US011352647B2

(12) United States Patent
Zhang et al.

(10) Patent No.: US 11,352,647 B2
(45) Date of Patent: *Jun. 7, 2022

(54) CRISPR ENZYMES AND SYSTEMS

(71) Applicants: THE BROAD INSTITUTE, INC., Cambridge, MA (US); MASSACHUSETTS INSTITUTE OF TECHNOLOGY, Cambridge, MA (US)

(72) Inventors: Feng Zhang, Cambridge, MA (US); David Arthur Scott, Cambridge, MA (US); Winston Xia Yan, Cambridge, MA (US); Sourav Choudhury, Cambridge, MA (US); Matthias Heidenreich, Cambridge, MA (US)

(73) Assignees: THE BROAD INSTITUTE, INC., Cambridge, MA (US); MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/325,898

(22) PCT Filed: Aug. 17, 2017

(86) PCT No.: PCT/US2017/047459
§ 371 (c)(1),
(2) Date: Feb. 15, 2019

(87) PCT Pub. No.: WO2018/035388
PCT Pub. Date: Feb. 22, 2018

(65) Prior Publication Data
US 2020/0080112 A1 Mar. 12, 2020

Related U.S. Application Data

(60) Provisional application No. 62/376,372, filed on Aug. 17, 2016, provisional application No. 62/437,023, filed on Dec. 20, 2016.

(51) Int. Cl.
| | | |
|---|---|---|
| *C12N 15/90* | (2006.01) | |
| *A61K 9/127* | (2006.01) | |
| *A61K 9/51* | (2006.01) | |
| *C12N 7/00* | (2006.01) | |
| *C12N 15/113* | (2010.01) | |
| *C12N 15/86* | (2006.01) | |

(52) U.S. Cl.
CPC .......... *C12N 15/907* (2013.01); *A61K 9/1271* (2013.01); *A61K 9/5184* (2013.01); *C12N 7/00* (2013.01); *C12N 15/113* (2013.01); *C12N 15/86* (2013.01); *C12N 2310/20* (2017.05); *C12N 2310/32* (2013.01); *C12N 2740/13042* (2013.01); *C12N 2740/13043* (2013.01); *C12N 2800/22* (2013.01)

(58) Field of Classification Search
None
See application file for complete search history.

(56) References Cited

U.S. PATENT DOCUMENTS

| | | | |
|---|---|---|---|
| 8,697,359 | B1 | 4/2014 | Zhang |
| 8,771,945 | B1 | 7/2014 | Zhang |
| 8,795,965 | B2 | 8/2014 | Zhang |
| 8,865,406 | B2 | 10/2014 | Zhang et al. |
| 8,871,445 | B2 | 10/2014 | Cong et al. |
| 8,889,356 | B2 | 11/2014 | Zhang |
| 8,889,418 | B2 | 11/2014 | Zhang et al. |

(Continued)

FOREIGN PATENT DOCUMENTS

| | | |
|---|---|---|
| EP | 2 764 103 A2 | 8/2014 |
| EP | 2 771 468 A1 | 9/2014 |

(Continued)

OTHER PUBLICATIONS

Sorek et al., "CRISPR-Mediated Adaptive Immune Systems in Bacteria and Archaea" 82 Annual Review of Biochemistry 217-266 (2013).*
Koonin et al., "Diveristy, classification and evolution of CRISPR-Cas systems" 37 Current Opinion in Microbiology 67-78 (2017).*
Hendel et al., "Chemically modified guide RNAs enhance CRISPR-Cas genome editing in human primary cells" 33(9) Nature Biotechnology 985-989, Online Methods (Jun. 29, 2015).*

(Continued)

*Primary Examiner* — Nancy J Leith
(74) *Attorney, Agent, or Firm* — Johnson, Marcou, Isaacs & Nix, LLC; F. Brent Nix, Esq.; Andrew R. Reeves

(57) ABSTRACT

Embodiments disclosed herein are directed to engineered CRISPR-Cas effector proteins that comprise at least one modification compared to an unmodified CRISPR-Cas effector protein that enhances binding of the of the CRISPR complex to the binding site and/or alters editing preference as compared to wild type. In certain example embodiments, the CRISPR-Cas effector protein is a Type V effector protein. In certain other example embodiments, the Type V effector protein is Cpf1. Embodiments disclosed herein are directed to viral vectors for delivery of CRISPR-Cas effector proteins, including Cpf1. In certain example embodiments, the vectors are designed so as to allow packaging of the CRISPR-Cas effector protein within a single vector. There is also an increased interest in the design of compact promoters for packing and thus expressing larger transgenes for targeted delivery and tissue-specificity. Thus, in another aspect certain embodiments disclosed herein are directed to delivery vectors, constructs, and methods of delivering larger genes for systemic delivery.

12 Claims, 66 Drawing Sheets
Specification includes a Sequence Listing.

(56) References Cited

U.S. PATENT DOCUMENTS

| | | |
|---|---|---|
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,790,490 B2 | 10/2017 | Zhang et al. |
| 2003/0053990 A1 | 3/2003 | Rabinowitz et al. |
| 2003/0100707 A1 | 5/2003 | Hwang et al. |
| 2005/0120395 A1 | 6/2005 | Burt et al. |
| 2010/0311124 A1 | 12/2010 | Liu et al. |
| 2011/0023145 A1 | 1/2011 | Weinstein et al. |
| 2011/0104051 A1 | 5/2011 | Francis et al. |
| 2011/0152957 A1 | 6/2011 | Shaquer |
| 2011/0158957 A1 | 6/2011 | Bonini et al. |
| 2011/0225664 A1 | 9/2011 | Smith |
| 2013/0185823 A1 | 7/2013 | Kuang et al. |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0287938 A1 | 9/2014 | Zhang et al. |
| 2014/0310830 A1 | 10/2014 | Zhang et al. |
| 2014/0359799 A1 | 12/2014 | Hao et al. |
| 2015/0030669 A1 | 1/2015 | Hoertner et al. |
| 2015/0184139 A1 | 7/2015 | Zhang et al. |
| 2016/0060691 A1 | 3/2016 | Giresi et al. |
| 2016/0082126 A1 | 3/2016 | Wang et al. |
| 2016/0208243 A1 | 7/2016 | Abudayyeh et al. |
| 2016/0237455 A1 | 8/2016 | Glucksmann et al. |

FOREIGN PATENT DOCUMENTS

| | | |
|---|---|---|
| EP | 2 784 162 A1 | 10/2014 |
| WO | 2008/042156 A1 | 4/2008 |
| WO | 2014/018423 A2 | 1/2014 |
| WO | 2014/093595 A1 | 6/2014 |
| WO | 2014/093622 A2 | 6/2014 |
| WO | 2014/093635 A1 | 6/2014 |
| WO | 2014/093655 A2 | 6/2014 |
| WO | 2014/093661 A2 | 6/2014 |
| WO | 2014/093694 A1 | 6/2014 |
| WO | 2014/093701 A1 | 6/2014 |
| WO | 2014/093709 A1 | 6/2014 |
| WO | 2014/093712 A1 | 6/2014 |
| WO | 2014/093718 A1 | 6/2014 |
| WO | 2014/204723 A1 | 12/2014 |
| WO | 2014/204724 A1 | 12/2014 |
| WO | 2014/204725 A1 | 12/2014 |
| WO | 2014/204726 A1 | 12/2014 |
| WO | 2014/204727 A1 | 12/2014 |
| WO | 2014/204728 A1 | 12/2014 |
| WO | 2014/204729 A1 | 12/2014 |
| WO | 2015/048577 A2 | 4/2015 |
| WO | 2015/070083 A1 | 5/2015 |
| WO | 2015/086795 A1 | 6/2015 |
| WO | 2015/089351 A1 | 6/2015 |
| WO | 2015/089354 A1 | 6/2015 |
| WO | 2015/089419 A2 | 6/2015 |
| WO | 2015/089427 A1 | 6/2015 |
| WO | 2015/089462 A1 | 6/2015 |
| WO | 2015/089465 A1 | 6/2015 |
| WO | 2015/089473 A1 | 6/2015 |
| WO | 2015/089486 A2 | 6/2015 |
| WO | 2015089364 A1 | 6/2015 |
| WO | 2015/134812 A1 | 9/2015 |
| WO | 2015/138510 A1 | 9/2015 |
| WO | 2015/148670 A1 | 10/2015 |
| WO | 2015/148860 A1 | 10/2015 |
| WO | 2015/148863 A2 | 10/2015 |
| WO | 2015/153780 A1 | 10/2015 |
| WO | 2015/161276 A2 | 10/2015 |
| WO | 2015200378 A1 | 12/2015 |
| WO | 2016011381 A1 | 1/2016 |
| WO | 2016/025131 A1 | 2/2016 |
| WO | 2016/028682 A1 | 2/2016 |
| WO | 2016/049024 A2 | 3/2016 |
| WO | 2016/049163 A2 | 3/2016 |
| WO | 2016/049258 A2 | 3/2016 |
| WO | 2016049251 A1 | 3/2016 |
| WO | 2016/073433 A1 | 5/2016 |
| WO | 2016/094872 A9 | 6/2016 |
| WO | 2016/094874 A1 | 6/2016 |
| WO | 2016/094880 A1 | 6/2016 |
| WO | 2016/099887 A1 | 6/2016 |
| WO | 2016/100272 A1 | 6/2016 |
| WO | 2016/100562 A1 | 6/2016 |
| WO | 2016/100568 A1 | 6/2016 |
| WO | 2016/100571 A1 | 6/2016 |
| WO | 2016/106236 A1 | 6/2016 |
| WO | 2016089433 A1 | 6/2016 |
| WO | 2016112242 A1 | 7/2016 |
| WO | 2016124765 A1 | 8/2016 |
| WO | 2017/019867 A1 | 2/2017 |
| WO | 2017/066175 A1 | 4/2017 |
| WO | 2017/070605 A1 | 4/2017 |
| WO | 2017/100158 A1 | 6/2017 |
| WO | 2017/105991 A1 | 6/2017 |
| WO | 2017/106414 A1 | 6/2017 |
| WO | 2018035388 A1 | 2/2018 |

OTHER PUBLICATIONS

Frock et al., "Genome-wide detection of DNA double-stranded breaks induced by engineered nucleases" 33(2) Nature Biotechnology 179-186, Online Methods (Dec. 15, 2014).*

Abudayeh, et al., "Reactive Crystals Have the Edge", Science Journals, vol. 353, Issue 6299, Aug. 5, 2016, 554-556.

Adamson, et al., "A Multiplexed Single-Cell CRISPR Screening Platform Enables Systematic Dissection of the Unfolded Protein Response", Cell, vol. 167, No. 7, Dec. 15, 2016, 1867-1882.

Bakondi, et al., "In Vivo CRISPR/Cas9 Gene Editing Corrects Retinal Dystrophy in the S334ter-3 Rat Model of Autosomal Dominant Retinitis Pigmentosa", Molecular Therapy, vol. 24, No. 3, Mar. 2016, 556-563.

Bikard, et al., "Exploiting CRISPR-Cas Nucleases to Produce Sequence-Specific Antimicrobials", Nature Biotechnology, vol. 32, No. 11, Nov. 2014, 1146-1151.

Brooks, et al., "Efficient Gene Editing in Tomato in the First Generation Using the Clustered Regularly Interspaced Short Palindromic Repeats/CRISPR-Associated9 System", Plant Physiology, vol. 166, Nov. 2014, 1292-1297.

Caliando, et al., "Targeted DNA Degradation using a CRISPR Device Stably Carried in the Host Genome", Nature Communications, vol. 6, No. 6989, May 19, 2015, 10 pages.

Canver, et al., "BCL11A Enhancer Dissection by Cas9-mediated in Situ Saturating Mutagenesis", Nature, vol. 527, No. 7577, Nov. 12, 2015, 192-197.

Chen, et al., "Genome-Wide CRISPR Screen in a Mouse Model of Tumor Growth and Metastasis", Cell, vol. 160, No. 6, Mar. 12, 2015, 1246-1260.

Chen, et al., "Predicting Peptide-Mediated Interactions on a Genome-Wide Scale", PLOS Computational Biology, vol. 11, No. 5, May 4, 2015, 13 pages.

Dong, et al., "Multiplex Genome Engineering Using CRISPR/Cas Systems", Science, vol. 339, No. 6121, Feb. 15, 2013, 819-823.

Dey, et al., "Toward a "Structural BLAST": Using Structural Relationships to Infer Function", Protein Science, vol. 22, No. 4, Apr. 2013, 359-366.

(56) References Cited

OTHER PUBLICATIONS

Dixit, et al., "Perturb-Seq: Dissecting Molecular Circuits with Scalable Singe-Cell RNA Profiling of Pooled Genetic Screens", Cell, vol. 167, Dec. 15, 2016, 1853-1866.
Dong, et al., "Targeting Hepatitis B virus cccDNA by CRISPR/Cas9 Nuclease Efficiently Inhibits Viral Replication", Antiviral Research, vol. 118, Apr. 3, 2015, 110-117.
Ebina, et al., "Harnessing the CRISPR/Cas9 system to Disrupt latent HIV-1 Provirus", Scientific Reports, vol. 3, No. 2510, 2013, 7 pages.
Esvelt, et al., "Concerning RNA-guided Gene Drives for the Alteration of Wild Populations", eLIFE, vol. 3, e03401, 2014, 21 pages.
Feng, et al., "Efficient Genome Editing in Plants using a CRISPR/Cas System", Cell Research, vol. 23, Aug. 20, 2013, 1229-1232.
Fine, et al., "Trans-Spliced Cas9 Allows Cleavage of HBB and CCR5 Genes in Human Cells Using Compact Expression Cassettes", Scientific Reports, vol. 5, No. 10777, Jul. 1, 2015, 9 pages.
Gantz, et al., "Highly Efficient Cas9-Mediated Gene Drive for Population Modification of the Malaria Vector Mosquito Anopheles Stephensi", Proceedings of the National Academy of Sciences, Nov. 23, 2015, E6736-E6743.
Gao, et al., "Engineered Cpf1 Enzymes with Altered PAM Specificities", BioRxiv, Dec. 4, 2016, 17 pages.
Genovese, et al., "Targeted Genome Editing in Human Repopulating Hematopoietic Stem Cells", Nature, vol. 510, No. 7504, Jun. 12, 2014, 235-240.
Ghorbal, et al., "Genome Editing in the Human Malaria Parasite Plasmodium Falciparumusing the CRISPR-Cas9 System", Nature Biotechnology, vol. 32, No. 8, Aug. 2014, 819-823.
Heo, et al., "CRISPR/Cas9 Nuclease-Mediated Gene Knock-In in Bovine-Induced Pluripotent Cells", Stem Cells Development, vol. 24, No. 3, Feb. 2015, 393-402.
Hsu, et al., "Development and Applications of CRISPR-Cas9 for Genome Engineering", Cell, vol. 157, No. 6, Jun. 5, 2014, 1262-1278.
Hsu, et al., "DNA Targeting Specificity of RNA-Guided Cas9 Nucleases", Nature Biotechnology, vol. 31, No. 9, Sep. 2013, 827-832.
Hur, et al., "Targeted Mutagenesis in Mice by Electroporation of Cpf1 Ribonucleoproteins", Nature Biotechnology, vol. 34, No. 8, Aug. 2016, 807-808.
Jiang, et al., "CRISPR-Assisted Editing of Bacterial Genomes", Nature Biotechnology, vol. 31, No. 3, Mar. 2013, 233-239.
Jiang, et al., "RNA-Guided Editing of Bacterial Genomes Using CRISPR-Cas Systems", Nature Biotechnology, vol. 31, No. 3, Mar. 2013, 233-239.
Kabadi, et al., "Multiplex CRISPR/Cas9-based Genome Engineering from a Single Lenttiviral Vector", Nucleic Acids Research, vol. 42, No. 19, e147, Aug. 13, 2014, 11 pages.
Karimova, et al., "CRISPR/Cas9 Nickase-Mediated Disruption of Hepatitis B Virus Open Reading Frame S and X", Scientific Reports, vol. 5, Sep. 3, 2015, 20 pages.
Kim, et al., "Genome-Wide Analysis Reveals Specificities of Cpf1 Endonucleases in Human Cells", Nature Biotechnology, vol. 34, No. 8, Aug. 2016, 863-888.
Konermann, et al., "Genome-Scale Transcriptional Activation by an Engineered CRISPR-Cas9 Complex", Nature, vol. 517, Jan. 29, 2015, 583-588.
Konermann, et al., "Optical Control of Mammalian Endogenous Transcription and Epigenetic States", Nature, vol. 500, No. 7463, Aug. 22, 2013, 472-476.
Li, et al., "In Vivo Genome Editing Restores Haemostasis in a Mouse Model of Haemophilia", Nature, vol. 475, Jul. 14, 2011, 217-221.
Li, et al., "Inhibition of HIV-1 Infection of Primary CD4+ T-Cells by Gene Editing Of CCR5 Using Adenovirus-Delivered CRISPR/Cas", Journal of General Virology, vol. 96, No. 8, Apr. 5, 2015, 2381-2393.
Lin, et al., "The CRISPR/Cas9 System Facilitates Clearance of the Intrahepatic HBV Templates in Vivo", Molecular Therapy—Nucleic Acids, vol. 3, e186, Aug. 19, 2014, 7 pages.
Liu, Y., et al., "Competing Loyalty Programs: Impact of Market Saturation, Market Share, and Category Expandability", Journal of Marketing, American Marketing Association, vol. 73, Jan. 2009, 93-108.
Liu, et al., "Inhibition of Hepatitis B Virus by the CRISPR/Cas9 System via Targeting the Conserved Regions of the Viral Genome", Journal of General Virology, vol. 96, 2015, 2252-2261.
Lowder, et al., "A CRISPR/Cas9 Toolbox for Multiplexed Plant Genome Editing and Transcriptional Regulation", Plant Physiology, vol. 169, Oct. 2015, 15 pages.
Ma, et al., "A Robust CRISPR/Cas9 System for Convenient, High-Efficiency Multiplex Genome Editing in Monocot and Dicot Plants", Molecular Plant, vol. 8, No. 8, Aug. 2015, 1274-1284.
Maji, et al., "Multidimensional Chemical Control of CRISPR-Cas9", Nature Chemical Biology, vol. 13, 2017, 9-11.
Makarova, et al., "Annotation and Classification of CRISPR-Cas Systems", Methods in Molecular Biology, vol. 1311, 2015, 47-75.
Mandal, et al., "Efficient Ablation of Genes in Human Hematopoietic Stem and Effector Cells Using CRISPR/Cas9", Cell Stem Cell, vol. 15, No. 5, Nov. 6, 2014, 643-652.
Nekrasov, et al., "Plant Genome Editing Made Easy: Targeted Mutagenesis In Model and Crop Plants Using the CRISPR/Cas System", Plant Methods, vol. 9, No. 39, 2013, 10 pages.
Nishimasu, et al., "Crystal Structure of Cas9 in Complex with Guide RNA and Target DNA", Cell, vol. 156, No. 5, Feb. 27, 2014, 935-949.
Nishimasu, et al., "Crystal Structure of Staphylococcus Aureus Cas9", Cell, vol. 162, Aug. 27, 2015, 1113-1126.
Parnas, et al., "A Genome-Wide CRISPR Screen in Primary Immune Cells to Dissect Regulatory Networks", Cell, vol. 162, No. 3, Jul. 30, 2015, 675-686.
Pattanayak, et al., "High-Throughput Profiling of Off-Target DNA Cleavage Reveals RNA-Programmed Cas9 Nuclease Specificity", Nature biotechnology, vol. 31, No. 9, Sep. 2013, 839-843.
Platt, et al., "CRISPR-Cas9 Knockin Mice for Genome Editing and Cancer Modelling", Cell, vol. 159, No. 2, Oct. 9, 2014, 440-455.
Ramakrishna, et al., "Gene Disruption by Cell-Penetrating Peptide-Mediated Delivery of Cas9 Protein and Guide RNA", Genome Research, vol. 24, No. 6, Jun. 2014, 1020-1027.
Ramanan, et al., "CRISPR/Cas9 Cleavage of Viral DNA Efficiently Suppresses Hepatitis B Virus", Scientific Reports, vol. 5, No. 10833, Jun. 2, 2015, 9 pages.
Park, Chui-Yong, et al., "Functional Correction of Large Factor VIII Gene Chromosomal Inversions in Hemopilia A Patient-Derived iPSC's Using CRISPR-Cas9," Cell Stem Cell vol. 17, pp. 213-220, Jul. 23, 2015.
Listgarten, J., et al., "Abstract No. 163: In Silico Predictive Modelling of CRISPR/Cas9 Guide Efficiency," 65th Annual Meeting American Society of Human Genetics (Methods Matter: Approaches for Genomic Analysis), Oct. 6, 2015, https://www.ashg.org/wp-content/uploads/2019/10/2015-platform-abstracts-min.pdf, pp. 1 and 78.
Partial Supplementary Search Report for corresponding European application No. 17842160.8 dated Jan. 17, 2020, all enclosed pages cited.
Zou, et al., "Generation of Gene-Target Dogs Using CRISPR/Cas9 System", Journal of Molecular Cell Biology, vol. 7, Issue 6, Dec. 2015, 580-583.
Ran, et al., "Double Nicking by RNA-Guided CRISPR Cas9 for Enhanced Genome Editing Specificity", Cell, vol. 154, No. 6, Sep. 12, 2013, 1380-1389.
Ran, et al., "Genome Engineering Using the CRISPR-Cas9 System", Nature Protocols, vol. 8, No. 11, Nov. 2013, 2281-2308.
Shalem, et al., "Genome-Scale CRISPR-Cas9 Knockout Screening in Human Cells", Science, vol. 343, No. 6166, Jan. 3, 2014, 84 87.
Shalem, et al., "High-Throughput Functional Genomics Using CRISPR-Cas9", Nature Reviews, vol. 16, May 2015, 299-311.
Shan, et al., "Targeted Genome Modification of Crop Plants Using a CRISPR-Cas System", Nature Biotechnology, vol. 31, No. 8, Aug. 2013, 686-688.

(56) References Cited

OTHER PUBLICATIONS

Shen, et al., "Efficient Gene Disruption in Diverse Strains of Toxoplasma Gondii Using CRISPR/Cas9", Mbio, vol. 5, Issue 3, May 2014, 11 pages.
Shmakov, et al., "Discovery and Functional Characterization of Diverse Class 2 CRISPR-Cas Systems", Molecular Cell, vol. 60, No. 3, Nov. 5, 2013, 385-397.
Sidik, et al., "Efficient Genome Engineering of Toxoplasma Gondii Using CRISPR/Cas9", PLOS one, vol. 9, Issue 6, Jun. 2014, 8 pages.
Song, et al., "Improved Hematopoietic Differentiation Efficiency of Gene-Corrected Beta-Thalassemia Induced Pluripotent Stem Cells by CRISPR/Cas9 System", Stem Cells and Development, vol. 24, No. 9, May 2015, 1053-1065.
Sugano, et al., "CRISPR/Cas9-Mediated Targeted Mutagenesis in the Liverwort Marchantia polymorpha L.", Plant and Cell Physiology, vol. 55, No. 3, 2014, 475-481.
Suhy, et al., "Safe, Long-term Hepatic Expression of Anti-HCV shRNA in a Nonhuman Primate Model", Molecular Therapy, vol. 20, No. 9, Sep. 2012, 1737-1749.
Swiech, et al., "In Vivo Interrogation of Gene Function in the Mammalian Brain Using CRISPR-Cas9", Nature Biotechnology, vol. 33, No. 1, Jan. 2015, 102-106.
Tsai, et al., "Dimeric CRISPR RNA-Guided FokI Nucleases for Highly Specific Genome Editing", Nature Biotechnology, vol. 32, No. 6, Jun. 2014, 569-577.
Vyas, et al., "A Candida Albicans CRISPR System Permits Genetic Engineering of Essential Genes and Gene Familiies", Science Advances, e1500248, Apr. 3, 2015, 6 pages.
Wagner, et al., "Efficient CRISPR/Cas9-Mediated Genome Editing in P. Falciparum", Nature Methods, vol. 11, No. 9, Sep. 2014, 915-918.
Wang, et al., "CCR5 Gene Disruption via Lentiviral Vectors Expressing Cas9 and Single Guided RNA Renders Cells Resistant to HIV-1 Infection", PLoS One, vol. 9, No. 12, e115987, Dec. 26, 2014, 26 pages.
Wang, et al., "Dual gRNAs Guided CRISPR/Cas9 System Inhibits Hepatitis B Virus Replication", World Journal of Gastroenterology, vol. 21, Issue 32, Aug. 28, 2015, 9554-9565.
Wang, et al., "Genetic Screens in Human Cells Using the CRISPR/Cas9 System", Science, vol. 343, No. 6166, Jan. 3, 2014, 80-84.
Wang, et al., "One-Step Generation of Mice Carrying Mutations in Multiple Genes by CRISPR/Cas-Mediated Genome Engineering", Cell, vol. 153, No. 4, May 9, 2013, 1-13.
Wang, et al., "Optimizing Multiplex CRISPR/Cas9-Based Genome Editing for Wheat", bioRxiv, May 12, 2016, 34 pages.
Whitworth, et al., "Gene-Edited Pigs are Protected from Porcine Reproductive and Respiratory Syndrome Virus", Nature Biotechnology, vol. 34, No. 1, Dec. 7, 2015, 20-22.
Wu, et al., "Correction of a Genetic Disease in Mouse via Use of CRISPR-Cas9", Cell Stem Cell, vol. 13, Dec. 5, 2013, 659-662.
Wu, et al., "Genome-Wide Binding of the CRISPR Endonuclease Cas9 in Mammalian Cells", Nature Biotechnology, vol. 32, No. 7, Jul. 2014, 670-676.
Xie, et al., "RNA-Guided Genome Editing in Plants Using a CRISPR-Cas System", Molecular Plant, vol. 6, No. 6, Nov. 2013, 1975-1983.
Xie, et al., "Seamless Gene Correction of ?-Thalassemia Mutations in Patient-Specific Ipscs Using CRISPR/Cas9 and Piggybac", Genome Research, vol. 24, No. 9, 2014, 1526-1533.
Xing, et al., "A CRISPR/Cas9 Toolkit for Multiplex Genome Editing in Plants", BMC Plant Biology, vol. 14, No. 327, 2014, 12 pages.
Xu, et al., "Both TALENs and CRISPR/Cas9 Directly Target the HBB IVS2-654 (C>T) Mutation in B-thalassemia-derived iPSCs", Scientific Reports, vol. 5, No. 12065, 2015, 15 pages.
Xu, et al., "Gene Targeting Using the Agrobacterium Tumefaciens-Mediated CRISPR-Cas System in Rice", Rice, vol. 7, No. 5, 2014, 4 pages.
Xu, et al., "Sequence Determinants of Improved CRISPR Sgrna Design", Genome Research, vol. 25, Aug. 2015, 1147-1157.
Yin, et al., "Genome Editing with Cas9 in Adult Mice Corrects a Disease Mutation and Phenotype", Nature Biotechnology, vol. 32, No. 6, Jun. 2014, 551-553.
Yosef, et al., "Temperate and Lytic Bacteriophages Programmed to Sensitize and Kill Antibiotic-Resistant Bacteria", Proceedings of the National Academy of Sciences, vol. 112, No. 23, Jun. 9, 2015, 7267-7272.
Zetsche, et al., "A Split-Cas9 Architecture for Inducible Genome Editing and Transcription Modulation", Nature Biotechnology, vol. 33, No. 2, 2015, 139-142.
Zetsche, et al., "Cpf1 is a Single RNA-Guided Endonuclease of a Class 2 CRISPR-Cas System", Cell, vol. 163, Oct. 22, 2015, 759-771.
Zhang, et al., "Efficient Editing of Malaria Parasite Genome Using the CRISPRJ/Cas9 System", MBio, vol. 5, No. 4, Jul. 1, 2014, 9 pages.
Zhang, et al., "Structure-Based Prediction of Protein-Protein Interactions on a Genome-Wide Scale", Nature, vol. 490, Oct. 25, 2012, 556-560.
Zhou, et al., "Exploiting SNPs for Biallelic CRISPR Mutations in the Outcrossing Woody Perennial Populus Reveals 4-coumarate:CoA ligase Specificity and Redundancy", New Phytologist, vol. 208, 2015, 298-301.
"International Search Report and Written Opinion", ISR/WO issued in International Patent Application No. PCT/US2017/047459, dated Dec. 1, 2017, 1-29.
Doench, et al., "Rational Design of Highly Active Sgmas for CRISPR-Cas9-Mediated Gene Inactivation", Nature Biotechnology, vol. 32, No. 12, Sep. 3, 2014, 1262-1267.
Mefherd, et al., "Expression of CRISPR/Cas Single Guide RNAs using Small tRNA Promoters", RNA; vol. 21, pp. 1683-1689, Jul. 17, 2015, Jul. 15, 2017, 1683-1689.
Ran, et al., "In Vivo Genome Editing using Staphylococcus aureau Cas9", Nature, vol. 520, No. 7546, Apr. 9, 2015, 186-191.
Slaymaker, et al., "Rationally Engineered Cas9 Nucleases with Improved Specificity", Science, vol. 351, Jan. 1, 2016, pp. 84-88 with supplementary materials, Jan. 1, 2016, 84-88.
Extended Search Report and Written Opinion from corresponding European patent application No. 17842160.8 dated Jun. 26, 2020, all enclosed pages cited.
Luo, et al., "Integrative Analysis of CRISPR/Cas9 Target Sites in the Human HBB Gene," BioMed Research International,, vol. 2015, Jan. 1, 2015, all enclosed pages cited.
Examination report for corresponding European application No. 17842160.8 dated Apr. 30, 2021,, all enclosed pages cited.

* cited by examiner

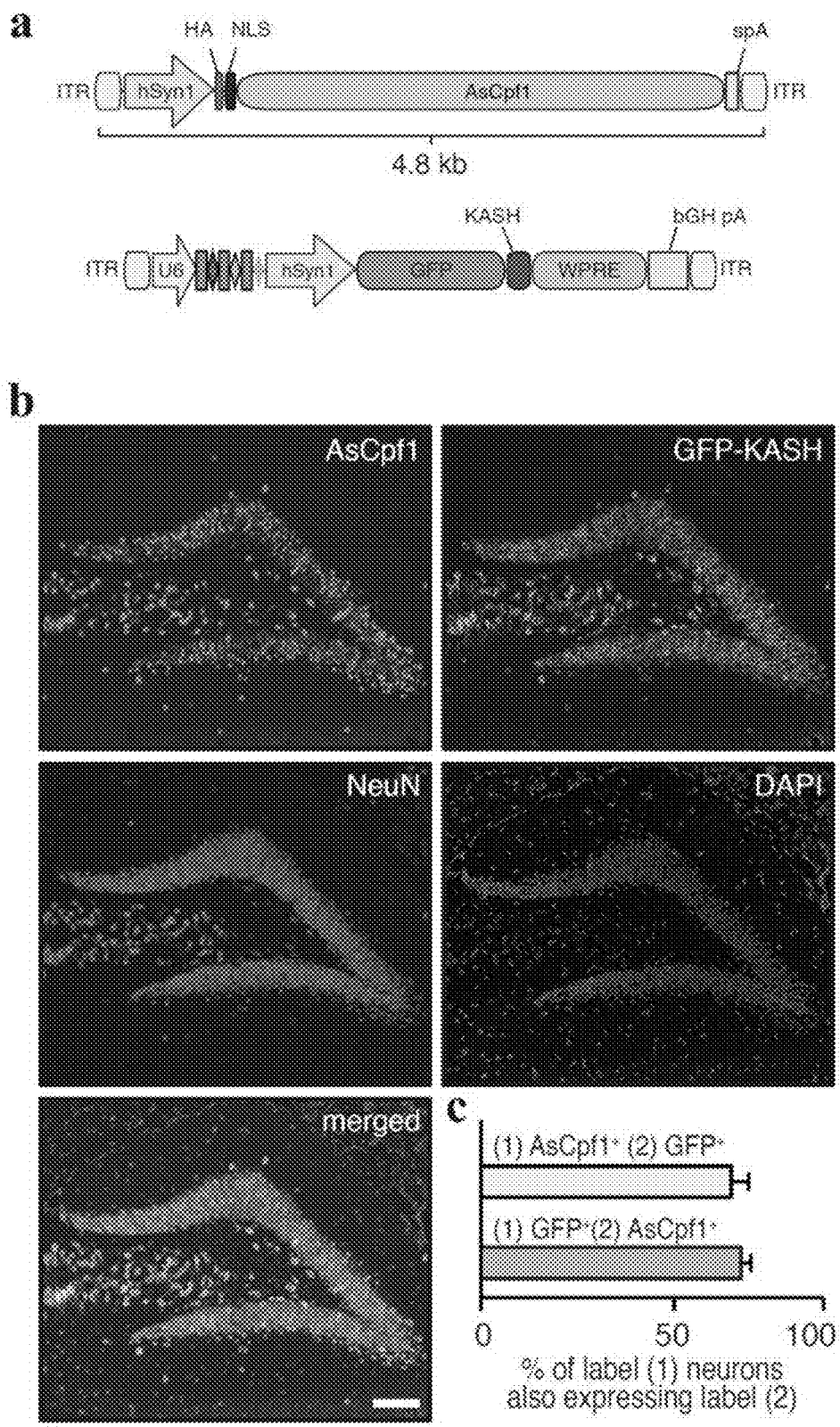
FIG. 4A-C

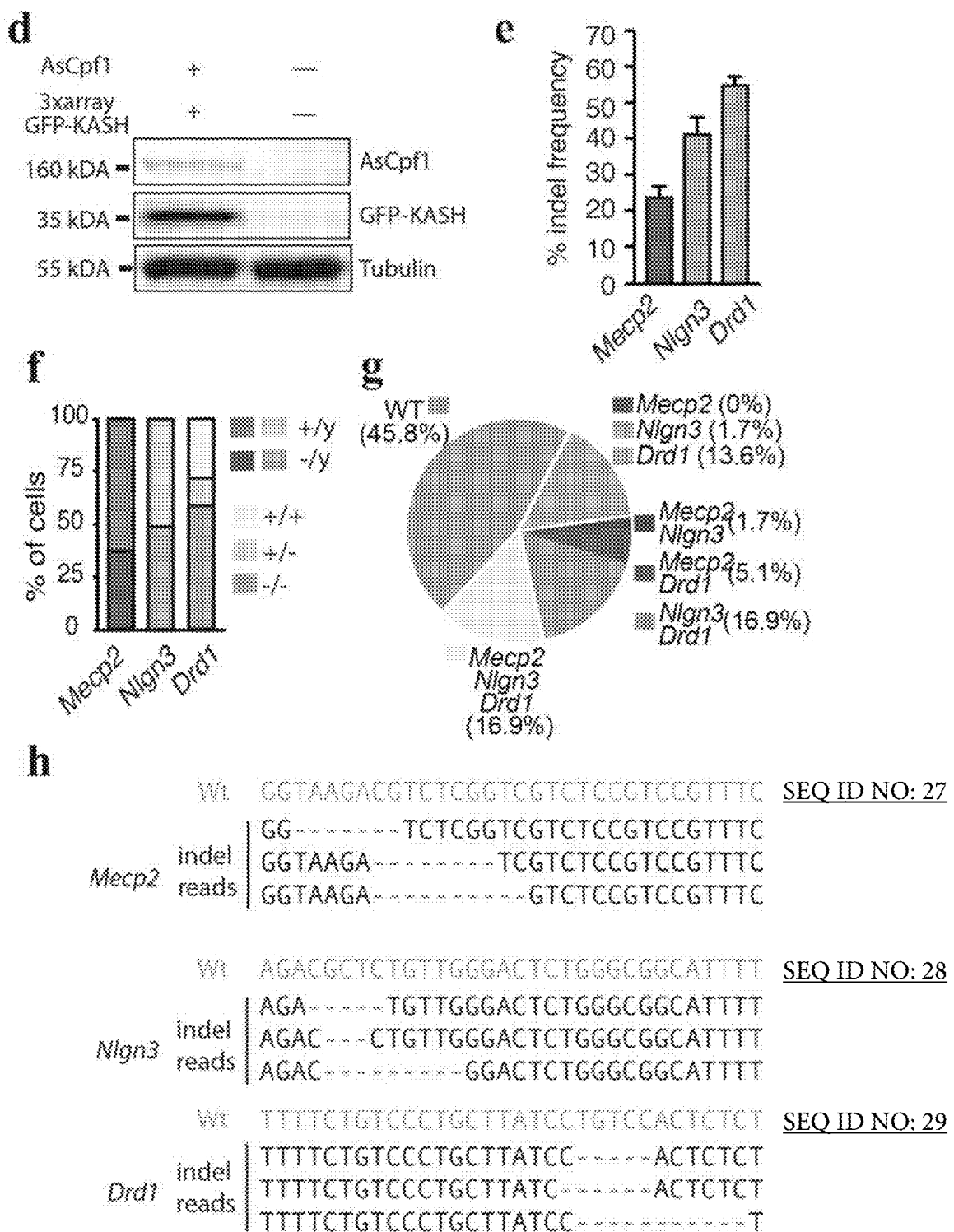
FIG. 4D-H

A   pLenti-AsCpf1 with single guide
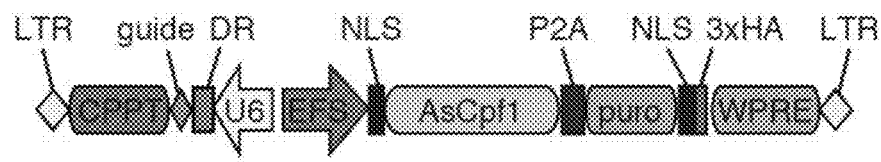
pLenti-AsCpf1 with guide array
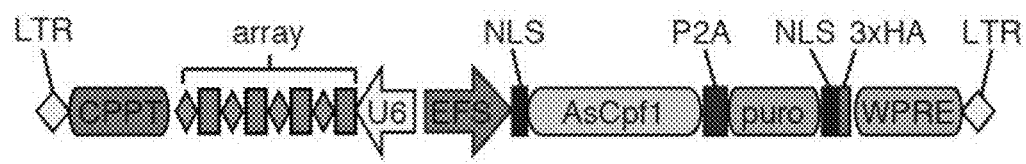
B
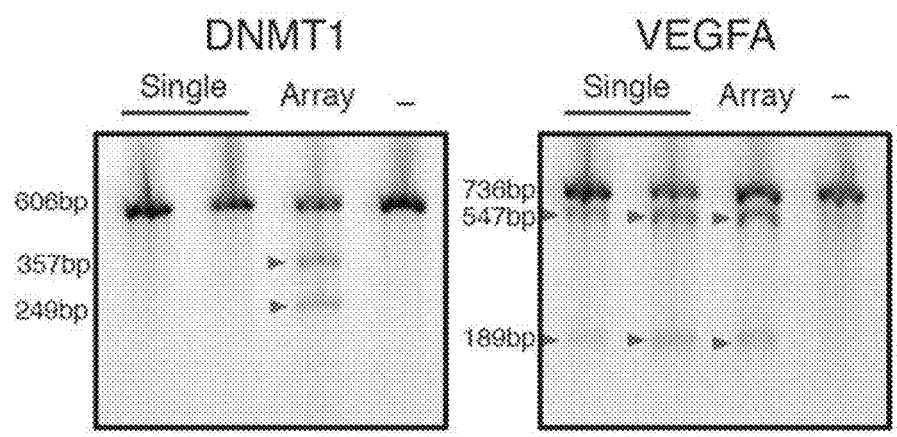
FIG. 6A-B

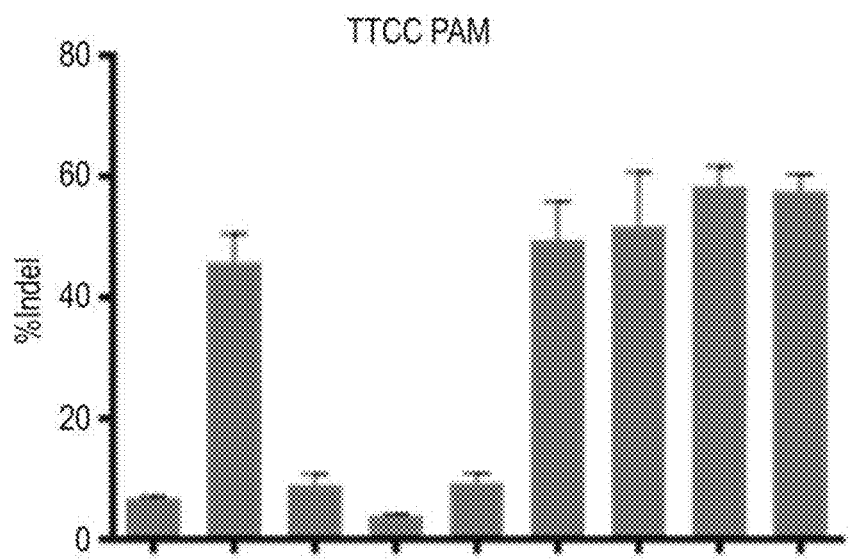
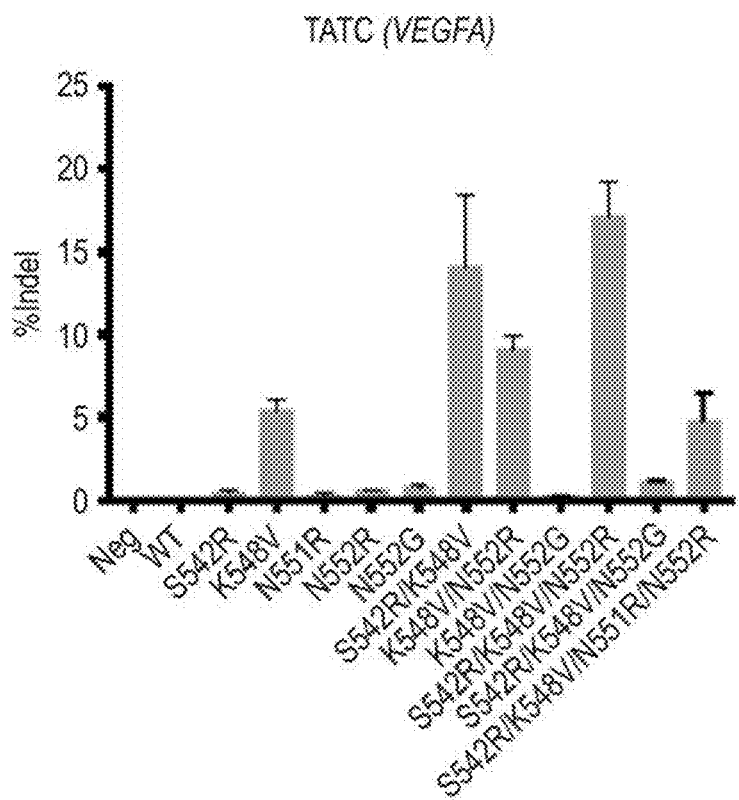
FIG. 22

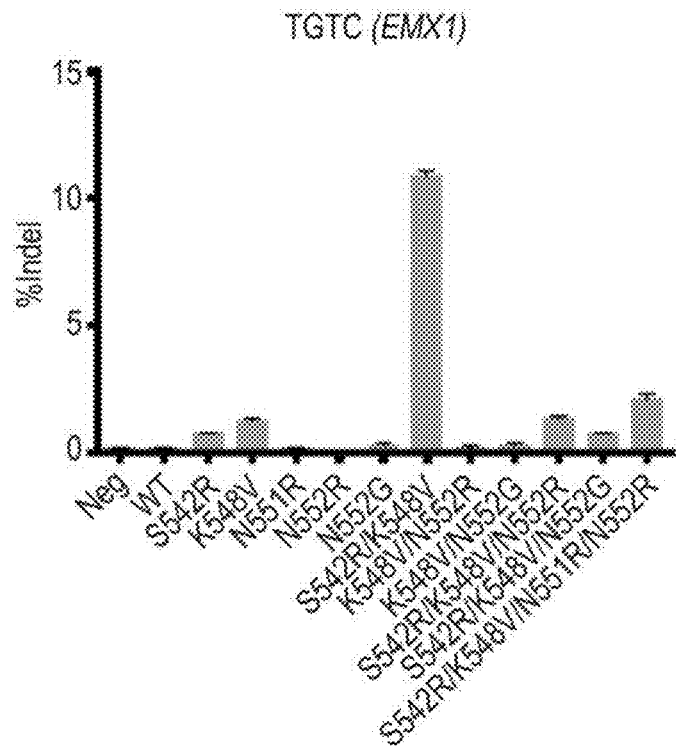
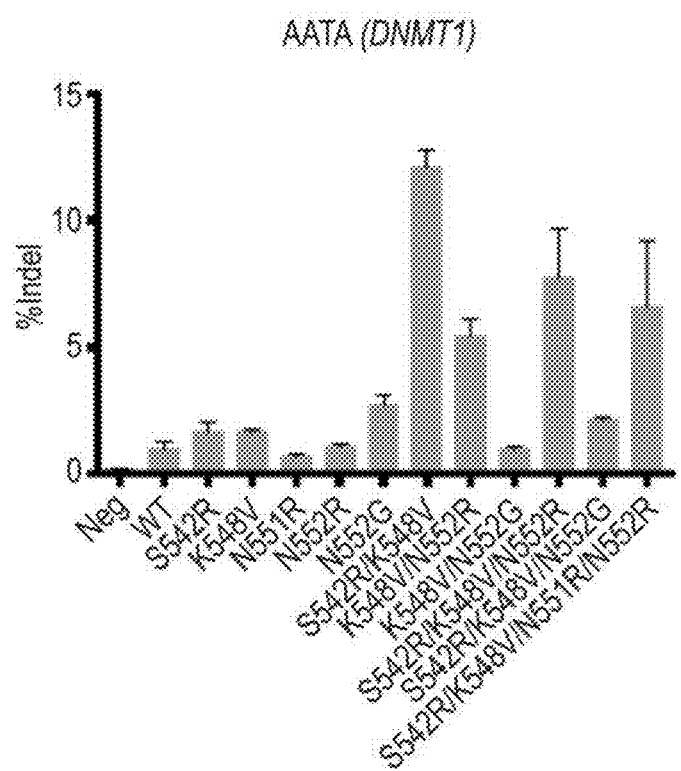
FIG. 22(continued)

SEQ ID NO: 38 AsCpf1
SEQ ID NO: 39 LbCpf1

| | | | |
|---|---|---|---|
| AsCpf1 | 1 | MTQFEGFTNLYQVSKTLRFELIPQGKTLKHIQEQGFIEEDKARNDHYKELKPIIDRIYKT | 60 |
| LbCpf1 | 1 | MSKLEKFTNCYSLSKTLRFKAIPVGKTQENIDNKRLLVEDEKRAEDYKGVKKLLDRYYLS | 60 |
| AsCpf1 | 61 | YADQCLQLVQLDWENLSAAIDSYRKEKTEETRNALIEE-QATYRNAIHDYFIGRTDNLTD | 119 |
| LbCpf1 | 61 | FINDVLHSIKL--KNLNNYISLFRKKTRTEKENKELENLRKEIAKAFKGN---------- | 112 |
| AsCpf1 | 120 | AINKRHAEIYKGLFKAELFNGKVLKQLGTVTTTEHENALLRSFDKFTTYFSGFYENRKNV | 179 |
| LbCpf1 | 113 | ------EGYKSLFKKDI----IETILPEFLDDKDEIALVNSFNGFTTAFTGFFDNRENM | 161 |
| AsCpf1 | 180 | FSAEDISTAIPHRIVQDNFPKFKENCHIFTRLITAVPSLREHFENVKKAIGIFVSTSIEE | 239 |
| LbCpf1 | 162 | FSEEAKSTSIAFRCINENLTRYISNMDIFEKVDAIFD--KHEVQEIKEKI-LNSDYDVED | 218 |
| AsCpf1 | 240 | VFSFPFYNQLLTQTQIDLYNQLLGGISREAGTEKIKGLNEVLNLAIQKNDETAHIIASLP | 299 |
| LbCpf1 | 219 | FFEGEFFNFVLTQEGIDVYNAIIGGFVTESG-EKIKGLNEYINLYNQKTKQ----KLP | 271 |
| AsCpf1 | 300 | HRFIPLFKQILSDRNTLSFILEEFKSDEEVIQSFCKYKTLLRNENVLETA--EALFNEL | 356 |
| LbCpf1 | 272 | -KFKPLYKQVLSDRESLSFYGEGYTSDEEVLEVF--RNTLNKNSEIFSSIKKLEKLFKNF | 328 |
| AsCpf1 | 357 | NSIDLTHIFISHK-KLETISSALCDHWDTLR---NALYERRISELTGKITKSAKEKVQRS | 412 |
| LbCpf1 | 329 | DEYSSAGIFVKNGPAISTISKDIFGEWNVIRDKWNAEYDDIHLKKKAVVTEKYEDDRRKS | 388 |
| AsCpf1 | 413 | LKH-EDINLQEITSAAGKELS------EAFKQKTSEIL------SHAHAALDQPLPTLKK | 460 |
| LbCpf1 | 389 | FKKIGSFSLEQLQEYADADLSVVEKLKEIIQKVDEIYKVYGSSEKLFDADFVLEKSLKK | 448 |
| AsCpf1 | 461 | QEEK-EILKSQLDSLLGLYHLLD-WFAVDESNEVDPEFSARLT--GIKLEMEPSLSFYN | 515 |
| LbCpf1 | 449 | NDAVVAIMKDLLDSVKSFENYIKAFFGEGKETNRDESFYGDFVLAYDILLKVD--HIYD | 505 |
| AsCpf1 | 516 | KARNYATKKPYSVEKFKLNFQMPTLASGWDVNKEKNNGAILFVKNGLYYLGIMPKQKGRY | 575 |
| LbCpf1 | 506 | AIRNYVTQKPYSKDKFKLYFQNPQFMGGWDKDKETDYRATILRYGSKYYLAIMDKKYA-- | 563 |
| AsCpf1 | 576 | KALSFEPTEKTSEGFDKMYYDYFPDAAKMIPKCSTQLKAVTAHFQTHTTPILLSNNFIEP | 635 |
| LbCpf1 | 564 | KCLQKIDKDDVNGNYEKINYKLLPGPNKMLPKVFFSKKWMAYY----------------- | 606 |
| AsCpf1 | 636 | LEITKEIYDLNNPEKEPKKFQTAYAKKTGDQKGYREALCKWIDFTRDFLSKYTKTTSIDL | 695 |
| LbCpf1 | 607 | --------NPSEDIQKIYKNGTFKKGDMFNLNDC-IKLIDFFKDSISRYPKWSNAYD | 654 |

FIG. 25

| | | |
|---|---|---|
| AsCpf1 | 696 | SSLRPSSQYKDLGEYYAELNPLLYHISFQRIAEKEIMDAVETGKLYLFQIYNKDFAKGHH | 755 |
| LbCpf1 | 655 | FNFSETEKYKDIAGFYREVEEQGYKVSFESASKKEVDKLVEEGKLYMFQIYNKDFSDKSH | 714 |
| AsCpf1 | 756 | GKPNLHTLYWTGLFSPENLAKTSIKLNGQAELFYRPKSRMKR--MAHRLGEKMLNKKLKD | 813 |
| LbCpf1 | 715 | GTPNLHTMYFKLLFDENNHGQ--IRLSGGAELFMRRASLKKEELVVHPANSPIANKN-- | 769 |
| AsCpf1 | 814 | QKTPIPDTILYQELYDYVNHRLSHDLSDEARALLPNVITKEVSHEIIKDRRFTSDKFFFHV | 873 |
| LbCpf1 | 770 | ---PDNPKK------------------TTTLSVYKDKRFSEDQYELHI | 798 |
| AsCpf1 | 874 | PITLNYQAANSPSKFNQRVNAYLKEHPETP-IGIDRGERNLIYITVIDSTGKILEQRSL | 932 |
| LbCpf1 | 799 | PIAIN--KCPKNIFNINTEVRVLLK-HDDNPYVIGIDRGERNLLYIVVVDGKGNIVEQYSL | 856 |
| AsCpf1 | 933 | NTI-------QQFDYQKKLDNREKERVAARQAWSVVGTIKDLKQGYLSQVIHEIVDLMI | 984 |
| LbCpf1 | 857 | NEIINNFNGIRIKTDYHSLLDKKEKERFEARQNWTSIENIKELKAGYISQVVHKICELVE | 916 |
| AsCpf1 | 985 | HYQAVVLENLNFGFKSKRTGIAEKAVYQQFEKMLIDKLNCLVLKDYPAEKVGGVLNPYQ | 1044 |
| | | KYDAVIALEDLNSGFKNSRVKV- |
| LbCpf1 | 917 | EKQVYQKFEKMLIDKLNYMVDKKSNPCATGGALKGYQ | 975 |
| AsCpf1 | 1045 | LTDQFTSFAKMGTQSGFLFYVPAPYTSKIDPLTGFVDPFVWKTIKNHESRKHFLEGFDFL | 1104 |
| LbCpf1 | 976 | ITNKFESFKSMSTQNGFIFYIPAWLTSKIDPSTGFVNLLKTKYTSIADSKK-FISSFDRI | 1034 |
| AsCpf1 | 1105 | HY--DVKTGDFILHFKMRNLSFQRGLPGFMPAWDIVFEKNETQFDAKGTPFIAGKRIVP | 1162 |
| LbCpf1 | 1035 | MYVPEEDLFEFALDYK-----NFSRTDADYIKKWKLYSYGNRIRIFRN-----PKKNNVF | 1084 |
| AsCpf1 | 1163 | VIENHRFTGRYRDLYPANELIALLEEKGIVFRDGSNILPKLLENDDSHAIDTMVALIRSV | 1222 |
| LbCpf1 | 1085 | DWEEVCLTSAYKELF--------NKYGINYQQG-DIRALLCEQSDKAFYSSFMALMSLM | 1134 |
| AsCpf1 | 1223 | LQMRNSITGEDYINSPVRDLNGVCFDSRF------QNPEWPMDADANGAYHIALKGQLL | 1277 |
| LbCpf1 | 1135 | LQMRNSITGRTDVDFLISPVKNSDGIFYDSRNYEAQENAILPKNADANGAYNIARKVLWA | 1194 |
| AsCpf1 | 1278 | LNHLKESKDLKLQN---GISNQDWLAYIQ | 1303 |
| LbCpf1 | 1195 | IGQFKKAEDEKLDKVKIAISNKEWLEYAQ | 1223 |

SEQ ID NO: 366

SEQUENCE LISTING

```
<160> NUMBER OF SEQ ID NOS: 367

<210> SEQ ID NO 1
<211> LENGTH: 7
<212> TYPE: PRT
<213> ORGANISM: Artificial
<220> FEATURE:
<223> OTHER INFORMATION: Synthetic

<400> SEQUENCE: 1

Glu Asn Leu Tyr Phe Gln Gly
1               5

<210> SEQ ID NO 2
<211> LENGTH: 7
<212> TYPE: PRT
<213> ORGANISM: Simian virus 40

<400> SEQUENCE: 2

Pro Lys Lys Lys Arg Lys Val
1               5

<210> SEQ ID NO 3
<211> LENGTH: 16
<212> TYPE: PRT
<213> ORGANISM: Artificial
```

```
<220> FEATURE:
<223> OTHER INFORMATION: Nucleoplasmin bipartite NLS

<400> SEQUENCE: 3

Lys Arg Pro Ala Ala Thr Lys Lys Ala Gly Gln Ala Lys Lys Lys Lys
1               5                   10                  15

<210> SEQ ID NO 4
<211> LENGTH: 9
<212> TYPE: PRT
<213> ORGANISM: Artificial
<220> FEATURE:
<223> OTHER INFORMATION: c-myc NLS from Homo sapiens

<400> SEQUENCE: 4

Pro Ala Ala Lys Arg Val Lys Leu Asp
1               5

<210> SEQ ID NO 5
<211> LENGTH: 11
<212> TYPE: PRT
<213> ORGANISM: Artificial
<220> FEATURE:
<223> OTHER INFORMATION: c-myc NLS from Homo sapiens

<400> SEQUENCE: 5

Arg Gln Arg Arg Asn Glu Leu Lys Arg Ser Pro
1               5                   10

<210> SEQ ID NO 6
<211> LENGTH: 38
<212> TYPE: PRT
<213> ORGANISM: Artificial
<220> FEATURE:
<223> OTHER INFORMATION: hRNPA1 M9 NLS from Homo sapiens

<400> SEQUENCE: 6

Asn Gln Ser Ser Asn Phe Gly Pro Met Lys Gly Gly Asn Phe Gly Gly
1               5                   10                  15

Arg Ser Ser Gly Pro Tyr Gly Gly Gly Gly Gln Tyr Phe Ala Lys Pro
            20                  25                  30

Arg Asn Gln Gly Gly Tyr
            35

<210> SEQ ID NO 7
<211> LENGTH: 42
<212> TYPE: PRT
<213> ORGANISM: Artificial
<220> FEATURE:
<223> OTHER INFORMATION: IBB domain from importin-alpha from Homo
      sapiens

<400> SEQUENCE: 7

Arg Met Arg Ile Glx Phe Lys Asn Lys Gly Lys Asp Thr Ala Glu Leu
1               5                   10                  15

Arg Arg Arg Arg Val Glu Val Ser Val Glu Leu Arg Lys Ala Lys Lys
            20                  25                  30

Asp Glu Gln Ile Leu Lys Arg Arg Asn Val
            35                  40

<210> SEQ ID NO 8
<211> LENGTH: 8
<212> TYPE: PRT
<213> ORGANISM: Artificial
<220> FEATURE:
```

<223> OTHER INFORMATION: Myoma T protein from Homo sapiens

<400> SEQUENCE: 8

Val Ser Arg Lys Arg Pro Arg Pro
1               5

<210> SEQ ID NO 9
<211> LENGTH: 8
<212> TYPE: PRT
<213> ORGANISM: Artificial
<220> FEATURE:
<223> OTHER INFORMATION: Myoma T protein from Homo sapiens

<400> SEQUENCE: 9

Pro Pro Lys Lys Ala Arg Glu Asp
1               5

<210> SEQ ID NO 10
<211> LENGTH: 8
<212> TYPE: PRT
<213> ORGANISM: Homo sapiens

<400> SEQUENCE: 10

Pro Gln Pro Lys Lys Lys Pro Leu
1               5

<210> SEQ ID NO 11
<211> LENGTH: 12
<212> TYPE: PRT
<213> ORGANISM: Mus sp.

<400> SEQUENCE: 11

Ser Ala Leu Ile Lys Lys Lys Lys Lys Met Ala Pro
1               5                   10

<210> SEQ ID NO 12
<211> LENGTH: 5
<212> TYPE: PRT
<213> ORGANISM: Influenza virus

<400> SEQUENCE: 12

Asp Arg Leu Arg Arg
1               5

<210> SEQ ID NO 13
<211> LENGTH: 7
<212> TYPE: PRT
<213> ORGANISM: Influenza virus

<400> SEQUENCE: 13

Pro Lys Gln Lys Lys Arg Lys
1               5

<210> SEQ ID NO 14
<211> LENGTH: 10
<212> TYPE: PRT
<213> ORGANISM: Hepatitis D virus

<400> SEQUENCE: 14

Arg Lys Leu Lys Lys Lys Ile Lys Lys Leu
1               5                   10

<210> SEQ ID NO 15
<211> LENGTH: 10
<212> TYPE: PRT

```
<213> ORGANISM: Mus sp.

<400> SEQUENCE: 15

Arg Glu Lys Lys Lys Phe Leu Lys Arg Arg
1               5                   10

<210> SEQ ID NO 16
<211> LENGTH: 20
<212> TYPE: PRT
<213> ORGANISM: Homo sapiens

<400> SEQUENCE: 16

Lys Arg Lys Gly Asp Glu Val Asp Gly Val Asp Glu Val Ala Lys Lys
1               5                   10                  15

Lys Ser Lys Lys
            20

<210> SEQ ID NO 17
<211> LENGTH: 17
<212> TYPE: PRT
<213> ORGANISM: Homo sapiens

<400> SEQUENCE: 17

Arg Lys Cys Leu Gln Ala Gly Met Asn Leu Glu Ala Arg Lys Thr Lys
1               5                   10                  15

Lys

<210> SEQ ID NO 18
<211> LENGTH: 4
<212> TYPE: PRT
<213> ORGANISM: Artificial
<220> FEATURE:
<223> OTHER INFORMATION: GlySer Linker

<400> SEQUENCE: 18

Gly Gly Gly Ser
1

<210> SEQ ID NO 19
<211> LENGTH: 15
<212> TYPE: PRT
<213> ORGANISM: Artificial
<220> FEATURE:
<223> OTHER INFORMATION: GlySer Linker

<400> SEQUENCE: 19

Gly Gly Gly Gly Ser Gly Gly Gly Ser Gly Gly Gly Gly Ser
1               5                   10                  15

<210> SEQ ID NO 20
<211> LENGTH: 30
<212> TYPE: PRT
<213> ORGANISM: Artificial
<220> FEATURE:
<223> OTHER INFORMATION: GlySer Linker

<400> SEQUENCE: 20

Gly Gly Gly Gly Ser Gly Gly Gly Gly Ser Gly Gly Gly Gly Ser Gly
1               5                   10                  15

Gly Gly Ser Gly Gly Gly Gly Ser Gly Gly Gly Gly Ser
            20                  25                  30

<210> SEQ ID NO 21
<211> LENGTH: 45
```

```
<212> TYPE: PRT
<213> ORGANISM: Artificial
<220> FEATURE:
<223> OTHER INFORMATION: GlySer Linker

<400> SEQUENCE: 21

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser Gly Gly Gly Ser Gly Gly Gly Ser
        35                  40                  45

<210> SEQ ID NO 22
<211> LENGTH: 60
<212> TYPE: PRT
<213> ORGANISM: Artificial
<220> FEATURE:
<223> OTHER INFORMATION: GlySer Linker

<400> SEQUENCE: 22

Gly Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Ser Gly Gly Gly Gly Ser Gly Gly Gly Ser Gly Gly
        35                  40                  45

Gly Ser Gly Gly Gly Ser Gly Gly Gly Gly Ser
    50                  55                  60

<210> SEQ ID NO 23
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 23
gagtccgagc agaagaagaa                                           20

<210> SEQ ID NO 24
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 24
gagtcctagc aggagaagaa                                           20

<210> SEQ ID NO 25
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 25
gagtctaagc agaagaagaa                                           20

<210> SEQ ID NO 26
<211> LENGTH: 9
<212> TYPE: PRT
<213> ORGANISM: Artificial
```

```
<220> FEATURE:
<223> OTHER INFORMATION: Synthetic Peptide

<400> SEQUENCE: 26

Leu Ala Gly Leu Ile Asp Ala Asp Gly
1               5

<210> SEQ ID NO 27
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 27
ggtaagacgt ctcggtcgtc tccgtccgtt tc                              32

<210> SEQ ID NO 28
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 28
agacgctctg ttgggactct gggcggcatt tt                              32

<210> SEQ ID NO 29
<211> LENGTH: 32
<212> TYPE: DNA
<213> ORGANISM: Artificial
<220> FEATURE:
<223> OTHER INFORMATION: Synthetic Oligonucleotide

<400> SEQUENCE: 29
ttttctgtcc ctgcttatcc tgtccactct ct                              32

<210> SEQ ID NO 30
<211> LENGTH: 23
<212> TYPE: DNA
<213> ORGANISM: Homo sapiens

<400> SEQUENCE: 30
tacataccca ccaccgtgcc tgg                                        23

<210> SEQ ID NO 31
<211> LENGTH: 23
<212> TYPE: DNA
<213> ORGANISM: Homo sapiens

<400> SEQUENCE: 31
tagacgccca ccaccatgcc tgg                                        23

<210> SEQ ID NO 32
<211> LENGTH: 23
<212> TYPE: DNA
<213> ORGANISM: Homo sapiens

<400> SEQUENCE: 32
tagatgccca ccaccgtgcc tgg                                        23

<210> SEQ ID NO 33
<211> LENGTH: 23
<212> TYPE: DNA
<213> ORGANISM: Homo sapiens
```

-continued

<210> SEQ ID NO 33
<211> LENGTH: 23
<212> TYPE: DNA
<213> ORGANISM: Homo sapiens

<400> SEQUENCE: 33
tagacgccca ccaccgtgcc tgg                                             23

<210> SEQ ID NO 34
<211> LENGTH: 23
<212> TYPE: DNA
<213> ORGANISM: Homo sapiens

<400> SEQUENCE: 34
tagacaccca ccaccatgcc tgg                                             23

<210> SEQ ID NO 35
<211> LENGTH: 24
<212> TYPE: DNA
<213> ORGANISM: Homo sapiens

<400> SEQUENCE: 35
ctgatggtcc atggtctgtt actc                                            24

<210> SEQ ID NO 36
<211> LENGTH: 23
<212> TYPE: DNA
<213> ORGANISM: Homo sapiens

<400> SEQUENCE: 36
ctgatggtcc atggtctgtt act                                             23

<210> SEQ ID NO 37
<211> LENGTH: 14
<212> TYPE: DNA
<213> ORGANISM: Homo sapiens

<400> SEQUENCE: 37
ctgatggtcc atgg                                                       14

<210> SEQ ID NO 38
<211> LENGTH: 1325
<212> TYPE: PRT
<213> ORGANISM: Acidaminococcus sp. BV3L6

<400> SEQUENCE: 38

Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45

Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

```
Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560
```

-continued

```
Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
```

```
                      980             985             990
        Glu Asn Leu Asn Phe Gly Phe Lys  Ser Lys Arg Thr Gly  Ile Ala Glu
                          995              1000             1005

Lys Ala  Val Tyr Gln Gln Phe  Glu Lys Met Leu Ile  Asp Lys Leu
            1010                 1015                 1020

Asn Cys Leu Val Leu Lys Asp  Tyr Pro Ala Glu Lys  Val Gly Gly
            1025                 1030                 1035

Val Leu Asn Pro Tyr Gln Lys  Tyr Asp Ala Val Ile  Ala Leu Glu
            1040                 1045                 1050

Asp Leu Asn Ser Gly Phe Lys  Asn Ser Arg Val Lys  Val Leu Thr
            1055                 1060                 1065

Asp Gln Phe Thr Ser Phe Ala  Lys Met Gly Thr Gln  Ser Gly Phe
            1070                 1075                 1080

Leu Phe Tyr Val Pro Ala Pro  Tyr Thr Ser Lys Ile  Asp Pro Leu
            1085                 1090                 1095

Thr Gly Phe Val Asp Pro Phe  Val Trp Lys Thr Ile  Lys Asn His
            1100                 1105                 1110

Glu Ser Arg Lys His Phe Leu  Glu Gly Phe Asp Phe  Leu His Tyr
            1115                 1120                 1125

Asp Val Lys Thr Gly Asp Phe  Ile Leu His Phe Lys  Met Asn Arg
            1130                 1135                 1140

Asn Leu Ser Phe Gln Arg Gly  Leu Pro Gly Phe Met  Pro Ala Trp
            1145                 1150                 1155

Asp Ile Val Phe Glu Lys Asn  Glu Thr Gln Phe Asp  Ala Lys Gly
            1160                 1165                 1170

Thr Pro Phe Ile Ala Gly Lys  Arg Ile Val Pro Val  Ile Glu Asn
            1175                 1180                 1185

His Arg Phe Thr Gly Arg Tyr  Arg Asp Leu Tyr Pro  Ala Asn Glu
            1190                 1195                 1200

Leu Ile Ala Leu Leu Glu Glu  Lys Gly Ile Val Phe  Arg Asp Gly
            1205                 1210                 1215

Ser Asn Ile Leu Pro Lys Leu  Leu Glu Asn Asp Asp  Ser His Ala
            1220                 1225                 1230

Ile Asp Thr Met Val Ala Leu  Ile Arg Ser Val Leu  Gln Met Arg
            1235                 1240                 1245

Asn Ser Asn Ala Ala Thr Gly  Glu Asp Tyr Ile Asn  Ser Pro Val
            1250                 1255                 1260

Arg Asp Leu Asn Gly Val Cys  Phe Asp Ser Arg Phe  Gln Asn Pro
            1265                 1270                 1275

Glu Trp Pro Met Asp Ala Asp  Ala Asn Gly Ala Tyr  His Ile Ala
            1280                 1285                 1290

Leu Lys Gly Gln Leu Leu Leu  Asn His Leu Lys Glu  Ser Lys Asp
            1295                 1300                 1305

Leu Lys Leu Gln Asn Gly Ile  Ser Asn Gln Asp Trp  Leu Ala Tyr
            1310                 1315                 1320

Ile Gln
            1325

<210> SEQ ID NO 39
<211> LENGTH: 1201
<212> TYPE: PRT
<213> ORGANISM: Lachnospiraceae bacterium ND2006

<400> SEQUENCE: 39
```

```
Met Ser Lys Leu Glu Lys Phe Thr Asn Cys Tyr Ser Leu Ser Lys Thr
1               5                   10                  15

Leu Arg Phe Lys Ala Ile Pro Val Gly Lys Thr Gln Glu Asn Ile Asp
            20                  25                  30

Asn Lys Arg Leu Leu Val Glu Asp Glu Lys Arg Ala Glu Asp Tyr Lys
            35                  40                  45

Gly Val Lys Lys Leu Leu Asp Arg Tyr Tyr Leu Ser Phe Ile Asn Asp
        50                  55                  60

Val Leu His Ser Ile Lys Leu Lys Asn Leu Asn Asn Tyr Ile Ser Leu
65                  70                  75                  80

Phe Arg Lys Lys Thr Arg Thr Glu Lys Glu Asn Lys Glu Leu Glu Asn
                85                  90                  95

Leu Glu Ile Asn Leu Arg Lys Glu Ile Ala Lys Ala Phe Lys Gly Asn
            100                 105                 110

Glu Gly Tyr Lys Ser Leu Phe Lys Lys Asp Ile Ile Glu Thr Ile Leu
            115                 120                 125

Pro Glu Phe Leu Asp Asp Lys Asp Glu Ile Ala Leu Val Asn Ser Phe
            130                 135                 140

Asn Gly Phe Thr Thr Ala Phe Thr Gly Phe Phe Asp Asn Arg Glu Asn
145                 150                 155                 160

Met Phe Ser Glu Glu Ala Lys Ser Thr Ser Ile Ala Phe Arg Cys Ile
                165                 170                 175

Asn Glu Asn Leu Thr Arg Tyr Ile Ser Asn Met Asp Ile Phe Glu Lys
            180                 185                 190

Val Asp Ala Ile Phe Asp Lys His Glu Val Gln Glu Ile Lys Glu Lys
            195                 200                 205

Ile Leu Asn Ser Asp Tyr Asp Val Glu Asp Phe Phe Glu Gly Glu Phe
            210                 215                 220

Phe Asn Phe Val Leu Thr Gln Glu Gly Ile Asp Val Tyr Asn Ala Ile
225                 230                 235                 240

Ile Gly Gly Phe Val Thr Glu Ser Gly Glu Lys Ile Lys Gly Leu Asn
                245                 250                 255

Glu Tyr Ile Asn Leu Tyr Asn Gln Lys Thr Lys Gln Lys Leu Pro Lys
            260                 265                 270

Phe Lys Pro Leu Tyr Lys Gln Val Leu Ser Asp Arg Glu Ser Leu Ser
            275                 280                 285

Phe Tyr Gly Glu Gly Tyr Thr Ser Asp Glu Glu Val Leu Glu Val Phe
            290                 295                 300

Arg Asn Thr Leu Asn Lys Asn Ser Glu Ile Phe Ser Ser Ile Lys Lys
305                 310                 315                 320

Leu Glu Lys Leu Phe Lys Asn Phe Asp Glu Tyr Ser Ser Ala Gly Ile
            325                 330                 335

Phe Val Lys Asn Gly Pro Ala Ile Ser Thr Ile Ser Lys Asp Ile Phe
            340                 345                 350

Gly Glu Trp Asn Val Ile Arg Asp Lys Trp Asn Ala Glu Tyr Asp Asp
            355                 360                 365

Ile His Leu Lys Lys Lys Ala Val Val Thr Glu Lys Tyr Glu Asp Asp
            370                 375                 380

Arg Arg Lys Ser Phe Lys Lys Ile Gly Ser Phe Ser Leu Glu Gln Leu
385                 390                 395                 400

Gln Glu Tyr Ala Asp Ala Asp Leu Ser Val Val Glu Lys Leu Lys Glu
            405                 410                 415

Ile Ile Ile Gln Lys Val Asp Glu Ile Tyr Lys Val Tyr Gly Ser Ser
```

```
                420             425             430
Glu Lys Leu Phe Asp Ala Asp Phe Val Leu Glu Lys Ser Leu Lys Lys
        435                 440                 445

Asn Asp Ala Val Val Ala Ile Met Lys Asp Leu Leu Asp Ser Val Lys
450                 455                 460

Ser Phe Glu Asn Tyr Ile Lys Ala Phe Phe Gly Glu Gly Lys Glu Thr
465                 470                 475                 480

Asn Arg Asp Glu Ser Phe Tyr Gly Asp Phe Val Leu Ala Tyr Asp Ile
                485                 490                 495

Leu Leu Lys Val Asp His Ile Tyr Asp Ala Ile Arg Asn Tyr Val Thr
                500                 505                 510

Gln Lys Pro Tyr Ser Lys Asp Lys Phe Lys Leu Tyr Phe Gln Asn Pro
        515                 520                 525

Gln Phe Met Gly Gly Trp Asp Lys Asp Lys Glu Thr Asp Tyr Arg Ala
        530                 535                 540

Thr Ile Leu Arg Tyr Gly Ser Lys Tyr Tyr Leu Ala Ile Met Asp Lys
545                 550                 555                 560

Lys Tyr Ala Lys Cys Leu Gln Lys Ile Asp Lys Asp Asp Val Asn Gly
                565                 570                 575

Asn Tyr Glu Lys Ile Asn Tyr Lys Leu Leu Pro Gly Pro Asn Lys Met
                580                 585                 590

Leu Pro Lys Val Phe Phe Ser Lys Lys Trp Met Ala Tyr Tyr Asn Pro
        595                 600                 605

Ser Glu Asp Ile Gln Lys Ile Tyr Lys Asn Gly Thr Phe Lys Lys Gly
        610                 615                 620

Asp Met Phe Asn Leu Asn Asp Cys His Lys Leu Ile Asp Phe Phe Lys
625                 630                 635                 640

Asp Ser Ile Ser Arg Tyr Pro Lys Trp Ser Asn Ala Tyr Asp Phe Asn
                645                 650                 655

Phe Ser Glu Thr Glu Lys Tyr Lys Asp Ile Ala Gly Phe Tyr Arg Glu
                660                 665                 670

Val Glu Glu Gln Gly Tyr Lys Val Ser Phe Glu Ser Ala Ser Lys Lys
                675                 680                 685

Glu Val Asp Lys Leu Val Glu Glu Gly Lys Leu Tyr Met Phe Gln Ile
        690                 695                 700

Tyr Asn Lys Asp Phe Ser Asp Lys Ser His Gly Thr Pro Asn Leu His
705                 710                 715                 720

Thr Met Tyr Phe Lys Leu Leu Phe Asp Glu Asn Asn His Gly Gln Ile
                725                 730                 735

Arg Leu Ser Gly Gly Ala Glu Leu Phe Met Arg Arg Ala Ser Leu Lys
                740                 745                 750

Lys Glu Glu Leu Val Val His Pro Ala Asn Ser Pro Ile Ala Asn Lys
        755                 760                 765

Asn Pro Asp Asn Pro Lys Lys Thr Thr Thr Leu Ser Tyr Asp Val Tyr
        770                 775                 780

Lys Asp Lys Arg Phe Ser Glu Asp Gln Tyr Glu Leu His Ile Pro Ile
785                 790                 795                 800

Ala Ile Asn Lys Cys Pro Lys Asn Ile Phe Lys Ile Asn Thr Glu Val
                805                 810                 815

Arg Val Leu Leu Lys His Asp Asp Asn Pro Tyr Val Ile Gly Ile Asp
                820                 825                 830

Arg Gly Glu Arg Asn Leu Leu Tyr Ile Val Val Val Asp Gly Lys Gly
                835                 840                 845
```

Asn Ile Val Glu Gln Tyr Ser Leu Asn Glu Ile Ile Asn Asn Phe Asn
            850                 855                 860

Gly Ile Arg Ile Lys Thr Asp Tyr His Ser Leu Leu Asp Lys Lys Glu
865                 870                 875                 880

Lys Glu Arg Phe Glu Ala Arg Gln Asn Trp Thr Ser Ile Glu Asn Ile
                885                 890                 895

Lys Glu Leu Lys Ala Gly Tyr Ile Ser Gln Val Val His Lys Ile Cys
                900                 905                 910

Glu Leu Val Glu Glu Lys Gln Val Tyr Gln Lys Phe Glu Lys Met Leu
            915                 920                 925

Ile Asp Lys Leu Asn Tyr Met Val Asp Lys Lys Ser Asn Pro Cys Ala
        930                 935                 940

Thr Gly Gly Ala Leu Lys Gly Tyr Gln Ile Thr Asn Lys Phe Glu Ser
945                 950                 955                 960

Phe Lys Ser Met Ser Thr Gln Asn Gly Phe Ile Phe Tyr Ile Pro Ala
                965                 970                 975

Trp Leu Thr Ser Lys Ile Asp Pro Ser Thr Gly Phe Val Asn Leu Leu
            980                 985                 990

Lys Thr Lys Tyr Thr Ser Ile Ala Asp Ser Lys Lys Phe Ile Ser Ser
        995                 1000                1005

Phe Asp Arg Ile Met Tyr Val Pro Glu Glu Asp Leu Phe Glu Phe
    1010                1015                1020

Ala Leu Asp Tyr Lys Asn Phe Ser Arg Thr Asp Ala Asp Tyr Ile
    1025                1030                1035

Lys Lys Trp Lys Leu Tyr Ser Tyr Gly Asn Arg Ile Arg Ile Phe
    1040                1045                1050

Arg Asn Pro Lys Lys Asn Asn Val Phe Asp Trp Glu Glu Val Cys
    1055                1060                1065

Leu Thr Ser Ala Tyr Lys Glu Leu Phe Asn Lys Tyr Gly Ile Asn
    1070                1075                1080

Tyr Gln Gln Gly Asp Ile Arg Ala Leu Leu Cys Glu Gln Ser Asp
    1085                1090                1095

Lys Ala Phe Tyr Ser Ser Phe Met Ala Leu Met Ser Leu Met Leu
    1100                1105                1110

Gln Met Arg Asn Ser Ile Thr Gly Arg Thr Asp Val Asp Phe Leu
    1115                1120                1125

Ile Ser Pro Val Lys Asn Ser Asp Gly Ile Phe Tyr Asp Ser Arg
    1130                1135                1140

Asn Tyr Glu Ala Gln Glu Asn Ala Ile Leu Pro Lys Asn Ala Asp
    1145                1150                1155

Ala Asn Gly Ala Tyr Asn Ile Ala Arg Lys Val Leu Trp Ala Ile
    1160                1165                1170

Gly Gln Phe Lys Lys Ala Glu Asp Glu Lys Leu Asp Lys Val Lys
    1175                1180                1185

Ile Ala Ile Ser Asn Lys Glu Trp Leu Glu Tyr Ala Gln
    1190                1195                1200

<210> SEQ ID NO 40
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 40
tttgctagga atattgaagg gggcagg                      27

<210> SEQ ID NO 41
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 41
caagccagga atattaaaag gggttgg                      27

<210> SEQ ID NO 42
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 42
aaggctagga agctgggagg tggcagg                      27

<210> SEQ ID NO 43
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 43
catagcaggt attttgaagg gggcagg                      27

<210> SEQ ID NO 44
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 44
tttggtgctc aatgaaagga gataagg                      27

<210> SEQ ID NO 45
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 45
tttgaagaaa tattacaaca tataaaa                      27

<210> SEQ ID NO 46
<211> LENGTH: 26
<212> TYPE: DNA
<213> ORGANISM: Artificial
<220> FEATURE:
<223> OTHER INFORMATION: Synthetic Oligonucleotide

<400> SEQUENCE: 46
tccaaataaa tttacacat ttaaaa                        26

<210> SEQ ID NO 47
<211> LENGTH: 28
<212> TYPE: DNA

```
<213> ORGANISM: Artificial
<220> FEATURE:
<223> OTHER INFORMATION: Synthetic Oligonucleotide

<400> SEQUENCE: 47
gagaaagaaa cattacctaa tgataaaa                                              28

<210> SEQ ID NO 48
<211> LENGTH: 28
<212> TYPE: DNA
<213> ORGANISM: Artificial
<220> FEATURE:
<223> OTHER INFORMATION: Synthetic Oligonucleotide

<400> SEQUENCE: 48
aacaaagaaa tattagaaaa taattaaa                                              28

<210> SEQ ID NO 49
<211> LENGTH: 28
<212> TYPE: DNA
<213> ORGANISM: Artificial
<220> FEATURE:
<223> OTHER INFORMATION: Synthetic Oligonucleotide

<400> SEQUENCE: 49
cataaacaaa tatcactaat atataaaa                                              28

<210> SEQ ID NO 50
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 50
gagaaaaaaa tattaataca tatacag                                               27

<210> SEQ ID NO 51
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 51
tttgtcctcc ggttctggaa ccacacc                                               27

<210> SEQ ID NO 52
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 52
ttcatcctcc ggttctggaa ccagatt                                               27

<210> SEQ ID NO 53
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 53
ttcatcctcc ggttctggaa ccagatc                                               27
```

<210> SEQ ID NO 54
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 54
ttcatcctcc ggttctgaaa ccacact                                    27

<210> SEQ ID NO 55
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 55
ttcatcctcc ggttctgaaa ccagatc                                    27

<210> SEQ ID NO 56
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 56
ttcatcctct ggttctggaa ccaggtc                                    27

<210> SEQ ID NO 57
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 57
ttcatccttc ggttctggaa ccagatc                                    27

<210> SEQ ID NO 58
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 58
cctctcctct ggttctggaa cactgaa                                    27

<210> SEQ ID NO 59
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 59
tttggggtga tcagacccaa cagcagg                                    27

<210> SEQ ID NO 60
<211> LENGTH: 27
<212> TYPE: DNA
<213> ORGANISM: Artificial
<220> FEATURE:

<223> OTHER INFORMATION: Synthetic Oligonucleotide

<400> SEQUENCE: 60
tttggggtga tcagacccaa caccagg                27

<210> SEQ ID NO 61
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 61
tttggggtga tcagacccaa ccccagg                27

<210> SEQ ID NO 62
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 62
tttggggtga tcaggcccaa caccagg                27

<210> SEQ ID NO 63
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 63
tttgtcctcc ggttctggaa ccacacc                27

<210> SEQ ID NO 64
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 64
ttcatcctcc ggttctggaa ccagatt                27

<210> SEQ ID NO 65
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 65
ttcatcctcc ggttctggaa ccagatc                27

<210> SEQ ID NO 66
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 66
ttcatcctcc ggttctgaaa ccacact                27

```
<210> SEQ ID NO 67
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 67
ttcatcctcc ggttctgaaa ccagatc                                           27

<210> SEQ ID NO 68
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 68
ttcatcctct ggttctggaa ccaggtc                                           27

<210> SEQ ID NO 69
<211> LENGTH: 27
<212> TYPE: DNA
<213> ORGANISM: Artificial
<220> FEATURE:
<223> OTHER INFORMATION: Synthetic Oligonucleotide

<400> SEQUENCE: 69
ttcatccttc ggttctggaa ccagatc                                           27

<210> SEQ ID NO 70
<211> LENGTH: 5
<212> TYPE: PRT
<213> ORGANISM: Artificial
<220> FEATURE:
<223> OTHER INFORMATION: GlySer Linker

<400> SEQUENCE: 70

Gly Gly Gly Gly Ser
1               5

<210> SEQ ID NO 71
<211> LENGTH: 10
<212> TYPE: PRT
<213> ORGANISM: Artificial
<220> FEATURE:
<223> OTHER INFORMATION: GlySer Linker

<400> SEQUENCE: 71

Gly Gly Gly Gly Ser Gly Gly Gly Gly Ser
1               5                   10

<210> SEQ ID NO 72
<211> LENGTH: 12
<212> TYPE: PRT
<213> ORGANISM: Artificial
<220> FEATURE:
<223> OTHER INFORMATION: Synthetic Peptide

<400> SEQUENCE: 72

Phe Trp Tyr His Lys Met Ile Leu Val Ala Gly Cys
1               5                   10

<210> SEQ ID NO 73
<211> LENGTH: 12
<212> TYPE: PRT
<213> ORGANISM: Artificial
```

```
<220> FEATURE:
<223> OTHER INFORMATION: Synthetic Peptide

<400> SEQUENCE: 73

Trp Tyr His Lys Arg Glu Asp Cys Ser Thr Asn Gln
1               5                   10

<210> SEQ ID NO 74
<211> LENGTH: 9
<212> TYPE: PRT
<213> ORGANISM: Artificial
<220> FEATURE:
<223> OTHER INFORMATION: Synthetic Peptide

<400> SEQUENCE: 74

Val Cys Ala Gly Ser Pro Thr Asn Asp
1               5

<210> SEQ ID NO 75
<211> LENGTH: 4
<212> TYPE: PRT
<213> ORGANISM: Artificial
<220> FEATURE:
<223> OTHER INFORMATION: Synthetic Peptide

<400> SEQUENCE: 75

Phe Trp Tyr His
1

<210> SEQ ID NO 76

<400> SEQUENCE: 76

000

<210> SEQ ID NO 77
<211> LENGTH: 5
<212> TYPE: PRT
<213> ORGANISM: Artificial
<220> FEATURE:
<223> OTHER INFORMATION: Synthetic Peptide

<400> SEQUENCE: 77

His Lys Arg Glu Asp
1               5

<210> SEQ ID NO 78

<400> SEQUENCE: 78

000

<210> SEQ ID NO 79

<400> SEQUENCE: 79

000

<210> SEQ ID NO 80

<400> SEQUENCE: 80

000

<210> SEQ ID NO 81

<400> SEQUENCE: 81
```

000

<210> SEQ ID NO 82
<211> LENGTH: 20
<212> TYPE: PRT
<213> ORGANISM: Artificial
<220> FEATURE:
<223> OTHER INFORMATION: GlySer Linker

<400> SEQUENCE: 82

Gly Gly Gly Gly Ser Gly Gly Gly Gly Ser Gly Gly Gly Gly Ser Gly
1               5                   10                  15

Gly Gly Gly Ser
            20

<210> SEQ ID NO 83
<211> LENGTH: 25
<212> TYPE: PRT
<213> ORGANISM: Artificial
<220> FEATURE:
<223> OTHER INFORMATION: GlySer Linker

<400> SEQUENCE: 83

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 84

<400> SEQUENCE: 84

000

<210> SEQ ID NO 85
<211> LENGTH: 35
<212> TYPE: PRT
<213> ORGANISM: Artificial
<220> FEATURE:
<223> OTHER INFORMATION: GlySer Linker

<400> SEQUENCE: 85

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser
        35

<210> SEQ ID NO 86
<211> LENGTH: 40
<212> TYPE: PRT
<213> ORGANISM: Artificial
<220> FEATURE:
<223> OTHER INFORMATION: GlySer Linker

<400> SEQUENCE: 86

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser Gly Gly
            20                  25                  30

Gly Gly Ser Gly Gly Gly Gly Ser
        35                  40

<210> SEQ ID NO 87
<211> LENGTH: 50
<212> TYPE: PRT
<213> ORGANISM: Artificial
<220> FEATURE:
<223> OTHER INFORMATION: GlySer Linker

<400> SEQUENCE: 87

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser Gly Gly Gly Gly Ser Gly Gly Gly
        35                  40                  45
Gly Ser
    50

<210> SEQ ID NO 88
<211> LENGTH: 55
<212> TYPE: PRT
<213> ORGANISM: Artificial
<220> FEATURE:
<223> OTHER INFORMATION: GlySer Linker

<400> SEQUENCE: 88

Gly Gly Gly Gly Ser Gly Gly Gly Gly Ser Gly Gly Gly Gly Ser Gly
1               5                   10                  15
Gly Gly Gly Ser Gly Gly Gly Gly Ser Gly Gly Gly Gly Ser Gly Gly
            20                  25                  30
Gly Gly Ser Gly Gly Gly Gly Ser Gly Gly Gly Gly Ser Gly Gly Gly
        35                  40                  45
Gly Ser Gly Gly Gly Gly Ser
    50                  55

<210> SEQ ID NO 89
<211> LENGTH: 20
<212> TYPE: DNA
<213> ORGANISM: Homo sapiens

<400> SEQUENCE: 89
gccaaattgg acgaccctcg                                            20

<210> SEQ ID NO 90
<211> LENGTH: 20
<212> TYPE: DNA
<213> ORGANISM: Homo sapiens

<400> SEQUENCE: 90
cgaggagacc cccgtttcgg                                            20

<210> SEQ ID NO 91
<211> LENGTH: 20
<212> TYPE: DNA
<213> ORGANISM: Homo sapiens

<400> SEQUENCE: 91
cccgccgccg ccgtggctcg                                            20

<210> SEQ ID NO 92
<211> LENGTH: 20
<212> TYPE: DNA

<213> ORGANISM: Homo sapiens

<400> SEQUENCE: 92
tgagctctac gagatccaca                                               20

<210> SEQ ID NO 93
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 93
ggtctcatgt gtggcactca                                               20

<210> SEQ ID NO 94
<211> LENGTH: 20
<212> TYPE: DNA
<213> ORGANISM: Artificial
<220> FEATURE:
<223> OTHER INFORMATION: Synthetic Oligonucleotide

<400> SEQUENCE: 94
tgtccaacct tcaggcaagg                                               20

<210> SEQ ID NO 95
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 95
gtaacgtcct ggacactgtg g                                             21

<210> SEQ ID NO 96
<211> LENGTH: 21
<212> TYPE: DNA
<213> ORGANISM: Artificial
<220> FEATURE:
<223> OTHER INFORMATION: Synthetic Oligonucleotide

<400> SEQUENCE: 96
ttggtccaat aggtcatgac g                                             21

<210> SEQ ID NO 97
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 97
tggctaagcc tggccaagaa cg                                            22

<210> SEQ ID NO 98
<211> LENGTH: 22
<212> TYPE: DNA
<213> ORGANISM: Artificial
<220> FEATURE:
<223> OTHER INFORMATION: Synthetic Oligonucleotide

<400> SEQUENCE: 98
tcaggatgaa ggctgccttc gg                                            22

```
<210> SEQ ID NO 99
<211> LENGTH: 485
<212> TYPE: DNA
<213> ORGANISM: Homo sapiens

<400> SEQUENCE: 99
gtgtctagac tgcagagggc cctgcgtatg agtgcaagtg ggttttagga ccaggatgag    60
gcggggtggg ggtgcctacc tgacgaccga ccccgaccca ctggacaagc acccaacccc   120
cattccccaa attgcgcatc ccctatcaga gaggggagg ggaaacagga tgcggcgagg   180
cgcgtgcgca ctgccagctt cagcaccgcg acagtgcct tcgcccccgc ctggcggcgc    240
gcgccaccgc cgcctcagca ctgaaggcgc gctgacgtca ctcgccggtc ccccgcaaac   300
tccccttccc ggccaccttg gtcgcgtccg cgccgccgcc ggcccagccg gaccgcacca   360
cgcgaggcgc gagatagggg ggcacgggcg cgaccatctg cgctgcggcg ccggcgactc   420
agcgctgcct cagtctgcgg tgggcagcgg aggagtcgtg tcgtgcctga gagcgcagtc   480
gagaa                                                               485

<210> SEQ ID NO 100
<211> LENGTH: 229
<212> TYPE: DNA
<213> ORGANISM: Mus sp.

<400> SEQUENCE: 100
agctgaatgg ggtccgcctc ttttccctgc ctaaacagac aggaactcct gccaattgag    60
ggcgtcaccg ctaaggctcc gccccagcct gggctccaca accaatgaag gtaatctcg   120 acaaagagca aggggtgggg cgcggcgcg caggtgcagc agcacacagg ctggtcggga   180
gggcggggcg cgacgtctgc cgtgcggggt cccggcatcg gttgcgcgc                229

<210> SEQ ID NO 101
<211> LENGTH: 30
<212> TYPE: DNA
<213> ORGANISM: Unknown
<220> FEATURE:
<223> OTHER INFORMATION: Synthetic Oligonucleotide

<400> SEQUENCE: 101
atgtacccat acgatgttcc agattacgct                                     30

<210> SEQ ID NO 102
<211> LENGTH: 33
<212> TYPE: DNA
<213> ORGANISM: Unknown
<220> FEATURE:
<223> OTHER INFORMATION: Synthetic Oligonucleotide

<400> SEQUENCE: 102
tcgccgaaga aaaagcgcaa ggtcgaagcg tcc                                 33

<210> SEQ ID NO 103
<211> LENGTH: 48
<212> TYPE: DNA
<213> ORGANISM: Unknown
<220> FEATURE:
<223> OTHER INFORMATION: Synthetic Oligonucleotide

<400> SEQUENCE: 103
aataaaagat ctttattttc attagatctg tgtgttggtt ttttgtgt                 48

<210> SEQ ID NO 104
```

```
<211> LENGTH: 72
<212> TYPE: DNA
<213> ORGANISM: Unknown
<220> FEATURE:
<223> OTHER INFORMATION: Synthetic Oligonucleotide

<400> SEQUENCE: 104
ggctcgttgg tctaggggta tgattctcgc ttagggtgcg agaggtcccg ggttcaaatc      60
ccggacgagc cc                                                         72

<210> SEQ ID NO 105
<211> LENGTH: 249
<212> TYPE: DNA
<213> ORGANISM: Unknown
<220> FEATURE:
<223> OTHER INFORMATION: Synthetic Oligonucleotide

<400> SEQUENCE: 105
gagggcctat ttcccatgat tccttcatat ttgcatatac gatacaaggc tgttagagag      60
ataattggaa ttaatttgac tgtaaacaca aagatattag tacaaaatac gtgacgtaga     120
aagtaataat ttcttgggta gtttgcagtt ttaaaattat gttttaaaat ggactatcat     180
atgcttaccg taacttgaaa gtatttcgat ttcttggctt tatatatctt gtggaaagga     240
cgaaacacc                                                            249

<210> SEQ ID NO 106
<211> LENGTH: 49
<212> TYPE: DNA
<213> ORGANISM: Unknown
<220> FEATURE:
<223> OTHER INFORMATION: Synthetic Oligonucleotide

<400> SEQUENCE: 106
gtaatttcta ctgttgtaga tggaagagca tatatgctct tcttttttt                 49

<210> SEQ ID NO 107
<211> LENGTH: 122
<212> TYPE: DNA
<213> ORGANISM: Artificial
<220> FEATURE:
<223> OTHER INFORMATION: Synthetic Oligonucleotide

<400> SEQUENCE: 107
aacacaggac cggtgccacc atgtacccat acgatgttcc agattacgct tcgccgaaga      60
aaaagcgcaa ggtcgaagcg tccacacagt tcgagggctt taccaacctg tatcaggtga     120
gc                                                                   122

<210> SEQ ID NO 108
<211> LENGTH: 94
<212> TYPE: DNA
<213> ORGANISM: Unknown
<220> FEATURE:
<223> OTHER INFORMATION: Synthetic Oligonucleotide

<400> SEQUENCE: 108
gcggccgcac acaaaaaacc aacacacaga tctaatgaaa ataaagatct tttattgaat      60
tcttagttgc gcagctcctg gatgtaggcc agcc                                 94

<210> SEQ ID NO 109
<211> LENGTH: 118
<212> TYPE: DNA
<213> ORGANISM: Unknown
```

```
<220> FEATURE:
<223> OTHER INFORMATION: Synthetic Oligonucleotide

<400> SEQUENCE: 109
taccggatcc ccgggtaccg gtatgtaccc atacgatgtt ccagattacg cttcgccgaa      60
gaaaaagcgc aaggtcgaag cgtccagcaa gctggagaag tttacaaact gctactcc      118

<210> SEQ ID NO 110
<211> LENGTH: 115
<212> TYPE: DNA
<213> ORGANISM: Unknown
<220> FEATURE:
<223> OTHER INFORMATION: Synthetic Oligonucleotide

<400> SEQUENCE: 110
gcggccgcac acaaaaaacc aacacacaga tctaatgaaa ataaagatct tttattgaat      60
tcttagtgct tcacgctggt ctgggcgtac tccagccact ccttgttaga gatgg          115

<210> SEQ ID NO 111
<211> LENGTH: 397
<212> TYPE: DNA
<213> ORGANISM: Mus musculus

<400> SEQUENCE: 111
cctacgctag cctgagggcc tatttcccat gattccttca tatttgcata tacgatacaa      60
ggctgttaga gagataattg gaattaattt gactgtaaac acaagatat tagtacaaaa     120 tacgtgacgt agaaagtaat aatttcttgg gtagtttgca gttttaaaat tatgttttaa    180
aatggactat catatgctta ccgtaacttg aaagtatttc gatttcttgg ctttatatat    240
cttgtggaaa ggacgaaaca ccgtaatttc tactcttgta gatcctgcct ctgctggctc    300
tgctaatttc tactcttgta gatcggcggg tctcagggtt gtctaatttc tactcttgta    360
gattgtccct gcttatcctg tccttttttc gacgcgt                             397

<210> SEQ ID NO 112
<211> LENGTH: 397
<212> TYPE: DNA
<213> ORGANISM: Mus sp.

<400> SEQUENCE: 112
cctacgctag cctgagggcc tatttcccat gattccttca tatttgcata tacgatacaa      60
ggctgttaga gagataattg gaattaattt gactgtaaac acaagatat tagtacaaaa     120 tacgtgacgt agaaagtaat aatttcttgg gtagtttgca gttttaaaat tatgttttaa    180
aatggactat catatgctta ccgtaacttg aaagtatttc gatttcttgg ctttatatat    240
cttgtggaaa ggacgaaaca ccgtaatttc tactcttgta gatttcgcct tcttaaactt    300
cagtaatttc tactcttgta gatgtgtccc tatggtaggt ccctaatttc tactcttgta    360
gattcatctc tttagctgtg tcatttttttc gacgcgt                            397

<210> SEQ ID NO 113
<211> LENGTH: 316
<212> TYPE: DNA
<213> ORGANISM: Unknown
<220> FEATURE:
<223> OTHER INFORMATION: Synthetic Oligonucleotide

<400> SEQUENCE: 113
ccctacgcta gcctgagggc ctatttccca tgattccttc atatttgcat atacgataca      60
```

```
aggctgttag agagataatt ggaattaatt tgactgtaaa cacaaagata ttagtacaaa    120
atacgtgacg tagaaagtaa taatttcttg ggtagtttgc agttttaaaa ttatgtttta    180
aaatggacta tcatatgctt accgtaactt gaaagtattt cgatttcttg gctttatata    240
tcttgtggaa aggacgaaac accgtaattt ctactcttgt agatgaagag cgagctcttc    300 tttttttcgac gcgtgt                                                   316
```

<210> SEQ ID NO 114
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 114

```
ctgatggtcc atgtctgtta ctc                                             23
```

<210> SEQ ID NO 115
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 115

```
tggttgccca ccctagtcat tgg                                             23
```

<210> SEQ ID NO 116
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 116

```
ctaggaatat tgaaggggggc agg                                            23
```

<210> SEQ ID NO 117
<211> LENGTH: 23
<212> TYPE: DNA
<213> ORGANISM: Artificial
<220> FEATURE:
<223> OTHER INFORMATION: Synthetic Oligonucleotide

<400> SEQUENCE: 117

```
gtgctcaatg aaaggagata agg                                             23
```

<210> SEQ ID NO 118
<211> LENGTH: 57
<212> TYPE: DNA
<213> ORGANISM: Artificial
<220> FEATURE:
<223> OTHER INFORMATION: Synthetic Oligonucleotide

<400> SEQUENCE: 118

```
agatctgatg gtccatgtct gttactcaat ttctactctt gtagattggt tgcccac        57
```

<210> SEQ ID NO 119
<211> LENGTH: 96
<212> TYPE: DNA
<213> ORGANISM: Artificial
<220> FEATURE:
<223> OTHER INFORMATION: Synthetic Oligonucleotide

<400> SEQUENCE: 119
cctagtcatt ggaatttcta ctcttgtaga tctaggaata ttgaaggggg caggaatttc    60
tactcttgta gatgtgctca atgaaaggag ataagg                              96

<210> SEQ ID NO 120
<211> LENGTH: 57
<212> TYPE: DNA
<213> ORGANISM: Artificial
<220> FEATURE:
<223> OTHER INFORMATION: Synthetic Oligonucleotide

<400> SEQUENCE: 120
aaaaccttat ctcctttcat tgagcacatc tacaagagta gaaattcctg ccccctt      57

<210> SEQ ID NO 121
<211> LENGTH: 96
<212> TYPE: DNA
<213> ORGANISM: Artificial
<220> FEATURE:
<223> OTHER INFORMATION: Synthetic Oligonucleotide

<400> SEQUENCE: 121
caatattcct agatctacaa gagtagaaat tccaatgact agggtgggca accaatctac    60
aagagtagaa attgagtaac agacatggac catcag                              96

<210> SEQ ID NO 122
<211> LENGTH: 71
<212> TYPE: DNA
<213> ORGANISM: Artificial
<220> FEATURE:
<223> OTHER INFORMATION: Synthetic Oligonucleotide

<400> SEQUENCE: 122
agatctgatg gtccatgtct gttactcgcc tgtcaatttc tactcttgta gattggttgc    60
ccaccctagt c                                                         71

<210> SEQ ID NO 123
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 123
acactggccc ggggctggga cgtgaataag gagaagaaca at                        42

<210> SEQ ID NO 124
<211> LENGTH: 42
<212> TYPE: DNA
<213> ORGANISM: Artificial
<220> FEATURE:
<223> OTHER INFORMATION: Synthetic

<400> SEQUENCE: 124
acactggcct caggctggga cgtgaagaag gagaagaaca at                        42

<210> SEQ ID NO 125
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 125
acactggcct caggctggga cgtgaagaag gagaagaaca at    42

<210> SEQ ID NO 126
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 126
acactggcct caggctggga cgtgaatgcc gagaagaaca at    42

<210> SEQ ID NO 127
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 127
acactggcct caggctggga cgtgaatcac gagaagaaca at    42

<210> SEQ ID NO 128
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 128
acactggcct caggctggga cgtgaataac gagaagaaca at    42

<210> SEQ ID NO 129
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 129
acactggcct caggctggga cgtgaatcag gagaagaaca at    42

<210> SEQ ID NO 130

<400> SEQUENCE: 130

000

<210> SEQ ID NO 131
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 131
acactggcct caggctggga cgtgaataag gagtacaaca at    42

<210> SEQ ID NO 132
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 132

```
acactggcct caggctggga cgtgaataag gagaagcgga at                    42
```

<210> SEQ ID NO 133
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 133

```
acactggcct caggctggga cgtgaataag gagaagaacg gc                    42
```

<210> SEQ ID NO 134
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 134

```
acactggcct caggctggga cgtgaataag gagaagaaca ag                    42
```

<210> SEQ ID NO 135
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 135

```
acactggcct caggctggga cgtgaataag gagaagaacc gg                    42
```

<210> SEQ ID NO 136
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 136

```
acactggcct caggctggga cgtgaataag gagaagaaca gc                    42
```

<210> SEQ ID NO 137
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 137

```
acactggcct caggctggga cgtgaataag gagaagaaca cc                    42
```

<210> SEQ ID NO 138
<211> LENGTH: 44
<212> TYPE: DNA
<213> ORGANISM: Artificial
<220> FEATURE:
<223> OTHER INFORMATION: Synthetic Oligonucleotide

<400> SEQUENCE: 138

```
atgccgccaa gatgatccca gcctgcagca cccagctgaa ggcg                  44
```

<210> SEQ ID NO 139
<211> LENGTH: 44
<212> TYPE: DNA
<213> ORGANISM: Artificial

```
<220> FEATURE:
<223> OTHER INFORMATION: Synthetic Oligonucleotide

<400> SEQUENCE: 139
atgccgccaa gatgatccca cggtgcagca cccagctgaa ggcg                44

<210> SEQ ID NO 140
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 140
acactggccc ggggctggga cgtgaatcgg gagaagaaca at                  42

<210> SEQ ID NO 141
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 141
acactggcct caggctggga cgtgaatcgg gagaagaacc gg                  42

<210> SEQ ID NO 142
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 142
acactggccc ggggctggga cgtgaataag gagtacaaca at                  42

<210> SEQ ID NO 143
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 143
acactggccc ggggctggga cgtgaatcgg gagtacaaca at                  42

<210> SEQ ID NO 144
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 144
cggctggcct caggctggga cgtgaataag gagaagaaca at                  42

<210> SEQ ID NO 145
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 145
aagctggcct caggctggga cgtgaataag gagaagaaca at                  42
```

<210> SEQ ID NO 146
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 146
acactggcct caggctggga cgtgaatggc gagaagaaca at          42

<210> SEQ ID NO 147
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 147
acactggcct caggctggga cgtgaattgc gagaagaaca at          42

<210> SEQ ID NO 148
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 148
acactggcct caggctggga cgtgaatttc gagaagaaca at          42

<210> SEQ ID NO 149
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 149
acactggcct caggctggga cgtgaatatc gagaagaaca at          42

<210> SEQ ID NO 150
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 150
acactggcct caggctggga cgtgaatatg gagaagaaca at          42

<210> SEQ ID NO 151
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 151
acactggcct caggctggga cgtgaatagc gagaagaaca at          42

<210> SEQ ID NO 152
<211> LENGTH: 42
<212> TYPE: DNA
<213> ORGANISM: Artificial
<220> FEATURE:
<223> OTHER INFORMATION: Synthetic Oligonucleotide

```
<400> SEQUENCE: 152
acactggcct caggctggga cgtgaatacc gagaagaaca at                              42

<210> SEQ ID NO 153
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 153
acactggcct caggctggga cgtgaatgtg gagaagaaca at                              42

<210> SEQ ID NO 154
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 154
acactggcct caggctggga cgtgaattgg gagaagaaca at                              42

<210> SEQ ID NO 155
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 155
acactggcct caggctggga cgtgaattac gagaagaaca at                              42

<210> SEQ ID NO 156
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 156
acactggcct caggctggga cgtgaatgac gagaagaaca at                              42

<210> SEQ ID NO 157
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 157
acactggcct caggctggga cgtgaatgag gagaagaaca at                              42

<210> SEQ ID NO 158
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 158
acactggcct caggctggga cgtgaatctg gagaagaaca at                              42

<210> SEQ ID NO 159
```

```
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 159
acactggcct caggctggga cgtgaatccc gagaagaaca at          42

<210> SEQ ID NO 160
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 160
acactggccc ggggctggga cgtgaatgtg gagaagaaca at          42

<210> SEQ ID NO 161
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 161
acactggcct caggctggga cgtgaatgtg gagaagaacc gg          42

<210> SEQ ID NO 162
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 162
acactggccc ggggctggga cgtgaatgtg gagaagaacc gg          42

<210> SEQ ID NO 163
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 163
acactggccc ggggctggga cgtgaatgtg gagaagcggc gg          42

<210> SEQ ID NO 164
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 164
acactggccc ggggctggga cgtgaagaag gagaagaaca at          42

<210> SEQ ID NO 165
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 165
```

-continued acactggccc ggggctggga cgtgaatgtg gagaagaaca at    42

<210> SEQ ID NO 166
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 166
acactggccc ggggctggga cgtgaataag gagaagcgga at    42

<210> SEQ ID NO 167
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 167
acactggccc ggggctggga cgtgaataag gagaagaaca gc    42

<210> SEQ ID NO 168
<211> LENGTH: 42
<212> TYPE: DNA
<213> ORGANISM: Artificial
<220> FEATURE:
<223> OTHER INFORMATION: Synthetic

<400> SEQUENCE: 168
acactggccc ggggctggga cgtgaagaag gagtacaaca at    42

<210> SEQ ID NO 169
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 169
acactggccc ggggctggga cgtgaagaag gagaagcgga at    42

<210> SEQ ID NO 170
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 170
acactggccc ggggctggga cgtgaagaag gagaagaaca gc    42

<210> SEQ ID NO 171
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 171
acactggccc ggggctggga cgtgaataag gagtaccgga at    42

<210> SEQ ID NO 172
<211> LENGTH: 42
<212> TYPE: DNA

<213> ORGANISM: Artificial
<220> FEATURE:
<223> OTHER INFORMATION: Synthetic Oligonucleotide

<400> SEQUENCE: 172
acactggccc ggggctggga cgtgaataag gagtacaaca gc                42

<210> SEQ ID NO 173
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 173
acactggccc ggggctggga cgtgaataag gagaagcgga gc                42

<210> SEQ ID NO 174
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 174
acactggccc ggggctggga cgtgaagaag gagtaccgga gc                42

<210> SEQ ID NO 175
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 175
acactggcct caggctggga cgtgaatgtg gagaagaacg gc                42

<210> SEQ ID NO 176
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 176
acactggccc ggggctggga cgtgaatgtg gagaagaacg gc                42

<210> SEQ ID NO 177
<211> LENGTH: 42
<212> TYPE: DNA
<213> ORGANISM: Artificial
<220> FEATURE:
<223> OTHER INFORMATION: Synthetic Oligonucleotide

<400> SEQUENCE: 177
acactggccc ggggctggga cgtgaatgtg gagaagcggg gc                42

<210> SEQ ID NO 178
<211> LENGTH: 23
<212> TYPE: DNA
<213> ORGANISM: Acidaminococcus sp. BV3L6

<400> SEQUENCE: 178
aaggaggagg aagctgctaa gga                                     23

```
<210> SEQ ID NO 179
<211> LENGTH: 23
<212> TYPE: DNA
<213> ORGANISM: Acidaminococcus sp. BV3L6

<400> SEQUENCE: 179
actagggtgg gcaaccacaa acc                                         23

<210> SEQ ID NO 180
<211> LENGTH: 23
<212> TYPE: DNA
<213> ORGANISM: Acidaminococcus sp. BV3L6

<400> SEQUENCE: 180
cctctttagc cagagccggg gtg                                         23

<210> SEQ ID NO 181
<211> LENGTH: 23
<212> TYPE: DNA
<213> ORGANISM: Acidaminococcus sp. BV3L6

<400> SEQUENCE: 181
agggcgttgg agcggggaga agg                                         23

<210> SEQ ID NO 182
<211> LENGTH: 23
<212> TYPE: DNA
<213> ORGANISM: Acidaminococcus sp. BV3L6

<400> SEQUENCE: 182
gagcggggag aaggccaggg gtc                                         23

<210> SEQ ID NO 183
<211> LENGTH: 23
<212> TYPE: DNA
<213> ORGANISM: Acidaminococcus sp. BV3L6

<400> SEQUENCE: 183
aaattccagc accgagcgcc ctg                                         23

<210> SEQ ID NO 184
<211> LENGTH: 23
<212> TYPE: DNA
<213> ORGANISM: Acidaminococcus sp. BV3L6

<400> SEQUENCE: 184
tagctgtttg ggaggtcaga aat                                         23

<210> SEQ ID NO 185
<211> LENGTH: 23
<212> TYPE: DNA
<213> ORGANISM: Acidaminococcus sp. BV3L6

<400> SEQUENCE: 185
tctttagcca gagccggggt gtg                                         23

<210> SEQ ID NO 186
<211> LENGTH: 23
<212> TYPE: DNA
<213> ORGANISM: Acidaminococcus sp. BV3L6

<400> SEQUENCE: 186
cgctccaacg ccctcaaccc cac                                         23
```

```
<210> SEQ ID NO 187
<211> LENGTH: 23
<212> TYPE: DNA
<213> ORGANISM: Acidaminococcus sp. BV3L6

<400> SEQUENCE: 187
tggccaggct ttggggaggc ctg                                              23

<210> SEQ ID NO 188
<211> LENGTH: 23
<212> TYPE: DNA
<213> ORGANISM: Acidaminococcus sp. BV3L6

<400> SEQUENCE: 188
tctgtcaatg gcggccccgg gct                                              23

<210> SEQ ID NO 189
<211> LENGTH: 23
<212> TYPE: DNA
<213> ORGANISM: Acidaminococcus sp. BV3L6

<400> SEQUENCE: 189
gtcacccctg tttctggcac cag                                              23

<210> SEQ ID NO 190
<211> LENGTH: 23
<212> TYPE: DNA
<213> ORGANISM: Acidaminococcus sp. BV3L6

<400> SEQUENCE: 190
cccgctccaa cgccctcaac ccc                                              23

<210> SEQ ID NO 191
<211> LENGTH: 23
<212> TYPE: DNA
<213> ORGANISM: Acidaminococcus sp. BV3L6

<400> SEQUENCE: 191
gctaaagagg gaatgggctt tgg                                              23

<210> SEQ ID NO 192
<211> LENGTH: 23
<212> TYPE: DNA
<213> ORGANISM: Acidaminococcus sp. BV3L6

<400> SEQUENCE: 192
tgtgggtgag tgagtgtgtg cgt                                              23

<210> SEQ ID NO 193
<211> LENGTH: 23
<212> TYPE: DNA
<213> ORGANISM: Acidaminococcus sp. BV3L6

<400> SEQUENCE: 193
ccctcccgtc acccctgttt ctg                                              23

<210> SEQ ID NO 194
<211> LENGTH: 23
<212> TYPE: DNA
<213> ORGANISM: Acidaminococcus sp. BV3L6

<400> SEQUENCE: 194
aatggcggcc ccgggcttca agc                                              23
```

<210> SEQ ID NO 195
<211> LENGTH: 23
<212> TYPE: DNA
<213> ORGANISM: Acidaminococcus sp. BV3L6

<400> SEQUENCE: 195
ggtgagtgag tgtgtgcgtg tgg							23

<210> SEQ ID NO 196
<211> LENGTH: 23
<212> TYPE: DNA
<213> ORGANISM: Acidaminococcus sp. BV3L6

<400> SEQUENCE: 196
aaagcccatt ccctctttag cca							23

<210> SEQ ID NO 197
<211> LENGTH: 23
<212> TYPE: DNA
<213> ORGANISM: Acidaminococcus sp. BV3L6

<400> SEQUENCE: 197
ctctttagcc agagccgggg tgt							23

<210> SEQ ID NO 198
<211> LENGTH: 23
<212> TYPE: DNA
<213> ORGANISM: Acidaminococcus sp. BV3L6

<400> SEQUENCE: 198
tggtgccaga aacaggggtg acg							23

<210> SEQ ID NO 199
<211> LENGTH: 23
<212> TYPE: DNA
<213> ORGANISM: Acidaminococcus sp. BV3L6

<400> SEQUENCE: 199
ctgatggtcc atgtctgtta ctc							23

<210> SEQ ID NO 200
<211> LENGTH: 23
<212> TYPE: DNA
<213> ORGANISM: Acidaminococcus sp. BV3L6

<400> SEQUENCE: 200
gctgaaggga aataaaagga aaa							23

<210> SEQ ID NO 201
<211> LENGTH: 23
<212> TYPE: DNA
<213> ORGANISM: Acidaminococcus sp. BV3L6

<400> SEQUENCE: 201
gccaccacag ggaagctggg tga							23

<210> SEQ ID NO 202
<211> LENGTH: 23
<212> TYPE: DNA
<213> ORGANISM: Acidaminococcus sp. BV3L6

<400> SEQUENCE: 202

```
aattccagca ccgagcgccc tgg                                              23

<210> SEQ ID NO 203
<211> LENGTH: 23
<212> TYPE: DNA
<213> ORGANISM: Acidaminococcus sp. BV3L6

<400> SEQUENCE: 203
aaaattttac accacaaaat gtt                                              23

<210> SEQ ID NO 204
<211> LENGTH: 23
<212> TYPE: DNA
<213> ORGANISM: Acidaminococcus sp. BV3L6

<400> SEQUENCE: 204
tatttctgac ctcccaaaca gct                                              23

<210> SEQ ID NO 205
<211> LENGTH: 23
<212> TYPE: DNA
<213> ORGANISM: Acidaminococcus sp. BV3L6

<400> SEQUENCE: 205
atgaatatca aattccagca ccg                                              23

<210> SEQ ID NO 206
<211> LENGTH: 23
<212> TYPE: DNA
<213> ORGANISM: Acidaminococcus sp. BV3L6

<400> SEQUENCE: 206
catcaaccgg tggcgcattg cca                                              23

<210> SEQ ID NO 207
<211> LENGTH: 23
<212> TYPE: DNA
<213> ORGANISM: Acidaminococcus sp. BV3L6

<400> SEQUENCE: 207
gagccggggt gtgcagacgg cag                                              23

<210> SEQ ID NO 208
<211> LENGTH: 23
<212> TYPE: DNA
<213> ORGANISM: Acidaminococcus sp. BV3L6

<400> SEQUENCE: 208
ttaaagaaaa tatcatcttt ggt                                              23

<210> SEQ ID NO 209
<211> LENGTH: 23
<212> TYPE: DNA
<213> ORGANISM: Acidaminococcus sp. BV3L6

<400> SEQUENCE: 209 agcgcccccct agtgactgcc gtc                                             23

<210> SEQ ID NO 210
<211> LENGTH: 23
<212> TYPE: DNA
<213> ORGANISM: Acidaminococcus sp. BV3L6

<400> SEQUENCE: 210
```
tccccattgg cctgcttcgt ggc    23

<210> SEQ ID NO 211
<211> LENGTH: 23
<212> TYPE: DNA
<213> ORGANISM: Acidaminococcus sp. BV3L6

<400> SEQUENCE: 211
gtcagcggac tcaccggcca ggg    23

<210> SEQ ID NO 212
<211> LENGTH: 23
<212> TYPE: DNA
<213> ORGANISM: Acidaminococcus sp. BV3L6

<400> SEQUENCE: 212
ttccctcttt agccagagcc ggg    23

<210> SEQ ID NO 213
<211> LENGTH: 23
<212> TYPE: DNA
<213> ORGANISM: Acidaminococcus sp. BV3L6

<400> SEQUENCE: 213
ggcttcaagc cctgtggggc cat    23

<210> SEQ ID NO 214
<211> LENGTH: 23
<212> TYPE: DNA
<213> ORGANISM: Acidaminococcus sp. BV3L6

<400> SEQUENCE: 214
aagatgatat tttctttaat ggt    23

<210> SEQ ID NO 215
<211> LENGTH: 23
<212> TYPE: DNA
<213> ORGANISM: Acidaminococcus sp. BV3L6

<400> SEQUENCE: 215
ctgtggtggc cgagcgcccc cta    23

<210> SEQ ID NO 216
<211> LENGTH: 23
<212> TYPE: DNA
<213> ORGANISM: Acidaminococcus sp. BV3L6

<400> SEQUENCE: 216
tctgcacacc ccggctctgg cta    23

<210> SEQ ID NO 217
<211> LENGTH: 23
<212> TYPE: DNA
<213> ORGANISM: Acidaminococcus sp. BV3L6

<400> SEQUENCE: 217
atgtcctccc cattggcctg ctt    23

<210> SEQ ID NO 218
<211> LENGTH: 23
<212> TYPE: DNA
<213> ORGANISM: Acidaminococcus sp. BV3L6

```
<400> SEQUENCE: 218
caaatatgta gctgtttggg agg                                              23

<210> SEQ ID NO 219
<211> LENGTH: 23
<212> TYPE: DNA
<213> ORGANISM: Acidaminococcus sp. BV3L6

<400> SEQUENCE: 219
ctccattcac ccagcttccc tgt                                              23

<210> SEQ ID NO 220
<211> LENGTH: 23
<212> TYPE: DNA
<213> ORGANISM: Acidaminococcus sp. BV3L6

<400> SEQUENCE: 220
aggaaaactg agaacagaat gaa                                              23

<210> SEQ ID NO 221
<211> LENGTH: 23
<212> TYPE: DNA
<213> ORGANISM: Acidaminococcus sp. BV3L6

<400> SEQUENCE: 221
taaactcatt aatgcccttc ggc                                              23

<210> SEQ ID NO 222
<211> LENGTH: 23
<212> TYPE: DNA
<213> ORGANISM: Acidaminococcus sp. BV3L6

<400> SEQUENCE: 222
atgtcacctc caatgactag ggt                                              23

<210> SEQ ID NO 223
<211> LENGTH: 23
<212> TYPE: DNA
<213> ORGANISM: Acidaminococcus sp. BV3L6

<400> SEQUENCE: 223
tggcaatgcg ccaccggttg atg                                              23

<210> SEQ ID NO 224
<211> LENGTH: 23
<212> TYPE: DNA
<213> ORGANISM: Acidaminococcus sp. BV3L6

<400> SEQUENCE: 224
gcgatgtttt ttctggagat tta                                              23

<210> SEQ ID NO 225
<211> LENGTH: 23
<212> TYPE: DNA
<213> ORGANISM: Acidaminococcus sp. BV3L6

<400> SEQUENCE: 225
cagggaagct gggtgaatgg agc                                              23

<210> SEQ ID NO 226
<211> LENGTH: 23
<212> TYPE: DNA
<213> ORGANISM: Acidaminococcus sp. BV3L6
```

```
<400> SEQUENCE: 226
ccacagggaa gctgggtgaa tgg                                          23

<210> SEQ ID NO 227
<211> LENGTH: 23
<212> TYPE: DNA
<213> ORGANISM: Acidaminococcus sp. BV3L6

<400> SEQUENCE: 227
gggtgtgcag acggcagtca cta                                          23

<210> SEQ ID NO 228
<211> LENGTH: 23
<212> TYPE: DNA
<213> ORGANISM: Acidaminococcus sp. BV3L6

<400> SEQUENCE: 228
tgggctctct gtacatgaag caa                                          23

<210> SEQ ID NO 229
<211> LENGTH: 23
<212> TYPE: DNA
<213> ORGANISM: Acidaminococcus sp. BV3L6

<400> SEQUENCE: 229
gaaatagggg gtccaggagc aaa                                          23

<210> SEQ ID NO 230
<211> LENGTH: 23
<212> TYPE: DNA
<213> ORGANISM: Acidaminococcus sp. BV3L6

<400> SEQUENCE: 230
cctagtgact gccgtctgca cac                                          23

<210> SEQ ID NO 231
<211> LENGTH: 23
<212> TYPE: DNA
<213> ORGANISM: Acidaminococcus sp. BV3L6

<400> SEQUENCE: 231
gccagggcgc tcggtgctgg aat                                          23

<210> SEQ ID NO 232
<211> LENGTH: 23
<212> TYPE: DNA
<213> ORGANISM: Acidaminococcus sp. BV3L6

<400> SEQUENCE: 232
attccctctt tagccagagc cgg                                          23

<210> SEQ ID NO 233
<211> LENGTH: 23
<212> TYPE: DNA
<213> ORGANISM: Acidaminococcus sp. BV3L6

<400> SEQUENCE: 233
gctctggcta aagagggaat ggg                                          23

<210> SEQ ID NO 234
<211> LENGTH: 23
<212> TYPE: DNA
```

<213> ORGANISM: Acidaminococcus sp. BV3L6

<400> SEQUENCE: 234
cggctctggc taaagaggga atg  23

<210> SEQ ID NO 235
<211> LENGTH: 23
<212> TYPE: DNA
<213> ORGANISM: Acidaminococcus sp. BV3L6

<400> SEQUENCE: 235
tcactctcga agacgctgct cgc  23

<210> SEQ ID NO 236
<211> LENGTH: 23
<212> TYPE: DNA
<213> ORGANISM: Acidaminococcus sp. BV3L6

<400> SEQUENCE: 236
gcttccctgt ggtggccgag cgc  23

<210> SEQ ID NO 237
<211> LENGTH: 23
<212> TYPE: DNA
<213> ORGANISM: Acidaminococcus sp. BV3L6

<400> SEQUENCE: 237
agtcccaaat atgtagctgt ttg  23

<210> SEQ ID NO 238
<211> LENGTH: 23
<212> TYPE: DNA
<213> ORGANISM: Acidaminococcus sp. BV3L6

<400> SEQUENCE: 238 cccccttttcc aaagcccatt ccc  23

<210> SEQ ID NO 239
<211> LENGTH: 23
<212> TYPE: DNA
<213> ORGANISM: Acidaminococcus sp. BV3L6

<400> SEQUENCE: 239
aagacgctgc tcgctccatt cac  23

<210> SEQ ID NO 240
<211> LENGTH: 23
<212> TYPE: DNA
<213> ORGANISM: Acidaminococcus sp. BV3L6

<400> SEQUENCE: 240
gtccacctaa ccgctgcgcc tcc  23

<210> SEQ ID NO 241
<211> LENGTH: 23
<212> TYPE: DNA
<213> ORGANISM: Acidaminococcus sp. BV3L6

<400> SEQUENCE: 241
tggaccccct atttctgacc tcc  23

<210> SEQ ID NO 242
<211> LENGTH: 23

<212> TYPE: DNA
<213> ORGANISM: Acidaminococcus sp. BV3L6

<400> SEQUENCE: 242
ggaggcgcag cggttaggtg gac                                              23

<210> SEQ ID NO 243
<211> LENGTH: 23
<212> TYPE: DNA
<213> ORGANISM: Acidaminococcus sp. BV3L6

<400> SEQUENCE: 243
cctatttctg acctcccaaa cag                                              23

<210> SEQ ID NO 244
<211> LENGTH: 23
<212> TYPE: DNA
<213> ORGANISM: Acidaminococcus sp. BV3L6

<400> SEQUENCE: 244
tctttagcca gagccggggt gtg                                              23

<210> SEQ ID NO 245
<211> LENGTH: 23
<212> TYPE: DNA
<213> ORGANISM: Acidaminococcus sp. BV3L6

<400> SEQUENCE: 245
gtcccaaata tgtagctgtt tgg                                              23

<210> SEQ ID NO 246
<211> LENGTH: 23
<212> TYPE: DNA
<213> ORGANISM: Acidaminococcus sp. BV3L6

<400> SEQUENCE: 246 ctaggggcg ctcggccacc aca                                               23

<210> SEQ ID NO 247
<211> LENGTH: 23
<212> TYPE: DNA
<213> ORGANISM: Acidaminococcus sp. BV3L6

<400> SEQUENCE: 247
cctttccaaa gcccattccc tct                                              23

<210> SEQ ID NO 248
<211> LENGTH: 23
<212> TYPE: DNA
<213> ORGANISM: Acidaminococcus sp. BV3L6

<400> SEQUENCE: 248
ctccaacgcc ctcaacccca cac                                              23

<210> SEQ ID NO 249
<211> LENGTH: 23
<212> TYPE: DNA
<213> ORGANISM: Acidaminococcus sp. BV3L6

<400> SEQUENCE: 249
ctctttagcc agagccgggg tgt                                              23

<210> SEQ ID NO 250

<210> SEQ ID NO 250
<211> LENGTH: 23
<212> TYPE: DNA
<213> ORGANISM: Acidaminococcus sp. BV3L6

<400> SEQUENCE: 250
cacgtaacct cactttcctg ctc              23

<210> SEQ ID NO 251
<211> LENGTH: 23
<212> TYPE: DNA
<213> ORGANISM: Acidaminococcus sp. BV3L6

<400> SEQUENCE: 251
ccccaccccc tttccaaagc cca              23

<210> SEQ ID NO 252
<211> LENGTH: 23
<212> TYPE: DNA
<213> ORGANISM: Acidaminococcus sp. BV3L6

<400> SEQUENCE: 252
gtcacccctg tttctggcac cag              23

<210> SEQ ID NO 253
<211> LENGTH: 23
<212> TYPE: DNA
<213> ORGANISM: Acidaminococcus sp. BV3L6

<400> SEQUENCE: 253
tggtgccaga acaggggtg acg               23

<210> SEQ ID NO 254
<211> LENGTH: 23
<212> TYPE: DNA
<213> ORGANISM: Acidaminococcus sp. BV3L6

<400> SEQUENCE: 254
gctaaaataa aggaggagga agc              23

<210> SEQ ID NO 255
<211> LENGTH: 23
<212> TYPE: DNA
<213> ORGANISM: Acidaminococcus sp. BV3L6

<400> SEQUENCE: 255
cccccggaaa ctctgtccag aga              23

<210> SEQ ID NO 256
<211> LENGTH: 23
<212> TYPE: DNA
<213> ORGANISM: Acidaminococcus sp. BV3L6

<400> SEQUENCE: 256
atagatctgt gtgtccctct ccc              23

<210> SEQ ID NO 257
<211> LENGTH: 23
<212> TYPE: DNA
<213> ORGANISM: Acidaminococcus sp. BV3L6

<400> SEQUENCE: 257
gtctccgtga acgttccctt agc              23

```
<210> SEQ ID NO 258
<211> LENGTH: 23
<212> TYPE: DNA
<213> ORGANISM: Acidaminococcus sp. BV3L6

<400> SEQUENCE: 258
tggagtgacc cctggccttc tcc                                          23

<210> SEQ ID NO 259
<211> LENGTH: 23
<212> TYPE: DNA
<213> ORGANISM: Acidaminococcus sp. BV3L6

<400> SEQUENCE: 259
aaagcccatt ccctctttag cca                                          23

<210> SEQ ID NO 260
<211> LENGTH: 23
<212> TYPE: DNA
<213> ORGANISM: Acidaminococcus sp. BV3L6

<400> SEQUENCE: 260
ctttccaaag cccattccct ctt                                          23

<210> SEQ ID NO 261
<211> LENGTH: 23
<212> TYPE: DNA
<213> ORGANISM: Acidaminococcus sp. BV3L6

<400> SEQUENCE: 261
ggggcggatg ggtaattttc agg                                          23

<210> SEQ ID NO 262
<211> LENGTH: 23
<212> TYPE: DNA
<213> ORGANISM: Acidaminococcus sp. BV3L6

<400> SEQUENCE: 262
cggagactga acactcctca aac                                          23

<210> SEQ ID NO 263
<211> LENGTH: 23
<212> TYPE: DNA
<213> ORGANISM: Acidaminococcus sp. BV3L6

<400> SEQUENCE: 263
cccaccccct ttccaaagcc cat                                          23

<210> SEQ ID NO 264
<211> LENGTH: 23
<212> TYPE: DNA
<213> ORGANISM: Acidaminococcus sp. BV3L6

<400> SEQUENCE: 264
ccaccccctt tccaaagccc att                                          23

<210> SEQ ID NO 265
<211> LENGTH: 30
<212> TYPE: DNA
<213> ORGANISM: Homo sapiens

<400> SEQUENCE: 265
ccgatggtcc atgtctgtta ctcgcctgtc                                   30
```

<210> SEQ ID NO 266
<211> LENGTH: 23
<212> TYPE: DNA
<213> ORGANISM: Homo sapiens

<400> SEQUENCE: 266
aaattccagc accgagcgcc ctg                                              23

<210> SEQ ID NO 267
<211> LENGTH: 23
<212> TYPE: DNA
<213> ORGANISM: Homo sapiens

<400> SEQUENCE: 267
aagaaatatt acaacatata aaa                                              23

<210> SEQ ID NO 268
<211> LENGTH: 23
<212> TYPE: DNA
<213> ORGANISM: Homo sapiens

<400> SEQUENCE: 268
gtcacccctg tttctggcac cag                                              23

<210> SEQ ID NO 269
<211> LENGTH: 23
<212> TYPE: DNA
<213> ORGANISM: Homo sapiens

<400> SEQUENCE: 269
tggtgccaga aacagggtg acg                                               23

<210> SEQ ID NO 270
<211> LENGTH: 24
<212> TYPE: DNA
<213> ORGANISM: Homo sapiens

<400> SEQUENCE: 270
gagaagtcat ttaataaggc cact                                             24

<210> SEQ ID NO 271
<211> LENGTH: 23
<212> TYPE: DNA
<213> ORGANISM: Homo sapiens

<400> SEQUENCE: 271
gcagttgtcg cagttttaca acc                                              23

<210> SEQ ID NO 272
<211> LENGTH: 23
<212> TYPE: DNA
<213> ORGANISM: Homo sapiens

<400> SEQUENCE: 272
acccggataa caaggaggaa cgc                                              23

<210> SEQ ID NO 273
<211> LENGTH: 23
<212> TYPE: DNA
<213> ORGANISM: Homo sapiens

<400> SEQUENCE: 273
gagttgattg gattgagaat aga                                              23

```
<210> SEQ ID NO 274
<211> LENGTH: 23
<212> TYPE: DNA
<213> ORGANISM: Homo sapiens

<400> SEQUENCE: 274
gcctctccct gctcagaatc tgg                                              23

<210> SEQ ID NO 275
<211> LENGTH: 23
<212> TYPE: DNA
<213> ORGANISM: Homo sapiens

<400> SEQUENCE: 275
tagctgtttg ggaggtcaga aat                                              23

<210> SEQ ID NO 276
<211> LENGTH: 23
<212> TYPE: DNA
<213> ORGANISM: Homo sapiens

<400> SEQUENCE: 276
gacatgtccc atttgtggga act                                              23

<210> SEQ ID NO 277
<211> LENGTH: 23
<212> TYPE: DNA
<213> ORGANISM: Homo sapiens

<400> SEQUENCE: 277
ttcgggtgct gtgaacttcc ctc                                              23

<210> SEQ ID NO 278
<211> LENGTH: 23
<212> TYPE: DNA
<213> ORGANISM: Homo sapiens

<400> SEQUENCE: 278
acccactgcg tgggttccca tga                                              23

<210> SEQ ID NO 279
<211> LENGTH: 23
<212> TYPE: DNA
<213> ORGANISM: Homo sapiens

<400> SEQUENCE: 279
ccaagtcaaa cttctcttca gtc                                              23

<210> SEQ ID NO 280
<211> LENGTH: 23
<212> TYPE: DNA
<213> ORGANISM: Homo sapiens

<400> SEQUENCE: 280
cccttaggaa cacatgctgt cta                                              23

<210> SEQ ID NO 281
<211> LENGTH: 23
<212> TYPE: DNA
<213> ORGANISM: Homo sapiens

<400> SEQUENCE: 281
```

-continued agtgcacctt cggcgtgctg cag                    23

<210> SEQ ID NO 282
<211> LENGTH: 23
<212> TYPE: DNA
<213> ORGANISM: Homo sapiens

<400> SEQUENCE: 282
cccaccatga caggaagaac ggc                    23

<210> SEQ ID NO 283
<211> LENGTH: 23
<212> TYPE: DNA
<213> ORGANISM: Homo sapiens

<400> SEQUENCE: 283
aggcgcttcc ccagcacaaa ctg                    23

<210> SEQ ID NO 284
<211> LENGTH: 23
<212> TYPE: DNA
<213> ORGANISM: Homo sapiens

<400> SEQUENCE: 284
gcgatgtttt ttctggagat tta                    23

<210> SEQ ID NO 285
<211> LENGTH: 23
<212> TYPE: DNA
<213> ORGANISM: Homo sapiens

<400> SEQUENCE: 285
gctaaaataa aggaggagga agc                    23

<210> SEQ ID NO 286
<211> LENGTH: 23
<212> TYPE: DNA
<213> ORGANISM: Homo sapiens

<400> SEQUENCE: 286
gtcacccctg tttctggcac cag                    23

<210> SEQ ID NO 287
<211> LENGTH: 23
<212> TYPE: DNA
<213> ORGANISM: Homo sapiens

<400> SEQUENCE: 287
tggtgccaga aacaggggtg acg                    23

<210> SEQ ID NO 288
<211> LENGTH: 23
<212> TYPE: DNA
<213> ORGANISM: Homo sapiens

<400> SEQUENCE: 288
gtctccgtga acgttccctt agc                    23

<210> SEQ ID NO 289
<211> LENGTH: 23
<212> TYPE: DNA
<213> ORGANISM: Homo sapiens

<400> SEQUENCE: 289
cggagactga acactcctca aac					23

<210> SEQ ID NO 290
<211> LENGTH: 23
<212> TYPE: DNA
<213> ORGANISM: Homo sapiens

<400> SEQUENCE: 290
tggcaatgcg ccaccggttg atg					23

<210> SEQ ID NO 291
<211> LENGTH: 23
<212> TYPE: DNA
<213> ORGANISM: Homo sapiens

<400> SEQUENCE: 291
ctgtggtggc cgagcgcccc cta					23

<210> SEQ ID NO 292
<211> LENGTH: 23
<212> TYPE: DNA
<213> ORGANISM: Homo sapiens

<400> SEQUENCE: 292
gtcccaaata tgtagctgtt tgg					23

<210> SEQ ID NO 293
<211> LENGTH: 23
<212> TYPE: DNA
<213> ORGANISM: Homo sapiens

<400> SEQUENCE: 293
cacgtaacct cactttcctg ctc					23

<210> SEQ ID NO 294
<211> LENGTH: 23
<212> TYPE: DNA
<213> ORGANISM: Homo sapiens

<400> SEQUENCE: 294
tctttagcca gagccggggt gtg					23

<210> SEQ ID NO 295
<211> LENGTH: 23
<212> TYPE: DNA
<213> ORGANISM: Homo sapiens

<400> SEQUENCE: 295
cccccggaaa ctctgtccag aga					23

<210> SEQ ID NO 296
<211> LENGTH: 23
<212> TYPE: DNA
<213> ORGANISM: Homo sapiens

<400> SEQUENCE: 296
ggggcggatg ggtaattttc agg					23

<210> SEQ ID NO 297
<211> LENGTH: 23
<212> TYPE: DNA
<213> ORGANISM: Homo sapiens

<400> SEQUENCE: 297
atagatctgt gtgtccctct ccc                                            23

<210> SEQ ID NO 298
<211> LENGTH: 23
<212> TYPE: DNA
<213> ORGANISM: Homo sapiens

<400> SEQUENCE: 298
aaagcccatt ccctctttag cca                                            23

<210> SEQ ID NO 299
<211> LENGTH: 23
<212> TYPE: DNA
<213> ORGANISM: Homo sapiens

<400> SEQUENCE: 299
cccaccccct ttccaaagcc cat                                            23

<210> SEQ ID NO 300
<211> LENGTH: 23
<212> TYPE: DNA
<213> ORGANISM: Homo sapiens

<400> SEQUENCE: 300
aaaattttac accacaaaat gtt                                            23

<210> SEQ ID NO 301
<211> LENGTH: 23
<212> TYPE: DNA
<213> ORGANISM: Homo sapiens

<400> SEQUENCE: 301
aagatgatat tttctttaat ggt                                            23

<210> SEQ ID NO 302
<211> LENGTH: 23
<212> TYPE: DNA
<213> ORGANISM: Homo sapiens

<400> SEQUENCE: 302
ttaaagaaaa tatcatcttt ggt                                            23

<210> SEQ ID NO 303
<211> LENGTH: 23
<212> TYPE: DNA
<213> ORGANISM: Homo sapiens

<400> SEQUENCE: 303
taaactcatt aatgcccttc ggc                                            23

<210> SEQ ID NO 304
<211> LENGTH: 23
<212> TYPE: DNA
<213> ORGANISM: Homo sapiens

<400> SEQUENCE: 304
aggaaaactg agaacagaat gaa                                            23

<210> SEQ ID NO 305
<211> LENGTH: 23
<212> TYPE: DNA
<213> ORGANISM: Homo sapiens

```
<400> SEQUENCE: 305
catcaaccgg tggcgcattg cca                                              23

<210> SEQ ID NO 306
<211> LENGTH: 23
<212> TYPE: DNA
<213> ORGANISM: Homo sapiens

<400> SEQUENCE: 306
tccccattgg cctgcttcgt ggc                                              23

<210> SEQ ID NO 307
<211> LENGTH: 23
<212> TYPE: DNA
<213> ORGANISM: Homo sapiens

<400> SEQUENCE: 307
ggcttcaagc cctgtggggc cat                                              23

<210> SEQ ID NO 308
<211> LENGTH: 23
<212> TYPE: DNA
<213> ORGANISM: Homo sapiens

<400> SEQUENCE: 308
atgtcacctc caatgactag ggt                                              23

<210> SEQ ID NO 309
<211> LENGTH: 23
<212> TYPE: DNA
<213> ORGANISM: Homo sapiens

<400> SEQUENCE: 309
atgtcctccc cattggcctg ctt                                              23

<210> SEQ ID NO 310
<211> LENGTH: 23
<212> TYPE: DNA
<213> ORGANISM: Homo sapiens

<400> SEQUENCE: 310
ttccctcttt agccagagcc ggg                                              23

<210> SEQ ID NO 311
<211> LENGTH: 23
<212> TYPE: DNA
<213> ORGANISM: Homo sapiens

<400> SEQUENCE: 311
gccaccacag ggaagctggg tga                                              23

<210> SEQ ID NO 312
<211> LENGTH: 23
<212> TYPE: DNA
<213> ORGANISM: Homo sapiens

<400> SEQUENCE: 312
caaatatgta gctgtttggg agg                                              23

<210> SEQ ID NO 313
<211> LENGTH: 23
<212> TYPE: DNA
```

<213> ORGANISM: Homo sapiens

<400> SEQUENCE: 313
agcgccccct agtgactgcc gtc                                              23

<210> SEQ ID NO 314
<211> LENGTH: 23
<212> TYPE: DNA
<213> ORGANISM: Homo sapiens

<400> SEQUENCE: 314
attccctctt tagccagagc cgg                                              23

<210> SEQ ID NO 315
<211> LENGTH: 23
<212> TYPE: DNA
<213> ORGANISM: Homo sapiens

<400> SEQUENCE: 315
gctctggcta aagagggaat ggg                                              23

<210> SEQ ID NO 316
<211> LENGTH: 23
<212> TYPE: DNA
<213> ORGANISM: Homo sapiens

<400> SEQUENCE: 316
gagccggggt gtgcagacgg cag                                              23

<210> SEQ ID NO 317
<211> LENGTH: 23
<212> TYPE: DNA
<213> ORGANISM: Homo sapiens

<400> SEQUENCE: 317
ctccattcac ccagcttccc tgt                                              23

<210> SEQ ID NO 318
<211> LENGTH: 23
<212> TYPE: DNA
<213> ORGANISM: Homo sapiens

<400> SEQUENCE: 318
gaaatagggg gtccaggagc aaa                                              23

<210> SEQ ID NO 319
<211> LENGTH: 23
<212> TYPE: DNA
<213> ORGANISM: Homo sapiens

<400> SEQUENCE: 319
agtcccaaat atgtagctgt ttg                                              23

<210> SEQ ID NO 320
<211> LENGTH: 23
<212> TYPE: DNA
<213> ORGANISM: Homo sapiens

<400> SEQUENCE: 320
tgggctctct gtacatgaag caa                                              23

<210> SEQ ID NO 321
<211> LENGTH: 23

```
<212> TYPE: DNA
<213> ORGANISM: Homo sapiens

<400> SEQUENCE: 321
cagggaagct gggtgaatgg agc                                          23

<210> SEQ ID NO 322
<211> LENGTH: 23
<212> TYPE: DNA
<213> ORGANISM: Homo sapiens

<400> SEQUENCE: 322
cggctctggc taaagaggga atg                                          23

<210> SEQ ID NO 323
<211> LENGTH: 23
<212> TYPE: DNA
<213> ORGANISM: Homo sapiens

<400> SEQUENCE: 323
gcttccctgt ggtggccgag cgc                                          23

<210> SEQ ID NO 324
<211> LENGTH: 23
<212> TYPE: DNA
<213> ORGANISM: Homo sapiens

<400> SEQUENCE: 324
tctgcacacc ccggctctgg cta                                          23

<210> SEQ ID NO 325
<211> LENGTH: 23
<212> TYPE: DNA
<213> ORGANISM: Homo sapiens

<400> SEQUENCE: 325
cctagtgact gccgtctgca cac                                          23

<210> SEQ ID NO 326
<211> LENGTH: 23
<212> TYPE: DNA
<213> ORGANISM: Homo sapiens

<400> SEQUENCE: 326
cctatttctg acctcccaaa cag                                          23

<210> SEQ ID NO 327
<211> LENGTH: 23
<212> TYPE: DNA
<213> ORGANISM: Homo sapiens

<400> SEQUENCE: 327
ccacagggaa gctgggtgaa tgg                                          23

<210> SEQ ID NO 328
<211> LENGTH: 23
<212> TYPE: DNA
<213> ORGANISM: Homo sapiens

<400> SEQUENCE: 328
tcactctcga agacgctgct cgc                                          23

<210> SEQ ID NO 329
```

```
<211> LENGTH: 23
<212> TYPE: DNA
<213> ORGANISM: Homo sapiens

<400> SEQUENCE: 329 ctaggggcg ctcggccacc aca                                            23

<210> SEQ ID NO 330
<211> LENGTH: 23
<212> TYPE: DNA
<213> ORGANISM: Homo sapiens

<400> SEQUENCE: 330
gggtgtgcag acggcagtca cta                                           23

<210> SEQ ID NO 331
<211> LENGTH: 23
<212> TYPE: DNA
<213> ORGANISM: Homo sapiens

<400> SEQUENCE: 331
aagacgctgc tcgctccatt cac                                           23

<210> SEQ ID NO 332
<211> LENGTH: 23
<212> TYPE: DNA
<213> ORGANISM: Homo sapiens

<400> SEQUENCE: 332
ctccaacgcc ctcaacccca cac                                           23

<210> SEQ ID NO 333
<211> LENGTH: 23
<212> TYPE: DNA
<213> ORGANISM: Homo sapiens

<400> SEQUENCE: 333 tggacccct atttctgacc tcc                                            23

<210> SEQ ID NO 334
<211> LENGTH: 23
<212> TYPE: DNA
<213> ORGANISM: Homo sapiens

<400> SEQUENCE: 334
tggagtgacc cctggccttc tcc                                           23

<210> SEQ ID NO 335
<211> LENGTH: 23
<212> TYPE: DNA
<213> ORGANISM: Homo sapiens

<400> SEQUENCE: 335
cctttccaaa gcccattccc tct                                           23

<210> SEQ ID NO 336
<211> LENGTH: 23
<212> TYPE: DNA
<213> ORGANISM: Homo sapiens

<400> SEQUENCE: 336 ccacccctt tccaaagccc att                                            23
```

-continued

```
<210> SEQ ID NO 337
<211> LENGTH: 23
<212> TYPE: DNA
<213> ORGANISM: Homo sapiens

<400> SEQUENCE: 337
ctaggaatat tgaagggggc agg                                               23

<210> SEQ ID NO 338
<211> LENGTH: 23
<212> TYPE: DNA
<213> ORGANISM: Homo sapiens

<400> SEQUENCE: 338
gtgctcaatg aaaggagata agg                                               23

<210> SEQ ID NO 339
<211> LENGTH: 23
<212> TYPE: DNA
<213> ORGANISM: Homo sapiens

<400> SEQUENCE: 339
aagaaatatt acaacatata aaa                                               23

<210> SEQ ID NO 340
<211> LENGTH: 23
<212> TYPE: DNA
<213> ORGANISM: Homo sapiens

<400> SEQUENCE: 340
tcctccggtt ctggaaccac acc                                               23

<210> SEQ ID NO 341
<211> LENGTH: 23
<212> TYPE: DNA
<213> ORGANISM: Homo sapiens

<400> SEQUENCE: 341
gggtgatcag acccaacagc agg                                               23

<210> SEQ ID NO 342
<211> LENGTH: 23
<212> TYPE: DNA
<213> ORGANISM: Homo sapiens

<400> SEQUENCE: 342
atggtgccag gcataatcca gga                                               23

<210> SEQ ID NO 343
<211> LENGTH: 23
<212> TYPE: DNA
<213> ORGANISM: Homo sapiens

<400> SEQUENCE: 343
ccttcagcta aaataaagga gga                                               23

<210> SEQ ID NO 344
<211> LENGTH: 23
<212> TYPE: DNA
<213> ORGANISM: Homo sapiens

<400> SEQUENCE: 344
aggagtgttc agtctccgtg aac                                               23
```

```
<210> SEQ ID NO 345
<211> LENGTH: 23
<212> TYPE: DNA
<213> ORGANISM: Homo sapiens

<400> SEQUENCE: 345
ctgatggtcc atgtctgtta ctc                                              23

<210> SEQ ID NO 346
<211> LENGTH: 23
<212> TYPE: DNA
<213> ORGANISM: Homo sapiens

<400> SEQUENCE: 346
gctgaaggga aataaaagga aaa                                              23

<210> SEQ ID NO 347
<211> LENGTH: 23
<212> TYPE: DNA
<213> ORGANISM: Homo sapiens

<400> SEQUENCE: 347
gggaggcctg gagtcatggc ccc                                              23

<210> SEQ ID NO 348
<211> LENGTH: 23
<212> TYPE: DNA
<213> ORGANISM: Homo sapiens

<400> SEQUENCE: 348
tggttgccca ccctagtcat tgg                                              23

<210> SEQ ID NO 349
<211> LENGTH: 23
<212> TYPE: DNA
<213> ORGANISM: Homo sapiens

<400> SEQUENCE: 349
gccagagccg gggtgtgcag acg                                              23

<210> SEQ ID NO 350
<211> LENGTH: 23
<212> TYPE: DNA
<213> ORGANISM: Homo sapiens

<400> SEQUENCE: 350
caaagcccat tccctcttta gcc                                              23

<210> SEQ ID NO 351
<211> LENGTH: 23
<212> TYPE: DNA
<213> ORGANISM: Homo sapiens

<400> SEQUENCE: 351
gtcccaggag gatggcctgg ctg                                              23

<210> SEQ ID NO 352
<211> LENGTH: 23
<212> TYPE: DNA
<213> ORGANISM: Homo sapiens

<400> SEQUENCE: 352
aggaggatgg cctggctgat gag                                              23
```

<210> SEQ ID NO 353
<211> LENGTH: 23
<212> TYPE: DNA
<213> ORGANISM: Homo sapiens

<400> SEQUENCE: 353
atctgtagcc tctgggtctc ctc                                   23

<210> SEQ ID NO 354
<211> LENGTH: 23
<212> TYPE: DNA
<213> ORGANISM: Homo sapiens

<400> SEQUENCE: 354
tggcttcttg gtgaagatga gca                                   23

<210> SEQ ID NO 355
<211> LENGTH: 23
<212> TYPE: DNA
<213> ORGANISM: Homo sapiens

<400> SEQUENCE: 355
tcaatgtact ccacatgggg caa                                   23

<210> SEQ ID NO 356
<211> LENGTH: 23
<212> TYPE: DNA
<213> ORGANISM: Homo sapiens

<400> SEQUENCE: 356
tgggatgctc tgggcgaaga caa                                   23

<210> SEQ ID NO 357
<211> LENGTH: 23
<212> TYPE: DNA
<213> ORGANISM: Homo sapiens

<400> SEQUENCE: 357
gatgggcacc ctggatgctg gta                                   23

<210> SEQ ID NO 358
<211> LENGTH: 23
<212> TYPE: DNA
<213> ORGANISM: Homo sapiens

<400> SEQUENCE: 358
ggccgctgac cacacctgcc agg                                   23

<210> SEQ ID NO 359
<211> LENGTH: 23
<212> TYPE: DNA
<213> ORGANISM: Homo sapiens

<400> SEQUENCE: 359
gatgggcacc cactgctctg cgt                                   23

<210> SEQ ID NO 360
<211> LENGTH: 23
<212> TYPE: DNA
<213> ORGANISM: Homo sapiens

<400> SEQUENCE: 360

```
ttcaatctgt agcctctggg tct                                    23
```

<210> SEQ ID NO 361
<211> LENGTH: 23
<212> TYPE: DNA
<213> ORGANISM: Homo sapiens

<400> SEQUENCE: 361

```
tgacctcttc cctggcttct tgg                                    23
```

<210> SEQ ID NO 362
<211> LENGTH: 23
<212> TYPE: DNA
<213> ORGANISM: Homo sapiens

<400> SEQUENCE: 362

```
tcttcgccca gagcatccca tgg                                    23
```

<210> SEQ ID NO 363
<211> LENGTH: 122
<212> TYPE: DNA
<213> ORGANISM: Artificial
<220> FEATURE:
<223> OTHER INFORMATION: Synthetic oligonucleotide

<400> SEQUENCE: 363

```
aacacaggac cggtgccacc atgtacccat acgatgttcc agattacgct tcgccgaaga    60
aaaagcgcaa ggtcgaagcg tccacacagt tcgagggctt taccaacctg tatcaggtga   120
gc                                                                  122
```

<210> SEQ ID NO 364
<211> LENGTH: 94
<212> TYPE: DNA
<213> ORGANISM: Artificial
<220> FEATURE:
<223> OTHER INFORMATION: Synthetic Oligonucleotide

<400> SEQUENCE: 364

```
gcggccgcac acaaaaaacc aacacacaga tctaatgaaa ataaagatct tttattgaat    60
tcttagttgc gcagctcctg gatgtaggcc agcc                               94
```

<210> SEQ ID NO 365
<211> LENGTH: 9464
<212> TYPE: DNA
<213> ORGANISM: Artificial
<220> FEATURE:
<223> OTHER INFORMATION: Synthetic Oligonucleotide

<400> SEQUENCE: 365

```
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420
attgacgtca atgggtggag tatttacggt aaactgccca cttggcagta catcaagtgt   480
atcatatgcc aagtacgccc cctattgacg tcaatgacgg taaatggccc gcctggcatt   540
```

```
atgcccagta catgaccttg tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta caactccgc cccattgacg caaatgggcg       780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttggta ccgccaccat gacacagttc gagggcttta ccaacctgta      960
tcaggtgagc aagacactgc ggtttgagct gatcccacag ggcaagaccc tgaagcacat     1020
ccaggagcag ggcttcatcg aggaggacaa ggcccgcaat gatcactaca aggagctgaa     1080
gcccatcatc gatcggatct acaagaccta tgccgaccag tgcctgcagc tggtgcagct     1140
ggattgggag aacctgagcg ccgccatcga ctcctataga aaggagaaaa ccgaggagac     1200
aaggaacgcc ctgatcgagg agcaggccac atatcgcaat gccatccacg actacttcat     1260
cggccggaca gacaacctga ccgatgccat caataagaga cacgccgaga tctacaaggg     1320
cctgttcaag gccgagctgt ttaatggcaa ggtgctgaag cagctgggca ccgtgaccac     1380
aaccgagcac gagaacgccc tgctgcggag cttcgacaag tttacaacct acttctccgg     1440
cttttatgag aacaggaaga acgtgttcag cgccgaggat atcagcacag ccatcccaca     1500
ccgcatcgtg caggacaact cccccaagtt taaggagaat tgtcacatct tcacacgcct     1560
gatcaccgcc gtgcccagcc tgcgggagca ctttgagaac gtgaagaagg ccatcggcat     1620
cttcgtgagc acctccatcg aggaggtgtt ttccttccct ttttataacc agctgctgac     1680
acagacccag atcgacctgt ataaccagct gctgggagga tctctcgggg aggcaggcac     1740
cgagaagatc aagggcctga acgaggtgct gaatctggcc atccagaaga tgatgagac      1800
agccccacatc atcgcctccc tgccacacag attcatcccc ctgtttaagc agatcctgtc     1860
cgataggaac accctgtctt tcatcctgga ggagtttaag agcgacgagg aagtgatcca     1920
gtccttctgc aagtacaaga cactgctgag aaacgagaac gtgctggaga cagccgaggc     1980
cctgtttaac gagctgaaca gcatcgacct gacacacatc ttcatcagcc acaagaagct     2040
ggagacaatc agcagcgccc tgtgcgacca ctgggatca ctgaggaatg ccctgtatga     2100
gcggagaatc tccgagctga caggcaagat caccaagtct gccaaggaga aggtgcagcg     2160
cagcctgaag cacgaggata tcaacctgca ggagatcatc tctgccgcag gcaaggagct     2220
gagcgaggcc ttcaagcaga aaaccagcga gatcctgtcc cacgcacacg ccgccctgga     2280
tcagccactg cctacaaccc tgaagaagca ggaggagaag gagatcctga gtctcagct      2340
ggacagcctg ctgggcctgt accacctgct ggactggttt gccgtggatg agtccaacga     2400
ggtggacccc gagttctctg cccggctgac cggcatcaag ctggagatgg agccgtctct     2460
gagcttctac aacaaggcca gaaattatgc caccaagaag ccctactccg tggagaagtt     2520
caagctgaac tttcagatgc ctacactggc ccggggctgg gacgtgaata aggagaagaa     2580
caatggcgcc atcctgtttg tgaagaacgg cctgtactat ctgggcatca tgccaaagca     2640
gaagggcagg tataaggccc tcagcttcga gcccacagag aaaccagcg agggctttga     2700
taagatgtac tatgactact ttccggatgc cgccaagatg atcccacggt gcagcaccca     2760
gctgaaggcg gtgaccgccc actttcagac ccacacaacc cccatcctgc tgtccaacaa     2820
tttcatcgag cctctgggaga tcacaaagga gatctacgac ctgaacaatc ctgagaagga     2880
```

-continued

```
gccaaagaag tttcagacag cgtacgccaa gaaaaccggc gaccagaagg gctacagaga    2940
ggccctgtgc aagtggatcg acttcacaag ggattttctg tccaagtata ccaagacaac    3000
ctctatcgat ctgtctagcc tgcggccatc tctcagtat aaggacctgg gcgagtacta     3060
tgccgagctg aatcccctgc tgtaccacat cagcttccag agaatcgccg agaaggagat    3120
catggatgcc gtggagacag gcaagctgta cctgttccag atctataaca aggactttgc    3180
caagggccac cacggcaagc ctaatctgca cacactgtat tggaccggtc tgttttctcc    3240
agagaacctg gccaagacaa gcatcaagct gaatggccag gccgagctgt ctaccgccc     3300 taagtccagg atgaagagga tggcacaccg gctgggagag aagatgctga caagaagct     3360 gaaggatcag aaaaccccaa tccccgacac cctgtaccag gagctgtacg actatgtgaa    3420
tcacagactg tccacgacc tgtctgatga ggccagggcc ctgctgccca acgtgatcac     3480
caaggaggtg tctcacgaga tcatcaagga taggcgcttt accagcgaca gttctttttt    3540
ccacgtgcct atcacactga actatcaggc cgccaattcc ccatctaagt tcaaccagag    3600
ggtgaatgcc tacctgaagg agcaccccga cacctatc atcggcatcg atcggggcga      3660
gagaaacctg atctatatca cagtgatcga ctccaccggc aagatcctgg agcagcggag    3720
cctgaacacc atccagcagt ttgattacca gaagaagctg gacaacaggg agaaggagag    3780
ggtggcagca aggcaggcct ggtctgtggt gggcacaatc aaggatctga agcagggcta    3840
tctgagccag gtcatccacg agatcgtgga cctgatgatc cactaccagg ccgtggtggt    3900
gctggagaac ctgaatttcg gctttaagag caagaggacc ggcatcgccg agaaggccgt    3960
gtaccagcag ttcgagaaga tgctgatcga taagctgaat tgcctggtgc tgaaggacta    4020
tccagcagag aaagtgggag gcgtgctgaa cccataccag ctgacagacc agttcacctc    4080 cttttgccaag atgggcaccc agtctggctt cctgttttac gtgcctgccc catatacatc    4140
taagatcgat ccctgaccg gcttcgtgga ccccttcgtg tggaaaacca tcaagaatca    4200
cgagagccgc aagcacttcc tggagggctt cgactttctg cactacgacg tgaaaaccgg    4260
cgacttcatc ctgcacttta agatgaacag aaatctgtcc ttccagaggg gcctgcccgg    4320
ctttatgcct gcatgggata tcgtgttcga gaagaacgag acacagtttg acgccaaggg    4380
cacccctttc atcgccggca agagaatcgt gccagtgatc gagaatcaca gattcaccgg    4440
cagataccgg gacctgtatc ctgccaacga gctgatcgcc ctgctggagg agaagggcat    4500
cgtgttcagg gatggctcca acatcctgcc aaagctgctg gagaatgacg attctcacgc    4560
catcgacacc atggtggccc tgatccgcag cgtgctgcag atgcggaact ccaatgccgc    4620
cacaggcgag gactatatca cagcccccgt gcgcgatctg aatggcgtgt gcttcgactc    4680
ccggtttcag aaccccagagt ggcccatgga cgccgatgcc aatggcgcct accacatcgc    4740
cctgaagggc cagctgctgc tgaatcacct gaaggagagc aaggatctga agctgcagaa    4800
cggcatctcc aatcaggact ggctggccta catccaggag ctgcgcaaca aaaggccggc    4860
ggccacgaaa aaggccggcc aggcaaaaaa gaaaaaggga tcctacccat acgatgttcc    4920
agattacgct tatccctacg acgtgcctga ttatgcatac ccatatgatg tccccgacta    4980
tgcctaagaa ttctgcagat atccagcaca gtggcggccg ctcgagtcta gagggcccgt    5040
ttaaacccgc tgatcagcct cgactgtgcc ttctagttgc cagccatctg ttgtttgccc    5100
ctcccccgtg ccttccttga ccctggaagg tgccactccc actgtccttt cctaataaaa    5160
tgaggaaatt gcatcgcatt gtctgagtag gtgtcattct attctggggg gtggggtggg    5220
gcaggacagc aagggggagg attgggaaga caatagcagg catgctgggg atgcggtggg    5280
```

```
ctctatggct tctgaggcgg aaagaaccag ctggggctct aggggtatc cccacgcgcc     5340
ctgtagcggc gcattaagcg cggcgggtgt ggtggttacg cgcagcgtga ccgctacact     5400
tgccagcgcc ctagcgcccg ctcctttcgc tttcttccct tcctttctcg ccacgttcgc     5460
cggctttccc cgtcaagctc taaatcgggg gctcccttta gggttccgat ttagtgcttt     5520
acggcacctc gaccccaaaa aacttgatta gggtgatggt tcacgtagtg gccatcgcc      5580
ctgatagacg gttttcgcc ctttgacgtt ggagtccacg ttctttaata gtggactctt      5640
gttccaaact ggaacaacac tcaaccctat ctcggtctat tcttttgatt tataagggat     5700
tttgccgatt tcggcctatt ggttaaaaaa tgagctgatt taacaaaaat ttaacgcgaa     5760
ttaattctgt ggaatgtgtg tcagttaggg tgtggaaagt ccccaggctc cccagcaggc    5820
agaagtatgc aaagcatgca tctcaattag tcagcaacca ggtgtggaaa gtccccaggc    5880
tccccagcag gcagaagtat gcaaagcatg catctcaatt agtcagcaac catagtcccg    5940
cccctaactc cgcccatccc gcccctaact ccgcccagtt ccgcccattc tccgccccat    6000
ggctgactaa ttttttttat ttatgcagag gccgaggccg cctctgcctc tgagctattc    6060
cagaagtagt gaggaggctt ttttggaggc ctaggctttt gcaaaaagct cccgggagct    6120
tgtatatcca ttttcggatc tgatcaagag acaggatgag gatcgtttcg catgattgaa    6180
caagatggat tgcacgcagg ttctccggcc gcttgggtgg agaggctatt cggctatgac    6240
tgggcacaac agacaatcgg ctgctctgat gccgccgtgt tccggctgtc agcgcagggg    6300
cgcccggttc tttttgtcaa gaccgacctg tccggtgccc tgaatgaact gcaggacgag    6360
gcagcgcggc tatcgtggct ggccacgacg ggcgttcctt gcgcagctgt gctcgacgtt    6420
gtcactgaag cgggaaggga ctggctgcta ttgggcgaag tgccggggca ggatctcctg    6480
tcatctcacc ttgctcctgc cgagaaagta tccatcatgg ctgatgcaat gcggcggctg    6540
catacgcttg atccggctac ctgcccattc gaccaccaag cgaaacatcg catcgagcga    6600
gcacgtactc ggatggaagc cggtcttgtc gatcaggatg atctggacga agagcatcag    6660
gggctcgcgc cagccgaact gttcgccagg ctcaaggcgc gcatgcccga cggcgaggat    6720
ctcgtcgtga cccatggcga tgcctgcttg ccgaatatca tggtggaaaa tggccgcttt    6780
tctggattca tcgactgtgg ccggctgggt gtggcggacc gctatcagga catagcgttg    6840
gctacccgtg atattgctga agagcttggc ggcgaatggg ctgaccgctt cctcgtgctt    6900
tacggtatcg ccgctcccga ttcgcagcgc atcgccttct atcgccttct tgacgagttc    6960
ttctgagcgg gactctgggg ttcgaaatga ccgaccaagc gacgcccaac ctgccatcac    7020
gagatttcga ttccaccgcc gccttctatg aaaggttggg cttcggaatc gttttccggg    7080
acgccggctg gatgatcctc cagcgcgggg atctcatgct ggagttcttc gcccaccca     7140
acttgtttat tgcagcttat aatggttaca aataaagcaa tagcatcaca aatttcacaa    7200
ataaagcatt ttttcactg cattctagtt gtggtttgtc caaactcatc aatgtatctt     7260
atcatgtctg tataccgtcg acctctagct agagcttggc gtaatcatgg tcatagctgt    7320
ttcctgtgtg aaattgttat ccgctcacaa ttccacacaa catacgagcc ggaagcataa    7380
agtgtaaagc ctggggtgcc taatgagtga gctaactcac attaattgcg ttgcgctcac    7440
tgcccgcttt ccagtcggga aacctgtcgt gccagctgca ttaatgaatc ggccaacgcg    7500
cggggagagg cggtttgcgt attgggcgct cttccgcttc ctcgctcact gactcgctgc    7560
gctcggtcgt tcggctgcgg cgagcggtat cagctcactc aaaggcggta atacggttat    7620
```

| | |
|---|---|
| ccacagaatc agggataac gcaggaaaga acatgtgagc aaaaggccag caaaaggcca | 7680 |
| ggaaccgtaa aaaggccgcg ttgctggcgt ttttccatag gctccgcccc cctgacgagc | 7740 |
| atcacaaaaa tcgacgctca agtcagaggt ggcgaaaccc gacaggacta taaagatacc | 7800 |
| aggcgtttcc ccctggaagc tccctcgtgc gctctcctgt tccgaccctg ccgcttaccg | 7860 |
| gatacctgtc cgcctttctc ccttcgggaa gcgtggcgct ttctcatagc tcacgctgta | 7920 |
| ggtatctcag ttcggtgtag gtcgttcgct ccaagctggg ctgtgtgcac gaaccccccg | 7980 |
| ttcagcccga ccgctgcgcc ttatccggta actatcgtct tgagtccaac ccggtaagac | 8040 |
| acgacttatc gccactggca gcagccactg gtaacaggat tagcagagcg aggtatgtag | 8100 |
| gcggtgctac agagttcttg aagtggtggc ctaactacgg ctacactaga agaacagtat | 8160 |
| ttggtatctg cgctctgctg aagccagtta ccttcggaaa aagagttggt agctcttgat | 8220 |
| ccggcaaaca aaccaccgct ggtagcggtt ttttgtttg caagcagcag attacgcgca | 8280 |
| gaaaaaaagg atctcaagaa gatcctttga tcttttctac ggggtctgac gctcagtgga | 8340 |
| acgaaaactc acgttaaggg attttggtca tgagattatc aaaaaggatc ttcacctaga | 8400 |
| tccttttaaa ttaaaaatga agttttaaat caatctaaag tatatatgag taaacttggt | 8460 |
| ctgacagtta ccaatgctta atcagtgagg cacctatctc agcgatctgt ctatttcgtt | 8520 |
| catccatagt tgcctgactc cccgtcgtgt agataactac gatacgggag ggcttaccat | 8580 |
| ctggccccag tgctgcaatg ataccgcgag acccacgctc accggctcca gatttatcag | 8640 |
| caataaacca gccagccgga agggccgagc gcagaagtgg tcctgcaact ttatccgcct | 8700 |
| ccatccagtc tattaattgt tgccgggaag ctagagtaag tagttcgcca gttaatagtt | 8760 |
| tgcgcaacgt tgttgccatt gctacaggca tcgtggtgtc acgctcgtcg tttggtatgg | 8820 |
| cttcattcag ctccggttcc caacgatcaa ggcgagttac atgatccccc atgttgtgca | 8880 |
| aaaaagcggt tagctccttc ggtcctccga tcgttgtcag aagtaagttg gccgcagtgt | 8940 |
| tatcactcat ggttatggca gcactgcata attctcttac tgtcatgcca tccgtaagat | 9000 |
| gcttttctgt gactggtgag tactcaacca agtcattctg agaatagtgt atgcggcgac | 9060 |
| cgagttgctc ttgcccggcg tcaatacggg ataataccgc gccacatagc agaactttaa | 9120 |
| aagtgctcat cattggaaaa cgttcttcgg ggcgaaaact ctcaaggatc ttaccgctgt | 9180 |
| tgagatccag ttcgatgtaa cccactcgtg cacccaactg atcttcagca tcttttactt | 9240 |
| tcaccagcgt ttctgggtga gcaaaaacag gaaggcaaaa tgccgcaaaa aagggaataa | 9300 |
| gggcgacacg gaaatgttga atactcatac tcttcctttt tcaatattat tgaagcattt | 9360 |
| atcagggtta ttgtctcatg agcggataca tatttgaatg tatttagaaa aataaacaaa | 9420 |
| taggggttcc gcgcacattt ccccgaaaag tgccacctga cgtc | 9464 |

<210> SEQ ID NO 366
<211> LENGTH: 9464
<212> TYPE: DNA
<213> ORGANISM: Artificial
<220> FEATURE:
<223> OTHER INFORMATION: Synthetic Oligonucleotide

<400> SEQUENCE: 366

| | |
|---|---|
| gacgtcaggt ggcacttttc ggggaaatgt gcgcggaacc cctatttgtt tatttttcta | 60 |
| aatacattca aatatgtatc cgctcatgag acaataaccc tgataaatgc ttcaataata | 120 |
| ttgaaaaagg aagagtatga gtattcaaca tttccgtgtc gcccttattc ccttttttgc | 180 |
| ggcattttgc cttcctgttt ttgctcaccc agaaacgctg gtgaaagtaa aagatgctga | 240 |

```
agatcagttg ggtgcacgag tgggttacat cgaactggat ctcaacagcg gtaagatcct    300
tgagagtttt cgccccgaag aacgttttcc aatgatgagc acttttaaag ttctgctatg    360
tggcgcggta ttatcccgta ttgacgccgg gcaagagcaa ctcggtcgcc gcatacacta    420
ttctcagaat gacttggttg agtactcacc agtcacagaa aagcatctta cggatggcat    480
gacagtaaga gaattatgca gtgctgccat aaccatgagt gataacactg cggccaactt    540
acttctgaca cgatcggag gaccgaagga gctaaccgct tttttgcaca acatgggga    600
tcatgtaact cgccttgatc gttgggaacc ggagctgaat gaagccatac caaacgacga    660
gcgtgacacc acgatgcctg tagcaatggc aacaacgttg cgcaaactat taactggcga    720
actacttact ctagcttccc ggcaacaatt aatagactgg atggaggcgg ataaagttgc    780
aggaccactt ctgcgctcgg cccttccggc tggctggttt attgctgata aatctggagc    840
cggtgagcgt gggtctcgcg gtatcattgc agcactgggg ccagatggta agccctcccg    900
tatcgtagtt atctacacga cggggagtca ggcaactatg gatgaacgaa atagacagat    960
cgctgagata ggtgcctcac tgattaagca ttggtaactg tcagaccaag tttactcata   1020
tatactttag attgatttaa aacttcattt ttaatttaaa aggatctagg tgaagatcct   1080
ttttgataat ctcatgacca aaatccctta acgtgagttt tcgttccact gagcgtcaga   1140
ccccgtagaa aagatcaaag gatcttcttg agatcctttt tttctgcgcg taatctgctg   1200
cttgcaaaca aaaaaaccgc taccagcggt ggtttgtttg ccggatcaag agctaccaac   1260
tcttttccg aaggtaactg gcttcagcag agcgcagata ccaaatactg ttcttctagt   1320
gtagccgtag ttaggccacc acttcaagaa ctctgtagca ccgcctacat acctcgctct   1380
gctaatcctg ttaccagtgg ctgctgccag tggcgataag tcgtgtctta ccgggttgga   1440
ctcaagacga tagttaccgg ataaggcgca gcggtcgggc tgaacggggg gttcgtgcac   1500
acagcccagc ttggagcgaa cgacctacac cgaactgaga tacctacagc gtgagctatg   1560
agaaagcgcc acgcttcccg aagggagaaa ggcggacagg tatccggtaa gcggcagggt   1620
cggaacagga gagcgcacga gggagcttcc agggggaaac gcctggtatc tttatagtcc   1680
tgtcgggttt cgccacctct gacttgagcg tcgatttttg tgatgctcgt cagggggggcg   1740
agcctatgg aaaaacgcca gcaacgcggc cttttacgg ttcctggcct tttgctggcc   1800
ttttgctcac atgttctttc ctgcgttatc ccctgattct gtggataacc gtattaccgc   1860
ctttgagtga gctgataccg ctcgccgcag ccgaacgacc gagcgcagcg agtcagtgag   1920
cgaggaagcg gaagagcgcc caatacgcaa accgcctctc cccgcgcgtt ggccgattca   1980
ttaatgcagc tggcacgaca ggtttcccga ctggaaagcg ggcagtgagc gcaacgcaat   2040
taatgtgagt tagctcactc attaggcacc ccaggcttta cactttatgc ttccggctcg   2100
tatgttgtgt ggaattgtga gcggataaca atttcacaca ggaaacagct atgaccatga   2160
ttacgccaag ctctagctag aggtcgacgg tatacagaca tgataagata cattgatgag   2220
tttggacaaa ccacaactag aatgcagtga aaaaaatgct ttatttgtga aatttgtgat   2280
gctattgctt tatttgtaac cattataagc tgcaataaac aagttggggt gggcgaagaa   2340
ctccagcatg agatccccgc gctggaggat catccagccg gcgtcccgga aaacgattcc   2400
gaagcccaac ctttcataga aggcggcggt ggaatcgaaa tctcgtgatg gcaggttggg   2460
cgtcgcttgg tcggtcattt cgaacccag agtcccgctc agaagaactc gtcaagaagg   2520
cgatagaagg cgatgcgctg cgaatcggga gcggcgatac cgtaaagcac gaggaagcgg   2580
```

```
tcagcccatt cgccgccaag ctcttcagca atatcacggg tagccaacgc tatgtcctga    2640
tagcggtccg ccacacccag ccggccacag tcgatgaatc cagaaaagcg gccattttcc    2700
accatgatat tcggcaagca ggcatcgcca tgggtcacga cgagatcctc gccgtcgggc    2760
atgcgcgcct tgagcctggc gaacagttcg gctggcgcga gccctgatg ctcttcgtcc     2820
agatcatcct gatcgacaag accggcttcc atccgagtac gtgctcgctc gatgcgatgt    2880
ttcgcttggt ggtcgaatgg gcaggtagcc ggatcaagcg tatgcagccg ccgcattgca    2940
tcagccatga tggatacttt ctcggcagga gcaaggtgag atgacaggag atcctgcccc    3000
ggcacttcgc ccaatagcag ccagtcccct cccgcttcag tgacaacgtc gagcacagct    3060
gcgcaaggaa cgcccgtcgt ggccagccac gatagccgcg ctgcctcgtc ctgcagttca    3120
ttcagggcac cggacaggtc ggtcttgaca aaagaaccg ggcgccctg cgctgacagc      3180
cggaacacgg cggcatcaga gcagccgatt gtctgttgtg cccagtcata gccgaatagc    3240
ctctccaccc aagcggccgg agaacctgcg tgcaatccat cttgttcaat catgcgaaac    3300
gatcctcatc ctgtctcttg atcagatccg aaaatggata tacaagctcc cgggagcttt    3360
ttgcaaaagc ctaggcctcc aaaaaagcct cctcactact tctggaatag ctcagaggca    3420
gaggcggcct cggcctctgc ataaataaaa aaattagtc agccatgggg cggagaatgg     3480
gcggaactgg gcggagttag gggcgggatg ggcggagtta ggggcgggac tatggttgct    3540
gactaattga gatgcatgct ttgcatactt ctgcctgctg gggagcctgg ggactttcca    3600
cacctggttg ctgactaatt gagatgcatg ctttgcatac ttctgcctgc tggggagcct    3660
ggggactttc cacaccctaa ctgacacaca ttccacagaa ttaattcgcg ttaaattttt     3720
gttaaatcag ctcattttt aaccaatagg ccgaaatcgg caaaatccct tataaatcaa     3780
aagaatagac cgagataggg ttgagtgttg ttccagtttg gaacaagagt ccactattaa    3840
agaacgtgga ctccaacgtc aaagggcgaa aaaccgtcta tcagggcgat ggcccactac    3900
gtgaaccatc accctaatca agttttttgg ggtcgaggtg ccgtaaagca ctaaatcgga    3960
accctaaagg gagcccccga tttagagctt gacggggaaa gccggcgaac gtggcgagaa    4020
aggaagggaa gaaagcgaaa ggagcgggcg ctagggcgct ggcaagtgta gcggtcacgc    4080
tgcgcgtaac caccacaccc gccgcgctta atgcgccgct acagggcgcg tgggatacc     4140
ccctagagcc ccagctggtt cttttccgcct cagaagccat agagcccacc gcatccccag   4200
catgcctgct attgtcttcc caatcctccc ccttgctgtc ctgccccacc ccaccccca    4260
gaatagaatg acacctactc agacaatgcg atgcaatttc ctcattttat taggaaagga    4320
cagtgggagt ggcaccttcc agggtcaagg aaggcacggg ggaggggcaa acaacagatg   4380
gctggcaact agaaggcaca gtcgaggctg atcagcgggt ttaaacgggc cctctagact    4440
cgagcggccg ccactgtgct ggatatctgc agaattctta ggcatagtcg gggacatcat   4500
atgggtatgc ataatcaggc acgtcgtagg gataagcgta atctggaaca tcgtatgggt    4560
aggatcccctt tttctttttt gcctggccgg cctttttcgt ggccgccggc cttttgttgc    4620
gcagctcctg gatgtaggcc agccagtcct gattggagat gccgttctgc agcttcagat    4680
ccttgctctc cttcaggtga ttcagcagca gctggccctt cagggcgatg tggtaggcgc    4740
cattggcatc ggcgtccatg ggccactctg ggttctgaaa ccgggagtcg aagcacacgc    4800
cattcagatc gcgcacgggg ctgttgatat agtcctcgcc tgtggcggca ttggagttcc    4860
gcatctgcag cacgctgcgg atcagggcca ccatggtgtc gatggcgtga gaatcgtcat    4920
tctccagcag cttttggcagg atgttggagc catccctgaa cacgatgccc ttctcctcca    4980
```

```
gcagggcgat cagctcgttg gcaggataca ggtcccggta tctgccggtg aatctgtgat    5040
tctcgatcac tggcacgatt ctcttgccgg cgatgaaagg ggtgcccttg gcgtcaaact    5100
gtgtctcgtt cttctcgaac acgatatccc atgcaggcat aaagccgggc aggcccctct    5160
ggaaggacag atttctgttc atcttaaagt gcaggatgaa gtcgccggtt ttcacgtcgt    5220
agtgcagaaa gtcgaagccc tccaggaagt gcttgcggct ctcgtgattc ttgatggttt    5280
tccacacgaa ggggtccacg aagccggtca ggggatcgat cttagatgta tatgggcag    5340 gcacgtaaaa caggaagcca gactgggtgc ccatcttggc aaaggaggtg aactggtctg    5400
tcagctggta tgggttcagc acgcctccca ctttctctgc tggatagtcc ttcagcacca    5460
ggcaattcag cttatcgatc agcatcttct cgaactgctg gtacacggcc ttctcggcga    5520
tgccggtcct cttgctctta aagccgaaat tcaggttctc cagcaccacc acggcctggt    5580
agtggatcat caggtccacg atctcgtgga tgacctggct cagatagccc tgcttcagat    5640
ccttgattgt gcccaccaca gaccaggcct gccttgctgc caccctctcc ttctccctgt    5700
tgtccagctt cttctggtaa tcaaactgct ggatggtgtt caggctccgc tgctccagga    5760
tcttgccggt ggagtcgatc actgtgatat agatcaggtt tctctcgccc cgatcgatgc    5820
cgatgatagg tgtctcgggg tgctccttca ggtaggcatt caccctctgg ttgaacttag    5880
atggggaatt ggcggcctga tagttcagtg tgataggcac gtggaaaaag aacttgtcgc    5940
tggtaaagcg cctatccttg atgatctcgt gagacacctc cttggtgatc acgttgggca    6000
gcagggccct ggcctcatca gacaggtcgt gggacagtct gtgattcaca tagtcgtaca    6060
gctcctggta cagggtgtcg gggattgggg ttttctgatc cttcagcttc ttgttcagca    6120
tcttctctcc cagccggtgt gccatcctct tcatcctgga cttagggcgg tagaacagct    6180
cggcctggcc attcagcttg atgcttgtct tggccaggtt ctctggagaa aacagaccgg    6240
tccaatacag tgtgtgcaga ttaggcttgc cgtggtggcc cttggcaaag tccttgttat    6300
agatctggaa caggtacagc ttgcctgtct ccacggcatc catgatctcc ttctcggcga    6360
ttctctggaa gctgatgtgg tacagcaggg gattcagctc ggcatagtac tcgcccaggt    6420
ccttatactg agaggatggc cgcaggctag acagatcgat agaggttgtc ttggtatact    6480
tggacagaaa atcccttgtg aagtcgatcc acttgcacag ggcctctctg tagcccttct    6540
ggtcgccggt tttcttggcg tacgctgtct gaaacttctt tggctccttc tcaggattgt    6600
tcaggtcgta gatctccttt gtgatctcca gaggctcgat gaaattgttg acagcagga    6660 tgggggttgt gtgggtctga aagtgggcgg tcaccgcctt cagctgggtg ctgcaccgtg    6720
ggatcatctt ggcggcatcc ggaaagtagt catagtacat cttatcaaag ccctcgctgg    6780
ttttctctgt gggctcgaag ctgagggcct tatacctgcc cttctgcttt ggcatgatgc    6840
ccagatagta caggccgttc ttcacaaaca ggatggcgcc attgttcttc tccttattca    6900
cgtcccagcc ccgggccagt gtaggcatct gaaagttcag cttgaacttc tccacggagt    6960
agggcttctt ggtggcataa tttctggcct tgttgtagaa gctcagagac ggctccatct    7020
ccagcttgat gccggtcagc cgggcagaga actcggggtc cacctcgttg gactcatcca    7080
cggcaaacca gtccagcagg tggtacaggc ccagcaggct gtccagctga gacttcagga    7140
tctccttctc ctcctgcttc ttcagggttg taggcagtgg ctgatccagg cggcgtgtg    7200 cgtgggacag gatctcgctg gttttctgct gaaggcctc gctcagctcc ttgcctgcgg    7260
cagagatgat ctcctgcagg ttgatatcct cgtgcttcag gctgcgctgc accttctcct    7320
```

-continued

| | |
|---|---|
| tggcagactt ggtgatcttg cctgtcagct cggagattct ccgctcatac agggcattcc | 7380 |
| tcagtgtatc ccagtggtcg cacagggcgc tgctgattgt ctccagcttc ttgtggctga | 7440 |
| tgaagatgtg tgtcaggtcg atgctgttca gctcgttaaa cagggcctcg gctgtctcca | 7500 |
| gcacgttctc gtttctcagc agtgtcttgt acttgcagaa ggactggatc acttcctcgt | 7560 |
| cgctcttaaa ctcctccagg atgaaagaca gggtgttcct atcggacagg atctgcttaa | 7620 |
| acagggggat gaatctgtgt ggcagggagg cgatgatgtg ggctgtctca tcattcttct | 7680 |
| ggatggccag attcagcacc tcgttcaggc ccttgatctt ctcggtgcct gcctcccgag | 7740 |
| agattcctcc cagcagctgg ttatacaggt cgatctgggt ctgtgtcagc agctggttat | 7800 |
| aaaaagggaa ggaaaacacc tcctcgatgg aggtgctcac gaagatgccg atggccttct | 7860 |
| tcacgttctc aaagtgctcc cgcaggctgg cacggcggt gatcaggcgt gtgaagatgt | 7920 |
| gacaattctc cttaaacttg gggaagttgt cctgcacgat gcggtgtggg atggctgtgc | 7980 |
| tgatatcctc ggcgctgaac acgttcttcc tgttctcata aaagccggag aagtaggttg | 8040 |
| taaacttgtc gaagctccgc agcagggcgt tctcgtgctc ggttgtggtc acggtgccca | 8100 |
| gctgcttcag caccttgcca ttaaacagct cggccttgaa caggcccttg tagatctcgg | 8160 |
| cgtgtctctt attgatggca tcggtcaggt tgtctgtccg gccgatgaag tagtcgtgga | 8220 |
| tggcattgcg atatgtggcc tgctcctcga tcagggcgtt ccttgtctcc tcggttttct | 8280 |
| cctttctata ggagtcgatg gcggcgctca ggttctccca atccagctgc accagctgca | 8340 |
| ggcactggtc ggcataggtc ttgtagatcc gatcgatgat gggcttcagc tccttgtagt | 8400 |
| gatcattgcg ggccttgtcc tcctcgatga agccctgctc ctggatgtgc ttcagggtct | 8460 |
| tgccctgtgg gatcagctca accgcagtg tcttgctcac ctgatacagg ttggtaaagc | 8520 |
| cctcgaactg tgtcatggtg gcggtaccaa gcttaagttt aaacgctagc cagcttgggt | 8580 |
| ctccctatag tgagtcgtat taatttcgat aagccagtaa gcagtgggtt ctctagttag | 8640 |
| ccagagagct ctgcttatat agacctccca ccgtacacgc ctaccgccca tttgcgtcaa | 8700 |
| tggggcggag ttgttacgac attttggaaa gtcccgttga ttttggtgcc aaaacaaact | 8760 |
| cccattgacg tcaatgggt ggagacttgg aaatccccgt gagtcaaacc gctatccacg | 8820 |
| cccattgatg tactgccaaa accgcatcac catggtaata gcgatgacta atacgtagat | 8880 |
| gtactgccaa gtaggaaagt cccataaggt catgtactgg cataatgcc aggcgggcca | 8940 |
| tttaccgtca ttgacgtcaa tagggggcgt acttggcata tgatacactt gatgtactgc | 9000 |
| caagtgggca gtttaccgta aatactccac ccattgacgt caatggaaag tcccattgg | 9060 |
| cgttactatg ggaacatacg tcattattga cgtcaatggg cggggtcgt tggcggtca | 9120 |
| gccaggcggg ccatttaccg taagttatgt aacgcggaac tccatatatg gctatgaac | 9180 |
| taatgacccc gtaattgatt actattaata actagtcaat aatcaatgtc aacgcgtata | 9240 |
| tctgccccgt acatcgcgaa gcagcgcaaa acgcctaacc ctaagcagat tcttcatgca | 9300 |
| attgtcggtc aagccttgcc ttgttgtagc ttaaattttg ctcgcgcact actcagcgac | 9360 |
| ctccaacaca caagcaggga gcagatactg gcttaactat gcggcatcag agcagattgt | 9420 |
| actgagagtg caccataggg gatcgggaga tctcccgatc cgtc | 9464 |

<210> SEQ ID NO 367
<211> LENGTH: 1352
<212> TYPE: PRT
<213> ORGANISM: Homo sapiens

<400> SEQUENCE: 367

```
Met Thr Gln Phe Glu Gly Phe Thr Asn Leu Tyr Gln Val Ser Lys Thr
1               5                   10                  15
Leu Arg Phe Glu Leu Ile Pro Gln Gly Lys Thr Leu Lys His Ile Gln
            20                  25                  30
Glu Gln Gly Phe Ile Glu Asp Lys Ala Arg Asn Asp His Tyr Lys
        35                  40                  45
Glu Leu Lys Pro Ile Ile Asp Arg Ile Tyr Lys Thr Tyr Ala Asp Gln
    50                  55                  60
Cys Leu Gln Leu Val Gln Leu Asp Trp Glu Asn Leu Ser Ala Ala Ile
65                  70                  75                  80
Asp Ser Tyr Arg Lys Glu Lys Thr Glu Glu Thr Arg Asn Ala Leu Ile
            85                  90                  95
Glu Glu Gln Ala Thr Tyr Arg Asn Ala Ile His Asp Tyr Phe Ile Gly
        100                 105                 110
Arg Thr Asp Asn Leu Thr Asp Ala Ile Asn Lys Arg His Ala Glu Ile
        115                 120                 125
Tyr Lys Gly Leu Phe Lys Ala Glu Leu Phe Asn Gly Lys Val Leu Lys
    130                 135                 140
Gln Leu Gly Thr Val Thr Thr Thr Glu His Glu Asn Ala Leu Leu Arg
145                 150                 155                 160
Ser Phe Asp Lys Phe Thr Thr Tyr Phe Ser Gly Phe Tyr Glu Asn Arg
            165                 170                 175
Lys Asn Val Phe Ser Ala Glu Asp Ile Ser Thr Ala Ile Pro His Arg
            180                 185                 190
Ile Val Gln Asp Asn Phe Pro Lys Phe Lys Glu Asn Cys His Ile Phe
        195                 200                 205
Thr Arg Leu Ile Thr Ala Val Pro Ser Leu Arg Glu His Phe Glu Asn
210                 215                 220
Val Lys Lys Ala Ile Gly Ile Phe Val Ser Thr Ser Ile Glu Glu Val
225                 230                 235                 240
Phe Ser Phe Pro Phe Tyr Asn Gln Leu Leu Thr Gln Thr Gln Ile Asp
            245                 250                 255
Leu Tyr Asn Gln Leu Leu Gly Gly Ile Ser Arg Glu Ala Gly Thr Glu
        260                 265                 270
Lys Ile Lys Gly Leu Asn Glu Val Leu Asn Leu Ala Ile Gln Lys Asn
    275                 280                 285
Asp Glu Thr Ala His Ile Ile Ala Ser Leu Pro His Arg Phe Ile Pro
        290                 295                 300
Leu Phe Lys Gln Ile Leu Ser Asp Arg Asn Thr Leu Ser Phe Ile Leu
305                 310                 315                 320
Glu Glu Phe Lys Ser Asp Glu Glu Val Ile Gln Ser Phe Cys Lys Tyr
            325                 330                 335
Lys Thr Leu Leu Arg Asn Glu Asn Val Leu Glu Thr Ala Glu Ala Leu
        340                 345                 350
Phe Asn Glu Leu Asn Ser Ile Asp Leu Thr His Ile Phe Ile Ser His
        355                 360                 365
Lys Lys Leu Glu Thr Ile Ser Ser Ala Leu Cys Asp His Trp Asp Thr
    370                 375                 380
Leu Arg Asn Ala Leu Tyr Glu Arg Arg Ile Ser Glu Leu Thr Gly Lys
385                 390                 395                 400
Ile Thr Lys Ser Ala Lys Glu Lys Val Gln Arg Ser Leu Lys His Glu
            405                 410                 415
```

```
Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460

Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Arg Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Arg Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
```

```
                835                 840                 845
Val Ile Thr Lys Glu Val Ser His Glu Ile Ile Lys Asp Arg Arg Phe
            850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
                915                 920                 925

Gln Arg Ser Leu Asn Thr Ile Gln Gln Phe Asp Tyr Gln Lys Lys Leu
            930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys Ser Lys Arg Thr Gly Ile Ala Glu
                995                 1000                1005

Lys Ala Val Tyr Gln Gln Phe Glu Lys Met Leu Ile Asp Lys Leu
            1010                1015                1020

Asn Cys Leu Val Leu Lys Asp Tyr Pro Ala Glu Lys Val Gly Gly
            1025                1030                1035

Val Leu Asn Pro Tyr Gln Leu Thr Asp Gln Phe Thr Ser Phe Ala
            1040                1045                1050

Lys Met Gly Thr Gln Ser Gly Phe Leu Phe Tyr Val Pro Ala Pro
            1055                1060                1065

Tyr Thr Ser Lys Ile Asp Pro Leu Thr Gly Phe Val Asp Pro Phe
            1070                1075                1080

Val Trp Lys Thr Ile Lys Asn His Glu Ser Arg Lys His Phe Leu
            1085                1090                1095

Glu Gly Phe Asp Phe Leu His Tyr Asp Val Lys Thr Gly Asp Phe
            1100                1105                1110

Ile Leu His Phe Lys Met Asn Arg Asn Leu Ser Phe Gln Arg Gly
            1115                1120                1125

Leu Pro Gly Phe Met Pro Ala Trp Asp Ile Val Phe Glu Lys Asn
            1130                1135                1140

Glu Thr Gln Phe Asp Ala Lys Gly Thr Pro Phe Ile Ala Gly Lys
            1145                1150                1155

Arg Ile Val Pro Val Ile Glu Asn His Arg Phe Thr Gly Arg Tyr
            1160                1165                1170

Arg Asp Leu Tyr Pro Ala Asn Glu Leu Ile Ala Leu Leu Glu Glu
            1175                1180                1185

Lys Gly Ile Val Phe Arg Asp Gly Ser Asn Ile Leu Pro Lys Leu
            1190                1195                1200

Leu Glu Asn Asp Asp Ser His Ala Ile Asp Thr Met Val Ala Leu
            1205                1210                1215

Ile Arg Ser Val Leu Gln Met Arg Asn Ser Asn Ala Ala Thr Gly
            1220                1225                1230

Glu Asp Tyr Ile Asn Ser Pro Val Arg Asp Leu Asn Gly Val Cys
            1235                1240                1245
```

-continued

```
Phe Asp Ser Arg Phe Gln Asn Pro Glu Trp Pro Met Asp Ala Asp
    1250            1255            1260

Ala Asn Gly Ala Tyr His Ile Ala Leu Lys Gly Gln Leu Leu Leu
    1265            1270            1275

Asn His Leu Lys Glu Ser Lys Asp Leu Lys Leu Gln Asn Gly Ile
    1280            1285            1290

Ser Asn Gln Asp Trp Leu Ala Tyr Ile Gln Glu Leu Arg Asn Lys
    1295            1300            1305

Arg Pro Ala Ala Thr Lys Lys Ala Gly Gln Ala Lys Lys Lys Lys
    1310            1315            1320

Gly Ser Tyr Pro Tyr Asp Val Pro Asp Tyr Ala Tyr Pro Tyr Asp
    1325            1330            1335

Val Pro Asp Tyr Ala Tyr Pro Tyr Asp Val Pro Asp Tyr Ala
    1340            1345            1350
```

CRISPR ENZYMES AND SYSTEMS

CROSS-REFERENCE TO RELATED APPLICATIONS

This application is a national phase entry of International Application No. PCT/US2017/047459 filed Aug. 17, 2017, which claims the benefit of U.S. Provisional Application No. 62/376,372 filed Aug. 17, 2016, and U.S. Provisional Application No. 62/437,023 filed Dec. 20, 2016.

STATEMENT AS TO FEDERALLY SPONSORED RESEARCH

This invention was made with government support under grant numbers MH100706 and MH110049 awarded by the National Institutes of Health. The government has certain rights in the invention.

REFERENCE TO AN ELECTRONIC SEQUENCE LISTING

The contents of the electronic sequence listing ("BROD-0961US_Corrected_2020-10-01_ST25.txt"; Size is 125,525 bytes; was created on Oct. 1, 2020) is herein incorporated by reference in its entirety.

FIELD OF THE INVENTION

The present invention generally relates to systems, methods and compositions related to Clustered Regularly Interspaced Short Palindromic Repeats (CRISPR) and components thereof. The present invention also generally relates to delivery of large payloads and includes novel delivery particles, particularly using lipid and viral particle, and also novel viral capsids, both suitable to deliver large payloads, such as Clustered Regularly Interspaced Short Palindromic Repeats (CRISPR), CRISPR protein (e.g., Cas, Cas9, Cpf1, Cas13a, Cas13b and the like), CRISPR-Cas or CRISPR system or CRISPR-Cas complex, components thereof, nucleic acid molecules, e.g., vectors, involving the same and uses of all of the foregoing, amongst other aspects. Additionally, the present invention relates to methods for developing or designing CRISPR-Cas system based therapy or therapeutics.

BACKGROUND OF THE INVENTION

Recent advances in genome sequencing techniques and analysis methods have significantly accelerated the ability to catalog and map genetic factors associated with a diverse range of biological functions and diseases. Precise genome targeting technologies are needed to enable systematic reverse engineering of causal genetic variations by allowing selective perturbation of individual genetic elements, as well as to advance synthetic biology, biotechnological, and medical applications. Although genome-editing techniques such as designer zinc fingers, transcription activator-like effectors (TALEs), or homing meganucleases are available for producing targeted genome perturbations, there remains a need for new genome engineering technologies that employ novel strategies and molecular mechanisms and are affordable, easy to set up, scalable, and amenable to targeting multiple positions within the eukaryotic genome. This would provide a major resource for new applications in genome engineering and biotechnology.

The CRISPR-Cas systems of bacterial and archaeal adaptive immunity show extreme diversity of protein composition and genomic loci architecture. The CRISPR-Cas system loci has more than 50 gene families and there is no strictly universal genes indicating fast evolution and extreme diversity of loci architecture. So far, adopting a multi-pronged approach, there is comprehensive cas gene identification of about 395 profiles for 93 Cas proteins. Classification includes signature gene profiles plus signatures of locus architecture. A new classification of CRISPR-Cas systems is proposed in which these systems are broadly divided into two classes, Class 1 with multisubunit effector complexes and Class 2 with single-subunit effector modules exemplified by the Cas9 protein. Novel effector proteins associated with Class 2 CRISPR-Cas systems may be developed as powerful genome engineering tools and the prediction of putative novel effector proteins and their engineering and optimization is important.

The development of CRISPR-Cas RNA-guided endonucleases for eukaryotic genome editing has sparked intense interest in the use of this technology for therapeutic applications.

Extensive research has led to the identification of different technologies which can address the challenges of safety and efficacy. In order to allow the translation of this genome editing technologies to the clinic. There is a need for the development of an algorithm for developing a CRISPR-Cas based therapeutic, which takes into account the different variables which need to be considered.

In contrast to small molecule therapies, which target highly conserved protein active sites, treatment of disease at the genomic level must contend with significant levels of genetic variation in patient populations. Recently, large scale sequencing datasets from the Exome Aggregation Consortium (ExAC) and 1000 Genomes Project have provided an unprecedented view of the landscape of human genetic variation. This variation can affect both the efficacy of a CRISPR-based therapeutic, by disrupting the target site, and its safety, by generating off-target candidate sites.

Citation or identification of any document in this application is not an admission that such document is available as prior art to the present invention.

SUMMARY OF THE INVENTION

In certain example embodiments, an engineered CRISPR-Cas effector protein that complexes with a nucleic acid comprising a guide sequence to form a CRISPR complex, and wherein in the CRISPR complex the nucleic acid molecule target one or more polynucleotide loci and the protein comprises at least one modification compared to the unmodified protein that enhances binding of the CRISPR complex to the binding site and/or alters editing preferences as compared to wildtype. The editing preference may relate to indel formation. In certain example embodiments, the at least one modification may increase formation of one or more specific indels at a target locus. The CRISPR-Cas effector protein may be Type V CRISPR-Cas effector protein. In certain example embodiments, the CRISPR-Cas protein is Cpf1 or orthologue thereof.

In certain other example embodiments, the invention is directed to vectors for delivery of the CRISPR-Cas system, including vector based systems allowing for encoding of both the effector protein and guide sequence in a single vector.

In certain other example embodiments, the invention relates to methods for developing or designing CRISPR-Cas systems. In an aspect, the present invention relates to methods for developing or designing CRISPR-Cas system based therapy or therapeutics. The present invention in particular relates to methods for improving CRISPR-Cas systems, such as CRISPR-Cas system based therapy or therapeutics. Key characteristics of successful CRISPR-Cas systems, such as CRISPR-Cas system based therapy or therapeutics involve high specificity, high efficacy, and high safety. High specificity and high safety can be achieved among others by reduction of off-target effects.

The methods of the present invention in particular involve optimization of selected parameters or variables associated with the CRISPR-Cas system and/or its functionality, as described herein further elsewhere. Optimization of the CRISPR-Cas system in the methods as described herein may depend on the target(s), such as the therapeutic target or therapeutic targets, the mode or type of CRISPR-Cas system modulation, such as CRISPR-Cas system based therapeutic target(s) modulation, modification, or manipulation, as well as the delivery of the CRISPR-Cas system components. One or more targets may be selected, depending on the genotypic and/or phenotypic outcome. For instance, one or more therapeutic targets may be selected, depending on (genetic) disease etiology or the desired therapeutic outcome. The (therapeutic) target(s) may be a single gene, locus, or other genomic site, or may be multiple genes, loci or other genomic sites. As is known in the art, a single gene, locus, or other genomic site may be targeted more than once, such as by use of multiple gRNAs.

These and other aspects, objects, features, and advantages of the example embodiments will become apparent to those having ordinary skill in the art upon consideration of the following detailed description of illustrated example embodiments.

BRIEF DESCRIPTION OF THE DRAWINGS

FIG. 4A-H illustrates Stereotactic injection of AAV1/2 dual vectors into adult mouse hippocampus. a) Vector design. b) Immunostaining 3 weeks after stereotactic AAV1/2 injection. c) Quantification of double infected neurons. d) Western blot showing AsCpf1 and GFP-KASH protein levels. e) NGS indel analysis 3 weeks after stereotactic injection on GFP+ sorted nuclei. f) Quantification of mono- and bi-allelic modification of Drd1 in male mice. Mecp2 and Nlgn3 are x-chromosomal genes, hence only one allele can be edited. g) Quantification of multiplex editing efficiency. h) Example NGS reads showing indels in all three targeted genes.

FIG. 6A-C illustrates a) Schematic of pLenti-Cpf1 constructs. The pLenti-Cpf1 Constructs are modified from the lentiCRISPRv2 plasmids. SpCas9 was replaced by AsCpf1 and the SpCas9 U6 guide expression cassette was replaced with a AsCpf1 U6 guide expression cassette. Unlike lentiCRISPRv2, the U6 guide expression cassette in pLenti-Cpf1 is in reverse orientation. This change was required because Cpf1 recognizes its corresponding direct repeat (DR) sequence and cleaves RNA molecules that exhibit this feature. Therefore, Lenti viral RNA is susceptible for Cpf1 mediated cleavage if it exhibits a direct repeat sequence. However, incorporating the U6 guide expression cassette in reverse order results in a RNA molecule without the direct repeat sequence. b) Surveyor assay results from two bioreps of HEK293T cells infected with pLenti-AsCpf1 carrying a single VEGFA guide and one biorep of HEK293T cells infected with pLenti-AsCpf1 encoding a DNMT1-EMX1-VEGFA-GRIN2b array. Cells were analyzed 5 days after puromycin selection. Robust cutting was observed in all lenti infected cells at the targeted loci. Red triangles indicate cleavage products. c) NGS results for DNMT1, EMX1, VEGFA, and GRIN2b from colonies grown for 10 days after single cell FACS sorting of HEK293T cells infected with pLenti-AsCpf1 encoding a DNMT1-EMX1-VEGFA-GRIN2b array. FACS was performed after 5 days of puromycin selection. Multiplex editing was observed in a subset of examined cells. Each column represent one clonal colony, blue squares indicate editing of ≥30%, while squares indicate editing <30%.

FIG. 18A-10C. Validation of PAM screen with wt AsCpf1. A. Colony growth in cam/amp media for clones containing the indicated PAM sequences. B. Bar graph showing sensitivity of wild-type AsCpf1 to substitutions mutations in the PAM. C. Screen readout, highlighting depleted hits. Each dot represents a distinct Cpf1 wildtype (WT) or mutant codon. The dashed line indicates 15-fold depletion. Red=stop codon; blue=WT codon.

FIG. 19A provides a key as to guide length depicted in panels B-D. FIG. 19B depicts activity of AsCpf1 with truncated guides targeting DNMT1-3. FIG. 19C depicts activity of AsCpf1 with truncated guides targeting DNMT1-4. FIG. 19D depicts activity of LbCpf1 with truncated guides targeting DNMT1-3. FIG. 19E depicts activity of AsCpf1 with truncated guides targeting DNMT1-4.

FIG. 20A provides a key as to partially binding guides depicted in panels B-D. FIG. 20B depicts activity of AsCpf1 with partially matching guides targeting DNMT1-3. FIG. 20C depicts activity of AsCpf1 with partially matching guides targeting DNMT1-4. FIG. 20D depicts activity of LbCpf1 with partially matching guides targeting DNMT1-3. FIG. 20E depicts activity of AsCpf1 with partially matching guides targeting DNMT1-4.

FIG. 25. Protein alignment of AsCpf1 (Acidaminococcus sp. BV3L6) and LbCpf1 (Lachnospiraceae bacterium ND2006).

TABLE 1

| Packaging A0060 | VP3 only loop3 Cre 1:10 |
| Packaging A0061 | VP3 only loop3 Cre 1:1 |
| Packaging A0062 | VP3 only loop3 Cas9 1:10 |
| Packaging A0063 | VP3 only loop3 Cas9 1:1 |
| Packaging A0064 | VP3 only loop4 Cre 1:10 |
| Packaging A0065 | VP3 only loop4 Cre 1:1 |
| A0068 | VSVG Cas9 gesicle |
| A0069 | VSVG Cre gesicle |
| A0070 | RVG Cas9 gesicle |

TABLE 1-continued

| A0071 | RVG Cre gesicle |
| Packaging A0072 | AAV9 loop6 (His)6 1:10 |
| Packaging A0073 | AAV9 loop6 (His)6 1:1 |
| Packaging A0074 | VP3 only loop4 Cas9 1:10 |
| Packaging A0075 | VP3 only loop4 Cas9 1:1 |
| A0084 | VSVG-CRE |
| A0085 | DNase treatment |
| A0086 | (+G −S) |
| A0087 | (−G +S) |

Figure 38:
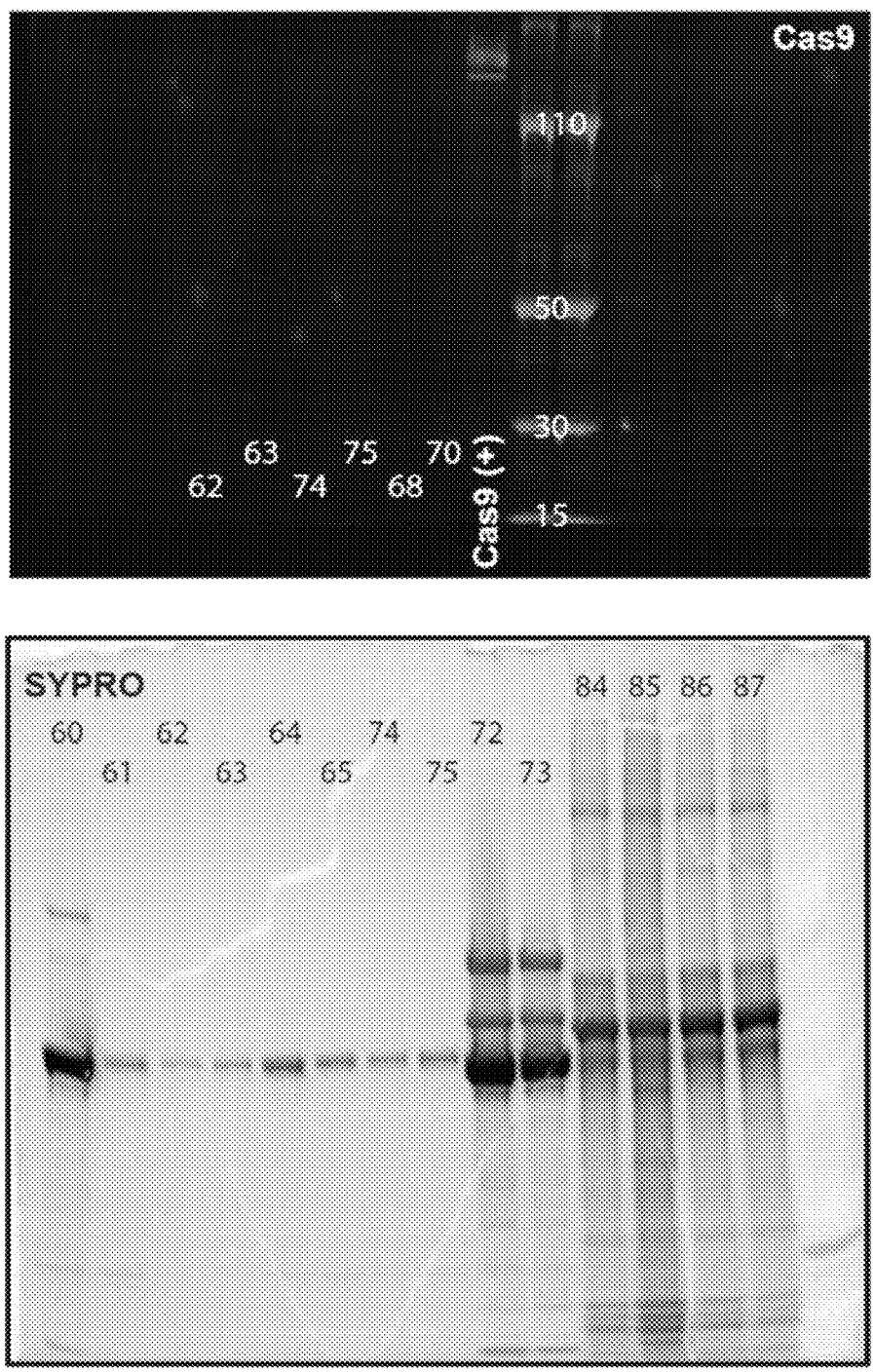

FIG. 38 shows Interior SunTag-GFP. Western blots detect VP3 (top left) and GFP (bottom left) for native VP3 and VP3-GFP fusion. Electron micrographs show GFP-filled capsid (103).

Figure 39:
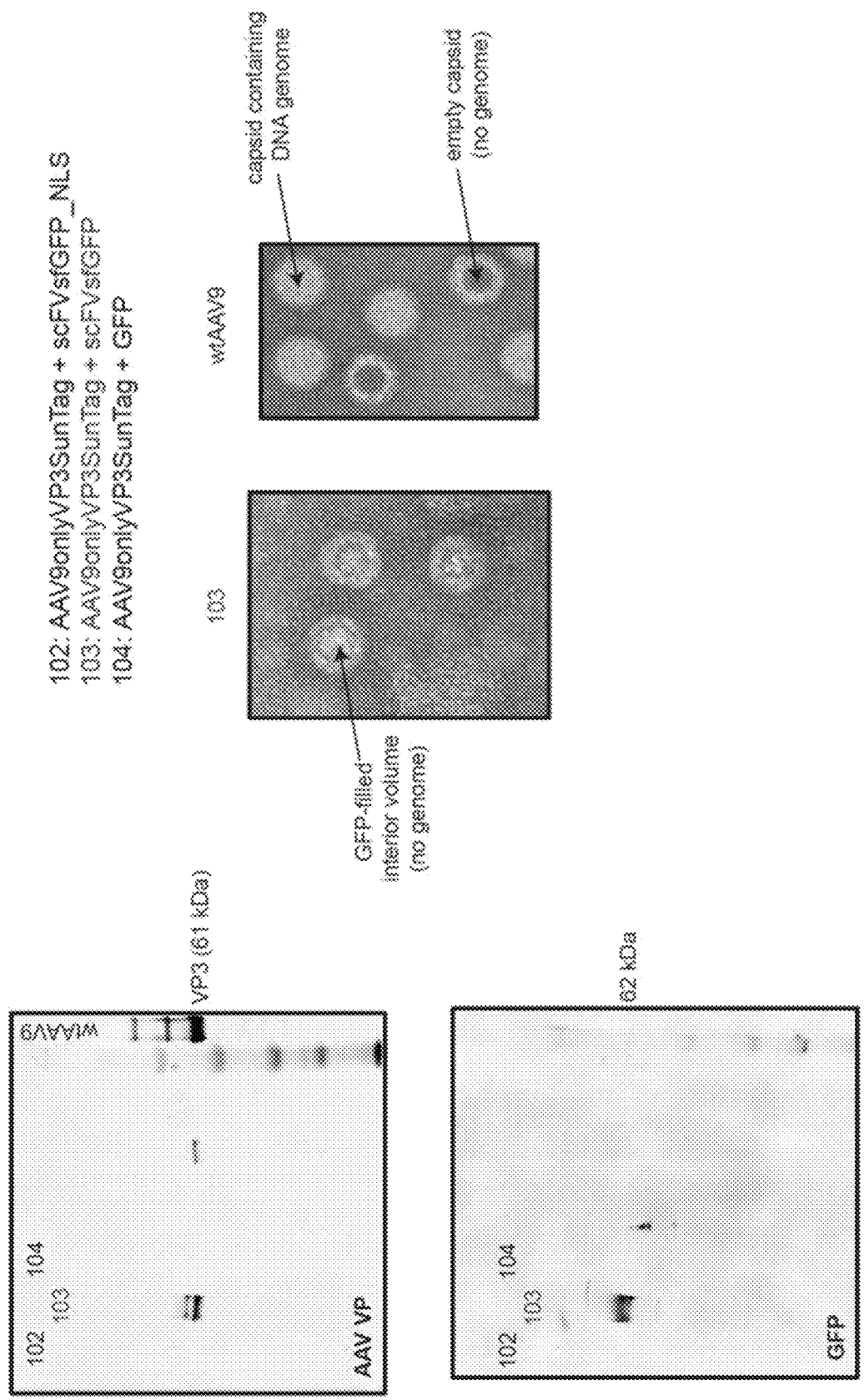

FIG. 39 depicts Vesicular stomatitis virus (VSV) and Rabies virus (RV) sources of packaging vesicles.

Figure 40:
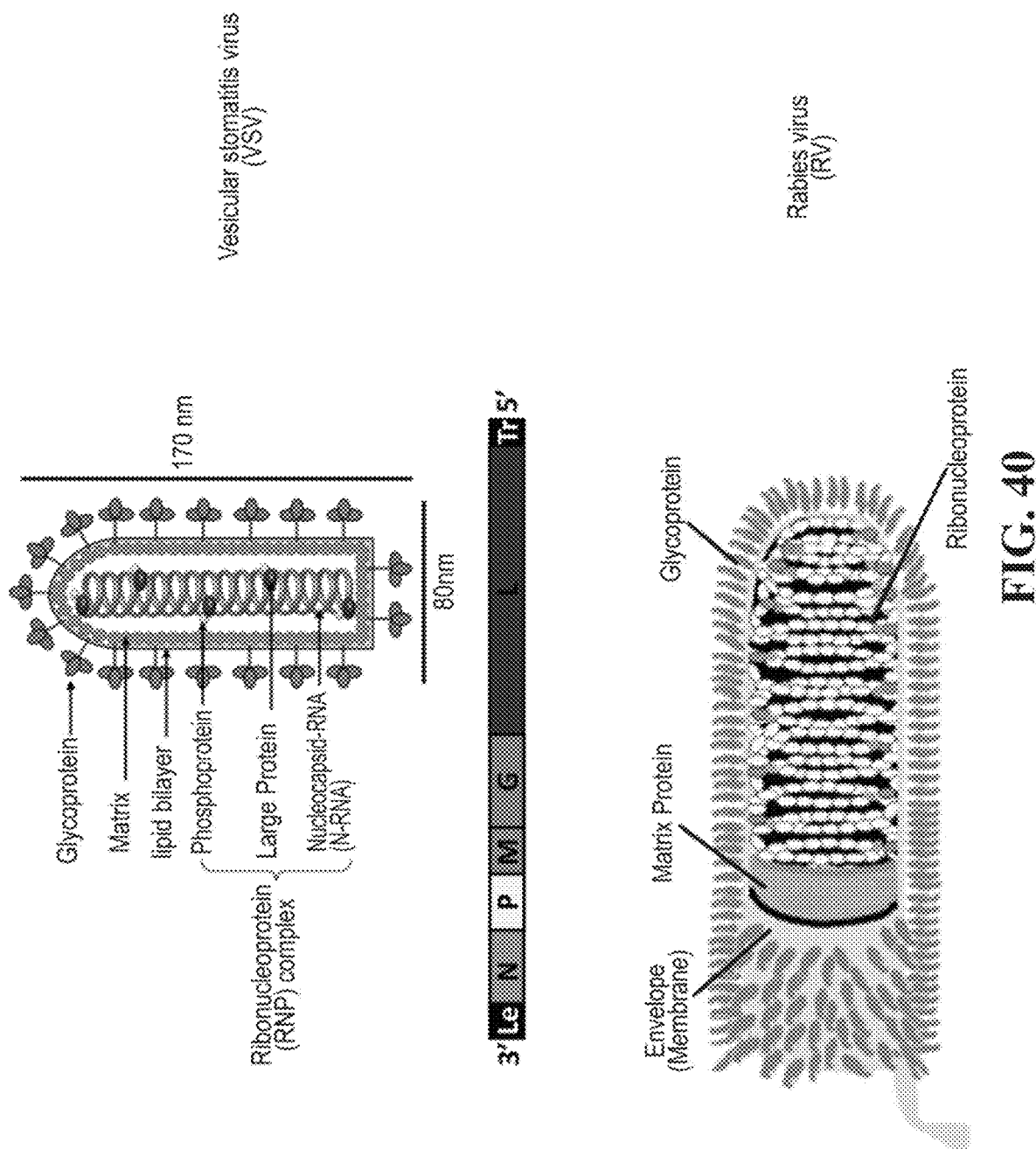

FIG. 40 shows a schematic for transduction of cells with lentiviral vectors packaged in vesicular stomatitis virus-G (VSVG) vesicles. (Cronin et al., Curr Gene Ther. 5(4):387-398 (2005)).

Figure 41:
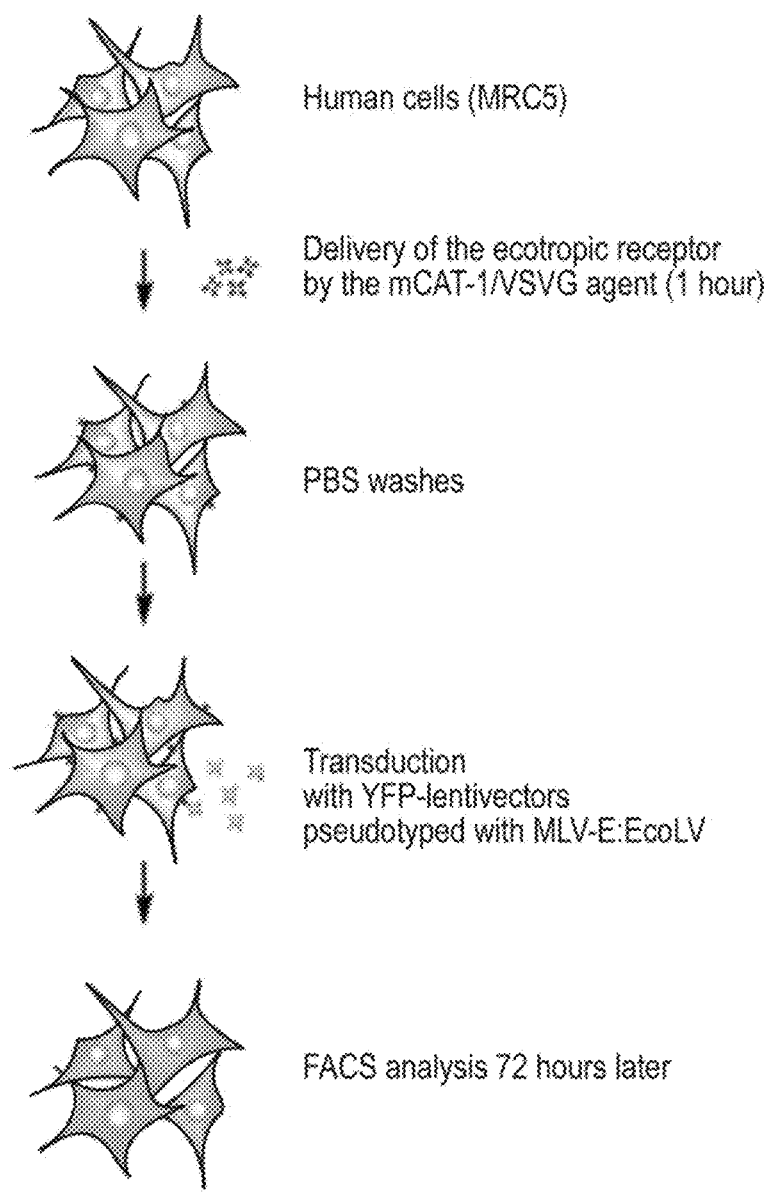

FIG. 41 depicts infection of TLR19 cells with VSVG and RVG vesicles harboring Cas9 and sgRNA inducing frameshift mutations to allow mCherry expression. Cas9 RNP vesicles were synthesized by contransfection of VSVG (or RVG) with eSpCas9(1.1) and plasmid GFPg2.

Figure 42:
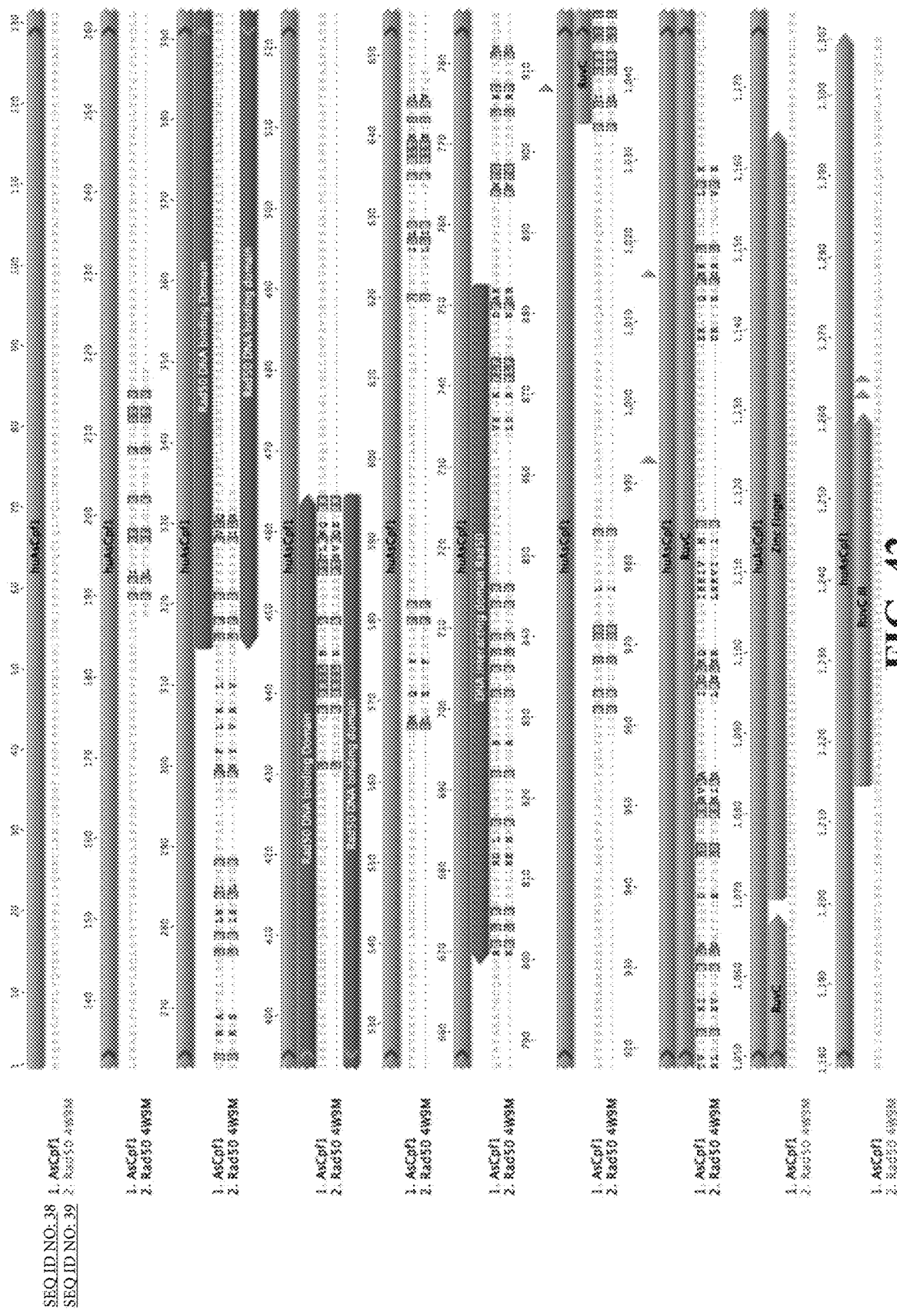

FIG. 42 provides an alignment of AsCpf1 and FnCpf1, identifying Rad50 binding domains and the arginines and lysines within.

Figure 43:
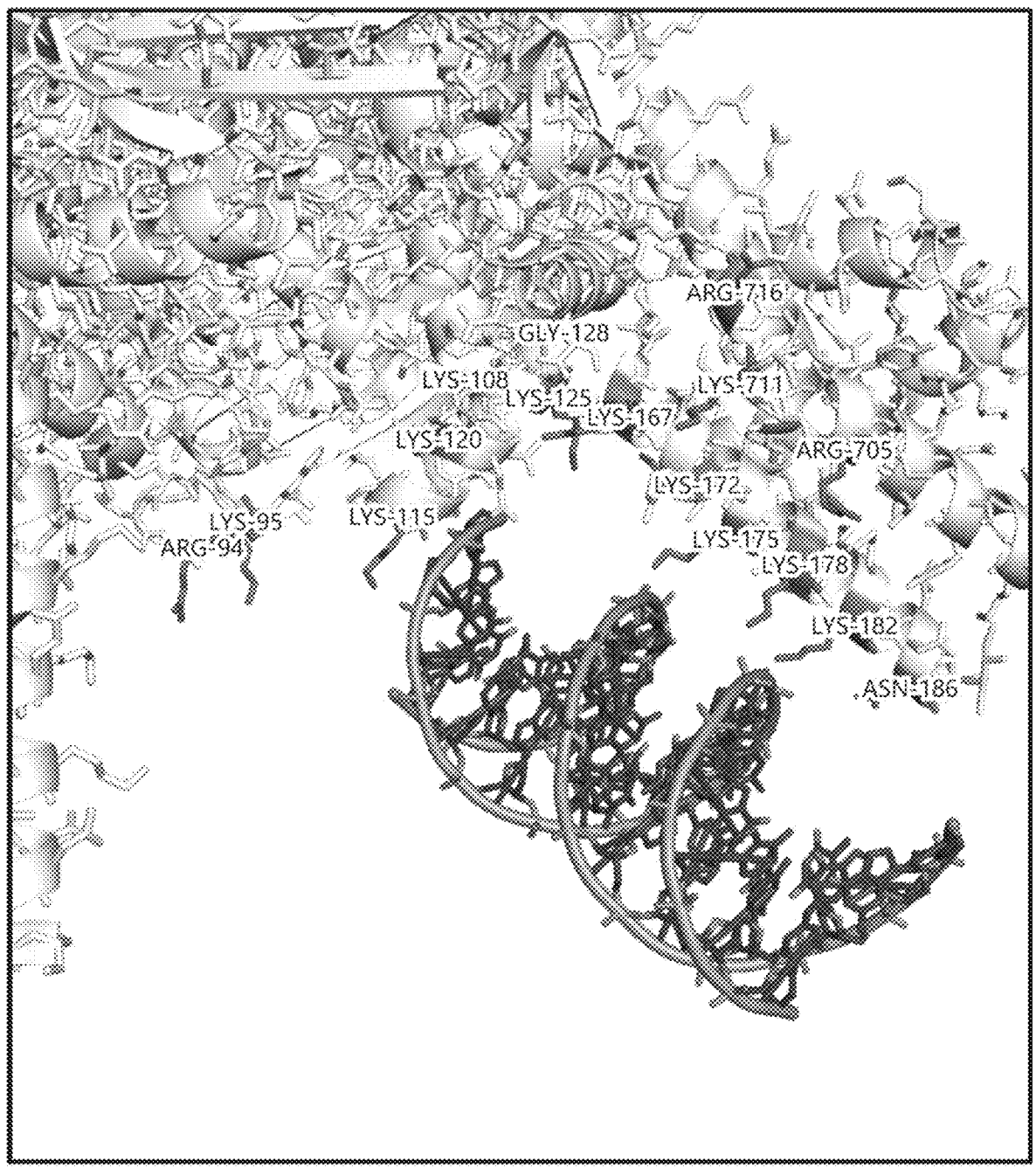

FIG. 43 provides a crystal structure of two similar domains as those found in Cpf1.

Figure 44:
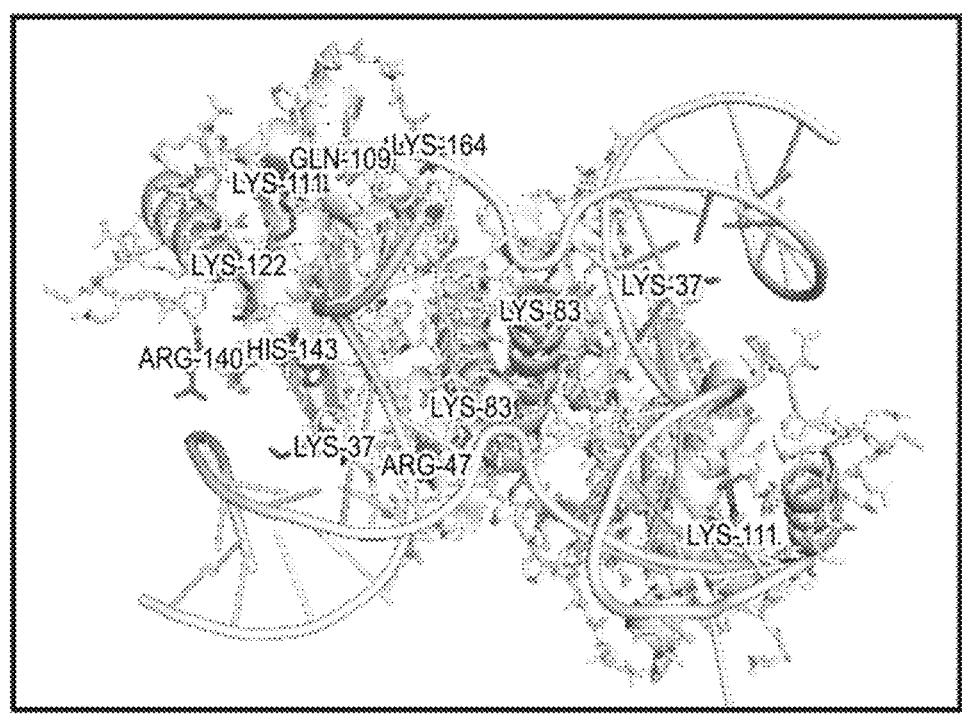

FIG. 44 provides a crystal structure of Aspf1 with regions that correspond to DNA binding regions annotated.

The figures herein are for illustrative purposes only and are not necessarily drawn to scale.

DETAILED DESCRIPTION OF THE INVENTION

General Definitions

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, $2^{nd}$ edition (1989) (Sambrook, Fritsch, and Maniatis); Molecular Cloning: A Laboratory Manual, $4^{th}$ edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2$^{nd}$ edition (2011).

As used herein, the singular forms "a", "an", and "the" include both singular and plural referents unless the context clearly dictates otherwise.

The term "optional" or "optionally" means that the subsequent described event, circumstance or substituent may or may not occur, and that the description includes instances where the event or circumstance occurs and instances where it does not.

The recitation of numerical ranges by endpoints includes all numbers and fractions subsumed within the respective ranges, as well as the recited endpoints.

The terms "about" or "approximately" as used herein when referring to a measurable value such as a parameter, an amount, a temporal duration, and the like, are meant to encompass variations of and from the specified value, such as variations of +/−10% or less, +/−5% or less, +/−1% or less, and +/−0.1% or less of and from the specified value, insofar such variations are appropriate to perform in the disclosed invention. It is to be understood that the value to which the modifier "about" or "approximately" refers is itself also specifically, and preferably, disclosed.

Reference throughout this specification to "one embodiment", "an embodiment," "an example embodiment," means that a particular feature, structure or characteristic described in connection with the embodiment is included in at least one embodiment of the present invention. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention. For example, in the appended claims, any of the claimed embodiments can be used in any combination.

It will be appreciated that the terms Cas enzyme, CRISPR enzyme, CRISPR protein, Cas protein and CRISPR-Cas are generally used interchangeably and at all points of reference herein refer by analogy to novel CRISPR effector proteins further described in this application, unless otherwise apparent, such as by specific reference to Cas9 or Cpf1. The CRISPR effector proteins described herein are preferably Cpf1 effector proteins.

All publications, published patent documents, and patent applications cited herein are hereby incorporated by reference to the same extent as though each individual publication, published patent document, or patent application was specifically and individually indicated as being incorporated by reference.

Overview

In one aspect, embodiments disclosed herein are directed to engineered CRISPR-Cas effector proteins that comprise at least one modification compared to an unmodified CRISPR-Cas effector protein that enhances binding of the CRISPR complex to the binding site and/or alters editing preference as compared to wild type. In certain example embodiments, the CRISPR-Cas effector protein is a Type V effector protein. In certain other example embodiments, the Type V effector protein is Cpf1. Example Cpf1 proteins suitable for use in the embodiments disclosed herein are discussed in further detail below.

In another aspect, embodiments disclosed herein are directed to viral vectors for delivery of CRISPR-Cas effector proteins, including Cpf1. In certain example embodiments, the vectors are designed so as to allow packaging of the CRISPR-Cas effector protein within a single vector. There is also an increased interest in the design of compact promoters for packing and thus expressing larger transgenes for targeted delivery and tissue-specificity. Thus, in another aspect certain embodiments disclosed herein are directed to delivery vectors, constructs, and methods of delivering larger genes for systemic delivery.

In another aspect, the present invention relates to methods for developing or designing CRISPR-Cas systems. In an aspect, the present invention relates to methods for developing or designing optimized CRISPR-Cas systems a wide range of applications including, but not limited to, therapeutic development, bioproduction, and plant and agricultural applications. In certain based therapy or therapeutics. The present invention in particular relates to methods for improving CRISPR-Cas systems, such as CRISPR-Cas system based therapy or therapeutics. Key characteristics of successful CRISPR-Cas systems, such as CRISPR-Cas system based therapy or therapeutics involve high specificity, high efficacy, and high safety. High specificity and high safety can be achieved among others by reduction of off-target effects. Improved specificity and efficacy likewise may be used to improve applications in plants and bioproduction.

Accordingly, in an aspect, the present invention relates to methods for increasing specificity of CRISPR-Cas systems, such as CRISPR-Cas system based therapy or therapeutics. In a further aspect, the invention relates to methods for increasing efficacy of CRISPR-Cas systems, such as CRISPR-Cas system based therapy or therapeutics. In a further aspect, the invention relates to methods for increasing safety of CRISPR-Cas systems, such as CRISPR-Cas system based therapy or therapeutics. In a further aspect, the present invention relates to methods for increasing specificity, efficacy, and/or safety, preferably all, of CRISPR-Cas systems, such as CRISPR-Cas system based therapy or therapeutics.

In certain embodiments, the CRISPR-Cas system comprises a CRISPR effector as defined herein elsewhere.

The methods of the present invention in particular involve optimization of selected parameters or variables associated with the CRISPR-Cas system and/or its functionality, as described herein further elsewhere. Optimization of the CRISPR-Cas system in the methods as described herein may depend on the target(s), such as the therapeutic target or therapeutic targets, the mode or type of CRISPR-Cas system modulation, such as CRISPR-Cas system based therapeutic target(s) modulation, modification, or manipulation, as well as the delivery of the CRISPR-Cas system components. One or more targets may be selected, depending on the genotypic and/or phenotypic outcome. For instance, one or more therapeutic targets may be selected, depending on (genetic) disease etiology or the desired therapeutic outcome. The (therapeutic) target(s) may be a single gene, locus, or other genomic site, or may be multiple genes, loci or other genomic sites. As is known in the art, a single gene, locus, or other genomic site may be targeted more than once, such as by use of multiple gRNAs.

CRISPR-Cas system activity, such as CRISPR-Cas system design may involve target disruption, such as target mutation, such as leading to gene knockout. CRISPR-Cas system activity, such as CRISPR-Cas system design may involve replacement of particular target sites, such as leading to target correction. CRISPR-Cas system design may involve removal of particular target sites, such as leading to target deletion. CRISPR-Cas system activity may involve modulation of target site functionality, such as target site activity or accessibility, leading for instance to (transcriptional and/or epigenetic) gene or genomic region activation or gene or genomic region silencing. The skilled person will understand that modulation of target site functionality may involve CRISPR effector mutation (such as for instance generation of a catalytically inactive CRISPR effector) and/or functionalization (such as for instance fusion of the CRISPR effector with a heterologous functional domain, such as a transcriptional activator or repressor), as described herein elsewhere.

Engineered CRISPR-Cas Systems

In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307:26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to *Aeropyrum, Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

General Features of Cpf1 Effector Protein

The present invention encompasses the use of a Cpf1 effector protein, derived from a Cpf1 locus denoted as subtype V-A. Herein such effector proteins are also referred to as "Cpf1p", e.g., a Cpf1 protein (and such effector protein or Cpf1 protein or protein derived from a Cpf1 locus is also called "CRISPR enzyme"). Presently, the subtype V-A loci encompasses cas1, cas2, a distinct gene denoted Cpf1 and a CRISPR array. Cpf1(CRISPR-associated protein Cpf1, subtype PREFRAN) is a large protein (about 1300 amino acids) that contains a RuvC-like nuclease domain homologous to the corresponding domain of Cas9 along with a counterpart to the characteristic arginine-rich cluster of Cas9. However, Cpf1 lacks the HNH nuclease domain that is present in all Cas9 proteins, and the RuvC-like domain is contiguous in the Cpf1 sequence, in contrast to Cas9 where it contains long inserts including the HNH domain. Accordingly, in particular embodiments, the CRISPR-Cas enzyme comprises only a RuvC-like nuclease domain.

Methods for Identifying New CRISPR-Cas Loci

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this novel CRISPR-Cas system appears to be similar to that of type II-B. Furthermore, similar to Cas9, the Cpf1 protein contains a readily identifiable C-terminal region that is homologous to the transposon ORF-B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF-B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin EV. Methods Mol Biol. 2015; 1311:47-75). However, as described herein, Cpf1 is denoted to be in subtype V-A to distinguish it from C2c1p which does not have an identical domain structure and is hence denoted to be in subtype V-B. The application describes methods for using CRISPR-Cas proteins in therapy. This is exemplified herein with Cpf1, whereby a number of Cpf1 orthologs or homologs have been identified. It will be apparent to the skilled person that further Cpf1 orthologs or homologs can be identified and that any of the functionalities described herein may be engineered into other Cpf1 orthologs, including chimeric enzymes comprising fragments from multiple orthologs.

For instance, computational methods of identifying novel CRISPR-Cas loci are described in EP3009511 or US2016208243 and may comprise the following steps: detecting all contigs encoding the Cas1 protein; identifying all predicted protein coding genes within 20 kB of the cas1 gene; comparing the identified genes with Cas protein-specific profiles and predicting CRISPR arrays; selecting unclassified candidate CRISPR-Cas loci containing proteins larger than 500 amino acids (>500 aa); analyzing selected candidates using methods such as PSI-BLAST and HHPred to screen for known protein domains, thereby identifying novel Class 2 CRISPR-Cas loci (see also Schmakov et al. 2015, Mol Cell. 60(3):385-97). In addition to the above mentioned steps, additional analysis of the candidates may be conducted by searching metagenomics databases for additional homologs. Additionally or alternatively, to expand the search to non-autonomous CRISPR-Cas systems, the same procedure can be performed with the CRISPR array used as the seed.

In one aspect the detecting all contigs encoding the Cas1 protein is performed by GenemarkS which a gene prediction program as further described in "GeneMarkS: a self-training method for prediction of gene starts in microbial genomes. Implications for finding sequence motifs in regulatory regions." John Besemer, Alexandre Lomsadze and Mark Borodovsky, Nucleic Acids Research (2001) 29, pp 2607-2618, herein incorporated by reference.

In one aspect the identifying all predicted protein coding genes is carried out by comparing the identified genes with Cas protein-specific profiles and annotating them according to NCBI Conserved Domain Database (CDD) which is a protein annotation resource that consists of a collection of well-annotated multiple sequence alignment models for ancient domains and full-length proteins. These are available as position-specific score matrices (PSSMs) for fast identification of conserved domains in protein sequences via RPS-BLAST. CDD content includes NCBI-curated domains, which use 3D-structure information to explicitly define domain boundaries and provide insights into sequence/structure/function relationships, as well as domain models imported from a number of external source databases (Pfam, SMART, COG, PRK, TIGRFAM). In a further aspect, CRISPR arrays were predicted using a PILER-CR program which is a public domain software for finding CRISPR repeats as described in "PILER-CR: fast and accurate identification of CRISPR repeats", Edgar, R. C., BMC Bioinformatics, January 20; 8:18(2007), herein incorporated by reference.

In a further aspect, the case by case analysis is performed using PSI-BLAST (Position-Specific Iterative Basic Local Alignment Search Tool). PSI-BLAST derives a position-specific scoring matrix (PSSM) or profile from the multiple sequence alignment of sequences detected above a given score threshold using protein-protein BLAST. This PSSM is used to further search the database for new matches, and is updated for subsequent iterations with these newly detected sequences. Thus, PSI-BLAST provides a means of detecting distant relationships between proteins.

In another aspect, the case by case analysis is performed using HHpred, a method for sequence database searching and structure prediction that is as easy to use as BLAST or PSI-BLAST and that is at the same time much more sensitive in finding remote homologs. In fact, HHpred's sensitivity is competitive with the most powerful servers for structure prediction currently available. HHpred is the first server that is based on the pairwise comparison of profile hidden Markov models (HMMs). Whereas most conventional sequence search methods search sequence databases such as UniProt or the NR, HHpred searches alignment databases, like Pfam or SMART. This greatly simplifies the list of hits to a number of sequence families instead of a clutter of single sequences. All major publicly available profile and alignment databases are available through HHpred. HHpred accepts a single query sequence or a multiple alignment as input. Within only a few minutes it returns the search results in an easy-to-read format similar to that of PSI-BLAST. Search options include local or global alignment and scoring secondary structure similarity. HHpred can produce pairwise query-template sequence alignments, merged query-template multiple alignments (e.g. for transitive searches), as well as 3D structural models calculated by the MODELLER software from HHpred alignments.

In certain example embodiments, methods for identifying novel CRISPR loci may include comparison to properties and elements of known CRISPR loci. Example methods are disclosed in U.S. Provisional Application No. 62/376,387 filed Aug. 17, 2016 and entitled "Methods for identifying Class 2 CRISPR-Cas systems," U.S. Provisional Application No. 62/376,383 filed Aug. 17, 2016 and entitled "Methods for Identifying Novel Gene Editing Elements," and Shmakov et al. "Diversity and evolution of class 2 CRISPR-Cas systems," Nat Rev Microbiol. 2017 15(3):169-182. Finally, methods such as those disclosed above may also be adaptive to identify genomic structures comprising repeating motifs in general as opposed to specific known CRISPR objects such as Cas9 or Cpf1.

It should be further recognized that putative novel CRISPR-Cas loci may be further discovered and/or integrated, in particular for relevant nuclease activity, using the methods disclosed in the section below under the header "Methods for determining on/off target activity and selecting suitable sequences/guides."

Orthologs of Cpf1

The terms "orthologue" (also referred to as "ortholog" herein) and "homologue" (also referred to as "homolog" herein) are well known in the art. By means of further guidance, a "homologue" of a protein as used herein is a protein of the same species which performs the same or a similar function as the protein it is a homologue of. Homologous proteins may but need not be structurally related, or are only partially structurally related. An "orthologue" of a protein as used herein is a protein of a different species which performs the same or a similar function as the protein it is an orthologue of Orthologous proteins may but need not be structurally related, or are only partially structurally related. Homologs and orthologs may be identified by homology modelling (see, e.g., Greer, Science vol. 228 (1985) 1055, and Blundell et al. Eur J Biochem vol 172 (1988), 513) or "structural BLAST" (Dey F, Cliff Zhang Q, Petrey D, Honig B. Toward a "structural BLAST": using structural relationships to infer function. Protein Sci. 2013 April; 22(4):359-66. doi: 10.1002/pro.2225.). See also Shmakov et al. (2015) for application in the field of CRISPR-Cas loci. Homologous proteins may but need not be structurally related, or are only partially structurally related.

The Cpf1 gene is found in several diverse bacterial genomes, typically in the same locus with cas1, cas2, and cas4 genes and a CRISPR cassette (for example, FNFX1_1431-FNFX1_1428 of *Francisella* cf. *novicida* Fx1). Thus, the layout of this putative novel CRISPR-Cas system appears to be similar to that of type II-B. Furthermore, similar to Cas9, the Cpf1 protein contains a readily identifiable C-terminal region that is homologous to the transposon ORF-B and includes an active RuvC-like nuclease, an arginine-rich region, and a Zn finger (absent in Cas9). However, unlike Cas9, Cpf1 is also present in several genomes without a CRISPR-Cas context and its relatively high similarity with ORF-B suggests that it might be a transposon component. It was suggested that if this was a genuine CRISPR-Cas system and Cpf1 is a functional analog of Cas9 it would be a novel CRISPR-Cas type, namely type V (See Annotation and Classification of CRISPR-Cas Systems. Makarova K S, Koonin EV. Methods Mol Biol. 2015; 1311:47-75). However, as described herein, Cpf1 is denoted to be in subtype V-A to distinguish it from C2c1p which does not have an identical domain structure and is hence denoted to be in subtype V-B.

In particular embodiments, the effector protein is a Cpf1 effector protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Leptotrichia, Francisella, Legionella, Alicyclobacillus, Methanomethyophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*.

In further particular embodiments, the Cpf1 effector protein is from an organism selected from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii.*

The effector protein may comprise a chimeric effector protein comprising a first fragment from a first effector protein (e.g., a Cpf1) ortholog and a second fragment from a second effector (e.g., a Cpf1) protein ortholog, and wherein the first and second effector protein orthologs are different. At least one of the first and second effector protein (e.g., a Cpf1) orthologs may comprise an effector protein (e.g., a Cpf1) from an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Leptotrichia, Francisella, Legionella, Alicyclobacillus, Methanomethyophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*; e.g., a chimeric effector protein comprising a first fragment and a second fragment wherein each of the first and second fragments is selected from a Cpf1 of an organism comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Leptotrichia, Francisella, Legionella, Alicyclobacillus, Methanomethyophilus, Porphyromonas, Prevotella, Bacteroidetes, Helcococcus, Leptospira, Desulfovibrio, Desulfonatronum, Opitutaceae, Tuberibacillus, Bacillus, Brevivacillus, Methylobacterium* or *Acidaminococcus* wherein the first and second fragments are not from the same bacteria; for instance a chimeric effector protein comprising a first fragment and a second fragment wherein each of the first and second fragments is selected from a Cpf1 of *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44 _17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas creviorica-nis* 3, *Prevotella disiens* and *Porphyromonas macacae*, wherein the first and second fragments are not from the same bacteria.

In a more preferred embodiment, the Cpf1p is derived from a bacterial species selected from *Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011 GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas creviorica-nis* 3, *Prevotella disiens* and *Porphyromonas macacae*. In certain embodiments, the Cpf1p is derived from a bacterial species selected from *Acidaminococcus* sp. BV3L6, *Lachnospiraceae bacterium* MA2020. In certain embodiments, the effector protein is derived from a subspecies of *Francisella tularensis* 1, including but not limited to *Francisella tularensis* subsp. *Novicida*.

In particular embodiments, the homologue or orthologue of Cpf1 as referred to herein has a sequence homology or identity of at least 80%, more preferably at least 85%, even more preferably at least 90%, such as for instance at least 95% with Cpf1. In further embodiments, the homologue or orthologue of Cpf1 as referred to herein has a sequence identity of at least 80%, more preferably at least 85%, even more preferably at least 90%, such as for instance at least 95% with the wild type Cpf1. Where the Cpf1 has one or more mutations (mutated), the homologue or orthologue of said Cpf1 as referred to herein has a sequence identity of at least 80%, more preferably at least 85%, even more preferably at least 90%, such as for instance at least 95% with the mutated Cpf1.

In an embodiment, the Cpf1 protein may be an ortholog of an organism of a genus which includes, but is not limited to *Acidaminococcus* sp, *Lachnospiraceae bacterium* or *Moraxella bovoculi*; in particular embodiments, the type V Cas protein may be an ortholog of an organism of a species which includes, but is not limited to *Acidaminococcus* sp. BV3L6; *Lachnospiraceae bacterium* ND2006 (LbCpf1) or *Moraxella bovoculi* 237.In particular embodiments, the homologue or orthologue of Cpf1 as referred to herein has a sequence homology or identity of at least 80%, more preferably at least 85%, even more preferably at least 90%, such as for instance at least 95% with one or more of the Cpf1 sequences disclosed herein. In further embodiments, the homologue or orthologue of Cpf as referred to herein has a sequence identity of at least 80%, more preferably at least 85%, even more preferably at least 90%, such as for instance at least 95% with the wild type FnCpf1, AsCpf1 or LbCpf1.

In particular embodiments, the Cpf1 protein of the invention has a sequence homology or identity of at least 60%, more particularly at least 70, such as at least 80%, more preferably at least 85%, even more preferably at least 90%, such as for instance at least 95% with FnCpf1, AsCpf1 or LbCpf1. In further embodiments, the Cpf1 protein as referred to herein has a sequence identity of at least 60%, such as at least 70%, more particularly at least 80%, more preferably at least 85%, even more preferably at least 90%, such as for instance at least 95% with the wild type AsCpf1 or LbCpf1. In particular embodiments, the Cpf1 protein of the present invention has less than 60% sequence identity with FnCpf1. The skilled person will understand that this includes truncated forms of the Cpf1 protein whereby the sequence identity is determined over the length of the truncated form.

In an embodiment of the invention, the effector protein comprises at least one HEPN domain, including but not limited to HEPN domains described herein, HEPN domains known in the art, and domains recognized to be HEPN domains by comparison to consensus sequences and motifs.

Determination of PAM

Determination of PAM can be ensured as follows This experiment closely parallels similar work in *E. coli* for the heterologous expression of StCas9 (Sapranauskas, R. et al. Nucleic Acids Res 39, 9275-9282 (2011)). Applicants introduce a plasmid containing both a PAM and a resistance gene into the heterologous *E. coli*, and then plate on the corresponding antibiotic. If there is DNA cleavage of the plasmid, Applicants observe no viable colonies.

In further detail, the assay is as follows for a DNA target. Two *E. coli* strains are used in this assay. One carries a plasmid that encodes the endogenous effector protein locus from the bacterial strain. The other strain carries an empty plasmid (e.g. pACYC184, control strain). All possible 7 or 8 bp PAM sequences are presented on an antibiotic resistance plasmid (pUC19 with ampicillin resistance gene). The PAM is located next to the sequence of proto-spacer 1 (the DNA target to the first spacer in the endogenous effector protein locus). Two PAM libraries were cloned. One has a 8 random bp 5' of the proto-spacer (e.g. total of 65536 different PAM sequences=complexity). The other library has 7 random bp 3' of the proto-spacer (e.g. total complexity is 16384 different PAMs). Both libraries were cloned to have in average 500 plasmids per possible PAM. Test strain and control strain were transformed with 5'PAM and 3'PAM library in separate transformations and transformed cells were plated separately on ampicillin plates. Recognition and subsequent cutting/interference with the plasmid renders a cell vulnerable to ampicillin and prevents growth. Approximately 12h after transformation, all colonies formed by the test and control strains where harvested and plasmid DNA was isolated. Plasmid DNA was used as template for PCR amplification and subsequent deep sequencing. Representation of all PAMs in the untransfomed libraries showed the expected representation of PAMs in transformed cells. Representation of all PAMs found in control strains showed the actual representation. Representation of all PAMs in test strain showed which PAMs are not recognized by the enzyme and comparison to the control strain allows extracting the sequence of the depleted PAM.

For the Cpf1 orthologues identified to date, the following PAMs have been identified: the *Acidaminococcus* sp. BV3L6 Cpf1 (AsCpf1) and *Lachnospiraceae bacterium* ND2006 Cpf1 (LbCpf1) can cleave target sites preceded by a TTTV PAM, FnCpf1p, can cleave sites preceded by TTN, where N is A/C/G or T.

Codon Optimized Nucleic Acid Sequences

Where the effector protein is to be administered as a nucleic acid, the application envisages the use of codon-optimized Cpf1 sequences. An example of a codon optimized sequence, is in this instance a sequence optimized for expression in a eukaryote, e.g., humans (i.e. being optimized for expression in humans), or for another eukaryote, animal or mammal as herein discussed; see, e.g., SaCas9 human codon optimized sequence in WO 2014/093622 (PCT/US2013/074667) as an example of a codon optimized sequence (from knowledge in the art and this disclosure, codon optimizing coding nucleic acid molecule(s), especially as to effector protein (e.g., Cpf1) is within the ambit of the skilled artisan). Whilst this is preferred, it will be appreciated that other examples are possible and codon optimization for a host species other than human, or for codon optimization for specific organs is known. In some embodiments, an enzyme coding sequence encoding a DNA/RNA-targeting Cas protein is codon optimized for expression in particular cells, such as eukaryotic cells. The eukaryotic cells may be those of or derived from a particular organism, such as a plant or a mammal, including but not limited to human, or non-human eukaryote or animal or mammal as herein discussed, e.g., mouse, rat, rabbit, dog, livestock, or non-human mammal or primate. In some embodiments, processes for modifying the germ line genetic identity of human beings and/or processes for modifying the genetic identity of animals which are likely to cause them suffering without any substantial medical benefit to man or animal, and also animals resulting from such processes, may be excluded. In general, codon optimization refers to a process of modifying a nucleic acid sequence for enhanced expression in the host cells of interest by replacing at least one codon (e.g., about or more than about 1, 2, 3, 4, 5, 10, 15, 20, 25, 50, or more codons) of the native sequence with codons that are more frequently or most frequently used in the genes of that host cell while maintaining the native amino acid sequence. Various species exhibit particular bias for certain codons of a particular amino acid. Codon bias (differences in codon usage between organisms) often correlates with the efficiency of translation of messenger RNA (mRNA), which is in turn believed to be dependent on, among other things, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization. Codon usage tables are readily available, for example, at the "Codon Usage Database" available at www.kazuka.or.jp/codon and these tables can be adapted in a number of ways. See Nakamura, Y., et al. "Codon usage tabulated from the international DNA sequence databases: status for the year 2000" Nucl. Acids Res. 28:292 (2000). Computer algorithms for codon optimizing a particular sequence for expression in a particular host cell are also available, such as Gene Forge (Aptagen; Jacobus, Pa.), are also available. In some embodiments, one or more codons (e.g., 1, 2, 3, 4, 5, 10, 15, 20, 25, 50, or more, or all codons) in a sequence encoding a DNA/RNA-targeting Cas protein corresponds to the most frequently used codon for a particular amino acid. As to codon usage in yeast, reference is made to the online Yeast Genome database available at www.yeastgenome.org/community/codon_usage.shtml, or Codon selection in yeast, Bennetzen and Hall, J Biol Chem. 1982 Mar. 25; 257(6):3026-31. As to codon usage in plants including algae, reference is made to Codon usage in higher plants, green algae, and cyanobacteria, Campbell and Gown, Plant Physiol. 1990 January; 92(1): 1-11.; as well as Codon usage in plant genes, Murray et al, Nucleic Acids Res. 1989 Jan. 25; 17(2):477-98; or Selection on the codon bias of chloroplast and cyanelle genes in different plant and algal lineages, Morton B R, J Mol Evol. 1998 April; 46(4):449-59.

Modified Cpf1 Enzymes

In particular embodiments, it is of interest to make us of an engineered Cpf1 protein as defined herein, such as Cpf1, wherein the protein complexes with a nucleic acid molecule comprising RNA to form a CRISPR complex, wherein when in the CRISPR complex, the nucleic acid molecule targets one or more target polynucleotide loci, the protein comprises at least one modification compared to unmodified Cpf1 protein, and wherein the CRISPR complex comprising the modified protein has altered activity as compared to the complex comprising the unmodified Cpf1 protein. It is to be understood that when referring herein to CRISPR "protein", the Cpf1 protein preferably is a modified CRISPR enzyme (e.g. having increased or decreased (or no) enzymatic activity, such as without limitation including Cpf1. The term "CRISPR protein" may be used interchangeably with "CRISPR enzyme", irrespective of whether the CRISPR protein has altered, such as increased or decreased (or no) enzymatic activity, compared to the wild type CRISPR protein.

Computational analysis of the primary structure of Cpf1 nucleases reveals three distinct regions. First a C-terminal RuvC like domain, which is the only functional characterized domain. Second a N-terminal alpha-helical region and third a mixed alpha and beta region, located between the RuvC like domain and the alpha-helical region.

Figure 10:
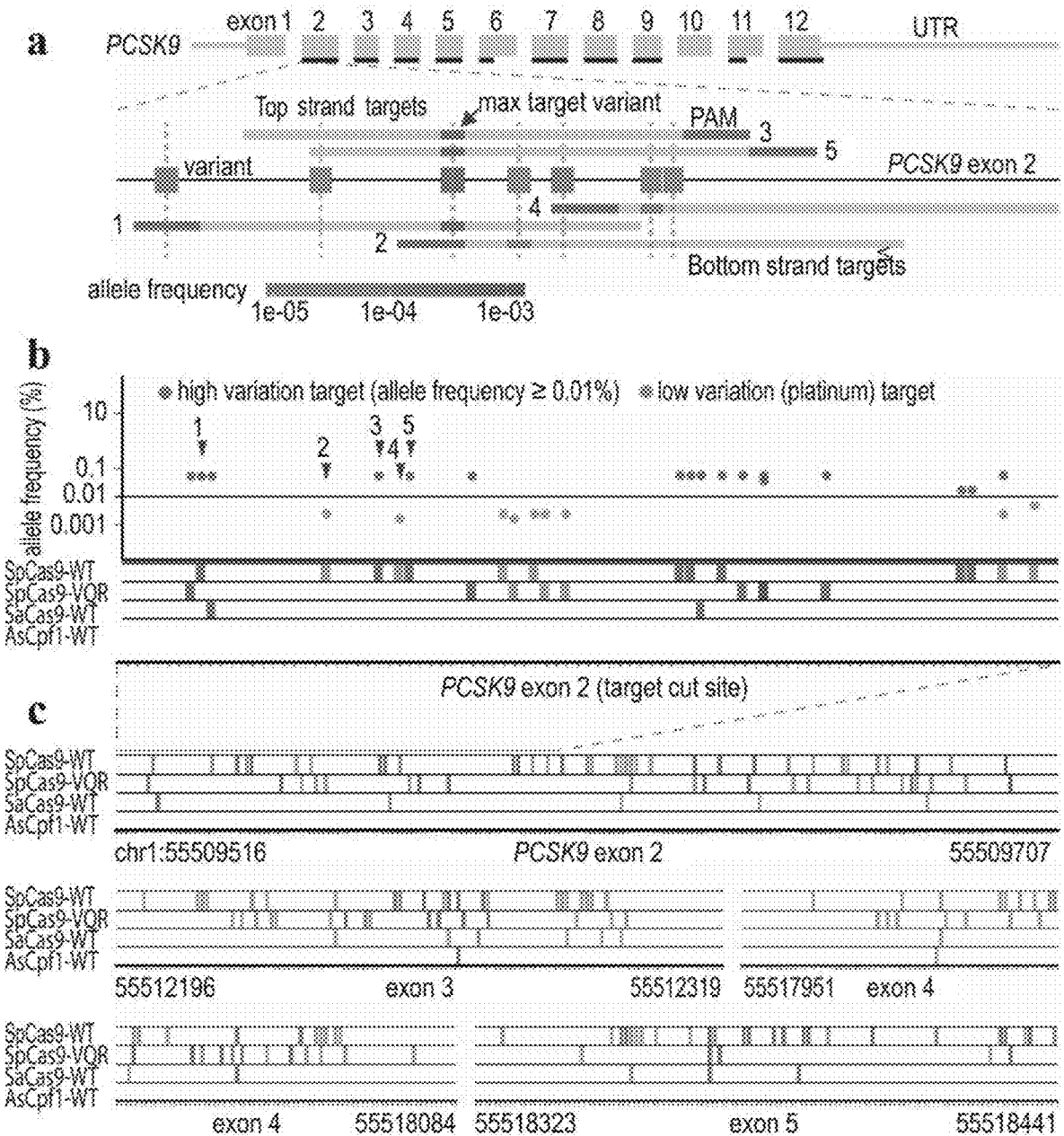
FIG. 10A-C depicts how a selection of platinum targets maximizes population efficacy. a) Schematic showing target variation within exon 2 of PCSK9-001, with regions containing high coverage in the ExAC dataset indicated (black lines below exons). b) Frequency of target variation plotted by cut site position for targets spanning the start of PCSK9-001 exon 2, with targets shown in (a) indicated by arrows. The horizontal line at 0.01% separates platinum targets (grey) from targets with high variation (red). The classification for each target is depicted below for each enzyme (grey or red boxes). c) Classification of targets for each enzyme spanning exons 2-5 of PCSK9-001.
Figure 11:
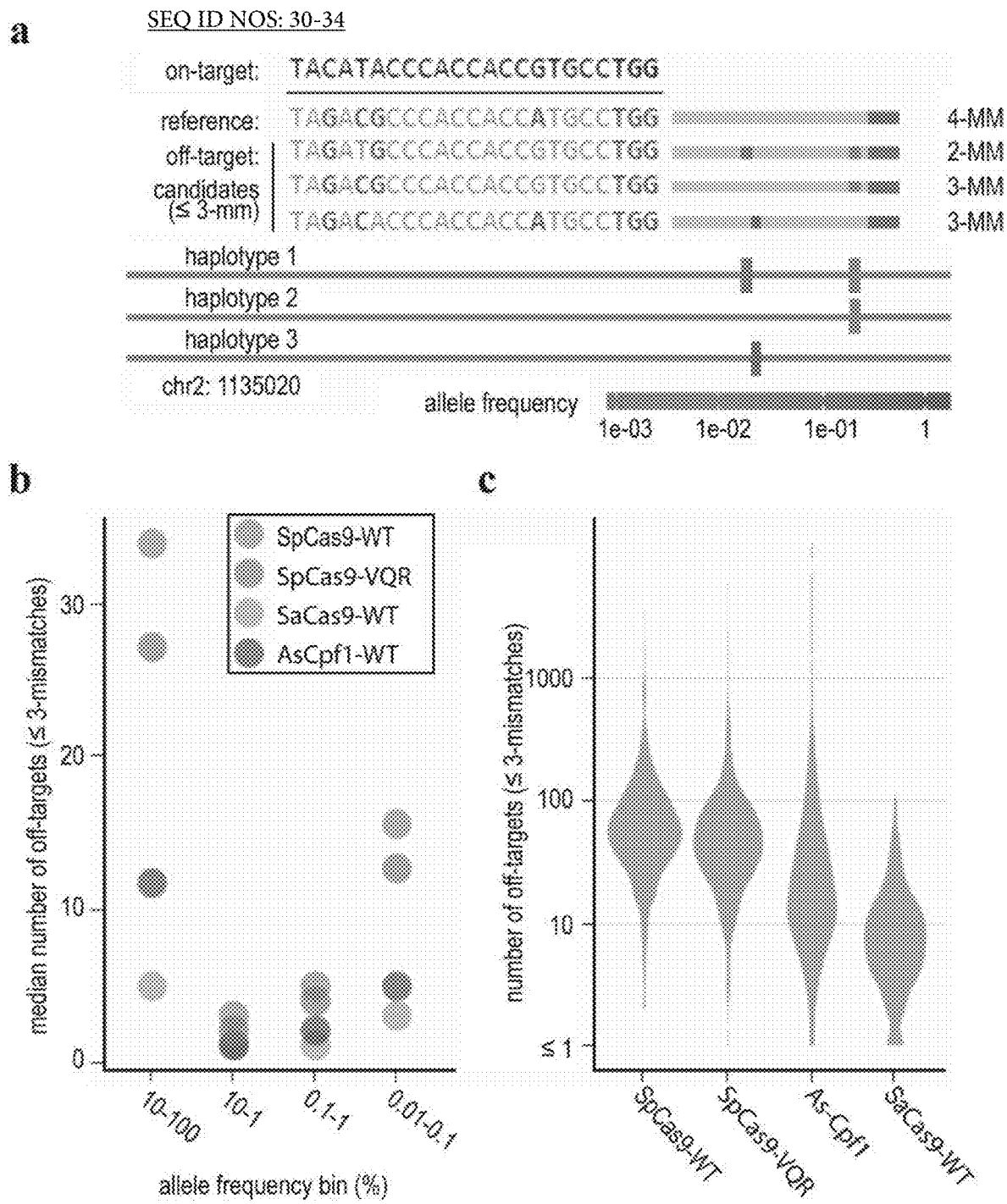
FIG. 11A-C depicts how human genetic variation significantly impacts CRISPR endonuclease therapeutic safety. a) Schematic illustrating off-target candidates arising due to multiple different haplotypes. b) Number of off-target candidates for each CRISPR endonuclease at different allele frequencies. c) Distribution of the number of off-target candidates per platinum target for each CRISPR endonuclease.

Several small stretches of unstructured regions are predicted within the Cpf1 primary structure. Unstructured regions, which are exposed to the solvent and not conserved within different Cpf1 orthologs, are preferred sides for splits and insertions of small protein sequences (FIGS. 10 and 11). In addition, these sides can be used to generate chimeric proteins between Cpf1 orthologs.

In certain example embodiments, a modified Cpf1 protein comprises at least one modification that alters editing preference as compared to wild type. In certain example embodiments, the editing preference is for a specific insert or deletion within the target region. In certain example embodiments, the at least one modification increases formation of one or more specific indels. In certain example embodiments, the at least one modification is in a C-terminal RuvC like domain, the N-terminal alpha-helical region, the mixed alpha and beta region, or a combination thereof. In certain example embodiments the altered editing preference is indel formation. In certain example embodiments, the at least one modification increases formation of one or more specific insertions.

In certain example embodiments, the at least one modification increases formation of one or more specific insertions. In certain example embodiments, the at least one modification results in an insertion of an A adjacent to an A, T, G, or C in the target region. In another example embodiment, the at least one modification results in insertion of a T adjacent to an A, T, G, or C in the target region. In another example embodiment, the at least one modification results in insertion of a G adjacent to an A, T, G, or C in the target region. In another example embodiment, the at least one modification results in insertion of a C adjacent to an A, T, C, or G in the target region. The insertion may be 5' or 3' to the adjacent nucleotide. In one example embodiment, the one or more modification direct insertion of a T adjacent to an existing T. In certain example embodiments, the existing T corresponds to the 4th position in the binding region of a guide sequence. In certain example embodiments, the one or more modifications result in an enzyme which ensures more precise one-base insertions or deletions, such as those described above. More particularly, the one or more modifications may reduce the formations of other types of indels by the enzyme. The ability to generate one-base insertions or deletions can be of interest in a number of applications, such as correction of genetic mutants in diseases caused by small deletions, more particularly where HDR is not possible. For example correction of the F508del mutation in CFTR via delivery of three sRNA directing insertion of three T's, which is the most common genotype of cystic fibrosis, or correction of Alia Jafar's single nucleotide deletion in CDKL5 in the brain. As the editing method only requires NHEJ, the editing would be possible in post-mitotic cells such as the brain. The ability to generate one base pair insertions/deletions may also be useful in genome-wide CRISPR-Cas negative selection screens. In certain example embodiments, the at least one modification, is a mutation. In certain other example embodiment, the one or more modification may be combined with one or more additional modifications or mutations described below including modifications to increase binding specificity and/or decrease off-target effects.

In certain example embodiments, the engineered CRISPR-Cas effector comprising at least one modification that alters editing preference as compared to wild type may further comprise one or more additional modifications that alters the binding property as to the nucleic acid molecule comprising RNA or the target polypeptide loci, altering binding kinetics as to the nucleic acid molecule or target molecule or target polynucleotide or alters binding specificity as to the nucleic acid molecule. Example of such modifications are summarized in the following paragraph. Based on the above information, mutants can be generated which lead to inactivation of the enzyme or which modify the double strand nuclease to nickase activity. In alternative embodiments, this information is used to develop enzymes with reduced off-target effects (described elsewhere herein).

In certain of the above-described Cpf1 enzymes, the enzyme is modified by mutation of one or more residues including but not limited to positions D917, E1006, E1028, D1227, D1255A, N1257, according to FnCpf1 protein or any corresponding ortholog. In an aspect the invention provides a herein-discussed composition wherein the Cpf1 enzyme is an inactivated enzyme which comprises one or more mutations selected from the group consisting of D917A, E1006A, E1028A, D1227A, D1255A, N1257A, D917A, E1006A, E1028A, D1227A, D1255A and N1257A according to FnCpf1 protein or corresponding positions in a Cpf1 ortholog. In an aspect the invention provides a herein-discussed composition, wherein the CRISPR enzyme comprises D917, or E1006 and D917, or D917 and D1255, according to FnCpf1 protein or a corresponding position in a Cpf1 ortholog.

In certain of the above-described Cpf1 enzymes, the enzyme is modified by mutation of one or more residues (in the RuvC domain) including but not limited to positions R909, R912, R930, R947, K949, R951, R955, K965, K968, K1000, K1002, R1003, K1009, K1017, K1022, K1029, K1035, K1054, K1072, K1086, R1094, K1095, K1109, K1118, K1142, K1150, K1158, K1159, R1220, R1226, R1242, and/or R1252 with reference to amino acid position numbering of AsCpf1 (*Acidaminococcus* sp. BV3L6).

In certain of the above-described non-naturally-occurring CRISPR enzymes, the enzyme is modified by mutation of one or more residues (in the RAD50) domain including but not limited positions K324, K335, K337, R331, K369, K370, R386, R392, R393, K400, K404, K406, K408, K414, K429, K436, K438, K459, K460, K464, R670, K675, R681, K686, K689, R699, K705, R725, K729, K739, K748, and/or K752 with reference to amino acid position numbering of AsCpf1 (*Acidaminococcus* sp. BV3L6).

In certain of the Cpf1 enzymes, the enzyme is modified by mutation of one or more residues including but not limited positions R912, T923, R947, K949, R951, R955, K965, K968, K1000, R1003, K1009, K1017, K1022, K1029, K1072, K1086, F1103, R1226, and/or R1252 with reference to amino acid position numbering of AsCpf1 (*Acidaminococcus* sp. BV3L6).

In certain embodiments, the Cpf1 enzyme is modified by mutation of one or more residues including but not limited positions R833, R836, K847, K879, K881, R883, R887, K897, K900, K932, R935, K940, K948, K953, K960, K984, K1003, K1017, R1033, R1138, R1165, and/or R1252 with reference to amino acid position numbering of LbCpf1 (*Lachnospiraceae bacterium* ND2006).

In certain embodiments, the Cpf1 enzyme is modified by mutation of one or more residues including but not limited positions K15, R18, K26, Q34, R43, K48, K51, R56, R84, K85, K87, N93, R103, N104, T118, K123, K134, R176, K177, R192, K200, K226, K273, K275, T291, R301, K307, K369, S404, V409, K414, K436, K438, K468, D482, K516, R518, K524, K530, K532, K548, K559, K570, R574, K592, D596, K603, K607, K613, C647, R681, K686, H720, K739, K748, K757, T766, K780, R790, P791, K796, K809, K815, T816, K860, R862, R863, K868, K897, R909, K912, T923, R947, K949, R951, R955, K965, K968, K1000, R1003, K1009, K1017, K1022, K1029, A1053, K1072, K1086, F1103, S1209, R1226, R1252, K1273, K1282, and/or K1288 with reference to amino acid position numbering of AsCpf1 (*Acidaminococcus* sp. BV3L6).

In certain embodiments, the enzyme is modified by mutation of one or more residues including but not limited positions K15, R18, K26, R34, R43, K48, K51, K56, K87, K88, D90, K96, K106, K107, K120, Q125, K143, R186, K187, R202, K210, K235, K296, K298, K314, K320, K326, K397, K444, K449, E454, A483, E491, K527, K541, K581, R583, K589, K595, K597, K613, K624, K635, K639, K656, K660, K667, K671, K677, K719, K725, K730, K763, K782, K791, R800, K809, K823, R833, K834, K839, K852, K858, K859, K869, K871, R872, K877, K905, R918, R921, K932, I960, K962, R964, R968, K978, K981, K1013, R1016, K1021, K1029, K1034, K1041, K1065, K1084, and/or K1098 with reference to amino acid position numbering of FnCpf1 (*Francisella novicida* U112).

In certain embodiments, the enzyme is modified by mutation of one or more residues including but not limited positions K15, R18, K26, K34, R43, K48, K51, R56, K83, K84, R86, K92, R102, K103, K116, K121, R158, E159, R174, R182, K206, K251, K253, K269, K271, K278, P342, K380, R385, K390, K415, K421, K457, K471, A506, R508, K514, K520, K522, K538, Y548, K560, K564, K580, K584, K591, K595, K601, K634, K640, R645, K679, K689, K707, T716, K725, R737, R747, R748, K753, K768, K774, K775, K785, K787, R788, Q793, K821, R833, R836, K847, K879, K881, K883, K887, K897, K900, K932, R935, K940, K948, K953, K960, K984, K1003, K1017, R1033, K1121, R1138, R1165, K1190, K1199, and/or K1208 with reference to amino acid position numbering of LbCpf1 (*Lachnospiraceae bacterium* ND2006).

In certain embodiments, the enzyme is modified by mutation of one or more residues including but not limited positions K14, R17, R25, K33, M42, Q47, K50, D55, K85, N86, K88, K94, R104, K105, K118, K123, K131, R174, K175, R190, R198, I221, K267, Q269, K285, K291, K297, K357, K403, K409, K414, K448, K460, K501, K515, K550, R552, K558, K564, K566, K582, K593, K604, K608, K623, K627, K633, K637, E643, K780, Y787, K792, K830, Q846, K858, K867, K876, K890, R900, K901, M906, K921, K927, K928, K937, K939, R940, K945, Q975, R987, R990, K1001, R1034, I1036, R1038, R1042, K1052, K1055, K1087, R1090, K1095, N1103, K1108, K1115, K1139, K1158, R1172, K1188, K1276, K1293, A1319, K1340, K1349, and/or K1356 with reference to amino acid position numbering of MbCpf1 (*Moraxella bovoculi* 237).

Recently a method was described for the generation of Cas9 orthologs with enhanced specificity (Slaymaker et al. 2015). This strategy can be used to enhance the specificity of Cpf1 orthologs. The following modifications are presently considered to provide enhanced Cpf1 specificity.

TABLE 2

| Conserved Lysine and Arginine residues within RuvC. | |
| --- | --- |
| AsCpf1 | LbCpf1 |
| R912 | R833 |
| T923 | R836 |
| R947 | K847 |
| K949 | K879 |
| R951 | K881 |
| R955 | R883 |
| K965 | K887 |
| K968 | K897 |
| K1000 | K900 |
| R1003 | K932 |
| K1009 | R935 |
| K1017 | K940 |
| K1022 | K948 |
| K1029 | K953 |
| K1072 | K960 |
| K1086 | K984 |
| F1103 | K1003 |
| R1226 | K1017 |
| R1252 | R1033 |
| | R1138 |
| | R1165 |

Additional candidates are positive charged residues that are conserved between different orthologs.

TABLE 3

| Conserved Lysine and Arginine residues | | | | |
| --- | --- | --- | --- | --- |
| Residue | AsCpf1 | FnCpf1 | LbCpf1 | MbCpf1 |
| Lys | K15 | K15 | K15 | K14 |
| Arg | R18 | R18 | R18 | R17 |
| Lys/Arg | K26 | K26 | K26 | R25 |
| Lys/Arg | Q34 | R34 | K34 | K33 |
| Arg | R43 | R43 | R43 | M42 |
| Lys | K48 | K48 | K48 | Q47 |
| Lys | K51 | K51 | K51 | K50 |
| Lys/Arg | R56 | K56 | R56 | D55 |
| Lys/Arg | R84 | K87 | K83 | K85 |
| Lys/Arg | K85 | K88 | K84 | N86 |
| Lys/Arg | K87 | D90 | R86 | K88 |
| Arg | N93 | K96 | K92 | K94 |
| Lys/Arg | R103 | K106 | R102 | R104 |
| Lys | N104 | K107 | K103 | K105 |
| Lys | T118 | K120 | K116 | K118 |
| Lys/Arg | K123 | Q125 | K121 | K123 |
| Lys | K134 | K143 | — | K131 |
| Arg | R176 | R186 | R158 | R174 |
| Lys | K177 | K187 | E159 | K175 |
| Arg | R192 | R202 | R174 | R190 |
| Lys/Arg | K200 | K210 | R182 | R198 |
| Lys | K226 | K235 | K206 | I221 |
| Lys | K273 | K296 | K251 | K267 |
| Lys | K275 | K298 | K253 | Q269 |
| Lys | T291 | K314 | K269 | K285 |
| Lys/Arg | R301 | K320 | K271 | K291 |
| Lys | K307 | K326 | K278 | K297 |
| Lys | K369 | K397 | P342 | K357 |
| Lys | S404 | K444 | K380 | K403 |
| Lys/Arg | V409 | K449 | R385 | K409 |
| Lys | K414 | E454 | K390 | K414 |
| Lys | K436 | A483 | K415 | K448 |
| Lys | K438 | E491 | K421 | K460 |
| Lys | K468 | K527 | K457 | K501 |
| Lys | D482 | K541 | K471 | K515 |
| Lys | K516 | K581 | A506 | K550 |
| Arg | R518 | R583 | R508 | R552 |
| Lys | K524 | K589 | K514 | K558 |
| Lys | K530 | K595 | K520 | K564 |
| Lys | K532 | K597 | K522 | K566 |
| Lys | K548 | K613 | K538 | K582 |

TABLE 3-continued

Conserved Lysine and Arginine residues

| Residue | AsCpf1 | FnCpf1 | LbCpf1 | MbCpf1 |
|---|---|---|---|---|
| Lys | K559 | K624 | Y548 | K593 |
| Lys | K570 | K635 | K560 | K604 |
| Lys/Arg | R574 | K639 | K564 | K608 |
| Lys | K592 | K656 | K580 | K623 |
| Lys | D596 | K660 | K584 | K627 |
| Lys | K603 | K667 | K591 | K633 |
| Lys | K607 | K671 | K595 | K637 |
| Lys | K613 | K677 | K601 | E643 |
| Lys | C647 | K719 | K634 | K780 |
| Lys/Arg | R681 | K725 | K640 | Y787 |
| Lys/Arg | K686 | K730 | K645 | K792 |
| Lys | H720 | K763 | K679 | K830 |
| Lys | K739 | K782 | K689 | Q846 |
| Lys | K748 | K791 | K707 | K858 |
| Lys/Arg | K757 | R800 | T716 | K867 |
| Lys/Arg | T766 | K809 | K725 | K876 |
| Lys/Arg | K780 | K823 | K737 | K890 |
| Arg | R790 | R833 | R747 | R900 |
| Lys/Arg | P791 | K834 | K748 | K901 |
| Lys | K796 | K839 | K753 | M906 |
| Lys | K809 | K852 | K768 | K921 |
| Lys | K815 | K858 | K774 | K927 |
| Lys | T816 | K859 | K775 | K928 |
| Lys | K860 | K869 | K785 | K937 |
| Lys/Arg | R862 | K871 | K787 | K939 |
| Arg | R863 | R872 | R788 | R940 |
| Lys | K868 | K877 | Q793 | K945 |
| Lys | K897 | K905 | K821 | Q975 |
| Arg | R909 | R918 | R833 | R987 |
| Arg | R912 | R921 | R836 | R990 |
| Lys | T923 | K932 | K847 | K1001 |
| Lys/Arg | R947 | I960 | K879 | R1034 |
| Lys | K949 | K962 | K881 | I1036 |
| Arg | R951 | R964 | R883 | R1038 |
| Arg | R955 | R968 | R887 | R1042 |
| Lys | K965 | K978 | K897 | K1052 |
| Lys | K968 | K981 | K900 | K1055 |
| Lys | K1000 | K1013 | K932 | K1087 |
| Arg | R1003 | R1016 | R935 | R1090 |
| Lys | K1009 | K1021 | K940 | K1095 |
| Lys | K1017 | K1029 | K948 | N1103 |
| Lys | K1022 | K1034 | K953 | K1108 |
| Lys | K1029 | K1041 | K960 | K1115 |
| Lys | A1053 | K1065 | K984 | K1139 |
| Lys | K1072 | K1084 | K1003 | K1158 |
| Lys/Arg | K1086 | K1098 | K1017 | R1172 |
| Lys/Arg | F1103 | K1114 | R1033 | K1188 |
| Lys | S1209 | K1201 | K1121 | K1276 |
| Arg | R1226 | R1218 | R1138 | R1293 |
| Arg | R1252 | R1244 | R1165 | A1319 |
| Lys | K1273 | K1265 | K1190 | K1340 |
| Lys | K1282 | K1274 | K1199 | K1349 |
| Lys | K1288 | K1281 | K1208 | K1356 |

Table 3 provides the positions of conserved Lysine and Arginine residues in an alignment of Cpf1 nuclease from *Francisella novicida* U112 (FnCpf1), *Acidaminococcus* sp. BV3L6 (AsCpf1), *Lachnospiraceae bacterium* ND2006 (LbCpf1) and *Moraxella bovoculi* 237 (MbCpf1). These can be used to generate Cpf1 mutants with enhanced specificity.

With a similar strategy used to improve Cas9 specificity, specificity of Cpf1 can be improved by mutating residues that stabilize the non-targeted DNA strand. This may be accomplished without a crystal structure by using linear structure alignments to predict 1) which domain of Cpf1 binds to which strand of DNA and 2) which residues within these domains contact DNA.

However, this approach may be limited due to poor conservation of Cpf1 with known proteins. Thus it may be desirable to probe the function of all likely DNA interacting amino acids (lysine, histidine and arginine).

Positively charged residues in the RuvC domain are more conserved throughout Cpf1s than those in the Rad50 domain indicating that RuvC residues are less evolutionarily flexible. This suggests that rigid control of nucleic acid binding is needed in this domain (relative to the Rad50 domain). Therefore, it is possible this domain cuts the targeted DNA strand because of the requirement for RNA:DNA duplex stabilization (precedent in Cas9). Furthermore, more arginines are present in the RuvC domain (5% of RuvC residues 904 to 1307 vs 3.8% in the proposed Rad50 domains) suggesting again that RuvC targets the DNA strand complexed with the guide RNA. Arginines are more involved in binding nucleic acid major and minor grooves (Rohs et al. Nature (2009): Vol 461: 1248-1254). Major/minor grooves would only be present in a duplex (such as DNA:RNA targeting duplex), further suggesting that RuvC cuts the "targeted strand".

From these specific observations about AsCpf1 we can identify similar residues in Cpf1 from other species by sequence alignments. Example given in FIG. 42 of AsCpf1 and FnCpf1 aligned, identifying Rad50 binding domains and the Arginines and Lysines within.

FIG. 43 provides crystal structures of two similar domains as those found in Cpf1 (RuvC holiday junction resolvase and Rad50 DNA repair protein). Based on these structures, it can be deduced what the relevant domains look like in Cpf1, and infer which regions and residues may contact DNA. In each structure residues are highlighted that contact DNA. In the alignments in FIG. X4 the regions of AsCpf1 that correspond to these DNA binding regions are annotated. The list of residues in Table 4 are those found in the two binding domains.

TABLE 4 list of probable DNA interacting residues

| RuvC domain probable DNA interacting residues: AsCpf1 | Rad50 domain probable DNA interacting residues: AsCpf1 |
|---|---|
| R909 | K324 |
| R912 | K335 |
| R930 | K337 |
| R947 | R331 |
| K949 | K369 |
| R951 | K370 |
| R955 | R386 |
| K965 | R392 |
| K968 | R393 |
| K1000 | K400 |
| K1002 | K404 |
| R1003 | K406 |
| K1009 | K408 |
| K1017 | K414 |
| K1022 | K429 |
| K1029 | K436 |
| K1035 | K438 |
| K1054 | K459 |
| K1072 | K460 |
| K1086 | K464 |
| R1094 | R670 |
| K1095 | K675 |
| K1109 | R681 |
| K1118 | K686 |
| K1142 | K689 |
| K1150 | R699 |
| K1158 | K705 |
| K1159 | R725 |
| R1220 | K729 |
| R1226 | K739 |

TABLE 4-continued list of probable DNA interacting residues

| RuvC domain probable DNA interacting residues: AsCpf1 | Rad50 domain probable DNA interacting residues: AsCpf1 |
|---|---|
| R1242 | K748 |
| R1252 | K752 |
|  | R670 |

Deactivated/Inactivated Cpf1 Protein

Where the Cpf1 protein has nuclease activity, the Cpf1 protein may be modified to have diminished nuclease activity e.g., nuclease inactivation of at least 70%, at least 80%, at least 90%, at least 95%, at least 97%, or 100% as compared with the wild type enzyme; or to put in another way, a Cpf1 enzyme having advantageously about 0% of the nuclease activity of the non-mutated or wild type Cpf1 enzyme or CRISPR enzyme, or no more than about 3% or about 5% or about 10% of the nuclease activity of the non-mutated or wild type Cpf1 enzyme, e.g. of the non-mutated or wild type *Francisella novicida* U112 (FnCpf1), *Acidaminococcus* sp. BV3L6 (AsCpf1), *Lachnospiraceae bacterium* ND2006 (LbCpf1) or *Moraxella bovoculi* 237 (MbCpf1) Cpf1 enzyme or CRISPR enzyme. This is possible by introducing mutations into the nuclease domains of the Cpf1 and orthologs thereof In certain embodiments, the CRISPR enzyme is engineered and can comprise one or more mutations that reduce or eliminate a nuclease activity. The amino acid positions in the FnCpf1p RuvC domain include but are not limited to D917A, E1006A, E1028A, D1227A, D1255A, N1257A, D917A, E1006A, E1028A, D1227A, D1255A and N1257A. Applicants have also identified a putative second nuclease domain which is most similar to PD-(D/E)XK nuclease superfamily and HincII endonuclease like. The point mutations to be generated in this putative nuclease domain to substantially reduce nuclease activity include but are not limited to N580A, N584A, T587A, W609A, D610A, K613A, E614A, D616A, K624A, D625A, K627A and Y629A. In a preferred embodiment, the mutation in the FnCpf1p RuvC domain is D917A or E1006A, wherein the D917A or E1006A mutation completely inactivates the DNA cleavage activity of the FnCpf1 effector protein. In another embodiment, the mutation in the FnCpf1p RuvC domain is D1255A, wherein the mutated FnCpf1 effector protein has significantly reduced nucleolytic activity.

More particularly, the inactivated Cpf1 enzymes include enzymes mutated in amino acid positions As908, As993, As1263 of AsCpf1 or corresponding positions in Cpf1 orthologs. Additionally, the inactivated Cpf1 enzymes include enzymes mutated in amino acid position Lb832, 925, 947 or 1180 of LbCpf1 or corresponding positions in Cpf1 orthologs. More particularly, the inactivated Cpf1 enzymes include enzymes comprising one or more of mutations AsD908A, AsE993A, AsD1263A of AsCpf1 or corresponding mutations in Cpf1 orthologs. Additionally, the inactivated Cpf1 enzymes include enzymes comprising one or more of mutations LbD832A, E925A, D947A or D1180A of LbCpf1 or corresponding mutations in Cpf1 orthologs.

Mutations can also be made at neighboring residues, e.g., at amino acids near those indicated above that participate in the nuclease activity. In some embodiments, only the RuvC domain is inactivated, and in other embodiments, another putative nuclease domain is inactivated, wherein the effector protein complex functions as a nickase and cleaves only one DNA strand. In a preferred embodiment, the other putative nuclease domain is a HincII-like endonuclease domain. In some embodiments, two FnCpf1, AsCpf1 or LbCpf1 variants (each a different nickase) are used to increase specificity, two nickase variants are used to cleave DNA at a target (where both nickases cleave a DNA strand, while minimizing or eliminating off-target modifications where only one DNA strand is cleaved and subsequently repaired). In preferred embodiments the Cpf1 effector protein cleaves sequences associated with or at a target locus of interest as a homodimer comprising two Cpf1 effector protein molecules. In a preferred embodiment the homodimer may comprise two Cpf1 effector protein molecules comprising a different mutation in their respective RuvC domains.

The inactivated Cpf1 CRISPR enzyme may have associated (e.g., via fusion protein) one or more functional domains, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that gRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases it is advantageous that additionally at least one NLS is provided. In some instances, it is advantageous to position the NLS at the N terminus. When more than one functional domain is included, the functional domains may be the same or different.

In general, the positioning of the one or more functional domain on the inactivated Cpf1 enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the CRISPR enzyme.

Elements of the Nuclear Targeting System

In general, "nucleic acid-targeting system" as used in the present application refers collectively to transcripts and other elements involved in the expression of or directing the activity of nucleic acid-targeting CRISPR-associated ("Cas") genes (also referred to herein as an effector protein), including sequences encoding a nucleic acid-targeting Cas (effector) protein and a guide RNA (comprising crRNA sequence and a trans-activating CRISPR/Cas system RNA (tracrRNA) sequence), or other sequences and transcripts from a nucleic acid-targeting CRISPR locus. In some embodiments, one or more elements of a nucleic acid-targeting system are derived from a Type V/Type VI nucleic acid-targeting CRISPR system. In some embodiments, one or more elements of a nucleic acid-targeting system is derived from a particular organism comprising an endogenous nucleic acid-targeting CRISPR system. In general, a nucleic acid-targeting system is characterized by elements that promote the formation of a nucleic acid-targeting complex at the site of a target sequence. In the context of formation of a nucleic acid-targeting complex, "target sequence" refers to a sequence to which a guide sequence is designed to have complementarity, where hybridization between a target sequence and a guide RNA promotes the formation of a DNA or RNA-targeting complex. Full complementarity is not necessarily required, provided there is sufficient complementarity to cause hybridization and promote formation of a nucleic acid-targeting complex. A target sequence may comprise RNA polynucleotides. In some embodiments, a target sequence is located in the nucleus or cytoplasm of a cell. In some embodiments, the target sequence may be within an organelle of a eukaryotic cell, for example, mitochondrion or chloroplast. A sequence or template that may be used for recombination into the targeted locus comprising the target sequences is referred to as an "editing template" or "editing RNA" or "editing sequence". In aspects of the invention, an exogenous template RNA may be referred to as an editing template. In an aspect of the invention the recombination is homologous recombination.

Typically, in the context of an endogenous nucleic acid-targeting system, formation of a nucleic acid-targeting complex (comprising a guide RNA hybridized to a target sequence and complexed with one or more nucleic acid-targeting effector proteins) results in cleavage of one or both RNA strands in or near (e.g. within 1, 2, 3, 4, 5, 6, 7, 8, 9, 10, 20, 50, or more base pairs from) the target sequence. In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector protein and a guide RNA could each be operably linked to separate regulatory elements on separate vectors. Alternatively, two or more of the elements expressed from the same or different regulatory elements, may be combined in a single vector, with one or more additional vectors providing any components of the nucleic acid-targeting system not included in the first vector. Nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector protein and a guide RNA embedded within one or more intron sequences (e.g. each in a different intron, two or more in at least one intron, or all in a single intron). In some embodiments, the nucleic acid-targeting effector protein and guide RNA are operably linked to and expressed from the same promoter.

In general, a CRISPR system is characterized by elements that promote the formation of a CRISPR complex at the site of a target sequence (also referred to as a protospacer in the context of an endogenous CRISPR system). In the context of formation of a CRISPR complex, "target sequence" refers to a sequence to which a guide sequence is designed to target, e.g. have complementarity, where hybridization between a target sequence and a guide sequence promotes the formation of a CRISPR complex. The section of the guide sequence through which complementarity to the target sequence is important for cleavage activity is referred to herein as the seed sequence. A target sequence may comprise any polynucleotide, such as DNA or RNA polynucleotides and is comprised within a target locus of interest. In some embodiments, a target sequence is located in the nucleus or cytoplasm of a cell.

In general, the term "guide sequence" is any polynucleotide sequence having sufficient complementarity with a target polynucleotide sequence to hybridize with the target sequence and direct sequence-specific binding of a nucleic acid-targeting complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a nucleic acid-targeting complex to a target sequence may be assessed by any suitable assay (as described in EP3009511 or US2016208243). For example, the components of a nucleic acid-targeting system sufficient to form a nucleic acid-targeting complex, including the guide sequence to be tested, may be provided to a host cell having the corresponding target sequence, such as by transfection with vectors encoding the components of the nucleic acid-targeting CRISPR sequence, followed by an assessment of preferential cleavage within or in the vicinity of the target sequence, such as by Surveyor assay as described herein. Similarly, cleavage of a target polynucleotide sequence (or a sequence in the vicinity thereof) may be evaluated in a test tube by providing the target sequence, components of a nucleic acid-targeting complex, including the guide sequence to be tested and a control guide sequence different from the test guide sequence, and comparing binding or rate of cleavage at or in the vicinity of the target sequence between the test and control guide sequence reactions. Other assays are possible, and will occur to those skilled in the art.

A guide sequence may be selected to target any target sequence. In some embodiments, the target sequence is a sequence within a gene transcript or mRNA. In some embodiments, the target sequence is a sequence within a genome of a cell.

In some embodiments, a guide sequence is selected to reduce the degree of secondary structure within the guide sequence. Secondary structure may be determined by any suitable polynucleotide folding algorithm. Some programs are based on calculating the minimal Gibbs free energy. An example of one such algorithm is mFold, as described by Zuker and Stiegler (Nucleic Acids Res. 9 (1981), 133-148). Another example folding algorithm is the online webserver RNAfold, developed at Institute for Theoretical Chemistry at the University of Vienna, using the centroid structure prediction algorithm (see e.g. A. R. Gruber et al., 2008, *Cell* 106(1): 23-24; and P A Can and G M Church, 2009, *Nature Biotechnology* 27(12): 1151-62). Further algorithms may be found in U.S. application Ser. No. _____; incorporated herein by reference.

In certain embodiments, a guide RNA or crRNA may comprise, consist essentially of, or consist of a direct repeat (DR) sequence and a guide sequence or spacer sequence. In certain embodiments, the guide RNA or crRNA may comprise, consist essentially of, or consist of a direct repeat sequence fused or linked to a guide sequence or spacer sequence. In certain embodiments, the direct repeat sequence may be located upstream (i.e., 5') from the guide sequence or spacer sequence. In other embodiments, the direct repeat sequence may be located downstream (i.e., 3') from the guide sequence or spacer sequence. For the Cpf1 orthologs identified to date, the direct repeat is located upstream 5' of the guide sequence.

In relation to a nucleic acid-targeting complex or system preferably, the crRNA sequence has one or more stem loops or hairpins and is 30 or more nucleotides in length, 40 or more nucleotides in length, or 50 or more nucleotides in length. In certain embodiments, the crRNA sequence is between 42 and 44 nucleotides in length, and the nucleic acid-targeting Cas protein is Cpf1 of *Francisella tularensis* subsp. *novicida* U112. In certain embodiments, the crRNA comprises, consists essentially of, or consists of 19 nucleotides of a direct repeat and between 23 and 25 nucleotides of spacer sequence, and the nucleic acid-targeting Cas protein is Cpf1 of *Francisella tularensis* subsp. *novicida* U112.

In certain embodiments, the crRNA comprises a stem loop, preferably a single stem loop. In certain embodiments, the direct repeat sequence forms a stem loop, preferably a single stem loop.

In certain embodiments, the spacer length of the guide RNA is from 15 to 35 nt. In certain embodiments, the spacer length of the guide RNA is at least 15 nucleotides. In certain embodiments, the spacer length is from 15 to 17 nt, e.g., 15, 16, or 17 nt, from 17 to 20 nt, e.g., 17, 18, 19, or 20 nt, from 20 to 24 nt, e.g., 20, 21, 22, 23, or 24 nt, from 23 to 25 nt, e.g., 23, 24, or 25 nt, from 24 to 27 nt, e.g., 24, 25, 26, or 27 nt, from 27-30 nt, e.g., 27, 28, 29, or 30 nt, from 30-35 nt, e.g., 30, 31, 32, 33, 34, or 35 nt, or 35 nt or longer.

In some embodiments, the direct repeat has a minimum length of 16 nts and a single stem loop. In further embodiments the direct repeat has a length longer than 16 nts, preferably more than 17 nts, and has more than one stem loop or optimized secondary structures. In some embodiments, the guide sequence is at least 16, 17, 18, 19, 20, 25 nucleotides, or between 16-30, or between 16-25, or between 16-20 nucleotides in length.

In some embodiments, direct repeats may be identified in silico by searching for repetitive motifs that fulfill any or all of the following criteria: 1. found in a 2Kb window of genomic sequence flanking the type II CRISPR locus; 2. span from 20 to 50 bp; and 3. interspaced by 20 to 50 bp. In some embodiments, 2 of these criteria may be used, for instance 1 and 2, 2 and 3, or 1 and 3. In some embodiments, all 3 criteria may be used.

The "tracrRNA" sequence or analogous terms includes any polynucleotide sequence that has sufficient complementarity with a crRNA sequence to hybridize. As indicated herein above, in embodiments of the present invention, the tracrRNA is not required for cleavage activity of Cpf1 effector protein complexes.

In some embodiments, the nucleic acid-targeting effector protein is part of a fusion protein comprising one or more heterologous protein domains (e.g., about or more than about 1, 2, 3, 4, 5, 6, 7, 8, 9, 10, or more domains in addition to the nucleic acid-targeting effector protein). In some embodiments, the CRISPR effector protein is part of a fusion protein comprising one or more heterologous protein domains (e.g. about or more than about 1, 2, 3, 4, 5, 6, 7, 8, 9, 10, or more domains in addition to the CRISPR enzyme). A CRISPR enzyme fusion protein may comprise any additional protein sequence, and optionally a linker sequence between any two domains. Examples of protein domains that may be fused to a CRISPR enzyme include, without limitation, epitope tags, reporter gene sequences, and protein domains having one or more of the following activities: methylase activity, demethylase activity, transcription activation activity, transcription repression activity, transcription release factor activity, histone modification activity, RNA cleavage activity and nucleic acid binding activity. Non-limiting examples of epitope tags include histidine (His) tags, V5 tags, FLAG tags, influenza hemagglutinin (HA) tags, Myc tags, VSV-G tags, and thioredoxin (Trx) tags. Examples of reporter genes include, but are not limited to, glutathione-S-transferase (GST), horseradish peroxidase (HRP), chloramphenicol acetyltransferase (CAT) beta-galactosidase, beta-glucuronidase, luciferase, green fluorescent protein (GFP), HcRed, DsRed, cyan fluorescent protein (CFP), yellow fluorescent protein (YFP), and autofluorescent proteins including blue fluorescent protein (BFP). A CRISPR enzyme may be fused to a gene sequence encoding a protein or a fragment of a protein that bind DNA molecules or bind other cellular molecules, including but not limited to maltose binding protein (MBP), S-tag, Lex A DNA binding domain (DBD) fusions, GAL4 DNA binding domain fusions, and herpes simplex virus (HSV) BP16 protein fusions. Additional domains that may form part of a fusion protein comprising a CRISPR enzyme are described in US20110059502, incorporated herein by reference. In some embodiments, a tagged CRISPR enzyme is used to identify the location of a target sequence.

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome),In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283 and WO 2014/018423 and U.S. Pat. Nos. 8,889, 418, 8,895,308, US20140186919, US20140242700, US20140273234, US20140335620, WO2014093635, which is hereby incorporated by reference in its entirety.

In some embodiments, a recombination template is also provided. A recombination template may be a component of another vector as described herein, contained in a separate vector, or provided as a separate polynucleotide. In some embodiments, a recombination template is designed to serve as a template in homologous recombination, such as within or near a target sequence nicked or cleaved by a nucleic acid-targeting effector protein as a part of a nucleic acid-targeting complex.

In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by an Cpf1 mediated cleavage event. In an embodiment, the template nucleic acid may include sequence that corresponds to both, a first site on the target sequence that is cleaved in a first Cpf1 mediated event, and a second site on the target sequence that is cleaved in a second Cpf1 mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence.

A template polynucleotide may be of any suitable length, such as about or more than about 10, 15, 20, 25, 50, 75, 100, 150, 200, 500, 1000, or more nucleotides in length. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

In some embodiments, the template polynucleotide is complementary to a portion of a polynucleotide comprising the target sequence. When optimally aligned, a template polynucleotide might overlap with one or more nucleotides of a target sequences (e.g. about or more than about 1, 5, 10, 15, 20, 25, 30, 35, 40, 45, 50, 60, 70, 80, 90, 100 or more nucleotides). In some embodiments, when a template sequence and a polynucleotide comprising a target sequence are optimally aligned, the nearest nucleotide of the template polynucleotide is within about 1, 5, 10, 15, 20, 25, 50, 75, 100, 200, 300, 400, 500, 1000, 5000, 10000, or more nucleotides from the target sequence.

The exogenous polynucleotide template comprises a sequence to be integrated (e.g., a mutated gene). The sequence for integration may be a sequence endogenous or exogenous to the cell. Examples of a sequence to be integrated include polynucleotides encoding a protein or a non-coding RNA (e.g., a microRNA). Thus, the sequence for integration may be operably linked to an appropriate control sequence or sequences. Alternatively, the sequence to be integrated may provide a regulatory function.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

An upstream or downstream sequence may comprise from about 20 bp to about 2500 bp, for example, about 50, 100, 200, 300, 400, 500, 600, 700, 800, 900, 1000, 1100, 1200, 1300, 1400, 1500, 1600, 1700, 1800, 1900, 2000, 2100, 2200, 2300, 2400, or 2500 bp. In some methods, the exemplary upstream or downstream sequence have about 200 bp to about 2000 bp, about 600 bp to about 1000 bp, or more particularly about 700 bp to about 1000.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In some methods, the exogenous polynucleotide template may further comprise a marker. Such a marker may make it easy to screen for targeted integrations. Examples of suitable markers include restriction sites, fluorescent proteins, or selectable markers. The exogenous polynucleotide template of the invention can be constructed using recombinant techniques (see, for example, Sambrook et al., 2001 and Ausubel et al., 1996).

In certain embodiments, a template nucleic acids for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Suzuki et al. describe in vivo genome editing via CRISPR/Cas9 mediated homology-independent targeted integration (2016, Nature 540:144-149).

Accordingly, when referring to the CRISPR system herein, in some aspects or embodiments, the CRISPR system comprises (i) a CRISPR protein or a polynucleotide encoding a CRISPR effector protein and (ii) one or more polynucleotides engineered to: complex with the CRISPR protein to form a CRISPR complex; and to complex with the target sequence.

In some embodiments, the therapeutic is for delivery (or application or administration) to a eukaryotic cell, either in vivo or ex vivo.

In some embodiments, the CRISPR protein is a nuclease directing cleavage of one or both strands at the location of the target sequence, or wherein the CRISPR protein is a nickase directing cleavage at the location of the target sequence.

In some embodiments, the CRISPR protein is a Cpf1 protein complexed with a CRISPR-Cas system RNA polynucleotide sequence, wherein the polynucleotide sequence comprises: a) a guide RNA polynucleotide capable of hybridizing to a target HBV sequence; and (b) a direct repeat RNA polynucleotide.

In some embodiments, the CRISPR protein is a Cpf1, and the system comprises: I. a CRISPR-Cas system RNA polynucleotide sequence, wherein the polynucleotide sequence comprises: (a) a guide RNA polynucleotide capable of hybridizing to a target sequence, and (b) a direct repeat RNA polynucleotide, and II. a polynucleotide sequence encoding the Cpf1, optionally comprising at least one or more nuclear localization sequences, wherein the direct repeat sequence hybridizes to the guide sequence and directs sequence-specific binding of a CRISPR complex to the target sequence, and wherein the CRISPR complex comprises the CRISPR protein complexed with (1) the guide sequence that is hybridized or hybridizable to the target sequence, and (2) the direct repeat sequence, and the polynucleotide sequence encoding a CRISPR protein is DNA or RNA.

In some embodiments, the CRISPR protein is a Cpf1 from *Acidaminococcus* sp. BV3L6 (AsCpf1), *Lachnospiraceae bacterium* ND2006 (LbCpf1) or *Moraxella bovoculi* 237.

In some embodiments, the CRISPR protein further comprises one or more nuclear localization sequences (NLSs) capable of driving the accumulation of the CRISPR protein to a detectible amount in the nucleus of the cell of the organism.

In some embodiments, the CRISPR protein comprises one or more mutations.

In some embodiments, he CRISPR protein has one or more mutations in a catalytic domain, and wherein the protein further comprises a functional domain.

In some embodiments, the CRISPR system is comprised within a delivery system, optionally: a vector system comprising one or more vectors, optionally wherein the vectors comprise one or more viral vectors, optionally wherein the one or more viral vectors comprise one or more lentiviral, adenoviral or adeno-associated viral (AAV) vectors; or a particle or lipid particle, optionally wherein the CRISPR protein is complexed with the polynucleotides to form the CRISPR complex.

In some embodiments, the system, complex or protein is for use in a method of modifying an organism or a non-human organism by manipulation of a target sequence in a genomic locus of interest.

In some embodiments, the polynucleotides encoding the sequence encoding or providing the CRISPR system are delivered via liposomes, particles, cell penetrating peptides, exosomes, microvesicles, or a gene-gun. In some embodiments, a delivery system is included. In some embodiments, the delivery system comprises: a vector system comprising one or more vectors comprising the engineered polynucleotides and polynucleotide encoding the CRISPR protein, optionally wherein the vectors comprise one or more viral vectors, optionally wherein the one or more viral vectors comprise one or more lentiviral, adenoviral or adeno-associated viral (AAV) vectors; or a particle or lipid particle, containing the CRISPR system or the CRISPR complex.

In some embodiments, the CRISPR protein has one or more mutations in a catalytic domain, and wherein the enzyme further comprises a functional domain.

In some embodiments, a recombination/repair template is provided.

Cpf1 Vectors (10083)

In general, and throughout this specification, the term "vector" refers to a nucleic acid molecule capable of transporting another nucleic acid to which it has been linked. It is a replicon, such as a plasmid, phage, or cosmid, into which another DNA segment may be inserted so as to bring about the replication of the inserted segment. Generally, a vector is capable of replication when associated with the proper control elements.

Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Vectors for and that result in expression in a eukaryotic cell can be referred to herein as "eukaryotic expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Advantageous vectors include lentiviruses and adeno-associated viruses, and types of such vectors can also be selected for targeting particular types of cells.

With regards to recombination and cloning methods, mention is made of U.S. patent application Ser. No. 10/815,730, published Sep. 2, 2004 as US 2004-0171156 A1, the contents of which are herein incorporated by reference in their entirety.

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Advantageous vectors include lentiviruses and adeno-associated viruses, and types of such vectors can also be selected for targeting particular types of cells.

In particular embodiments, use is made of bicistronic vectors for guide RNA and (optionally modified or mutated) CRISPR enzymes (e.g. Cpf1). Bicistronic expression vectors for guide RNA and (optionally modified or mutated) CRISPR enzymes are preferred. In general and particularly in this embodiment (optionally modified or mutated) CRISPR enzymes are preferably driven by the CBh promoter. The RNA may preferably be driven by a Pol III promoter, such as a U6 promoter. Ideally the two are combined.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983.

Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the a-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system.

In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector enzyme and a nucleic acid-targeting guide RNA could each be operably linked to separate regulatory elements on separate vectors. RNA(s) of the nucleic acid-targeting system can be delivered to a transgenic nucleic acid-targeting effector protein animal or mammal, e.g., an animal or mammal that constitutively or inducibly or conditionally expresses nucleic acid-targeting effector protein; or an animal or mammal that is otherwise expressing nucleic acid-targeting effector proteins or has cells containing nucleic acid-targeting effector proteins, such as by way of prior administration thereto of a vector or vectors that code for and express in vivo nucleic acid-targeting effector proteins. Alternatively, two or more of the elements expressed from the same or different regulatory elements, may be combined in a single vector, with one or more additional vectors providing any components of the nucleic acid-targeting system not included in the first vector. Nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector protein and the nucleic acid-targeting guide RNA, embedded within one or more intron sequences (e.g., each in a different intron, two or more in at least one intron, or all in a single intron). In some embodiments, the nucleic acid-targeting effector protein and the nucleic acid-targeting guide RNA may be operably linked to and expressed from the same promoter. Delivery vehicles, vectors, particles, nanoparticles, formulations and components thereof for expression of one or more elements of a nucleic acid-targeting system are as used in the foregoing documents, such as WO 2014/093622 (PCT/US2013/074667). In some embodiments, a vector comprises one or more insertion sites, such as a restriction endonuclease recognition sequence (also referred to as a "cloning site"). In some embodiments, one or more insertion sites (e.g., about or more than about 1, 2, 3, 4, 5, 6, 7, 8, 9, 10, or more insertion sites) are located upstream and/or downstream of one or more sequence elements of one or more vectors. When multiple different guide sequences are used, a single expression construct may be used to target nucleic acid-targeting activity to multiple different, corresponding target sequences within a cell. For example, a single vector may comprise about or more than about 1, 2, 3, 4, 5, 6, 7, 8, 9, 10, 15, 20, or more guide sequences. In some embodiments, about or more than about 1, 2, 3, 4, 5, 6, 7, 8, 9, 10, or more such guide-sequence-containing vectors may be provided, and optionally delivered to a cell. In some embodiments, a vector comprises a regulatory element operably linked to an enzyme-coding sequence encoding a nucleic acid-targeting effector protein. Nucleic acid-targeting effector protein or nucleic acid-targeting guide RNA or RNA(s) can be delivered separately; and advantageously at least one of these is delivered via a particle complex. Nucleic acid-targeting effector protein mRNA can be delivered prior to the nucleic acid-targeting guide RNA to give time for nucleic acid-targeting effector protein to be expressed. Nucleic acid-targeting effector protein mRNA might be administered 1-12 hours (preferably around 2-6 hours) prior to the administration of nucleic acid-targeting guide RNA. Alternatively, nucleic acid-targeting effector protein mRNA and nucleic acid-targeting guide RNA can be administered together. Advantageously, a second booster dose of guide RNA can be administered 1-12 hours (preferably around 2-6 hours) after the initial administration of nucleic acid-targeting effector protein mRNA+ guide RNA. Additional administrations of nucleic acid-targeting effector protein mRNA and/or guide RNA might be useful to achieve the most efficient levels of genome modification.

In some embodiments, a vector encodes a Cpf1 effector protein comprising one or more nuclear localization sequences (NLSs), such as about or more than about 1, 2, 3, 4, 5, 6, 7, 8, 9, 10, or more NLSs. More particularly, vector comprises one or more NLSs not naturally present in the Cpf1 effector protein. Most particularly, the NLS is present in the vector 5' and/or 3' of the Cpf1 effector protein sequence In some embodiments, the RNA-targeting effector protein comprises about or more than about 1, 2, 3, 4, 5, 6, 7, 8, 9, 10, or more NLSs at or near the amino-terminus, about or more than about 1, 2, 3, 4, 5, 6, 7, 8, 9, 10, or more NLSs at or near the carboxy-terminus, or a combination of these (e.g., zero or at least one or more NLS at the amino-terminus and zero or at one or more NLS at the carboxy terminus). When more than one NLS is present, each may be selected independently of the others, such that a single NLS may be present in more than one copy and/or in combination with one or more other NLSs present in one or more copies. In some embodiments, an NLS is considered near the N- or C-terminus when the nearest amino acid of the NLS is within about 1, 2, 3, 4, 5, 10, 15, 20, 25, 30, 40, 50, or more amino acids along the polypeptide chain from the N- or C-terminus. Non-limiting examples of NLSs include an NLS sequence derived from: the NLS of the SV40 virus large T-antigen, having the amino acid sequence PKKKRKV (SEQ ID NO: 2); the NLS from nucleoplasmin (e.g., the nucleoplasmin bipartite NLS with the sequence KRPAATKKAGQAKKKK (SEQ ID NO: 3)); the c-myc NLS having the amino acid sequence PAAKRVKLD (SEQ ID NO: 4) or RQRRNELKRSP (SEQ ID NO: 5); the hRNPA1 M9 NLS having the sequence NQSSNFGPMKGGNFGGRSSGPYGGGGQYFAK-PRNQGGY (SEQ ID NO: 6); the sequence RMRIZFKNKGKDTAELRRRRVEVSVELRKAKKD-EQILKRRNV (SEQ ID NO: 7) of the IBB domain from importin-alpha; the sequences VSRKRPRP (SEQ ID NO: 8) and PPKKARED (SEQ ID NO: 9) of the myoma T protein; the sequence PQPKKKPL (SEQ ID NO: 10) of human p53; the sequence SALIKKKKKMAP (SEQ ID NO: 11) of mouse c-abl IV; the sequences DRLRR (SEQ ID NO: 12) and PKQKKRK (SEQ ID NO: 13) of the influenza virus NS1; the sequence RKLKKKIKKL (SEQ ID NO: 14) of the Hepatitis virus delta antigen; the sequence REKKKFLKRR (SEQ ID NO: 15) of the mouse Mx1 protein; the sequence KRKGDEVDGVDEVAKKKSKK (SEQ ID NO: 16) of the human poly(ADP-ribose) polymerase; and the sequence RKCLQAGMNLEARKTKK (SEQ ID NO: 17) of the steroid hormone receptors (human) glucocorticoid. In general, the one or more NLSs are of sufficient strength to drive accumulation of the DNA/RNA-targeting Cas protein in a detectable amount in the nucleus of a eukaryotic cell. In general, strength of nuclear localization activity may derive from the number of NLSs in the nucleic acid-targeting effector protein, the particular NLS(s) used, or a combination of these factors. Detection of accumulation in the nucleus may be performed by any suitable technique. For example, a detectable marker may be fused to the nucleic acid-targeting protein, such that location within a cell may be visualized, such as in combination with a means for detecting the location of the nucleus (e.g., a stain specific for the nucleus such as DAPI). Cell nuclei may also be isolated from cells, the contents of which may then be analyzed by any suitable process for detecting protein, such as immuno-histochemistry, Western blot, or enzyme activity assay.

Accumulation in the nucleus may also be determined indirectly, such as by an assay for the effect of nucleic acid-targeting complex formation (e.g., assay for DNA or RNA cleavage or mutation at the target sequence, or assay for altered gene expression activity affected by DNA or RNA-targeting complex formation and/or DNA or RNA-targeting Cas protein activity), as compared to a control not exposed to the nucleic acid-targeting Cas protein or nucleic acid-targeting complex, or exposed to a nucleic acid-targeting Cas protein lacking the one or more NLSs. In preferred embodiments of the herein described Cpf1 effector protein complexes and systems the codon optimized Cpf1 effector proteins comprise an NLS attached to the C-terminal of the protein. In certain embodiments, other localization tags may be fused to the Cas protein, such as without limitation for localizing the Cas to particular sites in a cell, such as organelles, such mitochondria, plastids, chloroplast, vesicles, golgi, (nuclear or cellular) membranes, ribosomes, nucleolus, ER, cytoskeleton, vacuoles, centrosome, nucleosome, granules, centrioles, etc.

The invention also provides a non-naturally occurring or engineered composition, or one or more polynucleotides encoding components of said composition, or vector systems comprising one or more polynucleotides encoding components of said composition for use in a therapeutic method of treatment. The therapeutic method of treatment may comprise gene or genome editing, or gene therapy.

The nucleic acids-targeting systems, the vector systems, the vectors and the compositions described herein may be used in various nucleic acids-targeting applications, altering or modifying synthesis of a gene product, such as a protein, nucleic acids cleavage, nucleic acids editing, nucleic acids splicing; trafficking of target nucleic acids, tracing of target nucleic acids, isolation of target nucleic acids, visualization of target nucleic acids, etc.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Vectors for and that result in expression in a eukaryotic cell can be referred to herein as "eukaryotic expression vectors." Common expression vectors of utility in recombinant DNA techniques are often in the form of plasmids.

In certain embodiments, a vector system includes promoter-guide expression cassette in reverse order.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed.

Advantageous vectors include lentiviruses and adeno-associated viruses, and types of such vectors can also be selected for targeting particular types of cells.

In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector module and a nucleic acid-targeting guide RNA could each be operably linked to separate regulatory elements on separate vectors. RNA(s) of the nucleic acid-targeting system can be delivered to a transgenic nucleic acid-targeting effector module animal or mammal, e.g., an animal or mammal that constitutively or inducibly or conditionally expresses nucleic acid-targeting effector module; or an animal or mammal that is otherwise expressing nucleic acid-targeting effector modules or has cells containing nucleic acid-targeting effector modules, such as by way of prior administration thereto of a vector or vectors that code for and express in vivo nucleic acid-targeting effector modules. Alternatively, two or more of the elements expressed from the same or different regulatory elements, may be combined in a single vector, with one or more additional vectors providing any components of the nucleic acid-targeting system not included in the first vector. Nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector module and the nucleic acid-targeting guide RNA, embedded within one or more intron sequences (e.g., each in a different intron, two or more in at least one intron, or all in a single intron). In some embodiments, the nucleic acid-targeting effector module and the nucleic acid-targeting guide RNA may be operably linked to and expressed from the same promoter.

In an aspect, the invention provides in a vector system comprising one or more vectors, wherein the one or more vectors comprises: a) a first regulatory element operably linked to a nucleotide sequence encoding the engineered CRISPR protein as defined herein; and optionally b) a second regulatory element operably linked to one or more nucleotide sequences encoding one or more nucleic acid molecules comprising a guide RNA comprising a guide sequence, a direct repeat sequence, optionally wherein components (a) and (b) are located on same or different vectors.

The invention also provides an engineered, non-naturally occurring Clustered Regularly Interspersed Short Palindromic Repeats (CRISPR)-CRISPR associated (Cas effector module) (CRISPR-Cas effector module) vector system comprising one or more vectors comprising: a) a first regulatory element operably linked to a nucleotide sequence encoding a non-naturally occurring CRISPR enzyme of any one of the inventive constructs herein; and b) a second regulatory element operably linked to one or more nucleotide sequences encoding one or more of the guide RNAs, the guide RNA comprising a guide sequence, a direct repeat sequence, wherein: components (a) and (b) are located on same or different vectors, the CRISPR complex is formed; the guide RNA targets the target polynucleotide loci and the enzyme alters the polynucleotide loci, and the enzyme in the CRISPR complex has reduced capability of modifying one or more off-target loci as compared to an unmodified enzyme and/or whereby the enzyme in the CRISPR complex has increased capability of modifying the one or more target loci as compared to an unmodified enzyme.

As used herein, a CRISPR-Cas effector module or CRISPR effector module includes, but is not limited to, Cas9, Cpf1, C2c2, Group 13b, and C2c1. In some embodiments, the CRISPR-Cas effector module may be engineered.

In such a system, component (II) may comprise a first regulatory element operably linked to a polynucleotide sequence which comprises the guide sequence, the direct repeat sequence, and wherein component (II) may comprise a second regulatory element operably linked to a polynucleotide sequence encoding the CRISPR enzyme. In such a system, where applicable the guide RNA may comprise a chimeric RNA.

In such a system, component (I) may comprise a first regulatory element operably linked to the guide sequence and the direct repeat sequence, and wherein component (II) may comprise a second regulatory element operably linked to a polynucleotide sequence encoding the CRISPR enzyme. Such a system may comprise more than one guide RNA, and each guide RNA has a different target whereby there is multiplexing. Components (a) and (b) may be on the same vector.

In any such systems comprising vectors, the one or more vectors may comprise one or more viral vectors, such as one or more retrovirus, lentivirus, adenovirus, adeno-associated virus or herpes simplex virus.

In any such systems comprising regulatory elements, at least one of said regulatory elements may comprise a tissue-specific promoter. The tissue-specific promoter may direct expression in a mammalian blood cell, in a mammalian liver cell or in a mammalian eye.

In any of the above-described compositions or systems the direct repeat sequence, may comprise one or more protein-interacting RNA aptamers. The one or more aptamers may be located in the tetraloop. The one or more aptamers may be capable of binding MS2 bacteriophage coat protein.

In any of the above-described compositions or systems the cell may be a eukaryotic cell or a prokaryotic cell; wherein the CRISPR complex is operable in the cell, and whereby the enzyme of the CRISPR complex has reduced capability of modifying one or more off-target loci of the cell as compared to an unmodified enzyme and/or whereby the enzyme in the CRISPR complex has increased capability of modifying the one or more target loci as compared to an unmodified enzyme.

The invention also provides a CRISPR complex of any of the above-described compositions or from any of the above-described systems.

The invention also provides a method of modifying a locus of interest in a cell comprising contacting the cell with any of the herein-described engineered CRISPR enzymes (e.g. engineered Cas effector module), compositions or any of the herein-described systems or vector systems, or wherein the cell comprises any of the herein-described CRISPR complexes present within the cell. In such methods the cell may be a prokaryotic or eukaryotic cell, preferably a eukaryotic cell. In such methods, an organism may comprise the cell. In such methods the organism may not be a human or other animal.

In certain embodiment, the invention also provides a non-naturally-occurring, engineered composition (e.g., engineered Cas9, Cpf1, C2c2, C2c1, Group 29/30, 13b, or any Cas protein which can fit into an AAV vector). Reference is made to FIGS. 19A, 19B, 19C, 19D, and 20A-F in U.S. Pat. No. 8,697,359 herein incorporated by reference to provide a list and guidance for other proteins which may also be used.

Any such method may be ex vivo or in vitro.

In certain embodiments, a nucleotide sequence encoding at least one of said guide RNA or Cpf1 effector module is operably connected in the cell with a regulatory element comprising a promoter of a gene of interest, whereby expression of at least one CRISPR-Cas effector module system component is driven by the promoter of the gene of interest. "operably connected" is intended to mean that the nucleotide sequence encoding the guide RNA and/or the Cas effector module is linked to the regulatory element(s) in a manner that allows for expression of the nucleotide sequence, as also referred to herein elsewhere. The term "regulatory element" is also described herein elsewhere. According to the invention, the regulatory element comprises a promoter of a gene of interest, such as preferably a promoter of an endogenous gene of interest. In certain embodiments, the promoter is at its endogenous genomic location. In such embodiments, the nucleic acid encoding the CRISPR and/or Cas effector module is under transcriptional control of the promoter of the gene of interest at its native genomic location. In certain other embodiments, the promoter is provided on a (separate) nucleic acid molecule, such as a vector or plasmid, or other extrachromosomal nucleic acid, i.e. the promoter is not provided at its native genomic location. In certain embodiments, the promoter is genomically integrated at a non-native genomic location.

The invention also provides a method of altering the expression of a genomic locus of interest in a mammalian cell comprising contacting the cell with the engineered CRISPR enzymes (e.g. engineered Cas effector module), compositions, systems or CRISPR complexes described herein and thereby delivering the CRISPR-Cas effector module (vector) and allowing the CRISPR-Cas effector module complex to form and bind to target, and determining if the expression of the genomic locus has been altered, such as increased or decreased expression, or modification of a gene product.

The invention further provides for a method of making mutations to a Cas effector module or a mutated or modified Cas effector module that is an ortholog of the CRISPR enzymes according to the invention as described herein, comprising ascertaining amino acid(s) in that ortholog may be in close proximity or may touch a nucleic acid molecule, e.g., DNA, RNA, gRNA, etc., and/or amino acid(s) analogous or corresponding to herein-identified amino acid(s) in CRISPR enzymes according to the invention as described herein for modification and/or mutation, and synthesizing or preparing or expressing the orthologue comprising, consisting of or consisting essentially of modification(s) and/or mutation(s) or mutating as herein-discussed, e.g., modifying, e.g., changing or mutating, a neutral amino acid to a charged, e.g., positively charged, amino acid, e.g., Alanine. The so modified ortholog can be used in CRISPR-Cas effector module systems; and nucleic acid molecule(s) expressing it may be used in vector systems that deliver molecules or encoding CRISPR-Cas effector module system components as herein-discussed.

In one aspect, the invention provides a kit comprising one or more of the components described herein. In some embodiments, the kit comprises a vector system and instructions for using the kit. In some embodiments, the vector system comprises (a) a first regulatory element operably linked to a direct repeat sequence and one or more insertion sites for inserting one or more guide sequences downstream of the DR sequence, wherein when expressed, the guide sequence directs sequence-specific binding of a CRISPR-Cas effector module complex to a target sequence in a eukaryotic cell, wherein the CRISPR-Cas effector module complex comprises a Cas effector module complexed with (1) the guide sequence that is hybridized to the target sequence, and (2) the DR sequence; and/or (b) a second regulatory element operably linked to an enzyme-coding sequence encoding said Cas effector module comprising a nuclear localization sequence and advantageously this includes a split Cas effector module. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR-Cas effector module complex to a different target sequence in a eukaryotic cell.

In one aspect, the invention provides a method of modifying a target polynucleotide in a eukaryotic cell. In some embodiments, the method comprises allowing a CRISPR-Cas effector module complex to bind to the target polynucleotide to effect cleavage of said target polynucleotide thereby modifying the target polynucleotide, wherein the CRISPR-Cas effector module complex comprises a Cas effector module complexed with a guide sequence hybridized to a target sequence within said target polynucleotide, wherein said guide sequence is linked to a direct repeat sequence. In some embodiments, said cleavage comprises cleaving one or two strands at the location of the target sequence by said Cas effector module; this includes a split Cas effector module. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the Cas effector module, and the guide sequence linked to the DR sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR-Cas effector module complex to bind to the polynucleotide such that said binding results in increased or decreased expression of said polynucleotide; wherein the CRISPR-Cas effector module complex comprises a Cas effector module complexed with a guide sequence hybridized to a target sequence within said polynucleotide, wherein said guide sequence is linked to a direct repeat sequence; which may include a split Cas effector module. In some embodiments, the method further comprises delivering one or more vectors to said eukaryotic cells, wherein the one or more vectors drive expression of one or more of: the Cas effector module, and the guide sequence linked to the DR sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: Cas effector module, and a guide sequence linked to a direct repeat sequence; and (b) allowing a CRISPR-Cas effector module complex to bind to a target polynucleotide to effect cleavage of the target polynucleotide within said disease gene, wherein the CRISPR-Cas effector module complex comprises a Cas effector module complexed with (1) the guide sequence that is hybridized to the target sequence within the target polynucleotide, and (2) the DR sequence, thereby generating a model eukaryotic cell comprising a mutated disease gene; this includes a split Cas effector module. In some embodiments, said cleavage comprises cleaving one or two strands at the location of the target sequence by said Cas effector module. In a preferred embodiment, the strand break is a staggered cut with a 5' overhang. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a Cas effector module, a guide sequence linked to a direct repeat sequence, and an editing template; wherein the editing template comprises the one or more mutations that abolish Cas effector module cleavage; allowing homologous recombination of the editing template with the target polynucleotide in the cell(s) to be selected; allowing a CRISPR-Cas effector module complex to bind to a target polynucleotide to effect cleavage of the target polynucleotide within said gene, wherein the CRISPR-Cas effector module complex comprises the Cas effector module complexed with (1) the guide sequence that is hybridized to the target sequence within the target polynucleotide, and (2) the direct repeat sequence, wherein binding of the Cas effector module CRISPR-Cas effector module complex to the target polynucleotide induces cell death, thereby allowing one or more cell(s) in which one or more mutations have been introduced to be selected; this includes a split Cas effector module. In another preferred embodiment of the invention the cell to be selected may be a eukaryotic cell. Aspects of the invention allow for selection of specific cells without requiring a selection marker or a two-step process that may include a counter-selection system.

Compositions comprising a Cas effector module, complex or system comprising multiple guide RNAs, preferably tandemly arranged, or the polynucleotide or vector encoding or comprising said Cas effector module, complex or system comprising multiple guide RNAs, preferably tandemly arranged, for use in the methods of treatment as defined herein elsewhere are also provided. A kit of parts may be provided including such compositions. Use of said composition in the manufacture of a medicament for such methods of treatment are also provided. Use of a Cas effector module CRISPR system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again. Using an inducible Cas effector module activator allows one to induce transcription right before the screen and therefore minimizes the chance of false negative hits. Accordingly, by use of the instant invention in screening, e.g., gain of function screens, the chance of false negative results may be minimized.

In another aspect, the invention provides an engineered, non-naturally occurring vector system comprising one or more vectors comprising a first regulatory element operably linked to the multiple Cas effector module CRISPR system guide RNAs that each specifically target a DNA molecule encoding a gene product and a second regulatory element operably linked coding for a CRISPR protein. Both regulatory elements may be located on the same vector or on different vectors of the system. The multiple guide RNAs target the multiple DNA molecules encoding the multiple gene products in a cell and the CRISPR protein may cleave the multiple DNA molecules encoding the gene products (it may cleave one or both strands or have substantially no nuclease activity), whereby expression of the multiple gene products is altered; and, wherein the CRISPR protein and the multiple guide RNAs do not naturally occur together. In a preferred embodiment the CRISPR protein is a Cas effector module, optionally codon optimized for expression in a eukaryotic cell. In a preferred embodiment the eukaryotic cell is a mammalian cell, a plant cell or a yeast cell and in a more preferred embodiment the mammalian cell is a human cell. In a further embodiment of the invention, the expression of each of the multiple gene products is altered, preferably decreased.

In one aspect, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the CRISPR complex to the one or more target sequence(s) in a eukaryotic cell, wherein the CRISPR complex comprises a Cas effector module complexed with the one or more guide sequence(s) that is hybridized to the one or more target sequence(s); and (b) a second regulatory element operably linked to an enzyme-coding sequence encoding said Cas effector module, preferably comprising at least one nuclear localization sequence and/or at least one NES; wherein components (a) and (b) are located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the CRISPR complex comprises one or more nuclear localization sequences and/or one or more NES of sufficient strength to drive accumulation of said CRISPR complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

Recombinant expression vectors can comprise the polynucleotides encoding the Cas effector module, system or complex for use in multiple targeting as defined herein in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

In some embodiments, a host cell is transiently or non-transiently transfected with one or more vectors comprising the polynucleotides encoding the Cas effector module, system or complex for use in multiple targeting as defined herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art and exemplified herein elsewhere. Cell lines are available from a variety of sources known to those with skill in the art (see, e.g., the American Type Culture Collection (ATCC) (Manassas, Va.)). In some embodiments, a cell transfected with one or more vectors comprising the polynucleotides encoding the Cas effector module, system or complex for use in multiple targeting as defined herein is used to establish a new cell line comprising one or more vector-derived sequences. In some embodiments, a cell transiently transfected with the components of a Cas effector module, system or complex for use in multiple targeting as described herein (such as by transient transfection of one or more vectors, or transfection with RNA), and modified through the activity of a Cas effector module, system or complex, is used to establish a new cell line comprising cells containing the modification but lacking any other exogenous sequence. In some embodiments, cells transiently or non-transiently transfected with one or more vectors comprising the polynucleotides encoding Cas effector module, system or complex for use in multiple targeting as defined herein, or cell lines derived from such cells are used in assessing one or more test compounds.

The term "regulatory element" is as defined herein elsewhere.

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a direct repeat sequence and one or more insertion sites for inserting one or more guide RNA sequences up- or downstream (whichever applicable) of the direct repeat sequence, wherein when expressed, the guide sequence(s) direct(s) sequence-specific binding of the CRISPR complex to the respective target sequence(s) in a eukaryotic cell, wherein the CRISPR complex comprises a Cas effector module complexed with the one or more guide sequence(s) that is hybridized to the respective target sequence(s); and/or (b) a second regulatory element operably linked to an enzyme-coding sequence encoding said Cas effector module comprising preferably at least one nuclear localization sequence and/or NES. In some embodiments, the host cell comprises components (a) and (b). In some embodiments, component (a), component (b), or components (a) and (b) are stably integrated into a genome of the host eukaryotic cell. In some embodiments, component (a) further comprises two or more guide sequences operably linked to the first regulatory element, and optionally separated by a direct repeat, wherein when expressed, each of the two or more guide sequences direct sequence specific binding of a CRISPR complex to a different target sequence in a eukaryotic cell. In some embodiments, the Cas effector module comprises one or more nuclear localization sequences and/or nuclear export sequences or NES of sufficient strength to drive accumulation of said CRISPR enzyme in a detectable amount in and/or out of the nucleus of a eukaryotic cell.

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

In certain aspects the invention involves vectors.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters—especially as to the numbers of RNAs or guides or sgRNAs discussed herein, without any undue experimentation.

The guide RNA(s), e.g., sgRNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Aspects of the invention relate to bicistronic vectors for guide RNA and (optionally modified or mutated) Cas effector modules. Bicistronic expression vectors for guide RNA and (optionally modified or mutated) CRISPR enzymes are preferred. In general and particularly in this embodiment (optionally modified or mutated) CRISPR enzymes are preferably driven by the CBh promoter. The RNA may preferably be driven by a Pol III promoter, such as a U6 promoter. Ideally the two are combined.

In some embodiments, a loop in the guide RNA is provided. This may be a stem loop or a tetra loop. The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG.

The term "regulatory element" is intended to include promoters, enhancers, internal ribosomal entry sites (IRES), and other expression control elements (e.g. transcription termination signals, such as polyadenylation signals and poly-U sequences).

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRES- SION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerevisiae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the a-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

Typically, in the context of an endogenous nucleic acid-targeting system, formation of a nucleic acid-targeting complex (comprising a guide RNA hybridized to a target sequence and complexed with one or more nucleic acid-targeting effector modules) results in cleavage of one or both RNA strands in or near (e.g. within 1, 2, 3, 4, 5, 6, 7, 8, 9, 10, 20, 50, or more base pairs from) the target sequence. In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector module and a guide RNA could each be operably linked to separate regulatory elements on separate vectors. Alternatively, two or more of the elements expressed from the same or different regulatory elements, may be combined in a single vector, with one or more additional vectors providing any components of the nucleic acid-targeting system not included in the first vector. Nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector module and a guide RNA embedded within one or more intron sequences (e.g. each in a different intron, two or more in at least one intron, or all in a single intron). In some embodiments, the nucleic acid-targeting effector module and guide RNA are operably linked to and expressed from the same promoter.

In certain embodiments, a nucleotide sequence encoding at least one of said guide RNA or Cpf1 effector module is operably connected in the cell with a regulatory element comprising a promoter of a gene of interest, whereby expression of at least one CRISPR-Cas effector module system component is driven by the promoter of the gene of interest. "operably connected" is intended to mean that the nucleotide sequence encoding the guide RNA and/or the Cas effector module is linked to the regulatory element(s) in a manner that allows for expression of the nucleotide sequence, as also referred to herein elsewhere. The term "regulatory element" is also described herein elsewhere. According to the invention, the regulatory element comprises a promoter of a gene of interest, such as preferably a promoter of an endogenous gene of interest. In certain embodiments, the promoter is at its endogenous genomic location. In such embodiments, the nucleic acid encoding the CRISPR and/or Cas effector module is under transcriptional control of the promoter of the gene of interest at its native genomic location. In certain other embodiments, the promoter is provided on a (separate) nucleic acid molecule, such as a vector or plasmid, or other extrachromosomal nucleic acid, i.e. the promoter is not provided at its native genomic location. In certain embodiments, the promoter is genomically integrated at a non-native genomic location.

The invention also provides a method of altering the expression of a genomic locus of interest in a mammalian cell comprising contacting the cell with the engineered CRISPR enzymes (e.g. engineered Cas effector module), compositions, systems or CRISPR complexes described herein and thereby delivering the CRISPR-Cas effector module (vector) and allowing the CRISPR-Cas effector module complex to form and bind to target, and determining if the expression of the genomic locus has been altered, such as increased or decreased expression, or modification of a gene product.

The invention further provides for a method of making mutations to a Cas effector module or a mutated or modified Cas effector module that is an ortholog of the CRISPR enzymes according to the invention as described herein, comprising ascertaining amino acid(s) in that ortholog may be in close proximity or may touch a nucleic acid molecule, e.g., DNA, RNA, gRNA, etc., and/or amino acid(s) analogous or corresponding to herein-identified amino acid(s) in CRISPR enzymes according to the invention as described herein for modification and/or mutation, and synthesizing or preparing or expressing the orthologue comprising, consisting of or consisting essentially of modification(s) and/or mutation(s) or mutating as herein-discussed, e.g., modifying, e.g., changing or mutating, a neutral amino acid to a charged, e.g., positively charged, amino acid, e.g., Alanine. The so modified ortholog can be used in CRISPR-Cas effector module systems; and nucleic acid molecule(s) expressing it may be used in vector systems that deliver molecules or encoding CRISPR-Cas effector module system components as herein-discussed.

In one aspect, the invention provides a kit comprising one or more of the components described herein. In some embodiments, the kit comprises a vector system and instructions for using the kit. In some embodiments, the vector system comprises (a) a first regulatory element operably linked to a direct repeat sequence and one or more insertion sites for inserting one or more guide sequences downstream of the DR sequence, wherein when expressed, the guide sequence directs sequence-specific binding of a CRISPR-Cas effector module complex to a target sequence in a eukaryotic cell, wherein the CRISPR-Cas effector module complex comprises a Cas effector module complexed with (1) the guide sequence that is hybridized to the target sequence, and (2) the DR sequence; and/or (b) a second regulatory element operably linked to an enzyme-coding sequence encoding said Cas effector module comprising a nuclear localization sequence and advantageously this includes a split Cas effector module. In some embodiments, the kit comprises components (a) and (b) located on the same or different vectors of the system. In some embodiments, component (a) further comprises two or more guide sequences operably linked to the first regulatory element, wherein when expressed, each of the two or more guide sequences direct sequence specific binding of a CRISPR-Cas effector module complex to a different target sequence in a eukaryotic cell.

In one aspect, the invention provides a method of modifying a target polynucleotide in a eukaryotic cell. In some embodiments, the method comprises allowing a CRISPR-Cas effector module complex to bind to the target polynucleotide to effect cleavage of said target polynucleotide thereby modifying the target polynucleotide, wherein the CRISPR-Cas effector module complex comprises a Cas effector module complexed with a guide sequence hybridized to a target sequence within said target polynucleotide, wherein said guide sequence is linked to a direct repeat sequence. In some embodiments, said cleavage comprises cleaving one or two strands at the location of the target sequence by said Cas effector module; this includes a split Cas effector module. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein the one or more vectors drive expression of one or more of: the Cas effector module, and the guide sequence linked to the DR sequence. In some embodiments, said vectors are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a CRISPR-Cas effector module complex to bind to the polynucleotide such that said binding results in increased or decreased expression of said polynucleotide; wherein the CRISPR-Cas effector module complex comprises a Cas effector module complexed with a guide sequence hybridized to a target sequence within said polynucleotide, wherein said guide sequence is linked to a direct repeat sequence; which may include a split Cas effector module. In some embodiments, the method further comprises delivering one or more vectors to said eukaryotic cells, wherein the one or more vectors drive expression of one or more of: the Cas effector module, and the guide sequence linked to the DR sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors drive expression of one or more of: Cas effector module, and a guide sequence linked to a direct repeat sequence; and (b) allowing a CRISPR-Cas effector module complex to bind to a target polynucleotide to effect cleavage of the target polynucleotide within said disease gene, wherein the CRISPR-Cas effector module complex comprises a Cas effector module complexed with (1) the guide sequence that is hybridized to the target sequence within the target polynucleotide, and (2) the DR sequence, thereby generating a model eukaryotic cell comprising a mutated disease gene; this includes a split Cas effector module. In some embodiments, said cleavage comprises cleaving one or two strands at the location of the target sequence by said Cas effector module. In a preferred embodiment, the strand break is a staggered cut with a 5' overhang. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect the invention provides for a method of selecting one or more cell(s) by introducing one or more mutations in a gene in the one or more cell (s), the method comprising: introducing one or more vectors into the cell (s), wherein the one or more vectors drive expression of one or more of: a Cas effector module, a guide sequence linked to a direct repeat sequence, and an editing template; wherein the editing template comprises the one or more mutations that abolish Cas effector module cleavage; allowing homologous recombination of the editing template with the target polynucleotide in the cell(s) to be selected; allowing a CRISPR-Cas effector module complex to bind to a target polynucleotide to effect cleavage of the target polynucleotide within said gene, wherein the CRISPR-Cas effector module complex comprises the Cas effector module complexed with (1) the guide sequence that is hybridized to the target sequence within the target polynucleotide, and (2) the direct repeat sequence, wherein binding of the Cas effector module CRISPR-Cas effector module complex to the target polynucleotide induces cell death, thereby allowing one or more cell(s) in which one or more mutations have been introduced to be selected; this includes a split Cas effector module. In another preferred embodiment of the invention the cell to be selected may be a eukaryotic cell. Aspects of the invention allow for selection of specific cells without requiring a selection marker or a two-step process that may include a counter-selection system.

Compositions comprising a Cas effector module, complex or system comprising multiple guide RNAs, preferably tandemly arranged, or the polynucleotide or vector encoding or comprising said Cas effector module, complex or system comprising multiple guide RNAs, preferably tandemly arranged, for use in the methods of treatment as defined herein elsewhere are also provided. A kit of parts may be provided including such compositions. Use of said composition in the manufacture of a medicament for such methods of treatment are also provided. Use of a Cas effector module CRISPR system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again. Using an inducible Cas effector module activator allows one to induce transcription right before the screen and therefore minimizes the chance of false negative hits. Accordingly, by use of the instant invention in screening, e.g., gain of function screens, the chance of false negative results may be minimized.

In another aspect, the invention provides an engineered, non-naturally occurring vector system comprising one or more vectors comprising a first regulatory element operably linked to the multiple Cas effector module CRISPR system guide RNAs that each specifically target a DNA molecule encoding a gene product and a second regulatory element operably linked coding for a CRISPR protein. Both regulatory elements may be located on the same vector or on different vectors of the system. The multiple guide RNAs target the multiple DNA molecules encoding the multiple gene products in a cell and the CRISPR protein may cleave the multiple DNA molecules encoding the gene products (it may cleave one or both strands or have substantially no nuclease activity), whereby expression of the multiple gene products is altered; and, wherein the CRISPR protein and the multiple guide RNAs do not naturally occur together. In a preferred embodiment the CRISPR protein is a Cas effector module, optionally codon optimized for expression in a eukaryotic cell. In a preferred embodiment the eukaryotic cell is a mammalian cell, a plant cell or a yeast cell and in a more preferred embodiment the mammalian cell is a human cell. In a further embodiment of the invention, the expression of each of the multiple gene products is altered, preferably decreased.

In one aspect, the invention provides a vector system comprising one or more vectors. In some embodiments, the system comprises: (a) a first regulatory element operably linked to a direct repeat sequence and one or more insertion sites for inserting one or more guide sequences up- or downstream (whichever applicable) of the direct repeat sequence, wherein when expressed, the one or more guide sequence(s) direct(s) sequence-specific binding of the CRISPR complex to the one or more target sequence(s) in a eukaryotic cell, wherein the CRISPR complex comprises a Cas effector module complexed with the one or more guide sequence(s) that is hybridized to the one or more target sequence(s); and (b) a second regulatory element operably linked to an enzyme-coding sequence encoding said Cas effector module, preferably comprising at least one nuclear localization sequence and/or at least one NES; wherein components (a) and (b) are located on the same or different vectors of the system. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the CRISPR complex comprises one or more nuclear localization sequences and/or one or more NES of sufficient strength to drive accumulation of said CRISPR complex in a detectable amount in or out of the nucleus of a eukaryotic cell. In some embodiments, the first regulatory element is a polymerase III promoter. In some embodiments, the second regulatory element is a polymerase II promoter. In some embodiments, each of the guide sequences is at least 16, 17, 18, 19, 20, 25 nucleotides, or between 16-30, or between 16-25, or between 16-20 nucleotides in length.

Recombinant expression vectors can comprise the polynucleotides encoding the Cas effector module, system or complex for use in multiple targeting as defined herein in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

In some embodiments, a host cell is transiently or non-transiently transfected with one or more vectors comprising the polynucleotides encoding the Cas effector module, system or complex for use in multiple targeting as defined herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art and exemplified herein elsewhere. Cell lines are available from a variety of sources known to those with skill in the art (see, e.g., the American Type Culture Collection (ATCC) (Manassas, Va.)). In some embodiments, a cell transfected with one or more vectors comprising the polynucleotides encoding the Cas effector module, system or complex for use in multiple targeting as defined herein is used to establish a new cell line comprising one or more vector-derived sequences. In some embodiments, a cell transiently transfected with the components of a Cas effector module, system or complex for use in multiple targeting as described herein (such as by transient transfection of one or more vectors, or transfection with RNA), and modified through the activity of a Cas effector module, system or complex, is used to establish a new cell line comprising cells containing the modification but lacking any other exogenous sequence. In some embodiments, cells transiently or non-transiently transfected with one or more vectors comprising the polynucleotides encoding Cas effector module, system or complex for use in multiple targeting as defined herein, or cell lines derived from such cells are used in assessing one or more test compounds.

The term "regulatory element" is as defined herein elsewhere.

Advantageous vectors include lentiviruses and adeno-associated viruses, and types of such vectors can also be selected for targeting particular types of cells.

In one aspect, the invention provides a eukaryotic host cell comprising (a) a first regulatory element operably linked to a direct repeat sequence and one or more insertion sites for inserting one or more guide RNA sequences up- or downstream (whichever applicable) of the direct repeat sequence, wherein when expressed, the guide sequence(s) direct(s) sequence-specific binding of the CRISPR complex to the respective target sequence(s) in a eukaryotic cell, wherein the CRISPR complex comprises a Cas effector module complexed with the one or more guide sequence(s) that is hybridized to the respective target sequence(s); and/or (b) a second regulatory element operably linked to an enzyme-coding sequence encoding said Cas effector module comprising preferably at least one nuclear localization sequence and/or NES. In some embodiments, the host cell comprises components (a) and (b). In some embodiments, component (a), component (b), or components (a) and (b) are stably integrated into a genome of the host eukaryotic cell. In some embodiments, component (a) further comprises two or more guide sequences operably linked to the first regulatory element, and optionally separated by a direct repeat, wherein when expressed, each of the two or more guide sequences direct sequence specific binding of a CRISPR complex to a different target sequence in a eukaryotic cell. In some embodiments, the Cas effector module comprises one or more nuclear localization sequences and/or nuclear export sequences or NES of sufficient strength to drive accumulation of said CRISPR enzyme in a detectable amount in and/or out of the nucleus of a eukaryotic cell.

Several aspects of the invention relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

In certain aspects the invention involves vectors. A used herein, a "vector" is a tool that allows or facilitates the transfer of an entity from one environment to another. It is a replicon, such as a plasmid, phage, or cosmid, into which another DNA segment may be inserted so as to bring about the replication of the inserted segment. Generally, a vector is capable of replication when associated with the proper control elements. In general, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g. circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g. retroviruses, replication defective retroviruses, adenoviruses, replication defective adenoviruses, and adeno-associated viruses (AAVs)). Viral vectors also include polynucleotides carried by a virus for transfection into a host cell. Certain vectors are capable of autonomous replication in a host cell into which they are introduced (e.g. bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g. in an in vitro transcription/translation system or in a host cell when the vector is introduced into the host cell). With regards to recombination and cloning methods, mention is made of U.S. patent application Ser. No. 10/815,730, published Sep. 2, 2004 as US 2004-0171156 A1, the contents of which are herein incorporated by reference in their entirety.

The vector(s) can include the regulatory element(s), e.g., promoter(s). The vector(s) can comprise Cas encoding sequences, and/or a single, but possibly also can comprise at least 3 or 8 or 16 or 32 or 48 or 50 guide RNA(s) (e.g., sgRNAs) encoding sequences, such as 1-2, 1-3, 1-4 1-5, 3-6, 3-7, 3-8, 3-9, 3-10, 3-8, 3-16, 3-30, 3-32, 3-48, 3-50 RNA(s) (e.g., sgRNAs). In a single vector there can be a promoter for each RNA (e.g., sgRNA), advantageously when there are up to about 16 RNA(s) (e.g., sgRNAs); and, when a single vector provides for more than 16 RNA(s) (e.g., sgRNAs), one or more promoter(s) can drive expression of more than one of the RNA(s) (e.g., sgRNAs), e.g., when there are 32 RNA(s) (e.g., sgRNAs), each promoter can drive expression of two RNA(s) (e.g., sgRNAs), and when there are 48 RNA(s) (e.g., sgRNAs), each promoter can drive expression of three RNA(s) (e.g., sgRNAs). By simple arithmetic and well established cloning protocols and the teachings in this disclosure one skilled in the art can readily practice the invention as to the RNA(s) (e.g., sgRNA(s) for a suitable exemplary vector such as AAV, and a suitable promoter such as the U6 promoter, e.g., U6-sgRNAs. For example, the packaging limit of AAV is ~4.7 kb. The length of a single U6-sgRNA (plus restriction sites for cloning) is 361 bp. Therefore, the skilled person can readily fit about 12-16, e.g., 13 U6-sgRNA cassettes in a single vector. This can be assembled by any suitable means, such as a golden gate strategy used for TALE assembly (www.genome-engineering.org/taleffectors/). The skilled person can also use a tandem guide strategy to increase the number of U6-sgRNAs by approximately 1.5 times, e.g., to increase from 12-16, e.g., 13 to approximately 18-24, e.g., about 19 U6-sgRNAs. Therefore, one skilled in the art can readily reach approximately 18-24, e.g., about 19 promoter-RNAs, e.g., U6-sgRNAs in a single vector, e.g., an AAV vector. A further means for increasing the number of promoters and RNAs, e.g., sgRNA(s) in a vector is to use a single promoter (e.g., U6) to express an array of RNAs, e.g., sgRNAs separated by cleavable sequences. And an even further means for increasing the number of promoter-RNAs, e.g., sgRNAs in a vector, is to express an array of promoter-RNAs, e.g., sgRNAs separated by cleavable sequences in the intron of a coding sequence or gene; and, in this instance it is advantageous to use a polymerase II promoter, which can have increased expression and enable the transcription of long RNA in a tissue specific manner. (see, e.g., nar.oxfordjournals.org/content/34/7/e53.short, www.nature.com/mt/journal/v16/n9/abs/mt2008144a.html). In an advantageous embodiment, AAV may package U6 tandem sgRNA targeting up to about 50 genes. Accordingly, from the knowledge in the art and the teachings in this disclosure the skilled person can readily make and use vector(s), e.g., a single vector, expressing multiple RNAs or guides or sgRNAs under the control or operatively or functionally linked to one or more promoters—especially as to the numbers of RNAs or guides or sgRNAs discussed herein, without any undue experimentation.

The guide RNA(s), e.g., sgRNA(s) encoding sequences and/or Cas encoding sequences, can be functionally or operatively linked to regulatory element(s) and hence the regulatory element(s) drive expression. The promoter(s) can be constitutive promoter(s) and/or conditional promoter(s) and/or inducible promoter(s) and/or tissue specific promoter(s). The promoter can be selected from the group consisting of RNA polymerases, pol I, pol II, pol III, T7, U6, H1, retroviral Rous sarcoma virus (RSV) LTR promoter, the cytomegalovirus (CMV) promoter, the SV40 promoter, the dihydrofolate reductase promoter, the β-actin promoter, the phosphoglycerol kinase (PGK) promoter, and the EF1α promoter. An advantageous promoter is the promoter is U6.

Aspects of the invention relate to bicistronic vectors for guide RNA and (optionally modified or mutated) Cas effector modules. Bicistronic expression vectors for guide RNA and (optionally modified or mutated) CRISPR enzymes are preferred. In general and particularly in this embodiment (optionally modified or mutated) CRISPR enzymes are preferably driven by the CBh promoter. The RNA may preferably be driven by a Pol III promoter, such as a U6 promoter. Ideally the two are combined.

In some embodiments, a loop in the guide RNA is provided. This may be a stem loop or a tetra loop. The loop is preferably GAAA, but it is not limited to this sequence or indeed to being only 4 bp in length. Indeed, preferred loop forming sequences for use in hairpin structures are four nucleotides in length, and most preferably have the sequence GAAA. However, longer or shorter loop sequences may be used, as may alternative sequences. The sequences preferably include a nucleotide triplet (for example, AAA), and an additional nucleotide (for example C or G). Examples of loop forming sequences include CAAA and AAAG.

The term "regulatory element" is intended to include promoters, enhancers, internal ribosomal entry sites (IRES), and other expression control elements (e.g. transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g. liver, pancreas), or particular cell types (e.g. lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g. 1, 2, 3, 4, 5, or more pol III promoters), one or more pol II promoters (e.g. 1, 2, 3, 4, 5, or more pol II promoters), one or more pol I promoters (e.g. 1, 2, 3, 4, 5, or more pol I promoters), or combinations thereof Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)], the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.). With regards to regulatory sequences, mention is made of U.S. patent application Ser. No. 10/491,026, the contents of which are incorporated by reference herein in their entirety. With regards to promoters, mention is made of PCT publication WO 2011/028929 and U.S. application Ser. No. 12/511,940, the contents of which are incorporated by reference herein in their entirety.

Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Vectors may be introduced and propagated in a prokaryote or prokaryotic cell. In some embodiments, a prokaryote is used to amplify copies of a vector to be introduced into a eukaryotic cell or as an intermediate vector in the production of a vector to be introduced into a eukaryotic cell (e.g. amplifying a plasmid as part of a viral vector packaging system). In some embodiments, a prokaryote is used to amplify copies of a vector and express one or more nucleic acids, such as to provide a source of one or more proteins for delivery to a host cell or host organism. Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, such as to the amino terminus of the recombinant protein. Such fusion vectors may serve one or more purposes, such as: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Example fusion expression vectors include pGEX (Pharmacia Biotech Inc; Smith and Johnson, 1988. Gene 67: 31-40), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein. Examples of suitable inducible non-fusion *E. coli* expression vectors include pTrc (Amrann et al., (1988) Gene 69:301-315) and pET 11d (Studier et al., GENE EXPRESSION TECHNOLOGY: METHODS IN ENZYMOLOGY 185, Academic Press, San Diego, Calif. (1990) 60-89). In some embodiments, a vector is a yeast expression vector. Examples of vectors for expression in yeast *Saccharomyces cerivisae* include pYepSec1 (Baldari, et al., 1987. EMBO J. 6: 229-234), pMFa (Kuijan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.). In some embodiments, a vector drives protein expression in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In some embodiments, a vector is capable of driving expression of one or more sequences in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In some embodiments, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Baneiji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the a-fetoprotein promoter (Campes and Tilghman, 1989. Genes Dev. 3: 537-546). With regards to these prokaryotic and eukaryotic vectors, mention is made of U.S. Pat. No. 6,750,059, the contents of which are incorporated by reference herein in their entirety. Other embodiments of the invention may relate to the use of viral vectors, with regards to which mention is made of U.S. patent application Ser. No. 13/092,085, the contents of which are incorporated by reference herein in their entirety. Tissue-specific regulatory elements are known in the art and in this regard, mention is made of U.S. Pat. No. 7,776,321, the contents of which are incorporated by reference herein in their entirety. In some embodiments, a regulatory element is operably linked to one or more elements of a CRISPR system so as to drive expression of the one or more elements of the CRISPR system. In general, CRISPRs (Clustered Regularly Interspaced Short Palindromic Repeats), also known as SPIDRs (SPacer Interspersed Direct Repeats), constitute a family of DNA loci that are usually specific to a particular bacterial species. The CRISPR locus comprises a distinct class of interspersed short sequence repeats (SSRs) that were recognized in *E. coli* (Ishino et al., J. Bacteriol., 169:5429-5433 [1987]; and Nakata et al., J. Bacteriol., 171:3553-3556 [1989]), and associated genes. Similar interspersed SSRs have been identified in *Haloferax mediterranei, Streptococcus pyogenes, Anabaena*, and *Mycobacterium tuberculosis* (See, Groenen et al., Mol. Microbiol., 10:1057-1065 [1993]; Hoe et al., Emerg. Infect. Dis., 5:254-263 [1999]; Masepohl et al., Biochim. Biophys. Acta 1307: 26-30 [1996]; and Mojica et al., Mol. Microbiol., 17:85-93 [1995]). The CRISPR loci typically differ from other SSRs by the structure of the repeats, which have been termed short regularly spaced repeats (SRSRs) (Janssen et al., OMICS J. Integ. Biol., 6:23-33 [2002]; and Mojica et al., Mol. Microbiol., 36:244-246 [2000]). In general, the repeats are short elements that occur in clusters that are regularly spaced by unique intervening sequences with a substantially constant length (Mojica et al., [2000], supra). Although the repeat sequences are highly conserved between strains, the number of interspersed repeats and the sequences of the spacer regions typically differ from strain to strain (van Embden et al., J. Bacteriol., 182:2393-2401 [2000]). CRISPR loci have been identified in more than 40 prokaryotes (See e.g., Jansen et al., Mol. Microbiol., 43:1565-1575 [2002]; and Mojica et al., [2005]) including, but not limited to Aeropyrum, *Pyrobaculum, Sulfolobus, Archaeoglobus, Haloarcula, Methanobacterium, Methanococcus, Methanosarcina, Methanopyrus, Pyrococcus, Picrophilus, Thermoplasma, Corynebacterium, Mycobacterium, Streptomyces, Aquifex, Porphyromonas, Chlorobium, Thermus, Bacillus, Listeria, Staphylococcus, Clostridium, Thermoanaerobacter, Mycoplasma, Fusobacterium, Azoarcus, Chromobacterium, Neisseria, Nitrosomonas, Desulfovibrio, Geobacter, Myxococcus, Campylobacter, Wolinella, Acinetobacter, Erwinia, Escherichia, Legionella, Methylococcus, Pasteurella, Photobacterium, Salmonella, Xanthomonas, Yersinia, Treponema*, and *Thermotoga*.

Typically, in the context of an endogenous nucleic acid-targeting system, formation of a nucleic acid-targeting complex (comprising a guide RNA hybridized to a target sequence and complexed with one or more nucleic acid-targeting effector modules) results in cleavage of one or both RNA strands in or near (e.g. within 1, 2, 3, 4, 5, 6, 7, 8, 9, 10, 20, 50, or more base pairs from) the target sequence. In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector module and a guide RNA could each be operably linked to separate regulatory elements on separate vectors. Alternatively, two or more of the elements expressed from the same or different regulatory elements, may be combined in a single vector, with one or more additional vectors providing any components of the nucleic acid-targeting system not included in the first vector. Nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector module and a guide RNA embedded within one or more intron sequences (e.g. each in a different intron, two or more in at least one intron, or all in a single intron). In some embodiments, the nucleic acid-targeting effector module and guide RNA are operably linked to and expressed from the same promoter.

Ways to package inventive Cpf1 coding nucleic acid molecules, e.g., DNA, into vectors, e.g., viral vectors, to mediate genome modification in vivo may include:
  To achieve NHEJ-mediated gene knockout:
  Single virus vector:
  Vector containing two or more expression cassettes:
  Promoter-Cpf1 coding nucleic acid molecule-terminator
  Promoter-gRNA 1-terminator
  Promoter-gRNA2-terminator
  Promoter-gRNA(N)-terminator (up to size limit of vector)
  Double virus vector:
  Vector 1 containing one expression cassette for driving the expression of Cpf1
  Promoter-Cpf1 coding nucleic acid molecule-terminator
  Vector 2 containing one more expression cassettes for driving the expression of one or more guideRNAs
  Promoter-gRNA 1-terminator
  Promoter-gRNA(N)-terminator (up to size limit of vector)
  To mediate homology-directed repair.
  In addition to the single and double virus vector approaches described above, an additional vector can be used to deliver a homology-direct repair template.
  The promoter used to drive Cpf1 coding nucleic acid molecule expression can include:
    AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cpf1.
    For ubiquitous expression, promoters that can be used include: CMV, CAG, CBh, PGK, SV40, Ferritin heavy or light chains, etc.
    For brain or other CNS expression, can use promoters: Synapsin I for all neurons, CaMKIIalpha for excitatory neurons, GAD67 or GAD65 or VGAT for GABAergic neurons, etc.
    For liver expression, can use Albumin promoter.
    For lung expression, can use SP-B.

For endothelial cells, can use ICAM.
For hematopoietic cells can use IFNbeta or CD45.
For Osteoblasts can one can use the OG-2.
The promoter used to drive guide RNA can include:
Pol III promoters such as U6 or
Use of Pol II promoter and intronic cassettes to express gRNA Adeno Associated Virus (AAV)

Cpf1 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cpf1 can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons:

Low toxicity (this may be due to the purification method not requiring ultra centrifugation of cell particles that can activate the immune response) and Low probability of causing insertional mutagenesis because it doesn't integrate into the host genome.

AAV has a packaging limit of 4.5 or 4.75 Kb. This means that Cpf1 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cpf1 that are shorter. For example:

TABLE 5

| Species | Cas9 Size (nt) |
|---|---|
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |

TABLE 5-continued

| Species | Cas9 Size (nt) |
|---|---|
| Parvibaculum lavamentivorans | 3111 |
| Staphylococcus aureus | 3159 |
| Nitratifractor salsuginis DSM 16511 | 3396 |
| Campylobacter lari CF89-12 | 3009 |
| Campylobacter jejuni | 2952 |
| Streptococcus thermophilus LMD-9 | 3396 | rAAV vectors are preferably produced in insect cells, e.g., Spodoptera frugiperda Sf9 insect cells, grown in serum-free suspension culture. Serum-free insect cells can be purchased from commercial vendors, e.g., Sigma Aldrich (EX-CELL 405).

These species are therefore, in general, preferred Cpf1 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

TABLE 6

| Cell Line | AAV-1 | AAV-2 | AAV-3 | AAV-4 | AAV-5 | AAV-6 | AAV-8 | AAV-9 |
|---|---|---|---|---|---|---|---|---|
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 μg of lentiviral transfer plasmid (pCasES10) and the following packaging plasmids: 5 μg of pMD2.G (VSV-g pseudotype), and 7.5 μg of psPAX2 (gag/poi/rev/tat). Transfection was done in 4 mL OptiMEM with a cationic lipid delivery agent (50 μL Lipofectamine 2000 and 100 µl Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 µm low protein binding (PVDF) filter. They were then spun in a ultracentrifuge for 2 hours at 24,000 rpm. Viral pellets were resuspended in 50 µl of DMEM overnight at 4 C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

Use of Minimal Promoters

The present application provides a vector for delivering an effector protein and at least one CRISPR guide RNA to a cell comprising a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4Kb. In an embodiment, the vector is an AAV vector. In another embodiment, the effector protein is a CRISPR enzyme. In a further embodiment, the CRISPR enzyme is SaCas9, Cpf1, Cas13b or C2c2.

In a related aspect, the invention provides a lentiviral vector for delivering an effector protein and at least one CRISPR guide RNA to a cell comprising a promoter operably linked to a polynucleotide sequence encoding Cpf1 and a second promoter operably linked to a polynucleotide sequence encoding at least one guide RNA, wherein the polynucleotide sequences are in reverse orientation.

In another aspect, the invention provides a method of expressing an effector protein and guide RNA in a cell comprising introducing the vector according any of the vector delivery systems disclosed herein. In an embodiment of the vector for delivering an effector protein, the minimal promoter is the Mecp2 promoter, tRNA promoter, or U6. In a further embodiment, the minimal promoter is tissue specific.

Optimization of CRISPR-Cas Systems

In another aspect, the present invention relates to methods for developing or designing CRISPR-Cas systems. In an aspect, the present invention relates to methods for developing or designing CRISPR-Cas system based therapy or therapeutics. The present invention in particular relates to methods for improving CRISPR-Cas systems, such as CRISPR-Cas system based therapy or therapeutics. Key characteristics of successful CRISPR-Cas systems, such as CRISPR-Cas system based therapy or therapeutics involve high specificity, high efficacy, and high safety. High specificity and high safety can be achieved among others by reduction of off-target effects.

Accordingly, in another aspect, the invention relates to a method as described herein, comprising selection of one or more (therapeutic) target, selecting one or more CRISPR-Cas system functionality, and optimization of selected parameters or variables associated with the CRISPR-Cas system and/or its functionality. In a related aspect, the invention relates to a method as described herein, comprising (a) selecting one or more (therapeutic) target loci, (b) selecting one or more CRISPR-Cas system functionalities, (c) optionally selecting one or more modes of delivery, and preparing, developing, or designing a CRISPR-Cas system selected based on steps (a)-(c).

In certain embodiments, CRISPR-Cas system functionality comprises genomic mutation. In certain embodiments, CRISPR-Cas system functionality comprises single genomic mutation. In certain embodiments, CRISPR-Cas system functionality comprises multiple genomic mutation. In certain embodiments, CRISPR-Cas system functionality comprises gene knockout. In certain embodiments, CRISPR-Cas system functionality comprises single gene knockout. In certain embodiments, CRISPR-Cas system functionality comprises multiple gene knockout. In certain embodiments, CRISPR-Cas system functionality comprises gene correction. In certain embodiments, CRISPR-Cas system functionality comprises single gene correction. In certain embodiments, CRISPR-Cas system functionality comprises multiple gene correction. In certain embodiments, CRISPR-Cas system functionality comprises genomic region correction. In certain embodiments, CRISPR-Cas system functionality comprises single genomic region correction. In certain embodiments, CRISPR-Cas system functionality comprises multiple genomic region correction. In certain embodiments, CRISPR-Cas system functionality comprises gene deletion. In certain embodiments, CRISPR-Cas system functionality comprises single gene deletion. In certain embodiments, CRISPR-Cas system functionality comprises multiple gene deletion. In certain embodiments, CRISPR-Cas system functionality comprises genomic region deletion. In certain embodiments, CRISPR-Cas system functionality comprises single genomic region deletion. In certain embodiments, CRISPR-Cas system functionality comprises multiple genomic region deletion. In certain embodiments, CRISPR-Cas system functionality comprises modulation of gene or genomic region functionality. In certain embodiments, CRISPR-Cas system functionality comprises modulation of single gene or genomic region functionality. In certain embodiments, CRISPR-Cas system functionality comprises modulation of multiple gene or genomic region functionality. In certain embodiments, CRISPR-Cas system functionality comprises gene or genomic region functionality, such as gene or genomic region activity. In certain embodiments, CRISPR-Cas system functionality comprises single gene or genomic region functionality, such as gene or genomic region activity. In certain embodiments, CRISPR-Cas system functionality comprises multiple gene or genomic region functionality, such as gene or genomic region activity. In certain embodiments, CRISPR-Cas system functionality comprises modulation gene activity or accessibility optionally leading to transcriptional and/or epigenetic gene or genomic region activation or gene or genomic region silencing. In certain embodiments, CRISPR-Cas system functionality comprises modulation single gene activity or accessibility optionally leading to transcriptional and/or epigenetic gene or genomic region activation or gene or genomic region silencing. In certain embodiments, CRISPR-Cas system functionality comprises modulation multiple gene activity or accessibility optionally leading to transcriptional and/or epigenetic gene or genomic region activation or gene or genomic region silencing.

The methods as described herein may further involve selection of the CRISPR-Cas system mode of delivery. In certain embodiments, gRNA (and tracr, if and where needed, optionally provided as a sgRNA) and/or CRISPR effector protein are or are to be delivered. In certain embodiments, gRNA (and tracr, if and where needed, optionally provided as a sgRNA) and/or CRISPR effector mRNA are or are to be delivered. In certain embodiments, gRNA (and tracr, if and where needed, optionally provided as a sgRNA) and/or CRISPR effector provided in a DNA-based expression system are or are to be delivered. In certain embodiments, delivery of the individual CRISPR-Cas system components comprises a combination of the above modes of delivery. In certain embodiments, delivery comprises delivering gRNA and/or CRISPR effector protein, delivering gRNA and/or CRISPR effector mRNA, or delivering gRNA and/or CRISPR effector as a DNA based expression system.

Accordingly, in an aspect, the invention relates to a method as described herein, comprising selection of one or more (therapeutic) target, selecting CRISPR-Cas system functionality, selecting CRISPR-Cas system mode of delivery, and optimization of selected parameters or variables associated with the CRISPR-Cas system and/or its functionality.

The methods as described herein may further involve selection of the CRISPR-Cas system delivery vehicle and/or expression system. Delivery vehicles and expression systems are described herein elsewhere. By means of example, delivery vehicles of nucleic acids and/or proteins include nanoparticles, liposomes, etc. Delivery vehicles for DNA, such as DNA-based expression systems include for instance biolistics, viral based vector systems (e.g. adenoviral, AAV, lentiviral), etc. the skilled person will understand that selection of the mode of delivery, as well as delivery vehicle or expression system may depend on for instance the cell or tissues to be targeted. In certain embodiments, a delivery vehicle and/or expression system for delivering the CRISPR-Cas systems or components thereof comprises liposomes, lipid particles, nanoparticles, biolistics, or viral-based expression/delivery systems.

Accordingly, in an aspect, the invention relates to a method as described herein, comprising selection of one or more (therapeutic) target, selecting CRISPR-Cas system functionality, selecting CRISPR-Cas system mode of delivery, selecting CRISPR-Cas system delivery vehicle or expression system, and optimization of selected parameters or variables associated with the CRISPR-Cas system and/or its functionality.

Optimization of selected parameters or variables in the methods as described herein may result in optimized or improved CRISPR-Cas system, such as CRISPR-Cas system based therapy or therapeutic, specificity, efficacy, and/or safety. In certain embodiments, one or more of the following parameters or variables are taken into account, are selected, or are optimized in the methods of the invention as described herein: CRISPR effector specificity, gRNA specificity, CRISPR-Cas complex specificity, PAM restrictiveness, PAM type (natural or modified), PAM nucleotide content, PAM length, CRISPR effector activity, gRNA activity, CRISPR-Cas complex activity, target cleavage efficiency, target site selection, target sequence length, ability of effector protein to access regions of high chromatin accessibility, degree of uniform enzyme activity across genomic targets, epigenetic tolerance, mismatch/budge tolerance, CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector protein size, CRISPR effector expression level, gRNA expression level, CRISPR-Cas complex expression level, CRISPR effector spatiotemporal expression, gRNA spatiotemporal expression, CRISPR-Cas complex spatiotemporal expression.

In certain embodiments, selecting one or more CRISP-Cas system functionalities comprises selecting one or more of an optimal effector protein, an optimal guide RNA, or both.

In certain embodiments, selecting an optimal effector protein comprises optimizing one or more of effector protein type, size, PAM specificity, effector protein stability, immunogenicity or toxicity, functional specificity, and efficacy, or other CRISPR effector associated parameters or variables as described herein elsewhere.

In certain embodiments, the effector protein is a naturally occurring or modified effector protein.

In certain embodiments, the modified effector protein is a nickase, a deaminase, or a deactivated effector protein.

In certain embodiments, optimizing size comprises selecting a protein effector having a minimal size.

In certain embodiments, optimizing a PAM specificity comprises selecting an effector protein having a modified PAM specificity.

In certain embodiments, optimizing effector protein stability comprises selecting an effector protein having a short half-life while maintaining sufficient activity, such as by selecting an appropriate CRISPR effector orthologue having a specific half-life or stability.

In certain embodiments, optimizing immunogenicity or toxicity comprises minimizing effector protein immunogenicity or toxicity by protein modifications.

In certain embodiments, optimizing functional specific comprises selecting a protein effector with reduced tolerance of mismatches and/or bulges between the guide RNA and one or more target loci.

In certain embodiments, optimizing efficacy comprises optimizing overall efficiency, epigenetic tolerance, or both.

In certain embodiments, maximizing overall efficiency comprises selecting an effector protein with uniform enzyme activity across target loci with varying chromatin complexity, selecting an effector protein with enzyme activity limited to areas of open chromatin accessibility.

In certain embodiments, chromatin accessibility is measured using one or more of ATAC-seq, or a DNA-proximity ligation assay.

In certain embodiments, optimizing epigenetic tolerance comprises optimizing methylation tolerance, epigenetic mark competition, or both.

In certain embodiments, optimizing methylation tolerance comprises selecting an effector protein that modify methylated DNA.

In certain embodiments, optimizing epigenetic tolerance comprises selecting an effector protein unable to modify silenced regions of a chromosome, selecting an effector protein able to modify silenced regions of a chromosome, or selecting target loci not enriched for epigenetic markers.

In certain embodiments, selecting an optimized guide RNA comprises optimizing gRNA stability, gRNA immunogenicity, or both, or other gRNA associated parameters or variables as described herein elsewhere.

In certain embodiments, optimizing gRNA stability and/or gRNA immunogenicity comprises RNA modification, or other gRNA associated parameters or variables as described herein elsewhere. In certain embodiments, the modification comprises removing 1-3 nucleotides form the 3' end of a target complementarity region of the gRNA. In certain embodiments, modification comprises an extended gRNA and/or trans RNA/DNA element that create stable structures in the gRNA that compete with gRNA base pairing at a target of off-target loci, or extended complimentary nucleotides between the gRNA and target sequence, or both.

In certain embodiments, the mode of delivery comprises delivering gRNA and/or CRISPR effector protein, delivering gRNA and/or CRISPR effector mRNA, or delivery gRNA and/or CRISPR effector as a DNA based expression system. In certain embodiments, the mode of delivery further comprises selecting a delivery vehicle and/or expression systems from the group consisting of liposomes, lipid particles, nanoparticles, biolistics, or viral-based expression/delivery systems. In certain embodiments, expression is spatiotemporal expression is optimized by choice of conditional and/or inducible expression systems, including controllable CRISPR effector activity optionally a destabilized CRISPR effector and/or a split CRISPR effector, and/or cell- or tissue-specific expression system.

The above described parameters or variables, as well as means for optimization are described herein elsewhere. By means of example, and without limitation, parameter or variable optimization may be achieved as follows. CRISPR effector specificity may be optimized by selecting the most specific CRISPR effector. This may be achieved for instance by selecting the most specific CRISPR effector orthologue or by specific CRISPR effector mutations which increase specificity. gRNA specificity may be optimized by selecting the most specific gRNA. This may be achieved for instance by selecting gRNA having low homology, i.e. at least one or preferably more, such as at least 2, or preferably at least 3, mismatches to off-target sites. CRISPR-Cas complex specificity may be optimized by increasing CRISPR effector specificity and/or gRNA specificity as above. PAM restrictiveness may be optimized by selecting a CRISPR effector having to most restrictive PAM recognition. This may be achieved for instance by selecting a CRISPR effector orthologue having more restrictive PAM recognition or by specific CRISPR effector mutations which increase or alter PAM restrictiveness. PAM type may be optimized for instance by selecting the appropriate CRISPR effector, such as the appropriate CRISPR effector recognizing a desired PAM type. The CRISPR effector or PAM type may be naturally occurring or may for instance be optimized based on CRISPR effector mutants having an altered PAM recognition, or PAM recognition repertoire. PAM nucleotide content may for instance be optimized by selecting the appropriate CRISPR effector, such as the appropriate CRISPR effector recognizing a desired PAM nucleotide content. The CRISPR effector or PAM type may be naturally occurring or may for instance be optimized based on CRISPR effector mutants having an altered PAM recognition, or PAM recognition repertoire. PAM length may for instance be optimized by selecting the appropriate CRISPR effector, such as the appropriate CRISPR effector recognizing a desired PAM nucleotide length. The CRISPR effector or PAM type may be naturally occurring or may for instance be optimized based on CRISPR effector mutants having an altered PAM recognition, or PAM recognition repertoire. Target length or target sequence length may for instance be optimized by selecting the appropriate CRISPR effector, such as the appropriate CRISPR effector recognizing a desired target or target sequence nucleotide length. Alternatively, or in addition, the target (sequence) length may be optimized by providing a target having a length deviating from the target (sequence) length typically associated with the CRISPR effector, such as the naturally occurring CRISPR effector. The CRISPR effector or target (sequence) length may be naturally occurring or may for instance be optimized based on CRISPR effector mutants having an altered target (sequence) length recognition, or target (sequence) length recognition repertoire. For instance, increasing or decreasing target (sequence) length may influence target recognition and/or off-target recognition. CRISPR effector activity may be optimized by selecting the most active CRISPR effector. This may be achieved for instance by selecting the most active CRISPR effector orthologue or by specific CRISPR effector mutations which increase activity. The ability of the CRISPR effector protein to access regions of high chromatin accessibility, may be optimized by selecting the appropriate CRISPR effector or mutant thereof, and may take into account the size of the CRISPR effector, charge, or other dimensional variables etc. The degree of uniform CRISPR effector activity may be optimized by selecting the appropriate CRISPR effector or mutant thereof, and may take into account CRISPR effector specificity and/or activity, PAM specificity, target length, mismatch tolerance, epigenetic tolerance, CRISPR effector and/or gRNA stability and/or half-life, CRISPR effector and/or gRNA immunogenicity and/or toxicity, etc. gRNA activity may be optimized by selecting the most active gRNA. This may be achieved for instance by increasing gRNA stability through RNA modification. CRISPR-Cas complex activity may be optimized by increasing CRISPR effector activity and/or gRNA activity as above. The target site selection may be optimized by selecting the optimal position of the target site within a gene, locus or other genomic region. The target site selection may be optimized by optimizing target location comprises selecting a target sequence with a gene, locus, or other genomic region having low variability. This may be achieved for instance by selecting a target site in an early and/or conserved exon or domain (i.e. having low variability, such as polymorphisms, within a population). Alternatively, the target site may be selected by minimization of off-target effects (e.g. off-targets qualified as having 1-5, 1-4, or preferably 1-3 mismatches compared to target and/or having one or more PAM mismatches, such as distal PAM mismatches), preferably also taking into account variability within a population. CRISPR effector stability may be optimized by selecting CRISPR effector having appropriate half-life, such as preferably a short half-life while still capable of maintaining sufficient activity. This may be achieved for instance by selecting an appropriate CRISPR effector orthologue having a specific half-life or by specific CRISPR effector mutations or modifications which affect half-life or stability, such as inclusion (e.g. fusion) of stabilizing or destabilizing domains or sequences. CRISPR effector mRNA stability may be optimized by increasing or decreasing CRISPR effector mRNA stability. This may be achieved for instance by increasing or decreasing CRISPR effector mRNA stability through mRNA modification. gRNA stability may be optimized by increasing or decreasing gRNA stability. This may be achieved for instance by increasing or decreasing gRNA stability through RNA modification. CRISPR-Cas complex stability may be optimized by increasing or decreasing CRISPR effector stability and/or gRNA stability as above. CRISPR effector protein or mRNA immunogenicity or toxicity may be optimized by decreasing CRISPR effector protein or mRNA immunogenicity or toxicity. This may be achieved for instance by mRNA or protein modifications. Similarly, in case of DNA based expression systems, DNA immunogenicity or toxicity may be decreased. gRNA immunogenicity or toxicity may be optimized by decreasing gRNA immunogenicity or toxicity. This may be achieved for instance by gRNA modifications. Similarly, in case of DNA based expression systems, DNA immunogenicity or toxicity may be decreased. CRISPR-Cas complex immunogenicity or toxicity may be optimized by decreasing CRISPR effector immunogenicity or toxicity and/or gRNA immunogenicity or toxicity as above, or by selecting the least immunogenic or toxic CRISPR effector/gRNA combination. Similarly, in case of DNA based expression systems, DNA immunogenicity or toxicity may be decreased. CRISPR effector protein or mRNA dose or titer may be optimized by selecting dosage or titer to minimize toxicity and/or maximize specificity and/or efficacy. gRNA dose or titer may be optimized by selecting dosage or titer to minimize toxicity and/or maximize specificity and/or efficacy. CRISPR-Cas complex dose or titer may be optimized by selecting dosage or titer to minimize toxicity and/or maximize specificity and/or efficacy. CRISPR effector protein size may be optimized by selecting minimal protein size to increase efficiency of delivery, in particular for virus mediated delivery. CRISPR effector, gRNA, or CRISPR-Cas complex expression level may be optimized by limiting (or extending) the duration of expression and/or limiting (or increasing) expression level. This may be achieved for instance by using self-inactivating CRISPR-Cas systems, such as including a self-targeting (e.g. CRISPR effector targeting) gRNA, by using viral vectors having limited expression duration, by using appropriate promoters for low (or high) expression levels, by combining different delivery methods for individual CRISP-Cas system components, such as virus mediated delivery of CRISPR-effector encoding nucleic acid combined with non-virus mediated delivery of gRNA, or virus mediated delivery of gRNA combined with non-virus mediated delivery of CRISPR effector protein or mRNA. CRISPR effector, gRNA, or CRISPR-Cas complex spatiotemporal expression may be optimized by appropriate choice of conditional and/or inducible expression systems, including controllable CRISPR effector activity optionally a destabilized CRISPR effector and/or a split CRISPR effector, and/or cell- or tissue-specific expression systems.

In an aspect, the invention relates to a method as described herein, comprising selection of one or more (therapeutic) target, selecting CRISPR-Cas system functionality, selecting CRISPR-Cas system mode of delivery, selecting CRISPR-Cas system delivery vehicle or expression system, and optimization of selected parameters or variables associated with the CRISPR-Cas system and/or its functionality, optionally wherein the parameters or variables are one or more selected from CRISPR effector specificity, gRNA specificity, CRISPR-Cas complex specificity, PAM restrictiveness, PAM type (natural or modified), PAM nucleotide content, PAM length, CRISPR effector activity, gRNA activity, CRISPR-Cas complex activity, target cleavage efficiency, target site selection, target sequence length, ability of effector protein to access regions of high chromatin accessibility, degree of uniform enzyme activity across genomic targets, epigenetic tolerance, mismatch/budge tolerance, CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector protein size, CRISPR effector expression level, gRNA expression level, CRISPR-Cas complex expression level, CRISPR effector spatiotemporal expression, gRNA spatiotemporal expression, CRISPR-Cas complex spatiotemporal expression.

In an aspect, the invention relates to a method as described herein, comprising optionally selecting one or more (therapeutic) target, optionally selecting one or more CRISPR-Cas system functionality, optionally selecting one or more CRISPR-Cas system mode of delivery, optionally selecting one or more CRISPR-Cas system delivery vehicle or expression system, and optimization of selected parameters or variables associated with the CRISPR-Cas system and/or its functionality, wherein specificity, efficacy, and/or safety are optimized, and optionally wherein optimization of specificity comprises optimizing one or more parameters or variables selected from CRISPR effector specificity, gRNA specificity, CRISPR-Cas complex specificity, PAM restrictiveness, PAM type (natural or modified), PAM nucleotide content, PAM length, wherein optimization of efficacy comprises optimizing one or more parameters or variables selected from CRISPR effector activity, gRNA activity, CRISPR-Cas complex activity, target cleavage efficiency, target site selection, target sequence length, CRISPR effector protein size, ability of effector protein to access regions of high chromatin accessibility, degree of uniform enzyme activity across genomic targets, epigenetic tolerance, mismatch/budge tolerance, and wherein optimization of safety comprises optimizing one or more parameters or variables selected from CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector expression level, gRNA expression level, CRISPR-Cas complex expression level, CRISPR effector spatiotemporal expression, gRNA spatiotemporal expression, CRISPR-Cas complex spatiotemporal expression.

In an aspect, the invention relates to a method as described herein, comprising selecting one or more (therapeutic) target, selecting one or more CRISPR-Cas system functionality, selecting one or more CRISPR-Cas system mode of delivery, selecting one or more CRISPR-Cas system delivery vehicle or expression system, and optimization of selected parameters or variables associated with the CRISPR-Cas system and/or its functionality, wherein specificity, efficacy, and/or safety are optimized, and optionally wherein optimization of specificity comprises optimizing one or more parameters or variables selected from CRISPR effector specificity, gRNA specificity, CRISPR-Cas complex specificity, PAM restrictiveness, PAM type (natural or modified), PAM nucleotide content, PAM length, wherein optimization of efficacy comprises optimizing one or more parameters or variables selected from CRISPR effector activity, gRNA activity, CRISPR-Cas complex activity, target cleavage efficiency, target site selection, target sequence length, CRISPR effector protein size, ability of effector protein to access regions of high chromatin accessibility, degree of uniform enzyme activity across genomic targets, epigenetic tolerance, mismatch/budge tolerance, and wherein optimization of safety comprises optimizing one or more parameters or variables selected from CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector expression level, gRNA expression level, CRISPR-Cas complex expression level, CRISPR effector spatiotemporal expression, gRNA spatiotemporal expression, CRISPR-Cas complex spatiotemporal expression.

In an aspect, the invention relates to a method as described herein, comprising optimization of selected parameters or variables associated with the CRISPR-Cas system and/or its functionality, wherein specificity, efficacy, and/or safety are optimized, and optionally wherein optimization of specificity comprises optimizing one or more parameters or variables selected from CRISPR effector specificity, gRNA specificity, CRISPR-Cas complex specificity, PAM restrictiveness, PAM type (natural or modified), PAM nucleotide content, PAM length, wherein optimization of efficacy comprises optimizing one or more parameters or variables selected from CRISPR effector activity, gRNA activity, CRISPR-Cas complex activity, target cleavage efficiency, target site selection, target sequence length, CRISPR effector protein size, ability of effector protein to access regions of high chromatin accessibility, degree of uniform enzyme activity across genomic targets, epigenetic tolerance, mismatch/budge tolerance, and wherein optimization of safety comprises optimizing one or more parameters or variables selected from CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector expression level, gRNA expression level, CRISPR-Cas complex expression level, CRISPR effector spatiotemporal expression, gRNA spatiotemporal expression, CRISPR-Cas complex spatiotemporal expression.

It will be understood that the parameters or variables to be optimized as well as the nature of optimization may depend on the (therapeutic) target, the CRISPR-Cas system functionality, the CRISPR-Cas system mode of delivery, and/or the CRISPR-Cas system delivery vehicle or expression system.

In an aspect, the invention relates to a method as described herein, comprising optimization of gRNA specificity at the population level. Preferably, said optimization of gRNA specificity comprises minimizing gRNA target site sequence variation across a population and/or minimizing gRNA off-target incidence across a population.

In an aspect, the invention relates to a method for developing or designing a CRISPR-Cas system, optionally a CRISPR-Cas system based therapy or therapeutic, comprising (a) selecting for a (therapeutic) locus of interest gRNA target sites, wherein said target sites have minimal sequence variation across a population, and from said selected target sites subselecting target sites, wherein a gRNA directed against said target sites recognizes a minimal number of off-target sites across said population, or (b) selecting for a (therapeutic) locus of interest gRNA target sites, wherein said target sites have minimal sequence variation across a population, or selecting for a (therapeutic) locus of interest gRNA target sites, wherein a gRNA directed against said target sites recognizes a minimal number of off-target sites across said population, and optionally estimating the number of (sub)selected target sites needed to treat or otherwise modulate or manipulate a population, optionally validating one or more of the (sub)selected target sites for an individual subject, optionally designing one or more gRNA recognizing one or more of said (sub)selected target sites.

In an aspect, the invention relates to a method for developing or designing a gRNA for use in a CRISPR-Cas system, optionally a CRISPR-Cas system based therapy or therapeutic, comprising (a)
selecting for a (therapeutic) locus of interest gRNA target sites, wherein said target sites have minimal sequence variation across a population, and from said selected target sites subselecting target sites, wherein a gRNA directed against said target sites recognizes a minimal number of off-target sites across said population, or (b) selecting for a (therapeutic) locus of interest gRNA target sites, wherein said target sites have minimal sequence variation across a population, or selecting for a (therapeutic) locus of interest gRNA target sites, wherein a gRNA directed against said target sites recognizes a minimal number of off-target sites across said population, and optionally estimating the number of (sub)selected target sites needed to treat or otherwise modulate or manipulate a population, optionally validating one or more of the (sub)selected target sites for an individual subject, optionally designing one or more gRNA recognizing one or more of said (sub)selected target sites.

In an aspect, the invention relates to a method for developing or designing a CRISPR-Cas system, optionally a CRISPR-Cas system based therapy or therapeutic in a population, comprising (a) selecting for a (therapeutic) locus of interest gRNA target sites, wherein said target sites have minimal sequence variation across a population, and from said selected target sites subselecting target sites, wherein a gRNA directed against said target sites recognizes a minimal number of off-target sites across said population, or (b) selecting for a (therapeutic) locus of interest gRNA target sites, wherein said target sites have minimal sequence variation across a population, or selecting for a (therapeutic)

locus of interest gRNA target sites, wherein a gRNA directed against said target sites recognizes a minimal number of off-target sites across said population, and optionally estimating the number of (sub)selected target sites needed to treat or otherwise modulate or manipulate a population, optionally validating one or more of the (sub)selected target sites for an individual subject, optionally designing one or more gRNA recognizing one or more of said (sub)selected target sites.

In an aspect, the invention relates to a method for developing or designing a gRNA for use in a CRISPR-Cas system, optionally a CRISPR-Cas system based therapy or therapeutic in a population, comprising (a) selecting for a locus of interest gRNA target sites, wherein said target sites have minimal sequence variation across a population, and from said selected target sites subselecting target sites, wherein a gRNA directed against said target sites recognizes a minimal number of off-target sites across said population, or (b) selecting for a (therapeutic) locus of interest gRNA target sites, wherein said target sites have minimal sequence variation across a population, or selecting for a (therapeutic) locus of interest gRNA target sites, wherein a gRNA directed against said target sites recognizes a minimal number of off-target sites across said population, and optionally estimating the number of (sub)selected target sites needed to treat or otherwise modulate or manipulate a population, optionally validating one or more of the (sub)selected target sites for an individual subject, optionally designing one or more gRNA recognizing one or more of said (sub)selected target sites.

In a further aspect, the invention relates to method for developing or designing a CRISPR-Cas system, such as a CRISPR-Cas system based therapy or therapeutic, optionally in a population; or for developing or designing a gRNA for use in a CRISPR-Cas system, optionally a CRISPR-Cas system based therapy or therapeutic, optionally in a population, comprising: selecting a set of target sequences for one or more loci in a target population, wherein the target sequences do not contain variants occurring above a threshold allele frequency in the target population (i.e. platinum target sequences); removing from said selected (platinum) target sequences any target sequences having high frequency off-target candidates (relative to other (platinum) targets in the set) to define a final target sequence set; preparing one or more, such as a set of CRISPR-Cas systems based on the final target sequence set, optionally wherein a number of CRISP-Cas systems prepared is based (at least in part) on the size of a target population.

In certain embodiments, off-target candidates/off-targets, PAM restrictiveness, target cleavage efficiency, or effector protein specificity is identified or determined using a sequencing-based double-strand break (DSB) detection assay, such as described herein elsewhere. In certain embodiments, off-target candidates/off-targets are identified or determined using a sequencing-based double-strand break (DSB) detection assay, such as described herein elsewhere. In certain embodiments, off-targets, or off target candidates have at least 1, preferably 1-3, mismatches or (distal) PAM mismatches, such as 1 or more, such as 1, 2, 3, or more (distal) PAM mismatches. In certain embodiments, sequencing-based DSB detection assay comprises labeling a site of a DSB with an adapter comprising a primer binding site, labeling a site of a DSB with a barcode or unique molecular identifier, or combination thereof, as described herein elsewhere.

It will be understood that the guide sequence of the gRNA is 100% complementary to the target site, i.e. does not comprise any mismatch with the target site. It will be further understood that "recognition" of an (off-)target site by a gRNA presupposes CRISPR-Cas system functionality, i.e. an (off-)target site is only recognized by a gRNA if binding of the gRNA to the (off-)target site leads to CRISPR-Cas system activity (such as induction of single or double strand DNA cleavage, transcriptional modulation, etc).

In certain embodiments, the target sites having minimal sequence variation across a population are characterized by absence of sequence variation in at least 99%, preferably at least 99.9%, more preferably at least 99.99% of the population. In certain embodiments, optimizing target location comprises selecting target sequences or loci having an absence of sequence variation in at least 99%, %, preferably at least 99.9%, more preferably at least 99.99% of a population. These targets are referred to herein elsewhere also as "platinum targets". In certain embodiments, said population comprises at least 1000 individuals, such as at least 5000 individuals, such as at least 10000 individuals, such as at least 50000 individuals.

In certain embodiments, the off-target sites are characterized by at least one mismatch between the off-target site and the gRNA. In certain embodiments, the off-target sites are characterized by at most five, preferably at most four, more preferably at most three mismatches between the off-target site and the gRNA. In certain embodiments, the off-target sites are characterized by at least one mismatch between the off-target site and the gRNA and by at most five, preferably at most four, more preferably at most three mismatches between the off-target site and the gRNA.

In certain embodiments, said minimal number of off-target sites across said population is determined for high-frequency haplotypes in said population. In certain embodiments, said minimal number of off-target sites across said population is determined for high-frequency haplotypes of the off-target site locus in said population. In certain embodiments, said minimal number of off-target sites across said population is determined for high-frequency haplotypes of the target site locus in said population. In certain embodiments, the high-frequency haplotypes are characterized by occurrence in at least 0.1% of the population.

In certain embodiments, the number of (sub)selected target sites needed to treat a population is estimated based on based low frequency sequence variation, such as low frequency sequence variation captured in large scale sequencing datasets. In certain embodiments, the number of (sub)selected target sites needed to treat a population of a given size is estimated.

In certain embodiments, the method further comprises obtaining genome sequencing data of a subject to be treated; and treating the subject with a CRISPR-Cas system selected from the set of CRISPR-Cas systems, wherein the CRISPR-Cas system selected is based (at least in part) on the genome sequencing data of the individual.

In certain embodiments, the ((sub)selected) target is validated by genome sequencing, preferably whole genome sequencing.

In certain embodiments, target sequences or loci as described herein are (further) selected based on optimization of one or more parameters consisting of; PAM type (natural or modified), PAM nucleotide content, PAM length, target sequence length, PAM restrictiveness, target cleavage efficiency, and target sequence position within a gene, a locus or other genomic region.

In certain embodiments, target sequences or loci as described herein are (further) selected based on optimization of one or more of target loci location, target length, target specificity, and PAM characteristics. As used herein, PAM characteristics may comprise for instance PAM sequence, PAM length, and/or PAM GC contents. In certain embodiments, optimizing PAM characteristics comprises optimizing nucleotide content of a PAM. In certain embodiments, optimizing nucleotide content of PAM is selecting a PAM with a motif that maximizes abundance in the one or more target loci, minimizes mutation frequency, or both. Minimizing mutation frequency can for instance be achieved by selecting PAM sequences devoid of or having low or minimal CpG.

In certain embodiments, the effector protein for each CRISPR-Cas system in the set of CRISPR-Cas systems is selected based on optimization of one or more parameters selected from the group consisting of; effector protein size, ability of effector protein to access regions of high chromatin accessibility, degree of uniform enzyme activity across genomic targets, epigenetic tolerance, mismatch/budge tolerance, effector protein specificity, effector protein stability or half-life, effector protein immunogenicity or toxicity.

In certain embodiments, optimizing target (sequence) length comprises selecting a target sequence within one or more target loci between 5 and 25 nucleotides. In certain embodiments, a target sequence is 20 nucleotides.

In certain embodiments, optimizing target specificity comprises selecting targets loci that minimize off-target candidates.

In certain embodiments, the gRNA is a tru gRNA, an escorted gRNA, or a protected gRNA.

It will be understood that the CRISPR-Cas systems according to the invention as described herein, such as the CRISPR-Cas systems for use in the methods according to the invention as described herein, may be suitably used for any type of application known for CRISPR-Cas systems, preferably in eukaryotes. In certain aspects, the application is therapeutic, preferably therapeutic in a eukaryote organism, such as including but not limited to animals (including human), plants, algae, fungi (including yeasts), etc. Alternatively, or in addition, in certain aspects, the application may involve accomplishing or inducing one or more particular traits or characteristics, such as genotypic and/or phenotypic traits or characteristics, as also described herein elsewhere.

For the invention described herein, the following criteria may be taken into account when optimizing the respective parameters or variables.

CRISPR Effector Choice
1. Size:

Currently, CRISPR single nuclease effectors demonstrating high efficiency mammalian genome editing range from 1053 amino acids (SaCas9) to 1368 amino acids (SpCas9), (AsCpf1, 1307aa; and LbCpf1, 1246). While smaller orthologs of Cas9 do exist and cleave DNA with high efficiency in vitro, Cas9 orthologs smaller than SaCas9 have shown diminished mammalian DNA cleavage efficiency. The large size of current single effector CRISPR nucleases is challenging for both nanoparticle protein delivery and viral vector delivery strategies. For protein delivery, payload per particle is a function of 3-D protein size, and for viral delivery of single effectors, large gene size limits flexibility for multiplexing or use of large cell-type specific promoters. Considerations relating to delivery are described detailed further herein below.

2. Protein Search:

The ability of the CRISPR effector to access regions of high chromatin complexity can be viewed in two ways 1) this increases the versatility of the CRISPR effector as a tool for genome editing or 2) this may be undesirable due to cellular dysregulation resulting from perturbation of the genomic structure of cells contacted with the CRISPR effector. There have been reports that the most active Cas9 guides are ones that target low nucleosomal occupancy positions: elifesciences.orgicontent/5/e12677, and elifesciences.orgicontent/5/e13450; however, over a longer time scale, cleavage can still occur (also cleavage can occur during replication when the nucleosomal occupancy is moved) Considerations relating to choice of Cpf1 and modifications thereof are described detailed further herein below.

3. Efficacy:

Overall efficiency: robust and uniform enzyme activity across genomic targets in regions of open chromatin is generally desirable for all single effector nucleases. On the other hand, robust and uniform enzyme activity across genomic targets with varying chromatin complexity and epigenetic marks may not be desirable for research and therapeutic applications. It has been shown that Cas9 shows robust cleavage of methylated DNA, and this increases the utility of the enzyme. On the other hand, CRISPR effector binding or cleavage at loci enriched for epigenetic marks may dysregulate cellular processes. A further aspect to be considered is whether enzymes that do not disturb chromatin structure are desirable. If cleaving a locus in a terminally differentiated cell, it may be desirable to utilize enzymes that are not capable of penetrating silenced regions of the genome. Alternatively, when cleaving a locus in a precursor of a differentiated cell type, then it may be advantageous to be able to penetrate regions of the genome inactive at the time of editing.

4. Specificity: Mismatch/Bulge Tolerance:

Naturally occurring Cas9 orthologs: naturally occurring CRISPR effectors show tolerance of mismatches or bulges between the RNA guide and DNA target. This tolerance is generally undesirable for therapeutic applications. For therapeutic applications, patients should be individually screened for perfect target guide RNA complementarity, and tolerance of bulges and mismatches will only increase the likelihood of off-target DNA cleavage. High specificity engineered variants have been developed, such as eSpCas9 and Cas9-HF1 for Cas9; these variants show decreased tolerance of mismatches between DNA targets and the RNA guide (relevant to mismatches in approximately the PAM distal 12-14 nucleotides of the guide RNA given 20nt of guide RNA target complementarity).

5. PAM Choice:

Natural PAM vs. Modified PAM: Targets for each single effector CRISPR DNA endonuclease discovered so far require a protospacer adjacent motif (PAM) flanking the guide RNA complimentary region of the target. For the DNA endonucleases discovered so far, the PAM motifs have at least 2 nucleotides of specificity, such as 2, 3, 4, 5 or more nucleotides of specificity, such as 2-4 or 2-5 nucleotides of specificity, which curtails the fraction of possible targets in the genome that can be cleaved with a single natural enzyme. Mutation of naturally occurring DNA endonucleases has resulted in protein variants with modified PAM specificities. Cumulatively, the more such variants exist for a given protein targeting different PAMs, the greater the density of genomic targets are available for use in therapeutic design (See population efficacy). Nucleotide content: Nucleotide content of PAMs can affect what fraction of the genome can be targeted with an individual protein due to differences in the abundance of a particular motif in the genome or in a specific therapeutic locus of the genome. Additionally, nucleotide content can affect PAM mutation frequencies in the genome (See population efficacy). Cpf1 proteins with altered PAM specificity can address this issue (as described further herein). Influence of PAM length/complexity on target specificity: Cas9 interrogates the genome by first binding to a PAM site before attempting to create a stable RNA/DNA duplex by melting the double stranded DNA. Since the complexity of the PAM limits the possible space of targets interrogated, a more complex PAM will have fewer possible sites at which off-target cleavage can occur.

6. crRNA Processing Capabilities of the Enzyme: Multiplexing:

For multiplexing, crRNA processing capabilities are desirable, as a transcript expressed from a single promoter can contain multiple different crRNAs. This transcript is then processed into multiple constituent crRNAs by the protein, and multiplexed editing proceeds for each target specified by the crRNA. On the other hand, the rules for RNA endonucleolytic processing of multi crRNA transcripts into crRNAs are not fully understood. Hence, for therapeutic applications, crRNA processing may be undesirable due to off-target cleavage of endogenous RNA transcripts.

Target Choice

1. Target Length:

Although most protospacer elements observed in naturally occurring Cas9 and Cpf1 CRISPR arrays are longer than 20nt, protospacer complimentary regions of resulting crRNA products are often processed to 20nt (Cas9) or do not confer specificity beyond 20nt (Cpf1). Extension of the target complimentary region of the guide RNA beyond 20nt likely is positioned outside of the footprint of the protein on the guide RNA and is often processed away by exonucleases (See protected guide RNAs for further discussion).

2. Efficiency Screening:

Screening for CRISPR effector efficacy has been performed by studying the efficacy of knockdown of cell surface proteins using different DNA targets. These studies show some evidence that position dependent nucleotide content in CRISPR effector targets and flanking nucleotides affects the efficacy of target cleavage.

3. Specificity Screening:

Unbiased investigation of genome-wide CRISPR nuclease activity suggests that most off-target activity occurs at loci with at most three mismatches to the RNA guide. Current approaches for CRISPR effector target selection rank off-target candidates found in the reference human genome by both the number and position of RNA guide mismatches, with the assumption that loci containing less than 3 mismatches or containing PAM distal mismatches are more likely to be cleaved. However, in a population of individuals, this strategy is complicated by the existence of multiple haplotypes (sets of associated variants), which will contain different positions or numbers of mismatches at candidate off-target sites (See: population safety).

Guide RNA Design

Several technologies have been developed to address different aspects of efficacy and specificity.

1. Tru Guide:

Trimming 1-3 nt off from the 3' end of the target complimentary region of the gRNA often decreases activity at off-target loci containing at least one mismatch to the guide RNA. Likely, with fewer nucleotides of base-pairing between the off-target and gRNA, each mismatch has a greater thermodynamic consequence to the stability of the CRISPR effector-gRNA complex with the off-target DNA. Percentage of successfully cleaved targets may be reduced in using tru guides: i.e., some sites that worked with a 20nt guide may not cut efficiently with a 17nt guide; but the ones that do work with 17nt generally cleavage as efficiently.

2. Protected Guide:

Protected guides utilize an extended guide RNA and/or trans RNA/DNA elements to 1) create stable structures in the sgRNA that compete with sgRNA base-pairing at a target or off-target site or 2) (optionally) extend complimentary nucleotides between the gRNA and target. For extended RNA implementations, secondary structure results from complementarity between the 3' extension of the guide RNA and another target complimentary region of the guide RNA. For trans implementations, DNA or RNA elements bind the extended or normal length guide RNA partially obscuring the target complimentary region of the sgRNA.

Dosage

The dosage of the CRISPR components should take into account the following factors.

1. Target Search:

CRISPR effector/guide RNA-enzyme complexes use 3-D stochastic search to locate targets. Given equal genomic accessibility, the probability of the complex finding an off-target or on-target is similar.

2. Binding (Target Dwell Time):

Once located, the binding kinetics of the complex at an on-target or an off-target with few mismatches differs only slightly. Hence, target search and binding are likely not the rate-limiting steps for DNA cleavage at on-target or off-target loci. ChIP data suggests that complex dwell time does decrease accompanying increasing mismatches between the off-target locus and RNA guide, particularly in the PAM-proximal 'seed' region of the RNA guide.

3. Cutting (Thermodynamic Barrier to Assuming an Active Conformation):

A major rate-limiting step for CRISPR effector enzymatic activity appears to be configuration of the target DNA and guide RNA-protein complex in an active conformation for DNA cleavage. Increasing mismatches at off-target loci decrease the likelihood of the complex achieving an active conformation at off-target loci.

The difference between binding and cutting is why ChIP has very low predictive power as a tool for evaluating the off-target cleavage of Cpf1.

If the probability of finding an off-target or on-target is similar, then the difference in rate of on and off-target cleavage is likely due to the fact that the probability of cleavage at on target sites is greater than off target sites. (See temporal control) The stochastic search means that Cpf1 suggests that an incorrect model is to view Cpf1 as preferentially cleaving the on-target site first and only moving onto off-target sites after on-target cleavage is saturated; instead, all sites are interrogated at random, and the probability of progression to cutting after PAM binding is what differentiates the propensity of on vs. off-target cutting.

4. Repetition in DNA Modification at an Individual Locus:

NHEJ repair of DNA double strand breaks is generally high fidelity (Should find exact error rate). Hence, it is likely that a nuclease must cut an individual locus many times before an error in NHEJ results in an indel at the cut site. The probability of observing an indel is the compounding probability of observing a double strand break based on 1) target search probability, 2) target dwell time, and 3) overcoming the thermodynamic barrier to DNA cleavage.

5. Enzyme Concentration:

Even at very low concentrations, search may still encounter an off-target prior to an on-target. Thereafter, the number and location of mismatches in an off-target, and likely the nucleotide content of the target will influence the likelihood of DNA cleavage.

Thinking about on/off target cleavage in probabilistic terms, each interaction that Cas9 or Cpf1 has with the genome can be thought of as having some probability of successful cleavage. Reducing the dose will reduce the number of effector molecules available for interacting with the genome, and thus will limit the additive probability of repeated interactions at off-target sites.

Temporal and Spatial Control of the CRISPR System

Various technologies have been developed which provide additional options for addressing efficacy, specificity and safety issues. More particularly these options can be used to allow for temporal control. More particularly these technologies allow for temporal/spatial control (as described further herein):

1. Double nickases
2. Escorted guides
3. Split-effector protein
4. "self-inactivating" systems or "governing guides"

In the following, the different variables and how they influence the design of a CRISPR-based editing system are described in more detail.

Specificity—Select Most Specific Guide RNA a. Guide Specificity

While early reports were fairly contradictory on the ability to accurately predict guide RNAs with limited off-target activity, statistical analysis based on a large number of data has made it possible to identify rules governing off-target effects. Doench et al. (Nat Biotechnol. 2016 February; 34(2):184-91) describe the profiling of the off-target activity of thousands of sgRNAs and the development of a metric to predict off-target sites.

Accordingly, in particular embodiments, the methods of the invention involve selecting a guide RNA which, based on statistical analysis, is less likely to generate off-target effects.

b. Guide Complementarity

It is generally envisaged that the degree of complementarity between a guide sequence and its corresponding target sequence should be as high as possible, such as more than about 50%, 60%, 75%, 80%, 85%, 90%, 95%, 97.5%, 99%, or 100%. However, in particular embodiments, a particular concern is reducing off-target interactions, e.g., reducing the guide interacting with a target sequence having low complementarity. It has been shown that certain mutations result in the CRISPR-Cas system being able to distinguish between target and off-target sequences that have greater than 80% to about 95% complementarity, e.g., 83%-84% or 88-89% or 94-95% complementarity (for instance, distinguishing between a target having 18 nucleotides from an off-target of 18 nucleotides having 1, 2 or 3 mismatches). Accordingly, in particular embodiments, the guide is selected such that the degree of complementarity between a guide sequence and its corresponding target sequence is greater than 94.5% or 95% or 95.5% or 96% or 96.5% or 97% or 97.5% or 98% or 98.5% or 99% or 99.5% or 99.9%, or 100%. Off target is less than 100% or 99.9% or 99.5% or 99% or 99% or 98.5% or 98% or 97.5% or 97% or 96.5% or 96% or 95.5% or 95% or 94.5% or 94% or 93% or 92% or 91% or 90% or 89% or 88% or 87% or 86% or 85% or 84% or 83% or 82% or 81% or 80% complementarity between the sequence and the guide, with it advantageous that off target is 100% or 99.9% or 99.5% or 99% or 99% or 98.5% or 98% or 97.5% or 97% or 96.5% or 96% or 95.5% or 95% or 94.5% complementarity between the sequence and the guide.

c. Select Guide/Enzyme Concentration

For minimization of toxicity and off-target effect, it will be important to control the concentration of Cpf1 protein and guide RNA delivered. Optimal concentrations of Cpf1 protein and guide RNA can be determined by testing different concentrations in a cellular or non-human eukaryote animal model and using deep sequencing the analyze the extent of modification at potential off-target genomic loci. For example, for the guide sequence targeting 5'-GAGTCCGAGCAGAAGAAGAA-3' (SEQ ID NO: 23) in the EMX1 gene of the human genome, deep sequencing can be used to assess the level of modification at the following two off-target loci, 1: 5'-GAGTCCTAGCAG-GAGAAGAA-3' (SEQ ID NO: 24) and 2: 5'-GAGTCTAAGCAGAAGAAGAA-3' (SEQ ID NO: 25). The concentration that gives the highest level of on-target modification while minimizing the level of off-target modification should be chosen for in vivo delivery.

Specificity—Select Most Specific Enzyme a. Enzyme Modifications to Enhance Specificity In particular embodiments, a reduction of off-target cleavage is ensured by destabilizing strand separation, more particularly by introducing mutations in the Cpf1 enzyme decreasing the positive charge in the DNA interacting regions (as described herein and further exemplified for Cas9 by Slaymaker et al. 2016 (Science, 1; 351(6268):84-8). In further embodiments, a reduction of off-target cleavage is ensured by introducing mutations into Cpf1 enzyme which affect the interaction between the target strand and the guide RNA sequence, more particularly disrupting interactions between Cpf1 and the phosphate backbone of the target DNA strand in such a way as to retain target specific activity but reduce off-target activity (as described for Cas9 by Kleinstiver et al. 2016, Nature, 28; 529(7587):490-5). In particular embodiments, the off-target activity is reduced by way of a modified Cpf1 wherein both interaction with target strand and non-target strand are modified compared to wild-type Cpf1.

The methods and mutations which can be employed in various combinations to increase or decrease activity and/or specificity of on-target vs. off-target activity, or increase or decrease binding and/or specificity of on-target vs. off-target binding, can be used to compensate or enhance mutations or modifications made to promote other effects. Such mutations or modifications made to promote other effects include mutations or modification to the Cpf1 effector protein and/or mutation or modification made to a guide RNA.

With a similar strategy used to improve Cas9 specificity (Slaymaker et al. 2015 "Rationally engineered Cas9 nucleases with improved specificity"), specificity of Cpf1 can be improved by mutating residues that stabilize the non-targeted DNA strand. This may be accomplished without a crystal structure by using linear structure alignments to predict 1) which domain of Cpf1 binds to which strand of DNA and 2) which residues within these domains contact DNA.

However, this approach may be limited due to poor conservation of Cpf1 with known proteins. Thus it may be desirable to probe the function of all likely DNA interacting amino acids (lysine, histidine and arginine).

Positively charged residues in the RuvC domain are more conserved throughout Cpf1s than those in the Rad50 domain indicating that RuvC residues are less evolutionarily flexible. This suggests that rigid control of nucleic acid binding is needed in this domain (relative to the Rad50 domain). Therefore, it is possible this domain cuts the targeted DNA strand because of the requirement for RNA:DNA duplex stabilization (precedent in Cas9). Furthermore, more arginines are present in the RuvC domain (5% of RuvC residues 904 to 1307 vs 3.8% in the proposed Rad50 domains) suggesting again that RuvC targets one of the DNA strands. Arginines are more involved in binding nucleic acid major and minor grooves (Rohs Nature 2009: rohslab.cmb.usc.edu/Papers/Rohs_etal_Nature.pdf). Major/minor grooves would only be present in a duplex (such as DNA:RNA targeting duplex), further suggesting that RuvC may be involved in cutting.

Based on the structural analysis of the RuvC and Rad50 domains, it can be deduced what the relevant domains look like in Cpf1, and infer which regions and residues may contact DNA. Accordingly, in certain embodiments the Cpf1 enzyme is modified by mutation of one or more residues (in the RuvC domain) including but not limited positions R909, R912, R930, R947, K949, R951, R955, K965, K968, K1000, K1002, R1003, K1009, K1017, K1022, K1029, K1035, K1054, K1072, K1086, R1094, K1095, K1109, K1118, K1142, K1150, K1158, K1159, R1220, R1226, R1242, and/or R1252 with reference to amino acid position numbering of AsCpf1 (*Acidaminococcus* sp. BV3L6). Additionally or alternatively, in certain embodiments, the Cpf1 enzyme is modified by mutation of one or more residues (in the RAD50) domain including but not limited positions K324, K335, K337, R331, K369, K370, R386, R392, R393, K400, K404, K406, K408, K414, K429, K436, K438, K459, K460, K464, R670, K675, R681, K686, K689, R699, K705, R725, K729, K739, K748, and/or K752 with reference to amino acid position numbering of AsCpf1 (*Acidaminococcus* sp. BV3L6).

From these specific observations about AsCpf1 similar residues can be identified in Cpf1 from other species by sequence alignments. In certain embodiments, the Cpf1 enzyme is modified by mutation of one or more residues including but not limited positions R912, T923, R947, K949, R951, R955, K965, K968, K1000, R1003, K1009, K1017, K1022, K1029, K1072, K1086, F1103, R1226, and/or R1252 with reference to amino acid position numbering of AsCpf1 (*Acidaminococcus* sp. BV3L6). In certain embodiments, the enzyme is modified by mutation of one or more residues including but not limited positions R833, R836, K847, K879, K881, R883, R887, K897, K900, K932, R935, K940, K948, K953, K960, K984, K1003, K1017, R1033, R1138, R1165, and/or R1252 with reference to amino acid position numbering of LbCpf1 (*Lachnospiraceae bacterium* ND2006).

b. Selecting Suitable PAM Recognition

The requirement of a protospacer adjacent motif (PAM) of most CRISPR effector proteins, ensures another level of specificity in that only the target which is preceded by the relevant motif for the enzyme, will be cleaved. Thus, in particular embodiments, where available it may be of interest to select an effector protein with a stringent PAM so as to reduce off-target effects. Such an effector protein may be a Cpf1 ortholog or an effector protein having altered specificity.

On the other hand, the use of a Cpf1 effector protein can be limited by its protospacer adjacent motif (PAM), in that it will only be able to robustly cleave target sites preceded by said motif. For instance, the *Acidaminococcus* sp. BV3L6 Cpf1 (AsCpf1), which has been successfully harnessed for genome editing can only cleave target sites precede by a TTTV protospacer adjacent motif (PAM), which limits its practical utility. Where broad applicability is desirable or required for multiplexing, the selection of an effector protein with a different PAM specificity may be of interest. Again, this altered specificity may be found in a Cpf1 ortholog. However, it has been found that the Cpf1 effector protein can be mutated to modify its PAM specificity.

Modification of PAM specificity has been performed by a structure-guided saturation mutagenesis screen to increase the targeting range of Cpf1 (Linyi et al. 2016, BioRxiv, dx.doi.org/10.1101/091611). Two variants of AsCpf1 were engineered with the mutations S542R/K607R and S542R/K548V/N552R that can cleave target sites with TYCV/CCCC and TATV PAMs, respectively, with enhanced activities in vitro and in human cells. Genome-wide assessment of off-target activity indicated that these variants retain a high level of DNA targeting specificity. It was found that by the provision of the additional AsCpf1 effector protein variants, this results in the addition of one cleavage site for every ~8.7 bp in non-repetitive regions of the human genome.

Further Cpf1 mutants are also envisaged herein. In particular embodiments, a mutated Cpf1 is used wherein said mutated Cpf1 comprises one or more mutated amino acid residue at position 11, 12, 13, 14, 15, 16, 17, 34, 36, 39, 40, 43, 46, 47, 50, 54, 57, 58, 111, 126, 127, 128, 129, 130, 131, 132, 133, 134, 135, 136, 157, 158, 159, 160, 161, 162, 163, 164, 165, 166, 167, 168, 169, 170, 171, 172, 173, 174, 175, 176, 177, 178, 532, 533, 534, 535, 536, 537, 538, 539, 540, 541, 542, 543, 544, 545, 546, 547, 548, 549, 550, 551, 552, 553, 554, 555, 556, 565, 566, 567, 568, 569, 570, 571, 572, 573, 574, 575, 592, 593, 594, 595, 596, 597, 598, 599, 600, 601, 602, 603, 604, 605, 606, 607, 608, 609, 610, 611, 612, 613, 614, 615, 616, 617, 618, 619, 620, 626, 627, 628, 629, 630, 631, 632, 633, 634, 635, 636, 637, 638, 642, 643, 644, 645, 646, 647, 648, 649, 651, 652, 653, 654, 655, 656, 676, 679, 680, 682, 683, 684, 685, 686, 687, 688, 689, 690, 691, 692, 693, 707, 711, 714, 715, 716, 717, 718, 719, 720, 721, 722, 739, 765, 768, 769, 773, 777, 778, 779, 780, 781, 782, 783, 784, 785, 786, 871, 872, 873, 874, 875, 876, 877, 878, 879, 880, 881, 882, 883, 884, or 1048; preferably, one or more mutated amino acid residue at position 130, 131, 132, 133, 134, 135, 136, 162, 163, 164, 165, 166, 167, 168, 169, 170, 171, 172, 173, 174, 175, 176, 177, 536, 537, 538, 539, 540, 541, 542, 543, 544, 545, 546, 547, 548, 549, 550, 551, 552, 570, 571, 572, 573, 595, 596, 597, 598, 599, 600, 601, 602, 603, 604, 605, 606, 607, 608, 609, 610, 611, 612, 613, 614, 615, 630, 631, 632, 646, 647, 648, 649, 650, 651, 652, 653, 683, 684, 685, 686, 687, 688, 689, or 690; more preferably one or more mutated amino acid residue at position 539, 542, 547, 548, 550, 551, 552, 167, 604, and/or 607 of AsCpf1, or the corresponding position of an AsCpf1 orthologue, homologue, or variant, preferably mutated amino acid residues at positions 542 or 542 and 607, wherein said mutations preferably are 542R and 607R, such as S542R and K607R; or preferably mutated amino acid residues at positions 542 and 548 (and optionally 552), wherein said mutations preferably are 542R and 548V (and optionally 552R), such as S542R and K548V (and optionally N552R); or at position 532, 538, 542, and/or 595 of LbCpf1, or the corresponding position of an AsCpf1 orthologue, homologue, or variant, preferably mutated amino acid residues at positions 532 or 532 and 595, wherein said mutations preferably are 532R and 595R, such as G532R and K595R; or preferably mutated amino acid residues at positions 532 and 538 (and optionally 542), wherein said mutations preferably are 532R and 538V (and optionally 542R), such as G532R and K538V (and optionally Y542R).

Accordingly, these variants increase the targeting range, providing a useful addition to the CRISPR/Cas genome engineering toolbox. At the same time, the provision of Cpf1 effector proteins with alternative PAM specificity allows for the selection of a particular variant with optimal specificity for a particular target sequence.

System Approaches to Reduce Off-Target Effects:

a. Double Nickase

Alternatively, to minimize the level of toxicity and off-target effect, a Cpf1 nickase can be used with a pair of guide RNAs targeting a site of interest. Guide sequences and strategies to minimize toxicity and off-target effects can be as in WO 2014/093622 (PCT/US2013/074667); or, via mutation as described herein.

The invention thus contemplates methods of using two or more nickases, in particular a dual or double nickase approach. In some aspects and embodiments, a single type FnCpf1, AsCpf1 or LbCpf1 nickase may be delivered, for example a modified FnCpf1, AsCpf1 or LbCpf1 or a modified FnCpf1, AsCpf1 or LbCpf1 nickase as described herein. This results in the target DNA being bound by two FnCpf1 nickases. In addition, it is also envisaged that different orthologs may be used, e.g., an FnCpf1, AsCpf1 or LbCpf1 nickase on one strand (e.g., the coding strand) of the DNA and an ortholog on the non-coding or opposite DNA strand. The ortholog can be, but is not limited to, a Cpf1 nickase such as a AsCpf1 nickase or a LbCpf1 nickase or FnCpf1 nickase. It may be advantageous to use two different orthologs that require different PAMs and may also have different guide requirements, thus allowing a greater deal of control for the user. In certain embodiments, DNA cleavage will involve at least four types of nickases, wherein each type is guided to a different sequence of target DNA, wherein each pair introduces a first nick into one DNA strand and the second introduces a nick into the second DNA strand. In such methods, at least two pairs of single stranded breaks are introduced into the target DNA wherein upon introduction of first and second pairs of single-strand breaks, target sequences between the first and second pairs of single-strand breaks are excised. In certain embodiments, one or both of the orthologs is controllable, i.e. inducible.

b. Escorted Guides

The methods provided herein may also involve the use of escorted Cpf1 CRISPR-Cas systems or complexes, especially such a system involving an escorted Cpf1 CRISPR-Cas system guide. By "escorted" is meant that the Cpf1 CRISPR-Cas system or complex or guide is delivered to a selected time or place within a cell, so that activity of the Cpf1 CRISPR-Cas system or complex or guide is spatially or temporally controlled. For example, the activity and destination of the Cpf1 CRISPR-Cas system or complex or guide may be controlled by an escort RNA aptamer sequence that has binding affinity for an aptamer ligand, such as a cell surface protein or other localized cellular component. Alternatively, the escort aptamer may for example be responsive to an aptamer effector on or in the cell, such as a transient effector, such as an external energy source that is applied to the cell at a particular time. The principle of escorted guides and embodiments thereof are described in detail in WO2016094874 incorporated by reference herein.

Aptamers are biomolecules that can be designed or selected to bind tightly to other ligands, for example using a technique called systematic evolution of ligands by exponential enrichment (SELEX; Tuerk C, Gold L: "Systematic evolution of ligands by exponential enrichment: RNA ligands to bacteriophage T4 DNA polymerase." Science 1990, 249:505-510). Nucleic acid aptamers can for example be selected from pools of random-sequence oligonucleotides, with high binding affinities and specificities for a wide range of biomedically relevant targets, suggesting a wide range of therapeutic utilities for aptamers (Keefe, Anthony D., Supriya Pai, and Andrew Ellington. "Aptamers as therapeutics." Nature Reviews Drug Discovery 9.7 (2010): 537-550). These characteristics also suggest a wide range of uses for aptamers as drug delivery vehicles (Levy-Nissenbaum, Etgar, et al. "Nanotechnology and aptamers: applications in drug delivery." Trends in biotechnology 26.8 (2008): 442-449; and, Hicke B J, Stephens A W. "Escort aptamers: a delivery service for diagnosis and therapy." J Clin Invest 2000, 106:923-928.). Aptamers may also be constructed that function as molecular switches, responding to a que by changing properties, such as RNA aptamers that bind fluorophores to mimic the activity of green fluorescent protein (Paige, Jeremy S., Karen Y. Wu, and Samie R. Jaffrey. "RNA mimics of green fluorescent protein." Science 333.6042 (2011): 642-646). It has also been suggested that aptamers may be used as components of targeted siRNA therapeutic delivery systems, for example targeting cell surface proteins (Zhou, Jiehua, and John J. Rossi. "Aptamer-targeted cell-specific RNA interference." Silence 1.1 (2010): 4). The aptamers used in this aspect are designed to improve gRNA delivery, including delivery across the cellular membrane, to intracellular compartments, or into the nucleus. Such a structure can include, either in addition to the one or more aptamer(s) or without such one or more aptamer(s), moiety(ies) so as to render the guide deliverable, inducible or responsive to a selected effector. In particular embodiments, a gRNA is designed that responds to normal or pathological physiological conditions, including without limitation pH, hypoxia, O2 concentration, temperature, protein concentration, enzymatic concentration, lipid structure, light exposure, mechanical disruption (e.g. ultrasound waves), magnetic fields, electric fields, or electromagnetic radiation. Accordingly, in particular embodiments, the escort aptamer has binding affinity for an aptamer ligand on or in the cell, or the escort aptamer is responsive to a localized aptamer effector on or in the cell, wherein the presence of the aptamer ligand or effector on or in the cell is spatially or temporally restricted.

Once intended alterations have been introduced, such as by editing intended copies of a gene in the genome of a cell, continued CRISPR/Cpf1 expression in that cell is no longer necessary. Indeed, sustained expression would be undesirable in certain cases in case of off-target effects at unintended genomic sites, etc. Thus time-limited expression is of interest.

Inducible expression offers one approach, but in addition Applicants have engineered a self-inactivating Cpf1 CRISPR-Cas system that relies on the use of a non-coding guide target sequence within the CRISPR vector itself Thus, after expression begins, the CRISPR system will lead to its own destruction, but before destruction is complete it will have time to edit the genomic copies of the target gene (which, with a normal point mutation in a diploid cell, requires at most two edits). Simply, the self-inactivating Cpf1 CRISPR-Cas system includes additional RNA (i.e., guide RNA) that targets the coding sequence for the CRISPR enzyme itself or that targets one or more non-coding guide target sequences complementary to unique sequences present in one or more of the following: (a) within the promoter driving expression of the non-coding RNA elements, (b) within the promoter driving expression of the Cpf1 gene, (c) within 100 bp of the ATG translational start codon in the Cpf1 coding sequence, (d) within the inverted terminal repeat (iTR) of a viral delivery vector, e.g., in an AAV genome.

Examples of inducible systems are light responsive systems. Light responsiveness of an inducible system are achieved via the activation and binding of cryptochrome-2 and CIB1. Blue light stimulation induces an activating conformational change in cryptochrome-2, resulting in recruitment of its binding partner CIB1. This binding is fast and reversible, achieving saturation in <15 sec following pulsed stimulation and returning to baseline <15 min after the end of stimulation. These rapid binding kinetics result in a system temporally bound only by the speed of transcription/translation and transcript/protein degradation, rather than uptake and clearance of inducing agents. Cryptochrome-2 activation is also highly sensitive, allowing for the use of low light intensity stimulation and mitigating the risks of phototoxicity. Further, in a context such as the intact mammalian brain, variable light intensity may be used to control the size of a stimulated region, allowing for greater precision than vector delivery alone may offer.

In particular embodiments, energy sources such as electromagnetic radiation, sound energy or thermal energy can induce the guide. Advantageously, the electromagnetic radiation is a component of visible light. In a preferred embodiment, the light is a blue light with a wavelength of about 450 to about 495 nm. In an especially preferred embodiment, the wavelength is about 488 nm. In another preferred embodiment, the light stimulation is via pulses. The light power may range from about 0-9 mW/cm2. In a preferred embodiment, a stimulation paradigm of as low as 0.25 sec every 15 sec should result in maximal activation.

In particular embodiments, the system is chemically inducible. Exemplary designs of chemical inducible systems include: 1. ABI-PYL based system inducible by Abscisic Acid (ABA) (see, e.g., stke.sciencemag.org/cgi/content/abstract/sigtrans; 4/164/rs2), 2. FKBP-FRB based system inducible by rapamycin (or related chemicals based on rapamycin) (see, e.g., www.nature.com/nmeth/journal/v2/n6/full/nmeth763.html), 3. GID1-GAI based system inducible by Gibberellin (GA) (see, e.g., www.nature.com/nchembio/journal/v8/n5/full/nchembio.922.html). Another chemical inducible system is an estrogen receptor (ER) based system inducible by 4-hydroxytamoxifen (4OHT) (see, e.g., www.pnas.org/content/104/3/1027.abstract). A mutated ligand-binding domain of the estrogen receptor called ERT2 translocates into the nucleus of cells upon binding of 4-hydroxytamoxifen. In further embodiments of the invention any naturally occurring or engineered derivative of any nuclear receptor, thyroid hormone receptor, retinoic acid receptor, estrogen receptor, estrogen-related receptor, glucocorticoid receptor, progesterone receptor, androgen receptor may be used in inducible systems analogous to the ER based inducible system.

In particular embodiments, the chemical inducible system is based on change in sub-cellular localization. The polypeptide can include a DNA binding domain comprising at least five or more Transcription activator-like effector (TALE) monomers and at least one or more half-monomers specifically ordered to target the genomic locus of interest linked to at least one or more effector domains are further linker to a chemical or energy sensitive protein. This protein will lead to a change in the sub-cellular localization of the entire polypeptide (i.e. transportation of the entire polypeptide from cytoplasm into the nucleus of the cells) upon the binding of a chemical or energy transfer to the chemical or energy sensitive protein. This transportation of the entire polypeptide from one sub-cellular compartments or organelles, in which its activity is sequestered due to lack of substrate for the effector domain, into another one in which the substrate is present would allow the entire polypeptide to come in contact with its desired substrate (i.e. genomic DNA in the mammalian nucleus) and result in activation or repression of target gene expression.

Another inducible system is based on the design using Transient receptor potential (TRP) ion channel based system inducible by energy, heat or radio-wave (see, e.g., www.sciencemag.org/content/336/6081/604). These TRP family proteins respond to different stimuli, including light and heat. When this protein is activated by light or heat, the ion channel will open and allow the entering of ions such as calcium into the plasma membrane. This influx of ions will bind to intracellular ion interacting partners linked to a polypeptide including the guide and the other components of the Cpf1 CRISPR-Cas complex or system, and the binding will induce the change of sub-cellular localization of the polypeptide, leading to the entire polypeptide entering the nucleus of cells. Once inside the nucleus, the guide protein and the other components of the Cpf1 CRISPR-Cas complex will be active and modulating target gene expression in cells. This type of system could also be used to induce the cleavage of a genomic locus of interest in a cell; and, in this regard, it is noted that the Cpf1 enzyme is a nuclease. The light could be generated with a laser or other forms of energy sources. The heat could be generated by raise of temperature results from an energy source, or from nano-particles that release heat after absorbing energy from an energy source delivered in the form of radio-wave.

Photoinducibility provides the potential for spatial precision. Taking advantage of the development of optrode technology, a stimulating fiber optic lead may be placed in a precise brain region. Stimulation region size may then be tuned by light intensity. This may be done in conjunction with the delivery of the Cpf1 CRISPR-Cas system or complex of the invention, or, in the case of transgenic Cpf1 animals, guide RNA of the invention may be delivered and the optrode technology can allow for the modulation of gene expression in precise brain regions. A culture medium for culturing host cells includes a medium commonly used for tissue culture, such as M199-earle base, Eagle MEM (E-MEM), Dulbecco MEM (DMEM), SC-UCM102, UP-SFM (GIBCO BRL), EX-CELL302 (Nichirei), EX-CELL293-S (Nichirei), TFBM-01 (Nichirei), ASF104, among others. Suitable culture media for specific cell types may be found at the American Type Culture Collection (ATCC) or the European Collection of Authenticated Cell Cultures (ECACC). Culture media may be supplemented with amino acids such as L-glutamine, salts, anti-fungal or anti-bacterial agents such as Fungizone®, penicillin-streptomycin, animal serum, and the like. The cell culture medium may optionally be serum-free.

Temporal precision can also be achieved in vivo. This may be used to alter gene expression during a particular stage of development. This may be used to time a genetic cue to a particular experimental window. For example, genes implicated in learning may be overexpressed or repressed only during the learning stimulus in a precise region of the intact rodent or primate brain. Further, the invention may be used to induce gene expression changes only during particular stages of disease development. For example, an oncogene may be overexpressed only once a tumor reaches a particular size or metastatic stage. Conversely, proteins suspected in the development of Alzheimer's may be knocked down only at defined time points in the animal's life and within a particular brain region. Although these examples do not exhaustively list the potential applications of the invention, they highlight some of the areas in which the invention may be a powerful technology.

(c) Protected Guide RNAs

In one aspect, it is of interest to further enhance the specificity of Cpf1 given individual guide RNAs through thermodynamic tuning of the binding specificity of the guide RNA to target DNA. This is a general approach of introducing mismatches, elongation or truncation of the guide sequence to increase/decrease the number of complimentary bases vs. mismatched bases shared between a genomic target and its potential off-target loci, in order to give thermodynamic advantage to targeted genomic loci over genomic off-targets. Thus it can be of interest to modify the guide sequence by secondary structure to increase the specificity of the Cpf1 CRISPR-Cas system whereby the secondary structure can protect against exonuclease activity. This can be ensured by hybridizing a "protector RNA" to a guide sequence, wherein the "protector RNA" is an RNA strand complementary to the 5' end of the guide RNA (gRNA), to thereby generate a partially double-stranded gRNA. Protecting the mismatched bases with a perfectly complementary protector sequence decreases the likelihood of target DNA binding to the mismatched base pairs at the 3' end. In particular embodiments, additional sequences comprising an extended length may also be present. The principle of using protected guide RNAs is described in detail in WO/2016/094867, which is incorporated herein by reference.

Guide RNA (gRNA) extensions matching the genomic target provide gRNA protection and enhance specificity. Extension of the gRNA with matching sequence distal to the end of the spacer seed for individual genomic targets thus provides enhanced specificity. In particular embodiments, stable forms arise from protective states, where the extension forms a closed loop with the gRNA seed due to complimentary sequences in the spacer extension and the spacer seed. Thus, the protected guide concept also includes sequences matching the genomic target sequence distal of the 20mer spacer-binding region. Thermodynamic prediction can be used to predict completely matching or partially matching guide extensions that result in protected gRNA states as described in WO/2016/094867.

An extension sequence which corresponds to the extended length (ExL) may optionally be attached directly to the guide sequence at the 3' end of the protected guide sequence. The extension sequence may be 2 to 12 nucleotides in length. Preferably ExL may be denoted as 0, 2, 4, 6, 8, 10 or 12 nucleotides in length. In a preferred embodiment the ExL is denoted as 0 or 4 nucleotides in length. In a more preferred embodiment the ExL is 4 nucleotides in length. The extension sequence may or may not be complementary to the target sequence. An extension sequence may further optionally be attached directly to the guide sequence at the 5' end of the protected guide sequence as well as to the 3' end of a protecting sequence. As a result, the extension sequence serves as a linking sequence between the protected sequence and the protecting sequence. Without wishing to be bound by theory, such a link may position the protecting sequence near the protected sequence for improved binding of the protecting sequence to the protected sequence.

(d) Formation of a RISC Through Guide Engineering

In some embodiments, the guide may be a protected guide (e.g. a pgRNA) or an escorted guide (e.g. an esgRNA) as described herein. Both of these, in some embodiments, make use of RISC. A RISC is a key component of RNAi. RISC (RNA-induced silencing complex) is a multiprotein, specifically a ribonucleoprotein, complex which incorporates one strand of a double-stranded RNA (dsRNA) fragment, such as small interfering RNA (siRNA) or microRNA (miRNA), which acts as a template for RISC to recognize a complementary messenger RNA (mRNA) transcript. The mRNA is thus cleaved by one of the components of the RISC.

As such, the formation of a RISC is advantageous in some embodiments. Guide RNAs according to various aspects of the present invention, including but not limited to protected and/or escorted guide RNAs, may be adapted to include RNA nucleotides that promote formation of a RISC, for example in combination with an siRNA or miRNA that may be provided or may, for instance, already be expressed in a cell. This may be useful, for instance, as a self-inactivating system to clear or degrade the guide.

Thus, the guide RNA may comprise a sequence complementary to a target miRNA or an siRNA, which may or may not be present within a cell. In this way, only when the miRNA or siRNA is present, for example through expression (by the cell or through human intervention), is there binding of the RNA sequence to the miRNA or siRNA which then results in cleavage of the guide RNA an RNA-induced silencing complex (RISC) within the cell. Therefore, in some embodiments, the guide RNA comprises an RNA sequence complementary to a target miRNA or siRNA, and binding of the guide RNA sequence to the target miRNA or siRNA results in cleavage of the guide RNA by an RNA-induced silencing complex (RISC) within the cell.

RISC formation through use of escorted guides is described in WO2016094874, RISC formation through use of protected guides is described in WO/2016/094867.

(e) Use of inducible Systems

In some embodiments, a CRISPR enzyme may form a component of an inducible system. The inducible nature of the system would allow for spatiotemporal control of gene editing or gene expression using a form of energy. The form of energy may include but is not limited to electromagnetic radiation, sound energy, chemical energy and thermal energy. Examples of inducible system include tetracycline inducible promoters (Tet-On or Tet-Off), small molecule two-hybrid transcription activations systems (FKBP, ABA, etc), or light inducible systems (Phytochrome, LOV domains, or cryptochrome). In one embodiment, the CRISPR enzyme may be a part of a Light Inducible Transcriptional Effector (LITE) to direct changes in transcriptional activity in a sequence-specific manner. The components of a light may include a CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, and WO 2014/018423 A2 which is hereby incorporated by reference in its entirety.

(f) Use of Inducible/Split Effector Enzymes

In an aspect the invention provides a (non-naturally occurring or engineered) inducible CRISPR protein according to the invention as described herein (CRISPR-Cas system), comprising: a first CRISPR protein fusion construct attached to a first half of an inducible dimer and a second CRISPR protein fusion construct attached to a second half of the inducible dimer, wherein the first Cpf1 fusion construct is operably linked to one or more nuclear localization signals, wherein the second CRISPR protein fusion construct is operably linked to one or more nuclear export signals, wherein contact with an inducer energy source brings the first and second halves of the inducible dimer together, wherein bringing the first and second halves of the inducible dimer together allows the first and second CRISPR protein fusion constructs to constitute a functional CRISPR protein (optionally wherein the CRISPR-Cas system comprises a guide RNA (gRNA) comprising a guide sequence capable of hybridizing to a target sequence in a genomic locus of interest in a cell, and wherein the functional CRISPR-Cas system binds to the target sequence and, optionally, edits the genomic locus to alter gene expression).

In an aspect of the invention in the inducible CRISPR-Cas system, the inducible dimer is or comprises or consists essentially of or consists of an inducible heterodimer. In an aspect, in inducible CRISPR-Cas system, the first half or a first portion or a first fragment of the inducible heterodimer is or comprises or consists of or consists essentially of an FKBP, optionally FKBP12. In an aspect of the invention, in the inducible CRISPR-Cas system, the second half or a second portion or a second fragment of the inducible heterodimer is or comprises or consists of or consists essentially of FRB. In an aspect of the invention, in the inducible CRISPR-Cas system, the arrangement of the first CRISPR fusion construct is or comprises or consists of or consists essentially of N' terminal CRISPR part-FRB-NES. In an aspect of the invention, in the inducible CRISPR-Cas system, the arrangement of the first CRISP fusion construct is or comprises or consists of or consists essentially of NES-N' terminal CRISP part-FRB-NES. In an aspect of the invention, in the inducible CRISPR-Cas system, the arrangement of the second CRISP fusion construct is or comprises or consists essentially of or consists of C' terminal CRISP part-FKBP-NLS. In an aspect the invention provides in the inducible Cpf1 CRISPR-Cas system, the arrangement of the second CRISP fusion construct is or comprises or consists of or consists essentially of NLS-C' terminal CRISP part-FKBP-NLS. In an aspect, in inducible CRISPR-Cas system there can be a linker that separates the CRISP part from the half or portion or fragment of the inducible dimer. In an aspect, in the inducible CRISPR-Cas system, the inducer energy source is or comprises or consists essentially of or consists of rapamycin. In an aspect, in inducible CRISPR-Cas system, the inducible dimer is an inducible homodimer. In an aspect, in an inducible Cpf1 CRISPR-Cas system, the Cpf1 is AsCpf1, LbCpf1 or FnCpf1.

In an aspect, the invention provides a (non-naturally occurring or engineered) inducible CRISPR-Cas system, comprising: a first CRISPR fusion construct attached to a first half of an inducible heterodimer and a second CRISPR fusion construct attached to a second half of the inducible heterodimer, wherein the first CRISPR fusion construct is operably linked to one or more nuclear localization signals, wherein the second CRISPR fusion construct is operably linked to a nuclear export signal, wherein contact with an inducer energy source brings the first and second halves of the inducible heterodimer together, wherein bringing the first and second halves of the inducible heterodimer together allows the first and second CRISPR fusion constructs to constitute a functional CRISPR (optionally wherein the CRISPR-Cas system comprises a guide RNA (gRNA) comprising a guide sequence capable of hybridizing to a target sequence in a genomic locus of interest in a cell, and wherein the functional CRISPR-Cas system edits the genomic locus to alter gene expression).

Accordingly, the invention comprehends inter alia homodimers as well as heterodimers, dead-CRISPR or CRISPR protein having essentially no nuclease activity, e.g., through mutation, systems or complexes wherein there is one or more NLS and/or one or more NES; functional domain(s) linked to split Cas9; methods, including methods of treatment, and uses.

An inducer energy source may be considered to be simply an inducer or a dimerizing agent. The term 'inducer energy source' is used herein throughout for consistency. The inducer energy source (or inducer) acts to reconstitute the enzyme. In some embodiments, the inducer energy source brings the two parts of the enzyme together through the action of the two halves of the inducible dimer. The two halves of the inducible dimer therefore are brought tougher in the presence of the inducer energy source. The two halves of the dimer will not form into the dimer (dimerize) without the inducer energy source.

Thus, the two halves of the inducible dimer cooperate with the inducer energy source to dimerize the dimer. This in turn reconstitutes the CRISPR by bringing the first and second parts of the CRISPR together.

The CRISPR protein fusion constructs each comprise one part of the split CRISPR protein. These are fused, preferably via a linker such as a GlySer linker described herein, to one of the two halves of the dimer. The two halves of the dimer may be substantially the same two monomers that together that form the homodimer, or they may be different monomers that together form the heterodimer. As such, the two monomers can be thought of as one half of the full dimer.

The CRISPR protein is split in the sense that the two parts of the CRISPR protein enzyme substantially comprise a functioning CRISPR protein. That CRISPR protein may function as a genome editing enzyme (when forming a complex with the target DNA and the guide), such as a nickase or a nuclease (cleaving both strands of the DNA), or it may be a dead- CRISPR protein which is essentially a DNA-binding protein with very little or no catalytic activity, due to typically mutation(s) in its catalytic domains.

The two parts of the split CRISPR protein can be thought of as the N' terminal part and the C' terminal part of the split CRISPR protein. The fusion is typically at the split point of the CRISPR protein. In other words, the C' terminal of the N' terminal part of the split CRISPR protein is fused to one of the dimer halves, whilst the N' terminal of the C' terminal part is fused to the other dimer half.

The CRISPR protein does not have to be split in the sense that the break is newly created. The split point is typically designed in silico and cloned into the constructs. Together, the two parts of the split CRISPR protein, the N' terminal and C' terminal parts, form a full CRISPR protein, comprising preferably at least 70% or more of the wildtype amino acids (or nucleotides encoding them), preferably at least 80% or more, preferably at least 90% or more, preferably at least 95% or more, and most preferably at least 99% or more of the wildtype amino acids (or nucleotides encoding them). Some trimming may be possible, and mutants are envisaged. Non-functional domains may be removed entirely. What is important is that the two parts may be brought together and that the desired CRISPR protein function is restored or reconstituted.

The dimer may be a homodimer or a heterodimer.

One or more, preferably two, NLSs may be used in operable linkage to the first CRISPR protein construct. One or more, preferably two, NESs may be used in operable linkage to the first Cpf1 construct. The NLSs and/or the NESs preferably flank the split Cpf1-dimer (i.e., half dimer) fusion, i.e., one NLS may be positioned at the N' terminal of the first CRISPR protein construct and one NLS may be at the C' terminal of the first CRISPR protein construct. Similarly, one NES may be positioned at the N' terminal of the second CRISPR construct and one NES may be at the C' terminal of the second CRISPR construct. Where reference is made to N' or C' terminals, it will be appreciated that these correspond to 5' ad 3' ends in the corresponding nucleotide sequence.

A preferred arrangement is that the first CRISPR protein construct is arranged 5'-NLS-(N' terminal CRISPR protein part)-linker-(first half of the dimer)-NLS-3'. A preferred arrangement is that the second CRISPR protein construct is arranged 5'-NES-(second half of the dimer)-linker-(C' terminal CRISPR protein part)-NES-3'. A suitable promoter is preferably upstream of each of these constructs. The two constructs may be delivered separately or together.

In some embodiments, one or all of the NES(s) in operable linkage to the second CPf1 construct may be swapped out for an NLS. However, this may be typically not preferred and, in other embodiments, the localization signal in operable linkage to the second Cpf1 construct is one or more NES(s).

It will also be appreciated that the NES may be operably linked to the N' terminal fragment of the split CRISPR protein and that the NLS may be operably linked to the C' terminal fragment of the split CRISPR protein. However, the arrangement where the NLS is operably linked to the N' terminal fragment of the split Cpf1 and that the NES is operably linked to the C' terminal fragment of the split CRISPR protein may be preferred.

The NES functions to localize the second CRISPR protein fusion construct outside of the nucleus, at least until the inducer energy source is provided (e.g., at least until an energy source is provided to the inducer to perform its function). The presence of the inducer stimulates dimerization of the two CRISPR protein fusions within the cytoplasm and makes it thermodynamically worthwhile for the dimerized, first and second, CRISPR protein fusions to localize to the nucleus. Without being bound by theory, Applicants believe that the NES sequesters the second CRISPR protein fusion to the cytoplasm (i.e., outside of the nucleus). The NLS on the first CRISPR protein fusion localizes it to the nucleus. In both cases, Applicants use the NES or NLS to shift an equilibrium (the equilibrium of nuclear transport) to a desired direction. The dimerization typically occurs outside of the nucleus (a very small fraction might happen in the nucleus) and the NLSs on the dimerized complex shift the equilibrium of nuclear transport to nuclear localization, so the dimerized and hence reconstituted CRISPR protein enters the nucleus.

Beneficially, Applicants are able to reconstitute function in the split CRISPR protein. Transient transfection is used to prove the concept and dimerization occurs in the background in the presence of the inducer energy source. No activity is seen with separate fragments of the CRISPR protein. Stable expression through lentiviral delivery is then used to develop this and show that a split CRISPR protein approach can be used.

This present split CRISPR protein approach is beneficial as it allows the CRISPR protein activity to be inducible, thus allowing for temporal control. Furthermore, different localization sequences may be used (i.e., the NES and NLS as preferred) to reduce background activity from auto-assembled complexes. Tissue specific promoters, for example one for each of the first and second CRISPR protein fusion constructs, may also be used for tissue-specific targeting, thus providing spatial control. Two different tissue specific promoters may be used to exert a finer degree of control if required. The same approach may be used in respect of stage-specific promoters or there may a mixture of stage and tissue specific promoters, where one of the first and second Cpf1 fusion constructs is under the control of (i.e. operably linked to or comprises) a tissue-specific promoter, whilst the other of the first and second Cpf1 fusion constructs is under the control of (i.e. operably linked to or comprises) a stage-specific promoter.

The inducible CRISPR protein CRISPR-Cas system comprises one or more nuclear localization sequences (NLSs), as described herein, for example as operably linked to the first CRISPR protein fusion construct. These nuclear localization sequences are ideally of sufficient strength to drive accumulation of said first CRISPR protein fusion construct in a detectable amount in the nucleus of a eukaryotic cell. Without wishing to be bound by theory, it is believed that a nuclear localization sequence is not necessary for CRISPR-Cas complex activity in eukaryotes, but that including such sequences enhances activity of the system, especially as to targeting nucleic acid molecules in the nucleus, and assists with the operation of the present 2-part system.

Equally, the second CRISPR protein fusion construct is operably linked to a nuclear export sequence (NES). Indeed, it may be linked to one or more nuclear export sequences. In other words, the number of export sequences used with the second CRISPR protein fusion construct is preferably 1 or 2 or 3. Typically 2 is preferred, but 1 is enough and so is preferred in some embodiments. Suitable examples of NLS and NES are known in the art. For example, a preferred nuclear export signal (NES) is human protein tyrosin kinase 2. Preferred signals will be species specific.

Where the FRB and FKBP system are used, the FKBP is preferably flanked by nuclear localization sequences (NLSs). Where the FRB and FKBP system are used, the preferred arrangement is N' terminal CRISPR protein-FRB-NES: C' terminal Cpf1-FKBP-NLS. Thus, the first CRISPR protein fusion construct would comprise the C' terminal CRISPR protein part and the second CRISPR protein fusion construct would comprise the N' terminal CRISPR protein part.

Another beneficial aspect to the present invention is that it may be turned on quickly, i.e. that is has a rapid response. It is believed, without being bound by theory, that CRISPR protein activity can be induced through dimerization of existing (already present) fusion constructs (through contact with the inducer energy source) more rapidly than through the expression (especially translation) of new fusion constructs. As such, the first and second CRISPR protein fusion constructs may be expressed in the target cell ahead of time, i.e. before CRISPR protein activity is required. CRISPR protein activity can then be temporally controlled and then quickly constituted through addition of the inducer energy source, which ideally acts more quickly (to dimerize the heterodimer and thereby provide CRISPR protein activity) than through expression (including induction of transcription) of CRISPR protein delivered by a vector, for example.

Applicants demonstrate that CRISPR protein can be split into two components, which reconstitute a functional nuclease when brought back together. Employing rapamycin sensitive dimerization domains, Applicants generate a chemically inducible CRISPR protein for temporal control of CRISPR protein-mediated genome editing and transcription modulation. Put another way, Applicants demonstrate that CRISPR protein can be rendered chemically inducible by being split into two fragments and that rapamycin-sensitive dimerization domains may be used for controlled reassembly of the CRISPR protein. Applicants show that the re-assembled CRISPR protein may be used to mediate genome editing (through nuclease/nickase activity) as well as transcription modulation (as a DNA-binding domain, the so-called "dead CRISPR protein").

As such, the use of rapamycin-sensitive dimerization domains is preferred. Reassembly of the CRISPR protein is preferred. Reassembly can be determined by restoration of binding activity. Where the CRISPR protein is a nickase or induces a double-strand break, suitable comparison percentages compared to a wildtype are described herein.

Rapamycin treatments can last 12 days. The dose can be 200 nm. This temporal and/or molar dosage is an example of an appropriate dose for Human embryonic kidney 293FT (HEK293FT) cell lines and this may also be used in other cell lines. This figure can be extrapolated out for therapeutic use in vivo into, for example, mg/kg. However, it is also envisaged that the standard dosage for administering rapamycin to a subject is used here as well. By the "standard dosage", it is meant the dosage under rapamycin's normal therapeutic use or primary indication (i.e. the dose used when rapamycin is administered for use to prevent organ rejection).

It is noteworthy that the preferred arrangement of CRISPR protein-FRB/FKBP pieces are separate and inactive until rapamycin-induced dimerization of FRB and FKBP results in reassembly of a functional full-length CRISPR protein nuclease. Thus, it is preferred that first CRISPR protein fusion construct attached to a first half of an inducible heterodimer is delivered separately and/or is localized separately from the second Cpf1 fusion construct attached to a first half of an inducible heterodimer.

To sequester the CRISPR protein (N)-FRB fragment in the cytoplasm, where it is less likely to dimerize with the nuclear-localized Cpf1 (C)-FKBP fragment, it is preferable to use on CRISPR protein (N)-FRB a single nuclear export sequence (NES) from the human protein tyrosin kinase 2 (CRISPR protein (N)—FRB-NES). In the presence of rapamycin, CRISPR protein (N)—FRB-NES dimerizes with CRISPR protein (C)-FKBP-2×NLS to reconstitute a complete CRISPR protein, which shifts the balance of nuclear trafficking toward nuclear import and allows DNA targeting.

In some aspects or embodiments, an inducible system for providing a CRISPR protein may be used. In some embodiments, the CRISPR protein is capable, in the presence of an inducer energy source, of forming a CRISPR complex with a target sequence and polynucleotides engineered to complex with the CRISPR protein and the target sequence. In some embodiments, the inducible system comprises: a first fusion protein, or polynucleotides encoding it; and a second fusion protein, or polynucleotides encoding it. In some embodiments, the first fusion protein comprises a first portion of the CRISPR protein, a first half of an inducible dimer and one or more Nuclear Localisation Sequences (NLS); and the second fusion protein comprises a second portion of the CRISPR protein, a second half of the inducible dimer and one or more Nuclear Export Sequences (NES). In some embodiments, contact with the inducer energy source brings the first and second portions of the inducible dimer together, so as to bring the first and second portions of the CRISPR protein together, such that the CRISPR protein is thereby capable of forming the CRISPR complex. In some embodiments, the CRISPR protein or the CRISPR system is inducible. In some embodiments, the CRISPR protein may be provided as a single 'part.' In some embodiments, delivery of the CRISPR protein is in protein (including in RNP complex with the polynucleotides) or in nucleotide form (including in mRNA form). In some embodiments, polynucleotides encoding the first fusion protein and polynucleotides encoding second fusion protein are provided on same or different constructs. WO2015/089427 describes an inducible CRISPR-Cas system based on an inducible dimer, which can be a homodimer or heterodimer. The system is also described in Zetsche et al. (Nature Biotechnology 33: 139-142 (2015) DOI: doi:10.1038/nbt.3149). Basically, the CRISPR effector protein is split into two parts, each of which is fused to one half of an inducible dimer, whereby contact with an inducer energy source brings the first and second halves of the inducible dimer together, and bringing the first and second halves of the inducible dimer together allows the first and second CRISPR effector fusion constructs to constitute a functional CRISPR-Cas system, wherein the CRISPR-Cas system comprises a guide RNA (gRNA) comprising a guide sequence capable of hybridizing to a target sequence in a genomic locus of interest in a cell, and wherein the functional CRISPR-Cas system binds to the genomic locus. In particular embodiments, the functional CRISPR-Cas system edits the genomic locus to alter gene expression. In particular embodiments the first half is an FKBP and the second half is an FRB. An inducer energy source may be considered to be simply an inducer or a dimerizing agent as it acts to reconstitute the CRISPR effector protein.

Examples of inducers include light and hormones. A preferred example of first and second light-inducible dimer halves is the CIB1 and CRY2 system. The CIB1 domain is a heterodimeric binding partner of the light-sensitive Cryptochrome 2 (CRY2). In another example, the blue light-responsive Magnet dimerization system (pMag and nMag) may be fused to the two parts of a split Cpf1 protein. In response to light stimulation, pMag and nMag dimerize and Cpf1 reassembles. For example, such system is described in connection with Cas9 in Nihongaki et al. (Nat. Biotechnol. 33, 755-790, 2015). The inducer energy source may be heat, ultrasound, electromagnetic energy or chemical. In a preferred embodiment the inducer energy source may be an antibiotic, a small molecule, a hormone, a hormone derivative, a steroid or a steroid derivative. In a more preferred embodiment, the inducer energy source maybe abscisic acid (ABA), doxycycline (DOX), cumate, rapamycin, 4-hydroxytamoxifen (4OHT), estrogen or ecdysone. The at least one switch may be selected from the group consisting of antibiotic based inducible systems, electromagnetic energy based inducible systems, small molecule based inducible systems, nuclear receptor based inducible systems and hormone based inducible systems. In a more preferred embodiment the at least one switch may be selected from the group consisting of tetracycline (Tet)/DOX inducible systems, light inducible systems, ABA inducible systems, cumate repressor/operator systems, 4OHT/estrogen inducible systems, ecdysone-based inducible systems and FKBP12/FRAP (FKBP12-rapamycin complex) inducible systems. Such inducers are also discussed herein and in PCT/US2013/051418, incorporated herein by reference.

Also, it is described in WO2015/089427 that the half of an inducible dimer can be linked to the effector protein with a linker. Optionally, the CRISPR effector protein has reduced or no nuclease activity, e.g. contains one or more inactivating mutations. Further it is described that one or more functional domains can be associated with one or both parts of the effector protein, WO2015/089427 identifies split points within SpCas9. Similar suitable split points can be identified for Cpf1.

The following table presents non-limiting potential split regions within As and LbCpf1. A split site within such a region may be opportune.

TABLE 7

| Split region | AsCpf1 | LbCpf1 |
|---|---|---|
| 1 | 575-588 | 566-571 |
| 2 | 631-645 | 754-757 |
| 3 | 653-664 | — |
| 4 | 818-844 | — |

For Fn, As and Lb Cpf1 mutants, it should be readily apparent what the corresponding position for a potential split site is, for example, based on a sequence alignment. For non-Fn, As and Lb enzymes one can use the crystal structure of an ortholog if a relatively high degree of homology exists between the ortholog and the intended Cpf1, or one can use computational prediction.

Further it is described that the first and second fusion constructs of the CRISPR effector protein can be delivered in the same or separate vectors. In particular embodiments, a first half of the inducible dimer is fused to one or more nuclear localization constructs while the second half is fused to one or more nuclear export signals.

The therapeutic methods which involve the use of the inducible dimer comprise the step of administering the vectors comprising the first and second fusion constructs to the subject and administering an inducer energy source to the subject. In particular embodiments, the inducer energy source is rapamycin. It is further envisaged that the methods can involve administering, a repair template, in the same or a different vector as the inducible dimer fragments. An exemplary treatment regimen with Rapamycin can last 12 days.

The use of the split Cpf1 effector protein system described herein allows a further control of the CRISPR-Cas activity. More particularly the use of an inducible system allows for temporal control. In addition, the use of different localization sequences (i.e., the NES and NLS as preferred) can reduce background activity from auto-assembled complexes. Tissue specific promoters, allow for spatial control. Two different tissue specific promoters may be used to exert a finer degree of control if required.

f) Use of Self-Inactivating Systems

Once all copies of a gene in the genome of a cell have been edited, continued CRISPR/Cpf1 expression in that cell is no longer necessary. Indeed, sustained expression is undesirable to avoid off-target effects and other toxicity issues. WO 2015089351 describes self-inactivating CRISPR systems which rely on the use of a non-coding guide target sequence within the CRISPR vector itself Thus, after expression begins, the CRISPR system will lead to its own destruction, but before destruction is complete it will have time to edit the genomic copies of the target gene (which, with a normal point mutation in a diploid cell, requires at most two edits). Accordingly, the methods may involve the use of a self-inactivating CRISPR-Cas system which includes one additional RNA (i.e., guide RNA) that targets the coding sequence for the CRISPR enzyme itself or that targets one or more non-coding guide target sequences complementary to unique sequences present in within the promoter driving expression of the non-coding RNA elements, within the promoter driving expression of the Cpf1 gene, within 100 bp of the ATG translational start codon in the Cpf1 coding sequence, or within the inverted terminal repeat (iTR) of a viral delivery vector, e.g., in the AAV genome.

Similarly, self-inactivating systems which make use of "governing guides" are exemplified in relation to Cas9 in US2015232881A1 (also published as WO2015070083 (A1) referenced elsewhere herein and incorporated herein by reference, and may be extrapolated to Cpf1. More particularly Methods and compositions that use, or include, a nucleic acid, e.g., a DNA, that encodes a Cpf1 molecule or a gRNA molecule, can, in addition, use or include a "governing gRNA molecule." The governing gRNA molecule can complex with the Cpf1 molecule to inactivate or silence a component of a Cpf1 system. The additional gRNA molecule, referred to herein as a governing gRNA molecule, comprises a targeting domain which targets a component of the Cpf1 system. In an embodiment, the governing gRNA molecule targets and silences (1) a nucleic acid that encodes a Cpf1 molecule (i.e., a Cpf1-targeting gRNA molecule), (2) a nucleic acid that encodes a gRNA molecule (i.e., a gRNA-targeting gRNA molecule), or (3) a nucleic acid sequence engineered into the Cpf1 components that is designed with minimal homology to other nucleic acid sequences in the cell to minimize off-target cleavage (i.e., an engineered control sequence-targeting gRNA molecule).

The targeting sequence for the governing gRNA can be selected to increase regulation or control of the Cpf1 system and/or to reduce or minimize off-target effects of the system. For example, a governing gRNA can minimize undesirable cleavage, e.g., "recleavage" after Cpf1 mediated alteration of a target nucleic acid or off-target cutting of Cpf1, by inactivating (e.g., cleaving) a nucleic acid that encodes a Cpf1 molecule. In an embodiment, a governing gRNA places temporal or other limit(s) on the level of expression or activity of the Cpf1 molecule/gRNA molecule complex. In an embodiment, the governing gRNA reduces off-target or other unwanted activity.

The additional guide RNA can be delivered via a vector, e.g., a separate vector or the same vector that is encoding the CRISPR complex. When provided by a separate vector, the CRISPR RNA that targets Cpf1 expression can be administered sequentially or simultaneously. When administered sequentially, the CRISPR RNA that targets Cpf1 expression is to be delivered after the CRISPR RNA that is intended for e.g. gene editing or gene engineering. This period may be a period of minutes (e.g. 5 minutes, 10 minutes, 20 minutes, 30 minutes, 45 minutes, 60 minutes). This period may be a period of hours (e.g. 2 hours, 4 hours, 6 hours, 8 hours, 12 hours, 24 hours). This period may be a period of days (e.g. 2 days, 3 days, 4 days, 7 days). This period may be a period of weeks (e.g. 2 weeks, 3 weeks, 4 weeks). This period may be a period of months (e.g. 2 months, 4 months, 8 months, 12 months). This period may be a period of years (2 years, 3 years, 4 years). In this fashion, the Cas enzyme associates with a first gRNA capable of hybridizing to a first target, such as a genomic locus or loci of interest and undertakes the function(s) desired of the CRISPR-Cas system (e.g., gene engineering); and subsequently the Cpf1 enzyme may then associate with the second gRNA capable of hybridizing to the sequence comprising at least part of the Cpf1 or CRISPR cassette. Where the gRNA targets the sequences encoding expression of the Cpf1 protein, the enzyme becomes impeded and the system becomes self-inactivating. In the same manner, CRISPR RNA that targets Cpf1 expression applied via, for example liposome, lipofection, nanoparticles, microvesicles as explained herein, may be administered sequentially or simultaneously. Similarly, self-inactivation may be used for inactivation of one or more guide RNA used to target one or more targets.

In some embodiments, a single gRNA is provided that is capable of hybridization to a sequence downstream of a CRISPR enzyme start codon, whereby after a period of time there is a loss of the CRISPR enzyme expression. In some embodiments, one or more gRNA(s) are provided that are capable of hybridization to one or more coding or non-coding regions of the polynucleotide encoding the CRISPR-Cas system, whereby after a period of time there is a inactivation of one or more, or in some cases all, of the CRISPR-Cas systems. In some aspects of the system, and not to be limited by theory, the cell may comprise a plurality of CRISPR-Cas complexes, wherein a first subset of CRISPR complexes comprise a first chiRNA capable of targeting a genomic locus or loci to be edited, and a second subset of CRISPR complexes comprise at least one second chiRNA capable of targeting the polynucleotide encoding the CRISPR-Cas system, wherein the first subset of CRISPR-Cas complexes mediate editing of the targeted genomic locus or loci and the second subset of CRISPR complexes eventually inactivate the CRISPR-Cas system, thereby inactivating further CRISPR-Cas expression in the cell.

Thus the invention provides a CRISPR-Cas system comprising one or more vectors for delivery to a eukaryotic cell, wherein the vector(s) encode(s): (i) a CRISPR enzyme; (ii) a first guide RNA capable of hybridizing to a target sequence in the cell; (iii) a second guide RNA capable of hybridizing to one or more target sequence(s) in the vector which encodes the CRISPR enzyme; (iv) at least one tracr mate sequence; and (v) at least one tracr sequence. The first and second complexes can use the same tracr and tracr mate, thus differing only by the guide sequence, wherein, when expressed within the cell: the first guide RNA directs sequence-specific binding of a first CRISPR complex to the target sequence in the cell; the second guide RNA directs sequence-specific binding of a second CRISPR complex to the target sequence in the vector which encodes the CRISPR enzyme; the CRISPR complexes comprise (a) a tracr mate sequence hybridised to a tracr sequence and (b) a CRISPR enzyme bound to a guide RNA, such that a guide RNA can hybridize to its target sequence; and the second CRISPR complex inactivates the CRISPR-Cas system to prevent continued expression of the CRISPR enzyme by the cell. The CRISPR enzyme can be Cpf1, particularly FnCpf1 or AsCpf1.

Further characteristics of the vector(s), the encoded enzyme, the guide sequences, etc. are disclosed elsewhere herein. For instance, one or both of the guide sequence(s) can be part of a chiRNA sequence which provides the guide, tracr mate and tracr sequences within a single RNA, such that the system can encode (i) a CRISPR enzyme; (ii) a first chiRNA comprising a sequence capable of hybridizing to a first target sequence in the cell, a first tracr mate sequence, and a first tracr sequence; (iii) a second guide RNA capable of hybridizing to the vector which encodes the CRISPR enzyme, a second tracr mate sequence, and a second tracr sequence. Similarly, the enzyme can include one or more NLS, etc.

The various coding sequences (CRISPR enzyme, guide RNAs, tracr and tracr mate) can be included on a single vector or on multiple vectors. For instance, it is possible to encode the enzyme on one vector and the various RNA sequences on another vector, or to encode the enzyme and one chiRNA on one vector, and the remaining chiRNA on another vector, or any other permutation. In general, a system using a total of one or two different vectors is preferred.

Where multiple vectors are used, it is possible to deliver them in unequal numbers, and ideally with an excess of a vector which encodes the first guide RNA relative to the second guide RNA, thereby assisting in delaying final inactivation of the CRISPR system until genome editing has had a chance to occur.

Thus the target sequence in the vector must be capable of inactivating expression of the CRISPR effector protein. Suitable target sequences can be, for instance, near to or within the translational start codon for the Cpf1 coding sequence, in a non-coding sequence in the promoter driving expression of the non-coding RNA elements, within the promoter driving expression of the Cpf1 gene, within 100 bp of the ATG translational start codon in the Cpf1 coding sequence, and/or within the inverted terminal repeat (iTR) of a viral delivery vector, e.g., in the AAV genome. A double stranded break near this region can induce a frame shift in the Cpf1 coding sequence, causing a loss of protein expression. An alternative target sequence for the "self-inactivating" guide RNA would aim to edit/inactivate regulatory regions/sequences needed for the expression of the CRISPR-Cpf1 system or for the stability of the vector. For instance, if the promoter for the Cpf1 coding sequence is disrupted then transcription can be inhibited or prevented. Similarly, if a vector includes sequences for replication, maintenance or stability then it is possible to target these. For instance, in a AAV vector a useful target sequence is within the iTR. Other useful sequences to target can be promoter sequences, polyadenylation sites, etc.

Furthermore, if the guide RNAs are expressed in array format, the "self-inactivating" guide RNAs that target both promoters simultaneously will result in the excision of the intervening nucleotides from within the CRISPR-Cas expression construct, effectively leading to its complete inactivation. Similarly, excision of the intervening nucleotides will result where the guide RNAs target both ITRs, or targets two or more other CRISPR-Cas components simultaneously. Self-inactivation as explained herein is applicable, in general, with CRISPR-Cpf1 systems in order to provide regulation of the CRISPR-Cpf1. For example, self-inactivation as explained herein may be applied to the CRISPR repair of mutations, for example expansion disorders, as explained herein. As a result of this self-inactivation, CRISPR repair is only transiently active.

Addition of non-targeting nucleotides to the 5' end (e.g. 1-10 nucleotides, preferably 1-5 nucleotides) of the "self-inactivating" guide RNA can be used to delay its processing and/or modify its efficiency as a means of ensuring editing at the targeted genomic locus prior to CRISPR-Cpf1 shutdown.

In one aspect of the self-inactivating AAV-CRISPR-Cpf1 system, plasmids that co-express one or more sgRNA targeting genomic sequences of interest (e.g. 1-2, 1-5, 1-10, 1-15, 1-20, 1-30) may be established with "self-inactivating" sgRNAs that target a Cpf1 sequence at or near the engineered ATG start site (e.g. within 5 nucleotides, within 15 nucleotides, within 30 nucleotides, within 50 nucleotides, within 100 nucleotides). A regulatory sequence in the U6 promoter region can also be targeted with an sgRNA. The U6-driven sgRNAs may be designed in an array format such that multiple sgRNA sequences can be simultaneously released. When first delivered into target tissue/cells (left cell) sgRNAs begin to accumulate while Cpf1 protein levels rise in the nucleus. Cpf1 complexes with all of the sgRNAs to mediate genome editing and self-inactivation of the CRISPR-Cpf1 plasmids.

One aspect of a self-inactivating CRISPR-Cpf1 system is expression of singly or in tandem array format from 1 up to 4 or more different guide sequences; e.g. up to about 20 or about 30 guides sequences. Each individual self-inactivating guide sequence may target a different target. Such may be processed from, e.g. one chimeric pol3 transcript. Pol3 promoters such as U6 or H1 promoters may be used. Pol2 promoters such as those mentioned throughout herein. Inverted terminal repeat (iTR) sequences may flank the Pol3 promoter-sgRNA(s)-Pol2 promoter-Cas9.

In particular embodiments one or more guide(s) edit the one or more target(s) while one or more self-inactivating guides inactivate the CRISPR/Cpf1 system. Thus, for example, the described CRISPR-Cpf1 system for repairing expansion disorders may be directly combined with the self-inactivating CRISPR-Cpf1 system described herein. Such a system may, for example, have two guides directed to the target region for repair as well as at least a third guide directed to self-inactivation of the CRISPR-Cpf1. Reference is made to Application Ser. No. PCT/US2014/069897, entitled "Compositions And Methods Of Use Of Crispr-Cas Systems In Nucleotide Repeat Disorders," published Dec. 12, 2014 as WO/2015/089351.

In particular embodiments, the gene editing systems described herein are placed under the control of a passcode kill switch, which is a mechanism which efficiently kills the host cell when the conditions of the cell are altered. This is ensured by introducing hybrid LacI-GalR family transcription factors, which require the presence of IPTG to be switched on (Chan et al. 2015 Nature Chemical Biology doi:10.1038/nchembio.1979 which can be used to drive a gene encoding an enzyme critical for cell-survival. By combining different transcription factors sensitive to different chemicals, a "code" can be generated. This system can be used to spatially and temporally control the extent of CRISPR-induced genetic modifications, which can be of interest in different fields including therapeutic applications and may also be of interest to avoid the "escape" of GMOs from their intended environment.

g) Use of "Off-Switches"

In particular embodiments, it may be possible to make use of specific inhibitors and/or agonist of Cpf1. Off-switches and On-switches may be any molecules (i.e. peptides, proteins, small molecules, nucleic acids) capable of interfering with or acting as an agonist for any aspect of the Cas9 effector protein. For instance, Pawluck et al. 2016 (Cell 167, 1-10) describe mobile elements from bacteria that encode protein inhibitors of Cas9. Three families of anti-CRISPRs were found to inhibit N. meningitidis Cas9 in vivo and in vitro. The anti-CRISPRs bind directly to NmeCas9. These proteins are described to be potent "off-switches" for Nme-Cas9 genome editing in human cells. Methods for identifying small molecules which affect efficiency of Cas9 are described for example by Yu et al. (Cell Stem Cell 16, 142-147, 2015). In certain embodiments small molecules may be used for control Cas9. Maji et al. describe a small molecule-regulated protein degron domain to control Cas9 system editing. Maji et al. "Multidimensional chemical control of CRISPR-Cas9" Nature Chemical Biology (2017) 13:9-12. In certain example embodiments, the inhibitor may be a bacteriophage derived protein. See Rauch et al. "Inhibition of CRISPR-Cas9 with Bacteriophage Proteins" Cell (2017) 168(2):150-158. In certain example embodiments, the anti-CRISPR may inhibit CRISPR-Cas systems by binding to guide molecules. See Shin et al. "Disabling Cas9 by an anti-CRISPR DNA mimic" bioRxiv, Apr. 22, 2017, doi: dx.doi.org/10.1101/129627.

In particular embodiments, intracellular DNA is removed by genetically encoded DNai which responds to a transcriptional input and degrades user-defined DNA as described in Caliando & Voigt, Nature Communications 6: 6989 (2015).

Efficacy— a. Enzyme Stability

The level of expression of a protein is dependent on many factors, including the quantity of mRNA, its stability and rates of ribosome initiation. The stability or degradation of mRNA is an important factor. Several strategies have been described to increase mRNA stability. One aspect is codon-optimization. It has been found that GC-rich genes are expressed several-fold to over a 100-fold more efficiently than their GC-poor counterparts. This effect could be directly attributed to increased steady-state mRNA levels, and more particularly to efficient transcription or mRNA processing (not decreased degradation) (Kudla et al. Plos Biology dx.doi.org/10.1371/journal.pbio.0040180). Also, it has been found that ribosomal density has a significant effect on the transcript half-life. More particularly, it was found that an increase in stability can be achieved through the incorporation of nucleotide sequences that are capable of forming secondary structures, which often recruit ribosomes, which impede mRNA degrading enzymes. WO2011/141027 describes that slowly-read codons can be positioned in such a way as to cause high ribosome occupancy across a critical region of the 5' end of the mRNA can increase the half-life of a message by as much as 25%, and produce a similar uplift in protein production. In contrast, positioning even a single slow-read codon before this critical region can significantly destabilize the mRNA and result in an attenuation of protein expression. This understanding enables the design of mRNAs so as to suit the desired functionality. In addition, chemical modifications such as those described for guide sequences herein can be envisaged to increase mRNA stability.

b. Guide Stability

In certain embodiments, the methods make use of chemically modified guide RNAs. Examples of guide RNA chemical modifications include, without limitation, incorporation of 2'-O-methyl (M), 2'-O-methyl 3'phosphorothioate (MS), or 2'-O-methyl 3'thioPACE (MSP) at one or more terminal nucleotides. Such chemically modified guide RNAs can comprise increased stability and increased activity as compared to unmodified guide RNAs, though on-target vs. off-target specificity is not predictable. (See, Hendel, 2015, Nat Biotechnol. 33(9):985-9, doi: 10.1038/nbt.3290, published online 29 Jun. 2015). Chemically modified guide RNAs father include, without limitation, RNAs with phosphorothioate linkages and locked nucleic acid (LNA) nucleotides comprising a methylene bridge between the 2' and 4' carbons of the ribose ring.

Select Best Target Site in Gene a) Selection within a Target Gene

Studies to date suggest that while sgRNA activity can be quite high, there is significant variability among sgRNAs in their ability to generate the desired target cleavage. Efforts have been made to identify design criteria to maximize guide RNA efficacy. Doench et al. (Nat Biotechnol. 2014 December; 32(12): 1262-1267 and Nat Biotechnol. PubMed PMID: 26780180) describe the development of a quantitative model to optimize sgRNA activity prediction, and a tool to use this model for sgRNA design. Accordingly, in particular embodiments, the methods provided herein comprise identifying an optimal guide sequence based on a statistical comparison of active guide RNAs, such as described by Doench et al. (above). In particular embodiments, at least five gRNAs are designed per target and these are tested empirically in cells to generate at least one which has sufficiently high activity.

Figure 9:
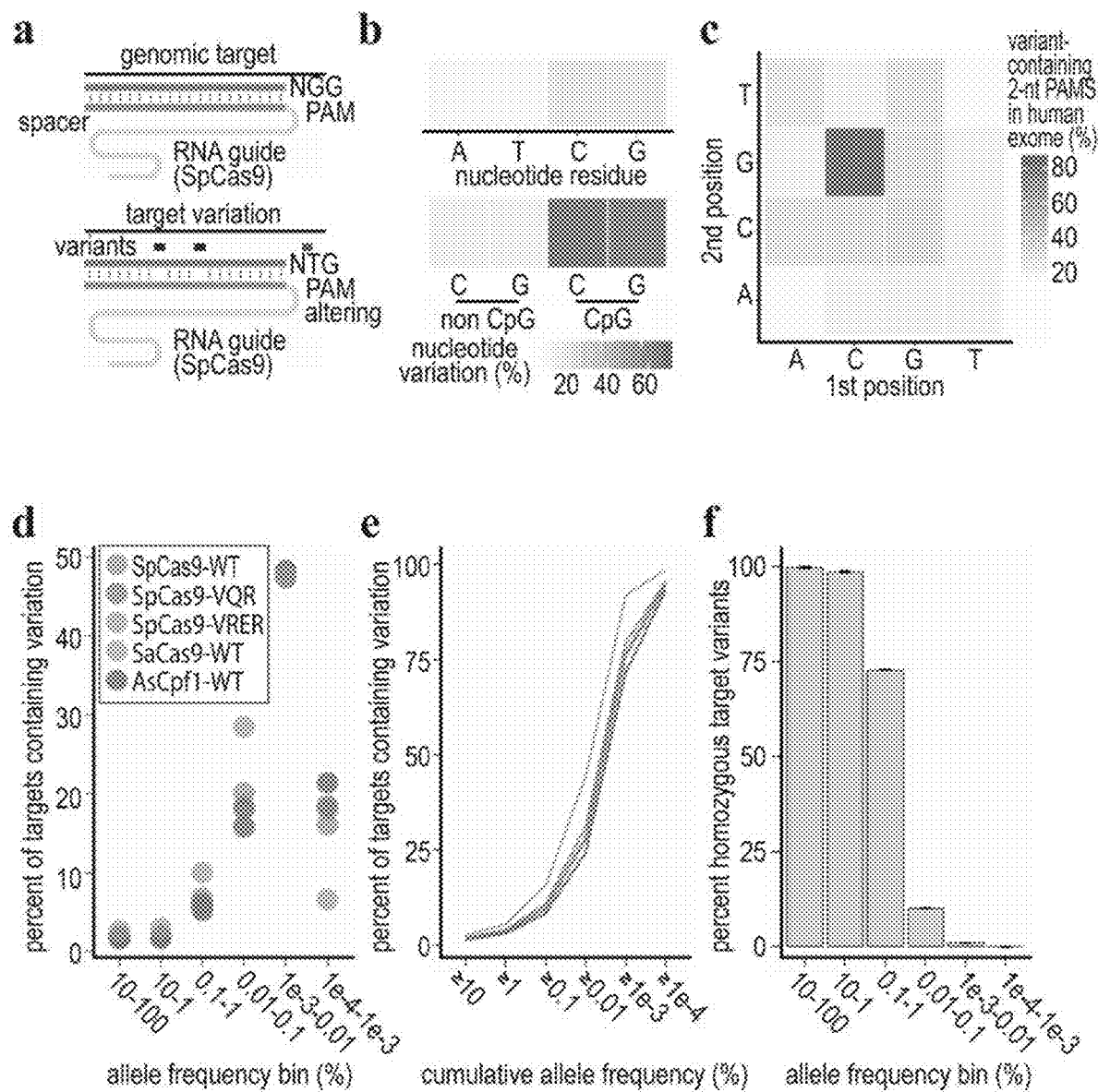
FIG. 9A-F depicts how human genetic variation significantly impacts the efficacy of RNA-guided endonucleases. a) Schematic illustrating the genomic target, RNA guide, and target variation. b) Fraction of residues for individual nucleotides containing variation in the ExAC dataset. c) Fraction of 2-nt PAM motifs altered by variants in the ExAC dataset. d) Percent of targets variants at different allele frequencies for each CRISPR endonuclease. e) Cumulative percent of targets containing variants for each enzyme. f) Fraction of targets containing homozygous variants at different allele frequencies. The mean and standard deviation for all enzymes is shown.

***Note that there is mention of a manual entitled "]"]How to design CRISPR crRNA for gene disruption "from integrated technologies which apparently mentions concept of "targeting an early 5' exon of your gene reduces the chances of functional [off-target]" but this link is no longer working.
b) Identification of Suitable Guide Sequence Currently RNA guides are designed using the reference human genome; however, failing to take into account variation in the human population may confound the therapeutic outcome for a given RNA guide. The recently released ExAC dataset, based on 60,706 individuals, contains on average one variant per eight nucleotides in the human exome (Lek, M. et al. Analysis of protein-coding genetic variation in 60,706 humans. Nature 536, 285-291 (2016)). This highlights the potential for genetic variation to impact the efficacy of certain RNA guides across patient populations for CRISPR-based gene therapy, due to the presence of mismatches between the RNA guide and variants present in the target site of specific patients. To assess this impact, we use the ExAC dataset to catalog variants present in all possible targets in the human reference exome that either (i) disrupt the target PAM sequence or (ii) introduce mismatches between the RNA guide and the genomic DNA, which can collectively be termed target variation (FIG. 9a). For treatment of a patient population, avoiding target variation for RNA guides administered to individual patients will maximize the consistency of outcomes for a genome editing therapeutic. The demonstration of the impact of target variation is illustrated in the examples section herein.

Figure 12:
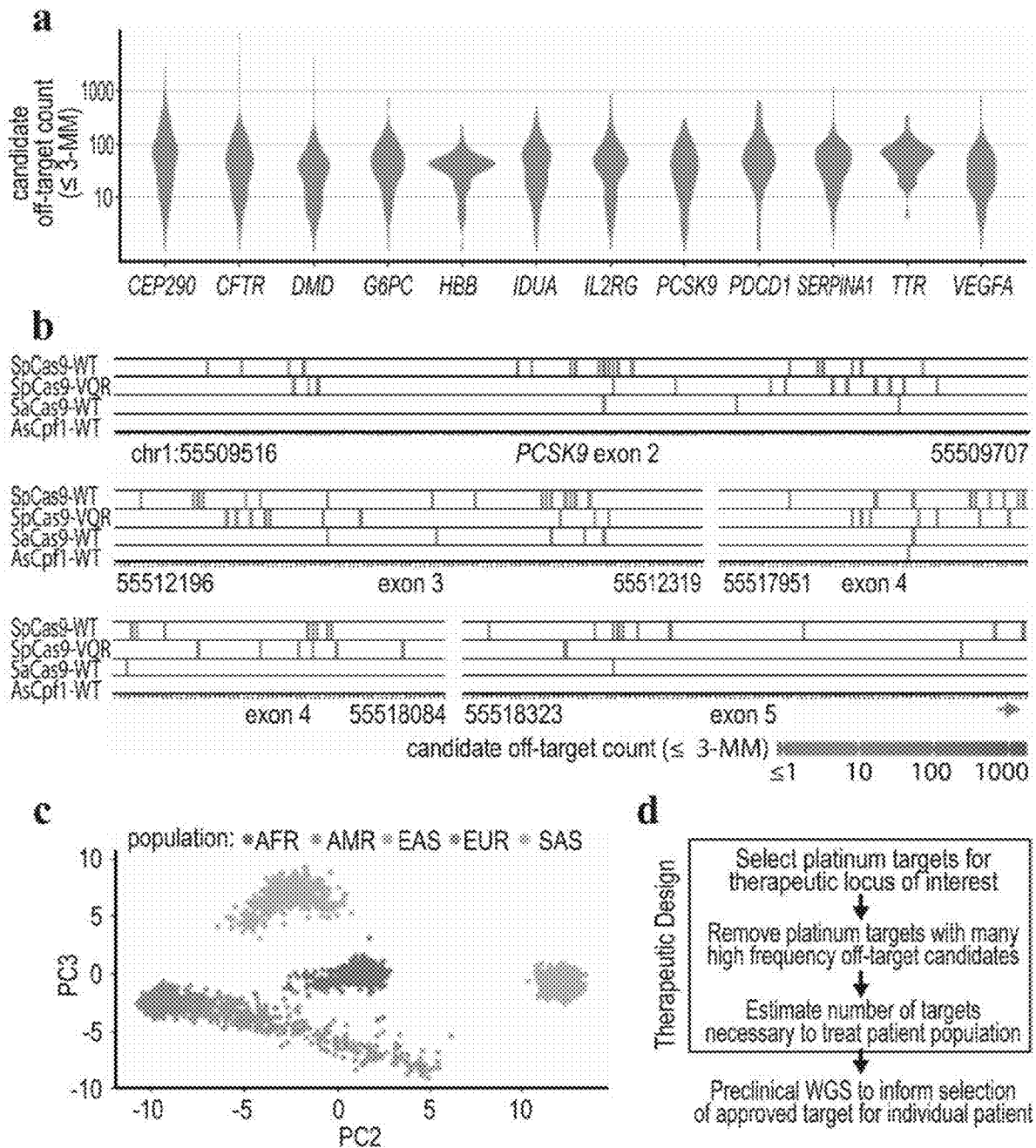
FIG. 12A-D depicts how gene- and population-specific variation informs therapeutic design. a) Distribution of the number of off-target candidates per platinum target for 12 therapeutically relevant genes. b) Total off-target candidates for platinum targets spanning exons 2-5 of PCSK9-001 are shown for each enzyme. c) Principal component analysis (PCA) separating 1000 Genomes individuals into super populations based on patient-specific off-target profiles for platinum targets spanning 12 therapeutically relevant genes. PC2 and PC3 are shown. AFR, African; AMR, Ad mixed American; EAS, East Asian; EUR, European; SAS, South Asian. d) Proposed therapeutic design framework.

Ideally, personalized genomic medicine would tailor RNA-guided endonuclease therapeutics for each patient. However, it would likely be cost-prohibitive and infeasible from a regulatory standpoint to design an individual RNA guide for each patient receiving a genome editing therapy. The analysis of the impact of genetic variation on the efficacy and safety of RNA-guided endonucleases motivates the following framework to streamline the design and testing of genome editing therapeutics (FIG. 12d). First, use of RNA guides for platinum targets would ensure perfect targeting for 99.99% of patients. Second, these RNA guides need to be further selected to minimize the number of off-target candidates occurring on high frequency haplotypes in the patient population. Third, low frequency variation captured in large scale sequencing datasets can be used to estimate the number of guide RNA-enzyme combinations required to effectively and safely treat different sizes of patient populations. Growth of large scale sequencing datasets will improve the accuracy of these estimates. Fourth, pre-therapeutic whole genome sequencing of individual patients will be needed to select a single approved guide RNA-enzyme combination for treatment. This combination should be a perfect match to the patient's genome and be free of patient-specific off-target candidates. This framework, in combination with rapidly accumulating human sequencing data, which will further refine these selection criteria, will enable the design and validation of genome editing therapeutics minimizing both the number of guide RNA-enzyme combinations necessary for approval and the cost of delivering effective and safe gene therapies to patients.

Accordingly, in particular embodiments, the methods provided herein comprise one or more of the following steps: (1) identifying platinum targets, (2) selection of the guides to minimize the number of off-target candidates occurring on high frequency haplotypes in the patient population; (3) select guide (and/or effector protein) based low frequency variation captured in large scale sequencing datasets to estimate the number of guide RNA-enzyme combinations required to effectively and safely treat different sizes of patient populations, and (4) confirm or select guide based on pre-therapeutic whole genome sequencing of individual patient. In particular embodiments, a "platinum" target is one that does not contain variants occurring at >0.01% allele frequency.

Methods for Determining on/Off-Target Activity and Selecting Suitable Target Sequences/Guides In certain example embodiments, parameters such as, but not limited to, off-target candidates, PAM restrictiveness, target cleavage efficiency, or effector protein specific may be determined using sequencing-based double-strand break (DSB) detection assays. Example sequencing-based DSB detection assay sChIP-seq (Szilard et al. Nat. Struct. Mol. Biol. 18, 299-305 (2010); Iacovoni et al. EMBO J. 29, 1446-1457 (2010)), BLESS (Crosetto et al. Nat. Methods 10, 361-365 (2013); Ran et al. Nature 520, 186-191 (2015); Slaymaker et al. Science 351, 84-88 (2016)), GUIDEseq (Tsai et al. Nat. Biotech 33, 187-197 (2015)), Digenome-seq (Kim et al. Nat. Methods 12, 237-43 (2015)), IDLV-mediated DNA break capture (Wang et al. Nat. Biotechnol. 33, 179-186 (2015), HTGTS (Frock et al. Nat. Biotechnol. 33, 179-186 (2015)), End-Seq (Canela et al. Mol. Cell 63, 898-911 (2016), and DSBCapture (Lensing et al. Nat. Methods 13, 855-857 (2016). Additional methods that may be used to assess target cleavage efficiency include SITE-Seq (Cameron et al. Nature Methods, 14, 600-606 (2017), and CIRCLE-seq (Tsai et al. Nature Methods 14, 607-614 (2017)).

Methods useful for assessing Cpf1 RNase activity include those disclosed in Zhong et al. Nature Chemical Biology Jun. 19, 2017 doi: 10.1038/NCHEMBIO.2410. Increased RNase activity and the ability to excise multiple CRISPR RNAs (crRNA) from a single RNA polymerase II-driven RNA transcript can simplify modification of multiple genomic targets and can be used to increase the efficiency of Cpf1-mediated editing.

Bliss

Other suitable assays include those described in Yan et al. ("BLISS: quantitative and versatile genome-wide profiling of DNA breaks in situ", BioRxiv, Dec. 4, 2016, doi: dx.doi.org/10.1101/091629) describe a versatile, sensitive and quantitative method for detecting DSBs applicable to low-input specimens of both cells and tissues that is scalable for high-throughput DSB mapping in multiple samples. Breaks Labeling In Situ and Sequencing (BLISS), features efficient in situ DSB labeling in fixed cells or tissue sections immobilized onto a solid surface, linear amplification of tagged DSBs via T7-mediated in vitro transcription (IVT) for greater sensitivity, and accurate DSB quantification by incorporation of unique molecular identifiers (UMIs).

Curtain

A further method, has been developed which may also be useful in assessing certain parameters disclosed herein. The method allowing on target and off target cutting of a nuclease to be assessed in a direct and unbiased way using in vitro cutting of immobilized nucleic acid molecules. Further reference is made to International Patent Application No. PCT/US2017/028009 entitled "Unbiased Detection of Nucleic Acid Modifications" filed on Jun. 16, 2017.

This method may also be used to select a suitable guide RNA. The method allows the detection of a nucleic acid modification, by performing the following steps: i) contacting one or more nucleic acid molecules immobilized on a solid support (immobilized nucleic acid molecules) with an agent capable of inducing a nucleic acid modification; and ii) sequencing at least part of said one or more immobilized nucleic acid molecules that comprises the nucleic acid modification using a primer specifically binding to a primer binding site. This method further allows the selection of a guide RNA from a plurality of guide RNAs specific for a selected target sequence. In particular embodiments, the method comprises contacting a plurality of nucleic acid molecules immobilized on a solid support (immobilized nucleic acid molecules) with a plurality of RNA-guided nuclease complexes capable of inducing a nucleic acid break, said plurality of RNA-guided nuclease complexes comprising a plurality of different guide RNA's, thereby inducing one or more nucleic acid breaks; attaching an adapter comprising a primer binding site to said one or more immobilized nucleic acid molecules comprising a nucleic acid break; sequencing at least part of said one or more immobilized nucleic acid molecules comprising a nucleic acid break using a primer specifically binding to said primer binding site; and selecting a guide RNA based on location and/or amount of said one or more breaks.

In particular embodiments, the method comprises determining one or more locations in said one or more immobilized nucleic acid molecules comprising a break other than a location comprising said selected target sequence (off-target breaks) and selecting a guide RNA based on said one or more locations. In particular embodiments, step v comprises determining a number of sites in said one or more immobilized nucleic acid molecules comprising off-target breaks and selecting a guide RNA based on said number of sites. In a further embodiment, step iv comprises both determining the location of off-targets breaks and the number of locations of off-target breaks.

Safety

1. Select Protein with Shortest Half-Life a) Inherent Half-Life of the Effector Protein The extended presence of an effector protein after having performed its function at the target site is a potential safety concern, both for off-target effects and direct toxicity of the effector protein. It has been reported that upon direct delivery to the cell by LNP, CRISPR effector proteins degrade rapidly within the cell (Kim et al. Genome Res. 2014 June; 24(6): 1012-1019). Where the effector protein is to be expressed from a plasmid, strategies to actively reduce the half-life of the protein may be of interest.

b) Use of Destabilized Domains

In certain embodiments, the methods provided herein involve the use of a Cpf1 effector protein which is associated with or fused to a destabilization domain (DD). The technology relating to the use of destabilizing domains is described in detail in WO2016/106244, which is incorporated by reference herein.

Destabilizing domains (DD) are domains which can confer instability to a wide range of proteins; see, e.g., Miyazaki, J Am Chem Soc. Mar. 7, 2012; 134(9): 3942-3945, and Chung H Nature Chemical Biology Vol. 11 Sep. 2015 pgs 713-720, incorporated herein by reference. DD can be associated with, e.g., fused to, advantageously with a linker, to a CRISPR enzyme, whereby the DD can be stabilized in the presence of a ligand and when there is the absence thereof the DD can become destabilized, whereby the CRISPR enzyme is entirely destabilized, or the DD can be stabilized in the absence of a ligand and when the ligand is present the DD can become destabilized; the DD allows the Cpf1 effector to be regulated or controlled, thereby providing means for regulation or control of the system. For instance, when a protein of interest is expressed as a fusion with the DD tag, it is destabilized and rapidly degraded in the cell, e.g., by proteasomes. Thus, absence of stabilizing ligand leads to a DD-associated Cpf1 being degraded. Peak activity of the Cpf1 effector is relevant to reduce off-target effects and for the general safety of the system. Advantages of the DD system include that it can be dosable, orthogonal (e.g., a ligand only affects its cognate DD so two or more systems can operate independently), transportable (e.g., may work in different cell types or cell lines) and allows for temporal control.

Suitable DD—stabilizing ligand pairs are known in the art and also described in WO2016/106244. The size of Destabilization Domain varies but is typically approx.-approx. 100-300 amino acids in size. Suitable examples include ER50 and/or DHFR50. A corresponding stabilizing ligand for ER50 is, for example, 4HT or CMP8. In some embodiments, one or two DDs may be fused to the N-terminal end of the CRISPR enzyme with one or two DDs fused to the C-terminal of the CRISPR enzyme. While the DD can be provided directly at N and/or C terminal(s) of the Cpf1 effector protein, they can also be fused via a linker, such as a GlySer linker, or an NLS and/or NES. A commercially available DD system is the CloneTech, ProteoTuner™ system; the stabilizing ligand is Shield1. In some embodiments, the stabilizing ligand is a 'small molecule', preferably it is cell-permeable and has a high affinity for its corresponding DD.

2. Select Least Immunogenic RNP

When administering an agent to a mammal, there is always the risk of an immune response to the agent and/or its delivery vehicle. Circumventing the immune response is a major challenge for most delivery vehicles. Viral vectors, which express immunogenic epitopes within the organism typically induce an immune response. Nanoparticle and lipid-based vectors to some extent address this problem. Yin et al. demonstrate a therapeutic approach combining viral delivery of the guide RNA with lipid nanoparticle-mediated delivery of the CRISPR effector protein (Nature Biotechnology 34:328-33(2016)). Ziris et al. describes cationic-lipid mediated delivery of Cas9:guideRNA nuclease complexes to cells. The CRISPR effector proteins, which are of bacterial origin, also inherently carry the risk of eliciting an immune response. This may be addressed by humanizing the Cpf1 effector protein.

3. Introduce Modifications in Guide RNA to Minimize Immunogenicity

Chemical modifications of RNAs have been used to avoid reactions of the innate immune system. Judge et al. (2006) demonstrated that immune stimulation by synthetic siRNA can be completely abrogated by selective incorporation of 2'-O-methyl (2'OMe) uridine or guanosine nucleosides into one strand of the siRNA duplex (Mol. Ther., 13 (2006), pp. 494-505). Cekaite et al. (J. Mol. Biol., 365 (2007), pp. 90-108) observed that replacement of only uridine bases of siRNA with either 2'-fluoro or 2'-O-methyl modified counterparts abrogated upregulation of genes involved in the regulation of the immune response. Similarly Hendel et al. tested sgRNAs with both backbone and sugar modifications that confer nuclease stability and can reduce immunostimulatory effects (Hendel et al., Nat. Biotechnol., 33 (2015), pp. 985-989).

Accordingly, in particular embodiments, the methods comprise modifying the guide RNA so as to minimize immunogenicity using one or more of these methods.

Identify Optimal Dosage to Minimize Toxicity and Maximize Specificity

It is generally accepted that the dosage of CRISPR components will be relevant to toxicity and specificity of the system (Pattanayak et al. Nat Biotechnol. 2013 September; 31(9): 839-843). Hsu et al. (Nat Biotechnol. 2013 September; 31(9): 827-832) demonstrated that the dosage of SpCas9 and sgRNA can be titrated to address these issues. In certain example embodiments, toxicity is minimized by saturating complex with guide by either pre-forming complex, putting guide under control of a strong promoter, or via timing of delivery to ensure saturating conditions available during expression of the effector protein.

Identifying Appropriate Delivery Vector

In some embodiments, the components of the CRISPR system may be delivered in various form, such as combinations of DNA/RNA or RNA/RNA or protein/RNA. For example, the Cpf1 may be delivered as a DNA-coding polynucleotide or an RNA-coding polynucleotide or as a protein. The guide may be delivered as a DNA-coding polynucleotide or an RNA. All possible combinations are envisioned, including mixed forms of delivery.

In some aspects, the invention provides methods comprising delivering one or more polynucleotides, such as or one or more vectors as described herein, one or more transcripts thereof, and/or one or proteins transcribed therefrom, to a host cell.

Vectors

Conventional viral and non-viral based gene transfer methods can be used to introduce nucleic acids in mammalian cells or target tissues. Such methods can be used to administer nucleic acids encoding components of a nucleic acid-targeting system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, Science 256:808-813 (1992); Nabel & Felgner, TIBTECH 11:211-217 (1993); Mitani & Caskey, TIBTECH 11:162-166 (1993); Dillon, TIBTECH 11:167-175 (1993); Miller, Nature 357:455-460 (1992); Van Brunt, Biotechnology 6(10):1149-1154 (1988); Vigne, Restorative Neurology and Neuroscience 8:35-36 (1995); Kremer & Perricaudet, British Medical Bulletin 51(1):31-44 (1995); Haddada et al., in Current Topics in Microbiology and Immunology, Doerfler and Bohm (eds) (1995); and Yu et al., Gene Therapy 1:13-26 (1994).

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424; WO 91/16024. Delivery can be to cells (e.g. in vitro or ex vivo administration) or target tissues (e.g. in vivo administration).

Plasmid delivery involves the cloning of a guide RNA into a CRISPR effector protein expressing plasmid and transfecting the DNA in cell culture. Plasmid backbones are available commercially and no specific equipment is required. They have the advantage of being modular, capable of carrying different sizes of CRISPR effector coding sequences (including those encoding larger sized proteins) as well as selection markers. Both an advantage of plasmids is that they can ensure transient, but sustained expression. However, delivery of plasmids is not straightforward such that in vivo efficiency is often low. The sustained expression can also be disadvantageous in that it can increase off-target editing. In addition excess build-up of the CRISPR effector protein can be toxic to the cells. Finally, plasmids always hold the risk of random integration of the dsDNA in the host genome, more particularly in view of the double-stranded breaks being generated (on and off-target).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). This is discussed more in detail below.

The advantages and disadvantages of Plasmid delivery are described by Plasmid delivery involves the cloning of a guide RNA into a CRISPR effector protein expressing plasmid and transfecting the DNA in cell culture. Plasmid backbones are available commercially and no specific equipment is required. They have the advantage of being modular, capable of carrying different sizes of CRISPR effector coding sequences (including those encoding larger sized proteins) as well as selection markers. Both an advantage of plasmids is that they can ensure transient, but sustained expression. However, delivery of plasmids is not straightforward such that in vivo efficiency is often low. The sustained expression can also be disadvantageous in that it can increase off-target editing. In addition excess build-up of the CRISPR effector protein can be toxic to the cells. Finally, plasmids always hold the risk of random integration of the dsDNA in the host genome, more particularly in view of the double-stranded breaks being generated (on and off-target). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787). This is discussed more in detail below.

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Virol. 66:2731-2739 (1992); Johann et al., J. Virol. 66:1635-1640 (1992); Sommnerfelt et al., Virol. 176:58-59 (1990); Wilson et al., J. Virol. 63:2374-2378 (1989); Miller et al., J. Virol. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Virol. 63:03822-3828 (1989).

The invention provides AAV that contains or consists essentially of an exogenous nucleic acid molecule encoding a CRISPR system, e.g., a plurality of cassettes comprising or consisting a first cassette comprising or consisting essentially of a promoter, a nucleic acid molecule encoding a CRISPR-associated (Cas) protein (putative nuclease or helicase proteins), e.g., Cpf1 and a terminator, and a two, or more, advantageously up to the packaging size limit of the vector, e.g., in total (including the first cassette) five, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector), or two or more individual rAAVs, each containing one or more than one cassette of a CRISPR system, e.g., a first rAAV containing the first cassette comprising or consisting essentially of a promoter, a nucleic acid molecule encoding Cas, e.g., Cas (Cpf1) and a terminator, and a second rAAV containing a plurality, four, cassettes comprising or consisting essentially of a promoter, nucleic acid molecule encoding guide RNA (gRNA) and a terminator (e.g., each cassette schematically represented as Promoter-gRNA1-terminator, Promoter-gRNA2-terminator Promoter-gRNA(N)-terminator (where N is a number that can be inserted that is at an upper limit of the packaging size limit of the vector). As rAAV is a DNA virus, the nucleic acid molecules in the herein discussion concerning AAV or rAAV are advantageously DNA. The promoter is in some embodiments advantageously human Synapsin I promoter (hSyn). Additional methods for the delivery of nucleic acids to cells are known to those skilled in the art. See, for example, US20030087817, incorporated herein by reference.

In another embodiment, Cocal vesiculovirus envelope pseudotyped retroviral vector particles are contemplated (see, e.g., US Patent Publication No. 20120164118 assigned to the Fred Hutchinson Cancer Research Center). Cocal virus is in the Vesiculovirus genus, and is a causative agent of vesicular stomatitis in mammals. Cocal virus was originally isolated from mites in Trinidad (Jonkers et al., Am. J. Vet. Res. 25:236-242 (1964)), and infections have been identified in Trinidad, Brazil, and Argentina from insects, cattle, and horses. Many of the vesiculoviruses that infect mammals have been isolated from naturally infected arthropods, suggesting that they are vector-borne. Antibodies to vesiculoviruses are common among people living in rural areas where the viruses are endemic and laboratory-acquired; infections in humans usually result in influenza-like symptoms. The Cocal virus envelope glycoprotein shares 71.5% identity at the amino acid level with VSV-G Indiana, and phylogenetic comparison of the envelope gene of vesiculoviruses shows that Cocal virus is serologically distinct from, but most closely related to, VSV-G Indiana strains among the vesiculoviruses. Jonkers et al., Am. J. Vet. Res. 25:236-242 (1964) and Travassos da Rosa et al., Am. J. Tropical Med. & Hygiene 33:999-1006 (1984). The Cocal vesiculovirus envelope pseudotyped retroviral vector particles may include for example, lentiviral, alpharetroviral, betaretroviral, gammaretroviral, deltaretroviral, and epsilonretroviral vector particles that may comprise retroviral Gag, Pol, and/or one or more accessory protein(s) and a Cocal vesiculovirus envelope protein. Within certain aspects of these embodiments, the Gag, Pol, and accessory proteins are lentiviral and/or gammaretroviral.

In some embodiments, a host cell is transiently or non-transiently transfected with one or more vectors described herein. In some embodiments, a cell is transfected as it naturally occurs in a subject optionally to be reintroduced therein. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLa-S3, Huh1, Huh4, Huh7, HUVEC, HASMC, HEKn, HEKa, MiaPaCell, Panc1, PC-3, TF1, CTLL-2, C1R, Rath, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRCS, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr −/−, COR-L23, COR-L23/CPR, COR-L2315010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A /PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)). In some embodiments, a cell transfected with one or more vectors described herein is used to establish a new cell line comprising one or more vector-derived sequences. In some embodiments, a cell transiently transfected with the components of a CRISPR system as described herein (such as by transient transfection of one or more vectors, or transfection with RNA), and modified through the activity of a CRISPR complex, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments it is envisaged to introduce the RNA and/or protein directly to the host cell. For instance, the CRISPR effector can be delivered as CRISPR effector-encoding mRNA together with an in vitro transcribed guide RNA. Such methods can reduce the time to ensure effect of the CRISPR effector protein and further prevents long-term expression of the CRISPR system components.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference. Delivery systems aimed specifically at the enhanced and improved delivery of siRNA into mammalian cells have been developed, (see, for example, Shen et al FEBS Let. 2003, 539: 111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Indeed, RNA delivery is a useful method of in vivo delivery. It is possible to deliver Cpf1 and gRNA (and, for instance, HR repair template) into cells using liposomes or nanoparticles. Thus delivery of the CRISPR enzyme, such as a Cpf1 and/or delivery of the RNAs of the invention may be in RNA form and via microvesicles, liposomes or particle or particles. For example, Cpf1 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via particles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E ($\alpha$-tocopherol) may be conjugated with CRISPR-Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mM posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR-Cas conjugated to $\alpha$-tocopherol and co-administered with HDL targeted to the brain may be contemplated for humans in the present invention, for example, about 3 nmol to about 3 $\mu$mol of CRISPR-Cas targeted to the brain may be contemplated. Zou et al. ((HUMAN GENE THERAPY 22:465-475 (April 2011)) describes a method of lentiviral-mediated delivery of short-hairpin RNAs targeting PKC$\gamma$ for in vivo gene silencing in the spinal cord of rats. Zou et al. administered about 10 $\mu$l of a recombinant lentivirus having a titer of 1×10$^9$ transducing units (TU)/ml by an intrathecal catheter. A similar dosage of CRISPR-Cas expressed in a lentiviral vector targeted to the brain may be contemplated for humans in the present invention, for example, about 10-50 ml of CRISPR-Cas targeted to the brain in a lentivirus having a titer of 1×10$^9$ transducing units (TU)/ml may be contemplated.

Vector delivery, e.g., plasmid, viral delivery: The CRISPR enzyme, for instance a Cpf1, and/or any of the present RNAs, for instance a guide RNA, can be delivered using any suitable vector, e.g., plasmid or viral vectors, such as adeno associated virus (AAV), lentivirus, adenovirus or other viral vector types, or combinations thereof. Cpf1 and one or more guide RNAs can be packaged into one or more vectors, e.g., plasmid or viral vectors. In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6 - 1 \times 10^{12}$ particles), more preferably at least about $1 \times 10^7$ particles, more preferably at least about $1 \times 10^8$ particles (e.g., about $1 \times 10^8 - 1 \times 10^{11}$ particles or about $1 \times 10^8 - 1 \times 10^{12}$ particles), and most preferably at least about $1 \times 10^0$ particles (e.g., about $1 \times 10^9 - 1 \times 10^{10}$ particles or about $1 \times 10^9 - 1 \times 10^{12}$ particles), or even at least about $1 \times 10^{10}$ particles (e.g., about $1 \times 10^{10} - 1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

Among vectors that may be used in the practice of the invention, integration in the host genome of a cell is possible with retrovirus gene transfer methods, often resulting in long term expression of the inserted transgene. In a preferred embodiment the retrovirus is a lentivirus. Additionally, high transduction efficiencies have been observed in many different cell types and target tissues. The tropism of a retrovirus can be altered by incorporating foreign envelope proteins, expanding the potential target population of target cells. A retrovirus can also be engineered to allow for conditional expression of the inserted transgene, such that only certain cell types are infected by the lentivirus. Cell type specific promoters can be used to target expression in specific cell types. Lentiviral vectors are retroviral vectors (and hence both lentiviral and retroviral vectors may be used in the practice of the invention). Moreover, lentiviral vectors are preferred as they are able to transduce or infect non-dividing cells and typically produce high viral titers. Selection of a retroviral gene transfer system may therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the desired nucleic acid into the target cell to provide permanent expression. Widely used retroviral vectors that may be used in the practice of the invention include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., (1992) J. Virol. 66:2731-2739; Johann et al., (1992) J. Virol. 66:1635-1640; Sommnerfelt et al., (1990) Virol. 176:58-59; Wilson et al., (1998) J. Virol. 63:2374-2378; Miller et al., (1991) J. Virol. 65:2220-2224; PCT/US94/05700). Zou et al. administered about 10 μl of a recombinant lentivirus having a titer of $1 \times 10^9$ transducing units (TU)/ml by an intrathecal catheter. These sort of dosages can be adapted or extrapolated to use of a retroviral or lentiviral vector in the present invention.

Vector Packaging of Cpf1

Ways to package inventive Cpf1 coding nucleic acid molecules, e.g., DNA, into vectors, e.g., viral vectors, to mediate genome modification in vivo include:

To achieve NHEJ-mediated gene knockout:

Single virus vector:

Vector containing two or more expression cassettes:

Promoter-Cpf1 coding nucleic acid molecule-terminator

Promoter-gRNA1-terminator

Promoter-gRNA2-terminator

Promoter-gRNA(N)-terminator (up to size limit of vector)

Double virus vector:

Vector 1 containing one expression cassette for driving the expression of Cpf1

Promoter-Cpf1 coding nucleic acid molecule-terminator
Vector 2 containing one more expression cassettes for driving the expression of one or more guideRNAs
Promoter-gRNA1-terminator
Promoter-gRNA(N)-terminator (up to size limit of vector)
To mediate homology-directed repair.

In addition to the single and double virus vector approaches described above, an additional vector can be used to deliver a homology-direct repair template. The promoter used to drive Cpf1 coding nucleic acid molecule expression can include:

AAV ITR can serve as a promoter: this is advantageous for eliminating the need for an additional promoter element (which can take up space in the vector). The additional space freed up can be used to drive the expression of additional elements (gRNA, etc.). Also, ITR activity is relatively weaker, so can be used to reduce potential toxicity due to over expression of Cpf1.

For ubiquitous expression, promoters that can be used include: CMV, CAG, CBh, PGK, SV40, Ferritin heavy or light chains, etc.

For brain or other CNS expression, can use promoters: Synapsin I for all neurons, CaMKIIalpha for excitatory neurons, GAD67 or GAD65 or VGAT for GABAergic neurons, etc.

For liver expression, can use Albumin promoter.
For lung expression, can use SP-B.
For endothelial cells, can use ICAM.
For hematopoietic cells can use IFNbeta or CD45.
For Osteoblasts can one can use the OG-2.
The promoter used to drive guide RNA can include:
Pol III promoters such as U6 or H1
Use of Pol II promoter and intronic cassettes to express gRNA Adeno Associated Virus (AAV)

Cpf1 and one or more guide RNA can be delivered using adeno associated virus (AAV), lentivirus, adenovirus or other plasmid or viral vector types, in particular, using formulations and doses from, for example, U.S. Pat. No. 8,454,972 (formulations, doses for adenovirus), U.S. Pat. No. 8,404,658 (formulations, doses for AAV) and U.S. Pat. No. 5,846,946 (formulations, doses for DNA plasmids) and from clinical trials and publications regarding the clinical trials involving lentivirus, AAV and adenovirus. For examples, for AAV, the route of administration, formulation and dose can be as in U.S. Pat. No. 8,454,972 and as in clinical trials involving AAV. For Adenovirus, the route of administration, formulation and dose can be as in U.S. Pat. No. 8,404,658 and as in clinical trials involving adenovirus. For plasmid delivery, the route of administration, formulation and dose can be as in U.S. Pat. No. 5,846,946 and as in clinical studies involving plasmids. Doses may be based on or extrapolated to an average 70 kg individual (e.g. a male adult human), and can be adjusted for patients, subjects, mammals of different weight and species. Frequency of administration is within the ambit of the medical or veterinary practitioner (e.g., physician, veterinarian), depending on usual factors including the age, sex, general health, other conditions of the patient or subject and the particular condition or symptoms being addressed. The viral vectors can be injected into the tissue of interest. For cell-type specific genome modification, the expression of Cpf1 can be driven by a cell-type specific promoter. For example, liver-specific expression might use the Albumin promoter and neuron-specific expression (e.g. for targeting CNS disorders) might use the Synapsin I promoter.

In terms of in vivo delivery, AAV is advantageous over other viral vectors for a couple of reasons:

Low toxicity (this may be due to the purification method not requiring ultra centrifugation of cell particles that can activate the immune response) and Low probability of causing insertional mutagenesis because it doesn't integrate into the host genome.

AAV has a packaging limit of 4.5 or 4.75 Kb. This means that Cpf1 as well as a promoter and transcription terminator have to be all fit into the same viral vector. Constructs larger than 4.5 or 4.75 Kb will lead to significantly reduced virus production. SpCas9 is quite large, the gene itself is over 4.1 Kb, which makes it difficult for packing into AAV. Therefore embodiments of the invention include utilizing homologs of Cpf1 that are shorter. For example:

TABLE 8

| Species | Cas9 Size (nt) |
| --- | --- |
| Corynebacter diphtheriae | 3252 |
| Eubacterium ventriosum | 3321 |
| Streptococcus pasteurianus | 3390 |
| Lactobacillus farciminis | 3378 |
| Sphaerochaeta globus | 3537 |
| Azospirillum B510 | 3504 |
| Gluconacetobacter diazotrophicus | 3150 |
| Neisseria cinerea | 3246 |
| Roseburia intestinalis | 3420 |
| Parvibaculum lavamentivorans | 3111 |
| Staphylococcus aureus | 3159 |
| Nitratifractor salsuginis DSM 16511 | 3396 |
| Campylobacter lar CF89-12 | 3009 |
| Campylobacter jejuni | 2952 |
| Streptococcus thermophilus LMD-9 | 3396 | rAAV vectors are preferably produced in insect cells, e.g., *Spodoptera frugiperda* Sf9 insect cells, grown in serum-free suspension culture. Serum-free insect cells can be purchased from commercial vendors, e.g., Sigma Aldrich (EX-CELL 405).

These species are therefore, in general, preferred Cpf1 species.

As to AAV, the AAV can be AAV1, AAV2, AAV5 or any combination thereof. One can select the AAV of the AAV with regard to the cells to be targeted; e.g., one can select AAV serotypes 1, 2, 5 or a hybrid capsid AAV1, AAV2, AAV5 or any combination thereof for targeting brain or neuronal cells; and one can select AAV4 for targeting cardiac tissue. AAV8 is useful for delivery to the liver. The herein promoters and vectors are preferred individually. A tabulation of certain AAV serotypes as to these cells (see Grimm, D. et al, J. Virol. 82: 5887-5911 (2008)) is as follows:

TABLE 9

| Cell Line | AAV-1 | AAV-2 | AAV-3 | AAV-4 | AAV-5 | AAV-6 | AAV-8 | AAV-9 |
| --- | --- | --- | --- | --- | --- | --- | --- | --- |
| Huh-7 | 13 | 100 | 2.5 | 0.0 | 0.1 | 10 | 0.7 | 0.0 |
| HEK293 | 25 | 100 | 2.5 | 0.1 | 0.1 | 5 | 0.7 | 0.1 |
| HeLa | 3 | 100 | 2.0 | 0.1 | 6.7 | 1 | 0.2 | 0.1 |
| HepG2 | 3 | 100 | 16.7 | 0.3 | 1.7 | 5 | 0.3 | ND |
| Hep1A | 20 | 100 | 0.2 | 1.0 | 0.1 | 1 | 0.2 | 0.0 |
| 911 | 17 | 100 | 11 | 0.2 | 0.1 | 17 | 0.1 | ND |
| CHO | 100 | 100 | 14 | 1.4 | 333 | 50 | 10 | 1.0 |
| COS | 33 | 100 | 33 | 3.3 | 5.0 | 14 | 2.0 | 0.5 |
| MeWo | 10 | 100 | 20 | 0.3 | 6.7 | 10 | 1.0 | 0.2 |
| NIH3T3 | 10 | 100 | 2.9 | 2.9 | 0.3 | 10 | 0.3 | ND |
| A549 | 14 | 100 | 20 | ND | 0.5 | 10 | 0.5 | 0.1 |
| HT1180 | 20 | 100 | 10 | 0.1 | 0.3 | 33 | 0.5 | 0.1 |

TABLE 9-continued

| Cell Line | AAV-1 | AAV-2 | AAV-3 | AAV-4 | AAV-5 | AAV-6 | AAV-8 | AAV-9 |
|---|---|---|---|---|---|---|---|---|
| Monocytes | 1111 | 100 | ND | ND | 125 | 1429 | ND | ND |
| Immature DC | 2500 | 100 | ND | ND | 222 | 2857 | ND | ND |
| Mature DC | 2222 | 100 | ND | ND | 333 | 3333 | ND | ND |

Lentivirus

Lentiviruses are complex retroviruses that have the ability to infect and express their genes in both mitotic and post-mitotic cells. The most commonly known lentivirus is the human immunodeficiency virus (HIV), which uses the envelope glycoproteins of other viruses to target a broad range of cell types.

Lentiviruses may be prepared as follows. After cloning pCasES10 (which contains a lentiviral transfer plasmid backbone), HEK293FT at low passage (p=5) were seeded in a T-75 flask to 50% confluence the day before transfection in DMEM with 10% fetal bovine serum and without antibiotics. After 20 hours, media was changed to OptiMEM (serum-free) media and transfection was done 4 hours later. Cells were transfected with 10 µg of lentiviral transfer plasmid (pCasES10) and the following packaging plasmids: 5 µg of pMD2.G (VSV-g pseudotype), and 7.5 µg of psPAX2 (gag/pol/rev/tat). Transfection was done in 4 mL OptiMEM with a cationic lipid delivery agent (50 µL Lipofectamine 2000 and 100 µl Plus reagent). After 6 hours, the media was changed to antibiotic-free DMEM with 10% fetal bovine serum. These methods use serum during cell culture, but serum-free methods are preferred.

Lentivirus may be purified as follows. Viral supernatants were harvested after 48 hours. Supernatants were first cleared of debris and filtered through a 0.45 µm low protein binding (PVDF) filter. They were then spun in a ultracentrifuge for 2 hours at 24,000 rpm. Viral pellets were resuspended in 50 µl of DMEM overnight at 4 C. They were then aliquoted and immediately frozen at −80° C.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285). In another embodiment, RetinoStat®, an equine infectious anemia virus-based lentiviral gene therapy vector that expresses angiostatic proteins endostatin and angiostatin that is delivered via a subretinal injection for the treatment of the web form of age-related macular degeneration is also contemplated (see, e.g., Binley et al., HUMAN GENE THERAPY 23:980-991 (September 2012)) and this vector may be modified for the CRISPR-Cas system of the present invention.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin,Takara Bio Inc.).

Lentiviral vectors have been disclosed as in the treatment for Parkinson's Disease, see, e.g., US Patent Publication No. 20120295960 and U.S. Pat. Nos. 7,303,910 and 7,351,585. Lentiviral vectors have also been disclosed for the treatment of ocular diseases, see e.g., US Patent Publication Nos. 20060281180, 20090007284, US20110117189; US20090017543; US20070054961, US20100317109. Lentiviral vectors have also been disclosed for delivery to the brain, see, e.g., US Patent Publication Nos. US20110293571; US20110293571, US20040013648, US20070025970, US20090111106 and U.S. Pat. No. 7,259,015.

Use of Minimal Promoters

The present application provides a vector for delivering an effector protein and at least one CRISPR guide RNA to a cell comprising a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4Kb. In an embodiment, the vector is an AAV vector. In another embodiment, the effector protein is a CRISPR enzyme. In a further embodiment, the CRISPR enzyme is SaCas9, Cpf1, Cas13b or C2c2.

In a related aspect, the invention provides a lentiviral vector for delivering an effector protein and at least one CRISPR guide RNA to a cell comprising a promoter operably linked to a polynucleotide sequence encoding Cpf1 and a second promoter operably linked to a polynucleotide sequence encoding at least one guide RNA, wherein the polynucleotide sequences are in reverse orientation.

In another aspect, the invention provides a method of expressing an effector protein and guide RNA in a cell comprising introducing the vector according any of the vector delivery systems disclosed herein. In an embodiment of the vector for delivering an effector protein, the minimal promoter is the Mecp2 promoter, tRNA promoter, or U6. In a further embodiment, the minimal promoter is tissue specific.

Dosage of Vectors

In some embodiments, the vector, e.g., plasmid or viral vector is delivered to the tissue of interest by, for example, an intramuscular injection, while other times the delivery is via intravenous, transdermal, intranasal, oral, mucosal, or other delivery methods. Such delivery may be either via a single dose, or multiple doses. One skilled in the art understands that the actual dosage to be delivered herein may vary greatly depending upon a variety of factors, such as the vector choice, the target cell, organism, or tissue, the general condition of the subject to be treated, the degree of transformation/modification sought, the administration route, the administration mode, the type of transformation/modification sought, etc.

Such a dosage may further contain, for example, a carrier (water, saline, ethanol, glycerol, lactose, sucrose, calcium phosphate, gelatin, dextran, agar, pectin, peanut oil, sesame oil, etc.), a diluent, a pharmaceutically-acceptable carrier (e.g., phosphate-buffered saline), a pharmaceutically-acceptable excipient, and/or other compounds known in the art. The dosage may further contain one or more pharmaceutically acceptable salts such as, for example, a mineral acid salt such as a hydrochloride, a hydrobromide, a phosphate, a sulfate, etc.; and the salts of organic acids such as acetates, propionates, malonates, benzoates, etc. Additionally, auxiliary substances, such as wetting or emulsifying agents, pH buffering substances, gels or gelling materials, flavorings, colorants, microspheres, polymers, suspension agents, etc. may also be present herein. In addition, one or more other conventional pharmaceutical ingredients, such as preservatives, humectants, suspending agents, surfactants, antioxidants, anticaking agents, fillers, chelating agents, coating agents, chemical stabilizers, etc. may also be present, especially if the dosage form is a reconstitutable form. Suitable exemplary ingredients include microcrystalline cellulose, carboxymethylcellulose sodium, polysorbate 80, phenylethyl alcohol, chlorobutanol, potassium sorbate, sorbic acid, sulfur dioxide, propyl gallate, the parabens, ethyl vanillin, glycerin, phenol, parachlorophenol, gelatin, albumin and a combination thereof. A thorough discussion of pharmaceutically acceptable excipients is available in REMINGTON'S PHARMACEUTICAL SCIENCES (Mack Pub. Co., N.J. 1991) which is incorporated by reference herein.

In an embodiment herein the delivery is via an adenovirus, which may be at a single booster dose containing at least $1 \times 10^5$ particles (also referred to as particle units, pu) of adenoviral vector. In an embodiment herein, the dose preferably is at least about $1 \times 10^6$ particles (for example, about $1 \times 10^6$-$1 \times 10^{12}$ particles), more preferably at least about $1 \times 10^7$ particles, more preferably at least about $1 \times 10^8$ particles (e.g., about $1 \times 10^8$-$1 \times 10^{11}$ particles or about $1 \times 10^8$-$1 \times 10^{12}$ particles), and most preferably at least about $1 \times 10^0$ particles (e.g., about $1 \times 10^9$-$1 \times 10^{10}$ particles or about $1 \times 10^9$-$1 \times 10^{12}$ particles), or even at least about $1 \times 10^{10}$ particles (e.g., about $1 \times 10^{10}$-$1 \times 10^{12}$ particles) of the adenoviral vector. Alternatively, the dose comprises no more than about $1 \times 10^{14}$ particles, preferably no more than about $1 \times 10^{13}$ particles, even more preferably no more than about $1 \times 10^{12}$ particles, even more preferably no more than about $1 \times 10^{11}$ particles, and most preferably no more than about $1 \times 10^{10}$ particles (e.g., no more than about $1 \times 10^9$ articles). Thus, the dose may contain a single dose of adenoviral vector with, for example, about $1 \times 10^6$ particle units (pu), about $2 \times 10^6$ pu, about $4 \times 10^6$ pu, about $1 \times 10^7$ pu, about $2 \times 10^7$ pu, about $4 \times 10^7$ pu, about $1 \times 10^8$ pu, about $2 \times 10^8$ pu, about $4 \times 10^8$ pu, about $1 \times 10^9$ pu, about $2 \times 10^9$ pu, about $4 \times 10^9$ pu, about $1 \times 10^{10}$ pu, about $2 \times 10^{10}$ pu, about $4 \times 10^{10}$ pu, about $1 \times 10^{11}$ pu, about $2 \times 10^{11}$ pu, about $4 \times 10^{11}$ pu, about $1 \times 10^{12}$ pu, about $2 \times 10^{12}$ pu, or about $4 \times 10^{12}$ pu of adenoviral vector. See, for example, the adenoviral vectors in U.S. Pat. No. 8,454,972 B2 to Nabel, et. al., granted on Jun. 4, 2013; incorporated by reference herein, and the dosages at col 29, lines 36-58 thereof. In an embodiment herein, the adenovirus is delivered via multiple doses.

In an embodiment herein, the delivery is via an AAV. A therapeutically effective dosage for in vivo delivery of the AAV to a human is believed to be in the range of from about 20 to about 50 ml of saline solution containing from about $1 \times 10^{10}$ to about $1 \times 10^{10}$ functional AAV/ml solution. The dosage may be adjusted to balance the therapeutic benefit against any side effects. In an embodiment herein, the AAV dose is generally in the range of concentrations of from about $1 \times 10^5$ to $1 \times 10^{50}$ genomes AAV, from about $1 \times 10^8$ to $1 \times 10^{20}$ genomes AAV, from about $1 \times 10^{10}$ to about $1 \times 10^{16}$ genomes, or about $1 \times 10^{11}$ to about $1 \times 10^{16}$ genomes AAV. A human dosage may be about $1 \times 10^{13}$ genomes AAV. Such concentrations may be delivered in from about 0.001 ml to about 100 ml, about 0.05 to about 50 ml, or about 10 to about 25 ml of a carrier solution. Other effective dosages can be readily established by one of ordinary skill in the art through routine trials establishing dose response curves. See, for example, U.S. Pat. No. 8,404,658 B2 to Hajjar, et al., granted on Mar. 26, 2013, at col. 27, lines 45-60.

In an embodiment herein the delivery is via a plasmid. In such plasmid compositions, the dosage should be a sufficient amount of plasmid to elicit a response. For instance, suitable quantities of plasmid DNA in plasmid compositions can be from about 0.1 to about 2 mg, or from about 1 μg to about 10 μg per 70 kg individual. Plasmids of the invention will generally comprise (i) a promoter; (ii) a sequence encoding a CRISPR enzyme, operably linked to said promoter; (iii) a selectable marker; (iv) an origin of replication; and (v) a transcription terminator downstream of and operably linked to (ii). The plasmid can also encode the RNA components of a CRISPR complex, but one or more of these may instead be encoded on a different vector.

The doses herein are based on an average 70 kg individual. The frequency of administration is within the ambit of the medical or veterinary practitioner (e.g., physician, veterinarian), or scientist skilled in the art. It is also noted that mice used in experiments are typically about 20 g and from mice experiments one can scale up to a 70 kg individual.

The dosage used for the compositions provided herein include dosages for repeated administration or repeat dosing. In particular embodiments, the administration is repeated within a period of several weeks, months, or years. Suitable assays can be performed to obtain an optimal dosage regime. Repeated administration can allow the use of lower dosage, which can positively affect off-target modifications.

RNA Delivery

In particular embodiments, RNA based delivery is used. In these embodiments, mRNA of the CRISPR effector protein is delivered together with in vitro transcribed guide RNA. Liang et al. describes efficient genome editing using RNA based delivery (Protein Cell. 2015 May; 6(5): 363-372).

RNA delivery: The CRISPR enzyme, for instance a Cpf1, and/or any of the present RNAs, for instance a guide RNA, can also be delivered in the form of RNA. Cpf1 mRNA can be generated using in vitro transcription. For example, Cpf1 mRNA can be synthesized using a PCR cassette containing the following elements: T7promoter-kozak sequence (GC-CACC)-Cpf1-3' UTR from beta globin-polyA tail (a string of 120 or more adenines). The cassette can be used for transcription by T7 polymerase. Guide RNAs can also be transcribed using in vitro transcription from a cassette containing T7 promoter-GG-guide RNA sequence.

To enhance expression and reduce possible toxicity, the CRISPR enzyme-coding sequence and/or the guide RNA can be modified to include one or more modified nucleoside e.g. using pseudo-U or 5-Methyl-C.

mRNA delivery methods are especially promising for liver delivery currently.

Much clinical work on RNA delivery has focused on RNAi or antisense, but these systems can be adapted for delivery of RNA for implementing the present invention. References below to RNAi etc. should be read accordingly.

CRISPR enzyme mRNA and guide RNA might also be delivered separately. CRISPR enzyme mRNA can be delivered prior to the guide RNA to give time for CRISPR enzyme to be expressed. CRISPR enzyme mRNA might be administered 1-12 hours (preferably around 2-6 hours) prior to the administration of guide RNA.

Alternatively, CRISPR enzyme mRNA and guide RNA can be administered together. Advantageously, a second booster dose of guide RNA can be administered 1-12 hours (preferably around 2-6 hours) after the initial administration of CRISPR enzyme mRNA+guide RNA.

RNP

In particular embodiments, pre-complexed guide RNA and CRISPR effector protein are delivered as a ribonucleoprotein (RNP). RNPs have the advantage that they lead to rapid editing effects even more so than the RNA method because this process avoids the need for transcription. An important advantage is that both RNP delivery is transient, reducing off-target effects and toxicity issues. Efficient genome editing in different cell types has been observed by Kim et al. (2014, Genome Res. 24(6):1012-9), Paix et al. (2015, Genetics 204(1):47-54), Chu et al. (2016, BMC Biotechnol. 16:4), and Wang et al. (2013, Cell. 9; 153(4): 910-8).

In particular embodiments, the ribonucleoprotein is delivered by way of a polypeptide-based shuttle agent as described in WO2016161516. WO2016161516 describes efficient transduction of polypeptide cargos using synthetic peptides comprising an endosome leakage domain (ELD) operably linked to a cell penetrating domain (CPD), to a histidine-rich domain and a CPD. Similarly these polypeptides can be used for the delivery of CRISPR-effector based RNPs in eukaryotic cells.

Indeed, RNA delivery is a useful method of in vivo delivery. It is possible to deliver Cpf1 and gRNA (and, for instance, HR repair template) into cells using liposomes or particles. Thus delivery of the CRISPR enzyme, such as a Cpf1 and/or delivery of the RNAs of the invention may be in RNA form and via microvesicles, liposomes or particles. For example, Cpf1 mRNA and gRNA can be packaged into liposomal particles for delivery in vivo. Liposomal transfection reagents such as lipofectamine from Life Technologies and other reagents on the market can effectively deliver RNA molecules into the liver.

Means of delivery of RNA also preferred include delivery of RNA via nanoparticles (Cho, S., Goldberg, M., Son, S., Xu, Q., Yang, F., Mei, Y., Bogatyrev, S., Langer, R. and Anderson, D., Lipid-like nanoparticles for small interfering RNA delivery to endothelial cells, Advanced Functional Materials, 19: 3112-3118, 2010) or exosomes (Schroeder, A., Levins, C., Cortez, C., Langer, R., and Anderson, D., Lipid-based nanotherapeutics for siRNA delivery, Journal of Internal Medicine, 267: 9-21, 2010, PMID: 20059641). Indeed, exosomes have been shown to be particularly useful in delivery siRNA, a system with some parallels to the CRISPR system. For instance, El-Andaloussi S, et al. ("Exosome-mediated delivery of siRNA in vitro and in vivo." Nat Protoc. 2012 December; 7(12):2112-26. doi: 10.1038/nprot.2012.131. Epub 2012 Nov. 15.) describe how exosomes are promising tools for drug delivery across different biological barriers and can be harnessed for delivery of siRNA in vitro and in vivo. Their approach is to generate targeted exosomes through transfection of an expression vector, comprising an exosomal protein fused with a peptide ligand. The exosomes are then purify and characterized from transfected cell supernatant, then RNA is loaded into the exosomes. Delivery or administration according to the invention can be performed with exosomes, in particular but not limited to the brain. Vitamin E (α-tocopherol) may be conjugated with CRISPR-Cas and delivered to the brain along with high density lipoprotein (HDL), for example in a similar manner as was done by Uno et al. (HUMAN GENE THERAPY 22:711-719 (June 2011)) for delivering short-interfering RNA (siRNA) to the brain. Mice were infused via Osmotic minipumps (model 1007D; Alzet, Cupertino, Calif.) filled with phosphate-buffered saline (PBS) or free TocsiBACE or Toc-siBACE/HDL and connected with Brain Infusion Kit 3 (Alzet). A brain-infusion cannula was placed about 0.5 mM posterior to the bregma at midline for infusion into the dorsal third ventricle. Uno et al. found that as little as 3 nmol of Toc-siRNA with HDL could induce a target reduction in comparable degree by the same ICV infusion method. A similar dosage of CRISPR-Cas conjugated to α-tocopherol and co-administered with HDL targeted to the brain may be contemplated for humans in the present invention, for example, about 3 nmol to about 3 μmol of CRISPR-Cas targeted to the brain may be contemplated.

Zou et al. ((HUMAN GENE THERAPY 22:465-475 (April 2011)) describes a method of lentiviral-mediated delivery of short-hairpin RNAs targeting PKCγ for in vivo gene silencing in the spinal cord of rats. Zou et al. administered about 10 μl of a recombinant lentivirus having a titer of 1×10⁹ transducing units (TU)/ml by an intrathecal catheter. A similar dosage of CRISPR-Cas expressed in a lentiviral vector may be contemplated for humans in the present invention, for example, about 10-50 ml of CRISPR-Cas in a lentivirus having a titer of 1×10⁹ transducing units (TU)/ml may be contemplated. A similar dosage of CRISPR-Cas expressed in a lentiviral vector targeted to the brain may be contemplated for humans in the present invention, for example, about 10-50 ml of CRISPR-Cas targeted to the brain in a lentivirus having a titer of 1×10⁹ transducing units (TU)/ml may be contemplated.

Anderson et al. (US 20170079916) provides a modified dendrimer nanoparticle for the delivery of therapeutic, prophylactic and/or diagnostic agents to a subject, comprising: one or more zero to seven generation alkylated dendrimers; one or more amphiphilic polymers; and one or more therapeutic, prophylactic and/or diagnostic agents encapsulated therein. One alkylated dendrimer may be selected from the group consisting of poly(ethyleneimine), poly (polypropylenimine), diaminobutane amine polypropylenimine tetramine and poly(amido amine). The therapeutic, prophylactic and diagnostic agent may be selected from the group consisting of proteins, peptides, carbohydrates, nucleic acids, lipids, small molecules and combinations thereof Anderson et al. (US 20160367686) provides a compound of Formula (I):

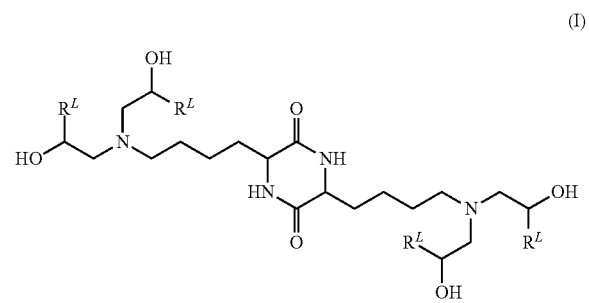

(I)

and salts thereof, wherein each instance of R L is independently optionally substituted C6-C40 alkenyl, and a composition for the delivery of an agent to a subject or cell comprising the compound, or a salt thereof; an agent; and optionally, an excipient. The agent may be an organic molecule, inorganic molecule, nucleic acid, protein, peptide, polynucleotide, targeting agent, an isotopically labeled chemical compound, vaccine, an immunological agent, or an agent useful in bioprocessing. The composition may further comprise cholesterol, a PEGylated lipid, a phospholipid, or an apolipoprotein.

Anderson et al. (US20150232883) provides a delivery particle formulations and/or systems, preferably nanoparticle delivery formulations and/or systems, comprising (a) a CRISPR-Cas system RNA polynucleotide sequence; or (b) Cas9; or (c) both a CRISPR-Cas system RNA polynucleotide sequence and Cas9; or (d) one or more vectors that contain nucleic acid molecule(s) encoding (a), (b) or (c), wherein the CRISPR-Cas system RNA polynucleotide sequence and the Cas9 do not naturally occur together. The delivery particle formulations may further comprise a surfactant, lipid or protein, wherein the surfactant may comprise a cationic lipid.

Anderson et al. (US20050123596) provides examples of microparticles that are designed to release their payload when exposed to acidic conditions, wherein the microparticles comprise at least one agent to be delivered, a pH triggering agent, and a polymer, wherein the polymer is selected from the group of polymethacrylates and polyacrylates.

Anderson et al (US 20020150626) provides lipid-protein-sugar particles for delivery of nucleic acids, wherein the polynucleotide is encapsulated in a lipid-protein-sugar matrix by contacting the polynucleotide with a lipid, a protein, and a sugar; and spray drying mixture of the polynucleotide, the lipid, the protein, and the sugar to make microparticles.

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797). It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

Particles

In some aspects or embodiments, a composition comprising a delivery particle formulation may be used. In some aspects or embodiments, the formulation comprises a CRISPR complex, the complex comprising a CRISPR protein and-a guide which directs sequence-specific binding of the CRISPR complex to a target sequence. In some embodiments, the delivery particle comprises a lipid-based particle, optionally a lipid nanoparticle, or cationic lipid and optionally biodegradable polymer. In some embodiments, the cationic lipid comprises 1,2-dioleoyl-3-trimethylammonium-propane (DOTAP). In some embodiments, the hydrophilic polymer comprises ethylene glycol or polyethylene glycol. In some embodiments, the delivery particle further comprises a lipoprotein, preferably cholesterol. In some embodiments, the delivery particles are less than 500 nm in diameter, optionally less than 250 nm in diameter, optionally less than 100 nm in diameter, optionally about 35 nm to about 60 nm in diameter.

Several types of particle delivery systems and/or formulations are known to be useful in a diverse spectrum of biomedical applications. In general, a particle is defined as a small object that behaves as a whole unit with respect to its transport and properties. Particles are further classified according to diameter. Coarse particles cover a range between 2,500 and 10,000 nanometers. Fine particles are sized between 100 and 2,500 nanometers. Ultrafine particles, or nanoparticles, are generally between 1 and 100 nanometers in size. The basis of the 100 nm limit is the fact that novel properties that differentiate particles from the bulk material typically develop at a critical length scale of under 100 nm.

As used herein, a particle delivery system/formulation is defined as any biological delivery system/formulation which includes a particle in accordance with the present invention. A particle in accordance with the present invention is any entity having a greatest dimension (e.g. diameter) of less than 100 microns (μm). In some embodiments, inventive particles have a greatest dimension of less than 10 μm. In some embodiments, inventive particles have a greatest dimension of less than 2000 nanometers (nm). In some embodiments, inventive particles have a greatest dimension of less than 1000 nanometers (nm). In some embodiments, inventive particles have a greatest dimension of less than 900 nm, 800 nm, 700 nm, 600 nm, 500 nm, 400 nm, 300 nm, 200 nm, or 100 nm. Typically, inventive particles have a greatest dimension (e.g., diameter) of 500 nm or less. In some embodiments, inventive particles have a greatest dimension (e.g., diameter) of 250 nm or less. In some embodiments, inventive particles have a greatest dimension (e.g., diameter) of 200 nm or less. In some embodiments, inventive particles have a greatest dimension (e.g., diameter) of 150 nm or less. In some embodiments, inventive particles have a greatest dimension (e.g., diameter) of 100 nm or less. Smaller particles, e.g., having a greatest dimension of 50 nm or less are used in some embodiments of the invention. In some embodiments, inventive particles have a greatest dimension ranging between 25 nm and 200 nm.

In terms of this invention, it is preferred to have one or more components of CRISPR complex, e.g., CRISPR enzyme or mRNA or guide RNA delivered using nanoparticles or lipid envelopes. Other delivery systems or vectors are may be used in conjunction with the nanoparticle aspects of the invention.

In general, a "nanoparticle" refers to any particle having a diameter of less than 1000 nm. In certain preferred embodiments, nanoparticles of the invention have a greatest dimension (e.g., diameter) of 500 nm or less. In other preferred embodiments, nanoparticles of the invention have a greatest dimension ranging between 25 nm and 200 nm. In other preferred embodiments, nanoparticles of the invention have a greatest dimension of 100 nm or less. In other preferred embodiments, nanoparticles of the invention have a greatest dimension ranging between 35 nm and 60 nm. It will be appreciated that reference made herein to particles or nanoparticles can be interchangeable, where appropriate.

It will be understood that the size of the particle will differ depending as to whether it is measured before or after loading. Accordingly, in particular embodiments, the term "nanoparticles" may apply only to the particles pre loading.

Nanoparticles encompassed in the present invention may be provided in different forms, e.g., as solid nanoparticles (e.g., metal such as silver, gold, iron, titanium), non-metal, lipid-based solids, polymers), suspensions of nanoparticles, or combinations thereof. Metal, dielectric, and semiconductor nanoparticles may be prepared, as well as hybrid structures (e.g., core-shell nanoparticles). Nanoparticles made of semiconducting material may also be labeled quantum dots if they are small enough (typically sub 10 nm) that quantization of electronic energy levels occurs. Such nanoscale particles are used in biomedical applications as drug carriers or imaging agents and may be adapted for similar purposes in the present invention.

Semi-solid and soft nanoparticles have been manufactured, and are within the scope of the present invention. A prototype nanoparticle of semi-solid nature is the liposome. Various types of liposome nanoparticles are currently used clinically as delivery systems for anticancer drugs and vaccines. Nanoparticles with one half hydrophilic and the other half hydrophobic are termed Janus particles and are particularly effective for stabilizing emulsions. They can self-assemble at water/oil interfaces and act as solid surfactants.

Particle characterization (including e.g., characterizing morphology, dimension, etc.) is done using a variety of different techniques. Common techniques are electron microscopy (TEM, SEM), atomic force microscopy (AFM), dynamic light scattering (DLS), X-ray photoelectron spectroscopy (XPS), powder X-ray diffraction (XRD), Fourier transform infrared spectroscopy (FTIR), matrix-assisted laser desorption/ionization time-of-flight mass spectrometry (MALDI-TOF), ultraviolet-visible spectroscopy, dual polarization interferometry and nuclear magnetic resonance (NMR). Characterization (dimension measurements) may be made as to native particles (i.e., preloading) or after loading of the cargo (herein cargo refers to e.g., one or more components of CRISPR-Cas system e.g., CRISPR enzyme or mRNA or guide RNA, or any combination thereof, and may include additional carriers and/or excipients) to provide particles of an optimal size for delivery for any in vitro, ex vivo and/or in vivo application of the present invention. In certain preferred embodiments, particle dimension (e.g., diameter) characterization is based on measurements using dynamic laser scattering (DLS). Mention is made of U.S. Pat. Nos. 8,709,843; 6,007,845; 5,855,913; 5,985,309; 5,543,158; and the publication by James E. Dahlman and Carmen Barnes et al. Nature Nanotechnology (2014) published online 11 May 2014, doi:10.1038/nnano.2014.84, concerning particles, methods of making and using them and measurements thereof.

Particles delivery systems within the scope of the present invention may be provided in any form, including but not limited to solid, semi-solid, emulsion, or colloidal particles. As such any of the delivery systems described herein, including but not limited to, e.g., lipid-based systems, liposomes, micelles, microvesicles, exosomes, or gene gun may be provided as particle delivery systems within the scope of the present invention.

CRISPR enzyme mRNA and guide RNA may be delivered simultaneously using particles or lipid envelopes; for instance, CRISPR enzyme and RNA of the invention, e.g., as a complex, can be delivered via a particle as in Dahlman et al., WO2015089419 A2 and documents cited therein, such as 7C1 (see, e.g., James E. Dahlman and Carmen Barnes et al. Nature Nanotechnology (2014) published online 11 May 2014, doi:10.1038/nnano 2014.84), e.g., delivery particle comprising lipid or lipidoid and hydrophilic polymer, e.g., cationic lipid and hydrophilic polymer, for instance wherein the cationic lipid comprises 1,2-dioleoyl-3-trimethylammonium-propane (DOTAP) or 1,2-ditetradecanoyl-sn-glycero-3-phosphocholine (DMPC) and/or wherein the hydrophilic polymer comprises ethylene glycol or polyethylene glycol (PEG); and/or wherein the particle further comprises cholesterol (e.g., particle from formulation 1=DOTAP 100, DMPC 0, PEG 0, Cholesterol 0; formulation number 2=DOTAP 90, DMPC 0, PEG 10, Cholesterol 0; formulation number 3=DOTAP 90, DMPC 0, PEG 5, Cholesterol 5), wherein particles are formed using an efficient, multistep process wherein first, effector protein and RNA are mixed together, e.g., at a 1:1 molar ratio, e.g., at room temperature, e.g., for 30 minutes, e.g., in sterile, nuclease free 1×PBS; and separately, DOTAP, DMPC, PEG, and cholesterol as applicable for the formulation are dissolved in alcohol, e.g., 100% ethanol; and, the two solutions are mixed together to form particles containing the complexes).

Nucleic acid-targeting effector proteins (such as a Type V protein such Cpf1) mRNA and guide RNA may be delivered simultaneously using particles or lipid envelopes. Examples of suitable particles include but are not limited to those described in U.S. Pat. No. 9,301,923.

For example, Su X, Fricke J, Kavanagh D G, Irvine D J ("In vitro and in vivo mRNA delivery using lipid-enveloped pH-responsive polymer nanoparticles" Mol Pharm. 2011 Jun. 6; 8(3):774-87. doi: 10.1021/mp100390w. Epub 2011 Apr. 1) describes biodegradable core-shell structured nanoparticles with a poly(β-amino ester) (PBAE) core enveloped by a phospholipid bilayer shell. These were developed for in vivo mRNA delivery. The pH-responsive PBAE component was chosen to promote endosome disruption, while the lipid surface layer was selected to minimize toxicity of the polycation core. Such are, therefore, preferred for delivering RNA of the present invention.

Liu et al. (US 20110212179) provides bimodal porous polymer microspheres comprising a base polymer, wherein the particle comprises macropores having a diameter ranging from about 20 to about 500 microns and micropores having a diameter ranging from about 1 to about 70 microns, and wherein the microspheres have a diameter ranging from about 50 to about 1100 microns.

Berg et al. (US20160174546) a nanolipid delivery system, in particular a nano-particle concentrate, comprising: a composition comprising a lipid, oil or solvent, the composition having a viscosity of less than 100 cP at 25.degree. C. and a Kauri Butanol solvency of greater than 25 Kb; and at least one amphipathic compound selected from the group consisting of an alkoxylated lipid, an alkoxylated fatty acid, an alkoxylated alcohol, a heteroatomic hydrophilic lipid, a heteroatomic hydrophilic fatty acid, a heteroatomic hydrophilic alcohol, a diluent, and combinations thereof, wherein the compound is derived from a starting compound having a viscosity of less than 1000 cP at 50.degree. C., wherein the concentrate is configured to provide a stable nano emulsion having a D50 and a mean average particle size distribution of less than 100 nm when diluted.

Liu et al. (US 20140301951) provides a protocell nanostructure comprising: a porous particle core comprising a plurality of pores; and at least one lipid bilayer surrounding the porous particle core to form a protocell, wherein the protocell is capable of loading one or more cargo components to the plurality of pores of the porous particle core and releasing the one or more cargo components from the porous particle core across the surrounding lipid bilayer.

Chromy et al. (US 20150105538) provides methods and systems for assembling, solubilizing and/or purifying a membrane associated protein in a nanolipoprotein particle, which comprise a temperature transition cycle performed in presence of a detergent, wherein during the temperature transition cycle the nanolipoprotein components are brought to a temperature above and below the gel to liquid crystalling transition temperature of the membrane forming lipid of the nanolipoprotein particle.

Bader et al. (US 20150250725), provides a method for producing a lipid particle comprising the following: i) providing a first solution comprising denatured apolipoprotein, ii) adding the first solution to a second solution comprising at least two lipids and a detergent but no apolipoprotein, and iii) removing the detergent from the solution obtained in ii) and thereby producing a lipid particle.

Mirkin et al., (US20100129793) provides a method of preparing a composite particle comprising the steps of (a) admixing a dielectric component and a magnetic component to form a first intermediate, (b) admixing the first intermediate and gold seeds to form a second intermediate, and (c) forming a gold shell on the second intermediate by admixing the second intermediate with a gold source and a reducing agent to form said composite particle.

In one embodiment, particles/nanoparticles based on self assembling bioadhesive polymers are contemplated, which may be applied to oral delivery of peptides, intravenous delivery of peptides and nasal delivery of peptides, all to the brain. Other embodiments, such as oral absorption and ocular delivery of hydrophobic drugs are also contemplated. The molecular envelope technology involves an engineered polymer envelope which is protected and delivered to the site of the disease (see, e.g., Mazza, M. et al. ACSNano, 2013. 7(2): 1016-1026; Siew, A., et al. Mol Pharm, 2012. 9(1):14-28; Lalatsa, A., et al. J Contr Rel, 2012. 161(2):523-36; Lalatsa, A., et al., Mol Pharm, 2012. 9(6):1665-80; Lalatsa, A., et al. Mol Pharm, 2012. 9(6):1764-74; Garrett, N. L., et al. J Biophotonics, 2012. 5(5-6):458-68; Garrett, N. L., et al. J Raman Spect, 2012. 43(5):681-688; Ahmad, S., et al. J Royal Soc Interface 2010. 7:S423-33; Uchegbu, I. F. Expert Opin Drug Deliv, 2006. 3(5):629-40; Qu, X., et al. Biomacromolecules, 2006. 7(12):3452-9 and Uchegbu, I. F., et al. Int J Pharm, 2001. 224:185-199). Doses of about 5 mg/kg are contemplated, with single or multiple doses, depending on the target tissue.

In one embodiment, particles/nanoparticles that can deliver RNA to a cancer cell to stop tumor growth developed by Dan Anderson's lab at MIT may be used/and or adapted to the CRISPR-Cas system of the present invention. In particular, the Anderson lab developed fully automated, combinatorial systems for the synthesis, purification, characterization, and formulation of new biomaterials and nanoformulations. See, e.g., Alabi et al., Proc Natl Acad Sci USA. 2013 Aug. 6; 110(32):12881-6; Zhang et al., Adv Mater. 2013 Sep. 6; 25(33):4641-5; Jiang et al., Nano Lett. 2013 Mar. 13; 13(3):1059-64; Karagiannis et al., ACS Nano. 2012 Oct. 23; 6(10):8484-7; Whitehead et al., ACS Nano. 2012 Aug. 28; 6(8):6922-9 and Lee et al., Nat Nanotechnol. 2012 Jun. 3; 7(6):389-93.

The lipid particles developed by the Qiaobing Xu's lab at Tufts University may be used/adapted to the present delivery system for cancer therapy. See Wang et al., J. Control Release, 2017 Jan. 31. pii: 50168-3659(17)30038-X. doi: 10.1016/jjconre1.2017.01.037. [Epub ahead of print]; Altmoglu et al., Biomater Sci., 4(12):1773-80, Nov. 15, 2016; Wang et al., PNAS, 113(11):2868-73 Mar. 15, 2016; Wang et al., PloS One, 10(11): e0141860. doi: 10.1371/journal.pone.0141860. eCollection 2015, Nov. 3, 2015; Takeda et al., Neural Regen Res. 10(5):689-90, May 2015; Wang et al., Adv. Health Mater., 3(9):1398-403, September 2014; and Wang et al., Agnew Chem Int Ed Engl., 53(11):2893-8, Mar. 10, 2014.

US patent application 20110293703 relates to lipidoid compounds are also particularly useful in the administration of polynucleotides, which may be applied to deliver the CRISPR-Cas system of the present invention. In one aspect, the aminoalcohol lipidoid compounds are combined with an agent to be delivered to a cell or a subject to form microparticles, nanoparticles, liposomes, or micelles. The agent to be delivered by the particles, liposomes, or micelles may be in the form of a gas, liquid, or solid, and the agent may be a polynucleotide, protein, peptide, or small molecule. The aminoalcohol lipidoid compounds may be combined with other aminoalcohol lipidoid compounds, polymers (synthetic or natural), surfactants, cholesterol, carbohydrates, proteins, lipids, etc. to form the particles. These particles may then optionally be combined with a pharmaceutical excipient to form a pharmaceutical composition.

US Patent Publication No. 20110293703 also provides methods of preparing the aminoalcohol lipidoid compounds. One or more equivalents of an amine are allowed to react with one or more equivalents of an epoxide-terminated compound under suitable conditions to form an aminoalcohol lipidoid compound of the present invention. In certain embodiments, all the amino groups of the amine are fully reacted with the epoxide-terminated compound to form tertiary amines. In other embodiments, all the amino groups of the amine are not fully reacted with the epoxide-terminated compound to form tertiary amines thereby resulting in primary or secondary amines in the aminoalcohol lipidoid compound. These primary or secondary amines are left as is or may be reacted with another electrophile such as a different epoxide-terminated compound. As will be appreciated by one skilled in the art, reacting an amine with less than excess of epoxide-terminated compound will result in a plurality of different aminoalcohol lipidoid compounds with various numbers of tails. Certain amines may be fully functionalized with two epoxide-derived compound tails while other molecules will not be completely functionalized with epoxide-derived compound tails. For example, a diamine or polyamine may include one, two, three, or four epoxide-derived compound tails off the various amino moieties of the molecule resulting in primary, secondary, and tertiary amines. In certain embodiments, all the amino groups are not fully functionalized. In certain embodiments, two of the same types of epoxide-terminated compounds are used. In other embodiments, two or more different epoxide-terminated compounds are used. The synthesis of the aminoalcohol lipidoid compounds is performed with or without solvent, and the synthesis may be performed at higher temperatures ranging from 30-100° C., preferably at approximately 50-90° C. The prepared aminoalcohol lipidoid compounds may be optionally purified. For example, the mixture of aminoalcohol lipidoid compounds may be purified to yield an aminoalcohol lipidoid compound with a particular number of epoxide-derived compound tails. Or the mixture may be purified to yield a particular stereo- or regioisomer. The aminoalcohol lipidoid compounds may also be alkylated using an alkyl halide (e.g., methyl iodide) or other alkylating agent, and/or they may be acylated.

US Patent Publication No. 20110293703 also provides libraries of aminoalcohol lipidoid compounds prepared by the inventive methods. These aminoalcohol lipidoid compounds may be prepared and/or screened using high-throughput techniques involving liquid handlers, robots, microtiter plates, computers, etc. In certain embodiments, the aminoalcohol lipidoid compounds are screened for their ability to transfect polynucleotides or other agents (e.g., proteins, peptides, small molecules) into the cell.

US Patent Publication No. 20130302401 relates to a class of poly(beta-amino alcohols) (PBAAs) has been prepared using combinatorial polymerization. The inventive PBAAs may be used in biotechnology and biomedical applications as coatings (such as coatings of films or multilayer films for medical devices or implants), additives, materials, excipients, non-biofouling agents, micropatterning agents, and cellular encapsulation agents. When used as surface coatings, these PBAAs elicited different levels of inflammation, both in vitro and in vivo, depending on their chemical structures. The large chemical diversity of this class of materials allowed us to identify polymer coatings that inhibit macrophage activation in vitro. Furthermore, these coatings reduce the recruitment of inflammatory cells, and reduce fibrosis, following the subcutaneous implantation of carboxylated polystyrene microparticles. These polymers may be used to form polyelectrolyte complex capsules for cell encapsulation. The invention may also have many other biological applications such as antimicrobial coatings, DNA or siRNA delivery, and stem cell tissue engineering. The teachings of US Patent Publication No. 20130302401 may be applied to the CRISPR-Cas system of the present invention.

In another embodiment, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR-Cas system of the present invention. Doses of about 0.01 to about 1 mg per kg of body weight administered intravenously are contemplated. Medications to reduce the risk of infusion-related reactions are contemplated, such as dexamethasone, acetaminophen, diphenhydramine or cetirizine, and ranitidine are contemplated. Multiple doses of about 0.3 mg per kilogram every 4 weeks for five doses are also contemplated.

Zhu et al. (US20140348900) provides for a process for preparing liposomes, lipid discs, and other lipid nanoparticles using a multi-port manifold, wherein the lipid solution stream, containing an organic solvent, is mixed with two or more streams of aqueous solution (e.g., buffer). In some aspects, at least some of the streams of the lipid and aqueous solutions are not directly opposite of each other. Thus, the process does not require dilution of the organic solvent as an additional step. In some embodiments, one of the solutions may also contain an active pharmaceutical ingredient (API). This invention provides a robust process of liposome manufacturing with different lipid formulations and different payloads. Particle size, morphology, and the manufacturing scale can be controlled by altering the port size and number of the manifold ports, and by selecting the flow rate or flow velocity of the lipid and aqueous solutions.

Cullis et al. (US 20140328759) provides limit size lipid nanoparticles with a diameter from 10-100 nm, in particular comprising a lipid bilayer surrounding an aqueous core. Methods and apparatus for preparing such limit size lipid nanoparticles are also disclosed.

Manoharan et al. (US 20140308304) provides cationic lipids of formula (I)

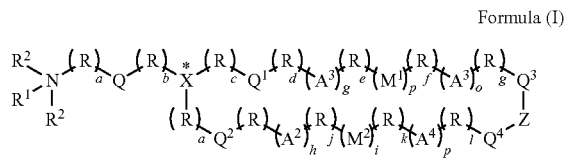

Formula (I)

or a salt thereof, wherein X is N or P; R' is absent, hydrogen, or alkyl; with respect to $R^1$ and $R^2$, (i) $R^1$ and $R^2$ are each, independently, optionally substituted alkyl, alkenyl, alkynyl, cycloalkyl, cycloalkylalkyl, heterocycle or $R^{10}$; (ii) $R^1$ and $R^2$, together with the nitrogen atom to which they are attached, form an optionally substituted heterocylic ring; or (iii) one of $R^1$ and $R^2$ is optionally substituted alkyl, alkenyl, alkynyl, cycloalkyl, cycloalkylalkyl, or heterocycle, and the other forms a 4-10 member heterocyclic ring or heteroaryl with (a) the adjacent nitrogen atom and (b) the $(R)_a$ group adjacent to the nitrogen atom; each occurrence of R is, independently, $—(CR^3R^4)—$; each occurrence of $R^3$ and $R^4$ are, independently H, halogen, OH, alkyl, alkoxy, —NH.sub.2, alkylamino, or dialkylamino; or $R^3$ and $R^4$, together with the carbon atom to which they are directly attached, form a cycloalkyl group, wherein no more than three R groups in each chain attached to the atom X* are cycloalkyl; each occurrence of R.sup.10 is independently selected from PEG and polymers based on poly(oxazoline), poly(ethylene oxide), poly(vinyl alcohol), poly(glycerol), poly(N-vinylpyrrolidone), poly[N-(2-hydroxypropyl)methacrylamide] and poly(amino acid)s, wherein (i) the PEG or polymer is linear or branched, (ii) the PEG or polymer is polymerized by n subunits, (iii) n is a number-averaged degree of polymerization between 10 and 200 units, and (iv) wherein the compound of formula has at most two $R^{10}$ groups; Q is absent or is —O—, —NH—, —C(O)O—, —OC(O)—, —C(O)N($R^4$)—, —N($R^5$)C(O)—, —S—S—, —OC(O)O—, —O—N.dbd.C($R^5$)—, —C($R^5$).dbd.N—O—, —OC(O)N($R^5$)—, —N($R^5$)C(O)N($R^5$)—, —N($R^5$)C(O)O—, —C(O)S—, —C(S)O— or —C($R^5$).dbd.N—O—C(O)—; $Q^1$ and $Q^2$ are each, independently, absent, —O—, —OC(O)—, —C(O)O—, —SC(O)—, —C(O)S—, —OC(S)—, —C(S)O—, —S—S—, —C(O)(N$R^5$)—, —N($R^5$)C(O)—, —C(S)(N$R^5$)—, —N($R^5$)C(O)—, —N($R^5$)C(O)N($R^5$)—, or —OC(O)O—; $Q^3$ and $Q^4$ are each, independently, H, $—(CR^3R^4)—$, aryl, or a cholesterol moiety; each occurrence of $A^1$, $A^2$, $A^3$ and $A^4$ is, independently, $—(CR^5R^5—CR^5.dbd.CR^5)—$; each occurrence of $R^5$ is, independently, H or alkyl; $M^1$ and $M^2$ are each, independently, a biodegradable group (e.g., —OC(O)—, —C(O)O—, —SC(O)—, —C(O)S—, —OC(S)—, —C(S)O—, —S—S—, —C($R^5$).dbd.N—, —N.dbd.C($R^5$)—, —C($R^5$).dbd.N—O—, —O—N.dbd.C(R5)-, —C(O)(NR5)-, —N(R5)C(O)—, —C(S)(N$R^5$)—, —N($R^5$)C(O)—, —N($R^5$)C(O)N($R^5$)—, —OC(O)O—, Si($R^5$).sub.2O—, —C(O)($CR^3R^4$)C(O)O—, or —OC(O)($CR^3R^4$)C(O)—); Z is absent, alkylene or —O—P(O)(OH)—O—; each ------ attached to Z is an optional bond, such that when Z is absent, $Q^3$ and $Q^4$ are not directly covalently bound together; a is 1, 2, 3, 4, 5 or 6; b is 0, 1, 2, or 3; c, d, e, f, i, j, m, n, q and r are each, independently, 0, 1, 2, 3, 4, 5, 6, 7, 8, 9, or 10; g and h are each, independently, 0, 1 or 2; k and l are each, independently, 0 or 1, where at least one of k and l is 1; and o and p are each, independently, 0, 1 or 2, wherein $Q^3$ and $Q^4$ are each, independently, separated from the tertiary atom marked with an asterisk (X*) by a chain of 8 or more atoms. The cationic lipid can be used with other lipid components such as cholesterol and PEG-lipids to form lipid nanoparticles with oligonucleotides, to facilitate the cellular uptake and endosomal escape, and to knockdown target mRNA both in vitro and in vivo.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR-Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethyl-ammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 µg/ml of LNP or CRISPR-Cas RNA in or associated with the LNP may be contemplated, especially for a formulation containing DLinKC2-DMA.

Preparation of LNPs and CRISPR-Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2"-(methoxypolyethyleneglycol 2000) succinoyl]-1,2-dimyristoyl-sn-glycol (PEG-S-DMG), and R-3-1(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR-Cas RNA may be encapsulated in LNPs containing DLinDAP, DLinDMA, DLinK-DMA, and DLinKC2-DMA (cationic lipid:DSPC:CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/1. This ethanol solution of lipid may be added drop-wise to 50 mmol/1 citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/1 citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a CRISPR-Cas system or components thereof Preparation of large LNPs may be used/and or adapted from Rosin et al, Molecular Therapy, vol. 19, no. 12, pages 1286-2200, December 2011. A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/1, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Preassembled recombinant CRISPR-Cpf1 complexes comprising Cpf1 and crRNA may be transfected, for example by electroporation, resulting in high mutation rates and absence of detectable off-target mutations. Hur, J. K. et al, Targeted mutagenesis in mice by electroporation of Cpf1 ribonucleoproteins, Nat Biotechnol. 2016 Jun. 6. doi: 10.1038/nbt.3596. [Epub ahead of print]

In terms of local delivery to the brain, this can be achieved in various ways. For instance, material can be delivered intrastriatally e.g. by injection. Injection can be performed stereotactically via a craniotomy.

Enhancing NHEJ or HR efficiency is also helpful for delivery. It is preferred that NHEJ efficiency is enhanced by co-expressing end-processing enzymes such as Trex2 (Dumitrache et al. Genetics. 2011 August; 188(4): 787-797).

It is preferred that HR efficiency is increased by transiently inhibiting NHEJ machineries such as Ku70 and Ku86. HR efficiency can also be increased by co-expressing prokaryotic or eukaryotic homologous recombination enzymes such as RecBCD, RecA.

In some embodiments, sugar-based particles may be used, for example GalNAc, as described herein and with reference to WO2014118272 (incorporated herein by reference) and Nair, J K et al., 2014, Journal of the American Chemical Society 136 (49), 16958-16961) and the teaching herein, especially in respect of delivery applies to all particles unless otherwise apparent. This may be considered to be a sugar-based particle and further details on other particle delivery systems and/or formulations are provided herein. GalNAc can therefore be considered to be a particle in the sense of the other particles described herein, such that general uses and other considerations, for instance delivery of said particles, apply to GalNAc particles as well. A solution-phase conjugation strategy may for example be used to attach triantennary GalNAc clusters (mol. wt. ~2000) activated as PFP (pentafluorophenyl) esters onto 5'-hexylamino modified oligonucleotides (5'-HA ASOs, mol. wt. ~8000 Da; Østergaard et al., Bioconjugate Chem., 2015, 26 (8), pp 1451-1455). Similarly, poly(acrylate) polymers have been described for in vivo nucleic acid delivery (see WO2013158141 incorporated herein by reference). In further alternative embodiments, pre-mixing CRISPR nanoparticles (or protein complexes) with naturally occurring serum proteins may be used in order to improve delivery (Akinc A et al, 2010, Molecular Therapy vol. 18 no. 7, 1357-1364).

Nanoclews

Further, the CRISPR system may be delivered using nanoclews, for example as described in Sun W et al, *Cocoon-like self-degradable DNA nanoclew for anticancer drug delivery.*, J Am Chem Soc. 2014 Oct. 22; 136(42): 14722-5. doi: 10.1021/ja5088024. Epub 2014 Oct. 13. ; or in Sun W et al, *Self-Assembled DNA Nanoclews for the Efficient Delivery of CRISPR-Cas9 for Genome Editing.*, Angew Chem Int Ed Engl. 2015 Oct. 5; 54(41):12029-33. doi: 10.1002/anie.201506030. Epub 2015 Aug. 27.

LNP

In some embodiments, delivery is by encapsulation of the Cpf1 protein or mRNA form in a lipid particle such as an LNP. In some embodiments, therefore, lipid nanoparticles (LNPs) are contemplated. An antitransthyretin small interfering RNA has been encapsulated in lipid nanoparticles and delivered to humans (see, e.g., Coelho et al., N Engl J Med 2013; 369:819-29), and such a system may be adapted and applied to the CRISPR-Cas system of the present invention. Doses of about 0.01 to about 1 mg per kg of body weight administered intravenously are contemplated. Medications to reduce the risk of infusion-related reactions are contemplated, such as dexamethasone, acetampinophen, diphenhydramine or cetirizine, and ranitidine are contemplated. Multiple doses of about 0.3 mg per kilogram every 4 weeks for five doses are also contemplated.

LNPs have been shown to be highly effective in delivering siRNAs to the liver (see, e.g., Tabernero et al., Cancer Discovery, April 2013, Vol. 3, No. 4, pages 363-470) and are therefore contemplated for delivering RNA encoding CRISPR-Cas to the liver. A dosage of about four doses of 6 mg/kg of the LNP every two weeks may be contemplated. Tabernero et al. demonstrated that tumor regression was observed after the first 2 cycles of LNPs dosed at 0.7 mg/kg, and by the end of 6 cycles the patient had achieved a partial response with complete regression of the lymph node metastasis and substantial shrinkage of the liver tumors. A complete response was obtained after 40 doses in this patient, who has remained in remission and completed treatment after receiving doses over 26 months. Two patients with RCC and extrahepatic sites of disease including kidney, lung, and lymph nodes that were progressing following prior therapy with VEGF pathway inhibitors had stable disease at all sites for approximately 8 to 12 months, and a patient with PNET and liver metastases continued on the extension study for 18 months (36 doses) with stable disease.

However, the charge of the LNP must be taken into consideration. As cationic lipids combined with negatively charged lipids to induce nonbilayer structures that facilitate intracellular delivery. Because charged LNPs are rapidly cleared from circulation following intravenous injection, ionizable cationic lipids with pKa values below 7 were developed (see, e.g., Rosin et al, Molecular Therapy, vol. 19, no. 12, pages 1286-2200, December 2011). Negatively charged polymers such as RNA may be loaded into LNPs at low pH values (e.g., pH 4) where the ionizable lipids display a positive charge. However, at physiological pH values, the LNPs exhibit a low surface charge compatible with longer circulation times. Four species of ionizable cationic lipids have been focused upon, namely 1,2-dilineoyl-3-dimethylammonium-propane (DLinDAP), 1,2-dilinoleyloxy-3-N,N-dimethylaminopropane (DLinDMA), 1,2-dilinoleyloxy-keto-N,N-dimethyl-3-aminopropane (DLinKDMA), and 1,2-dilinoleyl-4-(2-dimethylaminoethyl)-[1,3]-dioxolane (DLinKC2-DMA). It has been shown that LNP siRNA systems containing these lipids exhibit remarkably different gene silencing properties in hepatocytes in vivo, with potencies varying according to the series DLinKC2-DMA>DLinKDMA>DLinDMA>>DLinDAP employing a Factor VII gene silencing model (see, e.g., Rosin et al, Molecular Therapy, vol. 19, no. 12, pages 1286-2200, December 2011). A dosage of 1 µg/ml of LNP or CRISPR-Cas RNA in or associated with the LNP may be contemplated, especially for a formulation containing DLinKC2-DMA.

Preparation of LNPs and CRISPR-Cas encapsulation may be used/and or adapted from Rosin et al, Molecular Therapy, vol. 19, no. 12, pages 1286-2200, December 2011). The cationic lipids 1,2-dilineoyl-3-dimethylammonium-propane (DLinDAP), 1,2-dilinoleyloxy-3-N,N-dimethylaminopropane (DLinDMA), 1,2-dilinoleyloxyketo-N,N-dimethyl-3-aminopropane (DLinK-DMA), 1,2-dilinoleyl-4-(2-dimethylaminoethyl)-[1,3]-dioxolane (DLinKC2-DMA), (3-o-[2''-(methoxypolyethyleneglycol 2000) succinoyl]-1,2-dimyristoyl-sn-glycol (PEG-S-DMG), and R-3-1(ω-methoxy-poly(ethylene glycol)2000) carbamoyl]-1,2-dimyristyloxlpropyl-3-amine (PEG-C-DOMG) may be provided by Tekmira Pharmaceuticals (Vancouver, Canada) or synthesized. Cholesterol may be purchased from Sigma (St Louis, Mo.). The specific CRISPR-Cas RNA may be encapsulated in LNPs containing DLinDAP, DLinDMA, DLinK-DMA, and DLinKC2-DMA (cationic lipid:DSPC: CHOL: PEGS-DMG or PEG-C-DOMG at 40:10:40:10 molar ratios). When required, 0.2% SP-DiOC18 (Invitrogen, Burlington, Canada) may be incorporated to assess cellular uptake, intracellular delivery, and biodistribution. Encapsulation may be performed by dissolving lipid mixtures comprised of cationic lipid:DSPC:cholesterol:PEG-c-DOMG (40:10:40:10 molar ratio) in ethanol to a final lipid concentration of 10 mmol/1. This ethanol solution of lipid may be added drop-wise to 50 mmol/1 citrate, pH 4.0 to form multilamellar vesicles to produce a final concentration of 30% ethanol vol/vol. Large unilamellar vesicles may be formed following extrusion of multilamellar vesicles through two stacked 80 nm Nuclepore polycarbonate filters using the Extruder (Northern Lipids, Vancouver, Canada). Encapsulation may be achieved by adding RNA dissolved at 2 mg/ml in 50 mmol/1 citrate, pH 4.0 containing 30% ethanol vol/vol drop-wise to extruded preformed large unilamellar vesicles and incubation at 31° C. for 30 minutes with constant mixing to a final RNA/lipid weight ratio of 0.06/1 wt/wt. Removal of ethanol and neutralization of formulation buffer were performed by dialysis against phosphate-buffered saline (PBS), pH 7.4 for 16 hours using Spectra/Por 2 regenerated cellulose dialysis membranes. Nanoparticle size distribution may be determined by dynamic light scattering using a NICOMP 370 particle sizer, the vesicle/intensity modes, and Gaussian fitting (Nicomp Particle Sizing, Santa Barbara, Calif.). The particle size for all three LNP systems may be ~70 nm in diameter. RNA encapsulation efficiency may be determined by removal of free RNA using VivaPureD MiniH columns (Sartorius Stedim Biotech) from samples collected before and after dialysis. The encapsulated RNA may be extracted from the eluted nanoparticles and quantified at 260 nm. RNA to lipid ratio was determined by measurement of cholesterol content in vesicles using the Cholesterol E enzymatic assay from Wako Chemicals USA (Richmond, Va.). In conjunction with the herein discussion of LNPs and PEG lipids, PEGylated liposomes or LNPs are likewise suitable for delivery of a CRISPR-Cas system or components thereof A lipid premix solution (20.4 mg/ml total lipid concentration) may be prepared in ethanol containing DLinKC2-DMA, DSPC, and cholesterol at 50:10:38.5 molar ratios. Sodium acetate may be added to the lipid premix at a molar ratio of 0.75:1 (sodium acetate:DLinKC2-DMA). The lipids may be subsequently hydrated by combining the mixture with 1.85 volumes of citrate buffer (10 mmol/1, pH 3.0) with vigorous stirring, resulting in spontaneous liposome formation in aqueous buffer containing 35% ethanol. The liposome solution may be incubated at 37° C. to allow for time-dependent increase in particle size. Aliquots may be removed at various times during incubation to investigate changes in liposome size by dynamic light scattering (Zetasizer Nano ZS, Malvern Instruments, Worcestershire, UK). Once the desired particle size is achieved, an aqueous PEG lipid solution (stock=10 mg/ml PEG-DMG in 35% (vol/vol) ethanol) may be added to the liposome mixture to yield a final PEG molar concentration of 3.5% of total lipid. Upon addition of PEG-lipids, the liposomes should their size, effectively quenching further growth. RNA may then be added to the empty liposomes at an RNA to total lipid ratio of approximately 1:10 (wt:wt), followed by incubation for 30 minutes at 37° C. to form loaded LNPs. The mixture may be subsequently dialyzed overnight in PBS and filtered with a 0.45-µm syringe filter.

Spherical Nucleic Acid (SNA™) constructs and other nanoparticles (particularly gold nanoparticles) are also contemplated as a means to delivery CRISPR-Cas system to intended targets. Significant data show that AuraSense Therapeutics' Spherical Nucleic Acid (SNA™) constructs, based upon nucleic acid-functionalized gold nanoparticles, are useful.

Literature that may be employed in conjunction with herein teachings include: Cutler et al., J. Am. Chem. Soc. 2011 133:9254-9257, Hao et al., Small. 2011 7:3158-3162, Zhang et al., ACS Nano. 2011 5:6962-6970, Cutler et al., J. Am. Chem. Soc. 2012 134:1376-1391, Young et al., Nano Lett. 2012 12:3867-71, Zheng et al., Proc. Natl. Acad. Sci. USA. 2012 109:11975-80, Mirkin, Nanomedicine 2012 7:635-638 Zhang et al., J. Am. Chem. Soc. 2012 134:16488-1691, Weintraub, Nature 2013 495:S14-S16, Choi et al., Proc. Natl. Acad. Sci. USA. 2013 110(19):7625-7630, Jensen et al., Sci. Transl. Med. 5, 209ra152 (2013) and Mirkin, et al., Small, 10:186-192.

Self-assembling nanoparticles with RNA may be constructed with polyethyleneimine (PEI) that is PEGylated with an Arg-Gly-Asp (RGD) peptide ligand attached at the distal end of the polyethylene glycol (PEG). This system has been used, for example, as a means to target tumor neovasculature expressing integrins and deliver siRNA inhibiting vascular endothelial growth factor receptor-2 (VEGF R2) expression and thereby achieve tumor angiogenesis (see, e.g., Schiffelers et al., Nucleic Acids Research, 2004, Vol. 32, No. 19). Nanoplexes may be prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. A dosage of about 100 to 200 mg of CRISPR-Cas is envisioned for delivery in the self-assembling nanoparticles of Schiffelers et al.

The nanoplexes of Bartlett et al. (PNAS, Sep. 25, 2007, vol. 104, no. 39) may also be applied to the present invention. The nanoplexes of Bartlett et al. are prepared by mixing equal volumes of aqueous solutions of cationic polymer and nucleic acid to give a net molar excess of ionizable nitrogen (polymer) to phosphate (nucleic acid) over the range of 2 to 6. The electrostatic interactions between cationic polymers and nucleic acid resulted in the formation of polyplexes with average particle size distribution of about 100 nm, hence referred to here as nanoplexes. The DOTA-siRNA of Bartlett et al. was synthesized as follows: 1,4,7,10-tetraazacyclodo-decane-1,4,7,10-tetraacetic acid mono(N-hydroxysuccinim-ide ester) (DOTA-NHSester) was ordered from Macrocyclics (Dallas, Tex.). The amine modified RNA sense strand with a 100-fold molar excess of DOTA-NHS-ester in carbonate buffer (pH 9) was added to a microcentrifuge tube. The contents were reacted by stirring for 4 h at room temperature. The DOTA-RNAsense conjugate was ethanol-precipitated, resuspended in water, and annealed to the unmodified antisense strand to yield DOTA-siRNA. All liquids were pretreated with Chelex-100 (Bio-Rad, Hercules, Calif.) to remove trace metal contaminants. Tf-targeted and nontargeted siRNA nanoparticles may be formed by using cyclodextrin-containing polycations. Typically, nanoparticles were formed in water at a charge ratio of 3 (+/−) and an siRNA concentration of 0.5 g/liter. One percent of the adamantane-PEG molecules on the surface of the targeted nanoparticles were modified with Tf (adamantane-PEG-Tf). The nanoparticles were suspended in a 5% (wt/vol) glucose carrier solution for injection.

Davis et al. (Nature, Vol 464, 15 Apr. 2010) conducts a RNA clinical trial that uses a targeted nanoparticle-delivery system (clinical trial registration number NCT00689065). Patients with solid cancers refractory to standard-of-care therapies are administered doses of targeted nanoparticles on days 1, 3, 8 and 10 of a 21-day cycle by a 30-min intravenous infusion. The nanoparticles consist of a synthetic delivery system containing: (1) a linear, cyclodextrin-based polymer (CDP), (2) a human transferrin protein (TF) targeting ligand displayed on the exterior of the nanoparticle to engage TF receptors (TFR) on the surface of the cancer cells, (3) a hydrophilic polymer (polyethylene glycol (PEG) used to promote nanoparticle stability in biological fluids), and (4) siRNA designed to reduce the expression of the RRM2 (sequence used in the clinic was previously denoted siR2B+ 5). The TFR has long been known to be upregulated in malignant cells, and RRM2 is an established anti-cancer target. These nanoparticles (clinical version denoted as CALAA-01) have been shown to be well tolerated in multi-dosing studies in non-human primates. Although a single patient with chronic myeloid leukaemia has been administered siRNA by liposomal delivery, Davis et al.'s clinical trial is the initial human trial to systemically deliver siRNA with a targeted delivery system and to treat patients with solid cancer. To ascertain whether the targeted delivery system can provide effective delivery of functional siRNA to human tumors, Davis et al. investigated biopsies from three patients from three different dosing cohorts; patients A, B and C, all of whom had metastatic melanoma and received CALAA-01 doses of 18, 24 and 30 mg m-2 siRNA, respectively. Similar doses may also be contemplated for the CRISPR-Cas system of the present invention. The delivery of the invention may be achieved with nanoparticles containing a linear, cyclodextrin-based polymer (CDP), a human transferrin protein (TF) targeting ligand displayed on the exterior of the nanoparticle to engage TF receptors (TFR) on the surface of the cancer cells and/or a hydrophilic polymer (for example, polyethylene glycol (PEG) used to promote nanoparticle stability in biological fluids).

U.S. Pat. No. 8,709,843, incorporated herein by reference, provides a drug delivery system for targeted delivery of therapeutic agent-containing particles to tissues, cells, and intracellular compartments. The invention provides targeted particles comprising polymer conjugated to a surfactant, hydrophilic polymer or lipid.

U.S. Pat. No. 6,007,845, incorporated herein by reference, provides particles which have a core of a multiblock copolymer formed by covalently linking a multifunctional compound with one or more hydrophobic polymers and one or more hydrophilic polymers, and contain a biologically active material.

U.S. Pat. No. 5,855,913, incorporated herein by reference, provides a particulate composition having aerodynamically light particles having a tap density of less than 0.4 g/cm3 with a mean diameter of between 5 µm and 30 µm, incorporating a surfactant on the surface thereof for drug delivery to the pulmonary system.

U.S. Pat. No. 5,985,309, incorporated herein by reference, provides particles incorporating a surfactant and/or a hydrophilic or hydrophobic complex of a positively or negatively charged therapeutic or diagnostic agent and a charged molecule of opposite charge for delivery to the pulmonary system.

U.S. Pat. No. 5,543,158, incorporated herein by reference, provides biodegradable injectable particles having a biodegradable solid core containing a biologically active material and poly(alkylene glycol) moieties on the surface.

WO2012135025 (also published as US20120251560), incorporated herein by reference, describes conjugated polyethyleneimine (PEI) polymers and conjugated aza-macrocycles (collectively referred to as "conjugated lipomer" or "lipomers"). In certain embodiments, it can envisioned that such conjugated lipomers can be used in the context of the CRISPR-Cas system to achieve in vitro, ex vivo and in vivo genomic perturbations to modify gene expression, including modulation of protein expression.

In one embodiment, the nanoparticle may be epoxide-modified lipid-polymer, advantageously 7C1 (see, e.g., James E. Dahlman and Carmen Barnes et al. Nature Nanotechnology (2014) published online 11 May 2014, doi: 10.1038/nnano 2014.84). C71 was synthesized by reacting C15 epoxide-terminated lipids with PEI600 at a 14:1 molar ratio, and was formulated with C14PEG2000 to produce nanoparticles (diameter between 35 and 60 nm) that were stable in PBS solution for at least 40 days.

An epoxide-modified lipid-polymer may be utilized to deliver the CRISPR-Cas system of the present invention to pulmonary, cardiovascular or renal cells, however, one of skill in the art may adapt the system to deliver to other target organs. Dosage ranging from about 0.05 to about 0.6 mg/kg are envisioned. Dosages over several days or weeks are also envisioned, with a total dosage of about 2 mg/kg.

In some embodiments, the LNP for deliverting the RNA molecules is prepared by methods known in the art, such as those described in, for example, WO 2005/105152 (PCT/EP2005/004920), WO 2006/069782 (PCT/EP2005/014074), WO 2007/121947 (PCT/EP2007/003496), and WO 2015/082080 (PCT/EP2014/003274), which are herein incorporated by reference. LNPs aimed specifically at the enhanced and improved delivery of siRNA into mammalian cells are described in, for example, Aleku et al., Cancer Res., 68(23): 9788-98 (Dec. 1, 2008), Strumberg et al., Int. J. Clin. Pharmacol. Ther., 50(1): 76-8 (January 2012), Schultheis et al., J. Clin. Oncol., 32(36): 4141-48 (Dec. 20, 2014), and Fehring et al., Mol. Ther., 22(4): 811-20 (Apr. 22, 2014), which are herein incorporated by reference and may be applied to the present technology.

In some embodiments, the LNP includes any LNP disclosed in WO 2005/105152 (PCT/EP2005/004920), WO 2006/069782 (PCT/EP2005/014074), WO 2007/121947 (PCT/EP2007/003496), and WO 2015/082080 (PCT/EP2014/003274).

In some embodiments, the LNP includes at least one lipid having Formula I:

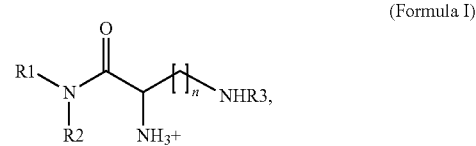
(Formula I)

wherein R1 and R2 are each and independently selected from the group comprising alkyl, n is any integer between 1 and 4, and R3 is an acyl selected from the group comprising lysyl, ornithyl, 2,4-diaminobutyryl, histidyl and an acyl moiety according to Formula II:

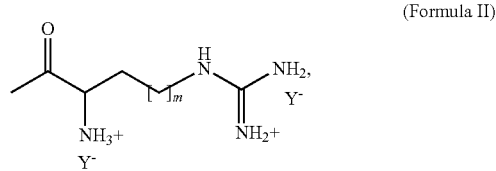
(Formula II)

wherein m is any integer from 1 to 3 and $Y^-$ is a pharmaceutically acceptable anion. In some embodiments, a lipid according to Formula I includes at least two asymmetric C atoms. In some embodiments, enantiomers of Formula I include, but are not limited to, R-R; S-S; R—S and S-R enantiomer.

In some embodiments, R1 is lauryl and R2 is myristyl. In another embodiment, R1 is palmityl and R2 is oleyl. In some embodiments, m is 1 or 2. In some embodiments, Y- is selected from halogenids, acetate or trifluoroacetate.

In some embodiments, the LNP comprises one or more lipids select from:

β-arginyl-2,3-diamino propionic acid-N-palmityl-N-oleyl-amide trihydrochloride (Formula III):

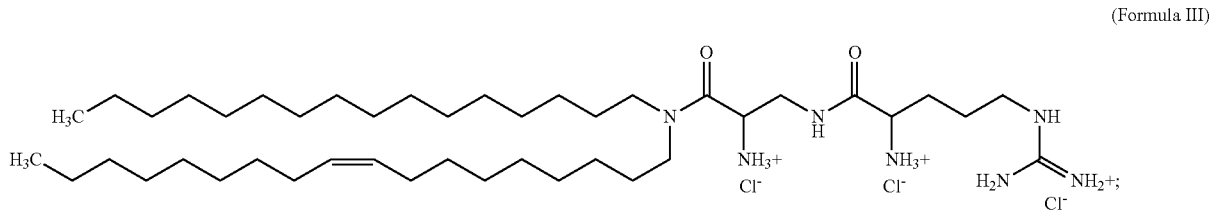

(Formula III)

β-arginyl-2,3-diamino propionic acid-N-lauryl-N-myristyl-amide trihydrochloride (Formula IV):

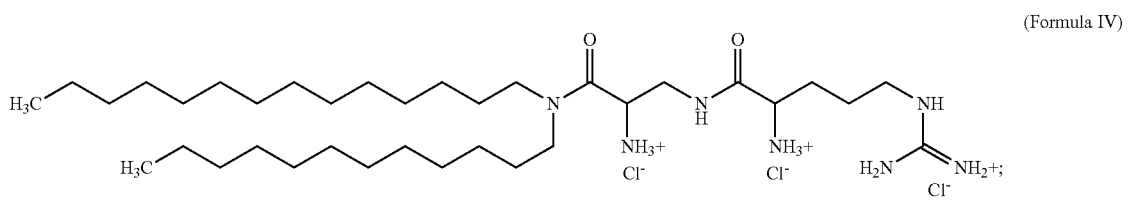

(Formula IV)

and
ε-arginyl-lysine-N-lauryl-N-myristyl-amide trihydrochloride (Formula V):

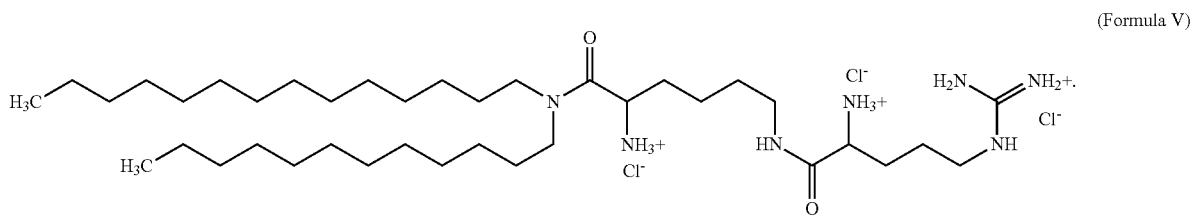

(Formula V)

In some embodiments, the LNP also includes a constituent. By way of example, but not by way of limitation, in some embodiments, the constituent is selected from peptides, proteins, oligonucleotides, polynucleotides, nucleic acids, or a combination thereof. In some embodiments, the constituent is an antibody, e.g., a monoclonal antibody. In some embodiments, the constituent is a nucleic acid selected from, e.g., ribozymes, aptamers, spiegelmers, DNA, RNA, PNA, LNA, or a combination thereof. In some embodiments, the nucleic acid is gRNA and/or mRNA.

In some embodiments, the constituent of the LNP comprises an mRNA encoding a CRISPR effector protein. In some embodiments, the constituent of the LNP comprises an mRNA encoding a Type-II, Type-V, or Type-VI CRISPR effector protein. In some embodiments, the constituent of the LNP comprises an mRNA encoding an RNA-guided DNA binding protein. In some embodiments, the constituent of the LNP comprises an mRNA encoding an RNA-guided RNA binding protein.

In some embodiments, the constituent of the LNP further comprises one or more guide RNA. In some embodiments, the LNP is configured to deliver the aforementioned mRNA and guide RNA to vascular endothelium. In some embodiments, the LNP is configured to deliver the aforementioned mRNA and guide RNA to pulmonary endothelium. In some embodiments, the LNP is configured to deliver the aforementioned mRNA and guide RNA to liver. In some embodiments, the LNP is configured to deliver the aforementioned mRNA and guide RNA to lung. In some embodiments, the LNP is configured to deliver the aforementioned mRNA and guide RNA to hearts. In some embodiments, the LNP is configured to deliver the aforementioned mRNA and guide RNA to spleen. In some embodiments, the LNP is configured to deliver the aforementioned mRNA and guide RNA to kidney. In some embodiments, the LNP is configured to deliver the aforementioned mRNA and guide RNA to pancreas. In some embodiments, the LNP is configured to deliver the aforementioned mRNA and guide RNA to brain. In some embodiments, the LNP is configured to deliver the aforementioned mRNA and guide RNA to macrophages.

In some embodiments, the LNP also includes at least one helper lipid. In some embodiments, the helper lipid is selected from phospholipids and steroids. In some embodiments, the phospholipids are di- and/or monoester of the phosphoric acid. In some embodiments, the phospholipids are phosphoglycerides and/or sphingolipids. In some embodiments, the steroids are naturally occurring and/or synthetic compounds based on the partially hydrogenated cyclopenta[a]phenanthrene. In some embodiments, the steroids contain 21 to 30 C atoms. In some embodiments, the steroid is cholesterol. In some embodiments, the helper lipid is selected from 1,2-diphytanoyl-sn-glycero-3-phosphoethanolamine (DPhyPE), ceramide, and 1,2-dioleyl-sn-glycero-3-phosphoethanolamine (DOPE).

In some embodiments, the at least one helper lipid comprises a moiety selected from the group comprising a PEG moiety, a HEG moiety, a polyhydroxyethyl starch (poly-HES) moiety and a polypropylene moiety. In some embodiments, the moiety has a molecule weight between about 500 to 10,000 Da or between about 2,000 to 5,000 Da. In some embodiments, the PEG moiety is selected from 1,2-distearoyl-sn-glycero-3 phosphoethanolamine, 1,2-dialkyl-sn-glycero-3-phosphoethanolamine, and Ceramide-PEG. In some embodiments, the PEG moiety has a molecular weight between about 500 to 10,000 Da or between about 2,000 to 5,000 Da. In some embodiments, the PEG moiety has a molecular weight of 2,000 Da.

In some embodiments, the helper lipid is between about 20 mol % to 80 mol % of the total lipid content of the composition. In some embodiments, the helper lipid component is between about 35 mol % to 65 mol % of the total lipid content of the LNP. In some embodiments, the LNP includes lipids at 50 mol % and the helper lipid at 50 mol % of the total lipid content of the LNP.

In some embodiments, the LNP includes any of -3-arginyl-2,3-diaminopropionic acid-N-palmityl-N-oleyl-amide trihydrochloride, -arginyl-2,3-diaminopropionic acid-N-lauryl-N-myristyl-amide trihydrochloride or arginyl-lysine-N-lauryl-N-myristyl-amide trihydrochloride in combination with DPhyPE, wherein the content of DPhyPE is about 80 mol %, 65 mol %, 50 mol % and 35 mol % of the overall lipid content of the LNP. In some embodiments, the LNP includes -arginyl-2,3-diamino propionic acid-N-pahnityl-N-oleyl-amide trihydrochloride (lipid) and 1,2-diphytanoyl-sn-glycero-3-phosphoethanolamine (helper lipid). In some embodiments, the LNP includes -arginyl-2,3-diamino propionic acid-N-palmityl-N-oleyl-amide trihydrochloride (lipid), 1,2-diphytanoyl-sn-glycero-3-phosphoethanolamine (first helper lipid), and 1,2-disteroyl-sn-glycero-3-phosphoethanolamine-PEG2000 (second helper lipid).

In some embodiments, the second helper lipid is between about 0.05 mol % to 4.9 mol % or between about 1 mol % to 3 mol % of the total lipid content. In some embodiments, the LNP includes lipids at between about 45 mol % to 50 mol % of the total lipid content, a first helper lipid between about 45 mol % to 50 mol % of the total lipid content, under the proviso that there is a PEGylated second helper lipid between about 0.1 mol % to 5 mol %, between about 1 mol % to 4 mol %, or at about 2 mol % of the total lipid content, wherein the sum of the content of the lipids, the first helper lipid, and of the second helper lipid is 100 mol % of the total lipid content and wherein the sum of the first helper lipid and the second helper lipid is 50 mol % of the total lipid content. In some embodiments, the LNP comprises: (a) 50 mol % of -arginyl-2,3-diamino propionic acid-N-palmityl-N-oleyl-amide trihydrochloride, 48 mol % of 1,2-diphytanoyl-sn-glycero-3-phosphoethanolamine; and 2 mol % 1,2-distearoyl-sn-glycero-3-phosphoethanolamine-PEG2000; or (b) 50 mol % of -arginyl-2,3-diamino propionic acid-N-palmityl-N-oleyl-amide trihydrochloride, 49 mol % 1,2-diphytanoyl-sn- glycerol-3-phosphoethanolamine; and 1 mol % N(Carbonyl-methoxypolyethylenglycol-2000)-1,2-distearoyl-sn-glycero3-phosphoethanolamine, or a sodium salt thereof In some embodiments, the LNP contains a nucleic acid, wherein the charge ratio of nucleic acid backbone phosphates to cationic lipid nitrogen atoms is about 1: 1.5-7 or about 1:4.

In some embodiments, the LNP also includes a shielding compound, which is removable from the lipid composition under in vivo conditions. In some embodiments, the shielding compound is a biologically inert compound. In some embodiments, the shielding compound does not carry any charge on its surface or on the molecule as such. In some embodiments, the shielding compounds are polyethylenglycoles (PEGs), hydroxyethylglucose (HEG) based polymers, polyhydroxyethyl starch (polyHES) and polypropylene. In some embodiments, the PEG, HEG, polyHES, and a polypropylene weight between about 500 to 10,000 Da or between about 2000 to 5000 Da. In some embodiments, the shielding compound is PEG2000 or PEG5000.

In some embodiments, the LNP includes at least one lipid, a first helper lipid, and a shielding compound that is removable from the lipid composition under in vivo conditions. In some embodiments, the LNP also includes a second helper lipid. In some embodiments, the first helper lipid is ceramide. In some embodiments, the second helper lipid is ceramide. In some embodiments, the ceramide comprises at least one short carbon chain substituent of from 6 to 10 carbon atoms. In some embodiments, the ceramide comprises 8 carbon atoms. In some embodiments, the shielding compound is attached to a ceramide. In some embodiments, the shielding compound is attached to a ceramide. In some embodiments, the shielding compound is covalently attached to the ceramide. In some embodiments, the shielding compound is attached to a nucleic acid in the LNP. In some embodiments, the shielding compound is covalently attached to the nucleic acid. In some embodiments, the shielding compound is attached to the nucleic acid by a linker. In some embodiments, the linker is cleaved under physiological conditions. In some embodiments, the linker is selected from ssRNA, ssDNA, dsRNA, dsDNA, peptide, S-S-linkers and pH sensitive linkers. In some embodiments, the linker moiety is attached to the 3' end of the sense strand of the nucleic acid. In some embodiments, the shielding compound comprises a pH-sensitive linker or a pH-sensitive moiety. In some embodiments, the pH-sensitive linker or pH-sensitive moiety is an anionic linker or an anionic moiety. In some embodiments, the anionic linker or anionic moiety is less anionic or neutral in an acidic environment. In some embodiments, the pH-sensitive linker or the pH-sensitive moiety is selected from the oligo (glutamic acid), oligophenolate(s) and diethylene triamine penta acetic acid.

In any of the LNP embodiments in the previous paragraph, the LNP can have an osmolality between about 50 to 600 mosmole/kg, between about 250 to 350 mosmole/kg, or between about 280 to 320 mosmole/kg, and/or wherein the LNP formed by the lipid and/or one or two helper lipids and the shielding compound have a particle size between about 20 to 200 nm, between about 30 to 100 nm, or between about 40 to 80 nm.

In some embodiments, the shielding compound provides for a longer circulation time in vivo and allows for a better biodistribution of the nucleic acid containing LNP. In some embodiments, the shielding compound prevents immediate interaction of the LNP with serum compounds or compounds of other bodily fluids or cytoplasma membranes, e.g., cytoplasma membranes of the endothelial lining of the vasculature, into which the LNP is administered. Additionally or alternatively, in some embodiments, the shielding compounds also prevent elements of the immune system from immediately interacting with the LNP. Additionally or alternatively, in some embodiments, the shielding compound acts as an anti-opsonizing compound. Without wishing to be bound by any mechanism or theory, in some embodiments, the shielding compound forms a cover or coat that reduces the surface area of the LNP available for interaction with its environment. Additionally or alternatively, in some embodiments, the shielding compound shields the overall charge of the LNP.

In another embodiment, the LNP includes at least one cationic lipid having Formula VI:

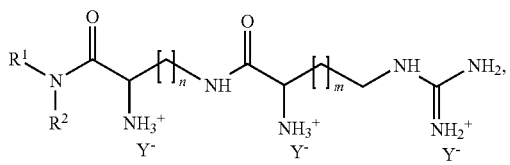

(Formula VI)

wherein n is 1, 2, 3, or 4, wherein m is 1, 2, or 3, wherein $Y^-$ is anion, wherein each of 10 and $R^2$ is individually and independently selected from the group consisting of linear C12-C18 alkyl and linear C12-C18 alkenyl, a sterol compound, wherein the sterol compound is selected from the group consisting of cholesterol and stigmasterol, and a PEGylated lipid, wherein the PEGylated lipid comprises a PEG moiety, wherein the PEGylated lipid is selected from the group consisting of:

a PEGylated phosphoethanolamine of Formula VII:

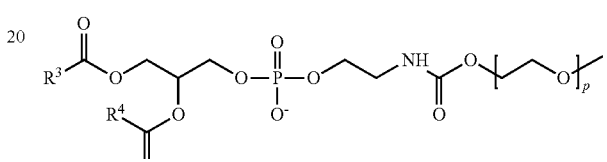

(Formula VII)

wherein $R^3$ and $R^4$ are individually and independently linear C13-C17 alkyl, and p is any integer between 15 to 130;

a PEGylated ceramide of Formula VIII:

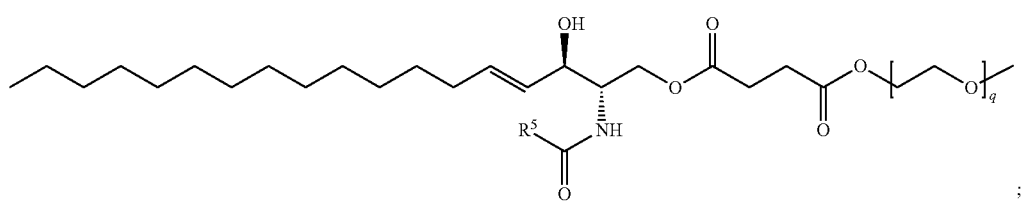

(Formula VIII)

wherein $R^5$ is linear C7-C15 alkyl, and q is any number between 15 to 130; and a PEGylated diacylglycerol of Formula IX:

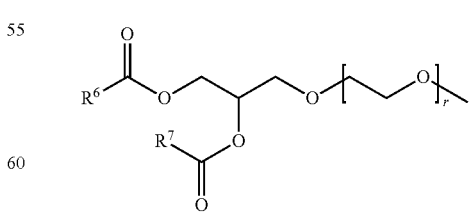

(Formula IX)

wherein each of $R^6$ and $R^7$ is individually and independently linear C11-C17 alkyl, and r is any integer from 15 to 130.

In some embodiments, $R^1$ and $R^2$ are different from each other. In some embodiments, $R^1$ is palmityl and $R^2$ is oleyl. In some embodiments, $R^1$ is lauryl and $R^2$ is myristyl. In some embodiments, $R^1$ and $R^2$ are the same. In some embodiments, each of $R^1$ and $R^2$ is individually and independently selected from the group consisting of C12 alkyl, C14 alkyl, C16 alkyl, C18 alkyl, C12 alkenyl, C14 alkenyl, C16 alkenyl and C18 alkenyl. In some embodiments, each of C12 alkenyl, C14 alkenyl, C16 alkenyl and C18 alkenyl comprises one or two double bonds. In some embodiments, C18 alkenyl is C18 alkenyl with one double bond between C9 and C10. In some embodiments, C18 alkenyl is cis-9-octadecyl.

In some embodiments, the cationic lipid is a compound of Formula X:

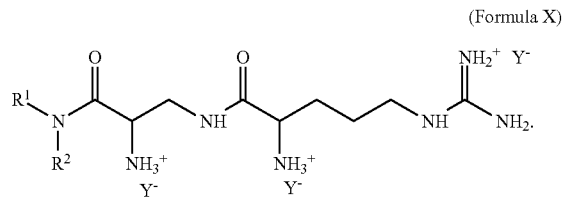

(Formula X)

In some embodiments, $Y^-$ is selected from halogenids, acetate and trifluoroacetate. In some embodiments, the cationic lipid is β-arginyl-2,3-diamino propionic acid-N-palmityl-N-oleyl-amide trihydrochloride of Formula III:

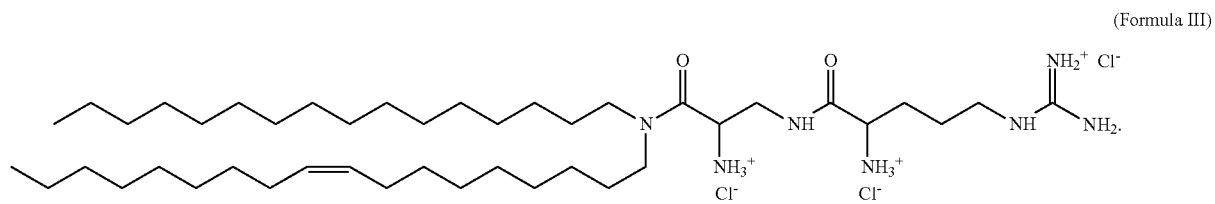 [SMILES: CCCCCCCC/C=C\CCCCCCCCN(CCCCCCCCCCCCCCCC)C(=O)C([NH3+])CNC(=O)C([NH3+])CCCNC(N)=[NH2+] ; [Cl-] ; [Cl-] ; [Cl-]]

(Formula III)

In some embodiments, the cationic lipid is β-arginyl-2,3-diamino propionic acid-N-lauryl-N-myristyl-amide trihydrochloride of Formula IV:

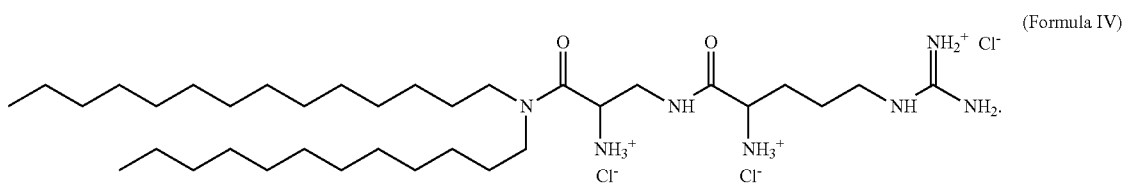 [SMILES: CCCCCCCCCCCCCCN(CCCCCCCCCCCC)C(=O)C([NH3+])CNC(=O)C([NH3+])CCCNC(N)=[NH2+] ; [Cl-] ; [Cl-] ; [Cl-]]

(Formula IV)

In some embodiments, the cationic lipid is c-arginyl-lysine-N-lauryl-N-myristyl-amide trihydrochloride of Formula V:

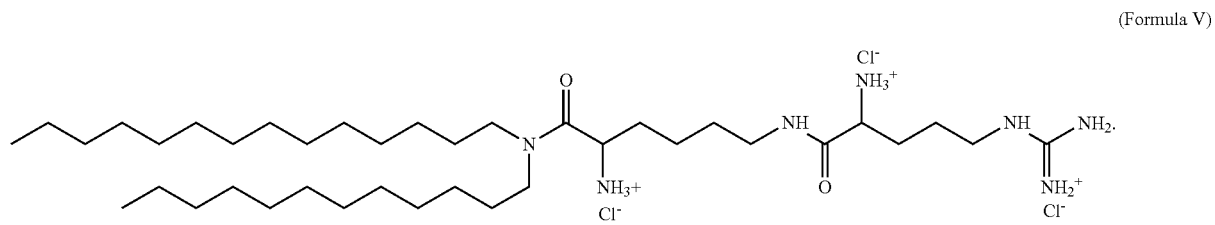 [SMILES: [Cl-] ; CCCCCCCCCCCCCCN(CCCCCCCCCCCC)C(=O)C([NH3+])CCCCNC(=O)C([NH3+])CCCNC(N)=[NH2+] ; [Cl-] ; [Cl-]]

(Formula V)

In some embodiments, the sterol compound is cholesterol. In some embodiments, the sterol compound is stigmasterin.

In some embodiments, the PEG moiety of the PEGylated lipid has a molecular weight from about 800 to 5,000 Da. In some embodiments, the molecular weight of the PEG moiety of the PEGylated lipid is about 800 Da. In some embodiments, the molecular weight of the PEG moiety of the PEGylated lipid is about 2,000 Da. In some embodiments, the molecular weight of the PEG moiety of the PEGylated lipid is about 5,000 Da. In some embodiments, the PEGylated lipid is a PEGylated phosphoethanolamine of Formula VII, wherein each of $R^3$ and $R^4$ is individually and independently linear C13-C17 alkyl, and p is any integer from 18, 19 or 20, or from 44, 45 or 46 or from 113, 114 or 115. In some embodiments, $R^3$ and $R^4$ are the same. In some embodiments, $R^3$ and $R^4$ are different. In some embodiments, each of $R^3$ and $R^4$ is individually and independently selected from the group consisting of C13 alkyl, C15 alkyl and C17 alkyl. In some embodiments, the PEGylated phosphoethanolamine of Formula VII is 1,2-distearoyl-sn-glycero-3-phosphoethanolamine-N-[methoxy(polyethylene glycol)-2000] (ammonium salt):

(Formula XI)

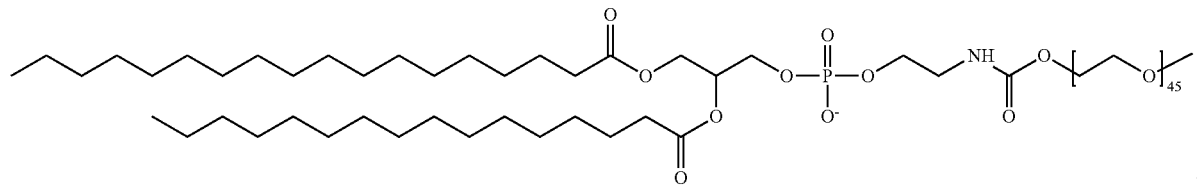

In some embodiments, the PEGylated phosphoethanolamine of Formula VII is 1,2-distearoyl-sn-glycero-3-phosphoethanolamine-N-[methoxy(polyethylene glycol)-5000] (ammonium salt):

(Formula XII)

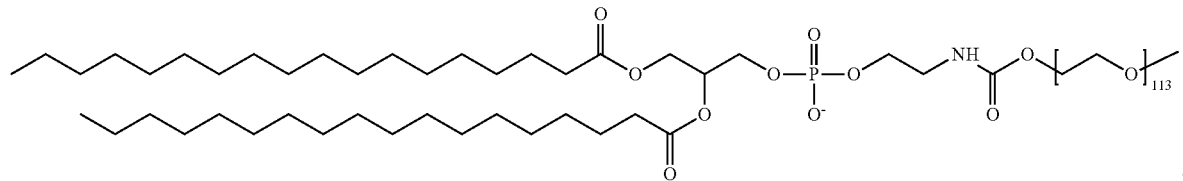

In some embodiments, the PEGylated lipid is a PEGylated ceramide of Formula VIII, wherein $R^5$ is linear C7-C15 alkyl, and q is any integer from 18, 19 or 20, or from 44, 45 or 46 or from 113, 114 or 115. In some embodiments, $R^5$ is linear C7 alkyl. In some embodiments, $R^5$ is linear C15 alkyl. In some embodiments, the PEGylated ceramide of Formula VIII is N-octanoyl-sphingosine-1- {succinyl[methoxy(polyethylene glycol)2000]}:

(Formula XIII)

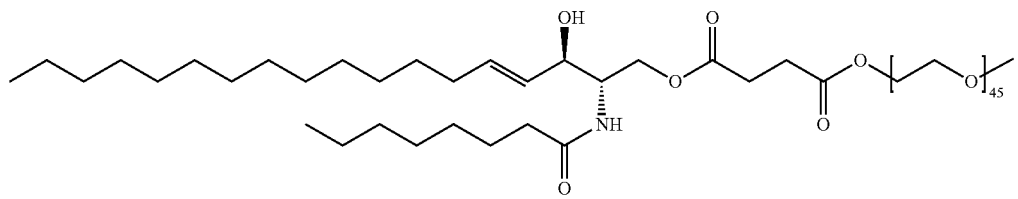

In some embodiments, the PEGylated ceramide of Formula VIII is N-palmitoyl-sphingosine-1- succinyl[methoxy(polyethylene glycol) 2000]}:

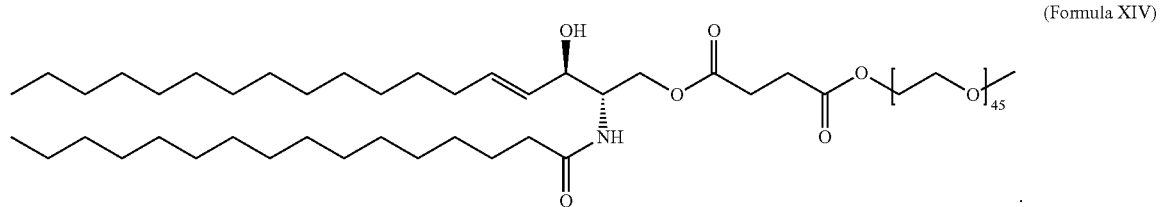
(Formula XIV)

In some embodiments, the PEGylated lipid is a PEGylated diacylglycerol of Formula IX, wherein each of $R^6$ and $R^7$ is individually and independently linear C11-C17 alkyl, and r is any integer from 18, 19 or 20, or from 44, 45 or 46 or from 113, 114 or 115. In some embodiments, $R^6$ and $R^7$ are the same. In some embodiments, $R^6$ and $R^7$ are different. In some embodiments, each of $R^6$ and $R^7$ is individually and independently selected from the group consisting of linear C17 alkyl, linear C15 alkyl and linear C13 alkyl. In some embodiments, the PEGylated diacylglycerol of Formula IX 1,2-Distearoyl-sn-glycerol [methoxy(polyethylene glycol) 2000]:

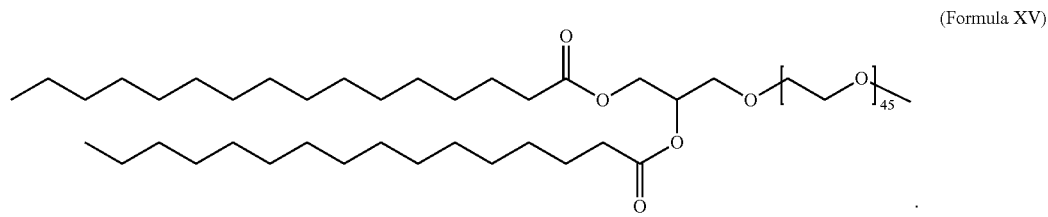
(Formula XV)

In some embodiments, the PEGylated diacylglycerol of Formula IX is 1,2-Dipalmitoyl-sn-glycerol [methoxy(polyethylene glycol)2000]:

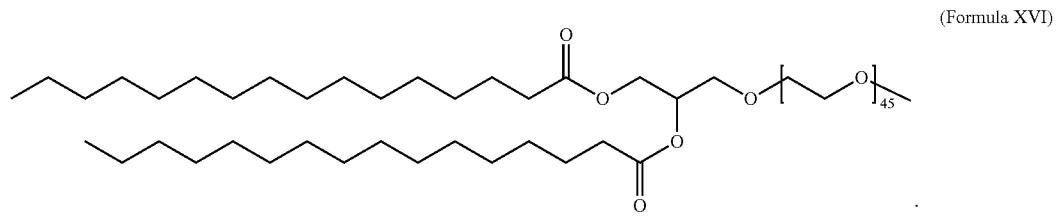
(Formula XVI)

In some embodiments, the PEGylated diacylglycerol of Formula IX is:

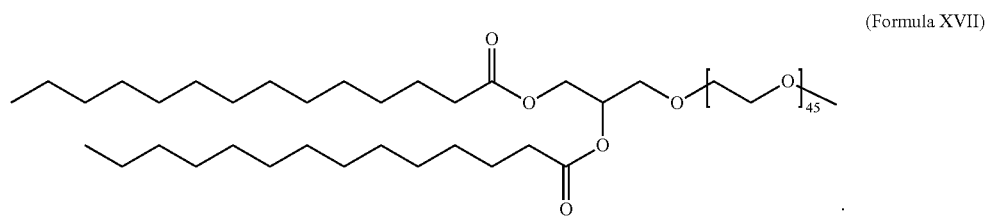
(Formula XVII)

In some embodiments, the LNP includes at least one cationic lipid selected from of Formulas III, IV, and V, at least one sterol compound selected from a cholesterol and stigmasterin, and wherein the PEGylated lipid is at least one selected from Formulas XI and XII. In some embodiments, the LNP includes at least one cationic lipid selected from Formulas III, IV, and V, at least one sterol compound selected from a cholesterol and stigmasterin, and wherein the PEGylated lipid is at least one selected from Formulas XIII and XIV. In some embodiments, the LNP includes at least one cationic lipid selected from Formulas III, IV, and V, at least one sterol compound selected from a cholesterol and stigmasterin, and wherein the PEGylated lipid is at least one selected from Formulas XV and XVI. In some embodiments, the LNP includes a cationic lipid of Formula III, a cholesterol as the sterol compound, and wherein the PEGylated lipid is Formula XI.

In any of the LNP embodiments in the previous paragraph, wherein the content of the cationic lipid composition is between about 65 mole % to 75 mole %, the content of the sterol compound is between about 24 mole % to 34 mole % and the content of the PEGylated lipid is between about 0.5 mole % to 1.5 mole %, wherein the sum of the content of the cationic lipid, of the sterol compound and of the PEGylated lipid for the lipid composition is 100 mole %. In some embodiments, the cationic lipid is about 70 mole %, the content of the sterol compound is about 29 mole % and the content of the PEGylated lipid is about 1 mole %. In some embodiments, the LNP is 70 mole % of Formula III, 29 mole % of cholesterol, and 1 mole % of Formula XI.

Exosomes

Exosomes are endogenous nano-vesicles that transport RNAs and proteins, and which can deliver RNA to the brain and other target organs. To reduce immunogenicity, Alvarez-Erviti et al. (2011, Nat Biotechnol 29: 341) used self-derived dendritic cells for exosome production. Targeting to the brain was achieved by engineering the dendritic cells to express Lamp2b, an exosomal membrane protein, fused to the neuron-specific RVG peptide. Purified exosomes were loaded with exogenous RNA by electroporation. Intravenously injected RVG-targeted exosomes delivered GAPDH siRNA specifically to neurons, microglia, oligodendrocytes in the brain, resulting in a specific gene knockdown. Pre-exposure to RVG exosomes did not attenuate knockdown, and non-specific uptake in other tissues was not observed. The therapeutic potential of exosome-mediated siRNA delivery was demonstrated by the strong mRNA (60%) and protein (62%) knockdown of BACE1, a therapeutic target in Alzheimer's disease.

To obtain a pool of immunologically inert exosomes, Alvarez-Erviti et al. harvested bone marrow from inbred C57BL/6 mice with a homogenous major histocompatibility complex (MHC) haplotype. As immature dendritic cells produce large quantities of exosomes devoid of T-cell activators such as MHC-II and CD86, Alvarez-Erviti et al. selected for dendritic cells with granulocyte/macrophage-colony stimulating factor (GM-CSF) for 7 d. Exosomes were purified from the culture supernatant the following day using well-established ultracentrifugation protocols. The exosomes produced were physically homogenous, with a size distribution peaking at 80 nm in diameter as determined by nanoparticle tracking analysis (NTA) and electron microscopy. Alvarez-Erviti et al. obtained 6-12 μg of exosomes (measured based on protein concentration) per $10^6$ cells.

Next, Alvarez-Erviti et al. investigated the possibility of loading modified exosomes with exogenous cargoes using electroporation protocols adapted for nanoscale applications. As electroporation for membrane particles at the nanometer scale is not well-characterized, nonspecific Cy5-labeled RNA was used for the empirical optimization of the electroporation protocol. The amount of encapsulated RNA was assayed after ultracentrifugation and lysis of exosomes. Electroporation at 400 V and 125 μF resulted in the greatest retention of RNA and was used for all subsequent experiments.

Alvarez-Erviti et al. administered 150 μg of each BACE1 siRNA encapsulated in 150 μg of RVG exosomes to normal C57BL/6 mice and compared the knockdown efficiency to four controls: untreated mice, mice injected with RVG exosomes only, mice injected with BACE1 siRNA complexed to an in vivo cationic liposome reagent and mice injected with BACE1 siRNA complexed to RVG-9R, the RVG peptide conjugated to 9 D-arginines that electrostatically binds to the siRNA. Cortical tissue samples were analyzed 3 d after administration and a significant protein knockdown (45%, P<0.05, versus 62%, P<0.01) in both siRNA-RVG-9R-treated and siRNARVG exosome-treated mice was observed, resulting from a significant decrease in BACE1 mRNA levels (66% [+ or −] 15%, P<0.001 and 61% [+ or −] 13% respectively, P<0.01). Moreover, Applicants demonstrated a significant decrease (55%, P<0.05) in the total [beta]-amyloid 1-42 levels, a main component of the amyloid plaques in Alzheimer's pathology, in the RVG-exosome-treated animals. The decrease observed was greater than the β-amyloid 1-40 decrease demonstrated in normal mice after intraventricular injection of BACE1 inhibitors. Alvarez-Erviti et al. carried out 5'-rapid amplification of cDNA ends (RACE) on BACE1 cleavage product, which provided evidence of RNAi-mediated knockdown by the siRNA.

Finally, Alvarez-Erviti et al. investigated whether RNA-RVG exosomes induced immune responses in vivo by assessing IL-6, IP-10, TNFα and IFN-α serum concentrations. Following exosome treatment, nonsignificant changes in all cytokines were registered similar to siRNA-transfection reagent treatment in contrast to siRNA-RVG-9R, which potently stimulated IL-6 secretion, confirming the immunologically inert profile of the exosome treatment. Given that exosomes encapsulate only 20% of siRNA, delivery with RVG-exosome appears to be more efficient than RVG-9R delivery as comparable mRNA knockdown and greater protein knockdown was achieved with fivefold less siRNA without the corresponding level of immune stimulation. This experiment demonstrated the therapeutic potential of RVG-exosome technology, which is potentially suited for long-term silencing of genes related to neurodegenerative diseases. The exosome delivery system of Alvarez-Erviti et al. may be applied to deliver the CRISPR-Cas system of the present invention to therapeutic targets, especially neurodegenerative diseases. A dosage of about 100 to 1000 mg of CRISPR-Cas encapsulated in about 100 to 1000 mg of RVG exosomes may be contemplated for the present invention.

El-Andaloussi et al. (Nature Protocols 7, 2112-2126 (2012)) discloses how exosomes derived from cultured cells can be harnessed for delivery of RNA in vitro and in vivo. This protocol first describes the generation of targeted exosomes through transfection of an expression vector, comprising an exosomal protein fused with a peptide ligand. Next, El-Andaloussi et al. explain how to purify and characterize exosomes from transfected cell supernatant. Next, El-Andaloussi et al. detail crucial steps for loading RNA into exosomes. Finally, El-Andaloussi et al. outline how to use exosomes to efficiently deliver RNA in vitro and in vivo in mouse brain. Examples of anticipated results in which exosome-mediated RNA delivery is evaluated by functional assays and imaging are also provided. The entire protocol takes ~3 weeks. Delivery or administration according to the invention may be performed using exosomes produced from self-derived dendritic cells. From the herein teachings, this can be employed in the practice of the invention.

In another embodiment, the plasma exosomes of Wahlgren et al. (Nucleic Acids Research, 2012, Vol. 40, No. 17 e130) are contemplated. Exosomes are nano-sized vesicles (30-90 nm in size) produced by many cell types, including dendritic cells (DC), B cells, T cells, mast cells, epithelial cells and tumor cells. These vesicles are formed by inward budding of late endosomes and are then released to the extracellular environment upon fusion with the plasma membrane. Because exosomes naturally carry RNA between cells, this property may be useful in gene therapy, and from this disclosure can be employed in the practice of the instant invention.

Exosomes from plasma can be prepared by centrifugation of buffy coat at 900 g for 20 min to isolate the plasma followed by harvesting cell supernatants, centrifuging at 300 g for 10 min to eliminate cells and at 16 500 g for 30 min followed by filtration through a 0.22 mM filter. Exosomes are pelleted by ultracentrifugation at 120 000 g for 70 min. Chemical transfection of siRNA into exosomes is carried out according to the manufacturer's instructions in RNAi Human/Mouse Starter Kit (Quiagen, Hilden, Germany). siRNA is added to 100 ml PBS at a final concentration of 2 mmol/ml. After adding HiPerFect transfection reagent, the mixture is incubated for 10 min at RT. In order to remove the excess of micelles, the exosomes are re-isolated using aldehyde/sulfate latex beads. The chemical transfection of CRISPR-Cas into exosomes may be conducted similarly to siRNA. The exosomes may be co-cultured with monocytes and lymphocytes isolated from the peripheral blood of healthy donors. Therefore, it may be contemplated that exosomes containing CRISPR-Cas may be introduced to monocytes and lymphocytes of and autologously reintroduced into a human. Accordingly, delivery or administration according to the invention may be performed using plasma exosomes.

Liposomes

The lipid, lipid particle, or lipid bilayer or lipid entity of the invention can be prepared by methods well known in the art. See Wang et al., ACS Synthetic Biology, 1, 403-07 (2012); Wang et al., PNAS, 113(11) 2868-2873 (2016); Manoharan, et al., WO 2008/042973; Zugates et al., U.S. Pat. No. 8,071,082; Xu et al., WO 2014/186366 A1 (US20160082126). Xu et provides a way to make a nanocomplex for the delivery of saporin wherein the nanocomplex comprising saporin and a lipid-like compound, and wherein the nanocomplex has a particle size of 50 nm to 1000 nm; the saporin binds to the lipid-like compound via non-covalent interaction or covalent bonding; and the lipid-like compound has a hydrophilic moiety, a hydrophobic moiety, and a linker joining the hydrophilic moiety and the hydrophobic moiety, the hydrophilic moiety being optionally charged and the hydrophobic moiety having 8 to 24 carbon atoms. Xu et al., WO 2014/186348 (US20160129120) provides examples of nanocomplexes of modified peptides or proteins comprising a cationic delivery agent and an anionic pharmaceutical agent, wherein the nanocomplex has a particle size of 50 to 1000 nm, the cationic delivery agent binds to the anionic pharmaceutical agent, and the anionic pharmaceutical agent is a modified peptide or protein formed of a peptide and a protein and an added chemical moiety that contains an anionic group. The added chemical moiety is linked to the peptide or protein via an amide group, an ester group, an ether group, a thioether group, a disulfide group, a hydrazone group, a sulfenate ester group, an amidine group, a urea group, a carbamate group, an imidoester group, or a carbonate group. More particularly these documents provide examples of lipid or lipid-like compounds that can be used to make the particle delivery system of the present invention, including compounds of the formula B1-K1-A-K2-B2, in which A, the hydrophilic moiety, is

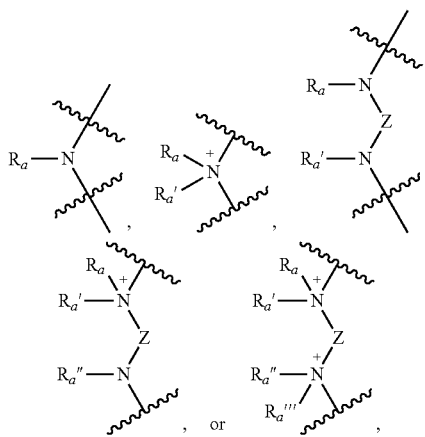

each of $R_a$, $R_a'$, $R_a''$, and $R_a'''$, independently, being a $C_1$-$C_{20}$ monovalent aliphatic radical, a $C_1$-$C_{20\ 0}$ monovalent heteroaliphatic radical, a monovalent aryl radical, or a monovalent heteroaryl radical; and Z being a $C_1$-$C_{20}$ bivalent aliphatic radical, a $C_1$-$C_{20}$ bivalent heteroaliphatic radical, a bivalent aryl radical, or a bivalent heteroaryl radical; each of $B_1$, the hydrophobic moiety, and B2, also the hydrophobic moiety, independently, is a $C_{12-20}$ aliphatic radical or a $c_{12-20}$ heteroaliphatic radical; and each of $K_1$, the linker, and $K_2$, also the linker, independently, is O, S, Si, $C_1$-$C_6$ alkylene

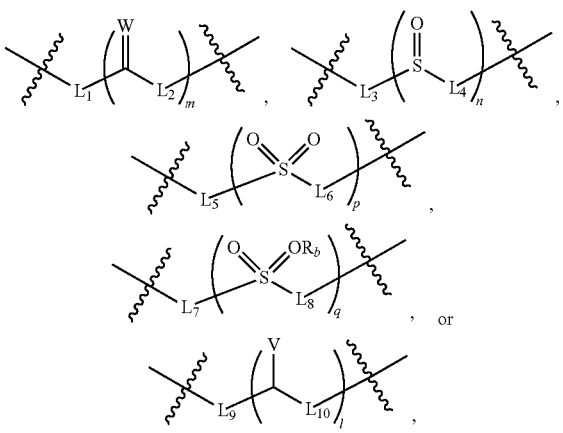

in which each of m, n, p, q, and t, independently, is 1-6; W is O, S, or $NR_c$; each of $L_1$, $L_3$, $L_5$, $L_7$, and $L_9$, independently, is a bond, O, S, or $NR_d$; each of L2, $L_4$, $L_6$, $L_8$, and $L_{10}$, independently, is a bond, O, S, or $NR_e$; and V is $OR_f$, $SR_g$, or $NR_hR_i$, each of $R_b$, $R_c$, $R_d$, $R_e$, $R_f$, $R_g$, $R_h$, and $R_i$, independently, being H, OH, a $C_1$-$C_{10}$ oxyaliphatic radical, a $C_1$-$C_{10}$ monovalent aliphatic radical, a $C_1$-$C_{10}$ monovalent heteroaliphatic radical, a monovalent aryl radical, or a monovalent heteroaryl radical and specific compounds:
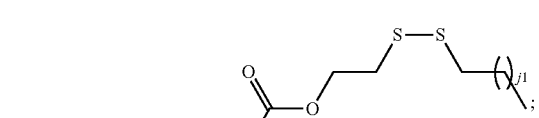
80-O14B, j1, j2 = 8;
80-O16B, j1, j2 = 10; and
80-O18B, j1, j2 = 12
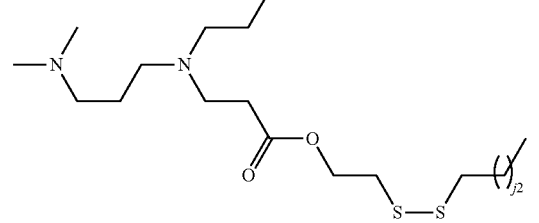
87-O14B, j1, j2 = 8;
87-O16B, j1, j2 = 10; and
87-O18B, j1, j2 = 12
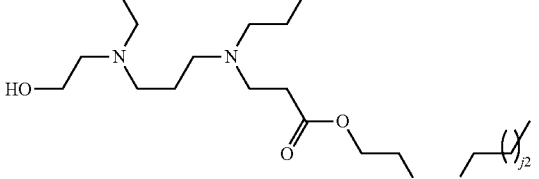
1-O16B, j1, j2 = 10; and
1-O18B, j1, j2 = 12
-continued
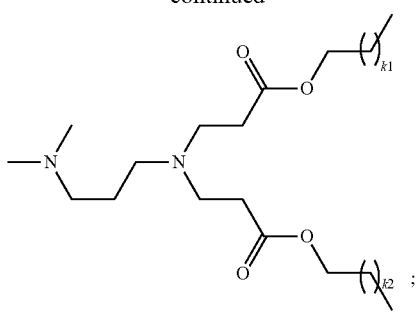
80-O14, k1, k2 = 12;
80-O16, k1, k2 = 14; and
80-O18, k1, k2 = 16
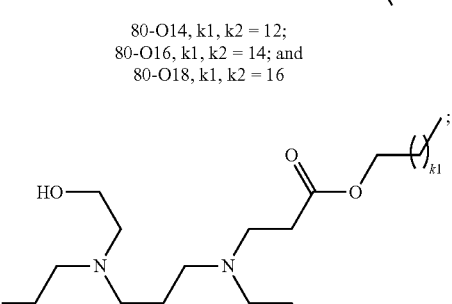
87-O14, k1, k2 = 12;
87-O16, k1, k2 = 14; and
87-O18, k1, k2 = 16.
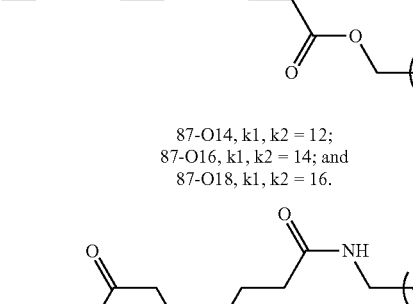
1-N16, k1, k2, k3, k4 = 14
1-N18, k1 = 12, k2 = 13, k3 = 15, and k4 = 16;
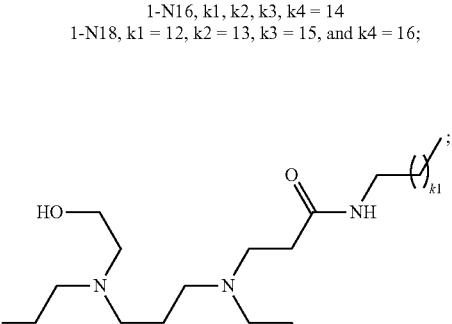
87-N17, k1 = 13 and k2 = 15;
87-N16, k1, k2 = 14; and
87-N18, k1, k2 = 16.

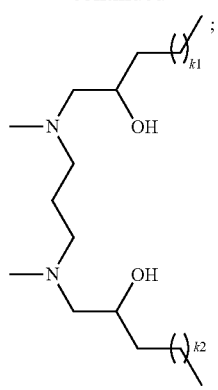

EC16-1, k1, k2 = 14;

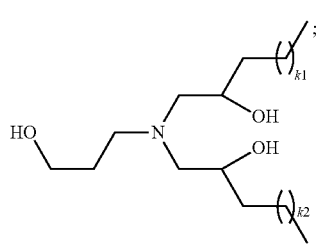

EC16-3, k1, k2 = 14

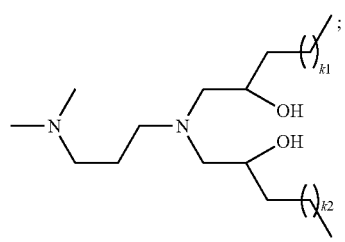

EC16-12, k1, k2 = 14

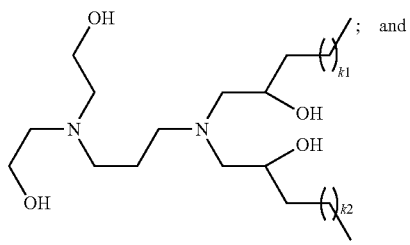

and

EC16-14, k1, k2 = 14

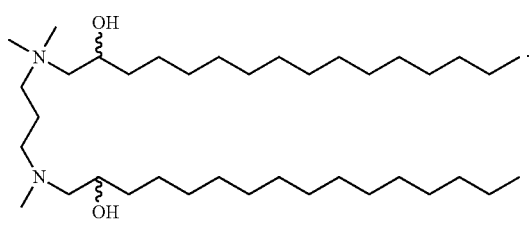

EC16-63

Additional examples of cationic lipid that can be used to make the particle delivery system of the invention can be found in US20150140070, wherein the cationic lipid has the formula

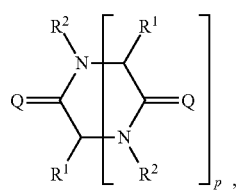

wherein p is an integer between 1 and 9, inclusive; each instance of Q is independently O, S, or $NR^Q$; $R^Q$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii) or (iii); each instance of $R^1$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, halogen, $-OR^{41}$, $-N(R^{41})_2$, $-SR^{41}$, or a group of formula:

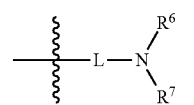

L is an optionally substituted alkylene, optionally substituted alkenylene, optionally substituted alkynylene, optionally substituted heteroalkylene, optionally substituted heteroalkenylene, optionally substituted heteroalkynylene, optionally substituted carbocyclylene, optionally substituted heterocyclylene, optionally substituted arylene, or optionally substituted heteroarylene, or combination thereof, and each of $R^6$ and $R^7$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of formula (i), (ii) or (iii); each occurrence of $R^{41}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to an sulfur atom, a nitrogen protecting group when attached to a nitrogen atom, or two $R^{41}$ groups, together with the nitrogen atom to which they are attached, are joined to form an optionally substituted heterocyclic or optionally substituted heteroaryl ring; each instance of $R^2$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, a nitrogen protecting group, or a group of the formula (i), (ii), or (iii); Formulae (i), (ii), and (iii) are:

(i) 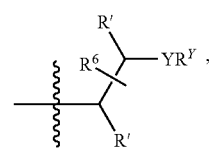

(ii) 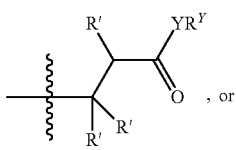, or (iii) 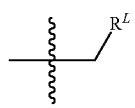, each instance of R' is independently hydrogen or optionally substituted alkyl; X is O, S, or $NR^X$; $R^X$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; Y is O, S, or $NR^Y$; $R^Y$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or a nitrogen protecting group; $R^P$ is hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, an oxygen protecting group when attached to an oxygen atom, a sulfur protecting group when attached to a sulfur atom, or a nitrogen protecting group when attached to a nitrogen atom; $R^L$ is optionally substituted $C_{1-50}$ alkyl, optionally substituted $C_{2-50}$ alkenyl, optionally substituted $C_{2-50}$ alkynyl, optionally substituted heteroC$_{1-50}$alkyl, optionally substituted heteroC$_{2-50}$alkenyl, optionally substituted heteroC$_{2-50}$ alkynyl, or a polymer; provided that at least one instance of $R^Q$, $R^2$, $R^6$, or $R^7$ is a group of the formula (i), (ii), or (iii); in Liu et al., (US 20160200779, US 20150118216, US 20150071903, and US 20150071903), which provide examples of cationic lipids to include polyethylenimine, polyamidoamine (PAMAM) starburst dendrimers, Lipofectin (a combination of DOTMA and DOPE), Lipofectase, LIPOFECTAMINE® (e.g., LIPOFECTAMINE® 2000, LIPOFECTAMINE® 3000, LIPOFECTAMINE® RNAiMAX, LIPOFECTAMINE® LTX), SAINT-RED (Synvolux Therapeutics, Groningen Netherlands), DOPE, Cytofectin (Gilead Sciences, Foster City, Calif.), and Eufectins (JBL, San Luis Obispo, Calif.). Exemplary cationic liposomes can be made from N-[1-(2,3-dioleoloxy)-propyl]-N,N,N-trimethylammonium chloride (DOTMA), N-[1-(2,3-dioleoloxy)-propyl]-N,N,N-trimethylammonium methylsulfate (DOTAP), 3.beta.-[N—(N',N'-dimethylaminoethane)carbamoyl] cholesterol (DC-Chol), 2,3,- dioleoyloxy-N-[2(sperminecarboxamido)ethyl]-N,N-dimethyl-1-propanamin- ium trifluoroacetate (DOSPA), 1,2-dimyristyloxypropyl-3-dimethyl-hydroxyethyl ammonium bromide; and dimethyldioctadecylammonium bromide (DDAB); in WO2013/093648 which provides cationic lipids of formula

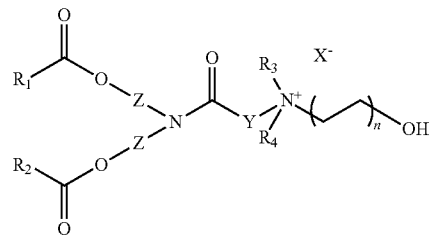

in which Z=an alkyl linker, $C_2$-$C_4$ alkyl, Y=an alkyl linker, $C_1$-$C_6$ alkyl, $R_1$ and $R_2$ are each independently $C_{10}$-$C_{30}$alkyl, $C_{10}$-$C_{30}$alkenyl, or $C_{10}$-$C_{30}$alkynyl, $C_{10}$-$C_{30}$alkyl, $C_{10}$-$C_{20}$alkyl, $C_{12}$- $C_{18}$alkyl, $C_{13}$- $C_{17}$alkyl, $C_{17}$alkyl, $C_{10}$-$C_{30}$alkenyl, $C_{10}$-$C_{20}$alkenyl. $C_{12}$-$C_{18}$alkenyl, $C_{13}$-$C_{17}$alkenyl, $C_{17}$alkenyl; R3 and R4 are each independently hydrogen, $C_1$-$C_6$ alkyl, or —$CH_2CH_2OH$, $C_1$-$C_6$ alkyl, $C_1$-$C_3$alkyl; n is 1-6; and X is a counterion, including any nitrogen counterion, as that term is readily understood in the art, and specific cationic lipids including

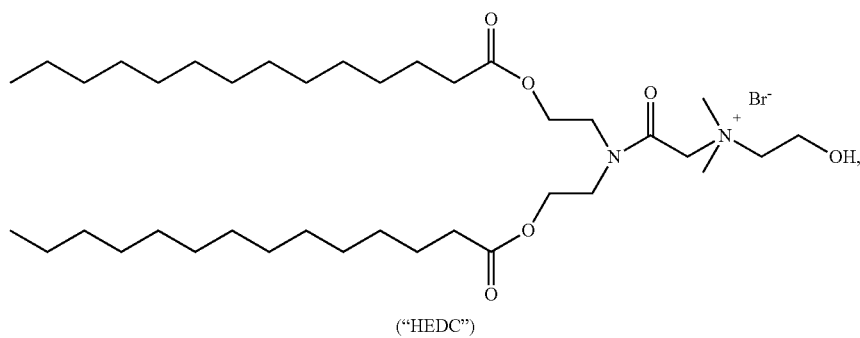

("HEDC")

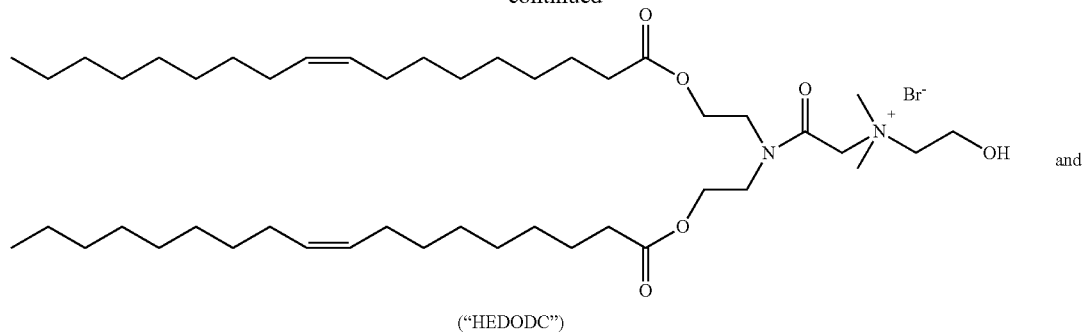

("HEDODC")

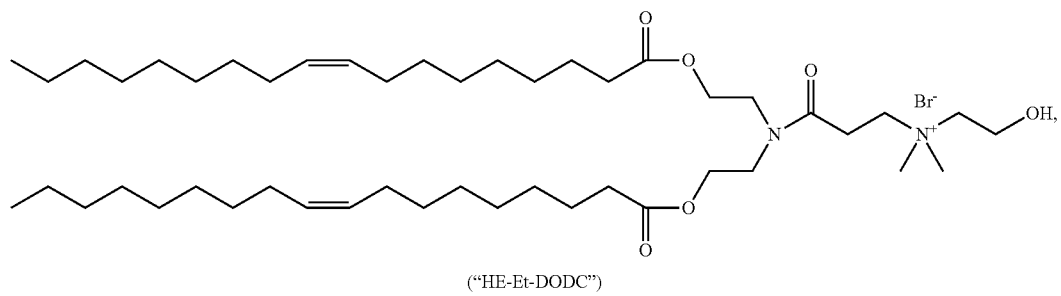

("HE-Et-DODC")

WO2013/093648 also provides examples of other cationic charged lipids at physiological pH including N,N-dioleyl-N,N-dimethylammonium chloride (DODAC), N,N-distearyl-N,N-dimethylammonium bromide (DDAB); N-(1,2-dimyristyloxyprop-3-yl)-N,N-dimethyl-N-hydroxyethylammonium bromide (DMRIE) and dioctadecylamidoglycyl carboxyspermidine (DOGS);in US 20160257951, which provides cationic lipids with a general formula

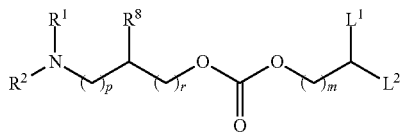

or a pharmacologically acceptable salt thereof, wherein $R^1$ and $R^2$ are each independently a hydrogen atom, a $C_1$-$C_6$ alkyl group optionally substituted with one or more substituents selected from substituent group a, a $C_2$-$C_6$ alkenyl group optionally substituted with one or more substituents selected from substituent group a, a $C_2$-$C_6$ alkynyl group optionally substituted with one or more substituents selected from substituent group a, or a $C_3$-$C_7$ cycloalkyl group optionally substituted with one or more substituents selected from substituent group α, or $R^1$ and $R^2$ form a 3- to 10-membered heterocyclic ring together with the nitrogen atom bonded thereto, wherein the heterocyclic ring is optionally substituted with one or more substituents selected from substituent group a and optionally contains one or more atoms selected from a nitrogen atom, an oxygen atom, and a sulfur atom, in addition to the nitrogen atom bonded to $R^1$ and $R^2$, as atoms constituting the heterocyclic ring; $R^8$ is a hydrogen atom or a $C_1$-$C_6$ alkyl group optionally substituted with one or more substituents selected from substituent group α; or $R^1$ and $R^8$ together are the group —$(CH_2)_q$—; substituent group a consists of a halogen atom, an oxo group, a hydroxy group, a sulfanyl group, an amino group, a cyano group, a $C_1$-$C_6$ alkyl group, a $C_1$-$C_6$ halogenated alkyl group, a C1-C6 alkoxy group, a $C_1$-$C_6$ alkylsulfanyl group, a $C_1$-$C_6$ alkylamino group, and a $C_1$-$C_7$ alkanoyl group; $L^1$ is a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, or a ($C_1$-$C_{10}$ alkyl)-$(Q)_k$-($C_1$-$C_{10}$ alkyl) group optionally substituted with one or more substituents selected from substituent group β1; $L^2$ is, independently of $L^1$, a $C_{10}$-$C_{24}$ alkyl group optionally substituted with one or more substituents selected from substituent group β1, a $C_{10}$-$C_{24}$ alkenyl group optionally substituted with one or more substituents selected from substituent group β1, a $C_3$-$C_{24}$ alkynyl group optionally substituted with one or more substituents selected from substituent group β1, a ($C_1$-$C_{10}$ alkyl)-$(Q)_k$-($C_1$-$C_{10}$ alkyl) group optionally substituted with having one or more substituents selected from substituent group β1, a ($C_{10}$-$C_{24}$ alkoxy)methyl group optionally substituted with one or more substituents selected from substituent group β1, a ($C_{10}$-$C_{24}$ alkenyl)oxymethyl group optionally substituted with one or more substituents selected from substituent group β1, a ($C_3$-$C_{24}$ alkynyl) oxymethyl group optionally substituted with one or more substituents selected from substituent group β1, or a ($C_1$-$C_{10}$ alkyl)-$(Q)_k$-($C_1$-$C_{10}$ alkoxy)methyl group optionally substituted with one or more substituents selected from substituent group β1; substituent group β1 consists of a halogen atom, an oxo group, a cyano group, a $C_1$-$C_6$ alkyl group, a $C_1$-$C_6$ halogenated alkyl group, a $C_1$-$C_6$ alkoxy group, a $C_1$-$C_6$ alkylsulfanyl group, a $C_1$-$C_7$ alkanoyl group, a $C_1$-$C_7$ alkanoyloxy group, a $C_3$-$C_7$ alkoxyalkoxy group, a ($C_1$-$C_6$ alkoxy)carbonyl group, a ($C_1$-$C_6$ alkoxy)carboxyl group, a ($C_1$-$C_6$ alkoxy)carbamoyl group, and a ($C_1$-$C_6$ alkylamino) carboxyl group; Q is a group of formula:

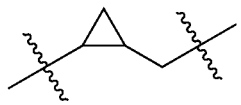 [SMILES: *CC1CC1*]

when $L^1$ and $L^2$ are each substituted with one or more substituents selected from substituent group β1 and substituent group β1 is a $C_1$-$C_6$ alkyl group, a $C_1$-$C_6$ alkoxy group, a $C_1$-$C_6$ alkylsulfanyl group, a $C_1$-$C_7$ alkanoyl group, or a $C_1$-$C_7$ alkanoyloxy group, the substituent or substituents selected from substituent group β1 in $L^1$ and the substituent or substituents selected from substituent group β1 in $L^2$ optionally bind to each other to form a cyclic structure; k is 1, 2, 3, 4, 5, 6, or 7; m is 0 or 1; p is 0, 1, or 2; q is 1, 2, 3, or 4; and r is 0, 1, 2, or 3, provided that p+r is 2 or larger, or q+r is 2 or larger, and specific cationic lipids including

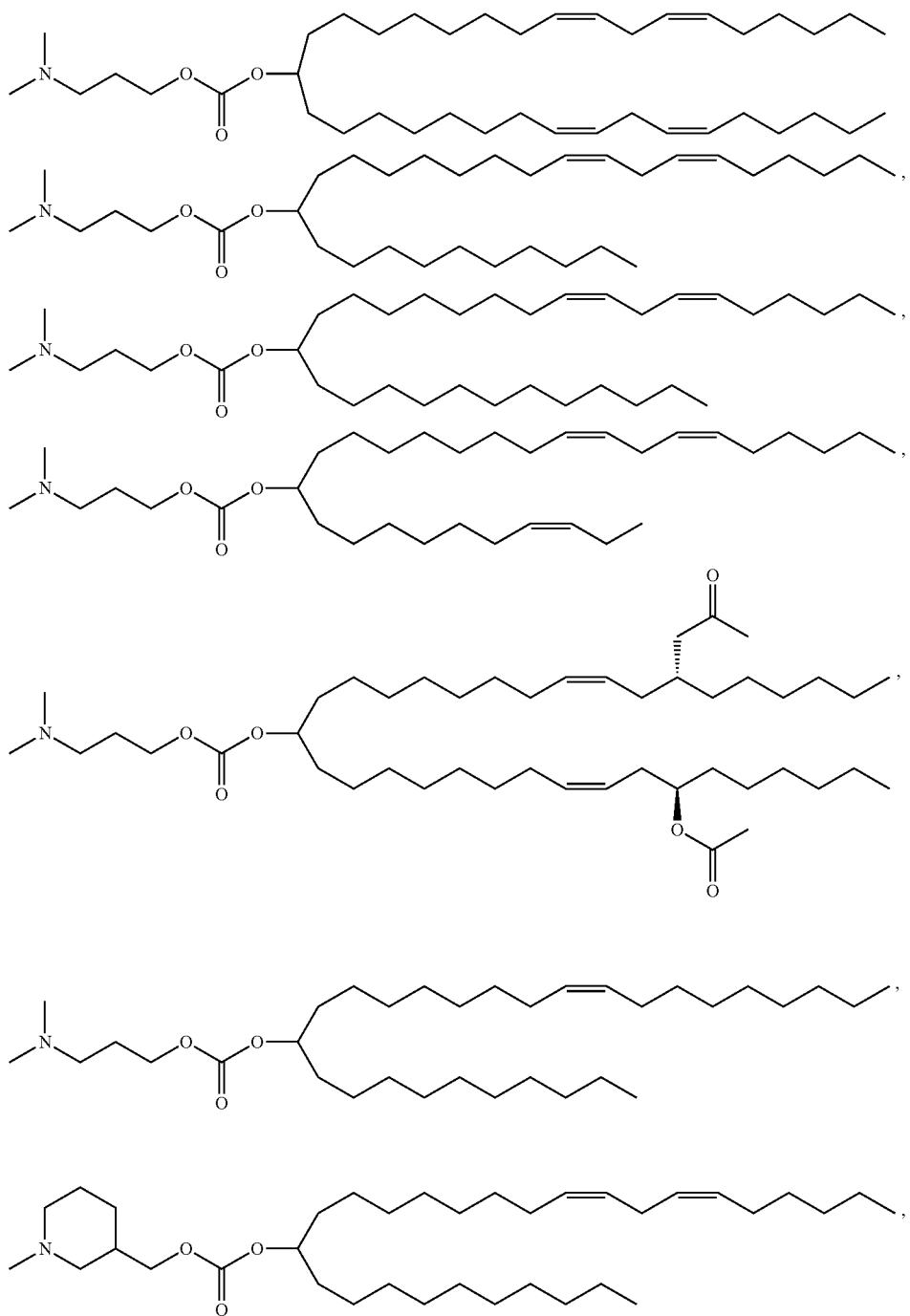

-continued

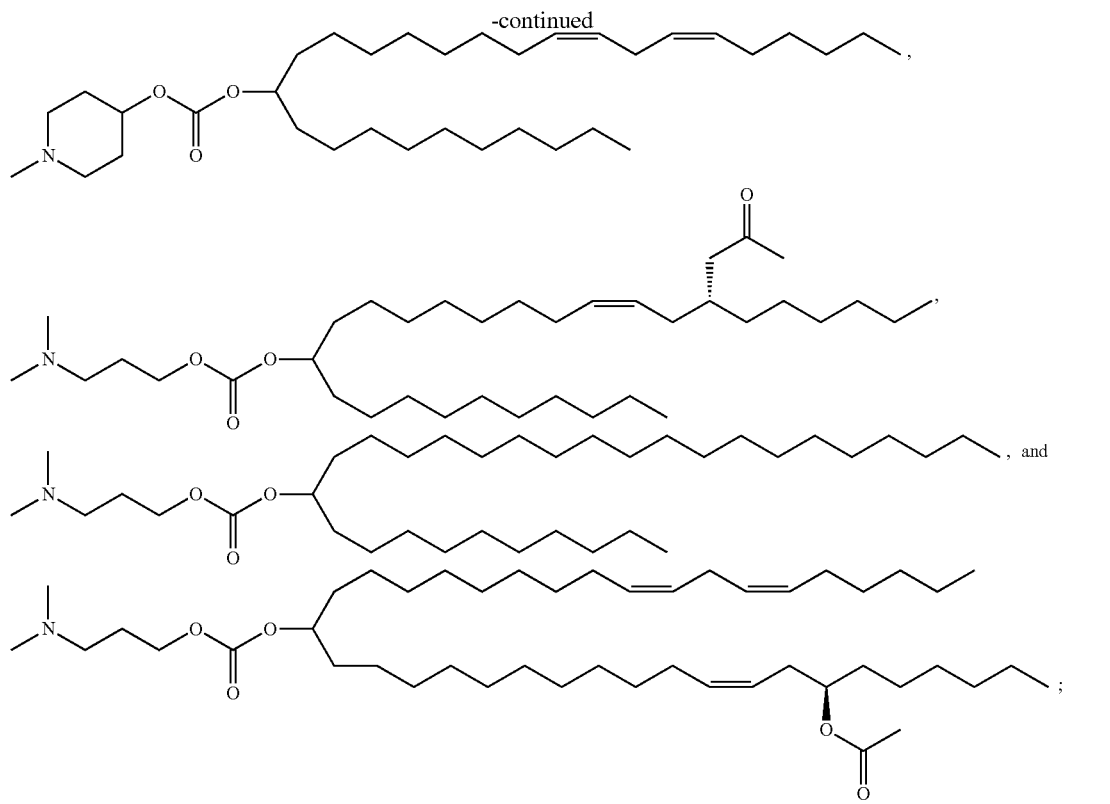

and in US 20160244761, which provides cationic lipids that include 1,2-distearyloxy-N,N-dimethyl-3-aminopropane (DSDMA), 1,2- dioleoyloxy-N,N-dimethyl-3-aminopropane (DODMA), 1,2-dilinoleyloxy-N,N-dimethyl-3-aminopropane (DLinDMA), 1,2-dilinolenyloxy-N,N-dimethyl-3-aminopropane (DLenDMA), 1,2-di-.gamma.-linolenyloxy-N,N-dimethylaminopropane (.gamma.-DLenDMA), 1,2-dilinoleyloxy-keto-N,N-dimethyl-3-aminopropane (DLin-K-DMA), 1,2-dilinoleyl-4-(2-dimethylaminoethyl)-[1,3]-dioxolane (DLin-K—C2-DMA) (also known as DLin-C2K-DMA, XTC2, and C2K), 2,2-dilinoleyl-4-(3-dimethylaminopropyl)-[1,3]-dioxolane (DLin-K-C3-DMA), 2,2-dilinoleyl-4-(4-dimethylaminobutyl)-[1,3]-dioxolane (DLin-K—C4-DMA), 1,2-dilinolenyloxy-4-(2-dimethylaminoethyl)-[1,3]-dioxolane (DLen-C2K-DMA), 1,2-di-.gamma.-linolenyloxy-4-(2-dimethylaminoethyl)-[1,3]-dioxolane (.gamma.-DLen-C2K-DMA), dilinoleylmethyl-3-dimethylaminopropionate (DLin-M-C2-DMA) (also known as MC2), (6Z,9Z,28Z,31Z)-heptatriaconta-6,9,28,31-tetraen-19-yl 4-(dimethylamino) butanoate (DLin-M-C3-DMA) (also known as MC3) and 3-(dilinoleylmethoxy)-N,N-dimethylpropan-1-amine (DLin-MP-DMA) (also known as 1-Bl 1).

In one embodiment, the lipid compound is preferably a bio-reducible material, e.g., a bio-reducible polymer and a bio-reducible lipid-like compound.

In embodiment, the lipid compound comprises a hydrophilic head, and a hydrophobic tail, and optionally a linker.

In one embodiment, the hydrophilic head contains one or more hydrophilic functional groups, e.g., hydroxyl, carboxyl, amino, sulfhydryl, phosphate, amide, ester, ether, carbamate, carbonate, carbamide and phosphodiester. These groups can form hydrogen bonds and are optionally positively or negatively charged, in particular at physiological conditions such as physiological pH.

In one embodiment, the hydrophobic tail is a saturated or unsaturated, linear or branched, acyclic or cyclic, aromatic or nonaromatic hydrocarbon moiety, wherein the saturated or unsaturated, linear or branched, acyclic or cyclic, aromatic or nonaromatic hydrocarbon moiety optionally contains a disulfide bond and/or 8-24 carbon atoms. One or more of the carbon atoms can be replaced with a heteroatom, such as N, O, P, B, S, Si, Sb, Al, Sn, As, Se, and Ge. The lipid or lipid-like compounds containing disulfide bond can be bioreducible.

In one embodiment, the linker of the lipid or lipid-like compound links the hydrophilic head and the hydrophobic tail. The linker can be any chemical group that is hydrophilic or hydrophobic, polar or non-polar, e.g., O, S, Si, amino, alkylene, ester, amide, carbamate, carbamide, carbonate phosphate, phosphite, sulfate, sulfite, and thiosulfate.

The lipid or lipid-like compounds described above include the compounds themselves, as well as their salts and solvates, if applicable. A salt, for example, can be formed between an anion and a positively charged group (e.g., amino) on a lipid-like compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a lipid-like compound. Suitable cations include sodium ion, potassium ion, magnesium ion, calcium ion, and an ammonium cation such as tetramethylammonium ion. The lipid-like compounds also include those salts containing quaternary nitrogen atoms. A solvate refers to a complex formed between a lipid-like compound and a pharmaceutically acceptable solvent. Examples of pharmaceutically acceptable solvents include water, ethanol, isopropanol, ethyl acetate, acetic acid, and ethanolamine.

Delivery or administration according to the invention can be performed with liposomes. Liposomes are spherical vesicle structures composed of a uni- or multi-lamellar lipid bilayer surrounding internal aqueous compartments and a relatively impermeable outer lipophilic phospholipid bilayer. Liposomes have gained considerable attention as drug delivery carriers because they are biocompatible, non-toxic, can deliver both hydrophilic and lipophilic drug molecules, protect their cargo from degradation by plasma enzymes, and transport their load across biological membranes and the blood brain barrier (BBB) (see, e.g., Spuch and Navarro, Journal of Drug Delivery, vol. 2011, Article ID 469679, 12 pages, 2011. doi:10.1155/2011/469679 for review).

Liposomes can be made from several different types of lipids; however, phospholipids are most commonly used to generate liposomes as drug carriers. Although liposome formation is spontaneous when a lipid film is mixed with an aqueous solution, it can also be expedited by applying force in the form of shaking by using a homogenizer, sonicator, or an extrusion apparatus (see, e.g., Spuch and Navarro, Journal of Drug Delivery, vol. 2011, Article ID 469679, 12 pages, 2011. doi:10.1155/2011/469679 for review).

Several other additives may be added to liposomes in order to modify their structure and properties. For instance, either cholesterol or sphingomyelin may be added to the liposomal mixture in order to help stabilize the liposomal structure and to prevent the leakage of the liposomal inner cargo. Further, liposomes are prepared from hydrogenated egg phosphatidylcholine or egg phosphatidylcholine, cholesterol, and dicetyl phosphate, and their mean vesicle sizes were adjusted to about 50 and 100 nm. (see, e.g., Spuch and Navarro, Journal of Drug Delivery, vol. 2011, Article ID 469679, 12 pages, 2011. doi:10.1155/2011/469679 for review).

A liposome formulation may be mainly comprised of natural phospholipids and lipids such as 1,2- distearoyl-sn-glycero-3-phosphatidyl choline (DSPC), sphingomyelin, egg phosphatidylcholines and monosialoganglioside. Since this formulation is made up of phospholipids only, liposomal formulations have encountered many challenges, one of the ones being the instability in plasma. Several attempts to overcome these challenges have been made, specifically in the manipulation of the lipid membrane. One of these attempts focused on the manipulation of cholesterol. Addition of cholesterol to conventional formulations reduces rapid release of the encapsulated bioactive compound into the plasma or 1,2-dioleoyl-sn-glycero-3-phosphoethanolamine (DOPE) increases the stability (see, e.g., Spuch and Navarro, Journal of Drug Delivery, vol. 2011, Article ID 469679, 12 pages, 2011. doi:10.1155/2011/469679 for review).

In a particularly advantageous embodiment, Trojan Horse liposomes (also known as Molecular Trojan Horses) are desirable and protocols may be found at cshprotocols.cshlp.org/content/2010/4/pdb.prot5407.long. These particles allow delivery of a transgene to the entire brain after an intravascular injection. Without being bound by limitation, it is believed that neutral lipid particles with specific antibodies conjugated to surface allow crossing of the blood brain barrier via endocytosis. Applicant postulates utilizing Trojan Horse Liposomes to deliver the CRISPR family of nucleases to the brain via an intravascular injection, which would allow whole brain transgenic animals without the need for embryonic manipulation. About 1-5 g of DNA or RNA may be contemplated for in vivo administration in liposomes.

In another embodiment, the CRISPR-Cas system or components thereof may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of a specific CRISPR-Cas targeted in a SNALP are contemplated. The daily treatment may be over about three days and then weekly for about five weeks. In another embodiment, a specific CRISPR-Cas encapsulated SNALP) administered by intravenous injection to at doses of about 1 or 2.5 mg/kg are also contemplated (see, e.g., Zimmerman et al., Nature Letters, Vol. 441, 4 May 2006). The SNALP formulation may contain the lipids 3-N-[(methoxypoly(ethylene glycol) 2000) carbamoyl]-1,2-dimyristyloxy-propylamine (PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar percent ratio (see, e.g., Zimmerman et al., Nature Letters, Vol. 441, 4 May 2006).

In another embodiment, stable nucleic-acid-lipid particles (SNALPs) have proven to be effective delivery molecules to highly vascularized HepG2-derived liver tumors but not in poorly vascularized HCT-116 derived liver tumors (see, e.g., Li, Gene Therapy (2012) 19, 775-780). The SNALP liposomes may be prepared by formulating D-Lin-DMA and PEG-C-DMA with distearoylphosphatidylcholine (DSPC), Cholesterol and siRNA using a 25:1 lipid/siRNA ratio and a 48/40/10/2 molar ratio of Cholesterol/D-Lin-DMA/DSPC/PEG-C-DMA. The resulted SNALP liposomes are about 80-100 nm in size.

In yet another embodiment, a SNALP may comprise synthetic cholesterol (Sigma-Aldrich, St Louis, Mo., USA), dipalmitoylphosphatidylcholine (Avanti Polar Lipids, Alabaster, Ala., USA), 3-N-1(methoxy poly(ethylene glycol) 2000)carbamoyl]-1,2-dimyrestyloxypropylamine, and cationic 1,2-dilinoleyloxy-3-N,N-dimethylaminopropane (see, e.g., Geisbert et al., Lancet 2010; 375: 1896-905). A dosage of about 2 mg/kg total CRISPR-Cas per dose administered as, for example, a bolus intravenous infusion may be contemplated.

In yet another embodiment, a SNALP may comprise synthetic cholesterol (Sigma-Aldrich), 1,2-distearoyl-sn-glycero-3-phosphocholine (DSPC; Avanti Polar Lipids Inc.), PEG-cDMA, and 1,2-dilinoleyloxy-3-(N,N-dimethyl)aminopropane (DLinDMA) (see, e.g., Judge, J. Clin. Invest. 119:661-673 (2009)). Formulations used for in vivo studies may comprise a final lipid/RNA mass ratio of about 9:1.

The safety profile of RNAi nanomedicines has been reviewed by Barros and Gollob of Alnylam Pharmaceuticals (see, e.g., Advanced Drug Delivery Reviews 64 (2012) 1730-1737). The stable nucleic acid lipid particle (SNALP) is comprised of four different lipids—an ionizable lipid (DLinDMA) that is cationic at low pH, a neutral helper lipid, cholesterol, and a diffusible polyethylene glycol (PEG)-lipid. The particle is approximately 80 nm in diameter and is charge-neutral at physiologic pH. During formulation, the ionizable lipid serves to condense lipid with the anionic RNA during particle formation. When positively charged under increasingly acidic endosomal conditions, the ionizable lipid also mediates the fusion of SNALP with the endosomal membrane enabling release of RNA into the cytoplasm. The PEG-lipid stabilizes the particle and reduces aggregation during formulation, and subsequently provides a neutral hydrophilic exterior that improves pharmacokinetic properties.

To date, two clinical programs have been initiated using SNALP formulations with RNA. Tekmira Pharmaceuticals recently completed a phase I single-dose study of SNALP-ApoB in adult volunteers with elevated LDL cholesterol. ApoB is predominantly expressed in the liver and jejunum and is essential for the assembly and secretion of VLDL and LDL. Seventeen subjects received a single dose of SNALP-ApoB (dose escalation across 7 dose levels). There was no evidence of liver toxicity (anticipated as the potential dose-limiting toxicity based on preclinical studies). One (of two) subjects at the highest dose experienced flu-like symptoms consistent with immune system stimulation, and the decision was made to conclude the trial.

Alnylam Pharmaceuticals has similarly advanced ALN-TTR01, which employs the SNALP technology described above and targets hepatocyte production of both mutant and wild-type TTR to treat TTR amyloidosis (ATTR). Three ATTR syndromes have been described: familial amyloidotic polyneuropathy (FAP) and familial amyloidotic cardiomyopathy (FAC)—both caused by autosomal dominant mutations in TTR; and senile systemic amyloidosis (SSA) cause by wildtype TTR. A placebo-controlled, single dose-escalation phase I trial of ALN-TTR01 was recently completed in patients with ATTR. ALN-TTR01 was administered as a 15-minute IV infusion to 31 patients (23 with study drug and 8 with placebo) within a dose range of 0.01 to 1.0 mg/kg (based on siRNA). Treatment was well tolerated with no significant increases in liver function tests. Infusion-related reactions were noted in 3 of 23 patients at≥0.4 mg/kg; all responded to slowing of the infusion rate and all continued on study. Minimal and transient elevations of serum cytokines IL-6, IP-10 and IL-1ra were noted in two patients at the highest dose of 1 mg/kg (as anticipated from preclinical and NHP studies). Lowering of serum TTR, the expected pharmacodynamics effect of ALN-TTR01, was observed at 1 mg/kg.

In yet another embodiment, a SNALP may be made by solubilizing a cationic lipid, DSPC, cholesterol and PEG-lipid e.g., in ethanol, e.g., at a molar ratio of 40:10:40:10, respectively (see, Semple et al., Nature Biotechnology, Volume 28 Number 2 Feb. 2010, pp. 172-177). The lipid mixture was added to an aqueous buffer (50 mM citrate, pH 4) with mixing to a final ethanol and lipid concentration of 30% (vol/vol) and 6.1 mg/ml, respectively, and allowed to equilibrate at 22° C. for 2 min before extrusion. The hydrated lipids were extruded through two stacked 80 nm pore-sized filters (Nuclepore) at 22° C. using a Lipex Extruder (Northern Lipids) until a vesicle diameter of 70-90 nm, as determined by dynamic light scattering analysis, was obtained. This generally required 1-3 passes. The siRNA (solubilized in a 50 mM citrate, pH 4 aqueous solution containing 30% ethanol) was added to the pre-equilibrated (35° C.) vesicles at a rate of ~5 ml/min with mixing. After a final target siRNA/lipid ratio of 0.06 (wt/wt) was reached, the mixture was incubated for a further 30 min at 35° C. to allow vesicle reorganization and encapsulation of the siRNA. The ethanol was then removed and the external buffer replaced with PBS (155 mM NaCl, 3 mM $Na_2HPO_4$, 1 mM $KH_2PO_4$, pH 7.5) by either dialysis or tangential flow diafiltration. siRNA were encapsulated in SNALP using a controlled step-wise dilution method process. The lipid constituents of KC2-SNALP were DLin-KC2-DMA (cationic lipid), dipalmitoylphosphatidylcholine (DPPC; Avanti Polar Lipids), synthetic cholesterol (Sigma) and PEG-DMA used at a molar ratio of 57.1:7.1:34.3:1.4. Upon formation of the loaded particles, SNALP were dialyzed against PBS and filter sterilized through a 0.2 µm filter before use. Mean particle sizes were 75-85 nm and 90-95% of the siRNA was encapsulated within the lipid particles. The final siRNA/lipid ratio in formulations used for in vivo testing was ~0.15 (wt/wt). LNP-siRNA systems containing Factor VII siRNA were diluted to the appropriate concentrations in sterile PBS immediately before use and the formulations were administered intravenously through the lateral tail vein in a total volume of 10 ml/kg. This method and these delivery systems may be extrapolated to the CRISPR-Cas system of the present invention.

Other Lipids

Other cationic lipids, such as amino lipid 2,2-dilinoleyl-4-dimethylaminoethyl-[1,3]-dioxolane (DLin-KC2-DMA) may be utilized to encapsulate CRISPR-Cas or components thereof or nucleic acid molecule(s) coding therefor e.g., similar to SiRNA (see, e.g., Jayaraman, Angew. Chem. Int. Ed. 2012, 51, 8529-8533), and hence may be employed in the practice of the invention. A preformed vesicle with the following lipid composition may be contemplated: amino lipid, distearoylphosphatidylcholine (DSPC), cholesterol and (R)-2,3-bis(octadecyloxy) propyl-1-(methoxy poly(ethylene glycol)2000)propylcarbamate (PEG-lipid) in the molar ratio 40/10/40/10, respectively, and a FVII siRNA/total lipid ratio of approximately 0.05 (w/w). To ensure a narrow particle size distribution in the range of 70-90 nm and a low polydispersity index of 0.11+0.04 (n=56), the particles may be extruded up to three times through 80 nm membranes prior to adding the guide RNA. Particles containing the highly potent amino lipid 16 may be used, in which the molar ratio of the four lipid components 16, DSPC, cholesterol and PEG-lipid (50/10/38.5/1.5) which may be further optimized to enhance in vivo activity.

Michael S D Kormann et al. ("Expression of therapeutic proteins after delivery of chemically modified mRNA in mice: Nature Biotechnology, Volume:29, Pages: 154-157 (2011)) describes the use of lipid envelopes to deliver RNA. Use of lipid envelopes is also preferred in the present invention.

In another embodiment, lipids may be formulated with the CRISPR-Cas system of the present invention or component (s) thereof or nucleic acid molecule(s) coding therefor to form lipid nanoparticles (LNPs). Lipids include, but are not limited to, DLin-KC2-DMA4, C12-200 and colipids disteroylphosphatidyl choline, cholesterol, and PEG-DMG may be formulated with CRISPR-Cas instead of siRNA (see, e.g., Novobrantseva, Molecular Therapy—Nucleic Acids (2012) 1, e4; doi:10.1038/mtna.2011.3) using a spontaneous vesicle formation procedure. The component molar ratio may be about 50/10/38.5/1.5 (DLin-KC2-DMA or C12-200/ disteroylphosphatidyl choline/cholesterol/PEG-DMG). The final lipid:siRNA weight ratio may be ~12:1 and 9:1 in the case of DLin-KC2-DMA and C12-200 lipid nanoparticles (LNPs), respectively. The formulations may have mean particle diameters of ~80 nm with >90% entrapment efficiency. A 3 mg/kg dose may be contemplated.

Tekmira has a portfolio of approximately 95 patent families, in the U.S. and abroad, that are directed to various aspects of LNPs and LNP formulations (see, e.g., U.S. Pat. Nos. 7,982,027; 7,799,565; 8,058,069; 8,283,333; 7,901,708; 7,745,651; 7,803,397; 8,101,741; 8,188,263; 7,915,399; 8,236,943 and 7,838,658 and European Pat. Nos 1766035; 1519714; 1781593 and 1664316), all of which may be used and/or adapted to the present invention.

The CRISPR-Cas system or components thereof or nucleic acid molecule(s) coding therefor may be delivered encapsulated in PLGA Microspheres such as that further described in US published applications 20130252281 and 20130245107 and 20130244279 (assigned to Moderna Therapeutics) which relate to aspects of formulation of compositions comprising modified nucleic acid molecules which may encode a protein, a protein precursor, or a partially or fully processed form of the protein or a protein precursor. The formulation may have a molar ratio 50:10:38.5:1.5-3.0 (cationic lipid:fusogenic lipid:cholesterol:PEG lipid). The PEG lipid may be selected from, but is not limited to PEG-c-DOMG, PEG-DMG. The fusogenic lipid may be DSPC. See also, Schrum et al., Delivery and Formulation of Engineered Nucleic Acids, US published application 20120251618.

Nanomerics' technology addresses bioavailability challenges for a broad range of therapeutics, including low molecular weight hydrophobic drugs, peptides, and nucleic acid based therapeutics (plasmid, siRNA, miRNA). Specific administration routes for which the technology has demonstrated clear advantages include the oral route, transport across the blood-brain-barrier, delivery to solid tumours, as well as to the eye. See, e.g., Mazza et al., 2013, ACS Nano. 2013 Feb. 26; 7(2):1016-26; Uchegbu and Siew, 2013, J Pharm Sci. 102(2):305-10 and Lalatsa et al., 2012, J Control Release. 2012 Jul. 20; 161(2):523-36.

US Patent Publication No. 20050019923 describes cationic dendrimers for delivering bioactive molecules, such as polynucleotide molecules, peptides and polypeptides and/or pharmaceutical agents, to a mammalian body. The dendrimers are suitable for targeting the delivery of the bioactive molecules to, for example, the liver, spleen, lung, kidney or heart (or even the brain). Dendrimers are synthetic 3-dimensional macromolecules that are prepared in a step-wise fashion from simple branched monomer units, the nature and functionality of which can be easily controlled and varied. Dendrimers are synthesised from the repeated addition of building blocks to a multifunctional core (divergent approach to synthesis), or towards a multifunctional core (convergent approach to synthesis) and each addition of a 3-dimensional shell of building blocks leads to the formation of a higher generation of the dendrimers. Polypropylenimine dendrimers start from a diaminobutane core to which is added twice the number of amino groups by a double Michael addition of acrylonitrile to the primary amines followed by the hydrogenation of the nitriles. This results in a doubling of the amino groups. Polypropylenimine dendrimers contain 100% protonable nitrogens and up to 64 terminal amino groups (generation 5, DAB 64). Protonable groups are usually amine groups which are able to accept protons at neutral pH. The use of dendrimers as gene delivery agents has largely focused on the use of the polyamidoamine, and phosphorous containing compounds with a mixture of amine/amide or N—P($O_2$)S as the conjugating units respectively with no work being reported on the use of the lower generation polypropylenimine dendrimers for gene delivery. Polypropylenimine dendrimers have also been studied as pH sensitive controlled release systems for drug delivery and for their encapsulation of guest molecules when chemically modified by peripheral amino acid groups. The cytotoxicity and interaction of polypropylenimine dendrimers with DNA as well as the transfection efficacy of DAB 64 has also been studied.

US Patent Publication No. 20050019923 is based upon the observation that, contrary to earlier reports, cationic dendrimers, such as polypropylenimine dendrimers, display suitable properties, such as specific targeting and low toxicity, for use in the targeted delivery of bioactive molecules, such as genetic material. In addition, derivatives of the cationic dendrimer also display suitable properties for the targeted delivery of bioactive molecules. See also, Bioactive Polymers, US published application 20080267903, which discloses "Various polymers, including cationic polyamine polymers and dendrimeric polymers, are shown to possess anti-proliferative activity, and may therefore be useful for treatment of disorders characterised by undesirable cellular proliferation such as neoplasms and tumours, inflammatory disorders (including autoimmune disorders), psoriasis and atherosclerosis. The polymers may be used alone as active agents, or as delivery vehicles for other therapeutic agents, such as drug molecules or nucleic acids for gene therapy. In such cases, the polymers' own intrinsic anti-tumour activity may complement the activity of the agent to be delivered." The disclosures of these patent publications may be employed in conjunction with herein teachings for delivery of CRISPR-Cas system(s) or component(s) thereof or nucleic acid molecule(s) coding therefor.

Supercharged Proteins

Supercharged proteins are a class of engineered or naturally occurring proteins with unusually high positive or negative net theoretical charge and may be employed in delivery of CRISPR-Cas system(s) or component(s) thereof or nucleic acid molecule(s) coding therefor. Both supernegatively and superpositively charged proteins exhibit a remarkable ability to withstand thermally or chemically induced aggregation. Superpositively charged proteins are also able to penetrate mammalian cells. Associating cargo with these proteins, such as plasmid DNA, RNA, or other proteins, can enable the functional delivery of these macromolecules into mammalian cells both in vitro and in vivo. David Liu's lab reported the creation and characterization of supercharged proteins in 2007 (Lawrence et al., 2007, Journal of the American Chemical Society 129, 10110-10112).

The nonviral delivery of RNA and plasmid DNA into mammalian cells are valuable both for research and therapeutic applications (Akinc et al., 2010, Nat. Biotech. 26, 561-569). Purified +36 GFP protein (or other superpositively charged protein) is mixed with RNAs in the appropriate serum-free media and allowed to complex prior addition to cells. Inclusion of serum at this stage inhibits formation of the supercharged protein-RNA complexes and reduces the effectiveness of the treatment. The following protocol has been found to be effective for a variety of cell lines (McNaughton et al., 2009, Proc. Natl. Acad. Sci. USA 106, 6111-6116) (However, pilot experiments varying the dose of protein and RNA should be performed to optimize the procedure for specific cell lines):

(1) One day before treatment, plate $1 \times 10^5$ cells per well in a 48-well plate.
(2) On the day of treatment, dilute purified +36 GFP protein in serumfree media to a final concentration 200 nm. Add RNA to a final concentration of 50 nm. Vortex to mix and incubate at room temperature for 10 min.
(3) During incubation, aspirate media from cells and wash once with PBS.
(4) Following incubation of +36 GFP and RNA, add the protein-RNA complexes to cells.
(5) Incubate cells with complexes at 37° C. for 4h.
(6) Following incubation, aspirate the media and wash three times with 20 U/mL heparin PBS. Incubate cells with serum-containing media for a further 48h or longer depending upon the assay for activity.
(7) Analyze cells by immunoblot, qPCR, phenotypic assay, or other appropriate method.

David Liu's lab has further found +36 GFP to be an effective plasmid delivery reagent in a range of cells. As plasmid DNA is a larger cargo than siRNA, proportionately more +36 GFP protein is required to effectively complex plasmids. For effective plasmid delivery Applicants have developed a variant of +36 GFP bearing a C-terminal HA2 peptide tag, a known endosome-disrupting peptide derived from the influenza virus hemagglutinin protein. The following protocol has been effective in a variety of cells, but as above it is advised that plasmid DNA and supercharged protein doses be optimized for specific cell lines and delivery applications:

(1) One day before treatment, plate $1 \times 10^5$ per well in a 48-well plate. (2) On the day of treatment, dilute purified þ 36 GFP protein in serumfree media to a final concentration 2 mM. Add 1 mg of plasmid DNA. Vortex to mix and incubate at room temperature for 10 min.
(3) During incubation, aspirate media from cells and wash once with PBS.
(4) Following incubation of þ 36 GFP and plasmid DNA, gently add the protein-DNA complexes to cells.
(5) Incubate cells with complexes at 37 C for 4h.
(6) Following incubation, aspirate the media and wash with PBS. Incubate cells in serum-containing media and incubate for a further 24-48h.
(7) Analyze plasmid delivery (e.g., by plasmid-driven gene expression) as appropriate.

See also, e.g., McNaughton et al., Proc. Natl. Acad. Sci. USA 106, 6111-6116 (2009); Cronican et al., ACS Chemical Biology 5, 747-752 (2010); Cronican et al., Chemistry & Biology 18, 833-838 (2011); Thompson et al., Methods in Enzymology 503, 293-319 (2012); Thompson, D. B., et al., Chemistry & Biology 19 (7), 831-843 (2012). The methods of the super charged proteins may be used and/or adapted for delivery of the CRISPR-Cas system of the present invention. These systems of Dr. Lui and documents herein in conjunction with herein teaching can be employed in the delivery of CRISPR-Cas system(s) or component(s) thereof or nucleic acid molecule(s) coding therefor.

Cell Penetrating Peptides (CPPs)

In yet another embodiment, cell penetrating peptides (CPPs) are contemplated for the delivery of the CRISPR-Cas system. CPPs are short peptides that facilitate cellular uptake of various molecular cargo (from nanosize particles to small chemical molecules and large fragments of DNA). The term "cargo" as used herein includes but is not limited to the group consisting of therapeutic agents, diagnostic probes, peptides, nucleic acids, antisense oligonucleotides, plasmids, proteins, particles, including nanoparticles, liposomes, chromophores, small molecules and radioactive materials. In aspects of the invention, the cargo may also comprise any component of the CRISPR-Cas system or the entire functional CRISPR-Cas system. Aspects of the present invention further provide methods for delivering a desired cargo into a subject comprising: (a) preparing a complex comprising the cell penetrating peptide of the present invention and a desired cargo, and (b) orally, intraarticularly, intraperitoneally, intrathecally, intraarterially, intranasally, intraparenchymally, subcutaneously, intramuscularly, intravenously, dermally, intrarectally, or topically administering the complex to a subject. The cargo is associated with the peptides either through chemical linkage via covalent bonds or through non-covalent interactions.

The function of the CPPs are to deliver the cargo into cells, a process that commonly occurs through endocytosis with the cargo delivered to the endosomes of living mammalian cells. Cell-penetrating peptides are of different sizes, amino acid sequences, and charges but all CPPs have one distinct characteristic, which is the ability to translocate the plasma membrane and facilitate the delivery of various molecular cargoes to the cytoplasm or an organelle. CPP translocation may be classified into three main entry mechanisms: direct penetration in the membrane, endocytosis-mediated entry, and translocation through the formation of a transitory structure. CPPs have found numerous applications in medicine as drug delivery agents in the treatment of different diseases including cancer and virus inhibitors, as well as contrast agents for cell labeling. Examples of the latter include acting as a carrier for GFP, MRI contrast agents, or quantum dots. CPPs hold great potential as in vitro and in vivo delivery vectors for use in research and medicine. CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPPs are the hydrophobic peptides, containing only apolar residues, with low net charge or have hydrophobic amino acid groups that are crucial for cellular uptake. One of the initial CPPs discovered was the trans-activating transcriptional activator (Tat) from Human Immunodeficiency Virus 1 (HIV-1) which was found to be efficiently taken up from the surrounding media by numerous cell types in culture. Since then, the number of known CPPs has expanded considerably and small molecule synthetic analogues with more effective protein transduction properties have been generated. CPPs include but are not limited to Penetratin, Tat (48-60), Transportan, and (R-AhX-R4) (Ahx=aminohexanoyl).

U.S. Pat. No. 8,372,951, provides a CPP derived from eosinophil cationic protein (ECP) which exhibits highly cell-penetrating efficiency and low toxicity. Aspects of delivering the CPP with its cargo into a vertebrate subject are also provided. Further aspects of CPPs and their delivery are described in U.S. Pat. Nos. 8,575,305; 8,614,194 and 8,044,019. CPPs can be used to deliver the CRISPR-Cas system or components thereof That CPPs can be employed to deliver the CRISPR-Cas system or components thereof is also provided in the manuscript "Gene disruption by cell-penetrating peptide-mediated delivery of Cas9 protein and guide RNA", by Suresh Ramakrishna, Abu-Bonsrah Kwaku Dad, Jagadish Beloor, et al. Genome Res. 2014 Apr. 2. [Epub ahead of print], incorporated by reference in its entirety, wherein it is demonstrated that treatment with CPP-conjugated recombinant Cas9 protein and CPP-complexed guide RNAs lead to endogenous gene disruptions in human cell lines. In the paper the Cas9 protein was conjugated to CPP via a thioether bond, whereas the guide RNA was complexed with CPP, forming condensed, positively charged particles. It was shown that simultaneous and sequential treatment of human cells, including embryonic stem cells, dermal fibroblasts, HEK293T cells, HeLa cells, and embryonic carcinoma cells, with the modified Cas9 and guide RNA led to efficient gene disruptions with reduced off-target mutations relative to plasmid transfections.

Implantable Devices

In another embodiment, implantable devices are also contemplated for delivery of the CRISPR-Cas system or component(s) thereof or nucleic acid molecule(s) coding therefor. For example, US Patent Publication 20110195123 discloses an implantable medical device which elutes a drug locally and in prolonged period is provided, including several types of such a device, the treatment modes of implementation and methods of implantation. The device comprising of polymeric substrate, such as a matrix for example, that is used as the device body, and drugs, and in some cases additional scaffolding materials, such as metals or additional polymers, and materials to enhance visibility and imaging. An implantable delivery device can be advantageous in providing release locally and over a prolonged period, where drug is released directly to the extracellular matrix (ECM) of the diseased area such as tumor, inflammation, degeneration or for symptomatic objectives, or to injured smooth muscle cells, or for prevention. One kind of drug is RNA, as disclosed above, and this system may be used/and or adapted to the CRISPR-Cas system of the present invention. The modes of implantation in some embodiments are existing implantation procedures that are developed and used today for other treatments, including brachytherapy and needle biopsy. In such cases the dimensions of the new implant described in this invention are similar to the original implant. Typically a few devices are implanted during the same treatment procedure.

US Patent Publication 20110195123, provides a drug delivery implantable or insertable system, including systems applicable to a cavity such as the abdominal cavity and/or any other type of administration in which the drug delivery system is not anchored or attached, comprising a biostable and/or degradable and/or bioabsorbable polymeric substrate, which may for example optionally be a matrix. It should be noted that the term "insertion" also includes implantation. The drug delivery system is preferably implemented as a "Loder" as described in US Patent Publication 20110195123.

The polymer or plurality of polymers are biocompatible, incorporating an agent and/or plurality of agents, enabling the release of agent at a controlled rate, wherein the total volume of the polymeric substrate, such as a matrix for example, in some embodiments is optionally and preferably no greater than a maximum volume that permits a therapeutic level of the agent to be reached. As a non-limiting example, such a volume is preferably within the range of 0.1 m$^3$ to 1000 mM$^3$, as required by the volume for the agent load. The Loder may optionally be larger, for example when incorporated with a device whose size is determined by functionality, for example and without limitation, a knee joint, an intra-uterine or cervical ring and the like.

The drug delivery system (for delivering the composition) is designed in some embodiments to preferably employ degradable polymers, wherein the main release mechanism is bulk erosion; or in some embodiments, non degradable, or slowly degraded polymers are used, wherein the main release mechanism is diffusion rather than bulk erosion, so that the outer part functions as membrane, and its internal part functions as a drug reservoir, which practically is not affected by the surroundings for an extended period (for example from about a week to about a few months). Combinations of different polymers with different release mechanisms may also optionally be used. The concentration gradient at the surface is preferably maintained effectively constant during a significant period of the total drug releasing period, and therefore the diffusion rate is effectively constant (termed "zero mode" diffusion). By the term "constant" it is meant a diffusion rate that is preferably maintained above the lower threshold of therapeutic effectiveness, but which may still optionally feature an initial burst and/or may fluctuate, for example increasing and decreasing to a certain degree. The diffusion rate is preferably so maintained for a prolonged period, and it can be considered constant to a certain level to optimize the therapeutically effective period, for example the effective silencing period.

The drug delivery system optionally and preferably is designed to shield the nucleotide based therapeutic agent from degradation, whether chemical in nature or due to attack from enzymes and other factors in the body of the subject.

The drug delivery system of US Patent Publication 20110195123 is optionally associated with sensing and/or activation appliances that are operated at and/or after implantation of the device, by non and/or minimally invasive methods of activation and/or acceleration/deceleration, for example optionally including but not limited to thermal heating and cooling, laser beams, and ultrasonic, including focused ultrasound and/or RF (radiofrequency) methods or devices.

According to some embodiments of US Patent Publication 20110195123, the site for local delivery may optionally include target sites characterized by high abnormal proliferation of cells, and suppressed apoptosis, including tumors, active and/or chronic inflammation and infection including autoimmune diseases states, degenerating tissue including muscle and nervous tissue, chronic pain, degenerative sites, and location of bone fractures and other wound locations for enhancement of regeneration of tissue, and injured cardiac, smooth and striated muscle.

The site for implantation of the composition, or target site, preferably features a radius, area and/or volume that is sufficiently small for targeted local delivery. For example, the target site optionally has a diameter in a range of from about 0.1 mM to about 5 cm.

The location of the target site is preferably selected for maximum therapeutic efficacy. For example, the composition of the drug delivery system (optionally with a device for implantation as described above) is optionally and preferably implanted within or in the proximity of a tumor environment, or the blood supply associated thereof For example the composition (optionally with the device) is optionally implanted within or in the proximity to pancreas, prostate, breast, liver, via the nipple, within the vascular system and so forth.

The target location is optionally selected from the group comprising, consisting essentially of, or consisting of (as non-limiting examples only, as optionally any site within the body may be suitable for implanting a Loder): 1. brain at degenerative sites like in Parkinson or Alzheimer disease at the basal ganglia, white and gray matter; 2. spine as in the case of amyotrophic lateral sclerosis (ALS); 3. uterine cervix to prevent HPV infection; 4. active and chronic inflammatory joints; 5. dermis as in the case of psoriasis; 6. sympathetic and sensoric nervous sites for analgesic effect; 7. Intra osseous implantation; 8. acute and chronic infection sites; 9. Intra vaginal; 10. Inner ear—auditory system, labyrinth of the inner ear, vestibular system; 11. Intra tracheal; 12. Intra-cardiac; coronary, epicardiac; 13. urinary bladder; 14. biliary system; 15. parenchymal tissue including and not limited to the kidney, liver, spleen; 16. lymph nodes; 17. salivary glands; 18. dental gums; 19. Intra-articular (into joints); 20. Intra-ocular; 21. Brain tissue; 22. Brain ventricles; 23. Cavities, including abdominal cavity (for example but without limitation, for ovary cancer); 24. Intra esophageal and 25. Intra rectal.

Optionally insertion of the system (for example a device containing the composition) is associated with injection of material to the ECM at the target site and the vicinity of that site to affect local pH and/or temperature and/or other biological factors affecting the diffusion of the drug and/or drug kinetics in the ECM, of the target site and the vicinity of such a site.

Optionally, according to some embodiments, the release of said agent could be associated with sensing and/or activation appliances that are operated prior and/or at and/or after insertion, by non and/or minimally invasive and/or else methods of activation and/or acceleration/deceleration, including laser beam, radiation, thermal heating and cooling, and ultrasonic, including focused ultrasound and/or RF (radiofrequency) methods or devices, and chemical activators.

According to other embodiments of US Patent Publication 20110195123, the drug preferably comprises a RNA, for example for localized cancer cases in breast, pancreas, brain, kidney, bladder, lung, and prostate as described below. Although exemplified with RNAi, many drugs are applicable to be encapsulated in Loder, and can be used in association with this invention, as long as such drugs can be encapsulated with the Loder substrate, such as a matrix for example, and this system may be used and/or adapted to deliver the CRISPR-Cas system of the present invention.

As another example of a specific application, neuro and muscular degenerative diseases develop due to abnormal gene expression. Local delivery of RNAs may have therapeutic properties for interfering with such abnormal gene expression. Local delivery of anti apoptotic, anti inflammatory and anti degenerative drugs including small drugs and macromolecules may also optionally be therapeutic. In such cases the Loder is applied for prolonged release at constant rate and/or through a dedicated device that is implanted separately. All of this may be used and/or adapted to the CRISPR-Cas system of the present invention.

As yet another example of a specific application, psychiatric and cognitive disorders are treated with gene modifiers. Gene knockdown is a treatment option. Loders locally delivering agents to central nervous system sites are therapeutic options for psychiatric and cognitive disorders including but not limited to psychosis, bi-polar diseases, neurotic disorders and behavioral maladies. The Loders could also deliver locally drugs including small drugs and macromolecules upon implantation at specific brain sites. All of this may be used and/or adapted to the CRISPR-Cas system of the present invention.

As another example of a specific application, silencing of innate and/or adaptive immune mediators at local sites enables the prevention of organ transplant rejection. Local delivery of RNAs and immunomodulating reagents with the Loder implanted into the transplanted organ and/or the implanted site renders local immune suppression by repelling immune cells such as CD8 activated against the transplanted organ. All of this may be used/and or adapted to the CRISPR-Cas system of the present invention.

As another example of a specific application, vascular growth factors including VEGFs and angiogenin and others are essential for neovascularization. Local delivery of the factors, peptides, peptidomimetics, or suppressing their repressors is an important therapeutic modality; silencing the repressors and local delivery of the factors, peptides, macromolecules and small drugs stimulating angiogenesis with the Loder is therapeutic for peripheral, systemic and cardiac vascular disease.

The method of insertion, such as implantation, may optionally already be used for other types of tissue implantation and/or for insertions and/or for sampling tissues, optionally without modifications, or alternatively optionally only with non-major modifications in such methods. Such methods optionally include but are not limited to brachytherapy methods, biopsy, endoscopy with and/or without ultrasound, such as ERCP, stereotactic methods into the brain tissue, Laparoscopy, including implantation with a laparoscope into joints, abdominal organs, the bladder wall and body cavities.

Implantable devices may also include cells, such as epidermal progenitor cells that have been edited or modified to express the CRISPR-Cas systems disclosed herein and embedded with an implantable device, such as a patch. See. Yue et al. "Engineered Epidermal Progenitor Cells Can Correct Diet-Induced Obesity and Diabetes" Cell Stem Cell (2017) 21(2):256-263.

Implantable device technology herein discussed can be employed with herein teachings and hence by this disclosure and the knowledge in the art, CRISPR-Cas system or components thereof or nucleic acid molecules thereof or encoding or providing components may be delivered via an implantable device.

Aerosol Delivery

Subjects treated for a lung disease may for example receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector.

Hybrid Viral Capsid Delivery Systems

In one aspect, the invention provides a particle delivery system comprising a hybrid virus capsid protein or hybrid viral outer protein, wherein the hybrid virus capsid or outer protein comprises a virus capsid or outer protein attached to at least a portion of a non-capsid protein or peptide. The genetic material of a virus is stored within a viral structure called the capsid. The capsid of certain viruses are enclosed in a membrane called the viral envelope. The viral envelope is made up of a lipid bilayer embedded with viral proteins including viral glycoproteins. As used herein, an "envelope protein" or "outer protein" means a protein exposed at the surface of a viral particle that is not a capsid protein. For example envelope or outer proteins typically comprise proteins embedded in the envelope of the virus. Non-limiting examples of outer or envelope proteins include, without limit, gp41 and gp120 of HIV, hemagglutinin, neuraminidase and M2 proteins of influenza virus.

In one example embodiment of the delivery system, the non-capsid protein or peptide has a molecular weight of up to a megadalton, or has a molecular weight in the range of 110 to 160 kDa, 160 to 200 kDa, 200 to 250 kDa, 250 to 300 kDa, 300 to 400 kDa, or 400 to 500 kDa, the non-capsid protein or peptide comprises a CRISPR protein.

The present application provides a vector for delivering an effector protein and at least one CRISPR guide RNA to a cell comprising a minimal promoter operably linked to a polynucleotide sequence encoding the effector protein and a second minimal promoter operably linked to a polynucleotide sequence encoding at least one guide RNA, wherein the length of the vector sequence comprising the minimal promoters and polynucleotide sequences is less than 4.4Kb. In an embodiment, the virus is an adeno-associated virus (AAV) or an adenovirus. In another embodiment, the effector protein is a CRISPR enzyme. In a further embodiment, the CRISPR enzyme is SaCas9, Cpf1, Cas13b or C2c2.

In a related aspect, the invention provides a lentiviral vector for delivering an effector protein and at least one CRISPR guide RNA to a cell comprising a promoter operably linked to a polynucleotide sequence encoding Cpf1 and a second promoter operably linked to a polynucleotide sequence encoding at least one guide RNA, wherein the polynucleotide sequences are in reverse orientation.

In an embodiment of the delivery system, the virus is lentivirus or murine leukemia virus (MuMLV).

In an embodiment of the delivery system, the virus is an Adenoviridae or a Parvoviridae or a retrovirus or a Rhabdoviridae or an enveloped virus having a glycoprotein protein (G protein).

In an embodiment of the delivery system, the virus is VSV or rabies virus.

In an embodiment of the delivery system, the capsid or outer protein comprises a capsid protein having VP1, VP2 or VP3.

In an embodiment of the delivery system, the capsid protein is VP3, and the non-capsid protein is inserted into or attached to VP3 loop 3 or loop 6.

In an embodiment of the delivery system, the virus is delivered to the interior of a cell.

In an embodiment of the delivery system, the capsid or outer protein and the non-capsid protein can dissociate after delivery into a cell.

In an embodiment of the delivery system, the capsid or outer protein is attached to the protein by a linker.

In an embodiment of the delivery system, the linker comprises amino acids.

In an embodiment of the delivery system, the linker is a chemical linker.

In an embodiment of the delivery system, the linker is cleavable.

In an embodiment of the delivery system, the linker is biodegradable.

In an embodiment of the delivery system, the linker comprises (GGGGS)1-3, ENLYFQG (SEQ ID NO: 1), or a disulfide.

In an embodiment, the delivery system comprises a protease or nucleic acid molecule(s) encoding a protease that is expressed, said protease being capable of cleaving the linker, whereby there can be cleavage of the linker. In an embodiment of the invention, a protease is delivered with a particle component of the system, for example packaged, mixed with, or enclosed by lipid and/or capsid. Entry of the particle into a cell is thereby accompanied or followed by cleavage and dissociation of payload from particle. In certain embodiments, an expressible nucleic acid encoding a protease is delivered, whereby at entry or following entry of the particle into a cell, there is protease expression, linker cleavage, and dissociation of payload from capsid. In certain embodiments, dissociation of payload occurs with viral replication. In certain embodiments, dissociation of payload occurs in the absence of productive virus replication.

In an embodiment of the delivery system, each terminus of a CRISPR protein is attached to the capsid or outer protein by a linker.

In an embodiment of the delivery system, the non-capsid protein is attached to the exterior portion of the capsid or outer protein.

In an embodiment of the delivery system, the non-capsid protein is attached to the interior portion of the capsid or outer protein.

In an embodiment of the delivery system, the capsid or outer protein and the non-capsid protein are a fusion protein.

In an embodiment of the delivery system, the non-capsid protein is encapsulated by the capsid or outer protein.

In an embodiment of the delivery system, the non-capsid protein is attached to a component of the capsid protein or a component of the outer protein prior to formation of the capsid or the outer protein.

In an embodiment of the delivery system, the protein is attached to the capsid or outer protein after formation of the capsid or outer protein.

In an embodiment, the delivery system comprises a targeting moiety, such as active targeting of a lipid entity of the invention, e.g., lipid particle or nanoparticle or liposome or lipid bilayer of the invention comprising a targeting moiety for active targeting.

With regard to targeting moieties, mention is made of Deshpande et al, "Current trends in the use of liposomes for tumor targeting," Nanomedicine (Lond). 8(9), doi:10.2217/nnm.13.118 (2013), and the documents it cites, all of which are incorporated herein by reference. Mention is also made of WO/2016/027264, and the documents it cites, all of which are incorporated herein by reference. And mention is made of Lorenzer et al, "Going beyond the liver: Progress and challenges of targeted delivery of siRNA therapeutics," Journal of Controlled Release, 203: 1-15 (2015), and the documents it cites, all of which are incorporated herein by reference.

An actively targeting lipid particle or nanoparticle or liposome or lipid bilayer delivery system (generally as to embodiments of the invention, "lipid entity of the invention" delivery systems) are prepared by conjugating targeting moieties, including small molecule ligands, peptides and monoclonal antibodies, on the lipid or liposomal surface; for example, certain receptors, such as folate and transferrin (Tf) receptors (TfR), are overexpressed on many cancer cells and have been used to make liposomes tumor cell specific. Liposomes that accumulate in the tumor microenvironment can be subsequently endocytosed into the cells by interacting with specific cell surface receptors. To efficiently target liposomes to cells, such as cancer cells, it is useful that the targeting moiety have an affinity for a cell surface receptor and to link the targeting moiety in sufficient quantities to have optimum affinity for the cell surface receptors; and determining these aspects are within the ambit of the skilled artisan. In the field of active targeting, there are a number of cell-, e.g., tumor-, specific targeting ligands.

Also as to active targeting, with regard to targeting cell surface receptors such as cancer cell surface receptors, targeting ligands on liposomes can provide attachment of liposomes to cells, e.g., vascular cells, via a noninternalizing epitope; and, this can increase the extracellular concentration of that which is being delivered, thereby increasing the amount delivered to the target cells. A strategy to target cell surface receptors, such as cell surface receptors on cancer cells, such as overexpressed cell surface receptors on cancer cells, is to use receptor-specific ligands or antibodies. Many cancer cell types display upregulation of tumor-specific receptors. For example, TfRs and folate receptors (FRs) are greatly overexpressed by many tumor cell types in response to their increased metabolic demand. Folic acid can be used as a targeting ligand for specialized delivery owing to its ease of conjugation to nanocarriers, its high affinity for FRs and the relatively low frequency of FRs, in normal tissues as compared with their overexpression in activated macrophages and cancer cells, e.g., certain ovarian, breast, lung, colon, kidney and brain tumors. Overexpression of FR on macrophages is an indication of inflammatory diseases, such as psoriasis, Crohn's disease, rheumatoid arthritis and atherosclerosis; accordingly, folate-mediated targeting of the invention can also be used for studying, addressing or treating inflammatory disorders, as well as cancers. Folate-linked lipid particles or nanoparticles or liposomes or lipid bilayers of the invention ("lipid entity of the invention") deliver their cargo intracellularly through receptor-mediated endocytosis. Intracellular trafficking can be directed to acidic compartments that facilitate cargo release, and, most importantly, release of the cargo can be altered or delayed until it reaches the cytoplasm or vicinity of target organelles. Delivery of cargo using a lipid entity of the invention having a targeting moiety, such as a folate-linked lipid entity of the invention, can be superior to nontargeted lipid entity of the invention. The attachment of folate directly to the lipid head groups may not be favorable for intracellular delivery of folate-conjugated lipid entity of the invention, since they may not bind as efficiently to cells as folate attached to the lipid entity of the invention surface by a spacer, which may can enter cancer cells more efficiently. A lipid entity of the invention coupled to folate can be used for the delivery of complexes of lipid, e.g., liposome, e.g., anionic liposome and virus or capsid or envelope or virus outer protein, such as those herein discussed such as adenovirus or AAV. Tf is a monomeric serum glycoprotein of approximately 80 KDa involved in the transport of iron throughout the body. Tf binds to the TfR and translocates into cells via receptor-mediated endocytosis. The expression of TfR is can be higher in certain cells, such as tumor cells (as compared with normal cells and is associated with the increased iron demand in rapidly proliferating cancer cells. Accordingly, the invention comprehends a TfR-targeted lipid entity of the invention, e.g., as to liver cells, liver cancer, breast cells such as breast cancer cells, colon such as colon cancer cells, ovarian cells such as ovarian cancer cells, head, neck and lung cells, such as head, neck and non-small-cell lung cancer cells, cells of the mouth such as oral tumor cells.

Also as to active targeting, a lipid entity of the invention can be multifunctional, i.e., employ more than one targeting moiety such as CPP, along with Tf; a bifunctional system; e.g., a combination of Tf and poly-L-arginine which can provide transport across the endothelium of the blood-brain barrier. EGFR, is a tyrosine kinase receptor belonging to the ErbB family of receptors that mediates cell growth, differentiation and repair in cells, especially non-cancerous cells, but EGF is overexpressed in certain cells such as many solid tumors, including colorectal, non-small-cell lung cancer, squamous cell carcinoma of the ovary, kidney, head, pancreas, neck and prostate, and especially breast cancer. The invention comprehends EGFR-targeted monoclonal antibody(ies) linked to a lipid entity of the invention. HER-2 is often overexpressed in patients with breast cancer, and is also associated with lung, bladder, prostate, brain and stomach cancers. HER-2, encoded by the ERBB2 gene. The invention comprehends a HER-2-targeting lipid entity of the invention, e.g., an anti-HER-2-antibody(or binding fragment thereof)-lipid entity of the invention, a HER-2-targeting-PEGylated lipid entity of the invention (e.g., having an anti-HER-2-antibody or binding fragment thereof), a HER-2-targeting-maleimide-PEG polymer- lipid entity of the invention (e.g., having an anti-HER-2-antibody or binding fragment thereof). Upon cellular association, the receptor-antibody complex can be internalized by formation of an endosome for delivery to the cytoplasm. With respect to receptor-mediated targeting, the skilled artisan takes into consideration ligand/target affinity and the quantity of receptors on the cell surface, and that PEGylation can act as a barrier against interaction with receptors. The use of antibody-lipid entity of the invention targeting can be advantageous. Multivalent presentation of targeting moieties can also increase the uptake and signaling properties of antibody fragments. In practice of the invention, the skilled person takes into account ligand density (e.g., high ligand densities on a lipid entity of the invention may be advantageous for increased binding to target cells). Preventing early by macrophages can be addressed with a sterically stabilized lipid entity of the invention and linking ligands to the terminus of molecules such as PEG, which is anchored in the lipid entity of the invention (e.g., lipid particle or nanoparticle or liposome or lipid bilayer). The microenvironment of a cell mass such as a tumor microenvironment can be targeted; for instance, it may be advantageous to target cell mass vasculature, such as the tumor vasculature microenvironment. Thus, the invention comprehends targeting VEGF. VEGF and its receptors are well-known proangiogenic molecules and are well-characterized targets for antiangiogenic therapy. Many small-molecule inhibitors of receptor tyrosine kinases, such as VEGFRs or basic FGFRs, have been developed as anticancer agents and the invention comprehends coupling any one or more of these peptides to a lipid entity of the invention, e.g., phage IVO peptide(s) (e.g., via or with a PEG terminus), tumor-homing peptide APRPG such as APRPG-PEG-modified. VCAM, the vascular endothelium plays a key role in the pathogenesis of inflammation, thrombosis and atherosclerosis. CAMs are involved in inflammatory disorders, including cancer, and are a logical target, E- and P-selectins, VCAM-1 and ICAMs. Can be used to target a lipid entity of the invention., e.g., with PEGylation. Matrix metalloproteases (MMPs) belong to the family of zinc-dependent endopeptidases. They are involved in tissue remodeling, tumor invasiveness, resistance to apoptosis and metastasis. There are four MMP inhibitors called TIMP1-4, which determine the balance between tumor growth inhibition and metastasis; a protein involved in the angiogenesis of tumor vessels is MT1-MMP, expressed on newly formed vessels and tumor tissues. The proteolytic activity of MT1-MMP cleaves proteins, such as fibronectin, elastin, collagen and laminin, at the plasma membrane and activates soluble MMPs, such as MMP-2, which degrades the matrix. An antibody or fragment thereof such as a Fab' fragment can be used in the practice of the invention such as for an antihuman MT1-MMP monoclonal antibody linked to a lipid entity of the invention, e.g., via a spacer such as a PEG spacer. αβ-integrins or integrins are a group of transmembrane glycoprotein receptors that mediate attachment between a cell and its surrounding tissues or extracellular matrix. Integrins contain two distinct chains (heterodimers) called α- and β-subunits. The tumor tissue-specific expression of integrin receptors can be been utilized for targeted delivery in the invention, e.g., whereby the targeting moiety can be an RGD peptide such as a cyclic RGD. Aptamers are ssDNA or RNA oligonucleotides that impart high affinity and specific recognition of the target molecules by electrostatic interactions, hydrogen bonding and hydro phobic interactions as opposed to the Watson-Crick base pairing, which is typical for the bonding interactions of oligonucleotides. Aptamers as a targeting moiety can have advantages over antibodies: aptamers can demonstrate higher target antigen recognition as compared with antibodies; aptamers can be more stable and smaller in size as compared with antibodies; aptamers can be easily synthesized and chemically modified for molecular conjugation; and aptamers can be changed in sequence for improved selectivity and can be developed to recognize poorly immunogenic targets. Such moieties as a sgc8 aptamer can be used as a targeting moiety (e.g., via covalent linking to the lipid entity of the invention, e.g., via a spacer, such as a PEG spacer). The targeting moiety can be stimuli-sensitive, e.g., sensitive to an externally applied stimuli, such as magnetic fields, ultrasound or light; and pH-triggering can also be used, e.g., a labile linkage can be used between a hydrophilic moiety such as PEG and a hydrophobic moiety such as a lipid entity of the invention, which is cleaved only upon exposure to the relatively acidic conditions characteristic of the particular environment or microenvironment such as an endocytic vacuole or the acidotic tumor mass. pH-sensitive copolymers can also be incorporated in embodiments of the invention can provide shielding; diortho esters, vinyl esters, cysteine-cleavable lipopolymers, double esters and hydrazones are a few examples of pH-sensitive bonds that are quite stable at pH 7.5, but are hydrolyzed relatively rapidly at pH 6 and below, e.g., a terminally alkylated copolymer of N-isopropylacrylamide and methacrylic acid that copolymer facilitates destabilization of a lipid entity of the invention and release in compartments with decreased pH value; or, the invention comprehends ionic polymers for generation of a pH-responsive lipid entity of the invention (e.g., poly (methacrylic acid), poly(diethylaminoethyl methacrylate), poly(acrylamide) and poly(acrylic acid)). Temperature-triggered delivery is also within the ambit of the invention. Many pathological areas, such as inflamed tissues and tumors, show a distinctive hyperthermia compared with normal tissues. Utilizing this hyperthermia is an attractive strategy in cancer therapy since hyperthermia is associated with increased tumor permeability and enhanced uptake. This technique involves local heating of the site to increase microvascular pore size and blood flow, which, in turn, can result in an increased extravasation of embodiments of the invention. Temperature-sensitive lipid entity of the invention can be prepared from thermosensitive lipids or polymers with a low critical solution temperature. Above the low critical solution temperature (e.g., at site such as tumor site or inflamed tissue site), the polymer precipitates, disrupting the liposomes to release. Lipids with a specific gel-to-liquid phase transition temperature are used to prepare these lipid entities of the invention; and a lipid for a thermosensitive embodiment can be dipalmitoylphosphatidylcholine. Thermosensitive polymers can also facilitate destabilization followed by release, and a useful thermosensitive polymer is poly (N-isopropylacrylamide). Another temperature triggered system can employ lysolipid temperature-sensitive liposomes. The invention also comprehends redox-triggered delivery: The difference in redox potential between normal and inflamed or tumor tissues, and between the intra- and extra-cellular environments has been exploited for delivery; e.g., GSH is a reducing agent abundant in cells, especially in the cytosol, mitochondria and nucleus. The GSH concentrations in blood and extracellular matrix are just one out of 100 to one out of 1000 of the intracellular concentration, respectively. This high redox potential difference caused by GSH, cysteine and other reducing agents can break the reducible bonds, destabilize a lipid entity of the invention and result in release of payload. The disulfide bond can be used as the cleavable/reversible linker in a lipid entity of the invention, because it causes sensitivity to redox owing to the disulfide to thiol reduction reaction; a lipid entity of the invention can be made reduction sensitive by using two (e.g., two forms of a disulfide-conjugated multifunctional lipid as cleavage of the disulfide bond (e.g., via tris(2-carboxyethyl)phosphine, dithiothreitol, L-cysteine or GSH), can cause removal of the hydrophilic head group of the conjugate and alter the membrane organization leading to release of payload. Calcein release from reduction-sensitive lipid entity of the invention containing a disulfide conjugate can be more useful than a reduction-insensitive embodiment. Enzymes can also be used as a trigger to release payload. Enzymes, including MMPs (e.g. MMP2), phospholipase A2, alkaline phosphatase, transglutaminase or phosphatidylinositol-specific phospholipase C, have been found to be overexpressed in certain tissues, e.g., tumor tissues. In the presence of these enzymes, specially engineered enzyme-sensitive lipid entity of the invention can be disrupted and release the payload. An MMP2-cleavable octapeptide (Gly-Pro-Leu-Gly-Ile-Ala-Gly-Gln) can be incorporated into a linker, and can have antibody targeting, e.g., antibody 2C5. The invention also comprehends light-or energy-triggered delivery, e.g., the lipid entity of the invention can be light-sensitive, such that light or energy can facilitate structural and conformational changes, which lead to direct interaction of the lipid entity of the invention with the target cells via membrane fusion, photo-isomerism, photofragmentation or photopolymerization; such a moiety therefor can be benzoporphyrin photosensitizer. Ultrasound can be a form of energy to trigger delivery; a lipid entity of the invention with a small quantity of particular gas, including air or perfluorated hydrocarbon can be triggered to release with ultrasound, e.g., low-frequency ultrasound (LFUS). Magnetic delivery: A lipid entity of the invention can be magnetized by incorporation of magnetites, such as $Fe_3O_4$ or $\gamma$-$Fe_2O_3$, e.g., those that are less than 10 nm in size. Targeted delivery can be then by exposure to a magnetic field.

Also as to active targeting, the invention also comprehends intracellular delivery. Since liposomes follow the endocytic pathway, they are entrapped in the endosomes (pH 6.5-6) and subsequently fuse with lysosomes (pH<5), where they undergo degradation that results in a lower therapeutic potential. The low endosomal pH can be taken advantage of to escape degradation. Fusogenic lipids or peptides, which destabilize the endosomal membrane after the conformational transition/activation at a lowered pH. Amines are protonated at an acidic pH and cause endosomal swelling and rupture by a buffer effect Unsaturated dioleoylphosphatidylethanolamine (DOPE) readily adopts an inverted hexagonal shape at a low pH, which causes fusion of liposomes to the endosomal membrane. This process destabilizes a lipid entity containing DOPE and releases the cargo into the cytoplasm; fusogenic lipid GALA, cholesteryl-GALA and PEG-GALA may show a highly efficient endosomal release; a pore-forming protein listeriolysin O may provide an endosomal escape mechanism; and, histidine-rich peptides have the ability to fuse with the endosomal membrane, resulting in pore formation, and can buffer the proton pump causing membrane lysis.

Also as to active targeting, cell-penetrating peptides (CPPs) facilitate uptake of macromolecules through cellular membranes and, thus, enhance the delivery of CPP-modified molecules inside the cell. CPPs can be split into two classes: amphipathic helical peptides, such as transportan and MAP, where lysine residues are major contributors to the positive charge; and Arg-rich peptides, such as TATp, Antennapedia or penetratin. TATp is a transcription-activating factor with 86 amino acids that contains a highly basic (two Lys and six Arg among nine residues) protein transduction domain, which brings about nuclear localization and RNA binding. Other CPPs that have been used for the modification of liposomes include the following: the minimal protein transduction domain of Antennapedia, a Drosophilia homeoprotein, called penetratin, which is a 16-mer peptide (residues 43-58) present in the third helix of the homeodomain; a 27-amino acid-long chimeric CPP, containing the peptide sequence from the amino terminus of the neuropeptide galanin bound via the Lys residue, mastoparan, a wasp venom peptide; VP22, a major structural component of HSV-1 facilitating intracellular transport and transportan (18-mer) amphipathic model peptide that translocates plasma membranes of mast cells and endothelial cells by both energy-dependent and -independent mechanisms. The invention comprehends a lipid entity of the invention modified with CPP(s), for intracellular delivery that may proceed via energy dependent macropinocytosis followed by endosomal escape. The invention further comprehends organelle-specific targeting. A lipid entity of the invention surface-functionalized with the triphenylphosphonium (TPP) moiety or a lipid entity of the invention with a lipophilic cation, rhodamine 123 can be effective in delivery of cargo to mitochondria. DOPE/sphingomyelin/stearyl-octa-arginine can delivers cargos to the mitochondrial interior via membrane fusion. A lipid entity of the invention surface modified with a lysosomotropic ligand, octadecyl rhodamine B can deliver cargo to lysosomes. Ceramides are useful in inducing lysosomal membrane permeabilization; the invention comprehends intracellular delivery of a lipid entity of the invention having a ceramide. The invention further comprehends a lipid entity of the invention targeting the nucleus, e.g., via a DNA-intercalating moiety. The invention also comprehends multifunctional liposomes for targeting, i.e., attaching more than one functional group to the surface of the lipid entity of the invention, for instance to enhances accumulation in a desired site and/or promotes organelle-specific delivery and/or target a particular type of cell and/or respond to the local stimuli such as temperature (e.g., elevated), pH (e.g., decreased), respond to externally applied stimuli such as a magnetic field, light, energy, heat or ultrasound and/or promote intracellular delivery of the cargo. All of these are considered actively targeting moieties.

An embodiment of the invention includes the delivery system comprising an actively targeting lipid particle or nanoparticle or liposome or lipid bilayer delivery system; or comprising a lipid particle or nanoparticle or liposome or lipid bilayer comprising a targeting moiety whereby there is active targeting or wherein the targeting moiety is an actively targeting moiety. A targeting moiety can be one or more targeting moieties, and a targeting moiety can be for any desired type of targeting such as, e.g., to target a cell such as any herein-mentioned; or to target an organelle such as any herein-mentioned; or for targeting a response such as to a physical condition such as heat, energy, ultrasound, light, pH, chemical such as enzymatic, or magnetic stimuli; or to target to achieve a particular outcome such as delivery of payload to a particular location, such as by cell penetration.

It should be understood that as to each possible targeting or active targeting moiety herein-discussed, there is an aspect of the invention wherein the delivery system comprises such a targeting or active targeting moiety. Likewise, the following table provides exemplary targeting moieties that can be used in the practice of the invention an as to each an aspect of the invention provides a delivery system that comprises such a targeting moiety.

TABLE 10

| Targeting Moiety | Target Molecule | Target Cell or Tissue |
| --- | --- | --- |
| folate | folate receptor | cancer cells |
| transferrin | transferrin receptor | cancer cells |
| Antibody CC52 | rat CC531 | rat colon adenocarcinoma CC531 |
| anti-HER2 antibody | HER2 | HER2-overexpressing tumors |
| anti-GD2 | GD2 | neuroblastoma, melanoma |

TABLE 10-continued

| Targeting Moiety | Target Molecule | Target Cell or Tissue |
| --- | --- | --- |
| anti-EGFR | EGFR | tumor cells overexpressing EGFR |
| pH-dependent fusogenic peptide diINF-7 | | ovarian carcinoma |
| anti-VEGFR | VEGF Receptor | tumor vasculature |
| anti-CD19 | CD19 (B cell marker) | leukemia, lymphoma |
| cell-penetrating peptide | | blood-brain barrier |
| cyclic arginine-glycine-aspartic acid-tyrosine-cysteine peptide (c(RGDyC)-LP) | $\alpha v\beta 3$ | glioblastoma cells, human umbilical vein endothelial cells, tumor angiogenesis |
| ASSHN peptide | | endothelial progenitor cells; anti-cancer |
| PR_b peptide | $\alpha_5\beta_1$ integrin | cancer cells |
| AG86 peptide | $\alpha_6\beta_4$ integrin | cancer cells |
| KCCYSL (P6.1 peptide) | HER-2 receptor | cancer cells |
| affinity peptide LN (YEVGHRC) | Aminopeptidase N (APN/CD13) | APN-positive tumor |
| synthetic somatostatin analogue | Somatostatin receptor 2 (SSTR2) | breast cancer |
| anti-CD20 monoclonal antibody | B-lymphocytes | B cell lymphoma |

Thus, in an embodiment of the delivery system, the targeting moiety comprises a receptor ligand, such as, for example, hyaluronic acid for CD44 receptor, galactose for hepatocytes, or antibody or fragment thereof such as a binding antibody fragment against a desired surface receptor, and as to each of a targeting moiety comprising a receptor ligand, or an antibody or fragment thereof such as a binding fragment thereof, such as against a desired surface receptor, there is an aspect of the invention wherein the delivery system comprises a targeting moiety comprising a receptor ligand, or an antibody or fragment thereof such as a binding fragment thereof, such as against a desired surface receptor, or hyaluronic acid for CD44 receptor, galactose for hepatocytes (see, e.g., Surace et al, "Lipoplexes targeting the CD44 hyaluronic acid receptor for efficient transfection of breast cancer cells," J. Mol Pharm 6(4):1062-73; doi: 10.1021/mp800215d (2009); Sonoke et al, "Galactose-modified cationic liposomes as a liver-targeting delivery system for small interfering RNA," Biol Pharm Bull. 34(8): 1338-42 (2011); Torchilin, "Antibody-modified liposomes for cancer chemotherapy," Expert Opin. Drug Deliv. 5 (9), 1003-1025 (2008); Manjappa et al, "Antibody derivatization and conjugation strategies: application in preparation of stealth immunoliposome to target chemotherapeutics to tumor," J. Control. Release 150 (1), 2-22 (2011); Sofou S "Antibody-targeted liposomes in cancer therapy and imaging," Expert Opin. Drug Deliv. 5 (2): 189-204 (2008); Gao J et al, "Antibody-targeted immunoliposomes for cancer treatment," Mini. Rev. Med. Chem. 13(14): 2026-2035 (2013); Molavi et al, "Anti-CD30 antibody conjugated liposomal doxorubicin with significantly improved therapeutic efficacy against anaplastic large cell lymphoma," Biomaterials 34(34):8718-25 (2013), each of which and the documents cited therein are hereby incorporated herein by reference).

Moreover, in view of the teachings herein the skilled artisan can readily select and apply a desired targeting moiety in the practice of the invention as to a lipid entity of the invention. The invention comprehends an embodiment wherein the delivery system comprises a lipid entity having a targeting moiety.

In an embodiment of the delivery system, the protein comprises a CRISPR protein, or portion thereof.

In some embodiments a non-capsid protein or protein that is not a virus outer protein or a virus envelope (sometimes herein shorthanded as "non-capsid protein"), such as a CRISPR protein or portion thereof, can have one or more functional moiety(ies) thereon, such as a moiety for targeting or locating, such as an NLS or NES, or an activator or repressor.

In an embodiment of the delivery system, a protein or portion thereof can comprise a tag.

In an aspect, the invention provides a virus particle comprising a capsid or outer protein having one or more hybrid virus capsid or outer proteins comprising the virus capsid or outer protein attached to at least a portion of a non-capsid protein or a CRISPR protein.

In an aspect, the invention provides an in vitro method of delivery comprising contacting the delivery system with a cell, optionally a eukaryotic cell, whereby there is delivery into the cell of constituents of the delivery system.

In an aspect, the invention provides an in vitro, a research or study method of delivery comprising contacting the delivery system with a cell, optionally a eukaryotic cell, whereby there is delivery into the cell of constituents of the delivery system, obtaining data or results from the contacting, and transmitting the data or results.

In an aspect, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results.

In an aspect, the invention provides a cell from or of an in vitro method of delivery, wherein the method comprises contacting the delivery system with a cell, optionally a eukaryotic cell, whereby there is delivery into the cell of constituents of the delivery system, and optionally obtaining data or results from the contacting, and transmitting the data or results; and wherein the cell product is altered compared to the cell not contacted with the delivery system, for example altered from that which would have been wild type of the cell but for the contacting.

In an embodiment, the cell product is non-human or animal.

In one aspect, the invention provides a particle delivery system comprising a composite virus particle, wherein the composite virus particle comprises a lipid, a virus capsid protein, and at least a portion of a non-capsid protein or peptide. The non-capsid peptide or protein can have a molecular weight of up to one megadalton.

In one embodiment, the particle delivery system comprises a virus particle adsorbed to a liposome or lipid particle or nanoparticle. In one embodiment, a virus is adsorbed to a liposome or lipid particle or nanoparticle either through electrostatic interactions, or is covalently linked through a linker. The lipid particle or nanoparticles (1 mg/ml) dissolved in either sodium acetate buffer (pH 5.2) or pure H2O (pH 7) are positively charged. The isoelectropoint of most viruses is in the range of 3.5-7. They have a negatively charged surface in either sodium acetate buffer (pH 5.2) or pure H2O. The electrostatic interaction between the virus and the liposome or synthetic lipid nanoparticle is the most significant factor driving adsorption. By modifying the charge density of the lipid nanoparticle, e.g. inclusion of neutral lipids into the lipid nanoparticle, it is possible to modulate the interaction between the lipid nanoparticle and the virus, hence modulating the assembly. In one embodiment, the liposome comprises a cationic lipid.

In one embodiment, the liposome of the particle delivery system comprises a CRISPR system component.

In one aspect, the invention provides a delivery system comprising one or more hybrid virus capsid proteins in combination with a lipid particle, wherein the hybrid virus capsid protein comprises at least a portion of a virus capsid protein attached to at least a portion of a non-capsid protein.

In one embodiment, the virus capsid protein of the delivery system is attached to a surface of the lipid particle. When the lipid particle is a bilayer, e.g., a liposome, the lipid particle comprises an exterior hydrophilic surface and an interior hydrophilic surface. In one embodiment, the virus capsid protein is attached to a surface of the lipid particle by an electrostatic interaction or by hydrophobic interaction.

In one embodiment, the particle delivery system has a diameter of 50-1000 nm, preferably 100-1000 nm.

In one embodiment, the delivery system comprises a non-capsid protein or peptide, wherein the non-capsid protein or peptide has a molecular weight of up to a megadalton. In one embodiment, the non-capsid protein or peptide has a molecular weight in the range of 110 to 160 kDa, 160 to 200 kDa, 200 to 250 kDa, 250 to 300 kDa, 300 to 400 kDa, or 400 to 500 kDa.

In one embodiment, the delivery system comprises a non-capsid protein or peptide, wherein the protein or peptide comprises a CRISPR protein or peptide. In one embodiment, the protein or peptide comprises a Cas9, a Cpf1 or a C2c2/Cas13a.

In one embodiment, a weight ratio of hybrid capsid protein to wild-type capsid protein is from 1:10 to 1:1, for example, 1:1, 1:2, 1:3, 1:4, 1:5, 1:6, 1:7, 1:8, 1:9 and 1:10.

In one embodiment, the virus of the delivery system is an Adenoviridae or a Parvoviridae or a Rhabdoviridae or an enveloped virus having a glycoprotein protein. In one embodiment, the virus is an adeno-associated virus (AAV) or an adenovirus or a VSV or a rabies virus. In one embodiment, the virus is a retrovirus or a lentivirus. In one embodiment, the virus is murine leukemia virus (MuMLV).

In one embodiment, the virus capsid protein of the delivery system comprises VP1, VP2 or VP3.

In one embodiment, the virus capsid protein of the delivery system is VP3, and the non-capsid protein is inserted into or tethered or connected to VP3 loop 3 or loop 6.

In one embodiment, the virus of the delivery system is delivered to the interior of a cell.

In one embodiment, the virus capsid protein and the non-capsid protein are capable of dissociating after delivery into a cell.

In one aspect of the delivery system, the virus capsid protein is attached to the non-capsid protein by a linker. In one embodiment, the linker comprises amino acids. In one embodiment, the linker is a chemical linker. In another embodiment, the linker is cleavable or biodegradable. In one embodiment, the linker comprises (GGGGS)1-3 (SEQ ID NO: 19), ENLYFQG (SEQ ID NO: 1), or a disulfide.

In one embodiment of the delivery system, each terminus of the non-capsid protein is attached to the capsid protein by a linker moiety.

In one embodiment, the non-capsid protein is attached to the exterior portion of the virus capsid protein. As used herein, "exterior portion" as it refers to a virus capsid protein means the outer surface of the virus capsid protein when it is in a formed virus capsid.

In one embodiment, the non-capsid protein is attached to the interior portion of the capsid protein or is encapsulated within the lipid particle. As used herein, "interior portion" as it refers to a virus capsid protein means the inner surface of the virus capsid protein when it is in a formed virus capsid. In one embodiment, the virus capsid protein and the non-capsid protein are a fusion protein.

In one embodiment, the fusion protein is attached to the surface of the lipid particle.

In one embodiment, the non-capsid protein is attached to the virus capsid protein prior to formation of the capsid.

In one embodiment, the non-capsid protein is attached to the virus capsid protein after formation of the capsid.

In one embodiment, the non-capsid protein comprises a targeting moiety.

In one embodiment, the targeting moiety comprises a receptor ligand.

In an embodiment, the non-capsid protein comprises a tag.

In an embodiment, the non-capsid protein comprises one or more heterologous nuclear localization signals(s) (NLSs).

In an embodiment, the protein or peptide comprises a Type II CRISPR protein or a Type V CRISPR protein.

In an embodiment, the delivery system further comprises guide RNS, optionally complexed with the CRISPR protein.

In an embodiment, the delivery system comprises a protease or nucleic acid molecule(s) encoding a protease that is expressed, whereby the protease cleaves the linker. In certain embodiments, there is protease expression, linker cleavage, and dissociation of payload from capsid in the absence of productive virus replication.

In an aspect, the invention provides a delivery system comprising a first hybrid virus capsid protein and a second hybrid virus capsid protein, wherein the first hybrid virus capsid protein comprises a virus capsid protein attached to a first part of a protein, and wherein the second hybrid virus capsid protein comprises a second virus capsid protein attached to a second part of the protein, wherein the first part of the protein and the second part of the protein are capable of associating to form a functional protein.

In an aspect, the invention provides a delivery system comprising a first hybrid virus capsid protein and a second hybrid virus capsid protein, wherein the first hybrid virus capsid protein comprises a virus capsid protein attached to a first part of a CRISPR protein, and wherein the second hybrid virus capsid protein comprises a second virus capsid protein attached to a second part of a CRISPR protein, wherein the first part of the CRISPR protein and the second part of the CRISPR protein are capable of associating to form a functional CRISPR protein.

In an embodiment of the delivery system, the first hybrid virus capsid protein and the second virus capsid protein are on the surface of the same virus particle.

In an embodiment of the delivery system, the first hybrid virus capsule protein is located at the interior of a first virus particle and the second hybrid virus capsid protein is located at the interior of a second virus particle.

In an embodiment of the delivery system, the first part of the protein or CRISPR protein is linked to a first member of a ligand pair, and the second part of the protein or CRISPR protein is linked to a second member of a ligand pair, wherein the first part of the ligand pair binds to the second part of the ligand pair in a cell. In an embodiment, the binding of the first part of the ligand pair to the second part of the ligand pair is inducible.

In an embodiment of the delivery system, either or both of the first part of the protein or CRISPR protein and the second part of the protein or CRISPR protein comprise one or more NLSs.

In an embodiment of the delivery system, either or both of the first part of the protein or CRISPR protein and the second part of the protein or CRISPR protein comprise one or more nuclear export signals (NESs).

In certain embodiments, the virus structural component comprises one or more capsid proteins including an entire capsid. In certain embodiments, such as wherein a viral capsid comprises multiple copies of different proteins, the delivery system can provide one or more of the same protein or a mixture of such proteins. For example, AAV comprises 3 capsid proteins, VP1, VP2, and VP3, thus delivery systems of the invention can comprise one or more of VP1, and/or one or more of VP2, and/or one or more of VP3. Accordingly, the present invention is applicable to a virus within the family Adenoviridae, such as Atadenovirus, e.g., Ovine atadenovirus D, Aviadenovirus, e.g., Fowl aviadenovirus A, Ichtadenovirus, e.g., Sturgeon ichtadenovirus A, Mastadenovirus (which includes adenoviruses such as all human adenoviruses), e.g., Human mastadenovirus C, and Siadenovirus, e.g., Frog siadenovirus A. Thus, a virus of within the family Adenoviridae is contemplated as within the invention with discussion herein as to adenovirus applicable to other family members. Target-specific AAV capsid variants can be used or selected. Non-limiting examples include capsid variants selected to bind to chronic myelogenous leukemia cells, human CD34 PBPC cells, breast cancer cells, cells of lung, heart, dermal fibroblasts, melanoma cells, stem cell, glioblastoma cells, coronary artery endothelial cells and keratinocytes. See, e.g., Buning et al, 2015, Current Opinion in Pharmacology 24, 94-104. From teachings herein and knowledge in the art as to modifications of adenovirus (see, e.g., U.S. Pat. Nos. 9,410,129, 7,344,872, 7,256,036, 6,911,199, 6,740,525; Matthews, "Capsid-Incorporation of Antigens into Adenovirus Capsid Proteins for a Vaccine Approach," Mol Pharm, 8(1): 3-11 (2011)), as well as regarding modifications of AAV, the skilled person can readily obtain a modified adenovirus that has a large payload protein or a CRISPR-protein, despite that heretofore it was not expected that such a large protein could be provided on an adenovirus. And as to the viruses related to adenovirus mentioned herein, as well as to the viruses related to AAV mentioned herein, the teachings herein as to modifying adenovirus and AAV, respectively, can be applied to those viruses without undue experimentation from this disclosure and the knowledge in the art.

In another aspect, the invention provides a non-naturally occurring or engineered CRISPR protein associated with Adeno Associated Virus (AAV), e.g., an AAV comprising a CRISPR protein as a fusion, with or without a linker, to or with an AAV capsid protein such as VP1, VP2, and/or VP3; and, for shorthand purposes, such a non-naturally occurring or engineered CRISPR protein is herein termed a "AAV-CRISPR protein" More in particular, modifying the knowledge in the art, e.g., Rybniker et al., "Incorporation of Antigens into Viral Capsids Augments Immunogenicity of Adeno-Associated Virus Vector-Based Vaccines," J Virol. December 2012; 86(24): 13800-13804, Lux K, et al. 2005. Green fluorescent protein-tagged adeno-associated virus particles allow the study of cytosolic and nuclear trafficking. J. Virol. 79:11776-11787, Munch R C, et al. 2012. "Displaying high-affinity ligands on adeno-associated viral vectors enables tumor cell-specific and safe gene transfer." Mol. Ther. [Epub ahead of print.] doi:10.1038/mt.2012.186 and Warrington K H, Jr, et al. 2004. Adeno-associated virus type 2 VP2 capsid protein is nonessential and can tolerate large peptide insertions at its N terminus. J. Virol. 78:6595-6609, each incorporated herein by reference, one can obtain a modified AAV capsid of the invention. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3). One can modify the cap gene to have expressed at a desired location a non-capsid protein advantageously a large payload protein, such as a CRISPR-protein. Likewise, these can be fusions, with the protein, e.g., large payload protein such as a CRISPR-protein fused in a manner analogous to prior art fusions. See, e.g., US Patent Publication 20090215879; Nance et al., "Perspective on Adeno-Associated Virus Capsid Modification for Duchenne Muscular Dystrophy Gene Therapy," Hum Gene Ther. 26(12):786-800 (2015) and documents cited therein, incorporated herein by reference. The skilled person, from this disclosure and the knowledge in the art can make and use modified AAV or AAV capsid as in the herein invention, and through this disclosure one knows now that large payload proteins can be fused to the AAV capsid. Applicants provide AAV capsid-CRISPR protein (e.g., Cas, Cas9, dCas9, Cpf1, Cas13a, Cas13b) fusions and those AAV-capsid CRISPR protein (e.g., Cas, Cas9) fusions can be a recombinant AAV that contains nucleic acid molecule(s) encoding or providing CRISPR-Cas or CRISPR system or complex RNA guide(s), whereby the CRISPR protein (e.g., Cas, Cas9) fusion delivers a CRISPR-Cas or CRISPR system complex (e.g., the CRISPR protein or Cas or Cas9 or Cpf1 is provided by the fusion, e.g., VP1, VP2, pr VP3 fusion, and the guide RNA is provided by the coding of the recombinant virus, whereby in vivo, in a cell, the CRISPR-Cas or CRISPR system is assembled from the nucleic acid molecule(s) of the recombinant providing the guide RNA and the outer surface of the virus providing the CRISPR-Enzyme or Cas or Cas9. Such as complex may herein be termed an "AAV-CRISPR system" or an "AAV-CRISPR-Cas" or "AAV-CRISPR complex" or AAV-CRISPR-Cas complex." Accordingly, the instant invention is also applicable to a virus in the genus Dependoparvovirus or in the family Parvoviridae, for instance, AAV, or a virus of Amdoparvovirus, e.g., Carnivore amdoparvovirus 1, a virus of Aveparvovirus, e.g., Galliform aveparvovirus 1, a virus of Bocaparvovirus, e.g., Ungulate bocaparvovirus 1, a virus of Copiparvovirus, e.g., Ungulate copiparvovirus 1, a virus of Dependoparvovirus, e.g., Adeno-associated dependoparvovirus A, a virus of Erythroparvovirus, e.g., Primate erythroparvovirus 1, a virus of Protoparvovirus, e.g., Rodent protoparvovirus 1, a virus of Tetraparvovirus, e.g., Primate tetraparvovirus 1. Thus, a virus of within the family Parvoviridae or the genus Dependoparvovirus or any of the other foregoing genera within Parvoviridae is contemplated as within the invention with discussion herein as to AAV applicable to such other viruses.

In one aspect, the invention provides a non-naturally occurring or engineered composition comprising a CRISPR enzyme which is part of or tethered to a AAV capsid domain, i.e., VP1, VP2, or VP3 domain of Adeno-Associated Virus (AAV) capsid. In some embodiments, part of or tethered to a AAV capsid domain includes associated with associated with a AAV capsid domain. In some embodiments, the CRISPR enzyme may be fused to the AAV capsid domain. In some embodiments, the fusion may be to the N-terminal end of the AAV capsid domain. As such, in some embodiments, the C-terminal end of the CRISPR enzyme is fused to the N-terminal end of the AAV capsid domain. In some embodiments, an NLS and/or a linker (such as a GlySer linker) may be positioned between the C-terminal end of the CRISPR enzyme and the N-terminal end of the AAV capsid domain. In some embodiments, the fusion may be to the C-terminal end of the AAV capsid domain. In some embodiments, this is not preferred due to the fact that the VP1, VP2 and VP3 domains of AAV are alternative splices of the same RNA and so a C- terminal fusion may affect all three domains. In some embodiments, the AAV capsid domain is truncated. In some embodiments, some or all of the AAV capsid domain is removed. In some embodiments, some of the AAV capsid domain is removed and replaced with a linker (such as a GlySer linker), typically leaving the N-terminal and C- terminal ends of the AAV capsid domain intact, such as the first 2, 5 or 10 amino acids. In this way, the internal (non-terminal) portion of the VP3 domain may be replaced with a linker. It is particularly preferred that the linker is fused to the CRISPR protein. A branched linker may be used, with the CRISPR protein fused to the end of one of the braches. This allows for some degree of spatial separation between the capsid and the CRISPR protein. In this way, the CRISPR protein is part of (or fused to) the AAV capsid domain.

Alternatively, the CRISPR enzyme may be fused in frame within, i.e. internal to, the AAV capsid domain. Thus in some embodiments, the AAV capsid domain again preferably retains its N-terminal and C- terminal ends. In this case, a linker is preferred, in some embodiments, either at one or both ends of the CRISPR enzyme. In this way, the CRISPR enzyme is again part of (or fused to) the AAV capsid domain. In certain embodiments, the positioning of the CRISPR enzyme is such that the CRISPR enzyme is at the external surface of the viral capsid once formed. In one aspect, the invention provides a non-naturally occurring or engineered composition comprising a CRISPR enzyme associated with a AAV capsid domain of Adeno-Associated Virus (AAV) capsid. Here, associated may mean in some embodiments fused, or in some embodiments bound to, or in some embodiments tethered to. The CRISPR protein may, in some embodiments, be tethered to the VP1, VP2, or VP3 domain. This may be via a connector protein or tethering system such as the biotin-streptavidin system. In one example, a biotinylation sequence (15 amino acids) could therefore be fused to the CRISPR protein. When a fusion of the AAV capsid domain, especially the N-terminus of the AAV capsid domain, with streptavidin is also provided, the two will therefore associate with very high affinity. Thus, in some embodiments, provided is a composition or system comprising a CRISPR protein-biotin fusion and a streptavidin-AAV capsid domain arrangement, such as a fusion. The CRISPR protein-biotin and streptavidin- AAV capsid domain forms a single complex when the two parts are brought together. NLSs may also be incorporated between the CRISPR protein and the biotin; and/or between the streptavidin and the AAV capsid domain.

An alternative tether may be to fuse or otherwise associate the AAV capsid domain to an adaptor protein which binds to or recognizes to a corresponding RNA sequence or motif. In some embodiments, the adaptor is or comprises a binding protein which recognizes and binds (or is bound by) an RNA sequence specific for said binding protein. In some embodiments, a preferred example is the MS2 (see Konermann et al. December 2014, cited infra, incorporated herein by reference) binding protein which recognizes and binds (or is bound by) an RNA sequence specific for the MS2 protein.

With the AAV capsid domain associated with the adaptor protein, the CRISPR protein may, in some embodiments, be tethered to the adaptor protein of the AAV capsid domain. The CRISPR protein may, in some embodiments, be tethered to the adaptor protein of the AAV capsid domain via the CRISPR enzyme being in a complex with a modified guide, see Konermann et al. The modified guide is, in some embodiments, a sgRNA. In some embodiments, the modified guide comprises a distinct RNA sequence; see, e.g., PCT/US14/70175, incorporated herein by reference.

In some embodiments, distinct RNA sequence is an aptamer. Thus, corresponding aptamer-adaptor protein systems are preferred. One or more functional domains may also be associated with the adaptor protein. An example of a preferred arrangement would be:
[AAV capsid domain-adaptor protein]-[modified guide-CRISPR protein]

In certain embodiments, the positioning of the CRISPR protein is such that the CRISPR protein is at the internal surface of the viral capsid once formed. In one aspect, the invention provides a non-naturally occurring or engineered composition comprising a CRISPR protein associated with an internal surface of an AAV capsid domain. Here again, associated may mean in some embodiments fused, or in some embodiments bound to, or in some embodiments tethered to. The CRISPR protein may, in some embodiments, be tethered to the VP1, VP2, or VP3 domain such that it locates to the internal surface of the viral capsid once formed. This may be via a connector protein or tethering system such as the biotin-streptavidin system as described above.

When the CRISPR protein fusion is designed so as to position the CRISPR protein at the internal surface of the capsid once formed, the CRISPR protein will fill most or all of internal volume of the capsid. Alternatively the CRISPR protein may be modified or divided so as to occupy a less of the capsid internal volume. Accordingly, in certain embodiments, the invention provides a CRISPR protein divided in two portions, one portion comprises in one viral particle or capsid and the second portion comprised in a second viral particle or capsid. In certain embodiments, by splitting the CRISPR protein in two portions, space is made available to link one or more heterologous domains to one or both CRISPR protein portions.

Split CRISPR proteins are set forth herein and in documents incorporated herein by reference in further detail herein. In certain embodiments, each part of a split CRISPR proteins are attached to a member of a specific binding pair, and when bound with each other, the members of the specific binding pair maintain the parts of the CRISPR protein in proximity. In certain embodiments, each part of a split CRISPR protein is associated with an inducible binding pair. An inducible binding pair is one which is capable of being switched "on" or "off" by a protein or small molecule that binds to both members of the inducible binding pair. In general, according to the invention, CRISPR proteins may preferably split between domains, leaving domains intact. Preferred, non-limiting examples of such CRISPR proteins include, without limitation, Cas9, Cpf1, C2c2, Cas13a, Cas13b, and orthologues. Preferred, non-limiting examples of split points include, with reference to SpCas9: a split position between 202A/203S; a split position between 255F/256D; a split position between 310E/311I; a split position between 534R/535K; a split position between 572E/573C; a split position between 713S/714G; a split position between 1003L/104E; a split position between 1054G/1055E; a split position between 1114N/1115S; a split position between 1152K/1153S; a split position between 1245K/1246G; or a split between 1098 and 1099.

In some embodiments, any AAV serotype is preferred. In some embodiments, the VP2 domain associated with the CRISPR enzyme is an AAV serotype 2 VP2 domain. In some embodiments, the VP2 domain associated with the CRISPR enzyme is an AAV serotype 8 VP2 domain. The serotype can be a mixed serotype as is known in the art.

The CRISPR enzyme may form part of a CRISPR-Cas system, which further comprises a guide RNA (sgRNA) comprising a guide sequence capable of hybridizing to a target sequence in a genomic locus of interest in a cell. In some embodiments, the functional CRISPR-Cas system binds to the target sequence. In some embodiments, the functional CRISPR-Cas system may edit the genomic locus to alter gene expression. In some embodiments, the functional CRISPR-Cas system may comprise further functional domains.

In some embodiments, the CRISPR enzyme is a Cpf1. In some embodiments, the CRISPR enzyme is an FnCpf1. In some embodiments, the CRISPR enzyme is an AsCpf1, although other orthologs are envisaged. FnCpf1 and AsCpf1 are particularly preferred, in some embodiments.

In some embodiments, the CRISPR enzyme is external to the capsid or virus particle. In the sense that it is not inside the capsid (enveloped or encompassed with the capsid), but is externally exposed so that it can contact the target genomic DNA). In some embodiments, the CRISPR enzyme cleaves both strands of DNA to produce a double strand break (DSB). In some embodiments, the CRISPR enzyme is a nickase. In some embodiments, the CRISPR enzyme is a dual nickase. In some embodiments, the CRISPR enzyme is a deadCpf1. In some general embodiments, the CRISPR enzyme is associated with one or more functional domains. In some more specific embodiments, the CRISPR enzyme is a deadCpf1 and is associated with one or more functional domains. In some embodiments, the CRISPR enzyme comprises a Rec2 or HD2 truncation. In some embodiments, the CRISPR enzyme is associated with the AAV VP2 domain by way of a fusion protein. In some embodiments, the CRISPR enzyme is fused to Destabilization Domain (DD). In other words, the DD may be associated with the CRISPR enzyme by fusion with said CRISPR enzyme. The AAV can then, by way of nucleic acid molecule(s) deliver the stabilizing ligand (or such can be otherwise delivered) In some embodiments, the enzyme may be considered to be a modified CRISPR enzyme, wherein the CRISPR enzyme is fused to at least one destabilization domain (DD) and VP2. In some embodiments, the association may be considered to be a modification of the VP2 domain. Where reference is made herein to a modified VP2 domain, then this will be understood to include any association discussed herein of the VP2 domain and the CRISPR enzyme. In some embodiments, the AAV VP2 domain may be associated (or tethered) to the CRISPR enzyme via a connector protein, for example using a system such as the streptavidin-biotin system. As such, provided is a fusion of a CRISPR enzyme with a connector protein specific for a high affinity ligand for that connector, whereas the AAV VP2 domain is bound to said high affinity ligand. For example, streptavidin may be the connector fused to the CRISPR enzyme, while biotin may be bound to the AAV VP2 domain. Upon co-localization, the streptavidin will bind to the biotin, thus connecting the CRISPR enzyme to the AAV VP2 domain. The reverse arrangement is also possible. In some embodiments, a biotinylation sequence (15 amino acids) could therefore be fused to the AAV VP2 domain, especially the N- terminus of the AAV VP2 domain. A fusion of the CRISPR enzyme with streptavidin is also preferred, in some embodiments. In some embodiments, the biotinylated AAV capsids with streptavidin-CRISPR enzyme are assembled in vitro. This way the AAV capsids should assemble in a straightforward manner and the CRISPR enzyme-streptavidin fusion can be added after assembly of the capsid. In other embodiments a biotinylation sequence (15 amino acids) could therefore be fused to the CRISPR enzyme, together with a fusion of the AAV VP2 domain, especially the N-terminus of the AAV VP2 domain, with streptavidin. For simplicity, a fusion of the CRISPR enzyme and the AAV VP2 domain is preferred in some embodiments. In some embodiments, the fusion may be to the N-terminal end of the CRISPR enzyme. In other words, in some embodiments, the AAV and CRISPR enzyme are associated via fusion. In some embodiments, the AAV and CRISPR enzyme are associated via fusion including a linker. Suitable linkers are discussed herein, but include GlySer linkers. Fusion to the N- term of AAV VP2 domain is preferred, in some embodiments. In some embodiments, the CRISPR enzyme comprises at least one Nuclear Localization Signal (NLS). In an aspect, the present invention provides a polynucleotide encoding the present CRISPR enzyme and associated AAV VP2 domain.

Viral delivery vectors, for example modified viral delivery vectors, are hereby provided. While the AAV may advantageously be a vehicle for providing RNA of the CRISPR-Cas Complex or CRISPR system, another vector may also deliver that RNA, and such other vectors are also herein discussed. In one aspect, the invention provides a non-naturally occurring modified AAV having a VP2-CRISPR enzyme capsid protein, wherein the CRISPR enzyme is part of or tethered to the VP2 domain. In some preferred embodiments, the CRISPR enzyme is fused to the VP2 domain so that, in another aspect, the invention provides a non-naturally occurring modified AAV having a VP2-CRISPR enzyme fusion capsid protein. The following embodiments apply equally to either modified AAV aspect, unless otherwise apparent. Thus, reference herein to a VP2-CRISPR enzyme capsid protein may also include a VP2-CRISPR enzyme fusion capsid protein. In some embodiments, the VP2-CRISPR enzyme capsid protein further comprises a linker. In some embodiments, the VP2-CRISPR enzyme capsid protein further comprises a linker, whereby the VP2-CRISPR enzyme is distanced from the remainder of the AAV. In some embodiments, the VP2-CRISPR enzyme capsid protein further comprises at least one protein complex, e.g., CRISPR complex, such as CRISPR-Cpf1 complex guide RNA that targets a particular DNA, TALE, etc. A CRISPR complex, such as CRISPR-Cas system comprising the VP2-CRISPR enzyme capsid protein and at least one CRISPR complex, such as CRISPR-Cpf1 complex guide RNA that targets a particular DNA, is also provided in one aspect. In general, in some embodiments, the AAV further comprises a repair template. It will be appreciated that comprises here may mean encompassed thin the viral capsid or that the virus encodes the comprised protein. In some embodiments, one or more, preferably two or more guide RNAs, may be comprised/encompassed within the AAV vector. Two may be preferred, in some embodiments, as it allows for multiplexing or dual nickase approaches. Particularly for multiplexing, two or more guides may be used. In fact, in some embodiments, three or more, four or more, five or more, or even six or more guide RNAs may be comprised/encompassed within the AAV. More space has been freed up within the AAV by virtue of the fact that the AAV no longer needs to comprise/encompass the CRISPR enzyme. In each of these instances, a repair template may also be provided comprised/encompassed within the AAV. In some embodiments, the repair template corresponds to or includes the DNA target.

In a further aspect, the present invention provides compositions comprising the CRISPR enzyme and associated AAV VP2 domain or the polynucleotides or vectors described herein. Also provides are CRISPR-Cas systems comprising guide RNAs.

Also provided is a method of treating a subject in need thereof, comprising inducing gene editing by transforming the subject with the polynucleotide encoding the system or any of the present vectors. A suitable repair template may also be provided, for example delivered by a vector comprising said repair template. In some embodiments, a single vector provides the CRISPR enzyme through (association with the viral capsid) and at least one of: guide RNA; and/or a repair template. Also provided is a method of treating a subject in need thereof, comprising inducing transcriptional activation or repression by transforming the subject with the polynucleotide encoding the present system or any of the present vectors, wherein said polynucleotide or vector encodes or comprises the catalytically inactive CRISPR enzyme and one or more associated functional domains. Compositions comprising the present system for use in said method of treatment are also provided. A kit of parts may be provided including such compositions. Use of the present system in the manufacture of a medicament for such methods of treatment are also provided.

Also provided is a pharmaceutical composition comprising the CRISPR enzyme which is part of or tethered to a VP2 domain of Adeno-Associated Virus (AAV) capsid; or the non-naturally occurring modified AAV; or a polynucleotide encoding them.

Also provided is a complex of the CRISPR enzyme with a guideRNA, such as sgRNA. The complex may further include the target DNA.

A split CRISPR enzyme, most preferably Cpf1, approach may be used. The so-called 'split Cpf1' approach Split Cpf1 allows for the following. The Cpf1is split into two pieces and each of these are fused to one half of a dimer. Upon dimerization, the two parts of the Cpf1 are brought together and the reconstituted Cpf1 has been shown to be functional. Thus, one part of the split Cpf1 may be associated with one VP2 domain and second part of the split Cpf1 may be associated with another VP2 domain. The two VP2 domains may be in the same or different capsid. In other words, the split parts of the Cpf1 could be on the same virus particle or on different virus particles.

In some embodiments, one or more functional domains may be associated with or tethered to CRISPR enzyme and/or may be associated with or tethered to modified guides via adaptor proteins. These can be used irrespective of the fact that the CRISPR enzyme may also be tethered to a virus outer protein or capsid or envelope, such as a VP2 domain or a capsid, via modified guides with aptamer RAN sequences that recognize correspond adaptor proteins.

In some embodiments, one or more functional domains comprise a transcriptional activator, repressor, a recombinase, a transposase, a histone remodeler, a demethylase, a DNA methyltransferase, a cryptochrome, a light inducible/controllable domain, a chemically inducible/controllable domain, an epigenetic modifying domain, or a combination thereof. Advantageously, the functional domain comprises an activator, repressor or nuclease.

In some embodiments, a functional domain can have methylase activity, demethylase activity, transcription activation activity, transcription repression activity, transcription release factor activity, histone modification activity, RNA cleavage activity or nucleic acid binding activity, or activity that a domain identified herein has.

Examples of activators include P65, a tetramer of the herpes simplex activation domain VP16, termed VP64, optimized use of VP64 for activation through modification of both the sgRNA design and addition of additional helper molecules, MS2, P65 and HSF1in the system called the synergistic activation mediator (SAM) (Konermann et al, "Genome-scale transcriptional activation by an engineered CRISPR-Cas9 complex," Nature 517(7536):583-8 (2015)); and examples of repressors include the KRAB (Kruppel-associated box) domain of Kox1 or SID domain (e.g. SID4X); and an example of a nuclease or nuclease domain suitable for a functional domain comprises Fok1.

Suitable functional domains for use in practice of the invention, such as activators, repressors or nucleases are also discussed in documents incorporated herein by reference, including the patents and patent publications herein-cited and incorporated herein by reference regarding general information on CRISPR-Cas Systems.

In some embodiments, the CRISPR enzyme comprises or consists essentially of or consists of a localization signal as, or as part of, the linker between the CRISPR enzyme and the AAV capsid, e.g., VP2. HA or Flag tags are also within the ambit of the invention as linkers as well as Glycine Serine linkers as short as GS up to (GGGGS)3 (SEQ ID NO: 19). In this regard it is mentioned that tags that can be used in embodiments of the invention include affinity tags, such as chitin binding protein (CBP), maltose binding protein (MBP), glutathione-S-transferase (GST), poly(His) tag; solubilization tags such as thioredoxin (TRX) and poly (NANP), MBP, and GST; chromatography tags such as those consisting of polyanionic amino acids, such as FLAG-tag; epitope tags such as V5-tag, Myc-tag, HA-tag and NE-tag; fluorescence tags, such as GFP and mCherry; protein tags that may allow specific enzymatic modification (such as biotinylation by biotin ligase) or chemical modification (such as reaction with FlAsH-EDT2 for fluorescence imaging).

Also provided is a method of treating a subject, e.g, a subject in need thereof, comprising inducing gene editing by transforming the subject with the AAV-CRISPR enzyme advantageously encoding and expressing in vivo the remaining portions of the CRISPR system (e.g., RNA, guides). A suitable repair template may also be provided, for example delivered by a vector comprising said repair template. Also provided is a method of treating a subject, e.g., a subject in need thereof, comprising inducing transcriptional activation or repression by transforming the subject with the AAV-CRISPR enzyme advantageously encoding and expressing in vivo the remaining portions of the CRISPR system (e.g., RNA, guides); advantageously in some embodiments the CRISPR enzyme is a catalytically inactive CRISPR enzyme and comprises one or more associated functional domains. Where any treatment is occurring ex vivo, for example in a cell culture, then it will be appreciated that the term 'subject' may be replaced by the phrase "cell or cell culture."

Compositions comprising the present system for use in said method of treatment are also provided. A kit of parts may be provided including such compositions. Use of the present system in the manufacture of a medicament for such methods of treatment are also provided. Use of the present system in screening is also provided by the present invention, e.g., gain of function screens. Cells which are artificially forced to overexpress a gene are be able to down regulate the gene over time (re-establishing equilibrium) e.g. by negative feedback loops. By the time the screen starts the unregulated gene might be reduced again.

In one aspect, the invention provides an engineered, non-naturally occurring CRISPR-Cas system comprising a AAV-Cas protein and a guide RNA that targets a DNA molecule encoding a gene product in a cell, whereby the guide RNA targets the DNA molecule encoding the gene product and the Cas protein cleaves the DNA molecule encoding the gene product, whereby expression of the gene product is altered; and, wherein the Cas protein and the guide RNA do not naturally occur together. The invention comprehends the guide RNA comprising a guide sequence fused to a tracr sequence. In an embodiment of the invention the Cas protein is a type II CRISPR-Cas protein and in a preferred embodiment the Cas protein is a Cpf1 protein. The invention further comprehends the coding for the Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides an engineered, non-naturally occurring vector system comprising one or more vectors comprising a first regulatory element operably linked to a CRISPR-Cas system guide RNA that targets a DNA molecule encoding a gene product and a AAV-Cas protein. The components may be located on same or different vectors of the system, or may be the same vector whereby the AAV-Cas protein also delivers the RNA of the CRISPR system. The guide RNA targets the DNA molecule encoding the gene product in a cell and the AAV-Cas protein may cleaves the DNA molecule encoding the gene product (it may cleave one or both strands or have substantially no nuclease activity), whereby expression of the gene product is altered; and, wherein the AAV-Cas protein and the guide RNA do not naturally occur together. The invention comprehends the guide RNA comprising a guide sequence fused to a tracr sequence. In an embodiment of the invention the AAV-Cas protein is a type II AAV-CRISPR-Cas protein and in a preferred embodiment the AAV-Cas protein is a AAV-Cpf1 protein. The invention further comprehends the coding for the AAV-Cas protein being codon optimized for expression in a eukaryotic cell. In a preferred embodiment the eukaryotic cell is a mammalian cell and in a more preferred embodiment the mammalian cell is a human cell. In a further embodiment of the invention, the expression of the gene product is decreased.

In another aspect, the invention provides a method of expressing an effector protein and guide RNA in a cell comprising introducing the vector according any of the vector delivery systems disclosed herein. In an embodiment of the vector for delivering an effector protein, the minimal promoter is the Mecp2 promoter, tRNA promoter, or U6. In a further embodiment, the minimal promoter is tissue specific.

The one or more polynucleotide molecules may be comprised within one or more vectors. The invention comprehends such polynucleotide molecule(s), for instance such polynucleotide molecules operably configured to express the protein and/or the nucleic acid component(s), as well as such vector(s).

In one aspect, the invention provides a vector system comprising one or more vectors. In some embodiments, the system comprises: (a) a first regulatory element operably linked to a tracr mate sequence and one or more insertion sites for inserting one or more guide sequences upstream of the tracr mate sequence, wherein when expressed, the guide sequence directs sequence-specific binding of a AAV- CRISPR complex to a target sequence in a eukaryotic cell, wherein the CRISPR complex comprises a AAV-CRISPR enzyme complexed with (1) the guide sequence that is hybridized to the target sequence, and (2) the tracr mate sequence that is hybridized to the tracr sequence; and (b) said AAV-CRISPR enzyme comprising at least one nuclear localization sequence and/or at least one NES; wherein components (a) and (b) are located on or in the same or different vectors of the system. In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a AAV-CRISPR complex to a different target sequence in a eukaryotic cell. In some embodiments, the system comprises the tracr sequence under the control of a third regulatory element, such as a polymerase III promoter. In some embodiments, the tracr sequence exhibits at least 50%, 60%, 70%, 80%, 90%, 95%, or 99% of sequence complementarity along the length of the tracr mate sequence when optimally aligned. Determining optimal alignment is within the purview of one of skill in the art. For example, there are publically and commercially available alignment algorithms and programs such as, but not limited to, ClustalW, Smith-Waterman in matlab, Bowtie, Geneious, Biopython and SeqMan. In some embodiments, the AAV-CRISPR complex comprises one or more nuclear localization sequences of sufficient strength to drive accumulation of said CRISPR complex in a detectable amount in the nucleus of a eukaryotic cell. Without wishing to be bound by theory, it is believed that a nuclear localization sequence is not necessary for AAV-CRISPR complex activity in eukaryotes, but that including such sequences enhances activity of the system, especially as to targeting nucleic acid molecules in the nucleus and/or having molecules exit the nucleus. In some embodiments, the AAV-CRISPR enzyme is a type II AAV-CRISPR system enzyme. In some embodiments, the AAV-CRISPR enzyme is a AAV-Cpf1 enzyme. In some embodiments, the AAV-Cpf1 enzyme is derived from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae* (e.g., a Cpf1 of one of these organisms modified to have or be associated with at least one AAV), and may include further mutations or alterations or be a chimeric Cpf1. The enzyme may be a AAV-Cpf1 homolog or ortholog. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks DNA strand cleavage activity. In some embodiments, the first regulatory element is a polymerase III promoter. In some embodiments, the second regulatory element is a polymerase II promoter.

In some embodiments, the guide sequence is at least 15, 16, 17, 18, 19, 20, 25 nucleotides, or between 10-30, or between 15-25, or between 15-20 nucleotides in length. In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Common expression vectors of utility in recombinant DNA techniques are often in the form of plasmids.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell). Again, the RNA of the CRISPR System, while advantageously delivered via the AAV-CRISPR enzyme can also be delivered separately, e.g. via a separate vector.

In one aspect, the invention provides an AAV-CRISPR enzyme comprising one or more nuclear localization sequences and/or NES. In some embodiments, said AAV-CRISPR enzyme includes a regulatory element that drives transcription of component(s) of the CRISPR system (e.g., RNA, such as guide RNA and/or HR template nucleic acid molecule) in a eukaryotic cell such that said AAV-CRISPR enzyme delivers the CRISPR system accumulates in a detectable amount in the nucleus of the eukaryotic cell and/or is exported from the nucleus. In some embodiments, the regulatory element is a polymerase II promoter. In some embodiments, the AAV-CRISPR enzyme is a type II AAV-CRISPR system enzyme. In some embodiments, the AAV-CRISPR enzyme is a AAV-Cpf1 enzyme. In some embodiments, the AAV-Cpf1 enzyme is derived from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocyto-*

*genes, L. ivanovii; C. botulinum, C. difficile, C. tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, Candidatus *Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae* (e.g., Cpf1 modified to have or associated with at least one AAV), and may include further alteration or mutation of the Cpf1, and can be a chimeric Cpf1. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity).

In one aspect, the invention provides a AAV-CRISPR enzyme comprising one or more nuclear localization sequences of sufficient strength to drive accumulation of said AAV-CRISPR enzyme in a detectable amount in the nucleus of a eukaryotic cell. In some embodiments, the AAV-CRISPR enzyme is a type II AAV-CRISPR system enzyme. In some embodiments, the AAV-CRISPR enzyme is a AAV-Cpf1 enzyme. In some embodiments, the AAV-Cpf1 enzyme is derived from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011 GWC2_44_17, *Smithella* sp. SCADC, *Acidaminococcus* sp. BV3L6, *Lachnospiraceae bacterium* MA2020, Candidatus *Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae* (e.g., Cpf1 modified to have or be associated with at least one AAV), and may include further alteration or mutation of the Cpf1, and can be a chimeric Cpf1. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity).

In one aspect, the invention provides a eukaryotic host cell comprising (a) a first regulatory element operably linked to a tracr mate sequence and one or more insertion sites for inserting one or more guide sequences upstream of the tracr mate sequence, wherein when expressed, the guide sequence directs sequence-specific binding of a AAV-CRISPR complex to a target sequence in a eukaryotic cell, wherein the AAV-CRISPR complex comprises a AAV-CRISPR enzyme complexed with (1) the guide sequence that is hybridized to the target sequence, and (2) the tracr mate sequence that is hybridized to the tracr sequence; and/or (b) a said AAV-CRISPR enzyme optionally comprising at least one nuclear localization sequence and/or NES. In some embodiments, the host cell comprises components (a) and (b). In some embodiments, component (a), component (b), or components (a) and (b) are stably integrated into a genome of the host eukaryotic cell. In some embodiments, component (b) includes or contains component (a). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a AAV-CRISPR complex to a different target sequence in a eukaryotic cell. In some embodiments, the eukaryotic host cell further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the AAV-CRISPR enzyme comprises one or more nuclear localization sequences and/or nuclear export sequences of sufficient strength to drive accumulation of said CRISPR enzyme in a detectable amount in of the nucleus of a eukaryotic cell. In some embodiments, the AAV- CRISPR enzyme is a type II CRISPR system enzyme. In some embodiments, the CRISPR enzyme is a Cpf1 enzyme. In some embodiments, the AAV-Cpf1 enzyme is derived from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011 GWC2_44_17, *Smithella* sp. SCADC, *Acidaminococcus* sp. BV3L6, *Lachnospiraceae bacterium* MA2020, Candidatus *Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae* (e.g., Cpf1 modified to have or be associated with at least one AAV), and may include further alteration or mutation of the Cpf1, and can be a chimeric Cpf1. In some embodiments, the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length. In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The organism also may be a plant. Further, the organism may be a fungus. Advantageously the organism is a host of AAV.

In one aspect, the invention provides a kit comprising one or more of the components described herein. In some embodiments, the kit comprises a vector system and instructions for using the kit. In some embodiments, the vector system comprises (a) a first regulatory element operably linked to a tracr mate sequence and one or more insertion sites for inserting one or more guide sequences upstream of the tracr mate sequence, wherein when expressed, the guide sequence directs sequence-specific binding of a CRISPR complex to a target sequence in a eukaryotic cell, wherein the CRISPR complex comprises a CRISPR enzyme complexed with (1) the guide sequence that is hybridized to the target sequence, and (2) the tracr mate sequence that is hybridized to the tracr sequence; and/or (b) said AAV-CRISPR enzyme optionally comprising a nuclear localization sequence. In some embodiments, the kit comprises components (a) and (b) located on or in the same or different vectors of the system, e.g., (a) can be contained in (b). In some embodiments, component (a) further comprises the tracr sequence downstream of the tracr mate sequence under the control of the first regulatory element. In some embodiments, component (a) further comprises two or more guide sequences operably linked to the first regulatory element, wherein when expressed, each of the two or more guide sequences direct sequence specific binding of a CRISPR complex to a different target sequence in a eukaryotic cell. In some embodiments, the system further comprises a third regulatory element, such as a polymerase III promoter, operably linked to said tracr sequence. In some embodiments, the tracr sequence exhibits at least 50%, 60%, 70%, 80%, 90%, 95%, or 99% of sequence complementarity along the length of the tracr mate sequence when optimally aligned. In some embodiments, the CRISPR enzyme comprises one or more nuclear localization sequences of sufficient strength to drive accumulation of said CRISPR enzyme in a detectable amount in the nucleus of a eukaryotic cell. In some embodiments, the CRISPR enzyme is a type II CRISPR system enzyme. In some embodiments, the CRISPR enzyme is a Cpf1 enzyme. In some embodiments, the Cpf1 enzyme is derived from *S. mutans, S. agalactiae, S. equisimilis, S. sanguinis, S. pneumonia; C. jejuni, C. coli; N. salsuginis, N. tergarcus; S. auricularis, S. carnosus; N. meningitides, N. gonorrhoeae; L. monocytogenes, L. ivanovii; C. botulinum, C. difficile, C. tetani, C. sordellii; Francisella tularensis* 1, *Prevotella albensis, Lachnospiraceae bacterium* MC2017 1, *Butyrivibrio proteoclasticus, Peregrinibacteria bacterium* GW2011_GWA2_33_10, *Parcubacteria bacterium* GW2011_GWC2_44_17, *Smithella* sp. SCADC, *Acidaminococcus* sp. BV3L6, *Lachnospiraceae bacterium* MA2020, *Candidatus Methanoplasma termitum, Eubacterium eligens, Moraxella bovoculi* 237, *Leptospira inadai, Lachnospiraceae bacterium* ND2006, *Porphyromonas crevioricanis* 3, *Prevotella disiens* and *Porphyromonas macacae* (e.g., Cpf1 modified to have or be associated with at least one AAV), and may include further alteration or mutation of the Cpf1, and can be a chimeric Cpf1. In some embodiments, the coding for the AAV-CRISPR enzyme is codon-optimized for expression in a eukaryotic cell. In some embodiments, the AAV-CRISPR enzyme directs cleavage of one or two strands at the location of the target sequence. In some embodiments, the AAV-CRISPR enzyme lacks or substantially DNA strand cleavage activity (e.g., no more than 5% nuclease activity as compared with a wild type enzyme or enzyme not having the mutation or alteration that decreases nuclease activity). In some embodiments, the first regulatory element is a polymerase III promoter. In some embodiments, the second regulatory element is a polymerase II promoter. In some embodiments, the guide sequence is at least 15, 16, 17, 18, 19, 20, 25 nucleotides, or between 10-30, or between 15-25, or between 15-20 nucleotides in length.

In one aspect, the invention provides a method of modifying a target polynucleotide in a eukaryotic cell. In some embodiments, the method comprises allowing a AAV-CRISPR complex to bind to the target polynucleotide, e.g., to effect cleavage of said target polynucleotide, thereby modifying the target polynucleotide, wherein the AAV-CRISPR complex comprises a AAV-CRISPR enzyme complexed with a guide sequence hybridized to a target sequence within said target polynucleotide, wherein said guide sequence is linked to a tracr mate sequence which in turn hybridizes to a tracr sequence. In some embodiments, said cleavage comprises cleaving one or two strands at the location of the target sequence by said AAV-CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expressed from a gene comprising the target sequence. In some embodiments, the method further comprises delivering one or more vectors to said eukaryotic cell, wherein one or more vectors comprise the AAV-CRISPR enzyme and one or more vectors drive expression of one or more of: the guide sequence linked to the tracr mate sequence, and the tracr sequence. In some embodiments, said AAV-CRISPR enzyme drive expression of one or more of: the guide sequence linked to the tracr mate sequence, and the tracr sequence. In some embodiments such AAV-CRISPR enzyme are delivered to the eukaryotic cell in a subject. In some embodiments, said modifying takes place in said eukaryotic cell in a cell culture. In some embodiments, the method further comprises isolating said eukaryotic cell from a subject prior to said modifying. In some embodiments, the method further comprises returning said eukaryotic cell and/or cells derived therefrom to said subject.

In one aspect, the invention provides a method of modifying expression of a polynucleotide in a eukaryotic cell. In some embodiments, the method comprises allowing a AAV-CRISPR complex to bind to the polynucleotide such that said binding results in increased or decreased expression of said polynucleotide; wherein the AAV-CRISPR complex comprises a AAV-CRISPR enzyme complexed with a guide sequence hybridized to a target sequence within said polynucleotide, wherein said guide sequence is linked to a tracr mate sequence which in turn hybridizes to a tracr sequence. In some embodiments, the method further comprises delivering one or more vectors to said eukaryotic cells, wherein the one or more vectors are the AAV-CRISPR enzyme and/or drive expression of one or more of: the guide sequence linked to the tracr mate sequence, and the tracr sequence.

In one aspect, the invention provides a method of generating a model eukaryotic cell comprising a mutated disease gene. In some embodiments, a disease gene is any gene associated an increase in the risk of having or developing a disease. In some embodiments, the method comprises (a) introducing one or more vectors into a eukaryotic cell, wherein the one or more vectors comprise the AAV-CRISPR enzyme and/or drive expression of one or more of: a guide sequence linked to a tracr mate sequence, and a tracr sequence; and (b) allowing a AAV-CRISPR complex to bind to a target polynucleotide, e.g., to effect cleavage of the target polynucleotide within said disease gene, wherein the AAV-CRISPR complex comprises the AAV-CRISPR enzyme complexed with (1) the guide sequence that is hybridized to the target sequence within the target polynucleotide, and (2) the tracr mate sequence that is hybridized to the tracr sequence, thereby generating a model eukaryotic cell comprising a mutated disease gene. Thus, in some embodiments the AAV-CRISPR enzyme contains nucleic acid molecules for and drives expression of one or more of: a guide sequence linked to a tracr mate sequence, and a tracr sequence and/or a Homologous Recombination template and/or a stabilizing ligand if the CRISPR enzyme has a destabilization domain. In some embodiments, said cleavage comprises cleaving one or two strands at the location of the target sequence by said AAV-CRISPR enzyme. In some embodiments, said cleavage results in decreased transcription of a target gene. In some embodiments, the method further comprises repairing said cleaved target polynucleotide by homologous recombination with an exogenous template polynucleotide, wherein said repair results in a mutation comprising an insertion, deletion, or substitution of one or more nucleotides of said target polynucleotide. In some embodiments, said mutation results in one or more amino acid changes in a protein expression from a gene comprising the target sequence.

In one aspect, the invention provides a method for developing a biologically active agent that modulates a cell signaling event associated with a disease gene. In some embodiments, a disease gene is any gene associated an increase in the risk of having or developing a disease. In some embodiments, the method comprises (a) contacting a test compound with a model cell of any one of the described embodiments; and (b) detecting a change in a readout that is indicative of a reduction or an augmentation of a cell signaling event associated with said mutation in said disease gene, thereby developing said biologically active agent that modulates said cell signaling event associated with said disease gene.

In one aspect, the invention provides a recombinant polynucleotide comprising a guide sequence upstream of a tracr mate sequence, wherein the guide sequence when expressed directs sequence-specific binding of a AAV-CRISPR complex to a corresponding target sequence present in a eukaryotic cell. The polynucleotide can be carried within and expressed in vivo from the AAV-CRISPR enzyme. In some embodiments, the target sequence is a viral sequence present in a eukaryotic cell. In some embodiments, the target sequence is a proto-oncogene or an oncogene.

In one aspect the invention provides for a method of selecting one or more cell(s) by introducing one or more mutations in a gene in the one or more cell (s), the method comprising: introducing one or more vectors into the cell (s), wherein the one or more vectors comprise a AAV-CRISPR enzyme and/or drive expression of one or more of: a guide sequence linked to a tracr mate sequence, a tracr sequence, and an editing template; wherein, for example that which is being expressed is within and expressed in vivo by the AAV-CRISPR enzyme and/or the editing template comprises the one or more mutations that abolish AAV-CRISPR enzyme cleavage; allowing homologous recombination of the editing template with the target polynucleotide in the cell(s) to be selected; allowing a CRISPR complex to bind to a target polynucleotide to effect cleavage of the target polynucleotide within said gene, wherein the AAV-CRISPR complex comprises the AAV-CRISPR enzyme complexed with (1) the guide sequence that is hybridized to the target sequence within the target polynucleotide, and (2) the tracr mate sequence that is hybridized to the tracr sequence, wherein binding of the AAV-CRISPR complex to the target polynucleotide induces cell death, thereby allowing one or more cell(s) in which one or more mutations have been introduced to be selected. In a preferred embodiment, the AAV-CRISPR enzyme is AAV-Cpf1. In another aspect of the invention the cell to be selected may be a eukaryotic cell. Aspects of the invention allow for selection of specific cells without requiring a selection marker or a two-step process that may include a counter-selection system. The cell(s) may be prokaryotic or eukaryotic cells.

With respect to mutations of the AAV-CRISPR enzyme, mutations may be made at any or all residues corresponding to positions 908, 993, and 1263 with reference to amino acid position numbering of AsCpf1 (which may be ascertained for instance by standard sequence comparison tools), or 917 and 1006 with reference to amino acid numbering of FnCpf1, or 832, 925, 947, 1180 with reference to amino acid position numbering of LbCpf1. In particular, any or all of the following mutations are preferred in AsCpf1: D908A, E993A, and D1263; in FnCpf1: D917A and H1006A; in LbCpf1: D832A, E925A, D947A, and D1180A; as well as conservative substitution for any of the replacement amino acids is also envisaged. In an aspect the invention provides as to any or each or all embodiments herein-discussed wherein the AAV-CRISPR enzyme comprises at least one or more, or at least two or more mutations, wherein the at least one or more mutation or the at least two or more mutations is as to D908, E993, or D1263 according to AsCpf1 protein, e.g., D908A, E993A, or D1263 as to AsCpf1, or D917 or H1006 according to FnCpf1, e.g., D917A or H1006A as to FnCpf1, or D832, E925, D947, or D1180 according to LbCpf1, e.g., D832A, E925A, D947A, or D1180A as to LbCpf1, or any corresponding mutation(s) in a Cpf1 of an ortholog to As or Fn or Lb, or the CRISPR enzyme comprises at least one mutation wherein at least D908A, E993A, or D1263 as to AsCpf1 or D917A or H1006A as to FnCpf1 or D832A, E925A, D947A, or D1180A as to LbCpf1 is mutated; or any corresponding mutation(s) in a Cpf1 of an ortholog to As protein or Fn protein or Lb protein.

Aspects of the invention encompass a non-naturally occurring or engineered composition that may comprise a guide RNA (sgRNA) comprising a guide sequence capable of hybridizing to a target sequence in a genomic locus of interest in a cell and a AAV-CRISPR enzyme that may comprise at least one or more nuclear localization sequences, wherein the AAV-CRISPR enzyme comprises one or two or more mutations, such that the enzyme has altered or diminished nuclease activity compared with the wild type enzyme, wherein at least one loop of the sgRNA is modified by the insertion of distinct RNA sequence(s) that bind to one or more adaptor proteins, and wherein the adaptor protein further recruits one or more heterologous functional domains. In an embodiment of the invention the AAV-CRISPR enzyme comprises one or two or more mutations in a residue selected from the group comprising, consisting essentially of, or consisting of D908, E993, or D1263 according to AsCpf1 protein; D917 or H1006 according to FnCpf1; or D832, E925, D947, or D1180 according to LbCpf1. In a further embodiment the AAV-CRISPR enzyme comprises one or two or more mutations selected from the group comprising D908A, E993A, or D1263 as to AsCpf1; D917A or H1006A as to FnCpf1; or D832A, E925A, D947A, or D1180A as to LbCpf1. In another embodiment, the functional domain comprise, consist essentially of a transcriptional activation domain, e.g., VP64. In another embodiment, the functional domain comprise, consist essentially of a transcriptional repressor domain, e.g., KRAB domain, SID domain or a SID4X domain. In embodiments of the invention, the one or more heterologous functional domains have one or more activities selected from the group comprising, consisting essentially of, or consisting of methylase activity, demethylase activity, transcription activation activity, transcription repression activity, transcription release factor activity, histone modification activity, RNA cleavage activity and nucleic acid binding activity. In further embodiments of the invention the cell is a eukaryotic cell or a mammalian cell or a human cell. In further embodiments, the adaptor protein is selected from the group comprising, consisting essentially of, or consisting of MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In another embodiment, the at least one loop of the sgRNA is tetraloop and/or loop2. An aspect of the invention encompasses methods of modifying a genomic locus of interest to change gene expression in a cell by introducing into the cell any of the compositions described herein. An aspect of the invention is that the above elements are comprised in a single composition or comprised in individual compositions, e.g., the AAV-CRISPR enzyme delivers the enzyme as discussed as well as the guide. These compositions may advantageously be applied to a host to elicit a functional effect on the genomic level. In general, the sgRNA are modified in a manner that provides specific binding sites (e.g., aptamers) for adapter proteins comprising one or more functional domains (e.g., via fusion protein) to bind to. The modified sgRNA are modified such that once the sgRNA forms a AAV-CRISPR complex (i.e. AAV-CRISPR enzyme binding to sgRNA and target) the adapter proteins bind and, the functional domain on the adapter protein is positioned in a spatial orientation which is advantageous for the attributed function to be effective. For example, if the functional domain comprise, consist essentially of a transcription activator (e.g., VP64 or p65), the transcription activator is placed in a spatial orientation which allows it to affect the transcription of the target. Likewise, a transcription repressor will be advantageously positioned to affect the transcription of the target and a nuclease (e.g., Fok1) will be advantageously positioned to cleave or partially cleave the target. Again, the AAV-CRISPR enzyme can deliver both the enzyme and the modified guide. The skilled person will understand that modifications to the sgRNA which allow for binding of the adapter+functional domain but not proper positioning of the adapter+functional domain (e.g., due to steric hindrance within the three dimensional structure of the CRISPR complex) are modifications which are not intended. The one or more modified sgRNA may be modified at the tetra loop, the stem loop 1, stem loop 2, or stem loop 3, as described herein, preferably at either the tetra loop or stem loop 2, and most preferably at both the tetra loop and stem loop 2.

As explained herein the functional domains may be, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). In some cases it is advantageous that additionally at least one NLS is provided. In some instances, it is advantageous to position the NLS at the N terminus. When more than one functional domain is included, the functional domains may be the same or different.

The sgRNA may be designed to include multiple binding recognition sites (e.g., aptamers) specific to the same or different adapter protein. The sgRNA may be designed to bind to the promoter region −1000-+1 nucleic acids upstream of the transcription start site (i.e. TSS), preferably −200 nucleic acids. This positioning improves functional domains which affect gene activation (e.g., transcription activators) or gene inhibition (e.g., transcription repressors). The modified sgRNA may be one or more modified sgRNAs targeted to one or more target loci (e.g., at least 1 sgRNA, at least 2 sgRNA, at least 5 sgRNA, at least 10 sgRNA, at least 20 sgRNA, at least 30 sg RNA, at least 50 sgRNA) comprised in a composition.

Further, the AAV-CRISPR enzyme with diminished nuclease activity is most effective when the nuclease activity is inactivated (e.g., nuclease inactivation of at least 70%, at least 80%, at least 90%, at least 95%, at least 97%, or 100% as compared with the wild type enzyme; or to put in another way, a AAV-Cpf1 enzyme or AAV-CRISPR enzyme having advantageously about 0% of the nuclease activity of the non-mutated or wild type Cpf1 enzyme or CRISPR enzyme, or no more than about 3% or about 5% or about 10% of the nuclease activity of the non-mutated or wild type Cpf1 enzyme or CRISPR enzyme). This is possible by introducing mutations into the RuvC and HNH nuclease domains of the AsCpf1 and orthologs thereof For example utilizing mutations in a residue selected from the group comprising, consisting essentially of, or consisting of D908, E993, or D1263 according to AsCpf1 protein; D917 or H1006 according to FnCpf1; or D832, E925, D947, or D1180 according to LbCpf1, and more preferably introducing one or more of the mutations selected from the group comprising, consisting essentially of, or consisting of D908A, E993A, or D1263 as to AsCpf1; D917A or H1006A as to FnCpf1; or D832A, E925A, D947A, or D1180A as to LbCpf1. The inactivated CRISPR enzyme may have associated (e.g., via fusion protein) one or more functional domains, e.g., at least one destabilizing domain; or, for instance like those as described herein for the modified sgRNA adaptor proteins, including for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that Fok1 is provided, it is advantageous that multiple Fok1 functional domains are provided to allow for a functional dimer and that sgRNAs are designed to provide proper spacing for functional use (Fok1) as specifically described in Tsai et al. Nature Biotechnology, Vol. 32, Number 6, June 2014). The adaptor protein may utilize known linkers to attach such functional domains. In some cases it is advantageous that additionally at least one NLS is provided. In some instances, it is advantageous to position the NLS at the N terminus. When more than one functional domain is included, the functional domains may be the same or different. In general, the positioning of the one or more functional domain on the inactivated AAV-CRISPR enzyme is one which allows for correct spatial orientation for the functional domain to affect the target with the attributed functional effect. For example, if the functional domain is a transcription activator (e.g., VP64 or p65), the transcription activator is placed in a spatial orientation which allows it to affect the transcription of the target. Likewise, a transcription repressor will be advantageously positioned to affect the transcription of the target, and a nuclease (e.g., Fok1) will be advantageously positioned to cleave or partially cleave the target. This may include positions other than the N-/C-terminus of the AAV-CRISPR enzyme. Positioning the functional domain in the Rec1 domain, the Rec2 domain, the HNH domain, or the PI domain of the AsCpf1 protein or any ortholog corresponding to these domains is advantageous; and again, it is mentioned that the functional domain can be a DD. Positioning of the functional domains to the Rec1 domain or the Rec2 domain, of the AsCpf1 protein or any ortholog corresponding to these domains, in some instances may be preferred. Fok1 functional domain may be attached at the N terminus. When more than one functional domain is included, the functional domains may be the same or different.

An adaptor protein may be any number of proteins that binds to an aptamer or recognition site introduced into the modified sgRNA and which allows proper positioning of one or more functional domains, once the sgRNA has been incorporated into the AAV-CRISPR complex, to affect the target with the attributed function. As explained in detail in this application such may be coat proteins, preferably bacteriophage coat proteins. The functional domains associated with such adaptor proteins (e.g., in the form of fusion protein) may include, for example, one or more domains from the group comprising, consisting essentially of, or consisting of methylase activity, demethylase activity, transcription activation activity, transcription repression activity, transcription release factor activity, histone modification activity, RNA cleavage activity, DNA cleavage activity, nucleic acid binding activity, and molecular switches (e.g., light inducible). Preferred domains are Fok1, VP64, P65, HSF1, MyoD1. In the event that the functional domain is a transcription activator or transcription repressor it is advantageous that additionally at least an NLS is provided and preferably at the N terminus. When more than one functional domain is included, the functional domains may be the same or different. The adaptor protein may utilize known linkers to attach such functional domains. Such linkers may be used to associate the AAV (e.g., capsid or VP2) with the CRISPR enzyme or have the CRISPR enzyme comprise the AAV (or vice versa).

Thus, sgRNA, e.g., modified sgRNA, the inactivated AAV-CRISPR enzyme (with or without functional domains), and the binding protein with one or more functional domains, may each individually be comprised in a composition and administered to a host individually or collectively. Alternatively, these components may be provided in a single composition for administration to a host, e.g., the AAV-CRISPR enzyme can deliver the RNA or guide or sgRNA or modified sgRNA and/or other components of the CRISPR system. Administration to a host may be performed via viral vectors, advantageously using the AAV-CRISPR enzyme as the delivery vehicle, although other vehicles can be used to deliver components other than the enzyme of the CRISPR system, and such viral vectors can be, for example, lentiviral vector, adenoviral vector, AAV vector. Several variations are appropriate to elicit a genomic locus event, including DNA cleavage, gene activation, or gene deactivation. Using the provided compositions, the person skilled in the art can advantageously and specifically target single or multiple loci with the same or different functional domains to elicit one or more genomic locus events. The compositions may be applied in a wide variety of methods for screening in libraries in cells and functional modeling in vivo (e.g., gene activation of lincRNA and identification of function; gain-of-function modeling; loss-of-function modeling; the use the compositions of the invention to establish cell lines and transgenic animals for optimization and screening purposes).

In an aspect, the invention provides a particle delivery system or the delivery system or the virus particle of any one of any one of the above embodiments or the cell of any one of the above embodiments for use in medicine or in therapy; or for use in a method of modifying an organism or a non-human organism by manipulation of a target sequence in a genomic locus associated with a disease or disorder; or for use in a method of treating or inhibiting a condition caused by one or more mutations in a genetic locus associated with a disease in a eukaryotic organism or a non-human organism.; or for use in in vitro, ex vivo or in vivo gene or genome editing; or for use in in vitro, ex vivo or in vivo gene therapy.

In an aspect, the invention provides a pharmaceutical composition comprising the particle delivery system or the delivery system or the virus particle of any one of the above embodiment or the cell of any one of the above embodiment.

In an aspect, the invention provides a method of treating or inhibiting a condition or a disease caused by one or more mutations in a genomic locus in a eukaryotic organism or a non-human organism comprising manipulation of a target sequence within a coding, non-coding or regulatory element of said genomic locus in a target sequence in a subject or a non-human subject in need thereof comprising modifying the subject or a non-human subject by manipulation of the target sequence and wherein the condition or disease is susceptible to treatment or inhibition by manipulation of the target sequence comprising providing treatment comprising delivering a composition comprising the particle delivery system or the delivery system or the virus particle of any one of the above embodiment or the cell of any one of the above embodiment.

In an aspect, the invention provides use of the particle delivery system or the delivery system or the virus particle of any one of the above embodiment or the cell of any one of the above embodiment in ex vivo or in vivo gene or genome editing; or for use in in vitro, ex vivo or in vivo gene therapy.

In an aspect, the invention provides use of the particle delivery system or the delivery system or the virus particle of any one of the above embodiment or the cell of any one of the above embodiment in the manufacture of a medicament for in vitro, ex vivo or in vivo gene or genome editing or for use in in vitro, ex vivo or in vivo gene therapy or for use in a method of modifying an organism or a non-human organism by manipulation of a target sequence in a genomic locus associated with a disease or in a method of treating or inhibiting a condition or disease caused by one or more mutations in a genomic locus in a eukaryotic organism or a non-human organism.

In an aspect, the invention provides a method of individualized or personalized treatment of a genetic disease in a subject in need of such treatment comprising:
  (a) introducing one or more mutations ex vivo in a tissue, organ or a cell line, or in vivo in a transgenic nonhuman mammal, comprising delivering to cell(s) of the tissue, organ, cell or mammal a composition comprising the particle delivery system or the delivery system or the virus particle of any one of the above embodiment or the cell of any one of the above embodiment, wherein the specific mutations or precise sequence substitutions are or have been correlated to the genetic disease;

(b) testing treatment(s) for the genetic disease on the cells to which the vector has been delivered that have the specific mutations or precise sequence substitutions correlated to the genetic disease; and (c) treating the subject based on results from the testing of treatment(s) of step (b).

In an aspect, the invention provides a method of modeling a disease associated with a genomic locus in a eukaryotic organism or a non-human organism comprising manipulation of a target sequence within a coding, non-coding or regulatory element of said genomic locus comprising delivering a non-naturally occurring or engineered composition comprising a viral vector system comprising one or more viral vectors operably encoding a composition for expression thereof, wherein the composition comprises particle delivery system or the delivery system or the virus particle of any one of the above embodiments or the cell of any one of the above embodiment.

In an aspect, the method provides a method of modifying an organism or a non-human organism by manipulation of a target sequence in a genomic locus of interest comprising administering a composition comprising the particle delivery system or the delivery system or the virus particle of any one of the above embodiment or the cell of any one of the above embodiment.

In any of the described methods the strand break may be a single strand break or a double strand break.

Regulatory elements may comprise inducible promotors. Polynucleotides and/or vector systems may comprise inducible systems.

The invention also provides a vector system comprising one or more vectors, the one or more vectors comprising one or more polynucleotide molecules encoding components of a non-naturally occurring or engineered composition which is a composition having the characteristics as discussed herein or defined in any of the herein described methods.

The invention also provides a non-naturally occurring or engineered composition, or one or more polynucleotides encoding components of said composition, or vector systems comprising one or more polynucleotides encoding components of said composition for use in a therapeutic method of treatment. The therapeutic method of treatment may comprise gene or genome editing, or gene therapy.

The nucleic acids-targeting systems, the vector systems, the vectors and the compositions described herein may be used in various nucleic acids-targeting applications, altering or modifying synthesis of a gene product, such as a protein, nucleic acids cleavage, nucleic acids editing, nucleic acids splicing; trafficking of target nucleic acids, tracing of target nucleic acids, isolation of target nucleic acids, visualization of target nucleic acids, etc.

In general, and throughout this specification, the term "vector" refers to a nucleic acid molecule capable of transporting another nucleic acid to which it has been linked. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides known in the art. One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors." Vectors for and that result in expression in a eukaryotic cell can be referred to herein as "eukaryotic expression vectors." Common expression vectors of utility in recombinant DNA techniques are often in the form of plasmids.

In certain embodiments, a vector system includes promoter-guide expression cassette in reverse order.

Recombinant expression vectors can comprise a nucleic acid of the invention in a form suitable for expression of the nucleic acid in a host cell, which means that the recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence (e.g., in an in vitro transcription/translation system or in a host cell when the vector is introduced into the host cell).

The term "regulatory element" is intended to include promoters, enhancers, internal ribosomal entry sites (IRES), and other expression control elements (e.g., transcription termination signals, such as polyadenylation signals and poly-U sequences). Such regulatory elements are described, for example, in Goeddel, GENE EXPRESSION TECHNOLOGY: METHODS IN ENZYMOLOGY 185, Academic Press, San Diego, Calif. (1990). Regulatory elements include those that direct constitutive expression of a nucleotide sequence in many types of host cell and those that direct expression of the nucleotide sequence only in certain host cells (e.g., tissue-specific regulatory sequences). A tissue-specific promoter may direct expression primarily in a desired tissue of interest, such as muscle, neuron, bone, skin, blood, specific organs (e.g., liver, pancreas), or particular cell types (e.g., lymphocytes). Regulatory elements may also direct expression in a temporal-dependent manner, such as in a cell-cycle dependent or developmental stage-dependent manner, which may or may not also be tissue or cell-type specific. In some embodiments, a vector comprises one or more pol III promoter (e.g., 1, 2, 3, 4, 5, or more pol III promoters), one or more pol II promoters (e.g., 1, 2, 3, 4, 5, or more pol II promoters), one or more pol I promoters (e.g., 1, 2, 3, 4, 5, or more pol I promoters), or combinations thereof. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer) [see, e.g., Boshart et al, Cell, 41:521-530 (1985)1, the SV40 promoter, the dihydrofolate reductase promoter, the β-actin promoter, the phosphoglycerol kinase (PGK) promoter, and the EF1α promoter. Also encompassed by the term "regulatory element" are enhancer elements, such as WPRE; CMV enhancers; the R-U5' segment in LTR of HTLV-I (Mol. Cell. Biol., Vol. 8(1), p. 466-472, 1988); SV40 enhancer; and the intron sequence between exons 2 and 3 of rabbit β-globin (Proc. Natl. Acad. Sci. USA., Vol. 78(3), p. 1527-31, 1981). It will be appreciated by those skilled in the art that the design of the expression vector can depend on such factors as the choice of the host cell to be transformed, the level of expression desired, etc. A vector can be introduced into host cells to thereby produce transcripts, proteins, or peptides, including fusion proteins or peptides, encoded by nucleic acids as described herein (e.g., clustered regularly interspersed short palindromic repeats (CRISPR) transcripts, proteins, enzymes, mutant forms thereof, fusion proteins thereof, etc.).

Advantageous vectors include lentiviruses and adenoassociated viruses, and types of such vectors can also be selected for targeting particular types of cells.

In some embodiments, one or more vectors driving expression of one or more elements of a nucleic acid-targeting system are introduced into a host cell such that expression of the elements of the nucleic acid-targeting system direct formation of a nucleic acid-targeting complex at one or more target sites. For example, a nucleic acid-targeting effector module and a nucleic acid-targeting guide RNA could each be operably linked to separate regulatory elements on separate vectors. RNA(s) of the nucleic acid-targeting system can be delivered to a transgenic nucleic acid-targeting effector module animal or mammal, e.g., an animal or mammal that constitutively or inducibly or conditionally expresses nucleic acid-targeting effector module; or an animal or mammal that is otherwise expressing nucleic acid-targeting effector modules or has cells containing nucleic acid-targeting effector modules, such as by way of prior administration thereto of a vector or vectors that code for and express in vivo nucleic acid-targeting effector modules. Alternatively, two or more of the elements expressed from the same or different regulatory elements, may be combined in a single vector, with one or more additional vectors providing any components of the nucleic acid-targeting system not included in the first vector. nucleic acid-targeting system elements that are combined in a single vector may be arranged in any suitable orientation, such as one element located 5' with respect to ("upstream" of) or 3' with respect to ("downstream" of) a second element. The coding sequence of one element may be located on the same or opposite strand of the coding sequence of a second element, and oriented in the same or opposite direction. In some embodiments, a single promoter drives expression of a transcript encoding a nucleic acid-targeting effector module and the nucleic acid-targeting guide RNA, embedded within one or more intron sequences (e.g., each in a different intron, two or more in at least one intron, or all in a single intron). In some embodiments, the nucleic acid-targeting effector module and the nucleic acid-targeting guide RNA may be operably linked to and expressed from the same promoter.

In an aspect, the invention provides in a vector system comprising one or more vectors, wherein the one or more vectors comprises:

a) a first regulatory element operably linked to a nucleotide sequence encoding the engineered CRISPR protein as defined herein; and optionally b) a second regulatory element operably linked to one or more nucleotide sequences encoding one or more nucleic acid molecules comprising a guide RNA comprising a guide sequence, a direct repeat sequence, optionally wherein components (a) and (b) are located on same or different vectors.

The invention also provides an engineered, non-naturally occurring Clustered Regularly Interspersed Short Palindromic Repeats (CRISPR)-CRISPR associated (Cas effector module) (CRISPR-Cas effector module) vector system comprising one or more vectors comprising:

a) a first regulatory element operably linked to a nucleotide sequence encoding a non-naturally-occurring CRISPR enzyme of any one of the inventive constructs herein; and b) a second regulatory element operably linked to one or more nucleotide sequences encoding one or more of the guide RNAs, the guide RNA comprising a guide sequence, a direct repeat sequence, wherein:

components (a) and (b) are located on same or different vectors, the CRISPR complex is formed;

the guide RNA targets the target polynucleotide loci and the enzyme alters the polynucleotide loci, and the enzyme in the CRISPR complex has reduced capability of modifying one or more off-target loci as compared to an unmodified enzyme and/or whereby the enzyme in the CRISPR complex has increased capability of modifying the one or more target loci as compared to an unmodified enzyme.

As used herein, a CRISPR-Cas effector module or CRISPR effector module includes, but is not limited to, Cas9, Cpf1, C2c2, Group 13b, and C2c1. In some embodiments, the CRISPR-Cas effector module may be engineered.

In such a system, component (II) may comprise a first regulatory element operably linked to a polynucleotide sequence which comprises the guide sequence, the direct repeat sequence, and wherein component (II) may comprise a second regulatory element operably linked to a polynucleotide sequence encoding the CRISPR enzyme. In such a system, where applicable the guide RNA may comprise a chimeric RNA.

In such a system, component (I) may comprise a first regulatory element operably linked to the guide sequence and the direct repeat sequence, and wherein component (II) may comprise a second regulatory element operably linked to a polynucleotide sequence encoding the CRISPR enzyme. Such a system may comprise more than one guide RNA, and each guide RNA has a different target whereby there is multiplexing. Components (a) and (b) may be on the same vector.

In any such systems comprising vectors, the one or more vectors may comprise one or more viral vectors, such as one or more retrovirus, lentivirus, adenovirus, adeno-associated virus or herpes simplex virus.

In any such systems comprising regulatory elements, at least one of said regulatory elements may comprise a tissue-specific promoter. The tissue-specific promoter may direct expression in a mammalian blood cell, in a mammalian liver cell or in a mammalian eye.

In any of the above-described compositions or systems the direct repeat sequence, may comprise one or more protein-interacting RNA aptamers. The one or more aptamers may be located in the tetraloop. The one or more aptamers may be capable of binding MS2 bacteriophage coat protein.

In any of the above-described compositions or systems the cell may be a eukaryotic cell or a prokaryotic cell; wherein the CRISPR complex is operable in the cell, and whereby the enzyme of the CRISPR complex has reduced capability of modifying one or more off-target loci of the cell as compared to an unmodified enzyme and/or whereby the enzyme in the CRISPR complex has increased capability of modifying the one or more target loci as compared to an unmodified enzyme.

The invention also provides a CRISPR complex of any of the above-described compositions or from any of the above-described systems.

The invention also provides a method of modifying a locus of interest in a cell comprising contacting the cell with any of the herein-described engineered CRISPR enzymes (e.g. engineered Cas effector module), compositions or any of the herein-described systems or vector systems, or wherein the cell comprises any of the herein-described CRISPR complexes present within the cell. In such methods the cell may be a prokaryotic or eukaryotic cell, preferably a eukaryotic cell. In such methods, an organism may comprise the cell. In such methods the organism may not be a human or other animal.

In certain embodiment, the invention also provides a non-naturally-occurring, engineered composition (e.g., engineered Cas9, Cpf1, C2c2, C2c1, Group 29/30, 13b, or any Cas protein which can fit into an AAV vector). Reference is made to FIGS. 19A, 19B, 19C, 19D, and 20A-F in U.S. Pat. No. 8,697,359 herein incorporated by reference to provide a list and guidance for other proteins which may also be used.

Any such method may be ex vivo or in vitro.

Methods for Applying the Crispr-Cas System

Effector Protein Acting as Nuclease

In some embodiments, the unmodified nucleic acid-targeting effector protein may have cleavage activity. In some embodiments, the RNA-targeting effector protein may direct cleavage of one or both nucleic acid (DNA or RNA) strands at the location of or near a target sequence, such as within the target sequence and/or within the complement of the target sequence or at sequences associated with the target sequence. In some embodiments, the nucleic acid-targeting effector protein may direct cleavage of one or both DNA or RNA strands within about 1, 2, 3, 4, 5, 6, 7, 8, 9, 10, 15, 20, 25, 50, 100, 200, 500, or more base pairs from the first or last nucleotide of a target sequence. In some embodiments, the cleavage may be staggered, i.e. generating sticky ends. In some embodiments, the cleavage is a staggered cut with a 5' overhang. In some embodiments, the cleavage is a staggered cut with a 5' overhang of 1 to 5 nucleotides, preferably of 4 or 5 nucleotides. In some embodiments, the cleavage site is distant from the PAM, e.g., the cleavage occurs after the 18th nucleotide on the non-target strand and after the 23rd nucleotide on the targeted strand. In some embodiments, the cleavage site occurs after the 18th nucleotide (counted from the PAM) on the non-target strand and after the 23rd nucleotide (counted from the PAM) on the targeted strand. In some embodiments, a vector encodes a nucleic acid-targeting effector protein that may be mutated with respect to a corresponding wild-type enzyme such that the mutated nucleic acid-targeting effector protein lacks the ability to cleave one or both DNA or RNA strands of a target polynucleotide containing a target sequence.

The methods according to the invention as described herein comprehend inducing one or more mutations in a eukaryotic cell (in vitro, i.e. in an isolated eukaryotic cell) as herein discussed comprising delivering to cell a vector as herein discussed. The mutation(s) can include the introduction, deletion, or substitution of one or more nucleotides at each target sequence of cell(s) via the guide(s) RNA(s) or sgRNA(s). The mutations can include the introduction, deletion, or substitution of 1-75 nucleotides at each target sequence of said cell(s) via the guide(s) RNA(s) or sgRNA(s). The mutations can include the introduction, deletion, or substitution of 1, 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 5, 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations include the introduction, deletion, or substitution of 10, 11, 12, 13, 14, 15, 16, 17, 18, 19, 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 20, 21, 22, 23, 24, 25, 26, 27, 28, 29, 30, 35, 40, 45, 50, or 75 nucleotides at each target sequence of said cell(s) via the guide(s) RNA(s) or sgRNA(s). The mutations can include the introduction, deletion, or substitution of 40, 45, 50, 75, 100, 200, 300, 400 or 500 nucleotides at each target sequence of said cell(s) via the guide(s) RNA(s) or sgRNA(s).

Effector Protein Functioning as Target-Binding Protein

Effector Protein Lacking Nuclease Activity

As described herein, corresponding catalytic domains of a Cpf1 effector protein may also be mutated to produce a mutated Cpf1 effector protein lacking all DNA cleavage activity or having substantially reduced DNA cleavage activity. In some embodiments, a nucleic acid-targeting effector protein may be considered to substantially lack all RNA cleavage activity when the RNA cleavage activity of the mutated enzyme is about no more than 25%, 10%, 5%, 1%, 0.1%, 0.01%, or less of the nucleic acid cleavage activity of the non-mutated form of the enzyme; an example can be when the nucleic acid cleavage activity of the mutated form is nil or negligible as compared with the non-mutated form. An effector protein may be identified with reference to the general class of enzymes that share homology to the biggest nuclease with multiple nuclease domains from the Type V/Type VI CRISPR system. Most preferably, the effector protein is Cpf1. In further embodiments, the effector protein is a Type V protein. By derived, Applicants mean that the derived enzyme is largely based, in the sense of having a high degree of sequence homology with, a wildtype enzyme, but that it has been mutated (modified) in some way as known in the art or as described herein.

In particular embodiments the Cpf1 effector protein comprise one or more heterologous functional domains. The one or more heterologous functional domains may comprise one or more nuclear localization signal (NLS) domains. The one or more heterologous functional domains may comprise at least two or more NLSs. The one or more heterologous functional domains may comprise one or more transcriptional activation domains. A transcriptional activation domain may comprise VP64. The one or more heterologous functional domains may comprise one or more transcriptional repression domains. A transcriptional repression domain may comprise a KRAB domain or a SID domain. The one or more heterologous functional domain may comprise one or more nuclease domains. The one or more nuclease domains may comprise Fok1.

For the purposes of the following discussion, reference to a functional domain could be a functional domain associated with the CRISPR enzyme or a functional domain associated with the adaptor protein.

In the practice of the invention and as will be described below, loops of the gRNA may be extended, without colliding with the Cas (e.g. Cpf1) protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease. In some preferred embodiments, the functional domain is a transcriptional activation domain, such as, without limitation, VP64, p65, MyoD1, HSF1, RTA, SETT/9 or a histone acetyltransferase. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain. In some embodiments, the functional domain is a deaminase, such as a cytidine deaminase. Cytidine deaminese may be directed to a target nucleic acid to where it directs conversion of cytidine to uridine, resulting in C to T substitutions (G to A on the complementary strand). In such an embodiment, nucleotide substitutions can be effected without DNA cleavage.

Guide RNAs Comprising a Dead Guide Sequence

In one aspect, the invention provides guide sequences which are modified in a manner which allows for formation of the CRISPR complex and successful binding to the target, while at the same time, not allowing for successful nuclease activity (i.e. without nuclease activity/without indel activity). For matters of explanation such modified guide sequences are referred to as "dead guides" or "dead guide sequences". These dead guides or dead guide sequences can be thought of as catalytically inactive or conformationally inactive with regard to nuclease activity. Nuclease activity may be measured using surveyor analysis or deep sequencing as commonly used in the art, preferably surveyor analysis. Similarly, dead guide sequences may not sufficiently engage in productive base pairing with respect to the ability to promote catalytic activity or to distinguish on-target and off-target binding activity.

The ability of a dead guide sequence to direct sequence-specific binding of a CRISPR complex to a target sequence may be assessed by any suitable assay. For example, the components of a CRISPR system sufficient to form a CRISPR complex, including the dead guide sequence to be tested, may be provided to a host cell having the corresponding target sequence, such as by transfection with vectors encoding the components of the CRISPR sequence, followed by an assessment of preferential cleavage within the target sequence, such as by Surveyor assay as described herein. Similarly, cleavage of a target polynucleotide sequence may be evaluated in a test tube by providing the target sequence, components of a CRISPR complex, including the dead guide sequence to be tested and a control guide sequence different from the test dead guide sequence, and comparing binding or rate of cleavage at the target sequence between the test and control guide sequence reactions. Other assays are possible, and will occur to those skilled in the art. A dead guide sequence may be selected to target any target sequence. In some embodiments, the target sequence is a sequence within a genome of a cell.

Several structural parameters allow for a proper framework to arrive at such dead guides. As known in the art, one aspect of gRNA-CRISPR effector protein specificity is the direct repeat sequence, which is to be appropriately linked to such guides. In particular, this implies that the direct repeat sequences are designed dependent on the origin of the CRISPR effector protein. Thus, structural data available for validated dead guide sequences may be used for designing Cpf1 specific equivalents. Structural similarity between, e.g., the orthologous nuclease domains RuvC of two or more Cpf1 effector proteins may be used to transfer design equivalent dead guides. In particular embodiments, the dead guide sequences are shorter than respective guide sequences which result in active Cpf1-specific indel formation. Dead guides are 5%, 10%, 20%, 30%, 40%, 50%, shorter than respective guides directed to the same Cpf1 leading to active Cpf1-specific indel formation.

The use of dead guides in the context herein as well as the state of the art provides a surprising and unexpected platform for network biology and/or systems biology in both in vitro, ex vivo, and in vivo applications, allowing for multiplex gene targeting, and in particular bidirectional multiplex gene targeting. Prior to the use of dead guides, addressing multiple targets, for example for activation, repression and/or silencing of gene activity, has been challenging and in some cases not possible. With the use of dead guides, multiple targets, and thus multiple activities, may be addressed, for example, in the same cell, in the same animal, or in the same patient. Such multiplexing may occur at the same time or staggered for a desired timeframe.

For example, the dead guides now allow for the first time to use gRNA as a means for gene targeting, without the consequence of nuclease activity, while at the same time providing directed means for activation or repression. Guide RNA comprising a dead guide may be modified to further include elements in a manner which allow for activation or repression of gene activity, in particular protein adaptors (e.g. aptamers) as described herein elsewhere allowing for functional placement of gene effectors (e.g. activators or repressors of gene activity). One example is the incorporation of aptamers, as explained herein and in the state of the art. By engineering the gRNA comprising a dead guide to incorporate protein-interacting aptamers (Konermann et al., "Genome-scale transcription activation by an engineered CRISPR-Cas9 complex," doi:10.1038/nature14136, incorporated herein by reference), one may assemble a synthetic transcription activation complex consisting of multiple distinct effector domains. Such may be modeled after natural transcription activation processes. For example, an aptamer, which selectively binds an effector (e.g. an activator or repressor; dimerized MS2 bacteriophage coat proteins as fusion proteins with an activator or repressor), or a protein which itself binds an effector (e.g. activator or repressor) may be appended to a dead gRNA tetraloop and/or a stem-loop 2. In the case of MS2, the fusion protein MS2-VP64 binds to the tetraloop and/or stem-loop 2 and in turn mediates transcriptional up-regulation, for example for Neurog2. Other transcriptional activators are, for example, VP64. P65, HSF1, and MyoD1. By mere example of this concept, replacement of the MS2 stem-loops with PP7-interacting stem-loops may be used to recruit repressive elements.

Accordingly, in particular embodiments of the methods provided herein, use is made of a dead guide, wherein the gRNA further comprises modifications which provide for gene activation or repression, as described herein. The dead gRNA may comprise one or more aptamers. The aptamers may be specific to gene effectors, gene activators or gene repressors. Alternatively, the aptamers may be specific to a protein which in turn is specific to and recruits/binds a specific gene effector, gene activator or gene repressor. If there are multiple sites for activator or repressor recruitment, it is preferred that the sites are specific to either activators or repressors. If there are multiple sites for activator or repressor binding, the sites may be specific to the same activators or same repressors. The sites may also be specific to different activators or different repressors. The gene effectors, gene activators, gene repressors may be present in the form of fusion proteins.

In particular embodiments, the dead gRNA includes a non-naturally occurring or engineered composition comprising two or more adaptor proteins, wherein each protein is associated with one or more functional domains and wherein the adaptor protein binds to the distinct RNA sequence(s) inserted into the at least one loop of the dead gRNA. In certain embodiments, the adaptor protein is a fusion protein comprising the functional domain, the fusion protein optionally comprising a linker between the adaptor protein and the functional domain, the linker optionally including a GlySer linker. In certain embodiments, the one or more functional domains associated with the adaptor protein are selected from: transcriptional activation domains and transcriptional repressor domains. In certain embodiments, the one or more functional domains associated with the adaptor protein are selected from: VP64, p65, MyoD1, HSF1, RTA or SETT/9, KRAB domain, NuE domain, NcoR domain, SID domain or a SID4X domain. In certain embodiments, at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity. In certain embodiments, the DNA cleavage activity is due to a Fok1 nuclease. In certain embodiments, the dead gRNA is modified so that, after dead gRNA binds the adaptor protein and further binds to the Cpf1 and target, the functional domain is in a spatial orientation allowing for the functional domain to function in its attributed function. In certain embodiments, the at least one loop of the dead gRNA is tetra loop and/or loop2. In certain embodiments, the tetra loop and loop 2 of the dead gRNA are modified by the insertion of the distinct RNA sequence(s). In certain embodiments, the insertion of distinct RNA sequence(s) that bind to one or more adaptor proteins is an aptamer sequence. In certain embodiments, the aptamer sequence is two or more aptamer sequences specific to the same adaptor protein. In certain embodiments, the aptamer sequence is two or more aptamer sequences specific to different adaptor protein. In certain embodiments, the adaptor protein comprises MS2, PP7, Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s, PRR1. In certain embodiments, a first adaptor protein is associated with a p65 domain and a second adaptor protein is associated with a HSF1 domain. In certain embodiments, the composition comprises a Cpf1 CRISPR-Cas complex having at least three functional domains, at least one of which is associated with the Cpf1 and at least two of which are associated with dead gRNA.

The use of two different aptamers (each associated with a distinct nucleic acid-targeting guide RNAs) allows an activator-adaptor protein fusion and a repressor-adaptor protein fusion to be used, with different nucleic acid-targeting guide RNAs, to activate expression of one DNA or RNA, whilst repressing another. They, along with their different guide RNAs can be administered together, or substantially together, in a multiplexed approach. A large number of such modified nucleic acid-targeting guide RNAs can be used all at the same time, for example 10 or 20 or 30 and so forth, whilst only one (or at least a minimal number) of effector protein molecules need to be delivered, as a comparatively small number of effector protein molecules can be used with a large number modified guides. The adaptor protein may be associated (preferably linked or fused to) one or more activators or one or more repressors. For example, the adaptor protein may be associated with a first activator and a second activator. The first and second activators may be the same, but they are preferably different activators. Three or more or even four or more activators (or repressors) may be used, but package size may limit the number being higher than 5 different functional domains. Linkers are preferably used, over a direct fusion to the adaptor protein, where two or more functional domains are associated with the adaptor protein. Suitable linkers might include the GlySer linker.

It is also envisaged that the nucleic acid-targeting effector protein-guide RNA complex as a whole may be associated with two or more functional domains. For example, there may be two or more functional domains associated with the nucleic acid-targeting effector protein, or there may be two or more functional domains associated with the guide RNA (via one or more adaptor proteins), or there may be one or more functional domains associated with the nucleic acid-targeting effector protein and one or more functional domains associated with the guide RNA (via one or more adaptor proteins).

The fusion between the adaptor protein and the activator or repressor may include a linker. For example, GlySer linkers GGGS (SEQ ID NO: 18) can be used. They can be used in repeats of 3 ((GGGGS)3 (SEQ ID NO: 19)) or 6 (SEQ ID NO: 20), 9 (SEQ ID NO: 21) or even 12 (SEQ ID NO: 22) or more, to provide suitable lengths, as required. Linkers can be used between the guide RNAs and the functional domain (activator or repressor), or between the nucleic acid-targeting Cas protein (Cas) and the functional domain (activator or repressor). The linkers the user to engineer appropriate amounts of "mechanical flexibility".

The invention comprehends a nucleic acid-targeting complex comprising a nucleic acid-targeting effector protein and a guide RNA, wherein the nucleic acid-targeting effector protein comprises at least one mutation, such that the nucleic acid-targeting effector protein has no more than 5% of the activity of the nucleic acid-targeting effector protein not having the at least one mutation and, optional, at least one or more nuclear localization sequences; the guide RNA comprises a guide sequence capable of hybridizing to a target sequence in a RNA of interest in a cell; and wherein: the nucleic acid-targeting effector protein is associated with two or more functional domains; or at least one loop of the guide RNA is modified by the insertion of distinct RNA sequence(s) that bind to one or more adaptor proteins, and wherein the adaptor protein is associated with two or more functional domains; or the nucleic acid-targeting Cas protein is associated with one or more functional domains and at least one loop of the guide RNA is modified by the insertion of distinct RNA sequence(s) that bind to one or more adaptor proteins, and wherein the adaptor protein is associated with one or more functional domains.

In certain embodiments, the methods may involve the use of a second gRNA, wherein the second gRNA is a live gRNA capable of hybridizing to a second target sequence such that a second Cpf1 CRISPR-Cas system is directed to a second genomic locus of interest in a cell with detectable indel activity at the second genomic locus resultant from nuclease activity of the Cpf1 enzyme of the system. Accordingly, in certain embodiments, the methods involve a plurality of dead gRNAs and/or a plurality of live gRNAs.

Methods for designing, evaluating, or selecting a dead guide RNA targeting sequence (dead guide sequence) for guiding a Cpf1 CRISPR-Cas system to a target gene locus are described e.g. in WO2016094872, incorporated herein by reference in its entirety.

In particular embodiments, the method of selecting a dead guide RNA targeting sequence for directing a functionalized Cpf1 to a gene locus in an organism, without cleavage, comprises a) locating one or more CRISPR motifs in the gene locus; b) analyzing the sequence downstream of each CRISPR motif by i) selecting 10 to 15 nt adjacent to the CRISPR motif, ii) determining the GC content of the sequence, and c) selecting the 10 to 15 nt sequence as a targeting sequence for use in a dead guide RNA if the GC content of the sequence is 30% more, 40% or more. In certain embodiments, the GC content of the targeting sequence is 35% or more, 40% or more, 45% or more, 50% or more, 55% or more, 60% or more, 65% or more, or 70% or more. In certain embodiments, the GC content of the targeting sequence is from 30% to 40% or from 40% to 50% or from 50% to 60% or from 60% to 70%. In an embodiment of the invention, two or more sequences in a gene locus are analyzed and the sequence having the highest GC content is selected. In an embodiment, the portion of the targeting sequence in which GC content is evaluated is 10 to 15 contiguous nucleotides of the 15 target nucleotides nearest to the PAM. In an embodiment of the invention, the portion of the guide in which GC content is considered is the 10 to 11 nucleotides or 11 to 12 nucleotides or 12 to 13 nucleotides or 13, or 14, or 15 contiguous nucleotides of the 15 nucleotides nearest to the PAM. It has been observed that increased GC content in dead guide RNAs of 16 to 20 nucleotides coincides with increased DNA cleavage and reduced functional activation.

It has been demonstrated herein that efficiency of functionalized Cpf1 can be increased by addition of nucleotides to the 3' end of a guide RNA which do not match a target sequence downstream of the CRISPR motif. For example, of dead guide RNA 11 to 15 nt in length, shorter guides may be less likely to promote target cleavage, but are also less efficient at promoting CRISPR system binding and functional control. It is believed that similar effects can be observed for Cpf1.

Multiplex (Tandem) Targeting Approach

The inventors have shown that CRISPR enzymes as defined herein can employ more than one RNA guide without losing activity. This enables the use of the CRISPR enzymes, systems or complexes as defined herein for targeting multiple DNA targets, genes or gene loci, with a single enzyme, system or complex as defined herein. The guide RNAs may be tandemly arranged, optionally separated by a nucleotide sequence such as a direct repeat as defined herein. The position of the different guide RNAs is the tandem does not influence the activity.

Accordingly, the Cpf1 enzyme may form part of a CRISPR system or complex, which further comprises tandemly arranged guide RNAs (gRNAs) comprising a series of 2, 3, 4, 5, 6, 7, 8, 9, 10, 15, 25, 25, 30, or more than 30 guide sequences, each capable of specifically hybridizing to a target sequence in a genomic locus of interest in a cell. In some embodiments, the functional Cpf1 CRISPR system or complex binds to the multiple target sequences. In some embodiments, the functional CRISPR system or complex may edit the multiple target sequences, e.g., the target sequences may comprise a genomic locus, and in some embodiments there may be an alteration of gene expression. In some embodiments, the functional CRISPR system or complex may comprise further functional domains. In some embodiments, the invention provides a method for altering or modifying expression of multiple gene products. The method may comprise introducing into a cell containing said target nucleic acids, e.g., DNA molecules, or containing and expressing target nucleic acid, e.g., DNA molecules; for instance, the target nucleic acids may encode gene products or provide for expression of gene products (e.g., regulatory sequences). In some general embodiments, the Cpf1 enzyme used for multiplex targeting is associated with one or more functional domains. In some more specific embodiments, the CRISPR enzyme used for multiplex targeting is a deadCpf1 as defined herein elsewhere. In some embodiments, each of the guide sequence is at least 16, 17, 18, 19, 20, 25 nucleotides, or between 16-30, or between 16-25, or between 16-20 nucleotides in length.

Examples of multiplex genome engineering using CRISPR effector proteins are provided in Cong et al. (Science February 15; 339(6121):819-23 (2013) and other publications cited herein. More specifically, multiplex gene editing using Cpf1 is described in Zetsche et al. 2016 (doi: dx.doi.org/10.1101/049122).

The application provides methods for developing the therapeutic use of a nucleic acid-targeting system. The nucleic acid-targeting complex an effective means for modifying a target DNA or RNA (single or double stranded, linear or super-coiled). The nucleic acid-targeting complex has a wide variety of utility including modifying (e.g., deleting, inserting, translocating, inactivating, activating) a target DNA or RNA in a multiplicity of cell types. As such the nucleic acid-targeting complex has a broad spectrum of applications in, e.g., gene therapy, drug screening, disease diagnosis, and prognosis. An exemplary nucleic acid-targeting complex comprises a DNA or RNA-targeting effector protein complexed with a guide RNA hybridized to a target sequence within the target locus of interest.

The invention involves developing a therapeutic based on the CRISPR system. In particular embodiments, the therapeutic comprises a DNA-targeting effector protein and/or a guide RNA capable of hybridizing to a target sequence of interest. In particular embodiments, the therapeutic is a vector system comprising one or more vectors, wherein the one or more vectors comprises: a) a first regulatory element operably linked to a nucleotide sequence encoding the Cpf1 effector protein; and b) a second regulatory element operably linked to one or more nucleotide sequences encoding one or more nucleic acid molecules comprising a guide RNA comprising a guide sequence, a direct repeat sequence; wherein components (a) and (b) are located on same or different vectors. In particular embodiments, the therapeutic is a composition comprising a delivery system operably configured to deliver CRISPR-Cpf1 complex components or one or more polynucleotide sequences comprising or encoding said components into a cell, and wherein said CRISPR-Cpf1 complex is operable in the cell; CRISPR-Cas complex components, the CRISPR-Cpf1 complex components, comprising (I) the Cpf1 effector protein as described herein; and guide RNA comprising the guide sequence, and a direct repeat sequence. In any such compositions, the delivery system may comprise a yeast system, a lipofection system, a microinjection system, a biolistic system, virosomes, liposomes, immunoliposomes, polycations, lipid:nucleic acid conjugates or artificial virions, or any other system as described herein. In particular embodiments, the delivery is via a particle, a nanoparticle, a lipid or a cell penetrating peptide (CPP).

In any such compositions, the composition may comprise more than one guide RNA, and each guide RNA has a different target whereby there is multiplexing. In any such systems comprising regulatory elements, at least one of said regulatory elements may comprise a tissue-specific promoter. The tissue-specific promoter may direct expression in a mammalian blood cell, in a mammalian liver cell or in a mammalian eye. In any of the above-described compositions or systems the direct repeat sequence, may comprise one or more protein-interacting RNA aptamers. The one or more aptamers may be located in the tetraloop. The one or more aptamers may be capable of binding MS2 bacteriophage coat protein.

In particular embodiments, the methods provided herein are methods of modifying a locus of interest in a cell comprising contacting the cell with any of the herein-described Cpf1 effector proteins. Any such method may be ex vivo or in vivo.

The invention thus provides a method of treating a disease, disorder or infection in an individual in need thereof comprising identifying suitable treatment conditions and administering an effective amount of the compositions, systems or CRISPR-Cpf1 complexes described herein. The disease, disorder or infection may comprise a viral infection. The viral infection may be HBV. The methods may also be methods for gene or genome editing.

Gene Editing or Altering a Target Loci with Cpf1

In an embodiment, the template nucleic acid alters the structure of the target position by participating in homologous recombination. In an embodiment, the template nucleic acid alters the sequence of the target position. In an embodiment, the template nucleic acid results in the incorporation of a modified, or non-naturally occurring base into the target nucleic acid.

The template sequence may undergo a breakage mediated or catalyzed recombination with the target sequence. In an embodiment, the template nucleic acid may include sequence that corresponds to a site on the target sequence that is cleaved by an Cpf1 mediated cleavage event. In an embodiment, the template nucleic acid may include sequence that corresponds to both, a first site on the target sequence that is cleaved in a first Cpf1 mediated event, and a second site on the target sequence that is cleaved in a second Cpf1 mediated event.

In certain embodiments, the template nucleic acid can include sequence which results in an alteration in the coding sequence of a translated sequence, e.g., one which results in the substitution of one amino acid for another in a protein product, e.g., transforming a mutant allele into a wild type allele, transforming a wild type allele into a mutant allele, and/or introducing a stop codon, insertion of an amino acid residue, deletion of an amino acid residue, or a nonsense mutation. In certain embodiments, the template nucleic acid can include sequence which results in an alteration in a non-coding sequence, e.g., an alteration in an exon or in a 5' or 3' non-translated or non-transcribed region. Such alterations include an alteration in a control element, e.g., a promoter, enhancer, and an alteration in a cis-acting or trans-acting control element.

A template nucleic acid having homology with a target position in a target gene may be used to alter the structure of a target sequence. The template sequence may be used to alter an unwanted structure, e.g., an unwanted or mutant nucleotide. The template nucleic acid may include sequence which, when integrated, results in: decreasing the activity of a positive control element; increasing the activity of a positive control element; decreasing the activity of a negative control element; increasing the activity of a negative control element; decreasing the expression of a gene; increasing the expression of a gene; increasing resistance to a disorder or disease; increasing resistance to viral entry; correcting a mutation or altering an unwanted amino acid residue conferring, increasing, abolishing or decreasing a biological property of a gene product, e.g., increasing the enzymatic activity of an enzyme, or increasing the ability of a gene product to interact with another molecule.

The template nucleic acid may include sequence which results in: a change in sequence of 1, 2, 3, 4, 5, 6, 7, 8, 9, 10, 11, 12 or more nucleotides of the target sequence. In an embodiment, the template nucleic acid may be 20+/−10, 30+/−10, 40+/−10, 50+/−10, 60+/−10, 70+/−10, 80+/−10, 90+/−10, 100+/−10, 1 10+/−10, 120+/−10, 130+/−10, 140+/−10, 150+/−10, 160+/−10, 170+/−10, 1 80+/−10, 190+/−10, 200+/−10, 210+/−10, of 220+/−10 nucleotides in length. In an embodiment, the template nucleic acid may be 30+/−20, 40+/−20, 50+/−20, 60+/−20, 70+/−20, 80+/−20, 90+/−20, 100+/−20, 1 10+/−20, 120+/−20, 130+/−20, 140+/−20, I 50+/−20, 160+/−20, 170+/−20, 180+/−20, 190+/−20, 200+/−20, 210+/−20, of 220+/−20 nucleotides in length. In an embodiment, the template nucleic acid is 10 to 1,000, 20 to 900, 30 to 800, 40 to 700, 50 to 600, 50 to 500, 50 to 400, 50 to 300, 50 to 200, or 50 to 100 nucleotides in length.

A template nucleic acid comprises the following components: [5' homology arm]-[replacement sequence]-[3' homology arm]. The homology arms provide for recombination into the chromosome, thus replacing the undesired element, e.g., a mutation or signature, with the replacement sequence. In an embodiment, the homology arms flank the most distal cleavage sites. In an embodiment, the 3' end of the 5' homology arm is the position next to the 5' end of the replacement sequence. In an embodiment, the 5' homology arm can extend at least 10, 20, 30, 40, 50, 100, 200, 300, 400, 500, 600, 700, 800, 900, 1000, 1500, or 2000 nucleotides 5' from the 5' end of the replacement sequence. In an embodiment, the 5' end of the 3' homology arm is the position next to the 3' end of the replacement sequence. In an embodiment, the 3' homology arm can extend at least 10, 20, 30, 40, 50, 100, 200, 300, 400, 500, 600, 700, 800, 900, 1000, 1500, or 2000 nucleotides 3' from the 3' end of the replacement sequence.

In certain embodiments, one or both homology arms may be shortened to avoid including certain sequence repeat elements. For example, a 5' homology arm may be shortened to avoid a sequence repeat element. In other embodiments, a 3' homology arm may be shortened to avoid a sequence repeat element. In some embodiments, both the 5' and the 3' homology arms may be shortened to avoid including certain sequence repeat elements.

In certain embodiments, a template nucleic acids for correcting a mutation may designed for use as a single-stranded oligonucleotide. When using a single-stranded oligonucleotide, 5' and 3' homology arms may range up to about 200 base pairs (bp) in length, e.g., at least 25, 50, 75, 100, 125, 150, 175, or 200 bp in length.

Cpf1 Effector Protein Complex System Promotes Non-Homologous End-Joining

In certain embodiments, nuclease-induced non-homologous end-joining (NHEJ) can be used to target gene-specific knockouts. Nuclease-induced NHEJ can also be used to remove (e.g., delete) sequence in a gene of interest. Generally, NHEJ repairs a double-strand break in the DNA by joining together the two ends; however, generally, the original sequence is restored only if two compatible ends, exactly as they were formed by the double-strand break, are perfectly ligated. The DNA ends of the double-strand break are frequently the subject of enzymatic processing, resulting in the addition or removal of nucleotides, at one or both strands, prior to rejoining of the ends. This results in the presence of insertion and/or deletion (indel) mutations in the DNA sequence at the site of the NHEJ repair. Two-thirds of these mutations typically alter the reading frame and, therefore, produce a non-functional protein. Additionally, mutations that maintain the reading frame, but which insert or delete a significant amount of sequence, can destroy functionality of the protein. This is locus dependent as mutations in critical functional domains are likely less tolerable than mutations in non-critical regions of the protein. The indel mutations generated by NHEJ are unpredictable in nature; however, at a given break site certain indel sequences are favored and are over represented in the population, likely due to small regions of microhomology. The lengths of deletions can vary widely; most commonly in the 1-50 bp range, but they can easily be greater than 50 bp, e.g., they can easily reach greater than about 100-200 bp. Insertions tend to be shorter and often include short duplications of the sequence immediately surrounding the break site. However, it is possible to obtain large insertions, and in these cases, the inserted sequence has often been traced to other regions of the genome or to plasmid DNA present in the cells.

Because NHEJ is a mutagenic process, it may also be used to delete small sequence motifs as long as the generation of a specific final sequence is not required. If a double-strand break is targeted near to a short target sequence, the deletion mutations caused by the NHEJ repair often span, and therefore remove, the unwanted nucleotides. For the deletion of larger DNA segments, introducing two double-strand breaks, one on each side of the sequence, can result in NHEJ between the ends with removal of the entire intervening sequence. Both of these approaches can be used to delete specific DNA sequences; however, the error-prone nature of NHEJ may still produce indel mutations at the site of repair.

Both double strand cleaving Cpf1 molecules and single strand, or nickase, Cpf1 molecules can be used in the methods and compositions described herein to generate NHEJ- mediated indels. NHEJ-mediated indels targeted to the gene, e.g., a coding region, e.g., an early coding region of a gene of interest can be used to knockout (i.e., eliminate expression of) a gene of interest. For example, early coding region of a gene of interest includes sequence immediately following a transcription start site, within a first exon of the coding sequence, or within 500 bp of the transcription start site (e.g., less than 500, 450, 400, 350, 300, 250, 200, 150, 100 or 50 bp).

In an embodiment, in which a guide RNA and Cpf1 nuclease generate a double strand break for the purpose of inducing NHEJ-mediated indels, a guide RNA may be configured to position one double-strand break in close proximity to a nucleotide of the target position. In an embodiment, the cleavage site may be between 0-500 bp away from the target position (e.g., less than 500, 400, 300, 200, 100, 50, 40, 30, 25, 20, 15, 10, 9, 8, 7, 6, 5, 4, 3, 2 or 1 bp from the target position).

In an embodiment, in which two guide RNAs complexing with Cpf1 nickases induce two single strand breaks for the purpose of inducing NHEJ-mediated indels, two guide RNAs may be configured to position two single-strand breaks to provide for NHEJ repair a nucleotide of the target position.

Cpf1 Effector Protein Complexes Can Deliver Functional Effectors

Unlike CRISPR-Cas-mediated gene knockout, which permanently eliminates expression by mutating the gene at the DNA level, CRISPR-Cas knockdown allows for temporary reduction of gene expression through the use of artificial transcription factors. Mutating key residues in both DNA cleavage domains of the Cpf1 protein, such as FnCpf1 protein (e.g. the D917A and H1006A mutations of the FnCpf1 protein or D908A, E993A, D1263A according to AsCpf1 protein or D832A, E925A, D947A or D1180A according to LbCpf1 protein) results in the generation of a catalytically inactive Cpf1. A catalytically inactive Cpf1 complexes with a guide RNA and localizes to the DNA sequence specified by that guide RNA's targeting domain, however, it does not cleave the target DNA. Fusion of the inactive Cpf1 protein, such as FnCpf1 protein (e.g. the D917A and H1006A mutations) to an effector domain, e.g., a transcription repression domain, enables recruitment of the effector to any DNA site specified by the guide RNA. In certain embodiments, Cpf1 may be fused to a transcriptional repression domain and recruited to the promoter region of a gene. Especially for gene repression, it is contemplated herein that blocking the binding site of an endogenous transcription factor would aid in downregulating gene expression. In another embodiment, an inactive Cpf1 can be fused to a chromatin modifying protein. Altering chromatin status can result in decreased expression of the target gene.

In an embodiment, a guide RNA molecule can be targeted to a known transcription response elements (e.g., promoters, enhancers, etc.), a known upstream activating sequences, and/or sequences of unknown or known function that are suspected of being able to control expression of the target DNA.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In certain embodiments, the CRISPR enzyme comprises one or more mutations selected from the group consisting of D917A, E1006A and D1225A and/or the one or more mutations is in a RuvC domain of the CRISPR enzyme or is a mutation as otherwise as discussed herein. In some embodiments, the CRISPR enzyme has one or more mutations in a catalytic domain, wherein when transcribed, the direct repeat sequence forms a single stem loop and the guide sequence directs sequence-specific binding of a CRISPR complex to the target sequence, and wherein the enzyme further comprises a functional domain. In some embodiments, the functional domain is a transcriptional activation domain, preferably VP64. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

Use of Inactivated CRISPR Cpf1 Enzyme for Detection Methods Such as FISH

In one aspect, the invention provides an engineered, non-naturally occurring CRISPR-Cas system comprising a catalytically inactivate Cas protein described herein, preferably an inactivate Cpf1 (dCpf1), and use this system in detection methods such as fluorescence in situ hybridization (FISH). dCpf1 which lacks the ability to produce DNA double-strand breaks may be fused with a marker, such as fluorescent protein, such as the enhanced green fluorescent protein (eEGFP) and co-expressed with small guide RNAs to target pericentric, centric and telomeric repeats in vivo. The dCpf1 system can be used to visualize both repetitive sequences and individual genes in the human genome. Such new applications of labelled dCpf1 CRISPR-cas systems may be important in imaging cells and studying the functional nuclear architecture, especially in cases with a small nucleus volume or complex 3-D structures. (Chen B, Gilbert L A, Cimini B A, Schnitzbauer J, Zhang W, Li G W, Park J, Blackburn E H, Weissman J S, Qi L S, Huang B. 2013. Dynamic imaging of genomic loci in living human cells by an optimized CRISPR/Cas system. Cell 155(7):1479-91. doi: 10.1016/j.cell.2013.12.001.)

Nucleic Acids, Amino Acids and Proteins, Regulatory Sequences, Vectors, Etc.

The invention uses nucleic acids to bind target DNA sequences. This is advantageous as nucleic acids are much easier and cheaper to produce than proteins, and the specificity can be varied according to the length of the stretch where homology is sought. Complex 3-D positioning of multiple fingers, for example is not required. The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. The term also encompasses nucleic-acid-like structures with synthetic backbones, see, e.g., Eckstein, 1991; Baserga et al., 1992; Milligan, 1993; WO 97/03211; WO 96/39154; Mata, 1997; Strauss-Soukup, 1997; and Samstag, 1996. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. As used herein the term "wild type" is a term of the art understood by skilled persons and means the typical form of an organism, strain, gene or characteristic as it occurs in nature as distinguished from mutant or variant forms. A "wild type" can be a base line. As used herein the term "variant" should be taken to mean the exhibition of qualities that have a pattern that deviates from what occurs in nature. The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. "Complementarity" refers to the ability of a nucleic acid to form hydrogen bond(s) with another nucleic acid sequence by either traditional Watson-Crick base pairing or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. As used herein, "stringent conditions" for hybridization refer to conditions under which a nucleic acid having complementarity to a target sequence predominantly hybridizes with the target sequence, and substantially does not hybridize to non-target sequences. Stringent conditions are generally sequence-dependent, and vary depending on a number of factors. In general, the longer the sequence, the higher the temperature at which the sequence specifically hybridizes to its target sequence. Non-limiting examples of stringent conditions are described in detail in Tijssen (1993), Laboratory Techniques In Biochemistry And Molecular Biology-Hybridization With Nucleic Acid Probes Part I, Second Chapter "Overview of principles of hybridization and the strategy of nucleic acid probe assay", Elsevier, N.Y. Where reference is made to a polynucleotide sequence, then complementary or partially complementary sequences are also envisaged. These are preferably capable of hybridising to the reference sequence under highly stringent conditions. Generally, in order to maximize the hybridization rate, relatively low-stringency hybridization conditions are selected: about 20 to 25° C. lower than the thermal melting point (Tm). The Tm is the temperature at which 50% of specific target sequence hybridizes to a perfectly complementary probe in solution at a defined ionic strength and pH. Generally, in order to require at least about 85% nucleotide complementarity of hybridized sequences, highly stringent washing conditions are selected to be about 5 to 15° C. lower than the Tm. In order to require at least about 70% nucleotide complementarity of hybridized sequences, moderately-stringent washing conditions are selected to be about 15 to 30° C. lower than the Tm. Highly permissive (very low stringency) washing conditions may be as low as 50° C. below the Tm, allowing a high level of mis-matching between hybridized sequences. Those skilled in the art will recognize that other physical and chemical parameters in the hybridization and wash stages can also be altered to affect the outcome of a detectable hybridization signal from a specific level of homology between target and probe sequences. Preferred highly stringent conditions comprise incubation in 50% formamide, 5×SSC, and 1% SDS at 42° C., or incubation in 5×SSC and 1% SDS at 65° C., with wash in 0.2×SSC and 0.1% SDS at 65° C. "Hybridization" refers to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may comprise two strands forming a duplex structure, three or more strands forming a multi stranded complex, a single self-hybridizing strand, or any combination of these. A hybridization reaction may constitute a step in a more extensive process, such as the initiation of PCR, or the cleavage of a polynucleotide by an enzyme. A sequence capable of hybridizing with a given sequence is referred to as the "complement" of the given sequence. As used herein, the term "genomic locus" or "locus" (plural loci) is the specific location of a gene or DNA sequence on a chromosome. A "gene" refers to stretches of DNA or RNA that encode a polypeptide or an RNA chain that has functional role to play in an organism and hence is the molecular unit of heredity in living organisms. For the purpose of this invention it may be considered that genes include regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions. As used herein, "expression of a genomic locus" or "gene expression" is the process by which information from a gene is used in the synthesis of a functional gene product. The products of gene expression are often proteins, but in non-protein coding genes such as rRNA genes or tRNA genes, the product is functional RNA. The process of gene expression is used by all known life—eukaryotes (including multicellular organisms), prokaryotes (bacteria and archaea) and viruses to generate functional products to survive. As used herein "expression" of a gene or nucleic acid encompasses not only cellular gene expression, but also the transcription and translation of nucleic acid(s) in cloning systems and in any other context. As used herein, "expression" also refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell. The terms "polypeptide", "peptide" and "protein" are used interchangeably herein to refer to polymers of amino acids of any length. The polymer may be linear or branched, it may comprise modified amino acids, and it may be interrupted by non amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. As used herein, the term "domain" or "protein domain" refers to a part of a protein sequence that may exist and function independently of the rest of the protein chain. As described in aspects of the invention, sequence identity is related to sequence homology. Homology comparisons may be conducted by eye, or more usually, with the aid of readily available sequence comparison programs. These commercially available computer programs may calculate percent (%) homology between two or more sequences and may also calculate the sequence identity shared by two or more amino acid or nucleic acid sequences.

As used herein the term "wild type" is a term of the art understood by skilled persons and means the typical form of an organism, strain, gene or characteristic as it occurs in nature as distinguished from mutant or variant forms. A "wild type" can be a base line.

As used herein the term "variant" should be taken to mean the exhibition of qualities that have a pattern that deviates from what occurs in nature.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature. In all aspects and embodiments, whether they include these terms or not, it will be understood that, preferably, the may be optional and thus preferably included or not preferably not included. Furthermore, the terms "non-naturally occurring" and "engineered" may be used interchangeably and so can therefore be used alone or in combination and one or other may replace mention of both together. In particular, "engineered" is preferred in place of "non-naturally occurring" or "non-naturally occurring and/or engineered."

Sequence homologies may be generated by any of a number of computer programs known in the art, for example BLAST or FASTA, etc. A suitable computer program for carrying out such an alignment is the GCG Wisconsin Bestfit package (University of Wisconsin, U.S.A; Devereux et al., 1984, Nucleic Acids Research 12:387). Examples of other software than may perform sequence comparisons include, but are not limited to, the BLAST package (see Ausubel et al., 1999 ibid—Chapter 18), FASTA (Atschul et al., 1990, J. Mol. Biol., 403-410) and the GENEWORKS suite of comparison tools. Both BLAST and FASTA are available for offline and online searching (see Ausubel et al., 1999 ibid, pages 7-58 to 7-60). However it is preferred to use the GCG Bestfit program. Percentage (%) sequence homology may be calculated over contiguous sequences, i.e., one sequence is aligned with the other sequence and each amino acid or nucleotide in one sequence is directly compared with the corresponding amino acid or nucleotide in the other sequence, one residue at a time. This is called an "ungapped" alignment. Typically, such ungapped alignments are performed only over a relatively short number of residues. Although this is a very simple and consistent method, it fails to take into consideration that, for example, in an otherwise identical pair of sequences, one insertion or deletion may cause the following amino acid residues to be put out of alignment, thus potentially resulting in a large reduction in % homology when a global alignment is performed. Consequently, most sequence comparison methods are designed to produce optimal alignments that take into consideration possible insertions and deletions without unduly penalizing the overall homology or identity score. This is achieved by inserting "gaps" in the sequence alignment to try to maximize local homology or identity. However, these more complex methods assign "gap penalties" to each gap that occurs in the alignment so that, for the same number of identical amino acids, a sequence alignment with as few gaps as possible—reflecting higher relatedness between the two compared sequences—may achieve a higher score than one with many gaps. "Affinity gap costs" are typically used that charge a relatively high cost for the existence of a gap and a smaller penalty for each subsequent residue in the gap. This is the most commonly used gap scoring system. High gap penalties may, of course, produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension. Calculation of maximum % homology therefore first requires the production of an optimal alignment, taking into consideration gap penalties. A suitable computer program for carrying out such an alignment is the GCG Wisconsin Bestfit package (Devereux et al., 1984 Nuc. Acids Research 12 p 387). Examples of other software than may perform sequence comparisons include, but are not limited to, the BLAST package (see Ausubel et al., 1999 Short Protocols in Molecular Biology, 4th Ed. —Chapter 18), FASTA (Altschul et al., 1990 J. Mol. Biol. 403-410) and the GENEWORKS suite of comparison tools. Both BLAST and FASTA are available for offline and online searching (see Ausubel et al., 1999, Short Protocols in Molecular Biology, pages 7-58 to 7-60). However, for some applications, it is preferred to use the GCG Bestfit program. A new tool, called BLAST 2 Sequences is also available for comparing protein and nucleotide sequences (see FEMS Microbiol Lett. 1999 174 (2): 247-50; FEMS Microbiol Lett. 1999 177(1): 187-8 and the website of the National Center for Biotechnology information at the website of the National Institutes for Health). Although the final % homology may be measured in terms of identity, the alignment process itself is typically not based on an all-or-nothing pair comparison. Instead, a scaled similarity score matrix is generally used that assigns scores to each pair-wise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table, if supplied (see user manual for further details). For some applications, it is preferred to use the public default values for the GCG package, or in the case of other software, the default matrix, such as BLOSUM62. Alternatively, percentage homologies may be calculated using the multiple alignment feature in DNASIS™ (Hitachi Software), based on an algorithm, analogous to CLUSTAL (Higgins D G & Sharp P M (1988), Gene 73(1), 237-244). Once the software has produced an optimal alignment, it is possible to calculate % homology, preferably % sequence identity. The software typically does this as part of the sequence comparison and generates a numerical result. The sequences may also have deletions, insertions or substitutions of amino acid residues which produce a silent change and result in a functionally equivalent substance. Deliberate amino acid substitutions may be made on the basis of similarity in amino acid properties (such as polarity, charge, solubility, hydrophobicity, hydrophilicity, and/or the amphipathic nature of the residues) and it is therefore useful to group amino acids together in functional groups. Amino acids may be grouped together based on the properties of their side chains alone. However, it is more useful to include mutation data as well. The sets of amino acids thus derived are likely to be conserved for structural reasons. These sets may be described in the form of a Venn diagram (Livingstone C. D. and Barton G. J. (1993) "Protein sequence alignments: a strategy for the hierarchical analysis of residue conservation" Comput. Appl. Biosci. 9: 745-756) (Taylor W. R. (1986) "The classification of amino acid conservation" J. Theor. Biol. 119; 205-218). Conservative substitutions may be made, for example according to the table below which describes a generally accepted Venn diagram grouping of amino acids.

TABLE 11

| Set | | Sub-set | |
|---|---|---|---|
| Hydrophobic | F W Y H K M I L V A G C (SEQ ID NO: 72) | Aromatic | F W Y H (SEQ ID NO: 75) |
| | | Aliphatic | I L V |
| Polar | W Y H K R E D C S T N Q (SEQ ID NO: 73) | Charged | H K R E D (SEQ ID NO: 77) |
| | | Positively charged | H K R |
| | | Negatively charged | E D |
| Small | V C A G S P T N D (SEQ ID NO: 74) | Tiny | A G S |

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

The practice of the present invention employs, unless otherwise indicated, conventional techniques of immunology, biochemistry, chemistry, molecular biology, microbiology, cell biology, genomics and recombinant DNA, which are within the skill of the art. See Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)).

Embodiments of the invention include sequences (both polynucleotide or polypeptide) which may comprise homologous substitution (substitution and replacement are both used herein to mean the interchange of an existing amino acid residue or nucleotide, with an alternative residue or nucleotide) that may occur i.e., like-for-like substitution in the case of amino acids such as basic for basic, acidic for acidic, polar for polar, etc. Non-homologous substitution may also occur i.e., from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyridylalanine, thienylalanine, naphthylalanine and phenylglycine. Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, which involves the presence of one or more amino acid residues in peptoid form, may be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., PNAS (1992) 89(20), 9367-9371 and Horwell D C, Trends Biotechnol. (1995) 13(4), 132-134.

Homology modelling: Corresponding residues in other Cpf1 orthologs can be identified by the methods of Zhang et al., 2012 (Nature; 490(7421): 556-60) and Chen et al., 2015 (PLoS Comput Biol; 11(5): e1004248)—a computational protein-protein interaction (PPI) method to predict interactions mediated by domain-motif interfaces. PrePPI (Predicting PPI), a structure based PPI prediction method, combines structural evidence with non-structural evidence using a Bayesian statistical framework. The method involves taking a pair a query proteins and using structural alignment to identify structural representatives that correspond to either their experimentally determined structures or homology models. Structural alignment is further used to identify both close and remote structural neighbours by considering global and local geometric relationships. Whenever two neighbors of the structural representatives form a complex reported in the Protein Data Bank, this defines a template for modelling the interaction between the two query proteins. Models of the complex are created by superimposing the representative structures on their corresponding structural neighbour in the template. This approach is further described in Dey et al., 2013 (Prot Sci; 22: 359-66).

For purpose of this invention, amplification means any method employing a primer and a polymerase capable of replicating a target sequence with reasonable fidelity. Amplification may be carried out by natural or recombinant DNA polymerases such as TaqGold™, T7 DNA polymerase, Klenow fragment of E. coli DNA polymerase, and reverse transcriptase. A preferred amplification method is PCR.

Functional Domains

In some embodiments, one or more functional domains are associated with the Cpf1 effector protein. In some embodiments, one or more functional domains are associated with an adaptor protein, for example as used with the modified guides of Konnerman et al. (Nature 517, 583-588, 29 Jan. 2015). In some embodiments, one or more functional domains are associated with a dead gRNA (dRNA). In some embodiments, a dRNA complex with active Cpf1 effector protein directs gene regulation by a functional domain at on gene locus while an gRNA directs DNA cleavage by the active Cpf1 effector protein at another locus, for example as described analogously in CRISPR-Cas9 systems by Dahlman et al., 'Orthogonal gene control with a catalytically active Cas9 nuclease' (in press). In some embodiments, dRNAs are selected to maximize selectivity of regulation for a gene locus of interest compared to off-target regulation. In some embodiments, dRNAs are selected to maximize target gene regulation and minimize target cleavage For the purposes of the following discussion, reference to a functional domain could be a functional domain associated with the Cpf1 effector protein or a functional domain associated with the adaptor protein.

In the practice of the invention, loops of the gRNA may be extended, without colliding with the Cpf1 protein by the insertion of distinct RNA loop(s) or distinct sequence(s) that may recruit adaptor proteins that can bind to the distinct RNA loop(s) or distinct sequence(s). The adaptor proteins may include but are not limited to orthogonal RNA-binding protein/aptamer combinations that exist within the diversity of bacteriophage coat proteins. A list of such coat proteins includes, but is not limited to: Qβ, F2, GA, fr, JP501, M12, R17, BZ13, JP34, JP500, KU1, M11, MX1, TW18, VK, SP, FI, ID2, NL95, TW19, AP205, φCb5, φCb8r, φCb12r, φCb23r, 7s and PRR1. These adaptor proteins or orthogonal RNA binding proteins can further recruit effector proteins or fusions which comprise one or more functional domains. In some embodiments, the functional domain may be selected from the group consisting of: transposase domain, integrase domain, recombinase domain, resolvase domain, invertase domain, protease domain, DNA methyltransferase domain, DNA hydroxylmethylase domain, DNA demethylase domain, histone acetylase domain, histone deacetylases domain, nuclease domain, repressor domain, activator domain, nuclear-localization signal domains, transcription-regulatory protein (or transcription complex recruiting) domain, cellular uptake activity associated domain, nucleic acid binding domain, antibody presentation domain, histone modifying enzymes, recruiter of histone modifying enzymes; inhibitor of histone modifying enzymes, histone methyltransferase, histone demethylase, histone kinase, histone phosphatase, histone ribosylase, histone deribosylase, histone ubiquitinase, histone deubiquitinase, histone biotinase and histone tail protease. In some preferred embodiments, the functional domain is a transcriptional activation domain, such as, without limitation, VP64, p65, MyoD1, HSF1, RTA, SETT/9 or a histone acetyltransferase. In some embodiments, the functional domain is a transcription repression domain, preferably KRAB. In some embodiments, the transcription repression domain is SID, or concatemers of SID (eg SID4X). In some embodiments, the functional domain is an epigenetic modifying domain, such that an epigenetic modifying enzyme is provided. In some embodiments, the functional domain is an activation domain, which may be the P65 activation domain.

In some embodiments, the one or more functional domains is an NLS (Nuclear Localization Sequence) or an NES (Nuclear Export Signal). In some embodiments, the one or more functional domains is a transcriptional activation domain comprises VP64, p65, MyoD1, HSF1, RTA, SET7/9 and a histone acetyltransferase. Other references herein to activation (or activator) domains in respect of those associated with the CRISPR enzyme include any known transcriptional activation domain and specifically VP64, p65, MyoD1, HSF1, RTA, SET7/9 or a histone acetyltransferase.

In some embodiments, the one or more functional domains is a transcriptional repressor domain. In some embodiments, the transcriptional repressor domain is a KRAB domain. In some embodiments, the transcriptional repressor domain is a NuE domain, NcoR domain, SID domain or a SID4X domain.

In some embodiments, the one or more functional domains have one or more activities comprising methylase activity, demethylase activity, transcription activation activity, transcription repression activity, transcription release factor activity, histone modification activity, RNA cleavage activity, DNA cleavage activity, DNA integration activity or nucleic acid binding activity.

Histone modifying domains are also preferred in some embodiments. Exemplary histone modifying domains are discussed below. Transposase domains, HR (Homologous Recombination) machinery domains, recombinase domains, and/or integrase domains are also preferred as the present functional domains. In some embodiments, DNA integration activity includes HR machinery domains, integrase domains, recombinase domains and/or transposase domains. Histone acetyltransferases are preferred in some embodiments.

In some embodiments, the DNA cleavage activity is due to a nuclease. In some embodiments, the nuclease comprises a Fok1 nuclease. See, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

In some embodiments, the one or more functional domains is attached to the Cpf1 effector protein so that upon binding to the sgRNA and target the functional domain is in a spatial orientation allowing for the functional domain to function in its attributed function.

In some embodiments, the one or more functional domains is attached to the adaptor protein so that upon binding of the Cpf1 effector protein to the gRNA and target, the functional domain is in a spatial orientation allowing for the functional domain to function in its attributed function.

In an aspect the invention provides a composition as herein discussed wherein the one or more functional domains is attached to the Cpf1 effector protein or adaptor protein via a linker, optionally a GlySer linker, as discussed herein.

Endogenous transcriptional repression is often mediated by chromatin modifying enzymes such as histone methyltransferases (HMTs) and deacetylases (HDACs). Repressive histone effector domains are known and an exemplary list is provided below. In the exemplary table, preference was given to proteins and functional truncations of small size to facilitate efficient viral packaging (for instance via AAV). In general, however, the domains may include HDACs, histone methyltransferases (HMTs), and histone acetyltransferase (HAT) inhibitors, as well as HDAC and HMT recruiting proteins. The functional domain may be or include, in some embodiments, HDAC Effector Domains, HDAC Recruiter Effector Domains, Histone Methyltransferase (HMT) Effector Domains, Histone Methyltransferase (HMT) Recruiter Effector Domains, or Histone Acetyltransferase Inhibitor Effector Domains.

TABLE 12

HDAC Effector Domains

| Subtype/Complex | Name | Substrate (if known) | Modification (if known) | Organism | Full size (aa) | Selected truncation (aa) | Final size (aa) | Catalytic domain |
|---|---|---|---|---|---|---|---|---|
| HDAC I | HDAC8 | — | — | X. laevis | 325 | 1-325 | 325 | 1-272: HDAC |
| HDAC I | RPD3 | — | — | S. cerevisiae | 433 | 19-340 | 322 (Vannier) | 19-331: HDAC |
| HDAC IV | MesoLo4 | — | — | M. loti | 300 | 1-300 (Gregoretti) | 300 | — |

TABLE 12-continued

HDAC Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| HDAC IV | HDAC11 | — | — | *H. sapiens* | 347 | 1-347 (Gao) | 347 | 14-326: HDAC |
| HD2 | HDT1 | — | — | *A. thaliana* | 245 | 1-211 (Wu) | 211 | — |
| SIRT I | SIRT3 | H3K9Ac H4K16Ac H3K56Ac | — | *H. sapiens* | 399 | 143-399 (Scher) | 257 | 126-382: SIRT |
| SIRT I | HST2 | — | — | *C. albicans* | 331 | 1-331 (Hnisz) | 331 | — |
| SIRT I | CobB | — | — | *E. coli* (K12) | 242 | 1-242 (Landry) | 242 | — |
| SIRT I | HST2 | — | — | *S. cerevisiae* | 357 | 8-298 (Wilson) | 291 | — |
| SIRT III | SIRT5 | H4K8Ac H4K16Ac | — | *H. sapiens* | 310 | 37-310 (Gertz) | 274 | 41-309: SIRT |
| SIRT III | Sir2A | — | — | *P. falciparum* | 273 | 1-273 (Zhu) | 273 | 19-273: SIRT |
| SIRT IV | SIRT6 | H3K9Ac H3K56Ac | — | *H. sapiens* | 355 | 1-289 (Tennen) | 289 | 35-274: SIRT |

Accordingly, the repressor domains of the present invention may be selected from histone methyltransferases (HMTs), histone deacetylases (HDACs), histone acetyltransferase (HAT) inhibitors, as well as HDAC and HMT recruiting proteins.

The HDAC domain may be any of those in the table above, namely: HDAC8, RPD3, MesoLo4, HDAC11, HDT1, SIRT3, HST2, CobB, HST2, SIRT5, Sir2A, or SIRT6.

In some embodiment, the functional domain may be a HDAC Recruiter Effector Domain. Preferred examples include those in the Table below, namely MeCP2, MBD2b, Sin3a, NcoR, SALL1, RCOR1. NcoR is exemplified in the present Examples and, although preferred, it is envisaged that others in the class will also be useful.

TABLE 13

Table of HDAC Recruiter Effector Domains

| Subtype/ Complex | Name | Substrate (if known) | Modification (if known) | Organism | Full size (aa) | Selected truncation (aa) | Final size (aa) | Catalytic domain |
|---|---|---|---|---|---|---|---|---|
| Sin3a | MeCP2 | — | — | *R. norvegicus* | 492 | 207-492 (Nan) | 286 | — |
| Sin3a | MBD2b | — | — | *H. sapiens* | 262 | 45-262 (Boeke) | 218 | — |
| Sin3a | Sin3a | — | — | *H. sapiens* | 1273 | 524-851 (Laherty) | 328 | 627-829: HDAC1 interaction |
| NcoR | NcoR | — | — | *H. sapiens* | 2440 | 420-488 (Zhang) | 69 | — |
| NuRD | SALL1 | — | — | *M. musculus* | 1322 | 1-93 (Lauberth) | 93 | — |
| CoREST | RCOR1 | — | — | *H. sapiens* | 482 | 81-300 (Gu, Ouyang) | 220 | — |

In some embodiment, the functional domain may be a Methyltransferase (HMT) Effector Domain. Preferred examples include those in the Table below, namely NUE, vSET, EHMT2/G9A, SUV39H1, dim-5, KYP, SUVR4, SET4, SET1, SETD8, and TgSET8. NUE is exemplified in the present Examples and, although preferred, it is envisaged that others in the class will also be useful.

TABLE 14

Table of Histone Methyltransferase (HMT) Effector Domains

| Subtype Complex | Name | Substrate (if known) | Modification (if known) | Organism | Full size (aa) | Selected truncation (aa) | Final size (aa) | Catalytic domain |
|---|---|---|---|---|---|---|---|---|
| SET | NUE | H2B, H3, H4 | — | *C. trachomatis* | 219 | 1-219 (Pennini) | 219 | — |
| SET | vSET | — | H3K27me3 | *P. bursaria chlorella virus* | 119 | 1-119 (Mujtaba) | 119 | 4-112: SET2 |
| SUV39 family | EHMT2/G9A | H1.4K2, H3K9, H3K27 | H3K9me1/2, H1K25me1 | *M. musculus* | 1263 | 969-1263 (Tachibana) | 295 | 1025-1233: preSET, SET, postSET |
| SUV39 | SUV39H1 | — | H3K9me2/3 | *H. sapiens* | 412 | 79-412 (Snowden) | 334 | 172-412: preSET, SET, postSET |
| Suvar3-9 | dim-5 | — | H3K9me3 | *N. crassa* | 331 | 1-331 (Rathert) | 331 | 77-331: preSET, SET, postSET |
| Suvar3-9 (SUVH subfamily) | KYP | — | H3K9me1/2 | *A. thaliana* | 624 | 335-601 | 267 (Jackson) | — |
| Suvar3-9 (SUVR subfamily) | SUVR4 | H3K9me1 | H3K9me2/3 | *A. thaliana* | 492 | 180-492 | 313 (Thorstensen) | 192-462: preSET, SET, postSET |
| Suvar4-20 | SET4 | — | H4K20me3 | *C. elegans* | 288 | 1-288 (Vielle) | 288 | — |
| SET8 | SET1 | — | H4K20me1 | *C. elegans* | 242 | 1-242 (Vielle) | 242 | — |
| SET8 | SETD8 | — | H4K20me1 | *H. sapiens* | 393 | 185-393 | 209 (Couture) | 256-382: SET |
| SET8 | TgSET8 | — | H4K20me1/2/3 | *T. gondii* | 1893 | 1590-1893 (Sautel) | 304 | 1749-1884: SET |

In some embodiment, the functional domain may be a Histone Methyltransferase (HMT) Recruiter Effector Domain. Preferred examples include those in the Table below, namely Hp1a, PHF19, and NIPP1.

TABLE 15

Table of Histone Methyltransferase (HMT) Recruiter Effector Domains

| Subtype Complex | Name | Substrate (if known) | Modification (if known) | Organism | Full size (aa) | Selected truncation (aa) | Final size (aa) | Catalytic domain |
|---|---|---|---|---|---|---|---|---|
| — | Hp1a | — | H3K9me3 | *M. musculus* | 191 | 73-191 | 119 (Hathaway) | 121-179: chromoshadow |
| — | PHF19 | — | H3K27me3 | *H. sapiens* | 580 | (1-250) + GGSG linker + (500-580) | 335 (Ballaré) | 163-250: PHD2 |
| — | NIPP1 | — | H3K27me3 | *H. sapiens* | 351 | 1-329 (Jin) | 329 | 310-329: EED |

In some embodiment, the functional domain may be Histone Acetyltransferase Inhibitor Effector Domain. Preferred examples include SET/TAF-1β listed in the Table below.

TABLE 16

Table of Histone Acetyltransferase Inhibitor Effector Domains

| Subtype Complex | Name | Substrate (if known) | Modification (if known) | Organism | Full size (aa) | Selected truncation (aa) | Final size (aa) | Catalytic domain |
|---|---|---|---|---|---|---|---|---|
| — | SET/TAF-1β | — | — | *M. musculus* | 289 | 1-289 (Cervoni) | 289 | — |

It is also preferred to target endogenous (regulatory) control elements (such as enhancers and silencers) in addition to a promoter or promoter-proximal elements. Thus, the invention can also be used to target endogenous control elements (including enhancers and silencers) in addition to targeting of the promoter. These control elements can be located upstream and downstream of the transcriptional start site (TSS), starting from 200 bp from the TSS to 100 kb away. Targeting of known control elements can be used to activate or repress the gene of interest. In some cases, a single control element can influence the transcription of multiple target genes. Targeting of a single control element could therefore be used to control the transcription of multiple genes simultaneously.

Targeting of putative control elements on the other hand (e.g. by tiling the region of the putative control element as well as 200 bp up to 100 kB around the element) can be used as a means to verify such elements (by measuring the transcription of the gene of interest) or to detect novel control elements (e.g. by tiling 100 kb upstream and downstream of the TSS of the gene of interest). In addition, targeting of putative control elements can be useful in the context of understanding genetic causes of disease. Many mutations and common SNP variants associated with disease phenotypes are located outside coding regions. Targeting of such regions with either the activation or repression systems described herein can be followed by readout of transcription of either a) a set of putative targets (e.g. a set of genes located in closest proximity to the control element) or b) whole-transcriptome readout by e.g. RNAseq or microarray. This would allow for the identification of likely candidate genes involved in the disease phenotype. Such candidate genes could be useful as novel drug targets.

Histone acetyltransferase (HAT) inhibitors are mentioned herein. However, an alternative in some embodiments is for the one or more functional domains to comprise an acetyltransferase, preferably a histone acetyltransferase. These are useful in the field of epigenomics, for example in methods of interrogating the epigenome. Methods of interrogating the epigenome may include, for example, targeting epigenomic sequences. Targeting epigenomic sequences may include the guide being directed to an epigenomic target sequence. Epigenomic target sequence may include, in some embodiments, include a promoter, silencer or an enhancer sequence.

Use of a functional domain linked to a Cpf1 effector protein as described herein, preferably a dead-Cpf1 effector protein, more preferably a dead-FnCpf1 effector protein, to target epigenomic sequences can be used to activate or repress promoters, silencer or enhancers.

Examples of acetyltransferases are known but may include, in some embodiments, histone acetyltransferases. In some embodiments, the histone acetyltransferase may comprise the catalytic core of the human acetyltransferase p300 (Gerbasch & Reddy, Nature Biotech 6 Apr. 2015).

In some preferred embodiments, the functional domain is linked to a dead-Cpf1 effector protein to target and activate epigenomic sequences such as promoters or enhancers. One or more guides directed to such promoters or enhancers may also be provided to direct the binding of the CRISPR enzyme to such promoters or enhancers.

The term "associated with" is used here in relation to the association of the functional domain to the Cpf1 effector protein or the adaptor protein. It is used in respect of how one molecule 'associates' with respect to another, for example between an adaptor protein and a functional domain, or between the Cpf1 effector protein and a functional domain. In the case of such protein-protein interactions, this association may be viewed in terms of recognition in the way an antibody recognizes an epitope. Alternatively, one protein may be associated with another protein via a fusion of the two, for instance one subunit being fused to another subunit. Fusion typically occurs by addition of the amino acid sequence of one to that of the other, for instance via splicing together of the nucleotide sequences that encode each protein or subunit. Alternatively, this may essentially be viewed as binding between two molecules or direct linkage, such as a fusion protein. In any event, the fusion protein may include a linker between the two subunits of interest (i.e. between the enzyme and the functional domain or between the adaptor protein and the functional domain). Thus, in some embodiments, the Cpf1 effector protein or adaptor protein is associated with a functional domain by binding thereto. In other embodiments, the Cpf1 effector protein or adaptor protein is associated with a functional domain because the two are fused together, optionally via an intermediate linker.

Attachment of a functional domain or fusion protein can be via a linker, e.g., a flexible glycine-serine (GlyGlyGlySer) or (GGGS)3 (SEQ ID NO: 18) or a rigid alpha-helical linker such as (Ala(GluAlaAlaAlaLys)Ala). Linkers such as (GGGGS)3 (SEQ ID NO: 19) are preferably used herein to separate protein or peptide domains. (GGGGS)3 (SEQ ID NO: 19) is preferable because it is a relatively long linker (15 amino acids). The glycine residues are the most flexible and the serine residues enhance the chance that the linker is on the outside of the protein. (GGGGS)$_6$ (SEQ ID NO: 20) (GGGGS)$_9$ (SEQ ID NO: 21) or (GGGGS)$_{12}$ (SEQ ID NO: 22) may preferably be used as alternatives. Other preferred alternatives are (GGGGS)$_1$ (SEQ ID NO: 70), (GGGGS)$_2$ (SEQ ID NO: 71), (GGGGS)$_4$ (SEQ ID NO: 82), (GGGGS)$_5$ (SEQ ID NO: 83), (GGGGS)$_7$ (SEQ ID NO: 85), (GGGGS)$_8$ (SEQ ID NO: 86), (GGGGS)$_{10}$ (SEQ ID NO: 87), or (GGGGS)$_{11}$ (SEQ ID NO: 88). Alternative linkers are available, but highly flexible linkers are thought to work best to allow for maximum opportunity for the 2 parts of the Cpf1 to come together and thus reconstitute Cpf1 activity. One alternative is that the NLS of nucleoplasmin can be used as a linker. For example, a linker can also be used between the Cpf1 and any functional domain. Again, a (GGGGS)$_3$ (SEQ ID NO: 19) linker may be used here (or the 6, 9, or 12 repeat versions therefore) or the NLS of nucleoplasmin can be used as a linker between Cpf1 and the functional domain.

Cpf1 Effector Protein Complexes can be Used in Non-Animal Organisms, Such as Plants, Algae, Fungi, Yeasts, Etc The Cpf1 effector protein system(s) (e.g., single or multiplexed) can be used in conjunction with recent advances in crop genomics. The systems described herein can be used to perform efficient and cost effective plant gene or genome interrogation or editing or manipulation—for instance, for rapid investigation and/or selection and/or interrogations and/or comparison and/or manipulations and/or transformation of plant genes or genomes; e.g., to create, identify, develop, optimize, or confer trait(s) or characteristic(s) to plant(s) or to transform a plant genome. There can accordingly be improved production of plants, new plants with new combinations of traits or characteristics or new plants with enhanced traits. The Cpf1 effector protein system(s) can be used with regard to plants in Site-Directed Integration (SDI) or Gene Editing (GE) or any Near Reverse Breeding (NRB) or Reverse Breeding (RB) techniques. Aspects of utilizing the herein described Cpf1 effector protein systems may be analogous to the use of the CRISPR-Cas (e.g. CRISPR-Cas9) system in plants, and mention is made of the University of Arizona website "CRISPR-PLANT" (www.genome.arizona.edu/crispr/) (supported by Penn State and AGI). Embodiments of the invention can be used in genome editing in plants or where RNAi or similar genome editing techniques have been used previously; see, e.g., Nekrasov, "Plant genome editing made easy: targeted mutagenesis in model and crop plants using the CRISPR-Cas system," Plant Methods 2013, 9:39 (doi:10.1186/1746-4811-9-39); Brooks, "Efficient gene editing in tomato in the first generation using the CRISPR-Cas9 system," Plant Physiology September 2014 pp 114.247577; Shan, "Targeted genome modification of crop plants using a CRISPR-Cas system," Nature Biotechnology 31, 686-688 (2013); Feng, "Efficient genome editing in plants using a CRISPR/Cas system," Cell Research (2013) 23:1229-1232. doi:10.1038/cr.2013.114; published online 20 Aug. 2013; Xie, "RNA-guided genome editing in plants using a CRISPR-Cas system," Mol Plant. 2013 November; 6(6):1975-83. doi: 10.1093/mp/sst119. Epub 2013 Aug. 17; Xu, "Gene targeting using the *Agrobacterium tumefaciens*-mediated CRISPR-Cas system in rice," Rice 2014, 7:5 (2014), Zhou et al., "Exploiting SNPs for biallelic CRISPR mutations in the outcrossing woody perennial *Populus* reveals 4-coumarate: CoA ligase specificity and Redundancy," New Phytologist (2015) (Forum) 1-4 (available online only at www.newphytologist.com); Caliando et al, "Targeted DNA degradation using a CRISPR device stably carried in the host genome, NATURE COMMUNICATIONS 6:6989, DOI: 10.1038/ncomms7989, www.nature.com/naturecommunications DOI: 10.1038/ncomms7989; U.S. Pat. No. 6,603,061-*Agrobacterium*-Mediated Plant Transformation Method; U.S. Pat. No. 7,868,149—Plant Genome Sequences and Uses Thereof and US 2009/0100536—Transgenic Plants with Enhanced Agronomic Traits, all the contents and disclosure of each of which are herein incorporated by reference in their entirety. In the practice of the invention, the contents and disclosure of Morrell et al "Crop genomics: advances and applications," Nat Rev Genet. 2011 Dec. 29; 13(2):85-96; each of which is incorporated by reference herein including as to how herein embodiments may be used as to plants. Accordingly, reference herein to animal cells may also apply, mutatis mutandis, to plant cells unless otherwise apparent; and, the enzymes herein having reduced off-target effects and systems employing such enzymes can be used in plant applications, including those mentioned herein.

Application of Cpf1 CRISPR System to Plants and Yeast

Definitions

In general, the term "plant" relates to any various photosynthetic, eukaryotic, unicellular or multicellular organism of the kingdom Plantae characteristically growing by cell division, containing chloroplasts, and having cell walls comprised of cellulose. The term plant encompasses monocotyledonous and dicotyledonous plants. Specifically, the plants are intended to comprise without limitation angiosperm and gymnosperm plants such as acacia, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, eucalyptus, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, papaya, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. The term plant also encompasses Algae, which are mainly photoautotrophs unified primarily by their lack of roots, leaves and other organs that characterize higher plants.

The methods for genome editing using the Cpf1 system as described herein can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the methods and CRISPR-Cas systems can be used over a broad range of plants, such as for example with dicotyledonous plants belonging to the orders Magnoliales, Illiciales, Laurales, Piperales, Aristochiales, Nymphaeales, Ranunculales, Papaveraceae, Sarraceniaceae, Trochodendrales, Hamamelidales, Eucommia, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales; the methods and CRISPR-Cas systems can be used with monocotyledonous plants such as those belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales, or with plants belonging to Gymnospermae, e.g those belonging to the orders Pinales, Ginkgoales, Cycadales, Araucariales, Cupressales and Gnetales.

The Cpf1 CRISPR systems and methods of use described herein can be used over a broad range of plant species, included in the non-limitative list of dicot, monocot or gymnosperm genera hereunder: *Atropa, Alseodaphne, Anacardium, Arachis, Beilschmiedia, Brassica, Carthamus, Cocculus, Croton, Cucumis, Citrus, Citrullus, Capsicum, Catharanthus, Cocos, Coffea, Cucurbita, Daucus, Duguetia, Eschscholzia, Ficus, Fragaria, Glaucium, Glycine, Gossypium, Helianthus, Hevea, Hyoscyamus, Lactuca, Landolphia, Linum, Litsea, Lycopersicon, Lupinus, Manihot, Majorana, Malus, Medicago, Nicotiana, Olea, Parthenium, Papaver, Persea, Phaseolus, Pistacia, Pisum, Pyrus, Prunus, Raphanus, Ricinus, Senecio, Sinomenium, Stephania, Sinapis, Solanum, Theobroma, Trifolium, Trigonella, Vicia, Vinca, Vilis,* and *Vigna*; and the genera *Allium, Andropogon, Eragrostis, Asparagus, Avena, Cynodon, Elaeis, Festuca, Festulolium, Heterocallis, Hordeum, Lemna, Lolium, Musa, Oryza, Panicum, Pennisetum, Phleum, Poa, Secale, Sorghum, Triticum, Zea, Abies, Cunninghamia, Ephedra, Picea, Pinus,* and *Pseudotsuga*.

The Cpf1 CRISPR systems and methods of use can also be used over a broad range of "algae" or "algae cells"; including for example algea selected from several eukaryotic phyla, including the Rhodophyta (red algae), Chlorophyta (green algae), Phaeophyta (brown algae), Bacillariophyta (diatoms), Eustigmatophyta and dinoflagellates as well as the prokaryotic phylum Cyanobacteria (blue-green algae). The term "algae" includes for example algae selected from: Amphora, *Anabaena, Anikstrodesmus, Botryococcus, Chaetoceros, Chlamydomonas, Chlorella, Chlorococcum, Cyclotella, Cylindrotheca, Dunaliella, Emiliana, Euglena, Haematococcus, Isochrysis, Monochrysis, Monoraphidium, Nannochloris, Nannnochloropsis, Navicula, Nephrochloris, Nephroselmis, Nitzschia, Nodularia, Nostoc, Oochromonas, Oocystis, Oscillrtoria, Pavlova, Phaeodactylum, Platymonas, Pleurochrysis, Porphyra, Pseudoanabaena, Pyramimonas, Stichococcus, Synechococcus, Synechocystis, Tetraselmis, Thalassiosira,* and *Trichodesmium*.

A part of a plant, i.e., a "plant tissue" may be treated according to the methods of the present invention to produce an improved plant. Plant tissue also encompasses plant cells. The term "plant cell" as used herein refers to individual units of a living plant, either in an intact whole plant or in an isolated form grown in in vitro tissue cultures, on media or agar, in suspension in a growth media or buffer or as a part of higher organized unites, such as, for example, plant tissue, a plant organ, or a whole plant.

A "protoplast" refers to a plant cell that has had its protective cell wall completely or partially removed using, for example, mechanical or enzymatic means resulting in an intact biochemical competent unit of living plant that can reform their cell wall, proliferate and regenerate grow into a whole plant under proper growing conditions.

The term "transformation" broadly refers to the process by which a plant host is genetically modified by the introduction of DNA by means of Agrobacteria or one of a variety of chemical or physical methods. As used herein, the term "plant host" refers to plants, including any cells, tissues, organs, or progeny of the plants. Many suitable plant tissues or plant cells can be transformed and include, but are not limited to, protoplasts, somatic embryos, pollen, leaves, seedlings, stems, calli, stolons, microtubers, and shoots. A plant tissue also refers to any clone of such a plant, seed, progeny, propagule whether generated sexually or asexually, and descendents of any of these, such as cuttings or seed.

The term "transformed" as used herein, refers to a cell, tissue, organ, or organism into which a foreign DNA molecule, such as a construct, has been introduced. The introduced DNA molecule may be integrated into the genomic DNA of the recipient cell, tissue, organ, or organism such that the introduced DNA molecule is transmitted to the subsequent progeny. In these embodiments, the "transformed" or "transgenic" cell or plant may also include progeny of the cell or plant and progeny produced from a breeding program employing such a transformed plant as a parent in a cross and exhibiting an altered phenotype resulting from the presence of the introduced DNA molecule. Preferably, the transgenic plant is fertile and capable of transmitting the introduced DNA to progeny through sexual reproduction.

The term "progeny", such as the progeny of a transgenic plant, is one that is born of, begotten by, or derived from a plant or the transgenic plant. The introduced DNA molecule may also be transiently introduced into the recipient cell such that the introduced DNA molecule is not inherited by subsequent progeny and thus not considered "transgenic". Accordingly, as used herein, a "non-transgenic" plant or plant cell is a plant which does not contain a foreign DNA stably integrated into its genome.

The term "plant promoter" as used herein is a promoter capable of initiating transcription in plant cells, whether or not its origin is a plant cell. Exemplary suitable plant promoters include, but are not limited to, those that are obtained from plants, plant viruses, and bacteria such as *Agrobacterium* or *Rhizobium* which comprise genes expressed in plant cells.

As used herein, a "fungal cell" refers to any type of eukaryotic cell within the kingdom of fungi. Phyla within the kingdom of fungi include Ascomycota, Basidiomycota, Blastocladiomycota, Chytridiomycota, Glomeromycota, Microsporidia, and Neocallimastigomycota. Fungal cells may include yeasts, molds, and filamentous fungi. In some embodiments, the fungal cell is a yeast cell.

As used herein, the term "yeast cell" refers to any fungal cell within the phyla Ascomycota and Basidiomycota. Yeast cells may include budding yeast cells, fission yeast cells, and mold cells. Without being limited to these organisms, many types of yeast used in laboratory and industrial settings are part of the phylum Ascomycota. In some embodiments, the yeast cell is an *S. cerevisiae, Kluyveromyces marxianus*, or *Issatchenkia orientalis* cell. Other yeast cells may include without limitation *Candida* spp. (e.g., *Candida albicans*), *Yarrowia* spp. (e.g., *Yarrowia lipolytica*), *Pichia* spp. (e.g., *Pichia pastoris*), *Kluyveromyces* spp. (e.g., *Kluyveromyces lactis* and *Kluyveromyces marxianus*), *Neurospora* spp. (e.g., *Neurospora crassa*), *Fusarium* spp. (e.g., *Fusarium oxysporum*), and *Issatchenkia* spp. (e.g., *Issatchenkia orientalis*, a.k.a. *Pichia kudriavzevii* and *Candida acidothermophilum*). In some embodiments, the fungal cell is a filamentous fungal cell. As used herein, the term "filamentous fungal cell" refers to any type of fungal cell that grows in filaments, i.e., hyphae or mycelia. Examples of filamentous fungal cells may include without limitation *Aspergillus* spp. (e.g., *Aspergillus niger*), *Trichoderma* spp. (e.g., *Trichoderma reesei*), *Rhizopus* spp. (e.g., *Rhizopus oryzae*), and *Mortierella* spp. (e.g., *Mortierella isabellina*).

In some embodiments, the fungal cell is an industrial strain. As used herein, "industrial strain" refers to any strain of fungal cell used in or isolated from an industrial process, e.g., production of a product on a commercial or industrial scale. Industrial strain may refer to a fungal species that is typically used in an industrial process, or it may refer to an isolate of a fungal species that may be also used for non-industrial purposes (e.g., laboratory research). Examples of industrial processes may include fermentation (e.g., in production of food or beverage products), distillation, biofuel production, production of a compound, and production of a polypeptide. Examples of industrial strains may include, without limitation, JAY270 and ATCC4124.

In some embodiments, the fungal cell is a polyploid cell. As used herein, a "polyploid" cell may refer to any cell whose genome is present in more than one copy. A polyploid cell may refer to a type of cell that is naturally found in a polyploid state, or it may refer to a cell that has been induced to exist in a polyploid state (e.g., through specific regulation, alteration, inactivation, activation, or modification of meiosis, cytokinesis, or DNA replication). A polyploid cell may refer to a cell whose entire genome is polyploid, or it may refer to a cell that is polyploid in a particular genomic locus of interest. Without wishing to be bound to theory, it is thought that the abundance of guideRNA may more often be a rate-limiting component in genome engineering of polyploid cells than in haploid cells, and thus the methods using the Cpf1 CRISPRS system described herein may take advantage of using a certain fungal cell type.

In some embodiments, the fungal cell is a diploid cell. As used herein, a "diploid" cell may refer to any cell whose genome is present in two copies. A diploid cell may refer to a type of cell that is naturally found in a diploid state, or it may refer to a cell that has been induced to exist in a diploid state (e.g., through specific regulation, alteration, inactivation, activation, or modification of meiosis, cytokinesis, or DNA replication). For example, the *S. cerevisiae* strain S228C may be maintained in a haploid or diploid state. A diploid cell may refer to a cell whose entire genome is diploid, or it may refer to a cell that is diploid in a particular genomic locus of interest. In some embodiments, the fungal cell is a haploid cell. As used herein, a "haploid" cell may refer to any cell whose genome is present in one copy. A haploid cell may refer to a type of cell that is naturally found in a haploid state, or it may refer to a cell that has been induced to exist in a haploid state (e.g., through specific regulation, alteration, inactivation, activation, or modification of meiosis, cytokinesis, or DNA replication). For example, the *S. cerevisiae* strain S228C may be maintained in a haploid or diploid state. A haploid cell may refer to a cell whose entire genome is haploid, or it may refer to a cell that is haploid in a particular genomic locus of interest.

As used herein, a "yeast expression vector" refers to a nucleic acid that contains one or more sequences encoding an RNA and/or polypeptide and may further contain any desired elements that control the expression of the nucleic acid(s), as well as any elements that enable the replication and maintenance of the expression vector inside the yeast cell. Many suitable yeast expression vectors and features thereof are known in the art; for example, various vectors and techniques are illustrated in Yeast Protocols, 2nd edition, Xiao, W., ed. (Humana Press, New York, 2007) and Buckholz, R. G. and Gleeson, M. A. (1991) Biotechnology (NY) 9(11): 1067-72. Yeast vectors may contain, without limitation, a centromeric (CEN) sequence, an autonomous replication sequence (ARS), a promoter, such as an RNA Polymerase III promoter, operably linked to a sequence or gene of interest, a terminator such as an RNA polymerase III terminator, an origin of replication, and a marker gene (e.g., auxotrophic, antibiotic, or other selectable markers). Examples of expression vectors for use in yeast may include plasmids, yeast artificial chromosomes, 2μ plasmids, yeast integrative plasmids, yeast replicative plasmids, shuttle vectors, and episomal plasmids.

Stable integration of Cpf1 CRISPR system components in the genome of plants and plant cells In particular embodiments, it is envisaged that the polynucleotides encoding the components of the Cpf1 CRISPR system are introduced for stable integration into the genome of a plant cell. In these embodiments, the design of the transformation vector or the expression system can be adjusted depending on for when, where and under what conditions the guide RNA and/or the Cpf1 gene are expressed.

In particular embodiments, it is envisaged to introduce the components of the Cpf1 CRISPR system stably into the genomic DNA of a plant cell. Additionally or alternatively, it is envisaged to introduce the components of the Cpf1 CRISPR system for stable integration into the DNA of a plant organelle such as, but not limited to a plastid, e mitochondrion or a chloroplast.

The expression system for stable integration into the genome of a plant cell may contain one or more of the following elements: a promoter element that can be used to express the RNA and/or Cpf1 enzyme in a plant cell; a 5' untranslated region to enhance expression; an intron element to further enhance expression in certain cells, such as monocot cells; a multiple-cloning site to provide convenient restriction sites for inserting the guide RNA and/or the Cpf1 gene sequences and other desired elements; and a 3' untranslated region to provide for efficient termination of the expressed transcript.

The elements of the expression system may be on one or more expression constructs which are either circular such as a plasmid or transformation vector, or non-circular such as linear double stranded DNA.

In a particular embodiment, a Cpf1 CRISPR expression system comprises at least:

(a) a nucleotide sequence encoding a guide RNA (gRNA) that hybridizes with a target sequence in a plant, and wherein the guide RNA comprises a guide sequence and a direct repeat sequence, and (b) a nucleotide sequence encoding a Cpf1 protein, wherein components (a) or (b) are located on the same or on different constructs, and whereby the different nucleotide sequences can be under control of the same or a different regulatory element operable in a plant cell.

DNA construct(s) containing the components of the Cpf1 CRISPR system, and, where applicable, template sequence may be introduced into the genome of a plant, plant part, or plant cell by a variety of conventional techniques. The process generally comprises the steps of selecting a suitable host cell or host tissue, introducing the construct(s) into the host cell or host tissue, and regenerating plant cells or plants therefrom.

In particular embodiments, the DNA construct may be introduced into the plant cell using techniques such as but not limited to electroporation, microinjection, aerosol beam injection of plant cell protoplasts, or the DNA constructs can be introduced directly to plant tissue using biolistic methods, such as DNA particle bombardment (see also Fu et al., Transgenic Res. 2000 February; 9(1):11-9). The basis of particle bombardment is the acceleration of particles coated with gene/s of interest toward cells, resulting in the penetration of the protoplasm by the particles and typically stable integration into the genome. (see e.g. Klein et al, Nature (1987), Klein et ah, Bio/Technology (1992), Casas et ah, Proc. Natl. Acad. Sci. USA (1993)).

In particular embodiments, the DNA constructs containing components of the Cpf1 CRISPR system may be introduced into the plant by *Agrobacterium*-mediated transformation. The DNA constructs may be combined with suitable T-DNA flanking regions and introduced into a conventional *Agrobacterium tumefaciens* host vector. The foreign DNA can be incorporated into the genome of plants by infecting the plants or by incubating plant protoplasts with *Agrobacterium* bacteria, containing one or more Ti (tumor-inducing) plasmids. (see e.g. Fraley et al., (1985), Rogers et al., (1987) and U.S. Pat. No. 5,563,055).

Plant Promoters

In order to ensure appropriate expression in a plant cell, the components of the Cpf1 CRISPR system described herein are typically placed under control of a plant promoter, i.e. a promoter operable in plant cells. The use of different types of promoters is envisaged.

A constitutive plant promoter is a promoter that is able to express the open reading frame (ORF) that it controls in all or nearly all of the plant tissues during all or nearly all developmental stages of the plant (referred to as "constitutive expression"). One non-limiting example of a constitutive promoter is the cauliflower mosaic virus 35S promoter. "Regulated promoter" refers to promoters that direct gene expression not constitutively, but in a temporally- and/or spatially-regulated manner, and includes tissue-specific, tissue-preferred and inducible promoters. Different promoters may direct the expression of a gene in different tissues or cell types, or at different stages of development, or in response to different environmental conditions. In particular embodiments, one or more of the Cpf1 CRISPR components are expressed under the control of a constitutive promoter, such as the cauliflower mosaic virus 35S promoter issue-preferred promoters can be utilized to target enhanced expression in certain cell types within a particular plant tissue, for instance vascular cells in leaves or roots or in specific cells of the seed. Examples of particular promoters for use in the Cpf1 CRISPR system are found in Kawamata et al., (1997) Plant Cell Physiol 38:792-803; Yamamoto et al., (1997) Plant J 12:255-65; Hire et al, (1992) Plant Mol Biol 20:207-18, Kuster et al, (1995) Plant Mol Biol 29:759-72, and Capana et al., (1994) Plant Mol Biol 25:681-91.

Examples of promoters that are inducible and that allow for spatiotemporal control of gene editing or gene expression may use a form of energy. The form of energy may include but is not limited to sound energy, electromagnetic radiation, chemical energy and/or thermal energy. Examples of inducible systems include tetracycline inducible promoters (Tet-On or Tet-Off), small molecule two-hybrid transcription activations systems (FKBP, ABA, etc), or light inducible systems (Phytochrome, LOV domains, or cryptochrome)., such as a Light Inducible Transcriptional Effector (LITE) that direct changes in transcriptional activity in a sequence-specific manner. The components of a light inducible system may include a Cpf1 CRISPR enzyme, a light-responsive cytochrome heterodimer (e.g. from *Arabidopsis thaliana*), and a transcriptional activation/repression domain. Further examples of inducible DNA binding proteins and methods for their use are provided in U.S. 61/736,465 and U.S. 61/721,283, which is hereby incorporated by reference in its entirety.

In particular embodiments, transient or inducible expression can be achieved by using, for example, chemical-regulated promotors, i.e. whereby the application of an exogenous chemical induces gene expression. Modulating of gene expression can also be obtained by a chemical-repressible promoter, where application of the chemical represses gene expression. Chemical-inducible promoters include, but are not limited to, the maize 1n2-2 promoter, activated by benzene sulfonamide herbicide safeners (De Veylder et al., (1997) Plant Cell Physiol 38:568-77), the maize GST promoter (GST-ll-27, WO93/01294), activated by hydrophobic electrophilic compounds used as pre-emergent herbicides, and the tobacco PR-1 a promoter (Ono et al., (2004) Biosci Biotechnol Biochem 68:803-7) activated by salicylic acid. Promoters which are regulated by antibiotics, such as tetracycline-inducible and tetracycline-repressible promoters (Gatz et al., (1991) Mol Gen Genet 227: 229-37; U.S. Pat. Nos. 5,814,618 and 5,789,156) can also be used herein.

Translocation to and/or Expression in Specific Plant Organelles

The expression system may comprise elements for translocation to and/or expression in a specific plant organelle.

Chloroplast Targeting

In particular embodiments, it is envisaged that the Cpf1 CRISPR system is used to specifically modify chloroplast genes or to ensure expression in the chloroplast. For this purpose use is made of chloroplast transformation methods or compartmentalization of the Cpf1 CRISPR components to the chloroplast. For instance, the introduction of genetic modifications in the plastid genome can reduce biosafety issues such as gene flow through pollen.

Methods of chloroplast transformation are known in the art and include Particle bombardment, PEG treatment, and microinjection. Additionally, methods involving the translocation of transformation cassettes from the nuclear genome to the plastid can be used as described in WO2010061186.

Alternatively, it is envisaged to target one or more of the Cpf1 CRISPR components to the plant chloroplast. This is achieved by incorporating in the expression construct a sequence encoding a chloroplast transit peptide (CTP) or plastid transit peptide, operably linked to the 5' region of the sequence encoding the Cpf1 protein. The CTP is removed in a processing step during translocation into the chloroplast. Chloroplast targeting of expressed proteins is well known to the skilled artisan (see for instance Protein Transport into Chloroplasts, 2010, Annual Review of Plant Biology, Vol. 61: 157-180). In such embodiments it is also desired to target the guide RNA to the plant chloroplast. Methods and constructs which can be used for translocating guide RNA into the chloroplast by means of a chloroplast localization sequence are described, for instance, in US 20040142476, incorporated herein by reference. Such variations of constructs can be incorporated into the expression systems of the invention to efficiently translocate the Cpf1-guide RNA.

Introduction of Polynucleotides Encoding the CRISPR-Cpf1 System in Algal Cells.

Transgenic algae (or other plants such as rape) may be particularly useful in the production of vegetable oils or biofuels such as alcohols (especially methanol and ethanol) or other products. These may be engineered to express or overexpress high levels of oil or alcohols for use in the oil or biofuel industries.

U.S. Pat. No. 8,945,839 describes a method for engineering Micro-Algae (*Chlamydomonas reinhardtii* cells) species) using Cas9. Using similar tools, the methods of the Cpf1 CRISPR system described herein can be applied on *Chlamydomonas* species and other algae. In particular embodiments, Cpf1 and guide RNA are introduced in algae expressed using a vector that expresses Cpf1 under the control of a constitutive promoter such as Hsp70A-Rbc S2 or Beta2-tubulin. Guide RNA is optionally delivered using a vector containing T7 promoter. Alternatively, Cpf1 mRNA and in vitro transcribed guide RNA can be delivered to algal cells. Electroporation protocols are available to the skilled person such as the standard recommended protocol from the GeneArt *Chlamydomonas* Engineering kit.

In particular embodiments, the endonuclease used herein is a Split Cpf1 enzyme. Split Cpf1 enzymes are preferentially used in Algae for targeted genome modification as has been described for Cas9 in WO 2015086795. Use of the Cpf1 split system is particularly suitable for an inducible method of genome targeting and avoids the potential toxic effect of the Cpf1 overexpression within the algae cell. In particular embodiments, Said Cpf1 split domains (RuvC and HNH domains) can be simultaneously or sequentially introduced into the cell such that said split Cpf1 domain(s) process the target nucleic acid sequence in the algae cell. The reduced size of the split Cpf1 compared to the wild type Cpf1 allows other methods of delivery of the CRISPR system to the cells, such as the use of Cell Penetrating Peptides as described herein. This method is of particular interest for generating genetically modified algae.

Introduction of Polynucleotides Encoding Cpf1 Components in Yeast Cells

In particular embodiments, the invention relates to the use of the Cpf1 CRISPR system for genome editing of yeast cells. Methods for transforming yeast cells which can be used to introduce polynucleotides encoding the Cpf1 CRISPR system components are well known to the artisan and are reviewed by Kawai et al., 2010, Bioeng Bugs. 2010 November-December; 1(6): 395-403). Non-limiting examples include transformation of yeast cells by lithium acetate treatment (which may further include carrier DNA and PEG treatment), bombardment or by electroporation.

Transient Expression of Cpf1 CRISP System Components in Plants and Plant Cell

In particular embodiments, it is envisaged that the guide RNA and/or Cpf1 gene are transiently expressed in the plant cell. In these embodiments, the Cpf1 CRISPR system can ensure modification of a target gene only when both the guide RNA and the Cpf1 protein is present in a cell, such that genomic modification can further be controlled. As the expression of the Cpf1 enzyme is transient, plants regenerated from such plant cells typically contain no foreign DNA. In particular embodiments the Cpf1 enzyme is stably expressed by the plant cell and the guide sequence is transiently expressed.

In particular embodiments, the Cpf1 CRISPR system components can be introduced in the plant cells using a plant viral vector (Scholthof et al. 1996, Annu Rev Phytopathol. 1996; 34:299-323). In further particular embodiments, said viral vector is a vector from a DNA virus. For example, geminivirus (e.g., cabbage leaf curl virus, bean yellow dwarf virus, wheat dwarf virus, tomato leaf curl virus, maize streak virus, tobacco leaf curl virus, or tomato golden mosaic virus) or nanovirus (e.g., *Faba* bean necrotic yellow virus). In other particular embodiments, said viral vector is a vector from an RNA virus. For example, tobravirus (e.g., tobacco rattle virus, tobacco mosaic virus), potexvirus (e.g., potato virus X), or hordeivirus (e.g., barley stripe mosaic virus). The replicating genomes of plant viruses are non-integrative vectors.

In particular embodiments, the vector used for transient expression of Cpf1 CRISPR constructs is for instance a pEAQ vector, which is tailored for *Agrobacterium*-mediated transient expression (Sainsbury F. et al., Plant Biotechnol J. 2009 September; 7(7):682-93) in the protoplast. Precise targeting of genomic locations was demonstrated using a modified Cabbage Leaf Curl virus (CaLCuV) vector to express gRNAs in stable transgenic plants expressing a CRISPR enzyme (Scientific Reports 5, Article number: 14926 (2015), doi:10.1038/srep14926).

In particular embodiments, double-stranded DNA fragments encoding the guide RNA and/or the Cpf1 gene can be transiently introduced into the plant cell. In such embodiments, the introduced double-stranded DNA fragments are provided in sufficient quantity to modify the cell but do not persist after a contemplated period of time has passed or after one or more cell divisions. Methods for direct DNA transfer in plants are known by the skilled artisan (see for instance Davey et al. Plant Mol Biol. 1989 September; 13(3):273-85.)

In other embodiments, an RNA polynucleotide encoding the Cpf1 protein is introduced into the plant cell, which is then translated and processed by the host cell generating the protein in sufficient quantity to modify the cell (in the presence of at least one guide RNA) but which does not persist after a contemplated period of time has passed or after one or more cell divisions. Methods for introducing mRNA to plant protoplasts for transient expression are known by the skilled artisan (see for instance in Gallie, Plant Cell Reports (1993), 13; 119-122).

Combinations of the different methods described above are also envisaged.

Delivery of Cpf1 CRISPR Components to the Plant Cell

In particular embodiments, it is of interest to deliver one or more components of the Cpf1 CRISPR system directly to the plant cell. This is of interest, inter alia, for the generation of non-transgenic plants (see below). In particular embodiments, one or more of the Cpf1 components is prepared outside the plant or plant cell and delivered to the cell. For instance in particular embodiments, the Cpf1 protein is prepared in vitro prior to introduction to the plant cell. Cpf1 protein can be prepared by various methods known by one of skill in the art and include recombinant production. After expression, the Cpf1 protein is isolated, refolded if needed, purified and optionally treated to remove any purification tags, such as a His-tag. Once crude, partially purified, or more completely purified Cpf1 protein is obtained, the protein may be introduced to the plant cell.

In particular embodiments, the Cpf1 protein is mixed with guide RNA targeting the gene of interest to form a pre-assembled ribonucleoprotein.

The individual components or pre-assembled ribonucleoprotein can be introduced into the plant cell via electroporation, by bombardment with Cpf1-associated gene product coated particles, by chemical transfection or by some other means of transport across a cell membrane. For instance, transfection of a plant protoplast with a pre-assembled CRISPR ribonucleoprotein has been demonstrated to ensure targeted modification of the plant genome (as described by Woo et al. Nature Biotechnology, 2015; DOI: 10.1038/nbt.3389).

In particular embodiments, the Cpf1 CRISPR system components are introduced into the plant cells using nanoparticles. The components, either as protein or nucleic acid or in a combination thereof, can be uploaded onto or packaged in nanoparticles and applied to the plants (such as for instance described in WO 2008042156 and US 20130185823). In particular, embodiments of the invention comprise nanoparticles uploaded with or packed with DNA molecule(s) encoding the Cpf1 protein, DNA molecules encoding the guide RNA and/or isolated guide RNA as described in WO2015089419.

Further means of introducing one or more components of the Cpf1 CRISPR system to the plant cell is by using cell penetrating peptides (CPP). Accordingly, in particular, embodiments the invention comprises compositions comprising a cell penetrating peptide linked to the Cpf1 protein. In particular embodiments of the present invention, the Cpf1 protein and/or guide RNA is coupled to one or more CPPs to effectively transport them inside plant protoplasts; see also Ramakrishna (20140Genome Res. 2014 June; 24(6):1020-7 for Cas9 in human cells). In other embodiments, the Cpf1 gene and/or guide RNA are encoded by one or more circular or non-circular DNA molecule(s) which are coupled to one or more CPPs for plant protoplast delivery. The plant protoplasts are then regenerated to plant cells and further to plants. CPPs are generally described as short peptides of fewer than 35 amino acids either derived from proteins or from chimeric sequences which are capable of transporting biomolecules across cell membrane in a receptor independent manner. CPP can be cationic peptides, peptides having hydrophobic sequences, amphipathic peptides, peptides having proline-rich and anti-microbial sequence, and chimeric or bipartite peptides (Pooga and Langel 2005). CPPs are able to penetrate biological membranes and as such trigger the movement of various biomolecules across cell membranes into the cytoplasm and to improve their intracellular routing, and hence facilitate interaction of the biomolecule with the target. Examples of CPP include amongst others: Tat, a nuclear transcriptional activator protein required for viral replication by HIV type1, penetratin, Kaposi fibroblast growth factor (FGF) signal peptide sequence, integrin (33 signal peptide sequence; polyarginine peptide Args sequence, Guanine rich-molecular transporters, sweet arrow peptide, etc. . . . .

Use of the Cpf1 CRISPR System to Make Genetically Modified Non-Transgenic Plants In particular embodiments, the methods described herein are used to modify endogenous genes or to modify their expression without the permanent introduction into the genome of the plant of any foreign gene, including those encoding CRISPR components, so as to avoid the presence of foreign DNA in the genome of the plant. This can be of interest as the regulatory requirements for non-transgenic plants are less rigorous.

In particular embodiments, this is ensured by transient expression of the Cpf1 CRISPR components. In particular embodiments one or more of the CRISPR components are expressed on one or more viral vectors which produce sufficient Cpf1 protein and guide RNA to consistently steadily ensure modification of a gene of interest according to a method described herein.

In particular embodiments, transient expression of Cpf1 CRISPR constructs is ensured in plant protoplasts and thus not integrated into the genome. The limited window of expression can be sufficient to allow the Cpf1 CRISPR system to ensure modification of a target gene as described herein.

In particular embodiments, the different components of the Cpf1 CRISPR system are introduced in the plant cell, protoplast or plant tissue either separately or in mixture, with the aid of particulate delivering molecules such as nanoparticles or CPP molecules as described herein above.

The expression of the Cpf1 CRISPR components can induce targeted modification of the genome, either by direct activity of the Cpf1 nuclease and optionally introduction of template DNA or by modification of genes targeted using the Cpf1 CRISPR system as described herein. The different strategies described herein above allow Cpf1-mediated targeted genome editing without requiring the introduction of the Cpf1 CRISPR components into the plant genome. Components which are transiently introduced into the plant cell are typically removed upon crossing.

Detecting Modifications in the Plant Genome-Selectable Markers

In particular embodiments, where the method involves modification of an endogenous target gene of the plant genome, any suitable method can be used to determine, after the plant, plant part or plant cell is infected or transfected with the Cpf1 CRISPR system, whether gene targeting or targeted mutagenesis has occurred at the target site. Where the method involves introduction of a transgene, a transformed plant cell, callus, tissue or plant may be identified and isolated by selecting or screening the engineered plant material for the presence of the transgene or for traits encoded by the transgene. Physical and biochemical methods may be used to identify plant or plant cell transformants containing inserted gene constructs or an endogenous DNA modification. These methods include but are not limited to: 1) Southern analysis or PCR amplification for detecting and determining the structure of the recombinant DNA insert or modified endogenous genes; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct or expression is affected by the genetic modification; 4) protein gel electrophoresis, Western blot techniques, immunoprecipitation, or enzyme-linked immunoassays, where the gene construct or endogenous gene products are proteins. Additional techniques, such as in situ hybridization, enzyme staining, and immunostaining, also may be used to detect the presence or expression of the recombinant construct or detect a modification of endogenous gene in specific plant organs and tissues. The methods for doing all these assays are well known to those skilled in the art.

Additionally (or alternatively), the expression system encoding the Cpf1 CRISPR components is typically designed to comprise one or more selectable or detectable markers that provide a means to isolate or efficiently select cells that contain and/or have been modified by the Cpf1 CRISPR system at an early stage and on a large scale.

In the case of *Agrobacterium*-mediated transformation, the marker cassette may be adjacent to or between flanking T-DNA borders and contained within a binary vector. In another embodiment, the marker cassette may be outside of the T-DNA. A selectable marker cassette may also be within or adjacent to the same T-DNA borders as the expression cassette or may be somewhere else within a second T-DNA on the binary vector (e.g., a 2 T-DNA system).

For particle bombardment or with protoplast transformation, the expression system can comprise one or more isolated linear fragments or may be part of a larger construct that might contain bacterial replication elements, bacterial selectable markers or other detectable elements. The expression cassette(s) comprising the polynucleotides encoding the guide and/or Cpf1 may be physically linked to a marker cassette or may be mixed with a second nucleic acid molecule encoding a marker cassette. The marker cassette is comprised of necessary elements to express a detectable or selectable marker that allows for efficient selection of transformed cells.

The selection procedure for the cells based on the selectable marker will depend on the nature of the marker gene. In particular embodiments, use is made of a selectable marker, i.e. a marker which allows a direct selection of the cells based on the expression of the marker. A selectable marker can confer positive or negative selection and is conditional or non-conditional on the presence of external substrates (Miki et al. 2004, 107(3): 193-232). Most commonly, antibiotic or herbicide resistance genes are used as a marker, whereby selection is to be performed by growing the engineered plant material on media containing an inhibitory amount of the antibiotic or herbicide to which the marker gene confers resistance. Examples of such genes are genes that confer resistance to antibiotics, such as hygromycin (hpt) and kanamycin (nptII), and genes that confer resistance to herbicides, such as phosphinothricin (bar) and chlorosulfuron (als), Transformed plants and plant cells may also be identified by screening for the activities of a visible marker, typically an enzyme capable of processing a colored substrate (e.g., the β-glucuronidase, luciferase, B or C1 genes). Such selection and screening methodologies are well known to those skilled in the art.

Plant Cultures and Regeneration

In particular embodiments, plant cells which have a modified genome and that are produced or obtained by any of the methods described herein, can be cultured to regenerate a whole plant which possesses the transformed or modified genotype and thus the desired phenotype. Conventional regeneration techniques are well known to those skilled in the art. Particular examples of such regeneration techniques rely on manipulation of certain phytohormones in a tissue culture growth medium, and typically relying on a biocide and/or herbicide marker which has been introduced together with the desired nucleotide sequences. In further particular embodiments, plant regeneration is obtained from cultured protoplasts, plant callus, explants, organs, pollens, embryos or parts thereof (see e.g. Evans et al. (1983), Handbook of Plant Cell Culture, Klee et al (1987) Ann. Rev. of Plant Phys.).

In particular embodiments, transformed or improved plants as described herein can be self-pollinated to provide seed for homozygous improved plants of the invention (homozygous for the DNA modification) or crossed with non-transgenic plants or different improved plants to provide seed for heterozygous plants. Where a recombinant DNA was introduced into the plant cell, the resulting plant of such a crossing is a plant which is heterozygous for the recombinant DNA molecule. Both such homozygous and heterozygous plants obtained by crossing from the improved plants and comprising the genetic modification (which can be a recombinant DNA) are referred to herein as "progeny". Progeny plants are plants descended from the original transgenic plant and containing the genome modification or recombinant DNA molecule introduced by the methods provided herein. Alternatively, genetically modified plants can be obtained by one of the methods described supra using the Cpf1 enzyme whereby no foreign DNA is incorporated into the genome. Progeny of such plants, obtained by further breeding may also contain the genetic modification. Breedings are performed by any breeding methods that are commonly used for different crops (e.g., Allard, Principles of Plant Breeding, John Wiley & Sons, NY, U. of CA, Davis, Calif., 50-98 (1960).

Generation of Plants with Enhanced Agronomic Traits

The Cpf1 based CRISPR systems provided herein can be used to introduce targeted double-strand or single-strand breaks and/or to introduce gene activator and/or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

In particular embodiments, the Cpf1 CRISPR system as described herein is used to introduce targeted double-strand breaks (DSB) in an endogenous DNA sequence. The DSB activates cellular DNA repair pathways, which can be harnessed to achieve desired DNA sequence modifications near the break site. This is of interest where the inactivation of endogenous genes can confer or contribute to a desired trait. In particular embodiments, homologous recombination with a template sequence is promoted at the site of the DSB, in order to introduce a gene of interest.

In particular embodiments, the Cpf1 CRISPR system may be used as a generic nucleic acid binding protein with fusion to or being operably linked to a functional domain for activation and/or repression of endogenous plant genes. Exemplary functional domains may include but are not limited to translational initiator, translational activator, translational repressor, nucleases, in particular ribonucleases, a spliceosome, beads, a light inducible/controllable domain or a chemically inducible/controllable domain. Typically in these embodiments, the Cpf1 protein comprises at least one mutation, such that it has no more than 5% of the activity of the Cpf1 protein not having the at least one mutation; the guide RNA comprises a guide sequence capable of hybridizing to a target sequence.

The methods described herein generally result in the generation of "improved plants" in that they have one or more desirable traits compared to the wildtype plant. In particular embodiments, the plants, plant cells or plant parts obtained are transgenic plants, comprising an exogenous DNA sequence incorporated into the genome of all or part of the cells of the plant. In particular embodiments, non-transgenic genetically modified plants, plant parts or cells are obtained, in that no exogenous DNA sequence is incorporated into the genome of any of the plant cells of the plant. In such embodiments, the improved plants are non-transgenic. Where only the modification of an endogenous gene is ensured and no foreign genes are introduced or maintained in the plant genome, the resulting genetically modified crops contain no foreign genes and can thus basically be considered non-transgenic. The different applications of the Cpf1 CRISPR system for plant genome editing are described more in detail below:

a) Introduction of One or More Foreign Genes to Confer an Agricultural Trait of Interest The invention provides methods of genome editing or modifying sequences associated with or at a target locus of interest wherein the method comprises introducing a Cpf1 effector protein complex into a plant cell, whereby the Cpf1 effector protein complex effectively functions to integrate a DNA insert, e.g. encoding a foreign gene of interest, into the genome of the plant cell. In preferred embodiments the integration of the DNA insert is facilitated by HR with an exogenously introduced DNA template or repair template. Typically, the exogenously introduced DNA template or repair template is delivered together with the Cpf1 effector protein complex or one component or a polynucleotide vector for expression of a component of the complex.

The Cpf1 CRISPR systems provided herein allow for targeted gene delivery. It has become increasingly clear that the efficiency of expressing a gene of interest is to a great extent determined by the location of integration into the genome. The present methods allow for targeted integration of the foreign gene into a desired location in the genome. The location can be selected based on information of previously generated events or can be selected by methods disclosed elsewhere herein.

In particular embodiments, the methods provided herein include (a) introducing into the cell a Cpf1 CRISPR complex comprising a guide RNA, comprising a direct repeat and a guide sequence, wherein the guide sequence hybridizes to a target sequence that is endogenous to the plant cell; (b) introducing into the plant cell a Cpf1 effector molecule which complexes with the guide RNA when the guide sequence hybridizes to the target sequence and induces a double strand break at or near the sequence to which the guide sequence is targeted; and (c) introducing into the cell a nucleotide sequence encoding an HDR repair template which encodes the gene of interest and which is introduced into the location of the DS break as a result of HDR. In particular embodiments, the step of introducing can include delivering to the plant cell one or more polynucleotides encoding Cpf1 effector protein, the guide RNA and the repair template. In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the Cpf1 effector protein, the guide RNA and the repair template, where the delivering is via *Agrobacterium*. The nucleic acid sequence encoding the Cpf1 effector protein can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the repair template i.e. the gene of interest has been introduced. In particular embodiments, the methods include the step of regenerating a plant from the plant cell. In further embodiments, the methods include cross breeding the plant to obtain a genetically desired plant lineage. Examples of foreign genes encoding a trait of interest are listed below.

b) Editing of Endogenous Genes to Confer an Agricultural Trait of Interest

The invention provides methods of genome editing or modifying sequences associated with or at a target locus of interest wherein the method comprises introducing a Cpf1 effector protein complex into a plant cell, whereby the Cpf1 complex modifies the expression of an endogenous gene of the plant. This can be achieved in different ways. In particular embodiments, the elimination of expression of an endogenous gene is desirable and the Cpf1 CRISPR complex is used to target and cleave an endogenous gene so as to modify gene expression. In these embodiments, the methods provided herein include (a) introducing into the plant cell a Cpf1 CRISPR complex comprising a guide RNA, comprising a direct repeat and a guide sequence, wherein the guide sequence hybridizes to a target sequence within a gene of interest in the genome of the plant cell; and (b) introducing into the cell a Cpf1 effector protein, which upon binding to the guide RNA comprises a guide sequence that is hybridized to the target sequence, ensures a double strand break at or near the sequence to which the guide sequence is targeted. In particular embodiments, the step of introducing can include delivering to the plant cell one or more polynucleotides encoding Cpf1 effector protein and the guide RNA.

In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the Cpf1 effector protein and the guide RNA, where the delivering is via *Agrobacterium*. The polynucleotide sequence encoding the components of the Cpf1 CRISPR system can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage.

In particular embodiments of the methods described above, disease resistant crops are obtained by targeted mutation of disease susceptibility genes or genes encoding negative regulators (e.g. Mlo gene) of plant defense genes. In a particular embodiment, herbicide-tolerant crops are generated by targeted substitution of specific nucleotides in plant genes such as those encoding acetolactate synthase (ALS) and protoporphyrinogen oxidase (PPO). In particular embodiments drought and salt tolerant crops by targeted mutation of genes encoding negative regulators of abiotic stress tolerance, low amylose grains by targeted mutation of Waxy gene, rice or other grains with reduced rancidity by targeted mutation of major lipase genes in aleurone layer, etc. In particular embodiments. A more extensive list of endogenous genes encoding a traits of interest are listed below.

c) Modulating of Endogenous Genes by the Cpf1 CRISPR System to Confer an Agricultural Trait of Interest Also provided herein are methods for modulating (i.e. activating or repressing) endogenous gene expression using the Cpf1 protein provided herein. Such methods make use of distinct RNA sequence(s) which are targeted to the plant genome by the Cpf1 complex. More particularly the distinct RNA sequence(s) bind to two or more adaptor proteins (e.g. aptamers) whereby each adaptor protein is associated with one or more functional domains and wherein at least one of the one or more functional domains associated with the adaptor protein have one or more activities comprising methylase activity, demethylase activity, transcription activation activity, transcription repression activity, transcription release factor activity, histone modification activity, DNA integration activity RNA cleavage activity, DNA cleavage activity or nucleic acid binding activity. The functional domains are used to modulate expression of an endogenous plant gene so as to obtain the desired trait. Typically, in these embodiments, the Cpf1 effector protein has one or more mutations such that it has no more than 5% of the nuclease activity of the Cpf1 effector protein not having the at least one mutation.

In particular embodiments, the methods provided herein include the steps of (a) introducing into the cell a Cpf1 CRISPR complex comprising a guide RNA, comprising a direct repeat and a guide sequence, wherein the guide sequence hybridizes to a target sequence that is endogenous to the plant cell; (b) introducing into the plant cell a Cpf1 effector molecule which complexes with the guide RNA when the guide sequence hybridizes to the target sequence; and wherein either the guide RNA is modified to comprise a distinct RNA sequence (aptamer) binding to a functional domain and/or the Cpf1 effector protein is modified in that it is linked to a functional domain. In particular embodiments, the step of introducing can include delivering to the plant cell one or more polynucleotides encoding the (modified) Cpf1 effector protein and the (modified) guide RNA. The details the components of the Cpf1 CRISPR system for use in these methods are described elsewhere herein.

In particular embodiments, the polynucleotides are delivered into the cell by a DNA virus (e.g., a geminivirus) or an RNA virus (e.g., a tobravirus). In particular embodiments, the introducing steps include delivering to the plant cell a T-DNA containing one or more polynucleotide sequences encoding the Cpf1 effector protein and the guide RNA, where the delivering is via *Agrobacterium*. The nucleic acid sequence encoding the one or more components of the Cpf1 CRISPR system can be operably linked to a promoter, such as a constitutive promoter (e.g., a cauliflower mosaic virus 35S promoter), or a cell specific or inducible promoter. In particular embodiments, the polynucleotide is introduced by microprojectile bombardment. In particular embodiments, the method further includes screening the plant cell after the introducing steps to determine whether the expression of the gene of interest has been modified. In particular embodiments, the methods include the step of regenerating a plant from the plant cell. In further embodiments, the methods include cross breeding the plant to obtain a genetically desired plant lineage. A more extensive list of endogenous genes encoding a traits of interest are listed below.

Use of Cpf1 to Modify Polyploid Plants

Many plants are polyploid, which means they carry duplicate copies of their genomes—sometimes as many as six, as in wheat. The methods according to the present invention, which make use of the Cpf1 CRISPR effector protein can be "multiplexed" to affect all copies of a gene, or to target dozens of genes at once. For instance, in particular embodiments, the methods of the present invention are used to simultaneously ensure a loss of function mutation in different genes responsible for suppressing defences against a disease. In particular embodiments, the methods of the present invention are used to simultaneously suppress the expression of the TaMLO-A1, TaMLO-B1 and TaMLO-D1 nucleic acid sequence in a wheat plant cell and regenerating a wheat plant therefrom, in order to ensure that the wheat plant is resistant to powdery mildew (see also WO2015109752).

Exemplary Genes Conferring Agronomic Traits

As described herein above, in particular embodiments, the invention encompasses the use of the Cpf1 CRISPR system as described herein for the insertion of a DNA of interest, including one or more plant expressible gene(s). In further particular embodiments, the invention encompasses methods and tools using the Cpf1 system as described herein for partial or complete deletion of one or more plant expressed gene(s). In other further particular embodiments, the invention encompasses methods and tools using the Cpf1 system as described herein to ensure modification of one or more plant-expressed genes by mutation, substitution, insertion of one of more nucleotides. In other particular embodiments, the invention encompasses the use of Cpf1 CRISPR system as described herein to ensure modification of expression of one or more plant-expressed genes by specific modification of one or more of the regulatory elements directing expression of said genes.

In particular embodiments, the invention encompasses methods which involve the introduction of exogenous genes and/or the targeting of endogenous genes and their regulatory elements, such as listed below:

1. Genes that Confer Resistance to Pests or Diseases:

Plant disease resistance genes. A plant can be transformed with cloned resistance genes to engineer plants that are resistant to specific pathogen strains. See, e.g., Jones et al., Science 266:789 (1994) (cloning of the tomato Cf-9 gene for resistance to *Cladosporium fulvum*); Martin et al., Science 262:1432 (1993) (tomato Pto gene for resistance to *Pseudomonas syringae* pv. tomato encodes a protein kinase); Mindrinos et al., Cell 78:1089 (1994) (Arabidops may be RSP2 gene for resistance to *Pseudomonas syringae*). A plant gene that is upregulated or down regulated during pathogen infection can be engineered for pathogen resistance. See, e.g., Thomazella et al., bioRxiv 064824; doi: doi.org/10.1101/064824 Epub. Jul. 23, 2016 (tomato plants with deletions in the SlDMR6-1 which is normally upregulated during pathogen infection).

Genes conferring resistance to a pest, such as soybean cyst nematode. See e.g., PCT Application WO 96/30517; PCT Application WO 93/19181.

*Bacillus thuringiensis* proteins see, e.g., Geiser et al., Gene 48:109 (1986).

Lectins, see, for example, Van Damme et al., Plant Molec. Biol. 24:25 (1994.

Vitamin-binding protein, such as avidin, see PCT application US93/06487, teaching the use of avidin and avidin homologues as larvicides against insect pests.

Enzyme inhibitors such as protease or proteinase inhibitors or amylase inhibitors. See, e.g., Abe et al., J. Biol. Chem. 262:16793 (1987), Huub et al., Plant Molec. Biol. 21:985 (1993)), Sumitani et al., Biosci. Biotech. Biochem. 57:1243 (1993) and U.S. Pat. No. 5,494,813.

Insect-specific hormones or pheromones such as ecdysteroid or juvenile hormone, a variant thereof, a mimetic based thereon, or an antagonist or agonist thereof. See, for example Hammock et al., Nature 344:458 (1990).

Insect-specific peptides or neuropeptides which, upon expression, disrupts the physiology of the affected pest. For example Regan, J. Biol. Chem. 269:9 (1994) and Pratt et al., Biochem. Biophys. Res. Comm. 163:1243 (1989). See also U.S. Pat. No. 5,266,317.

Insect-specific venom produced in nature by a snake, a wasp, or any other organism. For example, see Pang et al., Gene 116: 165 (1992).

Enzymes responsible for a hyperaccumulation of a monoterpene, a sesquiterpene, a steroid, hydroxamic acid, a phenylpropanoid derivative or another nonprotein molecule with insecticidal activity.

Enzymes involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO93/02197, Kramer et al., Insect Biochem. Molec. Biol. 23:691 (1993) and Kawalleck et al., Plant Molec. Biol. 21:673 (1993).

Molecules that stimulates signal transduction. For example, see Botella et al., Plant Molec. Biol. 24:757 (1994), and Griess et al., Plant Physiol. 104:1467 (1994).

Viral-invasive proteins or a complex toxin derived therefrom. See Beachy et al., Ann. rev. Phytopathol. 28:451 (1990).

Developmental-arrestive proteins produced in nature by a pathogen or a parasite. See Lamb et al., Bio/Technology 10:1436 (1992) and Toubart et al., Plant J. 2:367 (1992).

A developmental-arrestive protein produced in nature by a plant. For example, Logemann et al., Bio/Technology 10:305 (1992).

In plants, pathogens are often host-specific. For example, some *Fusarium* species will causes tomato wilt but attacks only tomato, and other *Fusarium* species attack only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible or there can be partial resistance against all races of a pathogen, typically controlled by many genes and/or also complete resistance to some races of a pathogen but not to other races. Such resistance is typically controlled by a few genes. Using methods and components of the CRISP-cpf1 system, a new tool now exists to induce specific mutations in anticipation hereon. Accordingly, one can analyze the genome of sources of resistance genes, and in plants having desired characteristics or traits, use the method and components of the Cpf1 CRISPR system to induce the rise of resistance genes. The present systems can do so with more precision than previous mutagenic agents and hence accelerate and improve plant breeding programs.

2. Genes Involved in Plant Diseases, Such as Those Listed in WO 2013046247:

Rice diseases: *Magnaporthe grisea, Cochliobolus miyabeanus, Rhizoctonia solani, Gibberella fujikuroi*; Wheat diseases: *Erysiphe graminis, Fusarium graminearum, F. avenaceum, F. culmorum, Microdochium nivale, Puccinia striiformis, P. graminis, P. recondita, Micronectriella nivale, Typhula* sp., *Ustilago tritici, Tilletia caries, Pseudocercosporella herpotrichoides, Mycosphaerella graminicola, Stagonospora nodorum, Pyrenophora tritici-repentis*; Barley diseases: *Erysiphe graminis, Fusarium graminearum, F. avenaceum, F. culmorum, Microdochium nivale, Puccinia striiformis, P. graminis, P. hordei, Ustilago nuda, Rhynchosporium secalis, Pyrenophora teres, Cochliobolus sativus, Pyrenophora graminea, Rhizoctonia solani*; Maize diseases: *Ustilago maydis, Cochliobolus heterostrophus, Gloeocercospora sorghi, Puccinia polysora, Cercospora zeae-maydis, Rhizoctonia solani*;

Citrus diseases: *Diaporthe citri, Elsinoe fawcetti, Penicillium digitatum, P. italicum, Phytophtora parasitica, Phytophtora citrophthora*; Apple diseases: *Monilinia mali, Valsa ceratosperma, Podosphaera leucotricha, Alternaria alternata* apple pathotype, *Venturia inaequalis, Colletotrichum acutatum, Phytophtora cactorum*;

Pear diseases: *Venturia nashicola, V. pirina, Alternaria alternata* Japanese pear pathotype, *Gymnosporangium haraeanum, Phytophtora cactorum*;

Peach diseases: *Monilinia fructicola, Cladosporium carpophilum, Phomopsis* sp.;

Grape diseases: *Elsinoe ampelina, Glomerella cingulata, Uncinula necator, Phakopsora ampelopsidis, Guignardia bidwellii, Plasmopara viticola*;

Persimmon diseases: *Gloeosporium kaki, Cercospora kaki, Mycosphaerella nawae*;

Gourd diseases: *Colletotrichum lagenarium, Sphaerotheca fuliginea, Mycosphaerella melonis, Fusarium oxysporum, Pseudoperonospora cubensis, Phytophthora* sp., *Pythium* sp.;

Tomato diseases: *Alternaria solani, Cladosporium fulvum, Phytophthora infestans; Pseudomonas syringae* pv. Tomato; *Phytophthora capsici; Xanthomonas*

Eggplant diseases: *Phomopsis vexans, Erysiphe cichoracearum*; Brassicaceous vegetable diseases: *Alternaria japonica, Cercosporella brassicae, Plasmodiophora brassicae, Peronospora parasitica*;

Welsh onion diseases: *Puccinia allii, Peronospora destructor*;

Soybean diseases: *Cercospora kikuchii, Elsinoe glycines, Diaporthe phaseolorum* var. *sojae, Septoria glycines, Cercospora sojina, Phakopsora pachyrhizi, Phytophthora sojae, Rhizoctonia solani, Corynespora cassiicola, Sclerotinia sclerotiorum*;

Kidney bean diseases: *Colletotrichum lindemuthianum*.

Peanut diseases: *Cercospora personata, Cercospora arachidicola, Sclerotium rolfsii*;

Pea diseases pea: *Erysiphe pisi*;

Potato diseases: *Alternaria solani, Phytophthora infestans, Phytophthora erythroseptica, Spongospora subterranean*, f. sp. *Subterranean*;

Strawberry diseases: *Sphaerotheca humuli, Glomerella cingulata*;

Tea diseases: *Exobasidium reticulatum, Elsinoe leucospila, Pestalotiopsis* sp., *Colletotrichum theae-sinensis*;

Tobacco diseases: *Alternaria longipes, Erysiphe cichoracearum, Colletotrichum tabacum, Peronospora tabacina, Phytophthora nicotianae*;

Rapeseed diseases: *Sclerotinia sclerotiorum, Rhizoctonia solani*;

Cotton diseases: *Rhizoctonia solani*;

Beet diseases: *Cercospora beticola, Thanatephorus cucumeris, Thanatephorus cucumeris, Aphanomyces cochlioides*;

Rose diseases: *Diplocarpon rosae, Sphaerotheca pannosa, Peronospora sparsa*;

Diseases of *chrysanthemum* and asteraceae: *Bremia lactuca, Septoria chrysanthemi-indici, Puccinia horiana*;

Diseases of various plants: *Pythium aphanidermatum, Pythium debarianum, Pythium graminicola, Pythium irregulare, Pythium ultimum, Botrytis cinerea, Sclerotinia sclerotiorum;*

Radish diseases: *Alternaria brassicicola;*

Zoysia diseases: *Sclerotinia homoeocarpa, Rhizoctonia solani;*

Banana diseases: *Mycosphaerella fijiensis, Mycosphaerella musicola;*

Sunflower diseases: *Plasmopara halstedii;*

Seed diseases or diseases in the initial stage of growth of various plants caused by *Aspergillus* spp., *Penicillium* spp., *Fusarium* spp., *Gibberella* spp., *Tricoderma* spp., *Thielaviopsis* spp., *Rhizopus* spp., *Mucor* spp., *Corticium* spp., *Phoma* spp., *Rhizoctonia* spp., *Diplodia* spp., or the like;

Virus diseases of various plants mediated by *Polymyxa* spp., *Olpidium* spp., or the like.

3. Examples of Genes that Confer Resistance to Herbicides:

Resistance to herbicides that inhibit the growing point or meristem, such as an imidazolinone or a sulfonylurea, for example, by Lee et al., EMBO J. 7:1241 (1988), and Miki et al., Theor. Appl. Genet. 80:449 (1990), respectively.

Glyphosate tolerance (resistance conferred by, e.g., mutant 5-enolpyruvylshikimate-3-phosphate synthase (EPSPs) genes, aroA genes and glyphosate acetyl transferase (GAT) genes, respectively), or resistance to other phosphono compounds such as by glufosinate (phosphinothricin acetyl transferase (PAT) genes from *Streptomyces* species, including *Streptomyces hygroscopicus* and *Streptomyces viridochromogenes*), and to pyridinoxy or phenoxy propionic acids and cyclohexones by ACCase inhibitor-encoding genes. See, for example, U.S. Pat. Nos. 4,940,835 and 6,248,876, 4,769,061, EP No. 0 333 033 and U.S. Pat. No. 4,975,374. See also EP No. 0242246, DeGreef et al., Bio/Technology 7:61 (1989), Marshall et al., Theor. Appl. Genet. 83:435 (1992), WO 2005012515 to Castle et. al. and WO 2005107437.

Resistance to herbicides that inhibit photosynthesis, such as a triazine (psbA and gs+ genes) or a benzonitrile (nitrilase gene), and glutathione S-transferase in Przibila et al., Plant Cell 3:169 (1991), U.S. Pat. No. 4,810,648, and Hayes et al., Biochem. J. 285: 173 (1992).

Genes encoding Enzymes detoxifying the herbicide or a mutant glutamine synthase enzyme that is resistant to inhibition, e.g. n U.S. patent application Ser. No. 11/760,602. Or a detoxifying enzyme is an enzyme encoding a phosphinothricin acetyltransferase (such as the bar or pat protein from *Streptomyces* species). Phosphinothricin acetyltransferases are for example described in U.S. Pat. Nos. 5,561,236; 5,648,477; 5,646,024; 5,273,894; 5,637,489; 5,276,268; 5,739,082; 5,908,810 and 7,112,665.

Hydroxyphenylpyruvatedioxygenases (HPPD) inhibitors, ie naturally occurring HPPD resistant enzymes, or genes encoding a mutated or chimeric HPPD enzyme as described in WO 96/38567, WO 99/24585, and WO 99/24586, WO 2009/144079, WO 2002/046387, or U.S. Pat. No. 6,768,044.

4. Examples of Genes Involved in Abiotic Stress Tolerance:

Transgene capable of reducing the expression and/or the activity of poly(ADP-ribose) polymerase (PARP) gene in the plant cells or plants as described in WO 00/04173 or, WO/2006/045633.

Transgenes capable of reducing the expression and/or the activity of the PARG encoding genes of the plants or plants cells, as described e.g. in WO 2004/090140.

Transgenes coding for a plant-functional enzyme of the nicotineamide adenine dinucleotide salvage synthesis pathway including nicotinamidase, nicotinate phosphoribosyltransferase, nicotinic acid mononucleotide adenyl transferase, nicotinamide adenine dinucleotide synthetase or nicotine amide phosphoribosyltransferase as described e.g. in EP 04077624.7, WO 2006/133827, PCT/EP07/002,433, EP 1999263, or WO 2007/107326.

Enzymes involved in carbohydrate biosynthesis include those described in e.g. EP 0571427, WO 95/04826, EP 0719338, WO 96/15248, WO 96/19581, WO 96/27674, WO 97/11188, WO 97/26362, WO 97/32985, WO 97/42328, WO 97/44472, WO 97/45545, WO 98/27212, WO 98/40503, WO 99/58688, WO 99/58690, WO 99/58654, WO 00/08184, WO 00/08185, WO 00/08175, WO 00/28052, WO 00/77229, WO 01/12782, WO 01/12826, WO 02/101059, WO 03/071860, WO 2004/056999, WO 2005/030942, WO 2005/030941, WO 2005/095632, WO 2005/095617, WO 2005/095619, WO 2005/095618, WO 2005/123927, WO 2006/018319, WO 2006/103107, WO 2006/108702, WO 2007/009823, WO 00/22140, WO 2006/063862, WO 2006/072603, WO 02/034923, EP 06090134.5, EP 06090228.5, EP 06090227.7, EP 07090007.1, EP 07090009.7, WO 01/14569, WO 02/79410, WO 03/33540, WO 2004/078983, WO 01/19975, WO 95/26407, WO 96/34968, WO 98/20145, WO 99/12950, WO 99/66050, WO 99/53072, U.S. Pat. No. 6,734,341, WO 00/11192, WO 98/22604, WO 98/32326, WO 01/98509, WO 01/98509, WO 2005/002359, U.S. Pat. Nos. 5,824,790, 6,013,861, WO 94/04693, WO 94/09144, WO 94/11520, WO 95/35026 or WO 97/20936 or enzymes involved in the production of polyfructose, especially of the inulin and levan-type, as disclosed in EP 0663956, WO 96/01904, WO 96/21023, WO 98/39460, and WO 99/24593, the production of alpha-1,4-glucans as disclosed in WO 95/31553, US 2002031826, U.S. Pat. Nos. 6,284,479, 5,712,107, WO 97/47806, WO 97/47807, WO 97/47808 and WO 00/14249, the production of alpha-1,6 branched alpha-1,4-glucans, as disclosed in WO 00/73422, the production of alternan, as disclosed in e.g. WO 00/47727, WO 00/73422, EP 06077301.7, U.S. Pat. No. 5,908,975 and EP 0728213, the production of hyaluronan, as for example disclosed in WO 2006/032538, WO 2007/039314, WO 2007/039315, WO 2007/039316, JP 2006304779, and WO 2005/012529.

Genes that improve drought resistance. For example, WO 2013122472 discloses that the absence or reduced level of functional Ubiquitin Protein Ligase protein (UPL) protein, more specifically, UPL3, leads to a decreased need for water or improved resistance to drought of said plant. Other examples of transgenic plants with increased drought tolerance are disclosed in, for example, US 2009/0144850, US 2007/0266453, and WO 2002/083911. US2009/0144850 describes a plant displaying a drought tolerance phenotype due to altered expression of a DRO2 nucleic acid. US 2007/0266453 describes a plant displaying a drought tolerance phenotype due to altered expression of a DRO3 nucleic acid and WO 2002/08391 1 describes a plant having an increased tolerance to drought stress due to a reduced activity of an ABC transporter which is expressed in guard cells. Another example is the work by Kasuga and co-authors (1999), who describe that overexpression of cDNA encoding DREB1 A in transgenic plants activated the expression of many stress tolerance genes under normal growing conditions and resulted in improved tolerance to drought, salt loading, and freezing. However, the expression of DREB1A also resulted in severe growth retardation under normal growing conditions (Kasuga (1999) Nat Biotechnol 17(3) 287-291).

In further particular embodiments, crop plants can be improved by influencing specific plant traits. For example, by developing pesticide-resistant plants, improving disease resistance in plants, improving plant insect and nematode resistance, improving plant resistance against parasitic weeds, improving plant drought tolerance, improving plant nutritional value, improving plant stress tolerance, avoiding self-pollination, plant forage digestibility biomass, grain yield etc. A few specific non-limiting examples are provided hereinbelow.

In addition to targeted mutation of single genes, Cpf1 CRISPR complexes can be designed to allow targeted mutation of multiple genes, deletion of chromosomal fragment, site-specific integration of transgene, site-directed mutagenesis in vivo, and precise gene replacement or allele swapping in plants. Therefore, the methods described herein have broad applications in gene discovery and validation, mutational and cisgenic breeding, and hybrid breeding. These applications facilitate the production of a new generation of genetically modified crops with various improved agronomic traits such as herbicide resistance, disease resistance, abiotic stress tolerance, high yield, and superior quality.

Use of Cpf1 Gene to Create Male Sterile Plants

Hybrid plants typically have advantageous agronomic traits compared to inbred plants. However, for self-pollinating plants, the generation of hybrids can be challenging. In different plant types, genes have been identified which are important for plant fertility, more particularly male fertility. For instance, in maize, at least two genes have been identified which are important in fertility (Amitabh Mohanty International Conference on New Plant Breeding Molecular Technologies Technology Development And Regulation, Oct. 9-10, 2014, Jaipur, India; Svitashev et al. Plant Physiol. 2015 October; 169(2):931-45; Djukanovic et al. Plant J. 2013 December; 76(5):888-99). The methods provided herein can be used to target genes required for male fertility so as to generate male sterile plants which can easily be crossed to generate hybrids. In particular embodiments, the Cpf1 CRISPR system provided herein is used for targeted mutagenesis of the cytochrome P450-like gene (MS26) or the meganuclease gene (MS45) thereby conferring male sterility to the maize plant. Maize plants which are as such genetically altered can be used in hybrid breeding programs.

Increasing the Fertility Stage in Plants

In particular embodiments, the methods provided herein are used to prolong the fertility stage of a plant such as of a rice plant. For instance, a rice fertility stage gene such as Ehd3 can be targeted in order to generate a mutation in the gene and plantlets can be selected for a prolonged regeneration plant fertility stage (as described in CN 104004782).

Use of Cpf1 to Generate Genetic Variation in a Crop of Interest

The availability of wild germplasm and genetic variations in crop plants is the key to crop improvement programs, but the available diversity in germplasms from crop plants is limited. The present invention envisages methods for generating a diversity of genetic variations in a germplasm of interest. In this application of the Cpf1 CRISPR system a library of guide RNAs targeting different locations in the plant genome is provided and is introduced into plant cells together with the Cpf1 effector protein. In this way a collection of genome-scale point mutations and gene knockouts can be generated. In particular embodiments, the methods comprise generating a plant part or plant from the cells so obtained and screening the cells for a trait of interest. The target genes can include both coding and non-coding regions. In particular embodiments, the trait is stress tolerance and the method is a method for the generation of stress-tolerant crop varieties.

Use of Cpf1 to Affect Fruit-Ripening

Ripening is a normal phase in the maturation process of fruits and vegetables. Only a few days after it starts it renders a fruit or vegetable inedible. This process brings significant losses to both farmers and consumers. In particular embodiments, the methods of the present invention are used to reduce ethylene production. This is ensured by ensuring one or more of the following: a. Suppression of ACC synthase gene expression. ACC (1-aminocyclopropane-1-carboxylic acid) synthase is the enzyme responsible for the conversion of S-adenosylmethionine (SAM) to ACC; the second to the last step in ethylene biosynthesis. Enzyme expression is hindered when an antisense ("mirror-image") or truncated copy of the synthase gene is inserted into the plant's genome; b. Insertion of the ACC deaminase gene. The gene coding for the enzyme is obtained from *Pseudomonas chlororaphis*, a common nonpathogenic soil bacterium. It converts ACC to a different compound thereby reducing the amount of ACC available for ethylene production; c. Insertion of the SAM hydrolase gene. This approach is similar to ACC deaminase wherein ethylene production is hindered when the amount of its precursor metabolite is reduced; in this case SAM is converted to homoserine. The gene coding for the enzyme is obtained from *E. coli* T3 bacteriophage and d. Suppression of ACC oxidase gene expression. ACC oxidase is the enzyme which catalyzes the oxidation of ACC to ethylene, the last step in the ethylene biosynthetic pathway. Using the methods described herein, down regulation of the ACC oxidase gene results in the suppression of ethylene production, thereby delaying fruit ripening. In particular embodiments, additionally or alternatively to the modifications described above, the methods described herein are used to modify ethylene receptors, so as to interfere with ethylene signals obtained by the fruit. In particular embodiments, expression of the ETR1 gene, encoding an ethylene binding protein is modified, more particularly suppressed. In particular embodiments, additionally or alternatively to the modifications described above, the methods described herein are used to modify expression of the gene encoding Polygalacturonase (PG), which is the enzyme responsible for the breakdown of pectin, the substance that maintains the integrity of plant cell walls. Pectin breakdown occurs at the start of the ripening process resulting in the softening of the fruit. Accordingly, in particular embodiments, the methods described herein are used to introduce a mutation in the PG gene or to suppress activation of the PG gene in order to reduce the amount of PG enzyme produced thereby delaying pectin degradation.

Thus in particular embodiments, the methods comprise the use of the Cpf1 CRISPR system to ensure one or more modifications of the genome of a plant cell such as described above, and regenerating a plant therefrom. In particular embodiments, the plant is a tomato plant.

Increasing Storage Life of Plants

In particular embodiments, the methods of the present invention are used to modify genes involved in the production of compounds which affect storage life of the plant or plant part. More particularly, the modification is in a gene that prevents the accumulation of reducing sugars in potato tubers. Upon high-temperature processing, these reducing sugars react with free amino acids, resulting in brown, bitter-tasting products and elevated levels of acrylamide, which is a potential carcinogen. In particular embodiments, the methods provided herein are used to reduce or inhibit expression of the vacuolar invertase gene (VInv), which encodes a protein that breaks down sucrose to glucose and fructose (Clasen et al. DOI: 10.1111/pbi.12370).

The Use of the Cpf1 CRISPR System to Ensure a Value Added Trait

In particular embodiments the Cpf1 CRISPR system is used to produce nutritionally improved agricultural crops. In particular embodiments, the methods provided herein are adapted to generate "functional foods", i.e. a modified food or food ingredient that may provide a health benefit beyond the traditional nutrients it contains and/or "nutraceutical", i.e. substances that may be considered a food or part of a food and provides health benefits, including the prevention and treatment of disease. In particular embodiments, the nutraceutical is useful in the prevention and/or treatment of one or more of cancer, diabetes, cardiovascular disease, and hypertension.

Examples of nutritionally improved crops include (Newell-McGloughlin, Plant Physiology, July 2008, Vol. 147, pp. 939-953):

modified protein quality, content and/or amino acid composition, such as have been described for Bahiagrass (Luciani et al. 2005, Florida Genetics Conference Poster), Canola (Roesler et al., 1997, Plant Physiol 113 75-81), Maize (Cromwell et al, 1967, 1969 J Anim Sci 26 1325-1331, O'Quin et al. 2000 J Anim Sci 78 2144-2149, Yang et al. 2002, Transgenic Res 11 11-20, Young et al. 2004, Plant J 38 910-922), Potato (Yu J and Ao, 1997 Acta Bot Sin 39 329-334; Chakraborty et al. 2000, Proc Natl Acad Sci USA 97 3724-3729; Li et al. 2001) Chin Sci Bull 46 482-484, Rice (Katsube et al. 1999, Plant Physiol 120 1063-1074), Soybean (Dinkins et al. 2001, Rapp 2002, In Vitro Cell Dev Biol Plant 37 742-747), Sweet Potato (Egnin and Prakash 1997, In Vitro Cell Dev Biol 33 52A).

essential amino acid content, such as has been described for Canola (Falco et al. 1995, Bio/Technology 13 577-582), Lupin (White et al. 2001, J Sci Food Agric 81 147-154), Maize (Lai and Messing, 2002, Agbios 2008 GM crop database (Mar. 11, 2008)), Potato (Zeh et al. 2001, Plant Physiol 127 792-802), Sorghum (Zhao et al. 2003, Kluwer Academic Publishers, Dordrecht, The Netherlands, pp 413-416), Soybean (Falco et al. 1995 Bio/Technology 13 577-582; Galili et al. 2002 Crit Rev Plant Sci 21 167-204).

Oils and Fatty acids such as for Canola (Dehesh et al. (1996) Plant J 9 167-172 [PubMed]; Del Vecchio (1996) INFORM International News on Fats, Oils and Related Materials 7 230-243; Roesler et al. (1997) Plant Physiol 113 75-81 [PMC free article] [PubMed]; Froman and Ursin (2002, 2003) Abstracts of Papers of the American Chemical Society 223 U35; James et al. (2003) Am J Clin Nutr 77 1140-1145 [PubMed]; Agbios (2008, above); coton (Chapman et al. (2001). J Am Oil Chem Soc 78 941-947; Liu et al. (2002) J Am Coll Nutr 21 205S-211S [PubMed]; O'Neill (2007) Australian Life Scientist. www.biotechnews.com.au/index.php/id; 866694817; fp; 4; fpid; 2 (Jun. 17, 2008), Linseed (Abbadi et al., 2004, Plant Cell 16: 2734-2748), Maize (Young et al., 2004, Plant J 38 910-922), oil palm (Jalani et al. 1997, J Am Oil Chem Soc 74 1451-1455; Parveez, 2003, AgBiotechNet 113 1-8), Rice (Anai et al., 2003, Plant Cell Rep 21 988-992), Soybean (Reddy and Thomas, 1996, Nat Biotechnol 14 639-642; Kinney and Kwolton, 1998, Blackie Academic and Professional, London, pp 193-213), Sunflower (Arcadia, Biosciences 2008).

Carbohydrates, such as Fructans described for Chicory (Smeekens (1997) Trends Plant Sci 2 286-287, Sprenger et al. (1997) FEBS Lett 400 355-358, Sèvenier et al. (1998) Nat Biotechnol 16 843-846), Maize (Caimi et al. (1996) Plant Physiol 110 355-363), Potato (Hellwege et al., 1997 Plant J 12 1057-1065), Sugar Beet (Smeekens et al. 1997, above), Inulin, such as described for Potato (Hellewege et al. 2000, Proc Natl Acad Sci USA 97 8699-8704), Starch, such as described for Rice (Schwall et al. (2000) Nat Biotechnol 18 551-554, Chiang et al. (2005) Mol Breed 15 125-143).

Vitamins and carotenoids, such as described for Canola (Shintani and DellaPenna (1998) Science 282 2098-2100), Maize (Rocheford et al. (2002). J Am Coll Nutr 21 191S-198S, Cahoon et al. (2003) Nat Biotechnol 21 1082-1087, Chen et al. (2003) Proc Natl Acad Sci USA 100 3525-3530), Mustardseed (Shewmaker et al. (1999) Plant J 20 401-412, Potato (Ducreux et al., 2005, J Exp Bot 56 81-89), Rice (Ye et al. (2000) Science 287 303-305, Strawberry (Agius et al. (2003), Nat Biotechnol 21 177-181), Tomato (Rosati et al. (2000) Plant J 24 413-419, Fraser et al. (2001) J Sci Food Agric 81 822-827, Mehta et al. (2002) Nat Biotechnol 20 613-618, Diaz de la Garza et al. (2004) Proc Natl Acad Sci USA 101 13720-13725, Enfissi et al. (2005) Plant Biotechnol J 3 17-27, DellaPenna (2007) Proc Natl Acad Sci USA 104 3675-3676.

Functional secondary metabolites, such as described for Apple (stilbenes, Szankowski et al. (2003) Plant Cell Rep 22: 141-149), Alfalfa (resveratrol, Hipskind and Paiva (2000) Mol Plant Microbe Interact 13 551-562), Kiwi (resveratrol, Kobayashi et al. (2000) Plant Cell Rep 19 904-910), Maize and Soybean (flavonoids, Yu et al. (2000) Plant Physiol 124 781-794), Potato (anthocyanin and alkaloid glycoside, Lukaszewicz et al. (2004) J Agric Food Chem 52 1526-1533), Rice (flavonoids & resveratrol, Stark-Lorenzen et al. (1997) Plant Cell Rep 16 668-673, Shin et al. (2006) Plant Biotechnol J 4 303-315), Tomato (+resveratrol, chlorogenic acid, flavonoids, stilbene; Rosati et al. (2000) above, Muir et al. (2001) Nature 19 470-474, Niggeweg et al. (2004) Nat Biotechnol 22 746-754, Giovinazzo et al. (2005) Plant Biotechnol J 3 57-69), wheat (caffeic and ferulic acids, resveratrol; United Press International (2002)); and Mineral availabilities such as described for Alfalfa (phytase, Austin-Phillips et al. (1999) www.molecularfarming.com/nonmedical.html), Lettuce (iron, Goto et al. (2000) Theor Appl Genet 100 658-664), Rice (iron, Lucca et al. (2002) J Am Coll Nutr 21 184S-190S), Maize, Soybean and wheat (phytase, Drakakaki et al. (2005) Plant Mol Biol 59 869-880, Denbow et al. (1998) Poult Sci 77 878-881, Brinch-Pedersen et al. (2000) Mol Breed 6 195-206).

In particular embodiments, the value-added trait is related to the envisaged health benefits of the compounds present in the plant. For instance, in particular embodiments, the value-added crop is obtained by applying the methods of the invention to ensure the modification of or induce/increase the synthesis of one or more of the following compounds:

Carotenoids, such as α-Carotene present in carrots which Neutralizes free radicals that may cause damage to cells or β-Carotene present in various fruits and vegetables which neutralizes free radicals Lutein present in green vegetables which contributes to maintenance of healthy vision Lycopene present in tomato and tomato products, which is believed to reduce the risk of prostate cancer Zeaxanthin, present in citrus and maize, which contributes to maintenance of healthy vision Dietary fiber such as insoluble fiber present in wheat bran which may reduce the risk of breast and/or colon cancer and β-Glucan present in oat, soluble fiber present in Psylium and whole cereal grains which may reduce the risk of cardiovascular disease (CVD)

Fatty acids, such as ω-3 fatty acids which may reduce the risk of CVD and improve mental and visual functions, Conjugated linoleic acid, which may improve body composition, may decrease risk of certain cancers and GLA which may reduce inflammation risk of cancer and CVD, may improve body composition Flavonoids such as Hydroxycinnamates, present in wheat which have Antioxidant-like activities, may reduce risk of degenerative diseases, flavonols, catechins and tannins present in fruits and vegetables which neutralize free radicals and may reduce risk of cancer Glucosinolates, indoles, isothiocyanates, such as Sulforaphane, present in Cruciferous vegetables (broccoli, kale), horseradish, which neutralize free radicals, may reduce risk of cancer Phenolics, such as stilbenes present in grape which May reduce risk of degenerative diseases, heart disease, and cancer, may have longevity effect and caffeic acid and ferulic acid present in vegetables and citrus which have Antioxidant-like activities, may reduce risk of degenerative diseases, heart disease, and eye disease, and epicatechin present in cacao which has Antioxidant-like activities, may reduce risk of degenerative diseases and heart disease Plant stanols/sterols present in maize, soy, wheat and wooden oils which May reduce risk of coronary heart disease by lowering blood cholesterol levels Fructans, inulins, fructo-oligosaccharides present in Jerusalem artichoke, shallot, onion powder which may improve gastrointestinal health Saponins present in soybean, which may lower LDL cholesterol Soybean protein present in soybean which may reduce risk of heart disease Phytoestrogens such as isoflavones present in soybean which May reduce menopause symptoms, such as hot flashes, may reduce osteoporosis and CVD and lignans present in flax, rye and vegetables, which May protect against heart disease and some cancers, may lower LDL cholesterol, total cholesterol.

Sulfides and thiols such as diallyl sulphide present in onion, garlic, olive, leek and scallion and Allyl methyl trisulfide, dithiolthiones present in cruciferous vegetables which may lower LDL cholesterol, helps to maintain healthy immune system Tannins, such as proanthocyanidins, present in cranberry, cocoa, which may improve urinary tract health, may reduce risk of CVD and high blood pressure.

In addition, the methods of the present invention also envisage modifying protein/starch functionality, shelf life, taste/aesthetics, fiber quality, and allergen, antinutrient, and toxin reduction traits.

Accordingly, the invention encompasses methods for producing plants with nutritional added value, said methods comprising introducing into a plant cell a gene encoding an enzyme involved in the production of a component of added nutritional value using the Cpf1 CRISPR system as described herein and regenerating a plant from said plant cell, said plant characterized in an increase expression of said component of added nutritional value. In particular embodiments, the Cpf1 CRISPR system is used to modify the endogenous synthesis of these compounds indirectly, e.g. by modifying one or more transcription factors that controls the metabolism of this compound. Methods for introducing a gene of interest into a plant cell and/or modifying an endogenous gene using the Cpf1 CRISPR system are described herein above.

Some specific examples of modifications in plants that have been modified to confer value-added traits are: plants with modified fatty acid metabolism, for example, by transforming a plant with an antisense gene of stearyl-ACP desaturase to increase stearic acid content of the plant. See Knultzon et al., Proc. Natl. Acad. Sci. U.S.A. 89:2624 (1992). Another example involves decreasing phytate content, for example by cloning and then reintroducing DNA associated with the single allele which may be responsible for maize mutants characterized by low levels of phytic acid. See Raboy et al, Maydica 35:383 (1990).

Similarly, expression of the maize (Zea mays) Tfs C1 and R, which regulate the production of flavonoids in maize aleurone layers under the control of a strong promoter, resulted in a high accumulation rate of anthocyanins in Arabidopsis (Arabidopsis thaliana), presumably by activating the entire pathway (Bruce et al., 2000, Plant Cell 12:65-80). DellaPenna (Welsch et al., 2007 Annu Rev Plant Biol 57: 711-738) found that Tf RAP2.2 and its interacting partner SINAT2 increased carotenogenesis in Arabidopsis leaves. Expressing the Tf Dof1 induced the up-regulation of genes encoding enzymes for carbon skeleton production, a marked increase of amino acid content, and a reduction of the Glc level in transgenic Arabidopsis (Yanagisawa, 2004 Plant Cell Physiol 45: 386-391), and the DOF Tf AtDof1.1 (OBP2) up-regulated all steps in the glucosinolate biosynthetic pathway in Arabidopsis (Skirycz et al., 2006 Plant J 47: 10-24).

Reducing Allergen in Plants

In particular embodiments the methods provided herein are used to generate plants with a reduced level of allergens, making them safer for the consumer. In particular embodiments, the methods comprise modifying expression of one or more genes responsible for the production of plant allergens. For instance, in particular embodiments, the methods comprise down-regulating expression of a Lol p5 gene in a plant cell, such as a ryegrass plant cell and regenerating a plant therefrom so as to reduce allergenicity of the pollen of said plant (Bhalla et al. 1999, Proc. Natl. Acad. Sci. USA Vol. 96: 11676-11680).

Peanut allergies and allergies to legumes generally are a real and serious health concern. The Cpf1 effector protein system of the present invention can be used to identify and then edit or silence genes encoding allergenic proteins of such legumes. Without limitation as to such genes and proteins, Nicolaou et al. identifies allergenic proteins in peanuts, soybeans, lentils, peas, lupin, green beans, and mung beans. See, Nicolaou et al., Current Opinion in Allergy and Clinical Immunology 2011; 11(3):222).

Screening Methods for Endogenous Genes of Interest

The methods provided herein further allow the identification of genes of value encoding enzymes involved in the production of a component of added nutritional value or generally genes affecting agronomic traits of interest, across species, phyla, and plant kingdom. By selectively targeting e.g. genes encoding enzymes of metabolic pathways in plants using the Cpf1 CRISPR system as described herein, the genes responsible for certain nutritional aspects of a plant can be identified. Similarly, by selectively targeting genes which may affect a desirable agronomic trait, the relevant genes can be identified. Accordingly, the present invention encompasses screening methods for genes encoding enzymes involved in the production of compounds with a particular nutritional value and/or agronomic traits.

Further Applications of the Cpf1 CRISPR System in Plants and Yeasts

Use of Cpf1 CRISPR System in Biofuel Production

The term "biofuel" as used herein is an alternative fuel made from plant and plant-derived resources. Renewable biofuels can be extracted from organic matter whose energy has been obtained through a process of carbon fixation or are made through the use or conversion of biomass. This biomass can be used directly for biofuels or can be converted to convenient energy containing substances by thermal conversion, chemical conversion, and biochemical conversion. This biomass conversion can result in fuel in solid, liquid, or gas form. There are two types of biofuels: bioethanol and biodiesel. Bioethanol is mainly produced by the sugar fermentation process of cellulose (starch), which is mostly derived from maize and sugar cane. Biodiesel on the other hand is mainly produced from oil crops such as rapeseed, palm, and soybean. Biofuels are used mainly for transportation.

Enhancing Plant Properties for Biofuel Production

In particular embodiments, the methods using the Cpf1 CRISPR system as described herein are used to alter the properties of the cell wall in order to facilitate access by key hydrolysing agents for a more efficient release of sugars for fermentation. In particular embodiments, the biosynthesis of cellulose and/or lignin are modified. Cellulose is the major component of the cell wall. The biosynthesis of cellulose and lignin are co-regulated. By reducing the proportion of lignin in a plant the proportion of cellulose can be increased. In particular embodiments, the methods described herein are used to downregulate lignin biosynthesis in the plant so as to increase fermentable carbohydrates. More particularly, the methods described herein are used to downregulate at least a first lignin biosynthesis gene selected from the group consisting of 4-coumarate 3-hydroxylase (C3H), phenylalanine ammonia-lyase (PAL), cinnamate 4-hydroxylase (C4H), hydroxycinnamoyl transferase (HCT), caffeic acid O-methyltransferase (COMT), caffeoyl CoA 3-O-methyltransferase (CCoAOMT), ferulate 5-hydroxylase (F5H), cinnamyl alcohol dehydrogenase (CAD), cinnamoyl CoA-reductase (CCR), 4-coumarate-CoA ligase (4CL), monolignol-lignin-specific glycosyltransferase, and aldehyde dehydrogenase (ALDH) as disclosed in WO 2008064289 A2.

In particular embodiments, the methods described herein are used to produce plant mass that produces lower levels of acetic acid during fermentation (see also WO 2010096488). More particularly, the methods disclosed herein are used to generate mutations in homologs to CaslL to reduce polysaccharide acetylation.

Modifying Yeast for Biofuel Production

In particular embodiments, the Cpf1 enzyme provided herein is used for bioethanol production by recombinant micro-organisms. For instance, Cpf1 can be used to engineer micro-organisms, such as yeast, to generate biofuel or biopolymers from fermentable sugars and optionally to be able to degrade plant-derived lignocellulose derived from agricultural waste as a source of fermentable sugars. More particularly, the invention provides methods whereby the Cpf1 CRISPR complex is used to introduce foreign genes required for biofuel production into micro-organisms and/or to modify endogenous genes why may interfere with the biofuel synthesis. More particularly the methods involve introducing into a micro-organism such as a yeast one or more nucleotide sequence encoding enzymes involved in the conversion of pyruvate to ethanol or another product of interest. In particular embodiments the methods ensure the introduction of one or more enzymes which allows the micro-organism to degrade cellulose, such as a cellulase. In yet further embodiments, the Cpf1 CRISPR complex is used to modify endogenous metabolic pathways which compete with the biofuel production pathway.

Accordingly, in more particular embodiments, the methods described herein are used to modify a micro-organism as follows:

to introduce at least one heterologous nucleic acid or increase expression of at least one endogenous nucleic acid encoding a plant cell wall degrading enzyme, such that said micro-organism is capable of expressing said nucleic acid and of producing and secreting said plant cell wall degrading enzyme;

to introduce at least one heterologous nucleic acid or increase expression of at least one endogenous nucleic acid encoding an enzyme that converts pyruvate to acetaldehyde optionally combined with at least one heterologous nucleic acid encoding an enzyme that converts acetaldehyde to ethanol such that said host cell is capable of expressing said nucleic acid; and/or to modify at least one nucleic acid encoding for an enzyme in a metabolic pathway in said host cell, wherein said pathway produces a metabolite other than acetaldehyde from pyruvate or ethanol from acetaldehyde, and wherein said modification results in a reduced production of said metabolite, or to introduce at least one nucleic acid encoding for an inhibitor of said enzyme.

Modifying Algae and Plants for Production of Vegetable Oils or Biofuels

Transgenic algae or other plants such as rape may be particularly useful in the production of vegetable oils or biofuels such as alcohols (especially methanol and ethanol), for instance. These may be engineered to express or overexpress high levels of oil or alcohols for use in the oil or biofuel industries.

According to particular embodiments of the invention, the Cpf1 CRISPR system is used to generate lipid-rich diatoms which are useful in biofuel production.

In particular embodiments it is envisaged to specifically modify genes that are involved in the modification of the quantity of lipids and/or the quality of the lipids produced by the algal cell. Examples of genes encoding enzymes involved in the pathways of fatty acid synthesis can encode proteins having for instance acetyl-CoA carboxylase, fatty acid synthase, 3-ketoacyl_acyl-carrier protein synthase III, glycerol-3-phosphate dehydrogenase (G3PDH), Enoyl-acyl carrier protein reductase (Enoyl-ACP-reductase), glycerol-3-phosphate acyltransferase, lysophosphatidic acyl transferase or diacylglycerol acyltransferase, phospholipid: diacylglycerol acyltransferase, phosphatidate phosphatase, fatty acid thioesterase such as palmitoyl protein thioesterase, or malic enzyme activities. In further embodiments it is envisaged to generate diatoms that have increased lipid accumulation. This can be achieved by targeting genes that decrease lipid catabolisation. Of particular interest for use in the methods of the present invention are genes involved in the activation of both triacylglycerol and free fatty acids, as well as genes directly involved in β-oxidation of fatty acids, such as acyl-CoA synthetase, 3-ketoacyl-CoA thiolase, acyl-CoA oxidase activity and phosphoglucomutase. The Cpf1 CRISPR system and methods described herein can be used to specifically activate such genes in diatoms as to increase their lipid content.

Organisms such as microalgae are widely used for synthetic biology. Stovicek et al. (Metab. Eng. Comm., 2015; 2:13 describes genome editing of industrial yeast, for example, *Saccharomyces cerevisiae*, to efficiently produce robust strains for industrial production. Stovicek used a CRISPR-Cas9 system codon-optimized for yeast to simultaneously disrupt both alleles of an endogenous gene and knock in a heterologous gene. Cas9 and gRNA were expressed from genomic or episomal 2μ-based vector locations. The authors also showed that gene disruption efficiency could be improved by optimization of the levels of Cas9 and gRNA expression. Hlavová et al. (Biotechnol. Adv. 2015) discusses development of species or strains of microalgae using techniques such as CRISPR to target nuclear and chloroplast genes for insertional mutagenesis and screening. The methods of Stovicek and Hlavová may be applied to the Cpf1 effector protein system of the present invention.

U.S. Pat. No. 8,945,839 describes a method for engineering Micro-Algae (*Chlamydomonas reinhardtii* cells) species) using Cas9. Using similar tools, the methods of the Cpf1 CRISPR system described herein can be applied on *Chlamydomonas* species and other algae. In particular embodiments, Cpf1 and guide RNA are introduced in algae expressed using a vector that expresses Cpf1 under the control of a constitutive promoter such as Hsp70A-Rbc S2 or Beta2-tubulin. Guide RNA will be delivered using a vector containing T7 promoter. Alternatively, Cpf1 mRNA and in vitro transcribed guide RNA can be delivered to algal cells. Electroporation protocol follows standard recommended protocol from the GeneArt *Chlamydomonas* Engineering kit.

The Use of Cpf1 in the Generation of Micro-Organisms Capable of Fatty Acid Production In particular embodiments, the methods of the invention are used for the generation of genetically engineered micro-organisms capable of the production of fatty esters, such as fatty acid methyl esters ("FAME") and fatty acid ethyl esters ("FAEE").

Typically, host cells can be engineered to produce fatty esters from a carbon source, such as an alcohol, present in the medium, by expression or overexpression of a gene encoding a thioesterase, a gene encoding an acyl-CoA synthase, and a gene encoding an ester synthase. Accordingly, the methods provided herein are used to modify a micro-organisms so as to overexpress or introduce a thioesterase gene, a gene encoding an acyl-CoA synthase, and a gene encoding an ester synthase. In particular embodiments, the thioesterase gene is selected from tesA, 'tesA, tesB, fatB, fatB2, fatB3, fatA1, or fatA. In particular embodiments, the gene encoding an acyl-CoA synthase is selected from fadDJadK, BH3103, pfl-4354, EAV15023, fadD1, fadD2, RPC_4074, fadDD35, fadDD22, faa39, or an identified gene encoding an enzyme having the same properties. In particular embodiments, the gene encoding an ester synthase is a gene encoding a synthase/acyl-CoA:diacyl glycerol acyltransferase from *Simmondsia chinensis*, *Acinetobacter* sp. ADP, *Alcanivorax borkumensis*, *Pseudomonas aeruginosa*, *Fundibacter jadensis*, *Arabidopsis thaliana*, or *Alcaligenes eutrophus*, or a variant thereof. Additionally or alternatively, the methods provided herein are used to decrease expression in said micro-organism of at least one of a gene encoding an acyl-CoA dehydrogenase, a gene encoding an outer membrane protein receptor, and a gene encoding a transcriptional regulator of fatty acid biosynthesis. In particular embodiments one or more of these genes is inactivated, such as by introduction of a mutation. In particular embodiments, the gene encoding an acyl-CoA dehydrogenase is fadE. In particular embodiments, the gene encoding a transcriptional regulator of fatty acid biosynthesis encodes a DNA transcription repressor, for example, fabR.

Additionally or alternatively, said micro-organism is modified to reduce expression of at least one of a gene encoding a pyruvate formate lyase, a gene encoding a lactate dehydrogenase, or both. In particular embodiments, the gene encoding a pyruvate formate lyase is pflB. In particular embodiments, the gene encoding a lactate dehydrogenase is IdhA. In particular embodiments one or more of these genes is inactivated, such as by introduction of a mutation therein.

In particular embodiments, the micro-organism is selected from the genus *Escherichia*, *Bacillus*, *Lactobacillus*, *Rhodococcus*, *Synechococcus*, *Synechocystis*, *Pseudomonas*, *Aspergillus*, *Trichoderma*, *Neurospora*, *Fusarium*, *Humicola*, *Rhizomucor*, *Kluyveromyces*, *Pichia*, *Mucor*, *Myceliophthora*, *Penicillium*, *Phanerochaete*, *Pleurotus*, *Trametes*, *Chrysosporium*, *Saccharomyces*, *Stenotrophomonas*, *Schizosaccharomyces*, *Yarrowia*, or *Streptomyces*.

The Use of Cpf1 in the Generation of Micro-Organisms Capable of Organic Acid Production The methods provided herein are further used to engineer micro-organisms capable of organic acid production, more particularly from pentose or hexose sugars. In particular embodiments, the methods comprise introducing into a micro-organism an exogenous LDH gene. In particular embodiments, the organic acid production in said micro-organisms is additionally or alternatively increased by inactivating endogenous genes encoding proteins involved in an endogenous metabolic pathway which produces a metabolite other than the organic acid of interest and/or wherein the endogenous metabolic pathway consumes the organic acid. In particular embodiments, the modification ensures that the production of the metabolite other than the organic acid of interest is reduced. According to particular embodiments, the methods are used to introduce at least one engineered gene deletion and/or inactivation of an endogenous pathway in which the organic acid is consumed or a gene encoding a product involved in an endogenous pathway which produces a metabolite other than the organic acid of interest. In particular embodiments, the at least one engineered gene deletion or inactivation is in one or more gene encoding an enzyme selected from the group consisting of pyruvate decarboxylase (pdc), fumarate reductase, alcohol dehydrogenase (adh), acetaldehyde dehydrogenase, phosphoenolpyruvate carboxylase (ppc), D-lactate dehydrogenase (d-ldh), L-lactate dehydrogenase (l-ldh), lactate 2-monooxygenase.

In further embodiments the at least one engineered gene deletion and/or inactivation is in an endogenous gene encoding pyruvate decarboxylase (pdc).

In further embodiments, the micro-organism is engineered to produce lactic acid and the at least one engineered gene deletion and/or inactivation is in an endogenous gene encoding lactate dehydrogenase. Additionally or alternatively, the micro-organism comprises at least one engineered gene deletion or inactivation of an endogenous gene encoding a cytochrome-dependent lactate dehydrogenase, such as a cytochrome B2-dependent L-lactate dehydrogenase.

The Use of Cpf1 in the Generation of Improved Xylose or Cellobiose Utilizing Yeasts Strains In particular embodiments, the Cpf1 CRISPR system may be applied to select for improved xylose or cellobiose utilizing yeast strains. Error-prone PCR can be used to amplify one (or more) genes involved in the xylose utilization or cellobiose utilization pathways. Examples of genes involved in xylose utilization pathways and cellobiose utilization pathways may include, without limitation, those described in Ha, S. J., et al. (2011) Proc. Natl. Acad. Sci. USA 108(2):504-9 and Galazka, J. M., et al. (2010) Science 330(6000):84-6. Resulting libraries of double-stranded DNA molecules, each comprising a random mutation in such a selected gene could be co-transformed with the components of the Cpf1 CRISPR system into a yeast strain (for instance S288C) and strains can be selected with enhanced xylose or cellobiose utilization capacity, as described in WO2015138855.

The Use of Cpf1 in the Generation of Improved Yeasts Strains for Use in Isoprenoid Biosynthesis Tadas Jakočiūnas et al. described the successful application of a multiplex CRISPR/Cas9 system for genome engineering of up to 5 different genomic loci in one transformation step in baker's yeast *Saccharomyces cerevisiae* (Metabolic Engineering Volume 28, March 2015, Pages 213-222) resulting in strains with high mevalonate production, a key intermediate for the industrially important isoprenoid biosynthesis pathway. In particular embodiments, the Cpf1 CRISPR system may be applied in a multiplex genome engineering method as described herein for identifying additional high producing yeast strains for use in isoprenoid synthesis.

The Use of Cpf1 in the Generation of Lactic Acid Producing Yeasts Strains

In another embodiment, successful application of a multiplex Cpf1 CRISPR system is encompassed. In analogy with Vratislav Stovicek et al. (Metabolic Engineering Communications, Volume 2, December 2015, Pages 13-22), improved lactic acid-producing strains can be designed and obtained in a single transformation event. In a particular embodiment, the Cpf1 CRISPR system is used for simultaneously inserting the heterologous lactate dehydrogenase gene and disruption of two endogenous genes PDC1 and PDC5 genes.

Further Applications of the Cpf1 CRISPR System in Plants

In particular embodiments, the CRISPR system, and preferably the Cpf1 CRISPR system described herein, can be used for visualization of genetic element dynamics. For example, CRISPR imaging can visualize either repetitive or non-repetitive genomic sequences, report telomere length change and telomere movements and monitor the dynamics of gene loci throughout the cell cycle (Chen et al., Cell, 2013). These methods may also be applied to plants.

Other applications of the CRISPR system, and preferably the Cpf1 CRISPR system described herein, is the targeted gene disruption positive-selection screening in vitro and in vivo (Malina et al., Genes and Development, 2013). These methods may also be applied to plants.

In particular embodiments, fusion of inactive Cpf1 endonucleases with histone-modifying enzymes can introduce custom changes in the complex epigenome (Rusk et al., Nature Methods, 2014). These methods may also be applied to plants.

In particular embodiments, the CRISPR system, and preferably the Cpf1 CRISPR system described herein, can be used to purify a specific portion of the chromatin and identify the associated proteins, thus elucidating their regulatory roles in transcription (Waldrip et al., Epigenetics, 2014). These methods may also be applied to plants.

In particular embodiments, present invention can be used as a therapy for virus removal in plant systems as it is able to cleave both viral DNA and RNA. Previous studies in human systems have demonstrated the success of utilizing CRISPR in targeting the single strand RNA virus, hepatitis C (A. Price, et al., Proc. Natl. Acad. Sci, 2015) as well as the double stranded DNA virus, hepatitis B (V. Ramanan, et al., Sci. Rep, 2015). These methods may also be adapted for using the Cpf1 CRISPR system in plants.

In particular embodiments, present invention could be used to alter genome complexity. In further particular embodiment, the CRISPR system, and preferably the Cpf1 CRISPR system described herein, can be used to disrupt or alter chromosome number and generate haploid plants, which only contain chromosomes from one parent. Such plants can be induced to undergo chromosome duplication and converted into diploid plants containing only homozygous alleles (Karimi-Ashtiyani et al., PNAS, 2015; Anton et al., Nucleus, 2014). These methods may also be applied to plants.

In particular embodiments, the Cpf1 CRISPR system described herein, can be used for self-cleavage. In these embodiments, the promotor of the Cpf1 enzyme and gRNA can be a constitutive promotor and a second gRNA is introduced in the same transformation cassette, but controlled by an inducible promoter. This second gRNA can be designated to induce site-specific cleavage in the Cpf1 gene in order to create a non-functional Cpf1. In a further particular embodiment, the second gRNA induces cleavage on both ends of the transformation cassette, resulting in the removal of the cassette from the host genome. This system offers a controlled duration of cellular exposure to the Cas enzyme and further minimizes off-target editing. Furthermore, cleavage of both ends of a CRISPR/Cas cassette can be used to generate transgene-free T0 plants with bi-allelic mutations (as described for Cas9 e.g. Moore et al., Nucleic Acids Research, 2014; Schaeffer et al., Plant Science, 2015). The methods of Moore et al. may be applied to the Cpf1 CRISPR systems described herein.

Sugano et al. (Plant Cell Physiol. 2014 March; 55(3):475-81. doi: 10.1093/pcp/pcu014. Epub 2014 Jan. 18) reports the application of CRISPR-Cas9 to targeted mutagenesis in the liverwort *Marchantia polymorpha* L., which has emerged as a model species for studying land plant evolution. The U6 promoter of *M. polymorpha* was identified and cloned to express the gRNA. The target sequence of the gRNA was designed to disrupt the gene encoding auxin response factor 1 (ARF1) in *M. polymorpha*. Using *Agrobacterium*-mediated transformation, Sugano et al. isolated stable mutants in the gametophyte generation of *M. polymorpha*. CRISPR-Cas9-based site-directed mutagenesis in vivo was achieved using either the Cauliflower mosaic virus 35S or *M. polymorpha* EF1α promoter to express Cas9. Isolated mutant individuals showing an auxin-resistant phenotype were not chimeric. Moreover, stable mutants were produced by asexual reproduction of T1 plants. Multiple arf1 alleles were easily established using CRISPR-Cas9-based targeted mutagenesis. The methods of Sugano et al. may be applied to the Cpf1 effector protein system of the present invention.

Kabadi et al. (Nucleic Acids Res. 2014 Oct. 29; 42(19): e147. doi: 10.1093/nar/gku749. Epub 2014 Aug. 13) developed a single lentiviral system to express a Cas9 variant, a reporter gene and up to four sgRNAs from independent RNA polymerase III promoters that are incorporated into the vector by a convenient Golden Gate cloning method. Each sgRNA was efficiently expressed and can mediate multiplex gene editing and sustained transcriptional activation in immortalized and primary human cells. The methods of Kabadi et al. may be applied to the Cpf1 effector protein system of the present invention.

Ling et al. (BMC Plant Biology 2014, 14:327) developed a CRISPR-Cas9 binary vector set based on the pGreen or pCAMBIA backbone, as well as a gRNA This toolkit requires no restriction enzymes besides BsaI to generate final constructs harboring maize-codon optimized Cas9 and one or more gRNAs with high efficiency in as little as one cloning step. The toolkit was validated using maize protoplasts, transgenic maize lines, and transgenic *Arabidopsis* lines and was shown to exhibit high efficiency and specificity. More importantly, using this toolkit, targeted mutations of three *Arabidopsis* genes were detected in transgenic seedlings of the Ti generation. Moreover, the multiple-gene mutations could be inherited by the next generation, (guide RNA) module vector set, as a toolkit for multiplex genome editing in plants. The toolbox of Lin et al. may be applied to the Cpf1 effector protein system of the present invention.

Protocols for targeted plant genome editing via CRISPR-Cpf1 are also available based on those disclosed for the CRISPR-Cas9 system in volume 1284 of the series Methods in Molecular Biology pp 239-255 10 Feb. 2015. A detailed procedure to design, construct, and evaluate dual gRNAs for plant codon optimized Cas9 (pcoCas9) mediated genome editing using *Arabidopsis thaliana* and *Nicotiana benthamiana* protoplasts s model cellular systems are described. Strategies to apply the CRISPR-Cas9 system to generating targeted genome modifications in whole plants are also discussed. The protocols described in the chapter may be applied to the Cpf1 effector protein system of the present invention.

Ma et al. (Mol Plant. 2015 Aug. 3; 8(8):1274-84. doi: 10.1016/j.molp.2015.04.007) reports robust CRISPR-Cas9 vector system, utilizing a plant codon optimized Cas9 gene, for convenient and high-efficiency multiplex genome editing in monocot and dicot plants. Ma et al. designed PCR-based procedures to rapidly generate multiple sgRNA expression cassettes, which can be assembled into the binary CRISPR-Cas9 vectors in one round of cloning by Golden Gate ligation or Gibson Assembly. With this system, Ma et al. edited 46 target sites in rice with an average 85.4% rate of mutation, mostly in biallelic and homozygous status. Ma et al. provide examples of loss-of-function gene mutations in TO rice and Ti *Arabidopsis* plants by simultaneous targeting of multiple (up to eight) members of a gene family, multiple genes in a biosynthetic pathway, or multiple sites in a single gene. The methods of Ma et al. may be applied to the Cpf1 effector protein system of the present invention.

Lowder et al. (Plant Physiol. 2015 Aug. 21. pii: pp. 00636.2015) also developed a CRISPR-Cas9 toolbox enables multiplex genome editing and transcriptional regulation of expressed, silenced or non-coding genes in plants. This toolbox provides researchers with a protocol and reagents to quickly and efficiently assemble functional CRISPR-Cas9 T-DNA constructs for monocots and dicots using Golden Gate and Gateway cloning methods. It comes with a full suite of capabilities, including multiplexed gene editing and transcriptional activation or repression of plant endogenous genes. T-DNA based transformation technology is fundamental to modern plant biotechnology, genetics, molecular biology and physiology. As such, Applicants developed a method for the assembly of Cpf1 (WT, nickase or dCpf1) and gRNA(s) into a T-DNA destination-vector of interest. The assembly method is based on both Golden Gate assembly and MultiSite Gateway recombination. Three modules are required for assembly. The first module is a Cpf1 entry vector, which contains promoterless Cpf1 or its derivative genes flanked by attL1 and attR5 sites. The second module is a gRNA entry vector which contains entry gRNA expression cassettes flanked by attL5 and attL2 sites. The third module includes attR1-attR2-containing destination T-DNA vectors that provide promoters of choice for Cpf1 expression. The toolbox of Lowder et al. may be applied to the Cpf1 effector protein system of the present invention.

Wang et al. (bioRxiv 051342; doi: doi.org/10.1101/051342; Epub. May 12, 2016) demonstrate editing of homoeologous copies of four genes affecting important agronomic traits in hexaploid wheat using a multiplexed gene editing construct with several gRNA-tRNA units under the control of a single promoter.

In an advantageous embodiment, the plant may be a tree. The present invention may also utilize the herein disclosed CRISPR-Cas system for herbaceous systems (see, e.g., Belhaj et al., Plant Methods 9: 39 and Harrison et al., Genes & Development 28: 1859-1872). In a particularly advantageous embodiment, the CRISPR-Cas system of the present invention may target single nucleotide polymorphisms (SNPs) in trees (see, e.g., Zhou et al., New Phytologist, Volume 208, Issue 2, pages 298-301, October 2015). In the Zhou et al. study, the authors applied a CRISPR-Cas system in the woody perennial *Populus* using the 4-coumarate:CoA ligase (4CL) gene family as a case study and achieved 100% mutational efficiency for two 4CL genes targeted, with every transformant examined carrying biallelic modifications. In the Zhou et al., study, the CRISPR-Cas9 system was highly sensitive to single nucleotide polymorphisms (SNPs), as cleavage for a third 4CL gene was abolished due to SNPs in the target sequence. These methods may be applied to the Cpf1 effector protein system of the present invention.

The methods of Zhou et al. (New Phytologist, Volume 208, Issue 2, pages 298-301, October 2015) may be applied to the present invention as follows. Two 4CL genes, 4CL1 and 4CL2, associated with lignin and flavonoid biosynthesis, respectively are targeted for CRISPR-Cas9 editing. The *Populus tremula*×*alba* clone 717-1B4 routinely used for transformation is divergent from the genome-sequenced *Populus trichocarpa*. Therefore, the 4CL1 and 4CL2 gRNAs designed from the reference genome are interrogated with in-house 717 RNA-Seq data to ensure the absence of SNPs which could limit Cas efficiency. A third gRNA designed for 4CL5, a genome duplicate of 4CL1, is also included. The corresponding 717 sequence harbors one SNP in each allele near/within the PAM, both of which are expected to abolish targeting by the 4CL5-gRNA. All three gRNA target sites are located within the first exon. For 717 transformation, the gRNA is expressed from the *Medicago* U6.6 promoter, along with a human codon-optimized Cas under control of the CaMV 35S promoter in a binary vector. Transformation with the Cas-only vector can serve as a control. Randomly selected 4CL1 and 4CL2 lines are subjected to amplicon-sequencing. The data is then processed and biallelic mutations are confirmed in all cases. These methods may be applied to the Cpf1 effector protein system of the present invention.

In plants, pathogens are often host-specific. For example, *Fusarium oxysporum* f. sp. *lycopersici* causes tomato wilt but attacks only tomato, and *F. oxysporum* f. *dianthii* *Puccinia graminis* f. sp. *tritici* attacks only wheat. Plants have existing and induced defenses to resist most pathogens. Mutations and recombination events across plant generations lead to genetic variability that gives rise to susceptibility, especially as pathogens reproduce with more frequency than plants. In plants there can be non-host resistance, e.g., the host and pathogen are incompatible. There can also be Horizontal Resistance, e.g., partial resistance against all races of a pathogen, typically controlled by many genes and Vertical Resistance, e.g., complete resistance to some races of a pathogen but not to other races, typically controlled by a few genes. In a Gene-for-Gene level, plants and pathogens evolve together, and the genetic changes in one balance changes in other. Accordingly, using Natural Variability, breeders combine most useful genes for Yield, Quality, Uniformity, Hardiness, Resistance. The sources of resistance genes include native or foreign Varieties, Heirloom Varieties, Wild Plant Relatives, and Induced Mutations, e.g., treating plant material with mutagenic agents. Using the present invention, plant breeders are provided with a new tool to induce mutations. Accordingly, one skilled in the art can analyze the genome of sources of resistance genes, and in Varieties having desired characteristics or traits employ the present invention to induce the rise of resistance genes, with more precision than previous mutagenic agents and hence accelerate and improve plant breeding programs.

The following table provides additional references and related fields for which the CRISPR-Cas complexes, modified effector proteins, systems, and methods of optimization may be used to improve bioproduction.

TABLE 17

| | | |
|---|---|---|
| Feb. 17, 2014 | PCT/US15/63434 (WO2016/099887) | Compositions and methods for efficient gene editing in E. coli using guide RNA/Cas endonuclease systems in combination with circular polynucleotide modification templates. |
| Aug. 13, 2014 | PCT/US15/41256 (WO2016/025131) | Genetic targeting in non-conventional yeast using an RNA-guided endonuclease. |
| Nov. 6, 2014 | PCT/US15/58760 (WO2016/073433) | Peptide-mediated delivery of RNA-guided endonuclease into cells. |
| Oct. 12, 2015 | PCT/US16/56404 (WO2017/066175) | Protected DNA templates for gene modification and increased homologous recombination in cells and methods of use. |
| Dec. 11, 2015 | PCT/US16/65070 (WO2017/100158) | Methods and compositions for enhanced nuclease-mediated genome modification and reduced off-target site effects. |
| Dec. 18, 2015 | PCT/US16/65537 (WO2017/105991) | Methods and compositons for T-RNA based guide RNA expression. |
| Dec. 18, 2015 | PCT/US16/66772 (WO2017/106414) | Methods and compositions for polymerase II (Pol-II) based guide RNA expression. |
| Dec. 16, 2014 | PCT/US15/65693 (WO2016/100272) | Fungal genome modification systems and methods of use. |
| Dec. 16, 2014 | PCT/US15/66195 (WO2016/100571) | Fungal genome modification systems and methods of use |
| Dec. 16, 2014 | PCT/US15/66192 (WO2016/100568) | Fungal genome modification systems and methods of use. |
| Dec. 16, 2014 | PCT/US15/66178 (WO2016/100562) | Use of a helper strain with silenced NHEJ to improve homologous integration of targeted DNA cassettes in *Trichoderma reesei*. |
| Jul. 28, 2015 | PCT/US16/44489 (WO2017/019867) | Genome editing systems and methods of use. |

Improved Plants and Yeast Cells

The present invention also provides plants and yeast cells obtainable and obtained by the methods provided herein. The improved plants obtained by the methods described herein may be useful in food or feed production through expression of genes which, for instance ensure tolerance to plant pests, herbicides, drought, low or high temperatures, excessive water, etc.

The improved plants obtained by the methods described herein, especially crops and algae may be useful in food or feed production through expression of, for instance, higher protein, carbohydrate, nutrient or vitamin levels than would normally be seen in the wildtype. In this regard, improved plants, especially pulses and tubers are preferred.

Improved algae or other plants such as rape may be particularly useful in the production of vegetable oils or biofuels such as alcohols (especially methanol and ethanol), for instance. These may be engineered to express or over-express high levels of oil or alcohols for use in the oil or biofuel industries.

The invention also provides for improved parts of a plant. Plant parts include, but are not limited to, leaves, stems, roots, tubers, seeds, endosperm, ovule, and pollen. Plant parts as envisaged herein may be viable, nonviable, regeneratable, and/or non-regeneratable.

It is also encompassed herein to provide plant cells and plants generated according to the methods of the invention. Gametes, seeds, embryos, either zygotic or somatic, progeny or hybrids of plants comprising the genetic modification, which are produced by traditional breeding methods, are also included within the scope of the present invention. Such plants may contain a heterologous or foreign DNA sequence inserted at or instead of a target sequence. Alternatively, such plants may contain only an alteration (mutation, deletion, insertion, substitution) in one or more nucleotides. As such, such plants will only be different from their progenitor plants by the presence of the particular modification.

Thus, the invention provides a plant, animal or cell, produced by the present methods, or a progeny thereof. The progeny may be a clone of the produced plant or animal, or may result from sexual reproduction by crossing with other individuals of the same species to introgress further desirable traits into their offspring. The cell may be in vivo or ex vivo in the cases of multicellular organisms, particularly animals or plants.

The methods for genome editing using the Cpf1 system as described herein can be used to confer desired traits on essentially any plant, algae, fungus, yeast, etc. A wide variety of plants, algae, fungus, yeast, etc and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc of any foreign gene, including those encoding CRISPR components, so as to avoid the presence of foreign DNA in the genome of the plant. This can be of interest as the regulatory requirements for non-transgenic plants are less rigorous.

The CRISPR systems provided herein can be used to introduce targeted double-strand or single-strand breaks and/or to introduce gene activator and/or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

The methods described herein generally result in the generation of "improved plants, algae, fungi, yeast, etc" in that they have one or more desirable traits compared to the wildtype plant. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc. are non-transgenic. Where only the modification of an endogenous gene is ensured and no foreign genes are introduced or maintained in the plant, algae, fungi, yeast, etc. genome, the resulting genetically modified crops contain no foreign genes and can thus basically be considered non-transgenic. The different applications of the Cpf1 CRISPR system for plant, algae, fungi, yeast, etc. genome editing include, but are not limited to: introduction of one or more foreign genes to confer an agricultural trait of interest; editing of endogenous genes to confer an agricultural trait of interest; modulating of endogenous genes by the Cpf1 CRISPR system to confer an agricultural trait of interest. Exemplary genes conferring agronomic traits include, but are not limited to genes that confer resistance to pests or diseases; genes involved in plant diseases, such as those listed in WO 2013046247; genes that confer resistance to herbicides, fungicides, or the like; genes involved in (abiotic) stress tolerance. Other aspects of the use of the CRISPR-Cas system include, but are not limited to: create (male) sterile plants; increasing the fertility stage in plants/algae etc; generate genetic variation in a crop of interest; affect fruit-ripening; increasing storage life of plants/algae etc; reducing allergen in plants/algae etc; ensure a value added trait (e.g. nutritional improvement); Screening methods for endogenous genes of interest; biofuel, fatty acid, organic acid, etc production.

Cpf1 Effector Protein Complexes can be Used in Non-Human Organisms/Animals

In an aspect, the invention provides a non-human eukaryotic organism; preferably a multicellular eukaryotic organism, comprising a eukaryotic host cell according to any of the described embodiments. In other aspects, the invention provides a eukaryotic organism; preferably a multicellular eukaryotic organism, comprising a eukaryotic host cell according to any of the described embodiments. The organism in some embodiments of these aspects may be an animal; for example a mammal. Also, the organism may be an arthropod such as an insect. The present invention may also be extended to other agricultural applications such as, for example, farm and production animals. For example, pigs have many features that make them attractive as biomedical models, especially in regenerative medicine. In particular, pigs with severe combined immunodeficiency (SCID) may provide useful models for regenerative medicine, xenotransplantation (discussed also elsewhere herein), and tumor development and will aid in developing therapies for human SCID patients. Lee et al., (Proc Natl Acad Sci USA. 2014 May 20; 111(20):7260-5) utilized a reporter-guided transcription activator-like effector nuclease (TALEN) system to generated targeted modifications of recombination activating gene (RAG) 2 in somatic cells at high efficiency, including some that affected both alleles. The Cpf1 effector protein may be applied to a similar system.

The methods of Lee et al., (Proc Natl Acad Sci USA. 2014 May 20; 111(20):7260-5) may be applied to the present invention analogously as follows. Mutated pigs are produced by targeted modification of RAG2 in fetal fibroblast cells followed by SCNT and embryo transfer. Constructs coding for CRISPR-Cas and a reporter are electroporated into fetal-derived fibroblast cells. After 48 h, transfected cells expressing the green fluorescent protein are sorted into individual wells of a 96-well plate at an estimated dilution of a single cell per well. Targeted modification of RAG2 are screened by amplifying a genomic DNA fragment flanking any CRISPR-Cas cutting sites followed by sequencing the PCR products. After screening and ensuring lack of off-site mutations, cells carrying targeted modification of RAG2 are used for SCNT. The polar body, along with a portion of the adjacent cytoplasm of oocyte, presumably containing the metaphase II plate, are removed, and a donor cell are placed in the perivitelline. The reconstructed embryos are then electrically operated to fuse the donor cell with the oocyte and then chemically activated. The activated embryos are incubated in Porcine Zygote Medium 3 (PZM3) with 0.5 μM Scriptaid (S7817; Sigma-Aldrich) for 14-16 h. Embryos are then washed to remove the Scriptaid and cultured in PZM3 until they were transferred into the oviducts of surrogate pigs.

The present invention is also applicable to modifying SNPs of other animals, such as cows. Tan et al. (Proc Natl Acad Sci USA. 2013 Oct. 8; 110(41): 16526-16531) expanded the livestock gene editing toolbox to include transcription activator-like (TAL) effector nuclease (TALEN)- and clustered regularly interspaced short palindromic repeats (CRISPR)/Cas9-stimulated homology-directed repair (HDR) using plasmid, rAAV, and oligonucleotide templates. Gene specific gRNA sequences were cloned into the Church lab gRNA vector (Addgene ID: 41824) according to their methods (Mali P, et al. (2013) RNA-Guided Human Genome Engineering via Cas9. Science 339(6121):823-826). The Cas9 nuclease was provided either by co-transfection of the hCas9 plasmid (Addgene ID: 41815) or mRNA synthesized from RCIScript-hCas9. This RCIScript-hCas9 was constructed by sub-cloning the XbaI-AgeI fragment from the hCas9 plasmid (encompassing the hCas9 cDNA) into the RCIScript plasmid.

Heo et al. (Stem Cells Dev. 2015 Feb. 1; 24(3):393-402. doi: 10.1089/scd.2014.0278. Epub 2014 Nov. 3) reported highly efficient gene targeting in the bovine genome using bovine pluripotent cells and clustered regularly interspaced short palindromic repeat (CRISPR)/Cas9 nuclease. First, Heo et al. generate induced pluripotent stem cells (iPSCs) from bovine somatic fibroblasts by the ectopic expression of yamanaka factors and GSK3β and MEK inhibitor (2i) treatment. Heo et al. observed that these bovine iPSCs are highly similar to naïve pluripotent stem cells with regard to gene expression and developmental potential in teratomas. Moreover, CRISPR-Cas9 nuclease, which was specific for the bovine NANOG locus, showed highly efficient editing of the bovine genome in bovine iPSCs and embryos.

Igenity® provides a profile analysis of animals, such as cows, to perform and transmit traits of economic traits of economic importance, such as carcass composition, carcass quality, maternal and reproductive traits and average daily gain. The analysis of a comprehensive Igenity® profile begins with the discovery of DNA markers (most often single nucleotide polymorphisms or SNPs). All the markers behind the Igenity® profile were discovered by independent scientists at research institutions, including universities, research organizations, and government entities such as USDA. Markers are then analyzed at Igenity® in validation populations. Igenity® uses multiple resource populations that represent various production environments and biological types, often working with industry partners from the seedstock, cow-calf, feedlot and/or packing segments of the beef industry to collect phenotypes that are not commonly available. Cattle genome databases are widely available, see, e.g., the NAGRP Cattle Genome Coordination Program (www.animalgenome.org/cattle/maps/db.html). Thus, the present invention maybe applied to target bovine SNPs. One of skill in the art may utilize the above protocols for targeting SNPs and apply them to bovine SNPs as described, for example, by Tan et al. or Heo et al.

Qingjian Zou et al. (Journal of Molecular Cell Biology Advance Access published Oct. 12, 2015) demonstrated increased muscle mass in dogs by targeting the first exon of the dog Myostatin (MSTN) gene (a negative regulator of skeletal muscle mass). First, the efficiency of the sgRNA was validated, using cotransfection of the sgRNA targeting MSTN with a Cas9 vector into canine embryonic fibroblasts (CEFs). Thereafter, MSTN KO dogs were generated by micro-injecting embryos with normal morphology with a mixture of Cas9 mRNA and MSTN sgRNA and auto-transplantation of the zygotes into the oviduct of the same female dog. The knock-out puppies displayed an obvious muscular phenotype on thighs compared with its wild-type littermate sister. This can also be performed using the Cpf1 CRISPR systems provided herein.

Livestock—Pigs

Viral targets in livestock may include, in some embodiments, porcine CD163, for example on porcine macrophages. CD163 is associated with infection (thought to be through viral cell entry) by PRRSv (Porcine Reproductive and Respiratory Syndrome virus, an arterivirus). Infection by PRRSv, especially of porcine alveolar macrophages (found in the lung), results in a previously incurable porcine syndrome ("Mystery swine disease" or "blue ear disease") that causes suffering, including reproductive failure, weight loss and high mortality rates in domestic pigs. Opportunistic infections, such as enzootic pneumonia, meningitis and ear oedema, are often seen due to immune deficiency through loss of macrophage activity. It also has significant economic and environmental repercussions due to increased antibiotic use and financial loss (an estimated $660m per year).

As reported by Kristin M Whitworth and Dr Randall Prather et al. (Nature Biotech 3434 published online 7 Dec. 2015) at the University of Missouri and in collaboration with Genus Plc, CD163 was targeted using CRISPR-Cas9 and the offspring of edited pigs were resistant when exposed to PRRSv. One founder male and one founder female, both of whom had mutations in exon 7 of CD163, were bred to produce offspring. The founder male possessed an 11-bp deletion in exon 7 on one allele, which results in a frameshift mutation and missense translation at amino acid 45 in domain 5 and a subsequent premature stop codon at amino acid 64. The other allele had a 2-bp addition in exon 7 and a 377-bp deletion in the preceding intron, which were predicted to result in the expression of the first 49 amino acids of domain 5, followed by a premature stop code at amino acid 85. The sow had a 7 bp addition in one allele that when translated was predicted to express the first 48 amino acids of domain 5, followed by a premature stop codon at amino acid 70. The sow's other allele was unamplifiable. Selected offspring were predicted to be a null animal (CD163−/−), i.e. a CD163 knock out.

Accordingly, in some embodiments, porcine alveolar macrophages may be targeted by the CRISPR protein. In some embodiments, porcine CD163 may be targeted by the CRISPR protein. In some embodiments, porcine CD163 may be knocked out through induction of a DSB or through insertions or deletions, for example targeting deletion or modification of exon 7, including one or more of those described above, or in other regions of the gene, for example deletion or modification of exon 5.

An edited pig and its progeny are also envisaged, for example a CD163 knock out pig. This may be for livestock, breeding or modelling purposes (i.e. a porcine model). Semen comprising the gene knock out is also provided.

CD163 is a member of the scavenger receptor cysteine-rich (SRCR) superfamily. Based on in vitro studies SRCR domain 5 of the protein is the domain responsible for unpackaging and release of the viral genome. As such, other members of the SRCR superfamily may also be targeted in order to assess resistance to other viruses. PRRSV is also a member of the mammalian arterivirus group, which also includes murine lactate dehydrogenase-elevating virus, simian hemorrhagic fever virus and equine arteritis virus. The arteriviruses share important pathogenesis properties, including macrophage tropism and the capacity to cause both severe disease and persistent infection. Accordingly, arteriviruses, and in particular murine lactate dehydrogenase-elevating virus, simian hemorrhagic fever virus and equine arteritis virus, may be targeted, for example through porcine CD163 or homologues thereof in other species, and murine, simian and equine models and knockout also provided.

Indeed, this approach may be extended to viruses or bacteria that cause other livestock diseases that may be transmitted to humans, such as Swine Influenza Virus (SIV) strains which include influenza C and the subtypes of influenza A known as H1N1, H1N2, H2N1, H3N1, H3N2, and H2N3, as well as pneumonia, meningitis and oedema mentioned above.

Cpf1 Effector Protein Complexes can be Used in Non-Animal Organisms, Such as Plants, Algae, Fungi, Yeasts, Etc The methods for genome editing using the Cpf1 system as described herein can be used to confer desired traits on essentially any plant, algae, fungus, yeast, etc. A wide variety of plants, algae, fungus, yeast, etc and plant algae, fungus, yeast cell or tissue systems may be engineered for the desired physiological and agronomic characteristics described herein using the nucleic acid constructs of the present disclosure and the various transformation methods mentioned above.

In particular embodiments, the methods described herein are used to modify endogenous genes or to modify their expression without the permanent introduction into the genome of the plant, algae, fungus, yeast, etc of any foreign gene, including those encoding CRISPR components, so as to avoid the presence of foreign DNA in the genome of the plant. This can be of interest as the regulatory requirements for non-transgenic plants are less rigorous.

The CRISPR systems provided herein can be used to introduce targeted double-strand or single-strand breaks and/or to introduce gene activator and/or repressor systems and without being limitative, can be used for gene targeting, gene replacement, targeted mutagenesis, targeted deletions or insertions, targeted inversions and/or targeted translocations. By co-expression of multiple targeting RNAs directed to achieve multiple modifications in a single cell, multiplexed genome modification can be ensured. This technology can be used to high-precision engineering of plants with improved characteristics, including enhanced nutritional quality, increased resistance to diseases and resistance to biotic and abiotic stress, and increased production of commercially valuable plant products or heterologous compounds.

The methods described herein generally result in the generation of "improved plants, algae, fungi, yeast, etc" in that they have one or more desirable traits compared to the wildtype plant. In particular embodiments, the plants, algae, fungi, yeast, etc., cells or parts obtained are transgenic plants, comprising an exogenous DNA sequence incorporated into the genome of all or part of the cells. In particular embodiments, non-transgenic genetically modified plants, algae, fungi, yeast, etc., parts or cells are obtained, in that no exogenous DNA sequence is incorporated into the genome of any of the cells of the plant. In such embodiments, the improved plants, algae, fungi, yeast, etc. are non-transgenic. Where only the modification of an endogenous gene is ensured and no foreign genes are introduced or maintained in the plant, algae, fungi, yeast, etc. genome, the resulting genetically modified crops contain no foreign genes and can thus basically be considered non-transgenic. The different applications of the Cpf1 CRISPR system for plant, algae, fungi, yeast, etc. genome editing include, but are not limited to: introduction of one or more foreign genes to confer an agricultural trait of interest; editing of endogenous genes to confer an agricultural trait of interest; modulating of endogenous genes by the Cpf1 CRISPR system to confer an agricultural trait of interest. Exemplary genes conferring agronomic traits include, but are not limited to genes that confer resistance to pests or diseases; genes involved in plant diseases, such as those listed in WO 2013046247; genes that confer resistance to herbicides, fungicides, or the like; genes involved in (abiotic) stress tolerance. Other aspects of the use of the CRISPR-Cas system include, but are not limited to: create (male) sterile plants; increasing the fertility stage in plants/algae etc; generate genetic variation in a crop of interest; affect fruit-ripening; increasing storage life of plants/algae etc; reducing allergen in plants/algae etc; ensure a value added trait (e.g. nutritional improvement); Screening methods for endogenous genes of interest; biofuel, fatty acid, organic acid, etc production.

Therapeutic Targeting with RNA-Guided Cpf1 Effector Protein Complex

As will be apparent, it is envisaged that the present system can be used to target any polynucleotide sequence of interest. The invention provides a non-naturally occurring or engineered composition, or one or more polynucleotides encoding components of said composition, or vector or delivery systems comprising one or more polynucleotides encoding components of said composition for use in a modifying a target cell in vivo, ex vivo or in vitro and, may be conducted in a manner alters the cell such that once modified the progeny or cell line of the CRISPR modified cell retains the altered phenotype. The modified cells and progeny may be part of a multi-cellular organism such as a plant or animal with ex vivo or in vivo application of CRISPR system to desired cell types. The CRISPR invention may be a therapeutic method of treatment. The therapeutic method of treatment may comprise gene or genome editing, or gene therapy.

Treating Pathogens, Like Bacterial, Fungal and Parasitic Pathogens

The present invention may also be applied to treat bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

Jiang et al. ("RNA-guided editing of bacterial genomes using CRISPR-Cas systems," Nature Biotechnology vol. 31, p. 233-9, March 2013) used a CRISPR-Cas9 system to mutate or kill *S. pneumoniae* and *E. coli*. The work, which introduced precise mutations into the genomes, relied on dual-RNA:Cas9-directed cleavage at the targeted genomic site to kill unmutated cells and circumvented the need for selectable markers or counter-selection systems. CRISPR systems have be used to reverse antibiotic resistance and eliminate the transfer of resistance between strains. Bickard et al. showed that Cas9, reprogrammed to target virulence genes, kills virulent, but not avirulent, *S. aureus*. Reprogramming the nuclease to target antibiotic resistance genes destroyed staphylococcal plasmids that harbor antibiotic resistance genes and immunized against the spread of plasmid-borne resistance genes. (see, Bikard et al., "Exploiting CRISPR-Cas nucleases to produce sequence-specific antimicrobials," Nature Biotechnology vol. 32, 1146-1150, doi: 10.1038/nbt.3043, published online 5 Oct. 2014.) Bikard showed that CRISPR-Cas9 antimicrobials function in vivo to kill *S. aureus* in a mouse skin colonization model. Similarly, Yosef et al used a CRISPR system to target genes encoding enzymes that confer resistance to β-lactam antibiotics (see Yousef et al., "Temperate and lytic bacteriophages programmed to sensitize and kill antibiotic-resistant bacteria," Proc. Natl. Acad. Sci. USA, vol. 112, p. 7267-7272, doi: 10.1073/pnas.1500107112 published online May 18, 2015).

CRISPR systems can be used to edit genomes of parasites that are resistant to other genetic approaches. For example, a CRISPR-Cas9 system was shown to introduce double-stranded breaks into the in the *Plasmodium yoelii* genome (see, Zhang et al., "Efficient Editing of Malaria Parasite Genome Using the CRISPR/Cas9 System," mBio. vol. 5, e01414-14, July-August 2014). Ghorbal et al. ("Genome editing in the human malaria parasite *Plasmodium falciparum* using the CRISPR-Cas9 system," Nature Biotechnology, vol. 32, p. 819-821, doi: 10.1038/nbt.2925, published online Jun. 1, 2014) modified the sequences of two genes, orc1 and ketch13, which have putative roles in gene silencing and emerging resistance to artemisinin, respectively. Parasites that were altered at the appropriate sites were recovered with very high efficiency, despite there being no direct selection for the modification, indicating that neutral or even deleterious mutations can be generated using this system. CRISPR-Cas9 is also used to modify the genomes of other pathogenic parasites, including *Toxoplasma gondii* (see Shen et al., "Efficient gene disruption in diverse strains of *Toxoplasma gondii* using CRISPR/CAS9," mBio vol. 5:e01114-14, 2014; and Sidik et al., "Efficient Genome Engineering of *Toxoplasma gondii* Using CRISPR/Cas9," PLoS One vol. 9, e100450, doi: 10.1371/journal.pone.0100450, published online Jun. 27, 2014).

Vyas et al. ("A *Candida albicans* CRISPR system permits genetic engineering of essential genes and gene families," Science Advances, vol. 1, e1500248, DOI: 10.1126/sciadv.1500248, Apr. 3, 2015) employed a CRISPR system to overcome long-standing obstacles to genetic engineering in *C. albicans* and efficiently mutate in a single experiment both copies of several different genes. In an organism where several mechanisms contribute to drug resistance, Vyas produced homozygous double mutants that no longer displayed the hyper-resistance to fluconazole or cycloheximide displayed by the parental clinical isolate Can90. Vyas also obtained homozygous loss-of-function mutations in essential genes of *C. albicans* by creating conditional alleles. Null alleles of DCR1, which is required for ribosomal RNA processing, are lethal at low temperature but viable at high temperature. Vyas used a repair template that introduced a nonsense mutation and isolated dcr1/dcr1 mutants that failed to grow at 16° C.

The CRISPR system of the present invention for use in *P. falciparum* by disrupting chromosomal loci. Ghorbal et al. ("Genome editing in the human malaria parasite *Plasmo-*

*dium falciparum* using the CRISPR-Cas9 system", Nature Biotechnology, 32, 819-821 (2014), DOI: 10.1038/nbt.2925, Jun. 1, 2014) employed a CRISPR system to introduce specific gene knockouts and single-nucleotide substitutions in the malaria genome. To adapt the CRISPR-Cas9 system to *P. falciparum*, Ghorbal et al. generated expression vectors for under the control of plasmodial regulatory elements in the pUF1-Cas9 episome that also carries the drug-selectable marker ydhodh, which gives resistance to DSM1, a *P. falciparum* dihydroorotate dehydrogenase (PfDHODH) inhibitor and for transcription of the sgRNA, used *P. falciparum* U6 small nuclear (sn)RNA regulatory elements placing the guide RNA and the donor DNA template for homologous recombination repair on the same plasmid, pL7. See also, Zhang C. et al. ("Efficient editing of malaria parasite genome using the CRISPR/Cas9 system", MBio, 2014 Jul. 1; 5(4):E01414-14, doi: 10.1128/MbIO.01414-14) and Wagner et al. ("Efficient CRISPR-Cas9-mediated genome editing in *Plasmodium falciparum*, Nature Methods 11, 915-918 (2014), DOI: 10.1038/nmeth.3063).

Treating Pathogens, Like Viral Pathogens Such as HIV

Cas-mediated genome editing might be used to introduce protective mutations in somatic tissues to combat nongenetic or complex diseases. For example, NHEJ-mediated inactivation of the CCR5 receptor in lymphocytes (Lombardo et al., Nat Biotechnol. 2007 November; 25(11):1298-306) may be a viable strategy for circumventing HIV infection, whereas deletion of PCSK9 (Cohen et al., Nat Genet. 2005 February; 37(2):161-5) angiopoietin (Musunuru et al., N Engl J Med. 2010 December 2; 363(23):2220-7) may provide therapeutic effects against statin-resistant hypercholesterolemia or hyperlipidemia. Although these targets may be also addressed using siRNA-mediated protein knockdown, a unique advantage of NHEJ-mediated gene inactivation is the ability to achieve permanent therapeutic benefit without the need for continuing treatment. As with all gene therapies, it will of course be important to establish that each proposed therapeutic use has a favorable benefit-risk ratio.

Hydrodynamic delivery of plasmid DNA encoding Cas9 and guide RNA along with a repair template into the liver of an adult mouse model of tyrosinemia was shown to be able to correct the mutant Fah gene and rescue expression of the wild-type Fah protein in ~1 out of 250 cells (Nat Biotechnol. 2014 June; 32(6):551-3). In addition, clinical trials successfully used ZF nucleases to combat HIV infection by ex vivo knockout of the CCR5 receptor. In all patients, HIV DNA levels decreased, and in one out of four patients, HIV RNA became undetectable (Tebas et al., N Engl J Med. 2014 March 6; 370(10):901-10). Both of these results demonstrate the promise of programmable nucleases as a new therapeutic platform.

In another embodiment, self-inactivating lentiviral vectors with an siRNA targeting a common exon shared by HIV tat/rev, a nucleolar-localizing TAR decoy, and an anti-CCR5-specific hammerhead ribozyme (see, e.g., DiGiusto et al. (2010) Sci Transl Med 2:36ra43) may be used/and or adapted to the CRISPR-Cas system of the present invention. A minimum of 2.5×106 CD34+ cells per kilogram patient weight may be collected and prestimulated for 16 to 20 hours in X-VIVO 15 medium (Lonza) containing 2 µmol/L-glutamine, stem cell factor (100 ng/ml), Flt-3 ligand (Flt-3L) (100 ng/ml), and thrombopoietin (10 ng/ml) (CellGenix) at a density of 2×106 cells/ml. Prestimulated cells may be transduced with lentiviral at a multiplicity of infection of 5 for 16 to 24 hours in 75-cm2 tissue culture flasks coated with fibronectin (25 mg/cm2) (RetroNectin, Takara Bio Inc.).

With the knowledge in the art and the teachings in this disclosure the skilled person can correct HSCs as to immunodeficiency condition such as HIV/AIDS comprising contacting an HSC with a CRISPR-Cpf1 system that targets and knocks out CCR5. An guide RNA (and advantageously a dual guide approach, e.g., a pair of different guide RNAs; for instance, guide RNAs targeting of two clinically relevant genes, B2M and CCR5, in primary human CD4+ T cells and CD34+ hematopoietic stem and progenitor cells (HSPCs)) that targets and knocks out CCR5-and-Cpf1 protein containing particle is contacted with HSCs. The so contacted cells can be administered; and optionally treated/expanded; cf. Cartier. See also Kiem, "Hematopoietic stem cell-based gene therapy for HIV disease," Cell Stem Cell. Feb. 3, 2012; 10(2): 137-147; incorporated herein by reference along with the documents it cites; Mandal et al, "Efficient Ablation of Genes in Human Hematopoietic Stem and Effector Cells using CRISPR/Cas9," Cell Stem Cell, Volume 15, Issue 5, p643-652, 6 Nov. 2014; incorporated herein by reference along with the documents it cites. Mention is also made of Ebina, "CRISPR/Cas9 system to suppress HIV-1 expression by editing HIV-1 integrated proviral DNA" SCIENTIFIC REPORTS 3: 2510 DOI: 10.1038/srep02510, incorporated herein by reference along with the documents it cites, as another means for combatting HIV/AIDS using a CRISPR-Cpf1 system.

The rationale for genome editing for HIV treatment originates from the observation that individuals homozygous for loss of function mutations in CCR5, a cellular co-receptor for the virus, are highly resistant to infection and otherwise healthy, suggesting that mimicking this mutation with genome editing could be a safe and effective therapeutic strategy [Liu, R., et al. Cell 86, 367-377 (1996)]. This idea was clinically validated when an HIV infected patient was given an allogeneic bone marrow transplant from a donor homozygous for a loss of function CCR5 mutation, resulting in undetectable levels of HIV and restoration of normal CD4 T-cell counts [Hutter, G., et al. The New England journal of medicine 360, 692-698 (2009)]. Although bone marrow transplantation is not a realistic treatment strategy for most HIV patients, due to cost and potential graft vs. host disease, HIV therapies that convert a patient's own T-cells into CCR5 are desirable.

Early studies using ZFNs and NHEJ to knockout CCR5 in humanized mouse models of HIV showed that transplantation of CCR5 edited CD4 T cells improved viral load and CD4 T-cell counts [Perez, E. E., et al. Nature biotechnology 26, 808-816 (2008)]. Importantly, these models also showed that HIV infection resulted in selection for CCR5 null cells, suggesting that editing confers a fitness advantage and potentially allowing a small number of edited cells to create a therapeutic effect.

As a result of this and other promising preclinical studies, genome editing therapy that knocks out CCR5 in patient T cells has now been tested in humans [Holt, N., et al. Nature biotechnology 28, 839-847 (2010); Li, L., et al. Molecular therapy: the journal of the American Society of Gene Therapy 21, 1259-1269 (2013)]. In a recent phase I clinical trial, CD4+ T cells from patients with HIV were removed, edited with ZFNs designed to knockout the CCR5 gene, and autologously transplanted back into patients [Tebas, P., et al. The New England journal of medicine 370, 901-910 (2014)].

In another study (Mandal et al., Cell Stem Cell, Volume 15, Issue 5, p643-652, 6 Nov. 2014), CRISPR-Cas9 has targeted two clinical relevant genes, B2M and CCR5, in human CD4+ T cells and CD34+ hematopoietic stem and progenitor cells (HSPCs). Use of single RNA guides led to highly efficient mutagenesis in HSPCs but not in T cells. A dual guide approach improved gene deletion efficacy in both cell types. HSPCs that had undergone genome editing with CRISPR-Cas9 retained multilineage potential. Predicted on- and off-target mutations were examined via target capture sequencing in HSPCs and low levels of off-target mutagenesis were observed at only one site. These results demonstrate that CRISPR-Cas9 can efficiently ablate genes in HSPCs with minimal off-target mutagenesis, which have broad applicability for hematopoietic cell-based therapy.

Wang et al. (PLoS One. 2014 Dec. 26; 9(12):e115987. doi: 10.1371/journal.pone.0115987) silenced CCR5 via CRISPR associated protein 9 (Cas9) and single guided RNAs (guide RNAs) with lentiviral vectors expressing Cas9 and CCR5 guide RNAs. Wang et al. showed that a single round transduction of lentiviral vectors expressing Cas9 and CCR5 guide RNAs into HIV-1 susceptible human CD4+ cells yields high frequencies of CCR5 gene disruption. CCR5 gene-disrupted cells are not only resistant to R5-tropic HIV-1, including transmitted/founder (T/F) HIV-1 isolates, but also have selective advantage over CCR5 gene-undisrupted cells during R5-tropic HIV-1 infection. Genome mutations at potential off-target sites that are highly homologous to these CCR5 guide RNAs in stably transduced cells even at 84 days post transduction were not detected by a T7 endonuclease I assay.

Fine et al. (Sci Rep. 2015 Jul. 1; 5:10777. doi: 10.1038/srep10777) identified a two-cassette system expressing pieces of the *S. pyogenes* Cas9 (SpCas9) protein which splice together in cellula to form a functional protein capable of site-specific DNA cleavage. With specific CRISPR guide strands, Fine et al. demonstrated the efficacy of this system in cleaving the HBB and CCR5 genes in human HEK-293T cells as a single Cas9 and as a pair of Cas9 nickases. The trans-spliced SpCas9 (tsSpCas9) displayed ~35% of the nuclease activity compared with the wild-type SpCas9 (wtSpCas9) at standard transfection doses, but had substantially decreased activity at lower dosing levels. The greatly reduced open reading frame length of the tsSpCas9 relative to wtSpCas9 potentially allows for more complex and longer genetic elements to be packaged into an AAV vector including tissue-specific promoters, multiplexed guide RNA expression, and effector domain fusions to SpCas9.

Li et al. (J Gen Virol. 2015 August; 96(8):2381-93. doi: 10.1099/vir.0.000139. Epub 2015 Apr. 8) demonstrated that CRISPR-Cas9 can efficiently mediate the editing of the CCR5 locus in cell lines, resulting in the knockout of CCR5 expression on the cell surface. Next-generation sequencing revealed that various mutations were introduced around the predicted cleavage site of CCR5. For each of the three most effective guide RNAs that were analyzed, no significant off-target effects were detected at the 15 top-scoring potential sites. By constructing chimeric Ad5F35 adenoviruses carrying CRISPR-Cas9 components, Li et al. efficiently transduced primary CD4+T-lymphocytes and disrupted CCR5 expression, and the positively transduced cells were conferred with HIV-1 resistance.

One of skill in the art may utilize the above studies of, for example, Holt, N., et al. Nature biotechnology 28, 839-847 (2010), Li, L., et al. Molecular therapy: the journal of the American Society of Gene Therapy 21, 1259-1269 (2013), Mandal et al., Cell Stem Cell, Volume 15, Issue 5, p643-652, 6 Nov. 2014, Wang et al. (PLoS One. 2014 Dec. 26; 9(12):e115987. doi: 10.1371/journal.pone.0115987), Fine et al. (Sci Rep. 2015 Jul. 1; 5:10777. doi: 10.1038/srep10777) and Li et al. (J Gen Virol. 2015 August; 96(8):2381-93. doi: 10.1099/vir.0.000139. Epub 2015 Apr. 8) for targeting CCR5 with the CRISPR-Cas system of the present invention.

Treating Pathogens, Like Viral Pathogens, Such as HBV

The present invention may also be applied to treat hepatitis B virus (HBV). However, the CRISPR-Cas system must be adapted to avoid the shortcomings of RNAi, such as the risk of overstating endogenous small RNA pathways, by for example, optimizing dose and sequence (see, e.g., Grimm et al., Nature vol. 441, 26 May 2006). For example, low doses, such as about $1\text{-}10\times10^{14}$ particles per human are contemplated. In another embodiment, the CRISPR-Cas system directed against HBV may be administered in liposomes, such as a stable nucleic-acid-lipid particle (SNALP) (see, e.g., Morrissey et al., Nature Biotechnology, Vol. 23, No. 8, August 2005). Daily intravenous injections of about 1, 3 or 5 mg/kg/day of CRISPR-Cas targeted to HBV RNA in a SNALP are contemplated. The daily treatment may be over about three days and then weekly for about five weeks. In another embodiment, the system of Chen et al. (Gene Therapy (2007) 14, 11-19) may be used/and or adapted for the CRISPR-Cas system of the present invention. Chen et al. use a double-stranded adenoassociated virus 8-pseudotyped vector (dsAAV2/8) to deliver shRNA. A single administration of dsAAV2/8 vector (1×1012 vector genomes per mouse), carrying HBV-specific shRNA, effectively suppressed the steady level of HBV protein, mRNA and replicative DNA in liver of HBV transgenic mice, leading to up to 2-3 log 10 decrease in HBV load in the circulation. Significant HBV suppression sustained for at least 120 days after vector administration. The therapeutic effect of shRNA was target sequence dependent and did not involve activation of interferon. For the present invention, a CRISPR-Cas system directed to HBV may be cloned into an AAV vector, such as a dsAAV2/8 vector and administered to a human, for example, at a dosage of about 1×1015 vector genomes to about 1×1016 vector genomes per human. In another embodiment, the method of Wooddell et al. (Molecular Therapy vol. 21 no. 5, 973-985 May 2013) may be used/and or adapted to the CRISPR-Cas system of the present invention. Wooddell et al. show that simple coinjection of a hepatocyte-targeted, N-acetylgalactosamine-conjugated melittin-like peptide (NAG-MLP) with a liver-tropic cholesterol-conjugated siRNA (chol-siRNA) targeting coagulation factor VII (F7) results in efficient F7 knockdown in mice and nonhuman primates without changes in clinical chemistry or induction of cytokines. Using transient and transgenic mouse models of HBV infection, Wooddell et al. show that a single coinjection of NAG-MLP with potent chol-siRNAs targeting conserved HBV sequences resulted in multilog repression of viral RNA, proteins, and viral DNA with long duration of effect. Intraveinous coinjections, for example, of about 6 mg/kg of NAG-MLP and 6 mg/kg of HBV specific CRISPR-Cas may be envisioned for the present invention. In the alternative, about 3 mg/kg of NAG-MLP and 3 mg/kg of HBV specific CRISPR-Cas may be delivered on day one, followed by administration of about 2-3 mg/kg of NAG-MLP and 2-3 mg/kg of HBV specific CRISPR-Cas two weeks later.

In some embodiments, the target sequence is an HBV sequence. In some embodiments, the target sequences is comprised in an episomal viral nucleic acid molecule which is not integrated into the genome of the organism to thereby manipulate the episomal viral nucleic acid molecule. In some embodiments, the episomal nucleic acid molecule is a double-stranded DNA polynucleotide molecule or is a covalently closed circular DNA (cccDNA). In some embodiments, the CRISPR complex is capable of reducing the amount of episomal viral nucleic acid molecule in a cell of the organism compared to the amount of episomal viral nucleic acid molecule in a cell of the organism in the absence of providing the complex, or is capable of manipulating the episomal viral nucleic acid molecule to promote degradation of the episomal nucleic acid molecule. In some embodiments, the target HBV sequence is integrated into the genome of the organism. In some embodiments, when formed within the cell, the CRISPR complex is capable of manipulating the integrated nucleic acid to promote excision of all or part of the target HBV nucleic acid from the genome of the organism. In some embodiments, said at least one target HBV nucleic acid is comprised in a double-stranded DNA polynucleotide cccDNA molecule and/or viral DNA integrated into the genome of the organism and wherein the CRISPR complex manipulates at least one target HBV nucleic acid to cleave viral cccDNA and/or integrated viral DNA. In some embodiments, said cleavage comprises one or more double-strand break(s) introduced into the viral cccDNA and/or integrated viral DNA, optionally at least two double-strand break(s). In some embodiments, said cleavage is via one or more single-strand break(s) introduced into the viral cccDNA and/or integrated viral DNA, optionally at least two single-strand break(s). In some embodiments, said one or more double-strand break(s) or said one or more single-strand break(s) leads to the formation of one or more insertion or deletion mutations (INDELs) in the viral cccDNA sequences and/or integrated viral DNA sequences.

Lin et al. (Mol Ther Nucleic Acids. 2014 Aug. 19; 3:e186. doi: 10.1038/mtna.2014.38) designed eight gRNAs against HBV of genotype A. With the HBV-specific gRNAs, the CRISPR-Cas9 system significantly reduced the production of HBV core and surface proteins in Huh-7 cells transfected with an HBV-expression vector. Among eight screened gRNAs, two effective ones were identified. One gRNA targeting the conserved HBV sequence acted against different genotypes. Using a hydrodynamics-HBV persistence mouse model, Lin et al. further demonstrated that this system could cleave the intrahepatic HBV genome-containing plasmid and facilitate its clearance in vivo, resulting in reduction of serum surface antigen levels. These data suggest that the CRISPR-Cas9 system could disrupt the HBV-expressing templates both in vitro and in vivo, indicating its potential in eradicating persistent HBV infection.

Dong et al. (Antiviral Res. 2015 June; 118:110-7. doi: 10.1016/j.antiviral.2015.03.015. Epub 2015 Apr. 3) used the CRISPR-Cas9 system to target the HBV genome and efficiently inhibit HBV infection. Dong et al. synthesized four single-guide RNAs (guide RNAs) targeting the conserved regions of HBV. The expression of these guide RNAS with Cas9 reduced the viral production in Huh7 cells as well as in HBV-replication cell HepG2.2.15. Dong et al. further demonstrated that CRISPR-Cas9 direct cleavage and cleavage-mediated mutagenesis occurred in HBV cccDNA of transfected cells. In the mouse model carrying HBV cccDNA, injection of guide RNA-Cas9 plasmids via rapid tail vein resulted in the low level of cccDNA and HBV protein.

Liu et al. (J Gen Virol. 2015 August; 96(8):2252-61. doi: 10.1099/vir.0.000159. Epub 2015 Apr. 22) designed eight guide RNAs (gRNAs) that targeted the conserved regions of different HBV genotypes, which could significantly inhibit HBV replication both in vitro and in vivo to investigate the possibility of using the CRISPR-Cas9 system to disrupt the HBV DNA templates. The HBV-specific gRNA/Cpf1 system could inhibit the replication of HBV of different genotypes in cells, and the viral DNA was significantly reduced by a single gRNA/Cpf1 system and cleared by a combination of different gRNA/Cpf1 systems.

Wang et al. (World J Gastroenterol. 2015 Aug. 28; 21(32): 9554-65. doi: 10.3748/wjg.v21.i32.9554) designed 15 gRNAs against HBV of genotypes A-D. Eleven combinations of two above gRNAs (dual-gRNAs) covering the regulatory region of HBV were chosen. The efficiency of each gRNA and 11 dual-gRNAs on the suppression of HBV (genotypes A-D) replication was examined by the measurement of HBV surface antigen (HBsAg) or e antigen (HBeAg) in the culture supernatant. The destruction of HBV-expressing vector was examined in HuH7 cells co-transfected with dual-gRNAs and HBV-expressing vector using polymerase chain reaction (PCR) and sequencing method, and the destruction of cccDNA was examined in HepAD38 cells using KCl precipitation, plasmid-safe ATP-dependent DNase (PSAD) digestion, rolling circle amplification and quantitative PCR combined method. The cytotoxicity of these gRNAs was assessed by a mitochondrial tetrazolium assay. All of gRNAs could significantly reduce HBsAg or HBeAg production in the culture supernatant, which was dependent on the region in which gRNA against. All of dual gRNAs could efficiently suppress HBsAg and/or HBeAg production for HBV of genotypes A-D, and the efficacy of dual gRNAs in suppressing HBsAg and/or HBeAg production was significantly increased when compared to the single gRNA used alone. Furthermore, by PCR direct sequencing we confirmed that these dual gRNAs could specifically destroy HBV expressing template by removing the fragment between the cleavage sites of the two used gRNAs. Most importantly, gRNA-5 and gRNA-12 combination not only could efficiently suppressing HBsAg and/or HBeAg production, but also destroy the cccDNA reservoirs in HepAD38 cells.

Karimova et al. (Sci Rep. 2015 Sep. 3; 5:13734. doi: 10.1038/srep13734) identified cross-genotype conserved HBV sequences in the S and X region of the HBV genome that were targeted for specific and effective cleavage by a Cas9 nickase. This approach disrupted not only episomal cccDNA and chromosomally integrated HBV target sites in reporter cell lines, but also HBV replication in chronically and de novo infected hepatoma cell lines.

One of skill in the art may utilize the above studies of, for example, Lin et al. (Mol Ther Nucleic Acids. 2014 Aug. 19; 3:e186. doi: 10.1038/mtna.2014.38), Dong et al. (Antiviral Res. 2015 June; 118:110-7. doi: 10.1016/j.antiviral.2015.03.015. Epub 2015 Apr. 3), Liu et al. (J Gen Virol. 2015 August; 96(8):2252-61. doi: 10.1099/vir.0.000159. Epub 2015 Apr. 22), Wang et al. (World J Gastroenterol. 2015 Aug. 28; 21(32):9554-65. doi: 10.3748/ wjg.v21.i32.9554) and Karimova et al. (Sci Rep. 2015 Sep. 3; 5:13734. doi: 10.1038/srep13734) for targeting HBV with the CRISPR-Cas system of the present invention.

Chronic hepatitis B virus (HBV) infection is prevalent, deadly, and seldom cured due to the persistence of viral episomal DNA (cccDNA) in infected cells. Ramanan et al. (Ramanan V, Shlomai A, Cox D B, Schwartz R E, Michailidis E, Bhatta A, Scott D A, Zhang F, Rice C M, Bhatia S N, Sci Rep. 2015 Jun. 2; 5:10833. doi: 10.1038/srep10833, published online 2 Jun. 2015.) showed that the CRISPR/ Cas9 system can specifically target and cleave conserved regions in the HBV genome, resulting in robust suppression of viral gene expression and replication. Upon sustained expression of Cas9 and appropriately chosen guide RNAs, they demonstrated cleavage of cccDNA by Cas9 and a dramatic reduction in both cccDNA and other parameters of viral gene expression and replication. Thus, they showed that directly targeting viral episomal DNA is a novel therapeutic approach to control the virus and possibly cure patients. This is also described in WO2015089465 A1, in the name of The Broad Institute et al., the contents of which are hereby incorporated by reference As such targeting viral episomal DNA in HBV is preferred in some embodiments.

The present invention may also be applied to treat pathogens, e.g. bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

The present invention may also be applied to treat hepatitis C virus (HCV). The methods of Roelvinki et al. (Molecular Therapy vol. 20 no. 9, 1737-1749 Sep. 2012) may be applied to the CRISPR-Cas system. For example, an AAV vector such as AAV8 may be a contemplated vector and for example a dosage of about 1.25×1011 to 1.25×1013 vector genomes per kilogram body weight (vg/kg) may be contemplated. The present invention may also be applied to treat pathogens, e.g. bacterial, fungal and parasitic pathogens. Most research efforts have focused on developing new antibiotics, which once developed, would nevertheless be subject to the same problems of drug resistance. The invention provides novel CRISPR-based alternatives which overcome those difficulties. Furthermore, unlike existing antibiotics, CRISPR-based treatments can be made pathogen specific, inducing bacterial cell death of a target pathogen while avoiding beneficial bacteria.

Jiang et al. ("RNA-guided editing of bacterial genomes using CRISPR-Cas systems," Nature Biotechnology vol. 31, p. 233-9, March 2013) used a CRISPR-Cas9 system to mutate or kill *S. pneumoniae* and *E. coli*. The work, which introduced precise mutations into the genomes, relied on dual-RNA:Cas9-directed cleavage at the targeted genomic site to kill unmutated cells and circumvented the need for selectable markers or counter-selection systems. CRISPR systems have be used to reverse antibiotic resistance and eliminate the transfer of resistance between strains. Bickard et al. showed that Cas9, reprogrammed to target virulence genes, kills virulent, but not avirulent, *S. aureus*. Reprogramming the nuclease to target antibiotic resistance genes destroyed staphylococcal plasmids that harbor antibiotic resistance genes and immunized against the spread of plasmid-borne resistance genes. (see, Bikard et al., "Exploiting CRISPR-Cas nucleases to produce sequence-specific antimicrobials," Nature Biotechnology vol. 32, 1146-1150, doi: 10.1038/nbt.3043, published online 5 Oct. 2014.) Bikard showed that CRISPR-Cas9 antimicrobials function in vivo to kill *S. aureus* in a mouse skin colonization model. Similarly, Yosef et al used a CRISPR system to target genes encoding enzymes that confer resistance to β-lactam antibiotics (see Yousef et al., "Temperate and lytic bacteriophages programmed to sensitize and kill antibiotic-resistant bacteria," Proc. Natl. Acad. Sci. USA, vol. 112, p. 7267-7272, doi: 10.1073/pnas.1500107112 published online May 18, 2015).

CRISPR systems can be used to edit genomes of parasites that are resistant to other genetic approaches. For example, a CRISPR-Cas9 system was shown to introduce double-stranded breaks into the in the *Plasmodium yoelii* genome (see, Zhang et al., "Efficient Editing of Malaria Parasite Genome Using the CRISPR/Cas9 System," mBio. vol. 5, e01414-14, July-August 2014). Ghorbal et al. ("Genome editing in the human malaria parasite *Plasmodium falciparum* using the CRISPR-Cas9 system," Nature Biotechnology, vol. 32, p. 819-821, doi: 10.1038/nbt.2925, published online Jun. 1, 2014) modified the sequences of two genes, orc1 and ketch13, which have putative roles in gene silencing and emerging resistance to artemisinin, respectively. Parasites that were altered at the appropriate sites were recovered with very high efficiency, despite there being no direct selection for the modification, indicating that neutral or even deleterious mutations can be generated using this system. CRISPR-Cas9 is also used to modify the genomes of other pathogenic parasites, including *Toxoplasma gondii* (see Shen et al., "Efficient gene disruption in diverse strains of *Toxoplasma gondii* using CRISPR/CAS9," mBio vol. 5:e01114-14, 2014; and Sidik et al., "Efficient Genome Engineering of *Toxoplasma gondii* Using CRISPR/Cas9," PLoS One vol. 9, e100450, doi: 10.1371/journal.pone.0100450, published online Jun. 27, 2014).

Vyas et al. ("A *Candida albicans* CRISPR system permits genetic engineering of essential genes and gene families," Science Advances, vol. 1, e1500248, DOI: 10.1126/sciadv.1500248, Apr. 3, 2015) employed a CRISPR system to overcome long-standing obstacles to genetic engineering in *C. albicans* and efficiently mutate in a single experiment both copies of several different genes. In an organism where several mechanisms contribute to drug resistance, Vyas produced homozygous double mutants that no longer displayed the hyper-resistance to fluconazole or cycloheximide displayed by the parental clinical isolate Can90. Vyas also obtained homozygous loss-of-function mutations in essential genes of *C. albicans* by creating conditional alleles. Null alleles of DCR1, which is required for ribosomal RNA processing, are lethal at low temperature but viable at high temperature. Vyas used a repair template that introduced a nonsense mutation and isolated dcr1/dcr1 mutants that failed to grow at 16° C.

Treating Diseases with Genetic or Epigenetic Aspects

The CRISPR-Cas systems of the present invention can be used to correct genetic mutations that were previously attempted with limited success using TALEN and ZFN and have been identified as potential targets for Cas9 systems, including as in published applications of Editas Medicine describing methods to use Cas9 systems to target loci to therapeutically address diseases with gene therapy, including, WO 2015/048577 CRISPR-RELATED METHODS AND COMPOSITIONS of Gluckmann et al.; WO 2015/070083 CRISPR-RELATED METHODS AND COMPOSITIONS WITH GOVERNING gRNAS of Glucksmann et al. In some embodiments, the treatment, prophylaxis or diagnosis of Primary Open Angle Glaucoma (POAG) is provided. The target is preferably the MYOC gene. This is described in WO2015153780, the disclosure of which is hereby incorporated by reference.

Mention is made of WO2015/134812 CRISPR/CAS-RELATED METHODS AND COMPOSITIONS FOR TREATING USHER SYNDROME AND RETINITIS PIGMENTOSA of Maeder et al. Through the teachings herein the invention comprehends methods and materials of these documents applied in conjunction with the teachings herein. In an aspect of ocular and auditory gene therapy, methods and compositions for treating Usher Syndrome and Retinitis-Pigmentosa may be adapted to the CRISPR-Cas system of the present invention (see, e.g., WO 2015/134812). In an embodiment, the WO 2015/134812 involves a treatment or delaying the onset or progression of Usher Syndrome type IIA (USH2A, USH11A) and retinitis pigmentosa 39 (RP39) by gene editing, e.g., using CRISPR-Cas9 mediated methods to correct the guanine deletion at position 2299 in the USH2A gene (e.g., replace the deleted guanine residue at position 2299 in the USH2A gene). A similar effect can be achieved with Cpf1. In a related aspect, a mutation is targeted by cleaving with either one or more nuclease, one or more nickase, or a combination thereof, e.g., to induce HDR with a donor template that corrects the point mutation (e.g., the single nucleotide, e.g., guanine, deletion). The alteration or correction of the mutant USH2A gene can be mediated by any mechanism. Exemplary mechanisms that can be associated with the alteration (e.g., correction) of the mutant HSH2A gene include, but are not limited to, non-homologous end joining, microhomology-mediated end joining (MMEJ), homology-directed repair (e.g., endogenous donor template mediated), SDSA (synthesis dependent strand annealing), single-strand annealing or single strand invasion. In an embodiment, the method used for treating Usher Syndrome and Retinis-Pigmentosa can include acquiring knowledge of the mutation carried by the subject, e.g., by sequencing the appropriate portion of the USH2A gene.

Accordingly, in some embodiments, the treatment, prophylaxis or diagnosis of Retinitis Pigmentosa is provided. A number of different genes are known to be associated with or result in Retinitis Pigmentosa, such as RP1, RP2 and so forth. These genes are targeted in some embodiments and either knocked out or repaired through provision of suitable a template. In some embodiments, delivery is to the eye by injection.

One or more Retinitis Pigmentosa genes can, in some embodiments, be selected from: RP1 (Retinitis pigmentosa-1), RP2 (Retinitis pigmentosa-2), RPGR (Retinitis pigmentosa-3), PRPH2 (Retinitis pigmentosa-7), RP9 (Retinitis pigmentosa-9), IMPDH1 (Retinitis pigmentosa-10), PRPF31 (Retinitis pigmentosa-11), CRB1 (Retinitis pigmentosa-12, autosomal recessive), PRPF8 (Retinitis pigmentosa-13), TULP1 (Retinitis pigmentosa-14), CA4 (Retinitis pigmentosa-17), HPRPF3 (Retinitis pigmentosa-18), ABCA4 (Retinitis pigmentosa-19), EYS (Retinitis pigmentosa-25), CERKL (Retinitis pigmentosa-26), FSCN2 (Retinitis pigmentosa-30), TOPORS (Retinitis pigmentosa-31), SNRNP200 (Retinitis pigmentosa 33), SEMA4A (Retinitis pigmentosa-35), PRCD (Retinitis pigmentosa-36), NR2E3 (Retinitis pigmentosa-37), MERTK (Retinitis pigmentosa-38), USH2A (Retinitis pigmentosa-39), PROM1 (Retinitis pigmentosa-41), KLHL7 (Retinitis pigmentosa-42), CNGB1 (Retinitis pigmentosa-45), BEST1 (Retinitis pigmentosa-50), TTC8 (Retinitis pigmentosa 51), C2orf71 (Retinitis pigmentosa 54), ARL6 (Retinitis pigmentosa 55), ZNF513 (Retinitis pigmentosa 58), DHDDS (Retinitis pigmentosa 59), BEST1 (Retinitis pigmentosa, concentric), PRPH2 (Retinitis pigmentosa, digenic), LRAT (Retinitis pigmentosa, juvenile), SPATA7 (Retinitis pigmentosa, juvenile, autosomal recessive), CRX (Retinitis pigmentosa, late-onset dominant), and/or RPGR (Retinitis pigmentosa, X-linked, and sinorespiratory infections, with or without deafness).

In some embodiments, the Retinitis Pigmentosa gene is MERTK (Retinitis pigmentosa-38) or USH2A (Retinitis pigmentosa-39).

Mention is also made of WO 2015/138510 and through the teachings herein the invention (using a CRISPR-Cas9 system) comprehends providing a treatment or delaying the onset or progression of Leber's Congenital Amaurosis 10 (LCA 10). LCA 10 is caused by a mutation in the CEP290 gene, e.g., a c.2991+1655, adenine to guanine mutation in the CEP290 gene which gives rise to a cryptic splice site in intron 26. This is a mutation at nucleotide 1655 of intron 26 of CEP290, e.g., an A to G mutation. CEP290 is also known as: CT87; MKS4; POC3; rd16; BBS14; JBTSS; LCAJO; NPHP6; SLSN6; and 3H11Ag (see, e.g., WO 2015/138510). In an aspect of gene therapy, the invention involves introducing one or more breaks near the site of the LCA target position (e.g., c.2991+1655; A to G) in at least one allele of the CEP290 gene. Altering the LCA10 target position refers to (1) break-induced introduction of an indel (also referred to herein as NHEJ-mediated introduction of an indel) in close proximity to or including a LCA10 target position (e.g., c.2991+1655A to G), or (2) break-induced deletion (also referred to herein as NHEJ-mediated deletion) of genomic sequence including the mutation at a LCA10 target position (e.g., c.2991+1655A to G). Both approaches give rise to the loss or destruction of the cryptic splice site resulting from the mutation at the LCA 10 target position. Accordingly, the use of Cpf1 in the treatment of LCA is specifically envisaged.

Researchers are contemplating whether gene therapies could be employed to treat a wide range of diseases. The CRISPR systems of the present invention based on Cpf1 effector protein are envisioned for such therapeutic uses, including, but noted limited to further exemplified targeted areas and with delivery methods as below. Some examples of conditions or diseases that might be usefully treated using the present system are included in the examples of genes and references included herein and are currently associated with those conditions are also provided there. The genes and conditions exemplified are not exhaustive.

Treating Diseases of the Circulatory System

The present invention also contemplates delivering the CRISPR-Cas system, specifically the novel CRISPR effector protein systems described herein, to the blood or hematopoietic stem cells. The plasma exosomes of Wahlgren et al. (Nucleic Acids Research, 2012, Vol. 40, No. 17 e130) were previously described and may be utilized to deliver the CRISPR-Cas system to the blood. The nucleic acid-targeting system of the present invention is also contemplated to treat hemoglobinopathies, such as thalassemias and sickle cell disease. See, e.g., International Patent Publication No. WO 2013/126794 for potential targets that may be targeted by the CRISPR-Cas system of the present invention.

Drakopoulou, "Review Article, The Ongoing Challenge of Hematopoietic Stem Cell-Based Gene Therapy for β-Thalassemia," Stem Cells International, Volume 2011, Article ID 987980, 10 pages, doi:10.4061/2011/987980, incorporated herein by reference along with the documents it cites, as if set out in full, discuss modifying HSCs using a lentivirus that delivers a gene for β-globin or γ-globin. In contrast to using lentivirus, with the knowledge in the art and the teachings in this disclosure, the skilled person can correct HSCs as to β-Thalassemia using a CRISPR-Cas system that targets and corrects the mutation (e.g., with a suitable HDR template that delivers a coding sequence for β-globin or γ-globin, advantageously non-sickling β-globin or γ-globin); specifically, the guide RNA can target mutation that give rise to β-Thalassemia, and the HDR can provide coding for proper expression of β-globin or γ-globin. An guide RNA that targets the mutation-and-Cas protein containing particle is contacted with HSCs carrying the mutation. The particle also can contain a suitable HDR template to correct the mutation for proper expression of β-globin or γ-globin; or the HSC can be contacted with a second particle or a vector that contains or delivers the HDR template. The so contacted cells can be administered; and optionally treated/expanded; cf. Cartier. In this regard mention is made of: Cavazzana, "Outcomes of Gene Therapy for β-Thalassemia Major via Transplantation of Autologous Hematopoietic Stem Cells Transduced Ex Vivo with a Lentiviral βA-T87Q-Globin Vector." tif2014.org/abstractFiles/Jean %20Antoine %20Ribeil_Abstract.pdf; Cavazzana-Calvo, "Transfusion independence and HMGA2 activation after gene therapy of human β-thalassaemia", Nature 467, 318-322 (16 Sep. 2010) doi:10.1038/nature09328; Nienhuis, "Development of Gene Therapy for Thalassemia, Cold Spring Harbor Perspectives in Medicine, doi: 10.1101/cshperspect.a011833 (2012), LentiGlobin BB305, a lentiviral vector containing an engineered β-globin gene (βA-T87Q); and Xie et al., "Seamless gene correction of β-thalassaemia mutations in patient-specific iPSCs using CRISPR/Cas9 and piggyback" Genome Research gr.173427.114 (2014) www.genome.org/cgi/doi/10.1101/gr.173427.114 (Cold Spring Harbor Laboratory Press); that is the subject of Cavazzana work involving human β-thalassaemia and the subject of the Xie work, are all incorporated herein by reference, together with all documents cited therein or associated therewith. In the instant invention, the HDR template can provide for the HSC to express an engineered β-globin gene (e.g., βA-T87Q), or β-globin as in Xie.

Xu et al. (Sci Rep. 2015 Jul. 9; 5:12065. doi: 10.1038/srep12065) have designed TALENs and CRISPR-Cas9 to directly target the intron2 mutation site IVS2-654 in the globin gene. Xu et al. observed different frequencies of double-strand breaks (DSBs) at IVS2-654 loci using TALENs and CRISPR-Cas9, and TALENs mediated a higher homologous gene targeting efficiency compared to CRISPR-Cas9 when combined with the piggyBac transposon donor. In addition, more obvious off-target events were observed for CRISPR-Cas9 compared to TALENs. Finally, TALENs-corrected iPSC clones were selected for erythroblast differentiation using the OP9 co-culture system and detected relatively higher transcription of HBB than the uncorrected cells.

Song et al. (Stem Cells Dev. 2015 May 1; 24(9):1053-65. doi: 10.1089/scd.2014.0347. Epub 2015 Feb. 5) used CRISPR/Cas9 to correct β-Thal iPSCs; gene-corrected cells exhibit normal karyotypes and full pluripotency as human embryonic stem cells (hESCs) showed no off-targeting effects. Then, Song et al. evaluated the differentiation efficiency of the gene-corrected β-Thal iPSCs. Song et al. found that during hematopoietic differentiation, gene-corrected β-Thal iPSCs showed an increased embryoid body ratio and various hematopoietic progenitor cell percentages. More importantly, the gene-corrected β-Thal iPSC lines restored HBB expression and reduced reactive oxygen species production compared with the uncorrected group. Song et al.'s study suggested that hematopoietic differentiation efficiency of β-Thal iPSCs was greatly improved once corrected by the CRISPR-Cas9 system. Similar methods may be performed utilizing the CRISPR-Cas systems described herein, e.g. systems comprising Cpf1 effector proteins.

Sickle cell anemia is an autosomal recessive genetic disease in which red blood cells become sickle-shaped. It is caused by a single base substitution in the β-globin gene, which is located on the short arm of chromosome 11. As a result, valine is produced instead of glutamic acid causing the production of sickle hemoglobin (HbS). This results in the formation of a distorted shape of the erythrocytes. Due to this abnormal shape, small blood vessels can be blocked, causing serious damage to the bone, spleen and skin tissues. This may lead to episodes of pain, frequent infections, hand-foot syndrome or even multiple organ failure. The distorted erythrocytes are also more susceptible to hemolysis, which leads to serious anemia. As in the case of β-thalassaemia, sickle cell anemia can be corrected by modifying HSCs with the CRISPR-Cas system. The system allows the specific editing of the cell's genome by cutting its DNA and then letting it repair itself. The Cas protein is inserted and directed by a RNA guide to the mutated point and then it cuts the DNA at that point. Simultaneously, a healthy version of the sequence is inserted. This sequence is used by the cell's own repair system to fix the induced cut. In this way, the CRISPR-Cas allows the correction of the mutation in the previously obtained stem cells. With the knowledge in the art and the teachings in this disclosure, the skilled person can correct HSCs as to sickle cell anemia using a CRISPR-Cas system that targets and corrects the mutation (e.g., with a suitable HDR template that delivers a coding sequence for β-globin, advantageously non-sickling β-globin); specifically, the guide RNA can target mutation that give rise to sickle cell anemia, and the HDR can provide coding for proper expression of β-globin. An guide RNA that targets the mutation-and-Cas protein containing particle is contacted with HSCs carrying the mutation. The particle also can contain a suitable HDR template to correct the mutation for proper expression of β-globin; or the HSC can be contacted with a second particle or a vector that contains or delivers the HDR template. The so contacted cells can be administered; and optionally treated/expanded; cf. Cartier. The HDR template can provide for the HSC to express an engineered β-globin gene (e.g., βA-T87Q), or β-globin as in Xie.

Williams, "Broadening the Indications for Hematopoietic Stem Cell Genetic Therapies," Cell Stem Cell 13:263-264 (2013), incorporated herein by reference along with the documents it cites, as if set out in full, report lentivirus-mediated gene transfer into HSC/P cells from patients with the lysosomal storage disease metachromatic leukodystrophy disease (MLD), a genetic disease caused by deficiency of arylsulfatase A (ARSA), resulting in nerve demyelination; and lentivirus-mediated gene transfer into HSCs of patients with Wiskott-Aldrich syndrome (WAS) (patients with defective WAS protein, an effector of the small GTPase CDC42 that regulates cytoskeletal function in blood cell lineages and thus suffer from immune deficiency with recurrent infections, autoimmune symptoms, and thrombocytopenia with abnormally small and dysfunctional platelets leading to excessive bleeding and an increased risk of leukemia and lymphoma). In contrast to using lentivirus, with the knowledge in the art and the teachings in this disclosure, the skilled person can correct HSCs as to MLD (deficiency of arylsulfatase A (ARSA)) using a CRISPR-Cas system that targets and corrects the mutation (deficiency of arylsulfatase A (ARSA)) (e.g., with a suitable HDR template that delivers a coding sequence for ARSA); specifically, the guide RNA can target mutation that gives rise to MLD (deficient ARSA), and the HDR can provide coding for proper expression of ARSA. An guide RNA that targets the mutation-and-Cas protein containing particle is contacted with HSCs carrying the mutation. The particle also can contain a suitable HDR template to correct the mutation for proper expression of ARSA; or the HSC can be contacted with a second particle or a vector that contains or delivers the HDR template. The so contacted cells can be administered; and optionally treated/expanded; cf. Cartier. In contrast to using lentivirus, with the knowledge in the art and the teachings in this disclosure, the skilled person can correct HSCs as to WAS using a CRISPR-Cas system that targets and corrects the mutation (deficiency of WAS protein) (e.g., with a suitable HDR template that delivers a coding sequence for WAS protein); specifically, the guide RNA can target mutation that gives rise to WAS (deficient WAS protein), and the HDR can provide coding for proper expression of WAS protein. An guide RNA that targets the mutation-and-Cpf1 protein containing particle is contacted with HSCs carrying the mutation. The particle also can contain a suitable HDR template to correct the mutation for proper expression of WAS protein; or the HSC can be contacted with a second particle or a vector that contains or delivers the HDR template. The so contacted cells can be administered; and optionally treated/expanded; cf. Cartier.

Watts, "Hematopoietic Stem Cell Expansion and Gene Therapy" Cytotherapy 13(10):1164-1171. doi:10.3109/14653249.2011.620748 (2011), incorporated herein by reference along with the documents it cites, as if set out in full, discusses hematopoietic stem cell (HSC) gene therapy, e.g., virus-mediated HSC gene therapy, as an highly attractive treatment option for many disorders including hematologic conditions, immunodeficiencies including HIV/AIDS, and other genetic disorders like lysosomal storage diseases, including SCID-X1, ADA-SCID, β-thalassemia, X-linked CGD, Wiskott-Aldrich syndrome, Fanconi anemia, adrenoleukodystrophy (ALD), and metachromatic leukodystrophy (MLD).

US Patent Publication Nos. 20110225664, 20110091441, 20100229252, 20090271881 and 20090222937 assigned to Cellectis, relates to CREI variants, wherein at least one of the two I-CreI monomers has at least two substitutions, one in each of the two functional subdomains of the LAGLIDADG (SEQ ID NO: 26) core domain situated respectively from positions 26 to 40 and 44 to 77 of I-CreI, said variant being able to cleave a DNA target sequence from the human interleukin-2 receptor gamma chain (IL2RG) gene also named common cytokine receptor gamma chain gene or gamma C gene. The target sequences identified in US Patent Publication Nos. 20110225664, 20110091441, 20100229252, 20090271881 and 20090222937 may be utilized for the nucleic acid-targeting system of the present invention.

Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-109). Overall incidence is estimated to 1 in 75 000 births. Patients with untreated SCID are subject to multiple opportunist micro-organism infections, and do generally not live beyond one year. SCID can be treated by allogenic hematopoietic stem cell transfer, from a familial donor. Histocompatibility with the donor can vary widely. In the case of Adenosine Deaminase (ADA) deficiency, one of the SCID forms, patients can be treated by injection of recombinant Adenosine Deaminase enzyme.

Since the ADA gene has been shown to be mutated in SCID patients (Giblett et al., Lancet, 1972, 2, 1067-1069), several other genes involved in SCID have been identified (Cavazzana-Calvo et al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes involved in this process, result in the absence of mature T and B lymphocytes; and (iv) Mutations in other genes such as CD45, involved in T cell specific signaling have also been reported, although they represent a minority of cases (Cavazzana-Calvo et al., Annu. Rev. Med., 2005, 56, 585-602; Fischer et al., Immunol. Rev., 2005, 203, 98-109). Since when their genetic bases have been identified, the different SCID forms have become a paradigm for gene therapy approaches (Fischer et al., Immunol. Rev., 2005, 203, 98-109) for two major reasons. First, as in all blood diseases, an ex vivo treatment can be envisioned. Hematopoietic Stem Cells (HSCs) can be recovered from bone marrow, and keep their pluripotent properties for a few cell divisions. Therefore, they can be treated in vitro, and then reinjected into the patient, where they repopulate the bone marrow. Second, since the maturation of lymphocytes is impaired in SCID patients, corrected cells have a selective advantage. Therefore, a small number of corrected cells can restore a functional immune system. This hypothesis was validated several times by (i) the partial restoration of immune functions associated with the reversion of mutations in SCID patients (Hirschhorn et al., Nat. Genet., 1996, 13, 290-295; Stephan et al., N. Engl. J. Med., 1996, 335, 1563-1567; Bousso et al., Proc. Natl., Acad. Sci. USA, 2000, 97, 274-278; Wada et al., Proc. Natl. Acad. Sci. USA, 2001, 98, 8697-8702; Nishikomori et al., Blood, 2004, 103, 4565-4572), (ii) the correction of SCID-X1 deficiencies in vitro in hematopoietic cells (Candotti et al., Blood, 1996, 87, 3097-3102; Cavazzana-Calvo et al., Blood, 1996, Blood, 88, 3901-3909; Taylor et al., Blood, 1996, 87, 3103-3107; Hacein-Bey et al., Blood, 1998, 92, 4090-4097), (iii) the correction of SCID-X1 (Soudais et al., Blood, 2000, 95, 3071-3077; Tsai et al., Blood, 2002, 100, 72-79), JAK-3 (Bunting et al., Nat. Med., 1998, 4, 58-64; Bunting et al., Hum. Gene Ther., 2000, 11, 2353-2364) and RAG2 (Yates et al., Blood, 2002, 100, 3942-3949) deficiencies in vivo in animal models and (iv) by the result of gene therapy clinical trials (Cavazzana-Calvo et al., Science, 2000, 288, 669-672; Aiuti et al., Nat. Med., 2002; 8, 423-425; Gaspar et al., Lancet, 2004, 364, 2181-2187).

US Patent Publication No. 20110182867 assigned to the Children's Medical Center Corporation and the President and Fellows of Harvard College relates to methods and uses of modulating fetal hemoglobin expression (HbF) in a hematopoietic progenitor cells via inhibitors of BCL11A expression or activity, such as RNAi and antibodies. The targets disclosed in US Patent Publication No. 20110182867, such as BCL11A, may be targeted by the CRISPR-Cas system of the present invention for modulating fetal hemoglobin expression. See also Bauer et al. (Science 11 Oct. 2013: Vol. 342 no. 6155 pp. 253-257) and Xu et al. (Science 18 Nov. 2011: Vol. 334 no. 6058 pp. 993-996) for additional BCL11A targets.

With the knowledge in the art and the teachings in this disclosure, the skilled person can correct HSCs as to a genetic hematologic disorder, e.g., β-Thalassemia, Hemophilia, or a genetic lysosomal storage disease.

HSC—Delivery to and Editing of Hematopoietic Stem Cells; and Particular Conditions.

The term "Hematopoietic Stem Cell" or "HSC" is meant to include broadly those cells considered to be an HSC, e.g., blood cells that give rise to all the other blood cells and are derived from mesoderm; located in the red bone marrow, which is contained in the core of most bones. HSCs of the invention include cells having a phenotype of hematopoietic stem cells, identified by small size, lack of lineage (lin) markers, and markers that belong to the cluster of differentiation series, like: CD34, CD38, CD90, CD133, CD105, CD45, and also c-kit,—the receptor for stem cell factor. Hematopoietic stem cells are negative for the markers that are used for detection of lineage commitment, and are, thus, called Lin-; and, during their purification by FACS, a number of up to 14 different mature blood-lineage markers, e.g., CD13 & CD33 for myeloid, CD71 for erythroid, CD19 for B cells, CD61 for megakaryocytic, etc. for humans; and, B220 (murine CD45) for B cells, Mac-1 (CD11b/CD18) for monocytes, Gr-1 for Granulocytes, Ter119 for erythroid cells, Il7Ra, CD3, CD4, CD5, CD8 for T cells, etc. Mouse HSC markers: CD34lo/−, SCA-1+, Thy1.1+/lo, CD38+, C-kit+, lin−, and Human HSC markers: CD34+, CD59+, Thy1/CD90+, CD38lo/−, C-kit/CD117+, and lin−. HSCs are identified by markers. Hence in embodiments discussed herein, the HSCs can be CD34+ cells. HSCs can also be hematopoietic stem cells that are CD34−/CD38−. Stem cells that may lack c-kit on the cell surface that are considered in the art as HSCs are within the ambit of the invention, as well as CD133+ cells likewise considered HSCs in the art.

The CRISPR-Cas (eg Cpf1) system may be engineered to target genetic locus or loci in HSCs. Cas (eg Cpf1) protein, advantageously codon-optimized for a eukaryotic cell and especially a mammalian cell, e.g., a human cell, for instance, HSC, and sgRNA targeting a locus or loci in HSC, e.g., the gene EMX1, may be prepared. These may be delivered via particles. The particles may be formed by the Cas (eg Cpf1) protein and the gRNA being admixed. The gRNA and Cas (eg Cpf1) protein mixture may for example be admixed with a mixture comprising or consisting essentially of or consisting of surfactant, phospholipid, biodegradable polymer, lipoprotein and alcohol, whereby particles containing the gRNA and Cas (eg Cpf1) protein may be formed. The invention comprehends so making particles and particles from such a method as well as uses thereof.

More generally, particles may be formed using an efficient process. First, Cas (eg Cpf1) protein and gRNA targeting the gene EMX1 or the control gene LacZ may be mixed together at a suitable, e.g., 3:1 to 1:3 or 2:1 to 1:2 or 1:1 molar ratio, at a suitable temperature, e.g., 15-30C, e.g., 20-25C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g., 1,2-dioleoyl-3-trimethylammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol may be dissolved in an alcohol, advantageously a C1-6 alkyl alcohol, such as methanol, ethanol, isopropanol, e.g., 100% ethanol. The two solutions may be mixed together to form particles containing the Cas (eg Cpf1)-gRNA complexes. In certain embodiments the particle can contain an HDR template. That can be a particle co-administered with gRNA+Cas (eg Cpf1) protein-containing particle, or i.e., in addition to contacting an HSC with an gRNA+Cas (eg Cpf1) protein-containing particle, the HSC is contacted with a particle containing an HDR template; or the HSC is contacted with a particle containing all of the gRNA, Cas (eg Cpf1) and the HDR template. The HDR template can be administered by a separate vector, whereby in a first instance the particle penetrates an HSC cell and the separate vector also penetrates the cell, wherein the HSC genome is modified by the gRNA+Cas (eg Cpf1) and the HDR template is also present, whereby a genomic loci is modified by the HDR; for instance, this may result in correcting a mutation.

After the particles form, HSCs in 96 well plates may be transfected with 15 µg Cas (eg Cpf1) protein per well. Three days after transfection, HSCs may be harvested, and the number of insertions and deletions (indels) at the EMX1 locus may be quantified.

This illustrates how HSCs can be modified using CRISPR-Cas (eg Cpf1) targeting a genomic locus or loci of interest in the HSC. The HSCs that are to be modified can be in vivo, i.e., in an organism, for example a human or a non-human eukaryote, e.g., animal, such as fish, e.g., zebra fish, mammal, e.g., primate, e.g., ape, chimpanzee, macaque, rodent, e.g., mouse, rabbit, rat, canine or dog, livestock (cow/bovine, sheep/ovine, goat or pig), fowl or poultry, e.g., chicken. The HSCs that are to be modified can be in vitro, i.e., outside of such an organism. And, modified HSCs can be used ex vivo, i.e., one or more HSCs of such an organism can be obtained or isolated from the organism, optionally the HSC(s) can be expanded, the HSC(s) are modified by a composition comprising a CRISPR-Cas (eg Cpf1) that targets a genetic locus or loci in the HSC, e.g., by contacting the HSC(s) with the composition, for instance, wherein the composition comprises a particle containing the CRISPR enzyme and one or more gRNA that targets the genetic locus or loci in the HSC, such as a particle obtained or obtainable from admixing an gRNA and Cas (eg Cpf1) protein mixture with a mixture comprising or consisting essentially of or consisting of surfactant, phospholipid, biodegradable polymer, lipoprotein and alcohol (wherein one or more gRNA targets the genetic locus or loci in the HSC), optionally expanding the resultant modified HSCs and administering to the organism the resultant modified HSCs. In some instances the isolated or obtained HSCs can be from a first organism, such as an organism from a same species as a second organism, and the second organism can be the organism to which the resultant modified HSCs are administered, e.g., the first organism can be a donor (such as a relative as in a parent or sibling) to the second organism. Modified HSCs can have genetic modifications to address or alleviate or reduce symptoms of a disease or condition state of an individual or subject or patient. Modified HSCs, e.g., in the instance of a first organism donor to a second organism, can have genetic modifications to have the HSCs have one or more proteins e.g. surface markers or proteins more like that of the second organism. Modified HSCs can have genetic modifications to simulate a disease or condition state of an individual or subject or patient and would be re-administered to a non-human organism so as to prepare an animal model. Expansion of HSCs is within the ambit of the skilled person from this disclosure and knowledge in the art, see e.g., Lee, "Improved ex vivo expansion of adult hematopoietic stem cells by overcoming CUL4-mediated degradation of HOXB4." Blood. 2013 May 16; 121(20):4082-9. doi: 10.1182/blood-2012-09-455204. Epub 2013 Mar. 21.

As indicated to improve activity, gRNA may be pre-complexed with the Cas (eg Cpf1) protein, before formulating the entire complex in a particle. Formulations may be made with a different molar ratio of different components known to promote delivery of nucleic acids into cells (e.g.

1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. The invention accordingly comprehends admixing gRNA, Cas (eg Cpf1) protein and components that form a particle; as well as particles from such admixing.

In a preferred embodiment, particles containing the Cas (eg Cpf1)-gRNA complexes may be formed by mixing Cas (eg Cpf1) protein and one or more gRNAs together, preferably at a 1:1 molar ratio, enzyme: guide RNA. Separately, the different components known to promote delivery of nucleic acids (e.g. DOTAP, DMPC, PEG, and cholesterol) are dissolved, preferably in ethanol. The two solutions are mixed together to form particles containing the Cas (eg Cpf1)-gRNA complexes. After the particles are formed, Cas (eg Cpf1)-gRNA complexes may be transfected into cells (e.g. HSCs). Bar coding may be applied. The particles, the Cas-9 and/or the gRNA may be barcoded.

The invention in an embodiment comprehends a method of preparing an gRNA-and-Cas (eg Cpf1) protein containing particle comprising admixing an gRNA and Cas (eg Cpf1) protein mixture with a mixture comprising or consisting essentially of or consisting of surfactant, phospholipid, biodegradable polymer, lipoprotein and alcohol. An embodiment comprehends an gRNA-and-Cas (eg Cpf1) protein containing particle from the method. The invention in an embodiment comprehends use of the particle in a method of modifying a genomic locus of interest, or an organism or a non-human organism by manipulation of a target sequence in a genomic locus of interest, comprising contacting a cell containing the genomic locus of interest with the particle wherein the gRNA targets the genomic locus of interest; or a method of modifying a genomic locus of interest, or an organism or a non-human organism by manipulation of a target sequence in a genomic locus of interest, comprising contacting a cell containing the genomic locus of interest with the particle wherein the gRNA targets the genomic locus of interest. In these embodiments, the genomic locus of interest is advantageously a genomic locus in an HSC.

Considerations for Therapeutic Applications: A consideration in genome editing therapy is the choice of sequence-specific nuclease, such as a variant of a Cpf1 nuclease. Each nuclease variant may possess its own unique set of strengths and weaknesses, many of which must be balanced in the context of treatment to maximize therapeutic benefit. Thus far, two therapeutic editing approaches with nucleases have shown significant promise: gene disruption and gene correction. Gene disruption involves stimulation of NHEJ to create targeted indels in genetic elements, often resulting in loss of function mutations that are beneficial to patients. In contrast, gene correction uses HDR to directly reverse a disease causing mutation, restoring function while preserving physiological regulation of the corrected element. HDR may also be used to insert a therapeutic transgene into a defined 'safe harbor' locus in the genome to recover missing gene function. For a specific editing therapy to be efficacious, a sufficiently high level of modification must be achieved in target cell populations to reverse disease symptoms. This therapeutic modification 'threshold' is determined by the fitness of edited cells following treatment and the amount of gene product necessary to reverse symptoms. With regard to fitness, editing creates three potential outcomes for treated cells relative to their unedited counterparts: increased, neutral, or decreased fitness. In the case of increased fitness, for example in the treatment of SCID-X1, modified hematopoietic progenitor cells selectively expand relative to their unedited counterparts. SCID-X1 is a disease caused by mutations in the IL2RG gene, the function of which is required for proper development of the hematopoietic lymphocyte lineage [Leonard, W. J., et al. Immunological reviews 138, 61-86 (1994); Kaushansky, K. & Williams, W. J. Williams hematology, (McGraw-Hill Medical, New York, 2010)]. In clinical trials with patients who received viral gene therapy for SCID-X1, and a rare example of a spontaneous correction of SCID-X1 mutation, corrected hematopoietic progenitor cells may be able to overcome this developmental block and expand relative to their diseased counterparts to mediate therapy [Bousso, P., et al. Proceedings of the National Academy of Sciences of the United States of America 97, 274-278 (2000); Hacein-Bey-Abina, S., et al. The New England journal of medicine 346, 1185-1193 (2002); Gaspar, H. B., et al. Lancet 364, 2181-2187 (2004)]. In this case, where edited cells possess a selective advantage, even low numbers of edited cells can be amplified through expansion, providing a therapeutic benefit to the patient. In contrast, editing for other hematopoietic diseases, like chronic granulomatous disorder (CGD), would induce no change in fitness for edited hematopoietic progenitor cells, increasing the therapeutic modification threshold. CGD is caused by mutations in genes encoding phagocytic oxidase proteins, which are normally used by neutrophils to generate reactive oxygen species that kill pathogens [Mukherjee, S. & Thrasher, A. J. Gene 525, 174-181 (2013)]. As dysfunction of these genes does not influence hematopoietic progenitor cell fitness or development, but only the ability of a mature hematopoietic cell type to fight infections, there would be likely no preferential expansion of edited cells in this disease. Indeed, no selective advantage for gene corrected cells in CGD has been observed in gene therapy trials, leading to difficulties with long-term cell engraftment [Malech, H. L., et al. Proceedings of the National Academy of Sciences of the United States of America 94, 12133-12138 (1997); Kang, H. J., et al. Molecular therapy: the journal of the American Society of Gene Therapy 19, 2092-2101 (2011)]. As such, significantly higher levels of editing would be required to treat diseases like CGD, where editing creates a neutral fitness advantage, relative to diseases where editing creates increased fitness for target cells. If editing imposes a fitness disadvantage, as would be the case for restoring function to a tumor suppressor gene in cancer cells, modified cells would be outcompeted by their diseased counterparts, causing the benefit of treatment to be low relative to editing rates. This latter class of diseases would be particularly difficult to treat with genome editing therapy.

In addition to cell fitness, the amount of gene product necessary to treat disease also influences the minimal level of therapeutic genome editing that must be achieved to reverse symptoms. Haemophilia B is one disease where a small change in gene product levels can result in significant changes in clinical outcomes. This disease is caused by mutations in the gene encoding factor IX, a protein normally secreted by the liver into the blood, where it functions as a component of the clotting cascade. Clinical severity of haemophilia B is related to the amount of factor IX activity. Whereas severe disease is associated with less than 1% of normal activity, milder forms of the diseases are associated with greater than 1% of factor IX activity [Kaushansky, K. & Williams, W. J. Williams hematology, (McGraw-Hill Medical, New York, 2010); Lofqvist, T., et al. Journal of internal medicine 241, 395-400 (1997)]. This suggests that editing therapies that can restore factor IX expression to even a small percentage of liver cells could have a large impact on clinical outcomes. A study using ZFNs to correct a mouse model of haemophilia B shortly after birth demonstrated that 3-7% correction was sufficient to reverse disease symptoms, providing preclinical evidence for this hypothesis [Li, H., et al. Nature 475, 217-221 (2011)].

Disorders where a small change in gene product levels can influence clinical outcomes and diseases where there is a fitness advantage for edited cells, are ideal targets for genome editing therapy, as the therapeutic modification threshold is low enough to permit a high chance of success given the current technology. Targeting these diseases has now resulted in successes with editing therapy at the preclinical level and a phase I clinical trial. Improvements in DSB repair pathway manipulation and nuclease delivery are needed to extend these promising results to diseases with a neutral fitness advantage for edited cells, or where larger amounts of gene product are needed for treatment. The Table below shows some examples of applications of genome editing to therapeutic models, and the references of the below Table and the documents cited in those references are hereby incorporated herein by reference as if set out in full.

TABLE 18

| Disease Type | Nuclease Platform Employed | Therapeutic Strategy | References |
| --- | --- | --- | --- |
| Hemophilia B | ZFN | HDR-mediated insertion of correct gene sequence | Li, H., et al. Nature 475, 217-221 (2011) |
| SCID | ZFN | HDR-mediated insertion of correct gene sequence | Genovese, P., et al. Nature 510, 235-240 (2014) |
| Hereditary tyrosinemia | CRISPR | HDR-mediated correction of mutation in liver | Yin, H., et al. Nature biotechnology 32, 551-553 (2014) |

Addressing each of the conditions of the foregoing table, using the CRISPR-Cas (eg Cpf1) system to target by either HDR-mediated correction of mutation, or HDR-mediated insertion of correct gene sequence, advantageously via a delivery system as herein, e.g., a particle delivery system, is within the ambit of the skilled person from this disclosure and the knowledge in the art. Thus, an embodiment comprehends contacting a Hemophilia B, SCID (e.g., SCID-X1, ADA-SCID) or Hereditary tyrosinemia mutation-carrying HSC with an gRNA-and-Cas (eg Cpf1) protein containing particle targeting a genomic locus of interest as to Hemophilia B, SCID (e.g., SCID-X1, ADA-SCID) or Hereditary tyrosinemia (e.g., as in Li, Genovese or Yin). The particle also can contain a suitable HDR template to correct the mutation; or the HSC can be contacted with a second particle or a vector that contains or delivers the HDR template. In this regard, it is mentioned that Haemophilia B is an X-linked recessive disorder caused by loss-of-function mutations in the gene encoding Factor IX, a crucial component of the clotting cascade. Recovering Factor IX activity to above 1% of its levels in severely affected individuals can transform the disease into a significantly milder form, as infusion of recombinant Factor IX into such patients prophylactically from a young age to achieve such levels largely ameliorates clinical complications. With the knowledge in the art and the teachings in this disclosure, the skilled person can correct HSCs as to Haemophilia B using a CRISPR-Cas (eg Cpf1) system that targets and corrects the mutation (X-linked recessive disorder caused by loss-of-function mutations in the gene encoding Factor IX) (e.g., with a suitable HDR template that delivers a coding sequence for Factor IX); specifically, the gRNA can target mutation that give rise to Haemophilia B, and the HDR can provide coding for proper expression of Factor IX. An gRNA that targets the mutation-and-Cas (eg Cpf1) protein containing particle is contacted with HSCs carrying the mutation. The particle also can contain a suitable HDR template to correct the mutation for proper expression of Factor IX; or the HSC can be contacted with a second particle or a vector that contains or delivers the HDR template. The so contacted cells can be administered; and optionally treated/expanded; cf. Cartier, discussed herein.

In Cartier, "MINI-SYMPOSIUM: X-Linked Adrenoleukodystrophy, Hematopoietic Stem Cell Transplantation and Hematopoietic Stem Cell Gene Therapy in X-Linked Adrenoleukodystrophy," Brain Pathology 20 (2010) 857-862, incorporated herein by reference along with the documents it cites, as if set out in full, there is recognition that allogeneic hematopoietic stem cell transplantation (HSCT) was utilized to deliver normal lysosomal enzyme to the brain of a patient with Hurler's disease, and a discussion of HSC gene therapy to treat ALD. In two patients, peripheral CD34+ cells were collected after granulocyte-colony stimulating factor (G-CSF) mobilization and transduced with an myeloproliferative sarcoma virus enhancer, negative control region deleted, d1587rev primer binding site substituted (MND)-ALD lentiviral vector. CD34+ cells from the patients were transduced with the MND-ALD vector during 16 h in the presence of cytokines at low concentrations. Transduced CD34+ cells were frozen after transduction to perform on 5% of cells various safety tests that included in particular three replication-competent lentivirus (RCL) assays. Transduction efficacy of CD34+ cells ranged from 35% to 50% with a mean number of lentiviral integrated copy between 0.65 and 0.70. After the thawing of transduced CD34+ cells, the patients were reinfused with more than 4.106 transduced CD34+ cells/kg following full myeloablation with busulfan and cyclophos-phamide. The patient's HSCs were ablated to favor engraftment of the gene-corrected HSCs. Hematological recovery occurred between days 13 and 15 for the two patients. Nearly complete immunological recovery occurred at 12 months for the first patient, and at 9 months for the second patient. In contrast to using lentivirus, with the knowledge in the art and the teachings in this disclosure, the skilled person can correct HSCs as to ALD using a CRISPR-Cas (Cpf1) system that targets and corrects the mutation (e.g., with a suitable HDR template); specifically, the gRNA can target mutations in ABCD1, a gene located on the X chromosome that codes for ALD, a peroxisomal membrane transporter protein, and the HDR can provide coding for proper expression of the protein. An gRNA that targets the mutation-and-Cas (Cpf1) protein containing particle is contacted with HSCs, e.g., CD34+ cells carrying the mutation as in Cartier. The particle also can contain a suitable HDR template to correct the mutation for expression of the peroxisomal membrane transporter protein; or the HSC can be contacted with a second particle or a vector that contains or delivers the HDR template. The so contacted cells optionally can be treated as in Cartier. The so contacted cells can be administered as in Cartier.

Mention is made of WO 2015/148860, through the teachings herein the invention comprehends methods and materials of these documents applied in conjunction with the teachings herein. In an aspect of blood-related disease gene therapy, methods and compositions for treating beta thalassemia may be adapted to the CRISPR-Cas system of the present invention (see, e.g., WO 2015/148860). In an embodiment, WO 2015/148860 involves the treatment or prevention of beta thalassemia, or its symptoms, e.g., by altering the gene for B-cell CLL/lymphoma 11A (BCL11A). The BCL11A gene is also known as B-cell CLL/lymphoma 11A, BCL11A-L, BCL11A-S, BCL11AXL, CTIP 1, HBFQTL5 and ZNF. BCL11A encodes a zinc-finger protein that is involved in the regulation of globin gene expression. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating beta thalassemia disease phenotypes.

Mention is also made of WO 2015/148863 and through the teachings herein the invention comprehends methods and materials of these documents which may be adapted to the CRISPR-Cas system of the present invention. In an aspect of treating and preventing sickle cell disease, which is an inherited hematologic disease, WO 2015/148863 comprehends altering the BCL11A gene. By altering the BCL11A gene (e.g., one or both alleles of the BCL11A gene), the levels of gamma globin can be increased. Gamma globin can replace beta globin in the hemoglobin complex and effectively carry oxygen to tissues, thereby ameliorating sickle cell disease phenotypes.

In an aspect of the invention, methods and compositions which involve editing a target nucleic acid sequence, or modulating expression of a target nucleic acid sequence, and applications thereof in connection with cancer immunotherapy are comprehended by adapting the CRISPR-Cas system of the present invention. Reference is made to the application of gene therapy in WO 2015/161276 which involves methods and compositions which can be used to affect T-cell proliferation, survival and/or function by altering one or more T-cell expressed genes, e.g., one or more of FAS, BID, CTLA4, PDCD1, CBLB, PTPN6, TRAC and/or TRBC genes. In a related aspect, T-cell proliferation can be affected by altering one or more T-cell expressed genes, e.g., the CBLB and/or PTPN6 gene, FAS and/or BID gene, CTLA4 and/or PDCDI and/or TRAC and/or TRBC gene.

Chimeric antigen receptor (CAR)19 T-cells exhibit anti-leukemic effects in patient malignancies. However, leukemia patients often do not have enough T-cells to collect, meaning that treatment must involve modified T cells from donors. Accordingly, there is interest in establishing a bank of donor T-cells. Qasim et al. ("First Clinical Application of Talen Engineered Universal CAR19 T Cells in B-ALL" ASH 57th Annual Meeting and Exposition, Dec. 5-8, 2015, Abstract 2046 (ash.confex.com/ash/2015/webprogram/Paper81653.html published online November 2015) discusses modifying CAR19 T cells to eliminate the risk of graft-versus-host disease through the disruption of T-cell receptor expression and CD52 targeting. Furthermore, CD52 cells were targeted such that they became insensitive to Alemtuzumab, and thus allowed Alemtuzumab to prevent host-mediated rejection of human leukocyte antigen (HLA) mismatched CAR19 T-cells. Investigators used third generation self-inactivating lentiviral vector encoding a 4g7 CAR19 (CD19 scFv-4-1BB-CD3ζ) linked to RQR8, then electroporated cells with two pairs of TALEN mRNA for multiplex targeting for both the T-cell receptor (TCR) alpha constant chain locus and the CD52 gene locus. Cells which were still expressing TCR following ex vivo expansion were depleted using CliniMacs α/β TCR depletion, yielding a T-cell product (UCART19) with <1% TCR expression, 85% of which expressed CAR19, and 64% becoming CD52 negative. The modified CAR19 T cells were administered to treat a patient's relapsed acute lymphoblastic leukemia. The teachings provided herein provide effective methods for providing modified hematopoietic stem cells and progeny thereof, including but not limited to cells of the myeloid and lymphoid lineages of blood, including T cells, B cells, monocytes, macrophages, neutrophils, basophils, eosinophils, erythrocytes, dendritic cells, and megakaryocytes or platelets, and natural killer cells and their precursors and progenitors. Such cells can be modified by knocking out, knocking in, or otherwise modulating targets, for example to remove or modulate CD52 as described above, and other targets, such as, without limitation, CXCR4, and PD-1. Thus compositions, cells, and method of the invention can be used to modulate immune responses and to treat, without limitation, malignancies, viral infections, and immune disorders, in conjunction with modification of administration of T cells or other cells to patients.

Mention is made of WO 2015/148670 and through the teachings herein the invention comprehends methods and materials of this document applied in conjunction with the teachings herein. In an aspect of gene therapy, methods and compositions for editing of a target sequence related to or in connection with Human Immunodeficiency Virus (HIV) and Acquired Immunodeficiency Syndrome (AIDS) are comprehended. In a related aspect, the invention described herein comprehends prevention and treatment of HIV infection and AIDS, by introducing one or more mutations in the gene for C-C chemokine receptor type 5 (CCR5). The CCR5 gene is also known as CKR5, CCR-5, CD195, CKR-5, CCCKR5, CMKBR5, IDDM22, and CC-CKR-5. In a further aspect, the invention described herein comprehends provide for prevention or reduction of HIV infection and/or prevention or reduction of the ability for HIV to enter host cells, e.g., in subjects who are already infected. Exemplary host cells for HIV include, but are not limited to, CD4 cells, T cells, gut associated lymphatic tissue (GALT), macrophages, dendritic cells, myeloid precursor cell, and microglia. Viral entry into the host cells requires interaction of the viral glycoproteins gp41 and gp120 with both the CD4 receptor and a co-receptor, e.g., CCR5. If a co-receptor, e.g., CCR5, is not present on the surface of the host cells, the virus cannot bind and enter the host cells. The progress of the disease is thus impeded. By knocking out or knocking down CCR5 in the host cells, e.g., by introducing a protective mutation (such as a CCR5 delta 32 mutation), entry of the HIV virus into the host cells is prevented.

X-linked Chronic granulomatous disease (CGD) is a hereditary disorder of host defense due to absent or decreased activity of phagocyte NADPH oxidase. Using a CRISPR-Cas (Cpf1) system that targets and corrects the mutation (absent or decreased activity of phagocyte NADPH oxidase) (e.g., with a suitable HDR template that delivers a coding sequence for phagocyte NADPH oxidase); specifically, the gRNA can target mutation that gives rise to CGD (deficient phagocyte NADPH oxidase), and the HDR can provide coding for proper expression of phagocyte NADPH oxidase. An gRNA that targets the mutation-and-Cas (Cpf1) protein containing particle is contacted with HSCs carrying the mutation. The particle also can contain a suitable HDR template to correct the mutation for proper expression of phagocyte NADPH oxidase; or the HSC can be contacted with a second particle or a vector that contains or delivers the HDR template. The so contacted cells can be administered; and optionally treated/expanded; cf. Cartier.

Fanconi anemia: Mutations in at least 15 genes (FANCA, FANCB, FANCC, FANCD1/BRCA2, FANCD2, FANCE, FANCF, FANCG, FANCI, FANCFBACHVBRIP1, FANCL/PHF9/POG, FANCM, FANCN/PALB2, FANCO/Rad51C, and FANCP/SLX4/BTBD12) can cause Fanconi anemia. Proteins produced from these genes are involved in a cell process known as the FA pathway. The FA pathway is turned on (activated) when the process of making new copies of DNA, called DNA replication, is blocked due to DNA damage. The FA pathway sends certain proteins to the area of damage, which trigger DNA repair so DNA replication can continue. The FA pathway is particularly responsive to a certain type of DNA damage known as interstrand cross-links (ICLs). ICLs occur when two DNA building blocks (nucleotides) on opposite strands of DNA are abnormally attached or linked together, which stops the process of DNA replication. ICLs can be caused by a buildup of toxic substances produced in the body or by treatment with certain cancer therapy drugs. Eight proteins associated with Fanconi anemia group together to form a complex known as the FA core complex. The FA core complex activates two proteins, called FANCD2 and FANCI. The activation of these two proteins brings DNA repair proteins to the area of the ICL so the cross-link can be removed and DNA replication can continue. the FA core complex. More in particular, the FA core complex is a nuclear multiprotein complex consisting of FANCA, FANCB, FANCC, FANCE, FANCF, FANCG, FANCL, and FANCM, functions as an E3 ubiquitin ligase and mediates the activation of the ID complex, which is a heterodimer composed of FANCD2 and FANCI. Once monoubiquitinated, it interacts with classical tumor suppressors downstream of the FA pathway including FANCD1/BRCA2, FANCN/PALB2, FANCJ/BRIP1, and FANCO/Rad51C and thereby contributes to DNA repair via homologous recombination (HR). Eighty to 90 percent of FA cases are due to mutations in one of three genes, FANCA, FANCC, and FANCG. These genes provide instructions for producing components of the FA core complex. Mutations in such genes associated with the FA core complex will cause the complex to be nonfunctional and disrupt the entire FA pathway. As a result, DNA damage is not repaired efficiently and ICLs build up over time. Geiselhart, "Review Article, Disrupted Signaling through the Fanconi Anemia Pathway Leads to Dysfunctional Hematopoietic Stem Cell Biology: Underlying Mechanisms and Potential Therapeutic Strategies," Anemia Volume 2012 (2012), Article ID 265790, dx.doi.org/10.1155/2012/265790 discussed FA and an animal experiment involving intrafemoral injection of a lentivirus encoding the FANCC gene resulting in correction of HSCs in vivo. Using a CRISPR-Cas (Cpf1) system that targets and one or more of the mutations associated with FA, for instance a CRISPR-Cas (Cpf1) system having gRNA(s) and HDR template(s) that respectively targets one or more of the mutations of FANCA, FANCC, or FANCG that give rise to FA and provide corrective expression of one or more of FANCA, FANCC or FANCG; e.g., the gRNA can target a mutation as to FANCC, and the HDR can provide coding for proper expression of FANCC. An gRNA that targets the mutation(s) (e.g., one or more involved in FA, such as mutation(s) as to any one or more of FANCA, FANCC or FANCG)-and-Cas (Cpf1) protein containing particle is contacted with HSCs carrying the mutation(s). The particle also can contain a suitable HDR template(s) to correct the mutation for proper expression of one or more of the proteins involved in FA, such as any one or more of FANCA, FANCC or FANCG; or the HSC can be contacted with a second particle or a vector that contains or delivers the HDR template. The so contacted cells can be administered; and optionally treated/expanded; cf. Cartier.

The particle in the herein discussion (e.g., as to containing gRNA(s) and Cas (Cpf1), optionally HDR template(s), or HDR template(s); for instance as to Hemophilia B, SCID, SCID-X1, ADA-SCID, Hereditary tyrosinemia, β-thalassemia, X-linked CGD, Wiskott-Aldrich syndrome, Fanconi anemia, adrenoleukodystrophy (ALD), metachromatic leukodystrophy (MLD), HIV/AIDS, Immunodeficiency disorder, Hematologic condition, or genetic lysosomal storage disease) is advantageously obtained or obtainable from admixing an gRNA(s) and Cas (Cpf1) protein mixture (optionally containing HDR template(s) or such mixture only containing HDR template(s) when separate particles as to template(s) is desired) with a mixture comprising or consisting essentially of or consisting of surfactant, phospholipid, biodegradable polymer, lipoprotein and alcohol (wherein one or more gRNA targets the genetic locus or loci in the HSC).

Indeed, the invention is especially suited for treating hematopoietic genetic disorders with genome editing, and immunodeficiency disorders, such as genetic immunodeficiency disorders, especially through using the particle technology herein-discussed. Genetic immunodeficiencies are diseases where genome editing interventions of the instant invention can successful. The reasons include: Hematopoietic cells, of which immune cells are a subset, are therapeutically accessible. They can be removed from the body and transplanted autologously or allogenically. Further, certain genetic immunodeficiencies, e.g., severe combined immunodeficiency (SCID), create a proliferative disadvantage for immune cells. Correction of genetic lesions causing SCID by rare, spontaneous 'reverse' mutations indicates that correcting even one lymphocyte progenitor may be sufficient to recover immune function in patients . . . / . . . / . . . /Users/tkowalski/AppData/Local/Microsoft/Windows/Temporary Internet Files/Content.Outlook/GA8VY8LK/Treating SCID for Ellen.docx-_ENREF_1 See Bousso, P., et al. Diversity, functionality, and stability of the T cell repertoire derived in vivo from a single human T cell precursor. Proceedings of the National Academy of Sciences of the United States of America 97, 274-278 (2000). The selective advantage for edited cells allows for even low levels of editing to result in a therapeutic effect. This effect of the instant invention can be seen in SCID, Wiskott-Aldrich Syndrome, and the other conditions mentioned herein, including other genetic hematopoietic disorders such as alpha- and beta-thalassemia, where hemoglobin deficiencies negatively affect the fitness of erythroid progenitors.

The activity of NHEJ and HDR DSB repair varies significantly by cell type and cell state. NHEJ is not highly regulated by the cell cycle and is efficient across cell types, allowing for high levels of gene disruption in accessible target cell populations. In contrast, HDR acts primarily during S/G2 phase, and is therefore restricted to cells that are actively dividing, limiting treatments that require precise genome modifications to mitotic cells [Ciccia, A. & Elledge, S. J. Molecular cell 40, 179-204 (2010); Chapman, J. R., et al. Molecular cell 47, 497-510 (2012)].

The efficiency of correction via HDR may be controlled by the epigenetic state or sequence of the targeted locus, or the specific repair template configuration (single vs. double stranded, long vs. short homology arms) used [Hacein-Bey-Abina, S., et al. The New England journal of medicine 346, 1185-1193 (2002); Gaspar, H. B., et al. Lancet 364, 2181-2187 (2004); Beumer, K. J., et al. G3 (2013)]. The relative activity of NHEJ and HDR machineries in target cells may also affect gene correction efficiency, as these pathways may compete to resolve DSBs [Beumer, K. J., et al. Proceedings of the National Academy of Sciences of the United States of America 105, 19821-19826 (2008)]. HDR also imposes a delivery challenge not seen with NHEJ strategies, as it requires the concurrent delivery of nucleases and repair templates. In practice, these constraints have so far led to low levels of HDR in therapeutically relevant cell types. Clinical translation has therefore largely focused on NHEJ strategies to treat disease, although proof-of-concept preclinical HDR treatments have now been described for mouse models of haemophilia B and hereditary tyrosinemia [Li, H., et al. Nature 475, 217-221 (2011); Yin, H., et al. Nature biotechnology 32, 551-553 (2014)].

Any given genome editing application may comprise combinations of proteins, small RNA molecules, and/or repair templates, making delivery of these multiple parts substantially more challenging than small molecule therapeutics. Two main strategies for delivery of genome editing tools have been developed: ex vivo and in vivo. In ex vivo treatments, diseased cells are removed from the body, edited and then transplanted back into the patient. Ex vivo editing has the advantage of allowing the target cell population to be well defined and the specific dosage of therapeutic molecules delivered to cells to be specified. The latter consideration may be particularly important when off-target modifications are a concern, as titrating the amount of nuclease may decrease such mutations (Hsu et al., 2013). Another advantage of ex vivo approaches is the typically high editing rates that can be achieved, due to the development of efficient delivery systems for proteins and nucleic acids into cells in culture for research and gene therapy applications.

There may be drawbacks with ex vivo approaches that limit application to a small number of diseases. For instance, target cells must be capable of surviving manipulation outside the body. For many tissues, like the brain, culturing cells outside the body is a major challenge, because cells either fail to survive, or lose properties necessary for their function in vivo. Thus, in view of this disclosure and the knowledge in the art, ex vivo therapy as to tissues with adult stem cell populations amenable to ex vivo culture and manipulation, such as the hematopoietic system, by the CRISPR-Cas (Cpf1) system are enabled. [Bunn, H. F. & Aster, J. Pathophysiology of blood disorders, (McGraw-Hill, New York, 2011)]

In vivo genome editing involves direct delivery of editing systems to cell types in their native tissues. In vivo editing allows diseases in which the affected cell population is not amenable to ex vivo manipulation to be treated. Furthermore, delivering nucleases to cells in situ allows for the treatment of multiple tissue and cell types. These properties probably allow in vivo treatment to be applied to a wider range of diseases than ex vivo therapies.

To date, in vivo editing has largely been achieved through the use of viral vectors with defined, tissue-specific tropism. Such vectors are currently limited in terms of cargo carrying capacity and tropism, restricting this mode of therapy to organ systems where transduction with clinically useful vectors is efficient, such as the liver, muscle and eye [Kotterman, M. A. & Schaffer, D. V. Nature reviews. Genetics 15, 445-451 (2014); Nguyen, T. H. & Ferry, N. Gene therapy 11 Suppl 1, S76-84 (2004); Boye, S. E., et al. Molecular therapy: the journal of the American Society of Gene Therapy 21, 509-519 (2013)].

A potential barrier for in vivo delivery is the immune response that may be created in response to the large amounts of virus necessary for treatment, but this phenomenon is not unique to genome editing and is observed with other virus based gene therapies [Bessis, N., et al. Gene therapy 11 Suppl 1, S10-17 (2004)]. It is also possible that peptides from editing nucleases themselves are presented on MHC Class I molecules to stimulate an immune response, although there is little evidence to support this happening at the preclinical level. Another major difficulty with this mode of therapy is controlling the distribution and consequently the dosage of genome editing nucleases in vivo, leading to off-target mutation profiles that may be difficult to predict. However, in view of this disclosure and the knowledge in the art, including the use of virus- and particle-based therapies being used in the treatment of cancers, in vivo modification of HSCs, for instance by delivery by either particle or virus, is within the ambit of the skilled person.

Ex Vivo Editing Therapy: The long standing clinical expertise with the purification, culture and transplantation of hematopoietic cells has made diseases affecting the blood system such as SCID, Fanconi anemia, Wiskott-Aldrich syndrome and sickle cell anemia the focus of ex vivo editing therapy. Another reason to focus on hematopoietic cells is that, thanks to previous efforts to design gene therapy for blood disorders, delivery systems of relatively high efficiency already exist. With these advantages, this mode of therapy can be applied to diseases where edited cells possess a fitness advantage, so that a small number of engrafted, edited cells can expand and treat disease. One such disease is HIV, where infection results in a fitness disadvantage to CD4+ T cells.

Ex vivo editing therapy has been recently extended to include gene correction strategies. The barriers to HDR ex vivo were overcome in a recent paper from Genovese and colleagues, who achieved gene correction of a mutated IL2RG gene in hematopoietic stem cells (HSCs) obtained from a patient suffering from SCID-X1 [Genovese, P., et al. Nature 510, 235-240 (2014)]. Genovese et. al. accomplished gene correction in HSCs using a multimodal strategy. First, HSCs were transduced using integration-deficient lentivirus containing an HDR template encoding a therapeutic cDNA for IL2RG. Following transduction, cells were electroporated with mRNA encoding ZFNs targeting a mutational hotspot in IL2RG to stimulate HDR based gene correction. To increase HDR rates, culture conditions were optimized with small molecules to encourage HSC division. With optimized culture conditions, nucleases and HDR templates, gene corrected HSCs from the SCID-X1 patient were obtained in culture at therapeutically relevant rates. HSCs from unaffected individuals that underwent the same gene correction procedure could sustain long-term hematopoiesis in mice, the gold standard for HSC function. HSCs are capable of giving rise to all hematopoietic cell types and can be autologously transplanted, making them an extremely valuable cell population for all hematopoietic genetic disorders [Weissman, I. L. & Shizuru, J. A. Blood 112, 3543-3553 (2008)]. Gene corrected HSCs could, in principle, be used to treat a wide range of genetic blood disorders making this study an exciting breakthrough for therapeutic genome editing.

In Vivo Editing Therapy: In vivo editing can be used advantageously from this disclosure and the knowledge in the art. For organ systems where delivery is efficient, there have already been a number of exciting preclinical therapeutic successes. The first example of successful in vivo editing therapy was demonstrated in a mouse model of haemophilia B [Li, H., et al. Nature 475, 217-221 (2011)]. As noted earlier, Haemophilia B is an X-linked recessive disorder caused by loss-of-function mutations in the gene encoding Factor IX, a crucial component of the clotting cascade. Recovering Factor IX activity to above 1% of its levels in severely affected individuals can transform the disease into a significantly milder form, as infusion of recombinant Factor IX into such patients prophylactically from a young age to achieve such levels largely ameliorates clinical complications [Lofqvist, T., et al. Journal of internal medicine 241, 395-400 (1997)]. Thus, only low levels of HDR gene correction are necessary to change clinical outcomes for patients. In addition, Factor IX is synthesized and secreted by the liver, an organ that can be transduced efficiently by viral vectors encoding editing systems.

Using hepatotropic adeno-associated viral (AAV) serotypes encoding ZFNs and a corrective HDR template, up to 7% gene correction of a mutated, humanized Factor IX gene in the murine liver was achieved [Li, H., et al. Nature 475, 217-221 (2011)]. This resulted in improvement of clot formation kinetics, a measure of the function of the clotting cascade, demonstrating for the first time that in vivo editing therapy is not only feasible, but also efficacious. As discussed herein, the skilled person is positioned from the teachings herein and the knowledge in the art, e.g., Li to address Haemophilia B with a particle-containing HDR template and a CRISPR-Cas (Cpf1) system that targets the mutation of the X-linked recessive disorder to reverse the loss-of-function mutation.

Building on this study, other groups have recently used in vivo genome editing of the liver with CRISPR-Cas to successfully treat a mouse model of hereditary tyrosinemia and to create mutations that provide protection against cardiovascular disease. These two distinct applications demonstrate the versatility of this approach for disorders that involve hepatic dysfunction [Yin, H., et al. Nature biotechnology 32, 551-553 (2014); Ding, Q., et al. Circulation research 115, 488-492 (2014)]. Application of in vivo editing to other organ systems are necessary to prove that this strategy is widely applicable. Currently, efforts to optimize both viral and non-viral vectors are underway to expand the range of disorders that can be treated with this mode of therapy [Kotterman, M. A. & Schaffer, D. V. Nature reviews. Genetics 15, 445-451 (2014); Yin, H., et al. Nature reviews. Genetics 15, 541-555 (2014)]. As discussed herein, the skilled person is positioned from the teachings herein and the knowledge in the art, e.g., Yin to address hereditary tyrosinemia with a particle-containing HDR template and a CRISPR-Cas (Cpf1) system that targets the mutation.

Targeted deletion, therapeutic applications: Targeted deletion of genes may be preferred. Preferred are, therefore, genes involved in immunodeficiency disorder, hematologic condition, or genetic lysosomal storage disease, e.g., Hemophilia B, SCID, SCID-X1, ADA-SCID, Hereditary tyrosinemia, β-thalassemia, X-linked CGD, Wiskott-Aldrich syndrome, Fanconi anemia, adrenoleukodystrophy (ALD), metachromatic leukodystrophy (MLD), HIV/AIDS, other metabolic disorders, genes encoding mis-folded proteins involved in diseases, genes leading to loss-of-function involved in diseases; generally, mutations that can be targeted in an HSC, using any herein-discussed delivery system, with the particle system considered advantageous.

In the present invention, the immunogenicity of the CRISPR enzyme in particular may be reduced following the approach first set out in Tangri et al with respect to erythropoietin and subsequently developed. Accordingly, directed evolution or rational design may be used to reduce the immunogenicity of the CRISPR enzyme (for instance a Cpf1) in the host species (human or other species).

Genome editing: The CRISPR/Cas (Cpf1) systems of the present invention can be used to correct genetic mutations that were previously attempted with limited success using TALEN and ZFN and lentiviruses, including as herein discussed; see also WO2013163628.

Treating Disease of the Brain, Central Nervous and Immune Systems

The present invention also contemplates delivering the CRISPR-Cas system to the brain or neurons. For example, RNA interference (RNAi) offers therapeutic potential for this disorder by reducing the expression of HTT, the disease-causing gene of Huntington's disease (see, e.g., McBride et al., Molecular Therapy vol. 19 no. 12 Dec. 2011, pp. 2152-2162), therefore Applicant postulates that it may be used/and or adapted to the CRISPR-Cas system. The CRISPR-Cas system may be generated using an algorithm to reduce the off-targeting potential of antisense sequences. The CRISPR-Cas sequences may target either a sequence in exon 52 of mouse, rhesus or human huntingtin and expressed in a viral vector, such as AAV. Animals, including humans, may be injected with about three microinjections per hemisphere (six injections total): the first 1 mm rostral to the anterior commissure (12 µl) and the two remaining injections (12 µl and 10 µl, respectively) spaced 3 and 6 mm caudal to the first injection with 1e12 vg/ml of AAV at a rate of about 1 µl/minute, and the needle was left in place for an additional 5 minutes to allow the injectate to diffuse from the needle tip.

DiFiglia et al. (PNAS, Oct. 23, 2007, vol. 104, no. 43, 17204-17209) observed that single administration into the adult striatum of an siRNA targeting Htt can silence mutant Htt, attenuate neuronal pathology, and delay the abnormal behavioral phenotype observed in a rapid-onset, viral transgenic mouse model of HD. DiFiglia injected mice intrastriatally with 2 µl of Cy3-labeled cc-siRNA-Htt or unconjugated siRNA-Htt at 10 µM. A similar dosage of CRISPR-Cas targeted to Htt may be contemplated for humans in the present invention, for example, about 5-10 ml of 10 µM CRISPR-Cas targeted to Htt may be injected intrastriatally.

In another example, Boudreau et al. (Molecular Therapy vol. 17 no. 6 Jun. 2009) injects 5 µl of recombinant AAV serotype 2/1 vectors expressing htt-specific RNAi virus (at 4×1012 viral genomes/ml) into the straiatum. A similar dosage of CRISPR-Cas targeted to Htt may be contemplated for humans in the present invention, for example, about 10-20 ml of 4×1012 viral genomes/ml) CRISPR-Cas targeted to Htt may be injected intrastriatally.

In another example, a CRISPR-Cas targeted to HTT may be administered continuously (see, e.g., Yu et al., Cell 150, 895-908, Aug. 31, 2012). Yu et al. utilizes osmotic pumps delivering 0.25 ml/hr (Model 2004) to deliver 300 mg/day of ss-siRNA or phosphate-buffered saline (PBS) (Sigma Aldrich) for 28 days, and pumps designed to deliver 0.5 µl/hr (Model 2002) were used to deliver 75 mg/day of the positive control MOE ASO for 14 days. Pumps (Durect Corporation) were filled with ss-siRNA or MOE diluted in sterile PBS and then incubated at 37 C for 24 or 48 (Model 2004) hours prior to implantation. Mice were anesthetized with 2.5% isofluorane, and a midline incision was made at the base of the skull. Using stereotaxic guides, a cannula was implanted into the right lateral ventricle and secured with Loctite adhesive. A catheter attached to an Alzet osmotic mini pump was attached to the cannula, and the pump was placed subcutaneously in the midscapular area. The incision was closed with 5.0 nylon sutures. A similar dosage of CRISPR-Cas targeted to Htt may be contemplated for humans in the present invention, for example, about 500 to 1000 g/day CRISPR-Cas targeted to Htt may be administered.

In another example of continuous infusion, Stiles et al. (Experimental Neurology 233 (2012) 463-471) implanted an intraparenchymal catheter with a titanium needle tip into the right putamen. The catheter was connected to a SynchroMed® II Pump (Medtronic Neurological, Minneapolis, Minn.) subcutaneously implanted in the abdomen. After a 7 day infusion of phosphate buffered saline at 6 4/day, pumps were re-filled with test article and programmed for continuous delivery for 7 days. About 2.3 to 11.52 mg/d of siRNA were infused at varying infusion rates of about 0.1 to 0.5 4/min. A similar dosage of CRISPR-Cas targeted to Htt may be contemplated for humans in the present invention, for example, about 20 to 200 mg/day CRISPR-Cas targeted to Htt may be administered. In another example, the methods of US Patent Publication No. 20130253040 assigned to Sangamo may also be also be adapted from TALES to the nucleic acid-targeting system of the present invention for treating Huntington's Disease.

In another example, the methods of US Patent Publication No. 20130253040 (WO2013130824) assigned to Sangamo may also be also be adapted from TALES to the CRISPR-Cas system of the present invention for treating Huntington's Disease.

WO2015089354 A1 in the name of The Broad Institute et al., hereby incorporated by reference, describes a targets for Huntington's Disease (HP). Possible target genes of CRISPR complex in regard to Huntington's Disease: PRKCE; IGF1; EP300; RCOR1; PRKCZ; HDAC4; and TGM2. Accordingly, one or more of PRKCE; IGF1; EP300; RCOR1; PRKCZ; HDAC4; and TGM2 may be selected as targets for Huntington's Disease in some embodiments of the present invention.

Other trinucleotide repeat disorders. These may include any of the following: Category I includes Huntington's disease (HD) and the spinocerebellar ataxias; Category II expansions are phenotypically diverse with heterogeneous expansions that are generally small in magnitude, but also found in the exons of genes; and Category III includes fragile X syndrome, myotonic dystrophy, two of the spinocerebellar ataxias, juvenile myoclonic epilepsy, and Friedreich's ataxia.

A further aspect of the invention relates to utilizing the CRISPR-Cas system for correcting defects in the EMP2A and EMP2B genes that have been identified to be associated with Lafora disease. Lafora disease is an autosomal recessive condition which is characterized by progressive myoclonus epilepsy which may start as epileptic seizures in adolescence. A few cases of the disease may be caused by mutations in genes yet to be identified. The disease causes seizures, muscle spasms, difficulty walking, dementia, and eventually death. There is currently no therapy that has proven effective against disease progression. Other genetic abnormalities associated with epilepsy may also be targeted by the CRISPR-Cas system and the underlying genetics is further described in Genetics of Epilepsy and Genetic Epilepsies, edited by Giuliano Avanzini, Jeffrey L. Noebels, Mariani Foundation Paediatric Neurology:20; 2009).

The methods of US Patent Publication No. 20110158957 assigned to Sangamo BioSciences, Inc. involved in inactivating T cell receptor (TCR) genes may also be modified to the CRISPR-Cas system of the present invention. In another example, the methods of US Patent Publication No. 20100311124 assigned to Sangamo BioSciences, Inc. and US Patent Publication No. 20110225664 assigned to Cellectis, which are both involved in inactivating glutamine synthetase gene expression genes may also be modified to the CRISPR-Cas system of the present invention.

Delivery options for the brain include encapsulation of CRISPR enzyme and guide RNA in the form of either DNA or RNA into liposomes and conjugating to molecular Trojan horses for trans-blood brain barrier (BBB) delivery. Molecular Trojan horses have been shown to be effective for delivery of B-gal expression vectors into the brain of non-human primates. The same approach can be used to delivery vectors containing CRISPR enzyme and guide RNA. For instance, Xia C F and Boado R J, Pardridge W M ("Antibody-mediated targeting of siRNA via the human insulin receptor using avidin-biotin technology." Mol Pharm. 2009 May-June; 6(3):747-51. doi: 10.1021/mp800194) describes how delivery of short interfering RNA (siRNA) to cells in culture, and in vivo, is possible with combined use of a receptor-specific monoclonal antibody (mAb) and avidin-biotin technology. The authors also report that because the bond between the targeting mAb and the siRNA is stable with avidin-biotin technology, and RNAi effects at distant sites such as brain are observed in vivo following an intravenous administration of the targeted siRNA.

Zhang et al. (Mol Ther. 2003 January; 7(1):11-8.)) describe how expression plasmids encoding reporters such as luciferase were encapsulated in the interior of an "artificial virus" comprised of an 85 nm pegylated immunoliposome, which was targeted to the rhesus monkey brain in vivo with a monoclonal antibody (MAb) to the human insulin receptor (HIR). The HIRMAb enables the liposome carrying the exogenous gene to undergo transcytosis across the blood-brain barrier and endocytosis across the neuronal plasma membrane following intravenous injection. The level of luciferase gene expression in the brain was 50-fold higher in the rhesus monkey as compared to the rat. Widespread neuronal expression of the beta-galactosidase gene in primate brain was demonstrated by both histochemistry and confocal microscopy. The authors indicate that this approach makes feasible reversible adult transgenics in 24 hours. Accordingly, the use of immunoliposome is preferred. These may be used in conjunction with antibodies to target specific tissues or cell surface proteins.

Alzheimer's Disease

US Patent Publication No. 20110023153, describes use of zinc finger nucleases to genetically modify cells, animals and proteins associated with Alzheimer's Disease. Once modified cells and animals may be further tested using known methods to study the effects of the targeted mutations on the development and/or progression of AD using measures commonly used in the study of AD—such as, without limitation, learning and memory, anxiety, depression, addiction, and sensory motor functions as well as assays that measure behavioral, functional, pathological, metaboloic and biochemical function.

The present disclosure comprises editing of any chromosomal sequences that encode proteins associated with AD.

The AD-related proteins are typically selected based on an experimental association of the AD-related protein to an AD disorder. For example, the production rate or circulating concentration of an AD-related protein may be elevated or depressed in a population having an AD disorder relative to a population lacking the AD disorder. Differences in protein levels may be assessed using proteomic techniques including but not limited to Western blot, immunohistochemical staining, enzyme linked immunosorbent assay (ELISA), and mass spectrometry. Alternatively, the AD-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Examples of Alzheimer's disease associated proteins may include the very low density lipoprotein receptor protein (VLDLR) encoded by the VLDLR gene, the ubiquitin-like modifier activating enzyme 1 (UBA1) encoded by the UBA1 gene, or the NEDD8-activating enzyme E1 catalytic subunit protein (UBE1C) encoded by the UBA3 gene, for example.

By way of non-limiting example, proteins associated with AD include but are not limited to the proteins listed as follows: Chromosomal Sequence Encoded Protein ALAS2 Delta-aminolevulinate synthase 2 (ALAS2) ABCA1 ATP-binding cassette transporter (ABCA1) ACE Angiotensin I-converting enzyme (ACE) APOE Apolipoprotein E precursor (APOE) APP amyloid precursor protein (APP) AQP1 aquaporin 1 protein (AQP1) BIN1 Myc box-dependent-interacting protein 1 or bridging integrator 1 protein (BIN1) BDNF brain-derived neurotrophic factor (BDNF) BTNL8 Butyrophilin-like protein 8 (BTNL8) C1ORF49 chromosome 1 open reading frame 49 CDH4 Cadherin-4 CHRNB2 Neuronal acetylcholine receptor subunit beta-2 CKLFSF2 CKLF-like MARVEL transmembrane domain-containing protein 2 (CKLFSF2) CLEC4E C-type lectin domain family 4, member e (CLEC4E) CLU clusterin protein (also known as apolipoprotein J) CR1 Erythrocyte complement receptor 1 (CR1, also known as CD35, C3b/C4b receptor and immune adherence receptor) CR1L Erythrocyte complement receptor 1 (CR1L) CSF3R granulocyte colony-stimulating factor 3 receptor (CSF3R) CST3 Cystatin C or cystatin 3 CYP2C Cytochrome P450 2C DAPK1 Death-associated protein kinase 1 (DAPK1) ESR1 Estrogen receptor 1 FCAR Fc fragment of IgA receptor (FCAR, also known as CD89) FCGR3B Fc fragment of IgG, low affinity IIIb, receptor (FCGR3B or CD16b) FFA2 Free fatty acid receptor 2 (FFA2) FGA Fibrinogen (Factor I) GAB2 GRB2-associated-binding protein 2 (GAB2) GAB2 GRB2-associated-binding protein 2 (GAB2) GALP Galanin-like peptide GAPDHS Glyceraldehyde-3-phosphate dehydrogenase, spermatogenic (GAPDHS) GMPB GMBP HP Haptoglobin (HP) HTR7 5-hydroxytryptamine (serotonin) receptor 7 (adenylate cyclase-coupled) IDE Insulin degrading enzyme IF127 IF127 IFI6 Interferon, alpha-inducible protein 6 (IFI6) IFIT2 Interferon-induced protein with tetratricopeptide repeats 2 (IFIT2) IL1RN interleukin-1 receptor antagonist (IL-IRA) IL8RA Interleukin 8 receptor, alpha (IL8RA or CD181) IL8RB Interleukin 8 receptor, beta (IL8RB) JAG1 Jagged 1 (JAG1) KCNJ15 Potassium inwardly-rectifying channel, subfamily J, member 15 (KCNJ15) LRP6 Low-density lipoprotein receptor-related protein 6 (LRP6) MAPT microtubule-associated protein tau (MAPT) MARK4 MAP/microtubule affinity-regulating kinase 4 (MARK4) MPHOSPH1 M-phase phosphoprotein 1 MTHFR 5,10-methylenetetrahydrofolate reductase MX2 Interferon-induced GTP-binding protein Mx2 NBN Nibrin, also known as NBN NCSTN Nicastrin NIACR2 Niacin receptor 2 (NIACR2, also known as GPR109B) NMNAT3 nicotinamide nucleotide adenylyltransferase 3 NTM Neurotrimin (or HNT) ORM1 Orosomucoid 1 (ORM1) or Alpha-1-acid glycoprotein 1 P2RY13 P2Y purinoceptor 13 (P2RY13) PBEF1 Nicotinamide phosphoribosyltransferase (NAmPRTase or Nampt) also known as pre-B-cell colony-enhancing factor 1 (PBEF1) or visfatin PCK1 Phosphoenolpyruvate carboxykinase PICALM phosphatidylinositol binding clathrin assembly protein (PICALM) PLAU Urokinase-type plasminogen activator (PLAU) PLXNC1 Plexin C1 (PLXNC1) PRNP Prion protein PSEN1 presenilin 1 protein (PSEN1) PSEN2 presenilin 2 protein (PSEN2) PTPRA protein tyrosine phosphatase receptor type A protein (PTPRA) RALGPS2 Ral GEF with PH domain and SH3 binding motif 2 (RALGPS2) RGSL2 regulator of G-protein signaling like 2 (RGSL2) SELENBP1 Selenium binding protein 1 (SELENBP1) SLC25A37 Mitoferrin-1 SORL1 sortilin-related receptor L(DLR class) A repeats-containing protein (SORL1) TF Transferrin TFAM Mitochondrial transcription factor A TNF Tumor necrosis factor TNFRSF10C Tumor necrosis factor receptor superfamily member 10C (TNFRSF10C) TNFSF10 Tumor necrosis factor receptor superfamily, (TRAIL) member 10a (TNFSF10) UBA1 ubiquitin-like modifier activating enzyme 1 (UBA1) UBA3 NEDD8-activating enzyme E1 catalytic subunit protein (UBE1C) UBB ubiquitin B protein (UBB) UBQLN1 Ubiquilin-1 UCHL1 ubiquitin carboxyl-terminal esterase L1 protein (UCHL1) UCHL3 ubiquitin carboxyl-terminal hydrolase isozyme L3 protein (UCHL3) VLDLR very low density lipoprotein receptor protein (VLDLR).

In exemplary embodiments, the proteins associated with AD whose chromosomal sequence is edited may be the very low density lipoprotein receptor protein (VLDLR) encoded by the VLDLR gene, the ubiquitin-like modifier activating enzyme 1 (UBA1) encoded by the UBA1 gene, the NEDD8-activating enzyme E1 catalytic subunit protein (UBE1C) encoded by the UBA3 gene, the aquaporin 1 protein (AQP1) encoded by the AQP1 gene, the ubiquitin carboxyl-terminal esterase L1 protein (UCHL1) encoded by the UCHL1 gene, the ubiquitin carboxyl-terminal hydrolase isozyme L3 protein (UCHL3) encoded by the UCHL3 gene, the ubiquitin B protein (UBB) encoded by the UBB gene, the microtubule-associated protein tau (MAPT) encoded by the MAPT gene, the protein tyrosine phosphatase receptor type A protein (PTPRA) encoded by the PTPRA gene, the phosphatidylinositol binding clathrin assembly protein (PICALM) encoded by the PICALM gene, the clusterin protein (also known as apolipoprotein J) encoded by the CLU gene, the presenilin 1 protein encoded by the PSEN1 gene, the presenilin 2 protein encoded by the PSEN2 gene, the sortilin-related receptor L(DLR class) A repeats-containing protein (SORL1) protein encoded by the SORL1 gene, the amyloid precursor protein (APP) encoded by the APP gene, the Apolipoprotein E precursor (APOE) encoded by the APOE gene, or the brain-derived neurotrophic factor (BDNF) encoded by the BDNF gene. In an exemplary embodiment, the genetically modified animal is a rat, and the edited chromosomal sequence encoding the protein associated with AD is as follows: APP amyloid precursor protein (APP) NM_019288 AQP1 aquaporin 1 protein (AQP1) NM_012778 BDNF Brain-derived neurotrophic factor NM_012513 CLU clusterin protein (also known as NM_053021 apolipoprotein J) MAPT microtubule-associated protein NM_017212 tau (MAPT) PICALM phosphatidylinositol binding NM_053554 clathrin assembly protein (PICALM) PSEN1 presenilin 1 protein (PSEN1)

NM_019163 PSEN2 presenilin 2 protein (PSEN2) NM_031087 PTPRA protein tyrosine phosphatase NM_012763 receptor type A protein (PTPRA) SORL1 sortilin-related receptor L(DLR NM_053519, class) A repeats-containing XM_001065506, protein (SORL1) XM_217115 UBA1 ubiquitin-like modifier activating NM_001014080 enzyme 1 (UBA1) UBA3 NEDD8-activating enzyme E1 NM_057205 catalytic subunit protein (UBE1C) UBB ubiquitin B protein (UBB) NM_138895 UCHL1 ubiquitin carboxyl-terminal NM_017237 esterase L1 protein (UCHL1) UCHL3 ubiquitin carboxyl-terminal NM_001110165 hydrolase isozyme L3 protein (UCHL3) VLDLR very low density lipoprotein NM_013155 receptor protein (VLDLR)

The animal or cell may comprise 1, 2, 3, 4, 5, 6, 7, 8, 9, 10, 11, 12, 13, 14, 15 or more disrupted chromosomal sequences encoding a protein associated with AD and zero, 1, 2, 3, 4, 5, 6, 7, 8, 9, 10, 11, 12, 13, 14, 15 or more chromosomally integrated sequences encoding a protein associated with AD.

The edited or integrated chromosomal sequence may be modified to encode an altered protein associated with AD. A number of mutations in AD-related chromosomal sequences have been associated with AD. For instance, the V717I (i.e. valine at position 717 is changed to isoleucine) missense mutation in APP causes familial AD. Multiple mutations in the presenilin-1 protein, such as H163R (i.e. histidine at position 163 is changed to arginine), A246E (i.e. alanine at position 246 is changed to glutamate), L286V (i.e. leucine at position 286 is changed to valine) and C410Y (i.e. cysteine at position 410 is changed to tyrosine) cause familial Alzheimer's type 3. Mutations in the presenilin-2 protein, such as N141 I (i.e. asparagine at position 141 is changed to isoleucine), M239V (i.e. methionine at position 239 is changed to valine), and D439A (i.e. aspartate at position 439 is changed to alanine) cause familial Alzheimer's type 4. Other associations of genetic variants in AD-associated genes and disease are known in the art. See, for example, Waring et al. (2008) Arch. Neurol. 65:329-334, the disclosure of which is incorporated by reference herein in its entirety.

Secretase Disorders

US Patent Publication No. 20110023146, describes use of zinc finger nucleases to genetically modify cells, animals and proteins associated with secretase-associated disorders. Secretases are essential for processing pre-proteins into their biologically active forms. Defects in various components of the secretase pathways contribute to many disorders, particularly those with hallmark amyloidogenesis or amyloid plaques, such as Alzheimer's disease (AD).

A secretase disorder and the proteins associated with these disorders are a diverse set of proteins that effect susceptibility for numerous disorders, the presence of the disorder, the severity of the disorder, or any combination thereof. The present disclosure comprises editing of any chromosomal sequences that encode proteins associated with a secretase disorder. The proteins associated with a secretase disorder are typically selected based on an experimental association of the secretase—related proteins with the development of a secretase disorder. For example, the production rate or circulating concentration of a protein associated with a secretase disorder may be elevated or depressed in a population with a secretase disorder relative to a population without a secretase disorder. Differences in protein levels may be assessed using proteomic techniques including but not limited to Western blot, immunohistochemical staining, enzyme linked immunosorbent assay (ELISA), and mass spectrometry. Alternatively, the protein associated with a secretase disorder may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with a secretase disorder include PSENEN (presenilin enhancer 2 homolog (*C. elegans*)), CTSB (cathepsin B), PSEN1 (presenilin 1), APP (amyloid beta (A4) precursor protein), APH1B (anterior pharynx defective 1 homolog B (*C. elegans*)), PSEN2 (presenilin 2 (Alzheimer disease 4)), BACE1 (beta-site APP-cleaving enzyme 1), ITM2B (integral membrane protein 2B), CTSD (cathepsin D), NOTCH1 (Notch homolog 1, translocation-associated (*Drosophila*)), TNF (tumor necrosis factor (TNF superfamily, member 2)), INS (insulin), DYT10 (dystonia 10), ADAM17 (ADAM metallopeptidase domain 17), APOE (apolipoprotein E), ACE (angiotensin I converting enzyme (peptidyl-dipeptidase A) 1), STN (statin), TP53 (tumor protein p53), IL6 (interleukin 6 (interferon, beta 2)), NGFR (nerve growth factor receptor (TNFR superfamily, member 16)), IL1B (interleukin 1, beta), ACHE (acetylcholinesterase (Yt blood group)), CTNNB1 (catenin (cadherin-associated protein), beta 1, 88 kDa), IGF1 (insulin-like growth factor 1 (somatomedin C)), IFNG (interferon, gamma), NRG1 (neuregulin 1), CASP3 (caspase 3, apoptosis-related cysteine peptidase), MAPK1 (mitogen-activated protein kinase 1), CDH1 (cadherin 1, type 1, E-cadherin (epithelial)), APBB1 (amyloid beta (A4) precursor protein-binding, family B, member 1 (Fe65)), HMGCR (3-hydroxy-3-methylglutaryl-Coenzyme A reductase), CREB1 (cAMP responsive element binding protein 1), PTGS2 (prostaglandin-endoperoxide synthase 2 (prostaglandin G/H synthase and cyclooxygenase)), HES1 (hairy and enhancer of split 1, (*Drosophila*)), CAT (catalase), TGFB1 (transforming growth factor, beta 1), ENO2 (enolase 2 (gamma, neuronal)), ERBB4 (v-erb-a erythroblastic leukemia viral oncogene homolog 4 (avian)), TRAPPC10 (trafficking protein particle complex 10), MAOB (monoamine oxidase B), NGF (nerve growth factor (beta polypeptide)), MMP12 (matrix metallopeptidase 12 (macrophage elastase)), JAG1 (jagged 1 (Alagille syndrome)), CD40LG (CD40 ligand), PPARG (peroxisome proliferator-activated receptor gamma), FGF2 (fibroblast growth factor 2 (basic)), IL3 (interleukin 3 (colony-stimulating factor, multiple)), LRP1 (low density lipoprotein receptor-related protein 1), NOTCH4 (Notch homolog 4 (*Drosophila*)), MAPK8 (mitogen-activated protein kinase 8), PREP (prolyl endopeptidase), NOTCH3 (Notch homolog 3 (*Drosophila*)), PRNP (prion protein), CTSG (cathepsin G), EGF (epidermal growth factor (beta-urogastrone)), REN (renin), CD44 (CD44 molecule (Indian blood group)), SELP (selectin P (granule membrane protein 140 kDa, antigen CD62)), GHR (growth hormone receptor), ADCYAP1 (adenylate cyclase activating polypeptide 1 (pituitary)), INSR (insulin receptor), GFAP (glial fibrillary acidic protein), MMP3 (matrix metallopeptidase 3 (stromelysin 1, progelatinase)), MAPK10 (mitogen-activated protein kinase 10), SP1 (Sp1 transcription factor), MYC (v-myc myelocytomatosis viral oncogene homolog (avian)), CTSE (cathepsin E), PPARA (peroxisome proliferator-activated receptor alpha), JUN (jun oncogene), TIMP1 (TIMP metallopeptidase inhibitor 1), IL5 (interleukin 5 (colony-stimulating factor, eosinophil)), IL1A (interleukin 1, alpha), MMP9 (matrix metallopeptidase 9 (gelatinase B, 92 kDa gelatinase, 92 kDa type IV collagenase)), HTR4 (5-hydroxytryptamine (serotonin) receptor 4), HSPG2 (heparan sulfate proteoglycan 2), KRAS (v-Ki-ras2 Kirsten rat sarcoma viral oncogene homolog), CYCS (cytochrome c, somatic), SMG1 (SMG1 homolog, phosphatidylinositol 3-kinase-related kinase (*C. elegans*)), IL1R1 (interleukin 1 receptor, type I), PROK1 (prokineticin 1), MAPK3 (mitogen-activated protein kinase 3), NTRK1 (neurotrophic tyrosine kinase, receptor, type 1), IL13 (interleukin 13), MME (membrane metallo-endopeptidase), TKT (transketolase), CXCR2 (chemokine (C-X-C motif) receptor 2), IGF1R (insulin-like growth factor 1 receptor), RARA (retinoic acid receptor, alpha), CREBBP (CREB binding protein), PTGS1 (prostaglandin-endoperoxide synthase 1 (prostaglandin G/H synthase and cyclooxygenase)), GALT (galactose-1-phosphate uridylyltransferase), CHRM1 (cholinergic receptor, muscarinic 1), ATXN1 (ataxin 1), PAWR (PRKC, apoptosis, WT1, regulator), NOTCH2 (Notch homolog 2 (*Drosophila*)), M6PR (mannose-6-phosphate receptor (cation dependent)), CYP46A1 (cytochrome P450, family 46, subfamily A, polypeptide 1), CSNK1 D (casein kinase 1, delta), MAPK14 (mitogen-activated protein kinase 14), PRG2 (proteoglycan 2, bone marrow (natural killer cell activator, eosinophil granule major basic protein)), PRKCA (protein kinase C, alpha), L1 CAM (L1 cell adhesion molecule), CD40 (CD40 molecule, TNF receptor superfamily member 5), NR112 (nuclear receptor subfamily 1, group I, member 2), JAG2 (jagged 2), CTNND1 (catenin (cadherin-associated protein), delta 1), CDH2 (cadherin 2, type 1, N-cadherin (neuronal)), CMA1 (chymase 1, mast cell), SORT1 (sortilin 1), DLK1 (delta-like 1 homolog (*Drosophila*)), THEM4 (thioesterase superfamily member 4), JUP (junction plakoglobin), CD46 (CD46 molecule, complement regulatory protein), CCL11 (chemokine (C-C motif) ligand 11), CAV3 (caveolin 3), RNASE3 (ribonuclease, RNase A family, 3 (eosinophil cationic protein)), HSPA8 (heat shock 70 kDa protein 8), CASP9 (caspase 9, apoptosis-related cysteine peptidase), CYP3A4 (cytochrome P450, family 3, subfamily A, polypeptide 4), CCR3 (chemokine (C-C motif) receptor 3), TFAP2A (transcription factor AP-2 alpha (activating enhancer binding protein 2 alpha)), SCP2 (sterol carrier protein 2), CDK4 (cyclin-dependent kinase 4), HIF1A (hypoxia inducible factor 1, alpha subunit (basic helix-loop-helix transcription factor)), TCF7L2 (transcription factor 7-like 2 (T-cell specific, HMG-box)), IL1R2 (interleukin 1 receptor, type II), B3GALTL (beta 1,3-galactosyltransferase-like), MDM2 (Mdm2 p53 binding protein homolog (mouse)), RELA (v-rel reticuloendotheliosis viral oncogene homolog A (avian)), CASP7 (caspase 7, apoptosis-related cysteine peptidase), IDE (insulin-degrading enzyme), FABP4 (fatty acid binding protein 4, adipocyte), CASK (calcium/calmodulin-dependent serine protein kinase (MAGUK family)), ADCYAP1R1 (adenylate cyclase activating polypeptide 1 (pituitary) receptor type I), ATF4 (activating transcription factor 4 (tax-responsive enhancer element B67)), PDGFA (platelet-derived growth factor alpha polypeptide), C21 or f33 (chromosome 21 open reading frame 33), SCGS (secretogranin V (7B2 protein)), RNF123 (ring finger protein 123), NFKB1 (nuclear factor of kappa light polypeptide gene enhancer in B-cells 1), ERBB2 (v-erb-b2 erythroblastic leukemia viral oncogene homolog 2, neuro/glioblastoma derived oncogene homolog (avian)), CAV1 (caveolin 1, caveolae protein, 22 kDa), MMP7 (matrix metallopeptidase 7 (matrilysin, uterine)), TGFA (transforming growth factor, alpha), RXRA (retinoid X receptor, alpha), STX1A (syntaxin 1A (brain)), PSMC4 (proteasome (prosome, macropain) 26S subunit, ATPase, 4), P2RY2 (purinergic receptor P2Y, G-protein coupled, 2), TNFRSF21 (tumor necrosis factor receptor superfamily, member 21), DLG1 (discs, large homolog 1 (*Drosophila*)), NUMBL (numb homolog (*Drosophila*)-like), SPN (sialophorin), PLSCR1 (phospholipid scramblase 1), UBQLN2 (ubiquilin 2), UBQLN1 (ubiquilin 1), PCSK7 (proprotein convertase subtilisin/kexin type 7), SPON1 (spondin 1, extracellular matrix protein), SILV (silver homolog (mouse)), QPCT (glutaminyl-peptide cyclotransferase), HESS (hairy and enhancer of split 5 (*Drosophila*)), GCC1 (GRIP and coiled-coil domain containing 1), and any combination thereof.

The genetically modified animal or cell may comprise 1, 2, 3, 4, 5, 6, 7, 8, 9, 10 or more disrupted chromosomal sequences encoding a protein associated with a secretase disorder and zero, 1, 2, 3, 4, 5, 6, 7, 8, 9, 10 or more chromosomally integrated sequences encoding a disrupted protein associated with a secretase disorder.

ALS

US Patent Publication No. 20110023144, describes use of zinc finger nucleases to genetically modify cells, animals and proteins associated with amyotrophic lateral sclerosis (ALS) disease. ALS is characterized by the gradual steady degeneration of certain nerve cells in the brain cortex, brain stem, and spinal cord involved in voluntary movement.

Motor neuron disorders and the proteins associated with these disorders are a diverse set of proteins that effect susceptibility for developing a motor neuron disorder, the presence of the motor neuron disorder, the severity of the motor neuron disorder or any combination thereof. The present disclosure comprises editing of any chromosomal sequences that encode proteins associated with ALS disease, a specific motor neuron disorder. The proteins associated with ALS are typically selected based on an experimental association of ALS—related proteins to ALS. For example, the production rate or circulating concentration of a protein associated with ALS may be elevated or depressed in a population with ALS relative to a population without ALS. Differences in protein levels may be assessed using proteomic techniques including but not limited to Western blot, immunohistochemical staining, enzyme linked immunosorbent assay (ELISA), and mass spectrometry. Alternatively, the proteins associated with ALS may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with ALS include but are not limited to the following proteins: SOD1 superoxide dismutase 1, ALS3 amyotrophic lateral soluble sclerosis 3 SETX senataxin ALSS amyotrophic lateral sclerosis 5 FUS fused in sarcoma ALS7 amyotrophic lateral sclerosis 7 ALS2 amyotrophic lateral DPP6 Dipeptidyl-peptidase 6 sclerosis 2 NEFH neurofilament, heavy PTGS1 prostaglandin-polypeptide endoperoxide synthase 1 SLC1A2 solute carrier family 1 TNFRSF10B tumor necrosis factor (glial high affinity receptor superfamily, glutamate transporter), member 10b member 2 PRPH peripherin HSP90AA1 heat shock protein 90 kDa alpha (cytosolic), class A member 1 GRIA2 glutamate receptor, IFNG interferon, gamma ionotropic, AMPA 2 S100B S100 calcium binding FGF2 fibroblast growth factor 2 protein B AOX1 aldehyde oxidase 1 CS citrate synthase TARDBP TAR DNA binding protein TXN thioredoxin RAPH1 Ras association MAP3K5 mitogen-activated protein (RaIGDS/AF-6) and kinase 5 pleckstrin homology domains 1 NBEAL1 neurobeachin-like 1 GPX1 glutathione peroxidase 1 ICA 1L islet cell autoantigen RAC1 ras-related C3 botulinum 1.69 kDa-like toxin substrate 1 MAPT microtubule-associated ITPR2 inositol 1,4,5-protein tau triphosphate receptor, type 2

ALS2CR4 amyotrophic lateral sclerosis 2 (juvenile) chromosome region, candidate 4 ALS2CR8 amyotrophic lateral sclerosis 2 (juvenile) chromosome region, candidate 8 ALS2CR11 amyotrophic lateral sclerosis 2 (juvenile) chromosome region, candidate 11 FAM117B family with sequence similarity 117, member B CNTF ciliary neurotrophic factor SQSTM1 sequestosome 1 STRADB STE20-related kinase NAIP NLR family, apoptosis adaptor beta inhibitory protein YWHAQ tyrosine 3-SLC33A1 solute carrier family 33 monooxygenase/tryptophan (acetyl-CoA transporter), an 5-monooxygenase member 1 activation protein, theta polypeptide TRAK2 trafficking protein, homolog, SAC1 kinesin binding 2 lipid phosphatase domain containing NIF3L1 NIF3 NGG1 interacting INA internexin neuronal factor 3-like 1 intermediate filament protein, alpha PARD3B par-3 partitioning COX8A cytochrome c oxidase defective 3 homolog B subunit VIIIA CDK15 cyclin-dependent kinase HECW1 HECT, C2 and WW 15 domain containing E3 ubiquitin protein ligase 1 NOS1 nitric oxide synthase 1 MET met proto-oncogene SOD2 superoxide dismutase 2, HSPB1 heat shock 27 kDa mitochondrial protein 1 NEFL neurofilament, light CTSB cathepsin B polypeptide ANG angiogenin, HSPA8 heat shock 70 kDa ribonuclease, RNase A protein 8 family, 5 VAPB VAMP (vesicle-ESR1 estrogen receptor 1 associated membrane protein)-associated protein B and C SNCA synuclein, alpha HGF hepatocyte growth factor CAT catalase ACTB actin, beta NEFM neurofilament, medium TH tyrosine hydroxylase polypeptide BCL2 B-cell CLL/lymphoma 2 FAS Fas (TNF receptor superfamily, member 6) CASP3 caspase 3, apoptosis-CLU clusterin related cysteine peptidase SMN1 survival of motor neuron G6PD glucose-6-phosphate 1, telomeric dehydrogenase BAX BCL2-associated X HSF1 heat shock transcription protein factor 1 RNF19A ring finger protein 19A JUN jun oncogene ALS2CR12 amyotrophic lateral HSPA5 heat shock 70 kDa sclerosis 2 (juvenile) protein 5 chromosome region, candidate 12 MAPK14 mitogen-activated protein IL10 interleukin 10 kinase 14 APEX1 APEX nuclease TXNRD1 thioredoxin reductase 1 (multifunctional DNA repair enzyme) 1 NOS2 nitric oxide synthase 2, TIMP1 TIMP metallopeptidase inducible inhibitor 1 CASP9 caspase 9, apoptosis-XIAP X-linked inhibitor of related cysteine apoptosis peptidase GLG1 golgi glycoprotein 1 EPO erythropoietin VEGFA vascular endothelial ELN elastin growth factor A GDNF glial cell derived NFE2L2 nuclear factor (erythroid-neurotrophic factor derived 2)-like 2 SLC6A3 solute carrier family 6 HSPA4 heat shock 70 kDa (neurotransmitter protein 4 transporter, dopamine), member 3 APOE apolipoprotein E PSMB8 proteasome (prosome, macropain) subunit, beta type, 8 DCTN1 dynactin 1 TIMP3 TIMP metallopeptidase inhibitor 3 KIFAP3 kinesin-associated SLC1A1 solute carrier family 1 protein 3 (neuronal/epithelial high affinity glutamate transporter, system Xag), member 1 SMN2 survival of motor neuron CCNC cyclin C 2, centromeric MPP4 membrane protein, STUB1 STIP1 homology and U-palmitoylated 4 box containing protein 1 ALS2 amyloid beta (A4) PRDX6 peroxiredoxin 6 precursor protein SYP synaptophysin CABIN' calcineurin binding protein 1 CASP1 caspase 1, apoptosis-GART phosphoribosylglycinamide related cysteine de formyltransferase, peptidase phosphoribosylglycinamide synthetase, phosphoribosylaminoimidazole synthetase CDK5 cyclin-dependent kinase 5 ATXN3 ataxin 3 RTN4 reticulon 4 C 1QB complement component 1, q subcomponent, B chain VEGFC nerve growth factor HTT huntingtin receptor PARK? Parkinson disease 7 XDH xanthine dehydrogenase GFAP glial fibrillary acidic MAP2 microtubule-associated protein 2 CYCS cytochrome c, somatic FCGR3B Fc fragment of IgG, low affinity IIIb, CCS copper chaperone for UBL5 ubiquitin-like 5 superoxide dismutase MMP9 matrix metallopeptidase SLC18A3 solute carrier family 18 9 ((vesicular acetylcholine), member 3 TRPM7 transient receptor HSPB2 heat shock 27 kDa potential cation channel, protein 2 subfamily M, member 7 AKT1 v-akt murine thymoma DERL1 Derl-like domain family, viral oncogene homolog 1 member 1 CCL2 chemokine (C-C motif) NGRN neugrin, neurite ligand 2 outgrowth associated GSR glutathione reductase TPPP3 tubulin polymerization-promoting protein family member 3 APAF1 apoptotic peptidase BTBD10 BTB (POZ) domain activating factor 1 containing 10 GLUD1 glutamate CXCR4 chemokine (C-X-C motif) dehydrogenase 1 receptor 4 SLC1A3 solute carrier family 1 FLT1 fms-related tyrosine (glial high affinity glutamate transporter), member 3 kinase 1 PON1 paraoxonase 1 AR androgen receptor LIF leukemia inhibitory factor ERBB3 v-erb-b2 erythroblastic leukemia viral oncogene homolog 3 LGALS1 lectin, galactoside-CD44 CD44 molecule binding, soluble, 1 TP53 tumor protein p53 TLR3 toll-like receptor 3 GRIA1 glutamate receptor, GAPDH glyceraldehyde-3-ionotropic, AMPA 1 phosphate dehydrogenase GRIK1 glutamate receptor, DES desmin ionotropic, kainate 1 CHAT choline acetyltransferase FLT4 fms-related tyrosine kinase 4 CHMP2B chromatin modifying BAG1 BCL2-associated protein 2B athanogene MT3 metallothionein 3 CHRNA4 cholinergic receptor, nicotinic, alpha 4 GSS glutathione synthetase BAK1 BCL2-antagonist/killer 1 KDR kinase insert domain GSTP1 glutathione 5-transferase receptor (a type III pi 1 receptor tyrosine kinase) OGG1 8-oxoguanine DNA IL6 interleukin 6 (interferon, glycosylase beta 2).

The animal or cell may comprise 1, 2, 3, 4, 5, 6, 7, 8, 9, 10 or more disrupted chromosomal sequences encoding a protein associated with ALS and zero, 1, 2, 3, 4, 5, 6, 7, 8, 9, 10 or more chromosomally integrated sequences encoding the disrupted protein associated with ALS. Preferred proteins associated with ALS include SOD1 (superoxide dismutase 1), ALS2 (amyotrophic lateral sclerosis 2), FUS (fused in sarcoma), TARDBP (TAR DNA binding protein), VAGFA (vascular endothelial growth factor A), VAGFB (vascular endothelial growth factor B), and VAGFC (vascular endothelial growth factor C), and any combination thereof.

Autism

US Patent Publication No. 20110023145, describes use of zinc finger nucleases to genetically modify cells, animals and proteins associated with autism spectrum disorders (ASD). Autism spectrum disorders (ASDs) are a group of disorders characterized by qualitative impairment in social interaction and communication, and restricted repetitive and stereotyped patterns of behavior, interests, and activities. The three disorders, autism, Asperger syndrome (AS) and pervasive developmental disorder-not otherwise specified (PDD-NOS) are a continuum of the same disorder with varying degrees of severity, associated intellectual functioning and medical conditions. ASDs are predominantly genetically determined disorders with a heritability of around 90%.

US Patent Publication No. 20110023145 comprises editing of any chromosomal sequences that encode proteins associated with ASD which may be applied to the CRISPR-Cas system of the present invention. The proteins associated with ASD are typically selected based on an experimental association of the protein associated with ASD to an incidence or indication of an ASD. For example, the production rate or circulating concentration of a protein associated with ASD may be elevated or depressed in a population having an ASD relative to a population lacking the ASD. Differences in protein levels may be assessed using proteomic techniques including but not limited to Western blot, immunohistochemical staining, enzyme linked immunosorbent assay (ELISA), and mass spectrometry. Alternatively, the proteins associated with ASD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Non limiting examples of disease states or disorders that may be associated with proteins associated with ASD include autism, Asperger syndrome (AS), pervasive developmental disorder-not otherwise specified (PDD-NOS), Rett's syndrome, tuberous sclerosis, phenylketonuria, Smith-Lemli-Opitz syndrome and fragile X syndrome. By way of non-limiting example, proteins associated with ASD include but are not limited to the following proteins: ATP10C aminophospholipid-MET MET receptor transporting ATPase tyrosine kinase (ATP10C) BZRAP1 MGLUR5 (GRM5) Metabotropic glutamate receptor 5 (MGLUR5) CDH10 Cadherin-10 MGLUR6 (GRM6) Metabotropic glutamate receptor 6 (MGLUR6) CDH9 Cadherin-9 NLGN1 Neuroligin-1 CNTN4 Contactin-4 NLGN2 Neuroligin-2 CNTNAP2 Contactin-associated SEMA5A Neuroligin-3 protein-like 2 (CNTNAP2) DHCR7 7-dehydrocholesterol NLGN4X Neuroligin-4 X-reductase (DHCR7) linked DOC2A Double C2-like domain-NLGN4Y Neuroligin-4 Y-containing protein alpha linked DPP6 Dipeptidyl NLGN5 Neuroligin-5 aminopeptidase-like protein 6 EN2 engrailed 2 (EN2) NRCAM Neuronal cell adhesion molecule (NR-CAM) MDGA2 fragile X mental retardation NRXN1 Neurexin-1 1 (MDGA2) FMR2 (AFF2) AF4/FMR2 family member 2 OR4M2 Olfactory receptor (AFF2) 4M2 FOXP2 Forkhead box protein P2 OR4N4 Olfactory receptor (FOXP2) 4N4 FXR1 Fragile X mental OXTR oxytocin receptor retardation, autosomal (OXTR) homolog 1 (FXR1) FXR2 Fragile X mental PAH phenylalanine retardation, autosomal hydroxylase (PAH) homolog 2 (FXR2) GABRA1 Gamma-aminobutyric acid PTEN Phosphatase and receptor subunit alpha-1 tensin homologue (GABRA1) (PTEN) GABRA5 GABAA (.gamma.-aminobutyric PTPRZ1 Receptor-type acid) receptor alpha 5 tyrosine-protein subunit (GABRA5) phosphatase zeta (PTPRZ1) GABRB1 Gamma-aminobutyric acid RELN Reelin receptor subunit beta-1 (GABRB1) GABRB3 GABAA (.gamma.-aminobutyric RPL10 60S ribosomal acid) receptor.beta.3 subunit protein L10 (GABRB3) GABRG1 Gamma-aminobutyric acid SEMA5A Semaphorin-5A receptor subunit gamma-1 (SEMA5A) (GABRG1) HIRIP3 HIRA-interacting protein 3 SEZ6L2 seizure related 6 homolog (mouse)-like 2 HOXA1 Homeobox protein Hox-A 1 SHANK3 SH3 and multiple (HOXA1) ankyrin repeat domains 3 (SHANK3) IL6 Interleukin-6 SHBZRAP1 SH3 and multiple ankyrin repeat domains 3 (SHBZRAP1) LAMB1 Laminin subunit beta-1 SLC6A4 Serotonin (LAMB1) transporter (SERT) MAPK3 Mitogen-activated protein TAS2R1 Taste receptor kinase 3 type 2 member 1 TAS2R1 MAZ Myc-associated zinc finger TSC1 Tuberous sclerosis protein 1 MDGA2 MAM domain containing TSC2 Tuberous sclerosis glycosylphosphatidylinositol protein 2 anchor 2 (MDGA2) MECP2 Methyl CpG binding UBE3A Ubiquitin protein 2 (MECP2) ligase E3A (UBE3A) MECP2 methyl CpG binding WNT2 Wingless-type protein 2 (MECP2) MMTV integration site family, member 2 (WNT2)

The identity of the protein associated with ASD whose chromosomal sequence is edited can and will vary. In preferred embodiments, the proteins associated with ASD whose chromosomal sequence is edited may be the benzodiazapine receptor (peripheral) associated protein 1 (BZ-RAP1) encoded by the BZRAP1 gene, the AF4/FMR2 family member 2 protein (AFF2) encoded by the AFF2 gene (also termed MFR2), the fragile X mental retardation autosomal homolog 1 protein (FXR1) encoded by the FXR1 gene, the fragile X mental retardation autosomal homolog 2 protein (FXR2) encoded by the FXR2 gene, the MAM domain containing glycosylphosphatidylinositol anchor 2 protein (MDGA2) encoded by the MDGA2 gene, the methyl CpG binding protein 2 (MECP2) encoded by the MECP2 gene, the metabotropic glutamate receptor 5 (MGLUR5) encoded by the MGLUR5-1 gene (also termed GRM5), the neurexin 1 protein encoded by the NRXN1 gene, or the semaphorin-5A protein (SEMA5A) encoded by the SEMA5A gene. In an exemplary embodiment, the genetically modified animal is a rat, and the edited chromosomal sequence encoding the protein associated with ASD is as listed below: BZRAP1 benzodiazapine receptor XM_002727789, (peripheral) associated XM_213427, protein 1 (BZRAP1) XM_002724533, XM_001081125 AFF2 (FMR2) AF4/FMR2 family member 2 XM_219832, (AFF2) XM_001054673 FXR1 Fragile X mental NM_001012179 retardation, autosomal homolog 1 (FXR1) FXR2 Fragile X mental NM_001100647 retardation, autosomal homolog 2 (FXR2) MDGA2 MAM domain containing NM_199269 glycosylphosphatidylinositol anchor 2 (MDGA2) MECP2 Methyl CpG binding NM_022673 protein 2 (MECP2) MGLUR5 Metabotropic glutamate NM_017012 (GRM5) receptor 5 (MGLUR5) NRXN1 Neurexin-1 NM_021767 SEMA5A Semaphorin-5A (SEMA5A) NM_001107659.

Trinucleotide Repeat Expansion Disorders

US Patent Publication No. 20110016540, describes use of zinc finger nucleases to genetically modify cells, animals and proteins associated with trinucleotide repeat expansion disorders. Trinucleotide repeat expansion disorders are complex, progressive disorders that involve developmental neurobiology and often affect cognition as well as sensori-motor functions.

Trinucleotide repeat expansion proteins are a diverse set of proteins associated with susceptibility for developing a trinucleotide repeat expansion disorder, the presence of a trinucleotide repeat expansion disorder, the severity of a trinucleotide repeat expansion disorder or any combination thereof. Trinucleotide repeat expansion disorders are divided into two categories determined by the type of repeat. The most common repeat is the triplet CAG, which, when present in the coding region of a gene, codes for the amino acid glutamine (Q). Therefore, these disorders are referred to as the polyglutamine (polyQ) disorders and comprise the following diseases: Huntington Disease (HD); Spinobulbar Muscular Atrophy (SBMA); Spinocerebellar Ataxias (SCA types 1, 2, 3, 6, 7, and 17); and Dentatorubro-Pallidoluysian Atrophy (DRPLA). The remaining trinucleotide repeat expansion disorders either do not involve the CAG triplet or the CAG triplet is not in the coding region of the gene and are, therefore, referred to as the non-polyglutamine disorders. The non-polyglutamine disorders comprise Fragile X Syndrome (FRAXA); Fragile XE Mental Retardation (FRAXE); Friedreich Ataxia (FRDA); Myotonic Dystrophy (DM); and Spinocerebellar Ataxias (SCA types 8, and 12).

The proteins associated with trinucleotide repeat expansion disorders are typically selected based on an experimental association of the protein associated with a trinucleotide repeat expansion disorder to a trinucleotide repeat expansion disorder. For example, the production rate or circulating concentration of a protein associated with a trinucleotide repeat expansion disorder may be elevated or depressed in a population having a trinucleotide repeat expansion disorder relative to a population lacking the trinucleotide repeat expansion disorder. Differences in protein levels may be assessed using proteomic techniques including but not limited to Western blot, immunohistochemical staining, enzyme linked immunosorbent assay (ELISA), and mass spectrometry. Alternatively, the proteins associated with trinucleotide repeat expansion disorders may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

Non-limiting examples of proteins associated with trinucleotide repeat expansion disorders include AR (androgen receptor), FMR1 (fragile X mental retardation 1), HTT (huntingtin), DMPK (dystrophia myotonica-protein kinase), FXN (frataxin), ATXN2 (ataxin 2), ATN1 (atrophin 1), FEN1 (flap structure-specific endonuclease 1), TNRC6A (trinucleotide repeat containing 6A), PABPN1 (poly(A) binding protein, nuclear 1), JPH3 (junctophilin 3), MED15 (mediator complex subunit 15), ATXN1 (ataxin 1), ATXN3 (ataxin 3), TBP (TATA box binding protein), CACNA1A (calcium channel, voltage-dependent, P/Q type, alpha 1A subunit), ATXN8OS (ATXN8 opposite strand (non-protein coding)), PPP2R2B (protein phosphatase 2, regulatory subunit B, beta), ATXN7 (ataxin 7), TNRC6B (trinucleotide repeat containing 6B), TNRC6C (trinucleotide repeat containing 6C), CELF3 (CUGBP, Elav-like family member 3), MAB21L1 (mab-21-like 1 (C. elegans)), MSH2 (mutS homolog 2, colon cancer, nonpolyposis type 1 (E. coli)), TMEM185A (transmembrane protein 185A), SIX5 (SIX homeobox 5), CNPY3 (canopy 3 homolog (zebrafish)), FRAXE (fragile site, folic acid type, rare, fra(X)(q28) E), GNB2 (guanine nucleotide binding protein (G protein), beta polypeptide 2), RPL14 (ribosomal protein L14), ATXN8 (ataxin 8), INSR (insulin receptor), TTR (transthyretin), EP400 (E1A binding protein p400), GIGYF2 (GRB10 interacting GYF protein 2), OGG1 (8-oxoguanine DNA glycosylase), STC1 (stanniocalcin 1), CNDP1 (carnosine dipeptidase 1 (metallopeptidase M20 family)), C10orf2 (chromosome 10 open reading frame 2), MAML3 mastermind-like 3 (Drosophila), DKC1 (dyskeratosis congenita 1, dyskerin), PAXIP1 (PAX interacting (with transcription-activation domain) protein 1), CASK (calcium/calmodulin-dependent serine protein kinase (MAGUK family)), MAPT (microtubule-associated protein tau), SP1 (Sp1 transcription factor), POLG (polymerase (DNA directed), gamma), AFF2 (AF4/FMR2 family, member 2), THBS1 (thrombospondin 1), TP53 (tumor protein p53), ESR1 (estrogen receptor 1), CGGBP1 (CGG triplet repeat binding protein 1), ABT1 (activator of basal transcription 1), KLK3 (kallikrein-related peptidase 3), PRNP (prion protein), JUN (jun oncogene), KCNN3 (potassium intermediate/small conductance calcium-activated channel, subfamily N, member 3), BAX (BCL2-associated X protein), FRAXA (fragile site, folic acid type, rare, fra(X)(q27.3) A (macroorchidism, mental retardation)), KBTBD10 (kelch repeat and BTB (POZ) domain containing 10), MBNL1 (muscleblind-like (Drosophila)), RAD51 (RAD51 homolog (RecA homolog, E. coli) (S. cerevisiae)), NCOA3 (nuclear receptor coactivator 3), ERDA1 (expanded repeat domain, CAG/CTG 1), TSC1 (tuberous sclerosis 1), COMP (cartilage oligomeric matrix protein), GCLC (glutamate-cysteine ligase, catalytic subunit), RRAD (Ras-related associated with diabetes), MSH3 (mutS homolog 3 (E. coli)), DRD2 (dopamine receptor D2), CD44 (CD44 molecule (Indian blood group)), CTCF (CCCTC-binding factor (zinc finger protein)), CCND1 (cyclin D1), CLSPN (claspin homolog (Xenopus laevis)), MEF2A (myocyte enhancer factor 2A), PTPRU (protein tyrosine phosphatase, receptor type, U), GAPDH (glyceraldehyde-3-phosphate dehydrogenase), TRIM22 (tripartite motif-containing 22), WT1 (Wilms tumor 1), AHR (aryl hydrocarbon receptor), GPX1 (glutathione peroxidase 1), TPMT (thiopurine S-methyltransferase), NDP (Norrie disease (pseudoglioma)), ARX (aristaless related homeobox), MUS81 (MUS81 endonuclease homolog (S. cerevisiae)), TYR (tyrosinase (oculocutaneous albinism IA)), EGR1 (early growth response 1), UNG (uracil-DNA glycosylase), NUMBL (numb homolog (Drosophila)-like), FABP2 (fatty acid binding protein 2, intestinal), EN2 (engrailed homeobox 2), CRYGC (crystallin, gamma C), SRP14 (signal recognition particle 14 kDa (homologous Alu RNA binding protein)), CRYGB (crystallin, gamma B), PDCD1 (programmed cell death 1), HOXA1 (homeobox A1), ATXN2L (ataxin 2-like), PMS2 (PMS2 postmeiotic segregation increased 2 (S. cerevisiae)), GLA (galactosidase, alpha), CBL (Cas-Br-M (murine) ecotropic retroviral transforming sequence), FTH1 (ferritin, heavy polypeptide 1), IL12RB2 (interleukin 12 receptor, beta 2), OTX2 (orthodenticle homeobox 2), HOXA5 (homeobox A5), POLG2 (polymerase (DNA directed), gamma 2, accessory subunit), DLX2 (distal-less homeobox 2), SIRPA (signal-regulatory protein alpha), OTX1 (orthodenticle homeobox 1), AHRR (aryl-hydrocarbon receptor repressor), MANF (mesencephalic astrocyte-derived neurotrophic factor), TMEM158 (transmembrane protein 158 (gene/pseudogene)), and ENSG00000078687.

Preferred proteins associated with trinucleotide repeat expansion disorders include HTT (Huntingtin), AR (androgen receptor), FXN (frataxin), Atxn3 (ataxin), Atxn1 (ataxin), Atxn2 (ataxin), Atxn7 (ataxin), Atxn10 (ataxin), DMPK (dystrophia myotonica-protein kinase), Atn1 (atrophin 1), CBP (creb binding protein), VLDLR (very low density lipoprotein receptor), and any combination thereof.

Treating Hearing Diseases

The present invention also contemplates delivering the CRISPR-Cas system to one or both ears.

Researchers are looking into whether gene therapy could be used to aid current deafness treatments—namely, cochlear implants. Deafness is often caused by lost or damaged hair cells that cannot relay signals to auditory neurons. In such cases, cochlear implants may be used to respond to sound and transmit electrical signals to the nerve cells. But these neurons often degenerate and retract from the cochlea as fewer growth factors are released by impaired hair cells.

US patent application 20120328580 describes injection of a pharmaceutical composition into the ear (e.g., auricular administration), such as into the luminae of the cochlea (e.g., the Scala media, Sc vestibulae, and Sc tympani), e.g., using a syringe, e.g., a single-dose syringe. For example, one or more of the compounds described herein can be administered by intratympanic injection (e.g., into the middle ear), and/or injections into the outer, middle, and/or inner ear. Such methods are routinely used in the art, for example, for the administration of steroids and antibiotics into human ears. Injection can be, for example, through the round window of the ear or through the cochlear capsule. Other inner ear administration methods are known in the art (see, e.g., Salt and Plontke, Drug Discovery Today, 10:1299-1306, 2005).

In another mode of administration, the pharmaceutical composition can be administered in situ, via a catheter or pump. A catheter or pump can, for example, direct a pharmaceutical composition into the cochlear luminae or the round window of the ear and/or the lumen of the colon. Exemplary drug delivery apparatus and methods suitable for administering one or more of the compounds described herein into an ear, e.g., a human ear, are described by McKenna et al., (U.S. Publication No. 2006/0030837) and Jacobsen et al., (U.S. Pat. No. 7,206,639). In some embodiments, a catheter or pump can be positioned, e.g., in the ear (e.g., the outer, middle, and/or inner ear) of a patient during a surgical procedure. In some embodiments, a catheter or pump can be positioned, e.g., in the ear (e.g., the outer, middle, and/or inner ear) of a patient without the need for a surgical procedure.

Alternatively or in addition, one or more of the compounds described herein can be administered in combination with a mechanical device such as a cochlear implant or a hearing aid, which is worn in the outer ear. An exemplary cochlear implant that is suitable for use with the present invention is described by Edge et al., (U.S. Publication No. 2007/0093878).

In some embodiments, the modes of administration described above may be combined in any order and can be simultaneous or interspersed.

Alternatively or in addition, the present invention may be administered according to any of the Food and Drug Administration approved methods, for example, as described in CDER Data Standards Manual, version number 004 (which is available at fda.gov/cder/dsm/DRG/drg00301.htm).

In general, the cell therapy methods described in US patent application 20120328580 can be used to promote complete or partial differentiation of a cell to or towards a mature cell type of the inner ear (e.g., a hair cell) in vitro. Cells resulting from such methods can then be transplanted or implanted into a patient in need of such treatment. The cell culture methods required to practice these methods, including methods for identifying and selecting suitable cell types, methods for promoting complete or partial differentiation of selected cells, methods for identifying complete or partially differentiated cell types, and methods for implanting complete or partially differentiated cells are described below.

Cells suitable for use in the present invention include, but are not limited to, cells that are capable of differentiating completely or partially into a mature cell of the inner ear, e.g., a hair cell (e.g., an inner and/or outer hair cell), when contacted, e.g., in vitro, with one or more of the compounds described herein. Exemplary cells that are capable of differentiating into a hair cell include, but are not limited to stem cells (e.g., inner ear stem cells, adult stem cells, bone marrow derived stem cells, embryonic stem cells, mesenchymal stem cells, skin stem cells, iPS cells, and fat derived stem cells), progenitor cells (e.g., inner ear progenitor cells), support cells (e.g., Deiters' cells, pillar cells, inner phalangeal cells, tectal cells and Hensen's cells), and/or germ cells. The use of stem cells for the replacement of inner ear sensory cells is described in Li et al., (U.S. Publication No. 2005/0287127) and Li et al., (U.S. patent Ser. No. 11/953, 797). The use of bone marrow derived stem cells for the replacement of inner ear sensory cells is described in Edge et al., PCT/US2007/084654. iPS cells are described, e.g., at Takahashi et al., Cell, Volume 131, Issue 5, Pages 861-872 (2007); Takahashi and Yamanaka, Cell 126, 663-76 (2006); Okita et al., Nature 448, 260-262 (2007); Yu, J. et al., Science 318(5858):1917-1920 (2007); Nakagawa et al., Nat. Biotechnol. 26:101-106 (2008); and Zaehres and Scholer, Cell 131(5):834-835 (2007). Such suitable cells can be identified by analyzing (e.g., qualitatively or quantitatively) the presence of one or more tissue specific genes. For example, gene expression can be detected by detecting the protein product of one or more tissue-specific genes. Protein detection techniques involve staining proteins (e.g., using cell extracts or whole cells) using antibodies against the appropriate antigen. In this case, the appropriate antigen is the protein product of the tissue-specific gene expression. Although, in principle, a first antibody (i.e., the antibody that binds the antigen) can be labeled, it is more common (and improves the visualization) to use a second antibody directed against the first (e.g., an anti-IgG). This second antibody is conjugated either with fluorochromes, or appropriate enzymes for colorimetric reactions, or gold beads (for electron microscopy), or with the biotin-avidin system, so that the location of the primary antibody, and thus the antigen, can be recognized.

The CRISPR-Cas molecules of the present invention may be delivered to the ear by direct application of pharmaceutical composition to the outer ear, with compositions modified from US Published application, 20110142917. In some embodiments the pharmaceutical composition is applied to the ear canal. Delivery to the ear may also be referred to as aural or otic delivery.

In some embodiments the RNA molecules of the invention are delivered in liposome or lipofectin formulations and the like and can be prepared by methods well known to those skilled in the art. Such methods are described, for example, in U.S. Pat. Nos. 5,593,972, 5,589,466, and 5,580,859, which are herein incorporated by reference.

Delivery systems aimed specifically at the enhanced and improved delivery of siRNA into mammalian cells have been developed, (see, for example, Shen et al FEBS Let. 2003, 539:111-114; Xia et al., Nat. Biotech. 2002, 20:1006-1010; Reich et al., Mol. Vision. 2003, 9: 210-216; Sorensen et al., J. Mol. Biol. 2003, 327: 761-766; Lewis et al., Nat. Gen. 2002, 32: 107-108 and Simeoni et al., NAR 2003, 31, 11: 2717-2724) and may be applied to the present invention. siRNA has recently been successfully used for inhibition of gene expression in primates (see for example. Tolentino et al., Retina 24(4):660 which may also be applied to the present invention.

Qi et al. discloses methods for efficient siRNA transfection to the inner ear through the intact round window by a novel proteidic delivery technology which may be applied to the nucleic acid-targeting system of the present invention (see, e.g., Qi et al., Gene Therapy (2013), 1-9). In particular, a TAT double stranded RNA-binding domains (TAT-DRBDs), which can transfect Cy3-labeled siRNA into cells of the inner ear, including the inner and outer hair cells, crista ampullaris, macula utriculi and macula sacculi, through intact round-window permeation was successful for delivering double stranded siRNAs in vivo for treating various inner ear ailments and preservation of hearing function. About 40 µl of 10 mM RNA may be contemplated as the dosage for administration to the ear.

According to Rejali et al. (Hear Res. 2007 June; 228(1-2):180-7), cochlear implant function can be improved by good preservation of the spiral ganglion neurons, which are the target of electrical stimulation by the implant and brain derived neurotrophic factor (BDNF) has previously been shown to enhance spiral ganglion survival in experimentally deafened ears. Rejali et al. tested a modified design of the cochlear implant electrode that includes a coating of fibroblast cells transduced by a viral vector with a BDNF gene insert. To accomplish this type of ex vivo gene transfer, Rejali et al. transduced guinea pig fibroblasts with an adenovirus with a BDNF gene cassette insert, and determined that these cells secreted BDNF and then attached BDNF-secreting cells to the cochlear implant electrode via an agarose gel, and implanted the electrode in the scala tympani. Rejali et al. determined that the BDNF expressing electrodes were able to preserve significantly more spiral ganglion neurons in the basal turns of the cochlea after 48 days of implantation when compared to control electrodes and demonstrated the feasibility of combining cochlear implant therapy with ex vivo gene transfer for enhancing spiral ganglion neuron survival. Such a system may be applied to the nucleic acid-targeting system of the present invention for delivery to the ear.

Mukherjea et al. (Antioxidants & Redox Signaling, Volume 13, Number 5, 2010) document that knockdown of NOX3 using short interfering (si) RNA abrogated cisplatin ototoxicity, as evidenced by protection of OHCs from damage and reduced threshold shifts in auditory brainstem responses (ABRs). Different doses of siNOX3 (0.3, 0.6, and 0.9 µg) were administered to rats and NOX3 expression was evaluated by real time RT-PCR. The lowest dose of NOX3 siRNA used (0.3 µg) did not show any inhibition of NOX3 mRNA when compared to transtympanic administration of scrambled siRNA or untreated cochleae. However, administration of the higher doses of NOX3 siRNA (0.6 and 0.9 µg) reduced NOX3 expression compared to control scrambled siRNA. Such a system may be applied to the CRISPR-Cas system of the present invention for transtympanic administration with a dosage of about 2 mg to about 4 mg of CRISPR-Cas for administration to a human.

Jung et al. (Molecular Therapy, vol. 21 no. 4, 834-841 Apr. 2013) demonstrate that Hes5 levels in the utricle decreased after the application of siRNA and that the number of hair cells in these utricles was significantly larger than following control treatment. The data suggest that siRNA technology may be useful for inducing repair and regeneration in the inner ear and that the Notch signaling pathway is a potentially useful target for specific gene expression inhibition. Jung et al. injected 8 µg of Hes5 siRNA in 2 µl volume, prepared by adding sterile normal saline to the lyophilized siRNA to a vestibular epithelium of the ear. Such a system may be applied to the nucleic acid-targeting system of the present invention for administration to the vestibular epithelium of the ear with a dosage of about 1 to about 30 mg of CRISPR-Cas for administration to a human.

Gene Targeting in Non-Dividing Cells (Neurones & Muscle)

Non-dividing (especially non-dividing, fully differentiated) cell types present issues for gene targeting or genome engineering, for example because homologous recombination (HR) is generally suppressed in the G1 cell-cycle phase. However, while studying the mechanisms by which cells control normal DNA repair systems, Durocher discovered a previously unknown switch that keeps HR "off" in non-dividing cells and devised a strategy to toggle this switch back on. Orthwein et al. (Daniel Durocher's lab at the Mount Sinai Hospital in Ottawa, Canada) recently reported (Nature 16142, published online 9 Dec. 2015) have shown that the suppression of HR can be lifted and gene targeting successfully concluded in both kidney (293T) and osteosarcoma (U205) cells. Tumor suppressors, BRCA1, PALB2 and BRAC2 are known to promote DNA DSB repair by HR. They found that formation of a complex of BRCA1 with PALB2-BRAC2 is governed by a ubiquitin site on PALB2, such that action on the site by an E3 ubiquitin ligase. This E3 ubiquitin ligase is composed of KEAP1 (a PALB2-interacting protein) in complex with cullin-3 (CUL3)-RBX1. PALB2 ubiquitylation suppresses its interaction with BRCA1 and is counteracted by the deubiquitylase USP11, which is itself under cell cycle control. Restoration of the BRCA1-PALB2 interaction combined with the activation of DNA-end resection is sufficient to induce homologous recombination in G1, as measured by a number of methods including a CRISPR-Cas9-based gene-targeting assay directed at USP11 or KEAP1 (expressed from a pX459 vector). However, when the BRCA1-PALB2 interaction was restored in resection-competent G1 cells using either KEAP1 depletion or expression of the PALB2-KR mutant, a robust increase in gene-targeting events was detected.

Thus, reactivation of HR in cells, especially non-dividing, fully differentiated cell types is preferred, in some embodiments. In some embodiments, promotion of the BRCA1-PALB2 interaction is preferred in some embodiments. In some embodiments, the target ell is a non-dividing cell. In some embodiments, the target cell is a neurone or muscle cell. In some embodiments, the target cell is targeted in vivo. In some embodiments, the cell is in G1 and HR is suppressed. In some embodiments, use of KEAP1 depletion, for example inhibition of expression of KEAP1 activity, is preferred. KEAP1 depletion may be achieved through siRNA, for example as shown in Orthwein et al. Alternatively, expression of the PALB2-KR mutant (lacking all eight Lys residues in the BRCA1-interaction domain is preferred, either in combination with KEAP1 depletion or alone. PALB2-KR interacts with BRCA1 irrespective of cell cycle position. Thus, promotion or restoration of the BRCA1-PALB2 interaction, especially in G1 cells, is preferred in some embodiments, especially where the target cells are non-dividing, or where removal and return (ex vivo gene targeting) is problematic, for example neurone or muscle cells. KEAP1 siRNA is available from ThermoFischer. In some embodiments, a BRCA1-PALB2 complex may be delivered to the G1 cell. In some embodiments, PALB2 deubiquitylation may be promoted for example by increased expression of the deubiquitylase USP11, so it is envisaged that a construct may be provided to promote or up-regulate expression or activity of the deubiquitylase USP11.

Treating Diseases of the Eye

The present invention also contemplates delivering the CRISPR-Cas system to one or both eyes.

In particular embodiments of the invention, the CRISPR-Cas system may be used to correct ocular defects that arise from several genetic mutations further described in Genetic Diseases of the Eye, Second Edition, edited by Elias I. Traboulsi, Oxford University Press, 2012.

In some embodiments, the condition to be treated or targeted is an eye disorder. In some embodiments, the eye disorder may include glaucoma. In some embodiments, the eye disorder includes a retinal degenerative disease. In some embodiments, the retinal degenerative disease is selected from Stargardt disease, Bardet-Biedl Syndrome, Best disease, Blue Cone Monochromacy, Choroideremia, Cone-rod dystrophy, Congenital Stationary Night Blindness, Enhanced S-Cone Syndrome, Juvenile X-Linked Retinoschisis, Leber Congenital Amaurosis, Malattia Leventinese, Norrie Disease or X-linked Familial Exudative Vitreoretinopathy, Pattern Dystrophy, Sorsby Dystrophy, Usher Syndrome, Retinitis Pigmentosa, Achromatopsia or Macular dystrophies or degeneration, Retinitis Pigmentosa, Achromatopsia, and age related macular degeneration. In some embodiments, the retinal degenerative disease is Leber Congenital Amaurosis (LCA) or Retinitis Pigmentosa. In some embodiments, the CRISPR system is delivered to the eye, optionally via intravitreal injection or subretinal injection.

For administration to the eye, lentiviral vectors, in particular equine infectious anemia viruses (EIAV) are particularly preferred.

In another embodiment, minimal non-primate lentiviral vectors based on the equine infectious anemia virus (EIAV) are also contemplated, especially for ocular gene therapy (see, e.g., Balagaan, J Gene Med 2006; 8: 275-285, Published online 21 Nov. 2005 in Wiley InterScience (www.interscience.wiley.com). DOI: 10.1002/jgm.845). The vectors are contemplated to have cytomegalovirus (CMV) promoter driving expression of the target gene. Intracameral, subretinal, intraocular and intravitreal injections are all contemplated (see, e.g., Balagaan, J Gene Med 2006; 8: 275-285, Published online 21 Nov. 2005 in Wiley InterScience (www.interscience.wiley.com). DOI: 10.1002/jgm.845). Intraocular injections may be performed with the aid of an operating microscope. For subretinal and intravitreal injections, eyes may be prolapsed by gentle digital pressure and fundi visualised using a contact lens system consisting of a drop of a coupling medium solution on the cornea covered with a glass microscope slide coverslip. For subretinal injections, the tip of a 10 mm 34-gauge needle, mounted on a 5-µl Hamilton syringe may be advanced under direct visualisation through the superior equatorial sclera tangentially towards the posterior pole until the aperture of the needle was visible in the subretinal space. Then, 2 µl of vector suspension may be injected to produce a superior bullous retinal detachment, thus confirming subretinal vector administration. This approach creates a self-sealing sclerotomy allowing the vector suspension to be retained in the subretinal space until it is absorbed by the RPE, usually within 48 h of the procedure. This procedure may be repeated in the inferior hemisphere to produce an inferior retinal detachment. This technique results in the exposure of approximately 70% of neurosensory retina and RPE to the vector suspension. For intravitreal injections, the needle tip may be advanced through the sclera 1 mm posterior to the corneoscleral limbus and 2 µl of vector suspension injected into the vitreous cavity. For intracameral injections, the needle tip may be advanced through a corneoscleral limbal paracentesis, directed towards the central cornea, and 2 µl of vector suspension may be injected. For intracameral injections, the needle tip may be advanced through a corneoscleral limbal paracentesis, directed towards the central cornea, and 2 µl of vector suspension may be injected. These vectors may be injected at titres of either $1.0-1.4 \times 10^{10}$ or $1.0-1.4 \times 10^9$ transducing units (TU)/ml.

In another embodiment, RetinoStat®, an equine infectious anemia virus-based lentiviral gene therapy vector that expresses angiostatic proteins endostain and angiostatin that is delivered via a subretinal injection for the treatment of the web form of age-related macular degeneration is also contemplated (see, e.g., Binley et al., HUMAN GENE THERAPY 23:980-991 (September 2012)). Such a vector may be modified for the CRISPR-Cas system of the present invention. Each eye may be treated with either RetinoStat® at a dose of $1.1 \times 10^5$ transducing units per eye (TU/eye) in a total volume of 100

In another embodiment, an E1-, partial E3-, E4-deleted adenoviral vector may be contemplated for delivery to the eye. Twenty-eight patients with advanced neovascular agerelated macular degeneration (AMD) were given a single intravitreous injection of an E1-, partial E3-, E4-deleted adenoviral vector expressing human pigment ep-ithelium-derived factor (AdPEDF.11) (see, e.g., Campochiaro et al., Human Gene Therapy 17:167-176 (February 2006)). Doses ranging from 106 to 109.5 particle units (PU) were investigated and there were no serious adverse events related to AdPEDF.11 and no dose-limiting toxicities (see, e.g., Campochiaro et al., Human Gene Therapy 17:167-176 (February 2006)). Adenoviral vector mediated ocular gene transfer appears to be a viable approach for the treatment of ocular disorders and could be applied to the CRISPR-Cas system.

In another embodiment, the sd-rxRNA® system of RXi Pharmaceuticals may be used/and or adapted for delivering CRISPR-Cas to the eye. In this system, a single intravitreal administration of 3 of sd-rxRNA results in sequence-specific reduction of PPIB mRNA levels for 14 days. The sd-rxRNA® system may be applied to the nucleic acid-targeting system of the present invention, contemplating a dose of about 3 to 20 mg of CRISPR administered to a human.

Millington-Ward et al. (Molecular Therapy, vol. 19 no. 4, 642-649 Apr. 2011) describes adeno-associated virus (AAV) vectors to deliver an RNA interference (RNAi)-based rhodopsin suppressor and a codon-modified rhodopsin replacement gene resistant to suppression due to nucleotide alterations at degenerate positions over the RNAi target site. An injection of either $6.0 \times 10^8$ vp or $1.8 \times 10^{10}$ vp AAV were subretinally injected into the eyes by Millington-Ward et al. The AAV vectors of Millington-Ward et al. may be applied to the CRISPR-Cas system of the present invention, contemplating a dose of about $2 \times 10^{11}$ to about $6 \times 10^{13}$ vp administered to a human.

Dalkara et al. (Sci Transl Med 5, 189ra76 (2013)) also relates to in vivo directed evolution to fashion an AAV vector that delivers wild-type versions of defective genes throughout the retina after noninjurious injection into the eyes' vitreous humor. Dalkara describes a 7mer peptide display library and an AAV library constructed by DNA shuffling of cap genes from AAV1, 2, 4, 5, 6, 8, and 9. The rcAAV libraries and rAAV vectors expressing GFP under a CAG or Rho promoter were packaged and deoxyribonuclease-resistant genomic titers were obtained through quantitative PCR. The libraries were pooled, and two rounds of evolution were performed, each consisting of initial library diversification followed by three in vivo selection steps. In each such step, P30 rho-GFP mice were intravitreally injected with 2 ml of iodixanol-purified, phosphate-buffered saline (PBS)-dialyzed library with a genomic titer of about $1 \times 10^{12}$ vg/ml. The AAV vectors of Dalkara et al. may be applied to the nucleic acid-targeting system of the present invention, contemplating a dose of about $1 \times 10^{15}$ to about $1 \times 10^{16}$ vg/ml administered to a human.

In a particular embodiment, the rhodopsin gene may be targeted for the treatment of retinitis pigmentosa (RP), wherein the system of US Patent Publication No. 20120204282 assigned to Sangamo BioSciences, Inc. may be modified in accordance of the CRISPR-Cas system of the present invention.

In another embodiment, the methods of US Patent Publication No. 20130183282 assigned to Cellectis, which is directed to methods of cleaving a target sequence from the human rhodopsin gene, may also be modified to the nucleic acid-targeting system of the present invention.

US Patent Publication No. 20130202678 assigned to Academia Sinica relates to methods for treating retinopathies and sight-threatening ophthalmologic disorders relating to delivering of the Puf-A gene (which is expressed in retinal ganglion and pigmented cells of eye tissues and displays a unique anti-apoptotic activity) to the sub-retinal or intravitreal space in the eye. In particular, desirable targets are zgc:193933, prdm1a, spata2, tex10, rbb4, ddx3, zp2.2, Blimp-1 and HtrA2, all of which may be targeted by the nucleic acid-targeting system of the present invention.

Wu (Cell Stem Cell, 13:659-62, 2013) designed a guide RNA that led Cas9 to a single base pair mutation that causes cataracts in mice, where it induced DNA cleavage. Then using either the other wild-type allele or oligos given to the zygotes repair mechanisms corrected the sequence of the broken allele and corrected the cataract-causing genetic defect in mutant mouse.

US Patent Publication No. 20120159653, describes use of zinc finger nucleases to genetically modify cells, animals and proteins associated with macular degeneration (MD). Macular degeneration (MD) is the primary cause of visual impairment in the elderly, but is also a hallmark symptom of childhood diseases such as Stargardt disease, Sorsby fundus, and fatal childhood neurodegenerative diseases, with an age of onset as young as infancy. Macular degeneration results in a loss of vision in the center of the visual field (the macula) because of damage to the retina. Currently existing animal models do not recapitulate major hallmarks of the disease as it is observed in humans. The available animal models comprising mutant genes encoding proteins associated with MD also produce highly variable phenotypes, making translations to human disease and therapy development problematic.

One aspect of US Patent Publication No. 20120159653 relates to editing of any chromosomal sequences that encode proteins associated with MD which may be applied to the nucleic acid-targeting system of the present invention. The proteins associated with MD are typically selected based on an experimental association of the protein associated with MD to an MD disorder. For example, the production rate or circulating concentration of a protein associated with MD may be elevated or depressed in a population having an MD disorder relative to a population lacking the MD disorder. Differences in protein levels may be assessed using proteomic techniques including but not limited to Western blot, immunohistochemical staining, enzyme linked immunosorbent assay (ELISA), and mass spectrometry. Alternatively, the proteins associated with MD may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of non-limiting example, proteins associated with MD include but are not limited to the following proteins: (ABCA4) ATP-binding cassette, sub-family A (ABC1), member 4 ACHM1 achromatopsia (rod monochromacy) 1 ApoE Apolipoprotein E (ApoE) C1QTNF5 (CTRPS) C1q and tumor necrosis factor related protein 5 (C1QTNF5) C2 Complement component 2 (C2) C3 Complement components (C3) CCL2 Chemokine (C-C motif) Ligand 2 (CCL2) CCR2 Chemokine (C-C motif) receptor 2 (CCR2) CD36 Cluster of Differentiation 36 CFB Complement factor B CFH Complement factor CFH H CFHR1 complement factor H-related 1 CFHR3 complement factor H-related 3 CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair crosscomplementing rodent repair deficiency, complementation group 6 FBLN5 Fibulin-5 FBLN5 Fibulin 5 FBLN6 Fibulin 6 FSCN2 fascin (FSCN2) HMCN1 Hemicentin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domaincontaining family A member 1 (PLEKHA1) PROM1 Prominin 1(PROM1 or CD133) PRPH2 Peripherin-2 RPGR retinitis pigmentosa GTPase regulator SERPING1 serpin peptidase inhibitor, Glade G, member 1 (C1-inhibitor) TCOF1 Treacle TIMP3 Metalloproteinase inhibitor 3 (TIMP3) TLR3 Toll-like receptor 3.

The identity of the protein associated with MD whose chromosomal sequence is edited can and will vary. In preferred embodiments, the proteins associated with MD whose chromosomal sequence is edited may be the ATP-binding cassette, sub-family A (ABC1) member 4 protein (ABCA4) encoded by the ABCR gene, the apolipoprotein E protein (APOE) encoded by the APOE gene, the chemokine (C-C motif) Ligand 2 protein (CCL2) encoded by the CCL2 gene, the chemokine (C-C motif) receptor 2 protein (CCR2) encoded by the CCR2 gene, the ceruloplasmin protein (CP) encoded by the CP gene, the cathepsin D protein (CTSD) encoded by the CTSD gene, or the metalloproteinase inhibitor 3 protein (TIMP3) encoded by the TIMP3 gene. In an exemplary embodiment, the genetically modified animal is a rat, and the edited chromosomal sequence encoding the protein associated with MD may be: (ABCA4) ATPbinding cassette, NM_000350 sub-family A (ABC1), member 4 APOE Apolipoprotein E NM_138828 (APOE) CCL2 Chemokine (C-C NM_031530 motif) Ligand 2 (CCL2) CCR2 Chemokine (C-C NM_021866 motif) receptor 2 (CCR2) CP ceruloplasmin (CP) NM_012532 CTSD Cathepsin D (CTSD) NM_134334 TIMP3 Metalloproteinase NM_012886 inhibitor 3 (TIMP3) The animal or cell may comprise 1, 2, 3, 4, 5, 6, 7 or more disrupted chromosomal sequences encoding a protein associated with MD and zero, 1, 2, 3, 4, 5, 6, 7 or more chromosomally integrated sequences encoding the disrupted protein associated with MD.

The edited or integrated chromosomal sequence may be modified to encode an altered protein associated with MD. Several mutations in MD-related chromosomal sequences have been associated with MD. Non-limiting examples of mutations in chromosomal sequences associated with MD include those that may cause MD including in the ABCR protein, E471K (i.e. glutamate at position 471 is changed to lysine), R1129L (i.e. arginine at position 1129 is changed to leucine), T1428M (i.e. threonine at position 1428 is changed to methionine), R1517S (i.e. arginine at position 1517 is changed to serine), I1562T (i.e. isoleucine at position 1562 is changed to threonine), and G1578R (i.e. glycine at position 1578 is changed to arginine); in the CCR2 protein, V64I (i.e. valine at position 192 is changed to isoleucine); in CP protein, G969B (i.e. glycine at position 969 is changed to asparagine or aspartate); in TIMP3 protein, S156C (i.e. serine at position 156 is changed to cysteine), G166C (i.e. glycine at position 166 is changed to cysteine), G167C (i.e. glycine at position 167 is changed to cysteine), Y168C (i.e. tyrosine at position 168 is changed to cysteine), S170C (i.e. serine at position 170 is changed to cysteine), Y172C (i.e. tyrosine at position 172 is changed to cysteine) and S181C (i.e. serine at position 181 is changed to cysteine). Other associations of genetic variants in MD-associated genes and disease are known in the art.

CRISPR systems are useful to correct diseases resulting from autosomal dominant genes. For example, CRISPR/Cas9 was used to remove an autosomal dominant gene that causes receptor loss in the eye. Bakondi, B. et al., *In Vivo CRISPR/Cas9 Gene Editing Corrects Retinal Dystrophy in the S334ter-3 Rat Model of Autosomal Dominant Retinitis Pigmentosa. Molecular Therapy,* 2015; DOI: 10.1038/mt.2015.220.

Treating Circulatory and Muscular Diseases

The present invention also contemplates delivering the CRISPR-Cas system described herein, e.g. Cpf1 effector protein systems, to the heart. For the heart, a myocardium tropic adena-associated virus (AAVM) is preferred, in particular AAVM41 which showed preferential gene transfer in the heart (see, e.g., Lin-Yanga et al., PNAS, Mar. 10, 2009, vol. 106, no. 10). Administration may be systemic or local. A dosage of about $1-10 \times 10^{14}$ vector genomes are contemplated for systemic administration. See also, e.g., Eulalio et al. (2012) Nature 492: 376 and Somasuntharam et al. (2013) Biomaterials 34: 7790.

For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. Any chromosomal sequence involved in cardiovascular disease or the protein encoded by any chromosomal sequence involved in cardiovascular disease may be utilized in the methods described in this disclosure. The cardiovascular-related proteins are typically selected based on an experimental association of the cardiovascular-related protein to the development of cardiovascular disease. For example, the production rate or circulating concentration of a cardiovascular-related protein may be elevated or depressed in a population having a cardiovascular disorder relative to a population lacking the cardiovascular disorder. Differences in protein levels may be assessed using proteomic techniques including but not limited to Western blot, immunohistochemical staining, enzyme linked immunosorbent assay (ELISA), and mass spectrometry. Alternatively, the cardiovascular-related proteins may be identified by obtaining gene expression profiles of the genes encoding the proteins using genomic techniques including but not limited to DNA microarray analysis, serial analysis of gene expression (SAGE), and quantitative real-time polymerase chain reaction (Q-PCR).

By way of example, the chromosomal sequence may comprise, but is not limited to, IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), CTSK (cathepsin K), PTGIR (prostaglandin 12 (prostacyclin) receptor (IP)), KCNJ11 (potassium inwardly-rectifying channel, subfamily J, member 11), INS (insulin), CRP (C-reactive protein, pentraxin-related), PDGFRB (platelet-derived growth factor receptor, beta polypeptide), CCNA2 (cyclin A2), PDGFB (platelet-derived growth factor beta polypeptide (simian sarcoma viral (v-sis) oncogene homolog)), KCNJ5 (potassium inwardly-rectifying channel, subfamily J, member 5), KCNN3 (potassium intermediate/small conductance calcium-activated channel, subfamily N, member 3), CAPN10 (calpain 10), PTGES (prostaglandin E synthase), ADRA2B (adrenergic, alpha-2B-, receptor), ABCG5 (ATP-binding cassette, sub-family G (WHITE), member 5), PRDX2 (peroxiredoxin 2), CAPN5 (calpain 5), PARP14 (poly (ADP-ribose) polymerase family, member 14), MEX3C (mex-3 homolog C (*C. elegans*)), ACE angiotensin I converting enzyme (peptidyl-dipeptidase A) 1), TNF (tumor necrosis factor (TNF superfamily, member 2)), IL6 (interleukin 6 (interferon, beta 2)), STN (statin), SERPINE1 (serpin peptidase inhibitor, Glade E (nexin, plasminogen activator inhibitor type 1), member 1), ALB (albumin), ADIPOQ (adiponectin, C1Q and collagen domain containing), APOB (apolipoprotein B (including Ag(x) antigen)), APOE (apolipoprotein E), LEP (leptin), MTHFR (5,10-methylenetetrahydrofolate reductase (NADPH)), APOA1 (apolipoprotein A-I), EDN1 (endothelin 1), NPPB (natriuretic peptide precursor B), NOS3 (nitric oxide synthase 3 (endothelial cell)), PPARG (peroxisome proliferator-activated receptor gamma), PLAT (plasminogen activator, tissue), PTGS2 (prostaglandin-endoperoxide synthase 2 (prostaglandin G/H synthase and cyclooxygenase)), CETP (cholesteryl ester transfer protein, plasma), AGTR1 (angiotensin II receptor, type 1), HMGCR (3-hydroxy-3-methylglutaryl-Coenzyme A reductase), IGF1 (insulin-like growth factor 1 (somatomedin C)), SELE (selectin E), REN (renin), PPARA (peroxisome proliferator-activated receptor alpha), PON1 (paraoxonase 1), KNG1 (kininogen 1), CCL2 (chemokine (C-C motif) ligand 2), LPL (lipoprotein lipase), VWF (von Willebrand factor), F2 (coagulation factor II (thrombin)), ICAM1 (intercellular adhesion molecule 1), TGFB1 (transforming growth factor, beta 1), NPPA (natriuretic peptide precursor A), IL10 (interleukin 10), EPO (erythropoietin), SOD1 (superoxide dismutase 1, soluble), VCAM1 (vascular cell adhesion molecule 1), IFNG (interferon, gamma), LPA (lipoprotein, Lp(a)), MPO (myeloperoxidase), ESR1 (estrogen receptor 1), MAPK1 (mitogen-activated protein kinase 1), HP (haptoglobin), F3 (coagulation factor III (thromboplastin, tissue factor)), CST3 (cystatin C), COG2 (component of oligomeric golgi complex 2), MMP9 (matrix metallopeptidase 9 (gelatinase B, 92 kDa gelatinase, 92 kDa type IV collagenase)), SERPINC1 (serpin peptidase inhibitor, Glade C (antithrombin), member 1), F8 (coagulation factor VIII, procoagulant component), HMOX1 (heme oxygenase (decycling) 1), APOC3 (apolipoprotein C-III), IL8 (interleukin 8), PROK1 (prokineticin 1), CBS (cystathionine-beta-synthase), NOS2 (nitric oxide synthase 2, inducible), TLR4 (toll-like receptor 4), SELP (selectin P (granule membrane protein 140 kDa, antigen CD62)), ABCA1 (ATP-binding cassette, sub-family A (ABC1), member 1), AGT (angiotensinogen (serpin peptidase inhibitor, Glade A, member 8)), LDLR (low density lipoprotein receptor), GPT (glutamic-pyruvate transaminase (alanine aminotransferase)), VEGFA (vascular endothelial growth factor A), NR3C2 (nuclear receptor subfamily 3, group C, member 2), IL18 (interleukin 18 (interferon-gamma-inducing factor)), NOS1 (nitric oxide synthase 1 (neuronal)), NR3C1 (nuclear receptor subfamily 3, group C, member 1 (glucocorticoid receptor)), FGB (fibrinogen beta chain), HGF (hepatocyte growth factor (hepapoietin A; scatter factor)), ILIA (interleukin 1, alpha), RETN (resistin), AKT1 (v-akt murine thymoma viral oncogene homolog 1), LIPC (lipase, hepatic), HSPD1 (heat shock 60 kDa protein 1 (chaperonin)), MAPK14 (mitogen-activated protein kinase 14), SPP1 (secreted phosphoprotein 1), ITGB3 (integrin, beta 3 (platelet glycoprotein 111a, antigen CD61)), CAT (catalase), UTS2 (urotensin 2), THBD (thrombomodulin), F10 (coagulation factor X), CP (ceruloplasmin (ferroxidase)), TNFRSF11B (tumor necrosis factor receptor superfamily, member 11b), EDNRA (endothelin receptor type A), EGFR (epidermal growth factor receptor (erythroblastic leukemia viral (v-erb-b) oncogene homolog, avian)), MMP2 (matrix metallopeptidase 2 (gelatinase A, 72 kDa gelatinase, 72 kDa type IV collagenase)), PLG (plasminogen), NPY (neuropeptide Y), RHOD (ras homolog gene family, member D), MAPK8 (mitogen-activated protein kinase 8), MYC (v-myc myelocytomatosis viral oncogene homolog (avian)), FN1 (fibronectin 1), CMA1 (chymase 1, mast cell), PLAU (plasminogen activator, urokinase), GNB3 (guanine nucleotide binding protein (G protein), beta polypeptide 3), ADRB2 (adrenergic, beta-2-, receptor, surface), APOA5 (apolipoprotein A-V), SOD2 (superoxide dismutase 2, mitochondrial), F5 (coagulation factor V (proaccelerin, labile factor)), VDR (vitamin D (1,25-dihydroxyvitamin D3) receptor), ALOX5 (arachidonate 5-lipoxygenase), HLA-DRB1 (major histocompatibility complex, class II, DR beta 1), PARP1 (poly (ADP-ribose) polymerase 1), CD40LG (CD40 ligand), PON2 (paraoxonase 2), AGER (advanced glycosylation end product-specific receptor), IRS1 (insulin receptor substrate 1), PTGS1 (prostaglandin-endoperoxide synthase 1 (prostaglandin G/H synthase and cyclooxygenase)), ECE1 (endothelin converting enzyme 1), F7 (coagulation factor VII (serum prothrombin conversion accelerator)), URN (interleukin 1 receptor antagonist), EPHX2 (epoxide hydrolase 2, cytoplasmic), IGFBP1 (insulin-like growth factor binding protein 1), MAPK10 (mitogen-activated protein kinase 10), FAS (Fas (TNF receptor superfamily, member 6)), ABCB1 (ATP-binding cassette, sub-family B (MDR/TAP), member 1), JUN (jun oncogene), IGFBP3 (insulin-like growth factor binding protein 3), CD14 (CD14 molecule), PDE5A (phosphodiesterase 5A, cGMP-specific), AGTR2 (angiotensin II receptor, type 2), CD40 (CD40 molecule, TNF receptor superfamily member 5), LCAT (lecithin-cholesterol acyltransferase), CCR5 (chemokine (C-C motif) receptor 5), MMP1 (matrix metallopeptidase 1 (interstitial collagenase)), TIMP1 (TIMP metallopeptidase inhibitor 1), ADM (adrenomedullin), DYT10 (dystonia 10), STAT3 (signal transducer and activator of transcription 3 (acute-phase response factor)), MMP3 (matrix metallopeptidase 3 (stromelysin 1, progelatinase)), ELN (elastin), USF1 (upstream transcription factor 1), CFH (complement factor H), HSPA4 (heat shock 70 kDa protein 4), MMP12 (matrix metallopeptidase 12 (macrophage elastase)), MME (membrane metallo-endopeptidase), F2R (coagulation factor II (thrombin) receptor), SELL (selectin L), CTSB (cathepsin B), ANXA5 (annexin A5), ADRB1 (adrenergic, beta-1-, receptor), CYBA (cytochrome b-245, alpha polypeptide), FGA (fibrinogen alpha chain), GGT1 (gamma-glutamyltransferase 1), LIPG (lipase, endothelial), HIF1A (hypoxia inducible factor 1, alpha subunit (basic helix-loop-helix transcription factor)), CXCR4 (chemokine (C-X-C motif) receptor 4), PROC (protein C (inactivator of coagulation factors Va and VIIIa)), SCARB1 (scavenger receptor class B, member 1), CD79A (CD79a molecule, immunoglobulin-associated alpha), PLTP (phospholipid transfer protein), ADD1 (adducin 1 (alpha)), FGG (fibrinogen gamma chain), SAA1 (serum amyloid A1), KCNH2 (potassium voltage-gated channel, subfamily H (eag-related), member 2), DPP4 (dipeptidyl-peptidase 4), G6PD (glucose-6-phosphate dehydrogenase), NPR1 (natriuretic peptide receptor A/guanylate cyclase A (atrionatriuretic peptide receptor A)), VTN (vitronectin), KIAA0101 (KIAA0101), FOS (FBJ murine osteosarcoma viral oncogene homolog), TLR2 (toll-like receptor 2), PPIG (peptidylprolyl isomerase G (cyclophilin G)), IL1R1 (interleukin 1 receptor, type I), AR (androgen receptor), CYP1A1 (cytochrome P450, family 1, subfamily A, polypeptide 1), SERPINA1 (serpin peptidase inhibitor, Glade A (alpha-1 antiproteinase, antitrypsin), member 1), MTR (5-methyltetrahydrofolate-homocysteine methyltransferase), RBP4 (retinol binding protein 4, plasma), APOA4 (apolipoprotein A-IV), CDKN2A (cyclin-dependent kinase inhibitor 2A (melanoma, p16, inhibits CDK4)), FGF2 (fibroblast growth factor 2 (basic)), EDNRB (endothelin receptor type B), ITGA2 (integrin, alpha 2 (CD49B, alpha 2 subunit of VLA-2 receptor)), CABIN1 (calcineurin binding protein 1), SHBG (sex hormone-binding globulin), HMGB1 (high-mobility group box 1), HSP90B2P (heat shock protein 90 kDa beta (Grp94), member 2 (pseudogene)), CYP3A4 (cytochrome P450, family 3, subfamily A, polypeptide 4), GJA1 (gap junction protein, alpha 1, 43 kDa), CAV1 (caveolin 1, caveolae protein, 22 kDa), ESR2 (estrogen receptor 2 (ER beta)), LTA (lymphotoxin alpha (TNF superfamily, member 1)), GDF15 (growth differentiation factor 15), BDNF (brain-derived neurotrophic factor), CYP2D6 (cytochrome P450, family 2, subfamily D, polypeptide 6), NGF (nerve growth factor (beta polypeptide)), SP1 (Sp 1 transcription factor), TGIF1 (TGFB-induced factor homeobox 1), SRC (v-src sarcoma (Schmidt-Ruppin A-2) viral oncogene homolog (avian)), EGF (epidermal growth factor (beta-urogastrone)), PIK3CG (phosphoinositide-3-kinase, catalytic, gamma polypeptide), HLA-A (major histocompatibility complex, class I, A), KCNQ1 (potassium voltage-gated channel, KQT-like subfamily, member 1), CNR1 (cannabinoid receptor 1 (brain)), FBN1 (fibrillin 1), CHKA (choline kinase alpha), BEST1 (bestrophin 1), APP (amyloid beta (A4) precursor protein), CTNNB1 (catenin (cadherin-associated protein), beta 1, 88 kDa), IL2 (interleukin 2), CD36 (CD36 molecule (thrombospondin receptor)), PRKAB1 (protein kinase, AMP-activated, beta 1 non-catalytic subunit), TPO (thyroid peroxidase), ALDH7A1 (aldehyde dehydrogenase 7 family, member A1), CX3CR1 (chemokine (C-X3-C motif) receptor 1), TH (tyrosine hydroxylase), F9 (coagulation factor IX), GH1 (growth hormone 1), TF (transferrin), HFE (hemochromatosis), IL17A (interleukin 17A), PTEN (phosphatase and tensin homolog), GSTM1 (glutathione S-transferase mu 1), DMD (dystrophin), GATA4 (GATA binding protein 4), F13A1 (coagulation factor XIII, A1 polypeptide), TTR (transthyretin), FABP4 (fatty acid binding protein 4, adipocyte), PON3 (paraoxonase 3), APOC1 (apolipoprotein C-I), INSR (insulin receptor), TNFRSF1B (tumor necrosis factor receptor superfamily, member 1B), HTR2A (5-hydroxytryptamine (serotonin) receptor 2A), CSF3 (colony stimulating factor 3 (granulocyte)), CYP2C9 (cytochrome P450, family 2, subfamily C, polypeptide 9), TXN (thioredoxin), CYP11B2 (cytochrome P450, family 11, subfamily B, polypeptide 2), PTH (parathyroid hormone), CSF2 (colony stimulating factor 2 (granulocyte-macrophage)), KDR (kinase insert domain receptor (a type III receptor tyrosine kinase)), PLA2G2A (phospholipase A2, group IIA (platelets, synovial fluid)), B2M (beta-2-microglobulin), THBS1 (thrombospondin 1), GCG (glucagon), RHOA (ras homolog gene family, member A), ALDH2 (aldehyde dehydrogenase 2 family (mitochondrial)), TCF7L2 (transcription factor 7-like 2 (T-cell specific, HMG-box)), BDKRB2 (bradykinin receptor B2), NFE2L2 (nuclear factor (erythroid-derived 2)-like 2), NOTCH1 (Notch homolog 1, translocation-associated (*Drosophila*)), UGT1A1 (UDP glucuronosyltransferase 1 family, polypeptide A1), IFNA1 (interferon, alpha 1), PPARD (peroxisome proliferator-activated receptor delta), SIRT1 (sirtuin (silent mating type information regulation 2 homolog) 1 (*S. cerevisiae*)), GNRH1 (gonadotropin-releasing hormone 1 (luteinizing-releasing hormone)), PAPPA (pregnancy-associated plasma protein A, pappalysin 1), ARR3 (arrestin 3, retinal (X-arrestin)), NPPC (natriuretic peptide precursor C), AHSP (alpha hemoglobin stabilizing protein), PTK2 (PTK2 protein tyrosine kinase 2), IL13 (interleukin 13), MTOR (mechanistic target of rapamycin (serine/threonine kinase)), ITGB2 (integrin, beta 2 (complement component 3 receptor 3 and 4 subunit)), GSTT1 (glutathione S-transferase theta 1), IL6ST (interleukin 6 signal transducer (gp130, oncostatin M receptor)), CPB2 (carboxypeptidase B2 (plasma)), CYP1A2 (cytochrome P450, family 1, subfamily A, polypeptide 2), HNF4A (hepatocyte nuclear factor 4, alpha), SLC6A4 (solute carrier family 6 (neurotransmitter transporter, serotonin), member 4), PLA2G6 (phospholipase A2, group VI (cytosolic, calcium-independent)), TNFSF11 (tumor necrosis factor (ligand) superfamily, member 11), SLC8A1 (solute carrier family 8 (sodium/calcium exchanger), member 1), F2RL1 (coagulation factor II (thrombin) receptor-like 1), AKR1A1 (aldo-keto reductase family 1, member A1 (aldehyde reductase)), ALDH9A1 (aldehyde dehydrogenase 9 family, member A1), BGLAP (bone gamma-carboxyglutamate (gla) protein), MTTP (microsomal triglyceride transfer protein), MTRR (5-methyltetrahydrofolate-homocysteine methyltransferase reductase), SULT1A3 (sulfotransferase family, cytosolic, 1A, phenol-preferring, member 3), RAGE (renal tumor antigen), C4B (complement component 4B (Chido blood group), P2RY12 (purinergic receptor P2Y, G-protein coupled, 12), RNLS (renalase, FAD-dependent amine oxidase), CREB1 (cAMP responsive element binding protein 1), POMC (proopiomelanocortin), RAC1 (ras-related C3 botulinum toxin substrate 1 (rho family, small GTP binding protein Rac1)), LMNA (lamin NC), CD59 (CD59 molecule, complement regulatory protein), SCN5A (sodium channel, voltage-gated, type V, alpha subunit), CYP1B1 (cytochrome P450, family 1, subfamily B, polypeptide 1), MIF (macrophage migration inhibitory factor (glycosylation-inhibiting factor)), MMP13 (matrix metallopeptidase 13 (collagenase 3)), TIMP2 (TIMP metallopeptidase inhibitor 2), CYP19A1 (cytochrome P450, family 19, subfamily A, polypeptide 1), CYP21A2 (cytochrome P450, family 21, subfamily A, polypeptide 2), PTPN22 (protein tyrosine phosphatase, non-receptor type 22 (lymphoid)), MYH14 (myosin, heavy chain 14, non-muscle), MBL2 (mannose-binding lectin (protein C) 2, soluble (opsonic defect)), SELPLG (selectin P ligand), AOC3 (amine oxidase, copper containing 3 (vascular adhesion protein 1)), CTSL1 (cathepsin L1), PCNA (proliferating cell nuclear antigen), IGF2 (insulin-like growth factor 2 (somatomedin A)), ITGB1 (integrin, beta 1 (fibronectin receptor, beta polypeptide, antigen CD29 includes MDF2, MSK12)), CAST (calpastatin), CXCL12 (chemokine (C-X-C motif) ligand 12 (stromal cell-derived factor 1)), IGHE (immunoglobulin heavy constant epsilon), KCNE1 (potassium voltage-gated channel, Isk-related family, member 1), TFRC (transferrin receptor (p90, CD71)), COL1A1 (collagen, type I, alpha 1), COL1A2 (collagen, type I, alpha 2), IL2RB (interleukin 2 receptor, beta), PLA2G10 (phospholipase A2, group X), ANGPT2 (angiopoietin 2), PROCR (protein C receptor, endothelial (EPCR)), NOX4 (NADPH oxidase 4), HAMP (hepcidin antimicrobial peptide), PTPN11 (protein tyrosine phosphatase, non-receptor type 11), SLC2A1 (solute carrier family 2 (facilitated glucose transporter), member 1), IL2RA (interleukin 2 receptor, alpha), CCL5 (chemokine (C-C motif) ligand 5), IRF1 (interferon regulatory factor 1), CFLAR (CASP8 and FADD-like apoptosis regulator), CALCA (calcitonin-related polypeptide alpha), EIF4E (eukaryotic translation initiation factor 4E), GSTP1 (glutathione S-transferase pi 1), JAK2 (Janus kinase 2), CYP3A5 (cytochrome P450, family 3, subfamily A, polypeptide 5), HSPG2 (heparan sulfate proteoglycan 2), CCL3 (chemokine (C-C motif) ligand 3), MYD88 (myeloid differentiation primary response gene (88)), VIP (vasoactive intestinal peptide), SOAT1 (sterol O-acyltransferase 1), ADRBK1 (adrenergic, beta, receptor kinase 1), NR4A2 (nuclear receptor subfamily 4, group A, member 2), MMP8 (matrix metallopeptidase 8 (neutrophil collagenase)), NPR2 (natriuretic peptide receptor B/guanylate cyclase B (atrionatriuretic peptide receptor B)), GCH1 (GTP cyclohydrolase 1), EPRS (glutamyl-prolyl-tRNA synthetase), PPARGC1A (peroxisome proliferator-activated receptor gamma, coactivator 1 alpha), F12 (coagulation factor XII (Hageman factor)), PECAM1 (platelet/endothelial cell adhesion molecule), CCL4 (chemokine (C-C motif) ligand 4), SERPINA3 (serpin peptidase inhibitor, Glade A (alpha-1 antiproteinase, antitrypsin), member 3), CASR (calcium-sensing receptor), GJA5 (gap junction protein, alpha 5, 40 kDa), FABP2 (fatty acid binding protein 2, intestinal), TTF2 (transcription termination factor, RNA polymerase II), PROS1 (protein S (alpha)), CTF1 (cardiotrophin 1), SGCB (sarcoglycan, beta (43 kDa dystrophin-associated glycoprotein)), YME1L1 (YME1-like 1 (*S. cerevisiae*)), CAMP (cathelicidin antimicrobial peptide), ZC3H12A (zinc finger CCCH-type containing 12A), AKR1B1 (aldo-keto reductase family 1, member B1 (aldose reductase)), DES (desmin), MMP7 (matrix metallopeptidase 7 (matrilysin, uterine)), AHR (aryl hydrocarbon receptor), CSF1 (colony stimulating factor 1 (macrophage)), HDAC9 (histone deacetylase 9), CTGF (connective tissue growth factor), KCNMA1 (potassium large conductance calcium-activated channel, subfamily M, alpha member 1), UGT1A (UDP glucuronosyltransferase 1 family, polypeptide A complex locus), PRKCA (protein kinase C, alpha), COMT (catechol-.beta.-methyltransferase), S100B (S100 calcium binding protein B), EGR1 (early growth response 1), PRL (prolactin), IL15 (interleukin 15), DRD4 (dopamine receptor D4), CAMK2G (calcium/calmodulin-dependent protein kinase II gamma), SLC22A2 (solute carrier family 22 (organic cation transporter), member 2), CCL11 (chemokine (C-C motif) ligand 11), PGF (B321 placental growth factor), THPO (thrombopoietin), GP6 (glycoprotein VI (platelet)), TACR1 (tachykinin receptor 1), NTS (neurotensin), HNF1A (HNF1 homeobox A), SST (somatostatin), KCND1 (potassium voltage-gated channel, Shal-related subfamily, member 1), LOC646627 (phospholipase inhibitor), TBXAS1 (thromboxane A synthase 1 (platelet)), CYP2J2 (cytochrome P450, family 2, subfamily J, polypeptide 2), TBXA2R (thromboxane A2 receptor), ADH1C (alcohol dehydrogenase 1C (class I), gamma polypeptide), ALOX12 (arachidonate 12-lipoxygenase), AHSG (alpha-2-HS-glycoprotein), BHMT (betaine-homocysteine methyltransferase), GJA4 (gap junction protein, alpha 4, 37 kDa), SLC25A4 (solute carrier family 25 (mitochondrial carrier; adenine nucleotide translocator), member 4), ACLY (ATP citrate lyase), ALOX5AP (arachidonate 5-lipoxygenase-activating protein), NUMA1 (nuclear mitotic apparatus protein 1), CYP27B1 (cytochrome P450, family 27, subfamily B, polypeptide 1), CYSLTR2 (cysteinyl leukotriene receptor 2), SOD3 (superoxide dismutase 3, extracellular), LTC4S (leukotriene C4 synthase), UCN (urocortin), GHRL (ghrelin/obestatin prepropeptide), APOC2 (apolipoprotein C-II), CLEC4A (C-type lectin domain family 4, member A), KBTBD10 (kelch repeat and BTB (POZ) domain containing 10), TNC (tenascin C), TYMS (thymidylate synthetase), SHC1 (SHC (Src homology 2 domain containing) transforming protein 1), LRP1 (low density lipoprotein receptor-related protein 1), SOCS3 (suppressor of cytokine signaling 3), ADH1B (alcohol dehydrogenase 1B (class I), beta polypeptide), KLK3 (kallikrein-related peptidase 3), HSD11B1 (hydroxysteroid (11-beta) dehydrogenase 1), VKORC1 (vitamin K epoxide reductase complex, subunit 1), SERPINB2 (serpin peptidase inhibitor, Glade B (ovalbumin), member 2), TNS1 (tensin 1), RNF19A (ring finger protein 19A), EPOR (erythropoietin receptor), ITGAM (integrin, alpha M (complement component 3 receptor 3 subunit)), PITX2 (paired-like homeodomain 2), MAPK7 (mitogen-activated protein kinase 7), FCGR3A (Fc fragment of IgG, low affinity 111a, receptor (CD16a)), LEPR (leptin receptor), ENG (endoglin), GPX1 (glutathione peroxidase 1), GOT2 (glutamic-oxaloacetic transaminase 2, mitochondrial (aspartate aminotransferase 2)), HRH1 (histamine receptor H1), NR1I2 (nuclear receptor subfamily 1, group I, member 2), CRH (corticotropin releasing hormone), HTR1A (5-hydroxytryptamine (serotonin) receptor 1A), VDAC1 (voltage-dependent anion channel 1), HPSE (heparanase), SFTPD (surfactant protein D), TAP2 (transporter 2, ATP-binding cassette, sub-family B (MDR/TAP)), RNF123 (ring finger protein 123), PTK2B (PTK2B protein tyrosine kinase 2 beta), NTRK2 (neurotrophic tyrosine kinase, receptor, type 2), IL6R (interleukin 6 receptor), ACHE (acetylcholinesterase (Yt blood group)), GLP1R (glucagon-like peptide 1 receptor), GHR (growth hormone receptor), GSR (glutathione reductase), NQO1 (NAD(P)H dehydrogenase, quinone 1), NR5A1 (nuclear receptor subfamily 5, group A, member 1), GJB2 (gap junction protein, beta 2, 26 kDa), SLC9A1 (solute carrier family 9 (sodium/hydrogen exchanger), member 1), MAOA (monoamine oxidase A), PCSK9 (proprotein convertase subtilisin/kexin type 9), FCGR2A (Fc fragment of IgG, low affinity IIa, receptor (CD32)), SERPINF1 (serpin peptidase inhibitor, Glade F (alpha-2 antiplasmin, pigment epithelium derived factor), member 1), EDN3 (endothelin 3), DHFR (dihydrofolate reductase), GAS6 (growth arrest-specific 6), SMPD1 (sphingomyelin phosphodiesterase 1, acid lysosomal), UCP2 (uncoupling protein 2 (mitochondrial, proton carrier)), TFAP2A (transcription factor AP-2 alpha (activating enhancer binding protein 2 alpha)), C4BPA (complement component 4 binding protein, alpha), SERPINF2 (serpin peptidase inhibitor, Glade F (alpha-2 antiplasmin, pigment epithelium derived factor), member 2), TYMP (thymidine phosphorylase), ALPP (alkaline phosphatase, placental (Regan isozyme)), CXCR2 (chemokine (C-X-C motif) receptor 2), SLC39A3 (solute carrier family 39 (zinc transporter), member 3), ABCG2 (ATP-binding cassette, sub-family G (WHITE), member 2), ADA (adenosine deaminase), JAK3 (Janus kinase 3), HSPA1A (heat shock 70 kDa protein 1A), FASN (fatty acid synthase), FGF1 (fibroblast growth factor 1 (acidic)), F11 (coagulation factor XI), ATP7A (ATPase, Cu++ transporting, alpha polypeptide), CR1 (complement component (3b/4b) receptor 1 (Knops blood group)), GFAP (glial fibrillary acidic protein), ROCK1 (Rho-associated, coiled-coil containing protein kinase 1), MECP2 (methyl CpG binding protein 2 (Rett syndrome)), MYLK (myosin light chain kinase), BCHE (butyrylcholinesterase), LIPE (lipase, hormone-sensitive), PRDX5 (peroxiredoxin 5), ADORA1 (adenosine A1 receptor), WRN (Werner syndrome, RecQ helicase-like), CXCR3 (chemokine (C-X-C motif) receptor 3), CD81 (CD81 molecule), SMAD7 (SMAD family member 7), LAMC2 (laminin, gamma 2), MAP3K5 (mitogen-activated protein kinase kinase kinase 5), CHGA (chromogranin A (parathyroid secretory protein 1)), IAPP (islet amyloid polypeptide), RHO (rhodopsin), ENPP1 (ectonucleotide pyrophosphatase/phosphodiesterase 1), PTHLH (parathyroid hormone-like hormone), NRG1 (neuregulin 1), VEGFC (vascular endothelial growth factor C), ENPEP (glutamyl aminopeptidase (aminopeptidase A)), CEBPB (CCAAT/enhancer binding protein (C/EBP), beta), NAGLU (N-acetylglucosaminidase, alpha-), F2RL3 (coagulation factor II (thrombin) receptor-like 3), CX3CL1 (chemokine (C-X3-C motif) ligand 1), BDKRB1 (bradykinin receptor B1), ADAMTS13 (ADAM metallopeptidase with thrombospondin type 1 motif, 13), ELANE (elastase, neutrophil expressed), ENPP2 (ectonucleotide pyrophosphatase/phosphodiesterase 2), CISH (cytokine inducible SH2-containing protein), GAST (gastrin), MYOC (myocilin, trabecular meshwork inducible glucocorticoid response), ATP1A2 (ATPase, Na+/K+ transporting, alpha 2 polypeptide), NF1 (neurofibromin 1), GJB1 (gap junction protein, beta 1, 32 kDa), MEF2A (myocyte enhancer factor 2A), VCL (vinculin), BMPR2 (bone morphogenetic protein receptor, type II (serine/threonine kinase)), TUBB (tubulin, beta), CDC42 (cell division cycle 42 (GTP binding protein, 25 kDa)), KRT18 (keratin 18), HSF1 (heat shock transcription factor 1), MYB (v-myb myeloblastosis viral oncogene homolog (avian)), PRKAA2 (protein kinase, AMP-activated, alpha 2 catalytic subunit), ROCK2 (Rho-associated, coiled-coil containing protein kinase 2), TFPI (tissue factor pathway inhibitor (lipoprotein-associated coagulation inhibitor)), PRKG1 (protein kinase, cGMP-dependent, type I), BMP2 (bone morphogenetic protein 2), CTNND1 (catenin (cadherin-associated protein), delta 1), CTH (cystathionase (cystathionine gamma-lyase)), CTSS (cathepsin S), VAV2 (vav 2 guanine nucleotide exchange factor), NPY2R (neuropeptide Y receptor Y2), IGFBP2 (insulin-like growth factor binding protein 2, 36 kDa), CD28 (CD28 molecule), GSTA1 (glutathione S-transferase alpha 1), PPIA (peptidylprolyl isomerase A (cyclophilin A)), APOH (apolipoprotein H (beta-2-glycoprotein I)), S100A8 (S100 calcium binding protein A8), IL11 (interleukin 11), ALOX15 (arachidonate 15-lipoxygenase), FBLN1 (fibulin 1), NR1H3 (nuclear receptor subfamily 1, group H, member 3), SCD (stearoyl-CoA desaturase (delta-9-desaturase)), GIP (gastric inhibitory polypeptide), CHGB (chromogranin B (secretogranin 1)), PRKCB (protein kinase C, beta), SRD5A1 (steroid-5-alpha-reductase, alpha polypeptide 1 (3-oxo-5 alpha-steroid delta 4-dehydrogenase alpha 1)), HSD11B2 (hydroxysteroid (11-beta) dehydrogenase 2), CALCRL (calcitonin receptor-like), GALNT2 (UDP-N-acetyl-alpha-D-galactosamine:polypeptide N-acetylgalactosaminyltransferase 2 (GalNAc-T2)), ANGPTL4 (angiopoietin-like 4), KCNN4 (potassium intermediate/small conductance calcium-activated channel, subfamily N, member 4), PIK3C2A (phosphoinositide-3-kinase, class 2, alpha polypeptide), HBEGF (heparin-binding EGF-like growth factor), CYP7A1 (cytochrome P450, family 7, subfamily A, polypeptide 1), HLA-DRB5 (major histocompatibility complex, class II, DR beta 5), BNIP3 (BCL2/adenovirus E1B 19 kDa interacting protein 3), GCKR (glucokinase (hexokinase 4) regulator), S100A12 (S100 calcium binding protein A12), PADI4 (peptidyl arginine deiminase, type IV), HSPA14 (heat shock 70 kDa protein 14), CXCR1 (chemokine (C-X-C motif) receptor 1), H19 (H19, imprinted maternally expressed transcript (non-protein coding)), KRTAP19-3 (keratin associated protein 19-3), IDDM2 (insulin-dependent diabetes mellitus 2), RAC2 (ras-related C3 botulinum toxin substrate 2 (rho family, small GTP binding protein Rac2)), RYR1 (ryanodine receptor 1 (skeletal)), CLOCK (clock homolog (mouse)), NGFR (nerve growth factor receptor (TNFR superfamily, member 16)), DBH (dopamine beta-hydroxylase (dopamine beta-monooxygenase)), CHRNA4 (cholinergic receptor, nicotinic, alpha 4), CACNA1C (calcium channel, voltage-dependent, L type, alpha 1C subunit), PRKAG2 (protein kinase, AMP-activated, gamma 2 non-catalytic subunit), CHAT (choline acetyltransferase), PTGDS (prostaglandin D2 synthase 21 kDa (brain)), NR1H2 (nuclear receptor subfamily 1, group H, member 2), TEK (TEK tyrosine kinase, endothelial), VEGFB (vascular endothelial growth factor B), MEF2C (myocyte enhancer factor 2C), MAPKAPK2 (mitogen-activated protein kinase-activated protein kinase 2), TNFRSF11A (tumor necrosis factor receptor superfamily, member 11a, NFKB activator), HSPA9 (heat shock 70 kDa protein 9 (mortalin)), CYSLTR1 (cysteinyl leukotriene receptor 1), MAT1A (methionine adenosyltransferase I, alpha), OPRL1 (opiate receptor-like 1), IMPA1 (inositol (myo)-1(or 4)-monophosphatase 1), CLCN2 (chloride channel 2), DLD (dihydrolipoamide dehydrogenase), PSMA6 (proteasome (prosome, macropain) subunit, alpha type, 6), PSMB8 (proteasome (prosome, macropain) subunit, beta type, 8 (large multifunctional peptidase 7)), CHI3L1 (chitinase 3-like 1 (cartilage glycoprotein-39)), ALDH1B1 (aldehyde dehydrogenase 1 family, member B1), PARP2 (poly (ADP-ribose) polymerase 2), STAR (steroidogenic acute regulatory protein), LBP (lipopolysaccharide binding protein), ABCC6 (ATP-binding cassette, sub-family C(CFTR/MRP), member 6), RGS2 (regulator of G-protein signaling 2, 24 kDa), EFNB2 (ephrin-B2), GJB6 (gap junction protein, beta 6, 30 kDa), APOA2 (apolipoprotein A-II), AMPD1 (adenosine monophosphate deaminase 1), DYSF (dysferlin, limb girdle muscular dystrophy 2B (autosomal recessive)), FDFT1 (farnesyl-diphosphate farnesyltransferase 1), EDN2 (endothelin 2), CCR6 (chemokine (C-C motif) receptor 6), GJB3 (gap junction protein, beta 3, 31 kDa), IL1RL1 (interleukin 1 receptor-like 1), ENTPD1 (ectonucleoside triphosphate diphosphohydrolase 1), BBS4 (Bardet-Biedl syndrome 4), CELSR2 (cadherin, EGF LAG seven-pass G-type receptor 2 (flamingo homolog, *Drosophila*)), F11R (F11 receptor), RAPGEF3 (Rap guanine nucleotide exchange factor (GEF) 3), HYAL1 (hyaluronoglucosaminidase 1), ZNF259 (zinc finger protein 259), ATOX1 (ATX1 antioxidant protein 1 homolog (yeast)), ATF6 (activating transcription factor 6), KHK (ketohexokinase (fructokinase)), SAT1 (spermidine/spermine N1-acetyltransferase 1), GGH (gamma-glutamyl hydrolase (conjugase, folylpolygammaglutamyl hydrolase)), TIMP4 (TIMP metallopeptidase inhibitor 4), SLC4A4 (solute carrier family 4, sodium bicarbonate cotransporter, member 4), PDE2A (phosphodiesterase 2A, cGMP-stimulated), PDE3B (phosphodiesterase 3B, cGMP-inhibited), FADS1 (fatty acid desaturase 1), FADS2 (fatty acid desaturase 2), TMSB4X (thymosin beta 4, X-linked), TXNIP (thioredoxin interacting protein), LIMS1 (LIM and senescent cell antigen-like domains 1), RHOB (ras homolog gene family, member B), LY96 (lymphocyte antigen 96), FOXO1 (forkhead box 01), PNPLA2 (patatin-like phospholipase domain containing 2), TRH (thyrotropin-releasing hormone), GJC1 (gap junction protein, gamma 1, 45 kDa), SLC17A5 (solute carrier family 17 (anion/sugar transporter), member 5), FTO (fat mass and obesity associated), GJD2 (gap junction protein, delta 2, 36 kDa), PSRC1 (proline/serine-rich coiled-coil 1), CASP12 (caspase 12 (gene/pseudogene)), GPBAR1 (G protein-coupled bile acid receptor 1), PXK (PX domain containing serine/threonine kinase), IL33 (interleukin 33), TRIB1 (tribbles homolog 1 (*Drosophila*)), PBX4 (pre-B-cell leukemia homeobox 4), NUPR1 (nuclear protein, transcriptional regulator, 1), 15-Sep(15 kDa selenoprotein), CILP2 (cartilage intermediate layer protein 2), TERC (telomerase RNA component), GGT2 (gamma-glutamyltransferase 2), MT-CO1 (mitochondrially encoded cytochrome c oxidase I), and UOX (urate oxidase, pseudogene). Any of these sequences, may be a target for the CRISPR-Cas system, e.g., to address mutation.

In an additional embodiment, the chromosomal sequence may further be selected from Pon1 (paraoxonase 1), LDLR (LDL receptor), ApoE (Apolipoprotein E), Apo B-100 (Apolipoprotein B-100), ApoA (Apolipoprotein(a)), ApoA 1 (Apolipoprotein A1), CBS (Cystathionine B-synthase), Glycoprotein IIb/IIb, MTHRF (5,10-methylenetetrahydrofolate reductase (NADPH), and combinations thereof. In one iteration, the chromosomal sequences and proteins encoded by chromosomal sequences involved in cardiovascular disease may be chosen from Cacna1C, Sod1, Pten, Ppar(alpha), Apo E, Leptin, and combinations thereof as target(s) for the CRISPR-Cas system.

Treating Diseases of the Liver and Kidney

The present invention also contemplates delivering the CRISPR-Cas system described herein, e.g. Cpf1 effector protein systems, to the liver and/or kidney. Delivery strategies to induce cellular uptake of the therapeutic nucleic acid include physical force or vector systems such as viral-, lipid- or complex-based delivery, or nanocarriers. From the initial applications with less possible clinical relevance, when nucleic acids were addressed to renal cells with hydrodynamic high pressure injection systemically, a wide range of gene therapeutic viral and non-viral carriers have been applied already to target posttranscriptional events in different animal kidney disease models in vivo (Csaba Révész and Peter Hamar (2011). Delivery Methods to Target RNAs in the Kidney, Gene Therapy Applications, Prof. Chunsheng Kang (Ed.), ISBN: 978-953-307-541-9, InTech, Available from: www.intechopen.com/books/gene-therapy-applications/delivery-methods-to-target-mas-in the-kidney). Delivery methods to the kidney may include those in Yuan et al. (Am J Physiol Renal Physiol 295: F605-F617, 2008) investigated whether in vivo delivery of small interfering RNAs (siRNAs) targeting the 12/15-lipoxygenase (12/15-LO) pathway of arachidonate acid metabolism can ameliorate renal injury and diabetic nephropathy (DN) in a streptozotocin injected mouse model of type 1 diabetes. To achieve greater in vivo access and siRNA expression in the kidney, Yuan et al. used double-stranded 12/15-LO siRNA oligonucleotides conjugated with cholesterol. About 400 µg of siRNA was injected subcutaneously into mice. The method of Yuang et al. may be applied to the CRISPR-Cas system of the present invention contemplating a 1-2 g subcutaneous injection of CRISPR-Cas conjugated with cholesterol to a human for delivery to the kidneys.

Molitoris et al. (J Am Soc Nephrol 20: 1754-1764, 2009) exploited proximal tubule cells (PTCs), as the site of oligonucleotide reabsorption within the kidney to test the efficacy of siRNA targeted to p53, a pivotal protein in the apoptotic pathway, to prevent kidney injury. Naked synthetic siRNA to p53 injected intravenously 4 h after ischemic injury maximally protected both PTCs and kidney function. Molitoris et al.'s data indicates that rapid delivery of siRNA to proximal tubule cells follows intravenous administration. For dose-response analysis, rats were injected with doses of siP53, 0.33; 1, 3, or 5 mg/kg, given at the same four time points, resulting in cumulative doses of 1.32; 4, 12, and 20 mg/kg, respectively. All siRNA doses tested produced a SCr reducing effect on day one with higher doses being effective over approximately five days compared with PBS-treated ischemic control rats. The 12 and 20 mg/kg cumulative doses provided the best protective effect. The method of Molitoris et al. may be applied to the nucleic acid-targeting system of the present invention contemplating 12 and 20 mg/kg cumulative doses to a human for delivery to the kidneys.

Thompson et al. (Nucleic Acid Therapeutics, Volume 22, Number 4, 2012) reports the toxicological and pharmacokinetic properties of the synthetic, small interfering RNA I5NP following intravenous administration in rodents and nonhuman primates. I5NP is designed to act via the RNA interference (RNAi) pathway to temporarily inhibit expression of the pro-apoptotic protein p53 and is being developed to protect cells from acute ischemia/reperfusion injuries such as acute kidney injury that can occur during major cardiac surgery and delayed graft function that can occur following renal transplantation. Doses of 800 mg/kg I5NP in rodents, and 1,000 mg/kg I5NP in nonhuman primates, were required to elicit adverse effects, which in the monkey were isolated to direct effects on the blood that included a sub-clinical activation of complement and slightly increased clotting times. In the rat, no additional adverse effects were observed with a rat analogue of I5NP, indicating that the effects likely represent class effects of synthetic RNA duplexes rather than toxicity related to the intended pharmacologic activity of I5NP. Taken together, these data support clinical testing of intravenous administration of I5NP for the preservation of renal function following acute ischemia/reperfusion injury. The no observed adverse effect level (NOAEL) in the monkey was 500 mg/kg. No effects on cardiovascular, respiratory, and neurologic parameters were observed in monkeys following i.v. administration at dose levels up to 25 mg/kg. Therefore, a similar dosage may be contemplated for intravenous administration of CRISPR-Cas to the kidneys of a human.

Shimizu et al. (J Am Soc Nephrol 21: 622-633, 2010) developed a system to target delivery of siRNAs to glomeruli via poly(ethylene glycol)-poly(L-lysine)-based vehicles. The siRNA/nanocarrier complex was approximately 10 to 20 nm in diameter, a size that would allow it to move across the fenestrated endothelium to access to the mesangium. After intraperitoneal injection of fluorescence-labeled siRNA/nanocarrier complexes, Shimizu et al. detected siRNAs in the blood circulation for a prolonged time. Repeated intraperitoneal administration of a mitogen-activated protein kinase 1 (MAPK1) siRNA/nanocarrier complex suppressed glomerular MAPK1 mRNA and protein expression in a mouse model of glomerulonephritis. For the investigation of siRNA accumulation, Cy5-labeled siRNAs complexed with PIC nanocarriers (0.5 ml, 5 nmol of siRNA content), naked Cy5-labeled siRNAs (0.5 ml, 5 nmol), or Cy5-labeled siRNAs encapsulated in HVJ-E (0.5 ml, 5 nmol of siRNA content) were administered to BALBc mice. The method of Shimizu et al. may be applied to the nucleic acid-targeting system of the present invention contemplating a dose of about of 10-20 μmol CRISPR-Cas complexed with nanocarriers in about 1-2 liters to a human for intraperitoneal administration and delivery to the kidneys.

Delivery Methods to the Kidney are Summarized as Follows:

TABLE 19

| Delivery method | Carrier | Target RNA | Disease | Model | Functional assays | Author |
|---|---|---|---|---|---|---|
| Hydrodynamic/ Lipid | TransIT In Vivo Gene Delivery System, DOTAP | p85α | Acute renal injury | Ischemia-reperfusion | Uptake, biodistribution | Larson et al., Surgery, (August 2007), Vol. 142, No. 2, pp. (262-269) |
| Hydrodynamic/ Lipid | Lipofectamine 2000 | Fas | Acute renal injury | Ischemia-reperfusion | Blood urea nitrogen, Fas Immunohisto chemistry, apoptosis, histological scoring | Hamar et al., Proc Natl Acad Sci, (October 2004), Vol. 101, No. 41, pp. (14883-14888) |
| Hydrodynamic | n.a. | Apoptosis cascade elements | Acute renal injury | Ischemia-reperfusion | n.a. | Zheng et al., Am J Pathol, (October 2008), Vol. 173, No. 4, pp. (973-980) |
| Hydrodynamic | n.a. | Nuclear factor kappa-b (NFkB) | Acute renal injury | Ischemia-reperfusion | n.a. | Feng et al., Transplantation, (May 2009), Vol. 87, No. 9, pp. (1283-1289) |
| Hydrodynamic/ Viral | Lipofectamine 2000 | Apoptosis antagonizing transcription factor (AATF) | Acute renal injury | Ischemia-reperfusion | Apoptosis, oxidative stress, caspase activation, membrane lipid peroxidation | Xie & Guo, Am Soc Nephrol, (December 2006), Vol. 17, No. 12, pp. (3336-3346) |

TABLE 19-continued

| Delivery method | Carrier | Target RNA | Disease | Model | Functional assays | Author |
|---|---|---|---|---|---|---|
| Hydrodynamic | pBAsi mU6 Neo/TransIT-EE Hydrodynamic Delivery System | Gremlin | Diabetic nephropathy | Streptozotozin-induced diabetes | Proteinuria, serum creatinine, glomerular and tubular diameter, collagen type IV/BMP7 expression | Q. Zhang et al., PloS ONE, (July 2010), Vol. 5, No. 7, e11709, pp. (1-13) |
| Viral/Lipid | pSUPER vector/ Lipofectamine | TGF-β type II receptor | Interstitial renal fibrosis | Unilateral urethral obstruction | α-SMA expression, collagen content, | Kushibikia et al., J Controlled Release, (July 2005), Vol. 105, No. 3, pp. (318-331) |
| Viral | Adeno-associated virus-2 | Mineral corticoid receptor | Hypertension caused renal damage | Cold-induced hypertension | blood pressure, serum albumin, serum urea nitrogen, serum creatinine, kidney weight, urinary sodium uptake | Wang et al., Gene Therapy, (July 2006), Vol. 13, No. 14, pp. (1097-1103) |
| Hydrodynamic/ Viral | pU6 vector | Luciferase | n.a. | n.a. | | Kobayashi et al., Journal of Pharmacology and Experimental Therapeutics, (February 2004), Vol. 308, No. 2, pp. (688-693) |
| Lipid | Lipoproteins, albumin | apoB1, apoM | n.a. | n.a. | Uptake, binding affinity to lipoproteins and albumin | Wolfrum et al., Nature Biotechnology, (September 2007), Vol. 25, No. 10, pp. (1149-1157) |
| Lipid | Lipofectamine 2000 | p53 | Acute renal injury | Ischemic and cisplatin-induced acute injury | Histological scoring, apoptosis | Molitoris et al., J Am Soc Nephrol, (August 2009), Vol. 20, No. 8, pp. (1754-1764) |
| Lipid | DOTAP/DOPE, DOTAP/DOPE/ DOPE-PEG2000 | COX-2 | Breast adeno-carcinoma | MDA-MB-231 breast cancer xenograft-bearing mouse | Cell viability, uptake | Mikhaylova et al., Cancer Gene Therapy, (March 2011), Vol. 16, No. 3, pp. (217-226) |
| Lipid | Cholesterol | 12/15-lipoxygenase | Diabetic nephropathy | Streptozotocin-induced diabetes | Albuminuria, urinary creatinine, histology, type I and IV collagen, TGF-β, fibronectin, plasminogen activator inhibitor 1 | Yuan et al., Am J Physiol Renal Physiol, (June 2008), Vol. 295, pp. (F605-F617) |

TABLE 19-continued

| Delivery method | Carrier | Target RNA | Disease | Model | Functional assays | Author |
|---|---|---|---|---|---|---|
| Lipid | Lipofectamine 2000 | Mitochondrial membrane 44 (TIM44) | Diabetic nephropathy | Streptozotocin-induced diabetes | Cell proliferation and apoptosis, histology, ROS, mitochondrial import of Mn-SOD and glutathione peroxidase, cellular membrane polarization | Y. Zhang et al., J Am Soc Nephrol, (April 2006), Vol. 17, No. 4, pp. (1090-1101) |
| Hydrodynamic/ Lipid | Proteoliposome | RLIP76 | Renal carcinoma | Caki-2 kidney cancer xenograft-bearing mouse | uptake | Singhal et al., Cancer Res. (May 2009), Vol. 69, No. 10, pp. (4244-4251) |
| Polymer | PEGylated PEI | Luciferase pGL3 | n.a. | n.a. | Uptake, biodistribution, erythrocyte aggregation | Malek et al., Toxicology and Applied Pharmacology, (April 2009), Vol. 236, No. 1, pp. (97-108) |
| Polymer | PEGylated poly-L-lysine | MAPK1 | Lupus glomerulonephritis | Glomerulonephritis | Proteinuria, glomerulosclerosis, TGF-β, fibronectin, plasminogen activator inhibitor 1 | Shimizu et al., J Am Soc Nephrology, (Apil 2010), Vol. 21, No. 4, pp. (622-633) |
| Polymer/ Nano particle | Hyaluronic acid/ Quantum dot/PEI | VEGF | Kidney cancer/ melanoma | B16F1 melanoma tumor-bearing mouse | Biodistribution, citotoxicity, tumor volume, endocytosis | Jiang et al., Molecular Phaemaceutics, (May-June 2009), Vol. 6, No. 3, pp. (727-737) |
| Polymer/ Nano particle | PEGylated polycaprolactone nanofiber | GAPDH | n.a. | n.a. | cell viability, uptake | Cao et al, J Controlled Release, (June 2010), Vol. 144, No. 2, pp. (203-212) |
| Aptamer | Spiegelmer mNOX-E36 | CC chemokine ligand 2 | Glomerulo sclerosis | Uninephrectomized mouse | urinary albumin, urinary creatinine, histopathology, glomerular filtration rate, macrophage count, scrum Ccl2, Mac-2+, Ki-67+ | Ninichuk et al., Am J Pathol, (March 2008), Vol. 172, No. 3, pp. (628-637) |
| Aptamer | Aptamer NOX-F37 | vasopressin (AVP) | Congestive heart failure | n.a. | Binding affinity to D-AVP, Inhibition of AVP Signaling, Urine osmolality and sodium concentration, | Purschke et al., Proc Natl Acad Sci, (March 2006), Vol. 103, No. 13, pp. (5173-5178) |

Targeting the Liver or Liver Cells

Targeting liver cells is provided. This may be in vitro or in vivo. Hepatocytes are preferred. Delivery of the CRISPR protein, such as Cpf1 herein may be via viral vectors, especially AAV (and in particular AAV2/6) vectors. These may be administered by intravenous injection.

A preferred target for liver, whether in vitro or in vivo, is the albumin gene. This is a so-called 'safe harbor" as albumin is expressed at very high levels and so some reduction in the production of albumin following successful gene editing is tolerated. It is also preferred as the high levels of expression seen from the albumin promoter/enhancer allows for useful levels of correct or transgene production (from the inserted donor template) to be achieved even if only a small fraction of hepatocytes are edited.

Intron 1 of albumin has been shown by Wechsler et al. (reported at the 57th Annual Meeting and Exposition of the American Society of Hematology—abstract available online at ash.confex.com/ash/2015/webprogram/Paper86495.html and presented on 6th December 2015) to be a suitable target site. Their work used Zn Fingers to cut the DNA at this target site, and suitable guide sequences can be generated to guide cleavage at the same site by a CRISPR protein.

The use of targets within highly-expressed genes (genes with highly active enhancers/promoters) such as albumin may also allow a promoterless donor template to be used, as reported by Wechsler et al. and this is also broadly applicable outside liver targeting. Other examples of highly-expressed genes are known.

Other Disease of the Liver

In particular embodiments, the CRISPR proteins of the present invention are used in the treatment of liver disorders such as transthyretin amyloidosis (ATTR), alpha-1 antitrypsin deficiency and other hepatic-based inborn errors of metabolism. FAP is caused by a mutation in the gene that encodes transthyretin (TTR). While it is an autosomal dominant disease, not all carriers develop the disease. There are over 100 mutations in the TTR gene known to be associated with the disease. Examples of common mutations include V30M. The principle of treatment of TTR based on gene silencing has been demonstrated by studies with iRNA (Ueda et al. 2014 Transl Neurogener. 3:19). Wilson's Disease (WD) is caused by mutations in the gene encoding ATP7B, which is found exclusively in the hepatocyte. There are over 500 mutations associated with WD, with increased prevalence in specific regions such as East Asia. Other examples are A1ATD (an autosomal recessive disease caused by mutations in the SERPINA1 gene) and PKU (an autosomal recessive disease caused by mutations in the phenylalanine hydroxylase (PAH) gene).

Liver-Associated Blood Disorders, Especially Hemophilia and in Particular Hemophilia B Successful gene editing of hepatocytes has been achieved in mice (both in vitro and in vivo) and in non-human primates (in vivo), showing that treatment of blood disorders through gene editing/genome engineering in hepatocytes is feasible. In particular, expression of the human F9 (hF9) gene in hepatocytes has been shown in non-human primates indicating a treatment for Hemophilia B in humans.

Wechsler et al. reported at the 57th Annual Meeting and Exposition of the American Society of Hematology (abstract presented 6th December 2015 and available online at ash.confex.com/ash/2015/webprogram/Paper86495.html) that they has successfully expressed human F9 (hF9) from hepatocytes in non-human primates through in vivo gene editing. This was achieved using 1) two zinc finger nucleases (ZFNs) targeting intron 1 of the albumin locus, and 2) a human F9 donor template construct. The ZFNs and donor template were encoded on separate hepatotropic adeno-associated virus serotype 2/6 (AAV2/6) vectors injected intravenously, resulting in targeted insertion of a corrected copy of the hF9 gene into the albumin locus in a proportion of liver hepatocytes.

The albumin locus was selected as a "safe harbor" as production of this most abundant plasma protein exceeds 10 g/day, and moderate reductions in those levels are well-tolerated. Genome edited hepatocytes produced normal hFIX (hF9) in therapeutic quantities, rather than albumin, driven by the highly active albumin enhancer/promoter. Targeted integration of the hF9 transgene at the albumin locus and splicing of this gene into the albumin transcript was shown.

Mice studies: C57BL/6 mice were administered vehicle (n=20) or AAV2/6 vectors (n=25) encoding mouse surrogate reagents at $1.0 \times 10^{13}$ vector genome (vg)/kg via tail vein injection. ELISA analysis of plasma hFIX in the treated mice showed peak levels of 50-1053 ng/mL that were sustained for the duration of the 6-month study. Analysis of FIX activity from mouse plasma confirmed bioactivity commensurate with expression levels.

Non-human primate (NHP) studies: a single intravenous co-infusion of AAV2/6 vectors encoding the NHP targeted albumin-specific ZFNs and a human F9 donor at $1.2 \times 10^{13}$ vg/kg (n=5/group) resulted in >50 ng/mL (>1% of normal) in this large animal model. The use of higher AAV2/6 doses (up to $1.5 \times 10^{14}$ vg/kg) yielded plasma hFIX levels up to 1000 ng/ml (or 20% of normal) in several animals and up to 2000 ng/ml (or 50% of normal) in a single animal, for the duration of the study (3 months).

The treatment was well tolerated in mice and NHPs, with no significant toxicological findings related to AAV2/6 ZFN+donor treatment in either species at therapeutic doses. Sangamo (CA, USA) has since applied to the FDA, and been granted, permission to conduct the world's first human clinical trial for an in vivo genome editing application. This follows on the back of the EMEA's approval of the Glybera gene therapy treatment of lipoprotein lipase deficiency.

Accordingly, it is preferred, in some embodiments, that any or all of the following are used: AAV (especially AAV2/6) vectors, preferably administered by intravenous injection. Albumin as target for gene editing/insertion of transgene/template-especially at intron 1 of albumin; human F9 donor template; and/or a promoterless donor template.

Hemophilia B

Accordingly, in some embodiments, it is preferred that the present invention is used to treat Hemophilia B. As such it is preferred that F9 (Factor IX) is targeted through provision of a suitable guide RNA. The enzyme and the guide may ideally be targeted to the liver where F9 is produced, although they can be delivered together or separately. A template is provided, in some embodiments, and that this is the human F9 gene. It will be appreciated that the hF9 template comprises the wt or 'correct' version of hF9 so that the treatment is effective. In some embodiments, a two-vector system may be used-one vector for the Cpf1 and one vector for the repair template(s). The repair template may include two or more repair templates, for example, two F9 sequences from different mammalian species. In some embodiments, both a mouse and human F9 sequence are provided. This is may be delivered to mice. Yang Yang, John White, McMenamin Deirdre, and Peter Bell, PhD, presenting at 58th Annual American Society of Hematology Meeting (November 2016), report that this increases potency and accuracy. The second vector inserted the human sequence of factor IX into the mouse genome. In some embodiments, the targeted insertion leads to the expression of a chimeric hyperactive factor IX protein. In some embodiments, this is under the control of the native mouse factor IX promoter. Injecting this two-component system (vector 1 and vector 2) into newborn and adult "knock-out" mice at increasing doses led to expression and activity of stable factor IX activity at normal (or even higher) levels for over four months. In the case of treating humans, a native human F9 promoter may be used instead. In some embodiments, the wt phenotype is restored.

In an alternative embodiment, the hemophilia B version of F9 may be delivered so as to create a model organism, cell or cell line (for example a murine or non-human primate model organism, cell or cell line), the model organism, cell or cell line having or carrying the Hemophilia B phenotype, i.e. an inability to produce wt F9.

Hemophilia A

In some embodiments, the F9 (factor IX) gene may be replaced by the F8 (factor VIII) gene described above, leading to treatment of Hemophilia A (through provision of a correct F8 gene) and/or creation of a Hemophilia A model organism, cell or cell line (through provision of an incorrect, Hemophilia A version of the F8 gene).

Hemophilia C

In some embodiments, the F9 (factor IX) gene may be replaced by the F11 (factor XI) gene described above, leading to treatment of Hemophilia C (through provision of a correct F11 gene) and/or creation of a Hemophilia C model organism, cell or cell line (through provision of an incorrect, Hemophilia C version of the F11 gene).

Transthyretin Amyloidosis

Transthyretin is a protein, mainly produced in the liver, present in the serum and CSF which carries thyroxin hormone and retinol binding protein bound to retinol (Vitamin A). Over 120 different mutations can cause Transthyretin amyloidosis (ATTR), a heritable genetic disorder wherein mutant forms of the protein aggregate in tissues, particularly the peripheral nervous system, causing polyneuropathy. Familial amyloid polyneuropathy (FAP) is the most common TTR disorder and, in 2014, was thought to affect 47 per 100,000 people in Europe. A mutation in the TTR gene of Val30Met is thought be the most common mutation, causing an estimated 50% of FAP cases. In the absence a liver transplant, the only known cure to date, the disease is usually fatal within a decade of diagnosis. The majority of cases are monogenic.

In mouse models of ATTR, the TTR gene may be edited in a dose dependent manner by the delivery of CRISPR/Cas9. In some embodiments, the Cpf1 is provided as mRNA. In some embodiments, Cpf1 mRNA and guide RNA are packaged in LNPs. A system comprising Cpf1 mRNA and guide RNA packaged in LNPs achieved up to 60% editing efficiency in the liver, with serum TTR levels being reduced by up to 80%. In some embodiments, therefore, Transthyretin is targeted, in particular correcting for the Val30Met mutation. In some embodiments, therefore, ATTR is treated.

Alpha-1 Antitrypsin Deficiency

Alpha-1 Antitrypsin (A1AT) is a protein produced in the liver which primarily functions to decrease the activity of neutrophil elastase, an enzyme which degrades connective tissue, in the lungs. Alpha-1 Antitrypsin Deficiency (ATTD) is a disease caused by mutation of the SERPINA1 gene, which encodes A1AT. Impaired production of A1AT leads to a gradual degredation of the connective tissue of the lung resulting in emphysema like symptoms.

Several mutations can cause ATTD, though the most common mutations are Glu342Lys (referred to as Z allele, wild-type is referred to as M) or Glu264Val (referred to as the S allele), and each allele contributes equally to the disease state, with two affected alleles resulting in more pronounced pathophysiology. These results not only resulted in degradation of the connective tissue of sensitive organs, such as the lung, but accumulation of the mutants in the liver can result in proteotoxicity. Current treatments focus on the replacement of A1AT by injection of protein retrieved from donated human plasma. In severe cases a lung and/or liver transplant may be considered.

The common variants of the disease are again monogenic. In some embodiments, the SERPINA1 gene is targeted. In some embodiments, the Glu342Lys mutation (referred to as Z allele, wild-type is referred to as M) or the Glu264Val mutation (referred to as the S allele) are corrected for. In some embodiments, therefore, the faulty gene would require replacement by the wild-type functioning gene. In some embodiments, a knockout and repair approach is required, so a repair template is provided. In the case of bi-allelic mutations, in some embodiments only one guide RNA would be required for homozygous mutations, but in the case of heterozygous mutations two guide RNAs may be required. Delivery is, in some embodiments, to the lung or liver.

Inborn Errors of Metabolism

Inborn errors of metabolism (IEMs) are an umbrella group of diseases which affect metabolic processes. In some embodiments, an IEM is to be treated. The majority of these diseases are monogenic in nature (e.g. phenylketonuria) and the pathophysiology results from either the abnormal accumulation of substances which are inherently toxic, or mutations which result in an inability to synthesize essential substances. Depending on the nature of the IEM, CRISPR/Cpf1 may be used to facilitate a knock-out alone, or in combination with replacement of a faulty gene via a repair template. Exemplary diseases that may benefit from CRISPR/Cpf1 technology are, in some embodiments: primary hyperoxaluria type 1 (PHI), argininosuccinic lyase deficiency, ornithine transcarbamylase deficiency, phenylketonuria, or PKU, and maple syrup urine disease.

Treating Epithelial and Lung Diseases

The present invention also contemplates delivering the CRISPR-Cas system described herein, e.g. Cpf1 effector protein systems, to one or both lungs.

Although AAV-2-based vectors were originally proposed for CFTR delivery to CF airways, other serotypes such as AAV-1, AAV-5, AAV-6, and AAV-9 exhibit improved gene transfer efficiency in a variety of models of the lung epithelium (see, e.g., Li et al., Molecular Therapy, vol. 17 no. 12, 2067-277 December 2009). AAV-1 was demonstrated to be ~100-fold more efficient than AAV-2 and AAV-5 at transducing human airway epithelial cells in vitro, 5 although AAV-1 transduced murine tracheal airway epithelia in vivo with an efficiency equal to that of AAV-5. Other studies have shown that AAV-5 is 50-fold more efficient than AAV-2 at gene delivery to human airway epithelium (HAE) in vitro and significantly more efficient in the mouse lung airway epithelium in vivo. AAV-6 has also been shown to be more efficient than AAV-2 in human airway epithelial cells in vitro and murine airways in vivo.8 The more recent isolate, AAV-9, was shown to display greater gene transfer efficiency than AAV-5 in murine nasal and alveolar epithelia in vivo with gene expression detected for over 9 months suggesting AAV may enable long-term gene expression in vivo, a desirable property for a CFTR gene delivery vector.

Furthermore, it was demonstrated that AAV-9 could be readministered to the murine lung with no loss of CFTR expression and minimal immune consequences. CF and non-CF HAE cultures may be inoculated on the apical surface with 100 µl of AAV vectors for hours (see, e.g., Li et al., Molecular Therapy, vol. 17 no. 12, 2067-277 December 2009). The MOI may vary from $1\times10^3$ to $4\times10^5$ vector genomes/cell, depending on virus concentration and purposes of the experiments. The above cited vectors are contemplated for the delivery and/or administration of the invention.

Zamora et al. (Am J Respir Crit Care Med Vol 183. pp 531-538, 2011) reported an example of the application of an RNA interference therapeutic to the treatment of human infectious disease and also a randomized trial of an antiviral drug in respiratory syncytial virus (RSV)-infected lung transplant recipients. Zamora et al. performed a randomized, double-blind, placebo controlled trial in LTX recipients with RSV respiratory tract infection. Patients were permitted to receive standard of care for RSV. Aerosolized ALN-RSV01 (0.6 mg/kg) or placebo was administered daily for 3 days. This study demonstrates that an RNAi therapeutic targeting RSV can be safely administered to LTX recipients with RSV infection. Three daily doses of ALN-RSV01 did not result in any exacerbation of respiratory tract symptoms or impairment of lung function and did not exhibit any systemic proinflammatory effects, such as induction of cytokines or CRP. Pharmacokinetics showed only low, transient systemic exposure after inhalation, consistent with preclinical animal data showing that ALN-RSV01, administered intravenously or by inhalation, is rapidly cleared from the circulation through exonuclease mediated digestion and renal excretion. The method of Zamora et al. may be applied to the nucleic acid-targeting system of the present invention and an aerosolized CRISPR-Cas, for example with a dosage of 0.6 mg/kg, may be contemplated for the present invention.

Subjects treated for a lung disease may for example receive pharmaceutically effective amount of aerosolized AAV vector system per lung endobronchially delivered while spontaneously breathing. As such, aerosolized delivery is preferred for AAV delivery in general. An adenovirus or an AAV particle may be used for delivery. Suitable gene constructs, each operably linked to one or more regulatory sequences, may be cloned into the delivery vector. In this instance, the following constructs are provided as examples: CBh or EF1α promoter for Cas (Cpf1), U6 or H1 promoter for guide RNA),: A preferred arrangement is to use a CFTRdelta508 targeting guide, a repair template for deltaF508 mutation and a codon optimized Cpf1 enzyme, with optionally one or more nuclear localization signal or sequence(s) (NLS(s)), e.g., two (2) NLSs. Constructs without NLS are also envisaged.

Treating Diseases of the Muscular System

The present invention also contemplates delivering the CRISPR-Cas system described herein, e.g. Cpf1 effector protein systems, to muscle(s).

Bortolanza et al. (Molecular Therapy vol. 19 no. 11, 2055-264 November 2011) shows that systemic delivery of RNA interference expression cassettes in the FRG1 mouse, after the onset of facioscapulohumeral muscular dystrophy (FSHD), led to a dose-dependent long-term FRG1 knockdown without signs of toxicity. Bortolanza et al. found that a single intravenous injection of $5\times10^{12}$ vg of rAAV6-sh1FRG1 rescues muscle histopathology and muscle function of FRG1 mice. In detail, 200 containing $2\times10^{12}$ or $5\times10^{12}$ vg of vector in physiological solution were injected into the tail vein using a 25-gauge Terumo syringe. The method of Bortolanza et al. may be applied to an AAV expressing CRISPR-Cas and injected into humans at a dosage of about $2\times10^{15}$ or $2\times10^{16}$ vg of vector.

Dumonceaux et al. (Molecular Therapy vol. 18 no. 5, 881-887 May 2010) inhibit the myostatin pathway using the technique of RNA interference directed against the myostatin receptor AcvRIIb mRNA (sh-AcvRIIb). The restoration of a quasi-dystrophin was mediated by the vectorized U7 exon-skipping technique (U7-DYS). Adeno-associated vectors carrying either the sh-AcvrIIh construct alone, the U7-DYS construct alone, or a combination of both constructs were injected in the tibialis anterior (TA) muscle of dystrophic mdx mice. The injections were performed with $10^{11}$ AAV viral genomes. The method of Dumonceaux et al. may be applied to an AAV expressing CRISPR-Cas and injected into humans, for example, at a dosage of about $10^{14}$ to about $10^{15}$ vg of vector.

Kinouchi et al. (Gene Therapy (2008) 15, 1126-1130) report the effectiveness of in vivo siRNA delivery into skeletal muscles of normal or diseased mice through nanoparticle formation of chemically unmodified siRNAs with atelocollagen (ATCOL). ATCOL-mediated local application of siRNA targeting myostatin, a negative regulator of skeletal muscle growth, in mouse skeletal muscles or intravenously, caused a marked increase in the muscle mass within a few weeks after application. These results imply that ATCOL-mediated application of siRNAs is a powerful tool for future therapeutic use for diseases including muscular atrophy. Mst-siRNAs (final concentration, 10 mM) were mixed with ATCOL (final concentration for local administration, 0.5%) (AteloGene, Kohken, Tokyo, Japan) according to the manufacturer's instructions. After anesthesia of mice (20-week-old male C57BL/6) by Nembutal (25 mg/kg, i.p.), the Mst-siRNA/ATCOL complex was injected into the masseter and biceps femoris muscles. The method of Kinouchi et al. may be applied to CRISPR-Cas and injected into a human, for example, at a dosage of about 500 to 1000 ml of a 40 µM solution into the muscle. Hagstrom et al. (Molecular Therapy Vol. 10, No. 2, August 2004) describe an intravascular, nonviral methodology that enables efficient and repeatable delivery of nucleic acids to muscle cells (myofibers) throughout the limb muscles of mammals. The procedure involves the injection of naked plasmid DNA or siRNA into a distal vein of a limb that is transiently isolated by a tourniquet or blood pressure cuff. Nucleic acid delivery to myofibers is facilitated by its rapid injection in sufficient volume to enable extravasation of the nucleic acid solution into muscle tissue. High levels of transgene expression in skeletal muscle were achieved in both small and large animals with minimal toxicity. Evidence of siRNA delivery to limb muscle was also obtained. For plasmid DNA intravenous injection into a rhesus monkey, a threeway stopcock was connected to two syringe pumps (Model PHD 2000; Harvard Instruments), each loaded with a single syringe. Five minutes after a papaverine injection, pDNA (15.5 to 25.7 mg in 40-100 ml saline) was injected at a rate of 1.7 or 2.0 ml/s. This could be scaled up for plasmid DNA expressing CRISPR-Cas of the present invention with an injection of about 300 to 500 mg in 800 to 2000 ml saline for a human. For adenoviral vector injections into a rat, $2\times10^9$ infectious particles were injected in 3 ml of normal saline solution (NSS). This could be scaled up for an adenoviral vector expressing CRISPR-Cas of the present invention with an injection of about $1\times10^{13}$ infectious particles were injected in 10 liters of NSS for a human. For siRNA, a rat was injected into the great saphenous vein with 12.5 µg of a siRNA and a primate was injected into the great saphenous vein with 750 µg of a siRNA. This could be scaled up for a CRISPR-Cas of the present invention, for example, with an injection of about 15 to about 50 mg into the great saphenous vein of a human.

See also, for example, WO2013163628 A2, Genetic Correction of Mutated Genes, published application of Duke University describes efforts to correct, for example, a frameshift mutation which causes a premature stop codon and a truncated gene product that can be corrected via nuclease mediated non-homologous end joining such as those responsible for Duchenne Muscular Dystrophy, ("DMD") a recessive, fatal, X-linked disorder that results in muscle degeneration due to mutations in the dystrophin gene. The majority of dystrophin mutations that cause DMD are deletions of exons that disrupt the reading frame and cause premature translation termination in the dystrophin gene. Dystrophin is a cytoplasmic protein that provides structural stability to the dystroglycan complex of the cell membrane that is responsible for regulating muscle cell integrity and function. The dystrophin gene or "DMD gene" as used interchangeably herein is 2.2 megabases at locus Xp21. The primary transcription measures about 2,400 kb with the mature mRNA being about 14 kb. 79 exons code for the protein which is over 3500 amino acids. Exon 51 is frequently adjacent to frame-disrupting deletions in DMD patients and has been targeted in clinical trials for oligonucleotide-based exon skipping. A clinical trial for the exon 51 skipping compound eteplirsen recently reported a significant functional benefit across 48 weeks, with an average of 47% dystrophin positive fibers compared to baseline. Mutations in exon 51 are ideally suited for permanent correction by NHEJ-based genome editing.

The methods of US Patent Publication No. 20130145487 assigned to Cellectis, which relates to meganuclease variants to cleave a target sequence from the human dystrophin gene (DMD), may also be modified to for the nucleic acid-targeting system of the present invention.

Treating Diseases of the Skin

The present invention also contemplates delivering the CRISPR-Cas system described herein, e.g. Cpf1 effector protein systems, to the skin.

Hickerson et al. (Molecular Therapy—Nucleic Acids (2013) 2, e129) relates to a motorized microneedle array skin delivery device for delivering self-delivery (sd)-siRNA to human and murine skin. The primary challenge to translating siRNA-based skin therapeutics to the clinic is the development of effective delivery systems. Substantial effort has been invested in a variety of skin delivery technologies with limited success. In a clinical study in which skin was treated with siRNA, the exquisite pain associated with the hypodermic needle injection precluded enrollment of additional patients in the trial, highlighting the need for improved, more "patient-friendly" (i.e., little or no pain) delivery approaches. Microneedles represent an efficient way to deliver large charged cargos including siRNAs across the primary barrier, the stratum corneum, and are generally regarded as less painful than conventional hypodermic needles. Motorized "stamp type" microneedle devices, including the motorized microneedle array (MMNA) device used by Hickerson et al., have been shown to be safe in hairless mice studies and cause little or no pain as evidenced by (i) widespread use in the cosmetic industry and (ii) limited testing in which nearly all volunteers found use of the device to be much less painful than a flu shot, suggesting siRNA delivery using this device will result in much less pain than was experienced in the previous clinical trial using hypodermic needle injections. The MMNA device (marketed as Triple-M or Tri-M by Bomtech Electronic Co, Seoul, South Korea) was adapted for delivery of siRNA to mouse and human skin. sd-siRNA solution (up to 300 µl of 0.1 mg/ml RNA) was introduced into the chamber of the disposable Tri-M needle cartridge (Bomtech), which was set to a depth of 0.1 mm. For treating human skin, deidentified skin (obtained immediately following surgical procedures) was manually stretched and pinned to a cork platform before treatment. All intradermal injections were performed using an insulin syringe with a 28-gauge 0.5-inch needle. The MMNA device and method of Hickerson et al. could be used and/or adapted to deliver the CRISPR-Cas of the present invention, for example, at a dosage of up to 300 µl of 0.1 mg/ml CRISPR-Cas to the skin.

Leachman et al. (Molecular Therapy, vol. 18 no. 2, 442-446 February 2010) relates to a phase Ib clinical trial for treatment of a rare skin disorder pachyonychia congenita (PC), an autosomal dominant syndrome that includes a disabling plantar keratoderma, utilizing the first short-interfering RNA (siRNA)-based therapeutic for skin. This siRNA, called TD101, specifically and potently targets the keratin 6a (K6a) N171K mutant mRNA without affecting wild-type K6a mRNA.

Zheng et al. (PNAS, Jul. 24, 2012, vol. 109, no. 30, 11975-11980) show that spherical nucleic acid nanoparticle conjugates (SNA-NCs), gold cores surrounded by a dense shell of highly oriented, covalently immobilized siRNA, freely penetrate almost 100% of keratinocytes in vitro, mouse skin, and human epidermis within hours after application. Zheng et al. demonstrated that a single application of 25 nm epidermal growth factor receptor (EGFR) SNA-NCs for 60 h demonstrate effective gene knockdown in human skin. A similar dosage may be contemplated for CRISPR-Cas immobilized in SNA-NCs for administration to the skin.

Cancer

In some embodiments, the treatment, prophylaxis or diagnosis of cancer is provided. The target is preferably one or more of the FAS, BID, CTLA4, PDCD1, CBLB, PTPN6, TRAC or TRBC genes. The cancer may be one or more of lymphoma, chronic lymphocytic leukemia (CLL), B cell acute lymphocytic leukemia (B-ALL), acute lymphoblastic leukemia, acute myeloid leukemia, non-Hodgkin's lymphoma (NHL), diffuse large cell lymphoma (DLCL), multiple myeloma, renal cell carcinoma (RCC), neuroblastoma, colorectal cancer, breast cancer, ovarian cancer, melanoma, sarcoma, prostate cancer, lung cancer, esophageal cancer, hepatocellular carcinoma, pancreatic cancer, astrocytoma, mesothelioma, head and neck cancer, and medulloblastoma. This may be implemented with engineered chimeric antigen receptor (CAR) T cell. This is described in WO2015161276, the disclosure of which is hereby incorporated by reference and described herein below.

Target genes suitable for the treatment or prophylaxis of cancer may include, in some embodiments, those described in WO2015048577 the disclosure of which is hereby incorporated by reference.

Usher Syndrome or Retinitis Pigmentosa-39

In some embodiments, the treatment, prophylaxis or diagnosis of Usher Syndrome or retinitis pigmentosa-39 is provided. The target is preferably the USH2A gene. In some embodiments, correction of a G deletion at position 2299 (2299delG) is provided. This is described in WO2015134812A1, the disclosure of which is hereby incorporated by reference.

Autoimmune and Inflammatory Disorders

In some embodiments, autoimmune and inflammatory disorders are treated. These include Multiple Sclerosis (MS) or Rheumatoid Arthritis (RA), for example.

Cystic Fibrosis (CF)

In some embodiments, the treatment, prophylaxis or diagnosis of cystic fibrosis is provided. The target is preferably the SCNN1A or the CFTR gene. This is described in WO2015157070, the disclosure of which is hereby incorporated by reference.

Schwank et al. (Cell Stem Cell, 13:653-58, 2013) used CRISPR-Cas9 to correct a defect associated with cystic fibrosis in human stem cells. The team's target was the gene for an ion channel, cystic fibrosis transmembrane conductor receptor (CFTR). A deletion in CFTR causes the protein to misfold in cystic fibrosis patients. Using cultured intestinal stem cells developed from cell samples from two children with cystic fibrosis, Schwank et al. were able to correct the defect using CRISPR along with a donor plasmid containing the reparative sequence to be inserted. The researchers then grew the cells into intestinal "organoids," or miniature guts, and showed that they functioned normally. In this case, about half of clonal organoids underwent the proper genetic correction.

In some embodiments, Cystic fibrosis is treated, for example. Delivery to the lungs is therefore preferred. The F508 mutation (delta-F508, full name CFTRAF508 or F508del-CFTR) is preferably corrected. In some embodiments, the targets may be ABCC7, CF or MRP7.

Duchenne's Muscular Dystrophy

Duchenne's muscular dystrophy (DMD) is a recessive, sex-linked muscle wasting disease that affects approximately 1 in 5000 males at birth. Mutations of the dystrophin gene result in an absence of dystrophin in skeletal muscle, where it normally functions to connect the cytoskeleton of the muscle fiber to the basal lamina. The absence of dystrophin caused be these mutations results in excessive calcium entry into the soma which causes the mitochondria to rupture, destroying the cell. Current treatments are focused on easing the symptoms of DMD, and the average life expectancy is approximately 26 years.

CRISPR/Cas9 efficacy as a treatment for certain types of DMD has been demonstrated in mouse models. In one such study, the muscular dystrophy phenotype was partially corrected in the mouse by knocking-out a mutant exon resulting in a functional protein (see Nelson et al. (2016) Science, Long et al. (2016) Science, and Tabebordbar et al. (2016) Science).

In some embodiments, DMD is treated. In some embodiments, delivery is to the muscle by injection.

Glycogen Storage Diseases, Including 1a

Glycogen Storage Disease 1a is a genetic disease resulting from deficiency of the enzyme glucose-6-phosphatase. The deficiency impairs the ability of the liver to produce free glucose from glycogen and from gluconeogenesis. In some embodiments, the gene encoding the glucose-6-phosphatase enzyme is targeted. In some embodiments, Glycogen Storage Disease 1a is treated. In some embodiments, delivery is to the liver by encapsulation of the Cpf1 (in protein or mRNA form) in a lipid particle, such as an LNP.

In some embodiments, Glycogen Storage Diseases, including 1a, are targeted and preferably treated, for example by targeting polynucleotides associated with the condition/disease/infection. The associated polynucleotides include DNA, which may include genes (where genes include any coding sequence and regulatory elements such as enhancers or promoters). In some embodiments, the associated polynucleotides may include the SLC2A2, GLUT2, G6PC, G6PT, G6PT1, GAA, LAMP2, LAMPB, AGL, GDE, GBE1, GYS2, PYGL, or PFKM genes.

Hurler Syndrome

Hurler syndrome, also known as mucopolysaccharidosis type I (MPS I), Hurler's disease, is a genetic disorder that results in the buildup of glycosaminoglycans (formerly known as mucopolysaccharides) due to a deficiency of alpha-L iduronidase, an enzyme responsible for the degradation of mucopolysaccharides in lysosomes. Hurler syndrome is often classified as a lysosomal storage disease, and is clinically related to Hunter Syndrome. Hunter syndrome is X-linked while Hurler syndrome is autosomal recessive. MPS I is divided into three subtypes based on severity of symptoms. All three types result from an absence of, or insufficient levels of, the enzyme α-L-iduronidase. MPS I H or Hurler syndrome is the most severe of the MPS I subtypes. The other two types are MPS I S or Scheie syndrome and MPS I H-S or Hurler-Scheie syndrome. Children born to an MPS I parent carry a defective IDUA gene, which has been mapped to the 4p16.3 site on chromosome 4. The gene is named IDUA because of its iduronidase enzyme protein product. As of 2001, 52 different mutations in the IDUA gene have been shown to cause Hurler syndrome. Successful treatment of the mouse, dog, and cat models of MPS I by delivery of the iduronidase gene through retroviral, lentiviral, AAV, and even nonviral vectors.

In some embodiments, the α-L-iduronidase gene is targeted and a repair template preferably provided.

HIV and AIDS

In some embodiments, the treatment, prophylaxis or diagnosis of HIV and AIDS is provided. The target is preferably the CCR5 gene in HIV. This is described in WO2015148670A1, the disclosure of which is hereby incorporated by reference.

Beta Thalassaemia

In some embodiments, the treatment, prophylaxis or diagnosis of Beta Thalassaemia is provided. The target is preferably the BCL11A gene. This is described in WO2015148860, the disclosure of which is hereby incorporated by reference.

Sickle Cell Disease (SCD)

In some embodiments, the treatment, prophylaxis or diagnosis of Sickle Cell Disease (SCD) is provided. The target is preferably the HBB or BCL11A gene. This is described in WO2015148863, the disclosure of which is hereby incorporated by reference.

Herpes Simplex Virus 1 and 2

Herpesviridae are a family of viruses composed of linear double-stranded DNA genomes with 75-200 genes. For the purposes of gene editing, the most commonly studied family member is Herpes Simplex Virus-1 (HSV-1), a virus which has a distinct number of advantages over other viral vectors (reviewed in Vannuci et al. (2003)). Thus, in some embodiments, the viral vector is an HSV viral vector. In some embodiments, the HSV viral vector is HSV-1.

HSV-1 has a large genome of approximately 152 kb of double stranded DNA. This genome comprises of more than 80 genes, many of which can be replaced or removed, allowing a gene insert of between 30-150 kb. The viral vectors derived from HSV-1 are generally separated into 3 groups: replication-competent attenuated vectors, replication-incompetent recombinant vectors, and defective helper-dependent vectors known as amplicons. Gene transfer using HSV-1 as a vector has been demonstrated previously, for instance for the treatment of neuropathic pain (see, e.g., Wolfe et al. (2009) Gene Ther) and rheumatoid arthritis (see e.g., Burton et al. (2001) Stem Cells).

Thus, in some embodiments, the viral vector is an HSV viral vector. In some embodiments, the HSV viral vector is HSV-1. In some embodiments, the vector is used for delivery of one or more CRISPR components. It may be particularly useful for delivery of the Cpf1 and one or more guide RNAs, for example 2 or more, 3 or more, or 4 or more guide RNAs. In some embodiments, the vector is therefore useful in a multiplex system. In some embodiments, this delivery is for the treatment of treatment of neuropathic pain or rheumatoid arthritis.

In some embodiments, the treatment, prophylaxis or diagnosis of HSV-1 (Herpes Simplex Virus 1) is provided. The target is preferably the UL19, UL30, UL48 or UL50 gene in HSV-1. This is described in WO2015153789, the disclosure of which is hereby incorporated by reference.

In other embodiments, the treatment, prophylaxis or diagnosis of HSV-2 (Herpes Simplex Virus 2) is provided. The target is preferably the UL19, UL30, UL48 or UL50 gene in HSV-2. This is described in WO2015153791, the disclosure of which is hereby incorporated by reference.

In some embodiments, the treatment, prophylaxis or diagnosis of Primary Open Angle Glaucoma (POAG) is provided. The target is preferably the MYOC gene. This is described in WO2015153780, the disclosure of which is hereby incorporated by reference.

Adoptive Cell Therapies

The present invention also contemplates use of the CRISPR-Cas system described herein, e.g. Cpf1 effector protein systems, to modify cells for adoptive therapies. Aspects of the invention accordingly involve the adoptive transfer of immune system cells, such as T cells, specific for selected antigens, such as tumor associated antigens (see Maus et al., 2014, Adoptive Immunotherapy for Cancer or Viruses, Annual Review of Immunology, Vol. 32: 189-225; Rosenberg and Restifo, 2015, Adoptive cell transfer as personalized immunotherapy for human cancer, Science Vol. 348 no. 6230 pp. 62-68; and, Restifo et al., 2015, Adoptive immunotherapy for cancer: harnessing the T cell response. Nat. Rev. Immunol. 12(4): 269-281; and Jenson and Riddell, 2014, Design and implementation of adoptive therapy with chimeric antigen receptor-modified T cells. Immunol Rev. 257(1): 127-144). Various strategies may for example be employed to genetically modify T cells by altering the specificity of the T cell receptor (TCR) for example by introducing new TCR α and β chains with selected peptide specificity (see U.S. Pat. No. 8,697,854; PCT Patent Publications: WO2003020763, WO2004033685, WO2004044004, WO2005114215, WO2006000830, WO2008038002, WO2008039818, WO2004074322, WO2005113595, WO2006125962, WO2013166321, WO2013039889, WO2014018863, WO2014083173; U.S. Pat. No. 8,088,379).

As an alternative to, or addition to, TCR modifications, chimeric antigen receptors (CARs) may be used in order to generate immunoresponsive cells, such as T cells, specific for selected targets, such as malignant cells, with a wide variety of receptor chimera constructs having been described (see U.S. Pat. Nos. 5,843,728; 5,851,828; 5,912,170; 6,004,811; 6,284,240; 6,392,013; 6,410,014; 6,753,162; 8,211,422; and, PCT Publication WO9215322). Alternative CAR constructs may be characterized as belonging to successive generations. First-generation CARs typically consist of a single-chain variable fragment of an antibody specific for an antigen, for example comprising a VL linked to a VH of a specific antibody, linked by a flexible linker, for example by a CD8α hinge domain and a CD8α transmembrane domain, to the transmembrane and intracellular signaling domains of either CD3ζ or FcRγ (scFv-CD3ζ or scFv-FcRγ; see U.S. Pat. Nos. 7,741,465; 5,912,172; 5,906,936). Second-generation CARs incorporate the intracellular domains of one or more costimulatory molecules, such as CD28, OX40 (CD134), or 4-1BB (CD137) within the endodomain (for example scFv-CD28/OX40/4-1BB-CD3ζ; see U.S. Pat. Nos. 8,911,993; 8,916,381; 8,975,071; 9,101,584; 9,102,760; 9,102,761). Third-generation CARS include a combination of costimulatory endodomains, such a CD3ζ-chain, CD97, GDI la-CD18, CD2, ICOS, CD27, CD154, CD5, OX40, 4-1BB, or CD28 signaling domains (for example scFv-CD28-4-1BB-CD3ζ or scFv-CD28-OX40-CD3ζ; see U.S. Pat. Nos. 8,906,682; 8,399,645; 5,686,281; PCT Publication No. WO2014134165; PCT Publication No. WO2012079000). Alternatively, costimulation may be orchestrated by expressing CARS in antigen-specific T cells, chosen so as to be activated and expanded following engagement of their native αβTCR, for example by antigen on professional antigen-presenting cells, with attendant costimulation. In addition, additional engineered receptors may be provided on the immunoresponsive cells, for example to improve targeting of a T-cell attack and/or minimize side effects.

Alternative techniques may be used to transform target immunoresponsive cells, such as protoplast fusion, lipofection, transfection or electroporation. A wide variety of vectors may be used, such as retroviral vectors, lentiviral vectors, adenoviral vectors, adeno-associated viral vectors, plasmids or transposons, such as a Sleeping Beauty transposon (see U.S. Pat. Nos. 6,489,458; 7,148,203; 7,160,682; 7,985,739; 8,227,432), may be used to introduce CARs, for example using 2nd generation antigen-specific CARs signaling through CD3ζ and either CD28 or CD137. Viral vectors may for example include vectors based on HIV, SV40, EBV, HSV or BPV.

Cells that are targeted for transformation may for example include T cells, Natural Killer (NK) cells, cytotoxic T lymphocytes (CTL), regulatory T cells, human embryonic stem cells, tumor-infiltrating lymphocytes (TIL) or a pluripotent stem cell from which lymphoid cells may be differentiated. T cells expressing a desired CAR may for example be selected through co-culture with γ-irradiated activating and propagating cells (AaPC), which co-express the cancer antigen and co-stimulatory molecules. The engineered CAR T-cells may be expanded, for example by co-culture on AaPC in presence of soluble factors, such as IL-2 and IL-21. This expansion may for example be carried out so as to provide memory CAR+ T cells (which may for example be assayed by non-enzymatic digital array and/or multi-panel flow cytometry). In this way, CAR T cells may be provided that have specific cytotoxic activity against antigen-bearing tumors (optionally in conjunction with production of desired chemokines such as interferon-γ). CAR T cells of this kind may for example be used in animal models, for example to threat tumor xenografts.

Approaches such as the foregoing may be adapted to provide methods of treating and/or increasing survival of a subject having a disease, such as a neoplasia, for example by administering an effective amount of an immunoresponsive cell comprising an antigen recognizing receptor that binds a selected antigen, wherein the binding activates the immunoresponsive cell, thereby treating or preventing the disease (such as a neoplasia, a pathogen infection, an autoimmune disorder, or an allogeneic transplant reaction). Dosing in CAR T cell therapies may for example involve administration of from 106 to 109 cells/kg, with or without a course of lymphodepletion, for example with cyclophosphamide.

In one embodiment, the treatment can be administrated into patients undergoing an immunosuppressive treatment. The cells or population of cells, may be made resistant to at least one immunosuppressive agent due to the inactivation of a gene encoding a receptor for such immunosuppressive agent. Not being bound by a theory, the immunosuppressive treatment should help the selection and expansion of the immunoresponsive or T cells according to the invention within the patient.

The administration of the cells or population of cells according to the present invention may be carried out in any convenient manner, including by aerosol inhalation, injection, ingestion, transfusion, implantation or transplantation. The cells or population of cells may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of 104-109 cells per kg body weight, preferably 105 to 106 cells/kg body weight including all integer values of cell numbers within those ranges. Dosing in CAR T cell therapies may for example involve administration of from 106 to 109 cells/kg, with or without a course of lymphodepletion, for example with cyclophosphamide. The cells or population of cells can be administrated in one or more doses. In another embodiment, the effective amount of cells are administrated as a single dose. In another embodiment, the effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions are within the skill of one in the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, the effective amount of cells or composition comprising those cells are administrated parenterally. The administration can be an intravenous administration. The administration can be directly done by injection within a tumor.

To guard against possible adverse reactions, engineered immunoresponsive cells may be equipped with a transgenic safety switch, in the form of a transgene that renders the cells vulnerable to exposure to a specific signal. For example, the herpes simplex viral thymidine kinase (TK) gene may be used in this way, for example by introduction into allogeneic T lymphocytes used as donor lymphocyte infusions following stem cell transplantation (Greco, et al., Improving the safety of cell therapy with the TK-suicide gene. Front. Pharmacol. 2015; 6: 95). In such cells, administration of a nucleoside prodrug such as ganciclovir or acyclovir causes cell death. Alternative safety switch constructs include inducible caspase 9, for example triggered by administration of a small-molecule dimerizer that brings together two nonfunctional icasp9 molecules to form the active enzyme. A wide variety of alternative approaches to implementing cellular proliferation controls have been described (see U.S. Patent Publication No. 20130071414; PCT Patent Publication WO2011146862; PCT Patent Publication WO2014011987; PCT Patent Publication WO2013040371; Zhou et al. BLOOD, 2014, 123/25:3895-3905; Di Stasi et al., The New England Journal of Medicine 2011; 365:1673-1683; Sadelain M, The New England Journal of Medicine 2011; 365:1735-173; Ramos et al., Stem Cells 28(6):1107-15 (2010)).

In a further refinement of adoptive therapies, genome editing with a CRISPR-Cas system as described herein may be used to tailor immunoresponsive cells to alternative implementations, for example providing edited CAR T cells (see Poirot et al., 2015, Multiplex genome edited T-cell manufacturing platform for "off-the-shelf" adoptive T-cell immunotherapies, Cancer Res 75 (18): 3853). For example, immunoresponsive cells may be edited to delete expression of some or all of the class of HLA type II and/or type I molecules, or to knockout selected genes that may inhibit the desired immune response, such as the PD1 gene.

Cells may be edited using any CRISPR system and method of use thereof as described herein. CRISPR systems may be delivered to an immune cell by any method described herein. In preferred embodiments, cells are edited ex vivo and transferred to a subject in need thereof. Immunoresponsive cells, CAR T cells or any cells used for adoptive cell transfer may be edited. Editing may be performed to eliminate potential alloreactive T-cell receptors (TCR), disrupt the target of a chemotherapeutic agent, block an immune checkpoint, activate a T cell, and/or increase the differentiation and/or proliferation of functionally exhausted or dysfunctional CD8+ T-cells (see PCT Patent Publications: WO2013176915, WO2014059173, WO2014172606, WO2014184744, and WO2014191128). Editing may result in inactivation of a gene.

By inactivating a gene it is intended that the gene of interest is not expressed in a functional protein form. In a particular embodiment, the CRISPR system specifically catalyzes cleavage in one targeted gene thereby inactivating said targeted gene. The nucleic acid strand breaks caused are commonly repaired through the distinct mechanisms of homologous recombination or non-homologous end joining (NHEJ). However, NHEJ is an imperfect repair process that often results in changes to the DNA sequence at the site of the cleavage. Repair via non-homologous end joining (NHEJ) often results in small insertions or deletions (Indel) and can be used for the creation of specific gene knockouts. Cells in which a cleavage induced mutagenesis event has occurred can be identified and/or selected by well-known methods in the art.

T cell receptors (TCR) are cell surface receptors that participate in the activation of T cells in response to the presentation of antigen. The TCR is generally made from two chains, α and β, which assemble to form a heterodimer and associates with the CD3ζ-transducing subunits to form the T cell receptor complex present on the cell surface. Each α and β chain of the TCR consists of an immunoglobulin-like N-terminal variable (V) and constant (C) region, a hydrophobic transmembrane domain, and a short cytoplasmic region. As for immunoglobulin molecules, the variable region of the α and β chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of graft versus host disease (GVHD). The inactivation of TCRα or TCRβ can result in the elimination of the TCR from the surface of T cells preventing recognition of alloantigen and thus GVHD. However, TCR disruption generally results in the elimination of the CD3 signaling component and alters the means of further T cell expansion.

Allogeneic cells are rapidly rejected by the host immune system. It has been demonstrated that, allogeneic leukocytes present in non-irradiated blood products will persist for no more than 5 to 6 days (Boni, Muranski et al. 2008 Blood 1; 112(12):4746-54). Thus, to prevent rejection of allogeneic cells, the host's immune system usually has to be suppressed to some extent. However, in the case of adoptive cell transfer the use of immunosuppressive drugs also have a detrimental effect on the introduced therapeutic T cells. Therefore, to effectively use an adoptive immunotherapy approach in these conditions, the introduced cells would need to be resistant to the immunosuppressive treatment. Thus, in a particular embodiment, the present invention further comprises a step of modifying T cells to make them resistant to an immunosuppressive agent, preferably by inactivating at least one gene encoding a target for an immunosuppressive agent. An immunosuppressive agent is an agent that suppresses immune function by one of several mechanisms of action. An immunosuppressive agent can be, but is not limited to a calcineurin inhibitor, a target of rapamycin, an interleukin-2 receptor α-chain blocker, an inhibitor of inosine monophosphate dehydrogenase, an inhibitor of dihydrofolic acid reductase, a corticosteroid or an immunosuppressive antimetabolite. The present invention allows conferring immunosuppressive resistance to T cells for immunotherapy by inactivating the target of the immunosuppressive agent in T cells. As non-limiting examples, targets for an immunosuppressive agent can be a receptor for an immunosuppressive agent such as: CD52, glucocorticoid receptor (GR), a FKBP family gene member and a cyclophilin family gene member.

Immune checkpoints are inhibitory pathways that slow down or stop immune reactions and prevent excessive tissue damage from uncontrolled activity of immune cells. In certain embodiments, the immune checkpoint targeted is the programmed death-1 (PD-1 or CD279) gene (PDCD1). In other embodiments, the immune checkpoint targeted is cytotoxic T-lymphocyte-associated antigen (CTLA-4). In additional embodiments, the immune checkpoint targeted is another member of the CD28 and CTLA4 Ig superfamily such as BTLA, LAG3, ICOS, PDL1 or KIR. In further additional embodiments, the immune checkpoint targeted is a member of the TNFR superfamily such as CD40, OX40, CD137, GITR, CD27 or TIM-3.

Additional immune checkpoints include Src homology 2 domain-containing protein tyrosine phosphatase 1 (SHP-1) (Watson H A, et al., SHP-1: the next checkpoint target for cancer immunotherapy? Biochem Soc Trans. 2016 Apr. 15; 44(2):356-62). SHP-1 is a widely expressed inhibitory protein tyrosine phosphatase (PTP). In T-cells, it is a negative regulator of antigen-dependent activation and proliferation. It is a cytosolic protein, and therefore not amenable to antibody-mediated therapies, but its role in activation and proliferation makes it an attractive target for genetic manipulation in adoptive transfer strategies, such as chimeric antigen receptor (CAR) T cells. Immune checkpoints may also include T cell immunoreceptor with Ig and ITIM domains (TIGIT/Vstm3/WUCAM/VSIG9) and VISTA (Le Mercier I, et al., (2015) Beyond CTLA-4 and PD-1, the generation Z of negative checkpoint regulators. Front. Immunol. 6:418).

WO2014172606 relates to the use of MT1 and/or MT1 inhibitors to increase proliferation and/or activity of exhausted CD8+ T-cells and to decrease CD8+ T-cell exhaustion (e.g., decrease functionally exhausted or unresponsive CD8+ immune cells). In certain embodiments, metallothioneins are targeted by gene editing in adoptively transferred T cells.

In certain embodiments, targets of gene editing may be at least one targeted locus involved in the expression of an immune checkpoint protein. Such targets may include, but are not limited to CTLA4, PPP2CA, PPP2CB, PTPN6, PTPN22, PDCD1, ICOS (CD278), PDL1, KIR, LAG3, HAVCR2, BTLA, CD160, TIGIT, CD96, CRTAM, LAIR1, SIGLEC7, SIGLEC9, CD244 (2B4), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF, VISTA, GUCY1A2, GUCY1A3, GUCY1B2, GUCY1B3, MT1, MT2, CD40, OX40, CD137, GITR, CD27, SHP-1 or TIM-3. In preferred embodiments, the gene locus involved in the expression of PD-1 or CTLA-4 genes is targeted. In other preferred embodiments, combinations of genes are targeted, such as but not limited to PD-1 and TIGIT.

In other embodiments, at least two genes are edited. Pairs of genes may include, but are not limited to PD1 and TCRα, PD1 and TCRβ, CTLA-4 and TCRα, CTLA-4 and TCRβ, LAG3 and TCRα, LAG3 and TCRβ, Tim3 and TCRα, Tim3 and TCRβ, BTLA and TCRα, BTLA and TCRβ, BY55 and TCRα, BY55 and TCRβ, TIGIT and TCRα, TIGIT and TCRβ, B7H5 and TCRα, B7H5 and TCRβ, LAIR1 and TCRα, LAIR1 and TCRβ, SIGLEC10 and TCRα, SIGLEC10 and TCRβ, 2B4 and TCRα, 2B4 and TCRβ.

Whether prior to or after genetic modification of the T cells, the T cells can be activated and expanded generally using methods as described, for example, in U.S. Pat. Nos. 6,352,694; 6,534,055; 6,905,680; 5,858,358; 6,887,466; 6,905,681; 7,144,575; 7,232,566; 7,175,843; 5,883,223; 6,905,874; 6,797,514; 6,867,041; and 7,572,631. T cells can be expanded in vitro or in vivo.

The practice of the present invention employs, unless otherwise indicated, conventional techniques of immunology, biochemistry, chemistry, molecular biology, microbiology, cell biology, genomics and recombinant DNA, which are within the skill of the art. See MOLECULAR CLONING: A LABORATORY MANUAL, 2nd edition (1989) (Sambrook, Fritsch and Maniatis); MOLECULAR CLONING: A LABORATORY MANUAL, 4th edition (2012) (Green and Sambrook); CURRENT PROTOCOLS IN MOLECULAR BIOLOGY (1987) (F. M. Ausubel, et al. eds.); the series METHODS IN ENZYMOLOGY (Academic Press, Inc.); PCR 2: A PRACTICAL APPROACH (1995) (M. J. MacPherson, B. D. Hames and G. R. Taylor eds.); ANTIBODIES, A LABORATORY MANUAL (1988) (Harlow and Lane, eds.); ANTIBODIES A LABORATORY MANUAL, 2nd edition (2013) (E. A. Greenfield ed.); and ANIMAL CELL CULTURE (1987) (R. I. Freshney, ed.).

The practice of the present invention employs, unless otherwise indicated, conventional techniques for generation of genetically modified mice. See Marten H. Hofker and Jan van Deursen, TRANSGENIC MOUSE METHODS AND PROTOCOLS, 2nd edition (2011).

In some embodiments, the invention described herein relates to a method for adoptive immunotherapy, in which T cells are edited ex vivo by CRISPR to modulate at least one gene and subsequently administered to a patient in need thereof. In some embodiments, the CRISPR editing comprising knocking-out or knocking-down the expression of at least one target gene in the edited T cells. In some embodiments, in addition to modulating the target gene, the T cells are also edited ex vivo by CRISPR to (1) knock-in an exogenous gene encoding a chimeric antigen receptor (CAR) or a T-cell receptor (TCR), (2) knock-out or knock-down expression of an immune checkpoint receptor, (3) knock-out or knock-down expression of an endogenous TCR, (4) knock-out or knock-down expression of a human leukocyte antigen class I (HLA-I) proteins, and/or (5) knock-out or knock-down expression of an endogenous gene encoding an antigen targeted by an exogenous CAR or TCR.

In some embodiments, the T cells are contacted ex vivo with an adeno-associated virus (AAV) vector encoding a CRISPR effector protein, and a guide molecule comprising a guide sequence hybridizable to a target sequence, a tracr mate sequence, and a tracr sequence hybridizable to the tracr mate sequence. In some embodiments, the T cells are contacted ex vivo (e.g., by electroporation) with a ribonucleoprotein (RNP) comprising a CRISPR effector protein complexed with a guide molecule, wherein the guide molecule comprising a guide sequence hybridizable to a target sequence, a tracr mate sequence, and a tracr sequence hybridizable to the tracr mate sequence. See Rupp et al., Scientific Reports 7:737 (2017); Liu et al., Cell Research 27:154-157 (2017). In some embodiments, the T cells are contacted ex vivo (e.g., by electroporation) with an mRNA encoding a CRISPR effector protein, and a guide molecule comprising a guide sequence hybridizable to a target sequence, a tracr mate sequence, and a tracr sequence hybridizable to the tracr mate sequence. See Eyquem et al., Nature 543:113-117 (2017). In some embodiments, the T cells are not contacted ex vivo with a lentivirus or retrovirus vector.

In some embodiments, the method comprises editing T cells ex vivo by CRISPR to knock-in an exogenous gene encoding a CAR, thereby allowing the edited T cells to recognize cancer cells based on the expression of specific proteins located on the cell surface. In some embodiments, T cells are edited ex vivo by CRISPR to knock-in an exogenous gene encoding a TCR, thereby allowing the edited T cells to recognize proteins derived from either the surface or inside of the cancer cells. In some embodiments, the method comprising providing an exogenous CAR-encoding or TCR-encoding sequence as a donor sequence, which can be integrated by homology-directed repair (HDR) into a genomic locus targeted by a CRISPR guide sequence. In some embodiments, targeting the exogenous CAR or TCR to an endogenous TCR α constant (TRAC) locus can reduce tonic CAR signaling and facilitate effective internalization and re-expression of the CAR following single or repeated exposure to antigen, thereby delaying effector T-cell differentiation and exhaustion. See Eyquem et al., Nature 543:113-117 (2017).

In some embodiments, the method comprises editing T cells ex vivo by CRISPR to block one or more immune checkpoint receptors to reduce immunosuppression by cancer cells. In some embodiments, T cells are edited ex vivo by CRISPR to knock-out or knock-down an endogenous gene involved in the programmed death-1 (PD-1) signaling pathway, such as PD-1 and PD-L 1. In some embodiments, T cells are edited ex vivo by CRISPR to mutate the Pdcd1 locus or the CD274 locus. In some embodiments, T cells are edited ex vivo by CRISPR using one or more guide sequences targeting the first exon of PD-1. See Rupp et al., Scientific Reports 7:737 (2017); Liu et al., Cell Research 27:154-157 (2017).

In some embodiments, the method comprises editing T cells ex vivo by CRISPR to eliminate potential alloreactive TCRs to allow allogeneic adoptive transfer. In some embodiments, T cells are edited ex vivo by CRISPR to knock-out or knock-down an endogenous gene encoding a TCR (e.g., an αβ TCR) to avoid graft-versus-host-disease (GVHD). In some embodiments, T cells are edited ex vivo by CRISPR to mutate the TRAC locus. In some embodiments, T cells are edited ex vivo by CRISPR using one or more guide sequences targeting the first exon of TRAC. See Liu et al., Cell Research 27:154-157 (2017). In some embodiments, the method comprises use of CRISPR to knock-in an exogenous gene encoding a CAR or a TCR into the TRAC locus, while simultaneously knocking-out the endogenous TCR (e.g., with a donor sequence encoding a self-cleaving P2A peptide following the CAR cDNA). See Eyquem et al., Nature 543:113-117 (2017). In some embodiments, the exogenous gene comprises a promoter-less CAR-encoding or TCR-encoding sequence which is inserted operably downstream of an endogenous TCR promoter.

In some embodiments, the method comprises editing T cells ex vivo by CRISPR to knock-out or knock-down an endogenous gene encoding an HLA-I protein to minimize immunogenicity of the edited T cells. In some embodiments, T cells are edited ex vivo by CRISPR to mutate the beta-2 microglobulin (B2M) locus. In some embodiments, T cells are edited ex vivo by CRISPR using one or more guide sequences targeting the first exon of B2M. See Liu et al., Cell Research 27:154-157 (2017). In some embodiments, the method comprises use of CRISPR to knock-in an exogenous gene encoding a CAR or a TCR into the B2M locus, while simultaneously knocking-out the endogenous B2M (e.g., with a donor sequence encoding a self-cleaving P2A peptide following the CAR cDNA). See Eyquem et al., Nature 543:113-117 (2017). In some embodiments, the exogenous gene comprises a promoter-less CAR-encoding or TCR-encoding sequence which is inserted operably downstream of an endogenous B2M promoter.

In some embodiments, the method comprises editing T cells ex vivo by CRISPR to knock-out or knock-down an endogenous gene encoding an antigen targeted by an exogenous CAR or TCR. In some embodiments, the T cells are edited ex vivo by CRISPR to knock-out or knock-down the expression of a tumor antigen selected from human telomerase reverse transcriptase (hTERT), survivin, mouse double minute 2 homolog (MDM2), cytochrome P450 1B 1 (CYP1B), HER2/neu, Wilms' tumor gene 1 (WT1), livin, alphafetoprotein (AFP), carcinoembryonic antigen (CEA), mucin 16 (MUC16), MUC1, prostate-specific membrane antigen (PSMA), p53 or cyclin (DI) (see WO2016/011210). In some embodiments, the T cells are edited ex vivo by CRISPR to knock-out or knock-down the expression of an antigen selected from B cell maturation antigen (BCMA), transmembrane activator and CAML Interactor (TACI), or B-cell activating factor receptor (BAFF-R), CD38, CD138, CS-1, CD33, CD26, CD30, CD53, CD92, CD100, CD148, CD150, CD200, CD261, CD262, or CD362 (see WO2017/011804).

Gene Drives

The present invention also contemplates use of the CRISPR-Cas system described herein, e.g. Cpf1 effector protein systems, to provide RNA-guided gene drives, for example in systems analogous to gene drives described in PCT Patent Publication WO 2015/105928. Systems of this kind may for example provide methods for altering eukaryotic germline cells, by introducing into the germline cell a nucleic acid sequence encoding an RNA-guided DNA nuclease and one or more guide RNAs. The guide RNAs may be designed to be complementary to one or more target locations on genomic DNA of the germline cell. The nucleic acid sequence encoding the RNA guided DNA nuclease and the nucleic acid sequence encoding the guide RNAs may be provided on constructs between flanking sequences, with promoters arranged such that the germline cell may express the RNA guided DNA nuclease and the guide RNAs, together with any desired cargo-encoding sequences that are also situated between the flanking sequences. The flanking sequences will typically include a sequence which is identical to a corresponding sequence on a selected target chromosome, so that the flanking sequences work with the components encoded by the construct to facilitate insertion of the foreign nucleic acid construct sequences into genomic DNA at a target cut site by mechanisms such as homologous recombination, to render the germline cell homozygous for the foreign nucleic acid sequence. In this way, gene-drive systems are capable of introgressing desired cargo genes throughout a breeding population (Gantz et al., 2015, Highly efficient Cas9-mediated gene drive for population modification of the malaria vector mosquito *Anopheles stephensi*, PNAS 2015, published ahead of print Nov. 23, 2015, doi: 10.1073/pnas.1521077112; Esvelt et al., 2014, Concerning RNA-guided gene drives for the alteration of wild populations eLife 2014; 3:e03401). In select embodiments, target sequences may be selected which have few potential off-target sites in a genome. Targeting multiple sites within a target locus, using multiple guide RNAs, may increase the cutting frequency and hinder the evolution of drive resistant alleles. Truncated guide RNAs may reduce off-target cutting. Paired nickases may be used instead of a single nuclease, to further increase specificity. Gene drive constructs may include cargo sequences encoding transcriptional regulators, for example to activate homologous recombination genes and/or repress non-homologous end-joining. Target sites may be chosen within an essential gene, so that non-homologous end-joining events may cause lethality rather than creating a drive-resistant allele. The gene drive constructs can be engineered to function in a range of hosts at a range of temperatures (Cho et al. 2013, Rapid and Tunable Control of Protein Stability in *Caenorhabditis elegans* Using a Small Molecule, PLoS ONE 8(8): e72393. doi:10.1371/journal.pone.0072393).

Xenotransplantation

The present invention also contemplates use of the CRISPR-Cas system described herein, e.g. Cpf1 effector protein systems, to provide RNA-guided DNA nucleases adapted to be used to provide modified tissues for transplantation. For example, RNA-guided DNA nucleases may be used to knockout, knockdown or disrupt selected genes in an animal, such as a transgenic pig (such as the human heme oxygenase-1 transgenic pig line), for example by disrupting expression of genes that encode epitopes recognized by the human immune system, i.e. xenoantigen genes. Candidate porcine genes for disruption may for example include α(1, 3)-galactosyltransferase and cytidine monophosphate-N-acetylneuraminic acid hydroxylase genes (see PCT Patent Publication WO 2014/066505). In addition, genes encoding endogenous retroviruses may be disrupted, for example the genes encoding all porcine endogenous retroviruses (see Yang et al., 2015, Genome-wide inactivation of porcine endogenous retroviruses (PERVs), Science 27 Nov. 2015: Vol. 350 no. 6264 pp. 1101-1104). In addition, RNA-guided DNA nucleases may be used to target a site for integration of additional genes in xenotransplant donor animals, such as a human CD55 gene to improve protection against hyper-acute rejection.

General Gene Therapy Considerations

Examples of disease-associated genes and polynucleotides and disease specific information is available from McKusick-Nathans Institute of Genetic Medicine, Johns Hopkins University (Baltimore, Md.) and National Center for Biotechnology Information, National Library of Medicine (Bethesda, Md.), available on the World Wide Web.

Mutations in these genes and pathways can result in production of improper proteins or proteins in improper amounts which affect function. Further examples of genes, diseases and proteins are hereby incorporated by reference from U.S. Provisional application 61/736,527 filed Dec. 12, 2012. Such genes, proteins and pathways may be the target polynucleotide of a CRISPR complex of the present invention. Examples of disease-associated genes and polynucleotides are listed in Tables 20 and 21. Examples of signaling biochemical pathway-associated genes and polynucleotides are listed in Table 22.

TABLE 20

| DISEASE/DISORDERS | GENE(S) |
|---|---|
| Neoplasia | PTEN; ATM; ATR; EGFR: ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); Igf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Disorders | 5-HTT (Slc6a4); COMT; DRD (Drd1a); SLC6A3; DAOA; DTNBP1; Dao(Dao1) |

TABLE 20-continued

| DISEASE/DISORDERS | GENE(S) |
|---|---|
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP-global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion-related disorders | Prp |
| ALS | SOD1; ALS2; STEX; FUS; TARDBP; VEGF (VEGF-a; VEGF-b; VEGF-c) |
| Drug addiction | Prkce (alcohol); Drd2; Drd4; ABAT (alcohol); GRIA2; Grm5; Grin1; Htr1b; Grin2a; Drd3; Pdyn; Grial (alcohol) |
| Autism | Mecp2; BZRAP1; MDGA2; Sema5A; Neurexin 1: Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin 1); Uchl1: Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2: Parkin; PINK1 |

TABLE 21

| | |
|---|---|
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1). |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AFIQ, NPM1, NUMA1, ZNF145, PLZ, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN). |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), II-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4). |

TABLE 21-continued

| | |
|---|---|
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63). |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1). |
| Neurological and neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Nat1, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10). |
| Occular diseases and disorders | Age-related macular degeneration (Abcr, Ccl2. Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenita (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2). |

TABLE 22

| CELLULAR FUNCTION | GENES |
|---|---|
| PI3K/AKT Signaling | PRKCE; ITGAM; ITGA5; IRAK1; PRKAA2; EIF2AK2; PTEN; EIF4E; PRKCZ; GRK6; MAPK1; TSC1; PLK1; AKT2; IKBKB; PIK3CA; CDK8; CDKN1B; NFKB2; BCL2; PIK3CB; PPP2R1A; MAPK8; BCL2L1; MAPK3; TSC2; ITGA1; KRAS; EIF4EBP1; RELA; PRKCD; NOS3; PRKAA1; MAPK9; CDK2; PPP2CA; PIM1; ITGB7; YWHAZ; ILK; TP53; RAF1; IKBKG; RELB; DYRK1A; CDKN1A; ITGB1; MAP2K2; JAK1; AKT1; JAK2; PIK3R1; CHUK; PDPK1; PPP2R5C; CTNNB1; MAP2K1; NFKB1; PAK3; ITGB3; CCND1; GSK3A; FRAP1; SFN; ITGA2; TTK; CSNK1A1; BRAF; GSK3B; AKT3; FOX01; SGK; HSP90AA1; RPS6KB1 |
| ERK/MAPK Signaling | PRKCE; ITGAM; ITGA5; HSPB1; IRAK1; PRKAA2; EIF2AK2; RAC1; RAP1A; TLN1; EIF4E; ELK1; GRK6; MAPK1; RAC2; PLK1; AKT2; PIK3CA; CDK8; CREB1; PRKCI; PTK2; FOS; RPS6KA4; PIK3CB; PPP2R1A; PIK3C3; MAPK8; MAPK3; ITGA1; ETS1; KRAS; MYCN; EIF4EBP1; PPARG; PRKCD; PRKAA1; MAPK9; SRC; CDK2; PPP2CA; PIM1; PIK3C2A; ITGB7; YWHAZ; PPP1CC; KSR1; PXN; RAF1; FYN; DYRK1A; ITGB1; MAP2K2; PAK4; PIK3R1; STAT3; PPP2R5C; MAP2K1; PAK3; ITGB3; ESR1; ITGA2; MYC; TTK; CSNK1A1; CRKL; BRAF; ATF4; PRKCA; SRF; STAT1; SGK |
| Glucocorticoid Receptor Signaling | RAC1; TAF4B; EP300; SMAD2; TRAF6; PCAF; ELK1; MAPK1; SMAD3; AKT2; IKBKB; NCOR2; UBE2I; PIK3CA; CREB1; FOS; HSPA5; NFKB2; BCL2; MAP3K14; STAT5B; PIK3CB; PIK3C3; MAPK8; BCL2L1; MAPK3; T5C22D3; MAPK10; NRIP1; KRAS; MAPK13; RELA; STAT5A; MAPK9; NOS2A; PBX1; NR3C1; PIK3C2A; CDKN1C; TRAF2; SERPINE1; NCOA3; MAPK14; TNF; RAF1; IKBKG; MAP3K7; CREBBP; CDKN1A; MAP2K1; JAK1; IL8; NCOA2; AKT1; JAK2; PIK3R1; CHUK; STAT3; MAP2K1; NFKB1; TGFBR1; ESR1; SMAD4; CEBPB; JUN; AR; AKT3; CCL2; MMPl; STAT1; IL6; H5P90AA1 |
| Axonal Guidance Signaling | PRKCE; ITGAM; ROCK1; ITGA5; CXCR4; ADAM12; IGF1 ; RAC1 ; RAP1A; EIF4E; PRKCZ; NRP1 ; NTRK2; ARHGEF7; SMO; ROCK2; MAPK1; PGF; RAC2; PTPN11; GNAS; AKT2; PIK3CA; ERBB2; PRKCI; PTK2; CFL1; GNAQ; PIK3CB; CXCL12; PIK3C3; WNT11; PRKD1; GNB2L1; ABL1; MAPK3; ITGA1; KRAS; RHOA; PRKCD; PIK3C2A; ITGB7; GLI2; PXN; VASP; RAF1; FYN; ITGB1; MAP2K2; PAK4; ADAM17; AKT1; PIK3R1; GLI1; WNT5A; ADAM10; MAP2K1; PAK3; ITGB3; CDC42; VEGFA; ITGA2; EPHA8; CRKL; RND1; GSK3B; AKT3; PRKCA |
| Ephrin Receptor Signaling | PRKCE; ITGAM; ROCK1; ITGA5; CXCR4; IRAK1; PRKAA2; EIF2AK2; RAC1; RAP1A; GRK6; ROCK2; MAPK1; PGF; RAC2; PTPN11; GNAS; PLK1; AKT2; DOK1; CDK8; CREB1; PTK2; CFL1; GNAQ; MAP3K14; CXCL12; MAPK8; GNB2L1; ABL1; MAPK3; ITGA1; KRAS; RHOA; PRKCD; PRKAA1; MAPK9; SRC; CDK2; PIM1; ITGB7; PXN; RAF1; FYN; DYRK1A; ITGB1; MAP2K2; PAK4; AKT1; JAK2; STAT3; ADAM10; MAP2K1; PAK3; ITGB3; CDC42; VEGFA; ITGA2; EPHA8; TTK; CSNK1A1; CRKL; BRAF; PTPN13; ATF4; AKT3; SGK |
| Actin Cytoskeleton Signaling | ACTN4; PRKCE; ITGAM; ROCK1; ITGA5; IRAK1; PRKAA2; EIF2AK2; RAC1; INS; ARHGEF7; GRK6; ROCK2; MAPK1; RAC2; PLK1; AKT2; PIK3CA; CDK8; PTK2; CFL1; PIK3 CB; MYH9; DIAPH1; PIK3C3 ; MAPK8; F2R; MAPK3; SLC9A1; ITGA1; KRAS; RHOA; PRKCD; PRKAA1; MAPK9; CDK2; PIM1; PIK3C2A; ITGB7; PPP1CC; PXN; VIL2; RAF1; GSN; DYRK1A; ITGB1; MAP2K2; PAK4; PIP5K1A; PIK3R1; MAP2K1; PAK3; ITGB3; CDC42; APC; ITGA2; TTK; CSNK1A1; CRKL; BRAF; VAV3; SGK |
| Huntington's Disease Signaling | PRKCE; IGF1; EP300; RCOR1; PRKCZ; HDAC4; TGM2; MAPK1; CAPNS1; AKT2; EGFR; NCOR2; SP1; CAPN2; PIK3CA; HDAC5; CREB1; PRKCI; HSPA5; REST; GNAQ; PIK3CB; PIK3C3; MAPK8; IGF1R; PRKD1; GNB2L1; BCL2L1; CAPN1; MAPK3; CASP8; HDAC2; HDAC7A; PRKCD; HDAC11; MAPK9; HDAC9; PIK3C2A; HDAC3; TP53; CASP9; CREBBP; AKT1; PIK3R1; PDPK1; CASP1; APAF1; FRAP1; CASP2; JUN; BAX; ATF4; AKT3; PRKCA; CLTC; SGK; HDAC6; CASP3 |

TABLE 22-continued

| CELLULAR FUNCTION | GENES |
|---|---|
| Apoptosis Signaling | PRKCE; ROCK1; BID; IRAK1; PRKAA2; EIF2AK2; BAK1; BIRC4; GRK6; MAPK1; CAPNS1; PLK1; AKT2; IKBKB; CAPN2; CDK8; FAS; NFKB2; BCL2; MAP3K14; MAPK8; BCL2L1; CAPN1; MAPK3; CASP8; KRAS; RELA; PRKCD; PRKAA1; MAPK9; CDK2; PIM1; TP53; TNF; RAF1; IKBKG; RELB; CASP9; DYRK1A; MAP2K2; CHUK; APAF1; MAP2K1; NFKB1; PAK3; LMNA; CASP2; BIRC2; TTK; CSNK1A1; BRAF; BAX; PRKCA; SGK; CASP3; BIRC3; PARP1 |
| B Cell Receptor Signaling | RAC1; PTEN; LYN; ELK1; MAPK1; RAC2; PTPN11; AKT2; IKBKB; PIK3CA; CREB1; SYK; NFKB2; CAMK2A; MAP3K14; PIK3CB; PIK3C3; MAPK8; BCL2L1; ABL1; MAPK3; ETS1; KRAS; MAPK13; RELA; PTPN6; MAPK9; EGR1; PIK3C2A; BTK; MAPK14; RAF1; IKBKG; RELB; MAP3K7; MAP2K2; AKT1; PIK3R1; CHUK; MAP2K1; NFKB1; CDC42; GSK3A; FRAP1; BCL6; BCL10; JUN; GSK3B; ATF4; AKT3; VAV3; RPS6KB1 |
| Leukocyte Extravasation Signaling | ACTN4; CD44; PRKCE; ITGAM; ROCK1; CXCR4; CYBA; RAC1; RAP1A; PRKCZ; ROCK2; RAC2; PTPN11; MMP14; PIK3CA; PRKCI; PTK2; PIK3CB; CXCL12; PIK3C3; MAPK8; PRKD1; ABL1; MAPK10; CYBB; MAPK13; RHOA; PRKCD; MAPK9; SRC; PIK3C2A; BTK; MAPK14; NOX1; PXN; VIL2; VASP; ITGB1; MAP2K2; CTNND1; PIK3R1; CTNNB1; CLDN1; CDC42; F11R; ITK; CRKL; VAV3; CTTN; PRKCA; MMP1; MMP9 |
| Integrin Signaling | ACTN4; ITGAM; ROCK1; ITGA5; RAC1; PTEN; RAP1A; TLN1; ARHGEF7; MAPK1; RAC2; CAPNS1; AKT2; CAPN2; PIK3CA; PTK2; PIK3CB; PIK3C3; MAPK8; CAV1; CAPN1; ABL1; MAPK3; ITGA1; KRAS; RHOA; SRC; PIK3C2A; ITGB7; PPP1CC; ILK; PXN; VASP; RAF1; FYN; ITGB1; MAP2K2; PAK4; AKT1; PIK3R1; TNK2; MAP2K1; PAK3; ITGB3; CDC42; RND3; ITGA2; CRKL; BRAF; GSK3B; AKT3 |
| Acute Phase Response Signaling | IRAK1; SOD2; MYD88; TRAF6; ELK1; MAPK1; PTPN11; AKT2; IKBKB; PIK3CA; FOS; NFKB2; MAP3K14; PIK3CB; MAPK8; RIPK1; MAPK3; IL6ST; KRAS; MAPK13; IL6R; RELA; SOCS1; MAPK9; FTL; NR3C1; TRAF2; SERPINE1; MAPK14; TNF; RAF1; PDK1; IKBKG; RELB; MAP3K7; MAP2K2; AKT1; JAK2; PIK3R1; CHUK; STAT3; MAP2K1; NFKB1; FRAP1; CEBPB; JUN; AKT3; IL1R1; IL6 |
| PTEN Signaling | ITGAM; ITGA5; RAC1; PTEN; PRKCZ; BCL2L11; MAPK1; RAC2; AKT2; EGFR; IKBKB; CBL; PIK3CA; CDKN1B; PTK2; NFKB2; BCL2; PIK3CB; BCL2L1; MAPK3; ITGA1; KRAS; ITGB7; ILK; PDGFRB; INSR; RAF1; IKBKG; CASP9; CDKN1A; ITGB1; MAP2K2; AKT1; PIK3R1; CHUK; PDGFRA; PDPK1; MAP2K1; NFKB1; ITGB3; CDC42; CCND1; GSK3A; ITGA2; GSK3B; AKT3; FOXO1; CASP3; RP56KB1 |
| p53 Signaling | PTEN; EP300; BBC3; PCAF; FASN; BRCA1; GADD45A; BIRC5; AKT2; PIK3CA; CHEK1; TP53INP1; BCL2; PIK3CB; PIK3C3; MAPK8; THBS1; ATR; BCL2L1; E2F1; PMAIP1; CHEK2; TNFRSF10B; TP73; RB1; HDAC9; CDK2; PIK3C2A; MAPK14; TP53; LRDD; CDKN1A; HIPK2; AKT1; PIK3R1; RRM2B; APAF1; CTNNB1; SIRT1; CCND1; PRKDC; ATM; SFN; CDKN2A; JUN; SNAI2; GSK3B; BAX; AKT3 |
| Aryl Hydrocarbon Receptor Signaling | HSPB1; EP300; FASN; TGM2; RXRA; MAPK1; NQO1; NCOR2; SP1; ARNT; CDKN1B; FOS; CHEK1; SMARCA4; NFKB2; MAPK8; ALDH1A1; ATR; E2F1; MAPK3; NRIP1; CHEK2; RELA; TP73; GSTP1; RB1; SRC; CDK2; AHR; NFE2L2; NCOA3; TP53; TNF; CDKN1A; NCOA2; APAF1; NFKB1; CCND1; ATM; ESR1; CDKN2A; MYC; JUN; ESR2; BAX; IL6; CYP1B1; HSP90AA1 |
| Xenobiotic Metabolism Signaling | PRKCE; EP300; PRKCZ; RXRA; MAPK1; NQO1; NCOR2; PIK3CA; ARNT; PRKCI; NFKB2; CAMK2A; PIK3CB; PPP2R1A; PIK3C3; MAPK8; PRKD1; ALDH1A1; MAPK3; NRIP1; KRAS; MAPK13; PRKCD; GSTP1; MAPK9; NOS2A; ABCB1; AHR; PPP2CA; FTL; NFE2L2; PIK3C2A; PPARGC1A; MAPK14; TNF; RAF1; CREBBP; MAP2K2; PIK3R1; PPP2R5C; MAP2K1; NFKB1; KEAP1; PRKCA; EIF2AK3; IL6; CYP1B1; HSP90AA1 |
| SAPK/JNK Signaling | PRKCE; IRAK1; PRKAA2; EIF2AK2; RAC1; ELK1; GRK6; MAPK1; GADD45A; RAC2; PLK1; AKT2; PIK3CA; FADD; CDK8; PIK3CB; PIK3C3; MAPK8; RIPK1; |

TABLE 22-continued

| CELLULAR FUNCTION | GENES |
|---|---|
| | GNB2L1; IRS1; MAPK3; MAPK10; DAXX; KRAS; PRKCD; PRKAA1; MAPK9; CDK2; PIM1; PIK3C2A; TRAF2; TP53; LCK; MAP3K7; DYRK1A; MAP2K2; PIK3R1; MAP2K1; PAK3; CDC42; JUN; TTK; CSNK1A1; CRKL; BRAF; SGK |
| PPAr/RXR Signaling | PRKAA2; EP300; INS; SMAD2; TRAF6; PPARA; FASN; RXRA; MAPK1; SMAD3; GNAS; IKBKB; NCOR2; ABCA1; GNAQ; NFKB2; MAP3K14; STAT5B; MAPK8; IRS1; MAPK3; KRAS; RELA; PRKAA1; PPARGC1A; NCOA3; MAPK14; INSR; RAF1; IKBKG; RELB; MAP3K7; CREBBP; MAP2K2; JAK2; CHUK; MAP2K1; NFKB1; TGFBR1; SMAD4; JUN; IL1R1; PRKCA; IL6; H5P90AA1; ADIPOQ |
| NF-KB Signaling | IRAK1; EIF2AK2; EP300; INS; MYD88; PRKCZ; TRAF6; TBK1; AKT2; EGFR; IKBKB; PIK3CA; BTRC; NFKB2; MAP3K14; PIK3CB; PIK3C3; MAPK8; RIPK1; HDAC2; KRAS; RELA; PIK3C2A; TRAF2; TLR4; PDGFRB; TNF; INSR; LCK; IKBKG; RELB; MAP3K7; CREBBP; AKT1; PIK3R1; CHUK; PDGFRA; NFKB1; TLR2; BCL10; GSK3B; AKT3; TNFAIP3; IL1R1 |
| Neuregulin Signaling | ERBB4; PRKCE; ITGAM; ITGA5; PTEN; PRKCZ; ELK1; MAPK1; PTPN11; AKT2; EGFR; ERBB2; PRKCI; CDKN1B; STAT5B; PRKD1; MAPK3; ITGA1; KRAS; PRKCD; STAT5A; SRC; ITGB7; RAF1; ITGB1; MAP2K2; ADAM17; AKT1; PIK3R1; PDPK1; MAP2K1; ITGB3; EREG; FRAP1; PSEN1; ITGA2; MYC; NRG1; CRKL; AKT3; PRKCA; H5P90AA1; RP56KB1 |
| Wnt & Beta catenin Signaling | CD44; EP300; LRP6; DVL3; CSNK1E; GJA1; SMO; AKT2; PIN1; CDH1; BTRC; GNAQ; MARK2; PPP2R1A; WNT11; SRC; DKK1; PPP2CA; SOX6; SFRP2; ILK; LEF1; SOX9; TP53; MAP3K7; CREBBP; TCF7L2; AKT1; PPP2R5C; WNT5A; LRP5; CTNNB1; TGFBR1; CCND1; GSK3A; DVL1; APC; CDKN2A; MYC; CSNK1A1; GSK3B; AKT3; SOX2 |
| Insulin Receptor Signaling | PTEN; INS; EIF4E; PTPN1; PRKCZ; MAPK1; TSC1; PTPN11; AKT2; CBL; PIK3CA; PRKCI; PIK3CB; PIK3C3; MAPK8; IRS1; MAPK3; TSC2; KRAS; EIF4EBP1; SLC2A4; PIK3C2A; PPP1CC; INSR; RAF1; FYN; MAP2K2; JAK1; AKT1; JAK2; PIK3R1; PDPK1; MAP2K1; GSK3A; FRAP1; CRKL; GSK3B; AKT3; FOX01; SGK; RPS6KB1 |
| IL-6 Signaling | HSPB1; TRAF6; MAPKAPK2; ELK1; MAPK1; PTPN11; IKBKB; FOS; NFKB2; MAP3K14; MAPK8; MAPK3; MAPK10; IL6ST; KRAS; MAPK13; IL6R; RELA; SOCS1; MAPK9; ABCB1; TRAF2; MAPK14; TNF; RAF1; IKBKG; RELB; MAP3K7; MAP2K2; IL8; JAK2; CHUK; STAT3; MAP2K1; NFKB1; CEBPB; JUN; IL1R1; SRF; IL6 |
| Hepatic Cholestasis | PRKCE; IRAK1; INS; MYD88; PRKCZ; TRAF6; PPARA; RXRA; IKBKB; PRKCI; NFKB2; MAP3K14; MAPK8; PRKD1; MAPK10; RELA; PRKCD; MAPK9; ABCB1; TRAF2; TLR4; TNF; INSR; IKBKG; RELB; MAP3K7; IL8; CHUK; NR1H2; TJP2; NFKB1; ESR1; SREBF1; FGFR4; JUN; IL1R1; PRKCA; IL6 |
| IGF-1 Signaling | IGF1; PRKCZ; ELK1; MAPK1; PTPN11; NEDD4; AKT2; PIK3CA; PRKCI; PTK2; FOS; PIK3CB; PIK3C3; MAPK8; IGF1R; IRS1; MAPK3; IGFBP7; KRAS; PIK3C2A; YWHAZ; PXN; RAF1; CASP9; MAP2K2; AKT1; PIK3R1; PDPK1; MAP2K1; IGFBP2; SFN; JUN; CYR61; AKT3; FOXO1; SRF; CTGF; RP56KB1 |
| NRF2-mediated Oxidative Stress Response | PRKCE; EP300; SOD2; PRKCZ; MAPK1; SQSTM1; NQ01; PIK3CA; PRKCI; FOS; PIK3CB; PIK3C3; MAPK8; PRKD1; MAPK3; KRAS; PRKCD; GSTP1; MAPK9; FTL; NFE2L2; PIK3C2A; MAPK14; RAF1; MAP3K7; CREBBP; MAP2K2; AKT1; PIK3R1; MAP2K1; PPIB; JUN; KEAP1; GSK3B; ATF4; PRKCA; EIF2AK3; H5P90AA1 |
| Hepatic Fibrosis/Hepatic Stellate Cell Activation | EDN1; IGF1; KDR; FLT1; SMAD2; FGFR1; MET; PGF; SMAD3; EGFR; FAS; CSF1; NFKB2; BCL2; MYH9; IGF1R; IL6R; RELA; TLR4; PDGFRB; TNF; RELB; IL8; PDGFRA; NFKB1; TGFBR1; SMAD4; VEGFA; BAX; IL1R1; CCL2; HGF; MMP1; STAT1; IL6; CTGF; MMP9 |
| PPAR Signaling | EP300; INS; TRAF6; PPARA; RXRA; MAPK1; IKBKB; NCOR2; FOS; NFKB2; MAP3K14; STAT5B; MAPK3; NRIP1; KRAS; PPARG; RELA; STAT5A; TRAF2; PPARGC1A; PDGFRB; TNF; INSR; RAF1; IKBKG; RELB; MAP3K7; CREBBP; MAP2K2; CHUK; PDGFRA; MAP2K1; NFKB1; JUN; IL1R1; HSP90AA1 |

TABLE 22-continued

| CELLULAR FUNCTION | GENES |
|---|---|
| Fc Epsilon RI Signaling | PRKCE; RAC1; PRKCZ; LYN; MAPK1; RAC2; PTPN11; AKT2; PIK3CA; SYK; PRKCI; PIK3CB; PIK3C3; MAPK8; PRKD1; MAPK3; MAPK10; KRAS; MAPK13; PRKCD; MAPK9; PIK3C2A; BTK; MAPK14; TNF; RAF1; FYN; MAP2K2; AKT1; PIK3R1; PDPK1; MAP2K1; AKT3; VAV3; PRKCA |
| G-Protein Coupled Receptor Signaling | PRKCE; RAP1A; RGS16; MAPK1; GNAS; AKT2; IKBKB; PIK3CA; CREB1; GNAQ; NFKB2; CAMK2A; PIK3CB; PIK3C3; MAPK3; KRAS; RELA; SRC; PIK3C2A; RAF1; IKBKG; RELB; FYN; MAP2K2; AKT1; PIK3R1; CHUK; PDPK1; STAT3; MAP2K1; NFKB1; BRAF; ATF4; AKT3; PRKCA |
| Inositol Phosphate Metabolism | PRKCE; IRAK1; PRKAA2; EIF2AK2; PTEN; GRK6; MAPK1; PLK1; AKT2; PIK3CA; CDK8; PIK3CB; PIK3C3; MAPK8; MAPK3; PRKCD; PRKAA1; MAPK9; CDK2; PIM1; PIK3C2A; DYRK1A; MAP2K2; PIP5K1A; PIK3R1; MAP2K1; PAK3; ATM; TTK; CSNK1A1; BRAF; SGK |
| PDGF Signaling | EIF2AK2; ELK1; ABL2; MAPK1; PIK3CA; FOS; PIK3CB; PIK3C3; MAPK8; CAV1; ABL1; MAPK3; KRAS; SRC; PIK3C2A; PDGFRB; RAF1; MAP2K2; JAK1; JAK2; PIK3R1; PDGFRA; STAT3; SPHK1; MAP2K1; MYC; JUN; CRKL; PRKCA; SRF; STAT1; SPHK2 |
| VEGF Signaling | ACTN4; ROCK1; KDR; FLT1; ROCK2; MAPK1; PGF; AKT2; PIK3CA; ARNT; PTK2; BCL2; PIK3CB; PIK3C3; BCL2L1; MAPK3; KRAS; HIF1A; NOS3; PIK3C2A; PXN; RAF1; MAP2K2; ELAVL1; AKT1; PIK3R1; MAP2K1; SFN; VEGFA; AKT3; FOXO1; PRKCA |
| Natural Killer Cell Signaling | PRKCE; RAC1; PRKCZ; MAPK1; RAC2; PTPN11; KIR2DL3; AKT2; PIK3CA; SYK; PRKCI; PIK3CB; PIK3C3; PRKD1; MAPK3; KRAS; PRKCD; PTPN6; PIK3C2A; LCK; RAF1; FYN; MAP2K2; PAK4; AKT1; PIK3R1; MAP2K1; PAK3; AKT3; VAV3; PRKCA |
| Cell Cycle: G1/S Checkpoint Regulation | HDAC4; SMAD3; SUV39H1; HDAC5; CDKN1B; BTRC; ATR; ABL1; E2F1; HDAC2; HDAC7A; RB1; HDAC11; HDAC9; CDK2; E2F2; HDAC3; TP53; CDKN1A; CCND1; E2F4; ATM; RBL2; SMAD4; CDKN2A; MYC; NRG1; GSK3B; RBL1; HDAC6 |
| T Cell Receptor Signaling | RAC1; ELK1; MAPK1; IKBKB; CBL; PIK3CA; FOS; NFKB2; PIK3CB; PIK3C3; MAPK8; MAPK3; KRAS; RELA; PIK3C2A; BTK; LCK; RAF1; IKBKG; RELB; FYN; MAP2K2; PIK3R1; CHUK; MAP2K1; NFKB1; ITK; BCL10; JUN; VAV3 |
| Death Receptor Signaling | CRADD; HSPB1; BID; BIRC4; TBK1; IKBKB; FADD; FAS; NFKB2; BCL2; MAP3K14; MAPK8; RIPK1; CASP8; DAXX; TNFRSF10B; RELA; TRAF2; TNF; IKBKG; RELB; CASP9; CHUK; APAF1; NFKB1; CASP2; BIRC2; CASP3; BIRC3 |
| FGF Signaling | RAC1; FGFR1; MET; MAPKAPK2; MAPK1; PTPN11; AKT2; PIK3CA; CREB1; PIK3CB; PIK3C3; MAPK8; MAPK3; MAPK13; PTPN6; PIK3C2A; MAPK14; RAF1; AKT1; PIK3R1; STAT3; MAP2K1; FGFR4; CRKL; ATF4; AKT3; PRKCA; HGF |
| GM-CSF Signaling | LYN; ELK1; MAPK1; PTPN11; AKT2; PIK3CA; CAMK2A; STAT5B; PIK3CB; PIK3C3; GNB2L1; BCL2L1; MAPK3; ETS1; KRAS; RUNX1; PIM1; PIK3C2A; RAF1; MAP2K2; AKT1; JAK2; PIK3R1; STAT3; MAP2K1; CCND1; AKT3; STAT1 |
| Amyotrophic Lateral Sclerosis Signaling | BID; IGF1; RAC1; BIRC4; PGF; CAPNS1; CAPN2; PIK3CA; BCL2; PIK3CB; PIK3C3; BCL2L1; CAPN1; PIK3C2A; TP53; CASP9; PIK3R1; RAB5A; CASP1; APAF1; VEGFA; BIRC2; BAX; AKT3; CASP3; BIRC3 |
| JAK/Stat Signaling | PTPN1; MAPK1; PTPN11; AKT2; PIK3CA; STAT5B; PIK3CB; PIK3C3; MAPK3; KRAS; SOCS1; STAT5A; PTPN6; PIK3C2A; RAF1; CDKN1A; MAP2K2; JAK1; AKT1; JAK2; PIK3R1; STAT3; MAP2K1; FRAP1; AKT3; STAT1 |
| Nicotinate and Nicotinamide Metabolism | PRKCE; IRAK1; PRKAA2; EIF2AK2; GRK6; MAPK1; PLK1; AKT2; CDK8; MAPK8; MAPK3; PRKCD; PRKAA1; PBEF1; MAPK9; CDK2; PIM1; DYRK1A; MAP2K2; MAP2K1; PAK3; NT5E; TTK; CSNK1A1; BRAF; SGK |
| Chemokine Signaling | CXCR4; ROCK2; MAPK1; PTK2; FOS; CFL1; GNAQ; CAMK2A; CXCL12; MAPK8; MAPK3; KRAS; MAPK13; RHOA; CCR3; SRC; PPP1CC; MAPK14; NOX1; RAF1; MAP2K2; MAP2K1; JUN; CCL2; PRKCA |

TABLE 22-continued

| CELLULAR FUNCTION | GENES |
|---|---|
| IL-2 Signaling | ELK1; MAPK1; PTPN11; AKT2; PIK3CA; SYK; FOS; STAT5B; PIK3CB; PIK3C3; MAPK8; MAPK3; KRAS; SOCS1; STAT5A; PIK3C2A; LCK; RAF1; MAP2K2; JAK1; AKT1; PIK3R1; MAP2K1; JUN; AKT3 |
| Synaptic Long Term Depression | PRKCE; IGF1; PRKCZ; PRDX6; LYN; MAPK1; GNAS; PRKCI; GNAQ; PPP2R1A; IGF1R; PRKD1; MAPK3; KRAS; GRN; PRKCD; NOS3; NOS2A; PPP2CA; YWHAZ; RAF1; MAP2K2; PPP2R5C; MAP2K1; PRKCA |
| Estrogen Receptor Signaling | TAF4B; EP300; CARM1; PCAF; MAPK1; NCOR2; SMARCA4; MAPK3; NRIP1; KRAS; SRC; NR3C1; HDAC3; PPARGC1A; RBM9; NCOA3; RAF1; CREBBP; MAP2K2; NCOA2; MAP2K1; PRKDC; ESR1; ESR2 |
| Protein Ubiquitination Pathway | TRAF6; SMURF1; BIRC4; BRCA1; UCHL1; NEDD4; CBL; UBE2I; BTRC; HSPA5; USP7; USP10; FBXW7; USP9X; STUB1; U5P22; B2M; BIRC2; PARK2; USP8; USP1; VHL; H5P90AA1; BIRC3 |
| IL-10 Signaling | TRAF6; CCR1; ELK1; IKBKB; SP1; FOS; NFKB2; MAP3K14; MAPK8; MAPK13; RELA; MAPK14; TNF; IKBKG; RELB; MAP3K7; JAK1; CHUK; STAT3; NFKB1; JUN; IL1R1; IL6 |
| VDR/RXR Activation | PRKCE; EP300; PRKCZ; RXRA; GADD45A; HES1; NCOR2; SP1; PRKCI; CDKN1B; PRKD1; PRKCD; RUNX2; KLF4; YY1; NCOA3; CDKN1A; NCOA2; SPP1; LRP5; CEBPB; FOXO1; PRKCA |
| TGF-beta Signaling | EP300; SMAD2; SMURF1; MAPK1; SMAD3; SMAD1; FOS; MAPK8; MAPK3; KRAS; MAPK9; RUNX2; SERPINE1; RAF1; MAP3K7; CREBBP; MAP2K2; MAP2K1; TGFBR1; SMAD4; JUN; SMAD5 |
| Toll-like Receptor Signaling | IRAK1; EIF2AK2; MYD88; TRAF6; PPARA; ELK1; IKBKB; FOS; NFKB2; MAP3K14; MAPK8; MAPK13; RELA; TLR4; MAPK14; IKBKG; RELB; MAP3K7; CHUK; NFKB1; TLR2; JUN |
| p38 MAPK Signaling | HSPB1; IRAK1; TRAF6; MAPKAPK2; ELK1; FADD; FAS; CREB1; DDIT3; RPS6KA4; DAXX; MAPK13; TRAF2; MAPK14; TNF; MAP3K7; TGFBR1; MYC; ATF4; IL1R1; SRF; STAT1 |
| Neurotrophin/TRK Signaling | NTRK2; MAPK1; PTPN11; PIK3CA; CREB1; FOS; PIK3CB; PIK3C3; MAPK8; MAPK3; KRAS; PIK3C2A; RAF1; MAP2K2; AKT1; PIK3R1; PDPK1; MAP2K1; CDC42; JUN; ATF4 |
| FXR/RXR Activation | INS; PPARA; FASN; RXRA; AKT2; SDC1; MAPK8; APOB; MAPK10; PPARG; MTTP; MAPK9; PPARGC1A; TNF; CREBBP; AKT1; SREBF1; FGFR4; AKT3; FOXO1 |
| Synaptic Long Term Potentiation | PRKCE; RAP1A; EP300; PRKCZ; MAPK1; CREB1; PRKCI; GNAQ; CAMK2A; PRKD1; MAPK3; KRAS; PRKCD; PPP1CC; RAF1; CREBBP; MAP2K2; MAP2K1; ATF4; PRKCA |
| Calcium Signaling | RAP1A; EP300; HDAC4; MAPK1; HDAC5; CREB1; CAMK2A; MYH9; MAPK3; HDAC2; HDAC7A; HDAC11; HDAC9; FIDAC3; CREBBP; CALR; CAMKK2; ATF4; HDAC6 |
| EGF Signaling | ELK1; MAPK1; EGFR; PIK3CA; FOS; PIK3CB; PIK3C3; MAPK8; MAPK3; PIK3C2A; RAF1; JAK1; PIK3R1; STAT3; MAP2K1; JUN; PRKCA; SRF; STAT1 |
| Hypoxia Signaling in the Cardiovascular System | EDN1; PTEN; EP300; NQO1; UBE2I; CREB1; ARNT; HIF1A; SLC2A4; NOS3; TP53; LDHA; AKT1; ATM; VEGFA; JUN; ATF4; VHL; HSP90AA1 |
| LPS/IL-1 Mediated Inhibition of RXR Function | IRAK1; MYD88; TRAF6; PPARA; RXRA; ABCA1; MAPK8; ALDH1A1; GSTP1; MAPK9; ABCB1; TRAF2; TLR4; TNF; MAP3K7; NR1H2; SREBF1; JUN; IL1R1 |
| LXR/RXR Activation | FASN; RXRA; NCOR2; ABCA1; NFKB2; IRF3; RELA; NOS2A; TLR4; TNF; RELB; LDLR; NR1H2; NFKB1; SREBF1; IL1R1; CCL2; IL6; MMP9 |
| Amyloid Processing | PRKCE; CSNK1E; MAPK1; CAPNS1; AKT2; CAPN2; CAPN1; MAPK3; MAPK13; MAPT; MAPK14; AKT1; PSEN1; CSNK1A1; GSK3B; AKT3; APP |
| IL-4 Signaling | AKT2; PIK3CA; PIK3CB; PIK3C3; IRS1; KRAS; SOCS1; PTPN6; NR3C1; PIK3C2A; JAK1; AKT1; JAK2; PIK3R1; FRAP1; AKT3; RPS6KB1 |

TABLE 22-continued

| CELLULAR FUNCTION | GENES |
|---|---|
| Cell Cycle: G2/M DNA Damage Checkpoint Regulation | EP300; PCAF; BRCA1; GADD45A; PLK1; BTRC; CHEK1; ATR; CHEK2; YWHAZ; TP53; CDKN1A; PRKDC; ATM; SFN; CDKN2A |
| Nitric Oxide Signaling in the Cardiovascular System | KDR; FLT1; PGF; AKT2; PIK3CA; PIK3CB; PIK3C3; CAV1; PRKCD; NOS3; PIK3C2A; AKT1; PIK3R1; VEGFA; AKT3; HSP90AA1 |
| Purine Metabolism | NME2; SMARCA4; MYH9; RRM2; ADAR; EIF2AK4; PKM2; ENTPD1; RAD51; RRM2B; TJP2; RAD51C; NT5E; POLD1; NME1 |
| cAMP-mediated Signaling | RAP1A; MAPK1; GNAS; CREB1; CAMK2A; MAPK3; SRC; RAF1; MAP2K2; STAT3; MAP2K1; BRAF; ATF4 |
| Mitochondrial Dysfunction | SOD2; MAPK8; CASP8; MAPK10; MAPK9; CASP9; PARK7; PSEN1; PARK2; APP; CASP3 |
| Notch Signaling | HES1; JAG1; NUMB; NOTCH4; ADAM17; NOTCH2; PSEN1; NOTCH3; NOTCH1; DLL4 |
| Endoplasmic Reticulum Stress Pathway | HSPA5; MAPK8; XBP1; TRAF2; ATF6; CASP9; ATF4; EIF2AK3; CASP3 |
| Pyrimidine Metabolism | NME2; AICDA; RRM2; EIF2AK4; ENTPD1; RRM2B; NT5E; POLD1; NME1 |
| Parkinson's Signaling | UCHL1; MAPK8; MAPK13; MAPK14; CASP9; PARK7; PARK2; CASP3 |
| Cardiac & Beta Adrenergic Signaling | GNAS; GNAQ; PPP2R1A; GNB2L1; PPP2CA; PPP1CC; PPP2R5C |
| Glycolysis/Gluconeogenesis | HK2; GCK; GPI; ALDH1A1; PKM2; LDHA; HK1 |
| Interferon Signaling | IRF1; SOCS1; JAK1; JAK2; IFITM1; STAT1; IFIT3 |
| Sonic Hedgehog Signaling | ARRB2; SMO; GLI2; DYRK1A; GLI1; GSK3B; DYRK1B |
| Glycerophospholipid Metabolism | PLD1; GRN; GPAM; YWHAZ; SPHK1; SPHK2 |
| Phospholipid Degradation | PRDX6; PLD1; GRN; YWHAZ; SPHK1; SPHK2 |
| Tryptophan Metabolism | SIAH2; PRMT5; NEDD4; ALDH1A1; CYP1B1; SIAH1 |
| Lysine Degradation | SUV39H1; EHMT2; NSD1; SETD7; PPP2R5C |
| Nucleotide Excision Repair Pathway | ERCC5; ERCC4; XPA; XPC; ERCC1 |
| Starch and Sucrose Metabolism | UCHL1; HK2; GCK; GPI; HK1 |
| Aminosugars Metabolism | NQO1; FIK2; GCK; HK1 |
| Arachidonic Acid Metabolism | PRDX6; GRN; YWHAZ; CYP1B1 |
| Circadian Rhythm Signaling | CSNK1E; CREB1; ATF4; NR1D1 |
| Coagulation System | BDKRB1; F2R; SERPINE1; F3 |
| Dopamine Receptor Signaling | PPP2R1A; PPP2CA; PPP1CC; PPP2R5C |
| Glutathione Metabolism | IDH2; GSTP1; ANPEP; IDH1 |
| Glycerolipid Metabolism | ALDH1A1; GPAM; SPHK1; SPHK2 |
| Linoleic Acid Metabolism | PRDX6; GRN; YWHAZ; CYP1B1 |
| Methionine Metabolism | DNMT1; DNMT3B; AHCY; DNMT3A |
| Pyruvate Metabolism | GLO1; ALDH1A1; PKM2; LDHA |
| Arginine and Proline Metabolism | ALDH1A1; NOS3; NOS2A |
| Eicosanoid Signaling | PRDX6; GRN; YWHAZ |
| Fructose and Mannose Metabolism | FIK2; GCK; HK1 |
| Galactose Metabolism | HK2; GCK; HK1 |
| Stilbene, Coumarine and Lignin Biosynthesis | PRDX6; PRDX1; TYR |
| Antigen Presentation Pathway | CALR; B2M |
| Biosynthesis of Steroids | NQO1; DHCR7 |
| Butanoate Metabolism | ALDH1A1; NLGN1 |
| Citrate Cycle | IDH2; IDH1 |
| Fatty Acid Metabolism | ALDH1A1; CYP1B1 |
| Glycerophospholipid Metabolism | PRDX6; CHKA |
| Histidine Metabolism | PRMT5; ALDH1A1 |
| Inositol Metabolism | ERO1L; APEX1 |
| Metabolism of Xenobiotics by Cytochrome p450 | GSTP1; CYP1B1 |

TABLE 22-continued

| CELLULAR FUNCTION | GENES |
|---|---|
| Methane Metabolism | PRDX6; PRDX1 |
| Phenylalanine Metabolism | PRDX6; PRDX1 |
| Propanoate Metabolism | ALDH1A1; LDHA |
| Selenoamino Acid Metabolism | PRMT5; AHCY |
| Sphingolipid Metabolism | SPHK1; SPHK2 |
| Aminophosphonate Metabolism | PRMT5 |
| Androgen and Estrogen Metabolism | PRMT5 |
| Ascorbate and Aldarate Metabolism | ALDH1A1 |
| Bile Acid Biosynthesis | ALDH1A1 |
| Cysteine Metabolism | LDHA |
| Fatty Acid Biosynthesis | FASN |
| Glutamate Receptor Signaling | GNB2L1 |
| NRF2-mediated Oxidative Stress Response | PRDX1 |
| Pentose Phosphate Pathway | GPI |
| Pentose and Glucuronate Interconversions | UCHL1 |
| Retinol Metabolism | ALDH1A1 |
| Riboflavin Metabolism | TYR |
| Tyrosine Metabolism | PRMT5, TYR |
| Ubiquinone Biosynthesis | PRMT5 |
| Valine, Leucine and Isoleucine Degradation | ALDH1A1 |
| Glycine, Serine and Threonine Metabolism | CHKA |
| Lysine Degradation | ALDH1A1 |
| Pain/Taste | TRPM5; TRPA1 |
| Pain | TRPM7; TRPC5; TRPC6; TRPC1; Cnrl; cnr2; Grk2; Trpal; Pomc; Cgrp; Crf; Pka; Era; Nr2b; TRPM5; Prkaca; Prkacb; Prkar1a; Prkar2a |
| Mitochondrial Function | AIF; CytC; SMAC (Diablo); Aifm-1; Aifm-2 |
| Developmental Neurology | BMP-4; Chordin (Chrd); Noggin (Nog); WNT (Wnt2; Wnt2b; Wnt3a; Wnt4; Wnt5a; Wnt6; Wnt7b; Wnt8b; Wnt9a; Wnt9b; Wnt10a; Wnt10b; Wnt16); beta-catenin; Dkk-1; Frizzled related proteins; Otx-2; Gbx2; FGF-8; Reelin; Dab 1; unc-86 (Pou4f1 or Brn3a); Numb; Reln |

Embodiments of the invention also relate to methods and compositions related to knocking out genes, amplifying genes and repairing particular mutations associated with DNA repeat instability and neurological disorders (Robert D. Wells, Tetsuo Ashizawa, Genetic Instabilities and Neurological Diseases, Second Edition, Academic Press, Oct. 13, 2011—Medical). Specific aspects of tandem repeat sequences have been found to be responsible for more than twenty human diseases (New insights into repeat instability: role of RNA·DNA hybrids. McIvor EI, Polak U, Napierala M. RNA Biol. 2010 September-October; 7(5):551-8). The present effector protein systems may be harnessed to correct these defects of genomic instability.

Several further aspects of the invention relate to correcting defects associated with a wide range of genetic diseases which are further described on the website of the National Institutes of Health under the topic subsection Genetic Disorders (website at health.nih.gov/topic/GeneticDisorders). The genetic brain diseases may include but are not limited to Adrenoleukodystrophy, Agenesis of the Corpus Callosum, Aicardi Syndrome, Alpers' Disease, Alzheimer's Disease, Barth Syndrome, Batten Disease, CADASIL, Cerebellar Degeneration, Fabry's Disease, Gerstmann-Straussler-Scheinker Disease, Huntington's Disease and other Triplet Repeat Disorders, Leigh's Disease, Lesch-Nyhan Syndrome, Menkes Disease, Mitochondrial Myopathies and NINDS Colpocephaly. These diseases are further described on the website of the National Institutes of Health under the subsection Genetic Brain Disorders.

General Comments on Methods of Use of the CRISPR System

In particular embodiments, the methods described herein may involve targeting one or more polynucleotide targets of interest. The polynucleotide targets of interest may be targets which are relevant to a specific disease or the treatment thereof, relevant for the generation of a given trait of interest or relevant for the production of a molecule of interest. When referring to the targeting of a "polynucleotide target" this may include targeting one or more of a coding regions, an intron, a promoter and any other 5' or 3' regulatory regions such as termination regions, ribosome binding sites, enhancers, silencers etc. The gene may encode any protein or RNA of interest. Accordingly, the target may be a coding region which can be transcribed into mRNA, tRNA or rRNA, but also recognition sites for proteins involved in replication, transcription and regulation thereof.

In particular embodiments, the methods described herein may involve targeting one or more genes of interest, wherein at least one gene of interest encodes a long noncoding RNA (lncRNA). While lncRNAs have been found to be critical for cellular functioning. As the lncRNAs that are essential have been found to differ for each cell type (C. P. Fulco et al., 2016, Science, doi:10.1126/science.aag2445; N. E. Sanjana et al., 2016, Science, doi:10.1126/science.aaf8325), the methods provided herein may involve the step of determining the lncRNA that is relevant for cellular function for the cell of interest.

In an exemplary method for modifying a target polynucleotide by integrating an exogenous polynucleotide template, a double stranded break is introduced into the genome sequence by the CRISPR complex, the break is repaired via homologous recombination an exogenous polynucleotide template such that the template is integrated into the genome. The presence of a double-stranded break facilitates integration of the template.

In other embodiments, this invention provides a method of modifying expression of a polynucleotide in a eukaryotic cell. The method comprises increasing or decreasing expression of a target polynucleotide by using a CRISPR complex that binds to the polynucleotide.

In some methods, a target polynucleotide can be inactivated to effect the modification of the expression in a cell. For example, upon the binding of a CRISPR complex to a target sequence in a cell, the target polynucleotide is inactivated such that the sequence is not transcribed, the coded protein is not produced, or the sequence does not function as the wild-type sequence does. For example, a protein or microRNA coding sequence may be inactivated such that the protein is not produced.

In some methods, a control sequence can be inactivated such that it no longer functions as a control sequence. As used herein, "control sequence" refers to any nucleic acid sequence that effects the transcription, translation, or accessibility of a nucleic acid sequence. Examples of a control sequence include, a promoter, a transcription terminator, and an enhancer are control sequences. The inactivated target sequence may include a deletion mutation (i.e., deletion of one or more nucleotides), an insertion mutation (i.e., insertion of one or more nucleotides), or a nonsense mutation (i.e., substitution of a single nucleotide for another nucleotide such that a stop codon is introduced). In some methods, the inactivation of a target sequence results in "knockout" of the target sequence.

Also provided herein are methods of functional genomics which involve identifying cellular interactions by introducing multiple combinatorial perturbations and correlating observed genomic, genetic, proteomic, epigenetic and/or phenotypic effects with the perturbation detected in single cells, also referred to as "perturb-seq". In one embodiment, these methods combine single-cell RNA sequencing (RNA-seq) and clustered regularly interspaced short palindromic repeats (CRISPR)-based perturbations (Dixit et al. 2016, Cell 167, 1853-1866; Adamson et al. 2016, Cell 167, 1867-1882). Generally, these methods involve introducing a number of combinatorial perturbations to a plurality of cells in a population of cells, wherein each cell in the plurality of the cells receives at least 1 perturbation, detecting genomic, genetic, proteomic, epigenetic and/or phenotypic differences in single cells compared to one or more cells that did not receive any perturbation, and detecting the perturbation(s) in single cells; and determining measured differences relevant to the perturbations by applying a model accounting for co-variates to the measured differences, whereby intercellular and/or intracellular networks or circuits are inferred. More particularly, the single cell sequencing comprises cell barcodes, whereby the cell-of-origin of each RNA is recorded. More particularly, the single cell sequencing comprises unique molecular identifiers (UMI), whereby the capture rate of the measured signals, such as transcript copy number or probe binding events, in a single cell is determined.

These methods can be used for combinatorial probing of cellular circuits, for dissecting cellular circuitry, for delineating molecular pathways, and/or for identifying relevant targets for therapeutics development. More particularly, these methods may be used to identify groups of cells based on their molecular profiling. Similarities in gene-expression profiles between organic (e.g. disease) and induced (e.g. by small molecule) states may identify clinically-effective therapies.

Accordingly, in particular embodiments, therapeutic methods provided herein comprise, determining, for a population of cells isolated from a subject, optimal therapeutic target and/or therapeutic, using perturb-seq as described above.

In particular embodiments, perturb-seq methods as referred to herein elsewhere are used to determine, in an isolated cell or cell line, cellular circuits which may affect production of a molecule of interest.

Additional CRISPR-Cas Development and Use Considerations

The present invention may be further illustrated and extended based on aspects of CRISPR-Cas9 development and use as set forth in the following articles and particularly as relates to delivery of a CRISPR protein complex and uses of an RNA guided endonuclease in cells and organisms:

Multiplex genome engineering using CRISPR/Cas systems. Cong, L., Ran, F. A., Cox, D., Lin, S., Barretto, R., Habib, N., Hsu, P. D., Wu, X., Jiang, W., Marraffini, L. A., & Zhang, F. Science February 15; 339(6121):819-23 (2013);

RNA-guided editing of bacterial genomes using CRISPR-Cas systems. Jiang W., Bikard D., Cox D., Zhang F, Marraffini L A. Nat Biotechnol March; 31(3):233-9 (2013);

One-Step Generation of Mice Carrying Mutations in Multiple Genes by CRISPR/Cas-Mediated Genome Engineering. Wang H., Yang H., Shivalila C S., Dawlaty M M., Cheng A W., Zhang F., Jaenisch R. Cell May 9; 153(4): 910-8 (2013);

Optical control of mammalian endogenous transcription and epigenetic states. Konermann S, Brigham M D, Trevino A E, Hsu P D, Heidenreich M, Cong L, Platt R J, Scott D A, Church G M, Zhang F. Nature. August 22; 500(7463): 472-6. doi: 10.1038/Nature12466. Epub 2013 August 23 (2013);

Double Nicking by RNA-Guided CRISPR-Cas9 for Enhanced Genome Editing Specificity. Ran, F A., Hsu, P D., Lin, C Y., Gootenberg, J S., Konermann, S., Trevino, A E., Scott, D A., Inoue, A., Matoba, S., Zhang, Y., & Zhang, F. Cell August 28. pii: S0092-8674(13)01015-5 (2013-A);

DNA targeting specificity of RNA-guided Cas9 nucleases. Hsu, P., Scott, D., Weinstein, J., Ran, F A., Konermann, S., Agarwala, V., Li, Y., Fine, E., Wu, X., Shalem, O., Cradick, T J., Marraffini, L A., Bao, G., & Zhang, F. Nat Biotechnol doi:10.1038/nbt.2647 (2013);

Genome engineering using the CRISPR-Cas9 system. Ran, F A., Hsu, P D., Wright, J., Agarwala, V., Scott, D A., Zhang, F. Nature Protocols November; 8(11):2281-308 (2013-B);

Genome-Scale CRISPR-Cas9 Knockout Screening in Human Cells. Shalem, O., Sanjana, N E., Hartenian, E., Shi, X., Scott, D A., Mikkelson, T., Heckl, D., Ebert, B L., Root, D E., Doench, J G., Zhang, F. Science December 12. (2013). [Epub ahead of print];

Crystal structure of cas9 in complex with guide RNA and target DNA. Nishimasu, H., Ran, F A., Hsu, P D., Konermann, S., Shehata, S I., Dohmae, N., Ishitani, R., Zhang, F., Nureki, O. Cell February 27, 156(5):935-49 (2014);

Genome-wide binding of the CRISPR endonuclease Cas9 in mammalian cells. Wu X., Scott D A., Kriz A J., Chiu A C., Hsu P D., Dadon D B., Cheng A W., Trevino A E., Konermann S., Chen S., Jaenisch R., Zhang F., Sharp P A. Nat Biotechnol. April 20. doi: 10.1038/nbt.2889 (2014);

CRISPR-Cas9 Knockin Mice for Genome Editing and Cancer Modeling. Platt R J, Chen S, Zhou Y, Yim M J, Swiech L, Kempton H R, Dahlman J E, Parnas O, Eisenhaure T M, Jovanovic M, Graham D B, Jhunjhunwala S, Heidenreich M, Xavier R J, Langer R, Anderson D G, Hacohen N, Regev A, Feng G, Sharp P A, Zhang F. Cell 159(2): 440-455 DOI: 10.1016/j.cell.2014.09.014(2014);

Development and Applications of CRISPR-Cas9 for Genome Engineering, Hsu P D, Lander E S, Zhang F., Cell. June 5; 157(6):1262-78 (2014).

Genetic screens in human cells using the CRISPR/Cas9 system, Wang T, Wei J J, Sabatini D M, Lander E S., Science. January 3; 343(6166): 80-84. doi:10.1126/science.1246981 (2014);

Rational design of highly active sgRNAs for CRISPR-Cas9-mediated gene inactivation, Doench J G, Hartenian E, Graham D B, Tothova Z, Hegde M, Smith I, Sullender M, Ebert B L, Xavier R J, Root D E., (published online 3 Sep. 2014) Nat Biotechnol. December; 32(12):1262-7 (2014);

In vivo interrogation of gene function in the mammalian brain using CRISPR-Cas9, Swiech L, Heidenreich M, Banerjee A, Habib N, Li Y, Trombetta J, Sur M, Zhang F., (published online 19 Oct. 2014) Nat Biotechnol. January; 33(1):102-6 (2015);

Genome-scale transcriptional activation by an engineered CRISPR-Cas9 complex, Konermann S, Brigham M D, Trevino A E, Joung J, Abudayyeh O O, Barcena C, Hsu P D, Habib N, Gootenberg J S, Nishimasu H, Nureki O, Zhang F., Nature. January 29; 517(7536):583-8 (2015).

A split-Cas9 architecture for inducible genome editing and transcription modulation, Zetsche B, Volz S E, Zhang F., (published online 2 Feb. 2015) Nat Biotechnol. February; 33(2):139-42 (2015);

Genome-wide CRISPR Screen in a Mouse Model of Tumor Growth and Metastasis, Chen S, Sanjana N E, Zheng K, Shalem O, Lee K, Shi X, Scott D A, Song J, Pan J Q, Weissleder R, Lee H, Zhang F, Sharp P A. Cell 160, 1246-1260, Mar. 12, 2015 (multiplex screen in mouse), and In vivo genome editing using Staphylococcus aureus Cas9, Ran F A, Cong L, Yan W X, Scott D A, Gootenberg J S, Kriz A J, Zetsche B, Shalem O, Wu X, Makarova K S, Koonin E V, Sharp P A, Zhang F., (published online 1 Apr. 2015), Nature. April 9; 520(7546):186-91 (2015).

Shalem et al., "High-throughput functional genomics using CRISPR-Cas9," Nature Reviews Genetics 16, 299-311 (May 2015).

Xu et al., "Sequence determinants of improved CRISPR sgRNA design," Genome Research 25, 1147-1157 (August 2015).

Parnas et al., "A Genome-wide CRISPR Screen in Primary Immune Cells to Dissect Regulatory Networks," Cell 162, 675-686 (Jul. 30, 2015).

Ramanan et al., CRISPR/Cas9 cleavage of viral DNA efficiently suppresses hepatitis B virus," Scientific Reports 5:10833. doi: 10.1038/srep10833 (Jun. 2, 2015)

Nishimasu et al., Crystal Structure of *Staphylococcus aureus* Cas9," Cell 162, 1113-1126 (Aug. 27, 2015)

BCL11A enhancer dissection by Cas9-mediated in situ saturating mutagenesis, Canver et al., Nature 527(7577): 192-7 (Nov. 12, 2015) doi: 10.1038/nature15521. Epub 2015 Sep. 16.

*Cpf1 Is a Single RNA-Guided Endonuclease of a Class 2 CRISPR-Cas System*, Zetsche et al., Cell 163, 759-71 (Sep. 25, 2015).

*Discovery and Functional Characterization of Diverse Class 2 CRISPR-Cas Systems*, Shmakov et al., Molecular Cell, 60(3), 385-397 doi: 10.1016/j.molcel.2015.10.008 Epub Oct. 22, 2015.

*Rationally engineered Cas9 nucleases with improved specificity*, Slaymaker et al., Science 2016 January 1 351 (6268): 84-88 doi: 10.1126/science.aad5227. Epub 2015 Dec. 1. [Epub ahead of print].

Gao et al, "Engineered Cpf1 Enzymes with Altered PAM Specificities," bioRxiv 091611; doi: dx.doi.org/10.1101/091611 (Dec. 4, 2016)

each of which is incorporated herein by reference, may be considered in the practice of the instant invention, and discussed briefly below:

Cong et al. engineered type II CRISPR-Cas systems for use in eukaryotic cells based on both *Streptococcus thermophilus* Cas9 and also *Streptococcus pyogenes* Cas9 and demonstrated that Cas9 nucleases can be directed by short RNAs to induce precise cleavage of DNA in human and mouse cells. Their study further showed that Cas9 as converted into a nicking enzyme can be used to facilitate homology-directed repair in eukaryotic cells with minimal mutagenic activity. Additionally, their study demonstrated that multiple guide sequences can be encoded into a single CRISPR array to enable simultaneous editing of several at endogenous genomic loci sites within the mammalian genome, demonstrating easy programmability and wide applicability of the RNA-guided nuclease technology. This ability to use RNA to program sequence specific DNA cleavage in cells defined a new class of genome engineering tools. These studies further showed that other CRISPR loci are likely to be transplantable into mammalian cells and can also mediate mammalian genome cleavage. Importantly, it can be envisaged that several aspects of the CRISPR-Cas system can be further improved to increase its efficiency and versatility.

Jiang et al. used the clustered, regularly interspaced, short palindromic repeats (CRISPR)-associated Cas9 endonuclease complexed with dual-RNAs to introduce precise mutations in the genomes of *Streptococcus pneumoniae* and *Escherichia coli*. The approach relied on dual-RNA:Cas9-directed cleavage at the targeted genomic site to kill unmutated cells and circumvents the need for selectable markers or counter-selection systems. The study reported reprogramming dual-RNA:Cas9 specificity by changing the sequence of short CRISPR RNA (crRNA) to make single- and multinucleotide changes carried on editing templates. The study showed that simultaneous use of two crRNAs enabled multiplex mutagenesis. Furthermore, when the approach was used in combination with recombineering, in *S. pneumoniae*, nearly 100% of cells that were recovered using the described approach contained the desired mutation, and in *E. coli*, 65% that were recovered contained the mutation.

Wang et al. (2013) used the CRISPR-Cas system for the one-step generation of mice carrying mutations in multiple genes which were traditionally generated in multiple steps by sequential recombination in embryonic stem cells and/or time-consuming intercrossing of mice with a single mutation. The CRISPR-Cas system will greatly accelerate the in vivo study of functionally redundant genes and of epistatic gene interactions.

Konermann et al. (2013) addressed the need in the art for versatile and robust technologies that enable optical and chemical modulation of DNA-binding domains based CRISPR-Cas9 enzyme and also Transcriptional Activator Like Effectors Ran et al. (2013-A) described an approach that combined a Cas9 nickase mutant with paired guide RNAs to introduce targeted double-strand breaks. This addresses the issue of the Cas9 nuclease from the microbial CRISPR-Cas system being targeted to specific genomic loci by a guide sequence, which can tolerate certain mismatches to the DNA target and thereby promote undesired off-target mutagenesis. Because individual nicks in the genome are repaired with high fidelity, simultaneous nicking via appropriately offset guide RNAs is required for double-stranded breaks and extends the number of specifically recognized bases for target cleavage. The authors demonstrated that using paired nicking can reduce off-target activity by 50- to 1,500-fold in cell lines and to facilitate gene knockout in mouse zygotes without sacrificing on-target cleavage efficiency. This versatile strategy enables a wide variety of genome editing applications that require high specificity.

Hsu et al. (2013) characterized SpCas9 targeting specificity in human cells to inform the selection of target sites and avoid off-target effects. The study evaluated >700 guide RNA variants and SpCas9-induced indel mutation levels at >100 predicted genomic off-target loci in 293T and 293FT cells. The authors that SpCas9 tolerates mismatches between guide RNA and target DNA at different positions in a sequence-dependent manner, sensitive to the number, position and distribution of mismatches. The authors further showed that SpCas9-mediated cleavage is unaffected by DNA methylation and that the dosage of SpCas9 and gRNA can be titrated to minimize off-target modification. Additionally, to facilitate mammalian genome engineering applications, the authors reported providing a web-based software tool to guide the selection and validation of target sequences as well as off-target analyses.

Ran et al. (2013-B) described a set of tools for Cas9-mediated genome editing via non-homologous end joining (NHEJ) or homology-directed repair (HDR) in mammalian cells, as well as generation of modified cell lines for downstream functional studies. To minimize off-target cleavage, the authors further described a double-nicking strategy using the Cas9 nickase mutant with paired guide RNAs. The protocol provided by the authors experimentally derived guidelines for the selection of target sites, evaluation of cleavage efficiency and analysis of off-target activity. The studies showed that beginning with target design, gene modifications can be achieved within as little as 1-2 weeks, and modified clonal cell lines can be derived within 2-3 weeks.

Shalem et al. described a new way to interrogate gene function on a genome-wide scale. Their studies showed that delivery of a genome-scale CRISPR-Cas9 knockout (GeCKO) library targeted 18,080 genes with 64,751 unique guide sequences enabled both negative and positive selection screening in human cells. First, the authors showed use of the GeCKO library to identify genes essential for cell viability in cancer and pluripotent stem cells. Next, in a melanoma model, the authors screened for genes whose loss is involved in resistance to vemurafenib, a therapeutic that inhibits mutant protein kinase BRAF. Their studies showed that the highest-ranking candidates included previously validated genes NF1 and MED12 as well as novel hits NF2, CUL3, TADA2B, and TADA1. The authors observed a high level of consistency between independent guide RNAs targeting the same gene and a high rate of hit confirmation, and thus demonstrated the promise of genome-scale screening with Cas9.

Nishimasu et al. reported the crystal structure of *Streptococcus pyogenes* Cas9 in complex with sgRNA and its target DNA at 2.5 A° resolution. The structure revealed a bilobed architecture composed of target recognition and nuclease lobes, accommodating the sgRNA:DNA heteroduplex in a positively charged groove at their interface. Whereas the recognition lobe is essential for binding sgRNA and DNA, the nuclease lobe contains the HNH and RuvC nuclease domains, which are properly positioned for cleavage of the complementary and non-complementary strands of the target DNA, respectively. The nuclease lobe also contains a carboxyl-terminal domain responsible for the interaction with the protospacer adjacent motif (PAM). This high-resolution structure and accompanying functional analyses have revealed the molecular mechanism of RNA-guided DNA targeting by Cas9, thus paving the way for the rational design of new, versatile genome-editing technologies.

Wu et al. mapped genome-wide binding sites of a catalytically inactive Cas9 (dCas9) from *Streptococcus pyogenes* loaded with single guide RNAs (sgRNAs) in mouse embryonic stem cells (mESCs). The authors showed that each of the four sgRNAs tested targets dCas9 to between tens and thousands of genomic sites, frequently characterized by a 5-nucleotide seed region in the sgRNA and an NGG protospacer adjacent motif (PAM). Chromatin inaccessibility decreases dCas9 binding to other sites with matching seed sequences; thus 70% of off-target sites are associated with genes. The authors showed that targeted sequencing of 295 dCas9 binding sites in mESCs transfected with catalytically active Cas9 identified only one site mutated above background levels. The authors proposed a two-state model for Cas9 binding and cleavage, in which a seed match triggers binding but extensive pairing with target DNA is required for cleavage.

Platt et al. established a Cre-dependent Cas9 knockin mouse. The authors demonstrated in vivo as well as ex vivo genome editing using adeno-associated virus (AAV)-, lentivirus-, or particle-mediated delivery of guide RNA in neurons, immune cells, and endothelial cells.

Hsu et al. (2014) is a review article that discusses generally CRISPR-Cas9 history from yogurt to genome editing, including genetic screening of cells.

Wang et al. (2014) relates to a pooled, loss-of-function genetic screening approach suitable for both positive and negative selection that uses a genome-scale lentiviral single guide RNA (sgRNA) library.

Doench et al. created a pool of sgRNAs, tiling across all possible target sites of a panel of six endogenous mouse and three endogenous human genes and quantitatively assessed their ability to produce null alleles of their target gene by antibody staining and flow cytometry. The authors showed that optimization of the PAM improved activity and also provided an on-line tool for designing sgRNAs.

Swiech et al. demonstrate that AAV-mediated SpCas9 genome editing can enable reverse genetic studies of gene function in the brain.

Konermann et al. (2015) discusses the ability to attach multiple effector domains, e.g., transcriptional activator, functional and epigenomic regulators at appropriate positions on the guide such as stem or tetraloop with and without linkers.

Zetsche et al. demonstrates that the Cas9 enzyme can be split into two and hence the assembly of Cas9 for activation can be controlled.

Chen et al. relates to multiplex screening by demonstrating that a genome-wide in vivo CRISPR-Cas9 screen in mice reveals genes regulating lung metastasis.

Ran et al. (2015) relates to SaCas9 and its ability to edit genomes and demonstrates that one cannot extrapolate from biochemical assays.

Shalem et al. (2015) described ways in which catalytically inactive Cas9 (dCas9) fusions are used to synthetically repress (CRISPRi) or activate (CRISPRa) expression, showing. advances using Cas9 for genome-scale screens, including arrayed and pooled screens, knockout approaches that inactivate genomic loci and strategies that modulate transcriptional activity.

Xu et al. (2015) assessed the DNA sequence features that contribute to single guide RNA (sgRNA) efficiency in CRISPR-based screens. The authors explored efficiency of CRISPR/Cas9 knockout and nucleotide preference at the cleavage site. The authors also found that the sequence preference for CRISPRi/a is substantially different from that for CRISPR/Cas9 knockout.

Parnas et al. (2015) introduced genome-wide pooled CRISPR-Cas9 libraries into dendritic cells (DCs) to identify genes that control the induction of tumor necrosis factor (Tnf) by bacterial lipopolysaccharide (LPS). Known regulators of TLR4 signaling and previously unknown candidates were identified and classified into three functional modules with distinct effects on the canonical responses to LPS.

Ramanan et al (2015) demonstrated cleavage of viral episomal DNA (cccDNA) in infected cells. The HBV genome exists in the nuclei of infected hepatocytes as a 3.2 kb double-stranded episomal DNA species called covalently closed circular DNA (cccDNA), which is a key component in the HBV life cycle whose replication is not inhibited by current therapies. The authors showed that sgRNAs specifically targeting highly conserved regions of HBV robustly suppresses viral replication and depleted cccDNA.

Nishimasu et al. (2015) reported the crystal structures of SaCas9 in complex with a single guide RNA (sgRNA) and its double-stranded DNA targets, containing the 5'-TTGAAT-3' PAM and the 5'-TTGGGT-3' PAM. A structural comparison of SaCas9 with SpCas9 highlighted both structural conservation and divergence, explaining their distinct PAM specificities and orthologous sgRNA recognition.

Canver et al. (2015) demonstrated a CRISPR-Cas9-based functional investigation of non-coding genomic elements. The authors we developed pooled CRISPR-Cas9 guide RNA libraries to perform in situ saturating mutagenesis of the human and mouse BCL11A enhancers which revealed critical features of the enhancers.

Zetsche et al. (2015) reported characterization of Cpf1, a class 2 CRISPR nuclease from *Francisella novicida* U112 having features distinct from Cas9. Cpf1 is a single RNA-guided endonuclease lacking tracrRNA, utilizes a T-rich protospacer-adjacent motif, and cleaves DNA via a staggered DNA double-stranded break.

Shmakov et al. (2015) reported three distinct Class 2 CRISPR-Cas systems. Two system CRISPR enzymes (C2c1 and C2c3) contain RuvC-like endonuclease domains distantly related to Cpf1. Unlike Cpf1, C2c1 depends on both crRNA and tracrRNA for DNA cleavage. The third enzyme (C2c2) contains two predicted HEPN RNase domains and is tracrRNA independent.

Slaymaker et al (2016) reported the use of structure-guided protein engineering to improve the specificity of *Streptococcus pyogenes* Cas9 (SpCas9). The authors developed "enhanced specificity" SpCas9 (eSpCas9) variants which maintained robust on-target cleavage with reduced off-target effects.

The methods and tools provided herein are exemplified for Cpf1, a type II nuclease that does not make use of tracrRNA. Orthologs of Cpf1 have been identified in different bacterial species as described herein. Further type II nucleases with similar properties can be identified using methods described in the art (Shmakov et al. 2015, 60:385-397; Abudayeh et al. 2016, Science, 5; 353(6299)). In particular embodiments, such methods for identifying novel CRISPR effector proteins may comprise the steps of selecting sequences from the database encoding a seed which identifies the presence of a CRISPR-Cas locus, identifying loci located within 10 kb of the seed comprising Open Reading Frames (ORFs) in the selected sequences, selecting therefrom loci comprising ORFs of which only a single ORF encodes a novel CRISPR effector having greater than 700 amino acids and no more than 90% homology to a known CRISPR effector. In particular embodiments, the seed is a protein that is common to the CRISPR-Cas system, such as Cas1. In further embodiments, the CRISPR array is used as a seed to identify new effector proteins.

The effectiveness of the present invention has been demonstrated. Preassembled recombinant CRISPR-Cpf1 complexes comprising Cpf1 and crRNA may be transfected, for example by electroporation, resulting in high mutation rates and absence of detectable off-target mutations. Hur, J. K. et al, Targeted mutagenesis in mice by electroporation of Cpf1 ribonucleoproteins, Nat Biotechnol. 2016 Jun. 6. doi: 10.1038/nbt.3596. [Epub ahead of print]. Genome-wide analyses shows that Cpf1 is highly specific. By one measure, in vitro cleavage sites determined for SpCas9 in human HEK293T cells were significantly fewer that for SpCas9. Kim, D. et al., Genome-wide analysis reveals specificities of Cpf1 endonucleases in human cells, Nat Biotechnol. 2016 Jun. 6. doi: 10.1038/nbt.3609. [Epub ahead of print]. An efficient multiplexed system employing Cpf1 has been demonstrated in *Drosophila* employing gRNAs processed from an array containing inventing tRNAs. Port, F. et al, Expansion of the CRISPR toolbox in an animal with tRNA-flanked Cas9 and Cpf1 gRNAs. doi: dx.doi.org/10.1101/046417.

Also, "Dimeric CRISPR RNA-guided FokI nucleases for highly specific genome editing", Shengdar Q. Tsai, Nicolas Wyvekens, Cyd Khayter, Jennifer A. Foden, Vishal Thapar, Deepak Reyon, Mathew J. Goodwin, Martin J. Aryee, J. Keith Joung Nature Biotechnology 32(6): 569-77 (2014), relates to dimeric RNA-guided FokI Nucleases that recognize extended sequences and can edit endogenous genes with high efficiencies in human cells.

With respect to general information on CRISPR-Cas Systems, components thereof, and delivery of such components, including methods, materials, delivery vehicles, vectors, particles, AAV, and making and using thereof, including as to amounts and formulations, all useful in the practice of the instant invention, reference is made to: U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641; US Patent Publications US 2014-0310830 (U.S. application Ser. No. 14/105,031), US 2014-0287938 A1 (U.S. application Ser. No. 14/213, 991), US 2014-0273234 A1 (U.S. application Ser. No. 14/293,674), US2014-0273232 A1 (U.S. application Ser. No. 14/290,575), US 2014-0273231 (U.S. application Ser. No. 14/259,420), US 2014-0256046 A1 (U.S. application Ser. No. 14/226,274), US 2014-0248702 A1 (U.S. application Ser. No. 14/258,458), US 2014-0242700 A1 (U.S. application Ser. No. 14/222,930), US 2014-0242699 A1 (U.S. application Ser. No. 14/183,512), US 2014-0242664 A1 (U.S. application Ser. No. 14/104,990), US 2014-0234972 A1 (U.S. application Ser. No. 14/183,471), US 2014-0227787 A1 (U.S. application Ser. No. 14/256,912), US 2014-0189896 A1 (U.S. application Ser. No. 14/105, 035), US 2014-0186958 (U.S. application Ser. No. 14/105, 017), US 2014-0186919 A1 (U.S. application Ser. No. 14/104,977), US 2014-0186843 A1 (U.S. application Ser. No. 14/104,900), US 2014-0179770 A1 (U.S. application Ser. No. 14/104,837) and US 2014-0179006 A1 (U.S. application Ser. No. 14/183,486), US 2014-0170753 (U.S. application Ser. No. 14/183,429); US 2015-0184139 (U.S. application Ser. No. 14/324,960); Ser. No. 14/054,414 European Patent Applications EP 2 771 468 (EP13818570.7), EP 2 764 103 (EP13824232.6), and EP 2 784 162 (EP14170383.5); and PCT Patent Publications WO 2014/093661 (PCT/US2013/074743), WO 2014/093694 (PCT/US2013/074790), WO 2014/093595 (PCT/US2013/074611), WO 2014/093718 (PCT/US2013/074825), WO 2014/093709 (PCT/US2013/074812), WO 2014/093622 (PCT/US2013/074667), WO 2014/093635 (PCT/US2013/074691), WO 2014/093655 (PCT/US2013/074736), WO 2014/093712 (PCT/US2013/074819), WO 2014/093701 (PCT/US2013/074800), WO 2014/018423 (PCT/US2013/051418), WO 2014/204723 (PCT/US2014/041790), WO 2014/204724 (PCT/US2014/041800), WO 2014/204725 (PCT/US2014/041803), WO 2014/204726 (PCT/US2014/041804), WO 2014/204727 (PCT/US2014/041806), WO 2014/204728 (PCT/US2014/041808), WO 2014/204729 (PCT/US2014/041809), WO 2015/089351 (PCT/US2014/069897), WO 2015/089354 (PCT/US2014/069902), WO 2015/089364 (PCT/US2014/069925), WO 2015/089427 (PCT/US2014/070068), WO 2015/089462 (PCT/US2014/070127), WO 2015/089419 (PCT/US2014/070057), WO 2015/089465 (PCT/US2014/070135), WO 2015/089486 (PCT/US2014/070175), PCT/US2015/051691, PCT/US2015/051830. Reference is also made to U.S. provisional patent applications 61/758,468; 61/802,174; 61/806,375; 61/814,263; 61/819, 803 and 61/828,130, filed on Jan. 30, 2013; Mar. 15, 2013; Mar. 28, 2013; Apr. 20, 2013; May 6, 2013 and May 28, 2013 respectively. Reference is also made to U.S. provisional patent application 61/836,123, filed on Jun. 17, 2013. Reference is additionally made to U.S. provisional patent applications 61/835,931, 61/835,936, 61/835,973, 61/836, 080, 61/836,101, and 61/836,127, each filed Jun. 17, 2013. Further reference is made to U.S. provisional patent applications 61/862,468 and 61/862,355 filed on Aug. 5, 2013; 61/871,301 filed on Aug. 28, 2013; 61/960,777 filed on Sep. 25, 2013 and 61/961,980 filed on Oct. 28, 2013. Reference is yet further made to: PCT/US2014/62558 filed Oct. 28, 2014, and U.S. Provisional Patent Applications Ser. Nos. 61/915,148, 61/915,150, 61/915,153, 61/915,203, 61/915, 251, 61/915,301, 61/915,267, 61/915,260, and 61/915,397, each filed Dec. 12, 2013; 61/757,972 and 61/768,959, filed on Jan. 29, 2013 and Feb. 25, 2013; 62/010,888 and 62/010, 879, both filed Jun. 11, 2014; 62/010,329, 62/010,439 and 62/010,441, each filed Jun. 10, 2014; 61/939,228 and 61/939,242, each filed Feb. 12, 2014; 61/980,012, filed Apr. 15, 2014; 62/038,358, filed Aug. 17, 2014; 62/055,484, 62/055,460 and 62/055,487, each filed Sep. 25, 2014; and 62/069,243, filed Oct. 27, 2014. Reference is made to PCT application designating, inter alia, the United States, application No. PCT/US14/41806, filed Jun. 10, 2014. Reference is made to U.S. provisional patent application 61/930,214 filed on Jan. 22, 2014. Reference is made to PCT application designating, inter alia, the United States, application No. PCT/US14/41806, filed Jun. 10, 2014.

Mention is also made of U.S. application 62/180,709, 17 Jun. 15, PROTECTED GUIDE RNAS (PGRNAS); U.S. application 62/091,455, filed, 12 Dec. 14, PROTECTED GUIDE RNAS (PGRNAS); U.S. application 62/096,708, 24 Dec. 14, PROTECTED GUIDE RNAS (PGRNAS); U.S. applications 62/091,462, 12 Dec. 14, 62/096,324, 23 Dec. 14, 62/180,681, 17 Jun. 2015, and 62/237,496, 5 Oct. 2015, DEAD GUIDES FOR CRISPR TRANSCRIPTION FACTORS; U.S. application 62/091,456, 12 Dec. 14 and 62/180, 692, 17 Jun. 2015, ESCORTED AND FUNCTIONALIZED GUIDES FOR CRISPR-CAS SYSTEMS; U.S. application 62/091,461, 12 Dec. 14, DELIVERY, USE AND THERAPEUTIC APPLICATIONS OF THE CRISPR-CAS SYSTEMS AND COMPOSITIONS FOR GENOME EDITING AS TO HEMATOPOIETIC STEM CELLS (HSCs); U.S. application 62/094,903, 19 Dec. 14, UNBIASED IDENTIFICATION OF DOUBLE-STRAND BREAKS AND GENOMIC REARRANGEMENT BY GENOME-WIDE INSERT CAPTURE SEQUENCING; U.S. application 62/096,761, 24 Dec. 14, ENGINEERING OF SYSTEMS, METHODS AND OPTIMIZED ENZYME AND GUIDE SCAFFOLDS FOR SEQUENCE MANIPULATION; U.S. application 62/098,059, 30 Dec. 14, 62/181,641, 18 Jun. 2015, and 62/181,667, 18 Jun. 2015, RNA-TARGETING SYSTEM; U.S. application 62/096,656, 24 Dec. 14 and 62/181,151, 17 Jun. 2015, CRISPR HAVING OR ASSOCIATED WITH DESTABILIZATION DOMAINS; U.S. application 62/096,697, 24 Dec. 14, CRISPR HAVING OR ASSOCIATED WITH AAV; U.S. application 62/098,158, 30 Dec. 14, ENGINEERED CRISPR COMPLEX INSERTIONAL TARGETING SYSTEMS; U.S. application 62/151,052, 22 Apr. 15, CELLULAR TARGETING FOR EXTRACELLULAR EXOSOMAL REPORTING; U.S. application 62/054,490, 24 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS; U.S. application 61/939,154, 12 Feb. 14, SYSTEMS, METHODS AND COMPOSITIONS FOR SEQUENCE MANIPULATION WITH OPTIMIZED FUNCTIONAL CRISPR-CAS SYSTEMS; U.S. application 62/055,484, 25 Sep. 14, SYSTEMS, METHODS AND COMPOSITIONS FOR SEQUENCE MANIPULATION WITH OPTIMIZED FUNCTIONAL CRISPR-CAS SYSTEMS; U.S. application 62/087,537, 4 Dec. 14, SYSTEMS, METHODS AND COMPOSITIONS FOR SEQUENCE MANIPULATION WITH OPTIMIZED FUNCTIONAL CRISPR-CAS SYSTEMS; U.S. application 62/054,651, 24 Sep. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. application 62/067,886, 23 Oct. 14, DELIVERY, USE AND THERAPEUTIC APPLICATIONS OF THE CRISPR-CAS SYSTEMS AND COMPOSITIONS FOR MODELING COMPETITION OF MULTIPLE CANCER MUTATIONS IN VIVO; U.S. applications 62/054,675, 24 Sep. 14 and 62/181,002, 17 Jun. 2015, DELIVERY, USE AND THERAPEUTIC APPLICATIONS OF THE CRISPR-CAS SYSTEMS AND COMPOSITIONS IN NEURONAL CELLS/TISSUES; U.S. application 62/054,528, 24 Sep. 14, DELIVERY, USE AND THERAPEUTIC APPLICATIONS OF THE CRISPR-CAS SYSTEMS AND COMPOSITIONS IN IMMUNE DISEASES OR DISORDERS; U.S. application 62/055,454, 25 Sep. 14, DELIVERY, USE AND THERAPEUTIC APPLICATIONS OF THE CRISPR-CAS SYSTEMS AND COMPOSITIONS FOR TARGETING DISORDERS AND DISEASES USING CELL PENETRATION PEPTIDES (CPP); U.S. application 62/055,460, 25 Sep. 14, MULTIFUNCTIONAL-CRISPR COMPLEXES AND/OR OPTIMIZED ENZYME LINKED FUNCTIONAL-CRISPR COMPLEXES; U.S. application 62/087,475, 4 Dec. 14 and 62/181,690, 18 Jun. 2015, FUNCTIONAL SCREENING WITH OPTIMIZED FUNCTIONAL CRISPR-CAS SYSTEMS; U.S. application 62/055,487, 25 Sep. 14, FUNCTIONAL SCREENING WITH OPTIMIZED FUNCTIONAL CRISPR-CAS SYSTEMS; U.S. application 62/087,546, 4 Dec. 14 and 62/181,687, 18 Jun. 2015, MULTIFUNCTIONAL CRISPR COMPLEXES AND/OR OPTIMIZED ENZYME LINKED FUNCTIONAL-CRISPR COMPLEXES; and U.S. application 62/098,285, 30 Dec. 14, CRISPR MEDIATED IN VIVO MODELING AND GENETIC SCREENING OF TUMOR GROWTH AND METASTASIS.

Mention is made of U.S. applications 62/181,659, 18 Jun. 2015 and 62/207,318, 19 Aug. 2015, ENGINEERING AND OPTIMIZATION OF SYSTEMS, METHODS, ENZYME AND GUIDE SCAFFOLDS OF CAS9 ORTHOLOGS AND VARIANTS FOR SEQUENCE MANIPULATION. Mention is made of U.S. applications 62/181,663, 18 Jun. 2015 and 62/245,264, 22 Oct. 2015, NOVEL CRISPR ENZYMES AND SYSTEMS, U.S. applications 62/181,675, 18 Jun. 2015, 62/285,349, 22 Oct. 2015, 62/296,522, 17 Feb. 2016, and 62/320,231, 8 Apr. 2016, NOVEL CRISPR ENZYMES AND SYSTEMS, U.S. application 62/232,067, 24 Sep. 2015, U.S. application Ser. No. 14/975,085, 18 Dec. 2015, European application No. 16150428.7, U.S. application 62/205,733, 16 Aug. 2015, U.S. application 62/201,542, 5 Aug. 2015, U.S. application 62/193,507, 16 Jul. 2015, and U.S. application 62/181,739, 18 Jun. 2015, each entitled NOVEL CRISPR ENZYMES AND SYSTEMS and of U.S. application 62/245,270, 22 Oct. 2015, NOVEL CRISPR ENZYMES AND SYSTEMS. Mention is also made of U.S. application 61/939,256, 12 Feb. 2014, and WO 2015/089473 (PCT/US2014/070152), 12 Dec. 2014, each entitled ENGINEERING OF SYSTEMS, METHODS AND OPTIMIZED GUIDE COMPOSITIONS WITH NEW ARCHITECTURES FOR SEQUENCE MANIPULATION. Mention is also made of PCT/US2015/045504, 15 Aug. 2015, U.S. application 62/180,699, 17 Jun. 2015, and U.S. application 62/038,358, 17 Aug. 2014, each entitled GENOME EDITING USING CAS9 NICKASES.

In addition, mention is made of PCT application PCT/US14/70057, entitled "DELIVERY, USE AND THERAPEUTIC APPLICATIONS OF THE CRISPR-CAS SYSTEMS AND COMPOSITIONS FOR TARGETING DISORDERS AND DISEASES USING PARTICLE DELIVERY COMPONENTS (claiming priority from one or more or all of US provisional patent applications: 62/054,490, filed Sep. 24, 2014; 62/010,441, filed Jun. 10, 2014; and 61/915,118, 61/915,215 and 61/915,148, each filed on Dec. 12, 2013) ("the Particle Delivery PCT"), incorporated herein by reference, and of PCT application PCT/US14/70127, entitled "DELIVERY, USE AND THERAPEUTIC APPLICATIONS OF THE CRISPR-CAS SYSTEMS AND COMPOSITIONS FOR GENOME EDITING" (claiming priority from one or more or all of US provisional patent applications: 61/915,176; 61/915,192; 61/915,215; 61/915,107, 61/915,145; 61/915,148; and 61/915,153 each filed Dec. 12, 2013) ("the Eye PCT"), incorporated herein by reference, with respect to a method of preparing an sgRNA-and-Cpf1 protein containing particle comprising admixing a mixture comprising an sgRNA and Cpf1 protein (and optionally HDR template) with a mixture comprising or consisting essentially of or consisting of surfactant, phospholipid, biodegradable polymer, lipoprotein and alcohol; and particles from such a process. For example, wherein Cpf1 protein and sgRNA were mixed together at a suitable, e.g., 3:1 to 1:3 or 2:1 to 1:2 or 1:1 molar ratio, at a suitable temperature, e.g., 15-30 C, e.g., 20-25 C, e.g., room temperature, for a suitable time, e.g., 15-45, such as 30 minutes, advantageously in sterile, nuclease free buffer, e.g., 1×PBS. Separately, particle components such as or comprising: a surfactant, e.g., cationic lipid, e.g 1,2-dioleoyl-3-trimethyl-ammonium-propane (DOTAP); phospholipid, e.g., dimyristoylphosphatidylcholine (DMPC); biodegradable polymer, such as an ethylene-glycol polymer or PEG, and a lipoprotein, such as a low-density lipoprotein, e.g., cholesterol were dissolved in an alcohol, advantageously a C1-6 alkyl alcohol, such as methanol, ethanol, isopropanol, e.g., 100% ethanol. The two solutions were mixed together to form particles containing the Cas9-sgRNA complexes. Accordingly, sgRNA may be pre-complexed with the Cpf1 protein, before formulating the entire complex in a particle. Formulations may be made with a different molar ratio of different components known to promote delivery of nucleic acids into cells (e.g. 1,2-dioleoyl-3-trimethylammonium-propane (DOTAP), 1,2-ditetradecanoyl-sn-glycero-3-phosphocholine (DMPC), polyethylene glycol (PEG), and cholesterol) For example DOTAP:DMPC:PEG:Cholesterol Molar Ratios may be DOTAP 100, DMPC 0, PEG 0, Cholesterol 0; or DOTAP 90, DMPC 0, PEG 10, Cholesterol 0; or DOTAP 90, DMPC 0, PEG 5, Cholesterol 5. DOTAP 100, DMPC 0, PEG 0, Cholesterol 0. That application accordingly comprehends admixing sgRNA, Cpf1 protein and components that form a particle; as well as particles from such admixing. Aspects of the instant invention can involve particles; for example, particles using a process analogous to that of the Particle Delivery PCT or that of the Eye PCT, e.g., by admixing a mixture comprising sgRNA and/or Cpf1 as in the instant invention and components that form a particle, e.g., as in the Particle Delivery PCT or in the Eye PCT, to form a particle and particles from such admixing (or, of course, other particles involving sgRNA and/or Cpf1 as in the instant invention).

The subject invention may be used as part of a research program wherein there is transmission of results or data. A computer system (or digital device) may be used to receive, transmit, display and/or store results, analyze the data and/or results, and/or produce a report of the results and/or data and/or analysis. A computer system may be understood as a logical apparatus that can read instructions from media (e.g. software) and/or network port (e.g. from the internet), which can optionally be connected to a server having fixed media. A computer system may comprise one or more of a CPU, disk drives, input devices such as keyboard and/or mouse, and a display (e.g. a monitor). Data communication, such as transmission of instructions or reports, can be achieved through a communication medium to a server at a local or a remote location. The communication medium can include any means of transmitting and/or receiving data. For example, the communication medium can be a network connection, a wireless connection, or an internet connection. Such a connection can provide for communication over the World Wide Web. It is envisioned that data relating to the present invention can be transmitted over such networks or connections (or any other suitable means for transmitting information, including but not limited to mailing a physical report, such as a print-out) for reception and/or for review by a receiver. The receiver can be but is not limited to an individual, or electronic system (e.g. one or more computers, and/or one or more servers). In some embodiments, the computer system comprises one or more processors. Processors may be associated with one or more controllers, calculation units, and/or other units of a computer system, or implanted in firmware as desired. If implemented in software, the routines may be stored in any computer readable memory such as in RAM, ROM, flash memory, a magnetic disk, a laser disk, or other suitable storage medium. Likewise, this software may be delivered to a computing device via any known delivery method including, for example, over a communication channel such as a telephone line, the internet, a wireless connection, etc., or via a transportable medium, such as a computer readable disk, flash drive, etc. The various steps may be implemented as various blocks, operations, tools, modules and techniques which, in turn, may be implemented in hardware, firmware, software, or any combination of hardware, firmware, and/or software. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A client-server, relational database architecture can be used in embodiments of the invention. A client-server architecture is a network architecture in which each computer or process on the network is either a client or a server. Server computers are typically powerful computers dedicated to managing disk drives (file servers), printers (print servers), or network traffic (network servers). Client computers include PCs (personal computers) or workstations on which users run applications, as well as example output devices as disclosed herein. Client computers rely on server computers for resources, such as files, devices, and even processing power. In some embodiments of the invention, the server computer handles all of the database functionality. The client computer can have software that handles all the front-end data management and can also receive data input from users. A machine readable medium comprising computer-executable code may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution. Accordingly, the invention comprehends performing any method herein-discussed and storing and/or transmitting data and/or results therefrom and/or analysis thereof, as well as products from performing any method herein-discussed, including intermediates.

Throughout this disclosure there has been mention of CRISPR or CRISPR-Cas complexes or systems. CRISPR systems or complexes can target nucleic acid molecules, e.g., CRISPR-Cpf1 complexes can target and cleave or nick or simply sit upon a target DNA molecule (depending if the Cpf1 has mutations that render it a nickase or "dead"). Such systems or complexes are amenable for achieving tissue-specific and temporally controlled targeted deletion of candidate disease genes. Examples include but are not limited to genes involved in cholesterol and fatty acid metabolism, amyloid diseases, dominant negative diseases, latent viral infections, among other disorders. Accordingly, target sequences for such systems or complexes can be in candidate disease genes, e.g.:

TABLE 23

| Disease | GENE | SPACER | PAM | Mechanism | References |
|---|---|---|---|---|---|
| Hypercholesterolemia | HMG-CR | GCCAAA TTGGAC GACCCT CG (SEQ ID NO: 89) | CGG | Knock-out | Fluvastatin: a review of its pharmacology and use in the management of hypercholesterolaemia. (Plosker GL et al. Drugs 1996, 51(3): 433-459) |
| Hypercholesterolemia | SQLE | CGAGGA GACCCC CGTTTC GG (SEQ ID NO: 90) | TGG | Knock-out | Potential role of nonstatin cholesterol lowering agents (Trapani et al. IUBMB Life, Volume 63, Issue 11, pages 964-971, November 2011) |
| Hyperlipidemia | DGAT1 | CCCGCC GCCGCC GTGGCT CG (SEQ ID NO: 91) | AGG | Knock-out | DGAT1 inhibitors as anti-obesity and anti-diabetic agents. (Birch AM et al. Current Opinion in Drug Discovery & Development [2010, 13(4): 489-496) |

TABLE 23-continued

| Disease | GENE | SPACER | PAM | Mechanism | References |
|---|---|---|---|---|---|
| Leukemia | BCR-ABL | TGAGCT CTACGA GATCCA CA (SEQ ID NO: 92) | AGG | Knockout | Killing of leukemic cells with a BCR/ABL fusion gene by RNA interference (RNAi).(Fuchs et al. Oncogene 2002, 21(37): 5716-5724) |

Thus, the present invention, with regard to CRISPR or CRISPR-Cas complexes contemplates correction of hematopoietic disorders. For example, Severe Combined Immune Deficiency (SCID) results from a defect in lymphocytes T maturation, always associated with a functional defect in lymphocytes B (Cavazzana-Calvo et al., Annu. Rev. Med., 2005, 56, 585-602; Fischer et al., Immunol. Rev., 2005, 203, 98-109). In the case of Adenosine Deaminase (ADA) deficiency, one of the SCID forms, patients can be treated by injection of recombinant Adenosine Deaminase enzyme. Since the ADA gene has been shown to be mutated in SCID patients (Giblett et al., Lancet, 1972, 2, 1067-1069), several other genes involved in SCID have been identified (Cavazzana-Calvo et al., Annu. Rev. Med., 2005, 56, 585-602; Fischer et al., Immunol. Rev., 2005, 203, 98-109). There are four major causes for SCID: (i) the most frequent form of SCID, SCID-X1 (X-linked SCID or X-SCID), is caused by mutation in the IL2RG gene, resulting in the absence of mature T lymphocytes and NK cells. IL2RG encodes the gamma C protein (Noguchi, et al., Cell, 1993, 73, 147-157), a common component of at least five interleukin receptor complexes. These receptors activate several targets through the JAK3 kinase (Macchi et al., Nature, 1995, 377, 65-68), which inactivation results in the same syndrome as gamma C inactivation; (ii) mutation in the ADA gene results in a defect in purine metabolism that is lethal for lymphocyte precursors, which in turn results in the quasi absence of B, T and NK cells; (iii) V(D)J recombination is an essential step in the maturation of immunoglobulins and T lymphocytes receptors (TCRs). Mutations in Recombination Activating Gene 1 and 2 (RAG1 and RAG2) and Artemis, three genes oncogene in this process, result in the absence of mature T and B lymphocytes; and (iv) Mutations in other genes such as CD45, involved in T cell specific signaling have also been reported, although they represent a minority of cases (Cavazzana-Calvo et al., Annu. Rev. Med., 2005, 56, 585-602; Fischer et al., Immunol. Rev., 2005, 203, 98-109). In aspect of the invention, relating to CRISPR or CRISPR-Cas complexes contemplates system, the invention contemplates that it may be used to correct ocular defects that arise from several genetic mutations further described in Genetic Diseases of the Eye, Second Edition, edited by Elias I. Traboulsi, Oxford University Press, 2012. Non-limiting examples of ocular defects to be corrected include macular degeneration (MD), retinitis pigmentosa (RP). Non-limiting examples of genes and proteins associated with ocular defects include but are not limited to the following proteins: (ABCA4) ATP-binding cassette, sub-family A (ABC1), member 4 ACHM1 achromatopsia (rod monochromacy) 1 ApoE Apolipoprotein E (ApoE) C1QTNF5 (CTRPS) C1q and tumor necrosis factor related protein 5 (C1QTNF5) C2 Complement component 2 (C2) C3 Complement components (C3) CCL2 Chemokine (C-C motif) Ligand 2 (CCL2) CCR2 Chemokine (C-C motif) receptor 2 (CCR2) CD36 Cluster of Differentiation 36 CFB Complement factor B CFH Complement factor CFH H CFHR1 complement factor H-related 1 CFHR3 complement factor H-related 3 CNGB3 cyclic nucleotide gated channel beta 3 CP ceruloplasmin (CP) CRP C reactive protein (CRP) CST3 cystatin C or cystatin 3 (CST3) CTSD Cathepsin D (CTSD) CX3CR1 chemokine (C-X3-C motif) receptor 1 ELOVL4 Elongation of very long chain fatty acids 4 ERCC6 excision repair cross-complementing rodent repair deficiency, complementation group 6 FBLN5 Fibulin-5 FBLN5 Fibulin 5 FBLN6 Fibulin 6 FSCN2 fascin (FSCN2) HMCN1 Hemicentin 1 HMCN1 hemicentin 1 HTRA1 HtrA serine peptidase 1 (HTRA1) HTRA1 HtrA serine peptidase 1 IL-6 Interleukin 6 IL-8 Interleukin 8 LOC387715 Hypothetical protein PLEKHA1 Pleckstrin homology domain-containing family A member 1 (PLEKHA1) PROM1 Prominin 1(PROM1 or CD133) PRPH2 Peripherin-2 RPGR retinitis pigmentosa GTPase regulator SERPING1 serpin peptidase inhibitor, Glade G, member 1 (C1-inhibitor) TCOF1 Treacle TIMP3 Metalloproteinase inhibitor 3 (TIMP3) TLR3 Toll-like receptor 3 The present invention, with regard to CRISPR or CRISPR-Cas complexes contemplates also contemplates delivering to the heart. For the heart, a myocardium tropic adena-associated virus (AAVM) is preferred, in particular AAVM41 which showed preferential gene transfer in the heart (see, e.g., Lin-Yanga et al., PNAS, Mar. 10, 2009, vol. 106, no. 10). For example, US Patent Publication No. 20110023139, describes use of zinc finger nucleases to genetically modify cells, animals and proteins associated with cardiovascular disease. Cardiovascular diseases generally include high blood pressure, heart attacks, heart failure, and stroke and TIA. By way of example, the chromosomal sequence may comprise, but is not limited to, IL1B (interleukin 1, beta), XDH (xanthine dehydrogenase), TP53 (tumor protein p53), PTGIS (prostaglandin 12 (prostacyclin) synthase), MB (myoglobin), IL4 (interleukin 4), ANGPT1 (angiopoietin 1), ABCG8 (ATP-binding cassette, sub-family G (WHITE), member 8), CTSK (cathepsin K), PTGIR (prostaglandin 12 (prostacyclin) receptor (IP)), KCNJ11 (potassium inwardly-rectifying channel, subfamily J, member 11), INS (insulin), CRP (C-reactive protein, pentraxin-related), PDGFRB (platelet-derived growth factor receptor, beta polypeptide), CCNA2 (cyclin A2), PDGFB (platelet-derived growth factor beta polypeptide (simian sarcoma viral (v-sis) oncogene homolog)), KCNJ5 (potassium inwardly-rectifying channel, subfamily J, member 5), KCNN3 (potassium intermediate/small conductance calcium-activated channel, subfamily N, member 3), CAPN10 (calpain 10), PTGES (prostaglandin E synthase), ADRA2B (adrenergic, alpha-2B-, receptor), ABCG5 (ATP-binding cassette, sub-family G (WHITE), member 5), PRDX2 (peroxiredoxin 2), CAPN5 (calpain 5), PARP14 (poly (ADP-ribose) polymerase family, member 14), MEX3C (mex-3 homolog C (*C. elegans*)), ACE angiotensin I converting enzyme (peptidyl-dipeptidase A) 1), TNF (tumor necrosis factor (TNF superfamily, member 2)), IL6 (interleukin 6 (interferon, beta 2)), STN (statin), SERPINE1 (serpin peptidase inhibitor, Glade E (nexin, plasminogen activator inhibitor type 1), member 1), ALB (albumin), ADIPOQ (adiponectin, C1Q and collagen domain containing), APOB (apolipoprotein B (including Ag(x) antigen)), APOE (apolipoprotein E), LEP (leptin), MTHFR (5,10-methylenetetrahydrofolate reductase (NADPH)), APOA1 (apolipoprotein A-I), EDN1 (endothelin 1), NPPB (natriuretic peptide precursor B), NOS3 (nitric oxide synthase 3 (endothelial cell)), PPARG (peroxisome proliferator-activated receptor gamma), PLAT (plasminogen activator, tissue), PTGS2

(prostaglandin-endoperoxide synthase 2 (prostaglandin G/H synthase and cyclooxygenase)), CETP (cholesteryl ester transfer protein, plasma), AGTR1 (angiotensin II receptor, type 1), HMGCR (3-hydroxy-3-methylglutaryl-Coenzyme A reductase), IGF1 (insulin-like growth factor 1 (somatomedin C)), SELE (selectin E), REN (renin), PPARA (peroxisome proliferator-activated receptor alpha), PON1 (paraoxonase 1), KNG1 (kininogen 1), CCL2 (chemokine (C-C motif) ligand 2), LPL (lipoprotein lipase), VWF (von Willebrand factor), F2 (coagulation factor II (thrombin)), ICAM1 (intercellular adhesion molecule 1), TGFB1 (transforming growth factor, beta 1), NPPA (natriuretic peptide precursor A), IL10 (interleukin 10), EPO (erythropoietin), SOD1 (superoxide dismutase 1, soluble), VCAM1 (vascular cell adhesion molecule 1), IFNG (interferon, gamma), LPA (lipoprotein, Lp(a)), MPO (myeloperoxidase), ESR1 (estrogen receptor 1), MAPK1 (mitogen-activated protein kinase 1), HP (haptoglobin), F3 (coagulation factor III (thromboplastin, tissue factor)), CST3 (cystatin C), COG2 (component of oligomeric golgi complex 2), MMP9 (matrix metallopeptidase 9 (gelatinase B, 92 kDa gelatinase, 92 kDa type IV collagenase)), SERPINC1 (serpin peptidase inhibitor, Glade C (antithrombin), member 1), F8 (coagulation factor VIII, procoagulant component), HMOX1 (heme oxygenase (decycling) 1), APOC3 (apolipoprotein C-III), IL8 (interleukin 8), PROK1 (prokineticin 1), CBS (cystathionine-beta-synthase), NOS2 (nitric oxide synthase 2, inducible), TLR4 (toll-like receptor 4), SELP (selectin P (granule membrane protein 140 kDa, antigen CD62)), ABCA1 (ATP-binding cassette, sub-family A (ABC1), member 1), AGT (angiotensinogen (serpin peptidase inhibitor, Glade A, member 8)), LDLR (low density lipoprotein receptor), GPT (glutamic-pyruvate transaminase (alanine aminotransferase)), VEGFA (vascular endothelial growth factor A), NR3C2 (nuclear receptor subfamily 3, group C, member 2), IL18 (interleukin 18 (interferon-gamma-inducing factor)), NOS1 (nitric oxide synthase 1 (neuronal)), NR3C1 (nuclear receptor subfamily 3, group C, member 1 (glucocorticoid receptor)), FGB (fibrinogen beta chain), HGF (hepatocyte growth factor (hepapoietin A; scatter factor)), ILIA (interleukin 1, alpha), RETN (resistin), AKT1 (v-akt murine thymoma viral oncogene homolog 1), LIPC (lipase, hepatic), HSPD1 (heat shock 60 kDa protein 1 (chaperonin)), MAPK14 (mitogen-activated protein kinase 14), SPP1 (secreted phosphoprotein 1), ITGB3 (integrin, beta 3 (platelet glycoprotein 111a, antigen CD61)), CAT (catalase), UTS2 (urotensin 2), THBD (thrombomodulin), F10 (coagulation factor X), CP (ceruloplasmin (ferroxidase)), TNFRSF11B (tumor necrosis factor receptor superfamily, member 11b), EDNRA (endothelin receptor type A), EGFR (epidermal growth factor receptor (erythroblastic leukemia viral (v-erb-b) oncogene homolog, avian)), MMP2 (matrix metallopeptidase 2 (gelatinase A, 72 kDa gelatinase, 72 kDa type IV collagenase)), PLG (plasminogen), NPY (neuropeptide Y), RHOD (ras homolog gene family, member D), MAPK8 (mitogen-activated protein kinase 8), MYC (v-myc myelocytomatosis viral oncogene homolog (avian)), FN1 (fibronectin 1), CMA1 (chymase 1, mast cell), PLAU (plasminogen activator, urokinase), GNB3 (guanine nucleotide binding protein (G protein), beta polypeptide 3), ADRB2 (adrenergic, beta-2-, receptor, surface), APOA5 (apolipoprotein A-V), SOD2 (superoxide dismutase 2, mitochondrial), F5 (coagulation factor V (proaccelerin, labile factor)), VDR (vitamin D (1,25-dihydroxyvitamin D3) receptor), ALOX5 (arachidonate 5-lipoxygenase), HLA-DRB1 (major histocompatibility complex, class II, DR beta 1), PARP1 (poly (ADP-ribose) polymerase 1), CD40LG (CD40 ligand), PON2 (paraoxonase 2), AGER (advanced glycosylation end product-specific receptor), IRS1 (insulin receptor substrate 1), PTGS1 (prostaglandin-endoperoxide synthase 1 (prostaglandin G/H synthase and cyclooxygenase)), ECE1 (endothelin converting enzyme 1), F7 (coagulation factor VII (serum prothrombin conversion accelerator)), URN (interleukin 1 receptor antagonist), EPHX2 (epoxide hydrolase 2, cytoplasmic), IGFBP1 (insulin-like growth factor binding protein 1), MAPK10 (mitogen-activated protein kinase 10), FAS (Fas (TNF receptor superfamily, member 6)), ABCB1 (ATP-binding cassette, sub-family B (MDR/TAP), member 1), JUN (jun oncogene), IGFBP3 (insulin-like growth factor binding protein 3), CD14 (CD14 molecule), PDE5A (phosphodiesterase 5A, cGMP-specific), AGTR2 (angiotensin II receptor, type 2), CD40 (CD40 molecule, TNF receptor superfamily member 5), LCAT (lecithin-cholesterol acyltransferase), CCR5 (chemokine (C-C motif) receptor 5), MMP1 (matrix metallopeptidase 1 (interstitial collagenase)), TIMP1 (TIMP metallopeptidase inhibitor 1), ADM (adrenomedullin), DYT10 (dystonia 10), STAT3 (signal transducer and activator of transcription 3 (acute-phase response factor)), MMP3 (matrix metallopeptidase 3 (stromelysin 1, progelatinase)), ELN (elastin), USF1 (upstream transcription factor 1), CFH (complement factor H), HSPA4 (heat shock 70 kDa protein 4), MMP12 (matrix metallopeptidase 12 (macrophage elastase)), MME (membrane metallo-endopeptidase), F2R (coagulation factor II (thrombin) receptor), SELL (selectin L), CTSB (cathepsin B), ANXA5 (annexin A5), ADRB1 (adrenergic, beta-1-, receptor), CYBA (cytochrome b-245, alpha polypeptide), FGA (fibrinogen alpha chain), GGT1 (gamma-glutamyltransferase 1), LIPG (lipase, endothelial), HIF1A (hypoxia inducible factor 1, alpha subunit (basic helix-loop-helix transcription factor)), CXCR4 (chemokine (C-X-C motif) receptor 4), PROC (protein C (inactivator of coagulation factors Va and VIIIa)), SCARB1 (scavenger receptor class B, member 1), CD79A (CD79a molecule, immunoglobulin-associated alpha), PLTP (phospholipid transfer protein), ADD1 (adducin 1 (alpha)), FGG (fibrinogen gamma chain), SAA1 (serum amyloid A1), KCNH2 (potassium voltage-gated channel, subfamily H (eag-related), member 2), DPP4 (dipeptidyl-peptidase 4), G6PD (glucose-6-phosphate dehydrogenase), NPR1 (natriuretic peptide receptor A/guanylate cyclase A (atrionatriuretic peptide receptor A)), VTN (vitronectin), KIAA0101 (KIAA0101), FOS (FBJ murine osteosarcoma viral oncogene homolog), TLR2 (toll-like receptor 2), PPIG (peptidylprolyl isomerase G (cyclophilin G)), IL1R1 (interleukin 1 receptor, type I), AR (androgen receptor), CYP1A1 (cytochrome P450, family 1, subfamily A, polypeptide 1), SERPINA1 (serpin peptidase inhibitor, Glade A (alpha-1 antiproteinase, antitrypsin), member 1), MTR (5-methyltetrahydrofolate-homocysteine methyltransferase), RBP4 (retinol binding protein 4, plasma), APOA4 (apolipoprotein A-IV), CDKN2A (cyclin-dependent kinase inhibitor 2A (melanoma, p 16, inhibits CDK4)), FGF2 (fibroblast growth factor 2 (basic)), EDNRB (endothelin receptor type B), ITGA2 (integrin, alpha 2 (CD49B, alpha 2 subunit of VLA-2 receptor)), CABIN1 (calcineurin binding protein 1), SHBG (sex hormone-binding globulin), HMGB1 (high-mobility group box 1), HSP90B2P (heat shock protein 90 kDa beta (Grp94), member 2 (pseudogene)), CYP3A4 (cytochrome P450, family 3, subfamily A, polypeptide 4), GJA1 (gap junction protein, alpha 1, 43 kDa), CAV1 (caveolin 1, caveolae protein, 22 kDa), ESR2 (estrogen receptor 2 (ER beta)), LTA (lymphotoxin alpha (TNF superfamily, member 1)), GDF15 (growth differentiation factor 15), BDNF (brain-derived neurotrophic factor), CYP2D6 (cytochrome P450, family 2, subfamily D, polypeptide 6), NGF (nerve growth factor (beta polypeptide)), SP1 (Sp 1 transcription factor), TGIF1 (TGFB-induced factor homeobox 1), SRC (v-src sarcoma (Schmidt-Ruppin A-2) viral oncogene homolog (avian)), EGF (epidermal growth factor (beta-urogastrone)), PIK3CG (phosphoinositide-3-kinase, catalytic, gamma polypeptide), HLA-A (major histocompatibility complex, class I, A), KCNQ1 (potassium voltage-gated channel, KQT-like subfamily, member 1), CNR1 (cannabinoid receptor 1 (brain)), FBN1 (fibrillin 1), CHKA (choline kinase alpha), BEST1 (bestrophin 1), APP (amyloid beta (A4) precursor protein), CTNNB1 (catenin (cadherin-associated protein), beta 1, 88 kDa), IL2 (interleukin 2), CD36 (CD36 molecule (thrombospondin receptor)), PRKAB1 (protein kinase, AMP-activated, beta 1 non-catalytic subunit), TPO (thyroid peroxidase), ALDH7A1 (aldehyde dehydrogenase 7 family, member A1), CX3CR1 (chemokine (C-X3-C motif) receptor 1), TH (tyrosine hydroxylase), F9 (coagulation factor IX), GH1 (growth hormone 1), TF (transferrin), HFE (hemochromatosis), IL17A (interleukin 17A), PTEN (phosphatase and tensin homolog), GSTM1 (glutathione S-transferase mu 1), DMD (dystrophin), GATA4 (GATA binding protein 4), F13A1 (coagulation factor XIII, A1 polypeptide), TTR (transthyretin), FABP4 (fatty acid binding protein 4, adipocyte), PON3 (paraoxonase 3), APOC1 (apolipoprotein C-I), INSR (insulin receptor), TNFRSF1B (tumor necrosis factor receptor superfamily, member 1B), HTR2A (5-hydroxytryptamine (serotonin) receptor 2A), CSF3 (colony stimulating factor 3 (granulocyte)), CYP2C9 (cytochrome P450, family 2, subfamily C, polypeptide 9), TXN (thioredoxin), CYP11B2 (cytochrome P450, family 11, subfamily B, polypeptide 2), PTH (parathyroid hormone), CSF2 (colony stimulating factor 2 (granulocyte-macrophage)), KDR (kinase insert domain receptor (a type III receptor tyrosine kinase)), PLA2G2A (phospholipase A2, group IIA (platelets, synovial fluid)), B2M (beta-2-microglobulin), THBS1 (thrombospondin 1), GCG (glucagon), RHOA (ras homolog gene family, member A), ALDH2 (aldehyde dehydrogenase 2 family (mitochondrial)), TCF7L2 (transcription factor 7-like 2 (T-cell specific, HMG-box)), BDKRB2 (bradykinin receptor B2), NFE2L2 (nuclear factor (erythroid-derived 2)-like 2), NOTCH1 (Notch homolog 1, translocation-associated (*Drosophila*)), UGT1A1 (UDP glucuronosyltransferase 1 family, polypeptide A1), IFNA1 (interferon, alpha 1), PPARD (peroxisome proliferator-activated receptor delta), SIRT1 (sirtuin (silent mating type information regulation 2 homolog) 1 (*S. cerevisiae*)), GNRH1 (gonadotropin-releasing hormone 1 (luteinizing-releasing hormone)), PAPPA (pregnancy-associated plasma protein A, pappalysin 1), ARR3 (arrestin 3, retinal (X-arrestin)), NPPC (natriuretic peptide precursor C), AHSP (alpha hemoglobin stabilizing protein), PTK2 (PTK2 protein tyrosine kinase 2), IL13 (interleukin 13), MTOR (mechanistic target of rapamycin (serine/threonine kinase)), ITGB2 (integrin, beta 2 (complement component 3 receptor 3 and 4 subunit)), GSTT1 (glutathione S-transferase theta 1), IL6ST (interleukin 6 signal transducer (gp130, oncostatin M receptor)), CPB2 (carboxypeptidase B2 (plasma)), CYP1A2 (cytochrome P450, family 1, subfamily A, polypeptide 2), HNF4A (hepatocyte nuclear factor 4, alpha), SLC6A4 (solute carrier family 6 (neurotransmitter transporter, serotonin), member 4), PLA2G6 (phospholipase A2, group VI (cytosolic, calcium-independent)), TNFSF11 (tumor necrosis factor (ligand) superfamily, member 11), SLC8A1 (solute carrier family 8 (sodium/calcium exchanger), member 1), F2RL1 (coagulation factor II (thrombin) receptor-like 1), AKR1A1 (aldo-keto reductase family 1, member A1 (aldehyde reductase)), ALDH9A1 (aldehyde dehydrogenase 9 family, member A1), BGLAP (bone gamma-carboxyglutamate (gla) protein), MTTP (microsomal triglyceride transfer protein), MTRR (5-methyltetrahydrofolate-homocysteine methyltransferase reductase), SULT1A3 (sulfotransferase family, cytosolic, 1A, phenol-preferring, member 3), RAGE (renal tumor antigen), C4B (complement component 4B (Chido blood group)), P2RY12 (purinergic receptor P2Y, G-protein coupled, 12), RNLS (renalase, FAD-dependent amine oxidase), CREB1 (cAMP responsive element binding protein 1), POMC (proopiomelanocortin), RAC1 (ras-related C3 botulinum toxin substrate 1 (rho family, small GTP binding protein Rac1)), LMNA (lamin NC), CD59 (CD59 molecule, complement regulatory protein), SCN5A (sodium channel, voltage-gated, type V, alpha subunit), CYP1B1 (cytochrome P450, family 1, subfamily B, polypeptide 1), MIF (macrophage migration inhibitory factor (glycosylation-inhibiting factor)), MMP13 (matrix metallopeptidase 13 (collagenase 3)), TIMP2 (TIMP metallopeptidase inhibitor 2), CYP19A1 (cytochrome P450, family 19, subfamily A, polypeptide 1), CYP21A2 (cytochrome P450, family 21, subfamily A, polypeptide 2), PTPN22 (protein tyrosine phosphatase, non-receptor type 22 (lymphoid)), MYH14 (myosin, heavy chain 14, non-muscle), MBL2 (mannose-binding lectin (protein C) 2, soluble (opsonic defect)), SELPLG (selectin P ligand), AOC3 (amine oxidase, copper containing 3 (vascular adhesion protein 1)), CTSL1 (cathepsin L1), PCNA (proliferating cell nuclear antigen), IGF2 (insulin-like growth factor 2 (somatomedin A)), ITGB1 (integrin, beta 1 (fibronectin receptor, beta polypeptide, antigen CD29 includes MDF2, MSK12)), CAST (calpastatin), CXCL12 (chemokine (C-X-C motif) ligand 12 (stromal cell-derived factor 1)), IGHE (immunoglobulin heavy constant epsilon), KCNE1 (potassium voltage-gated channel, Isk-related family, member 1), TFRC (transferrin receptor (p90, CD71)), COL1A1 (collagen, type I, alpha 1), COL1A2 (collagen, type I, alpha 2), IL2RB (interleukin 2 receptor, beta), PLA2G10 (phospholipase A2, group X), ANGPT2 (angiopoietin 2), PROCR (protein C receptor, endothelial (EPCR)), NOX4 (NADPH oxidase 4), HAMP (hepcidin antimicrobial peptide), PTPN11 (protein tyrosine phosphatase, non-receptor type 11), SLC2A1 (solute carrier family 2 (facilitated glucose transporter), member 1), IL2RA (interleukin 2 receptor, alpha), CCL5 (chemokine (C-C motif) ligand 5), IRF1 (interferon regulatory factor 1), CFLAR (CASP8 and FADD-like apoptosis regulator), CALCA (calcitonin-related polypeptide alpha), EIF4E (eukaryotic translation initiation factor 4E), GSTP1 (glutathione 5-transferase pi 1), JAK2 (Janus kinase 2), CYP3A5 (cytochrome P450, family 3, subfamily A, polypeptide 5), HSPG2 (heparan sulfate proteoglycan 2), CCL3 (chemokine (C-C motif) ligand 3), MYD88 (myeloid differentiation primary response gene (88)), VIP (vasoactive intestinal peptide), SOAT1 (sterol O-acyltransferase 1), ADRBK1 (adrenergic, beta, receptor kinase 1), NR4A2 (nuclear receptor subfamily 4, group A, member 2), MMP8 (matrix metallopeptidase 8 (neutrophil collagenase)), NPR2 (natriuretic peptide receptor B/guanylate cyclase B (atrionatriuretic peptide receptor B)), GCH1 (GTP cyclohydrolase 1), EPRS (glutamyl-prolyl-tRNA synthetase), PPARGC1A (peroxisome proliferator-activated receptor gamma, coactivator 1 alpha), F12 (coagulation factor XII (Hageman factor)), PECAM1 (platelet/endothelial cell adhesion molecule), CCL4 (chemokine (C-C motif) ligand 4), SERPINA3 (serpin peptidase inhibitor, Glade A (alpha-1 antiproteinase, antitrypsin), member 3), CASR (calcium-sensing receptor), GJA5 (gap junction protein, alpha 5, 40 kDa), FABP2 (fatty acid binding protein 2, intestinal), TTF2 (transcription termination factor, RNA polymerase II), PROS1 (protein S (alpha)), CTF1 (cardiotrophin 1), SGCB (sarcoglycan, beta (43 kDa dystrophin-associated glycoprotein)), YME1L1 (YME1-like 1 (*S. cerevisiae*)), CAMP (cathelicidin antimicrobial peptide), ZC3H12A (zinc finger CCCH-type containing 12A), AKR1B1 (aldo-keto reductase family 1, member B1 (aldose reductase)), DES (desmin), MMP7 (matrix metallopeptidase 7 (matrilysin, uterine)), AHR (aryl hydrocarbon receptor), CSF1 (colony stimulating factor 1 (macrophage)), HDAC9 (histone deacetylase 9), CTGF (connective tissue growth factor), KCNMA1 (potassium large conductance calcium-activated channel, subfamily M, alpha member 1), UGT1A (UDP glucuronosyltransferase 1 family, polypeptide A complex locus), PRKCA (protein kinase C, alpha), COMT (catechol-.beta.-methyltransferase), S100B (S100 calcium binding protein B), EGR1 (early growth response 1), PRL (prolactin), IL15 (interleukin 15), DRD4 (dopamine receptor D4), CAMK2G (calcium/calmodulin-dependent protein kinase II gamma), SLC22A2 (solute carrier family 22 (organic cation transporter), member 2), CCL11 (chemokine (C-C motif) ligand 11), PGF (B321 placental growth factor), THPO (thrombopoietin), GP6 (glycoprotein VI (platelet)), TACR1 (tachykinin receptor 1), NTS (neurotensin), HNF1A (HNF1 homeobox A), SST (somatostatin), KCND1 (potassium voltage-gated channel, Shal-related subfamily, member 1), LOC646627 (phospholipase inhibitor), TBXAS1 (thromboxane A synthase 1 (platelet)), CYP2J2 (cytochrome P450, family 2, subfamily J, polypeptide 2), TBXA2R (thromboxane A2 receptor), ADH1C (alcohol dehydrogenase 1C (class I), gamma polypeptide), ALOX12 (arachidonate 12-lipoxygenase), AHSG (alpha-2-HS-glycoprotein), BHMT (betaine-homocysteine methyltransferase), GJA4 (gap junction protein, alpha 4, 37 kDa), SLC25A4 (solute carrier family 25 (mitochondrial carrier; adenine nucleotide translocator), member 4), ACLY (ATP citrate lyase), ALOX5AP (arachidonate 5-lipoxygenase-activating protein), NUMA1 (nuclear mitotic apparatus protein 1), CYP27B1 (cytochrome P450, family 27, subfamily B, polypeptide 1), CYSLTR2 (cysteinyl leukotriene receptor 2), SOD3 (superoxide dismutase 3, extracellular), LTC4S (leukotriene C4 synthase), UCN (urocortin), GHRL (ghrelin/obestatin prepropeptide), APOC2 (apolipoprotein C-II), CLEC4A (C-type lectin domain family 4, member A), KBTBD10 (kelch repeat and BTB (POZ) domain containing 10), TNC (tenascin C), TYMS (thymidylate synthetase), SHC1 (SHC (Src homology 2 domain containing) transforming protein 1), LRP1 (low density lipoprotein receptor-related protein 1), SOCS3 (suppressor of cytokine signaling 3), ADH1B (alcohol dehydrogenase 1B (class I), beta polypeptide), KLK3 (kallikrein-related peptidase 3), HSD11B1 (hydroxysteroid (11-beta) dehydrogenase 1), VKORC1 (vitamin K epoxide reductase complex, subunit 1), SERPINB2 (serpin peptidase inhibitor, Glade B (ovalbumin), member 2), TNS1 (tensin 1), RNF19A (ring finger protein 19A), EPOR (erythropoietin receptor), ITGAM (integrin, alpha M (complement component 3 receptor 3 subunit)), PITX2 (paired-like homeodomain 2), MAPK7 (mitogen-activated protein kinase 7), FCGR3A (Fc fragment of IgG, low affinity 111a, receptor (CD16a)), LEPR (leptin receptor), ENG (endoglin), GPX1 (glutathione peroxidase 1), GOT2 (glutamic-oxaloacetic transaminase 2, mitochondrial (aspartate aminotransferase 2)), HRH1 (histamine receptor H1), NR1I2 (nuclear receptor subfamily 1, group I, member 2), CRH (corticotropin releasing hormone), HTR1A (5-hydroxytryptamine (serotonin) receptor 1A), VDAC1 (voltage-dependent anion channel 1), HPSE (heparanase), SFTPD (surfactant protein D), TAP2 (transporter 2, ATP-binding cassette, sub-family B (MDR/TAP)), RNF123 (ring finger protein 123), PTK2B (PTK2B protein tyrosine kinase 2 beta), NTRK2 (neurotrophic tyrosine kinase, receptor, type 2), IL6R (interleukin 6 receptor), ACHE (acetylcholinesterase (Yt blood group)), GLP1R (glucagon-like peptide 1 receptor), GHR (growth hormone receptor), GSR (glutathione reductase), NQO1 (NAD(P)H dehydrogenase, quinone 1), NR5A1 (nuclear receptor subfamily 5, group A, member 1), GJB2 (gap junction protein, beta 2, 26 kDa), SLC9A1 (solute carrier family 9 (sodium/hydrogen exchanger), member 1), MAOA (monoamine oxidase A), PCSK9 (proprotein convertase subtilisin/kexin type 9), FCGR2A (Fc fragment of IgG, low affinity IIa, receptor (CD32)), SERPINF1 (serpin peptidase inhibitor, Glade F (alpha-2 antiplasmin, pigment epithelium derived factor), member 1), EDN3 (endothelin 3), DHFR (dihydrofolate reductase), GAS6 (growth arrest-specific 6), SMPD1 (sphingomyelin phosphodiesterase 1, acid lysosomal), UCP2 (uncoupling protein 2 (mitochondrial, proton carrier)), TFAP2A (transcription factor AP-2 alpha (activating enhancer binding protein 2 alpha)), C4BPA (complement component 4 binding protein, alpha), SERPINF2 (serpin peptidase inhibitor, Glade F (alpha-2 antiplasmin, pigment epithelium derived factor), member 2), TYMP (thymidine phosphorylase), ALPP (alkaline phosphatase, placental (Regan isozyme)), CXCR2 (chemokine (C-X-C motif) receptor 2), SLC39A3 (solute carrier family 39 (zinc transporter), member 3), ABCG2 (ATP-binding cassette, sub-family G (WHITE), member 2), ADA (adenosine deaminase), JAK3 (Janus kinase 3), HSPA1A (heat shock 70 kDa protein 1A), FASN (fatty acid synthase), FGF1 (fibroblast growth factor 1 (acidic)), F11 (coagulation factor XI), ATP7A (ATPase, Cu++ transporting, alpha polypeptide), CR1 (complement component (3b/4b) receptor 1 (Knops blood group)), GFAP (glial fibrillary acidic protein), ROCK1 (Rho-associated, coiled-coil containing protein kinase 1), MECP2 (methyl CpG binding protein 2 (Rett syndrome)), MYLK (myosin light chain kinase), BCHE (butyrylcholinesterase), LIPE (lipase, hormone-sensitive), PRDX5 (peroxiredoxin 5), ADORA1 (adenosine A1 receptor), WRN (Werner syndrome, RecQ helicase-like), CXCR3 (chemokine (C-X-C motif) receptor 3), CD81 (CD81 molecule), SMAD7 (SMAD family member 7), LAMC2 (laminin, gamma 2), MAP3K5 (mitogen-activated protein kinase kinase kinase 5), CHGA (chromogranin A (parathyroid secretory protein 1)), IAPP (islet amyloid polypeptide), RHO (rhodopsin), ENPP1 (ectonucleotide pyrophosphatase/phosphodiesterase 1), PTHLH (parathyroid hormone-like hormone), NRG1 (neuregulin 1), VEGFC (vascular endothelial growth factor C), ENPEP (glutamyl aminopeptidase (aminopeptidase A)), CEBPB (CCAAT/enhancer binding protein (C/EBP), beta), NAGLU (N-acetylglucosaminidase, alpha-), F2RL3 (coagulation factor II (thrombin) receptor-like 3), CX3CL1 (chemokine (C-X3-C motif) ligand 1), BDKRB1 (bradykinin receptor B1), ADAMTS13 (ADAM metallopeptidase with thrombospondin type 1 motif, 13), ELANE (elastase, neutrophil expressed), ENPP2 (ectonucleotide pyrophosphatase/phosphodiesterase 2), CISH (cytokine inducible SH2-containing protein), GAST (gastrin), MYOC (myocilin, trabecular meshwork inducible glucocorticoid response), ATP1A2 (ATPase, Na+/K+ transporting, alpha 2 polypeptide), NF1 (neurofibromin 1), GJB1 (gap junction protein, beta 1, 32 kDa), MEF2A (myocyte enhancer factor 2A), VCL (vinculin), BMPR2 (bone morphogenetic protein receptor, type II (serine/threonine kinase)), TUBB (tubulin, beta), CDC42 (cell division cycle 42 (GTP binding protein, 25 kDa)), KRT18 (keratin 18), HSF1 (heat shock transcription factor 1), MYB (v-myb myeloblastosis viral oncogene homolog (avian)), PRKAA2 (protein kinase, AMP-activated, alpha 2 catalytic subunit), ROCK2 (Rho-associated, coiled-coil containing protein kinase 2), TFPI (tissue factor pathway inhibitor (lipoprotein-associated coagulation inhibitor)), PRKG1 (protein kinase, cGMP-dependent, type I), BMP2 (bone morphogenetic protein 2), CTNND1 (catenin (cadherin-associated protein), delta 1), CTH (cystathionase (cystathionine gamma-lyase)), CTSS (cathepsin S), VAV2 (vav 2 guanine nucleotide exchange factor), NPY2R (neuropeptide Y receptor Y2), IGFBP2 (insulin-like growth factor binding protein 2, 36 kDa), CD28 (CD28 molecule), GSTA1 (glutathione S-transferase alpha 1), PPIA (peptidylprolyl isomerase A (cyclophilin A)), APOH (apolipoprotein H (beta-2-glycoprotein I)), S100A8 (S100 calcium binding protein A8), IL11 (interleukin 11), ALOX15 (arachidonate 15-lipoxygenase), FBLN1 (fibulin 1), NR1H3 (nuclear receptor subfamily 1, group H, member 3), SCD (stearoyl-CoA desaturase (delta-9-desaturase)), GIP (gastric inhibitory polypeptide), CHGB (chromogranin B (secretogranin 1)), PRKCB (protein kinase C, beta), SRD5A1 (steroid-5-alpha-reductase, alpha polypeptide 1 (3-oxo-5 alpha-steroid delta 4-dehydrogenase alpha 1)), HSD11B2 (hydroxysteroid (11-beta) dehydrogenase 2), CALCRL (calcitonin receptor-like), GALNT2 (UDP-N-acetyl-alpha-D-galactosamine:polypeptide N-acetylgalactosaminyltransferase 2 (GalNAc-T2)), ANGPTL4 (angiopoietin-like 4), KCNN4 (potassium intermediate/small conductance calcium-activated channel, subfamily N, member 4), PIK3C2A (phosphoinositide-3-kinase, class 2, alpha polypeptide), HBEGF (heparin-binding EGF-like growth factor), CYP7A1 (cytochrome P450, family 7, subfamily A, polypeptide 1), HLA-DRB5 (major histocompatibility complex, class II, DR beta 5), BNIP3 (BCL2/adenovirus E1B 19 kDa interacting protein 3), GCKR (glucokinase (hexokinase 4) regulator), S100A12 (S100 calcium binding protein A12), PADI4 (peptidyl arginine deiminase, type IV), HSPA14 (heat shock 70 kDa protein 14), CXCR1 (chemokine (C-X-C motif) receptor 1), H19 (H19, imprinted maternally expressed transcript (non-protein coding)), KRTAP19-3 (keratin associated protein 19-3), IDDM2 (insulin-dependent diabetes mellitus 2), RAC2 (ras-related C3 botulinum toxin substrate 2 (rho family, small GTP binding protein Rac2)), RYR1 (ryanodine receptor 1 (skeletal)), CLOCK (clock homolog (mouse)), NGFR (nerve growth factor receptor (TNFR superfamily, member 16)), DBH (dopamine beta-hydroxylase (dopamine beta-monooxygenase)), CHRNA4 (cholinergic receptor, nicotinic, alpha 4), CACNA1C (calcium channel, voltage-dependent, L type, alpha 1C subunit), PRKAG2 (protein kinase, AMP-activated, gamma 2 non-catalytic subunit), CHAT (choline acetyltransferase), PTGDS (prostaglandin D2 synthase 21 kDa (brain)), NR1H2 (nuclear receptor subfamily 1, group H, member 2), TEK (TEK tyrosine kinase, endothelial), VEGFB (vascular endothelial growth factor B), MEF2C (myocyte enhancer factor 2C), MAPKAPK2 (mitogen-activated protein kinase-activated protein kinase 2), TNFRSF11A (tumor necrosis factor receptor superfamily, member 11a, NFKB activator), HSPA9 (heat shock 70 kDa protein 9 (mortalin)), CYSLTR1 (cysteinyl leukotriene receptor 1), MAT1A (methionine adenosyltransferase I, alpha), OPRL1 (opiate receptor-like 1), IMPA1 (inositol (myo)-1(or 4)-monophosphatase 1), CLCN2 (chloride channel 2), DLD (dihydrolipoamide dehydrogenase), PSMA6 (proteasome (prosome, macropain) subunit, alpha type, 6), PSMB8 (proteasome (prosome, macropain) subunit, beta type, 8 (large multifunctional peptidase 7)), CHI3L1 (chitinase 3-like 1 (cartilage glycoprotein-39)), ALDH1B1 (aldehyde dehydrogenase 1 family, member B1), PARP2 (poly (ADP-ribose) polymerase 2), STAR (steroidogenic acute regulatory protein), LBP (lipopolysaccharide binding protein), ABCC6 (ATP-binding cassette, sub-family C(CFTR/MRP), member 6), RGS2 (regulator of G-protein signaling 2, 24 kDa), EFNB2 (ephrin-B2), GJB6 (gap junction protein, beta 6, 30 kDa), APOA2 (apolipoprotein A-II), AMPD1 (adenosine monophosphate deaminase 1), DYSF (dysferlin, limb girdle muscular dystrophy 2B (autosomal recessive)), FDFT1 (farnesyl-diphosphate farnesyltransferase 1), EDN2 (endothelin 2), CCR6 (chemokine (C-C motif) receptor 6), GJB3 (gap junction protein, beta 3, 31 kDa), IL1RL1 (interleukin 1 receptor-like 1), ENTPD1 (ectonucleoside triphosphate diphosphohydrolase 1), BBS4 (Bardet-Biedl syndrome 4), CELSR2 (cadherin, EGF LAG seven-pass G-type receptor 2 (flamingo homolog, *Drosophila*)), F11R (F11 receptor), RAPGEF3 (Rap guanine nucleotide exchange factor (GEF) 3), HYAL1 (hyaluronoglucosaminidase 1), ZNF259 (zinc finger protein 259), ATOX1 (ATX1 antioxidant protein 1 homolog (yeast)), ATF6 (activating transcription factor 6), KHK (ketohexokinase (fructokinase)), SAT1 (spermidine/spermine N1-acetyltransferase 1), GGH (gamma-glutamyl hydrolase (conjugase, folylpolygammaglutamyl hydrolase)), TIMP4 (TIMP metallopeptidase inhibitor 4), SLC4A4 (solute carrier family 4, sodium bicarbonate cotransporter, member 4), PDE2A (phosphodiesterase 2A, cGMP-stimulated), PDE3B (phosphodiesterase 3B, cGMP-inhibited), FADS1 (fatty acid desaturase 1), FADS2 (fatty acid desaturase 2), TMSB4X (thymosin beta 4, X-linked), TXNIP (thioredoxin interacting protein), LIMS1 (LIM and senescent cell antigen-like domains 1), RHOB (ras homolog gene family, member B), LY96 (lymphocyte antigen 96), FOXO1 (forkhead box O1), PNPLA2 (patatin-like phospholipase domain containing 2), TRH (thyrotropin-releasing hormone), GJC1 (gap junction protein, gamma 1, 45 kDa), SLC17A5 (solute carrier family 17 (anion/sugar transporter), member 5), FTO (fat mass and obesity associated), GJD2 (gap junction protein, delta 2, 36 kDa), PSRC1 (proline/serine-rich coiled-coil 1), CASP12 (caspase 12 (gene/pseudogene)), GPBAR1 (G protein-coupled bile acid receptor 1), PXK (PX domain containing serine/threonine kinase), IL33 (interleukin 33), TRIB1 (tribbles homolog 1 (*Drosophila*)), PBX4 (pre-B-cell leukemia homeobox 4), NUPR1 (nuclear protein, transcriptional regulator, 1), 15-Sep(15 kDa selenoprotein), CILP2 (cartilage intermediate layer protein 2), TERC (telomerase RNA component), GGT2 (gamma-glutamyltransferase 2), MT-CO1 (mitochondrially encoded cytochrome c oxidase I), and UOX (urate oxidase, pseudogene). In an additional embodiment, the chromosomal sequence may further be selected from Pon1 (paraoxonase 1), LDLR (LDL receptor), ApoE (Apolipoprotein E), Apo B-100 (Apolipoprotein B-100), ApoA (Apolipoprotein(a)), ApoA1 (Apolipoprotein A1), CBS (Cystathionine B-synthase), Glycoprotein IIb/IIb, MTHRF (5,10-methylenetetrahydrofolate reductase (NADPH), and combinations thereof. In one iteration, the chromosomal sequences and proteins encoded by chromosomal sequences involved in cardiovascular disease may be chosen from Cacna1C, Sod1, Pten, Ppar(alpha), Apo E, Leptin, and combinations thereof. The text herein accordingly provides exemplary targets as to CRISPR or CRISPR-Cas systems or complexes.

Each of these patents, patent publications, and applications, and all documents cited therein or during their prosecution ("appln cited documents") and all documents cited or referenced in the appln cited documents, together with any instructions, descriptions, product specifications, and product sheets for any products mentioned therein or in any document therein and incorporated by reference herein, are hereby incorporated herein by reference, and may be employed in the practice of the invention. All documents (e.g., these patents, patent publications and applications and the appln cited documents) are incorporated herein by reference to the same extent as if each individual document was specifically and individually indicated to be incorporated by reference.

Additional Example Embodiments

An aspect of the invention is captured by the below numbered statements.
1. A method for developing or designing a CRISPR-Cas system-based therapy or therapeutic, comprising:
   optionally, selecting one or more therapeutic targets,
   optionally, selecting one or more CRISPR-Cas system functionalities,
   optionally, selecting one or more CRISPR-Cas system mode of delivery,
   optionally, selecting one or more CRISPR-Cas system delivery vehicle or expression system, and
   optimization of selected parameters or variables associated with the CRISPR-Cas system and/or its functionality,
   wherein specificity, efficacy, and/or safety are optimized.
2. The method according to statement 1, wherein the selected parameters or variables are selected from the group comprising CRISPR effector specificity, gRNA specificity, CRISPR-Cas complex specificity, PAM restrictiveness, PAM type (natural or modified), PAM nucleotide content, PAM length, CRISPR effector activity, gRNA activity, CRISPR-Cas complex activity, target cleavage efficiency, target site selection, target sequence length, ability of effector protein to access regions of high chromatin accessibility, degree of uniform enzyme activity across genomic targets, epigenetic tolerance, mismatch/budge tolerance, CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector protein size, CRISPR effector expression level, gRNA expression level, CRISPR-Cas complex expression level, CRISPR effector spatiotemporal expression, gRNA spatiotemporal expression, CRISPR-Cas complex spatiotemporal expression.
3. The method according to statement 1 or 2,
   wherein optimization of specificity comprises optimizing one or more parameters or variables selected from CRISPR effector specificity, gRNA specificity, CRISPR-Cas complex specificity, PAM restrictiveness, PAM type (natural or modified), PAM nucleotide content, PAM length,
   wherein optimization of efficacy comprises optimizing one or more parameters or variables selected from CRISPR effector activity, gRNA activity, CRISPR-Cas complex activity, target cleavage efficiency, target site selection, target sequence length, CRISPR effector protein size, ability of effector protein to access regions of high chromatin accessibility, degree of uniform enzyme activity across genomic targets, epigenetic tolerance, mismatch/budge tolerance, and
   wherein optimization of safety comprises optimizing one or more parameters or variables selected from CRISPR effector stability, CRISPR effector mRNA stability, gRNA stability, CRISPR-Cas complex stability, CRISPR effector protein or mRNA immunogenicity or toxicity, gRNA immunogenicity or toxicity, CRISPR-Cas complex immunogenicity or toxicity, CRISPR effector protein or mRNA dose or titer, gRNA dose or titer, CRISPR-Cas complex dose or titer, CRISPR effector expression level, gRNA expression level, CRISPR-Cas complex expression level, CRISPR effector spatiotemporal expression, gRNA spatiotemporal expression, CRISPR-Cas complex spatiotemporal expression.
4. The method according to any of statements 1 to 3, wherein optimization of selected parameters or variables associated with the CRISPR-Cas system and/or its functionality depends on the therapeutic target or therapeutic targets, the mode or type of CRISPR-Cas system based therapeutic target(s) modulation, modification, or manipulation, and/or the delivery of the CRISPR-Cas system components.
5. The method according to any of statements 1 to 4, wherein the therapeutic target is a single gene, locus, or other genomic site, or multiple genes, loci or other genomic sites.
6. The method according to any of statements 1 to 5, wherein CRISPR-Cas system based therapy or therapeutics involve
   target disruption, such as target mutation, such as leading to gene knockout,
   replacement of particular target sites, such as leading to target correction,
   removal of particular target sites, such as leading to target deletion, and/or
   modulation of target site functionality, such as target site activity or accessibility, optionally leading to (transcriptional and/or epigenetic) gene or genomic region activation or gene or genomic region silencing.
7. The method according to any of statements 1 to 6, wherein CRISPR-Cas system functionality comprises
   genomic mutation, such as single genomic mutation or multiple genomic mutation,
   gene knockout, such as single gene knockout or multiple gene knockout,
   gene correction, such as single gene correction or multiple gene correction,
   genomic region deletion, such as single genomic region deletion of multiple genomic region deletion, and/or
   gene or genomic region functionality, such as single or multiple gene or genomic region activity.
8. The method according to any of statements 1 to 7, the mode of delivery comprises
   delivering gRNA and/or CRISPR effector protein,
   delivering gRNA and/or CRISPR effector mRNA, or
   delivering gRNA and/or CRISPR effector as a DNA based expression system.
9. The method according to any of statements 1 to 8, wherein the delivery vehicle and/or expression system comprises liposomes, lipid particles, nanoparticles, biolistics, or viral-based expression/delivery systems, optionally adenoviral, AAV, or lentiviral expression/delivery systems.
10. The method according to any of statements 1 to 9, wherein
   CRISPR effector specificity is optimized by selecting the most specific CRISPR effector, such as by selecting the most specific CRISPR effector orthologue or by specific CRISPR effector mutations which increase specificity,
   gRNA specificity is optimized by selecting the most specific gRNA, such as by selecting gRNA having low homology, i.e. at least one or preferably more, such as at least 2, or preferably at least 3, mismatches to off-target sites, PAM restrictiveness is optimized by selecting a CRISPR effector having to most restrictive PAM recognition, such as by selecting a CRISPR effector orthologue having more restrictive PAM recognition or by specific CRISPR effector mutations which increase or alter PAM restrictiveness, CRISPR effector activity is optimized by selecting the most active CRISPR effector, such as by selecting the most active CRISPR effector orthologue or by specific CRISPR effector mutations which increase activity, gRNA activity is optimized by selecting the most active gRNA such as by increasing gRNA stability through RNA modification, target site selection is optimized by selecting the optimal position of the target site within a gene, locus or other genomic region, such as by selecting a target site in an early and/or conserved exon or domain having low variability, such as polymorphisms, within a population, or by minimization of off-target effects, such as off-targets qualified as having 1-5, 1-4, or preferably 1-3 mismatches compared to target, preferably also taking into account variability within a population, CRISPR effector stability is optimized by selecting CRISPR effector having appropriate half-life, such as preferably a short half-life while still capable of maintaining sufficient activity, such as by selecting an appropriate CRISPR effector orthologue having a specific half-life or by specific CRISPR effector mutations or modifications which affect half-life or stability, such as inclusion of stabilizing or destabilizing domains or sequences, CRISPR effector mRNA stability is optimized by increasing or decreasing CRISPR effector mRNA stability, such as by increasing or decreasing CRISPR effector mRNA stability through mRNA modification, gRNA stability is optimized by increasing or decreasing gRNA stability, such as by increasing or decreasing gRNA stability through RNA modification, CRISPR effector protein or mRNA immunogenicity or toxicity is optimized by decreasing CRISPR effector protein or mRNA immunogenicity or toxicity, such as by mRNA or protein modifications, gRNA immunogenicity or toxicity is optimized by decreasing gRNA immunogenicity or toxicity, such as by gRNA modifications, CRISPR effector protein or mRNA dose or titer is optimized by selecting dosage or titer to minimize toxicity and/or maximize specificity and/or efficacy, gRNA dose or titer is optimized by selecting dosage or titer to minimize toxicity and/or maximize specificity and/or efficacy, CRISPR effector protein size is optimized by selecting minimal protein size to increase efficiency of delivery, in particular for virus mediated delivery, CRISPR effector, gRNA, and/or CRISPR-Cas complex expression level is optimized by limiting or extending the duration of expression and/or limiting or increasing expression level, such as by using self-inactivating CRISPR-Cas systems, such as including a self-targeting gRNA, by using viral vectors having limited expression duration, by using appropriate promoters for low or high expression levels, by combining different delivery methods for individual CRISP-Cas system components, such as virus mediated delivery of CRISPR-effector encoding nucleic acid combined with non-virus mediated delivery of gRNA, or virus mediated delivery of gRNA combined with non-virus mediated delivery of CRISPR effector protein or mRNA, and CRISPR effector, gRNA, or CRISPR-Cas complex spatiotemporal expression is optimized by appropriate choice of conditional and/or inducible expression systems, including controllable CRISPR effector activity optionally a destabilized CRISPR effector and/or a split CRISPR effector, and/or cell- or tissue-specific expression systems.

11. The method according to any of statements 1 to 10, wherein optimization of selected parameters or variables associated with the CRISPR-Cas system and/or its functionality depends on the choice of the therapeutic target, the CRISPR-Cas system functionality, the CRISPR-Cas system mode of delivery, and/or the CRISPR-Cas system delivery vehicle or expression system.

12. The method according to any of statements 1 to 11, wherein gRNA specificity is optimized at the population level of the target organism.

13. The method according to statement 12, wherein optimization of gRNA specificity comprises minimizing gRNA target site sequence variation across a population and/or minimizing gRNA off-target incidence across a population.

14. The method according to statement 12 or 13, comprising
(a) selecting for a therapeutic locus of interest gRNA target sites, wherein said target sites have minimal sequence variation across a population, and
from said selected target sites (sub)selecting target sites, wherein a gRNA directed against said target sites recognizes a minimal number of off-target sites across said population,
or
(b) selecting for a therapeutic locus of interest gRNA target sites, wherein said target sites have minimal sequence variation across a population, or
selecting for a therapeutic locus of interest gRNA target sites, wherein a gRNA directed against said target sites recognizes a minimal number of off-target sites across said population,
and
optionally estimating the number of (sub)selected target sites needed to treat a population,
optionally validating one or more of the (sub)selected target sites for an individual subject,
optionally designing one or more gRNA recognizing one or more of said (sub)selected target sites.

15. A method for developing or designing a CRISPR-Cas system based therapy or therapeutic or for developing or designing a gRNA for use in a CRISPR-Cas system based therapy or therapeutic, comprising
(a) selecting, for a therapeutic locus of interest, gRNA target sites, wherein said target sites have minimal sequence variation across a population of a target organism, and
(sub)selecting one or more target sites from said selected target sites, wherein a gRNA directed against said target sites recognizes a minimal number of off-target sites across said population,
or
(b) selecting, for a therapeutic locus of interest, gRNA target sites, wherein said target sites have minimal sequence variation across a population of a target organism, or
selecting, for a therapeutic locus of interest, gRNA target sites, wherein a gRNA directed against said target sites recognizes a minimal number of off-target sites across said population,
and
optionally estimating the number of (sub)selected target sites needed to treat a population, optionally validating one or more of the (sub)selected target sites for an individual subject, optionally designing one or more gRNA recognizing one or more of said (sub)selected target sites.

16. The method according to statement 15, wherein said method is a method for developing or designing a CRISPR-Cas system based therapy or therapeutic or for developing or designing a gRNA for use in a CRISPR-Cas system based therapy or therapeutic in a population of a target organism.

17. The method according to any of statements 12 to 16, wherein said target sites having minimal sequence variation across a population are characterized by absence of sequence variation in at least 99%, preferably at least 99.9%, more preferably at least 99.99% of the population.

18. The method according to any of statements 12 to 17, wherein said population comprises at least 1000 individuals, such as at least 5000 individuals, such as at least 10000 individuals, such as at least 50000 individuals.

19. The method according to any of statements 12 to 18, wherein said off-target sites are characterized by at least one mismatch between the off-target site and the gRNA, and/or the off-target sites are characterized by at most five, preferably at most four, more preferably at most three mismatches between the off-target site and the gRNA, preferably both.

20. The method according to any of statements 12 to 19, wherein said minimal number of off-target sites across said population is determined for high-frequency haplotypes in said population.

21. The method according to statement 20, wherein the high-frequency haplotypes are characterized by occurrence in at least 0.1% of the population.

22. The method according to any of statements 12 to 21, wherein the number of (sub)selected variation, such as low frequency sequence variation captured in large scale sequencing datasets.

23. The method according to any of statements 12 to 22, wherein the number of (sub)selected target sites needed to treat a population of a given size is estimated.

24. The method according to any of statements 12 to 23, wherein the (sub)selected target is validated by genome sequencing, preferably whole genome sequencing.

25. A method for developing or designing a CRISPR-Cas system based therapy or therapeutic, comprising:

selecting a set of target sequences for one or more loci in a target population, wherein the target sequences do not contain variants occurring above a threshold allele frequency in the target population;

removing any platinum target sequences having high frequency off-target candidates (relative to other platinum targets in the set) to define a final target sequence set;

preparing a set of CRISPR-Cas systems based on the final target sequence set, wherein a number of CRISP-Cas systems prepared is based at least in part a size of a target population.

26. The method of statement 25, further comprising;

obtaining genome sequencing data of a subject to be treated; and treating the subject with a CRISPR-Cas system selected from the set of CRISPR-Cas systems, wherein the CRISPR-Cas system selected is based at least in part on the genome sequencing data of the individual.

27. The method of statement 26, wherein the genome sequencing data is whole genome sequencing data.

28. The method of statements 2 to 27, wherein target sequences are further selected based on optimization of one or more parameters consisting of; PAM type (natural or modified), PAM nucleotide content, PAM length, target sequence length, PAM restrictiveness, target cleavage efficiency, and target sequence position within a gene, a locus or other genomic region.

29. The method of any one of statements 2 to 28, wherein the effector protein for each CRISPR-Cas system in the set of CRISPR-Cas systems is selected based on optimization of one or more parameters selected from the group consisting of; effector protein size, ability of effector protein to access regions of high chromatin accessibility, degree of uniform enzyme activity across genomic targets, epigenetic tolerance, mismatch/budge tolerance, effector protein specificity, effector protein stability or half-life, effector protein immunogenicity or toxicity 30. The method of any one of statements 2 to 29, wherein the guide RNA is a tru guide, an escorted guide, or a protected guide.

31. The method of any one of statements 1 to 30, wherein the CRISPR-Cas system functionality comprises genomic mutation, gene knockout, gene correction, genomic region deletion, modulation of gene or genomic region functionality.

32. The method of statement 31, wherein modulation of gene or genomic region functionality comprising modulation gene activity or accessibility optionally leading to transcriptional and/or epigenetic gene or genomic region activation or gene or genomic region silencing.

33. The method of any one of statements 1 to 32, wherein delivery comprises delivering gRNA and/or CRISPR effector protein, delivering gRNA and/or CRISPR effector mRNA, or delivering gRNA and/or CRISPR effector as a DNA based expression system.

34. The method of statement 33, wherein the delivery vehicle and/or expression system for delivering the CRISPR-Cas systems or components thereof comprises liposomes, lipid particles, nanoparticles, biolistics, or viral-based expression/delivery systems.

35. The method of any one of statements 1 to 34, wherein off-target candidates, PAM restrictiveness, target cleavage efficiency, or effector protein specificity is determined using a sequencing-based double-strand break detection assay.

36. Use of an engineered Cpf1 protein for reducing off-target activity of the Cas 9 protein, wherein the protein complexes with a nucleic acid molecule comprising RNA to form a CRISPR complex, wherein the nucleic acid molecule targets one or more target polynucleotide loci when in the CRISPR complex, wherein the protein comprises at least one modification compared to the unmodified protein that alter association of the Cpf1 protein with the nucleic acid molecule, or a strand of the target polynucleotide loci, or a strand of off-target polynucleotide loci.

37. A system for reducing off-target activity of Cpf1 protein comprising an engineered Cpf1 protein and a nucleic acid molecule comprising an RNA;

wherein the protein complexes with the nucleic acid molecule to form a CRISPR complex, wherein the nucleic acid molecule targets one or more target polynucleotide loci when in the CRISPR complex, wherein the protein comprises at least one modifications compared to the unmodified protein that alter association of the Cpf1 protein with the nucleic acid molecule, or a strand of the target polynucleotide loci, or a strand of off-target polynucleotide loci.

38. The use or system of statement 36 or 37, wherein the Cpf1 protein comprises at least two modifications compared to the unmodified protein that alter association of the Cpf1 protein with the nucleic acid molecule.

39. The use of system of any one of statements 36 to 38, wherein the modifications comprise one or more amino acid substitutions that alter PAM recognition.

40. The use of system of any one of statements 36 to 39, wherein the modifications comprise one or more amino acid substitutions at position 11, 12, 13, 14, 15, 16, 17, 34, 36, 39, 40, 43, 46, 47, 50, 54, 57, 58, 111, 126, 127, 128, 129, 130, 131, 132, 133, 134, 135, 136, 157, 158, 159, 160, 161, 162, 163, 164, 165, 166, 167, 168, 169, 170, 171, 172, 173, 174, 175, 176, 177, 178, 532, 533, 534, 535, 536, 537, 538, 539, 540, 541, 542, 543, 544, 545, 546, 547, 548, 549, 550, 551, 552, 553, 554, 555, 556, 565, 566, 567, 568, 569, 570, 571, 572, 573, 574, 575, 592, 593, 594, 595, 596, 597, 598, 599, 600, 601, 602, 603, 604, 605, 606, 607, 608, 609, 610, 611, 612, 613, 614, 615, 616, 617, 618, 619, 620, 626, 627, 628, 629, 630, 631, 632, 633, 634, 635, 636, 637, 638, 642, 643, 644, 645, 646, 647, 648, 649, 651, 652, 653, 654, 655, 656, 676, 679, 680, 682, 683, 684, 685, 686, 687, 688, 689, 690, 691, 692, 693, 707, 711, 714, 715, 716, 717, 718, 719, 720, 721, 722, 739, 765, 768, 769, 773, 777, 778, 779, 780, 781, 782, 783, 784, 785, 786, 871, 872, 873, 874, 875, 876, 877, 878, 879, 880, 881, 882, 883, 884, or 1048 with reference to amino acid position numbering of AsCpf1 (*Acidaminococcus* sp. BV3L6).

41. The use or system of any one of statements 36 to 40, wherein the modifications comprise one or more amino acid substitutions in a binding groove.

42. The use of system of any one of statements 36 to 41, wherein at least one of the protein modifications comprises an amino acid substitution at position R909, R912, R930, R947, K949, R951, R955, K965, K968, K1000, K1002, R1003, K1009, K1017, K1022, K1029, K1035, K1054, K1072, K1086, R1094, K1095, K1109, K1118, K1142, K1150, K1158, K1159, R1220, R1226, R1242, and/or R1252 with reference to amino acid position numbering of AsCpf1 (*Acidaminococcus* sp. BV3L6).

43. The use of system of any one of statements 36 to 42, wherein at least one of the protein modifications comprises an amino acid substitution at position K324, K335, K337, R331, K369, K370, R386, R392, R393, K400, K404, K406, K408, K414, K429, K436, K438, K459, K460, K464, R670, K675, R681, K686, K689, R699, K705, R725, K729, K739, K748, and/or K752 with reference to amino acid position numbering of AsCpf1 (*Acidaminococcus* sp. BV3L6).

44. The use of system of any one of statements 36 to 43, wherein at least one of the protein modifications comprises an amino acid substitution at position R912, T923, R947, K949, R951, R955, K965, K968, K1000, R1003, K1009, K1017, K1022, K1029, K1072, K1086, F1103, R1226, and/or R1252 with reference to amino acid position numbering of AsCpf1 (*Acidaminococcus* sp. BV3L6).

45. The use of system of any one of statements 36 to 44, wherein at least one of the protein modifications comprises an amino acid substitution at position R833, R836, K847, K879, K881, R883, R887, K897, K900, K932, R935, K940, K948, K953, K960, K984, K1003, K1017, R1033, R1138, R1165, and/or R1252 with reference to amino acid position numbering of LbCpf1 (*Lachnospiraceae bacterium* ND2006).

46. The use or system of any one of statements 36 to 45, wherein the modifications comprise an alanine substitution.

47. The use or system of any one of statements 36 to 46, wherein the modifications comprise K949A.

48. The use or system of any one of statements 36 to 47, wherein the Cpf1 protein comprises a Cpf1 protein from an organism from a genus comprising *Streptococcus, Campylobacter, Nitratifractor, Staphylococcus, Parvibaculum, Roseburia, Neisseria, Gluconacetobacter, Azospirillum, Sphaerochaeta, Lactobacillus, Eubacterium, Corynebacter, Carnobacterium, Rhodobacter, Listeria, Paludibacter, Clostridium, Lachnospiraceae, Leptotrichia, Francisella, Legionella, Alicyclobacillus, Methanomethylophilus, Porphyromonas, Prevotella, Bacteroidetes, Helcococcus, Leptospira, Desulfovibrio, Desulfonatronum, Opitutaceae, Tuberibacillus, Bacillus, Brevibacillus, Methylobacterium* or *Acidaminococcus*.

49. The use or system of any one of statements 36 to 48, wherein the Cpf1 protein comprises one or more nuclear localization signal (NLS) domains, preferably at least two or more NLS domains 50. The use or system of any one of statements 36 to 49, wherein the Cpf1 protein comprises modifications or mutations affecting Cpf1 catalytic activity and/or Cpf1 stability.

51. The use or system of any one statements 36 to 50, wherein the Cpf1 protein comprises one or more heterologous functional domains, which have one or more of the following activities: methylase activity, deaminase activity, demethylase activity, transcription activation activity, transcription repression activity, transcription release factor activity, histone modification activity, nuclease activity, single-strand RNA cleavage activity, double-strand RNA cleavage activity, single-strand DNA cleavage activity, double-strand DNA cleavage activity and nucleic acid binding activity.

52. The use or system according to any one statements 36 to 51, further comprising an exogenous template polynucleotide.

53. The system according to any one statements 36 to 52, wherein the system is comprised in a delivery system or encoded or delivered in whole or in part by one or more vectors; and optionally the one or more vectors are comprised in a delivery system, preferably a single vector.

54. The system according to statement 53, wherein the vector(s) comprise one or more viral vectors; or one or more retrovirus, lentivirus, adenovirus, adeno-associated virus or herpes simplex virus vectors.

55. The system according to statement 52, wherein the delivery system comprises particles (preferably comprising a lipid, a sugar, a metal or a protein), a yeast system, a lipofection system, a microinjection system, a biolistic system, virosomes, vesicles (preferably exosomes or liposomes), immunoliposomes, polycations, lipid:nucleic acid conjugates or artificial virions.

56. The system according to statement 55, wherein the particle comprises the engineered Cpf1 protein of any one of statements 36-51 complexed with guide RNA.

57. A eukaryotic cell comprising the system of any one of statements 36 to 56, preferably wherein the cell is an in vitro, ex vivo or in vivo host cell or cell line or progeny thereof, wherein the host cell or cell line is not a human germ cell line.

58. The cell of statement 57, wherein the cell comprises a stem cell or stem cell line.

59. The cell of statement 57 or 58, wherein the cell is an animal or plant cell, preferably a human cell.

60. A method of modulating gene expression or modifying a target locus of interest in a cell or cell line, wherein the method comprises introducing the system of any one of statements 36 to 59 into the cell or cell line, thereby obtaining a modified cell or cell line.

61. The method of statement 60, wherein the modified cell or cell line is further cultured to produce progeny.

62. A method of modifying a target locus of interest in vitro or ex vivo, the method comprising delivering to said locus a non-naturally occurring or engineered composition comprising the system of any one of statements 36 to 51, wherein the Cpf1 protein forms a complex with the one or more nucleic acid components and upon binding of the complex to a target locus of interest, the Cpf1 protein induces a modification of the target locus of interest.

63. A method of producing a plant having a modified trait of interest encoded by a gene of interest, said method comprising contacting a plant cell with a system according to any one of statements 36 to 56 or subjecting the plant cell to a method according to statement 62, thereby either modifying or introducing said gene of interest, and regenerating a plant from said plant cell.

64. A method of modifying an organism by manipulation of one or more target sequences at genomic loci of interest, comprising delivering to the organism the system according to any one of statements 36 to 63 thereby obtaining a modified organism.

65. A method according to statement 64, wherein the organism is a plant or algae.

66. An ex vivo method of modifying a cell or cell line by manipulation of one or more target sequences at genomic loci of interest comprising delivering to the cell the system according to any one of statements 36 to 65 thereby obtaining a modified cell or cell line, wherein the method does not comprise a process for modifying the germ line genetic identity of a human being.

67. The method of statement 66, wherein the modified cell or cell line is further cultured to produce progeny.

68. Use of the system according to any one of statements 36 to 67 for ex vivo gene or genome editing, wherein the use does not comprise a process for modifying the germ line genetic identity of a human being.

69. The system according to any one of statements 36 to 66, the cells according to statements 67-68, or the cells, cell line or progeny thereof produced by statements according to statements 60 to 71 or 66 to 67, for use in therapy.

70. The system or cells for use according to statement 69, wherein said therapy is for gene or genome editing, or gene therapy.

71. The system or cells for use according to statement 69 or 70, wherein said therapy is for the treatment of one or more of the following: blood and coagulation diseases and disorders; cell dysregulation and oncology diseases and disorders; inflammation and immune related diseases and disorders; metabolic, liver, kidney and protein diseases and disorders; muscular/skeletal diseases and disorders; neurological and neuronal diseases and disorders; and ocular diseases and disorders.

72. A cell or cell line obtained by or obtainable by the method of statement 60 to 61 or 66 to 67.

73. A method for developing or designing a CRISPR-Cas system-based therapy or therapeutic, comprising:
a. selecting one or more target loci
b. selecting one or more CRISPR-Cas system functionalities
c. optionally, selecting one or more modes of delivery
d. preparing a CRISPR-Cas system selected based on steps (a)-(c).

74. The method of any of the preceding statements, wherein selecting one or more target, target sequence, or target loci comprises optimizing one or more of target, target sequence, or target loci location, length, specificity, and PAM characteristics 75. The method of statement 74, wherein optimizing target location comprises selecting a target sequence with a gene, locus, or other genomic region having low variability.

76. The method of statement 75, wherein low variability comprises selecting an early and/or conserved exon or domain having low variability.

77. The method of statement 75, wherein optimizing target location comprises selecting target loci having an absence of sequence variation in at least 99%, of a population.

78. The method of statement 77, wherein the population comprises at least 1000 individuals.

79. The method of statement 74, wherein optimizing target length comprises selecting a target sequence within the one or more target loci between 5 and 25 nucleotides.

80. The method of statement 79 wherein target sequence length is 20 nucleotides.

81. The method of statement 74, wherein optimizing target specificity comprises selecting target loci that minimize off-target candidates.

82. The method of statement 81, wherein off-target candidates have 1-3 mismatches or distal PAM mismatches.

83. The method of statement 82, wherein off-target candidates are identified using a sequencing-based double-strand break (DSB) detection assay.

84. The method of statement 83, wherein the sequencing-based DSB detection assay comprises labeling a site of a DSB with an adapter comprising a primer binding site, labeling a site of a DSB with a barcode or unique molecular identifier, or combination thereof.

85. The method of statement 73, wherein optimizing PAM characteristics comprises optimizing nucleotide content of a PAM.

86. The method of statement 85, wherein optimizing nucleotide content of PAM is selecting a PAM with a motif that maximizes abundance in the one or more target loci, minimizes mutation frequency, or both.

87. The method of statement 73, wherein selecting one or more CRISP-Cas system functionalities comprises selecting one or more of an optimal effector protein, an optimal guide RNA, or both.

88. The method of statement 87, wherein selecting an optimal effector protein comprises optimizing one or more of effector protein type, size, PAM specificity, effector protein stability, immunogenicity or toxicity, functional specificity, and efficacy.

89. The method of statement 88, wherein the effector protein is a naturally occurring or modified effector protein.

90. The method of statement 89, wherein the modified effector protein is a nickase, a deaminase, or a deactivated effector protein.

91. The method of any one of statements 87 to 90, wherein optimizing size comprises selecting a protein effector having a minimal size.

92. The method of statement 88, wherein optimizing a PAM specificity comprises selecting an effector protein having a modified PAM specificity.

93. The method of statement 88, wherein optimizing effector protein stability comprises selecting an effector protein having a short half-life while maintaining sufficient activity, such as by selecting an appropriate CRISPR effector orthologue having a specific half-life or stability.

94. The method of statement 88, wherein optimizing immunogenicity or toxicity comprises minimizing effector protein immunogenicity or toxicity by protein modifications.

95. The method of statement 88 wherein optimizing functional specific comprises selecting a protein effector with reduced tolerance of mismatches and/or bulges between the guide RNA and one or more target loci.

96. The method of statement 88, wherein optimizing efficacy comprises optimizing overall efficiency, epigenetic tolerance, or both.

97. The method of statement 96, wherein maximizing overall efficiency comprises selecting an effector protein with uniform enzyme activity across target loci with varying chromatin complexity, selecting an effector protein with enzyme activity limited to areas of open chromatin accessibility.

98. The method of statement 97, wherein chromatin accessibility is measured using one or more of ATAC-seq, or a DNA-proximity ligation assay.

99. The method of statement 96, wherein optimizing epigenetic tolerance comprises optimizing methylation tolerance, epigenetic mark competition, or both.

100. The method of statement 96, wherein optimizing methylation tolerance comprises selecting an effector protein that modify methylated DNA.

101. The method of statement 96, wherein optimizing epigenetic tolerance comprises selecting an effector protein unable to modify silenced regions of a chromosome, selecting an effector protein able to modify silenced regions of a chromosome, or selecting target loci not enriched for epigenetic markers.

102. The method of statement 86, wherein selecting an optimized guide RNA comprises optimizing gRNA stability, gRNA immunogenicity, or both.

103. The method of statement 102, wherein optimizing gRNA stability and/or gRNA immunogenicity comprises RNA modification.

104. The method of statement 103, wherein the modification comprises removing 1-3 nucleotides form the 3' end of a target complementarity region of the gRNA.

105. The method of statement 103, wherein modification comprises an extended gRNA and/or trans RNA/DNA element that create stable structures in the gRNA that compete with gRNA base pairing at a target of off-target loci, or extended complimentary nucleotides between the gRNA and target sequence, or both.

106. The method of any one of the preceding statements, wherein the mode of delivery comprises delivering gRNA and/or CRISPR effector protein, delivering gRNA and/or CRISPR effector mRNA, or delivery gRNA and/or CRISPR effector as a DNA based expression system.

107. The method of statement 106, wherein the mode of delivery further comprises selecting a delivery vehicle and/or expression systems from the group consisting of liposomes, lipid particles, nanoparticles, biolistics, or viral-based expression/delivery systems.

108. The method of any one of statement 106 to 107 wherein expression is spatiotemporal expression is optimized by choice of conditional and/or inducible expression systems, including controllable CRISPR effector activity optionally a destabilized CRISPR effector and/or a split CRISPR effector, and/or cell- or tissue-specific expression system.

The present invention will be further illustrated in the following Examples which are given for illustration purposes only and are not intended to limit the invention in any way.

EXAMPLES

Example 1: Material and Methods Cpf1 In Vivo

DNA Constructs

The AAV hSyn-HA-NLS-AsCpf1-spA vector was generated by PCR amplifying the AsCpf1 encoding sequence (ref) using forward PCR primer including HA-NLS (aacacaggaccggtgccaccatgtacccatacgatgttccagat-tacgcttcgccgaagaaaaagcgcaaggtcgaagcgtccacacagttcgaggg ctttaccaacctgtatcaggtgagc) (SEQ ID NO: 363) (spA) (gcggccgcacacaaaaaaccaacacacagatctaatgaaaataaagatcttttat-tgaattcttagttgcgcagctcctggatgtag gccagcc) (SEQ ID NO: 364) (ref), and cloning of the resulting PCR template into AAV backbone under the human Synapsin promoter (hSyn) using. For the generation of AAV pU6-sgRNA(SapI)-hSyn-GFP-KASH-hGH and pU6-3×gRNA-hSyn-GFP-KASH-hGH vectors, gene blocks encoding for pU6-DR(SapI) and pU6-3×gRNA, respectively, have been cloned into AAV hSyn-GFP-KASH-hGH backbones (unpublished). All constructs were verified by sequencing. For the generation of AAV sMecp2-HA-NLS-AsCpf1-spA-tRNAp-3×gRNA vector, gene blocks encoding for tRNA promoter (tRNAp) and 3×gRNA repeats were assembled with PCR amplified sMecp2-HA-NLS-AsCpf1 and ligated into AAV backbone.

Production of AAV Vectors

AAV1 particles in DMEM culture medium were produced as described previously (ref). Briefly, HEK293FT cells were transfected with transgene plasmid, pAAV1 serotype plasmid and pDF6 helper plasmid using Poly(ethylenimine) (PEI). DMEM culture medium containing low titer AAV1 particles was collected after 48 h and sterile filtered. For high titer AAV1/2 production, HEK293FT cells were transfected with AAV1 and AAV2 serotype plasmids at equal ratios and pDF6 helper plasmid. 48 h after transfection, cells were harvested and high titer AAV1/2 virus was purified on heparin affinity column (ref). To generate high titer PHP.B viral vectors, HEK293T cells were cotransfected with the following mix of plasmids using PEI: 5.7 µg transgene plasmid, 10.4 µg adenoviral helper plasmid pAdDF6, 8.7 µg AAV-PHP.B rep-cap packaging plasmid, per $2.1 \times 10^7$ cells plated. 120 hours post-transfection, cells were harvested and cell lysates prepared by three cycles of freeze-thawing, combined with PEG-precipitated supernatant and treated with Benzonase (Sigma-Aldrich, St. Louis, Mo.) (50 U/ml cell lysate, 37° C., 30 minutes). AAV was purified from cell lysates by iodixanol density-gradient ultracentrifugation (Optiprep density-gradient medium, Axis-Shield, Oslo, Norway). Residual iodixanol was removed by replacing with PBS using a 100 kDa molecular weight cutoff centrifugation device (Amicon Ultra-15, Merck Millipore, Cork, Ireland) by three rounds of centrifugation at 1,500×g. After treatment of stocks with DNase I, the titer of AAV vectors was determined by real-time quantitative PCR (qPCR) using probe and primers specific for the mouse Mecp2 promoter sequence (Integrated DNA Technologies, Coralville, Iowa).

Primary Cortical Neuron Culture

Mice used to obtain neurons for tissue cultures were sacrificed according to the protocol approved by the Broad's Institutional Animal Care and Use Committee (IACUC). Primary neurons were prepared from postnatal day P0.5 mouse brains (ref) and plated on poly-D-lysine (PDL) coated 24-well plates (BD Biosciences) or laminin/PDL coated coverslips (VWR). Cultures were grown at 37° C. and 5% $CO_2$ in Neurobasal A medium, supplemented with B27, Glutamax (Life Technologies) and penicillin/streptomycin mix. For inhibition of glia cell proliferation, Cytosine-beta-D-arabinofuranoside (AraC, Sigma) at a final concentration of 10 µM has been added to the culture medium after 48 h and replaced by fresh culture medium after 72 h. For AAV1 transduction, cultured neurons were infected with low titer AAV1 as described previously (Ref). One week after transduction, neurons have been harvested for isolating genomic DNA (QuickExtract DNA extraction buffer (Epicentre)) or fixed in 4% paraformaldehyde (PFA) for immunofluorescent stainings.

Stereotactic Injection of AAV1/2 into the Mouse Brain

The Broad's Institutional Animal Care and Use Committee (IACUC) approved all animal procedures described here. Craniotomy was performed on adult (12-16 weeks) male C57BL/6N mice according to approved procedures, and 1 µl of 1:1 AAV mixture ($5.87 \times 10^{13}$ Vg/ml of single vector AAV-PHP.B sMecp2-HA-NLS-AsCpf1-spA-tRNAp-3×gRNA; $5.25 \times 10^{13}$ Vg/ml of hSyn-GFP-KASH) was injected into the dorsal dentate gyrus (anterior/posterior: −1.7; mediolateral: +/−0.6; dorsal/ventral: −2.15). The pipette was held in place for 3-5 minutes prior to retraction to prevent leakage. After injection, the incision was sutured and post-operative analgesics were administered according to approved IACUC protocol for three days following surgery.

Systemic Delivery of AAV-PHP.B into Mouse

AAV-PHP.B vectors were administered via the tail vein in a volume of 150 µl into 6-8-week-old male and female C57BL/6J mice (Charles River). A dose of $1 \times 10^{12}$ vg/mouse was administered for single vector AAV-PHP.B sMecp2-HA-NLS-AsCpf1-spA-tRNAp-3×gRNA. A dose of $5 \times 10^{11}$ vg/mouse was administered for each of AAV-PHP.B dual vectors.

Purification of Cell Nuclei from Intact Brain Tissue

Cell nuclei from AAV1/2 injected hippocampal tissue were purified as described previously (Ref). Briefly, dissected tissue was homogenized in ice-cold homogenization buffer (HB) (320 mM Sucrose, 5 mM CaCl, 3 mM Mg(Ac)$_2$, 10 mM Tris pH7.8, 0.1 mM EDTA, 0.1% NP40, 0.1 mM PMSF, 1 mM β-mercaptoethanol) using 2 ml Type A and B Dounce homogenizer (Sigma). For gradient centrifugation, OptiPrep™ density gradient medium (Sigma) has been used. Samples were centrifuged at 10,100×g (7,500 rpm) for 30 min at 4° C. (Beckman Coulter, SW28 rotor). Cell nuclei pellets were resuspended in 65 mM β-glycerophosphate (pH 7.0), 2 mM MgCl$_2$, 25 mM KCl, 340 mM sucrose and 5% glycerol. Finally, number and quality of purified nuclei was controlled using bright field microscopy.

Fluorescent Activated Cell Sorting (FACS) of Cell Nuclei

Purified cell nuclei were co-labeled with Vybrant® Dye-Cycle™ Ruby Stain (1:500, Life Technologies) and sorted using a Beckman Coulter MoFlo Astrios EQ cell sorter (Broad Institute Flow Cytometry Core). Single and population (500 nuclei) GFP-KASH$^+$ and GFP-KASH$^-$ nuclei were collected in 96 well plates containing 5 µl of QuickExtract DNA extraction buffer (Epicentre) and spined down at 2,000×g for 2 min. Each 96 well plate included two empty wells as negative control.

Genomic DNA Extraction and Indel Analysis

DNA in QuickExtract DNA extraction buffer (Epicentre) was used for PCR amplification of targeted genomic loci. Following PCR primers have been used together in one PCR reaction: Mecp2 fw GGTCTCATGTGTGGCACTCA (SEQ ID NO: 93), Mecp2 rv TGTCCAACCTTCAGGCAAGG (SEQ ID NO: 94), Nlgn3 fw GTAACGTCCTGGACACTGTGG (SEQ ID NO: 95), Nlgn3 ry TTGGTCCAATAGGTCATGACG (SEQ ID NO: 96), Drd1 fw TGGCTAAGCCTGGCCAAGAACG (SEQ ID NO: 97), Drd1 ry TCAGGATGAAGGCTGCCTTCGG (SEQ ID NO: 98). SURVEYOR nuclease assays (Transgenomics) of individual targets have been performed according to the manufacture's protocol. Band intensity quantification was performed as described before (ref). For next generation sequencing (NGS), PCR amplified targeted regions were attached with the Illumina P5 adapters as well as unique sample-specific barcode: to the target amplicons. Barcoded and purified DNA samples were quantified by Qubit 2.0 Fluorometer (Life Technologies) and pooled in an equimolar ratio. Sequencing libraries were then sequenced with the Illumina MiSeq Personal Sequencer (Life Technologies), with 300 bp reads length. The MiSeq reads for pooled and single nuclei were analyzed as described previously (ref).

Western Blot Analysis

AAV injected dentate gyrus tissues were lysed in 100 µl of ice-cold RIPA buffer (Cell Signaling) containing 0.1% SDS and proteases inhibitors (Roche, Sigma) and sonicated in a Bioruptor sonicater (Diagenode) for 1 min. Protein concentration was determined using the BCA Protein Assay Kit (Pierce Biotechnology, Inc.). Protein samples were separated under reducing conditions on 4-15% Tris-HCl gels (Bio-Rad) and analyzed by Western blotting using primary antibodies: mouse anti-HA (Cell Signaling 1:500), mouse anti-GFP (Roche, 1:500), rabbit anti-Tubulin (Cell Signaling, 1:10,000) followed by secondary anti-mouse and anti-rabbit HRP antibodies (Sigma-Aldrich, 1:10,000). Blots were imaged with Amersham Imager 600.

Immunofluorescent Staining 3-4 weeks after viral delivery, mice were transcardially perfused with PBS followed by PFA according to approved IACUC protocol. 30 µm free floating sections (Leica, VT1000S) were boiled for 2 min in sodium citrate buffer (10 mM tri-sodium citrate dehydrate, 0.05% Tween20, pH 6.0) and cooled down at RT for 20 min. Sections were blocked with 4% normal goat serum (NGS) in TBST (137 mM NaCl, 20 mM Tris pH 7.6, 0.2% Tween-20) for 1 hour. Primary antibodies were diluted in TBST with 4% NGS and sections were incubated overnight at 4° C. After 3 washes in TBST, samples were incubated with secondary antibodies for 1 h at RT. After 3 times washing with TBST, sections were mounted using VECTASHIELD HardSet Mounting Medium including DAPI and visualized with confocal microscope (Zeiss LSM 710, Ax10 ImagerZ2, Zen 2012 Software). Following primary antibodies were used: mouse anti-NeuN (Millipore, 1:50-1:400); chicken anti-GFP (Ayes labs, 1:200-1:400); rabbit anti-HA (Cell Signaling, 1:100). Anti-HA signaling was amplified using biotinylated anti-rabbit (1:200) followed by streptavidin AlexaFluor® 568 (1:500) (Life Technologies). Anti-chicken AlexaFluor®488 and anti-mouse AlexaFluor®647 secondary antibodies (Life Technologies) were used at 1:1000.

Statistical Analysis

All experiments were performed with a minimum of two independent biological replicates. Statistics were performed with Prism6 (GraphPad) using Student's two-tailed t-test.

Viral vectors for Cpf1 in vivo delivery:
1. hSyn-HA-NLS-AsCpf1-spA (dual vector AsCpf1)
2. sMecp2-HA-NLS-AsCpf1-spA-tRNAp-sgRNA(SapI) (single vector scaffold)
3. U6p-sgRNA(SapI)-hSyn-GFP-KASH-hGH (dual vector scaffold)
4. U6p-3×sgRNA(Mecp2, Nlgn3, Drd1)-hSyn-GFP-KASH-hGH (dual vector 3×sgRNA)
5. mMecp2-HA-NL S-AsCpf1-spA-tRNAp-3×sgRNA (Mecp2, Nlgn3, Drd1) (single vector 3×sgRNA)

hSyn: human Synapsin promoter (SEQ ID NO: 99)
gtgtctagactgcagagggccctgcgtatgagtgcaagtgggttttagga ccaggatgaggcggggtgggggtgcctacctgacgaccgaccccgaccca -continued ctggacaagcacccaaccccattccccaaattgcgcatccctatcaga gagggggagggaaacaggatgcggcgaggcgcgtgcgcactgccagctt cagcaccgcggacagtgccttcgccccgcctggcggcgcgcgccaccgc cgcctcagcactgaaggcgcgctgacgtcactcgccggtccccgcaaac tccccttcccggccaccttggtcgcgtccgcgccgccgccggcccagccg gaccgcaccacgcgaggcgcgagataggggggcacgggcgcgaccatctg cgctgcggcgccggcgactcagcgctgcctcagtctgcggtgggcagcgg aggagtcgtgtcgtgcctgagagcgcagtcgagaa sMecp2: short Mecp2 promoter (mouse)
(SEQ ID NO: 100)
agctgaatggggtccgcctcttttccctgcctaaacagacaggaactcct gccaattgagggcgtcaccgctaaggctccgccccagcctgggctccaca accaatgaagggtaatctcgacaaagagcaaggggtggggcgcgggcgcg caggtgcagcagcacacaggctggtcgggagggcggggcgcgacgtctgc cgtgcgggtcccggcatcggttgcgcgc HA: HA-Tag
(SEQ ID NO: 101)
atgtacccatacgatgttccagattacgct NLS: nuclear localization sequence
(SEQ ID NO: 102)
tcgccgaagaaaaagcgcaaggtcgaagcgtcc spA: short poly A signal
(SEQ ID NO: 103)
aataaaagatctttattttcattagatctgtgtgttggttttttgtgt tRNAp: tRNA promoter
(SEQ ID NO: 104)
ggctcgttggtctagggggtatgattctcgcttagggtgcgagaggtcccg ggttcaaatcccggacgagccc pU6: U6 promoter
(SEQ ID NO: 105)
gagggcctatttcccatgattccttcatatttgcatatacgatacaaggc tgttagagagataattggaattaatttgactgtaaacacaaagatattag tacaaaatacgtgacgtagaaagtaataatttcttgggtagtttgcagtt ttaaaattatgttttaaaatggactatcatatgcttaccgtaacttgaaa gtatttcgatttcttggctttatatcttgtggaaaggacgaaacacc sgRNA(SapI): AsCpf1 direct repeat and SapI
cloning site for spacer
(SEQ ID NO: 106)
gtaatttctactgttgtagatggaagagcatatatgctcttctttttt PCR primer:
AsCpf1 NLS-HA-fw
(SEQ ID NO: 107)
aacacaggaccggtGccAccatgtacccatacgatgttccagattacgct tcgccgaagaaaaagcgcaaggtcgaagcgtccACACAGTTCGAGGGCTT

TACCAACCTGTATCAGGTGAGC

AsCpf1-spA-rv
(SEQ ID NO: 108)
gcggccgcACACAAAAAACCAACACACAGATCTAATGAAAATAAAGATCT TTTATTgaattcttaGTTGCGCAGCTCCTGGATGTAGGCCAGCC LbCpf1 NLS-HA-fw
(SEQ ID NO: 109)
TACCGGATCCCCGGGTACCGGTATGTACCCATACGATGTTCCAGATTACG

CTTCGCCGAAGAAAAAGCGCAAGGTCGAAGCGTCCAGCAAGCTGGAGAAG

TTTACAAACTGCTACTCC

LbCpf1-spA-rv
(SEQ ID NO: 110)
GCGGCCGCACACAAAAAACCAACACACAGATCTAATGAAAATAAAGATCT

TTTATTGAATTCTTAGTGCTTCACGCTGGTCTGGGCGTACTCCAGCCACT

CCTTGTTAGAGATGG

Gene blocks (Mus musculus):
Cpf1mouse (vector 1) Mecp2/Nlgn3/Drd1
(SEQ ID NO: 111)
cctacgctagcctgagggcctatttcccatgattccttcatatttgcata tacgatacaaggctgttagagagataattggaattaatttgactgtaaac acaaagatattagtacaaaatacgtgacgtagaaagtaataatttcttgg gtagtttgcagttttaaaattatgttttaaaatggactatcatatgctta ccgtaacttgaaagtatttcgatttcttggctttatatcttgtggaaa ggacgaaacaccgTAATTTCTACTCTTGTAGATCCTGCCTCTGCTGGCTC

TGCTAATTTCTACTCTTGTAGATCGGCGGGTCTCAGGGTTGTCTAATTTC

TACTCTTGTAGATTGTCCCTGCTTATCCTGTCCTTTTTTcgACGCGT

Cpf1mouse (vector 2) Mecp2/Nlgn3/Drd1
(SEQ ID NO: 112)
cctacgctagcctgagggcctatttcccatgattccttcatatttgcata tacgatacaaggctgttagagagataattggaattaatttgactgtaaac acaaagatattagtacaaaatacgtgacgtagaaagtaataatttcttgg gtagtttgcagttttaaaattatgttttaaaatggactatcatatgctta ccgtaacttgaaagtatttcgatttcttggctttatatcttgtggaaa ggacgaaacaccgTAATTTCTACTCTTGTAGATTTCGCCTTCTTAAACTT

CAGTAATTTCTACTCTTGTAGATGTGTCCCTATGGTAGGTCCCTAATTTC

TACTCTTGTAGATTCATCTCTTTAGCTGTGTCATTTTTTcgACGCGT

Gene block (AsCpf1 direct repeat and SapI
cloning site)
(SEQ ID NO: 113)
Ccctacgctagcctgagggcctatttcccatgattccttcatatttgcat atacgatacaaggctgttagagagataattggaattaatttgactgtaaa cacaaagatattagtacaaaatacgtgacgtagaaagtaataatttcttg ggtagtttgcagttttaaaattatgttttaaaatggactatcatatgctt accgtaacttgaaagtatttcgatttcttggctttatatcttgtggaa aggacgaaacaccgTAATTTCTACTCTTGTAGATgaagagcgagctcttc

TTTTTTcgACGCGTgt
(Bold indicates SapI cloning site)

Pre-crRNA Array Design and Cloning crRNAs were designed as four oligos (IDT) consisting of direct-repeats, each one followed by a crRNA (Table 25). The oligos favored a one-directional annealing through their sticky-end design. The oligonucleotides (final concentration 10 μM) were annealed in 10×T4 ligase buffer (final concentration 1×; NEB) and T4 PNK (5 units; NEB). Thermocycler conditions were adjusted to 37° for 30 minutes, 95° for 5 minutes followed by a −5° C./minute ramp down to 25°. The annealed oligonucleotides were diluted 1:10 (final concentration 1 μM) and ligated into BsmBI-cut pcDNA-huAsCpf1-U6, utilizing T7 DNA ligase (Enzymatics), in room temperature for 30 minutes. The constructs were transformed into STBL3 bacteria and plated on ampicillin-containing (100 g/ml) agar plates. Single colonies were grown in standard LB media (Broad Facilities) for 16 hours. Plasmid DNA was harvested from bacteria according to QIAquick Spin Miniprep protocol (QIAGEN).

TABLE 24

Cpf1 guide sequences used for single and pre-crRNA array expression

| | |
|---|---|
| DNMT1 23nt guide | CTGATGGTCCATGTCTGTTACTC (SEQ ID NO: 114) |
| EMX1 23nt guide | TGGTTGCCCACCCTAGTCATTGG (SEQ ID NO: 115) |
| VEGFA 23nt guide | CTAGGAATATTGAAGGGGCAGG (SEQ ID NO: 116) |
| GRIN2b 23nt guide | GTGCTCAATGAAAGGAGATAAGG (SEQ ID NO: 117) |

TABLE 25

DNA oligonucleotides for array cloning

| | |
|---|---|
| array 1 T1 | AGATCTGATGGTCCATGTCTGTTACTCAATTTCTACTCTTGT AGATTGGTTGCCCAC (SEQ ID NO: 118) |
| array 1 T2 | CCTAGTCATTGGAATTTCTACTCTTGTAGATCTAGGAATAT TGAAGGGGCAGGAATTTCTACTCTTGTAGATGTGCTCAAT GAAAGGAGATAAGG (SEQ ID NO: 119) |
| array 1 B1 | AAAACCTTATCTCCTTTCATTGAGCACATCTACAAGAGTAG AAATTCCTGCCCCTT (SEQ ID NO: 120) |

TABLE 25-continued

DNA oligonucleotides for array cloning

| | |
|---|---|
| array 1 B2 | CAATATTCCTAGATCTACAAGAGTAGAAATTCCAATGACTA GGGTGGGCAACCAATCTACAAGAGTAGAAATTGAGTAACA GACATGGACCATCAG (SEQ ID NO: 121) |
| array 2 T1 | AGATCTGATGGTCCATGTCTGTTACTCGCCTGTCAATTTCTA CTCTTGTAGATTGGTTGCCCACCCTAGTC (SEQ ID NO: 122) |

Example 2: AsCpf1 is Efficiently Delivered to the Brain and Mediates Editing

Figure 1:
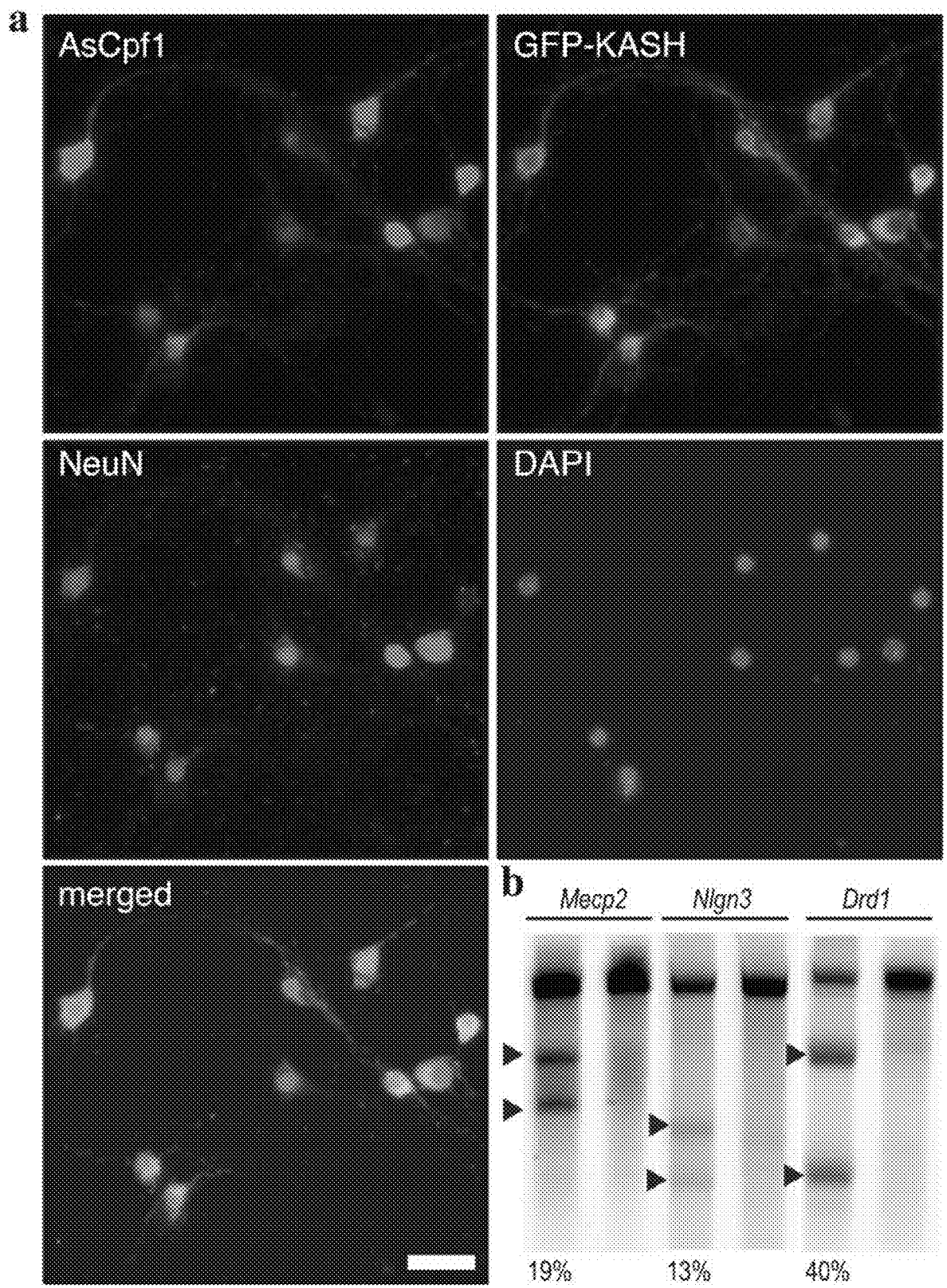
FIG. 1 illustrates AsCpf1 efficiency in primary neurons. a) AAV ½ infected primary cortical cultures stained with anti-HA (AsCpf1), anti-GFP (GFP-KASH) and NeuN (Neuronal marker) antibodies. b) Surveyor assay 7 days post infection.
Figure 2:
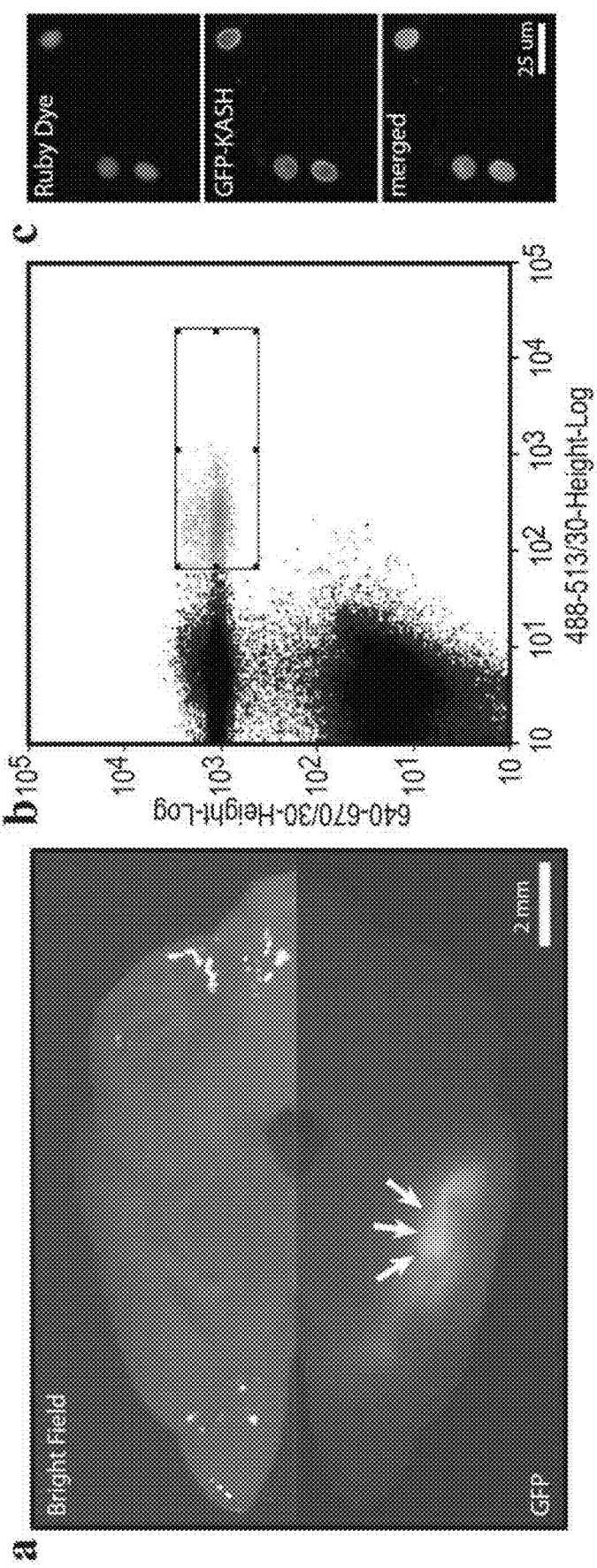
FIG. 2A-C illustrates Stereotactic AAV1/2 injection for AsCpf1 delivery into mouse hippocampus. a) Dissected mouse brain 3 weeks after viral delivery showing GFP fluorescence in hippocampus. b) FACS histogram of sorted GFP-KASH positive cell nuclei. c) Sorted GFP-KASH nuclei co-stained with nuclear marker Ruby Dye.
Figure 3A:
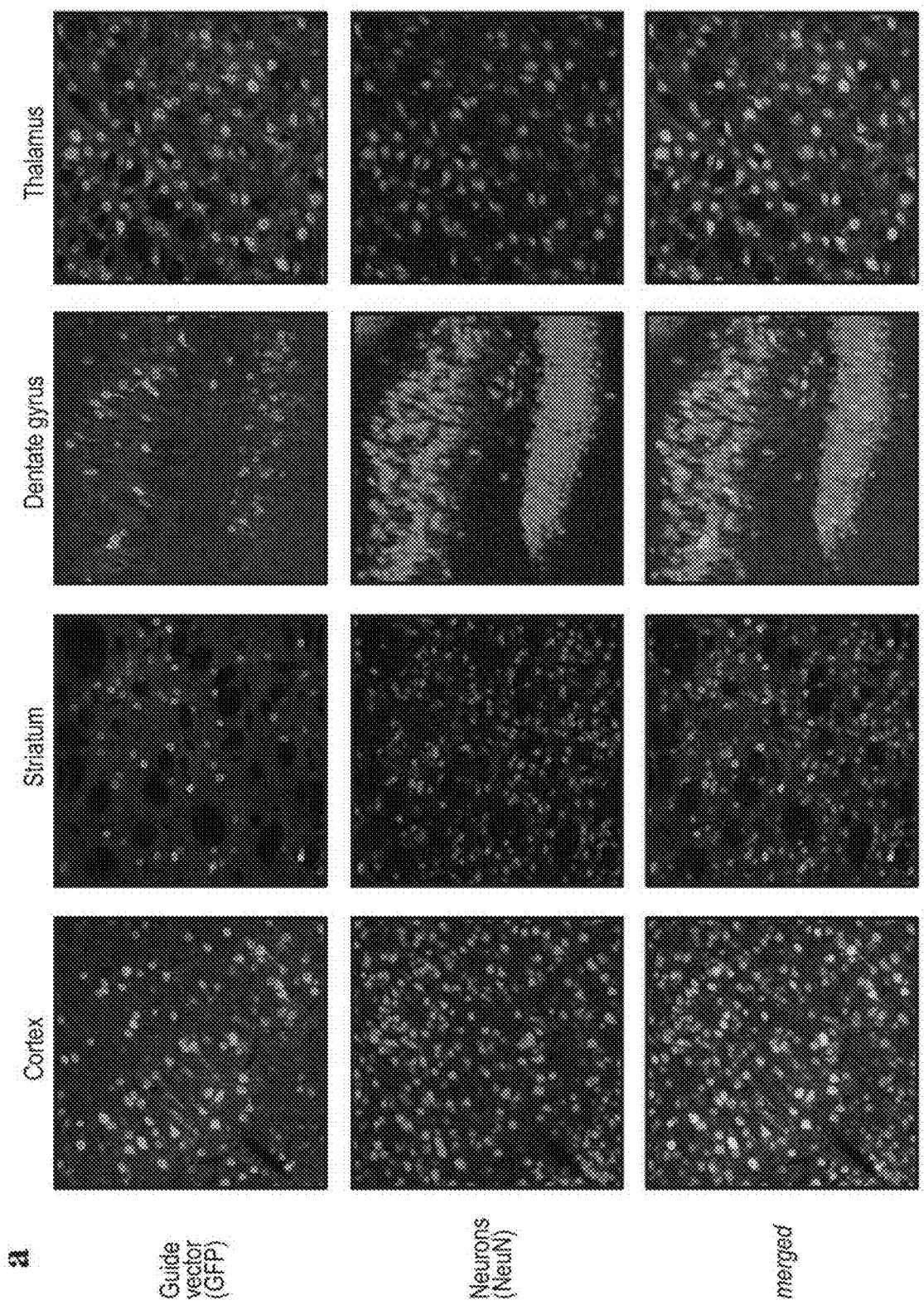
FIG. 3A-B illustrates Systemic delivery of AsCpf1 and GFP-KASH into adult mice using dual vector approach. a) Immunostaining 3 weeks after systemic tail vein injection showing delivery of Syn-GFP-KASH vector into neurons of various brain regions. b) NGS indel analysis of various brain regions dissected 3 weeks after systemic tail vein co-injection of dual vectors.
Figure 3B:
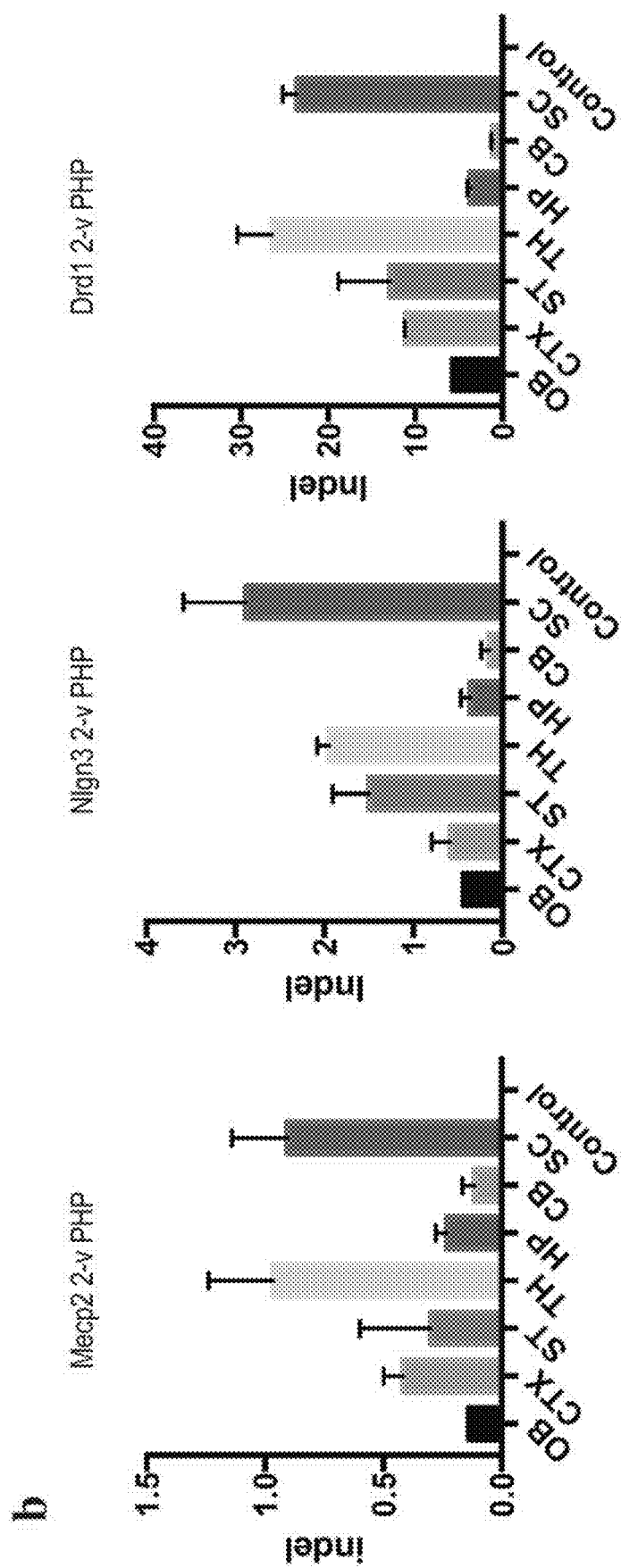
Figure 5:
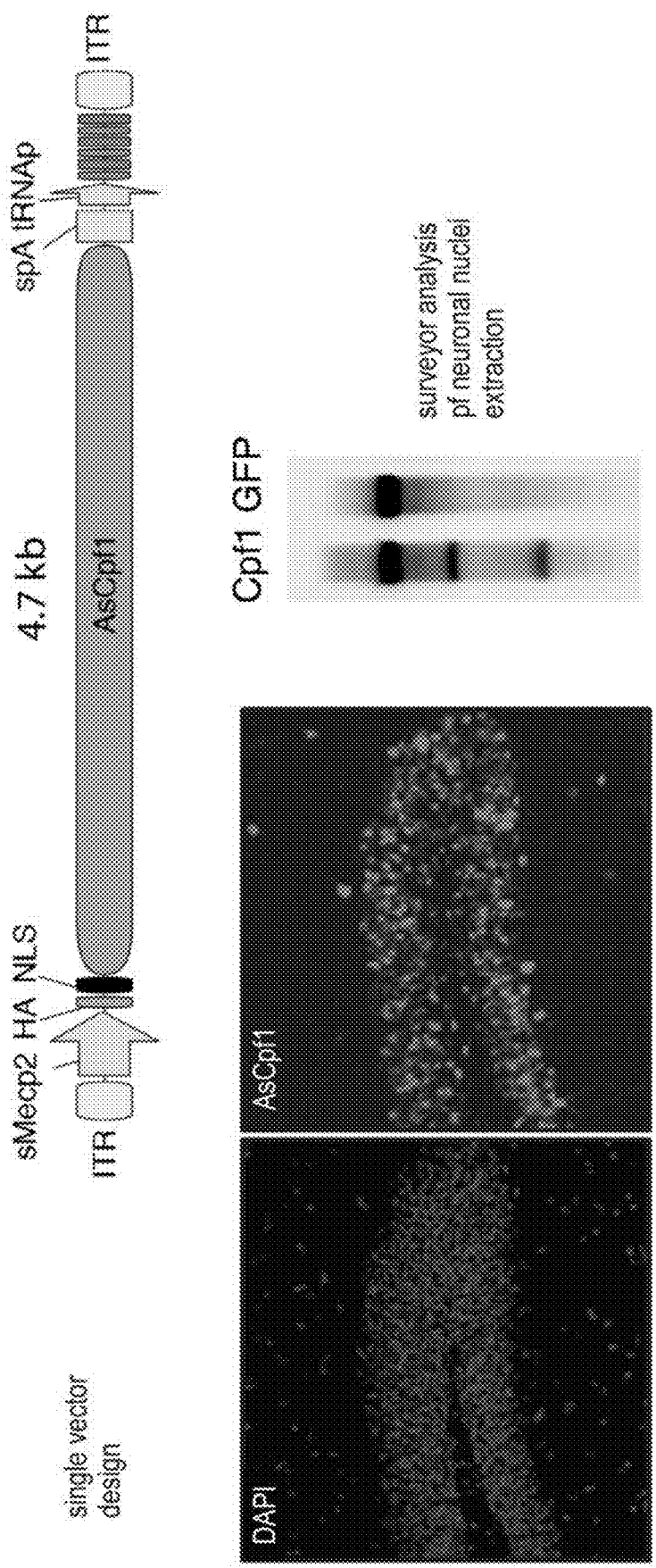
FIG. 5 illustrates packaging Cpf1 into a single AAV. (Top) single vector design. (bottom) Neurons express Cpf1 in nuclei and surveyor analysis shows guide RNA mediated cutting.
Figure 6C:
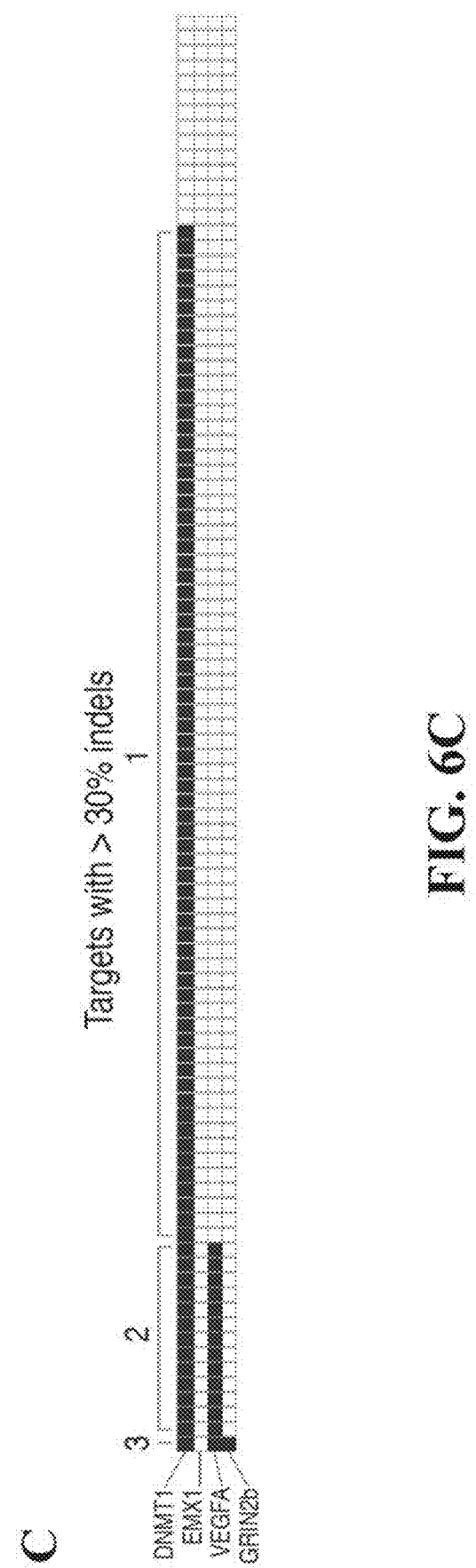
Figure 7:
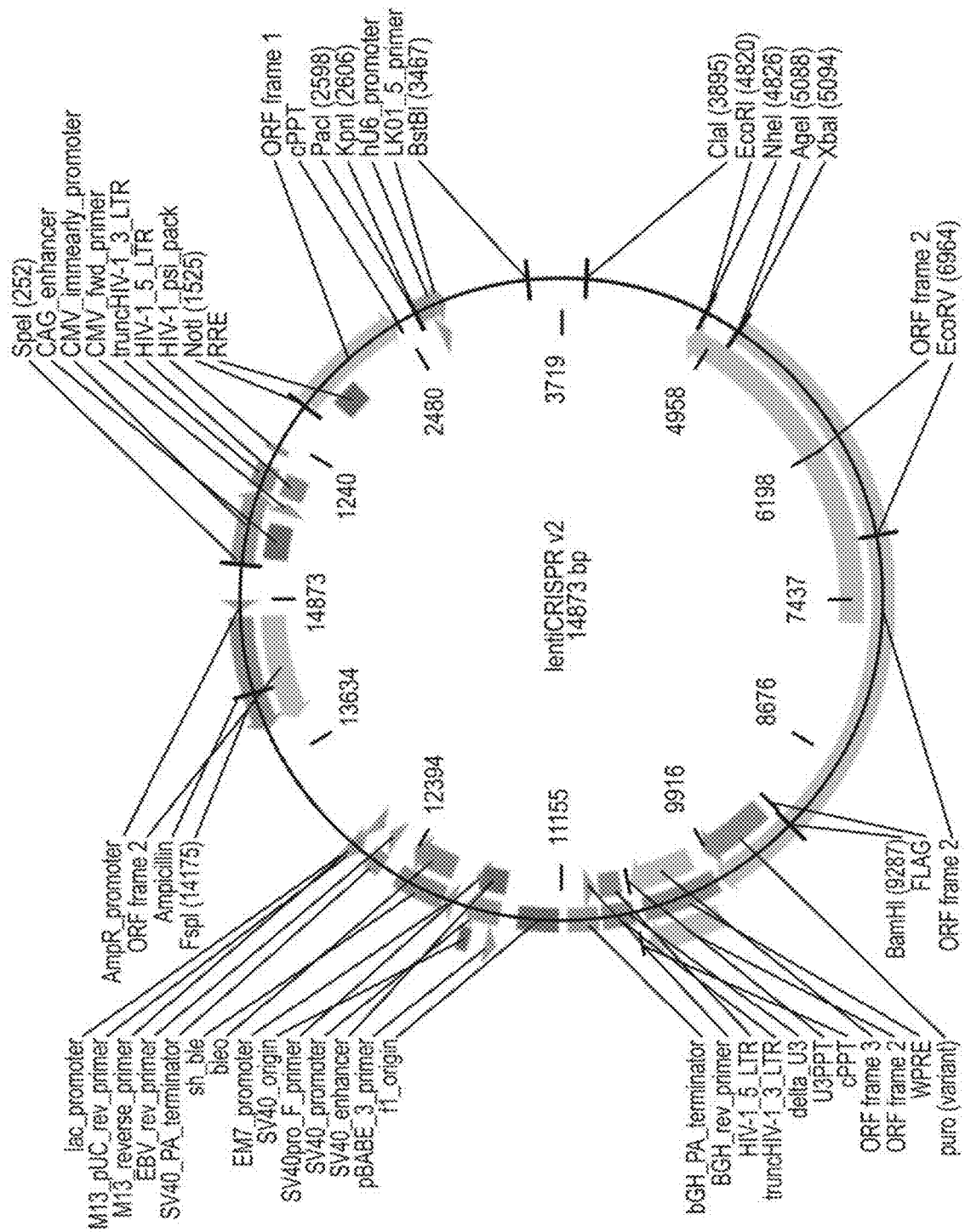
FIG. 7 illustrates lentiCRISPRv2 plasmid. Reference is made to Sanjana N E et al., Nat Methods. 2014 August; 11(8):783-4
Figure 8:
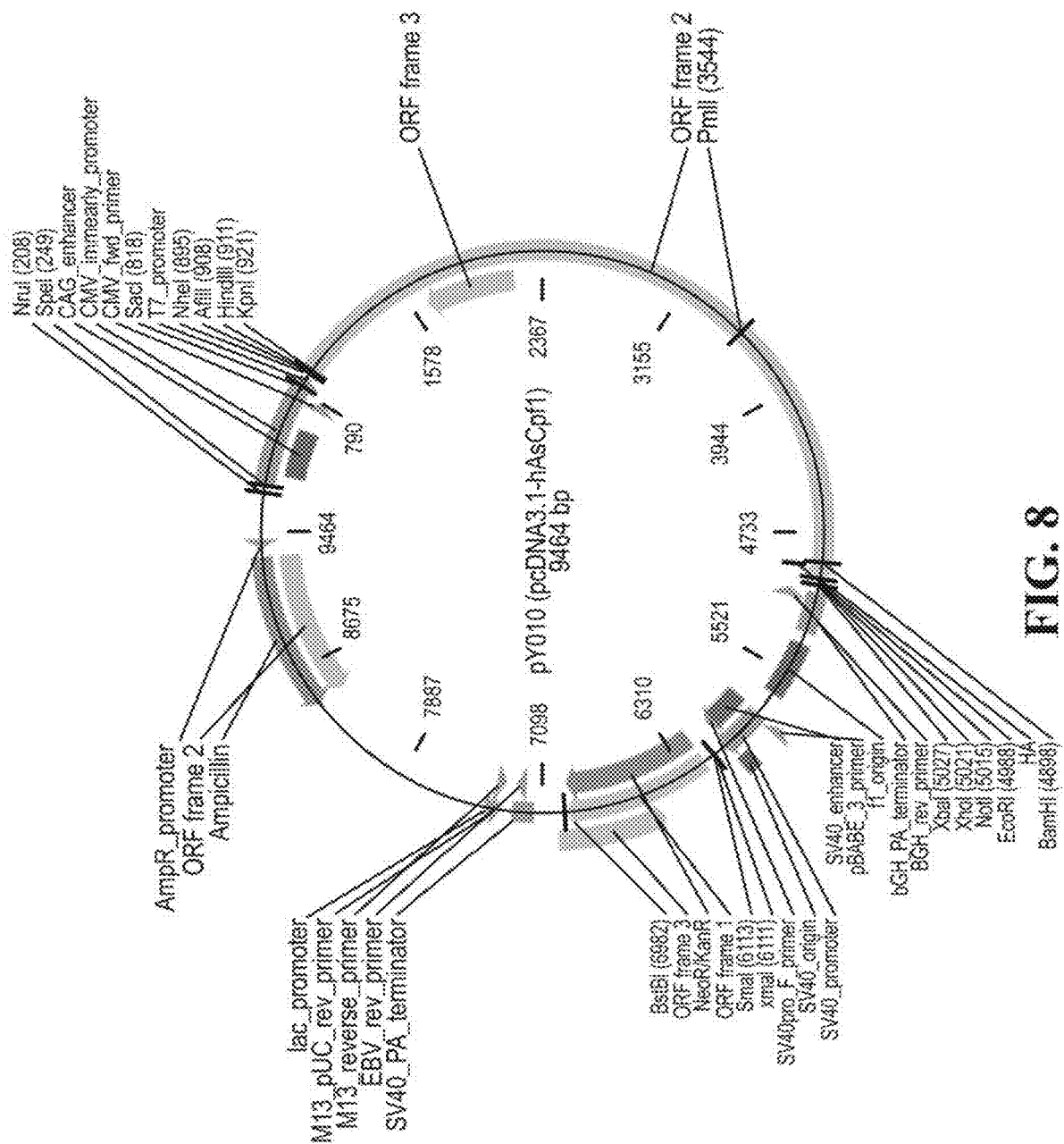
FIG. 8 illustrates AsCpf1. Reference is made Zetsche B et al., Cell. 2015 Sep. 23. pii: S0092-8674(15)01200-3.

AsCpf1 efficiently cuts in primary neurons (FIG. 1). AsCpf1 and guide RNAs are targeted to the nuclei of neurons after infection. Seven days post infection multiplex cutting is observed at three separate. Stereotactic AAV1/2 injection for AsCpf1 delivery into mouse hippocampus also shows viral delivery and 3 weeks after viral delivery GFP fluorescence (FIG. 2A). Systemic delivery of AsCpf1 and GFP-KASH into adult mice using the dual vector approach shows immunostaining 3 weeks after systemic tail vein injection, thus showing delivery of Syn-GFP-KASH vector into neurons of various brain regions (FIG. 3A). Next generation sequencing indel analysis of various brain regions dissected 3 weeks after systemic tail vein co-injection of dual vectors shows indels in various regions of the brain at three target loci. Stereotactic injection of AAV1/2 dual vectors into adult mouse hippocampus shows viral delivery by immunostaining and western blot (FIG. 4B-D). Next generation sequencing indel analysis 3 weeks after stereotactic injection on GFP+ sorted nuclei shows mono- and bi-allelic modification of Drd1 in male mice. Mecp2 and Nlgn3 are x-chromosomal genes, hence only one allele is edited (FIG. 4E-F). Multiplex editing efficiency is also shown. h) Example NGS reads showing indels in all three targeted genes (FIG. 4G). Cpf1 can be packaged into a single AAV, thus allowing high efficiency of editing in a cell (FIG. 5). Use of a single viral vector assures that every infected cell expresses enzyme and guide RNA. In the dual vector design, a cell needs to be infected by at least two separate viral vectors. (Top) single vector design. (bottom) Neurons express Cpf1 in nuclei and surveyor analysis shows guide RNA mediated cutting.

TABLE 26

| No. | Vector | Single/dual vectors | Description | Promoter for nuclease | Nuclease | Promoter for guide | Target genes for guides |
|---|---|---|---|---|---|---|---|
| 1 | mMecp2-HA-NLS-AsCpf1-spA-tRNAp-3xsgRNA(Mecp2, Nlgn3, Drd1) | Single | Single vector expressing AsCpf1 and 3 multiplexed guides | mMeCP2 | AsCpf1 | tRNA-Pro | Mecp2, Nlgn3, Drd1 |
| 2 | mMecp2-HA-NLS-AsCpf1-spA-tRNAp-sgRNA(SapI) | Single | Guide cloning vector, predecessor of Vector 1 (above) | mMeCP2 | AsCpf1 | tRNA-Pro | — |
| 3 | EFS-MVMI-HA-NLS-AsCpf1-spA-tRNAp-sgRNA(SapI) | Single | Guide cloning vector | EFS-MVMI | AsCpf1 | tRNA-Pro | — |
| 4 | EFS-MVMI-HA-NLS-AsCpf1(S542R/K548V/N552R)-spA-tRNAp-sgRNA(SapI) | Single | Guide cloning vector | EFS-MVMI | AsCpf1 mutant (S542R/K548V/N552R) | tRNA-Pro | — |
| 5 | EFS-MVMI-HA-NLS-AsCpf1(S542R/K548V)-spA-tRNAp-sgRNA(SapI) | Single | Guide cloning vector | EFS-MVMI | AsCpf1 mutant (S542R/K548V) | tRNA-Pro | — |
| 6 | EFS-MVMI-HA-NLS-AsCpf1(S542R/K607R)-spA-tRNAp-sgRNA(SapI) | Single | Guide cloning vector | EFS-MVMI | AsCpf1 mutant (S542R/K607R) | tRNA-Pro | — |

TABLE 26-continued

| No. | Vector | Single/dual vectors | Description | Promoter for nuclease | Nuclease | Promoter for guide | Target genes for guides |
|---|---|---|---|---|---|---|---|
| 7 | Syn-LwC2c2-U6-sgRNA(Bbs1) | Single | Guide cloning vector | Synapsin (Syn) | L. wadeii C2c2 | U6 | — |
| 8 | hSyn-HA-NLS-AsCpf1-spA | Dual | One half of dual vectors, expressing AsCpf1 | Synapsin (Syn) | AsCpf1 | — | — |
| 9 | hSyn-HA-NLS-LbCpf1-spA | Dual | One half of dual vectors, expressing LbCpf1 | Synapsin (Syn) | LbCpf1 | — | — |
| 10 | U6-3xsgRNA(Mecp2, Nlgn3, Drd1)-hSyn-GFP-KASH-hGH | Dual | One half of dual vectors, expressing 3 multiplexed guides | — | — | U6 | Mecp2, Nlgn3, Drd1 |
| 11 | U6-sgRNA(SapI)-hSyn-GFP-KASH-hGH | Dual | Guide cloning vector, predecessor of Vector 9 (above) | — | — | U6 | — |
| 12 | LP1-HA-AsCpf1-shortpA | Dual | One half of dual vectors, expressing AsCpf1 | LP1 | AsCpf1 | — | — |
| 13 | U6-sgRNA(SapI)-LP1-GFP-KASH-hGH | Dual | Guide cloning vector for one half of dual vectors, for expression of suitable guide/s | — | — | U6 | — |
| 14 | hSyn-HA-NLS-AsCpf1-NLS-spA | Dual | One half of dual vectors, expressing AsCpf1 | Synapsin (Syn) | AsCpf1 | — | — |
| 15 | hSyn-HA-NLS-LbCpf1-NLS-spA | Dual | One half of dual vectors, expressing LbCpf1 | Synapsin (Syn) | LbCpf1 | — | — |

With reference to Table 26, each of the sequence elements are described according to the following:

| Sequence element | Description |
|---|---|
| mMeCP2 | Short (229 bp) neuronal specific promoter |
| HA | Short tag for immunofluorescence or immunoblotting |
| NLS | Nuclear localization sequence |
| spA | Short (48 bp) polyadenylation signal |
| tRNA-Pro | Short (72 bp) Pol III promoter for small RNAs |
| EFS | EFS = Elongation factor-1α short: Short (238 bp) ubiquitous promoter |
| MVMI | Minute virus of mice intron (92 bp) (included downstream of promoter to increase promoter activity) |

For the following sequence elements, further details may be found according to the following sources: for mMeCP2, ncbi.nlm.nih.gov/pubmed/21476867. For tRNA-Pro, ncbi.nlm.nih.gov/pubmed/26187160, for EFS, science.sciencemag.org/content/343/6166/84.full; for MVMI, ncbi.nlm.nih.gov/pubmed/18059373

TABLE 27

A comprehensive census of Class 2 CRISPR-Cas systems in bacterial and archaeal genomes

| (Sub)type | II | V-A | V-B | V-U | VI-A | VI-B | VI-C |
|---|---|---|---|---|---|---|---|
| Effector | Cas9 | Cas12a (cpf1) | Cas12b (C2c1) | C2c4, C2c5; 5 distinct subgroups (V-U1-5) | Cas13a (C2c2) | Cas13b (C2c6) | Cas13c (C2c7) |
| Number of loci | 3822 2109 II-A 130 II-B 1573 II-C 10 unassigned | 70 | 18 | 92 | 30 | 94 | 6 |

TABLE 27-continued

A comprehensive census of Class 2 CRISPR-Cas systems in bacterial and archaeal genomes

| (Sub)type | II | V-A | V-B | V-U | VI-A | VI-B | VI-C |
|---|---|---|---|---|---|---|---|
| Representation | Diverse bacteria | Diverse bacteria + 2 archaea | Diverse bacteria | Diverse bacteria | Diverse bacteria | Bacteroidetes | Fusobacteria/Clostridia |
| Other cas genes | 85% cas1 + cas2; 55% csn2; 3% cas4 | 70% cas1 + cas2 55% cas4 | 65% cas1 + cas2 + cas4 | NONE | 25% cas1 + cas2 | NONE | NONE |
| % loci containing CRISPR array | 65% | 68% | 60% | ~50% | 73% | 90% | 83% |

Example 3: Implications of Human Genetic Variation for CRISPR-Based Therapeutic Genome Editing Methods Datasets Our target variation analysis was performed using the Exome Aggregation Consortium (ExAC) dataset from 60,706 globally diverse individuals. Our investigation of off-target candidates was performed using the 1000 Genomes Project phase 3 dataset containing phased whole genome sequences from 2504 globally diverse individuals.

Whole-Exome Target Variation Analysis

We included all targets for CRISPR enzymes SpCas9-WT, SpCas9-VQR, SpCas9-VRER, SaCas9, and AsCpf1 in the human exome that map to protein coding regions of exons with an average coverage of at least 20 reads per ExAC sample. For analysis of variation in these targets, we included all missense or synonymous variants passing quality filtering in the ExAC dataset as described previously. Because the publicly available ExAC dataset includes only summary information for each variant, it was not possible to determine if multiple variants occurring in a single genomic target occur on different haplotypes. Hence, we calculated target variation frequency as the maximum frequency of variants in an individual target. While accurately approximating the variation of most targets in the population, this approach does underestimate the variation frequency for rare targets containing multiple high frequency variants existing on separate haplotypes. Platinum targets were defined as those with a maximum variant frequency of less than 0.01% in the ExAC population.

Off-Target Candidate Analysis

Phased haplotypes included in the 1000 Genomes phase 3 dataset were used to create whole genome allele-specific references for 2504 individuals. We included in our analysis all single nucleotide polymorphisms passing quality filtering in the 1000 Genomes phase 3 dataset as described previously 2. Up to 100 protein-coding platinum targets for each therapeutically relevant gene, CEP290, CFTR, DMD, G6PC, HBB, IDUA, IL2RG, PCSK9, PDCD1, SERPINA1, TTR, VEGFA were selected for proteins SpCas9-WT, SpCas9-VQR, SaCas9, and AsCpf1. Targets for each gene were searched against the references for each of the 2504 1000 genomes individuals to profile off-target candidates specific to each individual. For the purpose of this study, off-target candidates are defined as unintended genome-wide targets for a specific guide RNA-enzyme combination with less than or equal to 3-mismatches with the guide RNA protospacer. Applicants performed principle component analysis (PCA) taking into account all off-target candidates present in less than 100% of the 1000 Genomes individuals.

A number of RNA-guided CRISPR nucleases have now been discovered and engineered as tools for genome editing, each with a different PAM (Cong, L. et al. Multiplex Genome Engineering Using CRISPR/Cas Systems. *Science* 339, 819-823 (2013); Mali, P. et al. RNA-Guided Human Genome Engineering via Cas9. *Science* 339, 823-826 (2013); Ran, F. A. et al. In vivo genome editing using *Staphylococcus aureus* Cas9. *Nature* 520, 186-191 (2015); Kleinstiver, B. P. et al. Engineered CRISPR-Cas9 nucleases with altered PAM specificities. *Nature* 523, 481-485 (2015); Zetsche, B. et al. Cpf1 Is a Single RNA-Guided Endonuclease of a Class 2 CRISPR-Cas System. *Cell* 163, 759-771 (2015)) (Table 28).

TABLE 28

| | | | Whole-exome PAM variation by allele frequency (%) | | | | | | |
|---|---|---|---|---|---|---|---|---|---|
| protein | PAM | orientation | ≥10% | ≥1 | ≥0.1 | ≥0.01 | ≥0.001 | total | n |
| AsCpf1-WT | TTTN | left | 0.15 | 0.26 | 0.61 | 1.81 | 8.91 | 21.04 | 2702056 |
| SpCas9-VQR | NGA | right | 0.11 | 0.25 | 0.69 | 2.28 | 11.39 | 23.19 | 9838603 |
| SpCas9-WT | NGG | right | 0.16 | 0.37 | 1.13 | 3.82 | 17.46 | 32.61 | 10286445 |
| SaCas9-WT | NNGRRT | right | 0.23 | 0.44 | 1.16 | 3.68 | 17.29 | 34.68 | 1938911 |
| SpCas9-VRER | NGGG | right | 0.77 | 1.86 | 5.79 | 20.72 | 66.67 | 80.16 | 981524 |

Table 28: Fraction of targets containing PAM altering variants for each CRISPR endonuclease (n specifies the number of protein coding targets in the human exome for each enzyme).

Figure 13:
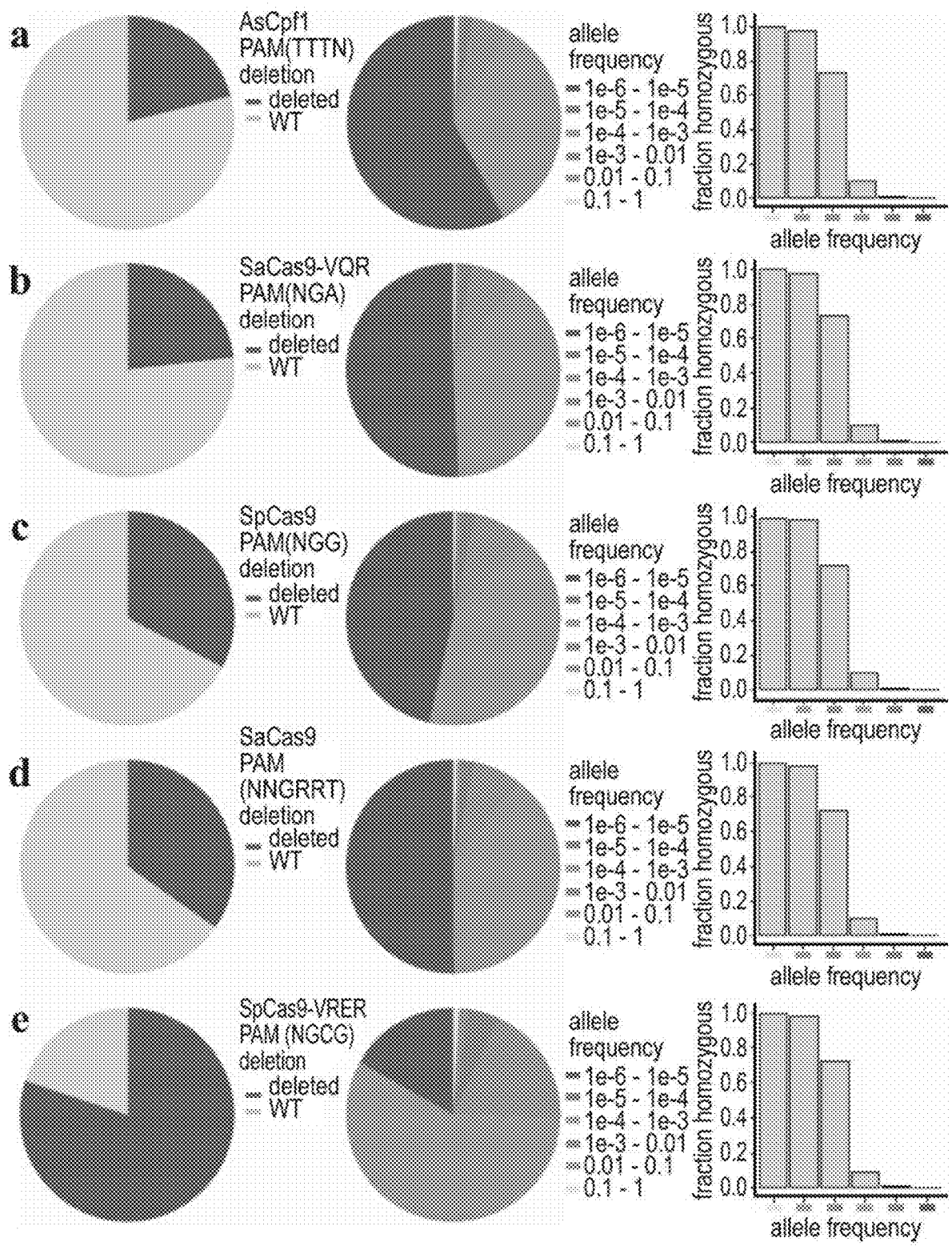
FIG. 13A-E: Left, fraction of PAMs altered by variants in the ExAC dataset; center, distribution of PAM-altering variant frequencies; right, fraction of homozygous variants by frequency. Data shown for AsCpf1 (a), SpCas9-VQR (b), SpCas9 (c), SaCas9 (d), and SpCas9-VRER (e).

For therapeutic design, consideration of multiple enzymes with different PAM requirements is advantageous as it increases the number of available genomic targets for therapeutic loci. We therefore assessed variation at each PAM in the human exome for SpCas9 (PAM=NGG), SpCas9-VQR (NGA), SpCas9-VRER (NGCG), SaCas9 (NNGRRT), and AsCpf1 (TTTN), all of which are currently being considered as candidate enzymes for CRISPR therapeutic development (the recently reported eSpCas9 and SpCas9-HF have the same NGG PAM as SpCas9, and are thus not considered separately here (Slaymaker, I. M. et al. Rationally engineered Cas9 nucleases with improved specificity. Science 351, 84-88 (2016); Kleinstiver, B. P. et al. High-fidelity CRISPR-Cas9 nucleases with no detectable genome-wide off-target effects. Nature 529, 490-495 (2016))). For each nuclease, we determined the fraction of exonic PAMs containing variants that alter PAM recognition. For the ExAC population, the total fraction of targets containing PAM-altering variants was similar for all enzymes (21-35%), except for SpCas9-VRER, which is impacted by PAM-altering variants in 80% of targets (Table 28, FIG. 13). The PAM for SpCas9-VRER contains a CpG motif, which has been shown to be highly mutable (Lek et al., 2016, above). Consistent with these results, we find that CG is the most highly mutable 2-nt PAM motif in the human exome, and 66% of cytosine and guanine residues contained in CpG motifs show variation for the 60,706 ExAC individuals (Lek et al., 2016, above) (FIG. 9b, c; Table 29). These results suggest that enzymes using PAMs containing CG motifs are significantly more affected by target variation in the human genome.

TABLE 29

Fraction of total residues and fraction of residues containing variation for individual nucleotides (nt) in the human exome.

| Source | nucleotide | A | T | C | G |
|---|---|---|---|---|---|
| ExAC | exome nt fraction (%) | 24.64 | 24.73 | 25.45 | 25.18 |
| | nt variation fraction (%) | 10.28 | 10.18 | 20.12 | 20.16 |
| | exome nt fraction (%) | 22.70 | 22.29 | 2.75 | 2.89 |
| | nt variation fraction (%) | 14.53 | 14.51 | 66.24 | 63.83 |
| | nucleotide | C (non CpG) | C (non CpG) | C (CpG) | G (CpG) |

Considering full target variation for all ExAC individuals, we find that 93-95% of targets in the human exome for SpCas9, SpCas9-VQR, SaCas9, and AsCpf1 contain variants likely to alter enzymatic activity (FIG. 9d, e; Table 30). Most (88%) of the target variation captured in the ExAC dataset is heterozygous, highlighting the fact that much of this target variation occurs at low frequencies in the population (FIG. 9d,f; Table 30).

TABLE 30

Fraction of targets containing target variation for each CRISPR endonuclease (n specifies the number of protein coding targets in the human exome for each enzyme).

| | | | Whole-exome target variation by allele frequency (%) | | | | | | |
|---|---|---|---|---|---|---|---|---|---|
| protein | PAM | orientation | ≥10% | ≥1 | ≥0.1 | ≥0.01 | ≥0.001 | total | n |
| SpCas9-WT | NGG | right | 2.03 | 4.16 | 11.03 | 31.14 | 79.39 | 95.44 | 10286445 |
| SpCas9-VQR | NGA | right | 1.81 | 3.66 | 9.65 | 27.66 | 75.77 | 94.27 | 9838603 |
| AsCpf1-WT | TTTN | left | 1.61 | 3.25 | 8.52 | 24.35 | 71.71 | 93.09 | 2702056 |
| SaCas9-WT | NNGRRT | right | 1.94 | 3.85 | 10.05 | 28.53 | 76.81 | 94.78 | 1938911 |
| SpCas9-VRER | NGCG | right | 2.70 | 5.72 | 15.77 | 44.21 | 91.82 | 98.44 | 981524 |

Figure 14:
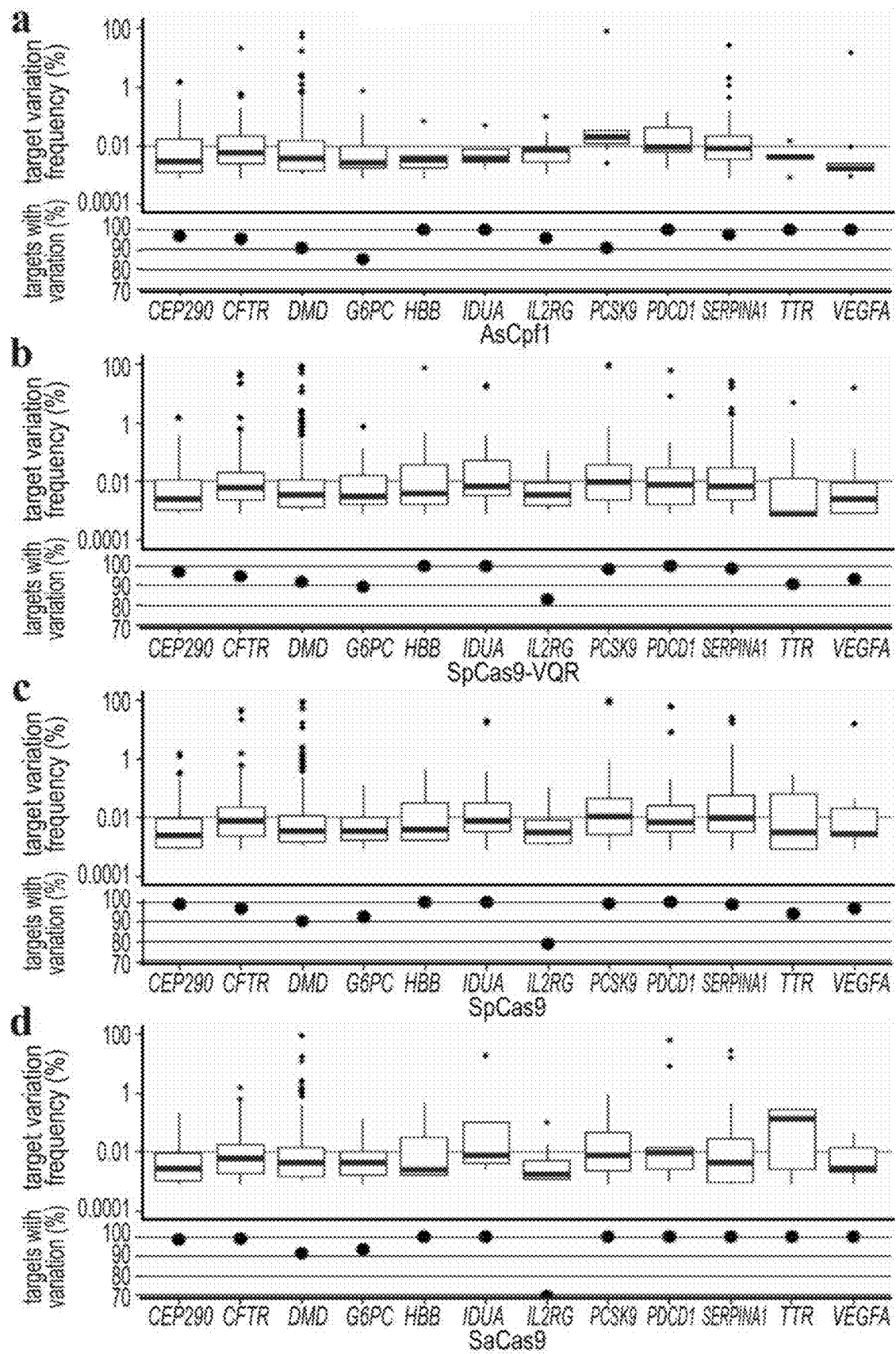
FIG. 14A-D: Top, distribution of target variation for therapeutically relevant genes. Targets with frequencies of variation less than 0.01% (red line) are considered platinum. Bottom, fraction of all targets in these genes containing variation. Data shown for AsCpf1 (a), SpCas9-VWR (b), SpCas9-WT (c), SaCas9-WT (d).
Figure 15:
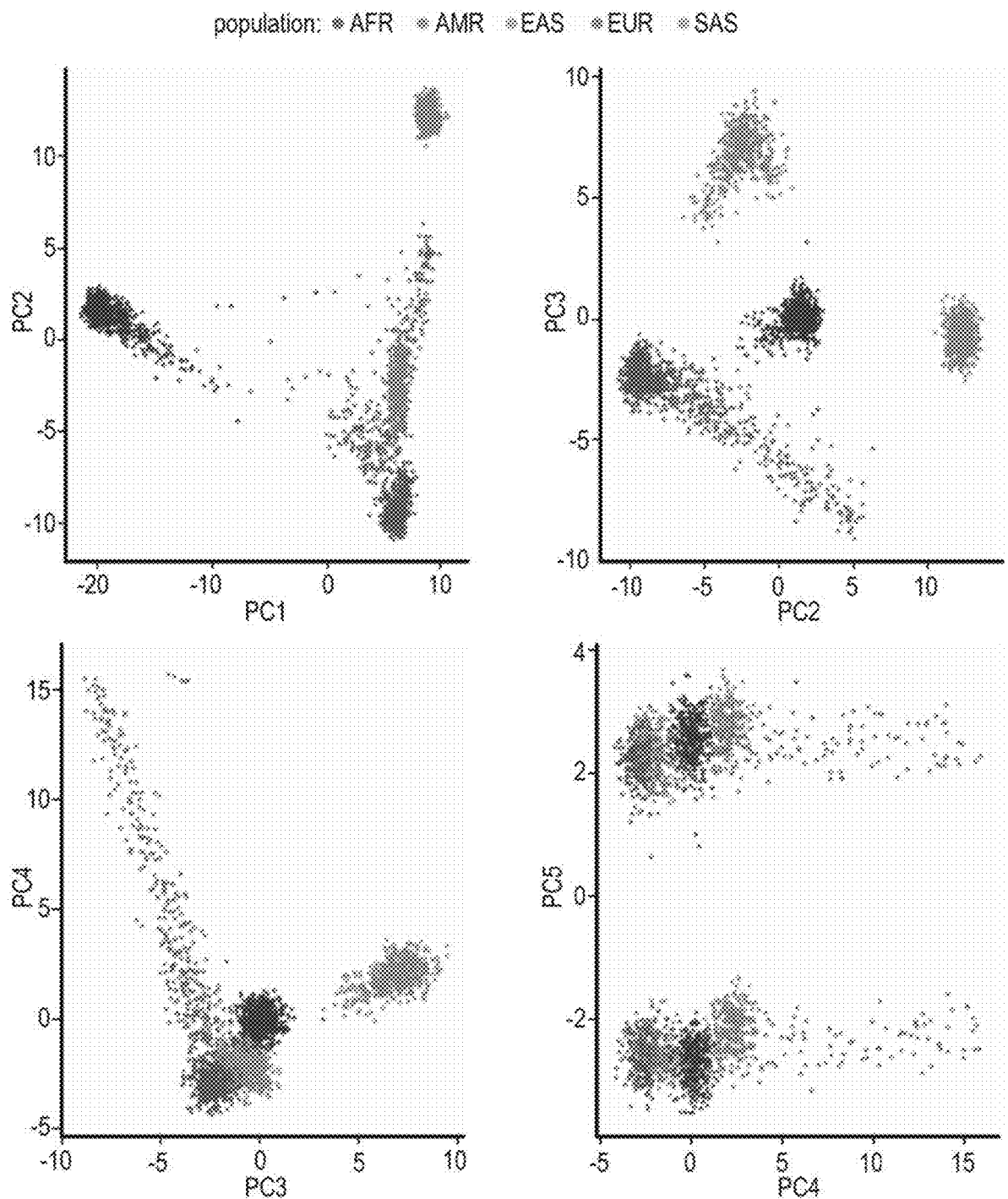
FIG. 15: Separation of 1000 Genomes individuals into super populations based on patient specific off-target profiles for targets spanning 12 therapeutically relevant genes. Principle components 1-5 shown. AFR, African; AMR, Ad mixed American; EAS, East Asian; EUR, European; SAS, South Asian.
Figure 16:
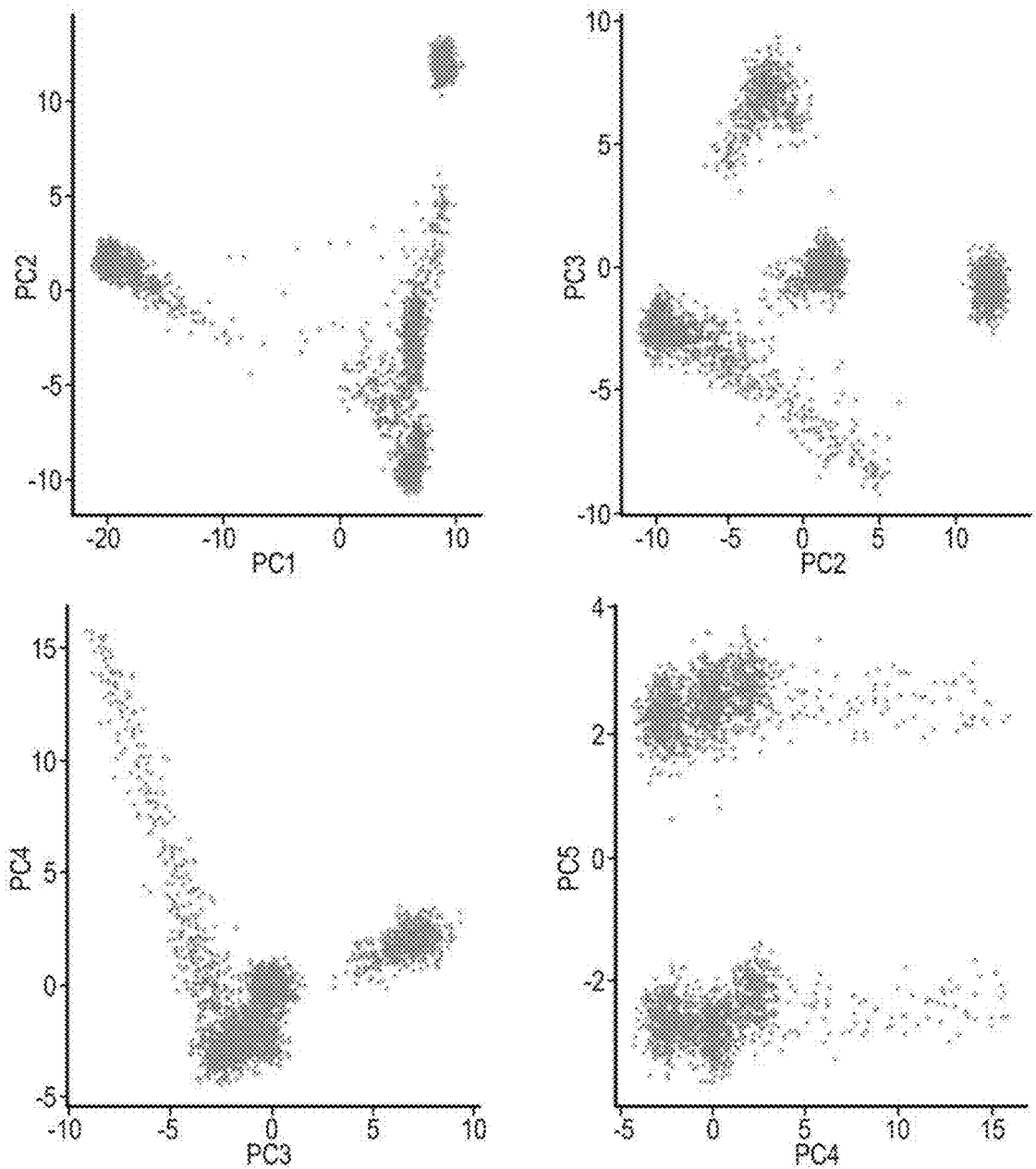
FIG. 16: Separation of 1000 Genomes individuals into populations based on patient specific off-target profiles for targets spanning 12 therapeutically relevant genes. Principle components 1-5 shown. CHB, Han Chinese in Beijing, China; JPT, Japanese in Tokyo, Japan; CHS, Southern Han Chinese; CDX, Chinese Dai in Xishuangbanna, China; KHV, Kinh in Ho Chi Minh City, Vietnam; CEU, Utah Residents (CEPH) with Northern and Western Ancestry; TSI, Toscani in Italia; FIN, Finnish in Finland; GBR, British in England and Scotland; IBS, Iberian Population in Spain; YRI, Yoruba in Ibadan, Nigeria; LWK, Luhya in Webuye, Kenya; GWD, Gambian in Western Divisions in the Gambia; MSL, Mende in Sierra Leone; ESN, Esan in Nigeria; ASW, Americans of African Ancestry in SW USA; ACB, African Caribbeans in Barbados; MXL, Mexican Ancestry from Los Angeles USA; PUR, Puerto Ricans from Puerto Rico; CLM, Colombians from Medellin, Colombia; PEL, Peruvians from Lima, Peru; GIH, Gujarati Indian from Houston, Tex.; PJL, Punjabi from Lahore, Pakistan; BEB, Bengali from Bangladesh; STU, Sri Lankan Tamil from the UK; ITU, Indian Telugu from the UK.
Figure 17:
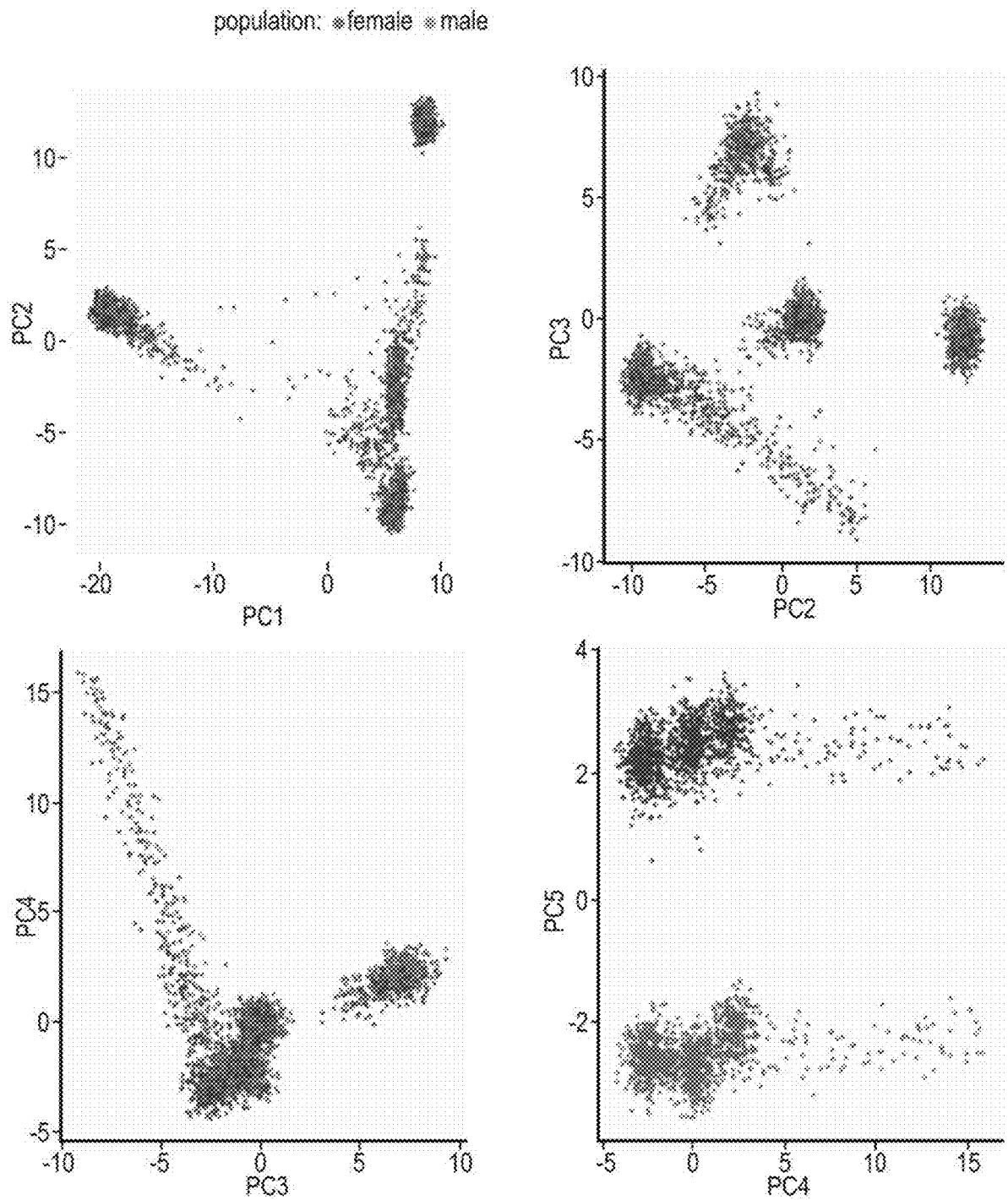
FIG. 17: Separation of 1000 Genomes individuals by sex based on patient specific off-target profiles for targets spanning 12 therapeutically relevant genes. Principle components 1 -5 shown.

The ExAC dataset is large enough that it provides near comprehensive coverage of variants in the protein coding genome occurring at allele frequencies of greater than or equal to 0.01% in the population (1 out of 10,000 alleles) (Lek et al. 2016, above). Hence, we used this dataset to compile a compendium of exome-wide target sites for SpCas9, Cas9-VQR, SaCas9, and AsCpf1 that do not contain variants occurring at >0.01% allele frequency (referred to as platinum targets; will be made available online) (FIG. 10a). These platinum targets are efficacious in >99.99% of the population (FIG. 10b). For further analysis, we focused on 12 therapeutically relevant genes, including those that are currently the focus of therapeutic development (See FIG. 14 for overview of genes included). For these genes, approximately two-thirds of possible protein coding targets meet our platinum criteria, with PCSK9 containing the smallest fraction of targets (50%) meeting our platinum criteria (Table 31).

TABLE 31

| enzyme | target classification | number of platinum targets and non-platinum targets for 12 therapeutically relevant genes | | | | | | | | | | | | |
|---|---|---|---|---|---|---|---|---|---|---|---|---|---|---|
| | | CEP290 | CFTR | DMD | G6PC | HBB | IDUA | IL2RG | PCSK9 | PDCD1 | SERPINA1 | TTR | VEGFA | total |
| AsCpf1 | platinum | 218 | 135 | 356 | 22 | 7 | 3 | 21 | 3 | 3 | 22 | 5 | 10 | 805 |
| AsCpf1 | not platinum | 97 | 90 | 133 | 5 | 1 | 1 | 3 | 8 | 2 | 18 | 1 | 1 | 360 |
| SpCas9 | platinum | 154 | 185 | 670 | 106 | 40 | 78 | 127 | 135 | 96 | 96 | 34 | 46 | 1767 |
| SpCas9 | not platinum | 45 | 134 | 213 | 32 | 22 | 40 | 7 | 137 | 55 | 93 | 18 | 19 | 815 |

TABLE 31-continued

| enzyme | target classi- fication | CEP290 | CFTR | DMD | G6PC | HBB | IDUA | IL2RG | PCSK9 | PDCD1 | SERPINA1 | TTR | VEGFA | total |
|---|---|---|---|---|---|---|---|---|---|---|---|---|---|---|
| | | \multicolumn{13}{c}{number of platinum targets and non-platinum targets for 12 therapeutically relevant genes} | | | | | | | | | | | | |
| SpCas9-VQR | platinum | 348 | 320 | 948 | 99 | 22 | 45 | 94 | 70 | 37 | 94 | 31 | 47 | 2155 |
| SpCas9-VQR | not platinum | 132 | 185 | 303 | 34 | 15 | 29 | 12 | 66 | 29 | 73 | 12 | 14 | 904 |
| SaCas9 | platinum | 53 | 67 | 160 | 23 | 9 | 5 | 29 | 20 | 9 | 21 | 3 | 11 | 410 |
| SaCas9 | not platinum | 16 | 35 | 65 | 8 | 4 | 4 | 4 | 12 | 4 | 13 | 5 | 1 | 174 |
| all | platinum | 773 | 707 | 2134 | 250 | 78 | 131 | 271 | 228 | 145 | 233 | 73 | 114 | 5137 |
| all | not platinum | 290 | 444 | 714 | 79 | 42 | 74 | 26 | 223 | 90 | 197 | 36 | 38 | 2253 |
| all | platinum/ total (%) | 72.7 | 61.4 | 74.9 | 76.0 | 65.0 | 63.9 | 91.2 | 50.6 | 61.7 | 54.2 | 67.0 | 75.0 | 69.5 |

While it is preferable to design RNA guides specifically for individual patients this may be challenging from a regulatory standpoint and cost prohibitive. Selecting from these platinum targets during therapeutic design will maximize efficacy across patient populations with the smallest number of RNA guides. When targeting regions with more than one high frequency haplotypes, it will be necessary to design multiple RNA guides for each independent haplotype.

We find that high variation targets or platinum targets cluster along exons for each of the 12 genes examined. For example, all targets in the 5' half of PCSK9 exon 4 are platinum, whereas very few platinum targets exist for exon 5 (FIG. 10c). Even for regions in PCSK9 exons 1-4 with high frequencies of variation, it is still possible to find small numbers of platinum targets for some enzymes (FIG. 10c). This observation for PCSK9 is representative of the other genes investigated in this study and suggests that considering multiple enzymes with distinct PAM requirements increases the likelihood of finding a platinum target.

When designing RNA guides, in addition to minimizing target variation, it is necessary to ensure safety by minimizing potential off-target activity due to sites in the genome similar to the target. Unbiased investigation of genome-wide CRISPR nuclease activity suggests that most off-target activity occurs at loci with at most three mismatches to the RNA guide12,18,19,20,8,21,22,23. Current approaches for Cas9 target selection rank off-target candidates found in the reference human genome by both the number and position of RNA guide mismatches, with the assumption that loci containing less than 3 mismatches or containing PAM distal mismatches are more likely to be cleaved12,13,14. However, in a population of individuals, this strategy is complicated by the existence of multiple haplotypes (sets of associated variants), which will contain different positions or numbers of mismatches at candidate off-target sites (FIG. 11a). We used phased single nucleotide variant calls to reconstruct allele-specific whole-genome sequences for each individual in the 1000 Genomes population[24]. For platinum targets in the 12 genes considered here, we quantified off-target candidates (defined as genomic loci with at most three mismatches to a given RNA guide) arising from all 1000 Genomes haplotypes. In this relatively small population (2504 individuals), more than half of the haplotypes containing off-target candidates are common (present in >10% of individuals) (FIG. 11b). However, in this population, the number of off-target candidates for each RNA guide is inversely correlated with haplotype frequency (FIG. 11b). This trend indicates that for large populations the majority of off-target candidates for a given RNA guide will differ between individuals.

For individual RNA guides in these 12 genes, we find that the number of off-target candidates for SpCas9, SpCas9-VQR, SaCas9, and AsCpf1 varies from 0 to greater than 10,000 in the 1000 Genomes population (FIG. 11c). Much of this large variation in the number of off-targets reflects how unique or repetitive an individual target sequence is within the human genome. For instance SaCas9, which has a longer PAM and hence fewer genomic targets, has on average fewer off-target candidates per RNA guide (FIG. 11c). Additionally, in a population, the number of off-target candidates at a given locus is further compounded by multiple haplotypes, such that as the size of a population increases so does the number of haplotypes for an individual off-target locus. Hence, for each off-target candidate present in a high frequency haplotype, in a large population, multiple lower frequency haplotypes are likely to exist with reduced numbers of RNA guide mismatches. These data indicate that minimizing the number of off-target candidates occurring in high frequency haplotypes is of critical importance for the selection of therapeutic RNA guides. By minimizing these off-target candidates in high frequency haplotypes, off-target candidates occurring in low frequency haplotypes that uniquely impact individual or small numbers of patients will also be minimized The current 1000 genomes dataset provides comprehensive coverage of alleles occurring at up to 0.1% in the population (considered to be the lower bound of high frequency variants), allowing us to identify platinum targets with minimal off-target candidates occurring in high frequency haplotypes in the human population24,4.

Of the 12 genes we considered, some are more repetitive relative to the rest of the human genome, which impacts the specificity of the underlying RNA guides for each gene (FIG. 12a). For example, within PCSK9 exons 2-5, we observed that platinum targets with high or low numbers of off-target candidates tend to cluster in regions of sequence that are either repetitive or unique within the genome, respectively (FIG. 12b) This pattern holds true for all 12 genes studied. Interestingly, within repetitive regions of exons, we identified platinum targets with significantly reduced quantities of off-target candidates. These findings further support the notion that utilizing multiple enzymes with distinct PAM requirements will enhance both safety and efficacy. Use of the enhanced specificity enzymes eSpCas9 and Cas9-HF1 will further reduce the likelihood of cleavage at off-target candidate sites, but it will still remain important to avoid repetitive therapeutic targets with large numbers of off-target candidates even with these enzymes[16,17].

Because the 1000 Genomes project provides demographic information for each individual, we used this data to explore how much off-target candidate variation for a given individual is explained by population demographics. For all off-target candidates for RNA guides targeting the 12 genes considered here, we performed principle component analysis (PCA) and find that the first five principle components separate individuals very effectively by continent, sub-continent, and sex (FIG. 12c, FIGS. 15-17). Cumulatively, population demographics account for 12% of the off-target candidates for a given individual, indicating that safety and efficacy of therapeutics can be enhanced by designing therapeutic targets for specific geographical or genotypic patient subpopulations.

Here we determine the impact of population genetic variation on therapeutic genome editing with *Streptococcus pyogenes* (Sp) Cas9, SpCas9 variants VQR and VRER, *Staphylococcus aureus* (Sa) Cas9, and *Acidaminococcus* sp. (As) Cpf1[1,2,8,9,3]. We find extensive variation likely to substantially alter the efficacy of these enzymes, and we show that unique, patient-specific off-target candidates will be the greatest challenge to safety. These results provide a framework for designing CRISPR-based therapeutics, highlight the need to develop multiple guide RNA-enzyme pairs for each target locus, and suggest that pre-therapeutic whole genome sequencing will be required to ensure uniform efficacy and safety for treatment across patient populations.

Example 4: Directed Evolution of AsCpf1 PAM Recognition

Cpf1 is a class 2 type V CRISPR effector. It is a single RNA-guided endonuclease and cleaves DNA via staggered double-stranded break. Multiplexed genome editing is efficient. Cpf1 cuts distal to PAM: 18 and 23 bp downstream (Zetsche et al. (2015) Cell; 163: 759-771).

Wild type AsCpf1 (such as AsCpf1 and LbCpf1) recognizes PAM sequence TTTV (wherein V is A, C, or G).

Alternate PAM sequences will broaden the PAM repertoire, and hence the amount of possible target sequences. Moreover, shorterPAM sequences will likewise allow increase of the amount of possible target sequences. The human genome contains 41% GC, 59% AT (29.5% T). Chances of 3 Ts in a row=0.0257 (2.57%). Approximately every 40 bases you will get a TTT. 0.00758 chance of 4 T in a row. So 1.81% chance of TTTV at any given starting location in genome. Approximately every 55 bases you will get TTTV.

Via mutagenesis of AsCpf1 (*Acidaminococcus* sp. BV3L6, UniProtKB/Swiss-Prot accession number U2UMQ6.1; genbank accession number 961512548), PAM recognition was broadened. The PI (PAM interacting) and REC1 domains of Cpf1 are in close proximity to the PAM sequence when bound to DNA. Point mutations across the entire PAM proximal region were generated and evaluated for alternate PAM recognition. A mutant Cpf1 library was created, in which different Cpf1 mutants were encoded on a CamR plasmid capable of expression in *E. coli* (pACYS Cpf1 plasmid). The plasmids also contained a spacer sequence flanked by direct repeats, for reconstitution of a functional CRISPR/Cpf1 complex, capable of binding to a DNA target locus. The library was transformed in *E. coli* to generate an *E. coli* containing Cpf1 mutant library.

A second plasmid comprising a target sequence flanked by a PAM sequence, and further comprising an AmpR marker was transformed in the mutant Cpf1 *E. coli* library. This was performed in parallel for a multitude of alternate PAM sequences.

Library complexity was 32,256 (84 positions*32codons*12PAMs)

Selection on Cam/Amp media allowed identification of alternate PAM sequences which were recognized by a particular Cpf1 mutant. If a PAM sequence was recognized by a particular Cpf1 mutant, the AmpR containing plasmid was cut and Amp resistance was lost. Accordingly there was a specific depletion of members of the library that recognized the particular PAM sequence. Sequencing of the plasmids comprising the Cpf1 mutants and which were depleted in the screen identified particular Cpf1 mutants recognizing alternate PAM sequences.

Figure 18A:
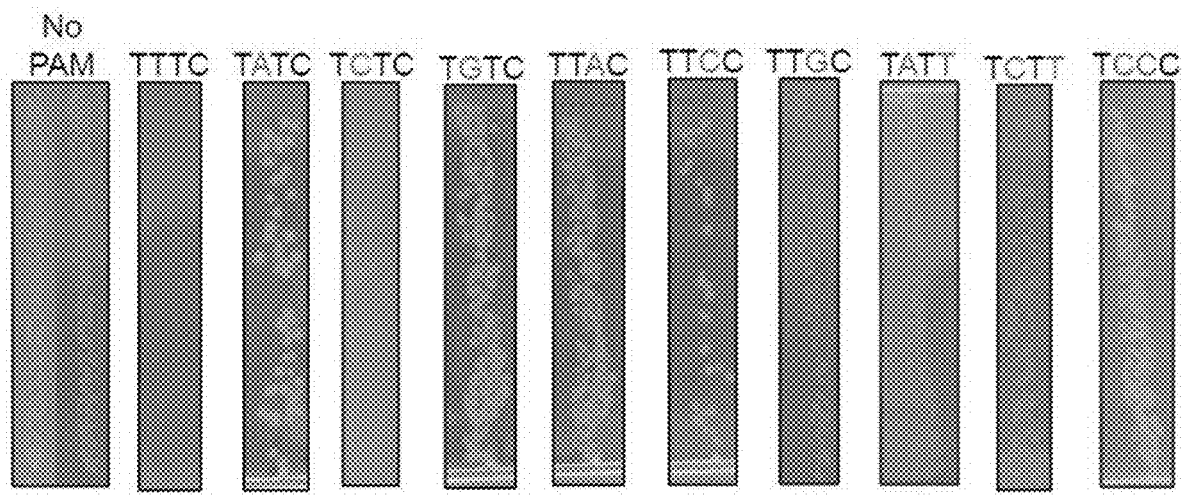
Figure 18B:
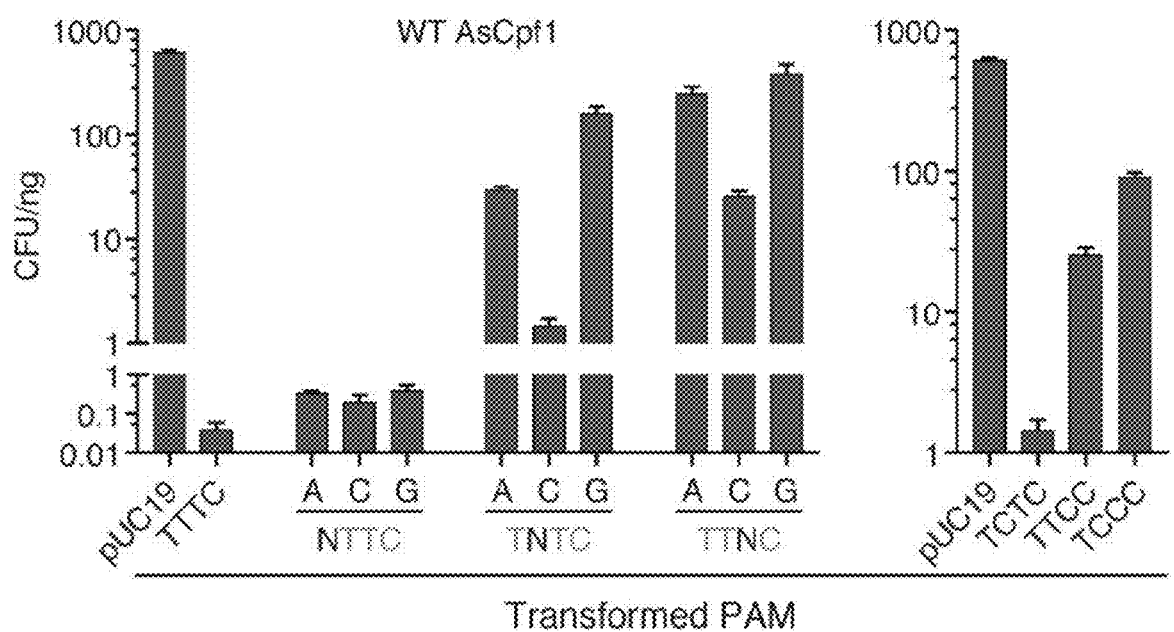

The above described approach was validated with wild type AsCpf1 (FIG. 18). Is was demonstrated that indeed the PAM sequence which is recognized by wild type AsCpf1 (TTTC) was unable to sustain bacterial growth on Cam/Amp media.

Figure 18C:
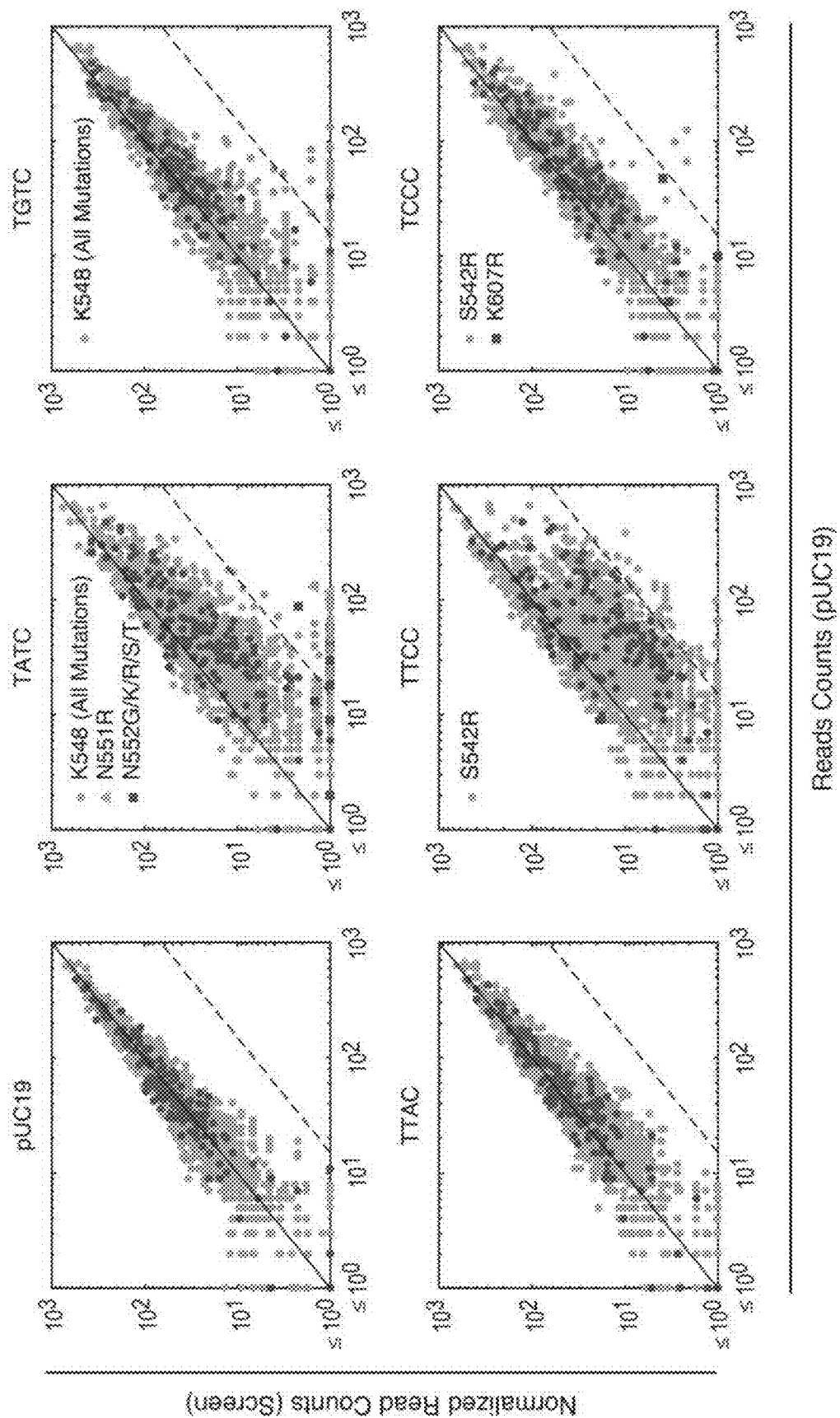
Figure 19:
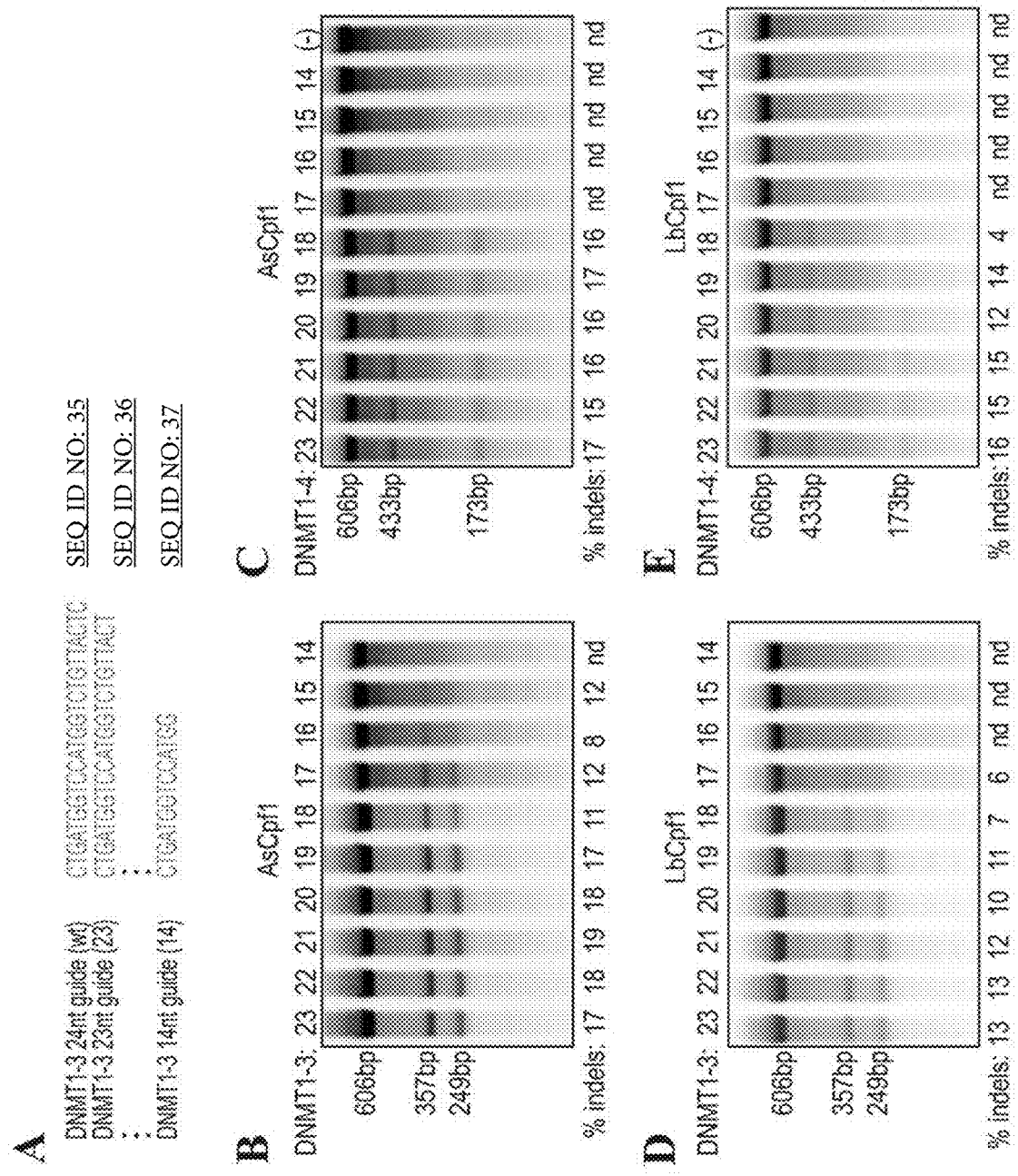
FIG. 19A-19E shows Cpf1 target nuclease activity of AsCpf1 and LbCpf1 with truncated guides.
Figure 20:
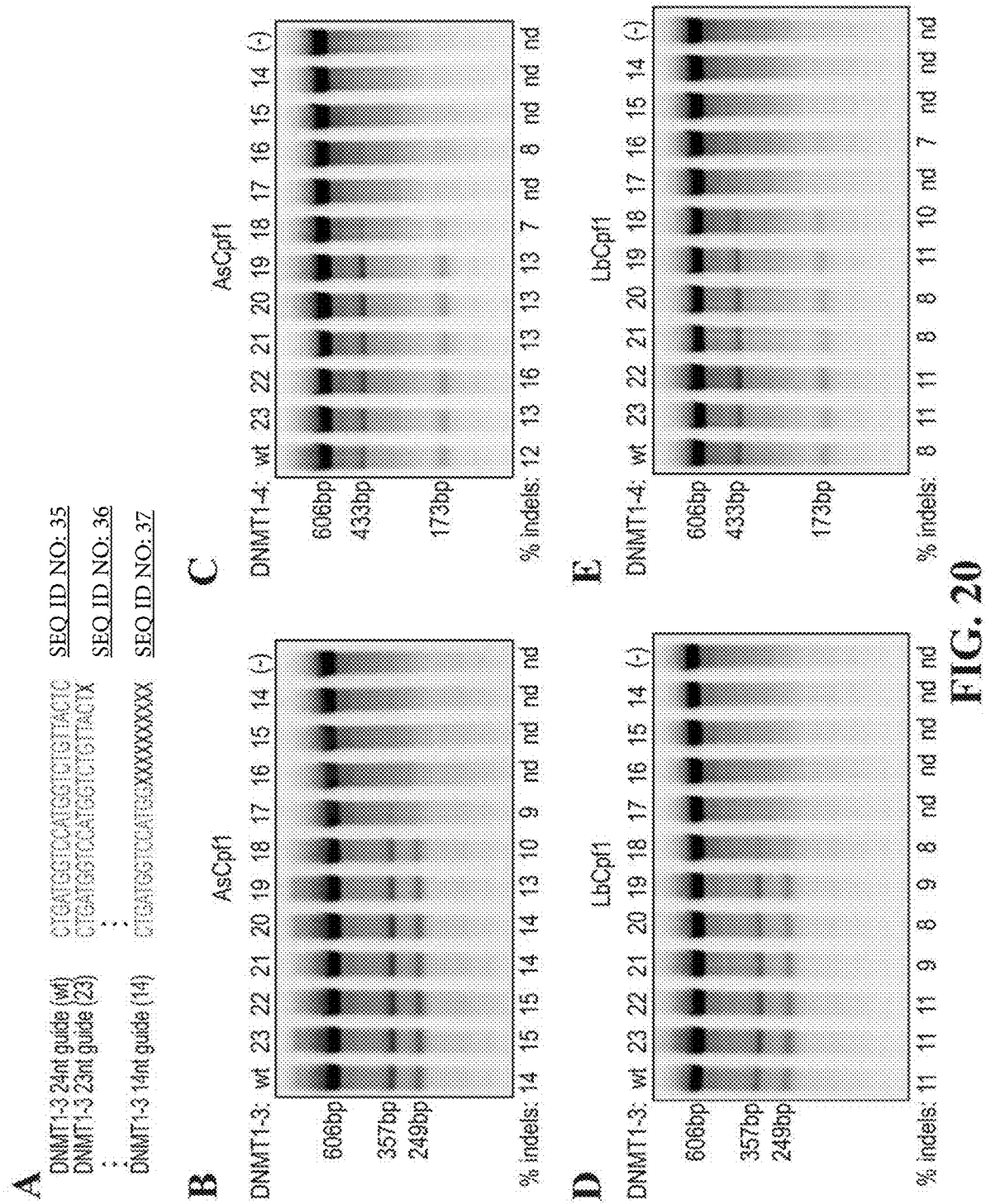
FIG. 20A-20E shows Cpf1 target nuclease activity of AsCpf1 and LbCpf1 with partially binding guides. All guides were 24nt in length, matching the target over a range from 24nt to 14nt.

The above described approach was then applied to the mutant AsCpf1 library. As a control, representation of the different Cpf1 mutants in a screen without PAM sequence demonstrated no significant over or underrepresentation of particular mutants, whereas representation of the different Cpf1 mutants in a screen with the PAM sequence that is recognized by the wild type Cpf1 demonstrated a significant underrepresentation (or depletion of wild type Cpf1). Representation of different Cpf1 mutants for various alternate PAM sequences is shown in FIG. 18C. From FIG. 18C, it is clear that various Cpf1 mutants recognize non-canonical PAM sequences.

It was observed that AsCpf1 mutant having the S542R mutation is capable of recognizing at least PAM sequence TCCC. Also, an AsCpf1 mutant having S542R is capable of recognizing at least PAM sequence TTCC.mutation. S542R allows for recognition of TCCC and TTCC (allows for C at 3rd position of PAM).

AsCpf1 mutants having various the K548 mutations are capable of recognizing at least PAM sequence TATC. At least mutants K548A, K548G, K548L, K548R, K548I, K548N, K548C, K548Q, K548H, K548F, K548S, K548T, K548 W, K548Y, K548V, are capable of recognizing PAM sequence TATC. AsCpf1 mutants having various the K548 mutations are capable of recognizing at least PAM sequence TGTC. At least mutants K548G, K548R, K548C, K548Q, K548H, K548S, K548T, K548 W, K548Y, K548V, are capable of recognizing PAM sequence TGTC. K548 provides thymine stringency for 2nd base of PAM. Many alternate aa allow for recognition of TATC or TGTC PAMs.

Further AsCpf1 mutants (data not shown) were identified which recognized additional alternate PAM sequences: 167A (recognizes NTTV or TTV), 604A (recognizes TTTV), 607A (recognizes TCCC).

An in vitro cleavage experiment was performed (essentially as described in Zetsche et al. (2015), Cell 163:1-13), in which lysate from mammalian cells expressing AsCpf1 was incubated in a test tube with a plasmid library containing a eight-bp randomized PAM preceding the target site. The members of the PAM library containing targetable PAMs was cut, while all other PAMs were left intact. The uncut PAMs were sequenced and compared to the negative control. PAMs depleted relative to the control represented those that Cpf1 can cleave—the sequence logo for the collective set of depleted PAM sequences is shown in FIG. 21.

Based on structural considerations of the Cpf1 protein and its interaction with gRNA and target sequence, the following amino acid residues of AsCpf1 (*Acidaminococcus* sp. BV3L6) were found in physical proximity of the PAM sequence (i.e. within 1.4 nm of the PAM): Y11, Q12, V13, S14, K15, T16, L17, Q34, F36, E39, D40, R43, H46, Y47, L50, 154, 157, Y58, I111, A126, E127, I128, Y129, K130, G131, L132, F133, K134, A135, E136, A157, L158, L159, R160, S161, F162, D163, K164, F165, T166, T167, Y168, F169, S170, G171, F172, Y173, E174, N175, R176, K177, N178, K532, L533, N534, F535, Q536, M537, P538, T539, L540, A541, S542, G543, W544, D545, V546, N547, K548, E549, K550, N551, N552, G553, A554, I555, L556, L565, G566, I567, M568, P569, K570, Q571, K572, G573, R574, Y575, K592, M593, Y594, Y595, D596, Y597, F598, P599, D600, A601, A602, K603, M604, I605, P606, K607, C608, S609, T610, Q611, L612, K613, A614, V615, T616, A617, H618, F619, Q620, I626, L627, L628, S629, N630, N631, F632, I633, E634, P635, L636, E637, I638, I642, Y643, D644, L645, N646, N647, P648, E649, E651, P652, K653, K654, F655, Q656, W676, F679, T680, D682, F683, L684, S685, K686, Y687, T688, K689, T690, T691, S692, I693, L707, Y711, L714, N715, P716, L717, L718, Y719, H720, I721, S722, K739, W765, L768, F769, N773, T777, S778, I779, K780, L781, N782, G783, Q784, A785, E786, F871, H872, V873, P874, I875, T876, L877, N878, Y879, Q880, A881, A882, N883, S884, and Q1048.

Mutations of one or more of these residues are expected to affect PAM recognition.

The following amino acid residues were selected for mutagenesis, and hence resulted in mutated Cpf1 proteins having the indicated amino acid residue mutated: K130, G131, L132, F133, K134, A135, E136, F162, D163, K164, F165, T166, T167, Y168, F169, S170, G171, F172, Y173, E174, N175, R176, K177, Q536, M537, P538, T539, L540, A541, S542, G543, W544, D545, V546, N547, K548, E549, K550, N551, N552, K570, Q571, K572, G573, Y595, D596, Y597, F598, P599, D600, A601, A602, K603, M604, I605, P606, K607, C608, S609, T610, Q611, L612, K613, A614, V615, N630, N631, F632, N646, N647, P648, E649, K650, E651, P652, K653, F683, L684, S685, K686, Y687, T688, K689, or T690.

The following PAM sequences were screened in a bacterial PAM screen with the AsCpf1 mutant library: TATC, TGTC, TATT, TTCC, TCCC, TTAC, TCTT, and TTGC.

The Table below indicates PAM sequences found to be associated with the indicated mutants (AsCpf1), as identified in a bacterial PAM screen (middle column), from which a putative PAM is postulated (right column). At least the indicated PAM sequences are recognized by the indicated mutants. Indicated in bold are mutants which have been generated and tested. PAM sequences of other mutants are postulated based on structural considerations as well as knowledge of the PAM sequence for the generated mutants.

TABLE 32

| Mutant | PAM screen | Putative PAM |
|---|---|---|
| S542R | TTCC, TCCC | TYCN |
| N547K | TTCC | TYCN or TTCN |
| K548A | TATC, TGTC | TNTN or TRTN |
| K548H | TATC, TGTC | TNTN or TRTN |
| K548N | TATC, TGTC | TNTN or TRTN |

TABLE 32-continued

| Mutant | PAM screen | Putative PAM |
|---|---|---|
| K548Q | TATC, TGTC | TNTN or TRTN |
| K548R | TATC, TGTC | TNTN or TRTN |
| K550Y | TTCC | TYCN or TCCN |
| N551R | TATC, TTCC | TRTN or TATN |
| N552G | TATC | TRTN or TATN |
| N552K | TATC | TRTN or TATN |
| N552R | TATC | TRTN or TATN |
| N552S | TATC | TRTN or TATN |
| N552T | TATC | TRTN or TATN |
| K607A | | TYCN or TYCC |
| K607R | TCCC | TYCN or TCCN |
| S542R/K548R | | TCCN |
| S542R/K607A | | TCCN |
| S542R/K607R | (T)YCV, (V)YCV | , (TYTV, and TYCT) |
| K548R/N552R | | TCCN |
| S542R/K550Y/K607R | | TCCN |
| S542R/K548R/K550Y/K607R | | TCCN |
| K548G | TATC, TGTC | TNTN or TRTN |
| K548C | TATC, TGTC | TNTN or TRTN |
| K548F | TATC | TNTN or TRTN |
| K548I | TATC, TGTC | TNTN or TRTN |
| K548M | TGTC | TNTN or TRTN |
| K548S | TATC, TGTC | TNTN or TRTN |
| K548T | TATC, TGTC | TNTN or TRTN |
| K548V | TATC, TGTC | TNTN or TRTN |
| K548W | TATC, TGTC | TNTN or TRTN |
| K548Y | TATC, TGTC | TNTN or TRTN |
| K548D | | TNTN |
| K548E | | TNTN |
| K548L | | TNTN |
| K548P | | TNTN |
| S542R/K548V | | TNTN |
| K548V/N552R | | TNTN |
| S542R/K548V/N552R | TATV | TNTN |
| S542R/K548V/N551R/N552R | | TNTN |
| S542R/K607R/N547K | | TYCC |
| S542R/K607R/K548V | | TYCC |
| S542R/K607R/N551R | | TYCC |
| S542R/K607R/N552S | | TYCC |
| S542R/K607R/N547K/K550Y | | TYCC |
| S542R/K607R/N547K/N551R | | TYCC |
| S542R/K607R/N547K/N552S | | TYCC |
| S542R/K607R/K550Y/N551R | | TYCC |
| S542R/K607R/K550Y/N552S | | TYCC |
| S542R/K607R/N551R/N552S | | TYCC |
| S542R/K607R/N547K/K550Y/N551R/N552S | | TYCC |
| K548V/N552G | | TNTN |
| S542R/K548V/N552G | | TNTN |
| S542R/K548V/N551R/N552G | | TNTN |
| T539R | | NTTN |
| T539K | | NTTN |

To assess global PAM preferences, variants, including S542R/K607R (hereinafter "RR"), S542R/K548V (hereinafter "RV"), and S542R/K548V/N552R (hereinafter "RVR") were compared to wild type by an in vitro PAM identification assay. Cell lysate from HEK293 cells expressing AsCpf1 (or a variant) was incubated with in vitro-transcribed crRNA and a library of plasmid DNA containing a constant target preceded by a degenerate sequence (5'-N NNNNNN-target). For each Cpf1 variant, ten replicates of the cleavage reaction were carried out, each incubated for a different amount of time, in order to determine cleavage kinetics.

WT AsCpf1 was most active at TTTV PAMs (FIG. 21A), with low cleavage rates observed for NTTV, TCTV, TTCV, and TTTT, consistent with observations in HEK293 cells.

Figure 21A:
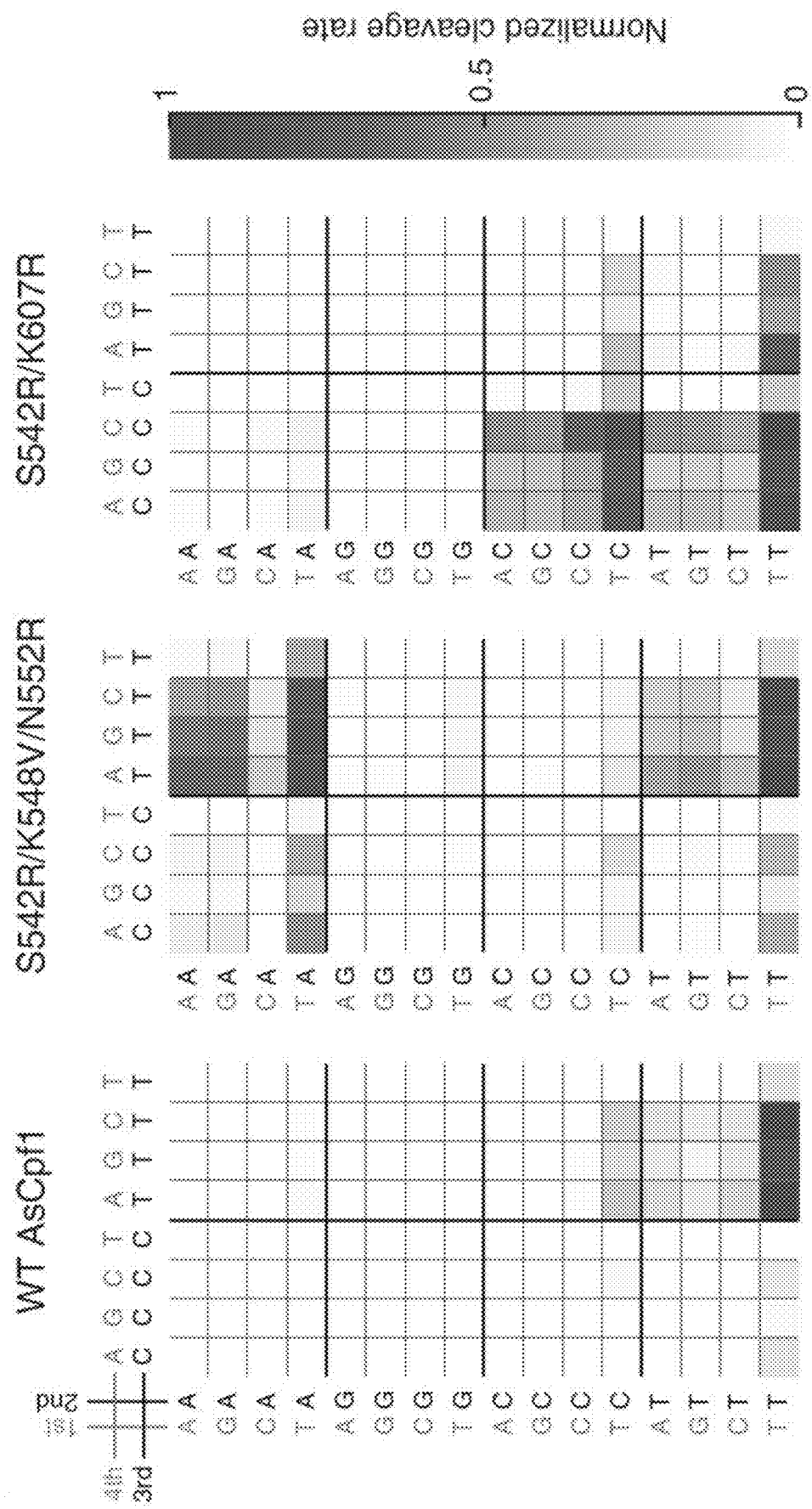
FIG. 21. In vitro cleavage assay. AsCpf1 PAM mutant S542R/K607R have altered PAM specificities in vitro. A. PAM preference of S542R/K607R (RR) and A542R/K548V/N552R (RVR) variants compared to wild type. Normalized cleavage rates are represented for all 4-base PAM motifs for wild-type, S542R/K607R, and S542R/K548V/N552R variants; B. Targeting range of Cpf1 variants in the human genome, including WT (dark blue), S542R/K607R (yellow), and S542R/K548V/N552R (light yellow). The percentages indicate the proportion of all non-repetitive guide sequences (both top and bottom strands) represented by the corresponding PAM; C. Distance between nearest target sites in non-repetitive regions of the human genome for TTTV PAMs (dark blue) and all PAMs cleavable by any of the variants (yellow).
Figure 21B:
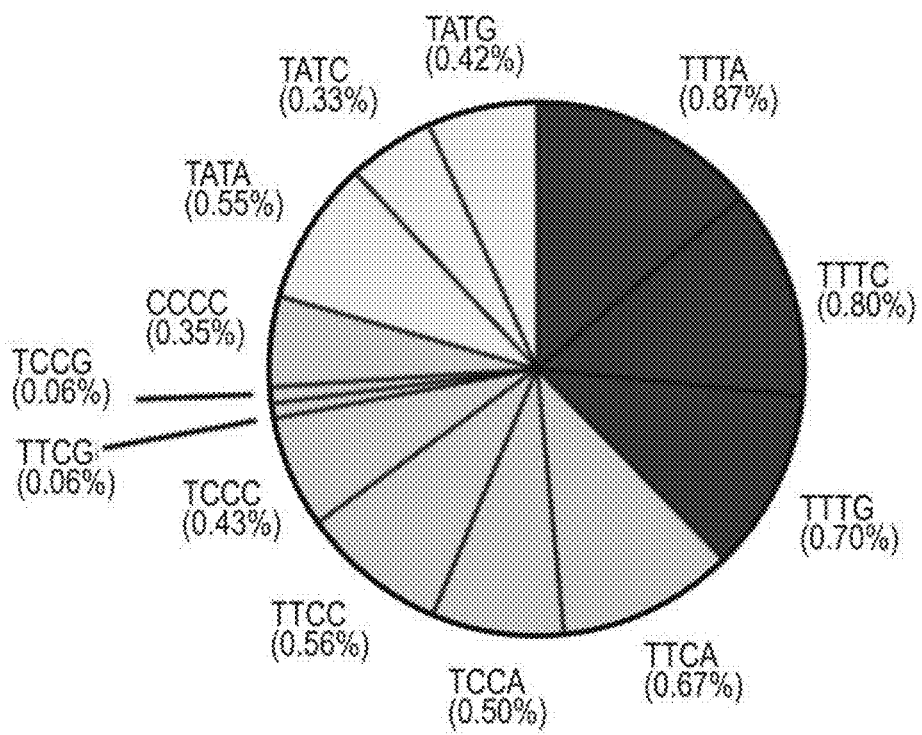
Figure 21C:
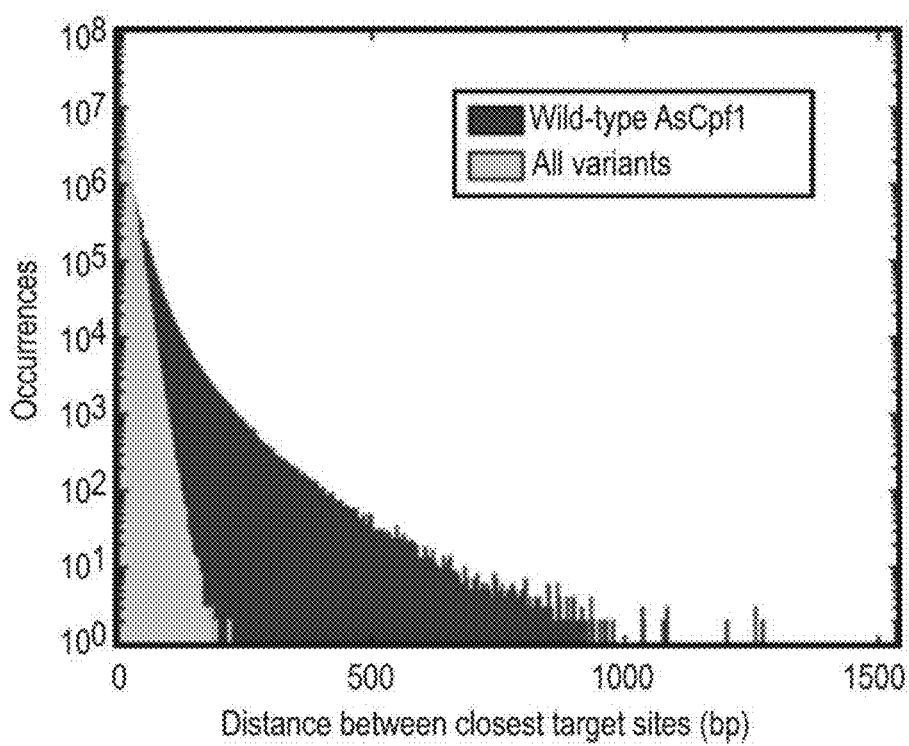

FIG. 21 shows the validation of the (N)YCV, such as TYCV, VYCV, or YCV PAM sequence for the S542R/K607R ("RR") AsCpf1 mutant as determined in an in vitro cleavage assay. Similarly, an in vitro cleavage assay validated the PAM sequence for the AsCpf1 mutant S542R/K548V as AYV, TYV, and TGYV. This mutant was also found to recognize the canonical PAM TTTV with higher efficiency than wild type AsCpf1, but with reduced specificity. FIG. 21A shows normalized cleavage rates for all 4-base PAM motifs for wild-type and the RR and RVR variants. The RVR variant had the highest activity at TATV PAM, compared to little or no activity for WT at this PAM. These PAMs increase the targeting range of Cpf1 in non-repetitive regions of the human genome (FIG. 21B) and reduce the sizes of genomic DNA stretches that cannot be targeted (FIG. 21C).

Example 5—Truncated Guides

HEK293FT cells were transfected in 24-well plagues with 400 ng AS or LbCpf1 encoding plasmids and 100 ng U6::crRNA PCR fragments per well. Guides targeting DNMT1-3 or DNMT1-4 were used, between 24 nt (full length) and 14 nt in length, truncated from the 3' end. Guides of 24 nt to 19 nt length demonstrated similar activity with both enzymes. Activity was somewhat reduced using 18 nt guides and further reduced using guides of 17 nt to 15 nt. Little or no activity was observed using guides of fewer than 15 nt. (FIG. 19B-E).

Example 6—Partially Binding Guides

HEK293FT cells were transfected in 24-well plagues with 400 ng AS or LbCpf1 encoding plasmids and 100 ng U6::crRNA PCR fragments per well. Guides targeting DNMT1-3 or DNMT1-4 were used, all 24 nt in length. The number of matching nucleotides was varied from 24 nt (full length) to 14 nt, with matching nucleotides closest to the PAM, and non-matching nucleotides at the 3' end.

Guides matching 24 nt to 19 nt demonstrated similar activity with both enzymes. Activity was somewhat reduced using guides matching 18 nt. Guides matching 17 nt to 15 nt showed little or no detectable activity. Activity was not detectable for guides matching fewer that 15 nt. (FIG. 20B-E).

Example 7—Validation of Cpf1 Mutants in Mammalian Cells

Different Cpf1 mutants (*Acidaminococcus* sp. BV3L6, essentially as described in Zetsche et al. (2015), Cell, 163:759-771) were cloned in eukaryotic expression vectors (as an example, the expression vectors used for evaluating AsCpf1 having 5542/K607R mutations is provided in FIG. 25; similar expression vectors were designed for the other Cpf1 mutants) and transfected in HEK293T cells, and genome editing was evaluated based on detection of indel percentage. The following Cpf1 mutants were generated, and comprised single or multiple point mutations (i.e. single or multiple amino acid mutations). Also indicated in the Table are the tested PAM sequences and Cpf1 nucleic acid sequences surrounding and including the recited amino acid mutation (from positions 539 to 552).

TABLE 33

| Mutation | PAM | Nucleic acid sequence |
|---|---|---|
| S542R | TYCC | ACACTGGCCCGGGGCTGGGACGTG AATAAGGAGAAGAACAAT (SEQ ID NO: 123) |
| N547K | TTCC | ACACTGGCCTCAGGCTGGGACGTGA AGAAGGAGAAGAACAAT (SEQ ID NO: 124) |
| K548A | TNTV | ACACTGGCCTCAGGCTGGGACGTGA ATGCCGAGAAGAACAAT (SEQ ID NO: 125) |
| K548H | TNTV | ACACTGGCCTCAGGCTGGGACGTGA ATCACGAGAAGAACAAT (SEQ ID NO: 126) |
| K548N | TNTV | ACACTGGCCTCAGGCTGGGACGTGA ATAACGAGAAGAACAAT (SEQ ID NO: 127) |
| K548Q | TNTV | ACACTGGCCTCAGGCTGGGACGTGA ATCAGGAGAAGAACAAT (SEQ ID NO: 128) |
| K548R | TNTV | ACACTGGCCTCAGGCTGGGACGTGA ATCGGGAGAAGAACAAT (SEQ ID NO: 129) |
| K548G | | |
| K548C | | |
| K548F | | |
| K548I | | |
| K548M | | |
| K548S | | |
| K548T | | |
| K548V | | |
| K548W | | |
| K548Y | | |
| K550Y | TCCC | ACACTGGCCTCAGGCTGGGACGTGA ATAAGGAGTACAACAAT (SEQ ID NO: 131) |
| N551R | TATC | ACACTGGCCTCAGGCTGGGACGTGA ATAAGGAGAAGCGGAAT (SEQ ID NO: 132) |
| N552G | TATC | ACACTGGCCTCAGGCTGGGACGTGA ATAAGGAGAAGAACGGC (SEQ ID NO: 133) |
| N552K | TATC | ACACTGGCCTCAGGCTGGGACGTGA ATAAGGAGAAGAACAAG (SEQ ID NO: 134) |
| N552R | TATC | ACACTGGCCTCAGGCTGGGACGTGA ATAAGGAGAAGAACCGG (SEQ ID NO: 135) |
| N552S | TATC | ACACTGGCCTCAGGCTGGGACGTGA ATAAGGAGAAGAACAGC (SEQ ID NO: 136) |
| N552T | TATC | ACACTGGCCTCAGGCTGGGACGTGA ATAAGGAGAAGAACACC (SEQ ID NO: 137) |

TABLE 33-continued

| Mutation | PAM | Nucleic acid sequence |
|---|---|---|
| K607A | TYCC | ATGCCGCCAAGATGATCCCAGCCTG<br>CAGCACCCAGCTGAAGGCG<br>(SEQ ID NO: 138) |
| K607R | TCCC | ATGCCGCCAAGATGATCCCACGGTG<br>CAGCACCCAGCTGAAGGCG<br>(SEQ ID NO: 139) |
| S542R/K548R | TCCC | ACACTGGCCCGGGGCTGGGACGTG<br>AATCGGGAGAAGAACAAT<br>(SEQ ID NO: 140) |
| S542R/K607A | TCCC | Same as S542R |
| S542R/K607R | TCCC | Same as S542R |
| K548R/N552R | TCCC | ACACTGGCCTCAGGCTGGGACGTGA<br>ATCGGGAGAAGAACCGG<br>(SEQ ID NO: 141) |
| S542R/K550Y/<br>K607R | TCCC | ACACTGGCCCGGGGCTGGGACGTG<br>AATAAGGAGTACAACAAT<br>(SEQ ID NO: 142) |
| S542R/K548R/<br>K550Y/K607R | TCCC | ACACTGGCCCGGGGCTGGGACGTG<br>AATCGGGAGTACAACAAT<br>(SEQ ID NO: 143) |
| T539R | NTTV | CGGCTGGCCTCAGGCTGGGACGTGA<br>ATAAGGAGAAGAACAAT<br>(SEQ ID NO: 144) |
| T539K | NTTV | AAGCTGGCCTCAGGCTGGGACGTGA<br>ATAAGGAGAAGAACAAT<br>(SEQ ID NO: 145) |
| T167A | NTTV | |
| T167A | NTTV | |
| T167R | NTTV | |
| T167R | NTTV | |
| K548G | TNTV | ACACTGGCCTCAGGCTGGGACGTGA<br>ATGGCGAGAAGAACAAT<br>(SEQ ID NO: 146) |
| K548C | TNTV | ACACTGGCCTCAGGCTGGGACGTGA<br>ATTGCGAGAAGAACAAT<br>(SEQ ID NO: 147) |
| K548F | TNTV | ACACTGGCCTCAGGCTGGGACGTGA<br>ATTTCGAGAAGAACAAT<br>(SEQ ID NO: 148) |
| K548I | TNTV | ACACTGGCCTCAGGCTGGGACGTGA<br>ATATCGAGAAGAACAAT<br>(SEQ ID NO: 149) |
| K548M | TNTV | ACACTGGCCTCAGGCTGGGACGTGA<br>ATATGGAGAAGAACAAT<br>(SEQ ID NO: 150) |
| K548S | TNTV | ACACTGGCCTCAGGCTGGGACGTGA<br>ATAGCGAGAAGAACAAT<br>(SEQ ID NO: 151) |
| K548T | TNTV | ACACTGGCCTCAGGCTGGGACGTGA<br>ATACCGAGAAGAACAAT<br>(SEQ ID NO: 152) |
| K548V | TNTV | ACACTGGCCTCAGGCTGGGACGTGA<br>ATGTGGAGAAGAACAAT<br>(SEQ ID NO: 153) |
| K548W | TNTV | ACACTGGCCTCAGGCTGGGACGTGA<br>ATTGGGAGAAGAACAAT<br>(SEQ ID NO: 154) |
| K548Y | TNTV | ACACTGGCCTCAGGCTGGGACGTGA<br>ATTACGAGAAGAACAAT<br>(SEQ ID NO: 155) |
| K548D | TNTV | ACACTGGCCTCAGGCTGGGACGTGA<br>ATGACGAGAAGAACAAT<br>(SEQ ID NO: 156) |
| K548E | TNTV | ACACTGGCCTCAGGCTGGGACGTGA<br>ATGAGGAGAAGAACAAT<br>(SEQ ID NO: 157) |
| K548L | TNTV | ACACTGGCCTCAGGCTGGGACGTGA<br>ATCTGGAGAAGAACAAT<br>(SEQ ID NO: 158) |
| K548P | TNTV | ACACTGGCCTCAGGCTGGGACGTGA<br>ATCCCGAGAAGAACAAT<br>(SEQ ID NO: 159) |
| S542R/K548V | TNTV | ACACTGGCCCGGGGCTGGGACGTG<br>AATGTGGAGAAGAACAAT<br>(SEQ ID NO: 160) |
| K548V/N552R | TNTV | ACACTGGCCTCAGGCTGGGACGTGA<br>ATGTGGAGAAGAACCGG<br>(SEQ ID NO: 161) |
| S542R/K548V/<br>N552R | TNTV | ACACTGGCCCGGGGCTGGGACGTG<br>AATGTGGAGAAGAACCGG<br>(SEQ ID NO: 162) |
| S542R/K548V/<br>N551R/N552R | TNTV | ACACTGGCCCGGGGCTGGGACGTG<br>AATGTGGAGAAGCGGCGG<br>(SEQ ID NO: 163) |
| S542R/K607R/<br>N547K | TYCC | ACACTGGCCCGGGGCTGGGACGTG<br>AAGAAGGAGAAGAACAAT<br>(SEQ ID NO: 164) |
| S542R/K607R/<br>K548V | TYCC | ACACTGGCCCGGGGCTGGGACGTG<br>AATGTGGAGAAGAACAAT<br>(SEQ ID NO: 165) |
| S542R/K607R/<br>N551R | TYCC | ACACTGGCCCGGGGCTGGGACGTG<br>AATAAGGAGAAGCGGAAT<br>(SEQ ID NO: 166) |
| S542R/K607R/<br>N552S | TYCC | ACACTGGCCCGGGGCTGGGACGTG<br>AATAAGGAGAAGAACAGC<br>(SEQ ID NO: 167) |
| S542R/K607R/<br>N547K/K550Y | TYCC | ACACTGGCCCGGGGCTGGGACGTG<br>AAGAAGGAGTACAACAAT<br>(SEQ ID NO: 168) |
| S542R/K607R/<br>N547K/N551R | TYCC | ACACTGGCCCGGGGCTGGGACGTG<br>AAGAAGGAGAAGCGGAAT<br>(SEQ ID NO: 169) |
| S542R/K607R/<br>N547K/N552S | TYCC | ACACTGGCCCGGGGCTGGGACGTG<br>AAGAAGGAGAAGAACAGC<br>(SEQ ID NO: 170) |
| S542R/K607R/<br>K550Y/N551R | TYCC | ACACTGGCCCGGGGCTGGGACGTG<br>AATAAGGAGTACCGGAAT<br>(SEQ ID NO: 171) |
| S542R/K607R/<br>K550Y/N552S | TYCC | ACACTGGCCCGGGGCTGGGACGTG<br>AATAAGGAGTACAACAGC<br>(SEQ ID NO: 172) |

TABLE 33-continued

| Mutation | PAM | Nucleic acid sequence |
|---|---|---|
| S542R/K607R/ N551R/N552S | TYCC | ACACTGGCCCGGGGCTGGGACGTG AATAAGGAGAAGCGGAGC (SEQ ID NO: 173) |
| S542R/K607R/ N547K/K550Y/ N551R/N552S | TYCC | ACACTGGCCCGGGGCTGGGACGTG AAGAAGGAGTACCGGAGC (SEQ ID NO: 174) |
| K548V/N552G | TNTV | ACACTGGCCTCAGGCTGGGACGTGA ATGTGGAGAAGAACGGC (SEQ ID NO: 175) |
| S542R/K548V/ N552G | TNTV | ACACTGGCCCGGGGCTGGGACGTG AATGTGGAGAAGAACGGC (SEQ ID NO: 176) |
| S542R/K548V/ N551R/N552G | TNTV | ACACTGGCCCGGGGCTGGGACGTG AATGTGGAGAAGCGGGC (SEQ ID NO: 177) |

Figure 22:
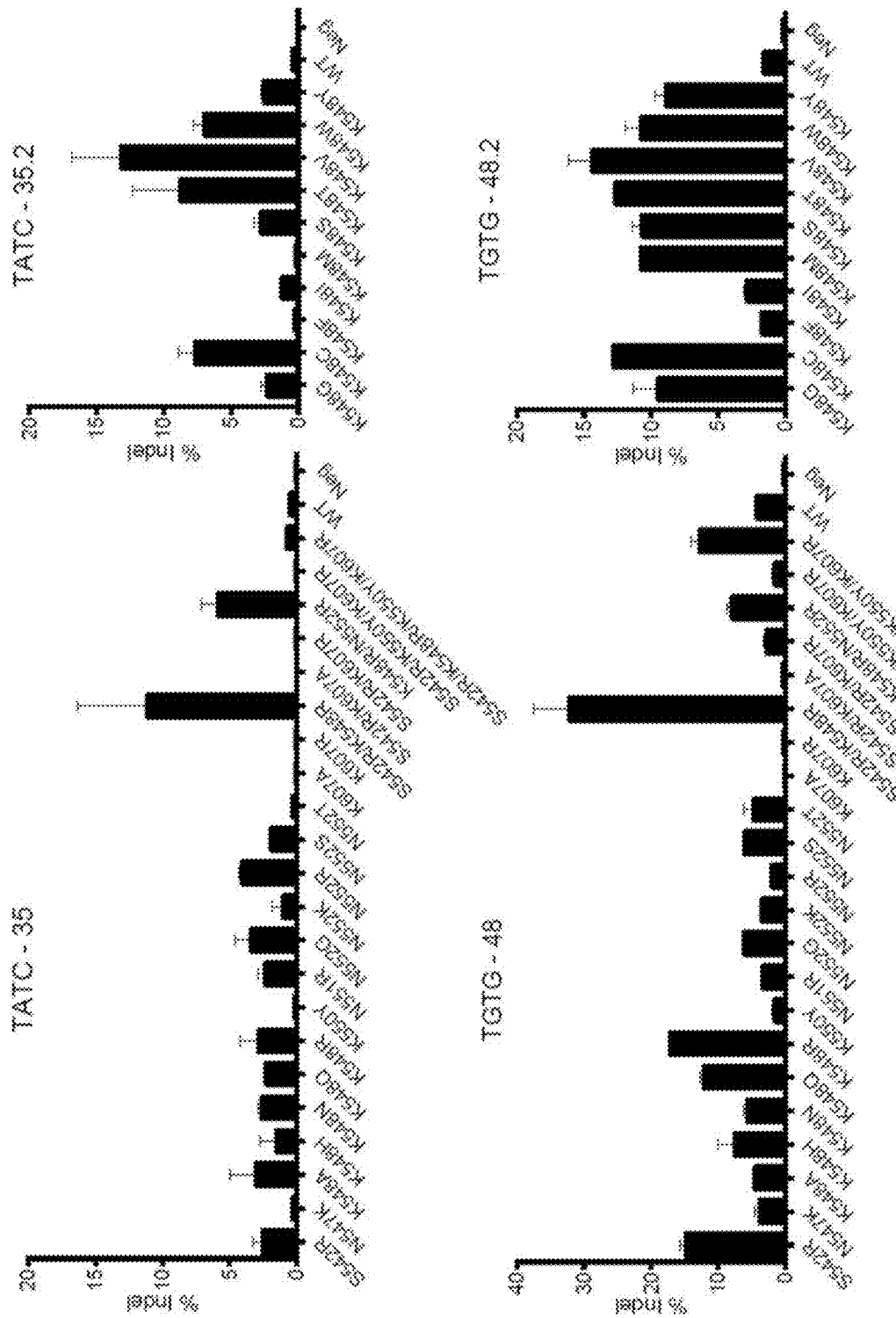
FIG. 22: Validation of AsCpf1 PAM mutants in HEK293 cells. % indel as determined for the indicated Cpf1 mutants and the indicated PAM sequence for indicated target genes. Numbers following the indicated PAM site represent different target sequences (e.g. TGTG-48) and different transfections for a given target sequence (e.g. TGTG-48.2). Co-transfection of plasmid expressing AsCpf1 (WT or mutant) and plasmid expressing AsCpf1 DR+spacer. Targeted deep sequencing of targeted genomic locus 3 days post-transfection.
Figure 22:
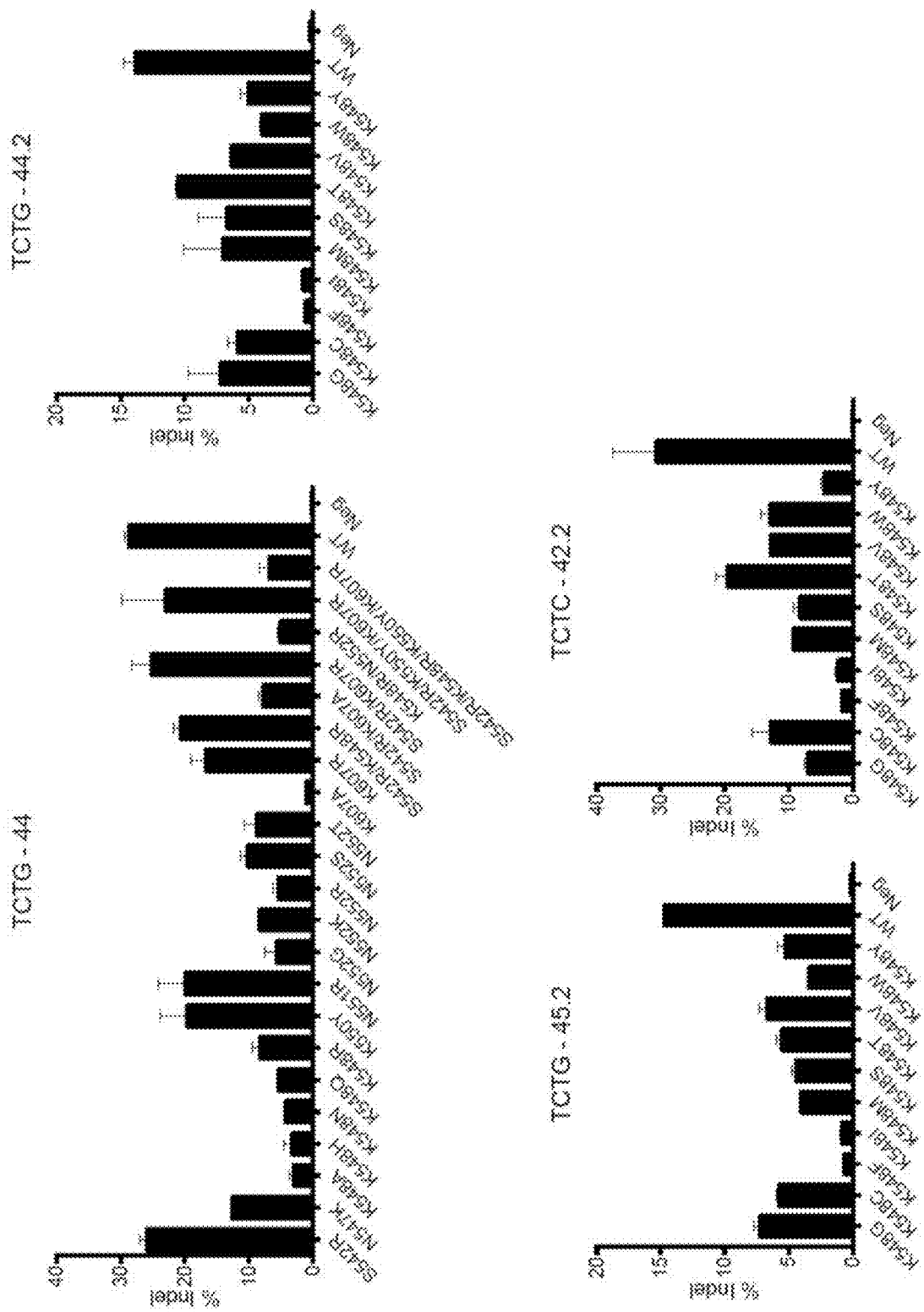
Figure 22:
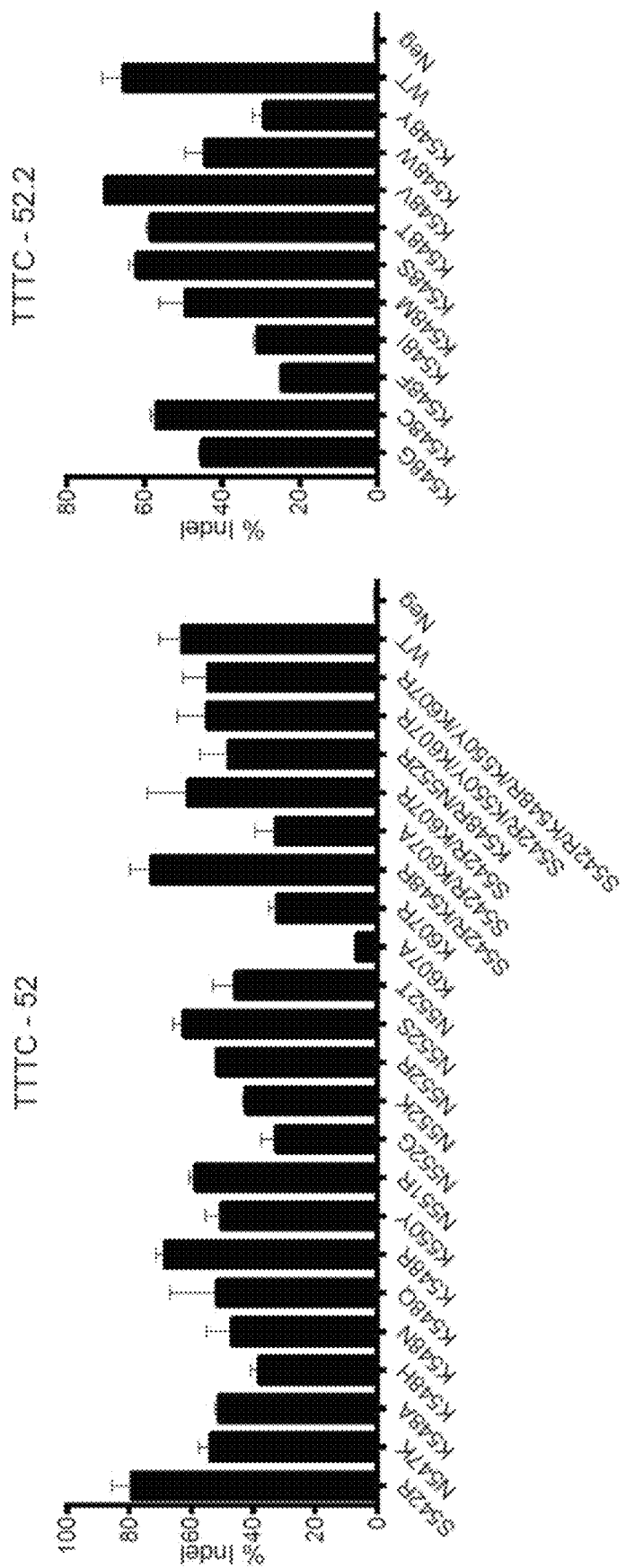
Figure 22:
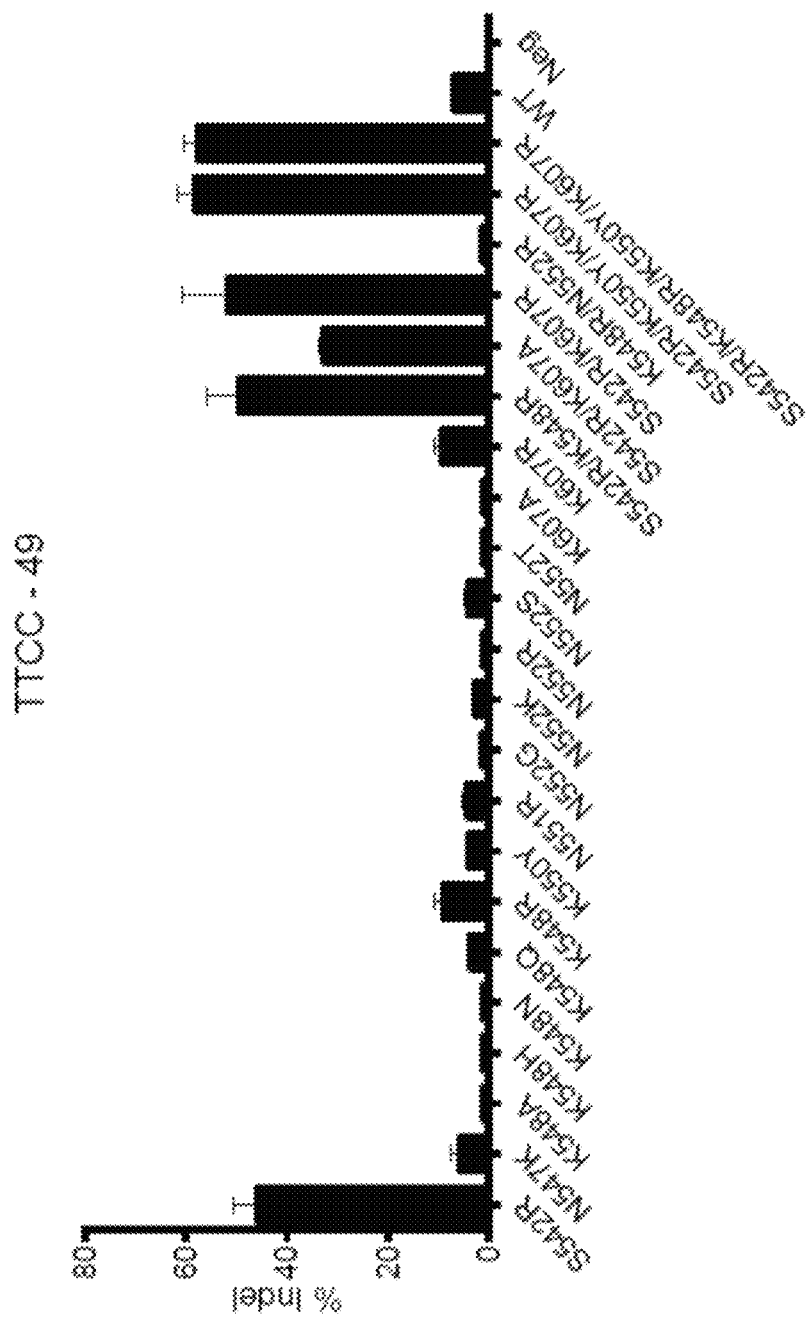

Target sequences corresponding to the indicated target sequence numbers in FIG. 22 are indicated in the Table below (not for every target sequence the results are shown in FIG. 22).

| # | Target sequence | |
|---|---|---|
| 13 | AAGGAGGAGGAAGCTGCTAAGGA | (SEQ ID NO: 178) |
| 25 | ACTAGGGTGGGCAACCACAAACC | (SEQ ID NO: 179) |
| 31 | CCTCTTTAGCCAGAGCCGGGGTG | (SEQ ID NO: 180) |
| 33 | AGGGCGTTGGAGCGGGGAGAAGG | (SEQ ID NO: 181) |
| 34 | GAGCGGGGAGAAGGCCAGGGGTC | (SEQ ID NO: 182) |
| 35 | AAATTCCAGCACCGAGCGCCCTG | (SEQ ID NO: 183) |
| 36 | TAGCTGTTTGGGAGGTCAGAAAT | (SEQ ID NO: 184) |
| 37 | TCTTTAGCCAGAGCCGGGGTGTG | (SEQ ID NO: 185) |
| 38 | CGCTCCAACGCCCTCAACCCCAC | (SEQ ID NO: 186) |
| 39 | TGGCCAGGCTTTGGGGAGGCCTG | (SEQ ID NO: 187) |
| 40 | TCTGTCAATGGCGGCCCCGGGCT | (SEQ ID NO: 188) |
| 41 | GTCACCCCTGTTTCTGGCACCAG | (SEQ ID NO: 189) |
| 42 | CCCGCTCCAACGCCCTCAACCCC | (SEQ ID NO: 190) |
| 44 | GCTAAAGAGGGAATGGGCTTTGG | (SEQ ID NO: 191) |
| 45 | TGTGGGTGAGTGAGTGTGTGCGT | (SEQ ID NO: 192) |
| 46 | CCCTCCCGTCACCCCTGTTTCTG | (SEQ ID NO: 193) |
| 47 | AATGGCGGCCCCGGGCTTCAAGC | (SEQ ID NO: 194) |
| 48 | GGTGAGTGAGTGTGTGCGTGTGG | (SEQ ID NO: 195) |
| 49 | AAAGCCCATTCCCTCTTTAGCCA | (SEQ ID NO: 196) |
| 50 | CTCTTTAGCCAGAGCCGGGGTGT | (SEQ ID NO: 197) |
| 51 | TGGTGCCAGAAACAGGGGTGACG | (SEQ ID NO: 198) |
| 52 | CTGATGGTCCATGTCTGTTACTC | (SEQ ID NO: 199) |
| 53 | GCTGAAGGGAAATAAAAGGAAAA | (SEQ ID NO: 200) |

Figure 23A:
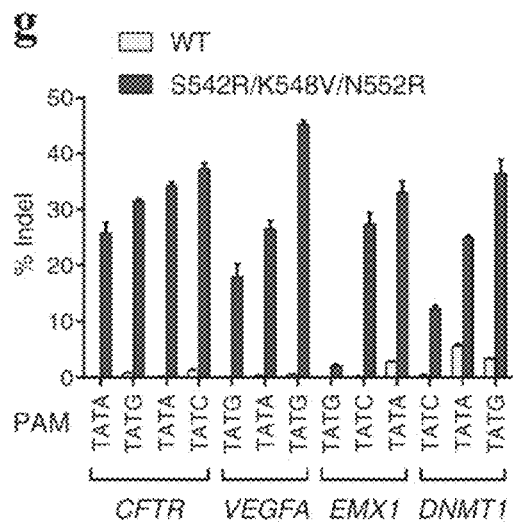
FIG. 23A-23D. A. Activity of the S542R/K548V/N552R variant at TATV target sites; B. Activity of the S542R/K607 variant at TYCV sites; C. Activity of the S542R/K607R variant at TYCV and CCCC target sites and activity of the S542R/K548V variant at TTTV target sites; D. Activity of the S542R/K607R variant at VYCV sites. All indel percentages were measured in HEK293 cells.
Figure 23B:
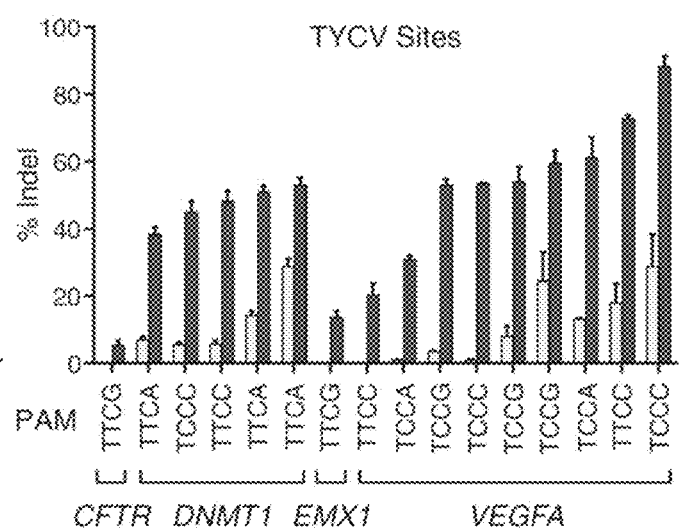
Figure 23C:
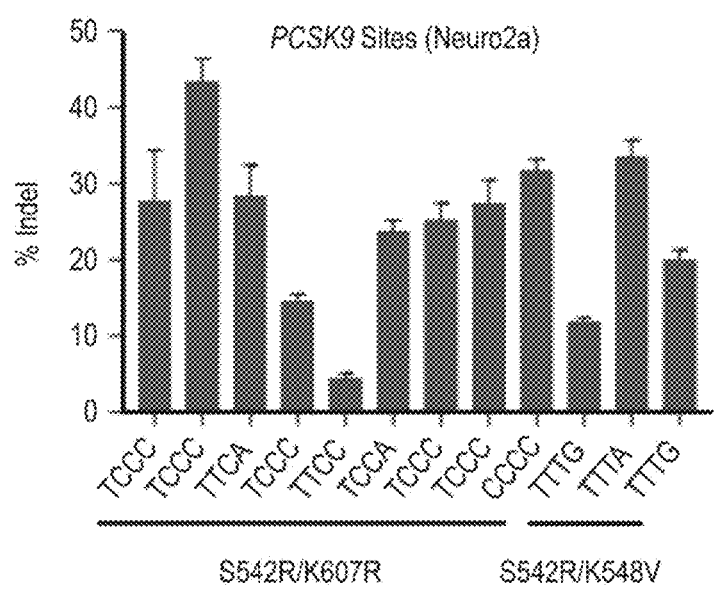
Figure 23D:
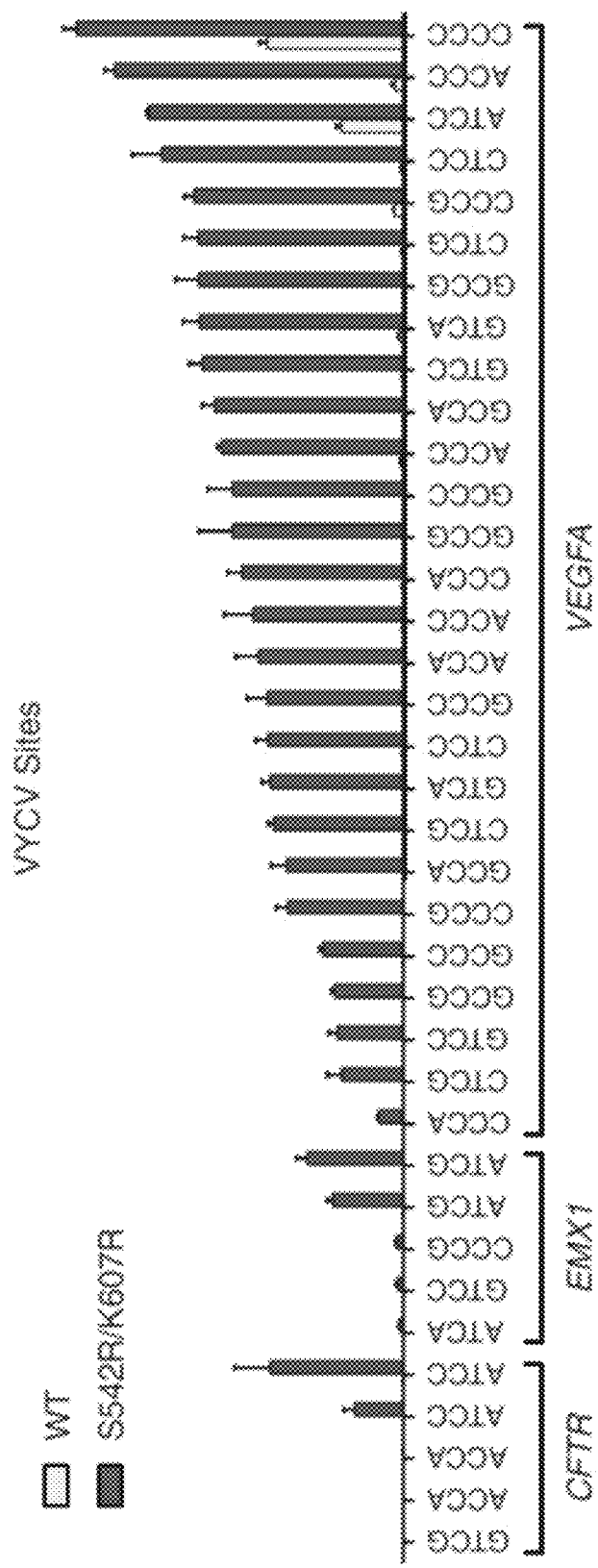

% indel activity in HEK cells was evaluated for target sequences (a guide RNA target site was selected within the DNMT1 gene) associated with a variety of PAM sequences, as indicated in FIG. 22 or for a variety of target sequences of different target genes associated with the indicated The RR and RVR variants were compared at their preferred PAMs in HEK293 cells (FIG. 23) and mediated robust editing across the four genes assessed (CFTR, DNMT1, EMX1, and VEGFA); in particular, 14/16 (88%) of TYCV target sites had >20% indel for RR (vs. 3/16 for WT), and 10/13 (77%) of TATV target sites had >20% indel for RVR (vs. 0/13 for WT). Moreover, the RR variant also had significant activity at VYCV target sites (>20% indel for 25/37 (68%) of sites) (FIG. 23), although this activity was somewhat lower than at TYCV sites, consistent with the in vitro cleavage assay. The RR variant was also tested in murine Neuro2a cells (FIG. 23C) and high rates of editing were observed (>20% indel for 7/9 TYCV or CCCC sites).

Figure 24:
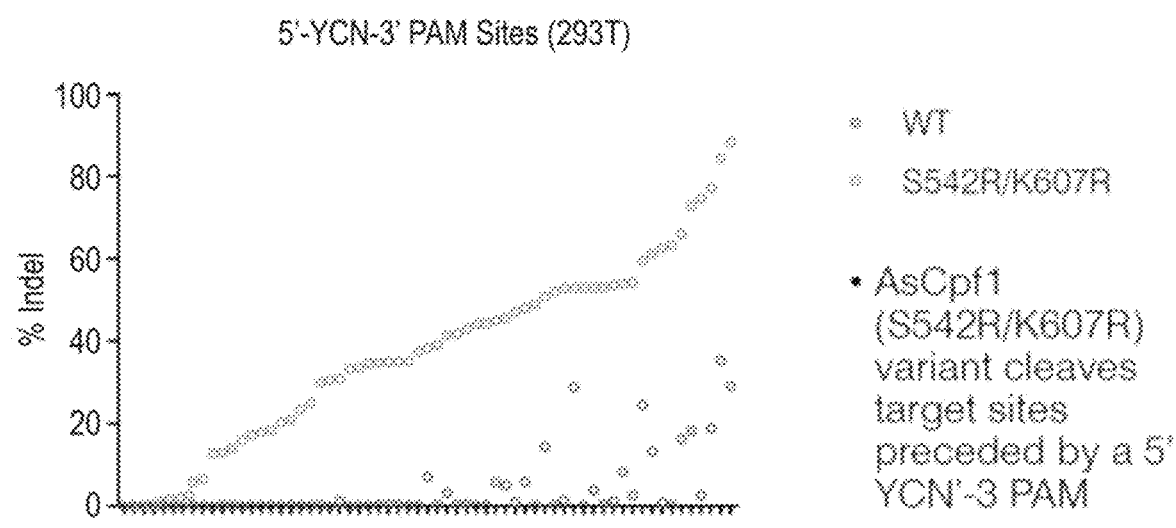
FIG. 24 Validation of AsCpf1 PAM mutant S542R/K607R in HEK293 cells. % indel as determined for the Cpf1 mutant and the indicated PAM sequence for 63 different target sites of various target genes. Co-transfection of plasmid expressing AsCpf1 (WT or mutant) and plasmid expressing AsCpf1 DR+spacer. Targeted deep sequencing of targeted genomic locus 3 days post-transfection.
Figure 26:
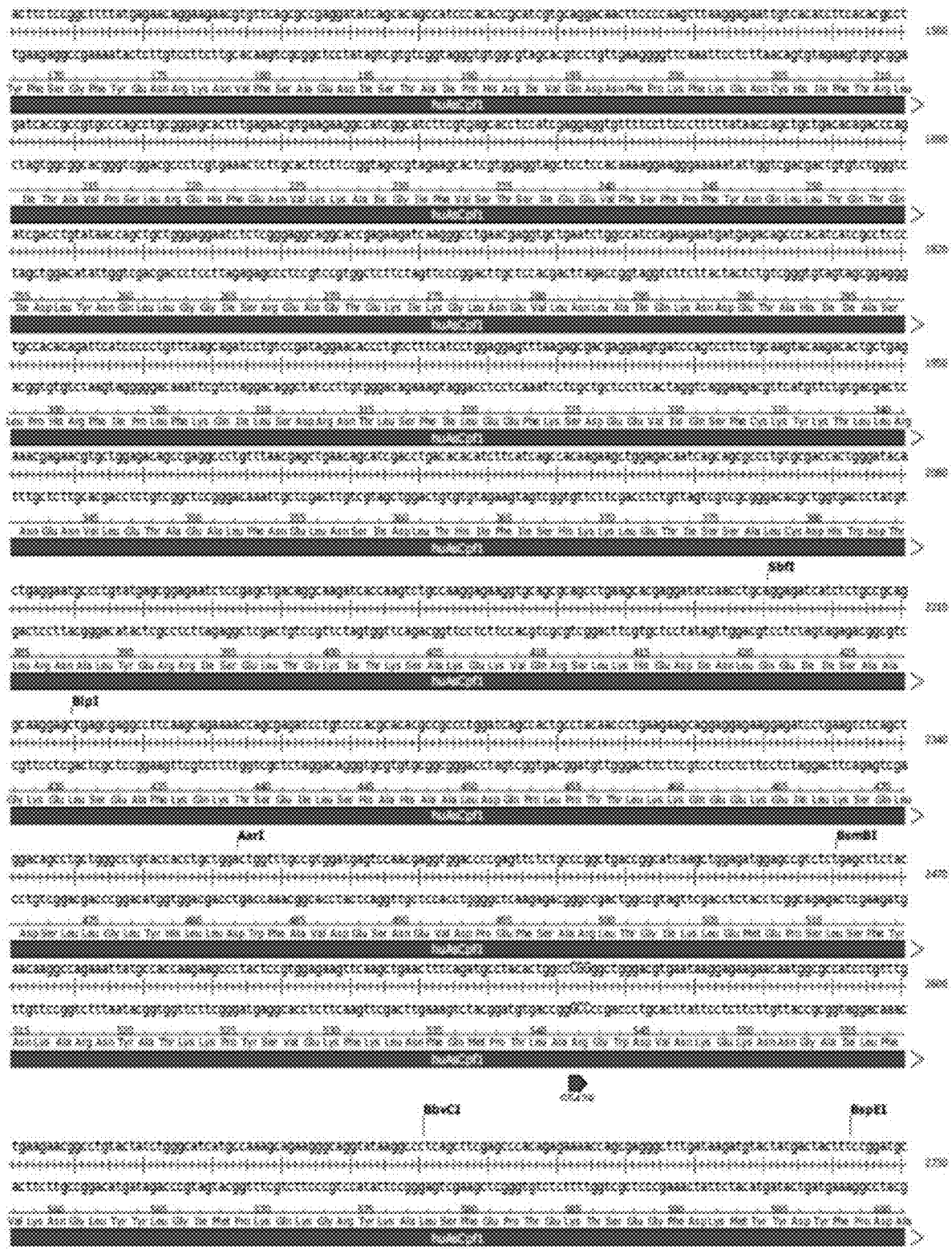
FIG. 26. Exemplary expression plasmids encoding mutant Cpf1 according to an embodiment of the invention. (A) pY036 encoding AsCpf1 mutant S542R/K607R. (B) pcDNA encoding AsCpf1 mutant S542R/K607R. Functional features are indicated on the respective maps and sequences.
Figure 26:
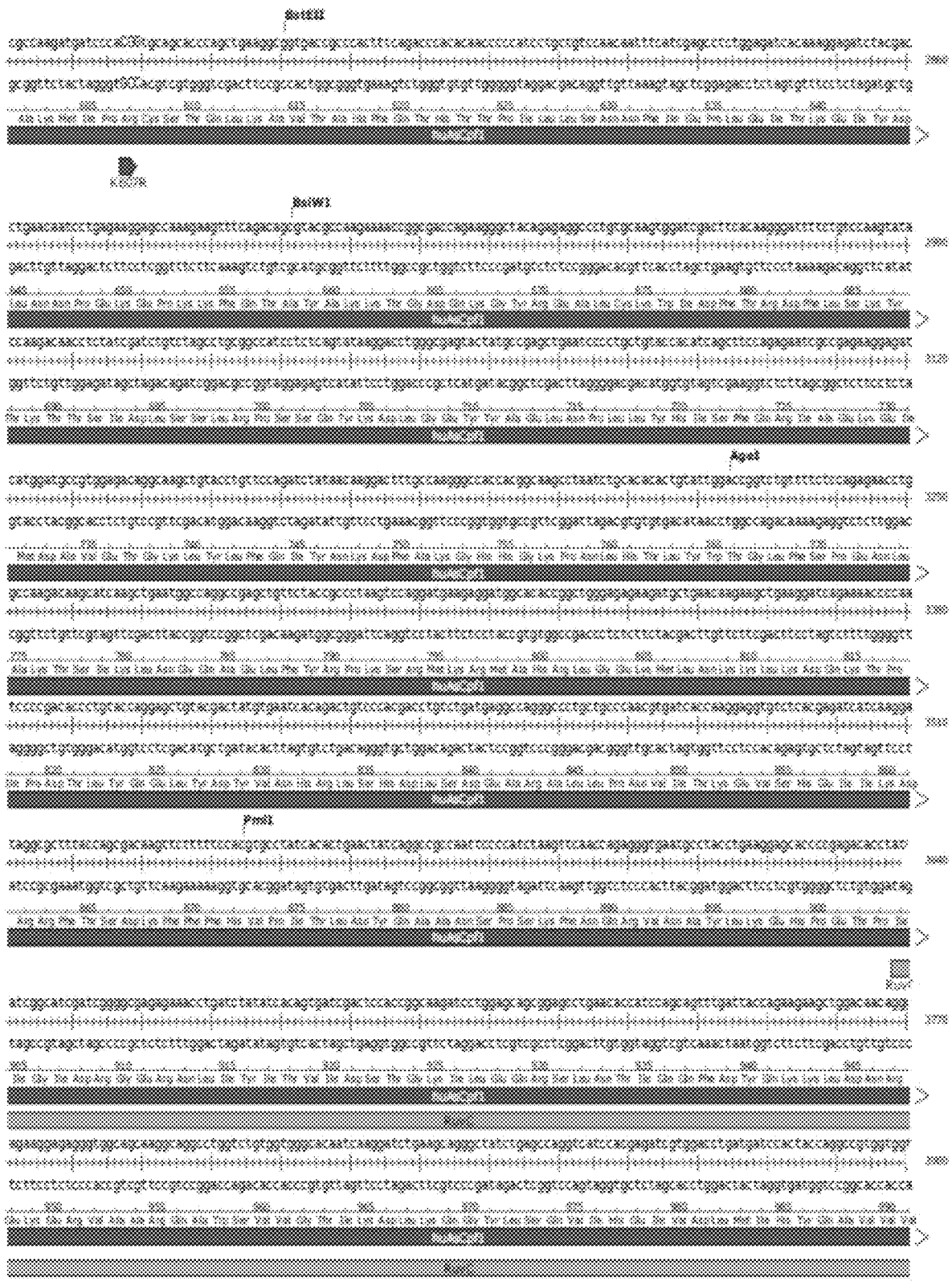
Figure 26:

YCN PAM sequence for the AsCpf1 S542R/K607R mutant as indicated in FIG. 24. Indel % of the indicated Cpf1 mutants was compared with indel % of the wild type Cpf1 or the negative control (no Cpf1 transfected).

The different target sequences and target genes of FIG. 24 are indicated in the Table below, as well as flanking PAM sequence, leading to the consensus PAM sequence YCN for the S542R/K607R mutant

| # | Target gene | PAM | Target sequence | |
|---|---|---|---|---|
| 1 | VEGFA | CTCG | GCCACCACAGGGAAGCTGGGTGA | (SEQ ID NO: 201) |
| 2 | VEGFA | ATCA | AATTCCAGCACCGAGCGCCCTGG | (SEQ ID NO: 202) |
| 3 | CFTR | GTCG | AAAATTTTACACCACAAAATGTT | (SEQ ID NO: 203) |
| 4 | VEGFA | CCCC | TATTTCTGACCTCCCAAACAGCT | (SEQ ID NO: 204) |
| 5 | VEGFA | ATCA | ATGAATATCAAATTCCAGCACCG | (SEQ ID NO: 205) |
| 6 | EMX1 | ATCA | CATCAACCGGTGGCGCATTGCCA | (SEQ ID NO: 206) |
| 7 | VEGFA | GCCA | GAGCCGGGGTGTGCAGACGGCAG | (SEQ ID NO: 207) |
| 8 | CFTR | ACCA | TTAAAGAAAATATCATCTTTGGT | (SEQ ID NO: 208) |
| 9 | VEGFA | GCCG | AGCGCCCCCTAGTGACTGCCGTC | (SEQ ID NO: 209) |

-continued

| # | Target gene | PAM | Target sequence |
|---|---|---|---|
| 10 | EMX1 | GTCC | TCCCCATTGGCCTGCTTCGTGGC (SEQ ID NO: 210) |
| 11 | VEGFA | ACCG | GTCAGCGGACTCACCGGCCAGGG (SEQ ID NO: 211) |
| 12 | VEGFA | CCCA | TTCCCTCTTTAGCCAGAGCCGGG (SEQ ID NO: 212) |
| 13 | EMX1 | CCCG | GGCTTCAAGCCCTGTGGGCCAT (SEQ ID NO: 213) |
| 14 | CFTR | ACCA | AAGATGATATTTTCTTTAATGGT (SEQ ID NO: 214) |
| 15 | VEGFA | TTCC | CTGTGGTGGCCGAGCGCCCCCTA (SEQ ID NO: 215) |
| 16 | VEGFA | GCCG | TCTGCACACCCCGGCTCTGGCTA (SEQ ID NO: 216) |
| 17 | EMX1 | ATCG | ATGTCCTCCCCATTGGCCTGCTT (SEQ ID NO: 217) |
| 18 | VEGFA | GTCC | CAAATATGTAGCTGTTTGGGAGG (SEQ ID NO: 218) |
| 19 | VEGFA | CTCG | CTCCATTCACCCAGCTTCCCTGT (SEQ ID NO: 219) |
| 20 | CFTR | ATCC | AGGAAAACTGAGAACAGAATGAA (SEQ ID NO: 220) |
| 21 | CFTR | ATCC | TAAACTCATTAATGCCCTTCGGC (SEQ ID NO: 221) |
| 22 | EMX1 | ATCG | ATGTCACCTCCAATGACTAGGGT (SEQ ID NO: 222) |
| 23 | EMX1 | TTCG | TGGCAATGCGCCACCGGTTGATG (SEQ ID NO: 223) |
| 24 | CFTR | TTCG | GCGATGTTTTTTCTGGAGATTTA (SEQ ID NO: 224) |
| 25 | VEGFA | ACCA | CAGGGAAGCTGGGTGAATGGAGC (SEQ ID NO: 225) |
| 26 | VEGFA | GCCA | CCACAGGGAAGCTGGGTGAATGG (SEQ ID NO: 226) |
| 27 | VEGFA | GCCG | GGGTGTGCAGACGGCAGTCACTA (SEQ ID NO: 227) |
| 28 | VEGFA | GCCC | TGGGCTCTCTGTACATGAAGCAA (SEQ ID NO: 228) |
| 29 | VEGFA | GTCA | GAAATAGGGGGTCCAGGAGCAAA (SEQ ID NO: 229) |
| 30 | VEGFA | GCCC | CCTAGTGACTGCCGTCTGCACAC (SEQ ID NO: 230) |
| 31 | VEGFA | ACCG | GCCAGGGCGCTCGGTGCTGGAAT (SEQ ID NO: 231) |
| 32 | VEGFA | GCCC | ATTCCCTCTTTAGCCAGAGCCGG (SEQ ID NO: 232) |
| 33 | VEGFA | CCCG | GCTCTGGCTAAAGAGGGAATGGG (SEQ ID NO: 233) |
| 34 | VEGFA | ACCC | CGGCTCTGGCTAAAGAGGGAATG (SEQ ID NO: 234) |
| 35 | VEGFA | GTCC | TCACTCTCGAAGACGCTGCTCGC (SEQ ID NO: 235) |
| 36 | VEGFA | CCCA | GCTTCCCTGTGGTGGCCGAGCGC (SEQ ID NO: 236) |
| 37 | VEGFA | CTCC | AGTCCCAAATATGTAGCTGTTTG (SEQ ID NO: 237) |
| 38 | VEGFA | CCCA | CCCCTTTCCAAAGCCCATTCCC (SEQ ID NO: 238) |
| 39 | VEGFA | CTCG | AAGACGCTGCTCGCTCCATTCAC (SEQ ID NO: 239) |
| 40 | VEGFA | ACCG | GTCCACCTAACCGCTGCGCCTCC (SEQ ID NO: 240) |
| 41 | VEGFA | CTCC | TGGACCCCCTATTTCTGACCTCC (SEQ ID NO: 241) |
| 42 | VEGFA | GTCG | GGAGGCGCAGCGGTTAGGTGGAC (SEQ ID NO: 242) |
| 43 | VEGFA | ACCC | CCTATTTCTGACCTCCCAAACAG (SEQ ID NO: 243) |
| 44 | VEGFA | TCCC | TCTTTAGCCAGAGCCGGGGTGTG (SEQ ID NO: 244) |
| 45 | VEGFA | TCCA | GTCCCAAATATGTAGCTGTTTGG (SEQ ID NO: 245) |
| 46 | VEGFA | GTCA | CTAGGGGGCGCTCGGCCACCACA (SEQ ID NO: 246) |
| 47 | VEGFA | ACCC | CCTTTCCAAAGCCCATTCCCTCT (SEQ ID NO: 247) |

-continued

| # | Target gene | PAM | Target sequence |
|---|---|---|---|
| 48 | VEGFA | CCCG | CTCCAACGCCCTCAACCCCACAC (SEQ ID NO: 248) |
| 49 | VEGFA | TTCC | CTCTTTAGCCAGAGCCGGGGTGT (SEQ ID NO: 249) |
| 50 | VEGFA | TCCG | CACGTAACCTCACTTTCCTGCTC (SEQ ID NO: 250) |
| 51 | VEGFA | CTCC | CCCCACCCCCTTTCCAAAGCCCA (SEQ ID NO: 251) |
| 52 | DNMT1 | TCCC | GTCACCCCTGTTTCTGGCACCAG (SEQ ID NO: 252) |
| 53 | DNMT1 | TTCC | TGGTGCCAGAAACAGGGGTGACG (SEQ ID NO: 253) |
| 54 | DNMT1 | TTCA | GCTAAAATAAAGGAGGAGGAAGC (SEQ ID NO: 254) |
| 55 | VEGFA | TCCG | CCCCCGGAAACTCTGTCCAGAGA (SEQ ID NO: 255) |
| 56 | VEGFA | TCCA | ATAGATCTGTGTGTCCCTCTCCC (SEQ ID NO: 256) |
| 57 | DNMT1 | TTCA | GTCTCCGTGAACGTTCCCTTAGC (SEQ ID NO: 257) |
| 58 | VEGFA | ATCC | TGGAGTGACCCCTGGCCTTCTCC (SEQ ID NO: 258) |
| 59 | VEGFA | TTCC | AAAGCCCATTCCCTCTTTAGCCA (SEQ ID NO: 259) |
| 60 | VEGFA | CCCC | CTTTCCAAAGCCCATTCCCTCTT (SEQ ID NO: 260) |
| 61 | VEGFA | TCCG | GGGGCGGATGGGTAATTTTCAGG (SEQ ID NO: 261) |
| 62 | DNMT1 | TTCA | CGGAGACTGAACACTCCTCAAAC (SEQ ID NO: 262) |
| 63 | VEGFA | TCCC | CCCACCCCTTTCCAAAGCCCAT (SEQ ID NO: 263) |
| 64 | VEGFA | CCCC | CCACCCCCTTTCCAAAGCCCATT (SEQ ID NO: 264) |

Figure 27A:
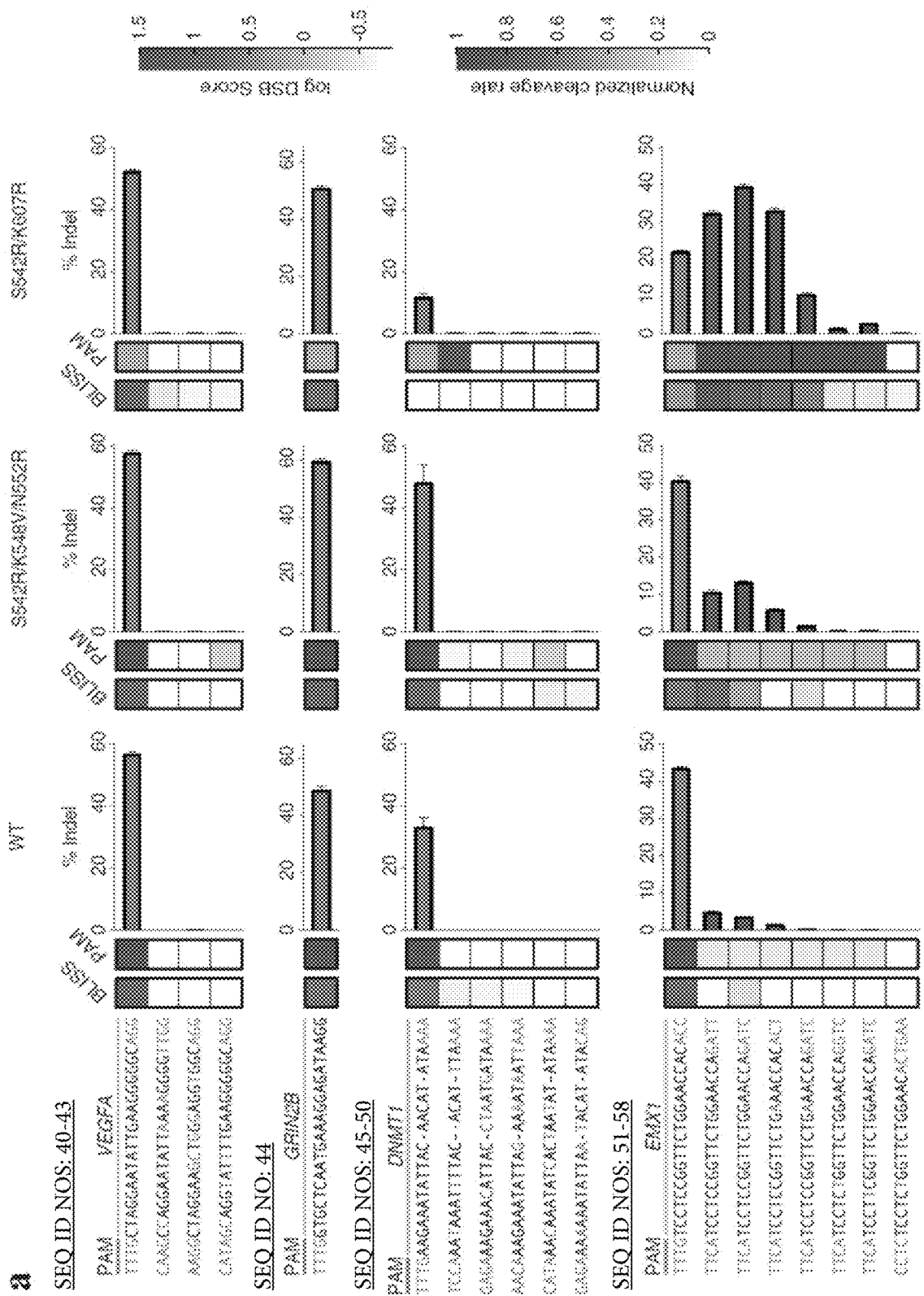
FIG. 27A-27D. DNA targeting specificity of Cpf1 PAM variants. A. DNA double-strand Breaks Labeling In Situ and Sequencing (BLISS) for 4 target sites (VEGFA, GRIN2B, EMX1, and DNMT1) in HEK293 cells. The log 10 double-strand break (DSB) scores for BLISS are indicated by the purple heat map, and the relative PAM cleavage rates from the in vitro cleavage assay are indicated by the blue heat map. Mismatches in the last three bases of the guide are not highlighted as they do not impact cleavage efficiency. B. Evaluation of an additional target site with known TTTV off-target sites, demonstrating the contribution of PAM preference to off-target activity. C. Addition of a K949A mutation reduces off-target DNA cleavage. D. Combining K949A with the S542R/K548V/N552R and S542R/K607R PAM variants retains high levels of on-target activity for their preferred PAMs.

Genome-wide editing specificity of the RR and RVR variants was evaluated using BLISS (double-strand breaks labeling in situ and sequencing), which quantifies DNA double-stranded breaks (DSBs) across the genome. To compare the variants to WT, analysis was restricted to target sites bearing PAMs that can be reliably cleaved by all three enzymes; TTTV was the only PAM that met this criterion, although it has lower activity for the RR variant. For three of the four target sites evaluated (VEGFA, GRIN2B, and DNMT1), no off-target activity was detected from deep sequencing of any of the BLISS-identified loci (FIG. 27a), either for WT or for the variants. For the fourth target site (EMX1), BLISS identified 6 off-target sites with detectable indels; all 6 sites had a TTCA PAM and no more than one mismatch in the first 19 bp of the guide. Both variants had increased activity at these off-target sites compared to WT, consistent with their increased ability to recognize TTCA PAMs. On the other hand, when targeting a different site with known TTTV off-target sites, the variants exhibited reduced off-target activity (FIG. 27b), which is also consistent with PAM preference. Collectively, these results indicate that the variants retain a high level of editing specificity that is comparable to WT AsCpf1.

Figures 27B, 27C, 27D:
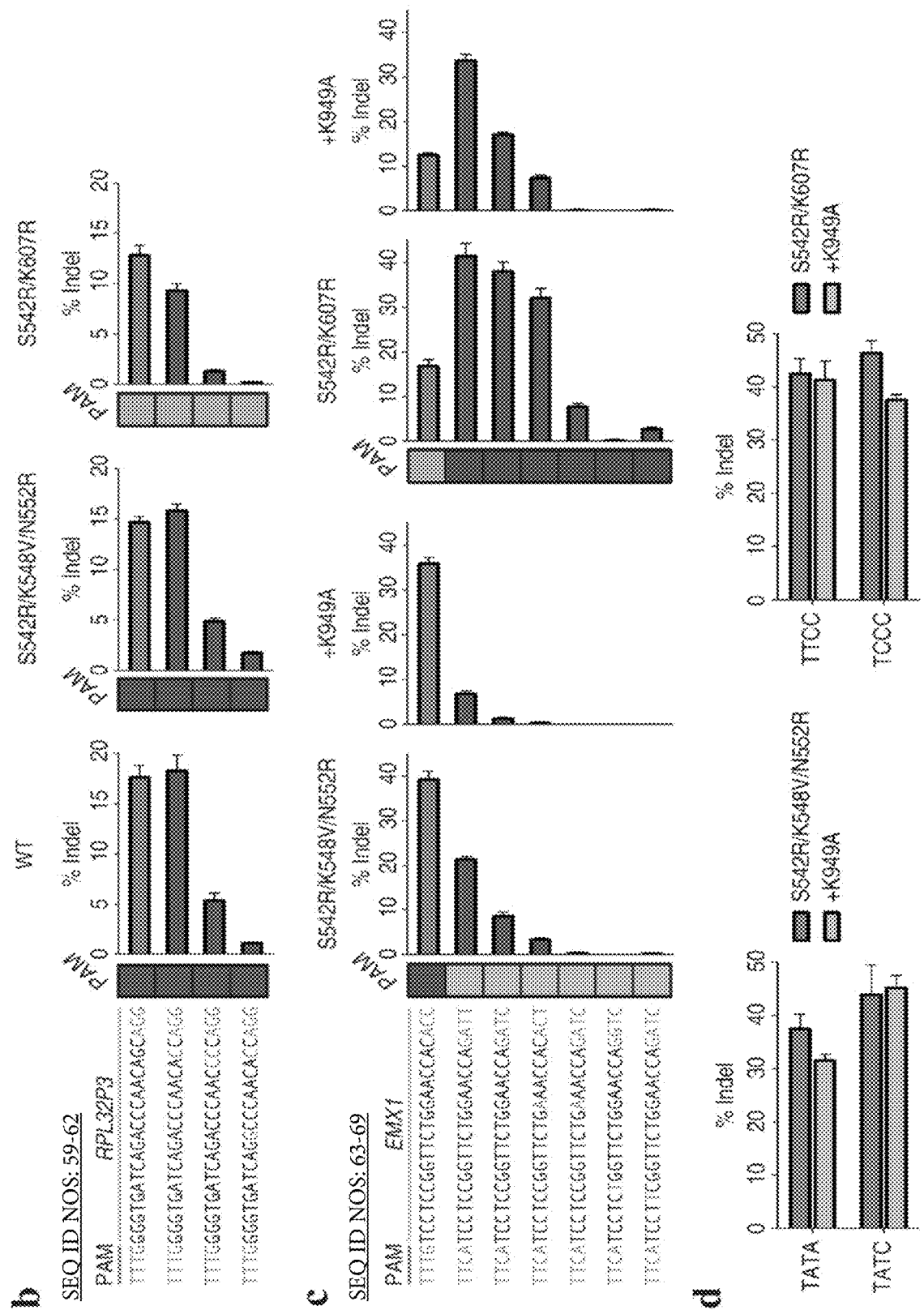
Figure 28:
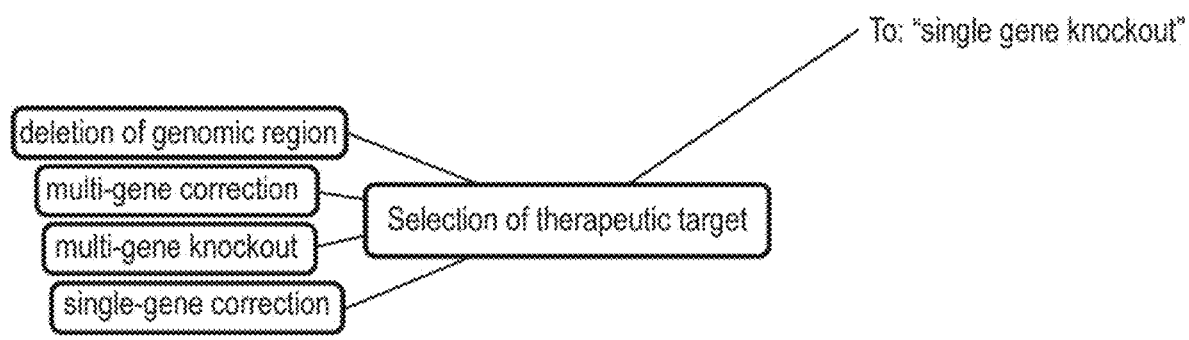
FIG. 28: Is a diagram depicting example parameters to be selected and optimized in accordance with certain example embodiments.
Figure 28:
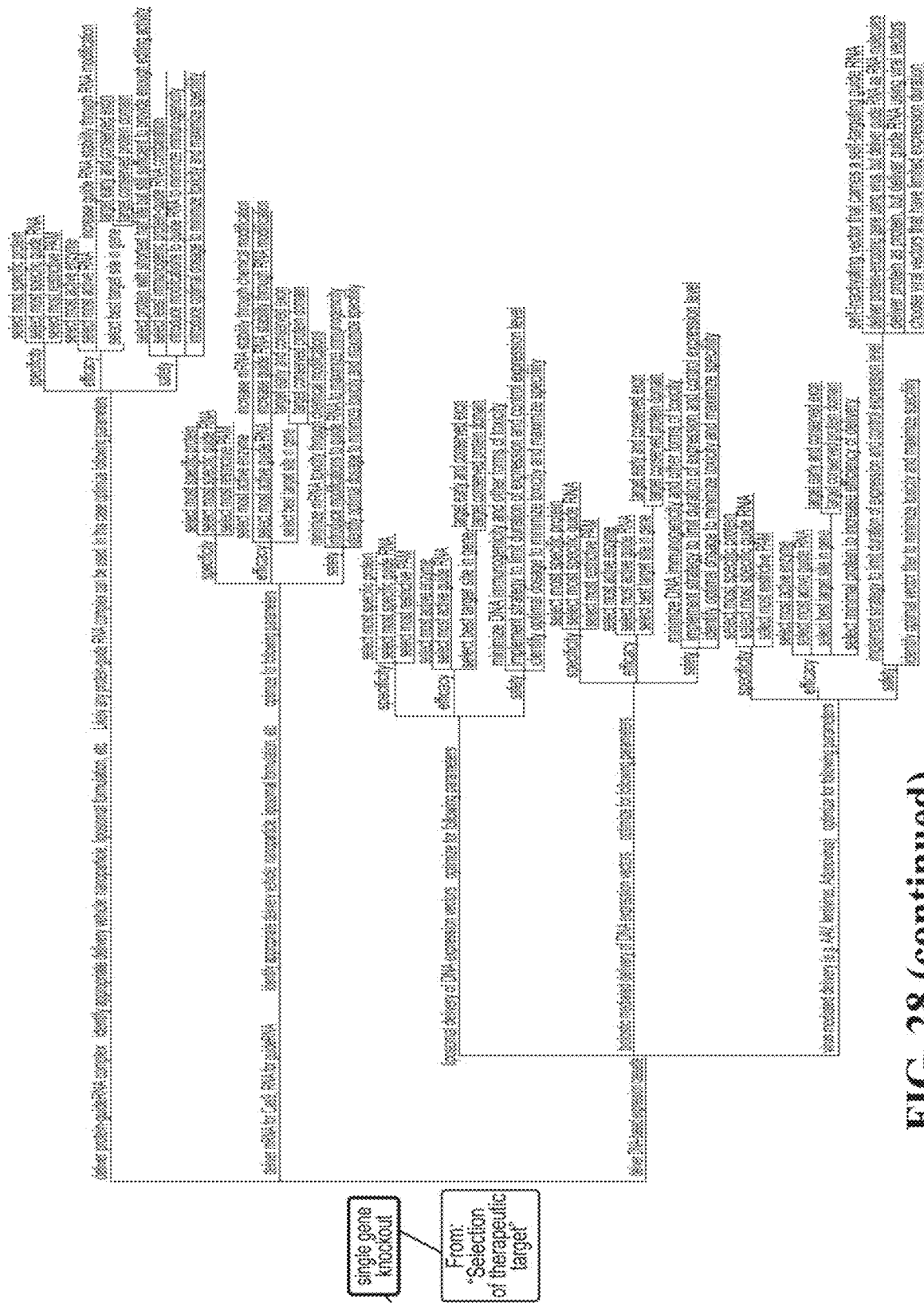
Figure 29:
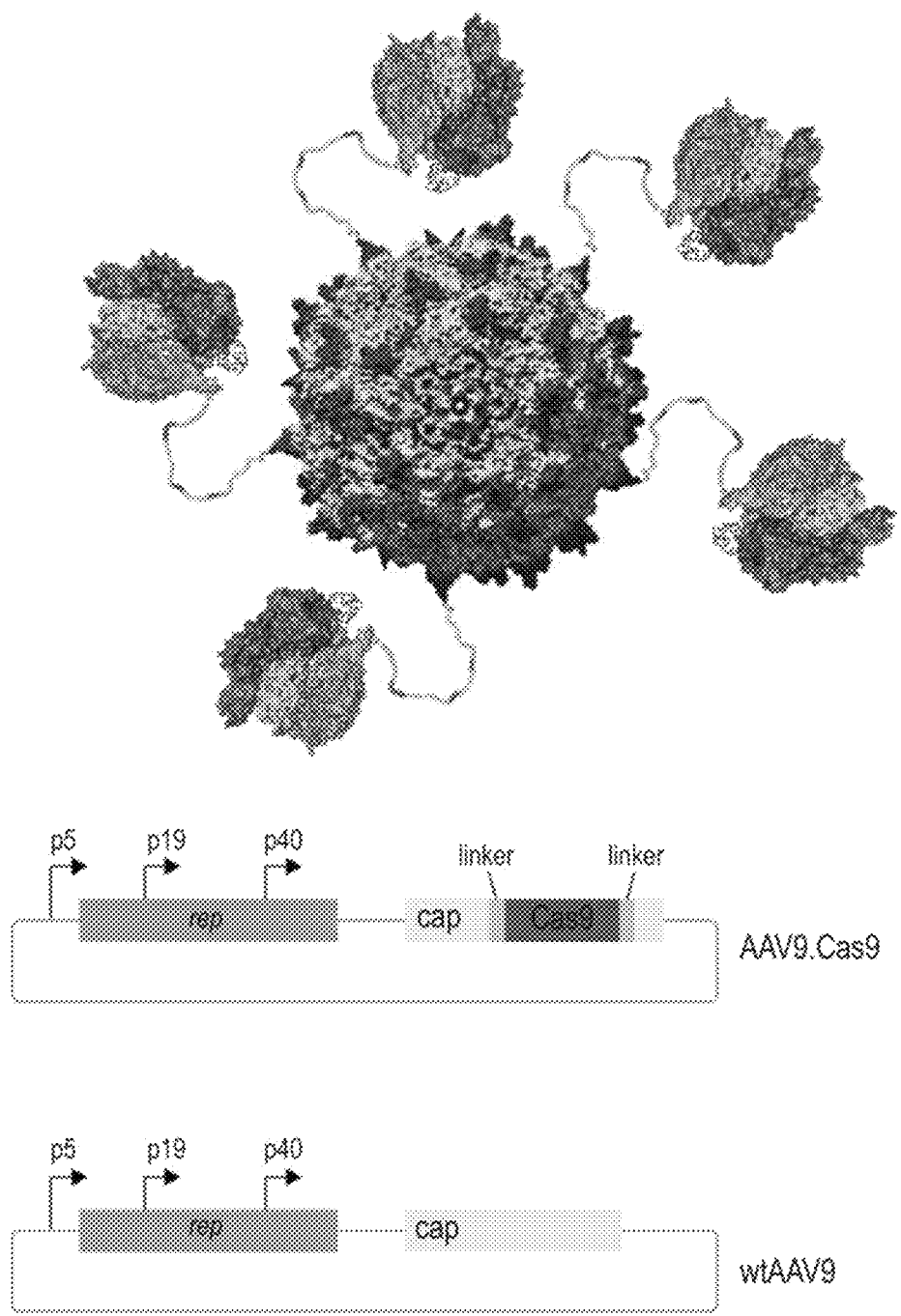
FIG. 29 shows illustrations of AAV-CRISPR protein of the invention, wherein Cas9 protein is fused or tethered to VP3, for example at the N-terminus of VP3. Cas9 is attached to some, but not all VP3 subunits to avoid steric blocking of cell entry sites on AAV surface. In the AAV9.Cas9 vector, a Cas9 protein fused or tethered to the C-term of VP1, VP2 or VP3 is depicted.
Figure 30A:
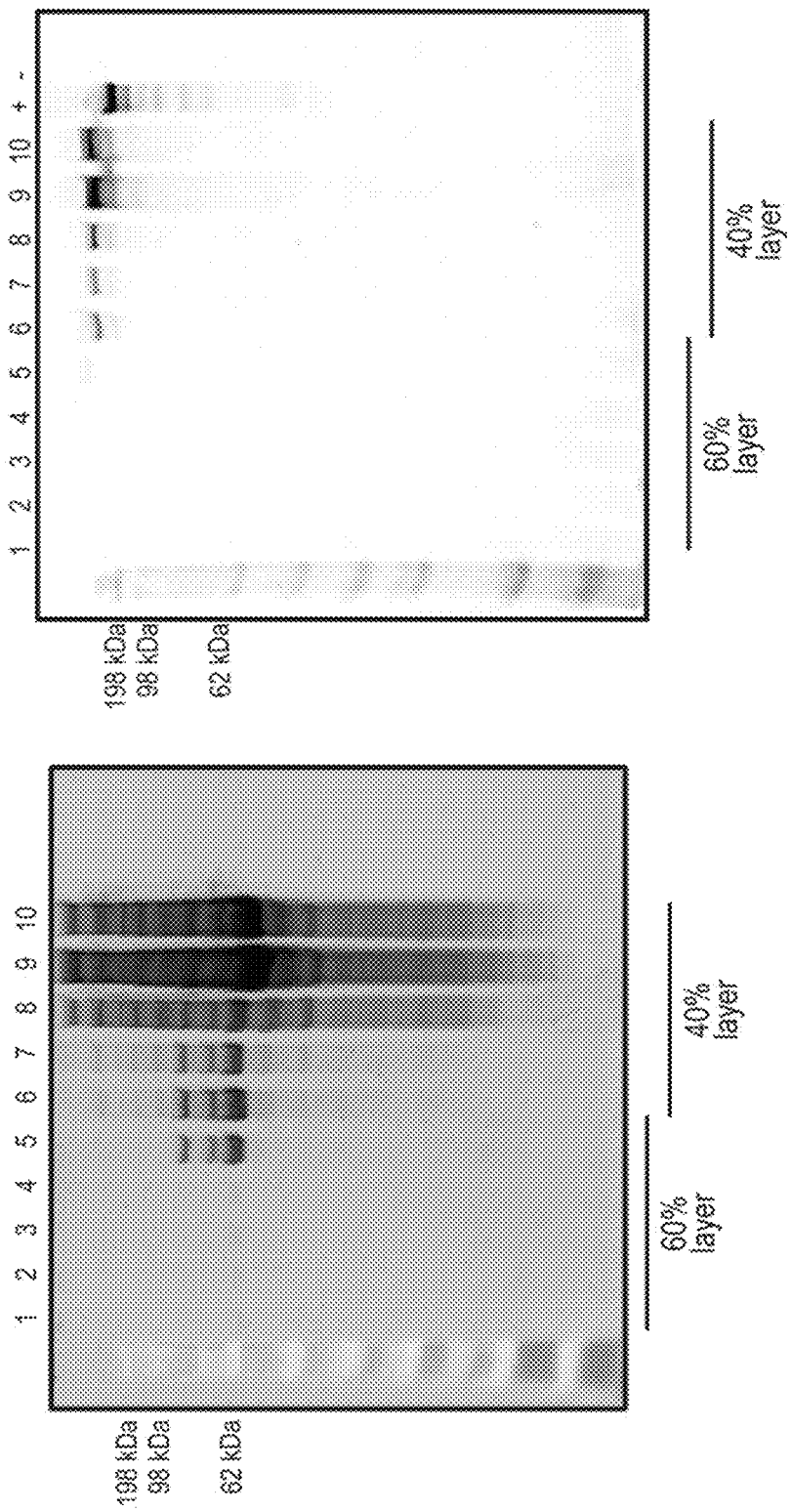
FIG. 30A-30B shows a Western blot confirming expression of Cas9-VP3 fusion proteins in cells transfected with plasmids encoding for Cas9 and Cas9-VP3 fusions (AAVCas9:wt 1:6). (A) Left panel: SYPRO Ruby protein staining of fractions from AAVCas9:wt 1:6. Right panel: Anti-SpCas9 blotting of fractions from AAVCas9:wt 1:6. (B) Left panel: SYPRO Ruby protein staining of fractions from wtAAV9. Right panel: Anti-SpCas9 blotting of fractions from wtAAV9.
Figure 30B:
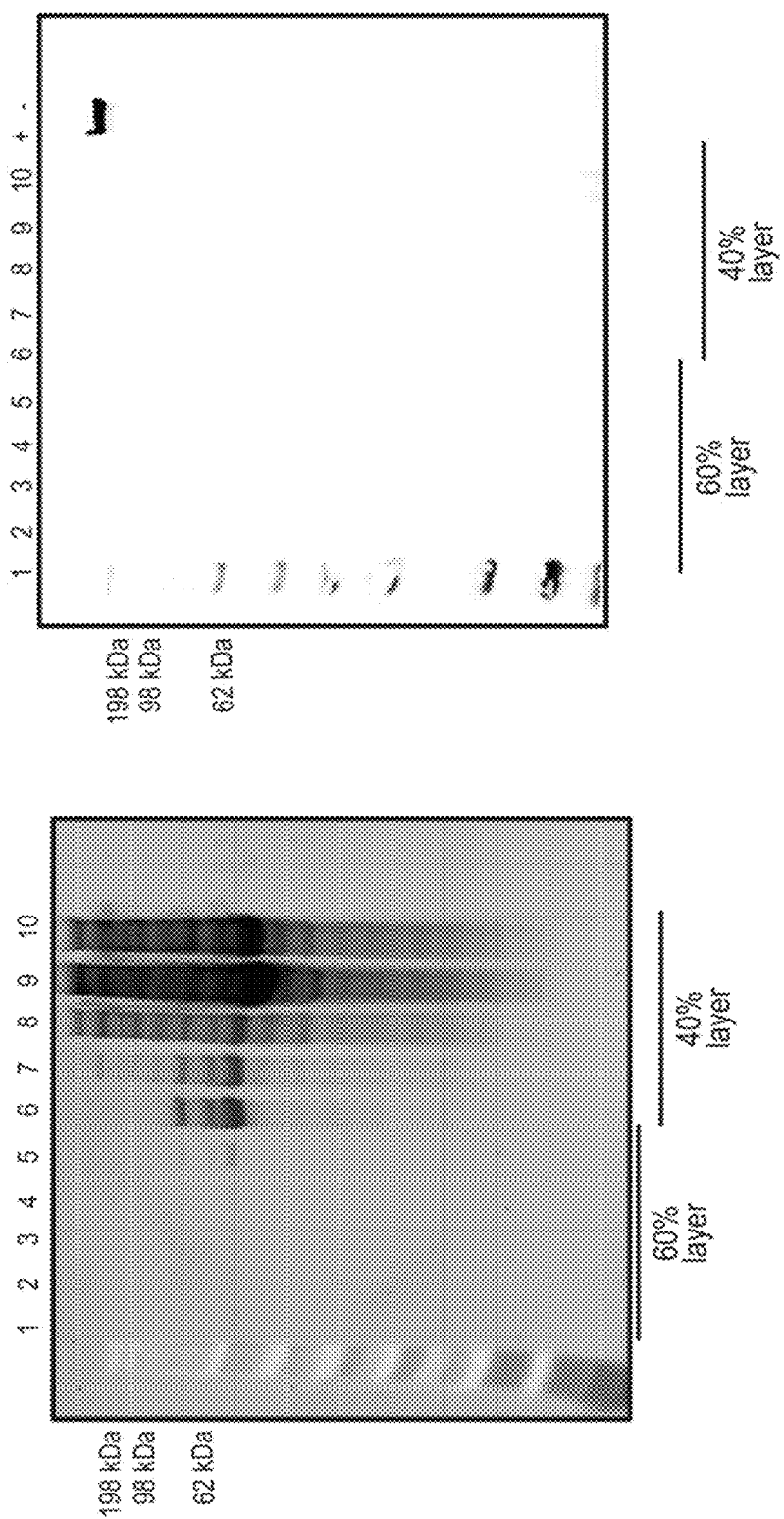
Figure 31:
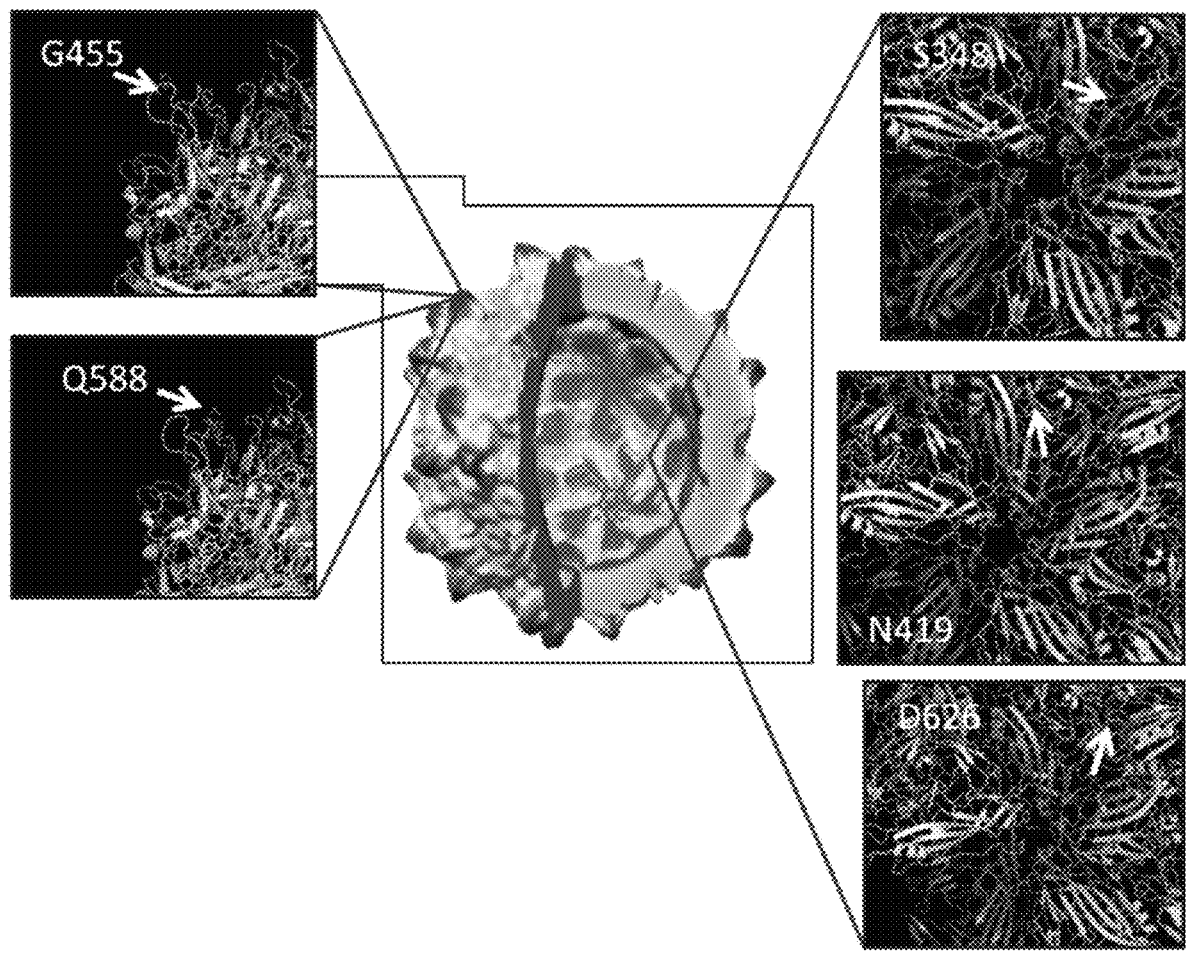
FIG. 31 illustrates exterior loops and interior sites in AAV9 VP3 for protein insertion.
Figure 32:
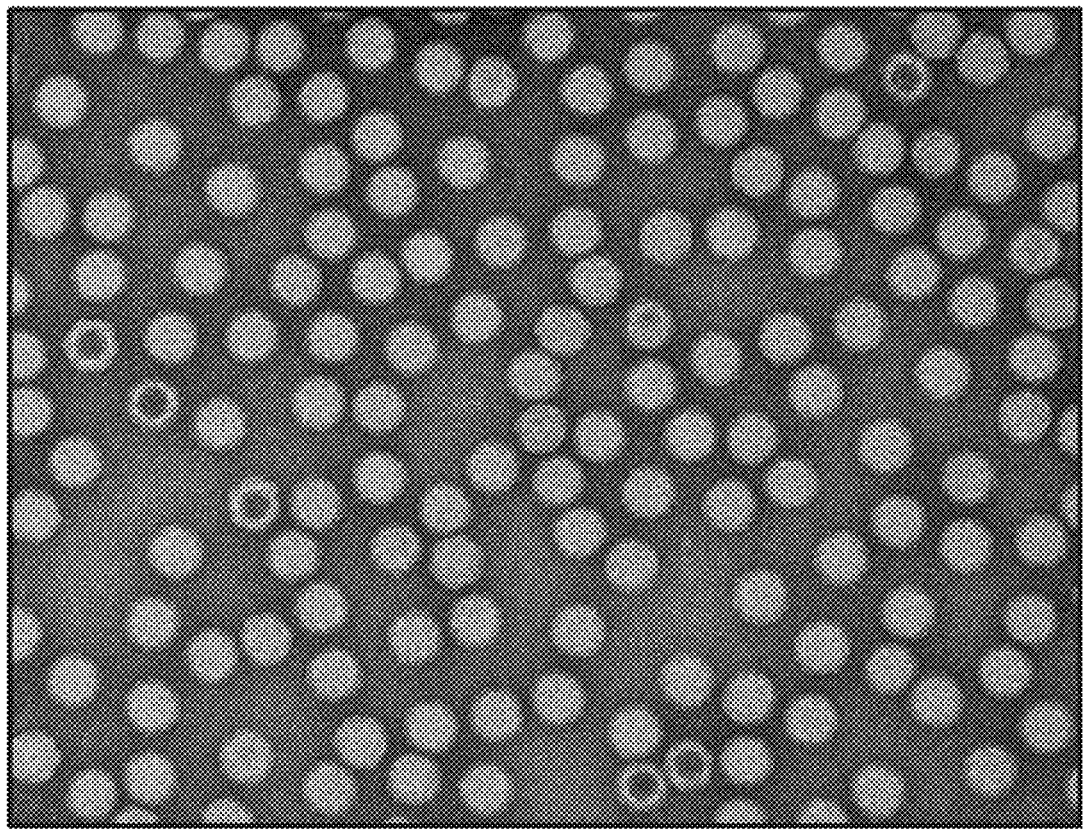
FIG. 32 depicts electron micrography of wtAAV. Dark particle centers indication empty particles.
Figure 33:
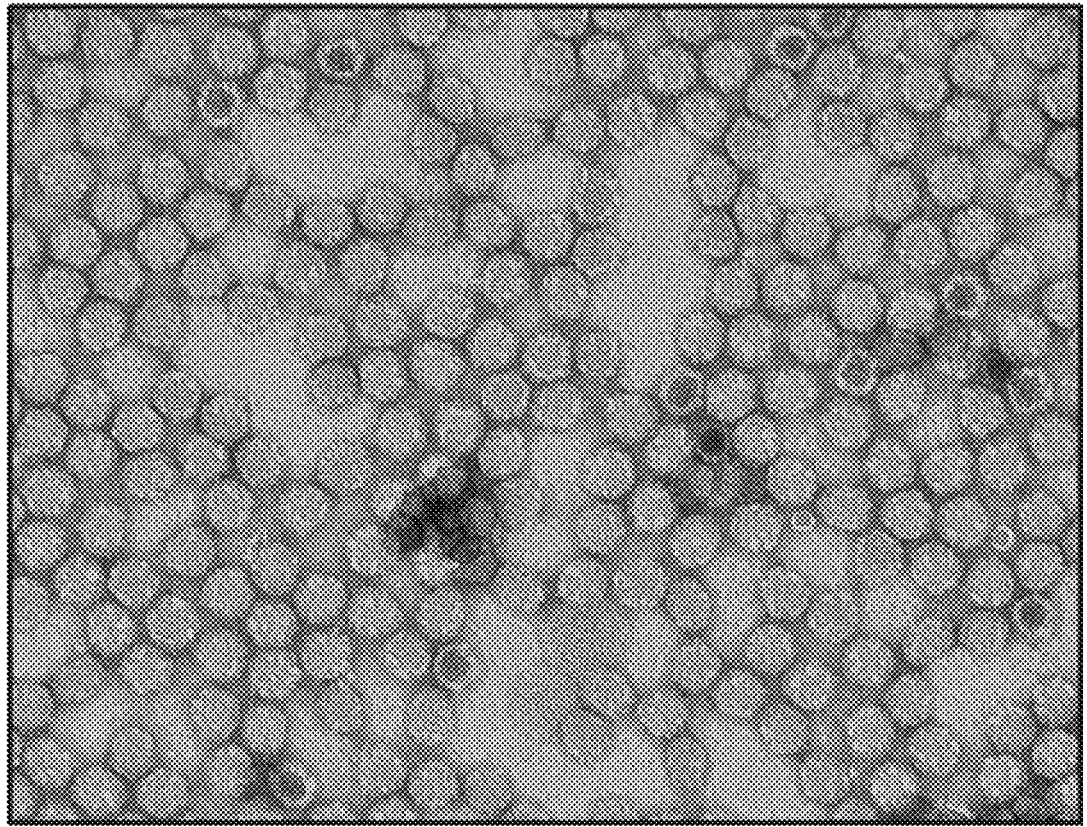
FIG. 33 depicts electron micrography of AAV.Cas9 virus particles comprising 50wtAAV:10AAVCas9.
Figure 34:
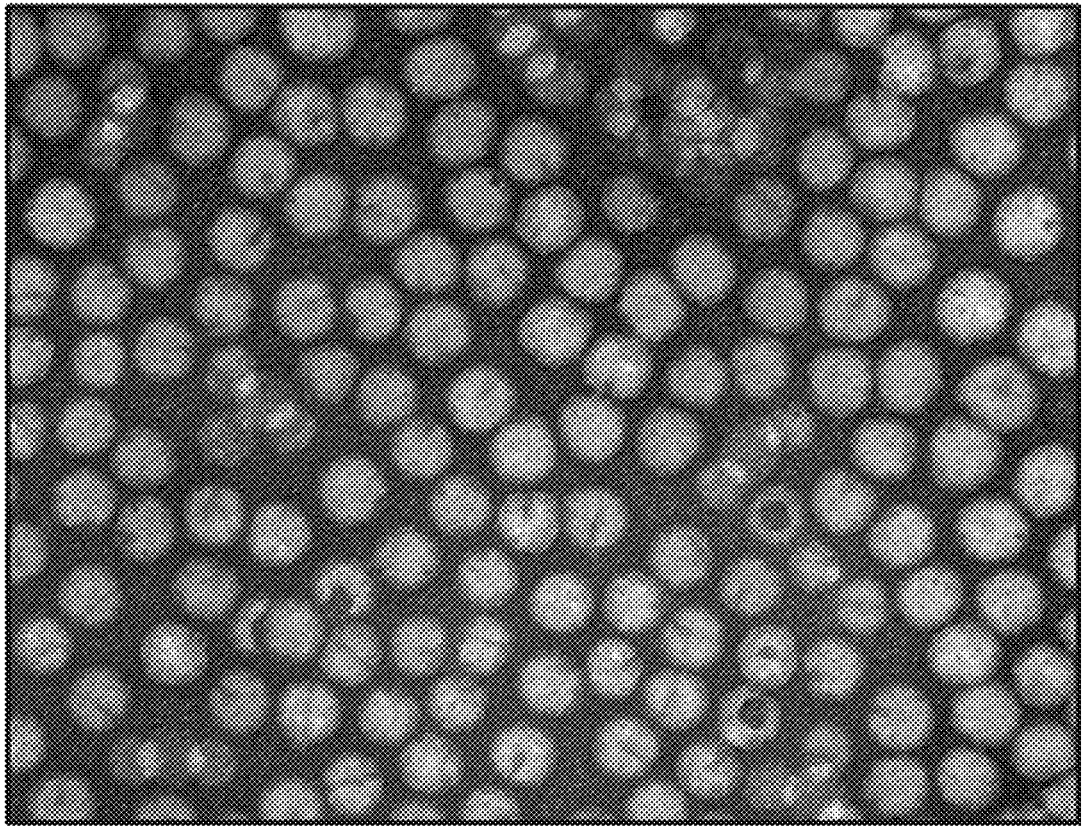
FIG. 34 depicts electron micrography of AAV.Cas9 virus particles comprising 30wtAAV:30AAVCas9.
Figure 35A:
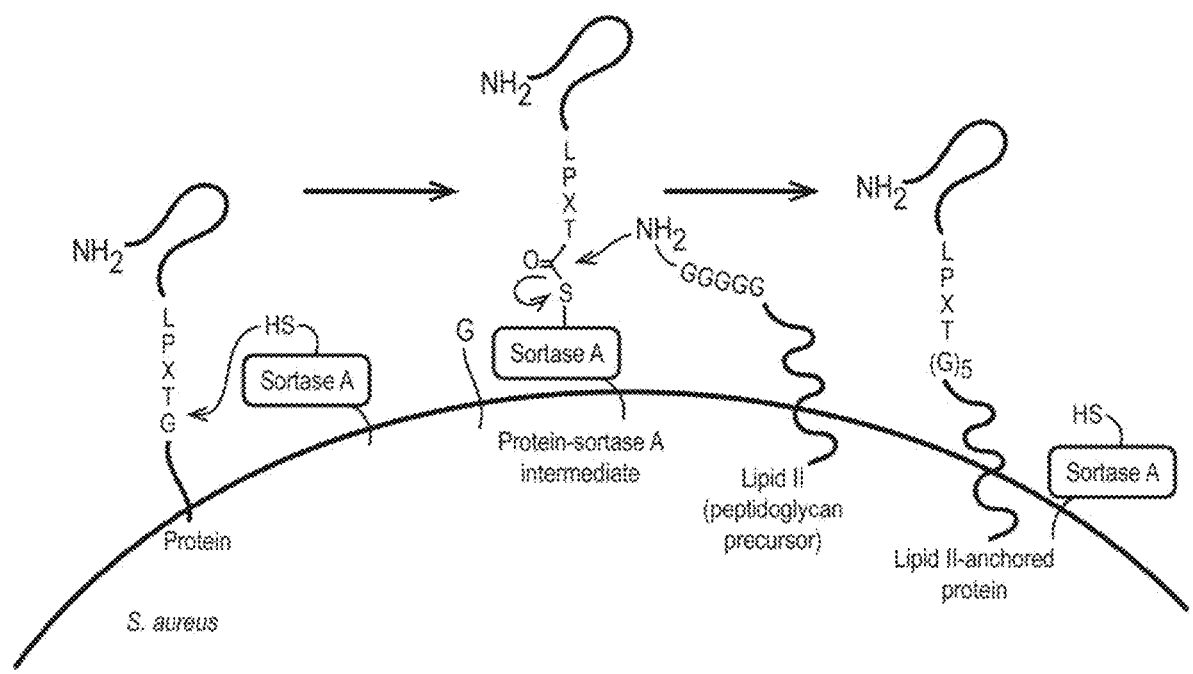
FIG. 35A-35B depicts sortase-mediated protein linkage. (A) schematic of proteins anchored to a cell wall via sortase in Gram-positive bacteria is shown (see, Guimares, et al., Nat. Prot. 2013). (B) linkage of Cas9 to AAV by TEV-sortase method. CRISPR protein modified at its C terminus with the LPXTG sortase-recognition motif followed by a handle for purification (often His6) is incubated with sortase A. Sortase cleaves the threonine-glycine bond and forms an acyl intermediate with threonine. Addition of TEV-cleaved AAV ("probe") comprising N-terminal glycine residues ligates the AAV to the C terminus of the CRISPR protein (see, Guimares, et al., Nat. Prot. 2013).
Figure 35B:
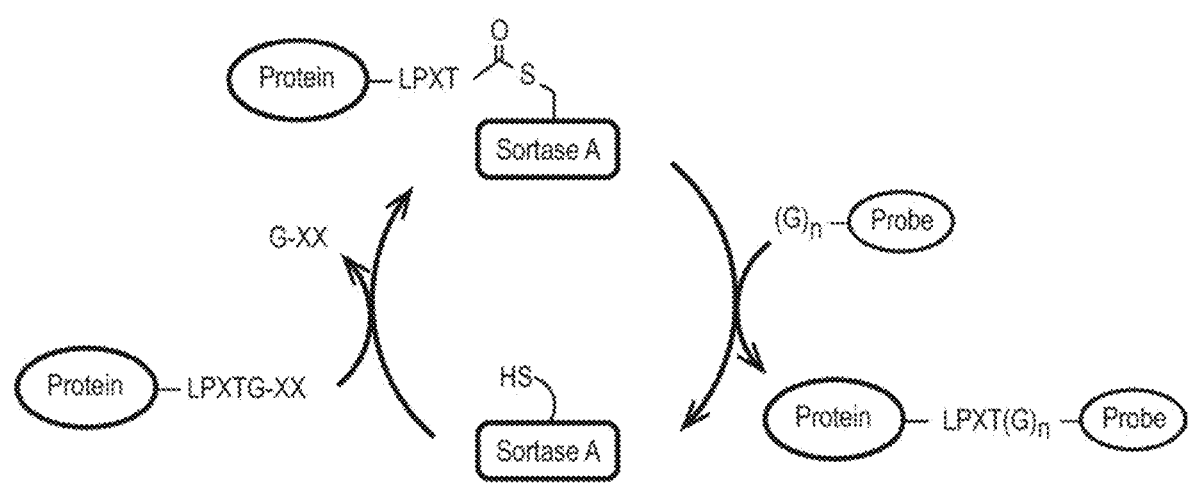
Figure 36:
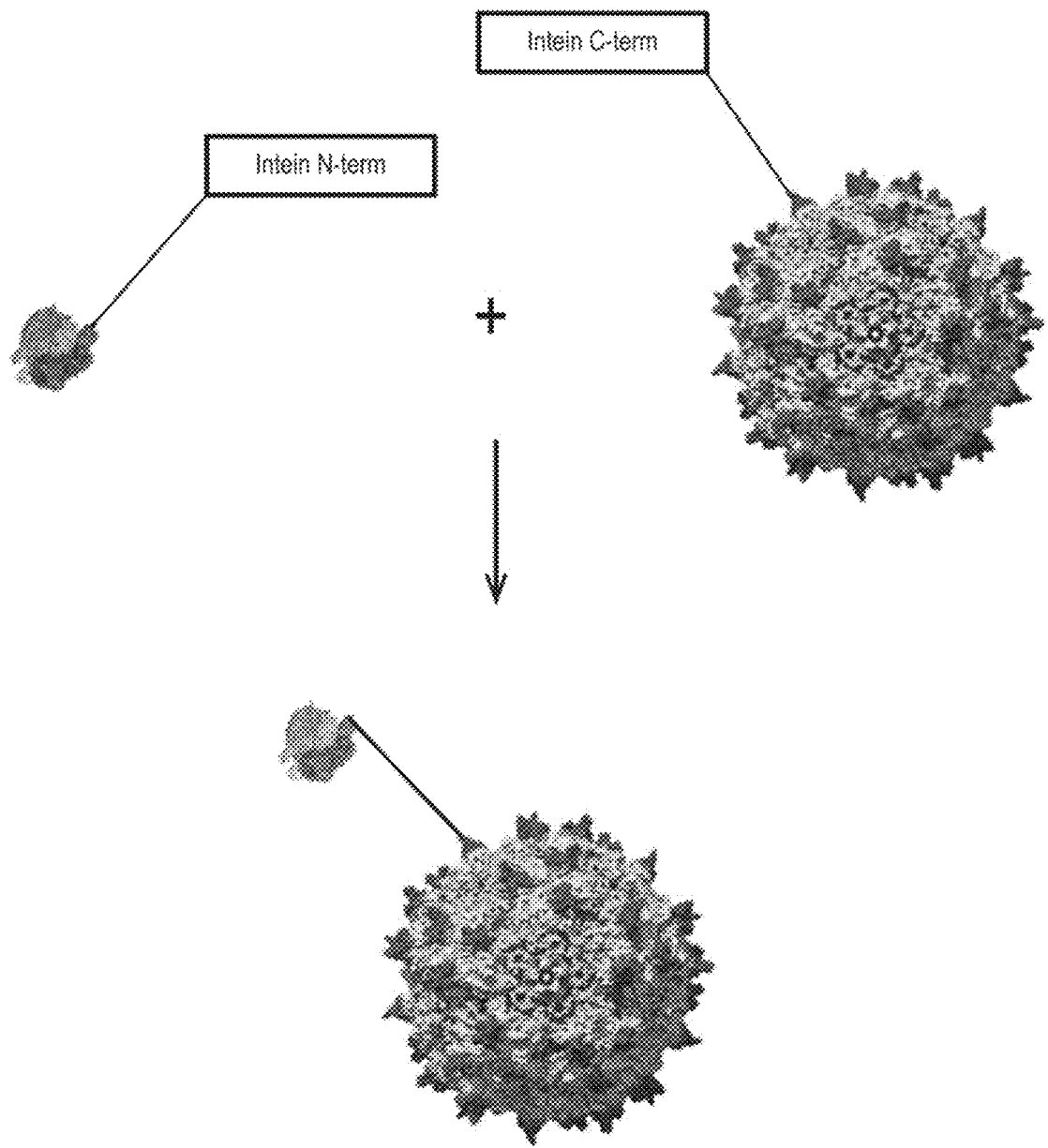
FIG. 36 depicts linkage of Cas9 to AAV by split intein reconstitution.
Figure 37:
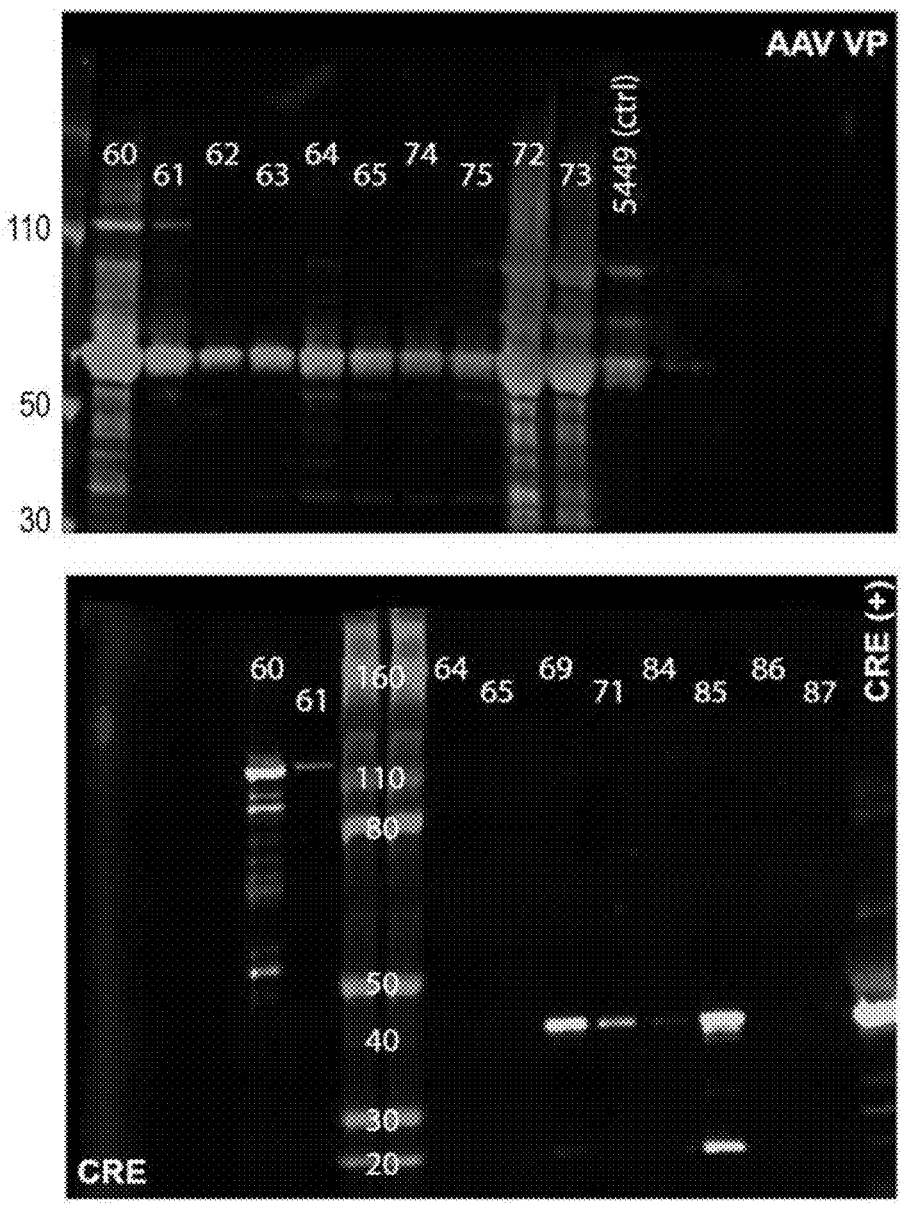
FIG. 37A-37B shows interior packaging of proteins.

Whether specificity can be improved by removing non-specific contacts, e.g. between positively-charged or polar residues and the target DNA, was tested. K949A, which is located in the cleft of the protein that is hypothesized to interact with the non-target DNA strand, was tested in combination with the RR and RVR variants, K949A reduced cleavage at all off-target sites assessed while maintaining high levels of on-target activity (FIG. 27C).

Because Cpf1-family enzymes have strong sequence and structural homology, the S542, K548, N552, and K607 positions in AsCpf1 have unambiguous correspondences in other Cpf1 orthologs. On the basis of crystal structure, LbCpf1 can similarly be engineered to recognize TYCV/CCCC and TATV PAMs, e.g., by the mutations G532R/K595R and G532R/K538V/Y542R, respectively.

TABLE

List of guide sequences used for BLISS and indel analysis.

| Gene or Description | PAM | Guide |
|---|---|---|
| Plasmid interference | Varies | CCGATGGTCCATGTCTGTTACTCGCCTGTC (SEQ ID NO: 265) |
| VEGFA | TATC | AAATTCCAGCACCGAGCGCCCTG (SEQ ID NO: 266) |
| DNMT1 | TATA | AAGAAATATTACAACATATAAAA (SEQ ID NO: 267) |
| DNMT1 | TCCC | GTCACCCCTGTTTCTGGCACCAG (SEQ ID NO: 268) |
| DNMT1 | TTCC | TGGTGCCAGAAACAGGGGTGACG (SEQ ID NO: 269) |
| In vitro cleavage | NNNN | GAGAAGTCATTTAATAAGGCCACT (SEQ ID NO: 270) |
| CFTR | TATA | GCAGTTGTCGCAGTTTTACAACC (SEQ ID NO: 271) |
| CFTR | TATG | ACCCGGATAACAAGGAGGAACGC (SEQ ID NO: 272) |

TABLE-continued

List of guide sequences used for BLISS and indel analysis.

| Gene or Description | PAM | Guide |
|---|---|---|
| CFTR | TATA | GAGTTGATTGGATTGAGAATAGA (SEQ ID NO: 273) |
| CFTR | TATC | GCCTCTCCCTGCTCAGAATCTGG (SEQ ID NO: 274) |
| VEGFA | TATG | TAGCTGTTTGGGAGGTCAGAAAT (SEQ ID NO: 275) |
| VEGFA | TATA | GACATGTCCCATTTGTGGGAACT (SEQ ID NO: 276) |
| VEGFA | TATG | TTCGGGTGCTGTGAACTTCCCTC (SEQ ID NO: 277) |
| EMX1 | TATG | ACCCACTGCGTGGGTTCCCATGA (SEQ ID NO: 278) |
| EMX1 | TATC | CCAAGTCAAACTTCTCTTCAGTC (SEQ ID NO: 279) |
| EMX1 | TATA | CCCTTTAGGACACATGCTGTCTA (SEQ ID NO: 280) |
| DNMT1 | TATC | AGTGCACCTTCGGCGTGCTGCAG (SEQ ID NO: 281) |
| DNMT1 | TATA | CCCACCATGACAGGAAGAACGGC (SEQ ID NO: 282) |
| DNMT1 | TATG | AGGCGCTTCCCCAGCACAAACTG (SEQ ID NO: 283) |
| CFTR | TTCG | GCGATGTTTTTTCTGGAGATTTA (SEQ ID NO: 284) |
| DNMT1 | TTCA | GCTAAAATAAAGGAGGAGGAAGC (SEQ ID NO: 285) |
| DNMT1 | TCCC | GTCACCCCTGTTTCTGGCACCAG (SEQ ID NO: 286) |
| DNMT1 | TTCC | TGGTGCCAGAAACAGGGGTGACG (SEQ ID NO: 287) |
| DNMT1 | TTCA | GTCTCCGTGAACGTTCCCTTAGC (SEQ ID NO: 288) |
| DNMT1 | TTCA | CGGAGACTGAACACTCCTCAAAC (SEQ ID NO: 289) |
| EMX1 | TTCG | TGGCAATGCGCCACCGGTTGATG (SEQ ID NO: 290) |
| VEGFA | TTCC | CTGTGGTGGCCGAGCGCCCCCTA (SEQ ID NO: 291) |
| VEGFA | TCCA | GTCCCAAATATGTAGCTGTTTGG (SEQ ID NO: 292) |
| VEGFA | TCCG | CACGTAACCTCACTTTCCTGCTC (SEQ ID NO: 293) |
| VEGFA | TCCC | TCTTTAGCCAGAGCCGGGGTGTG (SEQ ID NO: 294) |
| VEGFA | TCCG | CCCCCGGAAACTCTGTCCAGAGA (SEQ ID NO: 295) |
| VEGFA | TCCG | GGGGCGGATGGGTAATTTTCAGG (SEQ ID NO: 296) |
| VEGFA | TCCA | ATAGATCTGTGTGTCCCTCTCCC (SEQ ID NO: 297) |
| VEGFA | TTCC | AAAGCCCATTCCCTCTTTAGCCA (SEQ ID NO: 298) |
| VEGFA | TCCC | CCCACCCCCTTTCCAAAGCCCAT (SEQ ID NO: 299) |
| CFTR | GTCG | AAAATTTTACACCACAAAATGTT (SEQ ID NO: 300) |
| CFTR | ACCA | AAGATGATATTTTCTTTAATGGT (SEQ ID NO: 301) |
| CFTR | ACCA | TTAAAGAAAATATCATCTTTGGT (SEQ ID NO: 302) |
| CFTR | ATCC | TAAACTCATTAATGCCCTTCGGC (SEQ ID NO: 303) |
| CFTR | ATCC | AGGAAAACTGAGAACAGAATGAA (SEQ ID NO: 304) |
| EMX1 | ATCA | CATCAACCGGTGGCGCATTGCCA (SEQ ID NO: 305) |
| EMX1 | GTCC | TCCCCATTGGCCTGCTTCGTGGC (SEQ ID NO: 306) |
| EMX1 | CCCG | GGCTTCAAGCCCTGTGGGGCCAT (SEQ ID NO: 307) |
| EMX1 | ATCG | ATGTCACCTCCAATGACTAGGGT (SEQ ID NO: 308) |
| EMX1 | ATCG | ATGTCCTCCCCATTGGCCTGCTT (SEQ ID NO: 309) |
| VEGFA | CCCA | TTCCCTCTTTAGCCAGAGCCGGG (SEQ ID NO: 310) |
| VEGFA | CTCG | GCCACCACAGGGAAGCTGGGTGA (SEQ ID NO: 311) |
| VEGFA | GTCC | CAAATATGTAGCTGTTTGGGAGG (SEQ ID NO: 312) |
| VEGFA | GCCG | AGCGCCCCCTAGTGACTGCCGTC (SEQ ID NO: 313) |
| VEGFA | GCCC | ATTCCCTCTTTAGCCAGAGCCGG (SEQ ID NO: 314) |
| VEGFA | CCCG | GCTCTGGCTAAAGAGGGAATGGG (SEQ ID NO: 315) |
| VEGFA | GCCA | GAGCCGGGGTGTGCAGACGGCAG (SEQ ID NO: 316) |
| VEGFA | CTCG | CTCCATTCACCCAGCTTCCCTGT (SEQ ID NO: 317) |
| VEGFA | GTCA | GAAATAGGGGGTCCAGGAGCAAA (SEQ ID NO: 318) |
| VEGFA | CTCC | AGTCCCAAATATGTAGCTGTTTG (SEQ ID NO: 319) |
| VEGFA | GCCC | TGGGCTCTCTGTACATGAAGCAA (SEQ ID NO: 320) |
| VEGFA | ACCA | CAGGGAAGCTGGGTGAATGGAGC (SEQ ID NO: 321) |

TABLE-continued

List of guide sequences used for BLISS and indel analysis.

| Gene or Description | PAM | Guide |
|---|---|---|
| VEGFA | ACCC | CGGCTCTGGCTAAAGAGGGAATG (SEQ ID NO: 322) |
| VEGFA | CCCA | GCTTCCCTGTGGTGGCCGAGCGC (SEQ ID NO: 323) |
| VEGFA | GCCG | TCTGCACACCCCGGCTCTGGCTA (SEQ ID NO: 324) |
| VEGFA | GCCC | CCTAGTGACTGCCGTCTGCACAC (SEQ ID NO: 325) |
| VEGFA | ACCC | CCTATTTCTGACCTCCCAAACAG (SEQ ID NO: 326) |
| VEGFA | GCCA | CCACAGGGAAGCTGGGTGAATGG (SEQ ID NO: 327) |
| VEGFA | GTCC | TCACTCTCGAAGACGCTGCTCGC (SEQ ID NO: 328) |
| VEGFA | GTCA | CTAGGGGCGCTCGGCCACCACA (SEQ ID NO: 329) |
| VEGFA | GCCG | GGGTGTGCAGACGGCAGTCACTA (SEQ ID NO: 330) |
| VEGFA | CTCG | AAGACGCTGCTCGCTCCATTCAC (SEQ ID NO: 331) |
| VEGFA | CCCG | CTCCAACGCCCTCAACCCCACAC (SEQ ID NO: 332) |
| VEGFA | CTCC | TGGACCCCTATTTCTGACCTCC (SEQ ID NO: 333) |
| VEGFA | ATCC | TGGAGTGACCCCTGGCCTTCTCC (SEQ ID NO: 334) |
| VEGFA | ACCC | CCTTTCCAAAGCCCATTCCCTCT (SEQ ID NO: 335) |
| VEGFA | CCCC | CCACCCCTTTCCAAAGCCCATT (SEQ ID NO: 336) |
| VEGFA | TTTG | CTAGGAATATTGAAGGGGCAGG (SEQ ID NO: 337) |
| GRIN2B | TTTG | GTGCTCAATGAAAGGAGATAAGG (SEQ ID NO: 338) |
| DNMT1 | TTTG | AAGAAATATTACAACATATAAAA (SEQ ID NO: 339) |
| EMX1 | TTTG | TCCTCCGGTTCTGGAACCACACC (SEQ ID NO: 340) |
| RPL32P3 | TTTG | GGGTGATCAGACCCAACAGCAGG (SEQ ID NO: 341) |
| CFTR | TTTA | ATGGTGCCAGGCATAATCCAGGA (SEQ ID NO: 342) |
| DNMT1 | TTTC | CCTTCAGCTAAAATAAAGGAGGA (SEQ ID NO: 343) |
| DNMT1 | TTTG | AGGAGTGTTCAGTCTCCGTGAAC (SEQ ID NO: 344) |
| DNMT1 | TTTC | CTGATGGTCCATGTCTGTTACTC (SEQ ID NO: 345) |

TABLE-continued

List of guide sequences used for BLISS and indel analysis.

| Gene or Description | PAM | Guide |
|---|---|---|
| DNMT1 | TTTA | GCTGAAGGGAAATAAAAGGAAAA (SEQ ID NO: 346) |
| EMX1 | TTTG | GGGAGGCCTGGAGTCATGGCCCC (SEQ ID NO: 347) |
| EMX1 | TTTG | TGGTTGCCCACCCTAGTCATTGG (SEQ ID NO: 348) |
| VEGFA | TTTA | GCCAGAGCCGGGGTGTGCAGACG (SEQ ID NO: 349) |
| VEGFA | TTTC | CAAAGCCCATTCCCTCTTTAGCC (SEQ ID NO: 350) |
| PCSK9 (Neuro2a) | TCCC | GTCCCAGGAGGATGGCCTGGCTG (SEQ ID NO: 351) |
| PCSK9 (Neuro2a) | TCCC | AGGAGGATGGCCTGGCTGATGAG (SEQ ID NO: 352) |
| PCSK9 (Neuro2a) | TTCA | ATCTGTAGCCTCTGGGTCTCCTC (SEQ ID NO: 353) |
| PCSK9 (Neuro2a) | TCCC | TGGCTTCTTGGTGAAGATGAGCA (SEQ ID NO: 354) |
| PCSK9 (Neuro2a) | TTCC | TCAATGTACTCCACATGGGCAA (SEQ ID NO: 355) |
| PCSK9 (Neuro2a) | TCCA | TGGGATGCTCTGGGCGAAGACAA (SEQ ID NO: 356) |
| PCSK9 (Neuro2a) | TCCC | GATGGGCACCCTGGATGCTGGTA (SEQ ID NO: 357) |
| PCSK9 (Neuro2a) | TCCC | GGCCGCTGACCACACCTGCCAGG (SEQ ID NO: 358) |
| PCSK9 (Neuro2a) | CCCC | GATGGGCACCCACTGCTCTGCGT (SEQ ID NO: 359) |
| PCSK9 (Neuro2a) | TTTG | TTCAATCTGTAGCCTCTGGGTCT (SEQ ID NO: 360) |
| PCSK9 (Neuro2a) | TTTA | TGACCTCTTCCCTGGCTTCTTGG (SEQ ID NO: 361) |
| PCSK9 (Neuro2a) | TTTG | TCTTCGCCCAGAGCATCCCATGG (SEQ ID NO: 362) |

Activity of Cpf1 Cleavage in 293FT Cells

Cpf1 proteins codon optimized for human expression were synthesized with an N-terminal nuclear localization tag and cloned into the pcDNA3.1 CMV expression plasmid by Genscript. PCR amplicons comprised of a U6 promoter driving expression of the crRNA sequence were generated using Herculase II (Agilent Technologies). 400 ng of Cpf1 expression plasmids and 100 ng of the crRNA PCR products were transfected into 24-well plates of HEK293FT cells at 75-90% confluency using Lipofectamine 2000 reagent (Life Technologies). Genomic DNA was harvested using QuickExtract™ DNA Extraction Solution (Epicentre).

Deep Sequencing to Characterize Cpf1 Indel Patterns in 293FT Cells

HEK293FT cells were transfected and harvested as described for assessing activity of Cpf1 cleavage. The genomic region flanking DNMT1 targets were amplified using a two-round PCR region to add Illumina P5 adapters as well as unique sample-specific barcodes to the target amplicons. PCR products were ran on 2% E-gel (Invitrogen) and gel-extracted using QiaQuick Spin Column (Qiagen) as per the manufacturer's recommended protocol. Samples were pooled and quantified by Qubit 2.0 Fluorometer (Life Technologies). The prepared cDNA libraries were sequenced on a MiSeq (Illumina). Indels were mapped using a Python implementation of the Geneious 6.0.3 Read Mapper.

Example 8: Exemplary Lipid Particles

A lipid particle of the invention can be prepared as follows. Compound 80-014B is prepared using N,N'-dimethylpropane-1,3-diamine and 2-(decyldisulfanyl)ethyl acrylate. In a 5-mL Teflon-lined glass screw-top vial, the acrylate with disulfide bonds is added to the amine at a molar ratio of 2.4:1. The mixture is stirred at 90° C. for two days. After cooling, the lipid-like compound formed may be used without purification or purified using flash chromatography on silica gel. The prepared compound optionally is characterized by proton nuclear magnetic resonance.

The lipid-like compound prepared above is dissolved in sodium acetate solution (25 mM, pH=5.5) at a concentration of 1 mg/mL. Optionally, cholesterol and 1,2-dioleoyl-sn-glycero-3-phosphoethanolamine ("DOPE") is also included.

A synthetic lipid nanoparticle, comprising either pure synthetic lipid or synthetic lipid in combination with an excipient, such as cholesterol, PEGylated lipid or DOPE, at a particular concentration (for example, 0.1 mg/ml-2 mg/ml), is mixed with a viral particles (for example, an AAV viral particle). In a typical experiment, the AAV concentration is 109 AAV/μg lipid nanoparticle. After mixing, the mixture is left at room temperature for 15 min. Before imaging, the sample is mixed using vortex for 1 min.

In one embodiment, an AAV composition, comprising AAV capsids or capsid subunit proteins is introduced into the resulting mixture and incubated for 15 minutes at room temperature. (The AAV capsids and capsid subunit proteins can be wild type capsid subunits or further contain hybrid AAV capsid subunits comprising heterologous proteins or peptides.) The weight ratio between the lipid-like compound and AVV component is varied, for example 5:1, 10:1, 20:1, or 50:1. The complex composition thus prepared is ready for use in cells.

Example 9: Hybrid AA V-Lipid Particle

Hybrid AAV-lipid particles were formulated by mixing AAV8 vector with lipid nanoparticles encasing purified negatively supercharged CRE recombinase protein ($10^9$ AAV virions per μg lipid). The hybrid AAV-lipid particles were used to infect HEK293T cells. Protein delivery of CRE by the hybrid AAV-lipid particle was compared to lipid-CRE formulation 48 hours post transfection using a DsRed reporter for CRE activity. (FIG. 44).

Example 10: Determination of Particle Size Diameter for AAV/Lipid Nanocomplexes

Diameter of the AAV/lipid nanocomplexes in diameter can be determined by imaging the complexes using Transmission Electron Microscopy (TEM). See FIGS. 32, 33, 34, 38.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed:

1. A method for developing or designing a CRISPR-Cas system-based therapy or therapeutic, comprising:
   selecting a set of candidate therapeutic target sequences for one or more loci in a target population, wherein the candidate therapeutic target sequences do not contain variants occurring above a threshold allele frequency in the target population;
   removing any candidate therapeutic target sequences having off-target candidates in haplotypes that occur in at least 0.1% of the target population from the set of candidate therapeutic target sequences to thereby define a final therapeutic target sequence set,
   preparing a set of one or more CRISPR-Cas systems based on the final therapeutic target sequence set; and
   delivering the one or more CRISPR-Cas systems to a cell, wherein the delivery comprises delivering gRNA and/or CRISPR effector protein, delivering guide RNA (gRNA) and/or CRISPR effector mRNA, or delivering gRNA and/or CRISPR effector as a DNA based expression system,
   wherein the one or more CRISPR-Cas systems comprises a CRISPR effector and one or more gRNAs capable of binding and cleaving one or more of the final therapeutic target sequences and generating one or more insertions, deletions, or substitutions in the one or more final therapeutic target sequences of the cell, and
   wherein the one or more final therapeutic target sequences are associated with a genetic disease or disorder.

2. The method of claim 1, further comprising:
   obtaining genome sequencing data of a subject to be treated; and
   wherein the delivering the CRISPR-Cas system to the cell comprises delivering the CRISPR-Cas system to the subject, wherein the CRISPR-Cas system selected is based at least in part on the genome sequencing data of the subject.

3. The method of claim 2, wherein the genome sequencing data is whole genome sequencing data.

4. The method of claim 1, wherein the candidate target sequences are further selected based on optimization of one or more parameters selected from the group consisting of protospacer adjacent motif (PAM) type, PAM nucleotide content, PAM length, target sequence length, PAM restrictiveness, target cleavage efficiency, and target sequence position within a gene, a locus or other genomic region.

5. The method of claim 1, wherein an effector protein for each CRISPR-Cas system in the set of CRISPR-Cas systems is selected based on optimization of one or more parameters selected from the group consisting of: effector protein size, ability of the effector protein to access regions of high chromatin accessibility, degree of uniform enzyme activity across genomic targets, epigenetic tolerance, mismatch/budge tolerance, effector protein specificity, effector protein stability or half-life, effector protein immunogenicity, and toxicity.

6. The method of claim 1, wherein the one or more gRNAs are a tru guide, an escorted guide, or a protected guide.

7. The method of claim 1, wherein the CRISPR-Cas system functionality comprises genomic mutation, gene knockout, gene correction, genomic region deletion, modulation of gene or genomic region functionality.

8. The method of claim 7, wherein modulation of gene or genomic region functionality comprises modulation gene activity or accessibility, optionally leading to transcriptional and/or epigenetic gene or genomic region activation or gene or genomic region silencing.

9. The method of claim 1, wherein a delivery vehicle and/or expression system for delivering the CRISPR-Cas systems or components thereof comprises liposomes, lipid particles, nanoparticles, biolistics, or viral-based expression/delivery systems.

10. The method of claim 1, further comprising conducting a sequencing-based double-strand break detection assay wherein off-target candidates, PAM restrictiveness, target cleavage efficiency, or effector protein specificity is determined.

11. The method of claim 1, wherein the set of CRISPR-Cas systems is a set of class 2 Type V CRISPR-Cas systems.

12. The method of claim 11, wherein the set of class 2 Type V CRISPR-Cas systems is a set of CRISPR-Cpf1 systems.

* * * * *

UNITED STATES PATENT AND TRADEMARK OFFICE
CERTIFICATE OF CORRECTION

PATENT NO.         : 11,352,647 B2
APPLICATION NO.    : 16/325898
DATED              : June 7, 2022
INVENTOR(S)        : Feng Zhang et al.

It is certified that error appears in the above-identified patent and that said Letters Patent is hereby corrected as shown below:

In the Specification
Column 5, Line 57: "1 -5" should be -- 1-5 --.
Column 7, Line 2: "log 10" should be -- log10 --.
Column 15, Line 49: "44 _17," should be -- 44_17, --.
Column 15, Line 62: "GW2011 GWC2" should be -- GW2011_GWC2 --.
Column 18, Line 21: ".kazuka." should be -- .kazusa. --.
Column 25, Line 30: "thereof" should be -- thereof. --.
Column 29, Line 3: "Can" should be -- Carr --.
Column 30, Line 51: "cryptochrome),In" should be -- cryptochrome). In --.
Column 37, Line 40: "a-fetoprotein" should be -- α-fetoprotein --.
Column 51, Line 53: "a-fetoprotein" should be -- α-fetoprotein --.
Column 63, Line 2: "a-fetoprotein" should be -- α-fetoprotein --.
Column 64, Line 34: "gRNA 1" should be -- gRNA1 --.
Column 64, Line 43: "gRNA 1" should be -- gRNA1 --.
Column 65, Line 5: "or" should be -- or H1 --.
Column 80, Line 6: ".orgicontent/5" should be -- .org/content/5 --.
Column 80, Line 7: ".orgiconre1/5" should be -- .org/content/5 --.
Column 88, Line 51: "itself" should be -- itself. --.
Column 99, Line 49: "itself" should be -- itself. --.
Column 106, Line 6: ">0.01%" should be -- ≥0.01% --.
Column 112, Line 52: "MRCS," should be -- MRC5, --.
Column 112, Lines 61-62: "COR-L2315010," should be -- COR-L23/5010, --.
Column 115, Line 28: "thereof" should be -- thereof. --.
Column 116, Line 62: "gRNA 1" should be -- gRNA1 --.
Column 118 (Table 8): Line 30, "lar" should be -- lari --.
Column 122, Line 43: "T7promoter-" should be -- T7 promoter --.
Column 124, Line 39 (approx.): "thereof" should be -- thereof. --.
Column 127, Line 51: "/nnano 2014.84)," should be -- /nnano.2014.84), --.
Column 129, Line 48: "/jjconre1." should be -- /j.jconrel. --.
Column 132, Line 37: "Si(R5)$_2$O—,"should be -- —OSi(R5)$_2$O—, --.

Signed and Sealed this
Thirty-first Day of January, 2023

Katherine Kelly Vidal
*Director of the United States Patent and Trademark Office*

CERTIFICATE OF CORRECTION (continued)
U.S. Pat. No. 11,352,647 B2

Column 133, Line 45: "R-3-1(ω-" should be -- R-3-[(ω- --.
Column 133, Line 60: "mmol/1." should be -- mmol/l. --.
Column 133, Line 61: "mmol/1" should be -- mmol/l --.
Column 134, Line 1: "mmol/1" should be -- mmol/l --.
Column 134, Line 24: "thereof" should be -- thereof. --.
Column 134, Line 25: "used/and or" should be -- used and/or --.
Column 134, Line 34: "mmol/1," should be -- mmol/l, --.
Column 136, Line 49: "R-3-1(ω-" should be -- R-3-[(ω- --.
Column 136, Line 64: "mmol/1." should be -- mmol/l. --.
Column 136, Line 65: "mmol/1." should be -- mmol/l. --.
Column 137, Line 5: "mmol/1." should be -- mmol/l. --.
Column 137, Line 28: "thereof" should be -- thereof. --.
Column 137, Line 35: "mmol/1." should be -- mmol/l. --.
Column 140, Line 1: "/nnano 2014.84)." should be -- /nnano.2014.84), --.
Column 142, Line 64: "cyclopenta[alphenanthrene." should be -- cyclopenta[a]phenanthrene. --.
Column 144, Line 3: "thereof" should be -- thereof. --.
Column 146, Line 2: "10" should be -- R1 --.
Column 147, Line 5: "IV" should be -- R1 --.
Column 148, Line 40 (approx.): "c-arginyl" should be -- ε-arginyl --.
Column 156, Line 38 (approx.): "B2" should be -- B2, --.
Column 156, Line 39 (approx.): "c12-20" should be -- C12-20 --.
Column 156, Line 63 (approx.): "NRc;" should be -- NRC; --.
Column 161, Line 51: "heteroC1-50alkyl," should be -- heteroC1-50 alkyl, --.
Column 161, Line 51: "heteroC2-50alkenyl," should be -- heteroC2-50 alkenyl, --.
Column 162, Line 17 (approx.): "carbamoyl] cholesterol" should be -- carbamoyl]cholesterol --.
Column 162, Line 46: "C17alkyl," should be -- C13alkyl, --.
Column 163, Line 53: "a" should be -- α, --.
Column 163, Line 55: "a" should be -- α, --.
Column 163, Line 57: "a" should be -- α, --.
Column 163, Line 63: "a" should be -- α, --.
Column 164, Line 35: "a" should be -- α, --.
Column 164, Line 38: "C1-C6" should be -- $C_1$-$C_6$ --.
Column 170, Line 36: "3-N-1 (methoxy" should be -- 3-N-[(methoxy --.
Column 171, Line 30: "at≥0.4" should be -- at ≥0.4 --.
Column 176, Line 40: "thereof" should be -- thereof. --.
Column 178, Line 35: "thereof" should be -- thereof. --.
Column 203, Line 39: "GW2011 GWC2" should be -- GW2011_GWC2 --.
Column 204, Line 38: "GW2011 GWC2" should be -- GW2011_GWC2 --.
Column 210, Line 35: "thereof" should be -- thereof. --.
Column 215, Line 3: "(1985)1," should be -- (1985)], --.
Column 229, Line 56: ".ce11." should be -- .cell. --.
Column 237, Line 25: "SETT/9" should be -- SET7/9 --.
Column 252, Line 21: "1n2-2" should be -- ln2-2 --.
Column 255, Line 49: "(33" should be -- β3 --.
Column 266, Line 54: "2002/08391 1" should be -- 2002/083911 --.

CERTIFICATE OF CORRECTION (continued)
U.S. Pat. No. 11,352,647 B2

Column 278, Line 22: "TO" should be -- T0 --.
Column 278, Line 43: "Ti" should be -- T1 --.
Column 279, Line 2: "Ti" should be -- T1 --.
Column 279, Line 32: "TO" should be -- T0 --.
Column 279, Line 32: "Ti" should be -- T1 --.
Column 281 (Table 17), Line 4 (approx.): "compositons" should be -- compositions --.
Column 288, Line 33: "ketch13," should be -- kelch13, --.
Column 291, Line 56: "CD4+T-lymphocytes" should be -- CD4+ T-lymphocytes --.
Column 292, Line 29: "log 10" should be -- log10 --.
Column 296, Line 8: "ketch13," should be -- kelch13, --.
Column 298, Line 6: "JBTSS;" should be -- JBTS5; --.
Column 299, Line 8: "Antoine %20Ribeil" should be -- Antoine%20Ribeil --.
Column 311, Line 17: "FANCFBACHVBRIP1,"should be -- FANCJ/BACH1/BRIP1, --.
Column 312, Line 50: "/tkowalski/" should be -- /t_kowalski/ --.
Column 317, Line 21: "4/day," should be -- µL/day, --.
Column 317, Line 25: "4/min." should be -- µL/min. --.
Column 319, Line 32: "ClORF49" should be -- C1ORF49 --.
Column 319, Line 58: "(IL-IRA)" should be -- (IL-1RA) --.
Column 322, Line 64: "ILIA" should be -- IL1A --.
Column 323, Line 24: "NR1I2" should be -- NR1I2 --.
Column 323, Line 55: "SCGS" should be -- SCG5 --.
Column 324, Line 48: "ALSS" should be -- ALS5 --.
Column 324, Line 64: "ICA 1L" should be -- ICA1L --.
Column 325, Line 61: "CABIN'" should be -- CABIN1 --.
Column 325, Line 66: "C 1QB" should be -- C1QB --.
Column 326, Line 1: "PARK?" should be -- PARK7 --.
Column 326, Line 10: "Derl-" should be -- Der1- --.
Column 326, Line 33: "5-transferase" should be -- S-transferase --.
Column 327, Line 57: "Hox-A 1" should be -- Hox-A1 --.
Column 330, Line 31: "HOXAS" should be -- HOXA5 --.
Column 333, Line 67: "(U205)" should be -- (U2OS) --.
Column 334, Line 23: "ell" should be -- cell --.
Column 335, Line 65: "100" should be -- 100 µl. --.
Column 336, Line 17: "3" should be -- 3 µg --.
Column 337, Line 55: "(CTRPS)"should be -- (CTRP5) --.
Column 338, Line 12 (approx.): "Glade" should be -- clade --.
Column 340, Line 5: "Glade" should be -- clade --.
Column 340, Line 37: "Glade" should be -- clade --.
Column 340, Line 46: "Glade" should be -- clade --.
Column 341, Line 65: "Glade" should be -- clade --.
Column 342, Line 17: "(Sp 1" should be -- (Sp1 --.
Column 343, Line 63: "5-transferase" should be -- S-transferase --.
Column 344, Line 13: "Glade" should be -- clade --.
Column 345, Line 2: "Glade" should be -- clade --.
Column 345, Line 30: "Glade" should be -- clade --.
Column 345, Line 39: "Glade" should be -- clade --.

CERTIFICATE OF CORRECTION (continued)
U.S. Pat. No. 11,352,647 B2

Column 347, Line 52: "O1)," should be -- O1), --.
Column 348, Line 7: "ApoA 1" should be -- ApoA1 --.
Column 352-352 (Table 19 con't), Line 3 (approx.): "streptozotozin-" should be -- streptozotocin--.
Column 353-354 (Table 19 con't), Line 31 (approx.): "(Apil" should be -- (April --.
Column 353-354 (Table 19 con't), Line 37 (approx.): "Phaemaceutics," should be
-- Pharmaceutics, --.
Column 360, Line 10: "sh-AcvrIIh" should be -- sh-AcvrIIb --.
Column 363, Line 27: "CFTRAF508" should be -- CFTRΔF508 --.
Column 366, Line 10: "CARS" should be -- CARs --.
Column 366, Line 18: "CARS" should be -- CARs --.
Column 371, Line 66: "PD-L 1." should be -- PD-L1. --.
Column 375-376 (Table 21), Line 17 (approx.): "Leukocyde" should be -- Leukocyte --.
Column 375-376 (Table 21), Line 27 (approx.): "PLZ," should be -- PLZF, --.
Column 379-380 (Table 22), Line 12 (approx.): "FOX01;" should be -- FOXO1; --.
Column 379-380 (Table 22), Line 29 (approx.): "T5C22D3;" should be -- TSC22D3; --.
Column 379-380 (Table 22), Line 39 (approx.): "H5P90AA1" should be -- HSP90AA1 --.
Column 379-380 (Table 22), Line 62 (approx.): "PIK3 CB;" should be -- PIK3CB; --.
Column 381-382 (Table 22 con't), Line 50 (approx.): "FOX01;" should be -- FOXO1; --.
Column 381-382 (Table 22 con't), Line 50 (approx.): "RP56KB1" should be -- RPS6KB1 --.
Column 383-384 (Table 22 con't), Line 13 (approx.): "H5P90AA1;" should be -- HSP90AA1; --.
Column 383-384 (Table 22 con't), Line 28 (approx.): "H5P90AA1; RP56KB1" should be
-- HSP90AA1; RPS6KB1 --.
Column 383-384 (Table 22 con't), Line 41 (approx.): "FOX01;" should be -- FOXO1; --.
Column 383-384 (Table 22 con't), Line 60 (approx.): "RP56KB1" should be -- RPS6KB1 --.
Column 383-384 (Table 22 con't), Line 62 (approx.): "NQ01;" should be -- NQO1; --.
Column 383-384 (Table 22 con't), Line 66 (approx.): "H5P90AA1" should be -- HSP90AA1 --.
Column 385-386 (Table 22 con't), Line 9 (approx.): "RG516;" should be -- RGS16; --.
Column 385-386 (Table 22 con't), Line 16 (approx.): "U5P22;" should be -- USP22; --.
Column 387-388 (Table 22 con't), Line 17 (approx.): "H5P90AA1;" should be -- HSP90AA1; --.
Column 387-388 (Table 22 con't), Line 51 (approx.): "FIDAC3;" should be -- HDAC3; --.
Column 389-390, (Table 22 con't), Line 27 (approx.): "GUI;" should be -- GLI1; --.
Column 389-390, (Table 22 con't), Line 34 (approx.): "FIK2;" should be -- HK2; --.
Column 389-390, (Table 22 con't), Line 46 (approx.): "FIK2;" should be -- HK2; --.
Column 391-392, (Table 22 con't), Line 33 (approx.): "Dab 1;" should be -- Dab1; --.
Column 404, Line 30: "e.g" should be -- e.g., --.
Column 407, Line 63: "(CTRPS)" should be -- (CTRP5) --.
Column 408, Line 19: "Glade" should be -- clade --.
Column 408, Line 58: "Glade" should be -- clade --.
Column 409, Line 23: "Glade" should be -- clade --.
Column 409, Line 31: "Glade" should be -- clade --.
Column 410, Line 13: "PDESA" should be -- PDE5A --.
Column 410, Line 51: "Glade" should be -- clade --.
Column 410, Line 55: "p 16," should be -- p16, --.
Column 411, Line 2: "(Sp 1" should be -- (Sp1 --.
Column 412, Line 49: "5-transferase" should be -- S-transferase --.
Column 412, Line 66: "Glade" should be -- clade --.

Column 413, Line 55: "Glade" should be -- clade --.
Column 414, Line 16: "Glade" should be -- clade --.
Column 414, Line 25: "Glade" should be -- clade --.
Column 429, Line 59: "ry" should be -- rv --.
Column 429, Line 61: "ry" should be -- rv --.
Column 430, Line 1: "barcode:" should be -- barcodes --.
Column 430, Line 59: "NL S" should be -- NLS --.
Column 432, Line 65: "10×T4" should be -- 10X T4 --.
Column 432, Line 66: "1×;" should be -- 1X; --.
Column 440, Line 45 (approx.): ">0.01%" should be -- ≥0.01% --.
Column 414, Line 65: ">10%" should be -- ≥10% --.
Column 444, Line 47: "K548 W," should be -- K548W, --.
Column 444, Line 51: "K548 W," should be -- K548W, --.
Column 445, Line 12 (approx.): "1128," should be -- I128, --.
Column 445, Line 17 (approx.): "1555," should be -- I555, --.
Column 445, Line 18 (approx.): "1567," should be -- I567, --.
Column 445, Line 19 (approx.): "1605," should be -- I605, --.
Column 445, Line 22 (approx.): "1626," should be -- I626, --.
Column 445, Line 23 (approx.): "1633," should be -- I633, --.
Column 445, Line 23 (approx.): "1638," should be -- I638, --.
Column 445, Line 23 (approx.): "1642," should be -- I642, --.
Column 445, Line 26 (approx.): "1693," should be -- I693, --.
Column 445, Line 28 (approx.): "1721," should be -- I721, --.
Column 445, Line 29 (approx.): "1779," should be -- I779, --.
Column 445, Line 30 (approx.): "1875," should be -- I875, --.
Column 445, Line 42 (approx.): "1605," should be -- I605, --.
Column 447, Line 58: "5542/K607R" should be -- S542R/K607R --.
Column 449 (Table 13), Line 16 (approx.): "5542R/K607R" should be -- S542R/K607R --.
Column 462, Line 9 (approx.): "AA V" should be -- AAV --.